US012441708B2

(12) United States Patent
Crew et al.

(10) Patent No.: US 12,441,708 B2
(45) Date of Patent: Oct. 14, 2025

(54) CEREBLON LIGANDS AND BIFUNCTIONAL COMPOUNDS COMPRISING THE SAME

(71) Applicant: Arvinas Operations, Inc., New Haven, CT (US)

(72) Inventors: Andrew P. Crew, Chester, CT (US); Michael Berlin, Flemington, NJ (US); Keith R. Hornberger, Southbury, CT (US); Lawrence B. Snyder, Killingworth, CT (US); Jing Wang, Milford, CT (US); Yimin Qian, Plainsboro, NJ (US); Hanqing Dong, Madison, CT (US); Kurt Zimmermann, Durham, CT (US)

(73) Assignee: Arvinas Operations, Inc., New Haven, CT (US)

( * ) Notice: Subject to any disclaimer, the term of this patent is extended or adjusted under 35 U.S.C. 154(b) by 0 days.

(21) Appl. No.: 18/079,790

(22) Filed: Dec. 12, 2022

(65) Prior Publication Data

US 2023/0183209 A1 Jun. 15, 2023

Related U.S. Application Data

(63) Continuation of application No. 15/885,671, filed on Jan. 31, 2018, now abandoned.

(60) Provisional application No. 62/452,972, filed on Jan. 31, 2017.

(51) Int. Cl.

| | |
|---|---|
| ***C07D 401/14*** | (2006.01) |
| ***A61P 35/02*** | (2006.01) |
| ***C07D 417/14*** | (2006.01) |
| ***C07D 471/04*** | (2006.01) |
| ***C07D 471/10*** | (2006.01) |
| ***C07D 487/04*** | (2006.01) |
| ***C07D 495/14*** | (2006.01) |
| ***C07D 498/04*** | (2006.01) |

(52) U.S. Cl.

CPC ............ *C07D 401/14* (2013.01); *A61P 35/02* (2018.01); *C07D 417/14* (2013.01); *C07D 471/04* (2013.01); *C07D 471/10* (2013.01); *C07D 487/04* (2013.01); *C07D 495/14* (2013.01); *C07D 498/04* (2013.01)

(58) Field of Classification Search

CPC .................................................... C07D 401/14

See application file for complete search history.

(56) References Cited

U.S. PATENT DOCUMENTS

| | | | |
|---|---|---|---|
| 4,522,811 | A | 6/1985 | Eppstein et al. |
| 5,492,922 | A | 2/1996 | Palkowitz |
| 6,306,663 | B1 | 10/2001 | Kenten et al. |
| 6,642,251 | B1 | 11/2003 | Tang et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Dashaies et al. |
| 8,067,473 | B2 | 11/2011 | Erez et al. |
| 9,500,653 | B2 | 11/2016 | Crews et al. |
| 9,632,089 | B2 | 4/2017 | Crews et al. |
| 9,938,264 | B2 | 4/2018 | Crews et al. |
| 10,071,164 | B2 | 9/2018 | Crew et al. |
| 10,584,101 | B2 | 3/2020 | Crew et al. |
| 10,844,021 | B2 | 11/2020 | Crew et al. |
| 11,220,515 | B2 | 1/2022 | Crews et al. |
| 11,236,051 | B2 | 2/2022 | Crew et al. |
| 11,505,560 | B2 | 11/2022 | Nowak et al. |
| 11,883,393 | B2 | 1/2024 | Snyder et al. |
| 2007/0254933 | A1 | 11/2007 | Jung et al. |
| 2008/0051432 | A1 | 2/2008 | Zhang |
| 2008/0214501 | A1 | 9/2008 | Pan et al. |
| 2008/0219929 | A1 | 9/2008 | Wischik et al. |
| 2009/0035362 | A1 | 2/2009 | Shih et al. |
| 2009/0142297 | A1 | 6/2009 | Muller et al. |
| 2010/0048517 | A1 | 2/2010 | Hu et al. |

(Continued)

FOREIGN PATENT DOCUMENTS

| | | | |
|---|---|---|---|
| CA | 2945975 | A1 | 10/2015 |
| CL | 202200302 | A1 | 2/2023 |

(Continued)

OTHER PUBLICATIONS

Ahn, D., et al., "HIF-1α Peptide Derivatives with modifications at the hydroxyproline residue as activators of HIF-1α", Bioorganic & Medicinal Chemistry Letters (2009); 19(15): 4403-4405.

(Continued)

*Primary Examiner* — David K O'Dell

(74) *Attorney, Agent, or Firm* — LATHROP GPM LLP; Brian C. Trinque

(57) ABSTRACT

The description relates to cereblon E3 ligase binding compounds, including bifunctional compounds comprising the same, which find utility as modulators of targeted ubiquitination, especially inhibitors of a variety of polypeptides and other proteins which are degraded and/or otherwise inhibited by bifunctional compounds according to the present disclosure. In particular, the description provides compounds, which contain on one end a ligand which binds to the cereblon E3 ubiquitin ligase and on the other end a moiety which binds a target protein such that the target protein is placed in proximity to the ubiquitin ligase to effect degradation (and inhibition) of that protein. Compounds can be synthesized that exhibit a broad range of pharmacological activities consistent with the degradation/inhibition of targeted polypeptides of nearly any type.

20 Claims, 1 Drawing Sheet

(56) References Cited

U.S. PATENT DOCUMENTS

| | | | |
|---|---|---|---|
| 2010/0286127 | A1 | 11/2010 | Miyoshi et al. |
| 2011/0269793 | A1 | 11/2011 | Maccioni |
| 2012/0270800 | A1 | 10/2012 | Verdine et al. |
| 2014/0088143 | A1 | 3/2014 | Jain |
| 2014/0256700 | A1 | 9/2014 | Poss et al. |
| 2014/0302523 | A1 | 10/2014 | Crews et al. |
| 2014/0356322 | A1 | 12/2014 | Crews et al. |
| 2014/0371206 | A1 | 12/2014 | Albrecht et al. |
| 2015/0119435 | A1 | 4/2015 | Crews et al. |
| 2015/0141470 | A1 | 5/2015 | Garraway et al. |
| 2015/0148342 | A1 | 5/2015 | Yue et al. |
| 2015/0259288 | A1 | 9/2015 | Nam et al. |
| 2015/0291562 | A1 | 10/2015 | Crew et al. |
| 2015/0344473 | A1 | 12/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0136230 | A1 | 5/2016 | Campos et al. |
| 2016/0176864 | A1 | 6/2016 | Norris et al. |
| 2016/0214972 | A1 | 7/2016 | Jin et al. |
| 2016/0243247 | A1 | 8/2016 | Bradner et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |
| 2019/0233433 | A1 | 8/2019 | Crews et al. |
| 2021/0147387 | A1 | 5/2021 | Arlt et al. |
| 2021/0171470 | A1 | 6/2021 | Crew et al. |
| 2021/0196710 | A1 | 7/2021 | Snyder et al. |
| 2021/0380591 | A1 | 12/2021 | Koolman et al. |
| 2022/0112211 | A1 | 4/2022 | Crews et al. |
| 2022/0184078 | A1 | 6/2022 | Chirnomas et al. |
| 2022/0259154 | A1 | 8/2022 | Berlin et al. |
| 2022/0313826 | A1 | 10/2022 | Phillips et al. |
| 2023/0011726 | A1 | 1/2023 | Li et al. |
| 2023/0082997 | A1 | 3/2023 | Berlin et al. |
| 2023/0087008 | A1 | 3/2023 | Pouletty et al. |
| 2023/0111119 | A1 | 4/2023 | Lu et al. |
| 2023/0112499 | A1 | 4/2023 | Panknin et al. |
| 2023/0119316 | A1 | 4/2023 | Kurhade et al. |
| 2023/0142285 | A1 | 5/2023 | Cai et al. |
| 2023/0159519 | A1 | 5/2023 | Gerusz et al. |
| 2023/0203009 | A1 | 6/2023 | Waetzig et al. |
| 2024/0131023 | A1 | 4/2024 | Snyder |
| 2024/0180900 | A1 | 6/2024 | Peck et al. |
| 2024/0336566 | A1 | 10/2024 | Chen |
| 2025/0009737 | A1 | 1/2025 | Zhang et al. |

FOREIGN PATENT DOCUMENTS

| | | | |
|---|---|---|---|
| CL | 202200303 | A1 | 2/2023 |
| CL | 202201583 | A1 | 2/2023 |
| CL | 202201644 | A1 | 2/2023 |
| CL | 202203305 | A1 | 2/2023 |
| CL | 202201642 | A1 | 3/2023 |
| CL | 202201660 | A1 | 3/2023 |
| CL | 202201670 | A1 | 3/2023 |
| CL | 202201739 | A1 | 3/2023 |
| CL | 202203353 | A1 | 7/2023 |
| CN | 1844118 | A | 10/2006 |
| CN | 102477033 | A | 5/2012 |
| CN | 103688176 | A | 3/2014 |
| DE | 2460304 | A1 | 7/1976 |
| EP | 2985285 | A1 | 2/2016 |
| JP | 2002523455 | A | 7/2002 |
| JP | 2004525889 | A | 8/2004 |
| JP | 2010502627 | A | 1/2010 |
| JP | 2010515771 | A | 5/2010 |
| JP | 7061135 | B2 | 4/2022 |
| RU | 2310651 | C2 | 11/2007 |
| RU | 2008112221 | A | 10/2009 |
| RU | 2418800 | C2 | 5/2011 |
| RU | 2448101 | C2 | 4/2012 |
| RU | 2011121567 | A | 12/2012 |
| RU | 2012138709 | A | 3/2014 |
| WO | WO-9803502 | A1 | 1/1998 |
| WO | WO-9915521 | A1 | 4/1999 |
| WO | WO-9931061 | A1 | 6/1999 |
| WO | WO-0066119 | A1 | 11/2000 |
| WO | WO-0200617 | A2 | 1/2002 |
| WO | WO-0222577 | A2 | 3/2002 |
| WO | WO-02066512 | A1 | 8/2002 |
| WO | WO-02100845 | A1 | 12/2002 |
| WO | WO-03097052 | A2 | 11/2003 |
| WO | WO-2005007141 | A2 | 1/2005 |
| WO | WO-2006113942 | A2 | 10/2006 |
| WO | WO-2007106670 | A2 | 9/2007 |
| WO | WO-2008011392 | A2 | 1/2008 |
| WO | WO-2009015254 | A1 | 1/2009 |
| WO | WO-2010053732 | A1 | 5/2010 |
| WO | WO-2010141805 | A1 | 12/2010 |
| WO | WO-2011008260 | A2 | 1/2011 |
| WO | WO-2011119565 | A1 | 9/2011 |
| WO | WO-2011143660 | A2 | 11/2011 |
| WO | WO-2011143669 | A2 | 11/2011 |
| WO | WO-2012003281 | A2 | 1/2012 |
| WO | WO-2012040389 | A2 | 3/2012 |
| WO | WO-2012040527 | A2 | 3/2012 |
| WO | WO-2012078559 | A2 | 6/2012 |
| WO | WO-2012090104 | A1 | 7/2012 |
| WO | WO-2013097224 | A1 | 7/2013 |
| WO | WO-2013106643 | A2 | 7/2013 |
| WO | WO-2013106646 | A2 | 7/2013 |
| WO | WO-2013170147 | A1 | 11/2013 |
| WO | WO-2014001356 | A1 | 1/2014 |
| WO | WO-2014015157 | A2 | 1/2014 |
| WO | WO-2014108452 | A1 | 7/2014 |
| WO | WO-2014123418 | A1 | 8/2014 |
| WO | WO-2014128111 | A1 | 8/2014 |
| WO | WO-2015000868 | A1 | 1/2015 |
| WO | WO-2015011084 | A1 | 1/2015 |
| WO | WO-2015015318 | A2 | 2/2015 |
| WO | WO-2015022332 | A1 | 2/2015 |
| WO | WO-2015067770 | A1 | 5/2015 |
| WO | WO-2015074064 | A2 | 5/2015 |
| WO | WO-2015160845 | A2 | 10/2015 |
| WO | WO-2015188120 | A1 | 12/2015 |
| WO | WO-2015195863 | A1 | 12/2015 |
| WO | WO-2016050821 | A1 | 4/2016 |
| WO | WO-2016069578 | A1 | 5/2016 |
| WO | WO-2016097071 | A1 | 6/2016 |
| WO | WO-2016105518 | A1 | 6/2016 |
| WO | WO-2016118666 | A1 | 7/2016 |
| WO | WO-2016146985 | A1 | 9/2016 |
| WO | WO-2016149668 | A1 | 9/2016 |
| WO | WO-2016169989 | A1 | 10/2016 |
| WO | WO-2016172134 | A2 | 10/2016 |
| WO | WO-2016197032 | A1 | 12/2016 |
| WO | WO-2016197114 | A1 | 12/2016 |
| WO | WO-2017007612 | A1 | 1/2017 |
| WO | WO-2017011371 | A1 | 1/2017 |
| WO | WO-2017011590 | A1 | 1/2017 |
| WO | WO-2017024319 | A1 | 2/2017 |
| WO | WO-2017030814 | A1 | 2/2017 |
| WO | WO-2017046036 | A1 | 3/2017 |
| WO | WO-2017079267 | A1 | 5/2017 |

(56) References Cited

FOREIGN PATENT DOCUMENTS

| | | | |
|---|---|---|---|
| WO | WO-2017161119 | A1 | 9/2017 |
| WO | WO-2017176957 | A1 | 10/2017 |
| WO | WO-2017185036 | A1 | 10/2017 |
| WO | WO-2017197051 | A1 | 11/2017 |
| WO | WO-2018053354 | A1 | 3/2018 |
| WO | WO-2018071606 | A1 | 4/2018 |
| WO | WO-2018098280 | A1 | 5/2018 |
| WO | WO-2018144649 | A1 | 8/2018 |
| WO | WO-2018200981 | A1 | 11/2018 |
| WO | WO-2021127443 | A1 | 6/2021 |
| WO | WO-2022174134 | A1 | 8/2022 |
| WO | WO-2024091975 | A1 | 5/2024 |

OTHER PUBLICATIONS

Albrecht, B. K., et al., "Identification of a benzoisoxazoloazepine inhibitor (CPI-0610) of the bromodomain and extra-terminal (BET) family as a candidate for human clinical trials", Journal of Medicinal Chemistry (2016); 59: 1330-1339.

Allan, G. F., et al., "Therapeutic androgen receptor ligands", Nuclear Receptor Signaling (2003); 1(1): 1-4.

Ariza, M., et al., "Tau positron emission tomography (PET) imaging: past, present, and future", Journal of Medicinal Chemistry (2015); 58(11): 4365-4382.

Asangani, I. A., et al., "Therapeutic Targeting of BET Bromodomain Proteins in Castration-Resistant Prostate Cancer", Nature (2014); 510: 278-282.

[Author Unknown] "Cancer" Medline Plus Trusted Health Information for You [online] www.nlm.nih.gov/medlineplus/cancer.html (Jul. 6, 2007); 10 pages.

Azad, A. A., et al., "Androgen receptor gene aberrations in circulating cell-free DNA: biomarkers of therapeutic resistance in castration-resistant prostate cancer", Clinical Cancer Research (2015); 21(10): 2315-2324.

Banker, G. S., et al. (Ed.)., "Modern Pharmaceutics", Third Edition, Revised and Expanded, Marcel Dekker, Inc. (1996); pp. 450-453 and 596-597; 10 pages.

Baratta, M. G., et al., "An in-tumor genetic screen reveals that the BET bromodomain protein, BRD4, is a potential therapeutic target in ovarian carcinonoma", PNAS (2015); 112: 232-237.

Bargagna-Mohan, P., et al., "Use of PROTACS as molecular probes of angiogenesis", Bioorganic & Medicinal Chemistry Letters (2005); 15(11): 2724-2727.

Battista, M. J., et al., "Fulvestrant for the treatment of endometrial cancer." Expert Opinion on Investigational Drugs (2016); 25(4): 475-483.

Beaumont, K., et al., "Design of Ester Prodrugs to Enhance Oral Absorption of Poorly Permeable Compounds: Challenges to the Discovery Scientist", Current Drug Metabolism (2003); 4(6): 461-485.

Belkina, A. C., et al., "BET domain co-regulators in obesity, inflammation and cancer", Nature Reviews Cancer (2012); 12(7): 465-477.

Bogush, T. A., et al., "Expression of estrogen receptors in tumors other than cancer mammary gland", Antibiotics and Chemotherapy (2009); 54(7-8): 41-49; 10 pages with English summary.

Boi, M., et al., "The BET Bromodomain inhibitor OTX015 Affects pathogenetic Pathways in Preclinical B-cell Tumor Models and synergizes with Targeted Drugs", Clinical Cancer Research (2015); 21(7): 1628-1638.

Boichenko, I., et al., "A FRET-Based Assay for the Identification and Characterization of Cereblon Ligands", Journal of Medicinal Chemistry (2016); 59(2): 770-774.

Boitano, et al., "Aryl Hydrocarbon Receptor Antagonists Promote the Expansion of Human Hematopoietic Stem Cells", Science (2010); 329: 1345-1348.

Bondeson, D. P., et al., "Catalytic in vivo protein knockdown by small-molecule PROTACS", Nature Chemical Biology (2015); 11(8): 611-617.

Bondeson, D. P., et al., "Lessons in PROTAC design from selective degradation with a promiscuous warhead", Cell Chemical Biology (2018); 25(1): 78-87.

Bondeson, D. P., et al., "Targeted Protein Degradation by Small Molecules", Annual Review of Pharmacology and Toxicology (2017); 57 :107-123.

Bradbury, R. H., et. al., "Small-molecule androgen receptor downregulators as an approach to treatment of advanced prostate cancer", Bioorganic & Medicinal Chemistry Letters (2011); 21: 5442-5445.

Brough, P. A., et al., "4,5-Diarylisoxazole HSP90 Chaperone Inhibitors: Potential Therapeutic Agents for the Treatment of Cancer", Journal of Medicinal Chemistry (2008); 51(2): 196-218.

Buckley, D. L., et al., "HaloPROTACS: use of small molecule PROTACS to induce degradation of HaloTag fusion proteins", ACS Chemical Biology (2015); 10(8): 1831-1837.

Buckley, D. L., et al., "Small-molecule inhibitors of the interaction between the E3 ligase VHL and HIF1α", Angewandte Chemie (International Ed. in English) (2012); 51(46): 11463-11467.

Buckley, D. L., et al., "Targeting the von Hippel-Lindau E3 ubiquitin ligase using small molecules to disrupt the VHL/HIF-1α interaction", Journal of the American Chemical Society (2012); 134(10): 4465-4468.

Burslem, G. M., et al., "Small-Molecule Modulation of Protein Homeostasis", Chemical Reviews (2017); 117(17): 11269-11301.

Burslem, G. M., et al., "The Advantages of Targeted Protein Degradation Over Inhibition: An RTK Case Study", Cell Chemical Biology (2018); 25(1): 67-77.

Capitosti, S. M., et al., "Thalidomide analogues demonstrate dual inhibition of both angiogenesis and prostate cancer", Bioorganic & Medicinal Chemistry (2004); 12(2): 327-336.

Carmony, K. C., et al., "PROTAC-induced proteolytic targeting", Methods in Molecular Biology (2012); 832: 627-638.

Catalona, W. J., et al., "Comparison of digital rectal examination and serum prostate specific antigen in the early detection of prostate cancer: results of a multicenter clinical trial of 6,630 men", The Journal of Urology (1994); 151(5): 1283-1290.

Ceribelli, M., et al., "Blockade of oncongenic IKB kinase activity in diffuse large B-cell lymphoma by bromodomain and extraterminal domain protein inhibitors", PNAS (2014); 111(31): 11365-11370.

Chan, K., et al., "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (IBET726) Bet Inhibitor Scaffolds", Journal of Medicinal Chemistry (Jun. 8, 2018) ; 61(2): 504-513.

Chang, Y., et al., "Structural basis for G9a-like protein lysine methyltransferase inhibition by BIX-01294", Nature Structural & Molecular Biology (2009); 16(3): 312-317.

Chapuy, B., et al., "Discovery and characterization of super-enhancer-associated dependencies in diffuse large B cell lymphoma", Cancer Cell (2013); 24: 777-790.

Chen, C. D., et al., "Molecular determinants of resistance to antiandrogen therapy", Nature Medicine (2004); 10(1): 33-39.

Chung, C., et al., "Discovery and Characterization of Small Molecule Inhibitors of the BET Family Bromodomains", Journal of Medicinal Chemistry (2011); 54(11): 3827-3838.

Churcher, I., "Protac-Induced Protein Degradation in Drug Discovery: Breaking the Rules or Just Making New Ones?", Journal of Medicinal Chemistry (2018); 61(2): 444-452.

Cleutjens, K. B. J. M., et al., "Two Androgen Response Regions Cooperate in Steroid Hormone Regulated Activity of the Prostate-specific Antigen Promoter", Journal of Biological Chemistry (1996); 271(11): 6379-6388.

ClinicalTrials.gov Identifier: NCT01587703, "A Study to Investigate the Safety, Pharmacokinetics, Pharmacodynamics, and Clinical Activity of GSK525762 in Subjects With NUT Midline Carcinoma (NMC) and Other Cancers" [online] https://classic.clinicaltrials.gov/ct2/show/NCT01587703 (First Posted—Apr. 30, 2012, Access Date—Jul. 11, 2023); 59 pages.

ClinicalTrials.gov Identifier: NCT01713582, "A Dose-finding Study of the Bromodomain (Brd) Inhibitor OTX015/ Birabresib (MK-8628) in Hematologic Malignancies (MK-8628-001)" [online] https://classic.clinicaltrials.gov/ct2/show/NCT01713582 (First Posted—Oct. 22, 2012, Access Date—Jul. 11, 2023); 26 pages.

(56) References Cited

OTHER PUBLICATIONS

ClinicalTrials.gov Identifier: NCT01949883, "A Phase 1 Study Evaluating CPI-0610 in Patients With Progressive Lymphoma" [online] https://classic.clinicaltrials.gov/ct2/show/NCT01949883 (First Posted—Sep. 25, 2013, Access Date—Jul. 11, 2023); 12 pages.
ClinicalTrials.gov Identifier: NCT01987362, "A Two Part Study of RO6870810. Dose-Escalation Study in Participants With Advanced Solid Tumors and Expansion Study in Participants With Selected Malignancies" [online] https://classic.clinicaltrials.gov/ct2/show/NCT01987362 (First Posted—Nov. 19, 2013, Access Date—Jul. 11, 2023); 15 pages.
ClinicalTrials.gov Identifier: NCT05067140, "A Study of ARV-766 Given by Mouth in Men With Metastatic Castration-resistant Prostate Cancer Who Have Progressed on Prior Approved Systemic Therapies" [online] https://clinicaltrials.gov/ct2/show/NCT05067140?term=arv-766&draw=2&rank=1 (First Posted—Oct. 5, 2021, Last Update Posted—Feb. 2, 2023); 8 pages.
Contino-Pepin, C., et al., "Preliminary biological evaluations of new thalidomide analogues for multiple sclerosis application", Bioorganic & Medicinal Chemistry Letters (2009); 19(3): 878-881.
Co-pending U.S. Appl. No. 18/460,063, inventor Snyder; Lawrence B., filed Sep. 1, 2023.
Co-pending U.S. Appl. No. 18/493,773, inventors Peck; Ronald et al., filed Oct. 24, 2023.
Corson, T. W., et al., "Design and applications of bifunctional small molecules: why two heads are better than one", ACS Chemical Biology (2008); 3(11): 677-692.
Crew, A. P., et al., "Identification and Characterization of Von Hippel-Lindau-Recruiting Proteolysis Targeting Chimeras (PROTACs) of TANK-Binding Kinase 1", Journal of Medicinal Chemistry (2018); 61(2): 583-598.
Crews, C. M., "Targeting the undruggable proteome: the small molecules of my dreams", Chemistry & Biology (2010); 17(6): 551-555.
Cromm, P. M., et al., "Targeted protein degradation: from chemical biology to drug discovery", Cell chemical Biology (2017); 24(9): 1181-1190.
Cyrus, K., et al., "Impact of linker length on the activity of PROTACs", Molecular BioSystems (2011); 7(2): 359-364.
Cyrus, K., et al., "Jostling for position: Optimizing linker location in the design of estrogen receptor-targeting PROTACs", ChemMedChem (2010); 5(7): 979-985.
Cyrus, K., et al., "Two-Headed PROTAC: An Effective New Tool for Targeted Protein Degradation", Chembiochem (2010); 11(11): 1531-1534.
Database STN, CAS Registry No. 1004933-70-3, "2-Pyrrolidinecarboxamide, N-(4-bromo-2-fluorophenyl)-4-hydroxy-1-(2-naphthalenylsulfonyl)-, (2S,4R)-", Chemical Abstracts Service, American Chemical Society; entered Feb. 21, 2008; 1 page.
Database STN, CAS Registry No. 1226974-40-8, "Urea, N-[[2-(2,6-dioxo-3-piperidinyl)-2,3-dihydro-1-oxo-1H-isoindol-5-yl]methyl]-N'-(4-phenylcyclohexyl)-", Chemical Abstracts Service, American Chemical Society; entered Jun. 4, 2010; 1 page.
Database STN, CAS Registry No. 155180-53-3, "Benzonitrile, 4-[3-(4-hydroxybutyl)-4,4-dimethyl-5-oxo-2-thioxo-1-imidazolidinyl]-2-(trifluoromethyl)-", Chemical Abstracts Service, American Chemical Society; entered May 19, 1994; 1 page.
Database STN, CAS Registry No. 155255-73-5, "Benzonitrile, 4-[4,4-dimethyl-2,5-dioxo-3-[4-(triphenylmethoxy)butyl]-1-imidazolidinyl]-2-(trifluoromethyl)-", Chemical Abstracts Service, American Chemical Society; entered May 24, 1994; 1 page.
Database STN, CAS Registry No. 1818885-25-4, "Benzamide, N-[trans-3-(3-chloro-4-cyanophenoxy)-2,2,4,4-tetramethylcyclobutyl]-4-[[5-[3-[[2-(2,6-dioxo-3-piperidinyl)-2,3-dihydro-1,3-dioxo-1H-isoindol-4-yl]amino]propoxy]pentyl]oxy]-", Chemical Abstracts Service, American Chemical Society; entered Nov. 10, 2015; 1 page.
Database STN, CAS Registry No. 186040-53-9, "Benzenepropanoic acid, β-(benzoylamino)-α-hydroxy-, (2aR,4S,4aS,6R,9S,11S,12S,12aR,12bS)-6,12b-bis(acetyloxy)-12-(benzoyloxy)-4-[[[[2-[3-[4-cyano-3-(trifluoromethyl)phenyl]-5,5-dimethyl-4-oxo-2-thioxo-1-imidazolidinyl]ethyl]amino]carbonyl]oxy]-2a,3,4,4a,5,6,9,10,11,12,12a,12b-dodecahydro-11-hydroxy-4a,8,13,13-tetramethyl-5-oxo-7,11-methano-1H-cyclodeca[3,4]benz[1,2-b]oxet-9-ylester, (αR,βS)-", Chemical Abstracts Service, American Chemical Society; entered Feb. 13, 1997; 2 pages.
Database STN, CAS Registry No. 186798-71-0, "Glycinamide, N-[[(triphenylmethyl)thio]acetyl]glycyl-N-[2-[3-[4-cyano-3-(trifluoromethyl)phenyl]-5,5-dimethyl-4-oxo-2-thioxo-1-imidazolidinyl]ethyl]-", Chemical Abstracts Service, American Chemical Society; entered Mar. 7, 1997; 1 page.
Database STN, CAS Registry No. 186798-85-6, "Benzenepropanamide, N-[2-[3-[4-cyano-3-(trifluoromethyl)phenyl]-5,5-dimethyl-4-oxo-2-thioxo-1-imidazolidinyl]ethyl]-4-hydroxy-3,5-diiodo-", Chemical Abstracts Service, American Chemical Society; entered Mar. 7, 1997; 1 page.
Database STN, CAS Registry No. 534612-78-7, "Benzonitrile, 4-[3-[5-[4-[[2-[2-(2-methoxyethoxy)ethoxy]ethyl]sulfonyl]-1-piperazinyl]pentyl]-4,4-dimethyl-5-oxo-2-thioxo-1-imidazolidinyl]-2-(trifluoromethyl)-", Chemical Abstracts Service, American Chemical Society; entered Jun. 20, 2003; 1 page.
Database STN, CAS Registry No. 871986-52-6, "2-Pyrrolidinecarboxamide, N-[(1S)-3-[(3aR,6aS)-5-(2,6-dimethylbenzoyl)hexahydropyrrolo[3,4-c]pyrrol-2(1H)-yl]-1-phenylpropyl]-1-(2-furanylcarbonyl)-4-hydroxy-", Chemical Abstracts Service, American Chemical Society; entered Jan. 16, 2006; 1 page.
Dawson, M. A., et al., "Inhibition of BET recruitment to chromatin as an effective treatment for MLL-fusion leukemia", Nature (Oct. 2, 2011); 478; 529-533.
Delmore, J. E., et al., "BET Bromodomain inhibition as a therapeutic strategy to target c-Myc", Cell (2011); 146: 904-917.
Deroo, B. J., et al., "Estrogen receptors and human disease", Journal of Clinical Investigation (2006); 116(3): 561-570.
Di, J., et al., "Reactivation of p53 by inhibiting Mdm2 E3 Ligase: a novel antitumor approach", Current Cancer Drug Targets (2011); 11(8): 987-994.
Dixon, S. J., et al., "Identifying druggable disease-modifying gene products", Current Opinion in Chemical Biology (2009); 13(5-6): 549-555.
Durnov, L. A., et al., Pediatric Oncology, Second Edition, Moscow: Medicine Publishing House (2002); pp. 139-140; 5 pages with English summary.
Dyson, G. M., et al., "May's Chemistry of Synthetic Drugs", Longmans, Fifth Edition, Moscow, MIR (1964); pp. 12-19; 12 pages with English summary.
Filippakopoulos, P., et al., "Selective inhibition of BET bromodomains", Nature (Dec. 23, 2010); 468: 1067-1073.
Finnin, M. S., et al., "Structures of a histone deacetylase homologue bound to the TSA and SAHA inhibitors," Nature (Sep. 1999), vol. 401, pp. 188-193.
Fischer, E. S., et al., "Structure of the DDB1-CRBN E3 Ubiquitin ligase in complex with thalidomide", Nature (2014); 512(7512): 49-53.
French, C. A., et al., "BRD-NUT oncoproteins: a family of closely related nuclear proteins that block epithelial differentiation and maintain the growth of carcinoma cells", Oncogene (2008); 27: 2237-2242.
Gabay, M., et al., "MYC Activation is a hallmark of cancer initiation and maintenance", Cold Spring Harbor Perspectives in Medicine (2014); 4(a014241): 1-14.
Gadd, M. S., et al., "Structural basis of PROTAC cooperative recognition for selective protein degradation", Nature Chemical Biology (2017); 13(5): 514-521.
Galdeano, C., et al., "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities", Journal of Medicinal Chemistry (2014); 57(20): 8657-8663.
Gangjee, A., et al., "The contribution of a 2-amino group on receptor tyrosine kinase inhibition and antiangiogenic activity in 4-anilinosubstituted pyrrolo [2,3-d]pyrimidines", Bioorganic & Medicinal Chemistry Letters (2010); 20(10); 3177-3181.

(56) References Cited

OTHER PUBLICATIONS

Garrido, J., "Influencia de los agentes exteriores sobre la forma de los cristales", Forma y estructura de los cristales, Exedra (1973); Chapter V: 204-225; 34 pages with English Translation.
Giron, D., "Thermal analysis and calorimetric methods in the characterisation of polymorphs and solvates", Thermochimica Acta (1995); 248: 1-59.
Golub, T. R., et al., "Molecular classification of cancer: class discovery and class prediction by gene expression monitoring", Science (1991); 286: 531-537.
Gosink, M., et al., "Redirecting the specificity of ubiquitination by modifying ubiquitin-conjugating enzymes", Proceedings of the National Academy of Sciences (1995); 92(20): 9117-9121.
Gottlieb, B., et al., "The androgen receptor gene mutations database (ARDB): 2004 update", Human Mutation (2004); 23(6): 527-533.
Guo, C., et al., "Design of oxobenzimidazoles and oxindoles as novel androgen receptor antagonists", Bioorganic & Medicinal Chemistry Letters (2012); 22: 2572-2578.
Guo, C., et al., "Discovery of Aryloxy Tetramethylcyclobutanes as Novel Androgen Receptor Antagonists", Journal of Medicinal Chemistry (2011); 54: 7693-7704.
Gustafson, J. L., et al., "Small-molecule-mediated degradation of the androgen receptor through hydrophobic tagging", Angewandte Chemie (2015); 54: 9659-9662.
Heinlein, C. A., et al., "Androgen receptor in prostate cancer", Endocrine Reviews (2004); 25(2): 276-308.
Heinlein, C. A., et al., "The roles of androgen receptors and androgen-binding proteins in nongenomic androgen actions", Molecular Endocrinology (2002); 16(10): 2181-2187.
Hewings, D. S., et al., "3,5-Dimethylisoxazoles Act as Acetyllysine-mimetic Bromodomain", Journal of Medicinal Chemistry (Oct. 13, 2011); 54(19): 6761-6770.
Hines, J., et al., "Posttranslational protein knockdown coupled to receptor tyrosine kinase activation with phosphoPROTACs", Proceedings of the National Academy of Sciences (2013); 110(22): 8942-8947.
Hoffmann, J., et al., "Characterization of New Estrogen Receptor Destabilizing Compounds: Effects on Estrogen-Sensitive and Tamoxifen-Resistant Breast Cancer", JNCI Journal of the National Cancer Institute (2004); 96(3); 210-218.
Hon, W., et al., "Structural basis for the recognition of hydroxyproline in HIF-1α by pVHL", Nature (2002); 417(6892): 975-978.
Hu, et al., "Discovery of ERD-308 as a Highly Potent Proteolysis Targeting Chimera (PROTAC) Degrader of Estrogen Receptor (ER)", J. Med. Chem. Jan. 2019, 62:3, 1420-1442.
Huang, H. T., et al., "A Chemoproteomic Approach to Query the Degradable Kinome Using a Multi-kinase Degrader", Cell Chemical Biology (2018); 25(1): 88-99.
Huang, X. et al., "Drugging the undruggables: exploring the ubiquitin system for drug development", Cell Research (2016); 26(4): 484-498.
Hughes, S. J., et al., "Molecular recognition of ternary complexes: a new dimension in the structure-guided design of chemical degraders", Essays in Biochemistry (2017); 61(5): 505-516.
Ishikawa, T., et al., "Design and synthesis of novel human epidermal growth factor receptor 2 (HER2)/epidermal growth factor receptor (EGFR) dual inhibitors bearing a pyrrolo[3,2-d]pyrimidine scaffold", Journal of Medicinal Chemistry, 2011, 54(23), 8030-8050.
Ivan, M., et al., "HIFα targeted for VHL-mediated destruction by proline hydroxylation: implications for $O_2$ sensing", Science (2001); 292(5516): 464-468.
Jang, E. R., et al., "Targeted Degradation of Proteins by PROTACs", Current Protocols in Chemical Biology (2010); 2(2): 71-87.
Jenster, G., et al., "Functional domains of the human androgen receptor", The Journal of Steroid Biochemistry and Molecular Biology (1992); 41(3-8): 671-675.
Jung, M. E., et al., "Structure-activity relationship for thiohydantoin androgen receptor antagonists for castration-resistant prostate cancer (CRPC)", Journal of Medicinal Chemistry (2010); 53(7): 2779-2796.
Kim, L. S., et al., "Heat shock protein as molecular targets for breast cancer therapeutics", Journal of Breast Cancer (2011); 14(3): 167-174.
Kiselev, F. L., "Regarding Molecular Mechanisms of Tumors", Priroda (2014); 4: 19-20; 4 pages with English summary.
Klapproth, K., et al., "Advances in the understanding of MYC-induced lymphomagenesis", British Journal of Hematology (2010); 149: 484-497.
Kümmerer, K., "Pharmaceuticals in the Environment", Annual Review of Environment and Resources (2010); 35: 57-75.
Knott, E. B., "Compounds containing sulphur chromophores. Part I. The action of bases on heterocyclic sulphide quarternary salts", Journal of the Chemical Society (Resumed) (1955); 916-927.
Knott, E. B., et al., Accession No. 1957:56724, "Compounds containing sulfur chromophores. V. Complex cyanines" STN (Nov. 24, 2017); 1 page.
Konecny, G. E., et al., "Activity of the Dual Kinase Inhibitor Lapatinib (GW572016) against HER-2-Overexpressing and Trastuzumab-Treated Breast Cancer Cells", Cancer Research (2006); 66(3): 1630-1639.
Kronke, J., et al., "Lenalidomide causes selective degradation of IKZF1 and IKZF3 in multiple myeloma cells", Science (2014); 343(6168): 301-305.
Kurimchak, A. M., et al.," Resistance to BET Bromodomain Inhibitors Is Mediated by Kinome Reprogramming in Ovarian Cancer", Cell Reports (2016); 16: 1273-1286.
Lai, A. C., et al., "Induced protein degradation: an emerging drug discovery paradigm", Nature Reviews Drug Discovery (2017); 16(2): 101-114.
Lai, A. C., et al., "Modular PROTAC design for the degradation of oncogenic BCR-ABL", Angewandte Chemie International Edition (2016); 55(2): 807-810.
Lala, P. K., et al., "Role of nitric oxide in tumor progression: lessons from experimental tumors", Cancer and Metastasis Reviews (1998); 17: 91-106.
Lebraud, H., et al., "Protein degradation by in-cell self-assembly of proteolysis targeting chimeras", ACS Central Science (2016); 2(12): 927-934.
Ledet, E. M., et al., "Comprehensive analysis of AR alterations in circulating tumor DNA from patients with advanced prostate cancer", The Oncologist (2020); 25(4): 327-333.
Lee, B. Y., et al., "FAK signaling in human cancer as a target for therapeutics", Pharmacology & Therapeutics (2015); 146: 132-149.
Lee, H., et al., "Targeted degradation of the aryl hydrocarbon receptor by the PROTAC approach: a useful chemical genetic tool", Chembiochem (2007); 8(17): 2058-2062.
Lelais, G., et al., "Discovery of (R, E)-N-(7-Chloro-1-(1-[4-(dimethylamino) but-2-enoyl] azepan-3-yl)-1 H-benzo [d] imidazol-2-yl)-2-methylisonicotinamide (EGF816), a Novel, Potent, and WT Sparing Covalent Inhibitor of Oncogenic (L858R, ex19del) and Resistant (T790M) Egfr Mutants for the Treatment of EGFR Mutant Non-Small-Cell Lung Cancers", Journal of Medicinal Chemistry (2016); 59(14): 6671-6689.
Lemmon, M., et al., "Cell signaling by receptor tyrosine kinases", Cell (2010); 141(7): 1117-1134.
Levine, P. M., et al., "Targeting the androgen receptor with steroid conjugates: miniperspective", Journal of Medicinal Chemistry (2014); 57(20): 8224-8237.
Li, J., et al., "Aberrant corticosteroid metabolism in tumor cells enables GR takeover in enzalutamide resistant prostate cancer", eLife (2017); 6: e20183; 17 pages.
Li, Y., et al., "Single polymer-drug conjugate carrying two drugs for fixed-dose co-delivery", Medicinal Chemistry (2014); 4(10): 676-683.
Lien, E. J., "Atomic and Molecular Structure and the States of Matter", Remington's Pharmaceutical Sciences, $16^{th}$ Edition (1980); pp. 160-181.
Liu, F., et al., "Discovery of a 2,4-diamino-7-aminoalkoxyquinazoline as a potent and selective inhibitor of histone lysine methyltransferase G9a", Journal of Medicinal Chemistry (2009); 52(24): 7950-7953.

(56) References Cited

OTHER PUBLICATIONS

Liu, H., et al., "Bioactivation of the selective estrogen receptor modulator desmethylated arzoxifene to quinoids: 4'-fluoro substitution prevents quinoid formation", Chemical Research in Toxicology (2005); 18: 162-173.

Liu, K., et al., "Design and biological characterization of hybrid compounds of curcumin and thalidomide for multiple myeloma", Organic & Biomolecular Chemistry (2013); 11(29): 4757-4763.

Llinas-Brunet, M., et al., "Discovery of a potent and selective noncovalent linear inhibitor of the hepatitis C virus NS3 protease (BI 201335)", Journal of Medicinal Chemistry (2010); 53(17): 6466-6476.

Lopez-Girona, A. E. A., et al., "Cereblon is a direct protein target for immunomodulatory and antiproliferative activities of lenalidomide and pomalidomide", Leukemia (2012); 26(11): 2326-2335.

Lountos, G. T., et al., "Structural characterization of inhibitor complexes with checkpoint kinase 2 (Chk2), a drug target for cancer therapy", Journal of Structural Biology (2011); 176(3): 292-301.

Loven, J., et al., "Selective Inhibition of Tumor Oncogenes by Disruption of Super Enhancers", Cell (2013); 153: 320-334.

Lu, G., et al., "The myeloma drug lenalidomide promotes the cereblon-dependent destruction of Ikaros proteins", Science (2014); 343(6168): 305-309.

Lu, J., et al., "Hijacking the E3 ubiquitin ligase cereblon to efficiently target BRD4", Chemistry & Biology (2015); 22(6): 755-763.

Lu, N. Z., et al., "International Union of Pharmacology. LXV. The pharmacology and classification of the nuclear receptor superfamily: glucocorticoid, mineralocorticoid, progesterone, and androgen receptors", Pharmacological Reviews (2006); 58(4): 782-797.

Maclean, H. E., et al., "Localization of functional domains in the androgen receptor", The Journal of Steroid Biochemistry and Molecular Biology (1997); 62(4): 233-242.

Maniaci, C., et al., "Homo-PROTACs: bivalent small-molecule dimerizers of the VHL E3 ubiquitin ligase to induce self-degradation", Nature Communications (2017); 8(1): 1-14.

Marcelli, M., et al., "Androgen receptor mutations in prostate cancer", Cancer Research (2000); 60(4): 944-949.

Martin-Kohler, A., et al., "Furo [2,3-d] pyrimidines and Oxazolo [5,4-d] pyrimidines as Inhibitors of Receptor Tyrosine Kinases (RTK)", Helvetica Chimica Acta (2004); 87(4): 956-975.

Maximov, P. Y., et al., "The Discovery and Development of Selective Estrogen Receptor Modulators (SERMs) for Clinical Practice", Current Clinical Pharmacology (2013); 8: 135-155.

Mehellou, Y., et al., "Twenty-six years of anti-HIV drug discovery: where do we stand and where do we go?", Journal of Medicinal Chemistry (2010); 53(2): 521-538.

Mertz, J. A., et al., "Targeting MYC dependence in cancer by inhibiting BET bromodomains", PNAS (2011); 108(40): 16669-16674.

Millan, D. S., et al., "Design and Synthesis of Inhaled p38 Inhibitors for the Treatment of Chronic Obstructive Pulmonary Disease", Journal of Medicinal Chemistry (2011); 54(22): 7797-7814.

Min, J., et al., "Structure of an HIF-1α-pVHL complex: hydroxyproline recognition in signaling", Science (2002); 296(5574): 1886-1889.

Mohler, M. L., et al., "Androgen receptor antagonists: a patent review (2008-2011)", Expert Opinion on Therapeutic Patents (2012); 22(5): 541-565.

Mooradian, A. D., et al., "Biological actions of androgens", Endocrine Reviews (1987); 8(1): 1-28.

Muller, G. W., et al., "Amino-substituted thalidomide analogs: potent inhibitors of TNF-α production", Bioorganic & Medicinal Chemistry Letters (1999); 9(11): 1625-1630.

Nathan, M. R., et al., "A Review of Fulvestrant in Breast Cancer", Oncology and Therapy (2017); 5: 17-29.

Neklesa, T.K., et al., "Greasy tags for protein removal", Nature (2012); 487(7407): 308-309.

Neklesa, T. K., et al., "Targeted protein degradation by PROTACs," Pharmacology & Therapeutics, Jun. 1, 2017, vol. 174, pp. 138-144.

Nicodeme, E., et al., "Suppression of inflammation by a synthetic histone mimic", Nature (2010); 468: 1119-1123.

Nies, A. S., et al., "Principios de Terapeutica", Las Bases Farmacológicas De La Terapéutica (1996); Chapter 3; pp. 47; 2 pages with English Translation.

Noel, J. K., et al., "Abstract C244: Development of the BET Bromodomain inhibitor OTX015", Molecular Cancer Therapy (2013); 12(11 Suppl); 4 pages.

Ohoka, N., et al., "SNIPER (TACC3) induces cytoplasmic vacuolization and sensitizes cancer cells to Bortezomib", Cancer Science (2017); 108(5): 1032-1041.

Ottis, P., et al., "Assessing different E3 ligases for small molecule induced protein ubiquitination and degradation", ACS Chemical Biology (2017); 12(10): 2570-2578.

Ottis, P., et al., "Proteolysis-targeting chimeras: induced protein degradation as a therapeutic strategy", ACS Chemical Biology (2017); 12(4): 892-898.

Page, S. T., et al., "Persistent intraprostatic androgen concentrations after medical castration in healthy men", The Journal of Clinical Endocrinology & Metabolism (2006); 91(10): 3850-3856.

Pandian, R. S., et al., "In-silico analysis and QSAR studies of tacrine hybrids with ubiquitin ligase on Alzheimer's disease", International Journal of Bioinformatics Research and Applications (2010); 6(6): 556-570.

Pantoliano, M. W., et al., "High-density miniaturized thermal shift assays as a general strategy for drug discovery", Journal of Biomolecular Screening (2001); 6(6): 429-440.

Papulov, Y. G., "Relationship of Substance Properties and Molecular Structure: Mathematical Simulation", Advances of Contemporary Natural Science (2006); 2: 75-76; 3 pages with English summary.

Patch, R. J., et al., "Identification of diaryl ether-based ligands for estrogen-related receptor α as potential antidiabetic agents", Journal of Medicinal Chemistry (2011); 54(3): 788-808.

Pepe, A., et al., "Synthesis and structure-activity relationship studies of novel dihydropyridones as androgen receptor modulators", Journal of Medicinal Chemistry (2013); 56(21): 8280-8297.

Poutiainen, P. K., et al., "Design, synthesis, and biological evaluation of nonsteroidal cycloalkane [d] isoxazole-containing androgen receptor modulators", Journal of Medicinal Chemistry (2012); 55(14): 6316-6327.

Powell, C. E., et al., "Chemically Induced Degradation of Anaplastic Lymphoma Kinase (ALK)", Journal of Medicinal Chemistry (2018); 61: 4249-4255.

PubChem CID 46916268, "4-(4-((2,4-Dioxothiazolidin-5-ylidene)methyl)-2-methoxyphenoxy)-3-(trifluoromethyl)benzonitrile", National Center for Biotechnology Information, Create date Oct. 21, 2010 [online] https://pubchem.ncbi.nlm.nih.gov/compound/E3-ligase-Ligand-5; 13 pages.

Puissant, A., et al., "Targeting MYCN in neuroblastoma by BET bromodomain inhibition", Cancer Discovery (Mar. 2013); 3: 308-323.

Puppala, D., et al., "Development of an aryl hydrocarbon receptor antagonist using the proteolysis-targeting chimeric molecules approach: a potential tool for chemoprevention", Molecular Pharmacology (2008); 73(4): 1064-1071.

Qin, Z., et al., "Benzothiophene selective estrogen receptor modulators with modulated oxidative activity and receptor affinity", Journal of Medicinal Chemistry (2007); 50: 2682-2692.

Raina, K., et al., "PROTAC-induced BET protein degradation as a therapy for castration-resistant prostate cancer", Proceedings of the National Academy of Sciences (2016); 113(26): 7124-7129.

Raina, K., et al., "Targeted protein knockdown using small molecule degraders", Current Opinion in Chemical Biology (2017); 39: 46-53.

Rautio, J., et al., "Prodrugs: design and clinical applications", Nature Reviews Drug Discovery (Mar. 2008); 7: 255-270.

Remillard, D., et al., "Degradation of the BAF complex factor BRD9 by heterobifunctional ligands", Angewandte Chemie International Edition (2017); 56(21): 5738-5743.

Richters, A., et al., "Identification and further development of potent TBK1 inhibitors", ACS Chemical Biology (2014); 10(1): 289-298.

(56) References Cited

OTHER PUBLICATIONS

Robertson, J. F. R., "Fulvestrant (Faslodex)—how to make a good drug better", The Oncologist (2007); 12: 774-784.
Robinson, D., et al., "Integrative clinical genomics of advanced prostate cancer", Cell (2015); 161(5): 1215-1228.
Rodriguez-Gonzalez, A., et al., "Targeting steroid hormone receptors for ubiquitination and degradation in breast and prostate cancer", Oncogene (2008); 27(57): 7201-7211.
Romanel, A., et al., "Plasma AR and abiraterone-resistant prostate cancer", Science Translational Medicine (2015); 7(312): 312re10; 9 pages.
Rotili, D., et al., "Photoactivable peptides for identifying enzyme-substrate and protein-protein interactions", Chemical Communications (2011); 47(5): 1488-1490.
Roy, A. K., et al., "Regulation of androgen action", Vitamins & Hormones (1998); 55: 309-352.
Ruchelman, A., et al., "Isosteric analogs of lenalidomide and pomalidomide: Synthesis and biological activity", Bioorganic & Medicinal Chemistry Letters (2013); 23(1): 360-365.
Rusch, M., et al., "Identification of Acyl Protein Thioesterases 1 and 2 as the Cellular Targets of the Ras-Signaling Modulators Palmostatin B amd M", Angewandte Chemie International Edition (2011); 50: 9838-9842.
Sakamoto, K. M., et al., "Development of Protacs to target cancer-promoting proteins for ubiquitination and degradation", Molecular & Cellular Proteomics (2003); 2(12): 1350-1358.
Sakamoto, K. M., et al., "Protacs: Chimeric molecules that target proteins to the Skp1-Cullin-F box complex for ubiquitination and degradation", Proceedings of the National Academy of Sciences (2001); 98(15): 8554-8559.
Salami, J., et al., "Waste disposal—An attractive strategy for cancer therapy", Science (2017); 355(6330): 1163-1167.
Scagliotti, G., et al., "Phase III Multinational, Randomized, Double-Blind, Placebo-Controlled Study of Tivantinib (ARQ 197) Plus Erlotinib Versus Erlotinib Alone in Previously Treated Patients With Locally Advanced or Metastatic Nonsquamous Non-Small-Cell Lung Cancer", Journal of Clinical Oncology (2015); 33(24): 2667-2674.
Schenkel, L. B., et al., "Discovery of Potent and Highly Selective Thienopyridine Janus Kinase 2 Inhibitors", Journal of Medicinal Chemistry (2011); 54(24): 8440-8450.
Schiedel, M., et al., "Chemically induced degradation of sirtuin 2 (Sirt2) by a proteolysis targeting chimera (PROTAC) based on sirtuin rearranging ligands (SirReals)", Journal of Medicinal Chemistry (2018); 61(2): 482-491.
Schneekloth, A. R., et al., "Targeted intracellular protein degradation induced by a small molecule: En route to chemical proteomics", Bioorganic & Medicinal Chemistry Letters (2008); 18(22): 5904-5908.
Schneekloth Jr, J. S., et al., "Chemical genetic control of protein levels: selective in vivo targeted degradation", Journal of the American Chemical Society (2004); 126(12): 3748-3754.
Sequist, L.V., et al., "Randomized Phase II Study of Erlotinib Plus Tivantinib Versus Erlotinib Plus Placebo in Previously Treated Non-Small-Cell Lung Cancer", Journal of Clinical Oncology (2011); 29(24): 3307-3315.
Shangary, S et al., "Temporal activation of p53 by a specific MDM2 inhibitor is selectively toxic to tumors and leads to complete tumor growth inhabitation", PNAS (2008); 105(10): 3933-3938.
Shi, J., et al., "The mechanisms behind the therapeutic activity of BET bromodomain inhibition", Molecular Cell (2014); 54(5): 728-736.
Smith, A. R., et al., "Targeted Intracellular Protein Degradation Induced by a Small Molecule: En Route to Chemical Proteomics", Bioorganic & Medicinal Chemistry Letters (2008); 18(22): 5904-5908.
Stanton, B. Z., et al., "Chemically induced proximity in biology and medicine", Science (2018); 359(117): 1-11.
Stewart, S. G., et al., "Efforts toward elucidating Thalidomide's molecular target: an expedient synthesis of the first Thalidomide biotin analogue", Organic & Biomolecular Chemistry (2010); 8(18): 4059-4062.
Stoppler, M. C., "Endometriosis definition and facts", MedicineNet.com [online] http://www.medicinenet.com/endometriosis/article.htm (Retrieved on Apr. 5, 2017); 7 pages.
Stoppler, M. C., "What about surgery for Endometriosis?", MedicineNet.com [online] http://www.medicinenet.com/endometriosis/article.htm (Retrieved on Apr. 5, 2017); 7 pages.
Stuhlmiller, T. J., et al., "Inhibition of Lapatinib-Induced Kinome Reprogramming in ERBB2-Positive Breast Cancer by Targeting BET Family Bromodomains", Cell Reports (2015); 11: 390-404.
Suh, N., et al., "Arzoxifene, a new selective estrogen receptor modulator for chemoprevention of experimental breast cancer", Cancer Research (2001); 61: 8412-8415.
Sun, B., et al., "BET protein proteolysis targeting chimera (PROTAC) exerts potent lethal activity against mantle cell lymphoma cells", Leukemia (2018); 32: 343-352.
Suñé-Negre, J. M., "Nuevas aportaciones galénicas a las formas de administración", Formación Continuada para Farmacéuticos de Hospital (2002); 3(2): 1-29; 49 pages with English Translation.
Taplin, M., et al., "Mutation of the androgen-receptor gene in metastatic androgen-independent prostate cancer", New England Journal of Medicine (1995); 332(21): 1393-1398.
Toure, M., et al., "Small-molecule PROTACS: new approaches to protein degradation", Angewandte Chemie International Edition (2016); 55(6): 1966-1973.
Trewartha, D., et al., "Advances in prostate cancer treatment", Nature Reviews, Drug Discovery (2013); 12(11): 823-824.
Turk, B. E., et al., "Binding of thalidomide to alpha1-acid glycoprotein may be involved in its inhibition of tumor necrosis factor alpha production", Proceedings of the National Academy of Sciences (1996); 93(15): 7552-7556.
Vallee, F., et al., "Tricyclic Series of Heat Shock Protein 90 (HSP90) Inhibitors Part I: Discovery of Tricyclic Imidazo [4,5-c] Pyridines as Potent Inhibitors of the Hsp90 Molecular Chaperone", Journal of Medicinal Chemistry (2011); 54(20): 7206-7219.
Van Eis, M. J., et al., "2,6-Naphthyridines as potent and selective inhibitors of the novel protein kinase C isozymes", Bioorganic & Medicinal Chemistry Letters (2011); 21(24): 7367-7372.
Van Molle, I., et al., "Dissecting fragment-based lead discovery at the von Hippel-Lindau protein: hypoxia inducible factor 1α protein-protein interface", Chemistry & Biology (2012); 19(10): 1300-1312.
Vassilev, L. T., et al., "In vivo activation of the p53 pathway by small-molecule antagonists of MDM2", Science (Feb. 6, 2004); 303: 844-848.
Vu, B., et al., "Discovery of RG7112: a small-molecule MDM2 inhibitor in clinical development", ACS Medicinal Chemistry Letters (2013); 4: 466-469.
Wang, C., et al., "Estrogen induces c-myc gene expression via an upstream enhancer activated by the estrogen receptor and the AP-1 transcription factor", Molecular Endocrinology (Sep. 2011); 25(9): 1527-1538.
Willson, T.M., et al., "3-[4-(1,2-Diphenylbut-1-Enyl)Pheny1] Acrylic Acid: A non-steroidal estrogen with functional selectivity for bone over uterus in rats", Journal of Medicinal Chemistry (1994); 37 (11): 1550-1552.
Winter, G. E., et al., "Phthalimide conjugation as a strategy for in vivo target protein degradation", Science (2015); 348(6241): 1376-1381.
Wolff, M., "Burger's Medicinal Chemistry and Drug Discovery", Fifth Edition, John Wiley & Sons (1995); 1: 975-977.
Wright, L., et al., "Structure-Activity Relationships in Purine-Based Inhibitor Binding to HSP90 Isoforms", Chemistry & Biology (2004); 11(6): 775-785.
Wyatt, A. W., et al., "Genomic alterations in cell-free DNA and enzalutamide resistance in castration-resistant prostate cancer", JAMA Oncology (2016); 2(12): 1598-1606.
Wyce, A., et al., "Inhibition of BET bromodomain proteins as a therapeutic approach in prostate cancer", Oncotarget (Dec. 2013); 4(12): 2419-2429.

(56) References Cited

OTHER PUBLICATIONS

Zengerle, M., et al., "Selective small molecule induced degradation of the BET bromodomain protein BRD4", ACS Chemical Biology (2015); 10(8): 1770-1777.
Zhang, B., et al., "Small-molecule MDM2-p53 inhibitors: recent advances", Future Medicinal Chemistry (2015); 7(5): 631-645.
Zhang, D., et al., "Targeted Degradation of Proteins by Small Molecules: A Novel Tool for Functional Proteomics", Combinatorial Chemistry & High Throughput Screening (2004); 7(7): 689-697.
Zhao, Y., et al., "Small-molecule inhibitors of the MDM2-p53 protein-protein interaction (MDM2 inhibitors) in clinical trials for cancer treatment", Journal of Medicinal Chemistry (2015); 58: 1038-1052.
Zhou, B., et al., "Discovery of a Small-Molecule Degrader of Bromodomain and Extra-Terminal (BET) Proteins with Picomolar Cellular Potencies and Capable of Achieving Tumor Regression", Journal of Medicinal Chemistry 2018, 61, 462-481, published Mar. 24, 2017, DOI: 10.1021/acs.jmedchem.6b01816.
Zillhardt, M., et al., "Foretinib (GSK1363089), an Orally Available Multikinase Inhibitor of c-Met and VEGFR-2, Blocks Proliferation, Induces Anoikis, and Impairs Ovarian Cancer Metastasis", Clinical Cancer Research (2011); 17: 4042-4051.
Zuber, J., et al., "RNAi screen identifies Brd4 as a therapeutic target in acute myeloid leukaemia", Nature (2011); 478(7370): 524-528.
Alicea, J., et al., "The Effect of Food and the Proton Pump Inhibitor Esomeprazole on the Single-Dose Pharmacokinetics and Safety of ARV-766, a PROteolysis TArgeting Chimera (PROTAC) Androgen Receptor Degrader, in Healthy Volunteers", Poster 166, American College of Clinical Pharmacology (ACCP) Annual Meeting, Bellevue, WA (Sep. 10-12, 2023) [online] https://arvinasoncologymedical.com/wp-content/uploads/2023/10/Alicea-ACCP-2023-3.pdf (Access Date: Feb. 27, 2024); 3 pages.
Byrn, S., et al., "Pharmaceutical solids: a strategic approach to regulatory considerations", Pharmaceutical Research (1995); 12(7): 945-954.
ClinicalTrials.gov Identifier: NCT05067140, "Clinical Trial to Evaluate ARV-766 in Patients With Metastatic Castration-Resistant Prostate Cancer" [online] https://classic.clinicaltrials.gov/ct2/history/NCT05067140?V_3=View#StudyPageTop (First Posted—Oct. 5, 2021, Submitted Date—Mar. 16, 2022, Access Date—Feb. 27, 2024); 7 pages.
ClinicalTrials.gov Identifier: NCT05067140, "A Study of ARV-766 Given by Mouth in Men With Metastatic Castration-resistant Prostate Cancer Who Have Progressed on Prior Approved Systemic Therapies" [online] https://classic.clinicaltrials.gov/ct2/history/NCT05067140?V_4=View#StudyPageTop (First Posted - Oct. 5, 2021, Submitted Date - Oct. 2, 20228, Access Date - Feb. 2, 20247); 8 pages.
Co-pending U.S. Application No. 18/622, 152, inventor CHEN; Chungpin Herman, filed on Mar. 29, 2024.
Haleblian, J., et al., "Pharmaceutical applications of polymorphism", Journal of Pharmaceutical Sciences (1969); 58(8): 911-929.
He, M., et al., "PROTACs: great opportunities for academia and industry (an update from 2020 to 2021)", Signal Transduction and Targeted Therapy (Jun. 2022); 7(181); 64 pages.
Petrylak, D.P., et al., "A phase 2 expansion study of ARV-766, a PROTAC androgen receptor (AR) degrader, in metastatic castration-resistant prostate cancer (mCRPC)", Journal of Clinical Oncology (Feb. 16-18, 2023); 41(6); 1 page.
Snyder, L., et al., "Discovery of ARV-766, an androgen receptor degrading PROTAC® for the treatment of men with metastatic castration resistant prostate cancer", American Association of Cancer Research (AACR) Annual Meeting (Apr. 14-19, 2023) [online] https://arvinasoncologymedical.com/wp-content/uploads/2022/06/Snyder-AACR-2023.pdf (Access Date: Feb. 27, 2024); 15 pages.
Zhang, G. J., et al., "In Vitro Evaluation of PROTAC Androgen Receptor Degrader ARV-766 for Cytochrome P450- and Transporter-Mediated Drug-Drug Interaction", 25th North American ISSX Meeting, Boston, MA (Sep. 10-13, 2023) [online] https://arvinasoncologymedical.com/wp-content/uploads/2023/10/Zhang-ISSX-2023.pdf (Access Date: Feb. 27, 2024); 1 page.
Arvinas, Inc., "Arvinas Presents New Preclinical Data on Oral Androgen Receptor PROTAC at ASCO 2017 Genitourinary Cancers Symposium", Press Release (Feb. 17, 2017); 1 page.
Arvinas, Inc., "Arvinas Releases Updated Dose Escalation Data from Clinical Trial of PROTAC Protein Degrader ARV-110 in Patients with Metastatic Castration-Resistant Prostate Cancer", Press Release [online] https://ir.arvinas.com/node/7721/pdf (May 29, 2020); 2 pages.
Ciapetti, P., et al., "Chapter 15—Molecular Variations Based on Isosteric Replacements", The Practice of Medicinal Chemistry (Third Edition) (2008); pp. 290-342.
ClinicalTrials.gov Identifier: NCT05067140, "A Phase 1/2 Open-Label Study of ARV-766 in Patients with Metastatic Prostate Cancer", Clinical Trial Card ARV-766-mCRPC-101 [online] https://clinicaltrials.gov/study/NCT05067140?id=NCT05067140&rank=1&tab=history&a=1#version-content-panel (First Posted—Oct. 5, 2021, Submitted Date—Oct. 28, 2022, Access Date—Feb. 27, 2024); 1 page.
Co-pending U.S. Appl. No. 18/759,774, inventors Zhang; Jingang George et al., filed Jun. 28, 2024.
Gupta, A., et al., "Interactions of azole antifungal agents with the human breast cancer resistance protein (BCRP)", Journal of Pharmaceutical Sciences (2007); 96(12): 3226-3235.
Iusuf, D., et al., "Human OATP1B1, OATP1B3 and OATP1A2 can mediate the in vivo uptake and clearance of docetaxel", International Journal of Cancer (2015); 136(1): 225-233.
Jia, X., et al., " Targeting androgen receptor degradation with PROTACs from bench to bedside", Biomedicine & Pharmacotherapy (2023); 158(114112); 10 pages.
Petrylak, D. P., et al., "A phase 2 expansion study of ARV-766, a PROTAC androgen receptor degrader, in metastatic castration-resistant prostate cancer", Arvinas Presentation, TPS290, Presented at the ASCO Genitourinary Cancers Symposium, San Francisco, CA (Feb. 16-18, 2023); 1 page.
Zobniw, C. M., et al., "Clinical use of abiraterone in the treatment of metastatic castration-resistant prostate cancer", Research and Reports in Urology (2014): 97-105.
Han, X., et al., "Discovery of highly potent and efficient PROTAC degraders of androgen receptor (AR) by employing weak binding affinity VHL E3 ligase ligands", Journal of Medicinal Chemistry (2019); 62(24): 11218-11231.

CEREBLON LIGANDS AND BIFUNCTIONAL COMPOUNDS COMPRISING THE SAME

CROSS-REFERENCE TO RELATED APPLICATIONS

This application is a continuation of U.S. Non-Provisional patent application Ser. No. 15/885,671, filed on Jan. 31, 2018, which claims priority to, and the benefit of, U.S. Provisional Application No. 62/452,972, filed Jan. 31, 2017, each of which are incorporated herein by reference in their entireties for all purposes.

INCORPORATION BY REFERENCE

U.S. patent application Ser. No. 15/230,354, filed on Aug. 5, 2016, published as U.S. Patent Application Publication No. 2017/0065719; and U.S. patent application Ser. No. 15/801,243, filed on 1 Nov. 2017; and U.S. patent application Ser. No. 15/206,497 filed 11 Jul. 2016; and U.S. patent application Ser. No. 15/209,648 filed 13 Jul. 2016; and U.S. patent application Ser. No. 15/730,728, filed on Oct. 11, 2017; U.S. patent application Ser. No. 15/829,541, filed on Dec. 1, 2017; U.S. patent application Ser. No. 15/881,318, filed on Jan. 26, 2018; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639, are incorporated herein by reference in their entirety. Furthermore, all references cited herein are incorporated by reference herein in their entirety.

FIELD OF THE INVENTION

The description provides imide-based compounds, including bifunctional compounds comprising the same, and associated methods of use. The bifunctional compounds are useful as modulators of targeted ubiquitination, especially with respect to a variety of polypeptides and other proteins, which are degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped.

One E3 ligase with therapeutic potential is the von Hippel-Lindau (VHL) tumor suppressor. VHL comprises the substrate recognition subunit/E3 ligase complex VCB, which includes elongins B and C, and a complex including Cullin-2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. We generated the first small molecule ligands of Von Hippel Lindau (VHL) to the substrate recognition subunit of the E3 ligase, VCB, an important target in cancer, chronic anemia and ischemia, and obtained crystal structures confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Thalidomide, which has been approved for the treatment of a number of immunological indications, has also been approved for the treatment of certain neoplastic diseases, including multiple myeloma. In addition to multiple myeloma, thalidomide and several of its analogs are also currently under investigation for use in treating a variety of other types of cancer. While the precise mechanism of thalidomide's anti-tumor activity is still emerging, it is known to inhibit angiogenesis. Recent literature discussing the biology of the imides includes Lu et al Science 343, 305 (2014) and Krönke et al Science 343, 301 (2014).

Significantly, thalidomide and its analogs e.g. pomolinamiode and lenalinomide, are known to bind cereblon. These agents bind to cereblon, altering the specificity of the complex to induce the ubiquitination and degradation of Ikaros (IKZF1) and Aiolos (IKZF3), transcription factors essential for multiple myeloma growth. Indeed, higher expression of cereblon has been linked to an increase in efficacy of imide drugs in the treatment of multiple myeloma.

BRD4 has captured considerable attention from academia and Pharmaceutical industry alike due to its great potential as a novel target in multiple disease settings, particularly in cancer. BRD4 belongs to the bromodomain and extra-terminal domain (BET) family, which is characterized by two bromodomains (BD domain) at the N-terminus and an extraterminal domain (ET domain) at the C-terminus (J. Shi, et al. *Molecular cell,* 54 (2014) 728-736 and A. C. Belkina, et al., *Nat. Rev. Cancer,* 12 (2012) 465-477). The two BD domains recognize and interact with acetylated-lysine residues at the N-terminal tail of histone protein; the ET domain is not yet fully characterized, and is largely considered to serve a scaffolding function in recruiting diverse transcriptional regulators. Thus, BRD4 plays a key role in regulating gene expression by recruiting relevant transcription modulators to specific genomic loci. Several studies have establish that BRD4 is preferentially located at super-enhancer regions, which often reside upstream of important oncogenes, such as c-MYC, Bcl-xL and BCL-6, and play a key role in regulating their expressions (J. Loven, et al., *Cell,* 153 (2013) 320-334 and B. Chapuy, et al., *Cancer Cell,* 24 (2013) 777-790.). Owing to its pivotal role in modulating the expression of essential oncogenes, BRD4 emerges as a promising therapeutic target in multiple cancer types, including midline carcinoma, AML, MM, BL, and prostate cancer (J. Loven, et al., *Cell,* 153 (2013) 320-334; J. Zuber, et al., *Nature,* 478 (2011) 524-528; J. E. Delmore, et al., *Cell,* 146 (2011) 904-917; J. A. Mertz, et al., *PNAS,* 108 (2011) 16669-16674; A. Wyce, et al., *Oncotarget,* 4 (2013) 2419-2429; I. A. Asangani, et al., *Nature,* 510 (2014) 278-282; and C. A. French, et al., *Oncogene,* 27 (2008) 2237-2242). BRD4's distinct high occupancy of genomic loci proximal to specific oncogenes provide a potential therapeutic window that will allow specific targeting of tumor cells while sparing normal tissues. Particularly, BRD4 may serve as an alternative strategy of targeting c-MYC, which contributes to the development and maintenance of a majority of human cancers but has remained undruggable (J. E. Delmore, et al., *Cell,* 146 (2011) 904-917; J. A. Mertz, et al., *PNAS,* 108 (2011) 16669-16674; M. G. Baratta, et al., *PNAS,* 112 (2015) 232-237; and M. Gabay, et al., *Cold Spring Harb Perspect Med.* (2014) 4:a014241).

The development of small molecule BRD4 inhibitors, such as $JQ_1$, iBET and OTX15, has demonstrated promising therapeutic potential in preclinical models of various cancers, including BL (J. Loven, et al., *Cell,* 153 (2013) 320-334; B. Chapuy, et al., *Cancer Cell,* 24 (2013) 777-790; J. E. Delmore, et al., *Cell,* 146 (2011) 904-917; J. A. Mertz, et al., *PNAS,* 108 (2011) 16669-16674; I. A. Asangani, et al., *Nature,* 510 (2014) 278-282; M. G. Baratta, et al., *PNAS,* 112 (2015) 232-237; M. Boi, et al., *Clin. Cancer Res.*, (2015) 21(7):1628-38; and A. Puissant, et al., *Cancer discovery,* 3 (2013) 308-323). Indeed, BRD4 inhibitors have shown various anti-tumor activities with good tolerability in different mouse tumor models and, not surprisingly, high sensitivity to BRD4 inhibitors such as $JQ_1$, has been associated with high level of either c-MYC and N-MYC in different tumor types, including c-MYC driven BL. Almost all BL cases contain c-myc gene translocation that places it under control of a super-enhancer located upstream of IgH, thus driving an abnormally high level of c-MYC expression, tumor development and maintenance (K. Klapproth, et al., *British journal of haematology,* 149 (2010) 484-497).

Currently, four BET Bromodomain inhibitors are in phase I clinical trial with focus largely on midline carcinoma and hematological malignancies (CPI-0610, NCT01949883; GSK525762, NCT01587703; OTX015, NCT01713582; TEN-010, NCT01987362). Preclinical studies with BRD4 inhibitors demonstrate their value in suppressing c-MYC and proliferation in BL cell lines, albeit with $IC_{50}$ values often in the range of 100 nM to 1 uM (J. A. Mertz, et al., *PNAS,* 108 (2011) 16669-16674 and M. Ceribelli, et al., *PNAS,* 111 (2014) 11365-11370). Thus, despite the rapid progress of BRD4 inhibitors, the effect of BRD4 inhibition has been encouraging, but less than ideal, as the effect is mostly cytostatic and requires relatively high concentration of inhibitors.

An ongoing need exists in the art for effective treatments for disease, especially hyperplasias and cancers, such as multiple myeloma. However, non-specific effects, and the inability to target and modulate certain classes of proteins altogether, such as transcription factors, remain as obstacles to the development of effective anti-cancer agents. As such, small molecule therapeutic agents that leverage or potentiate cereblon's substrate specificity and, at the same time, are "tunable" such that a wide range of protein classes can be targetted and modulated with specificity would be very useful as a therapeutic.

BRIEF SUMMARY OF THE INVENTION

The present disclosure describes bifunctional compounds which function to recruit endogenous proteins to an E3 Ubiquitin Ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., multiple myeloma.

As such, in one aspect the disclosure provides novel imide-based compounds as described herein.

In an additional aspect, the disclosure provides bifunctional or PROTAC compounds, which comprise an E3 Ubiquitin Ligase binding moiety (i.e., a ligand for an E3 Ubiquitin Ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM is a cereblon E3 Ubiquitin Ligase binding moiety (i.e., a "CLM"). For example, the structure of the bifunctional compound can be depicted as:

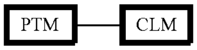

The respective positions of the PTM and CLM moieties as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

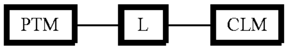

where PTM is a protein/polypeptide targeting moiety, L is a linker, and CLM is a cereblon E3 ubiquitin ligase binding moiety.

In certain preferred embodiments, the E3 Ubiquitin Ligase is cereblon. As such, in certain additional embodiments, the CLM of the bifunctional compound comprises chemistries such as imide, amide, thioamide, thioimide derived moieties. In additional embodiments, the CLM comprises a phthalimido group or an analog or derivative thereof. In still additional embodiments, the CLM comprises a phthalimido-glutarimide group or an analog or derivative thereof. In still other embodiments, the CLM comprises a member of the group consisting of thalidomide, lenalidomide, pomalidomide, and analogs or derivatives thereof.

In certain embodiments, the compounds as described herein comprise multiple CLMs, multiple PTMs, multiple chemical linkers or a combination thereof.

In any aspect or embodiment described herein, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM), or an IAP E3 ubiquitin ligase binding moiety (i.e., a "ILM"). In any aspect or embodiments described herein, the bifunctional compound includes at least one additional E3 ligase binding moiety selected from the group consisting of VLM,VLM', CLM, CLM', MLM, MLM', ILM, ILM', or a combination thereof. For example, there can be at least 1, 2, 3, 4, or 5 additional E3 ligase binding moieties.

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In yet another aspect, the present disclosure provides a method of ubiquitinating/degrading a target protein in a cell. In certain embodiments, the method comprises administering a bifunctional compound as described herein comprising an CLM and a PTM, preferably linked through a linker moiety, as otherwise described herein, wherein the CLM is coupled to the PTM and wherein the CLM recognizes a ubiquitin pathway protein (e.g., an ubiquitin ligase, preferably an E3 ubiquitin ligase such as, e.g., cereblon) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In an additional aspect, the description provides a method for assessing (i.e., determining and/or measuring) a CLM's binding affinity. In certain embodiments, the method comprises providing a test agent or compound of interest, for example, an agent or compound having an imide moiety, e.g., a phthalimido group, phthalimido-glutarimide group, derivatized thalidomide, derivatized lenalidomide or derivatized pomalidomide, and comparing the cereblon binding affinity and/or inhibitory activity of the test agent or compound as compared to an agent or compound known to bind and/or inhibit the activity of cereblon.

In still another aspect, the description provides methods for treating or emeliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present disclosure. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
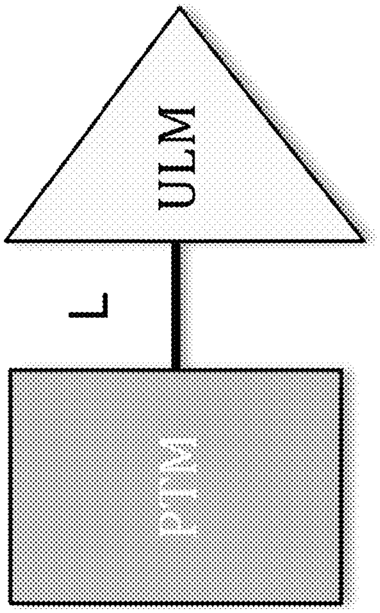
FIGS. 1A and 1B. Illustration of general principle for PROTAC function. (A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the PROTACs as described herein. Briefly, the ULM recognizes and binds to a specific E3 Ubiquitin Ligase, and the PTM binds and recruits a target protein bringing it into close proximity to the E3 Ubiquitin Ligase. Typically, the E3 Ubiquitin Ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degration by the proteosomal machinery of the cell.
Figure 1B:
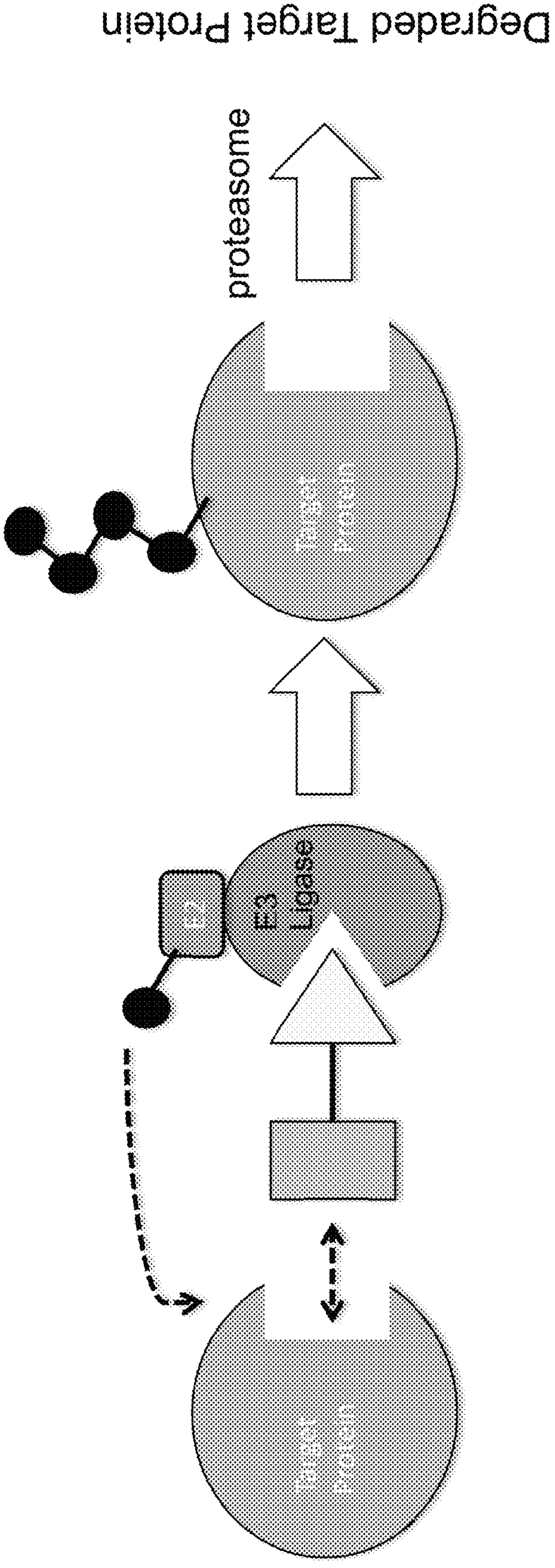

Presently described are compositions and methods that relate to the surprising and unexpected discovery that an E3 Ubiquitin Ligase protein, e.g., cereblon, ubiquitinates a target protein once it and the target protein are placed in proximity by a bifunctional or chimeric construct that binds the E3 Ubiquitin Ligase protein and the target protein. Accordingly the present disclosure provides such compounds and compositions comprising an E3 Ubiquintin Ligase binding moiety ("ULM") coupled to a protein target binding moiety ("PTM"), which result in the ubiquitination of a chosen target protein, which leads to degradation of the target protein by the proteasome (see FIGS. 1A and 1B). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHL, MDM2, or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anti-cancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "Ubiquitin Ligase" refers to a family of proteins that facilitate the transfer of ubiquitin to a specific substrate protein, targeting the substrate protein for degradation. For example, cereblon is an E3 Ubiquitin Ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 Ubiquitin Ligase binding moiety ("ULM") that is a cereblon E3 Ubiquitin Ligase binding moiety ("CLM"). In one embodiment, the CLM is coupled to a chemical linker (L) according to the structure:

(I) L-CLM wherein L is a chemical linker group and CLM is a cereblon E3 Ubiquitin Ligase binding moiety. The number and/or relative positions of the moieties in the compounds illustrated herein is provided by way of example only. As would be understood by the skilled artisan, compounds as described herein can be synthesized with any desired number and/or relative position of the respective functional moieties.

The terms ULM and CLM are used in their inclusive sense unless the context indicates otherwise. For example, the term ULM is inclusive of all ULMs, including those that bind cereblon (i.e., CLMs). Further, the term CLM is inclusive of all possible cereblon E3 Ubiquitin Ligase binding moieties.

In another aspect, the present disclosure provides bifunctional or multifunctional PROTAC compounds useful for regulating protein activity by inducing the degradation of a target protein. In certain embodiments, the compound comprises a CLM coupled, e.g., linked covalently, directly or indirectly, to a moiety that binds a target protein (i.e., protein targeting moiety or "PTM"). In certain embodiments, the CLM and PTM are joined or coupled via a chemical linker (L). The CLM recognizes the cereblon E3 ubiquitin ligase and the PTM recognizes a target protein and the interaction of the respective moieties with their targets facilitates the degradation of the target protein by placing the target protein in proximity to the ubiquitin ligase protein. An exemplary bifunctional compound can be depicted as:

(II) PTM-CLM

In certain embodiments, the bifunctional compound further comprises a chemical linker ("L"). For example, the bifunctional compound can be depicted as:

(III) PTM-L-CLM wherein PTM is a protein/polypeptide targeting moiety, L is a linker, and CLM is a cereblon E3 ligase binding moiety.

In certain embodiments, the compounds as described herein comprise multiple PTMs (targeting the same or different protein targets), multiple CLMs, one or more ULMs (i.e., moieties that bind specifically to another E3 Ubiquitin Ligase, e.g., VHL) or a combination thereof. In any of the aspects of embodiments described herein, the PTMs, CLMs, and ULMs can be coupled directly or via one or more chemical linkers or a combination thereof. In additional embodiments, where a compound has multiple ULMs, the ULMs can be for the same E3 Ubiquintin Ligase or each respective ULM can bind specifically to a different E3 Ubiquitin Ligase. In still further embodiments, where a compound has multiple PTMs, the PTMs can bind the same target protein or each respective PTM can bind specifically to a different target protein.

In another embodiment, the description provides a compound which comprises a plurality of CLMs coupled directly or via a chemical linker moiety (L). For example, a compound having two CLMs can be depicted as:

(IV) CLM-CLM or (V) CLM-L-CLM

In certain embodiments, where the compound comprises multiple CLMs, the CLMs are identical. In additional embodiments, the compound comprising a plurality of CLMs further comprises at least one PTM coupled to a CLM directly or via a chemical linker (L) or both. In certain additional embodiments, the compound comprising a plurality of CLMs further comprises multiple PTMs. In still additional embodiments, the PTMs are the same or, optionally, different. In still further embodiments, wherein the PTMs are different the respective PTMs may bind the same protein target or bind specifically to a different protein target.

In additional embodiments, the description provides a compound comprising at least two different CLMs coupled directly or via a chemical linker (L) or both. For example, such a compound having two different CLMs can be depicted as:

(VI) CLM-CLM' or (VII) CLM-L-CLM' wherein CLM' indicates a cereblon E3 Ubiquitin Ligase binding moiety that is structurally different from CLM. In certain embodiments, the compound may comprise a plurality of CLMs and/or a plurality of CLM's. In further embodiments, the compound comprising at least two different CLMs, a plurality of CLMs, and/or a plurality of CLM's further comprises at least one PTM coupled to a CLM or a CLM' directly or via a chemical linker or both. In any of the embodiments described herein, a compound comprising at least two different CLMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM or CLM (or ULM' or CLM').

In a preferred embodiment, the CLM comprises a moiety that is a ligand of the cereblon E3 Ubiquitin Ligase (CRBN). In certain embodiments, the CLM comprises a chemotype from the "imide" class of of molecules. In certain additional embodiments, the CLM comprises a phthalimido group or an analog or derivative thereof. In still additional embodiments, the CLM comprises a phthalimido-glutarimide group or an analog or derivative thereof. In still other embodiments, the CLM comprises a member of the group consisting of thalidomide, lenalidomide, pomalidomide, and analogs or derivatives thereof.

In additional embodiments, the description provides the compounds as described herein including their enantiomers, diastereomers, solvates and polymorphs, including pharmaceutically acceptable salt forms thereof, e.g., acid and base salt forms.

Exemplary Cereblon Binding and/or Inhibiting Compounds

In one aspect the description provides compounds useful for binding and/or inhibiting cereblon E3 Ubiquitin Ligase binding moiety. In certain embodiments, the compound has a chemical structure that includes at least one of (e.g., the compound has a chemical structure selected from the group consisting of):

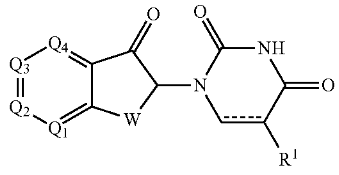
(a)

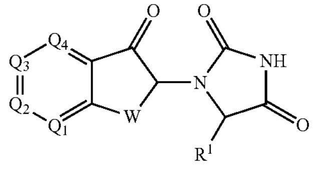
(b)

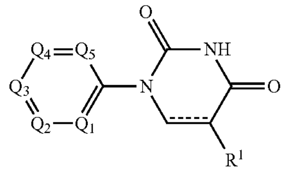
(c)

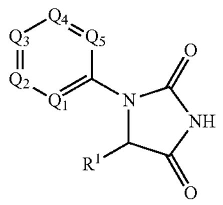
(d)

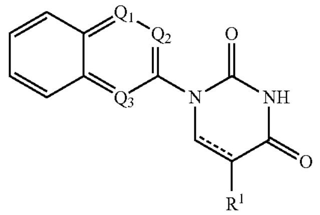
(e)

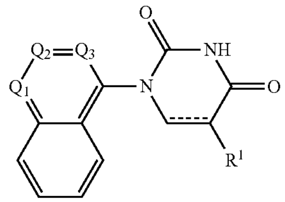
(f)

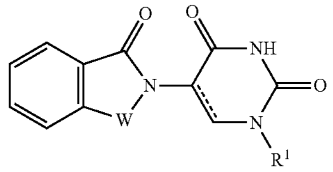
(g)

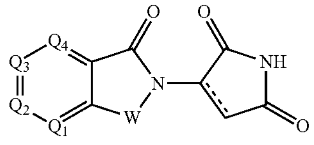
(h)

-continued
(i)
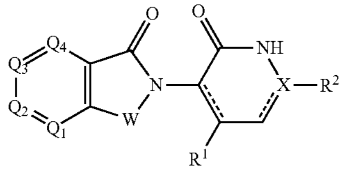
(j)
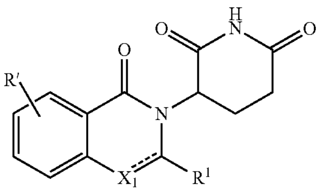
(k)
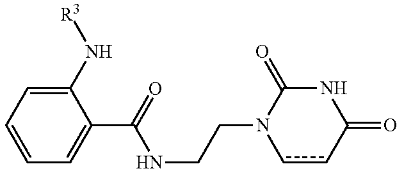
(l)
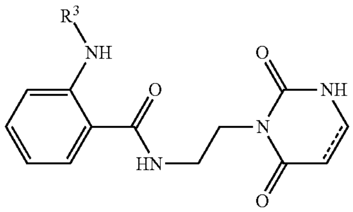
(m)
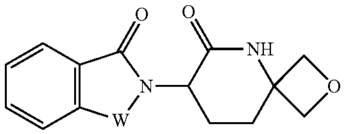
(n)
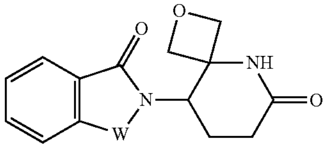
(o)
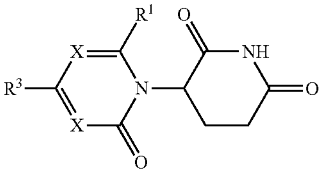
(p)
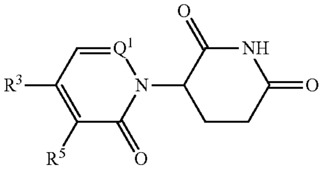
(q)
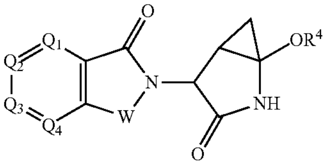
-continued
(r)
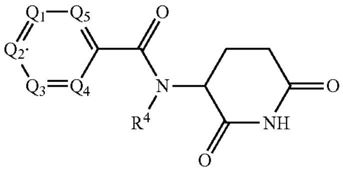
(s)
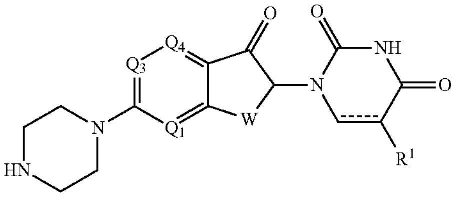
(t)
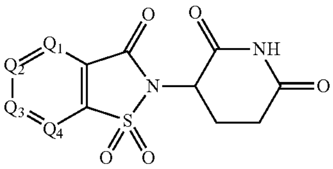
(ba)
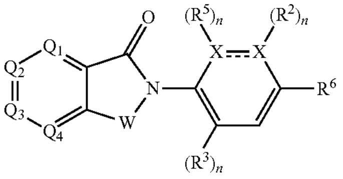
(bb)
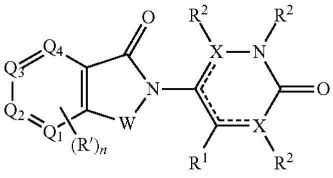
(bc)
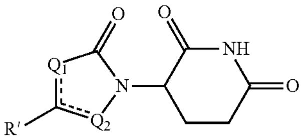
(bd)
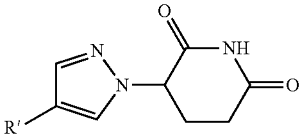
(be)
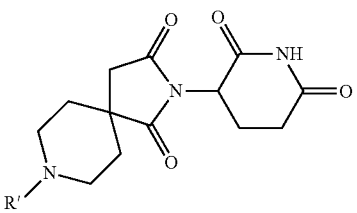
(bf)
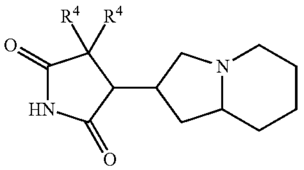

-continued (bg)

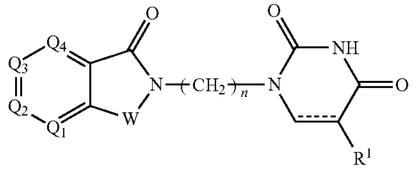

(bh)

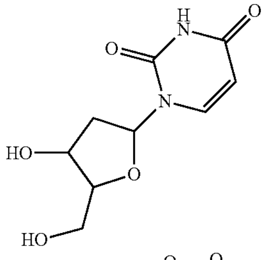

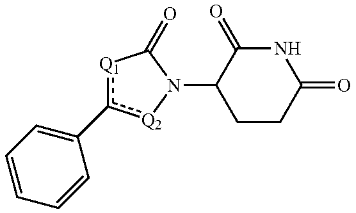

(j')

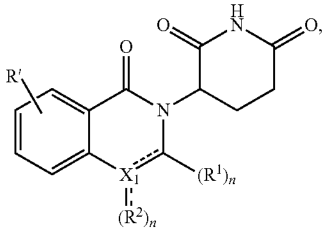

(p')

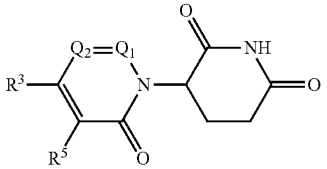

(h')

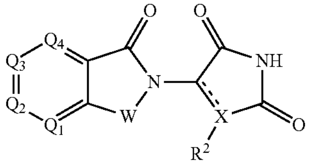

wherein:

W is independently selected from $CH_2$, CHR, C═O, $SO_2$, NH, and N-alkyl;

$Q_1$, $Q_2$, $Q_3$, $Q_4$, $Q_5$ are each independently represent a carbon C or N substituted with a group independently selected from R', N or N-oxide;

$R^1$ is selected from absent, H, OH, CN, $C_1$-$C_3$ alkyl, C═O;

$R^2$ is selected from the group absent, H, OH, CN, $C_1$-$C_3$ alkyl, $CHF_2$, $CF_3$, CHO, C(═O)$NH_2$;

$R^3$ is selected from absent, H, alkyl (e.g., $C_1$-$C_6$ or $C_1$-$C_3$ alkyl), substituted alkyl (e.g., substituted $C_1$-$C_6$ or $C_1$-$C_3$ alkyl), alkoxy (e.g., $C_1$-$C_6$ or $C_1$-$C_3$ alkoxyl), substituted alkoxy (e.g., substituted $C_1$-$C_6$ or $C_1$-$C_3$ alkoxyl);

$R^4$ is selected from H, alkyl, substituted alkyl;

$R^5$ and $R^6$ are each independently H, halogen, C(═O)R'; CN, OH, $CF_3$

X is C, CH, C═O, or N;

$X_1$ is C═O, N, CH, or $CH_2$;

R' is selected from H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, C(═O)$OR^2$, optionally substituted phenyl;

n is 0-4; and

 is a single or double bond.

Exemplary CLMs

In any of the compounds described herein, the CLM comprises a chemical structure selected from the group:

(a)

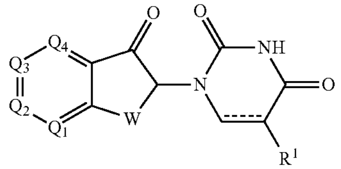

(b)

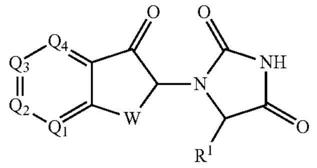

(c)

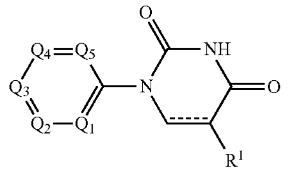

(d)

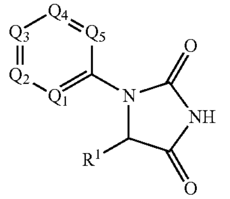

(e)

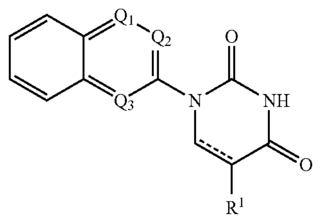

(f)

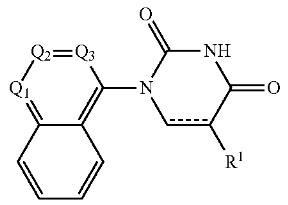

-continued
(g)
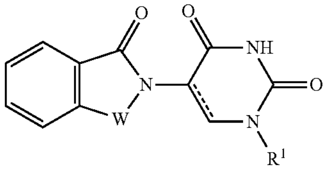
(h)
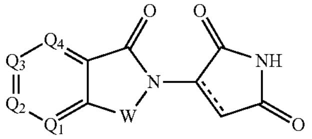
(i)
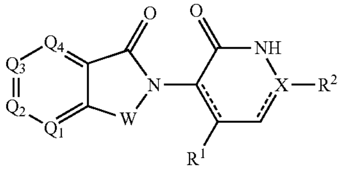
(j)
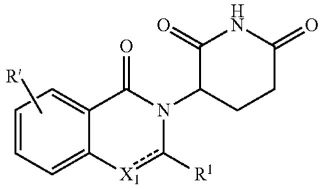
(k)
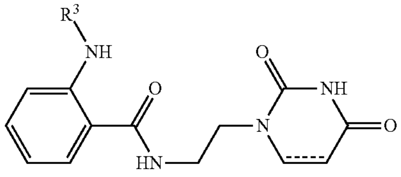
(l)
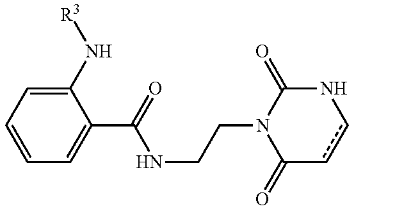
(m)
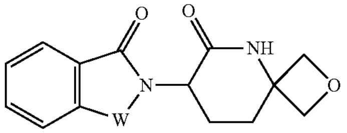
(n)
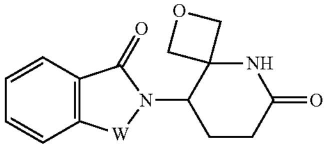
(o)
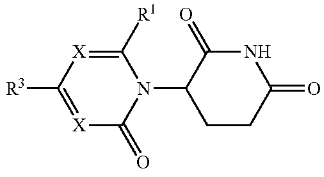
-continued
(p)
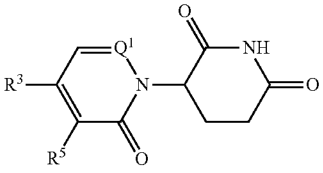
(q)
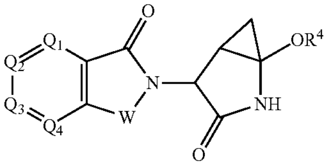
(r)
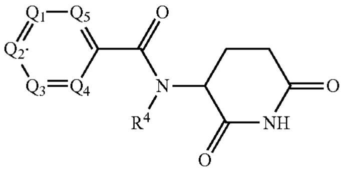
(s)
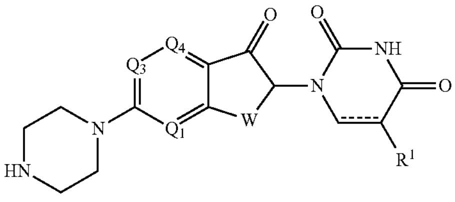
(t)
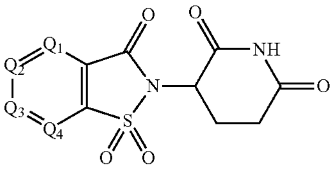
(ba)
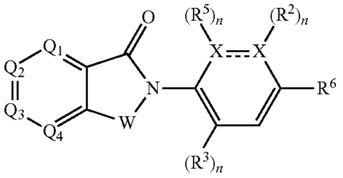
(bb)
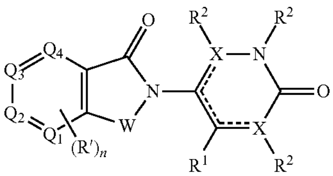
(bc)
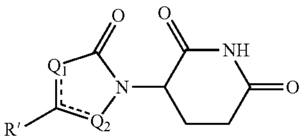
(bd)
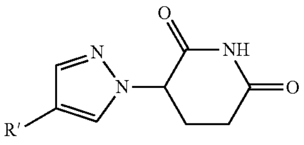

-continued (be)

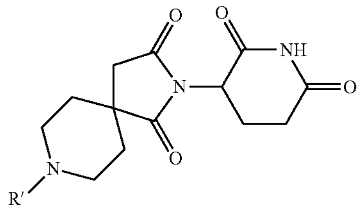

(bf)

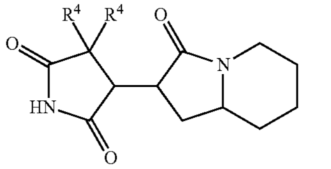

(bg)

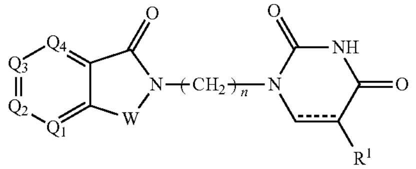

(bh)

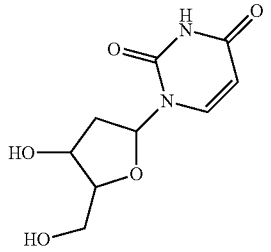

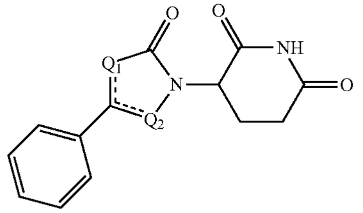

(j')

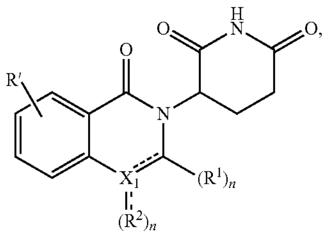

(p')

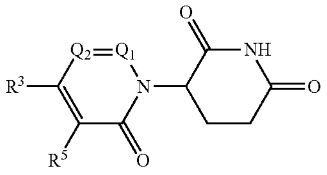

-continued (h')

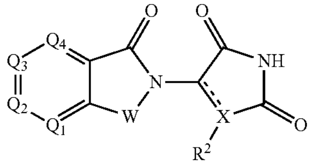

wherein:

W is independently selected from $CH_2$, CHR, C═O, $SO_2$, NH, and N-alkyl;

$Q_1$, $Q_2$, $Q_3$, $Q_4$, $Q_5$ are each independently represent a carbon C or N substituted with a group independently selected from R', N or N-oxide;

$R^1$ is selected from absent H, OH, CN, C1-C3 alkyl, C═O;

$R^2$ is selected from the group absent H, OH, CN, C1-C3 alkyl, $CHF_2$, $CF_3$, CHO, C(═O)$NH_2$;

$R^3$ is selected from H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), substituted alkoxy (e.g., substituted C1-C6 or C1-C3 alkoxyl);

$R^4$ is selected from H, alkyl, substituted alkyl;

$R^5$ and $R^6$ are each independently H, halogen, C(═O)R', CN, OH, $CF_3$;

X is C, CH, C═O, or N;

$X_1$ is C═O, N, CH, or $CH_2$;

R' is selected from H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, C(═O)$OR^2$, optionally substituted phenyl;

n is 0-4;

⁄⁄ is a single or double bond; and the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$.

In any of the embodiments described herein, the W, X, $R^1$, $R^2$, $R^3$, $R^4$, R', $Q_1$, $Q_2$, $Q_3$, $Q_4$, and $Q_5$ can independently be covalently coupled to a linker and/or a linker to which is attached to one or more PTM, ULM, ULM', CLM or CLM' groups.

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkoxy" refers to an alkyl group singularly bonded to oxygen.

The term "Alkenyl" refers to linear, branch-chained or cyclic $C_2$-$C_{10}$ (preferably $C_2$-$C_6$) hydrocarbon radicals containing at least one C═C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_{1sub}R_{2sub}R_{3sub}$ groups where each of $R_{1sub}$ and $R_{2sub}$ is as otherwise described herein and $R_{3sub}$ is H or a $C_1$-$C_6$ alkyl group, preferably $R_{1sub}$, $R_{2sub}$, $R_{3sub}$ in this context is a $C_1$-$C_3$ alkyl group (including an isopropyl or t-butyl group). Each of the above-described groups may be linked directly to the substituted moiety or alternatively, the sub stituent may be linked to the substituted moiety (preferably in the case of an aryl or heteraryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure, moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_{1sub}R_{2sub}$ or —N($R_{1sub}$)—C(O)—O—$R_{1sub}$, nitro, cyano and amine (especially including a $C_1$-$C_6$ alkylene-$NR_{1sub}R_{2sub}$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, ═O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_{1sub}$, —$(CH_2)_n$C(O)—$NR_{1sub}R_{2sub}$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_{1sub}$, —$(CH_2O)_n$C(O)—$NR_{1sub}R_{2sub}$, —$S(O)_2$—$R_S$, —S(O)—$R_S$ ($R_S$ is $C_1$-$C_6$ alkyl or a —$(CH_2)_m$—$NR_{1sub}R_{2sub}$ group), $NO_2$, CN or halogen (F, Cl, Br, I, preferably F or Cl), depending on the context of the use of the substituent. $R^{1sub}$ and $R_{2sub}$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_{1sub}R_{2sub}$ group where $R_{1sub}$ and $R_{2sub}$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$) alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

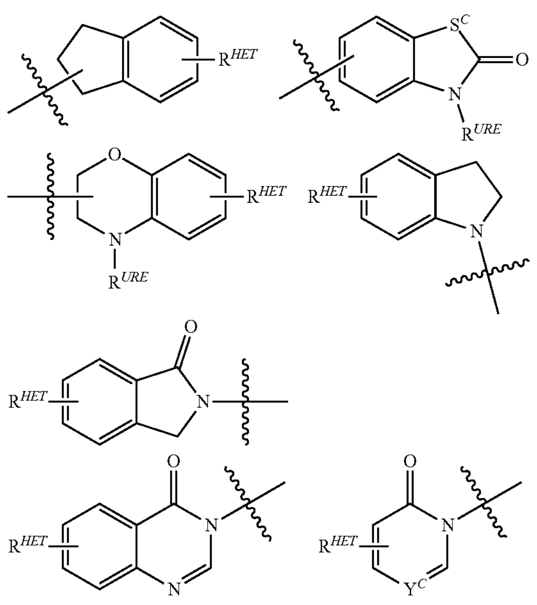

wherein $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxany, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carb oxy alkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (═O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defnied herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "lower alkyl" refers to methyl, ethyl or propyl

The term "lower alkoxy" refers to methoxy, ethoxy or propoxy.

More specifically, non-limiting examples of CLMs include those shown below as well as "hybrid" molecules or compounds that arise from combining 1 or more featrues of the following compounds:

(v)

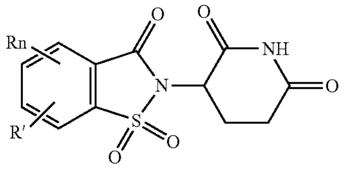

(w)

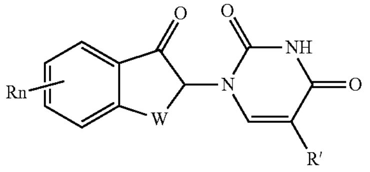

(x)

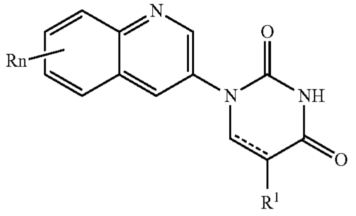

(y)

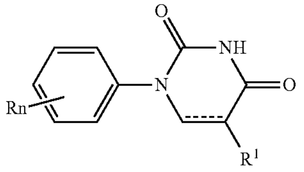

(z)

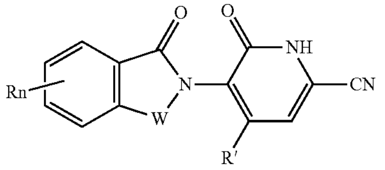

(aa)

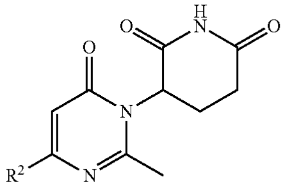

(ab)

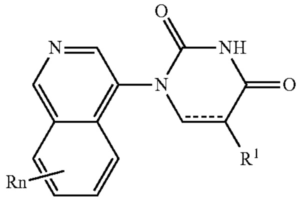

-continued (ac)

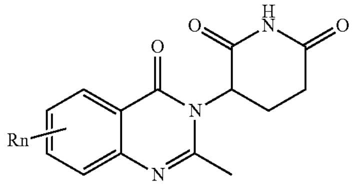

(ad)

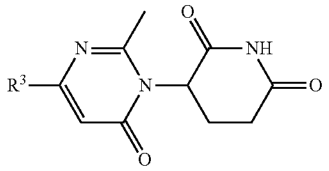

(ae)

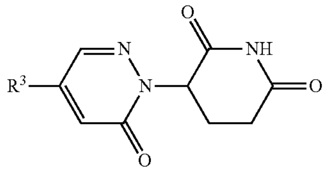

(af)

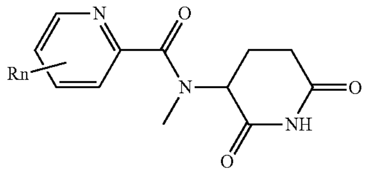

(ag)

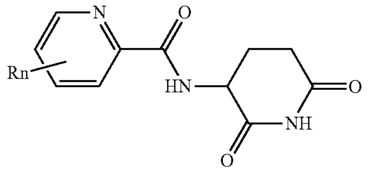

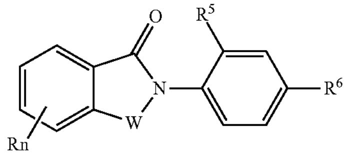

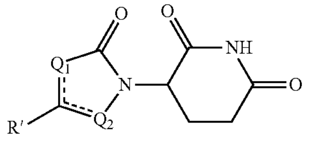

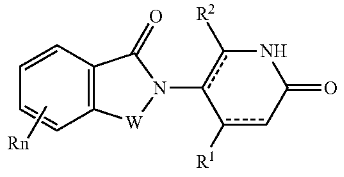

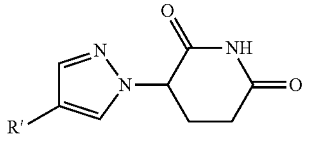

-continued

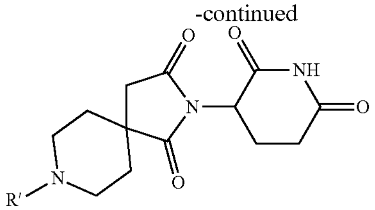

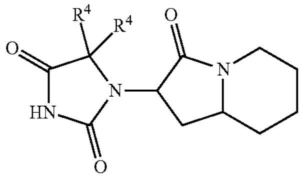

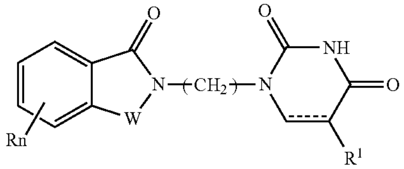

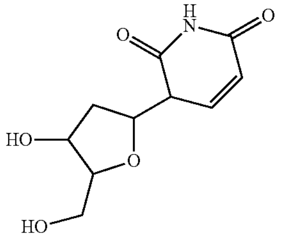

wherein:

W is independently selected from the group $CH_2$, CHR, C═O, $SO_2$, NH, and N-alkyl;

$R^1$ is selected from the group absent, H, CH, CN, C1-C3 alkyl;

$R^2$ is H or a C1-C3 alkyl;

$R^3$ is selected from H, alkyl, substituted alkyl, alkoxy, substituted alkoxy;

$R^4$ is methyl or ethyl;

$R^5$ is H or halo;

$R^6$ is H or halo;

R of the CLM is H;

R' is H or an attachment point for a PTM, a PTM', a chemical linker group (L), a ULM, a CLM, a CLM', Q1 and Q2 are each independently C or N substituted with a group independently selected from H or C1-C3 alkyl;

⋰ is a single or double bond; and

Rn comprises a functional group or an atom.

In any of the embodiments described herein, the W, $R^1$, $R^2$, $Q_1$, $Q_2$, $Q_3$, $Q_4$, and Rn can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and Rn can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and Rn can independently be covalently coupled to a linker and/or a linker to which is attached one or more PTM, ULM, ULM', CLM or CLM' groups.

In any aspect or embodiment described herein, $R_n$ is modified to be covalently joined to the linker group (L), a PTM, a ULM, a second CLM having the same chemical structure as the CLM, a CLM', a second linker, or any multiple or combination thereof In any aspect or embodiment described herein, the CLM is selected from:

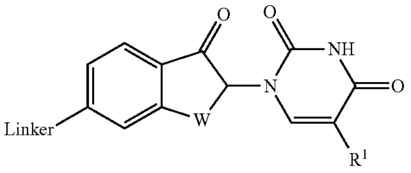

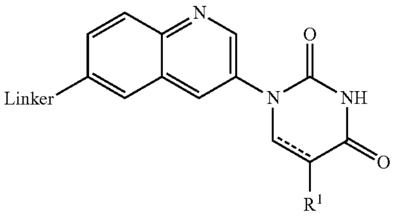

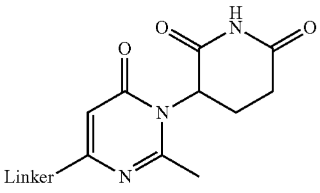

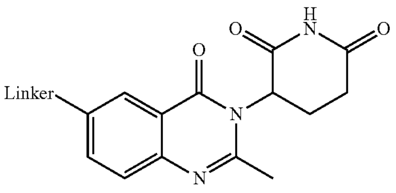

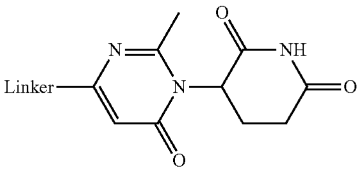

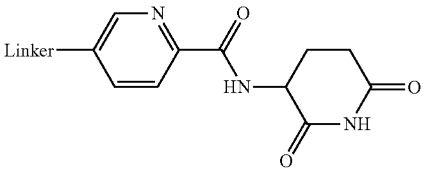

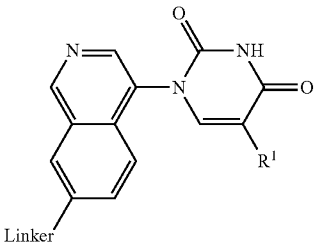

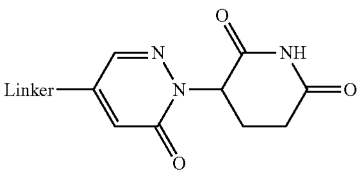

-continued
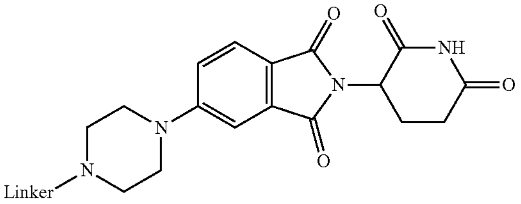
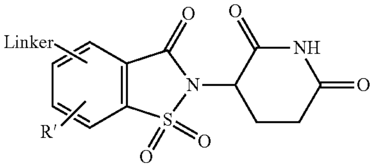
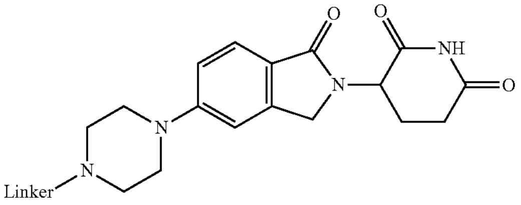
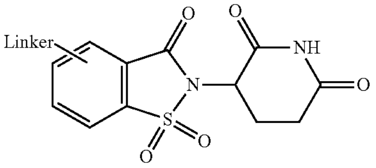
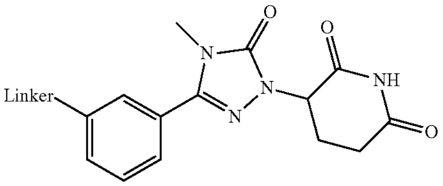
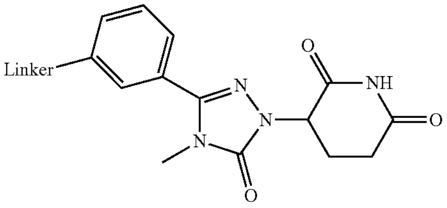
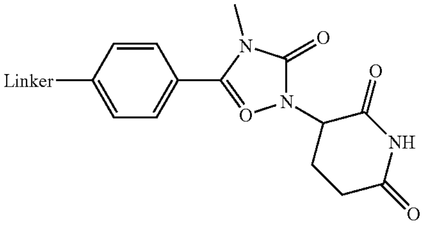
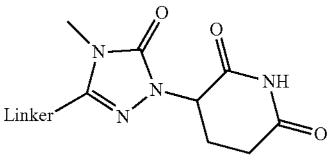
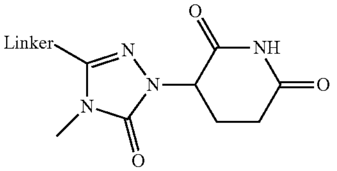
-continued
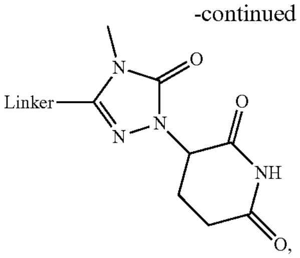
,
wherein R' is a halogen and $R^1$ is as described in any aspect or embodiment described herein.
In certain cases, "CLM" can be imides that bind to cereblon E3 ligase. These imides and linker attachment point can be but not limited to the following structures:
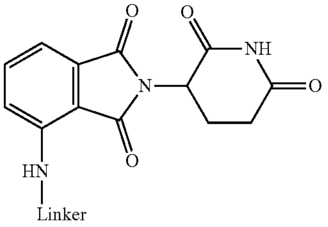
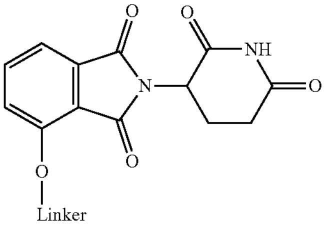
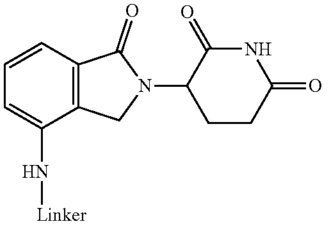
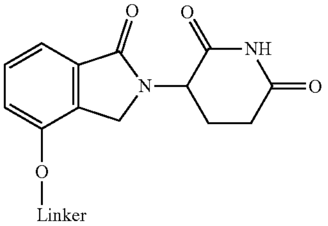
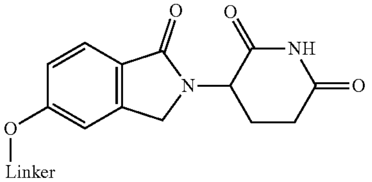
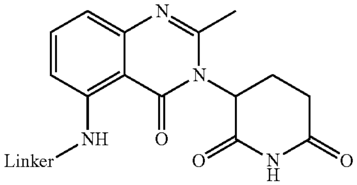

-continued

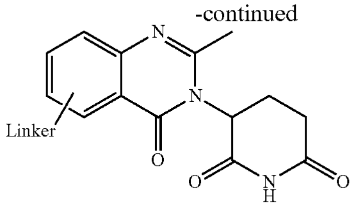

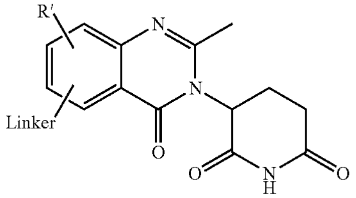

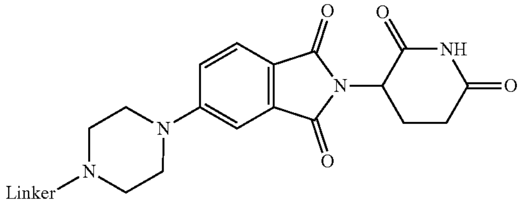

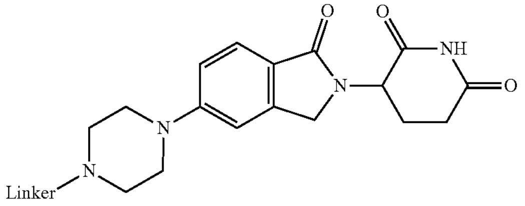

Exemplary Linkers

In certain embodiments, the compounds as described herein include one or more CLMs chemically linked or coupled to one or more PTMs (e.g., PTM and/or PTM'), ULMs (e.g., ULM, ULM', and/or CLM') via a chemical linker (L). In certain embodiments, the linker group L is a group comprising one or more covalently connected structural units (e.g., $-A^L_1 \ldots (A^L)_q$- or $-(A^L)_q$-), wherein $A_1$ is a group coupled to PTM, and Aq is a group coupled to at least one of a ULM, a ULM', a CLM, a CLM', or a combination thereof. In certain embodiments, $A^L_1$ links a CLM or CLM' directly to another ULM, PTM, or combination thereof. In other embodiments, $A^L_1$ links a CLM or CLM' indirectly to another ULM, PTM, or combination thereof through $A_q$.

In certain embodiments, the linker group is $-(A^L)_q$-, wherein $(A^L)_q$ is a group which is connected to at least one of a ULM moiety, a PTM moiety, or a combination thereof;

q of the linker is an integer greater than or equal to 1;

each $A^L$ is independently selected from the group consisting of a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{L3}C({=}NCN)NR^{L4}$, $NR^{L3}C({=}NCN)$, $NR^{L3}C({=}CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^1$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH═CH($C_{1-8}$alkyl), $C(C_{1-8}alkyl){=}CH(C_{1-8}alkyl)$, $C(C_{1-8}alkyl){=}C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)SO_2N(C_{1-8}alkyl)_2$, NH $SO_2NH(C_{1-8}alkyl)$, NH $SO_2N(C_{1-8}alkyl)_2$, NH $SO_2NH_2$.

In certain embodiments, q of the linker is an integer greater than or equal to 0. In certain embodiments, q is an integer greater than or equal to 1.

In certain embodiments, e.g., where q is greater than 2, $A^L_q$ is a group which is connected to a ULM or ULM' moiety (such as CLM or CLM'), and $A^L_1$ and $A^L_q$ are connected via structural units of the linker (L).

In certain embodiments, e.g., where q of the linker is 2, $A^L_q$ is a group which is connected to $A^L_1$ and to a ULM or a ULM' moiety (such as CLM or CLM').

In certain embodiments, e.g., where q of the linker is 1, the structure of the linker group L is $-A^L_1$-, and $A^L_1$ is a group which is connected to a ULM or ULM' moiety (such as CLM or CLM') and a PTM moiety.

In certain embodiments, the linker (L) comprises a group represented by a general structure selected from the group consisting of:

—$NR(CH_2)_n$-(lower alkyl)-, —$NR(CH_2)_n$-(lower alkoxyl)-, —$NR(CH_2)_n$-(lower alkoxyl)-$OCH_2$—, —$NR(CH_2)_n$-(lower alkoxyl)-(lower alkyl)-$OCH_2$—, —$NR(CH_2)$n-(cycloalkyl)-(lower alkyl)-$OCH_2$—, —$NR(CH_2)_n$-(hetero cycloalkyl)-, —$NR(CH_2CH_2O)_n$-(lower alkyl)-O—$CH_2$—, —$NR(CH_2CH_2O)_n$-(hetero cycloalkyl)-O—$CH_2$—, —$NR(CH_2CH_2O)_n$-Aryl-O—$CH_2$—, —$NR(CH_2CH_2O)_n$-(hetero aryl)-O—$CH_2$—, —$NR(CH_2CH_2O)_n$-(cyclo alkyl)-O-(hetero aryl)-O—$CH_2$—, —$NR(CH_2CH_2O)_n$-(cyclo alkyl)-O-Aryl-O—$CH_2$—, —$NR(CH_2CH_2O)_n$-(lower alkyl)-NH-Aryl-O—$CH_2$—, —$NR(CH_2CH_2O)_n$-(lower alkyl)-O-Aryl-$CH_2$, —$NR(CH_2CH_2O)_n$-cycloalkyl-O-Aryl-, —$NR(CH_2CH_2O)_n$-cycloalkyl-O-(heteroaryl)1-, —$NR(CH_2CH_2)_n$-(cycloalkyl)-O-(heterocycle)-$CH_2$, —$NR(CH_2CH_2)_n$-(heterocycle)-(heterocycle)-$CH_2$, —N(R1R2)-(heterocycle)-$CH_2$; where n of the linker can be 0 to 10;

R of the linker can be H, lower alkyl;

R1 and R2 of the linker can form a ring with the connecting N.

In certain embodiments, the linker (L) comprises a group represented by a general structure selected from the group consisting of:

—N(R)—$(CH2)_m$—$O(CH2)_n$—$O(CH2)_o$—$O(CH2)_p$—$O(CH2)_q$—$O(CH2)_r$—OCH2-,

—O—$(CH2)_m$—$O(CH2)_n$—$O(CH2)_o$—$O(CH2)_p$—$O(CH2)_q$—$O(CH2)_r$—OCH2-,

—O—$(CH2)_m$—$O(CH2)_n$—$O(CH2)_o$—$O(CH2)_p$—$O(CH2)_q$—$O(CH2)_r$—O—;

—N(R)—$(CH2)_m$—$O(CH2)_n$—$O(CH2)_o$—$O(CH2)_p$—O $(CH2)_q$—$O(CH2)_r$—O—;
—$(CH2)_m$—$O(CH2)_n$—$O(CH2)_o$—$O(CH2)_p$— $O(CH2)_q$—$O(CH2)_r$—O—;
—$(CH2)_m$—$O(CH2)_n$—$O(CH2)_o$—$O(CH2)_p$— $O(CH2)_q$—$O(CH2)_r$—OCH2—;
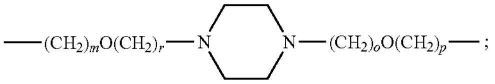
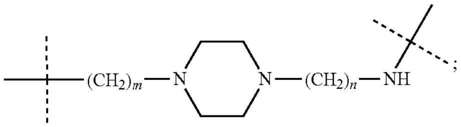
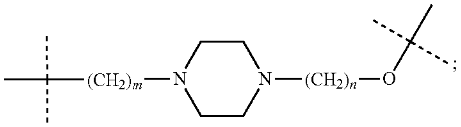
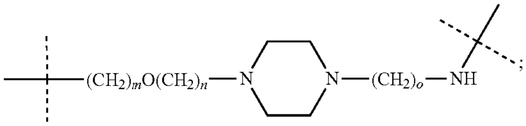
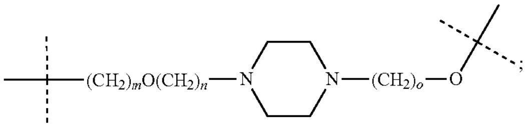
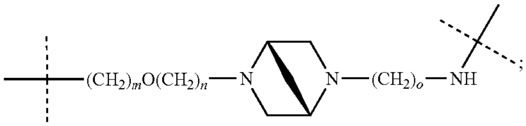
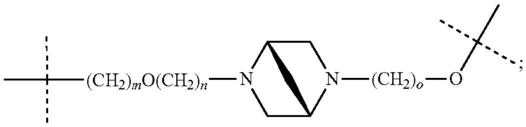
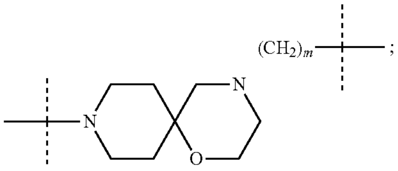
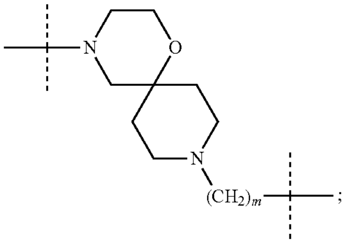
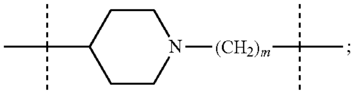
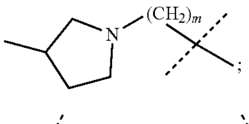
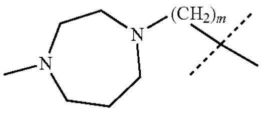
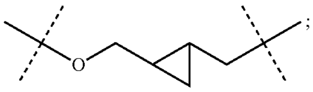
-continued
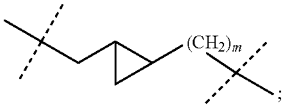
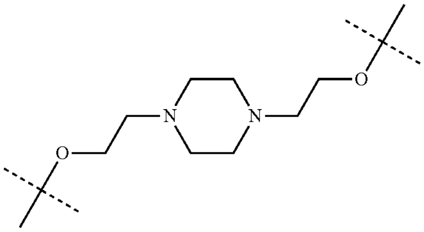
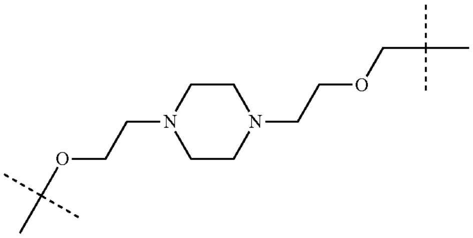
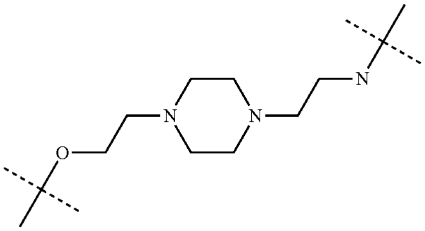
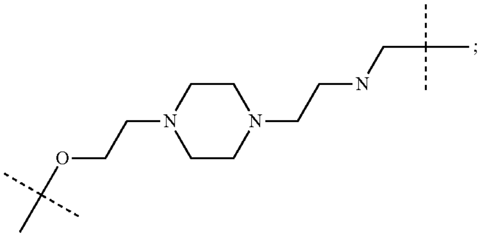
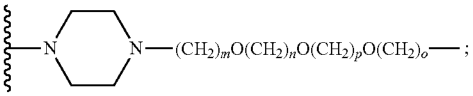
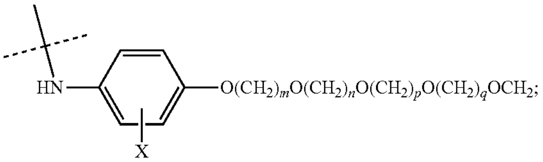
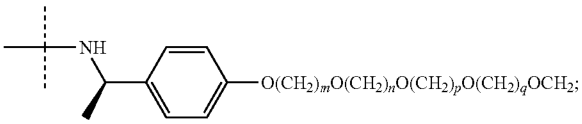
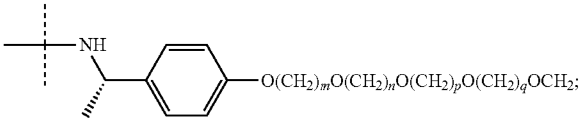
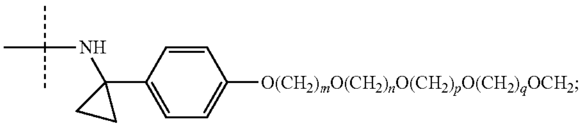

-continued
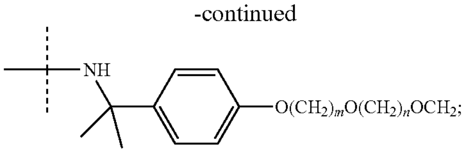
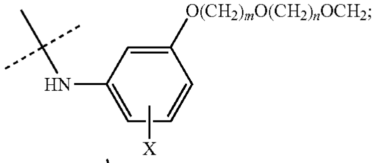
and
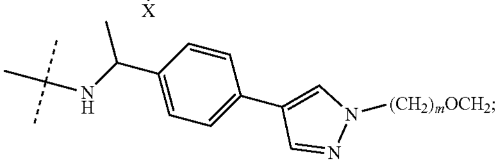
wherein
m, n, o, p, q, and r of the linker are independently 0, 1, 2, 3, 4, 5, 6; 7, 8, 9, 10, 11, 12, 13, 14, 15, 16, 17, 18, 19, or 20;
when the number is zero, there is no N—O or O—O bond
R of the linker is H, methyl and ethyl;
X of the linker is H and F
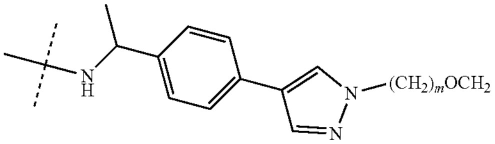
where m of the linker can be 2, 3, 4, 5
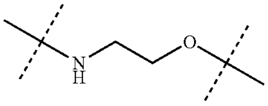
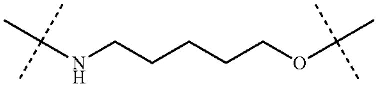
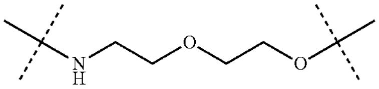
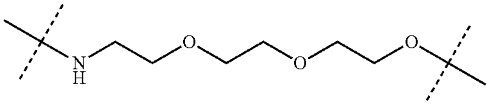
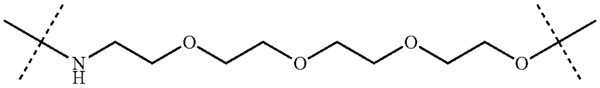
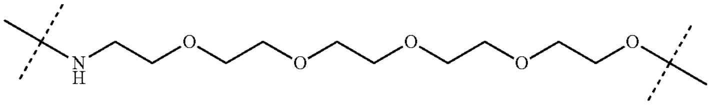
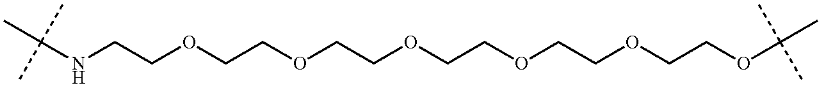
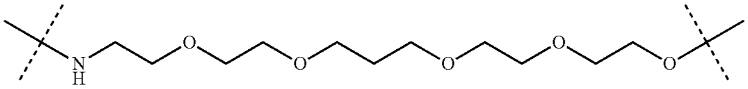
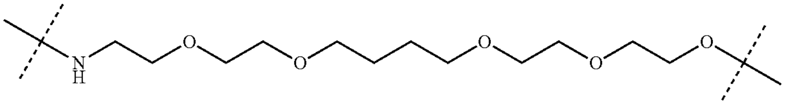
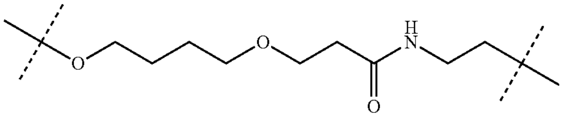
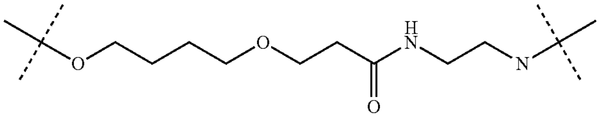
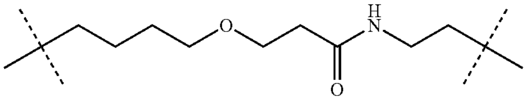
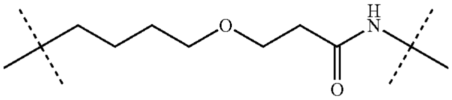
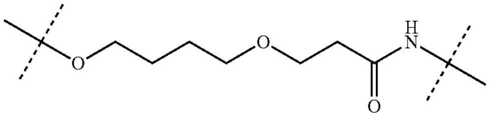
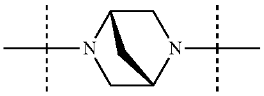
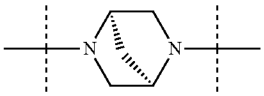

-continued
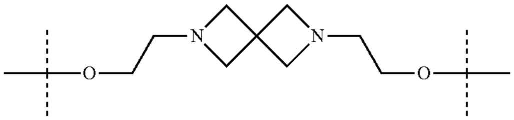
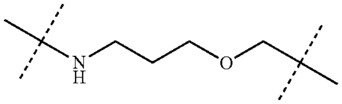
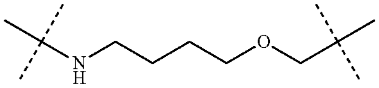
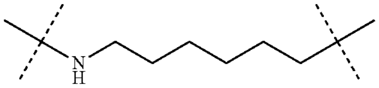
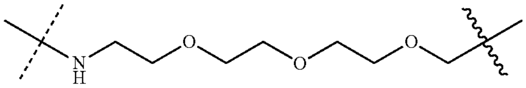
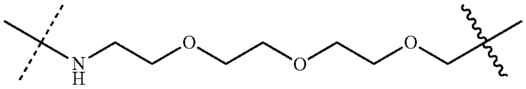
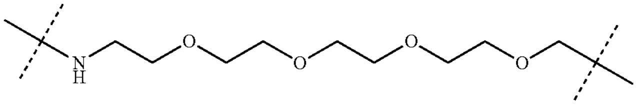
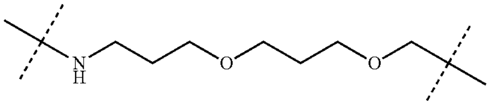
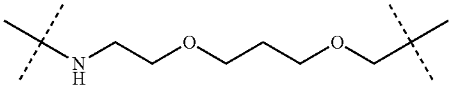
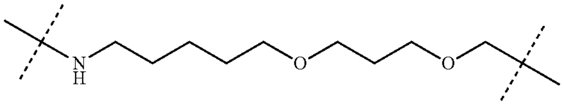
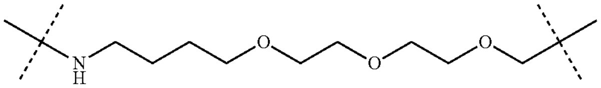
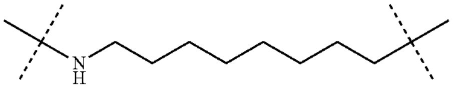
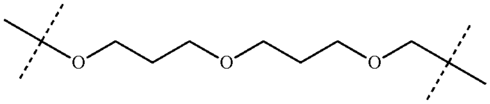
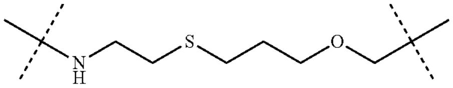
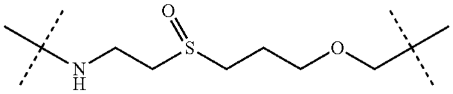
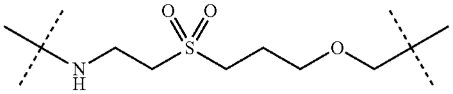
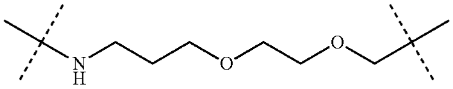
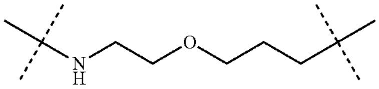
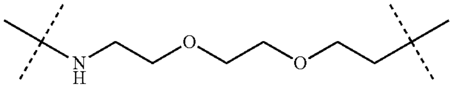
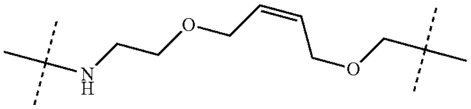
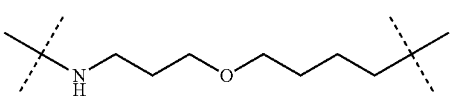
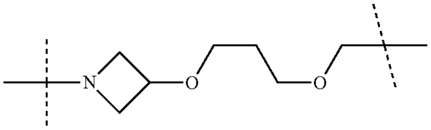
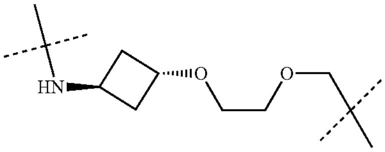
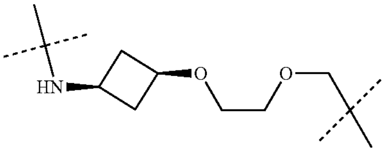
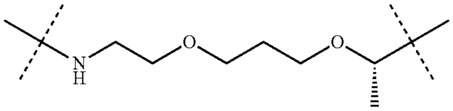
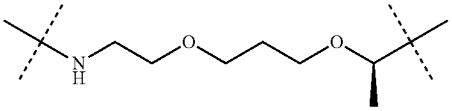
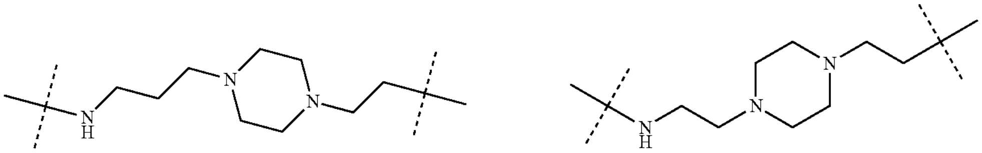

-continued
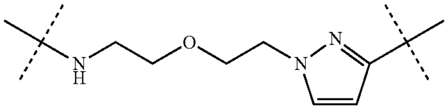
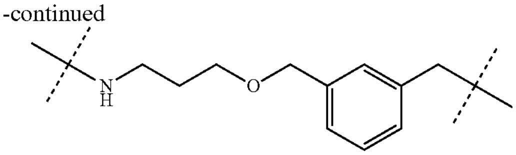
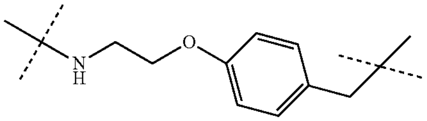
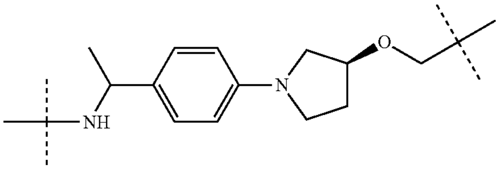
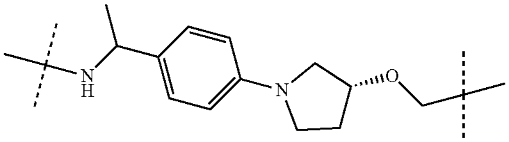
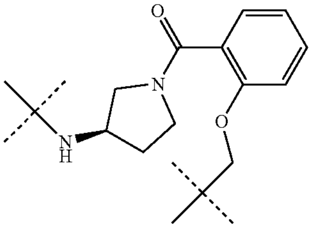
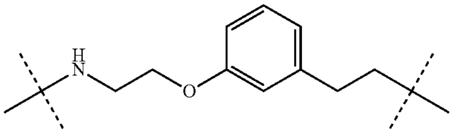
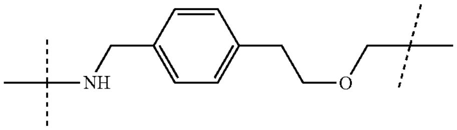
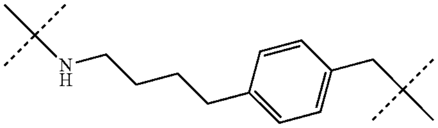
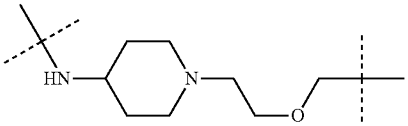
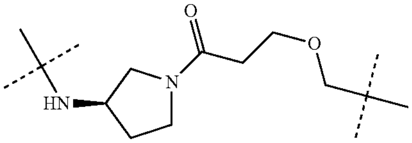
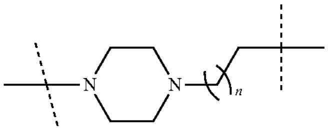
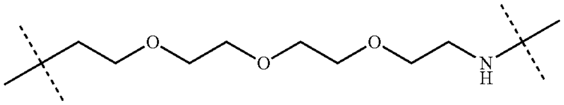
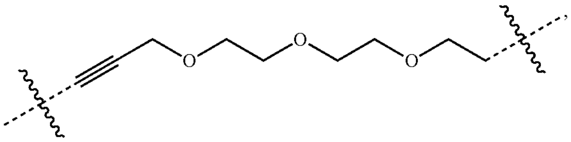,
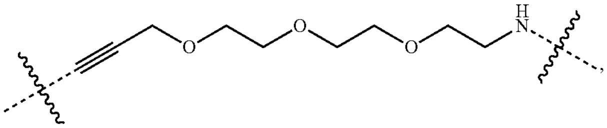,
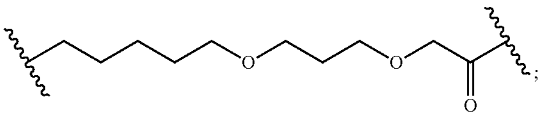;
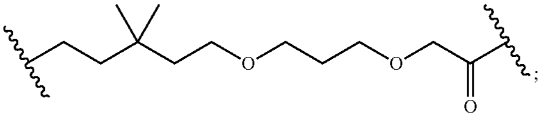;
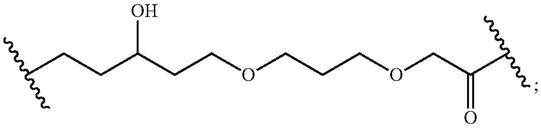;
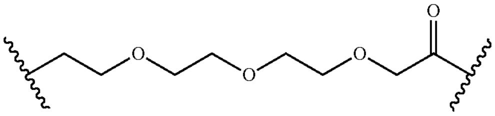;
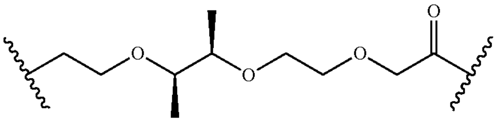;
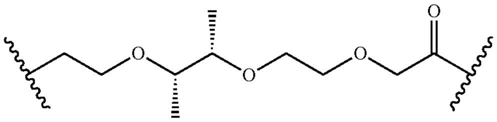;

-continued
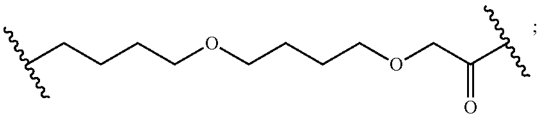 ;
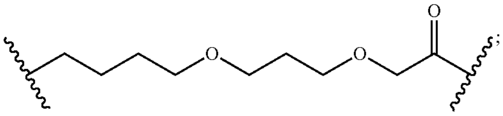 ;
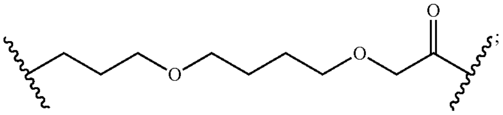 ;
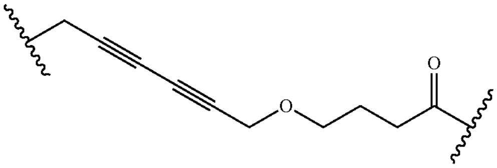 ;
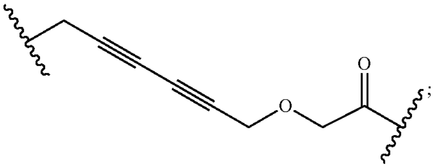 ;
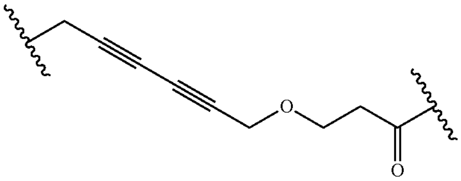 ;
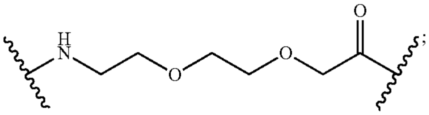 ;
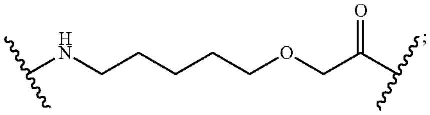 ;
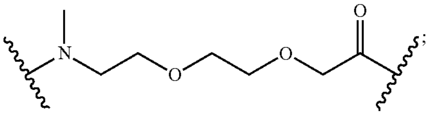 ;
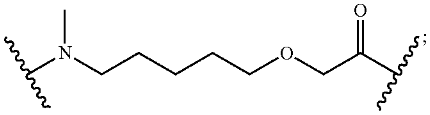 ;
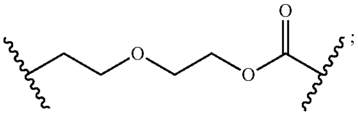 ;
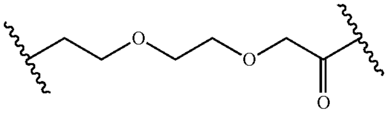 ;
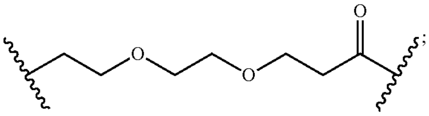 ;
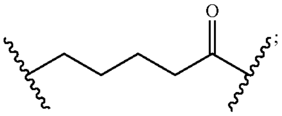 ;
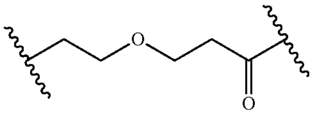 ;
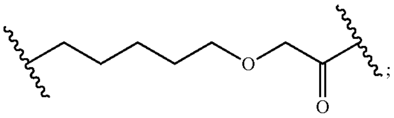 ;
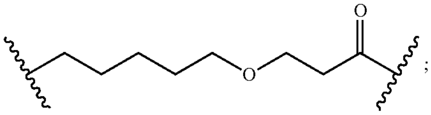 ;
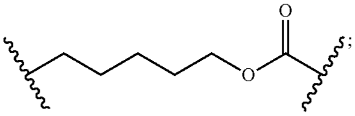 ;
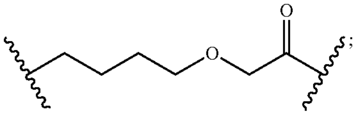 ;
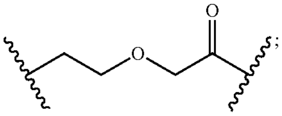 ;
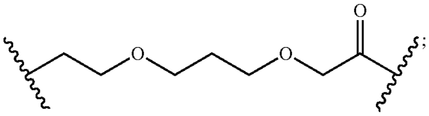 ;
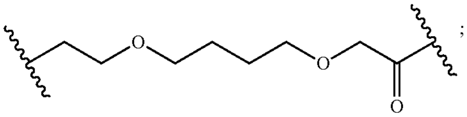 ;
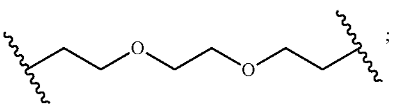 ;
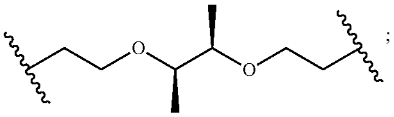 ;
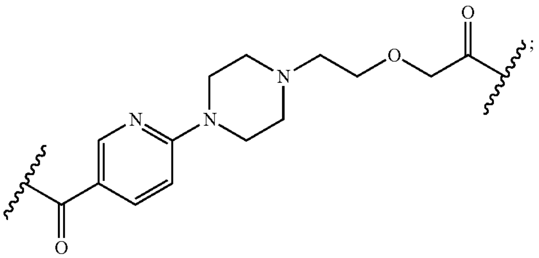 ;
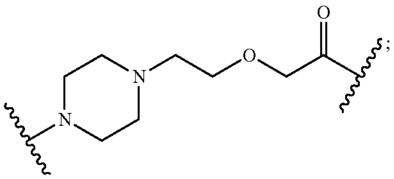 ;

-continued
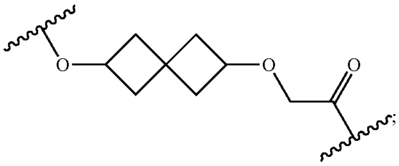;
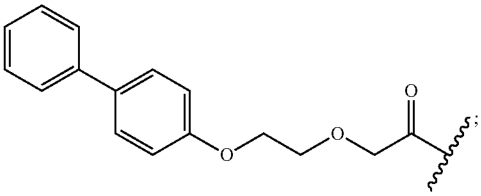;
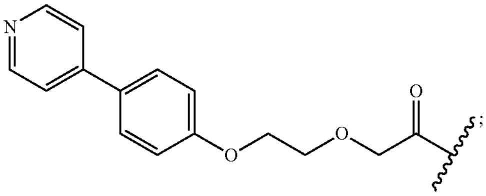;
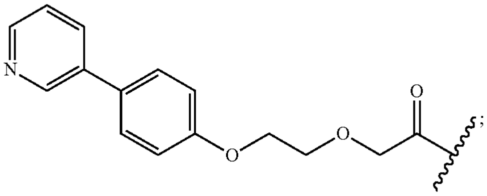;
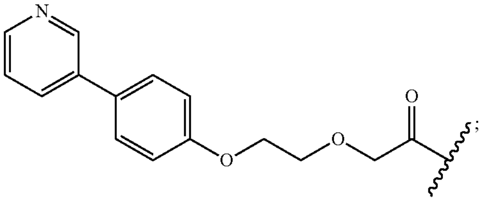;
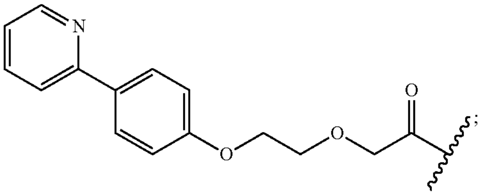;
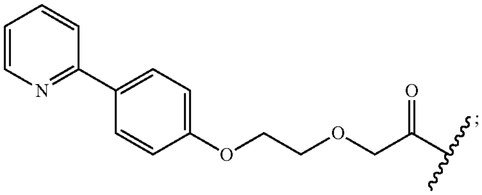;
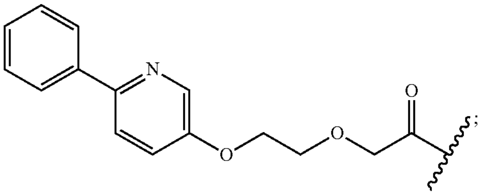;
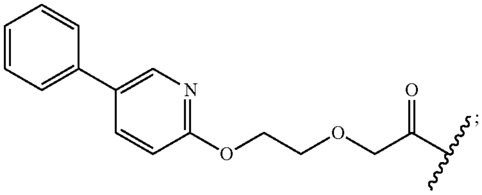;
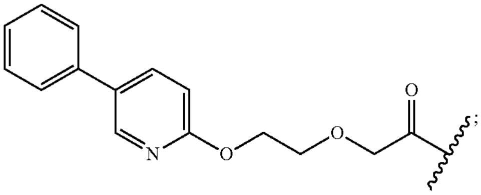;
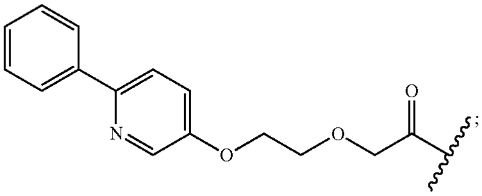;
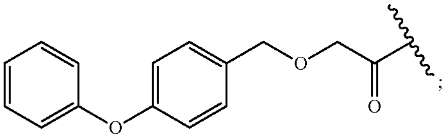;
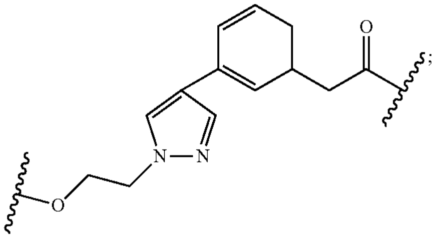;
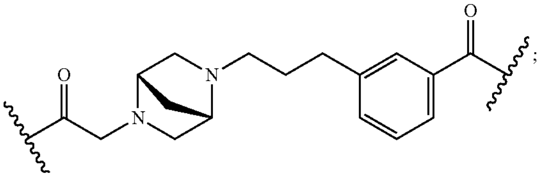;
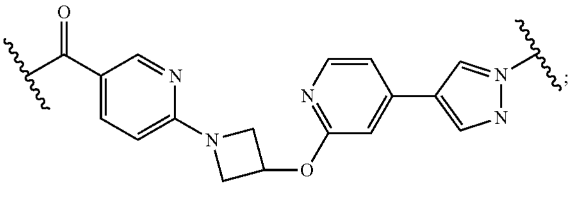;

-continued
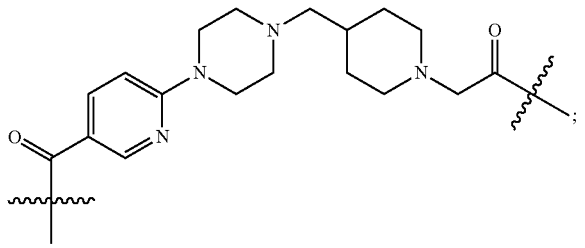
;
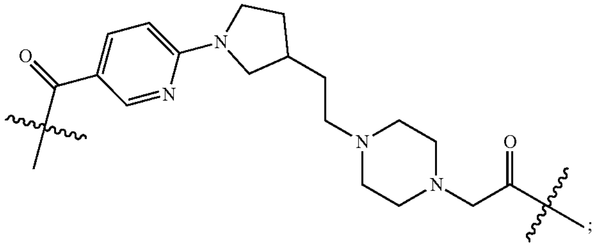
;
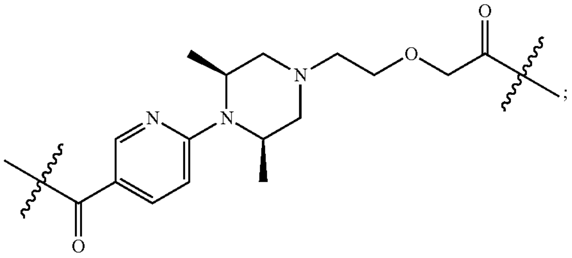
;
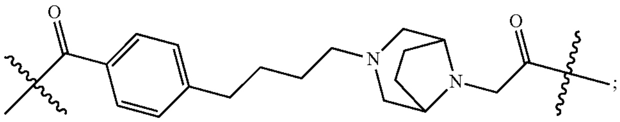
;
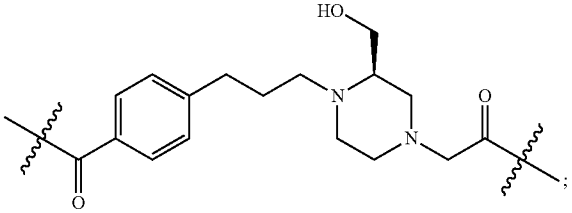
;
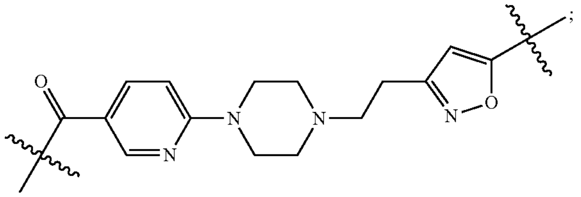
;
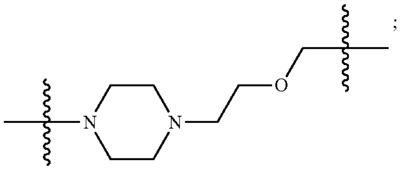
;
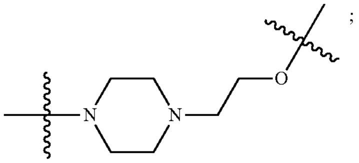
;
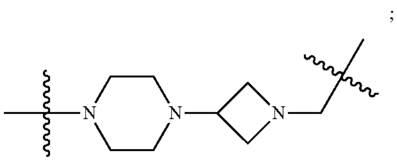
;
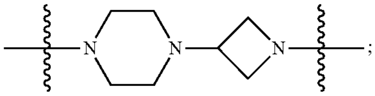
;
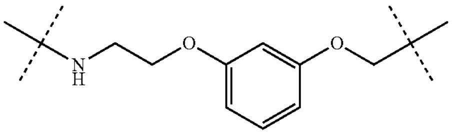

-continued
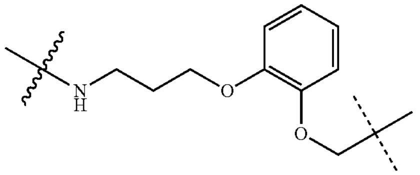
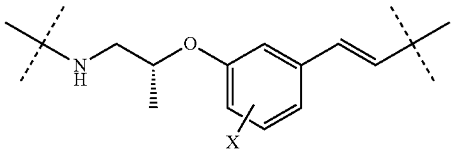
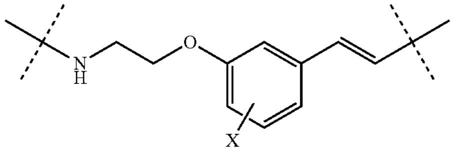
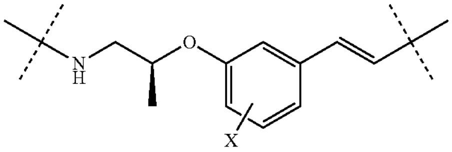
X = H, F
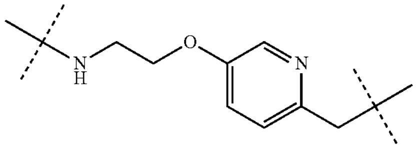
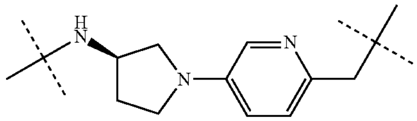
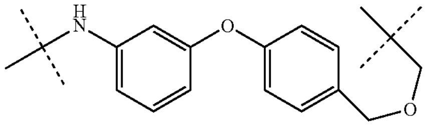
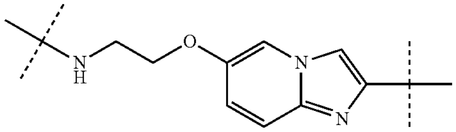
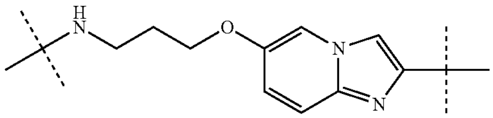
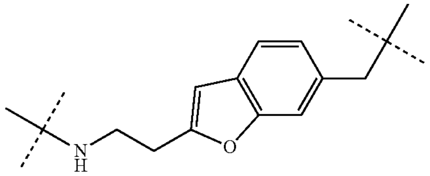
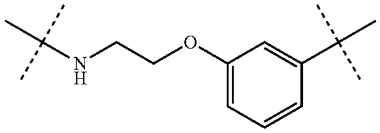
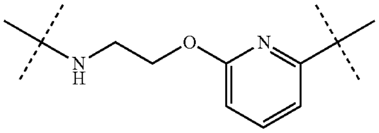
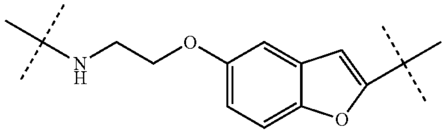
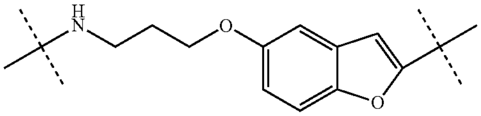
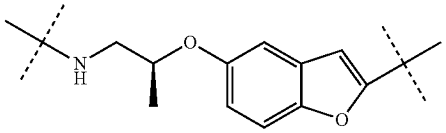
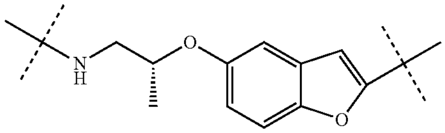
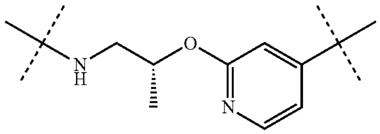
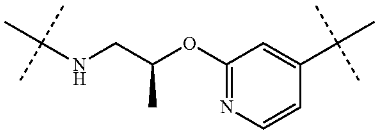
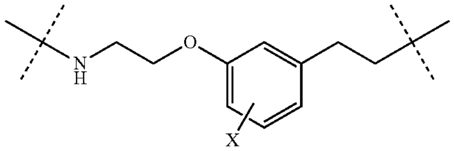
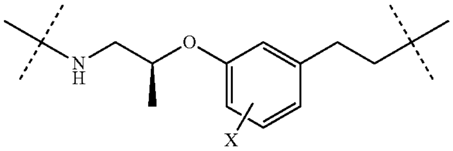
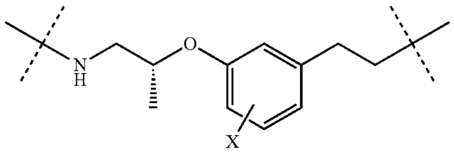
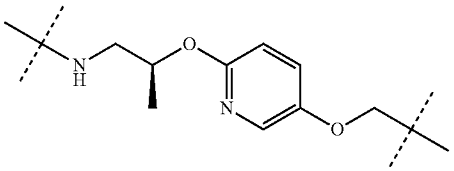

-continued
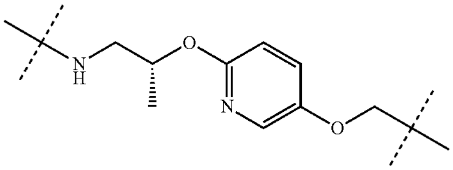
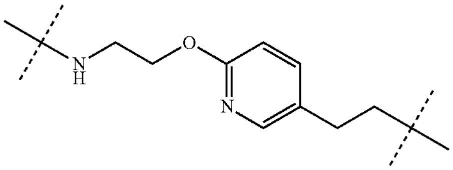
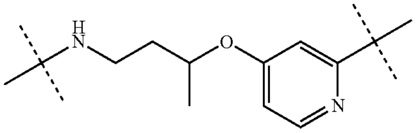
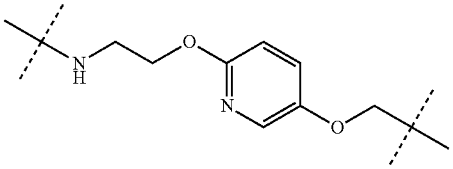
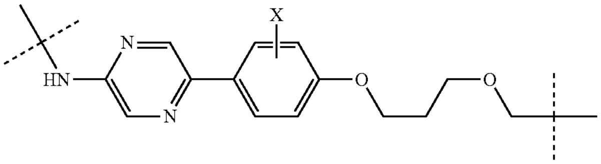
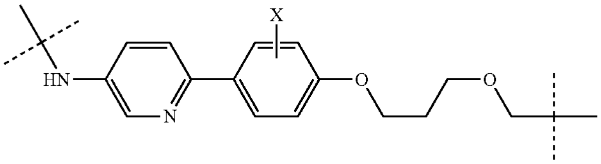
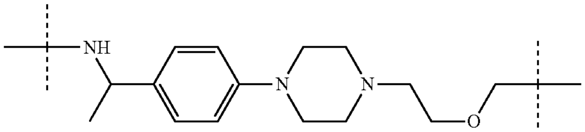
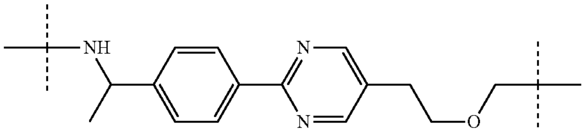
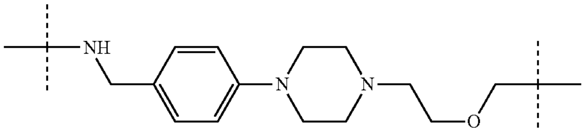
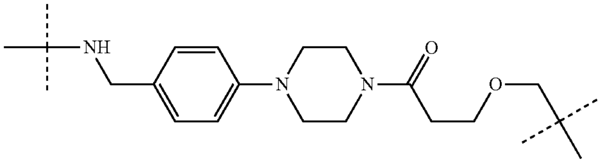
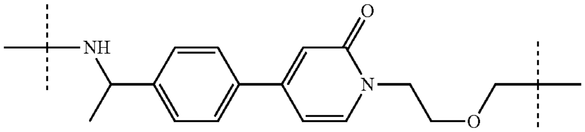
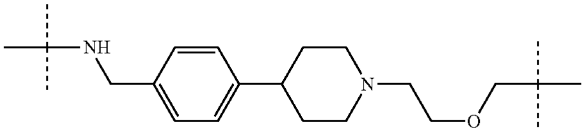
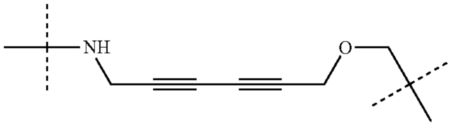
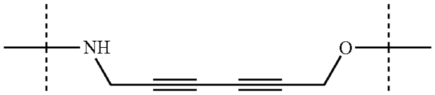

-continued
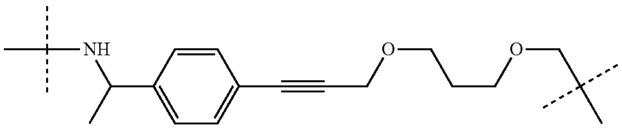
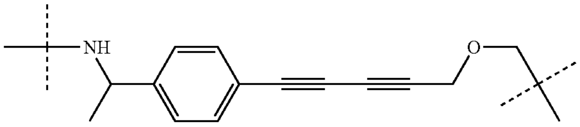
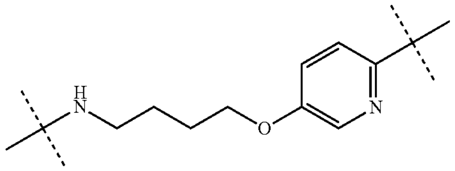
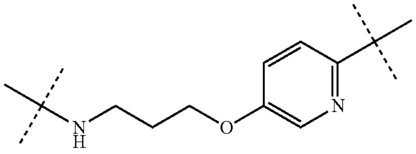
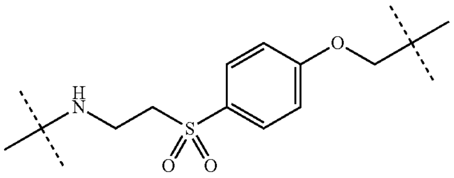
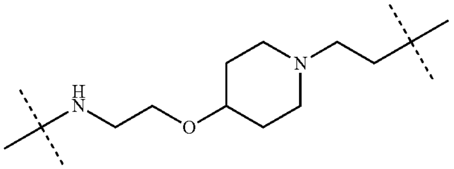
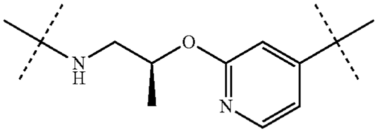
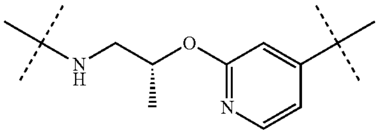
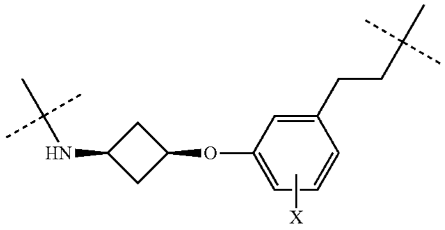
X = H, F
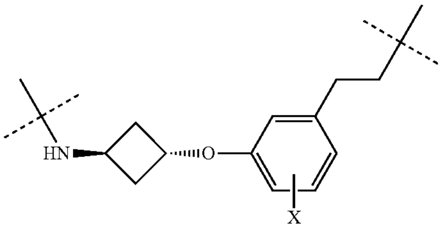
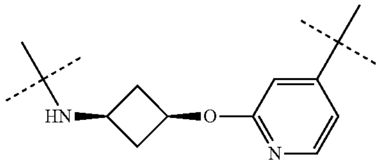
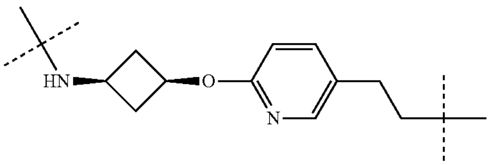
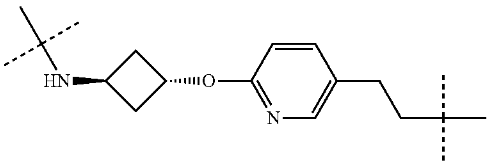
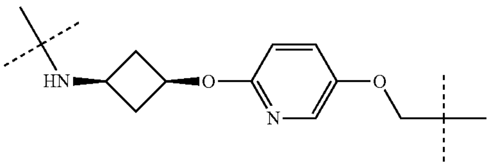
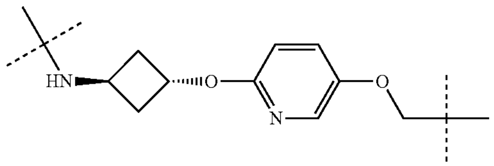
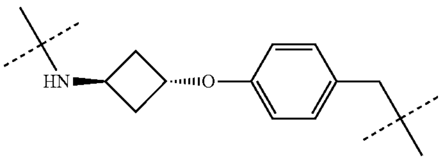
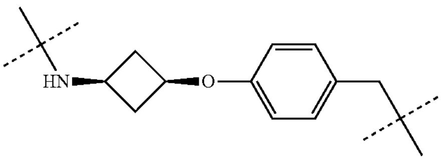

-continued
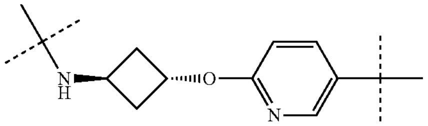
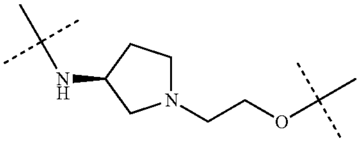
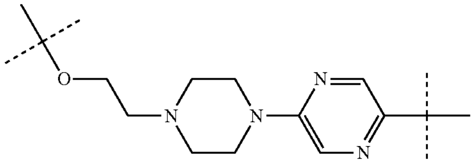
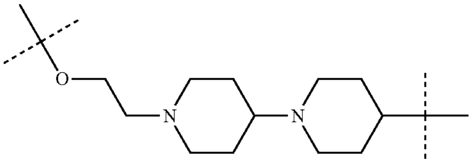
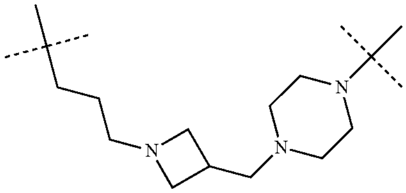
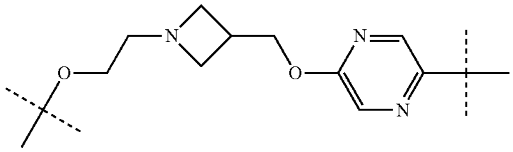
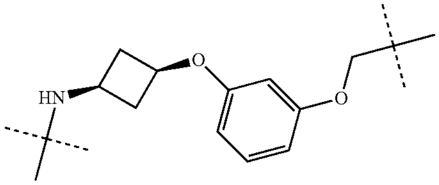
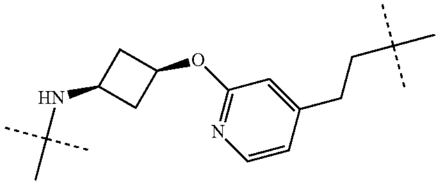
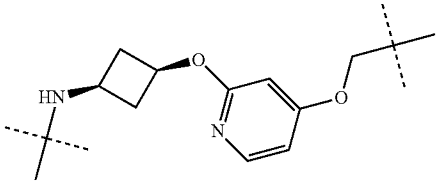
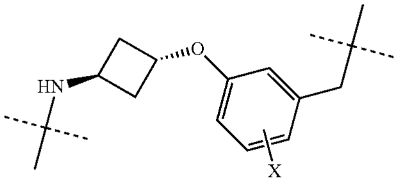
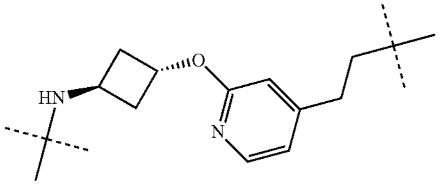
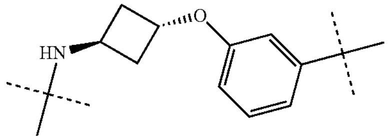
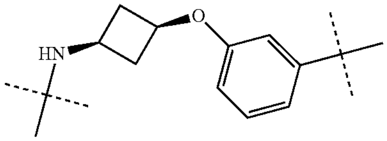
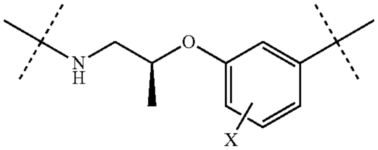
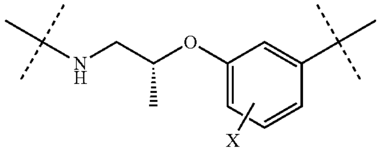
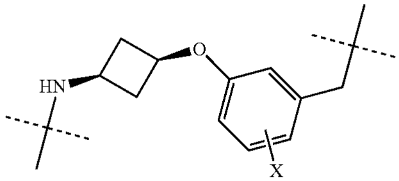
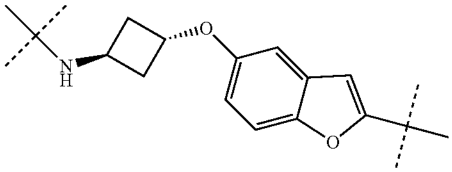
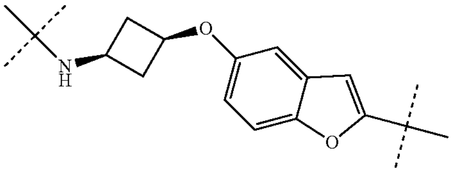
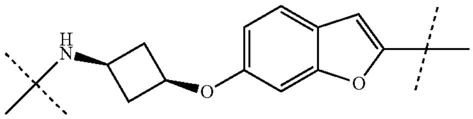
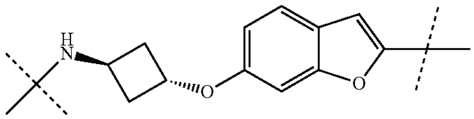

-continued
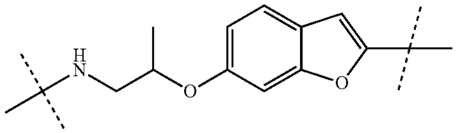
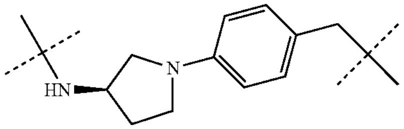
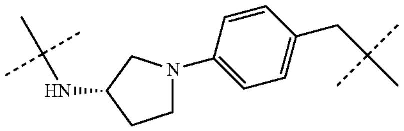
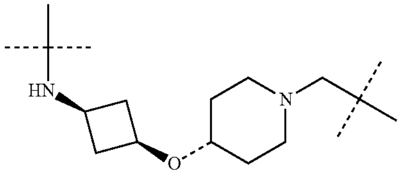
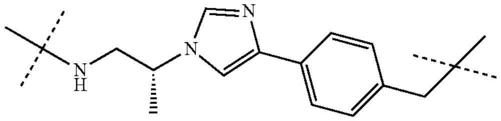
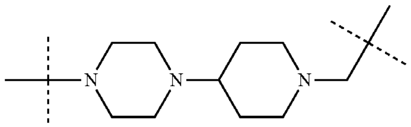
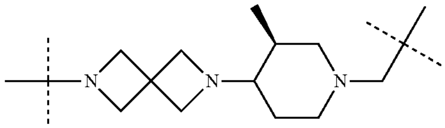
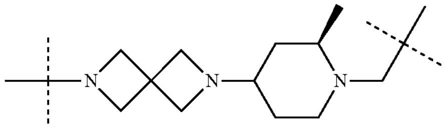
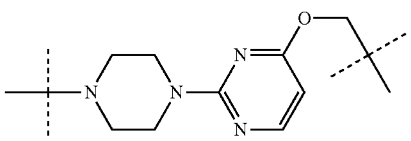
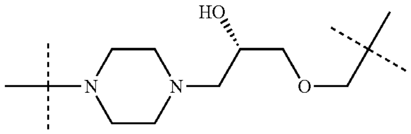
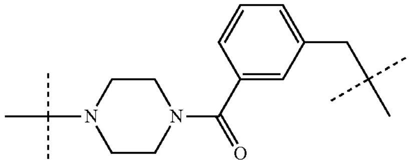
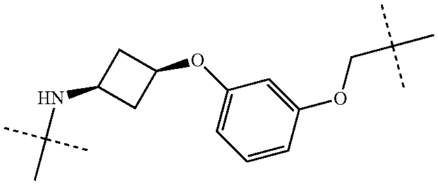
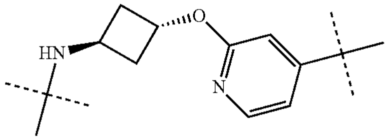
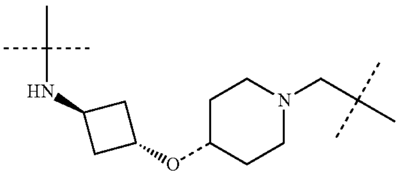
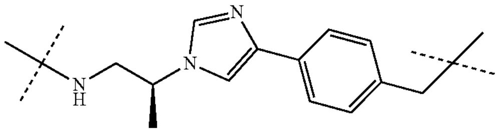
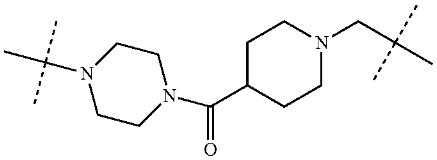
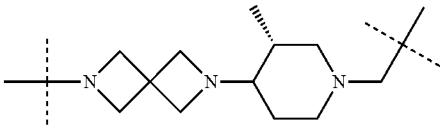
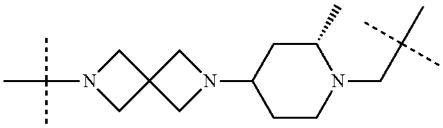
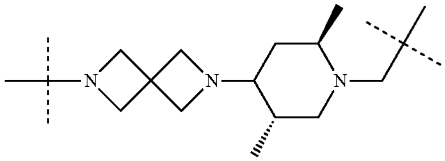
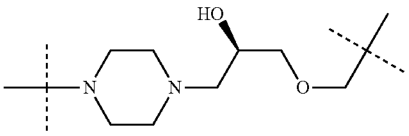
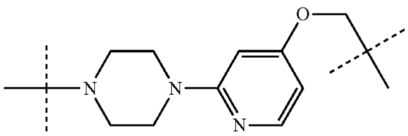
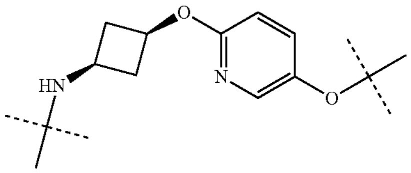

-continued
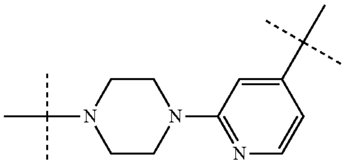
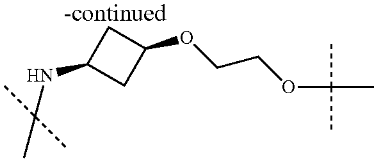
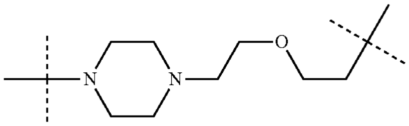
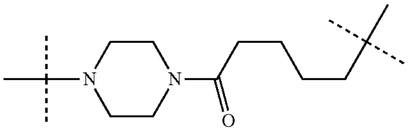
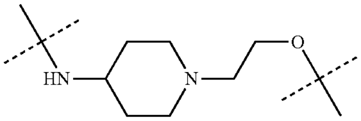
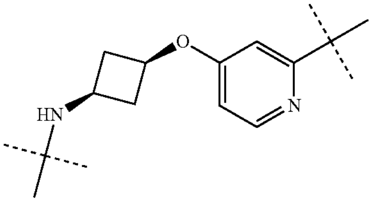
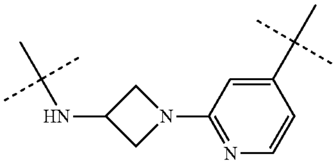
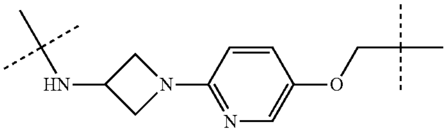
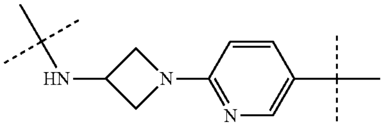
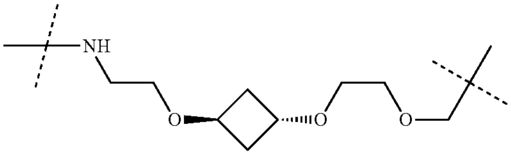
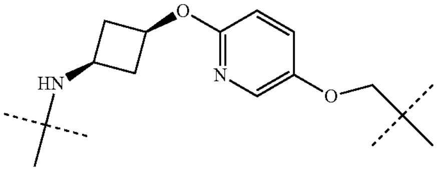
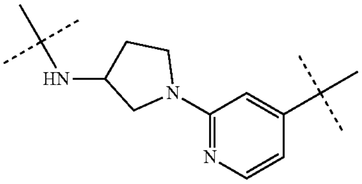
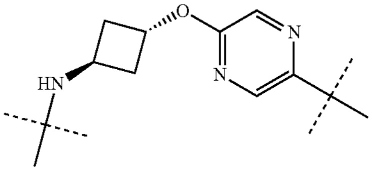
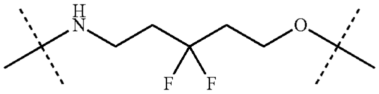
where each n and m of the linker can independently be 0, 1, 2, 3, 4, 5, 6.
In any aspect or embodiment described herein, the linker (L) is selected from the group consisting of:
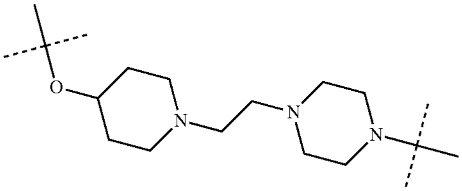
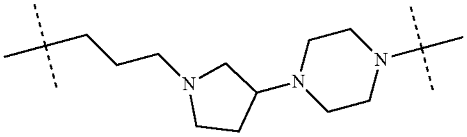
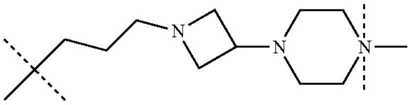
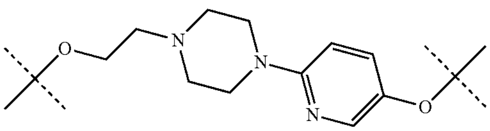

-continued
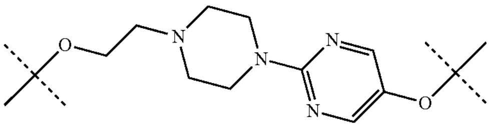
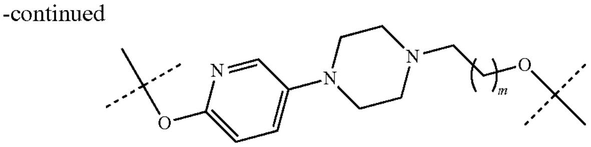
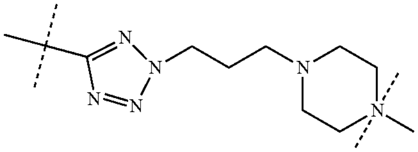
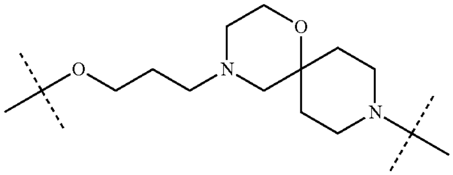
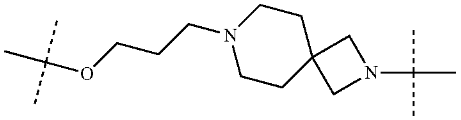
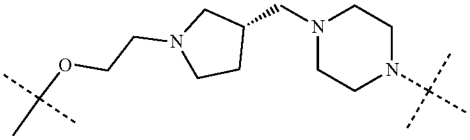
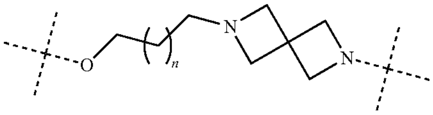
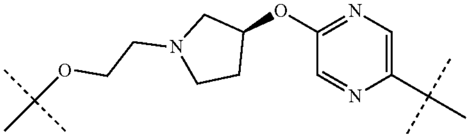
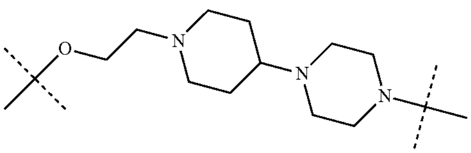
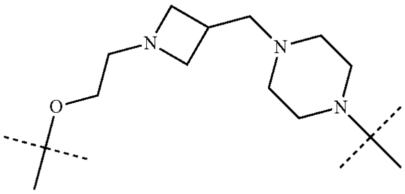
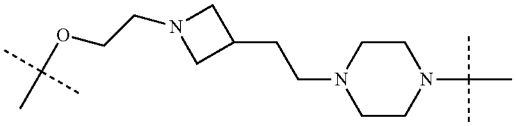
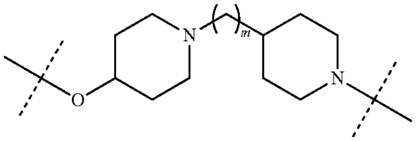
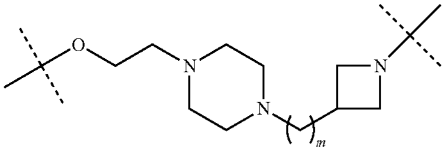
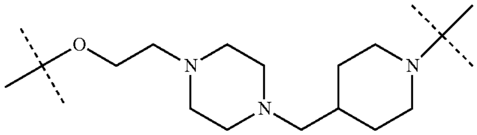
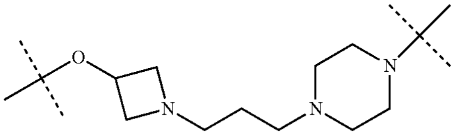
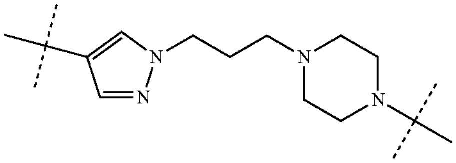
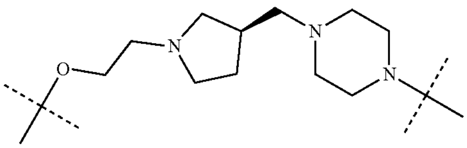
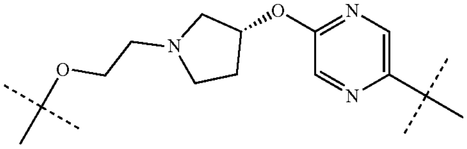
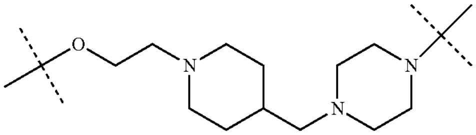
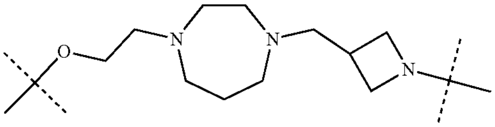
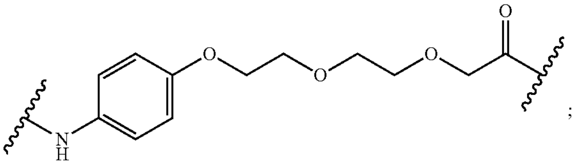
;

-continued
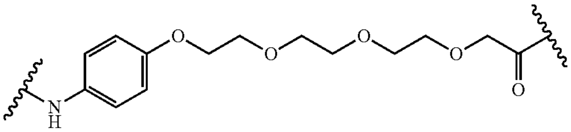
;
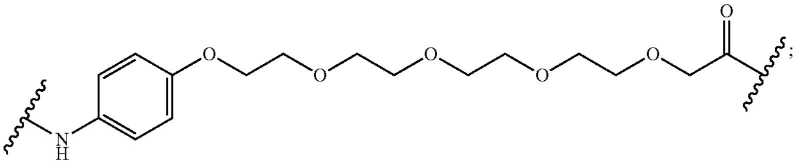
;
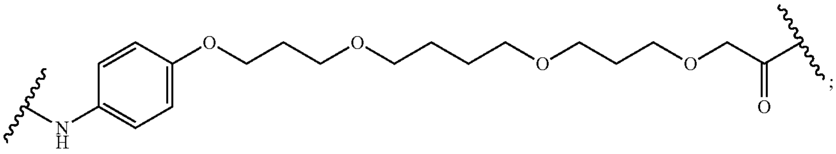
;
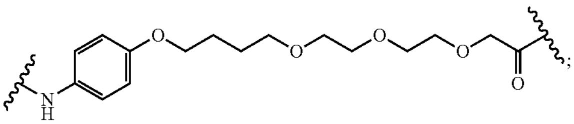
;
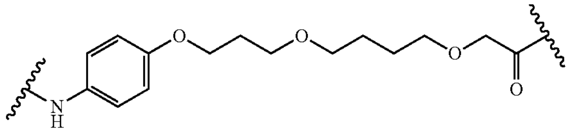
;
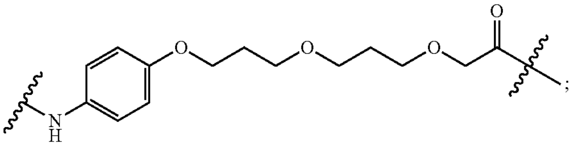
;
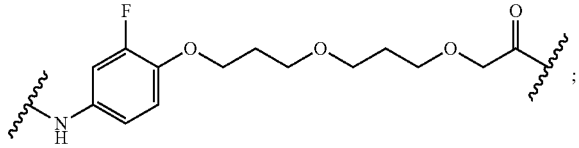
;
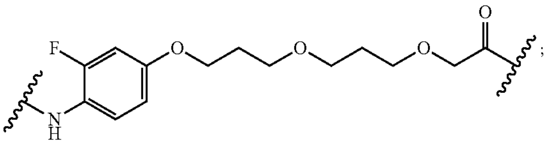
;
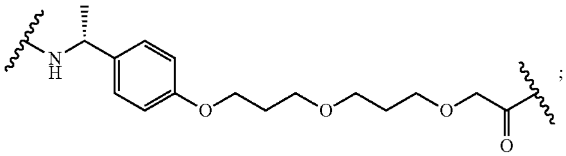
;
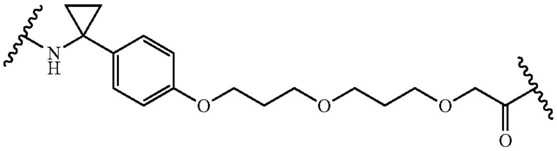
;
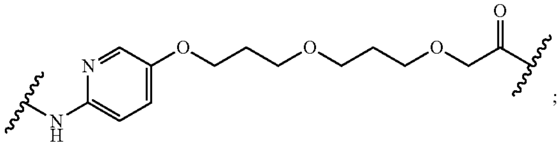
;
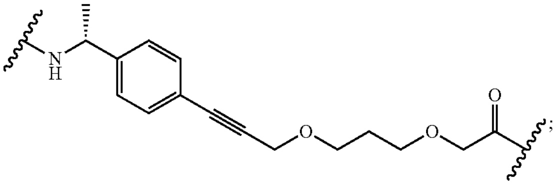
;
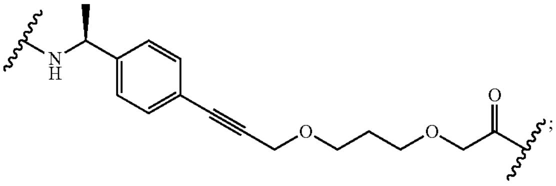
;
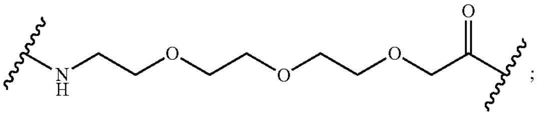
;
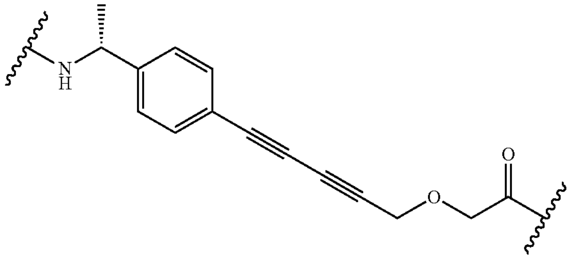
;
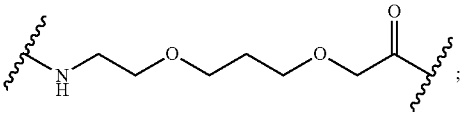
;
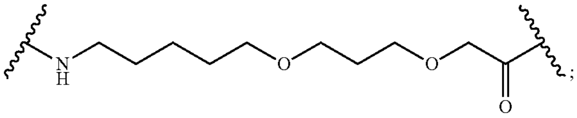
;

-continued
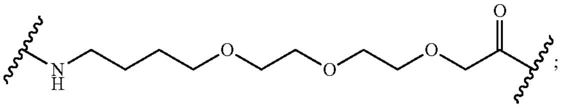
;
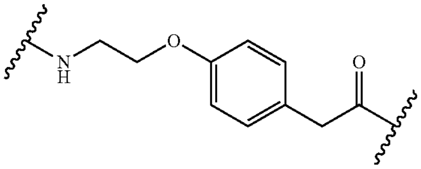
;
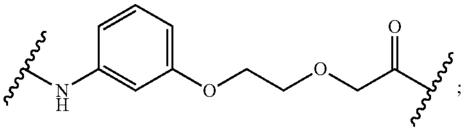
;
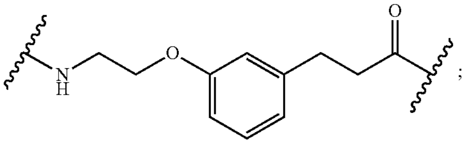
;
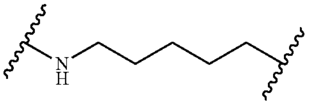
;
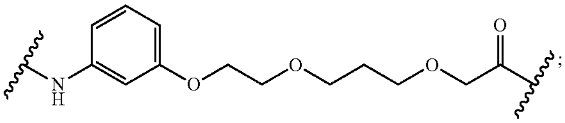
;
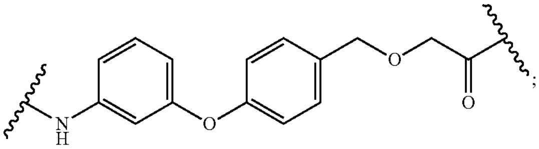
;
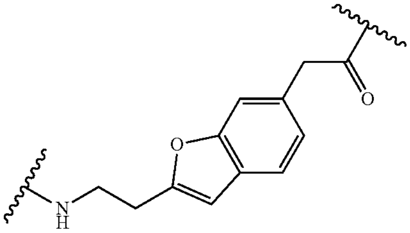
;
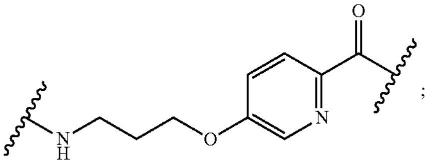
;
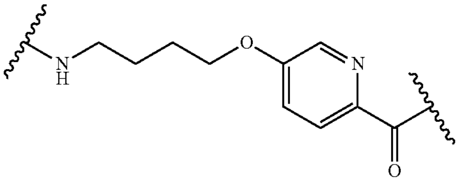
;
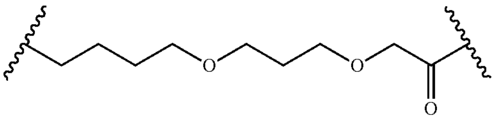
;
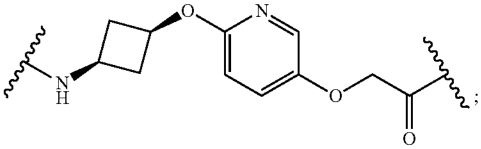
;
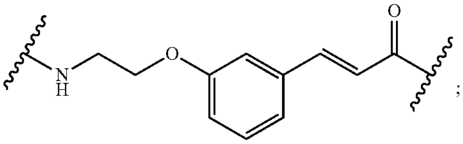
;
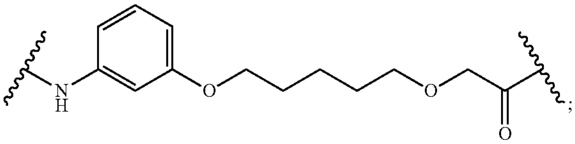
;
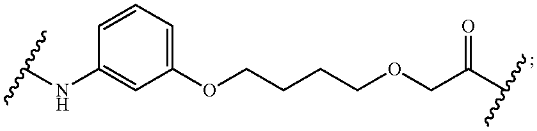
;
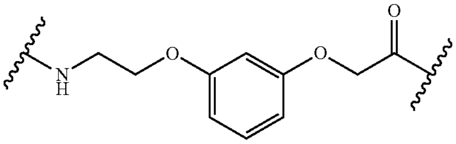
;
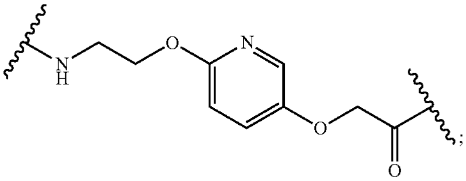
;
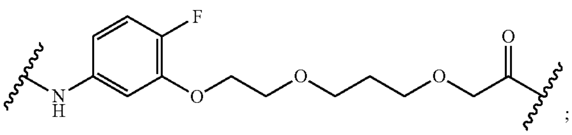
;
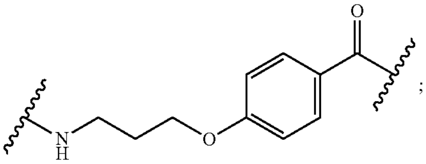
;
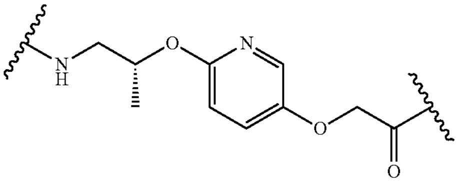
;

-continued
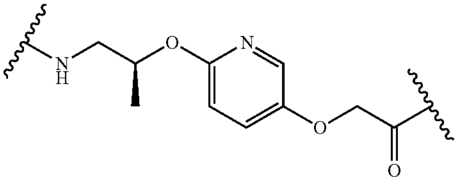 ; 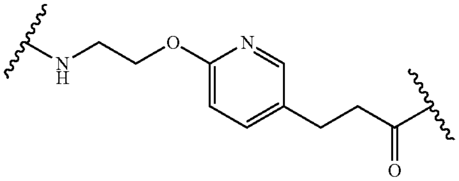 ;
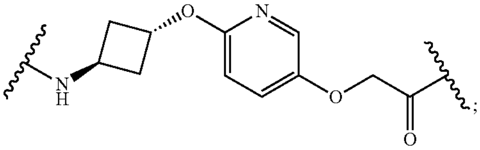 ; 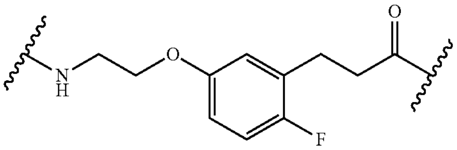 ;
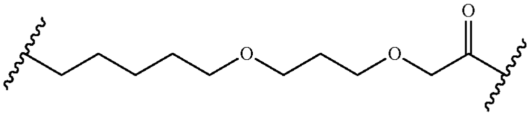 ; 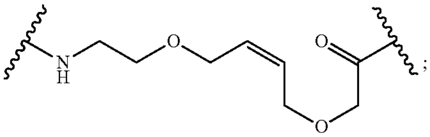 ;
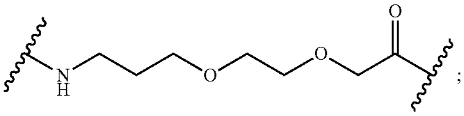 ; 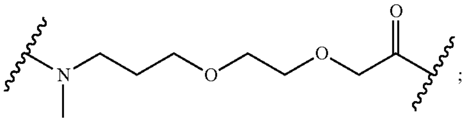 ;
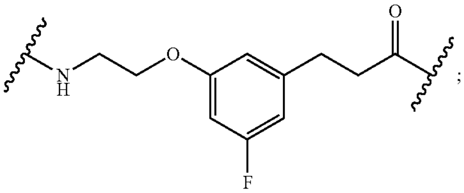 ; 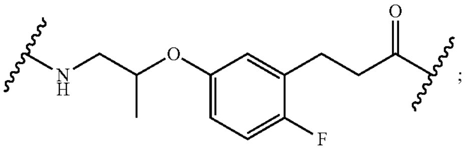 ;
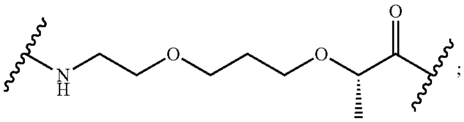 ; 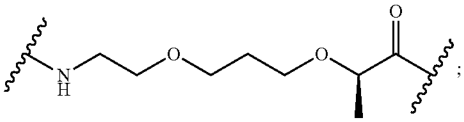 ;
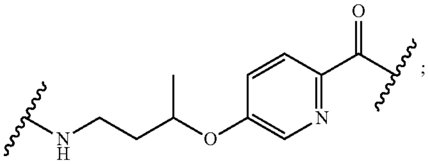 ; 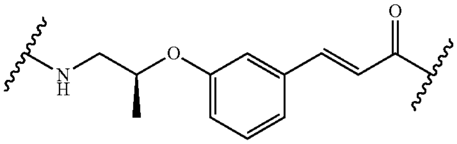 ;
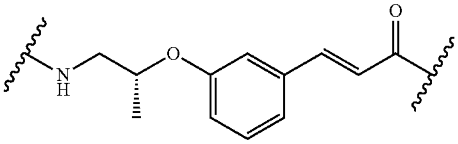 ; 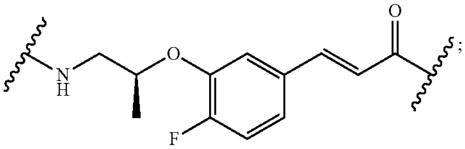 ;
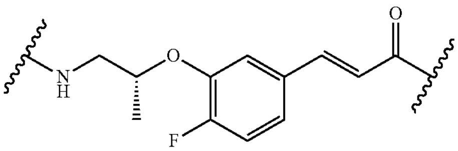 ; 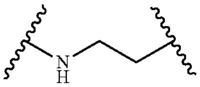 ;
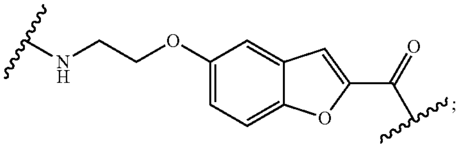 ; 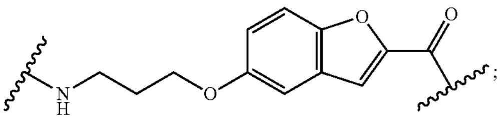 ;
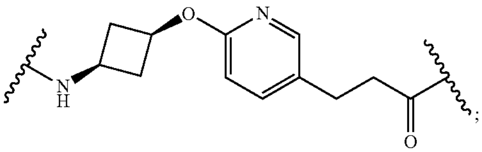 ; 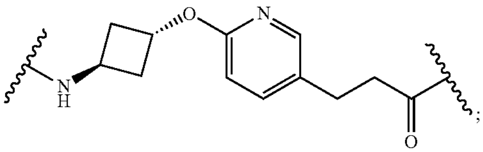 ;

-continued
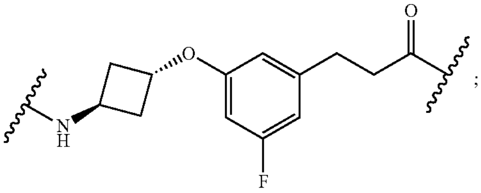
;
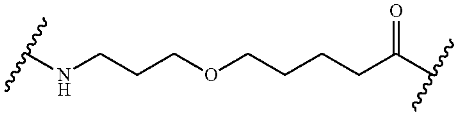
;
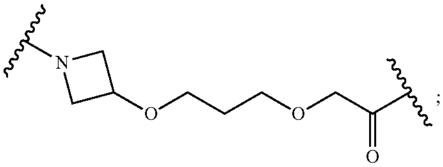
;
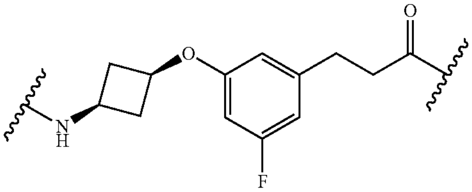
;
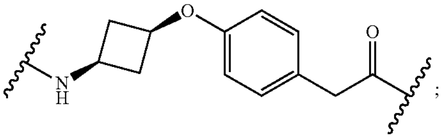
;
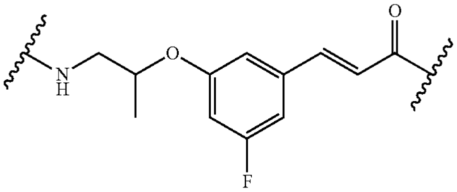
;
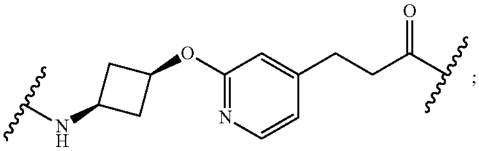
;
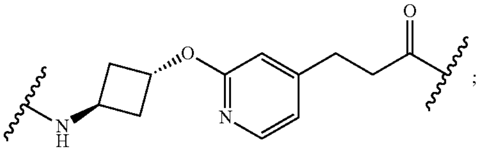
;
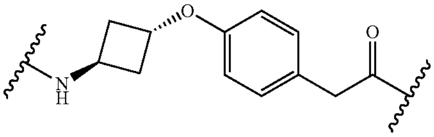
;
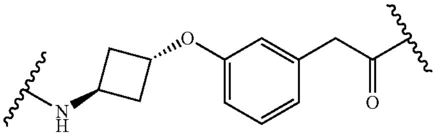
;
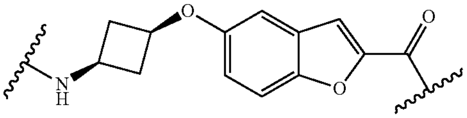
;
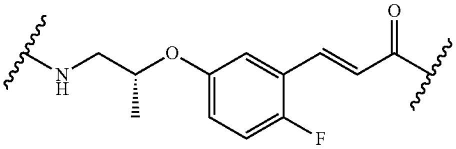
;
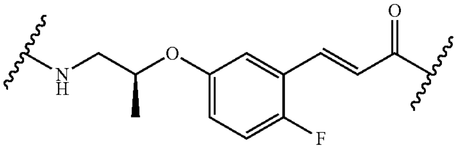
;
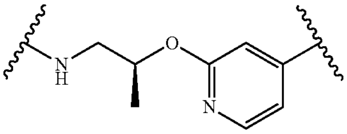
;
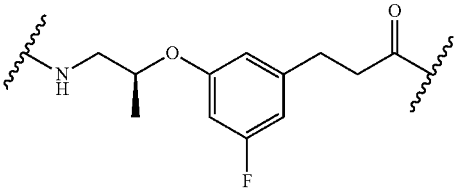
;
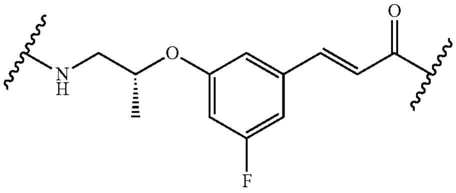
;
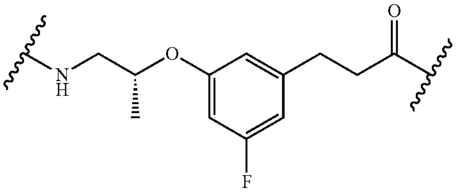
;
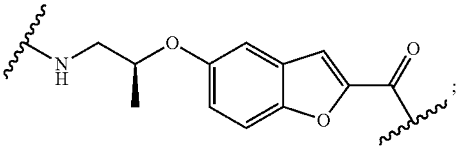
;
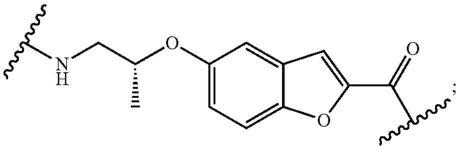
;
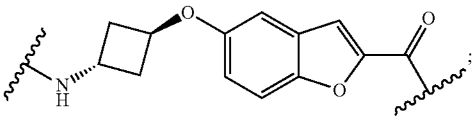
;

-continued
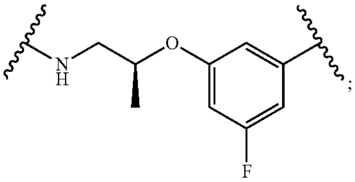;
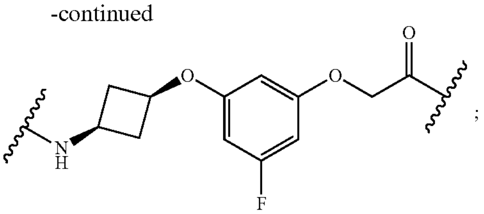;
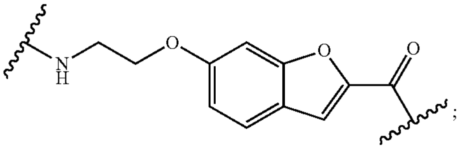;
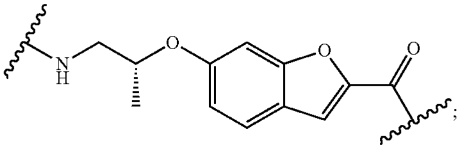;
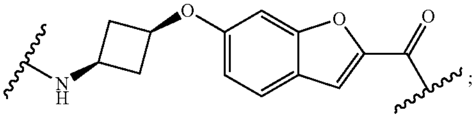;
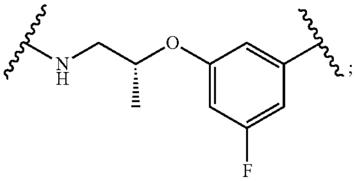;
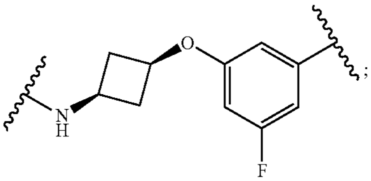;
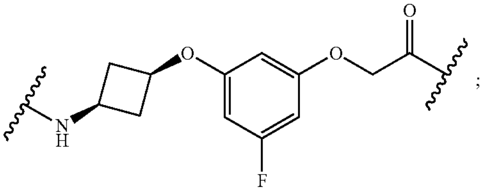;
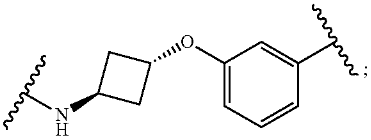;
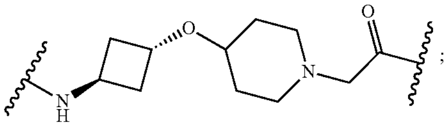;
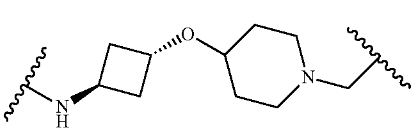
and
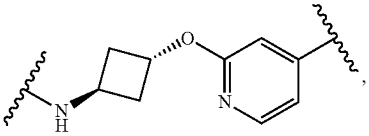,
wherein each m and n is independently selected from 0, 1, 2, 3, 4, 5, or 6.
In any aspect or embodiment described herein, the linker (L) is selected from the group consisting of:
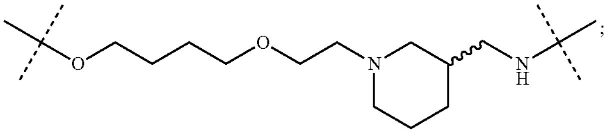;
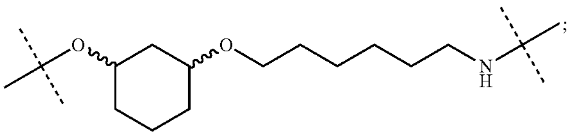;
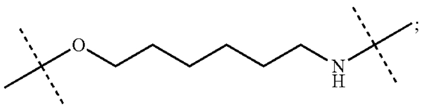;
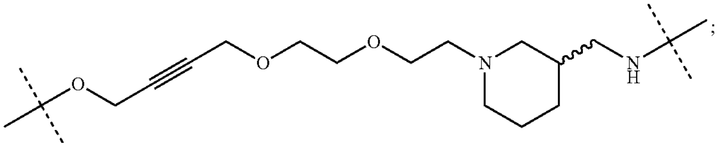;
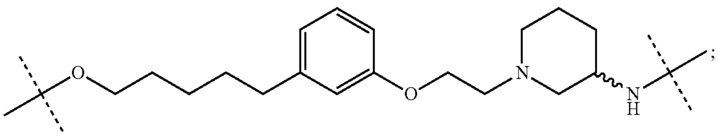;

-continued
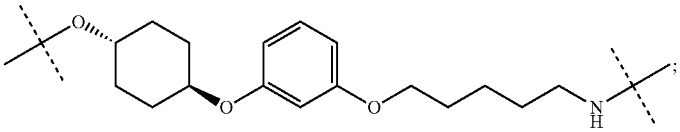;
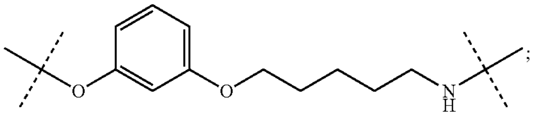; 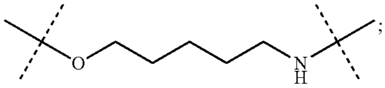;
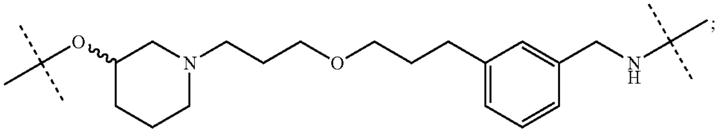;
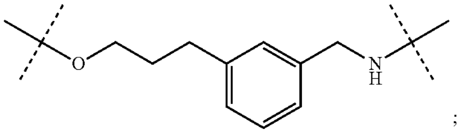; 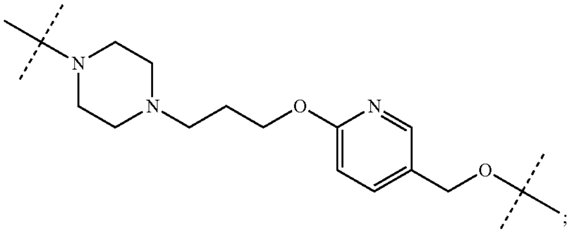;
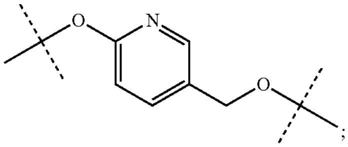; 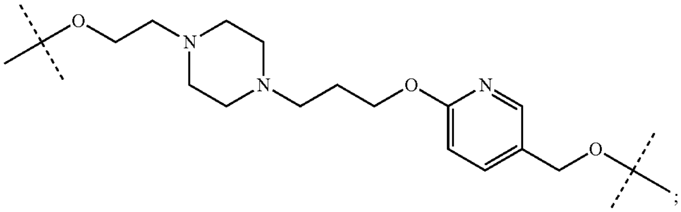;
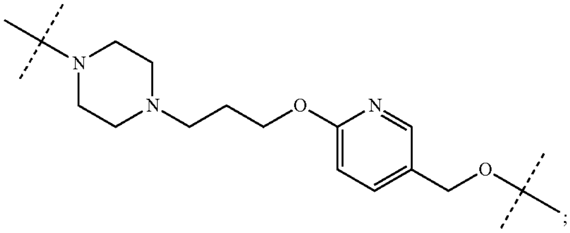;
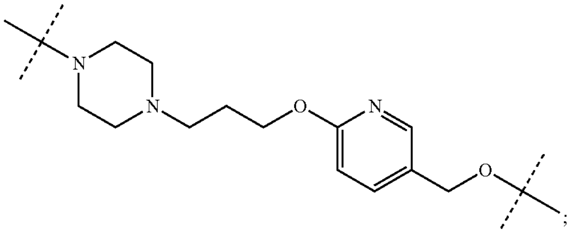;
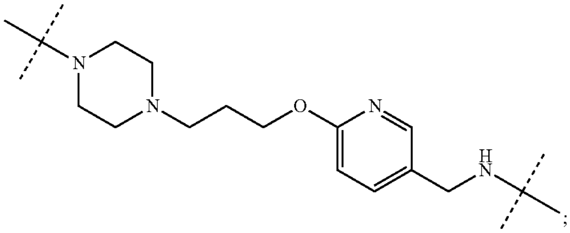; 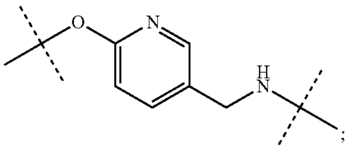;

-continued
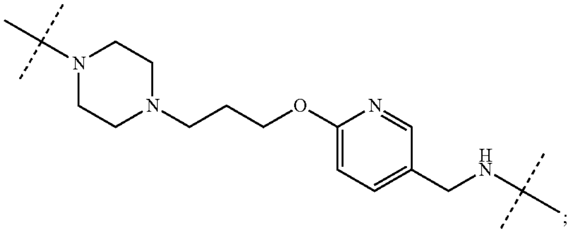
;
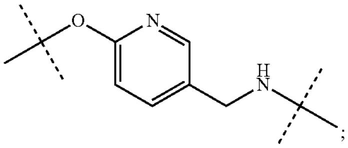
;
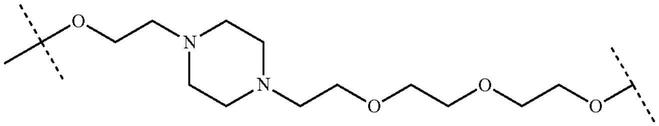
;
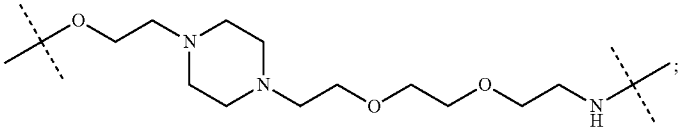
;
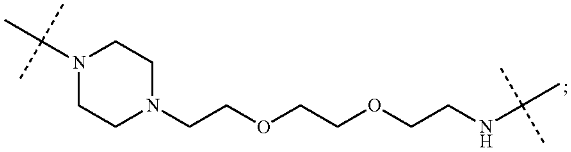
;
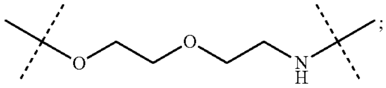
;
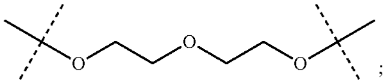
;
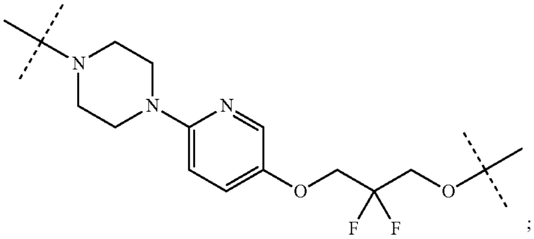
;
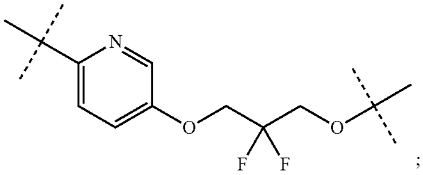
;
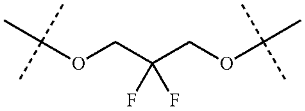
;
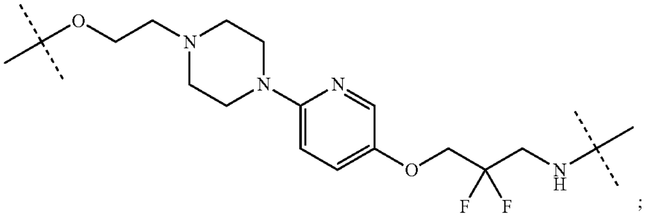
;
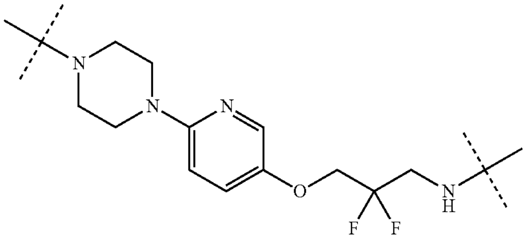
;
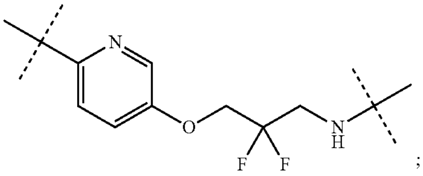
;
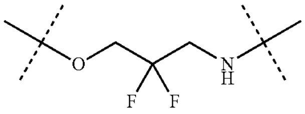
;
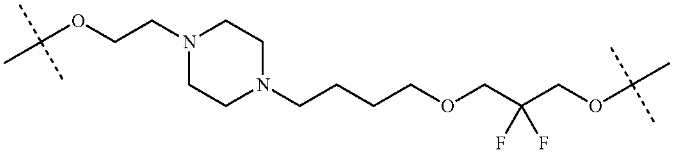
;

-continued
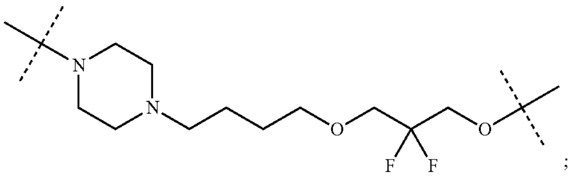
;
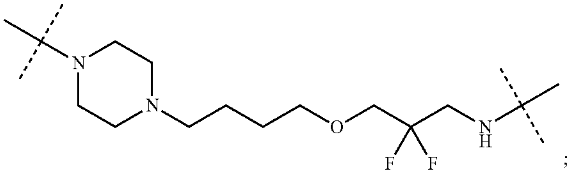
;
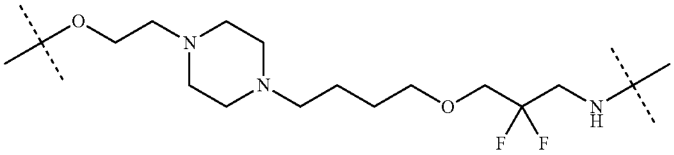
;
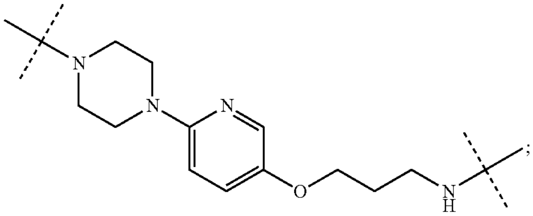
;
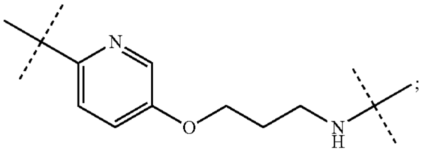
;
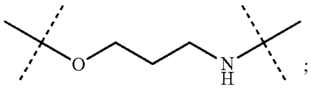
;
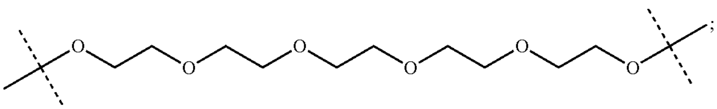
;
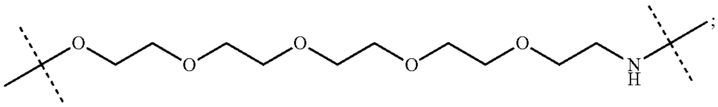
;
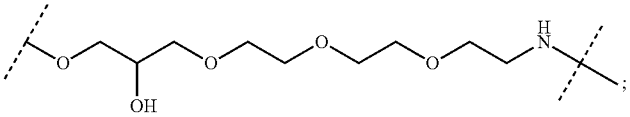
;
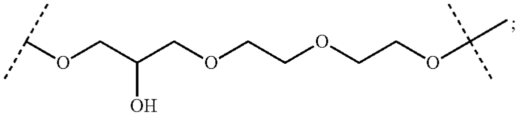
;
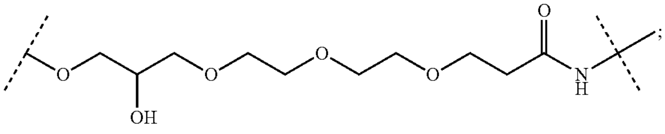
;
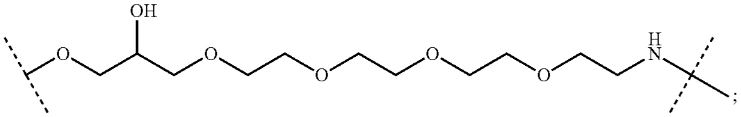
;
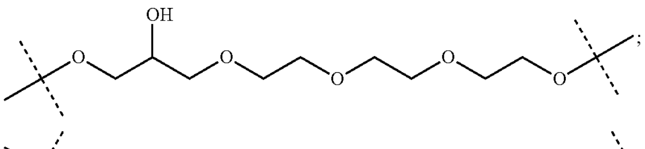
;
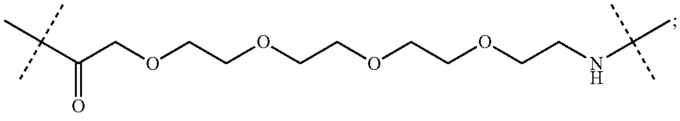
;

-continued
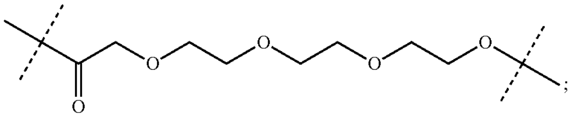
;
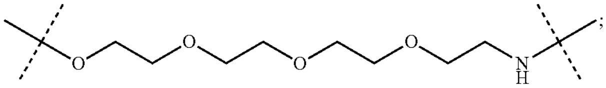
;
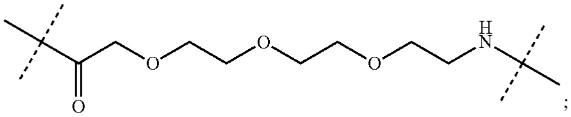
;
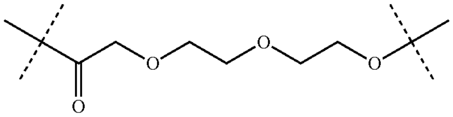
;
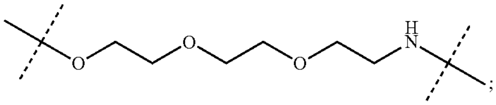
;
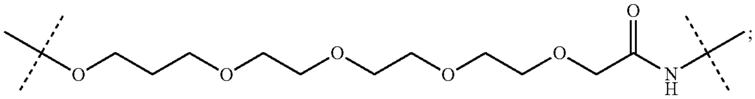
;
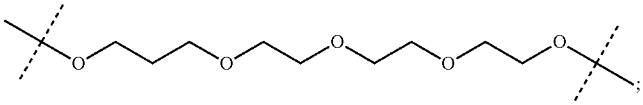
;
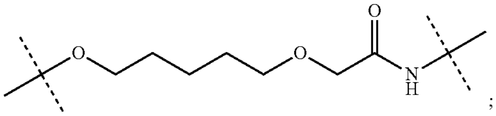
;
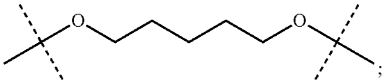
;
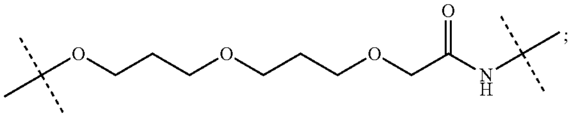
;
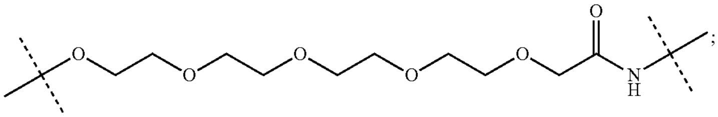
;
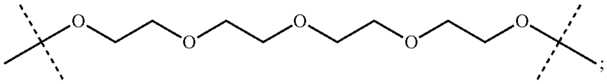
;
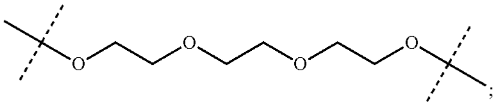
;
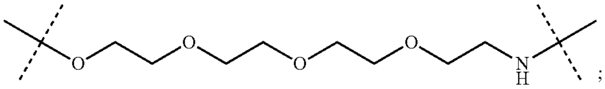
;
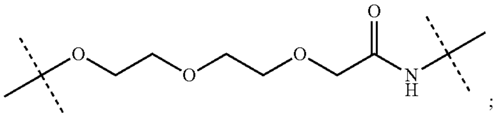
;
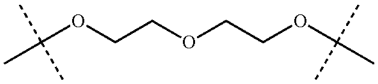
;
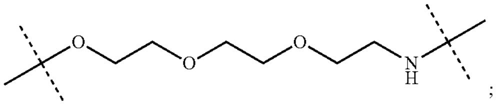
;
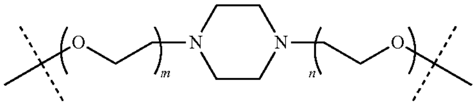
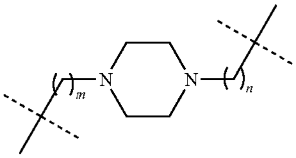
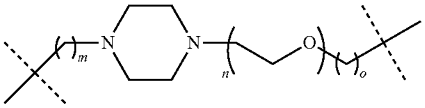
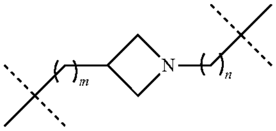

-continued
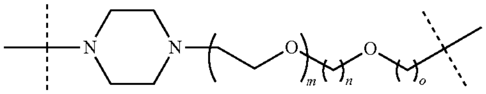
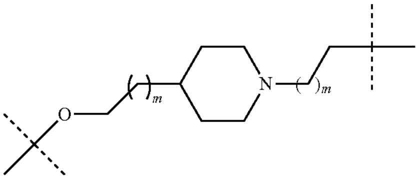
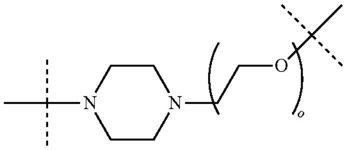
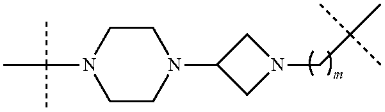
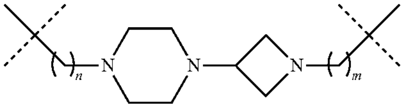
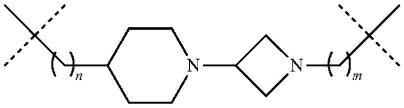
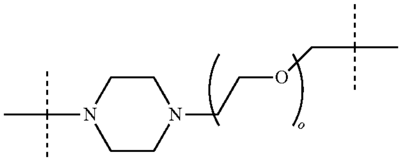
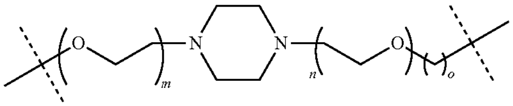
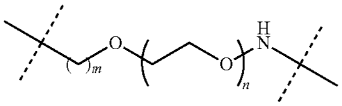
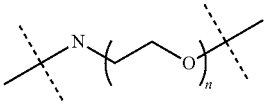
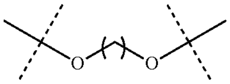
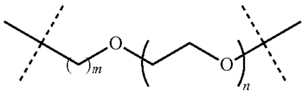
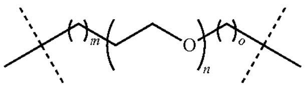
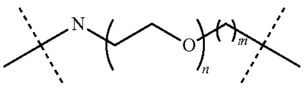
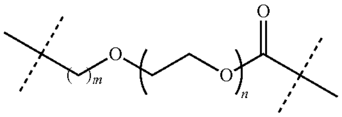
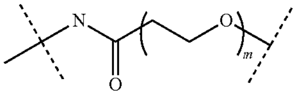
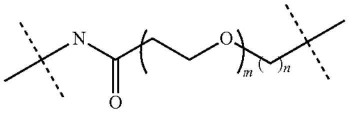
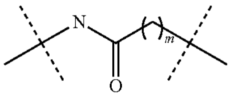
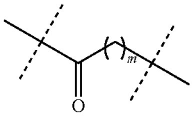
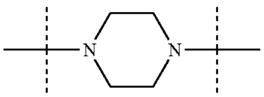
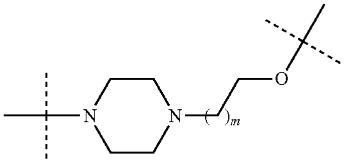
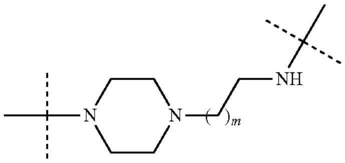
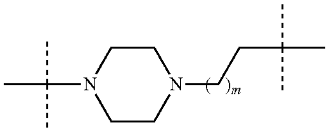
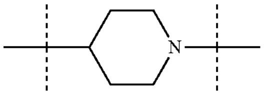
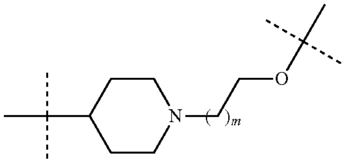
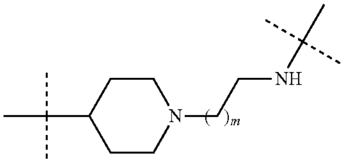
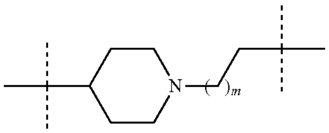
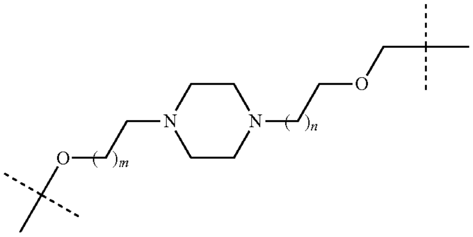
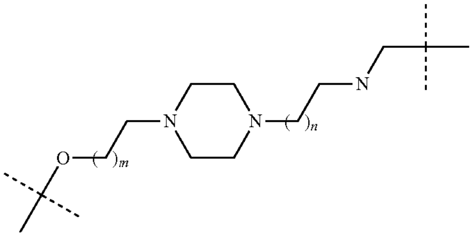

-continued
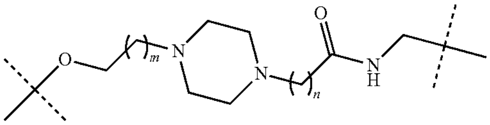
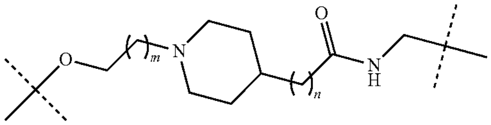
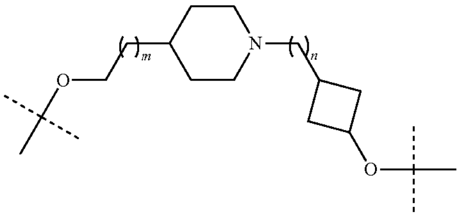
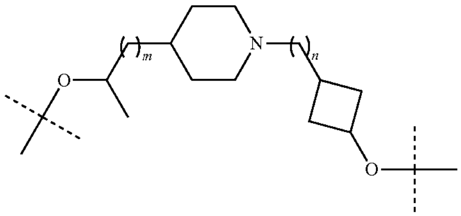
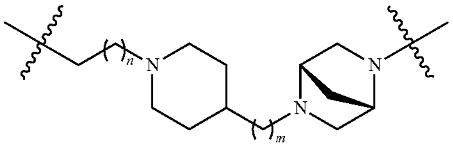
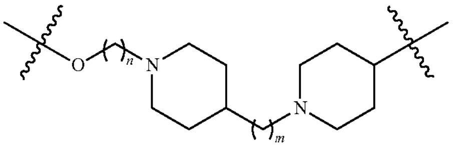
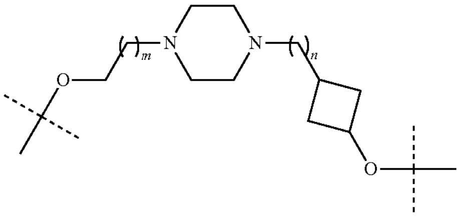
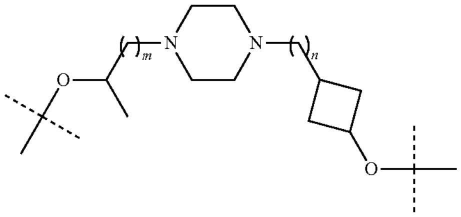
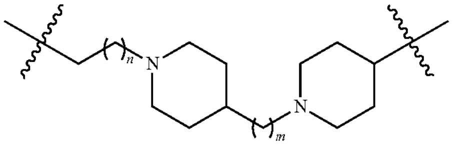
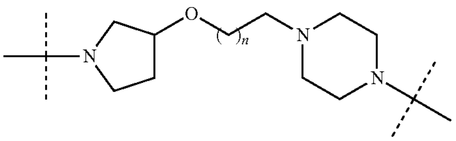
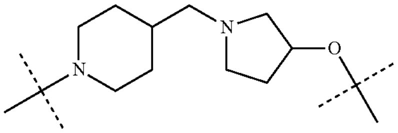
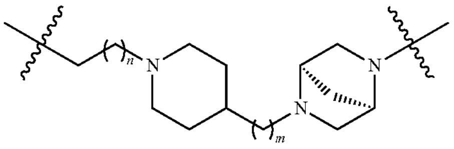
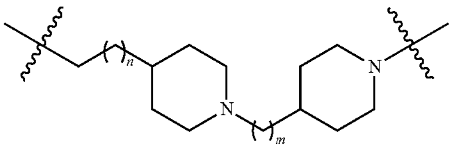
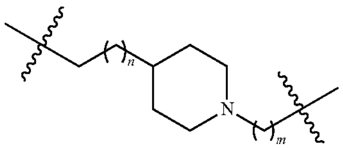
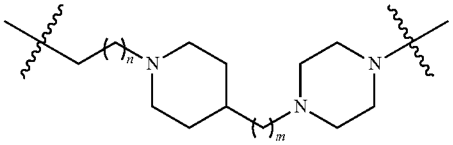
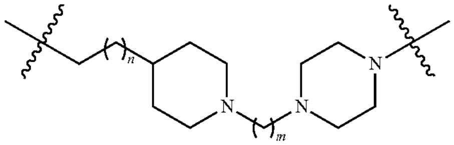
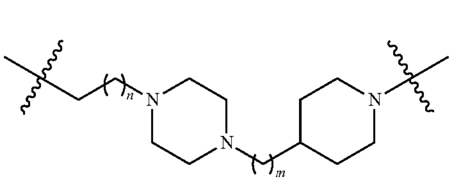
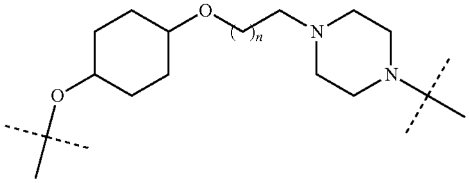
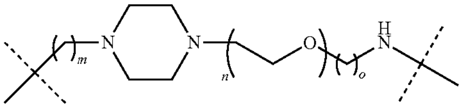
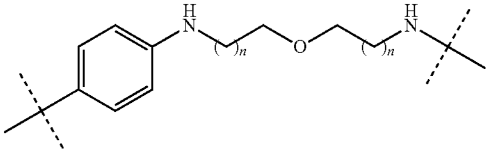

-continued
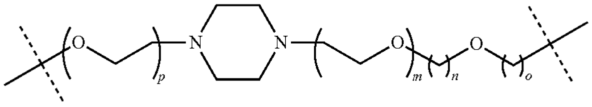
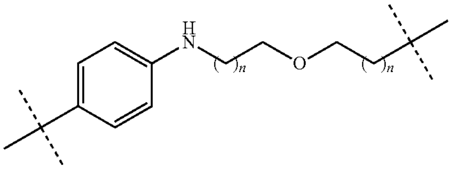
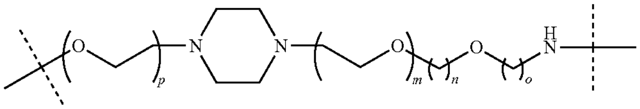
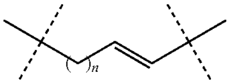
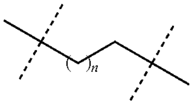
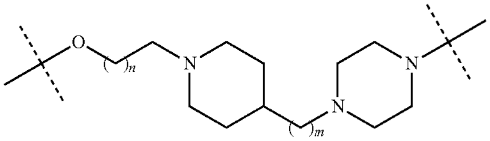
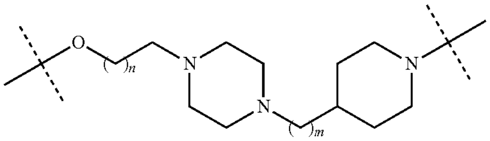
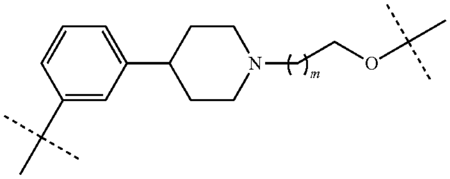
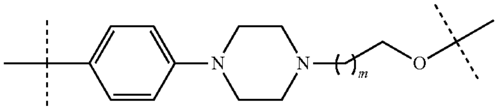
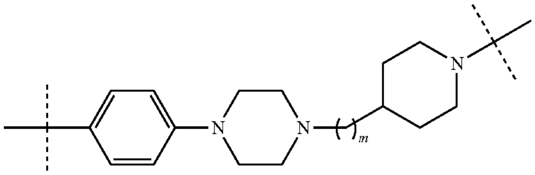
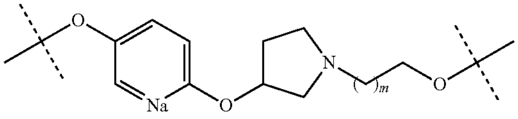
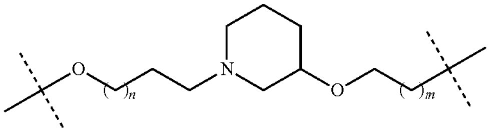
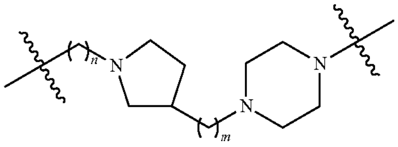
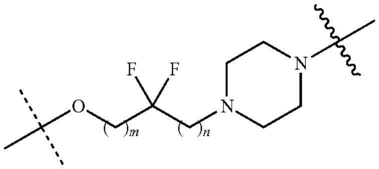
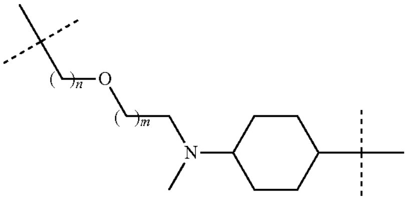
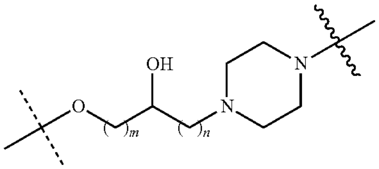
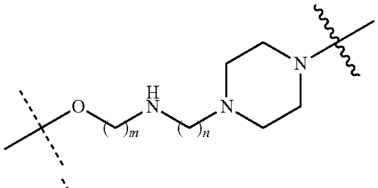
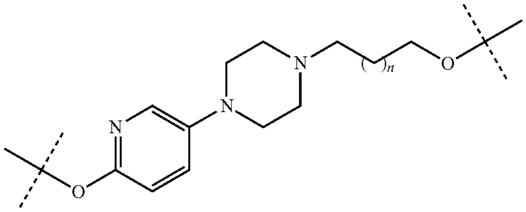
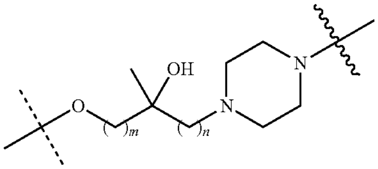
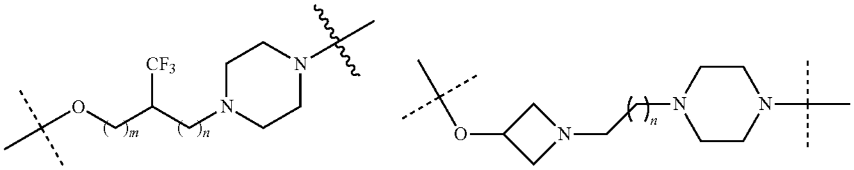

-continued
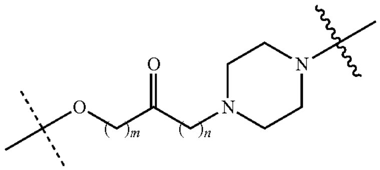
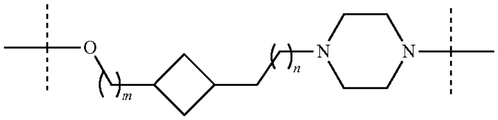
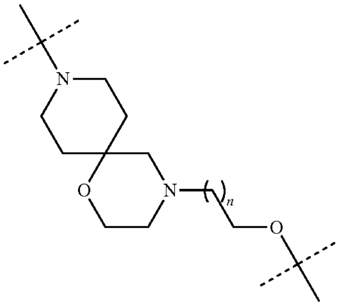
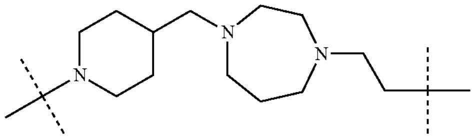
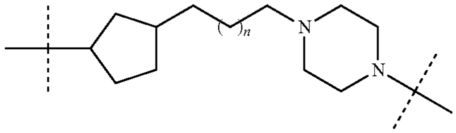
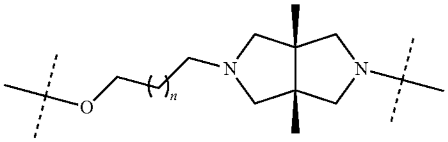
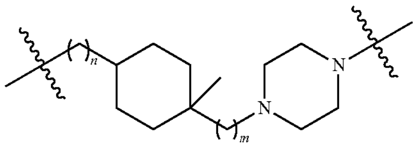
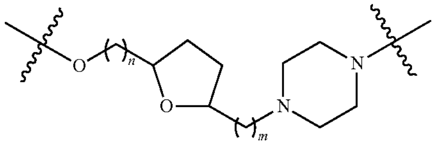
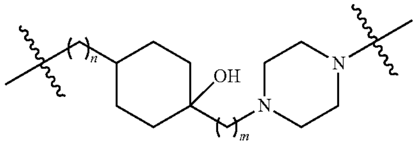
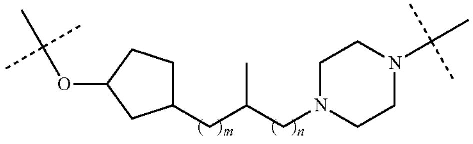
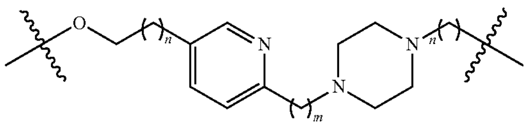
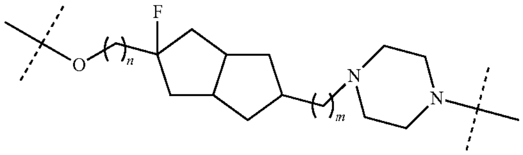
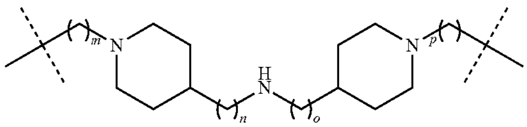
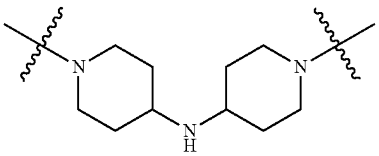
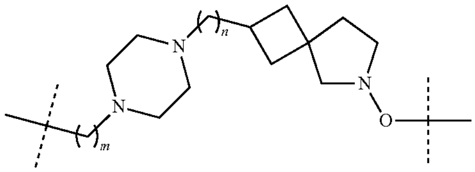
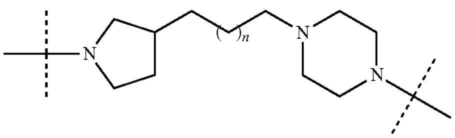
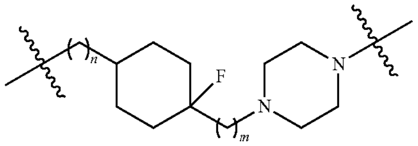
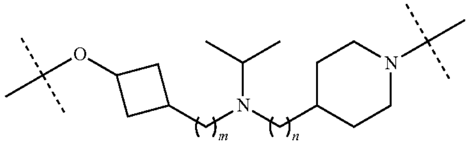
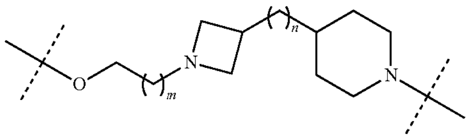
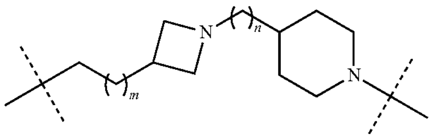

-continued
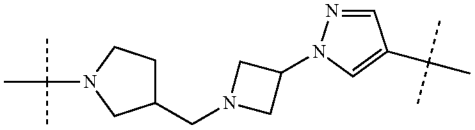
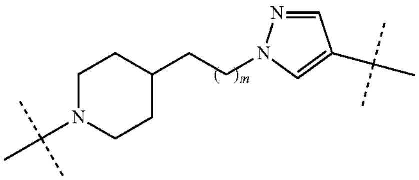
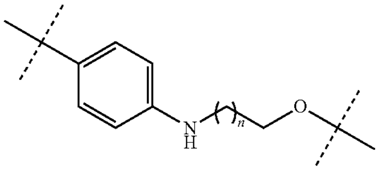
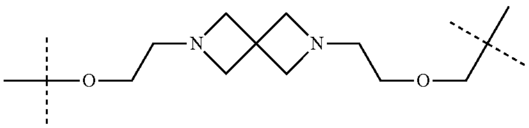
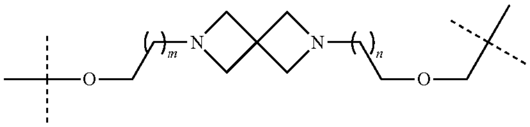
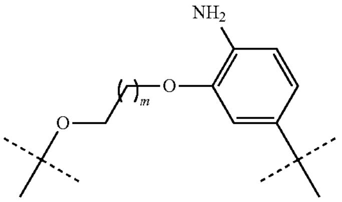
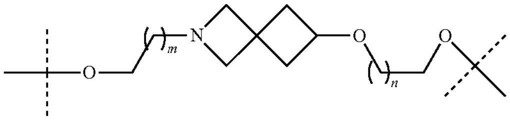
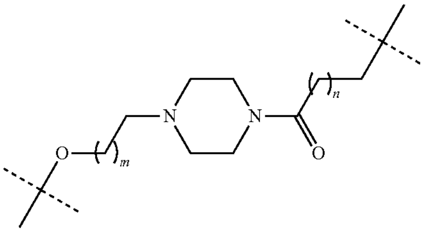
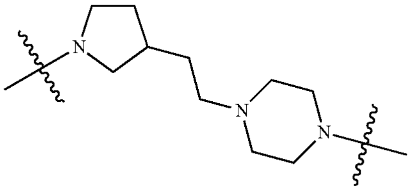
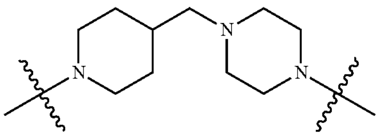
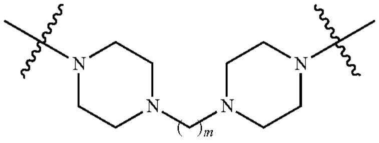
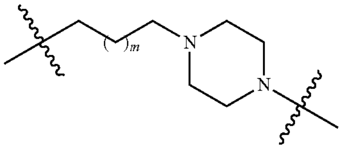
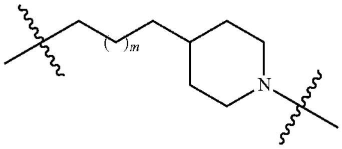
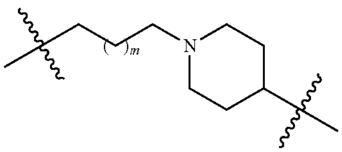
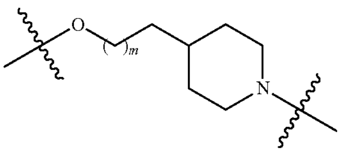
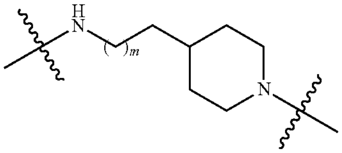
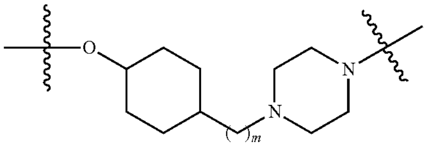
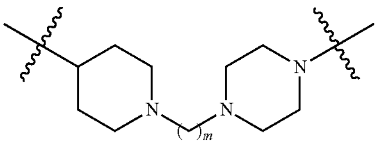
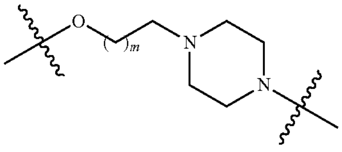
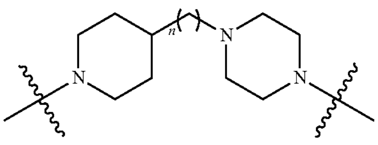
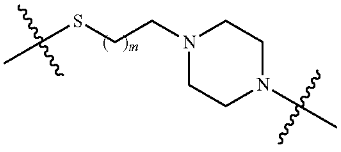

-continued
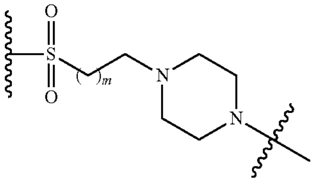
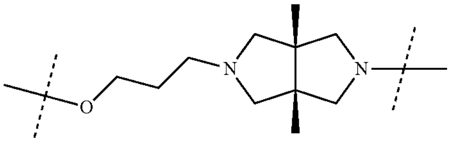
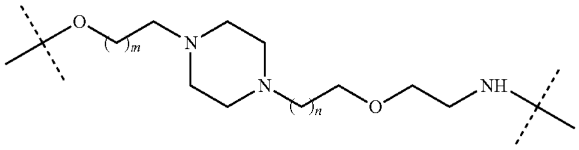
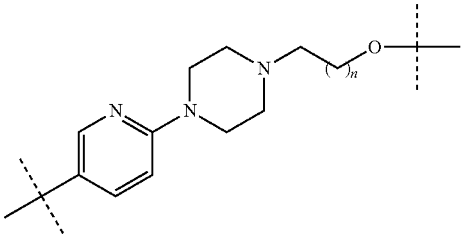
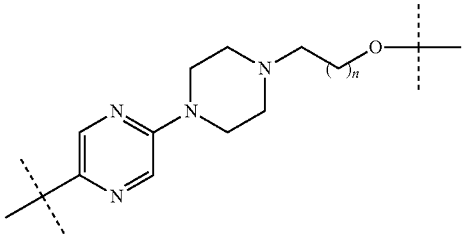
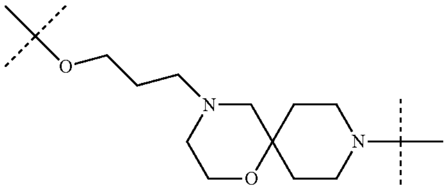
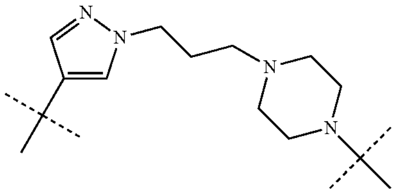
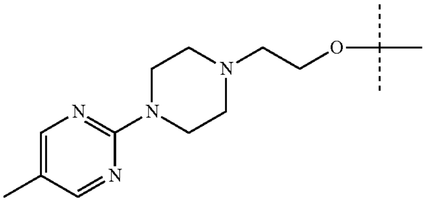
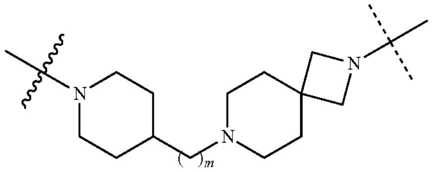
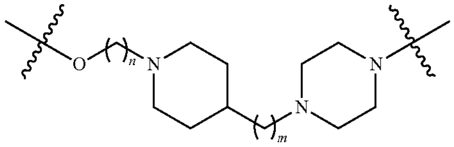
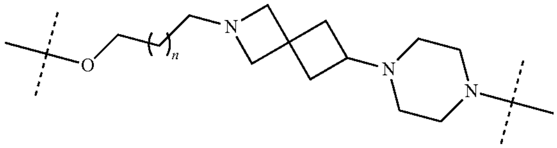
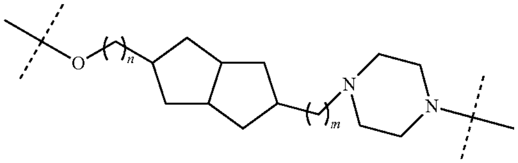
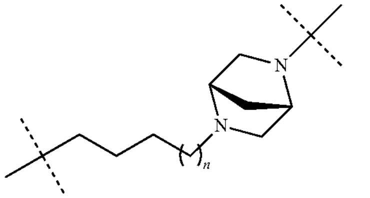
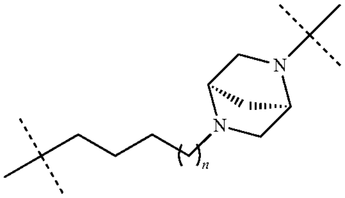
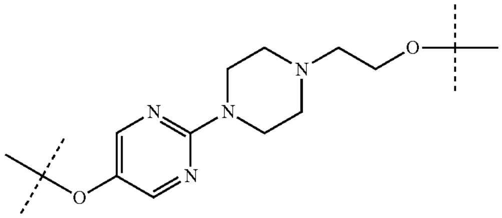
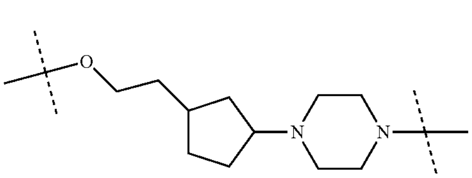

-continued
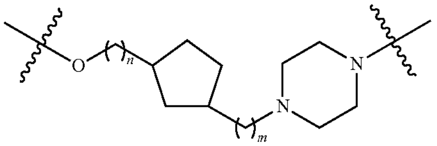
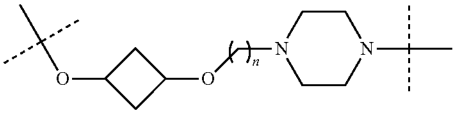
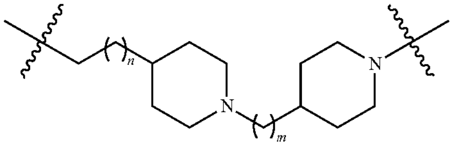
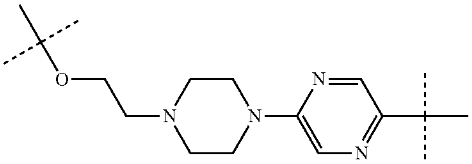
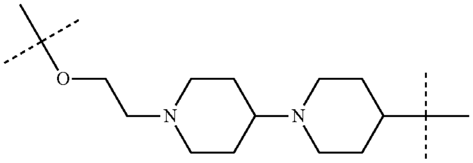
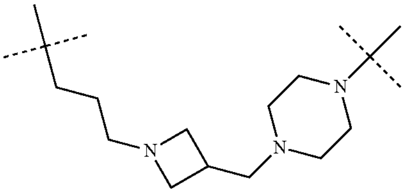
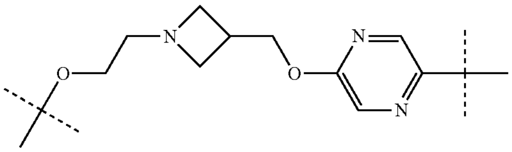
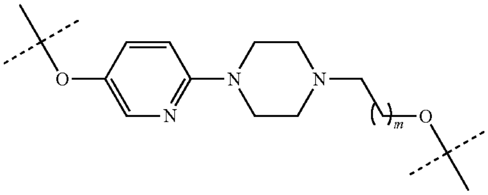
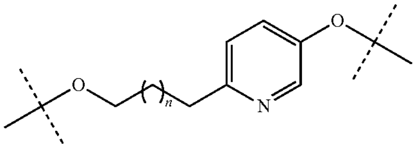
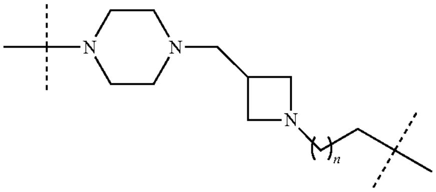
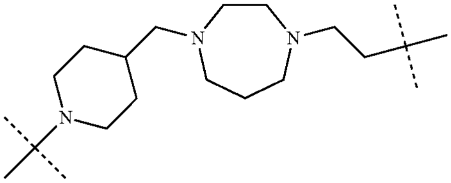
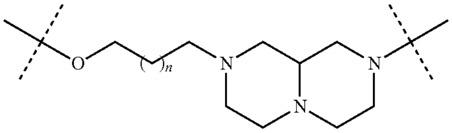
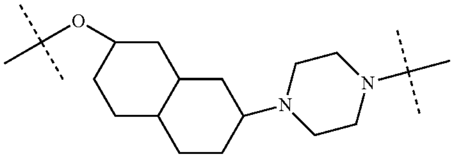
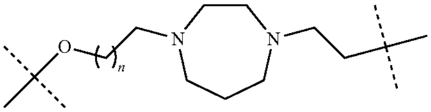
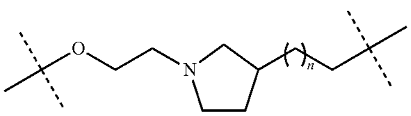
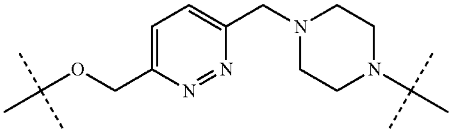
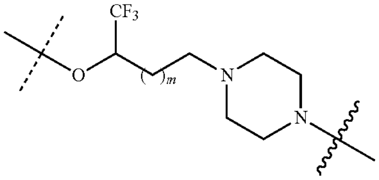
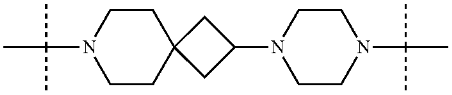
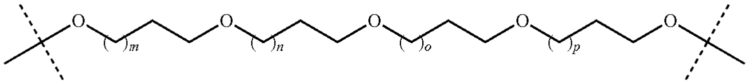
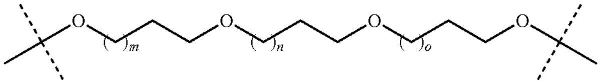
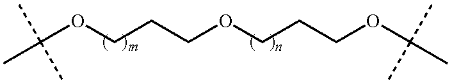

-continued
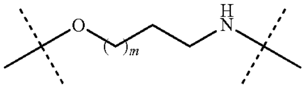
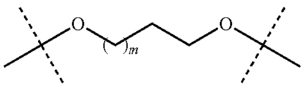
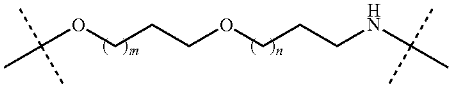
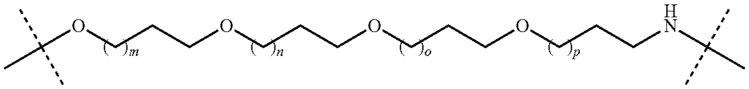
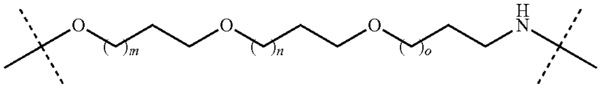
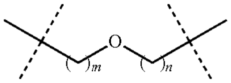
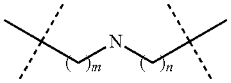
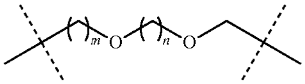
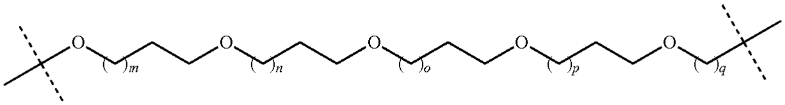
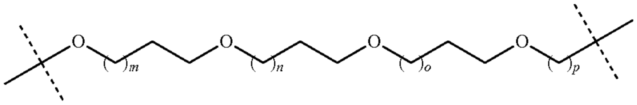
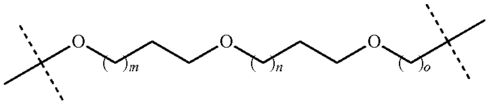
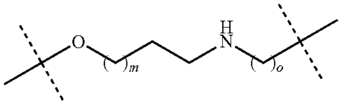
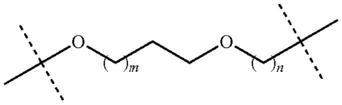
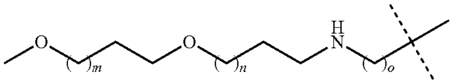
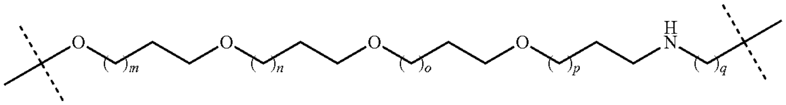
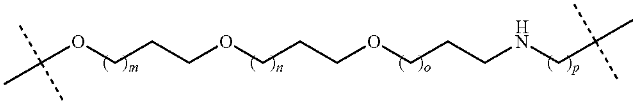
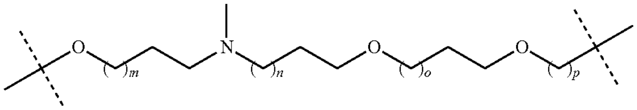
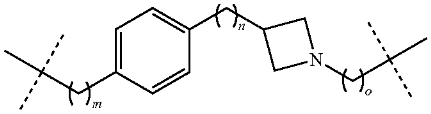
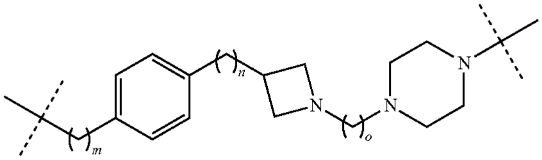
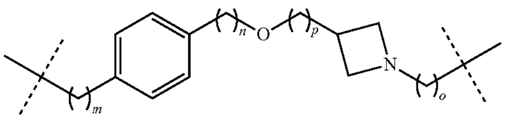
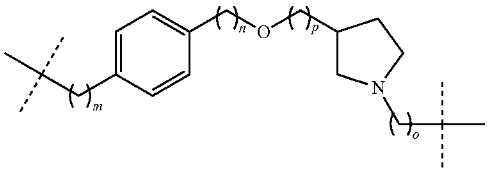
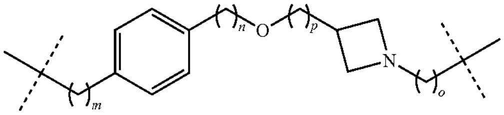
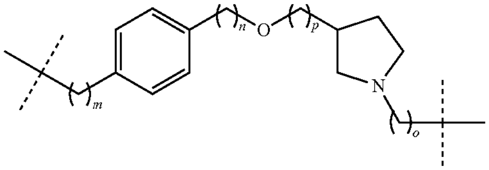
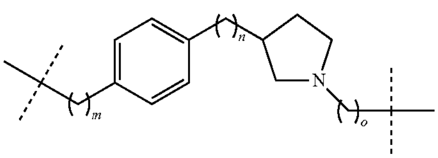
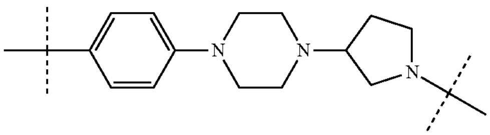
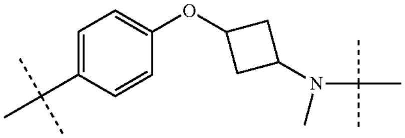

-continued
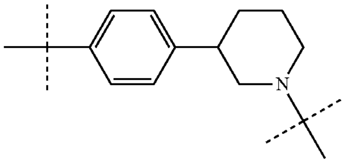
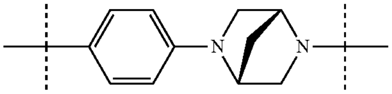
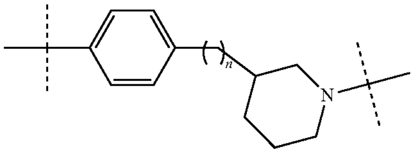
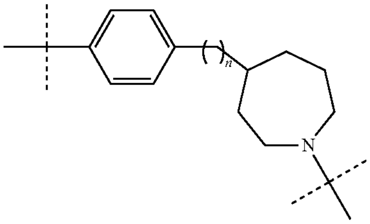
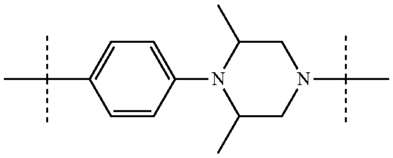
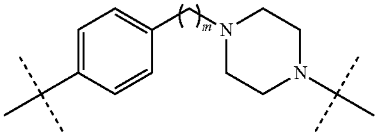
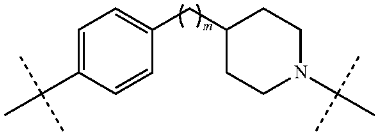
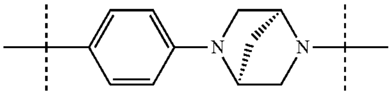
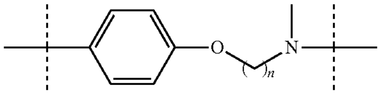
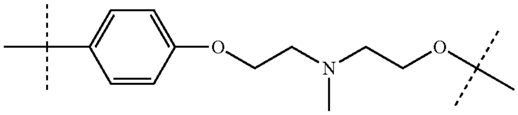
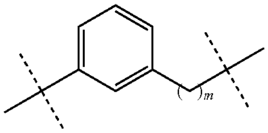
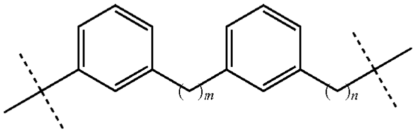
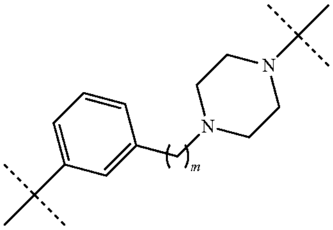
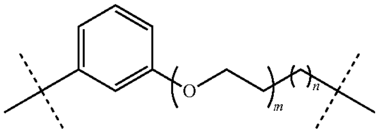
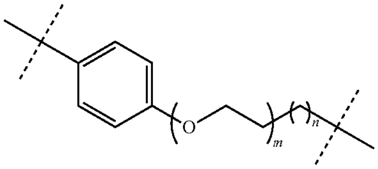
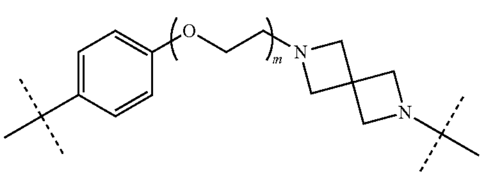
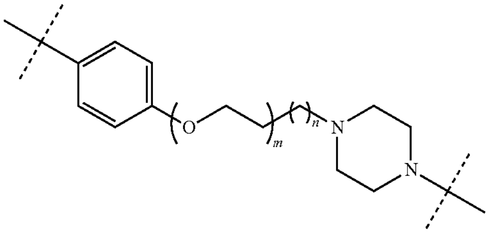
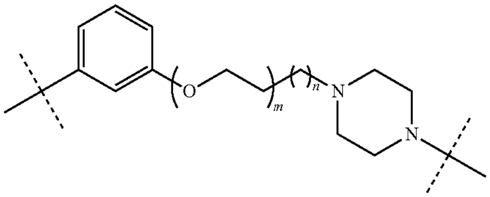
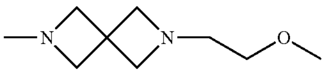

-continued
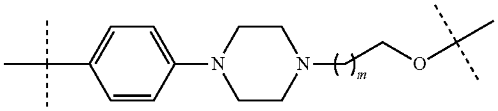
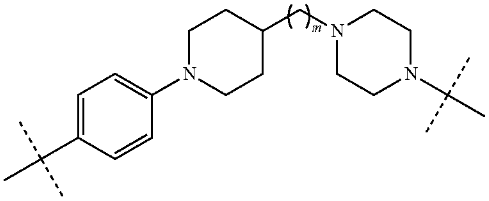
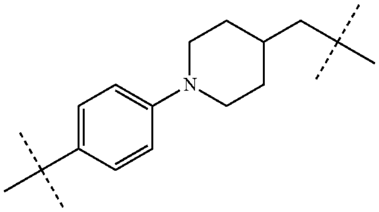
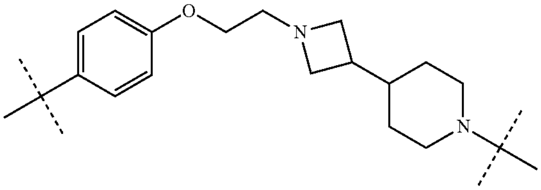
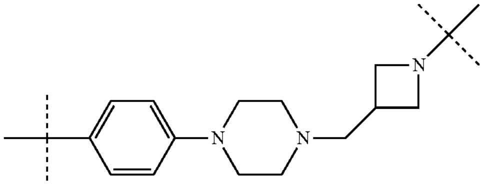
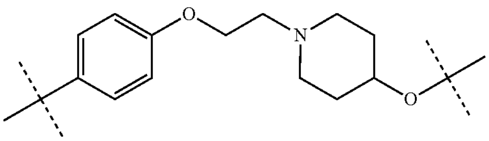
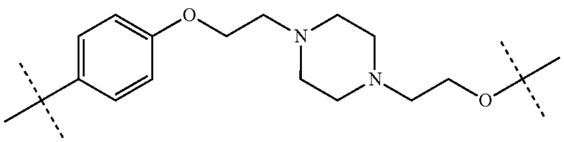
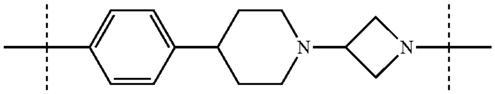
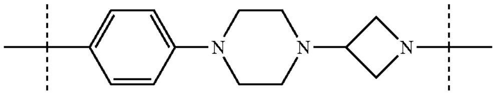
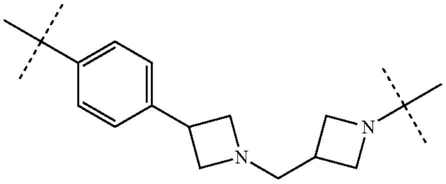
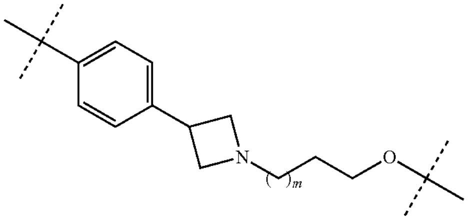
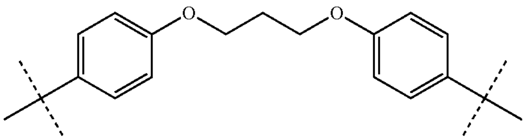
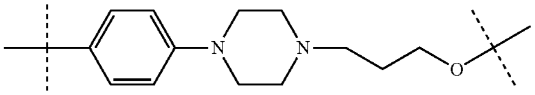
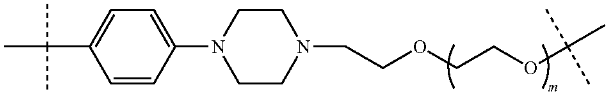
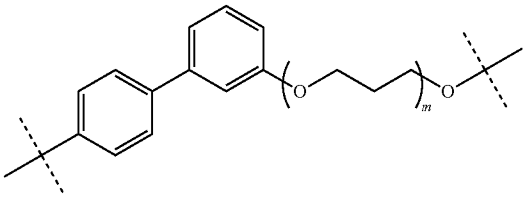
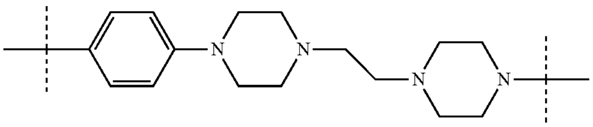
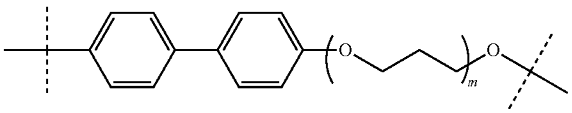

-continued
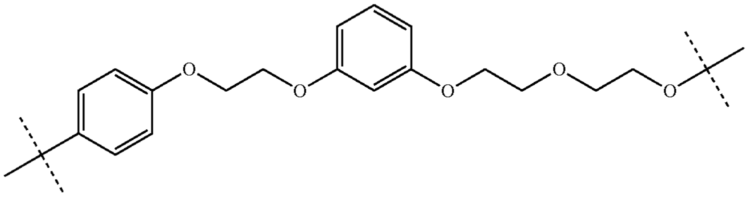
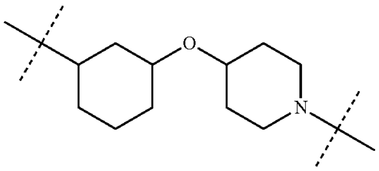
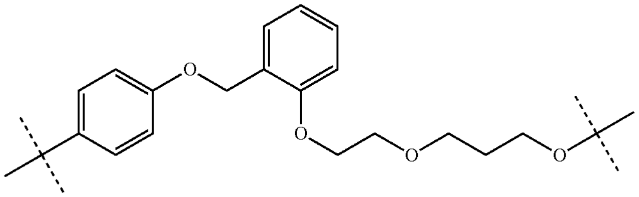
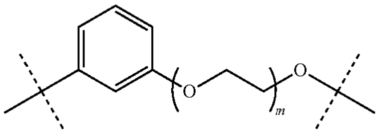
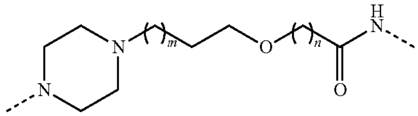
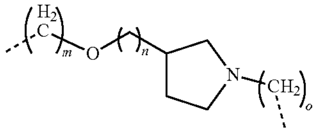
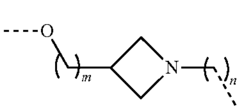
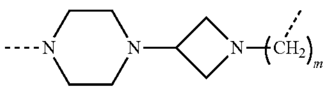
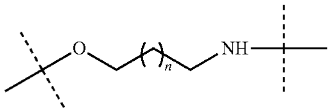
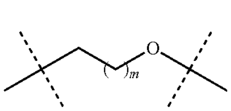
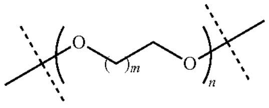
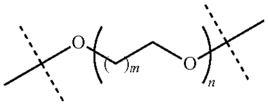
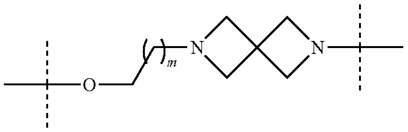
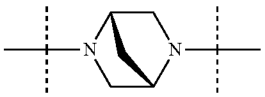
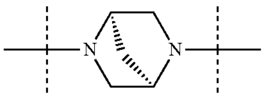
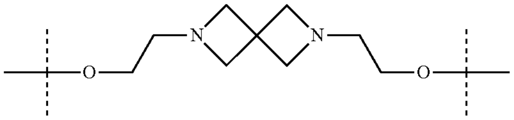
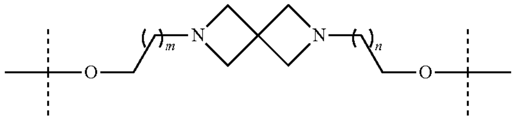
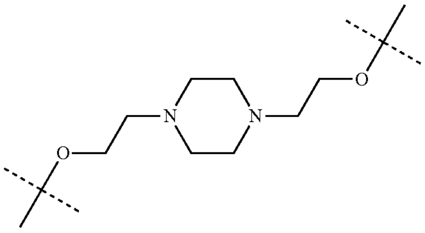
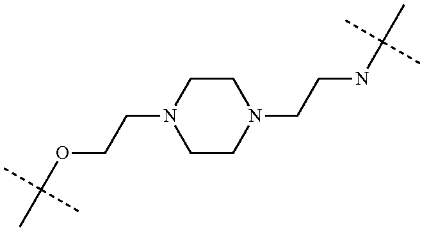
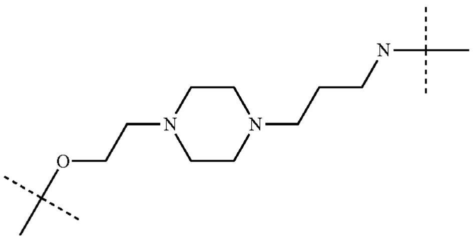
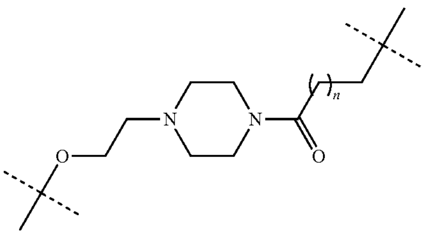
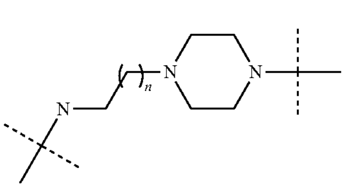
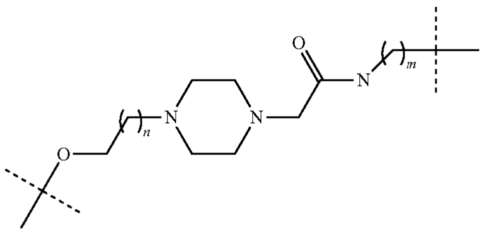

-continued
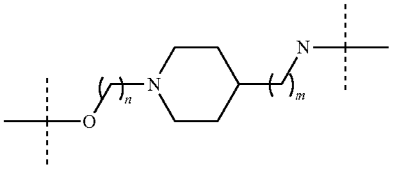
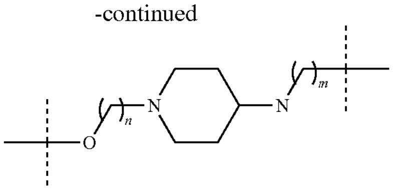
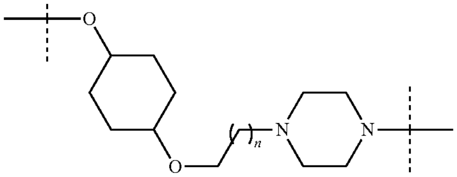
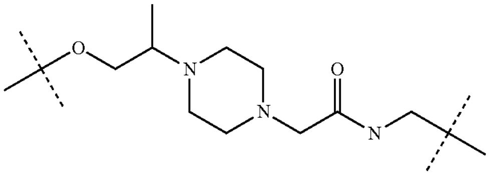
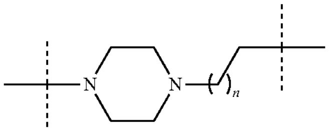
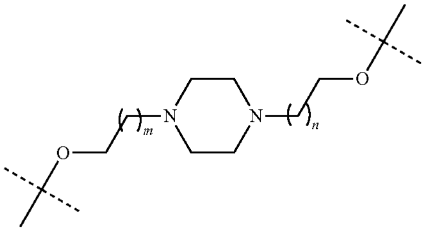
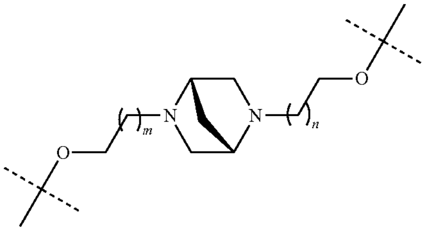
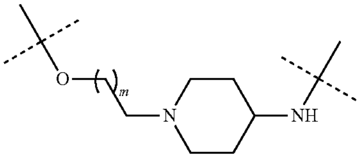
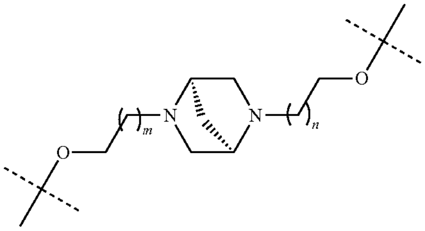
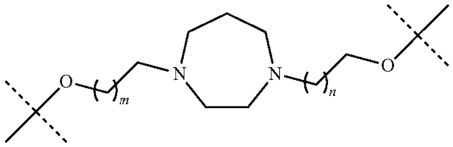
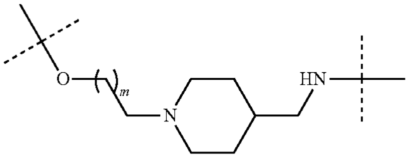
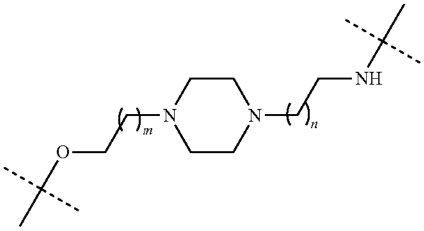
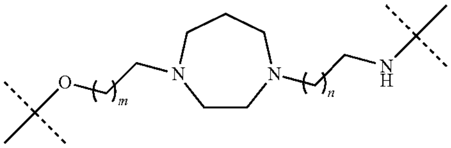
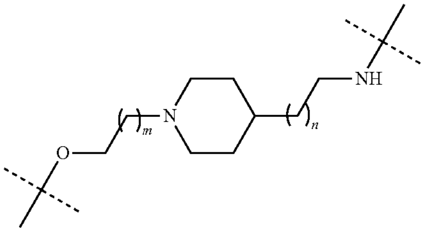
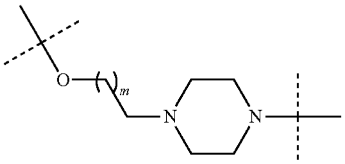
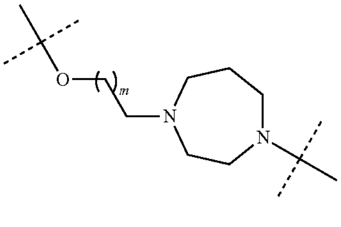
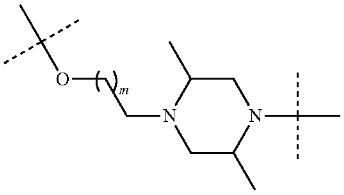

-continued
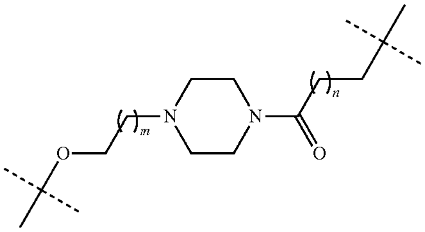
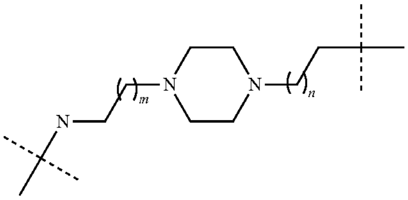
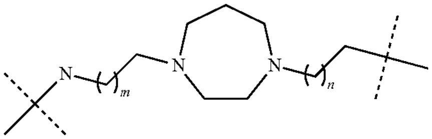
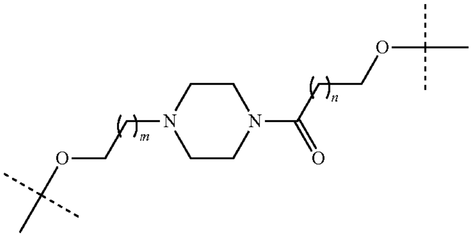
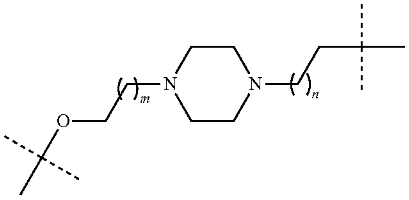
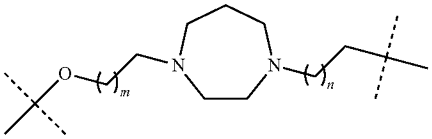
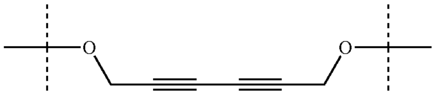
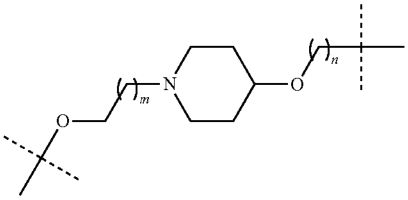
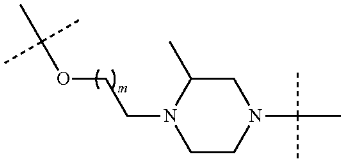
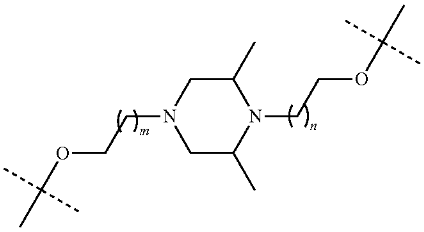
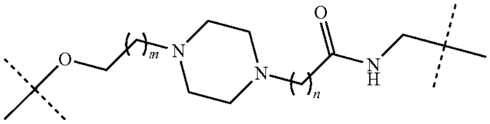
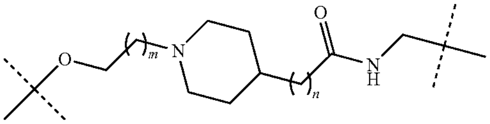
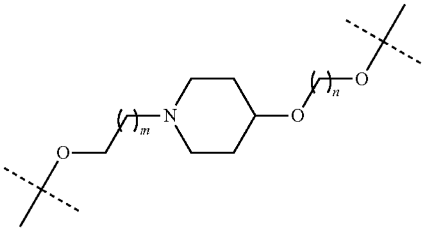
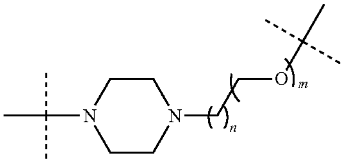
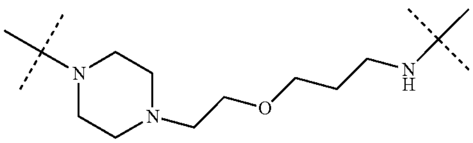
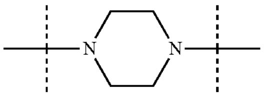
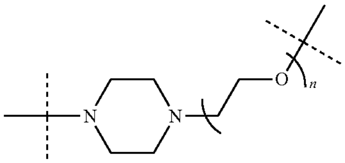
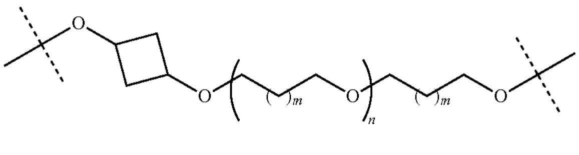

-continued
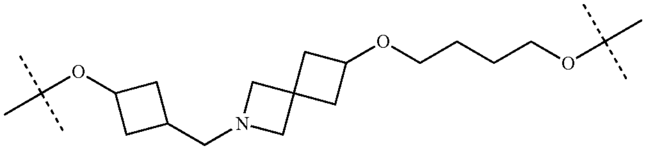
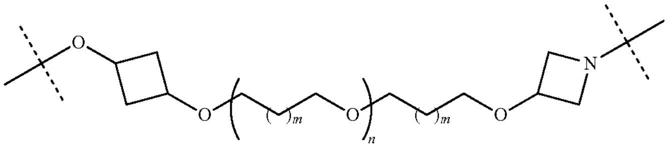
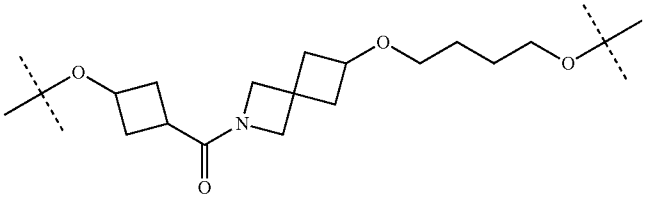
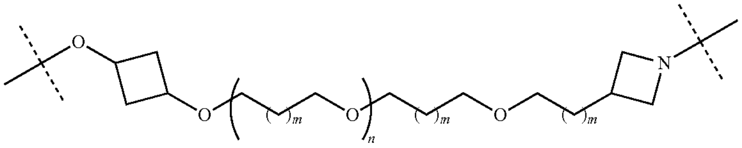
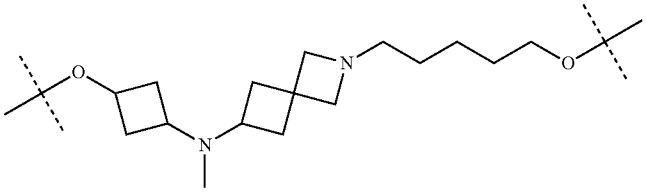
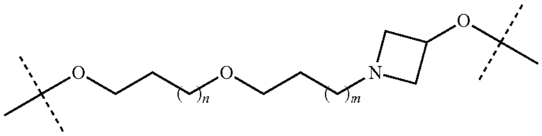
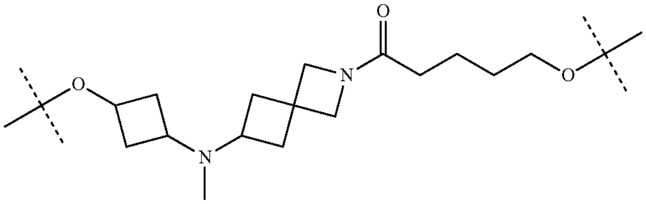
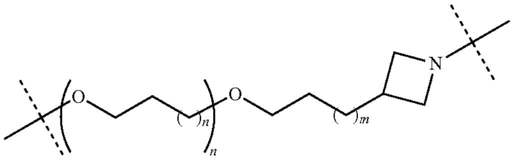
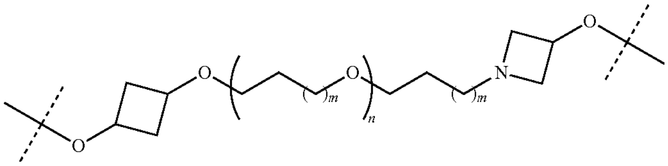
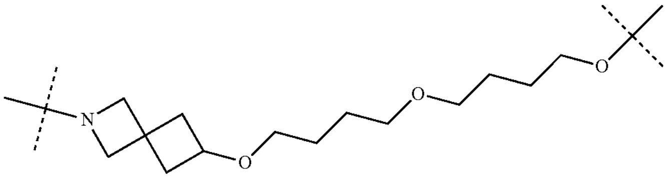

-continued
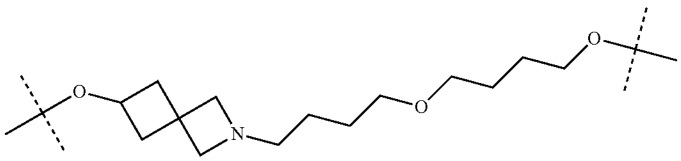
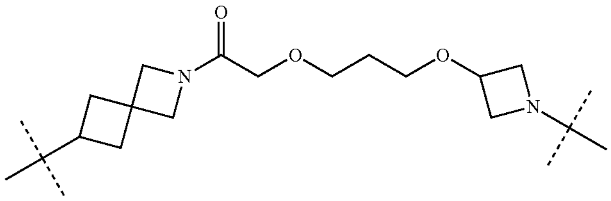
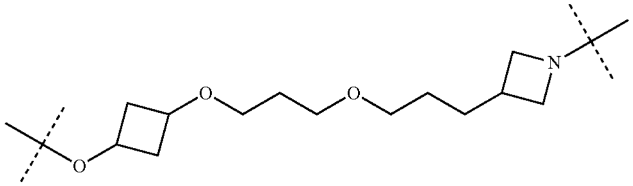
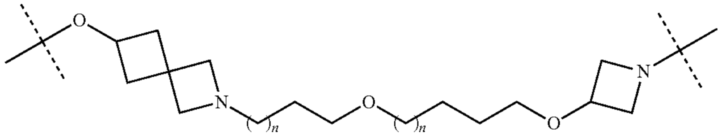
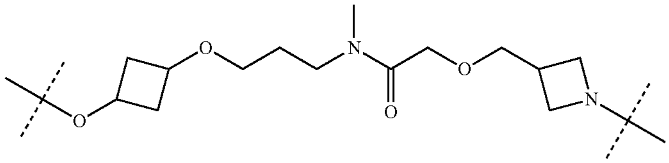
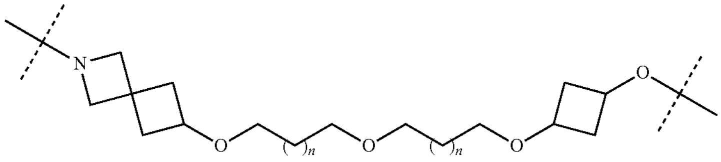
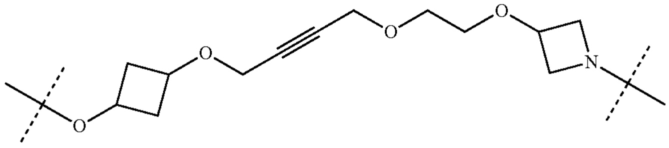
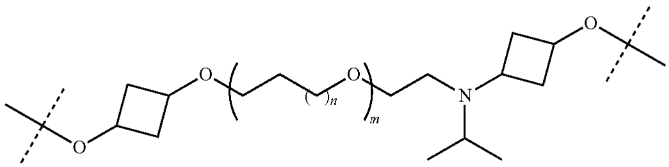
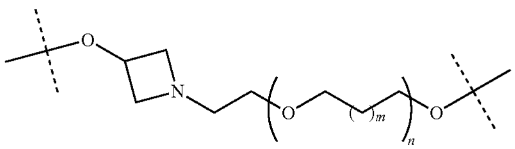
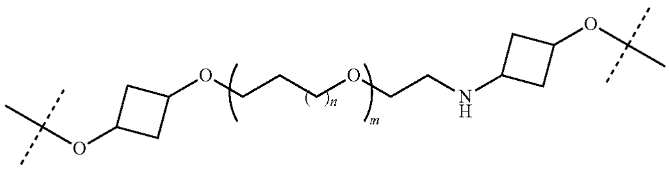

-continued
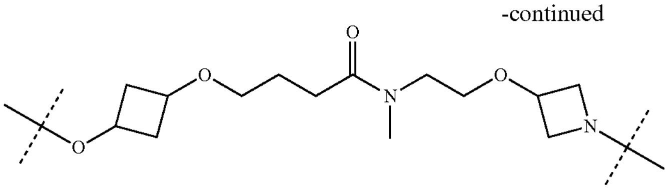
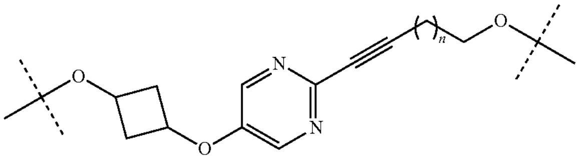
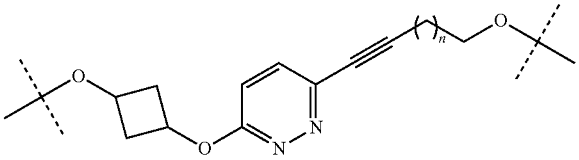
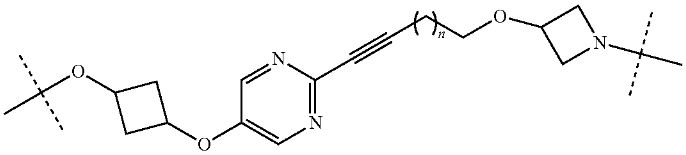
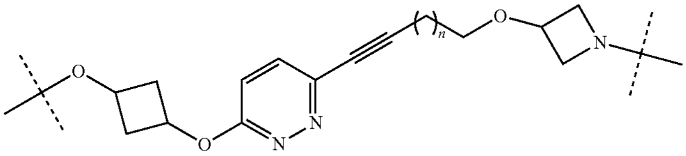
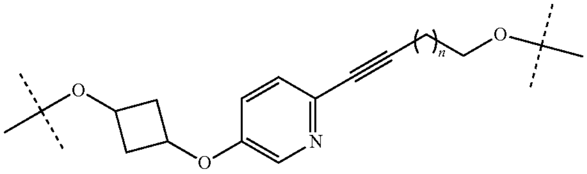
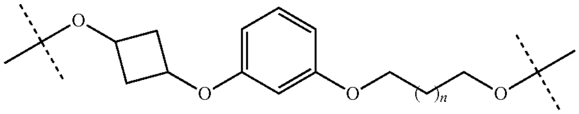
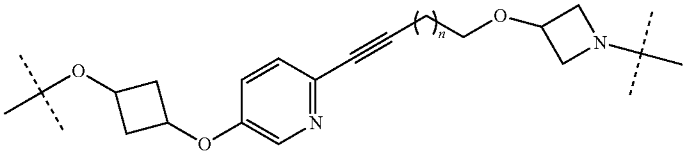
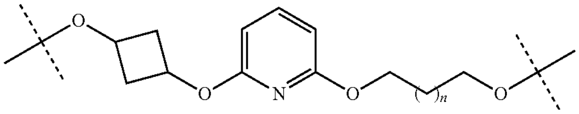
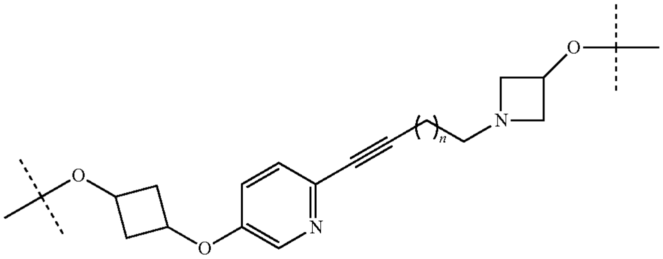
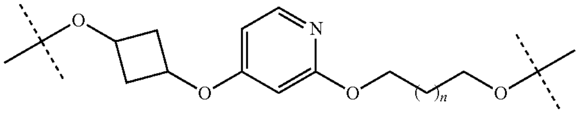

-continued
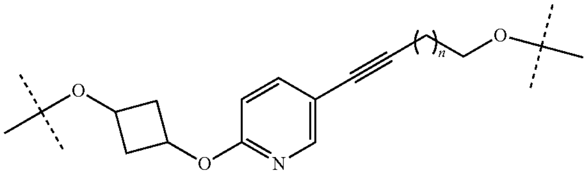
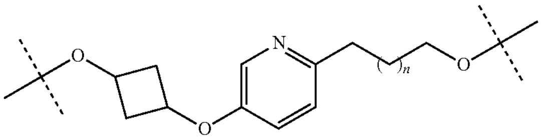
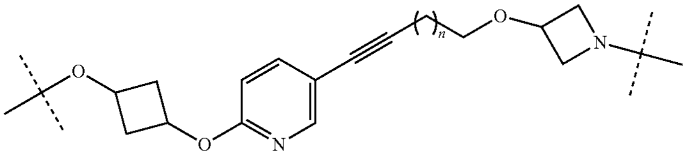
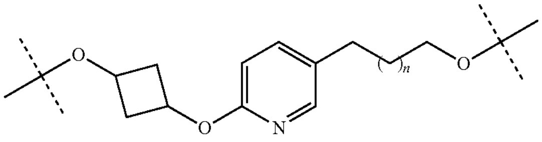
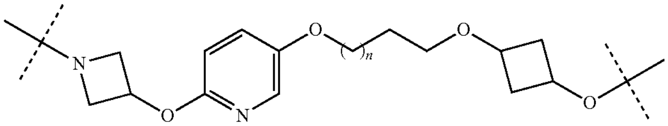
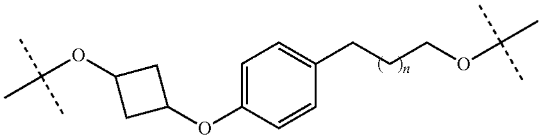
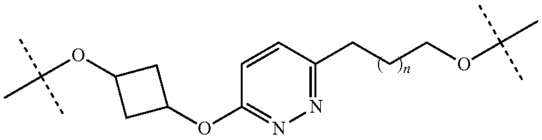
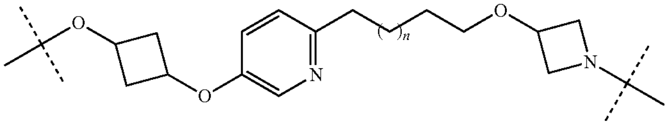
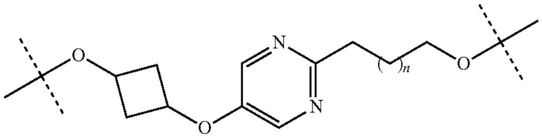
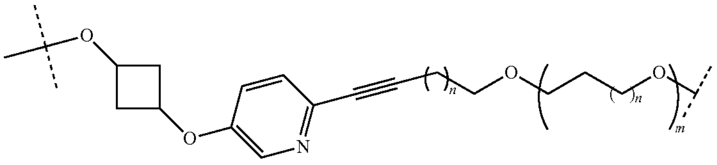
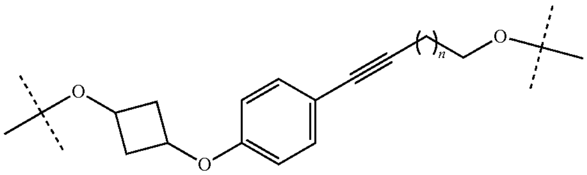
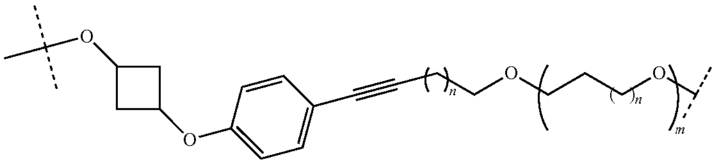
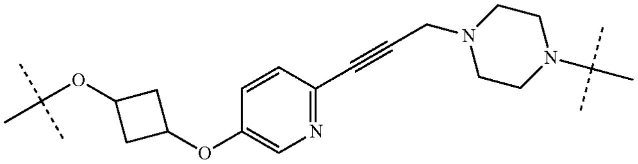

-continued
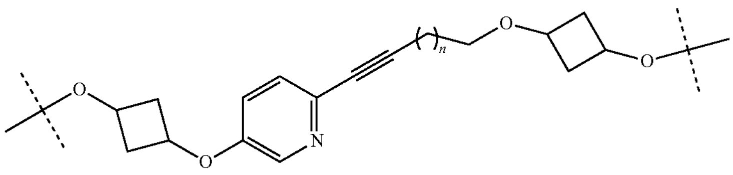
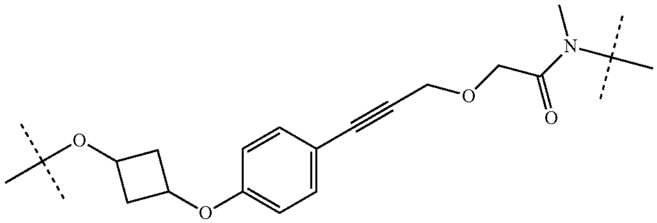
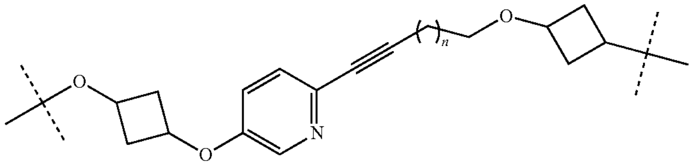
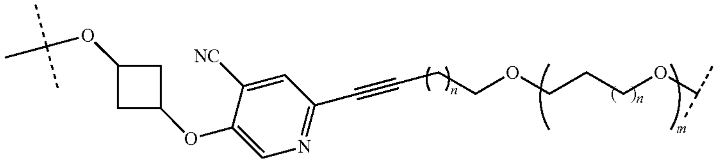
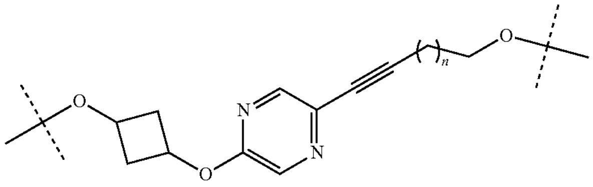
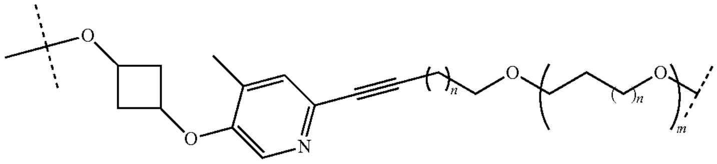
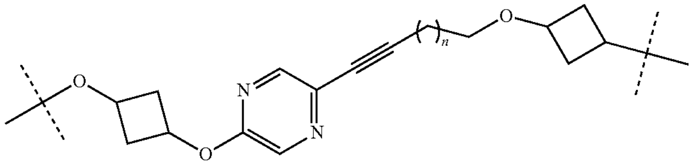
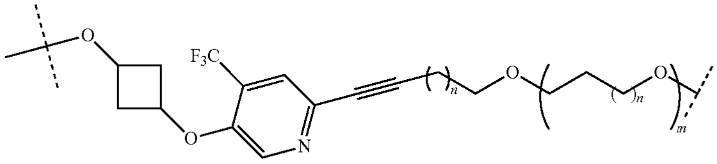
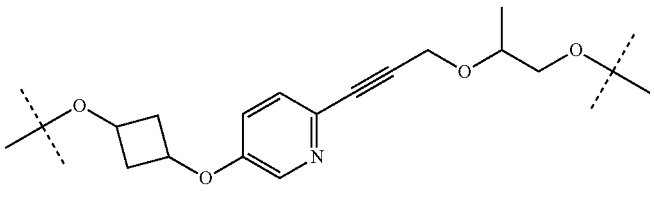

-continued
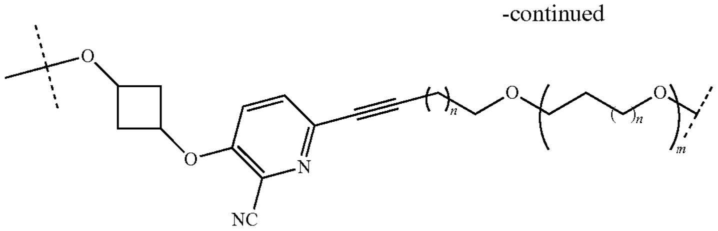
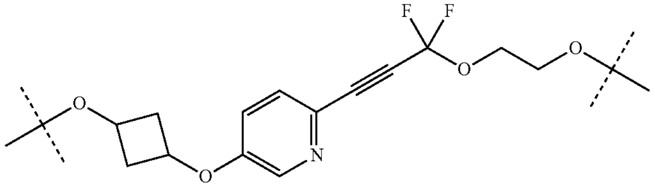
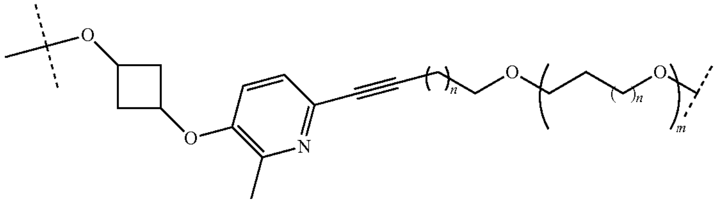
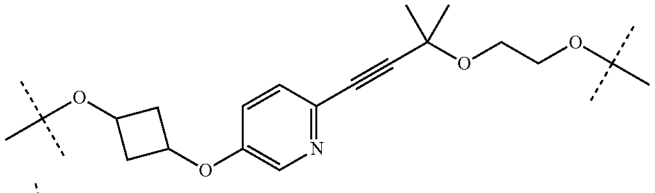
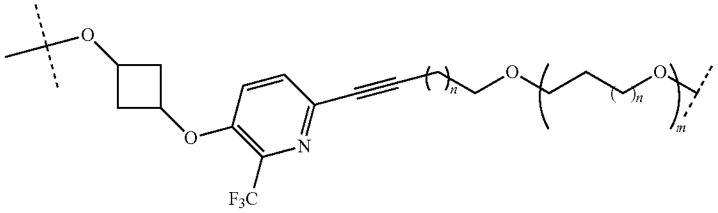
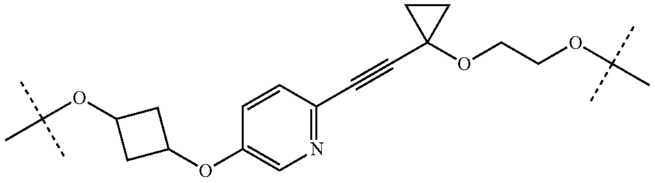
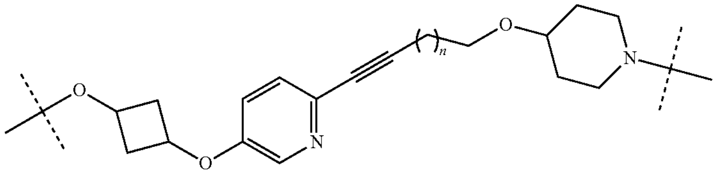
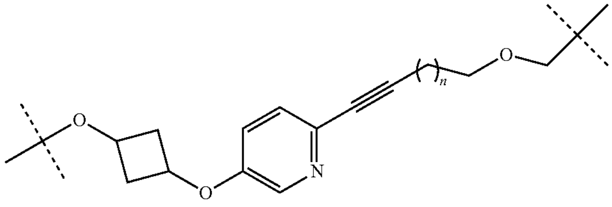
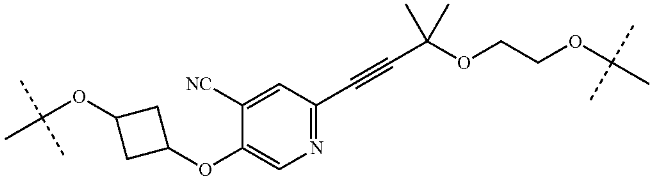

-continued
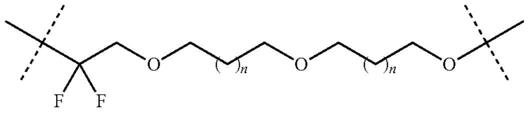
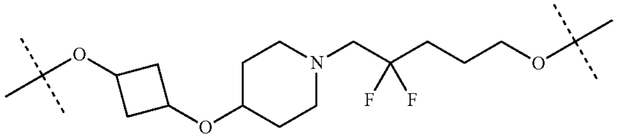
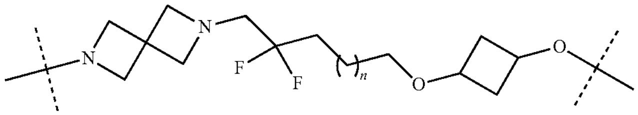
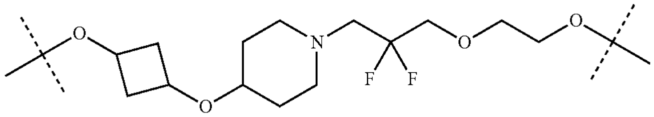
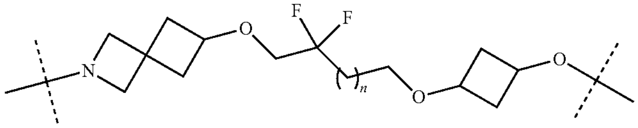
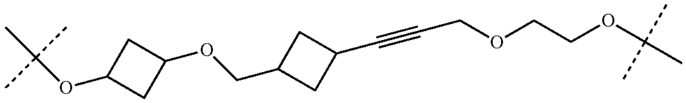
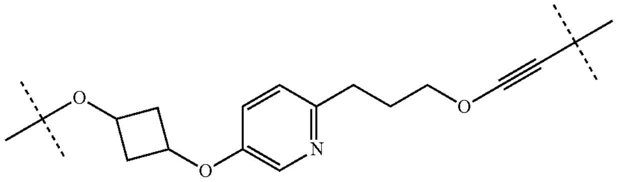
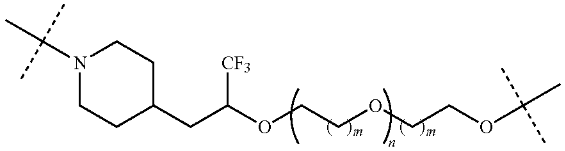
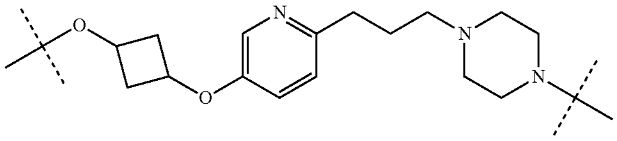
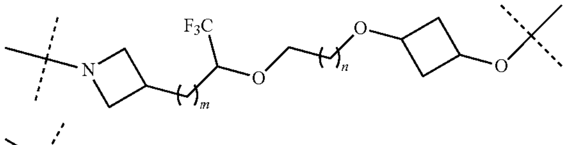
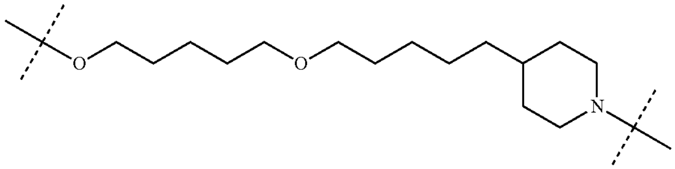
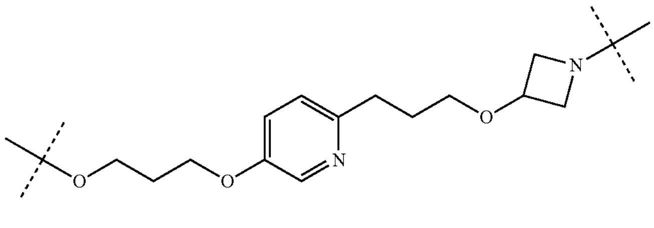

-continued
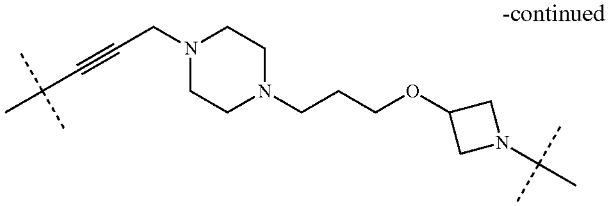
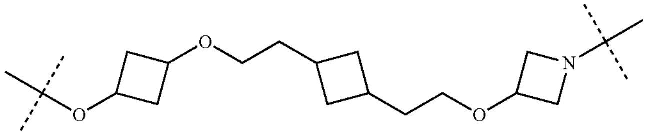
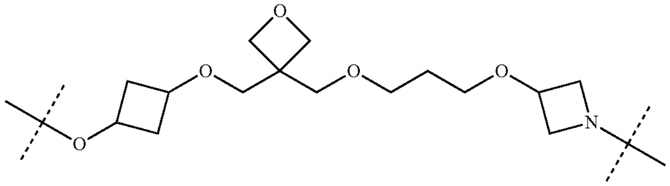
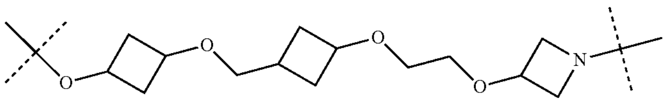
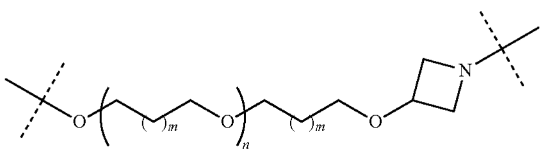
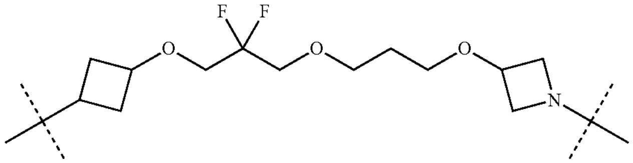
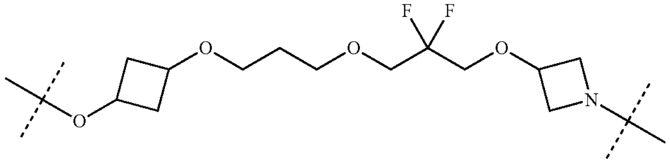
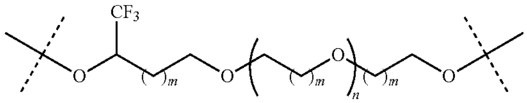
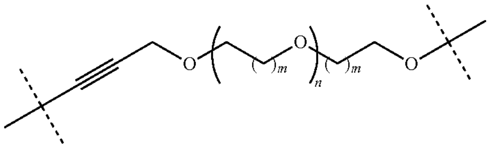
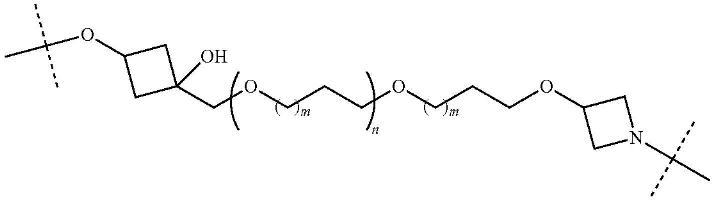
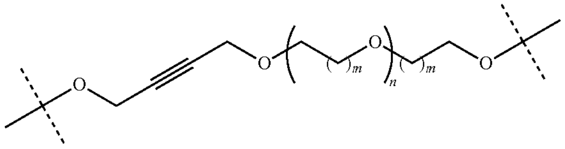
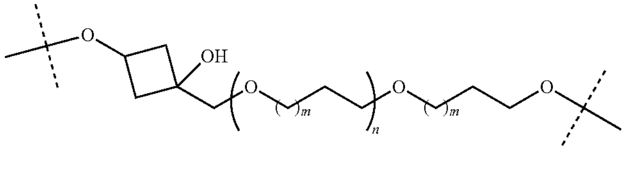

-continued
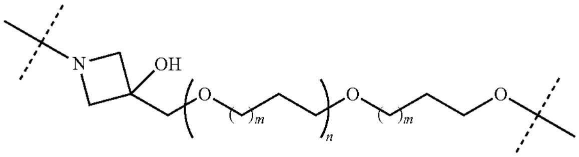
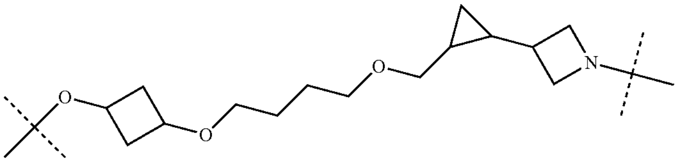
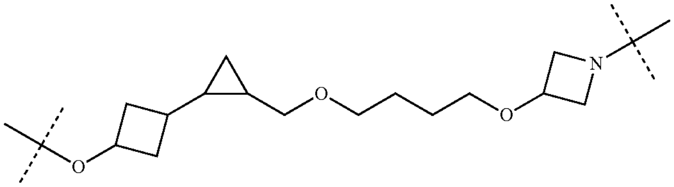
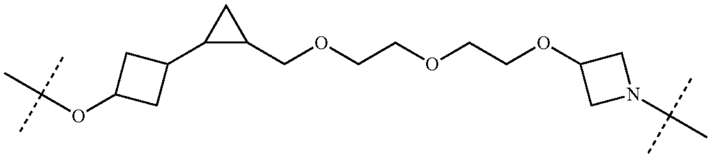
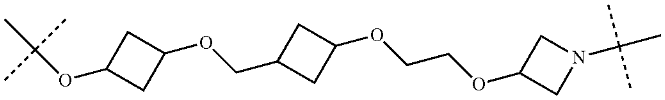
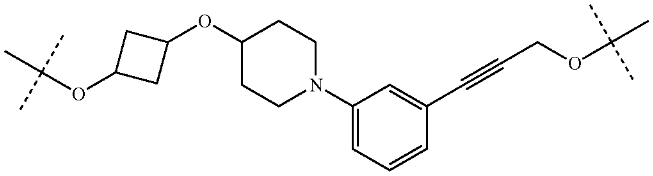
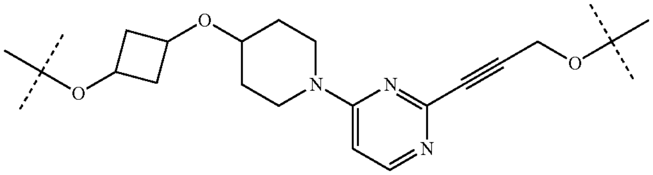
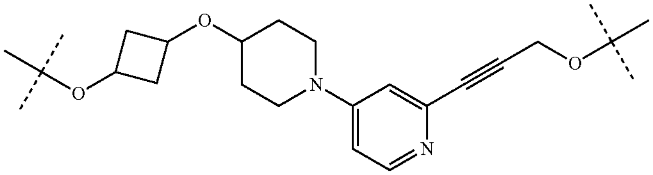
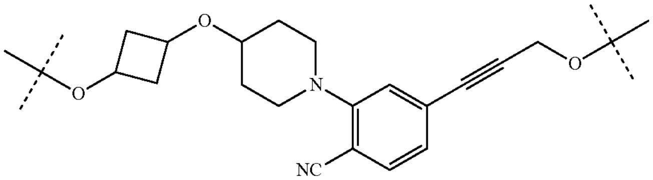
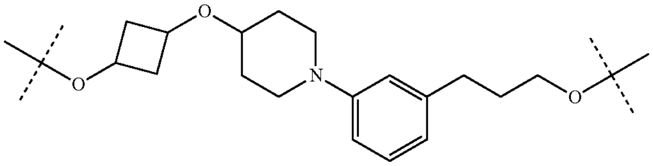

-continued
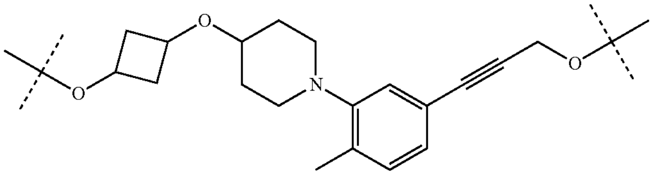
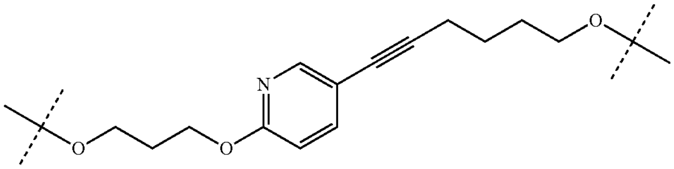
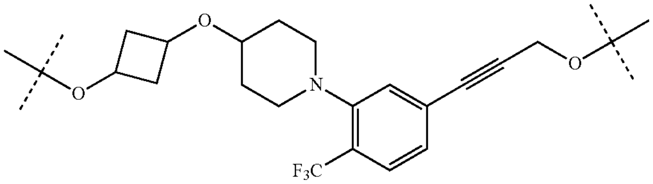
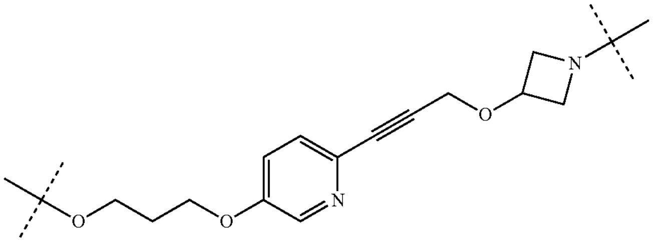
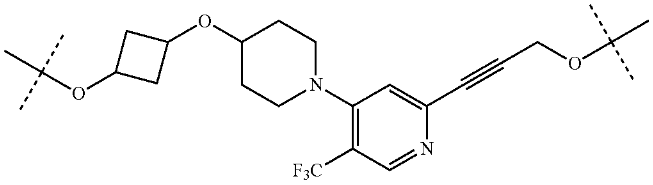
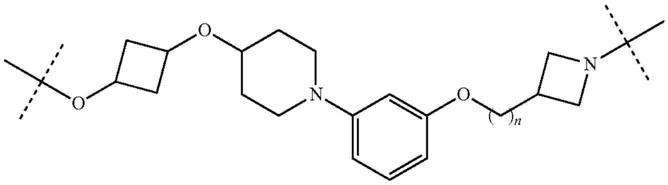
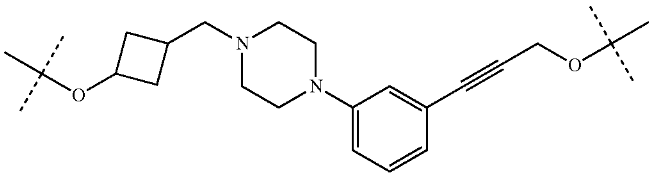
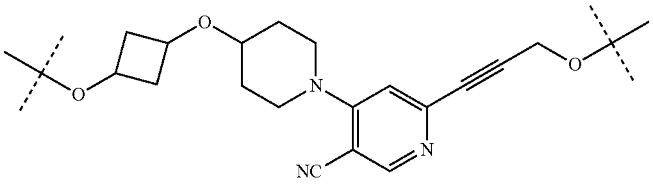
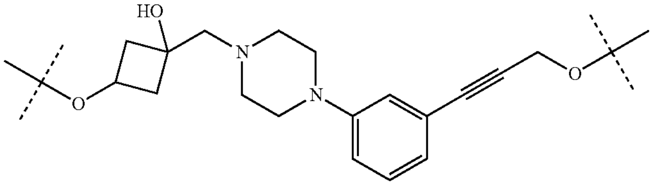

-continued
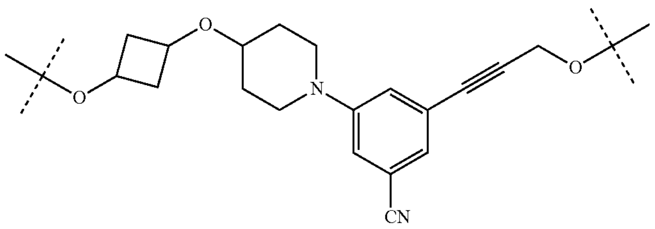
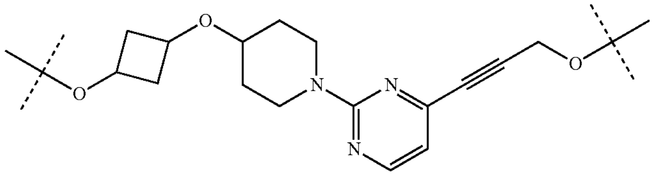
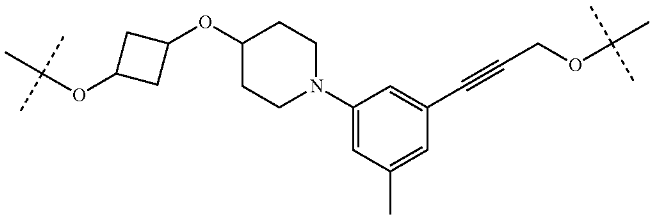
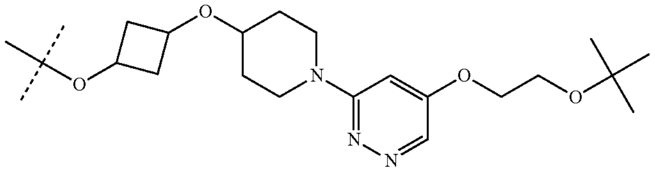
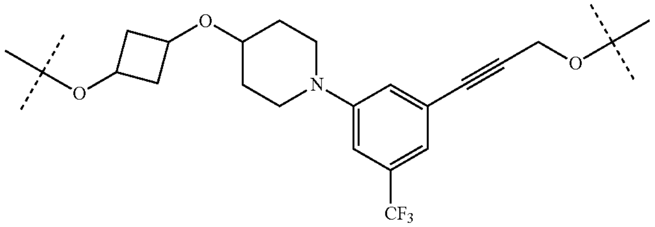
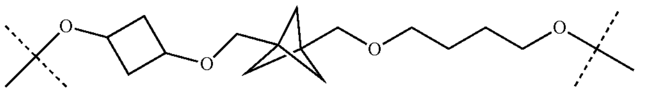
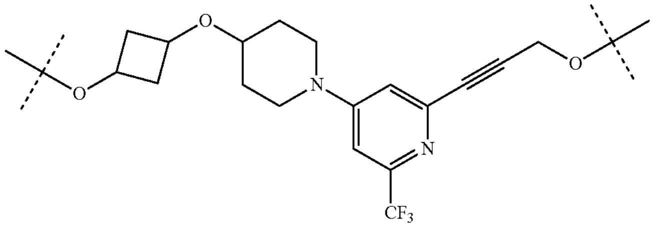
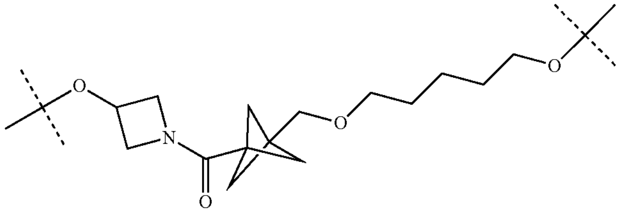

-continued
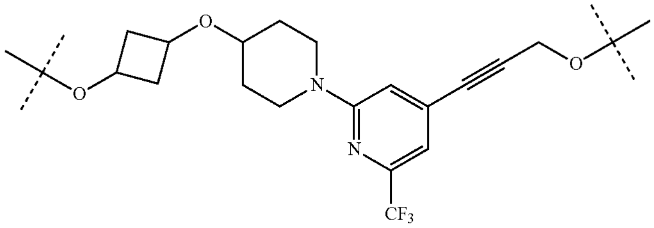
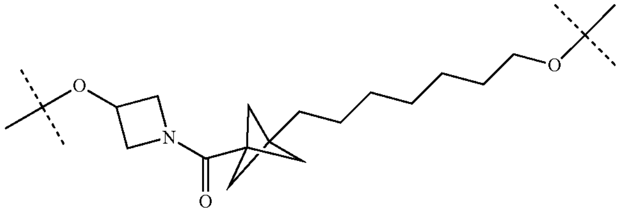
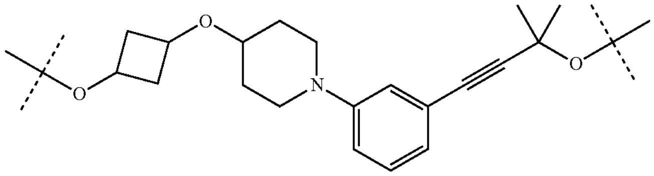
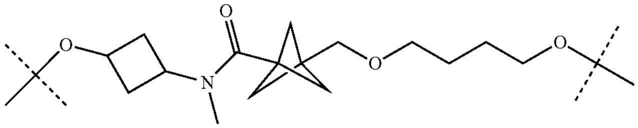
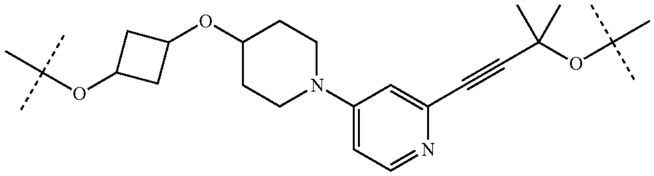
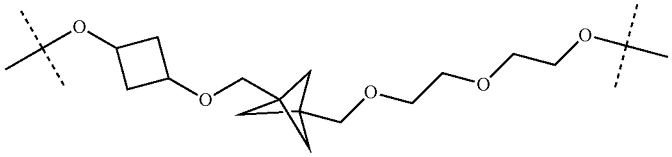
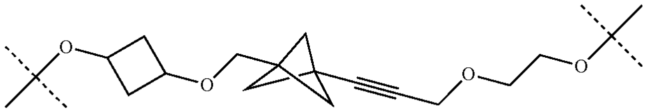
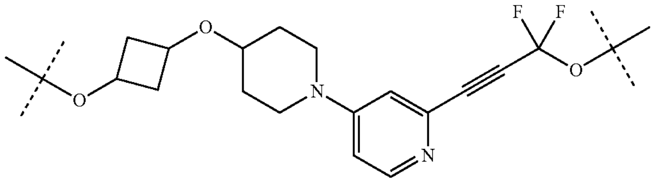
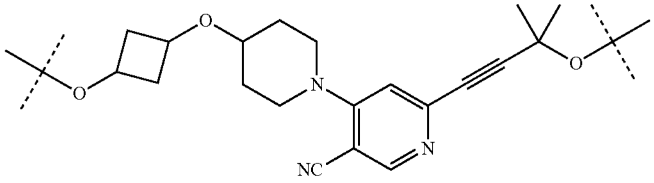
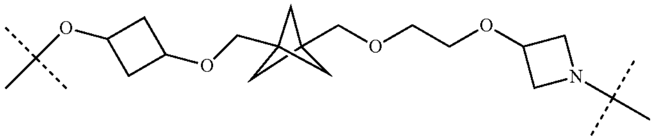

-continued
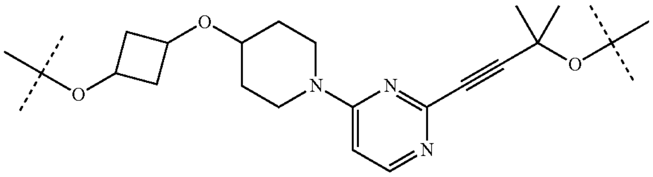
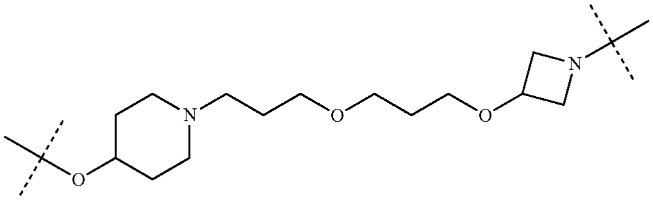
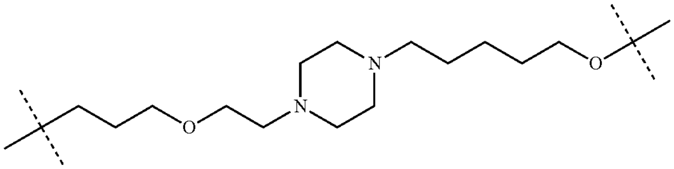
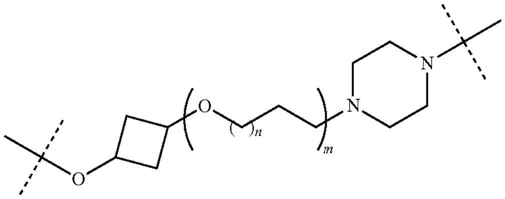
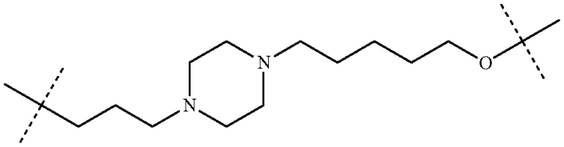
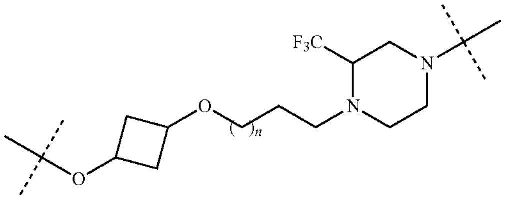
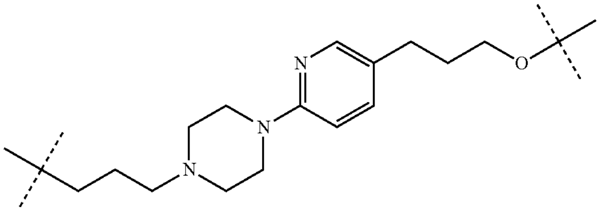
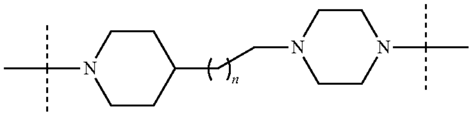
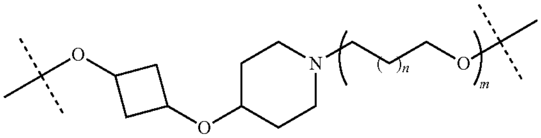
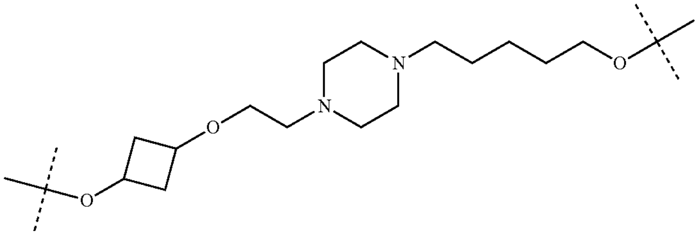
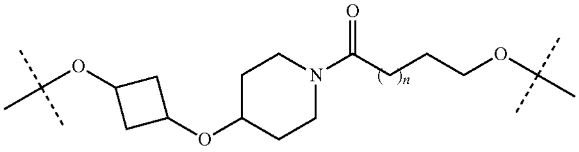
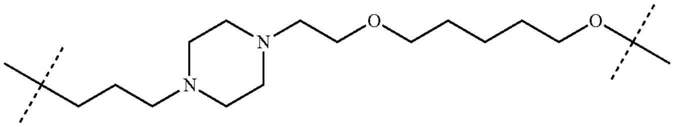

-continued
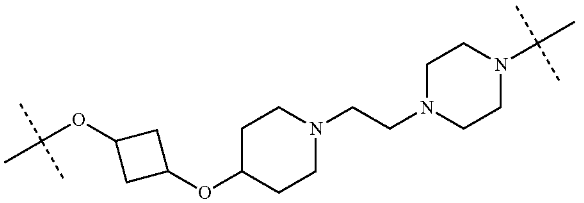
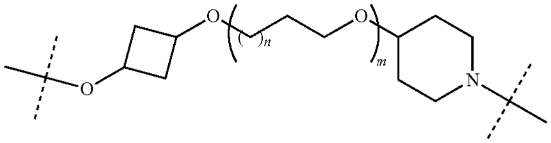
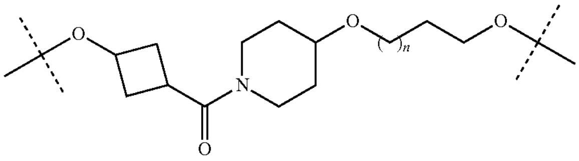
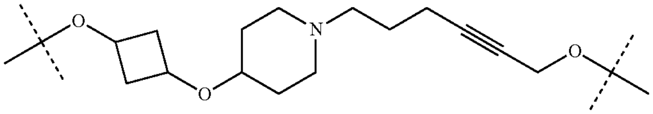
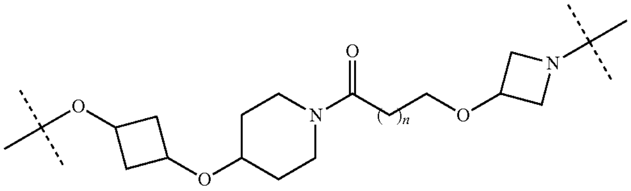
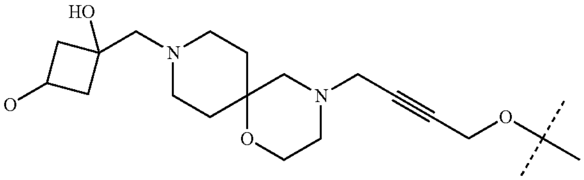
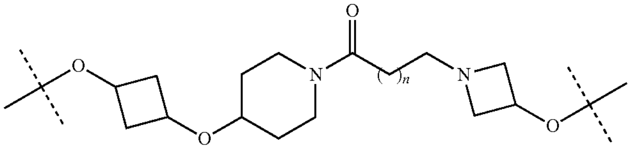
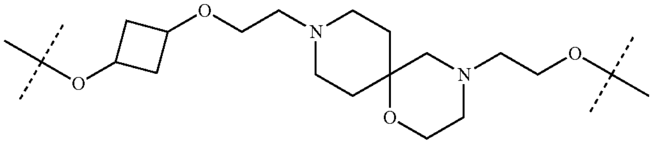
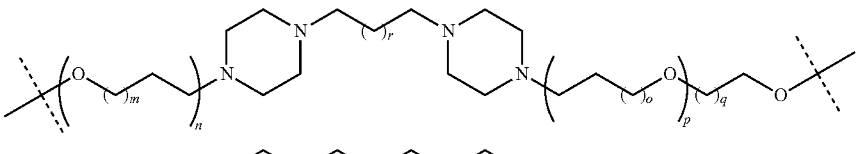
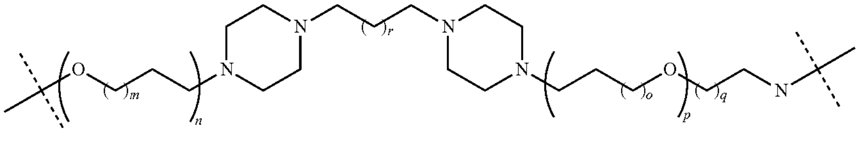
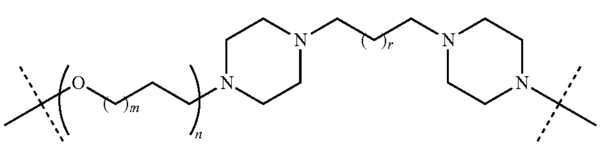
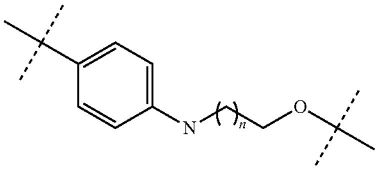

-continued
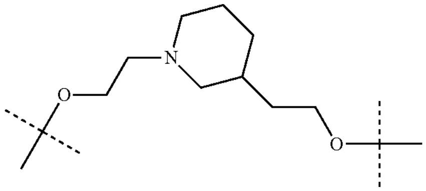
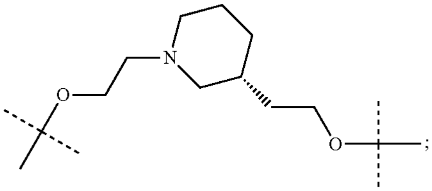
;
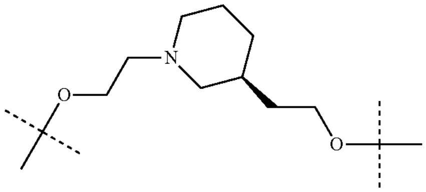
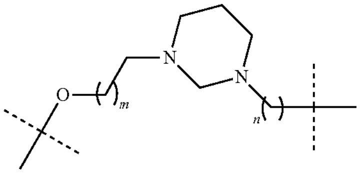
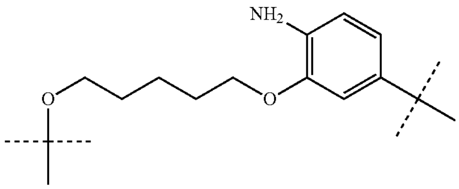
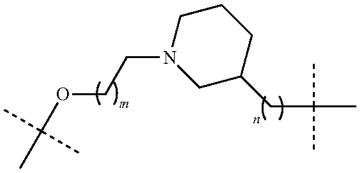
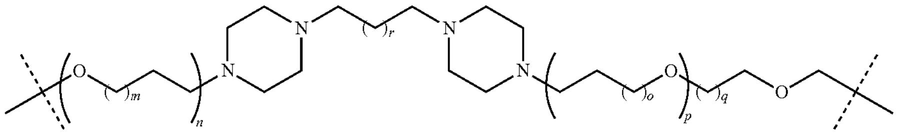
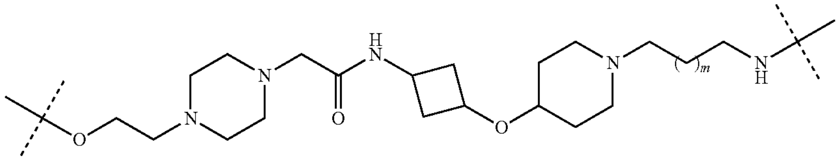
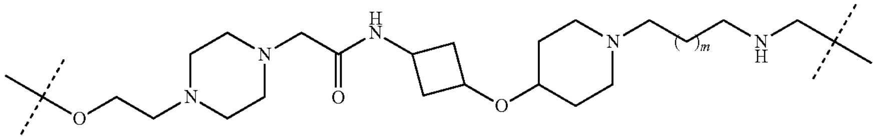
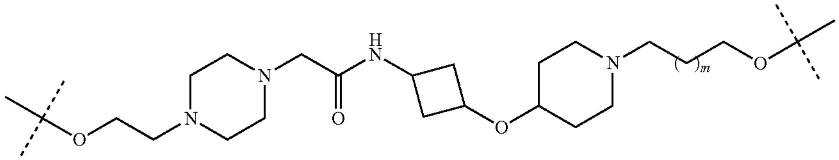
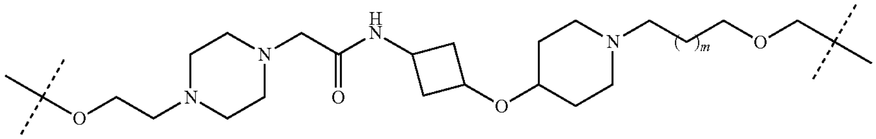
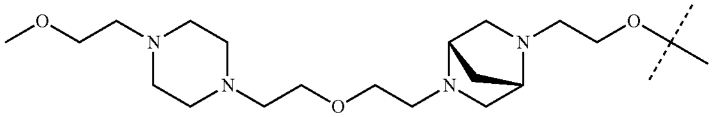
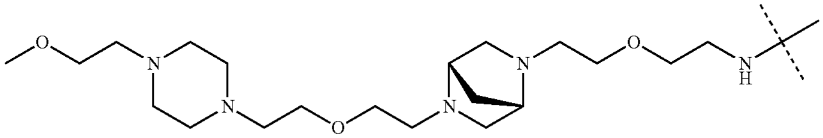
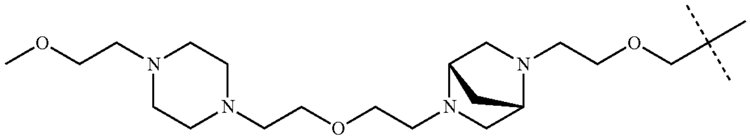

-continued
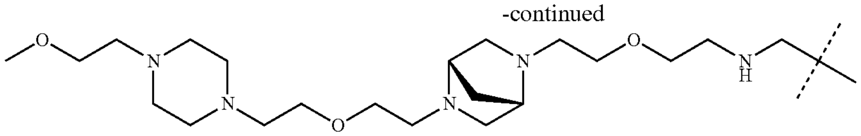
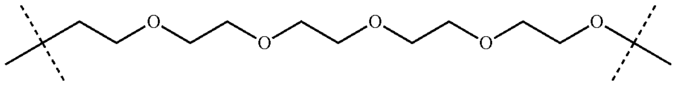
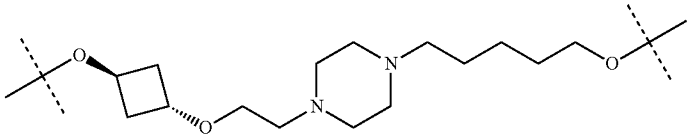
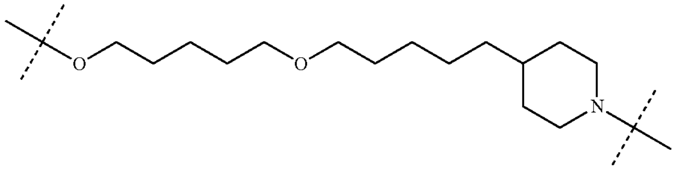
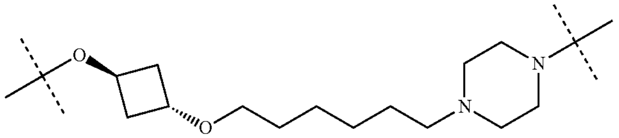
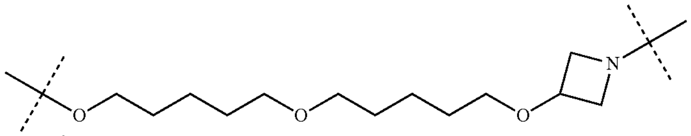
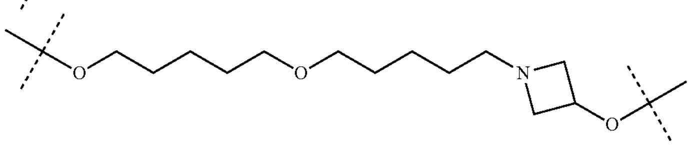
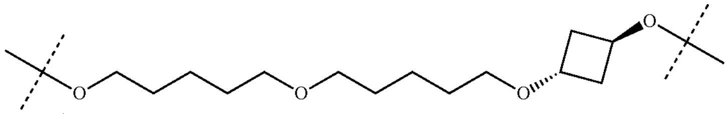
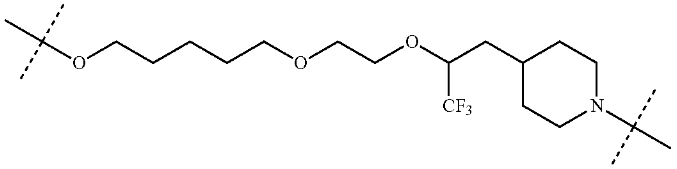
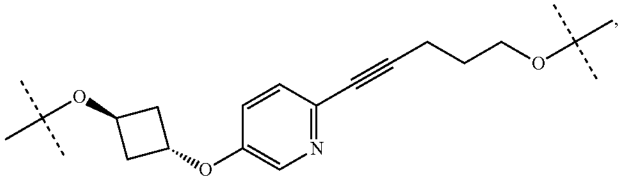
wherein each m, n, o, p, q, and r is independently 0, 1, 2, 3, 4, 5, 6, 7, 8, 9, 10, 11, 12, 13, 14, 15, 16, 17, 18, 19, or 20.
In any aspect or embodiment described herein, L is selected from the group consisting of:
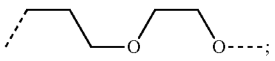
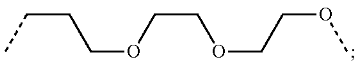
-continued
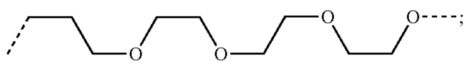
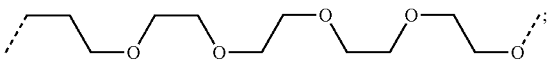
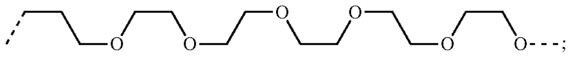
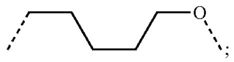
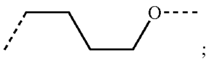

-continued
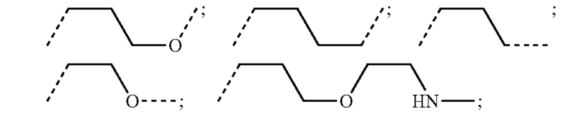
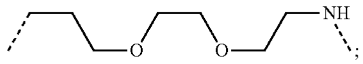
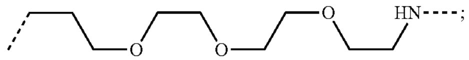
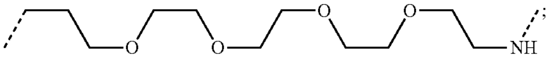
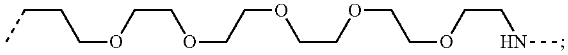
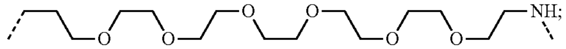
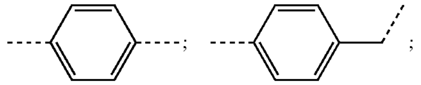
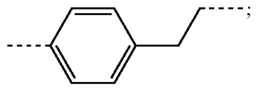
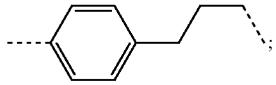
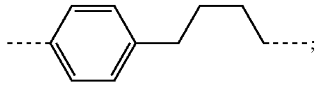
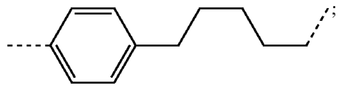
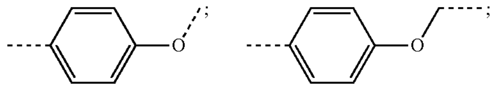
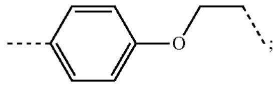
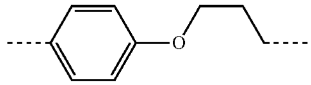
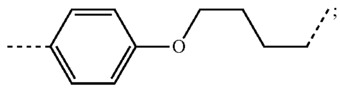
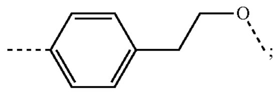
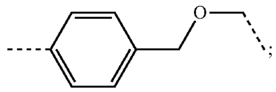
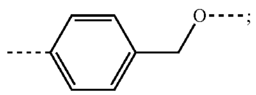
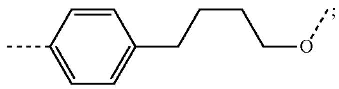
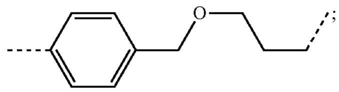
-continued
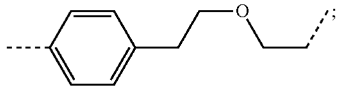
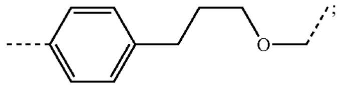
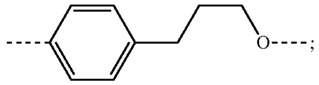
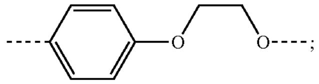
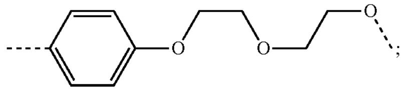
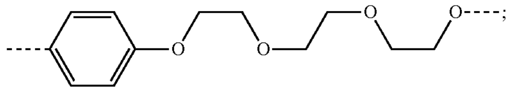
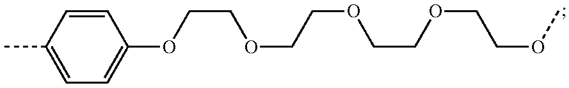
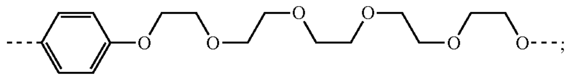
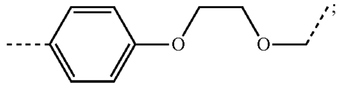
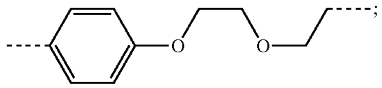
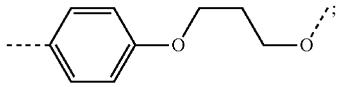
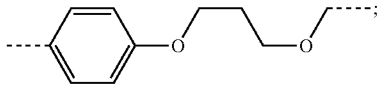
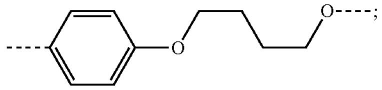
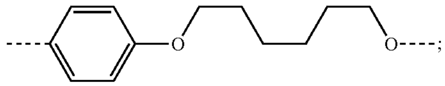
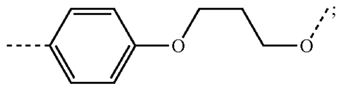
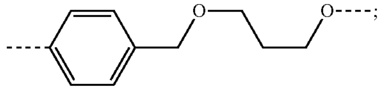
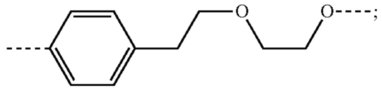
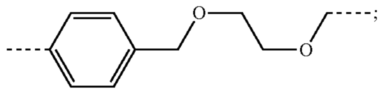
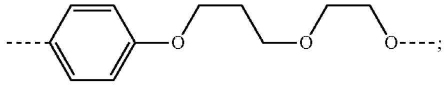

-continued
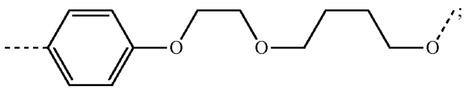
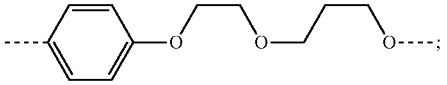
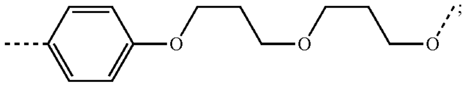
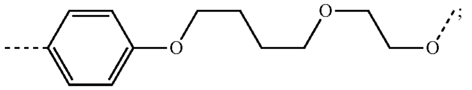
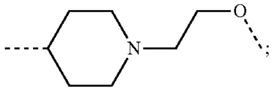
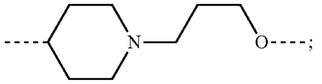
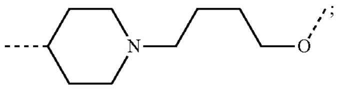
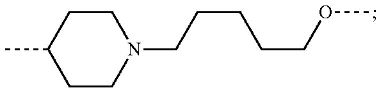
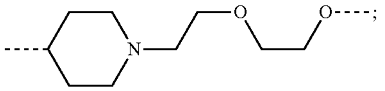
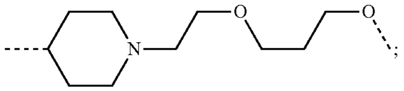
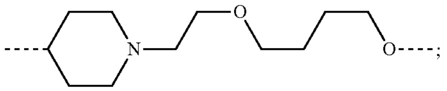
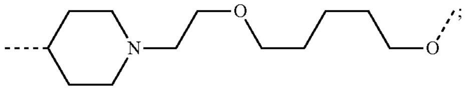
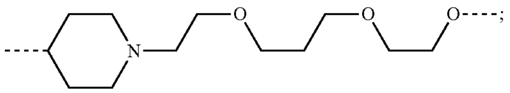
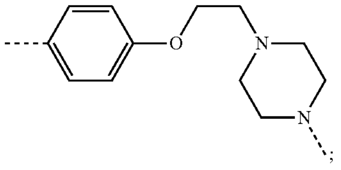
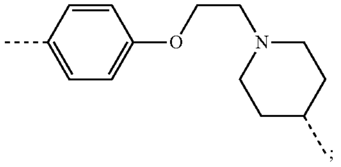
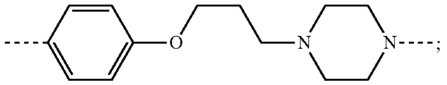
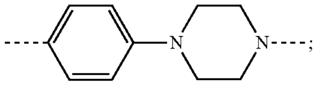
-continued
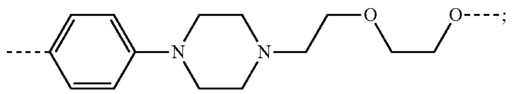
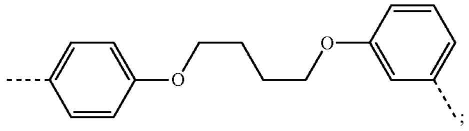
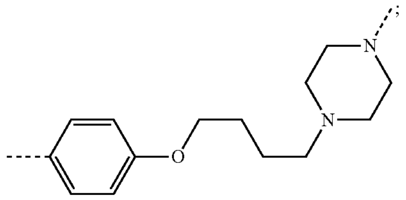
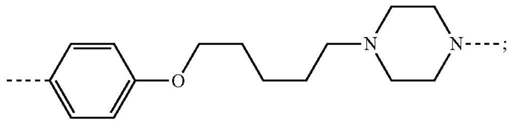
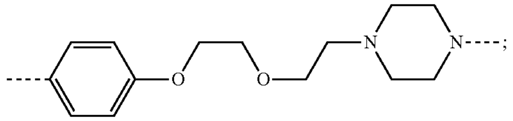
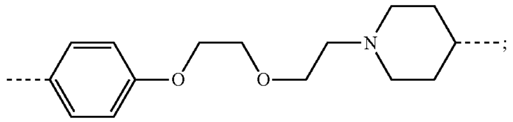
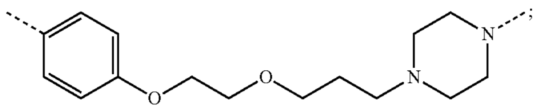
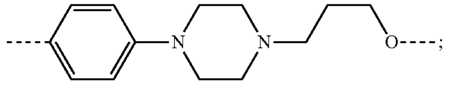
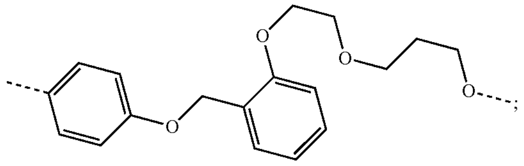
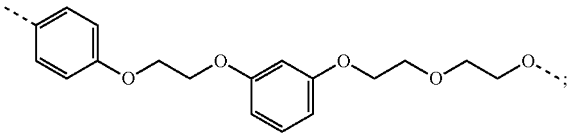
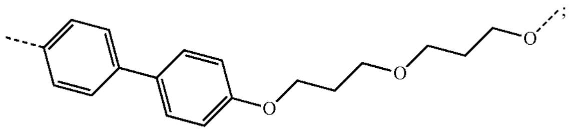
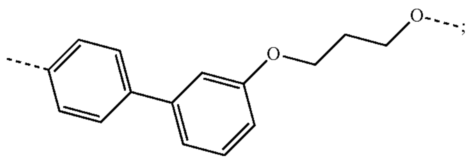
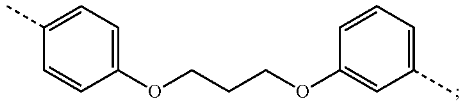

-continued
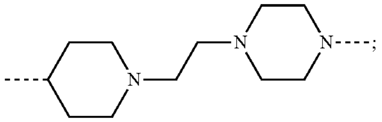
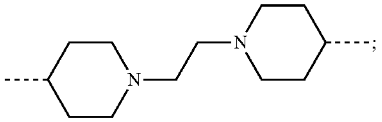
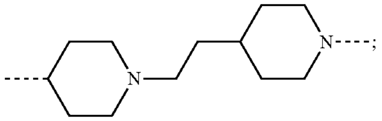
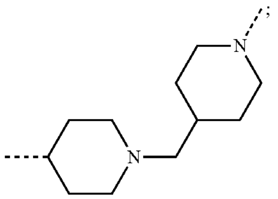
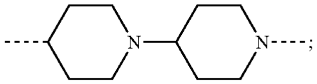
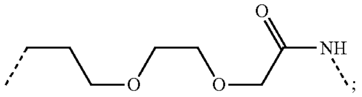
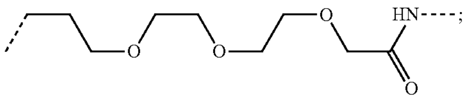
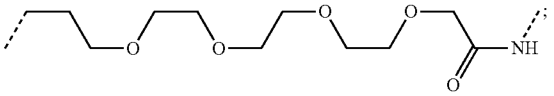
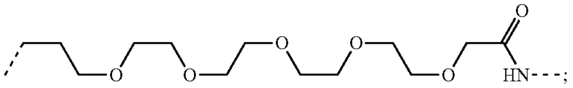
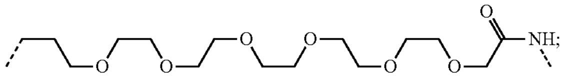
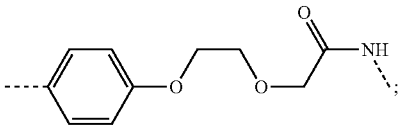
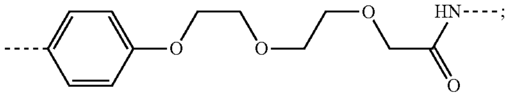
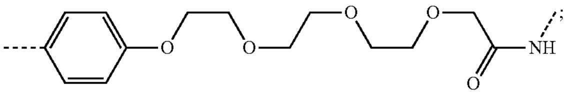
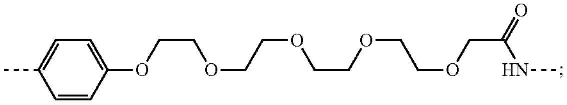
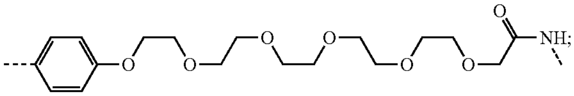
-continued
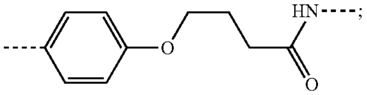
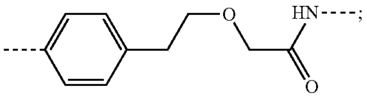
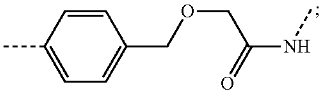
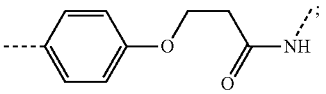
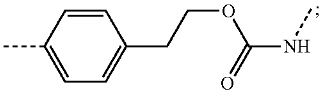
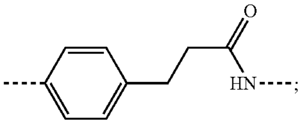
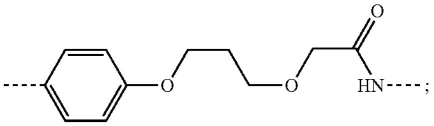
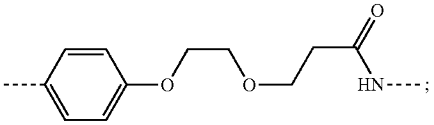
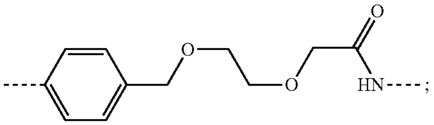
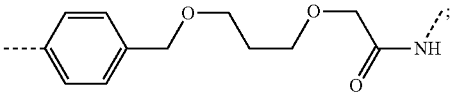
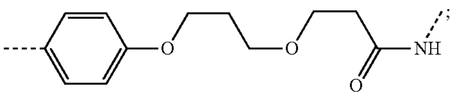
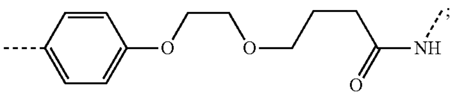
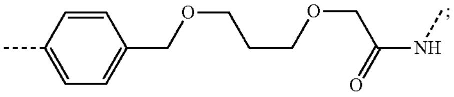
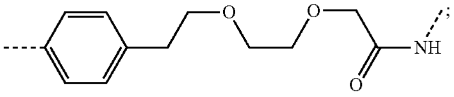
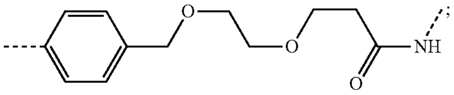
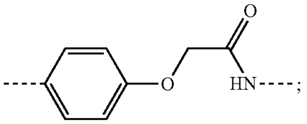

-continued
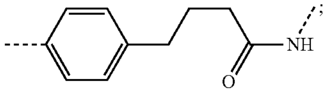
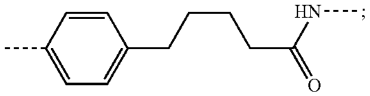
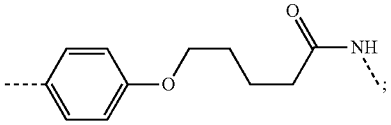
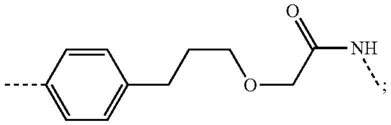
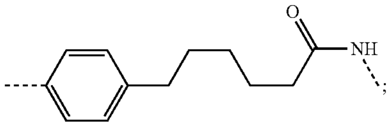
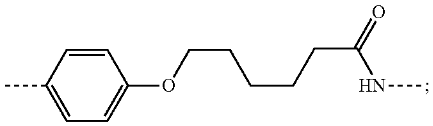
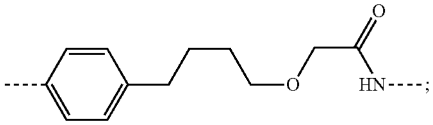
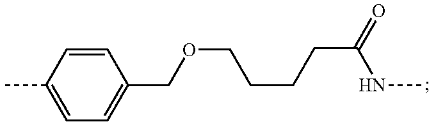
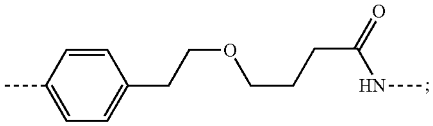
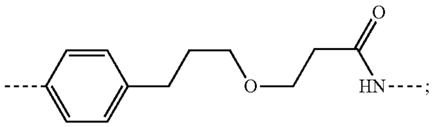
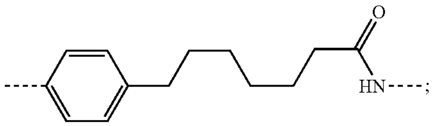
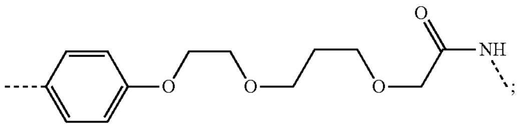
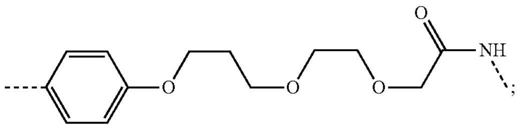
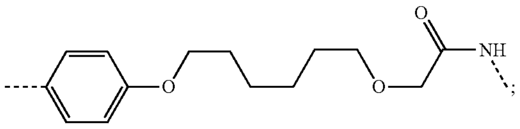
-continued
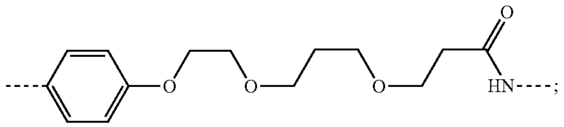
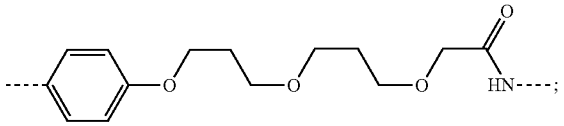
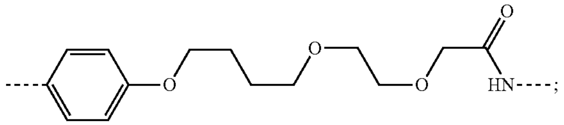
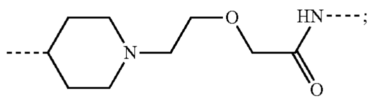
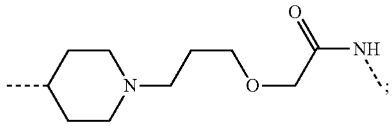
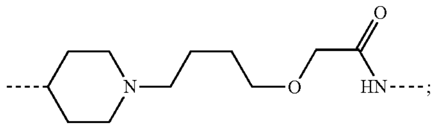
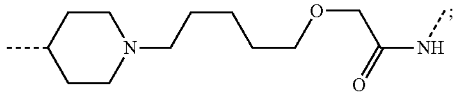
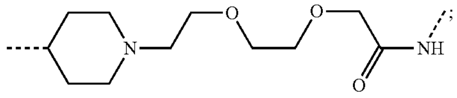
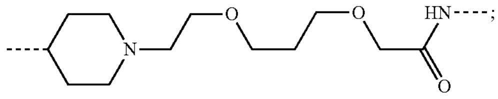
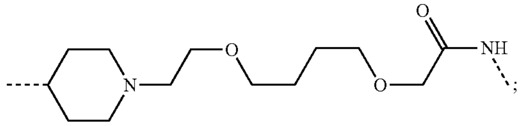
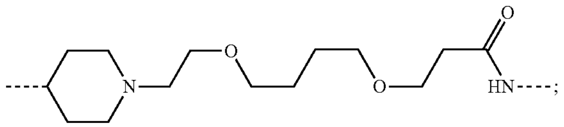
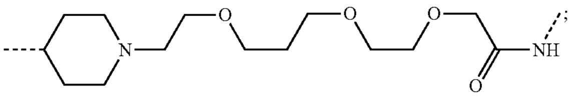
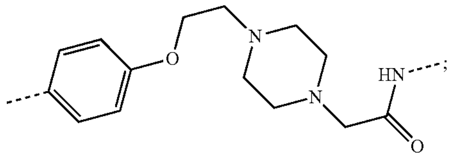
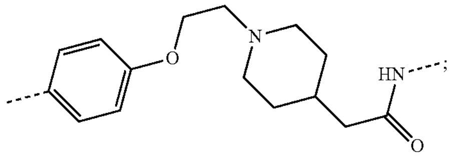

-continued
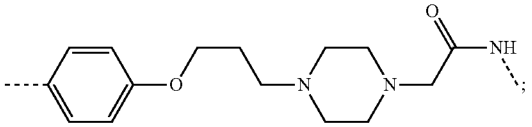
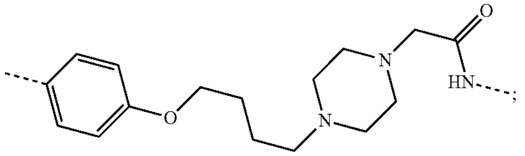
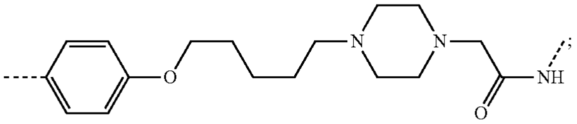
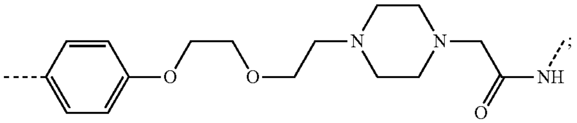
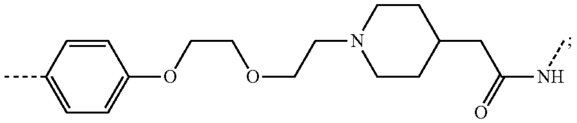
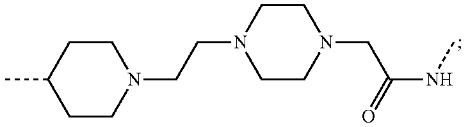
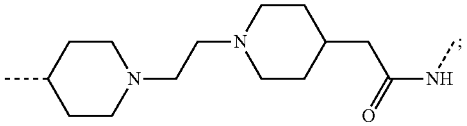
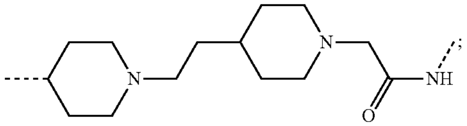
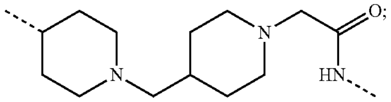
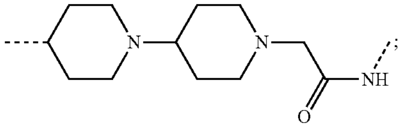
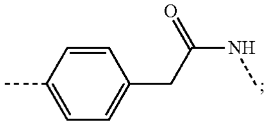
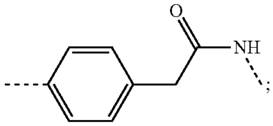
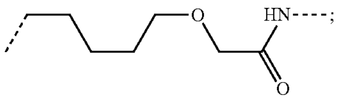
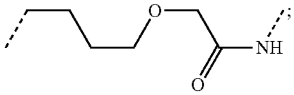
-continued
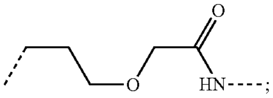
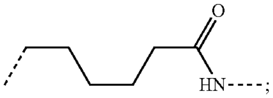
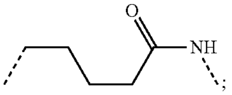
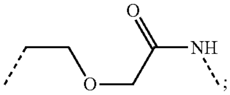
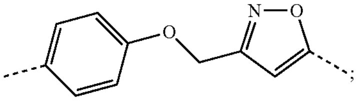
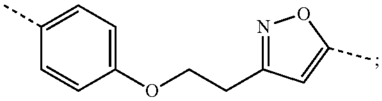
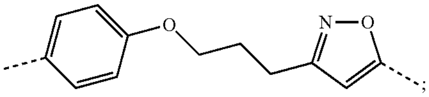
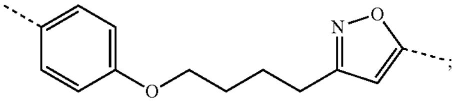
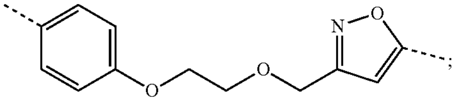
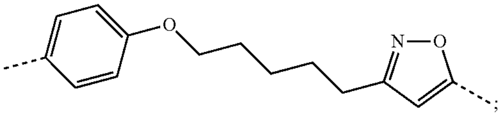
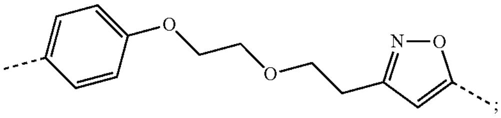
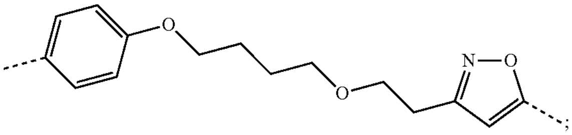
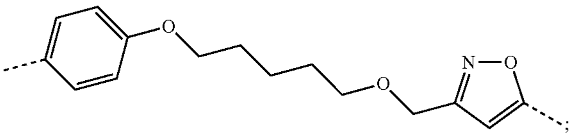
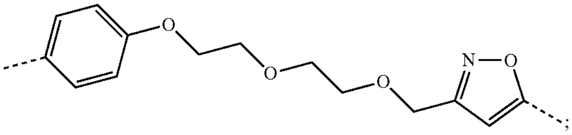
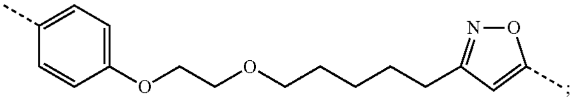
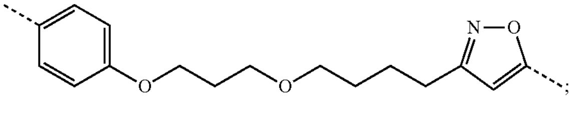

-continued
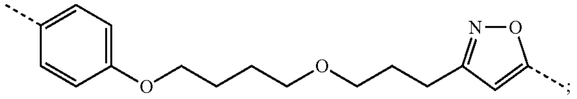
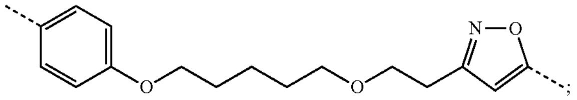
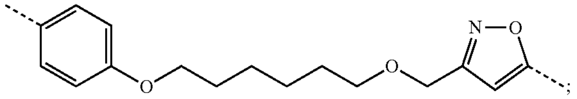
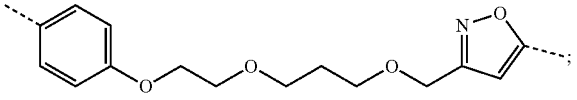
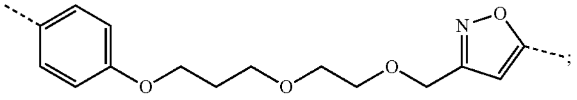
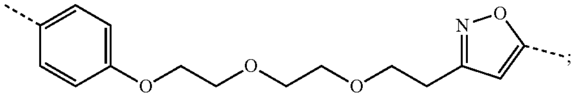
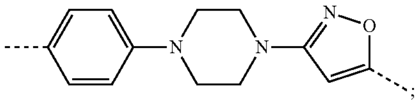
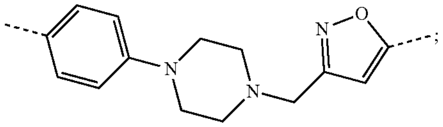
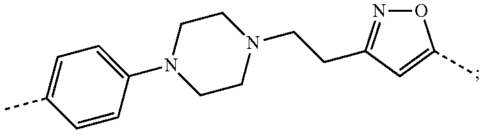
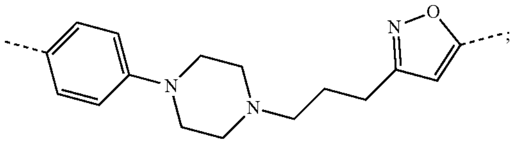
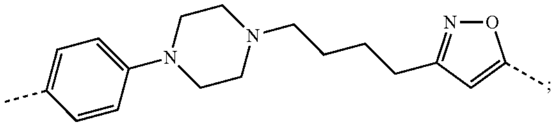
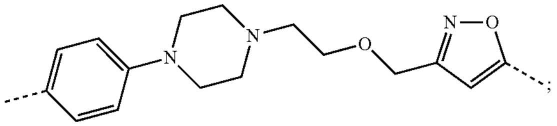
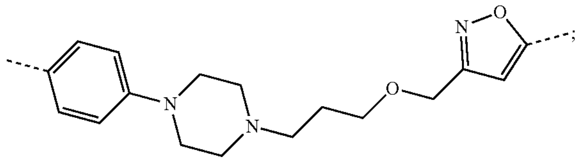
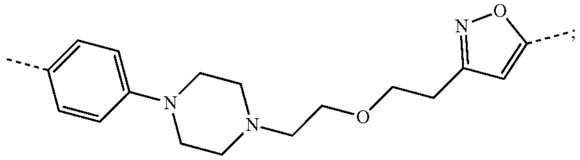
-continued
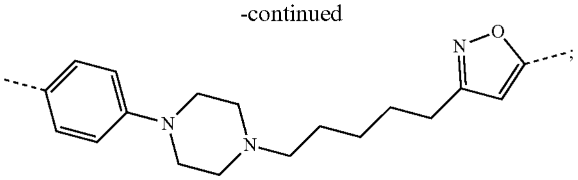
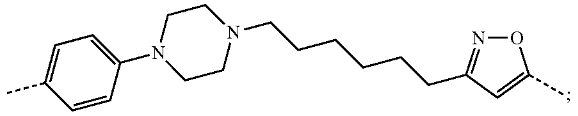
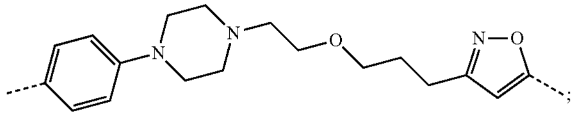
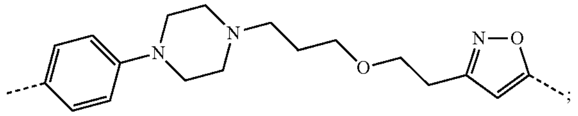
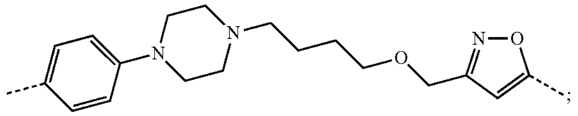
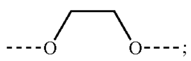
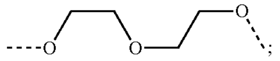
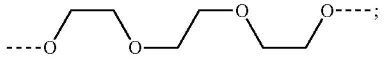
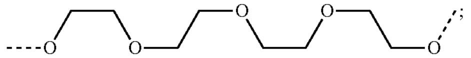
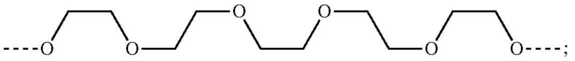
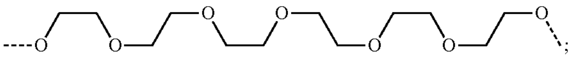
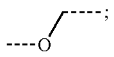
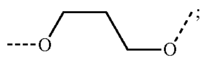
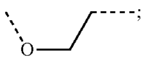
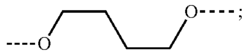
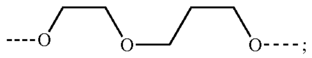
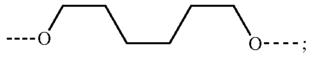
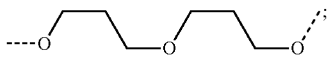
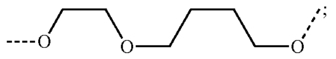
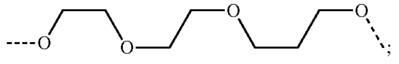
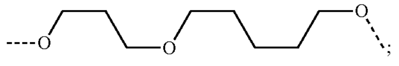
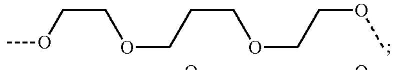
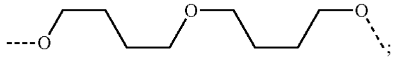
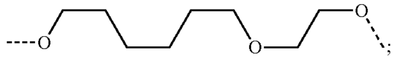
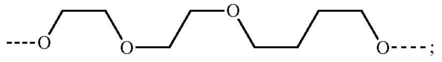
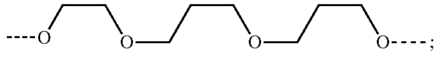

-continued
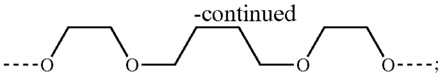
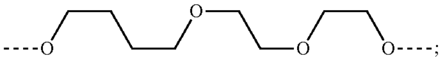
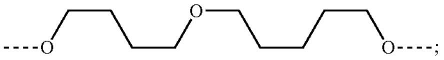
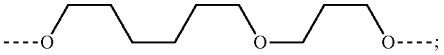
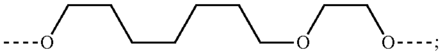
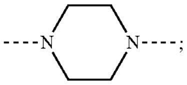
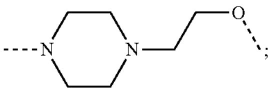
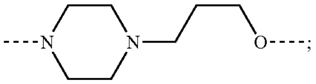
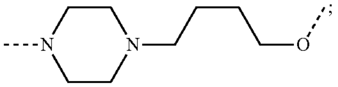
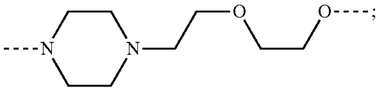
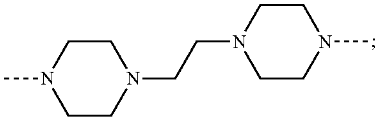
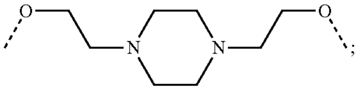
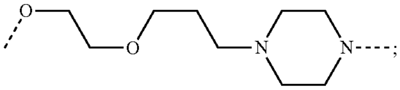
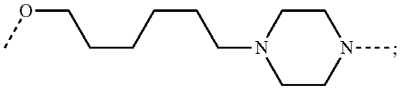
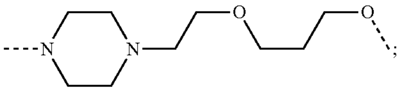
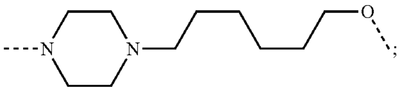
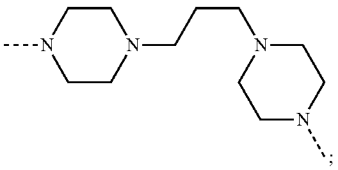
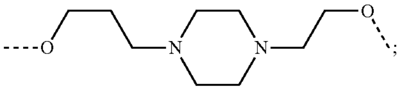
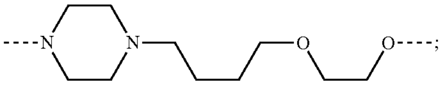
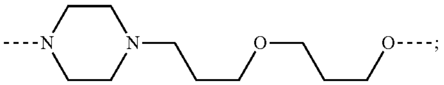
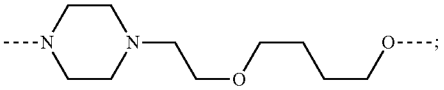
-continued
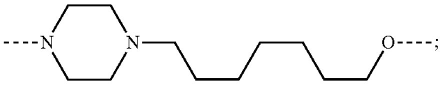
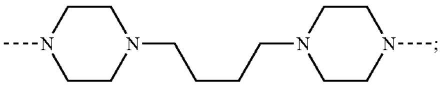
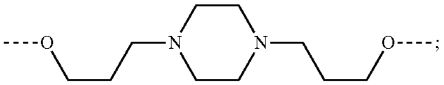
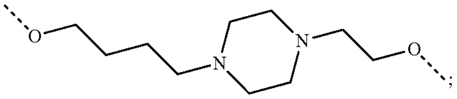
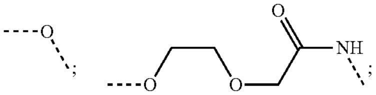
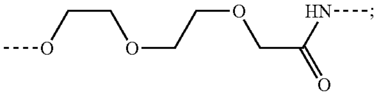
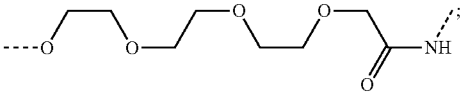
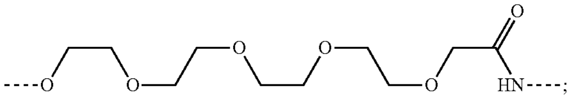
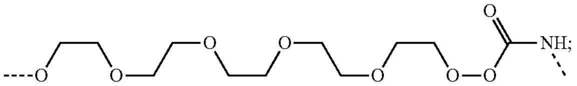
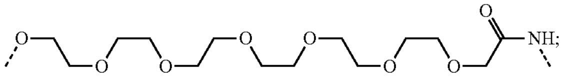
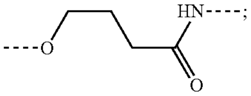
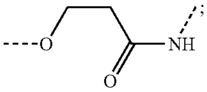
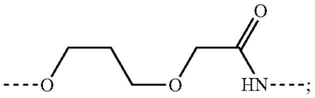
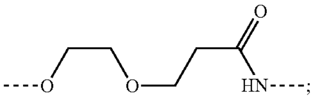
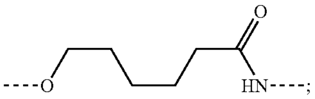
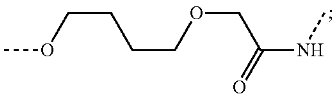
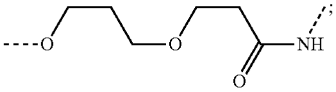
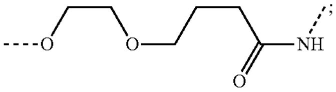
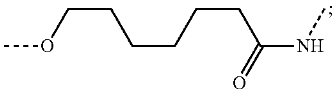

-continued
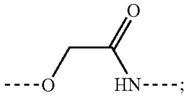
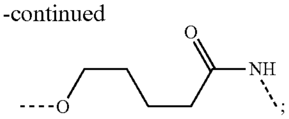
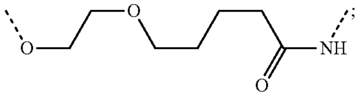
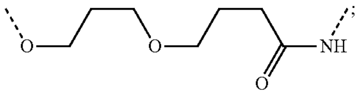
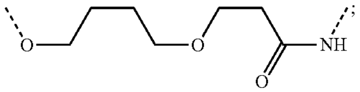
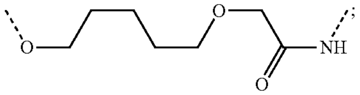
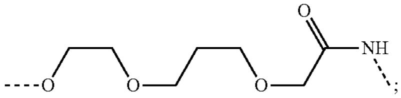
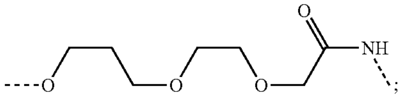
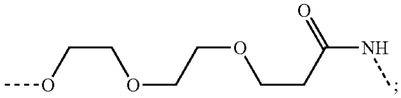
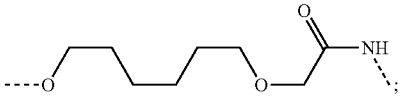
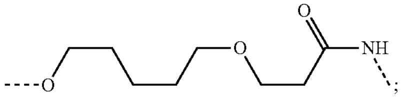
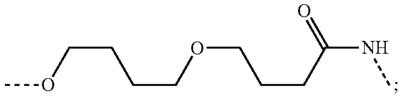
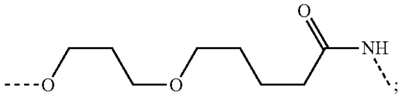
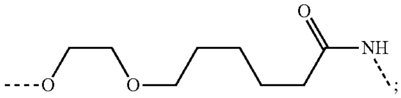
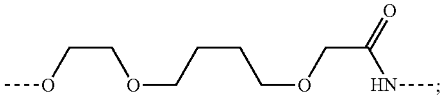
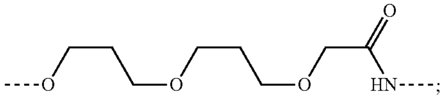
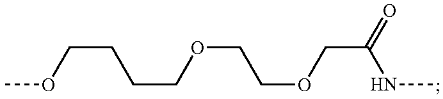
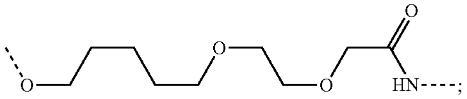
-continued
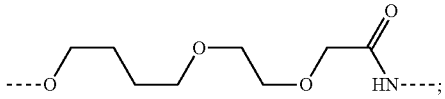
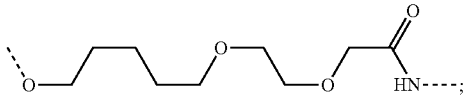
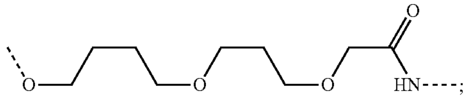
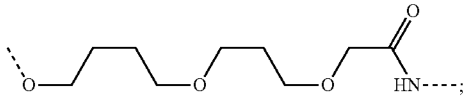
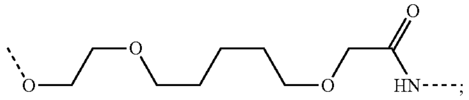
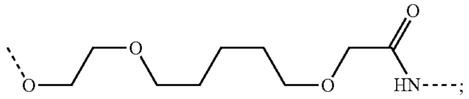
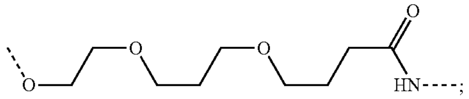
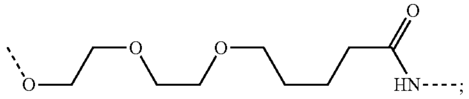
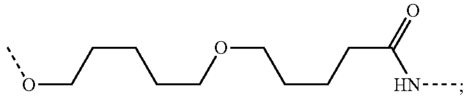
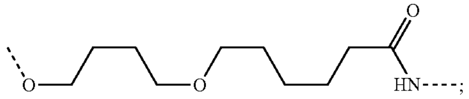
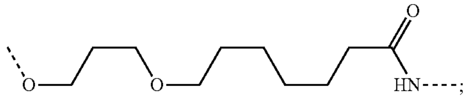
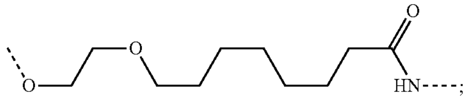
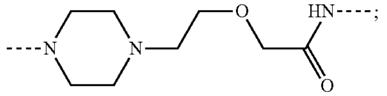
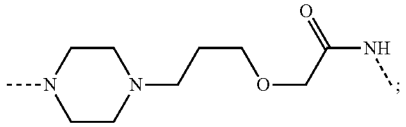
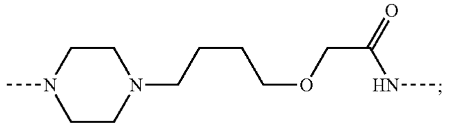
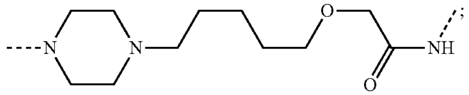

-continued
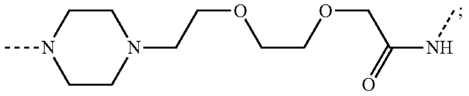
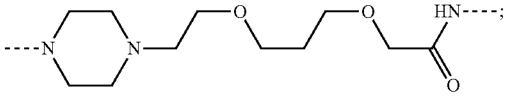
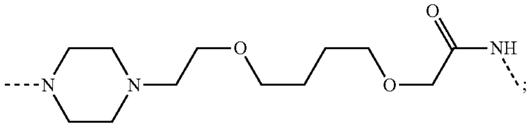
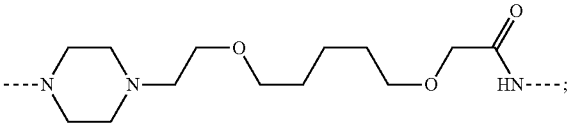
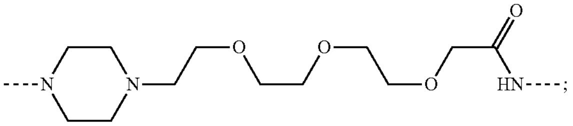
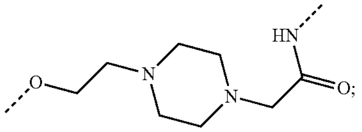
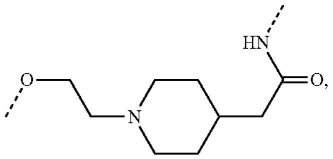
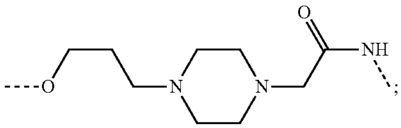
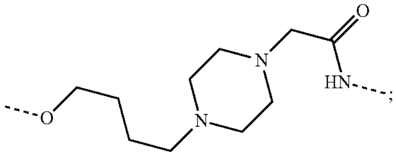
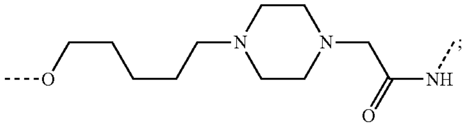
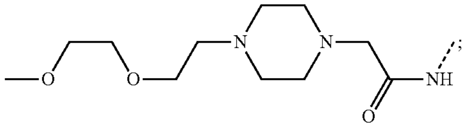
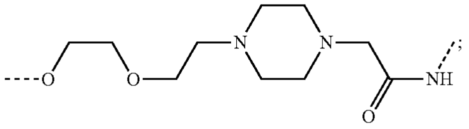
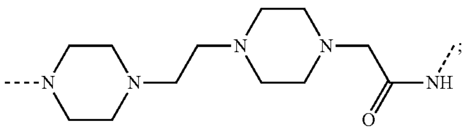
-continued
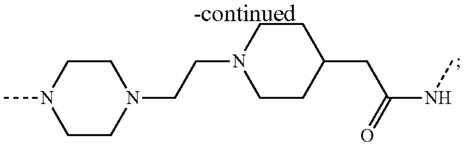
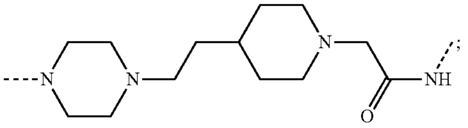
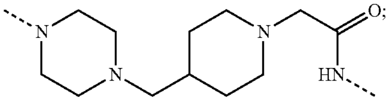
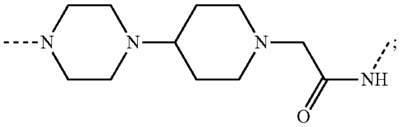
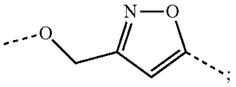
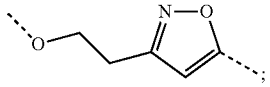
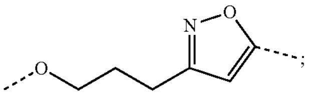
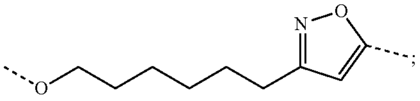
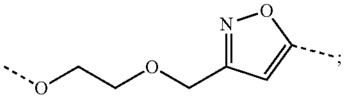
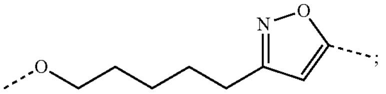
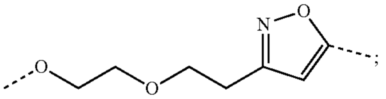
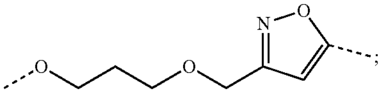
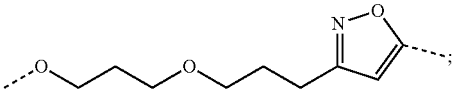
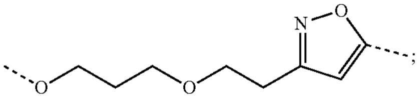
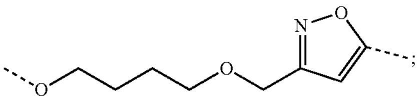
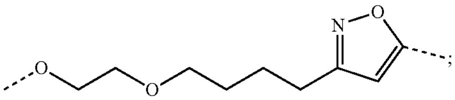
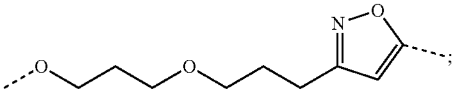
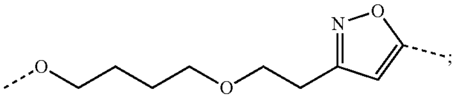

-continued

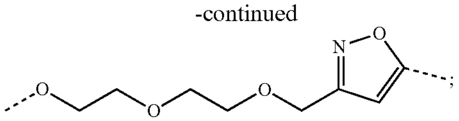
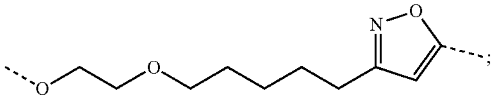
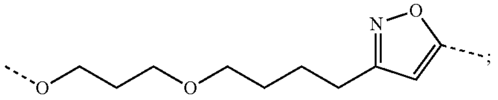
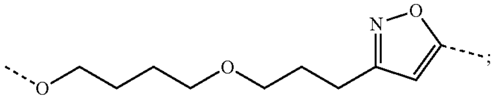
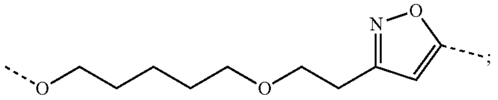
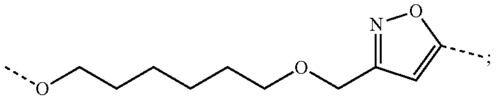
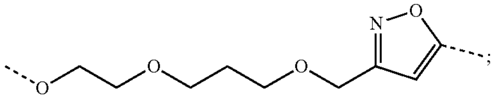
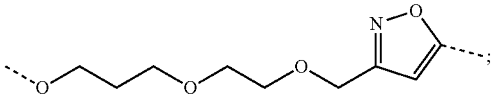
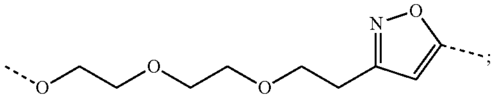
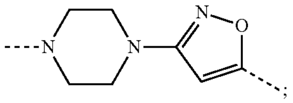
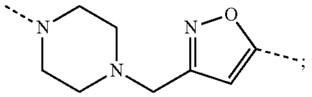
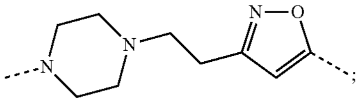
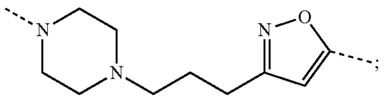
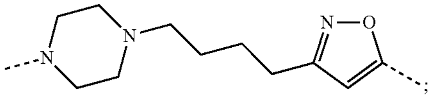
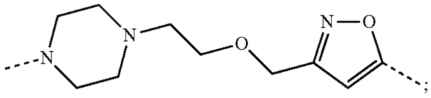
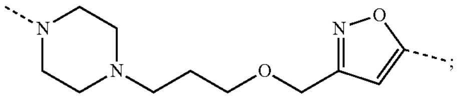
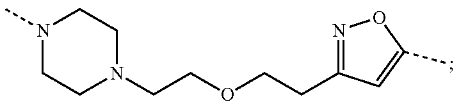

-continued

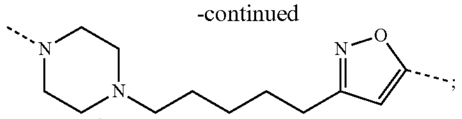
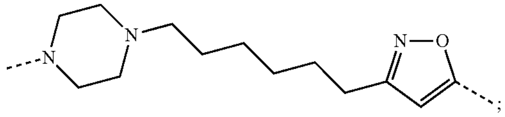
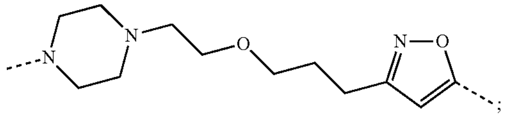
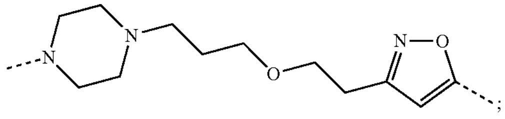
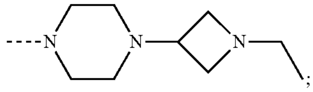
and
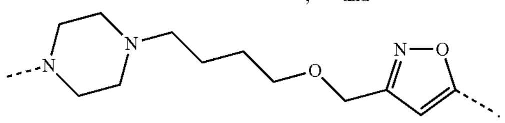

In additional embodiments, the linker (L) comprises a structure selected from, but not limited to the structure shown below, where a dashed line indicates the attachment point to the PTM or ULM moieties:

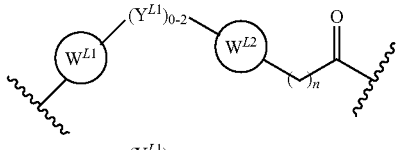
or
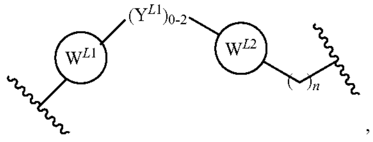
, wherein:

$W^{L1}$ and $W^{L2}$ are each independently a 4-8 membered ring with 0-4 heteroatoms, optionally substituted with $R^Q$, each $R^Q$ is independently a H, halo, OH, CN, $CF_3$, $C_1$-$C_6$ alkyl (linear, branched, optionally substituted), $C_1$-$C_6$ alkoxy (linear, branched, optionally substituted), or 2 $R^Q$ groups taken together with the atom they are attached to, form a 4-8 membered ring system containing 0-4 heteroatoms;

$Y^{L1}$ is each independently a bond, $C_1$-$C_6$ alkyl (linear, branched, optionally substituted) and optionally one or more C atoms are replaced with O; or $C_1$-$C_6$ alkoxy (linear, branched, optionally substituted);

n is 0-10; and a dashed line indicates the attachment point to the PTM or ULM moieties.

In additional embodiments, the linker (L) comprises a structure selected from, but not limited to the structure shown below, where a dashed line indicates the attachment point to the PTM or ULM moieties:

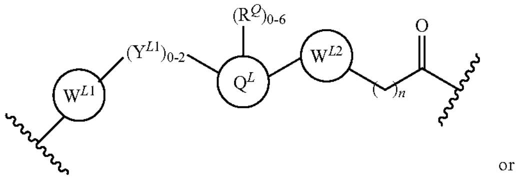

or

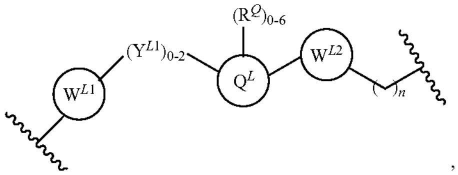

, wherein:

$W^{L1}$ and $W^{L2}$ are each independently aryl, heteroaryl, cyclic, heterocyclic, $C_{1-6}$ alkyl, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C═O, C═S, SO, $SO_2$, $C_1$-$C_6$ alkyl (linear, branched, optionally substituted) and optionally one or more C atoms are replaced with 0; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group, which binds to a target protein or polypeptide, which is ubiquitinated by an ubiquitin ligase and is chemically linked directly to the ULM group (such as CLM) or through a linker moiety L, or PTM is alternatively a ULM' group (such as CLM') which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

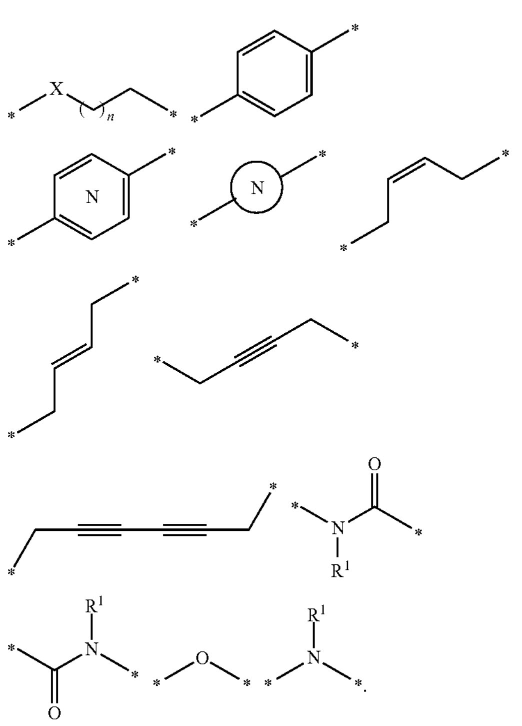

The X is selected from the group consisting of O, N, S, S(O) and $SO_2$; n is integer from 1 to 5; $R^{L1}$ is hydrogen or alkyl,

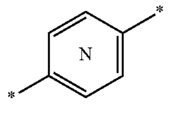

is a mono- or bicyclic aryl or heteroaryl optionally substituted with 1-3 substituents selected from alkyl, halogen, haloalkyl, hydroxy, alkoxy or cyano;

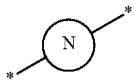

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the grou consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present dislcosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, the linker (L) is selected from the group consisting of:

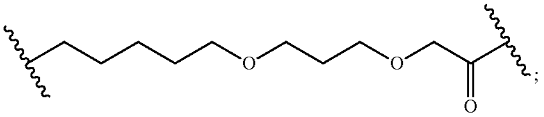

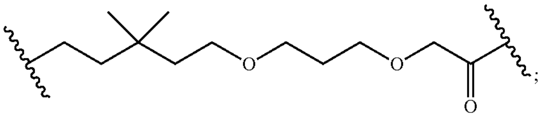

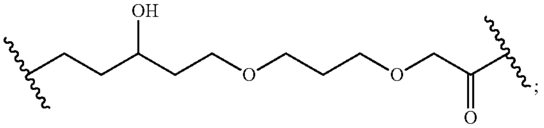

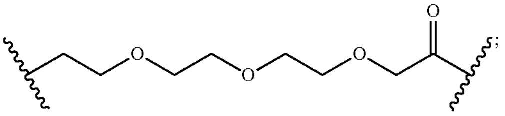

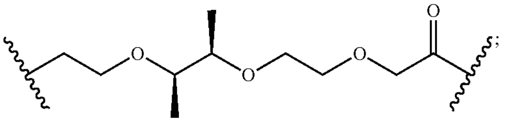

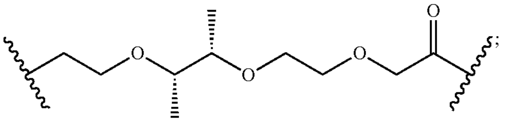

-continued

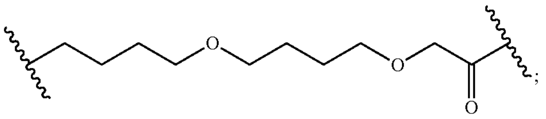

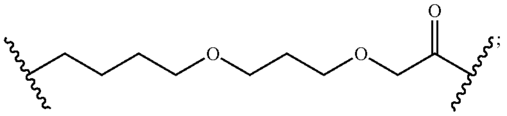

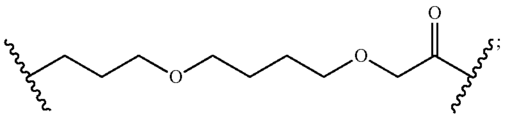

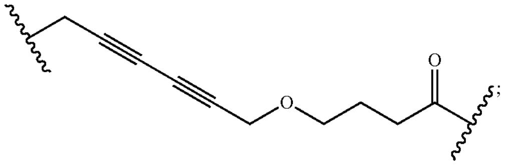

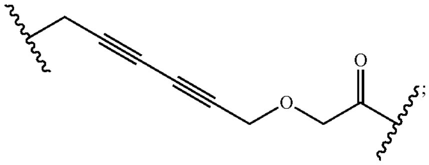

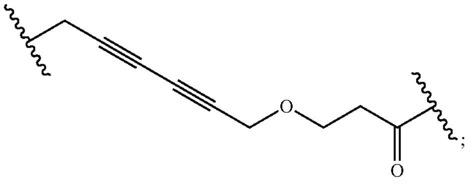

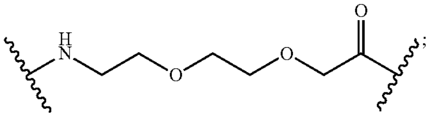

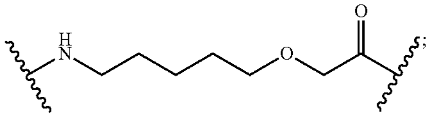

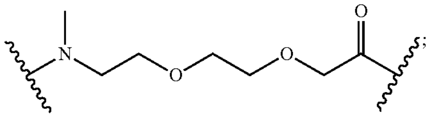

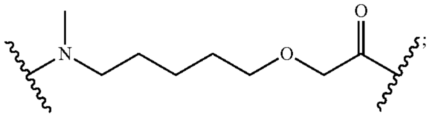

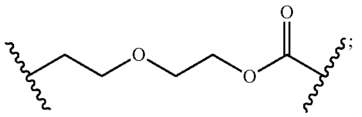

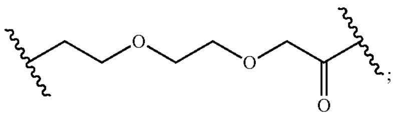

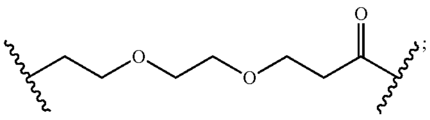

-continued

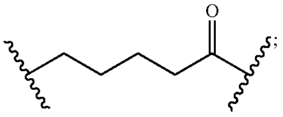

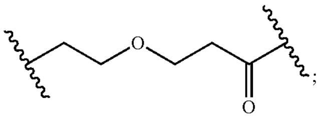

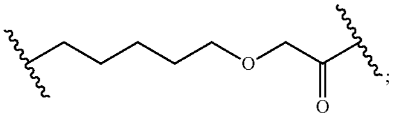

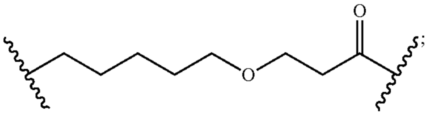

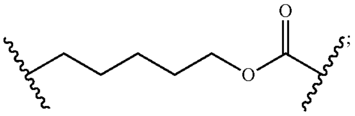

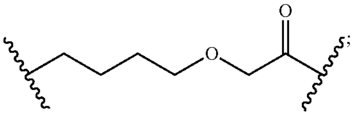

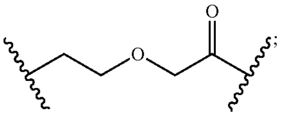

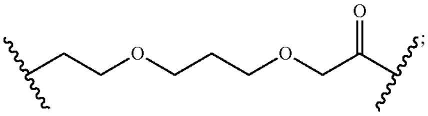

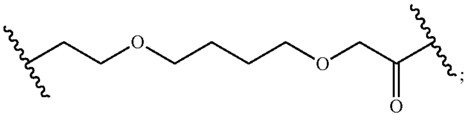

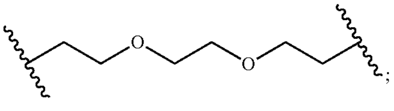

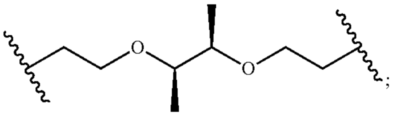

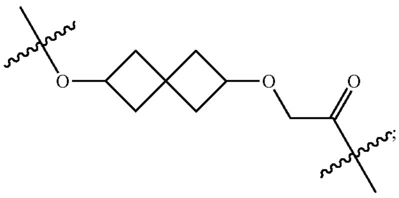

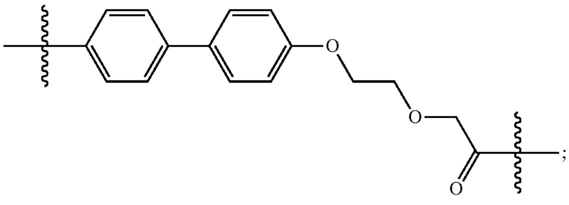

-continued

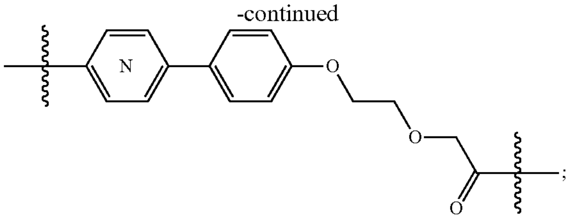

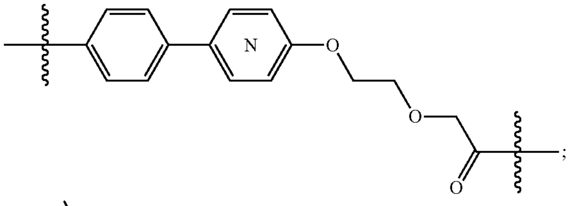

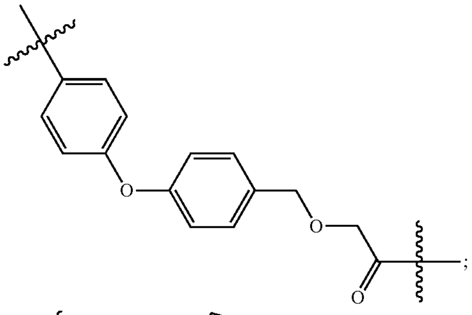

and

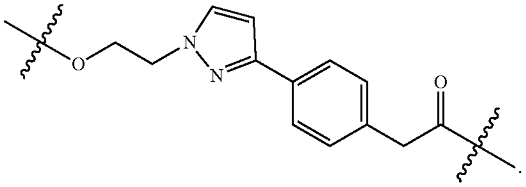

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

Although the CLM (or ULM) group and PTM group may be covalently linked to the linker group through any group which is appropriate and stable to the chemistry of the linker, in preferred aspects of the present disclosure, the linker is independently covalently bonded to the CLM group and the PTM group preferably through an amide, ester, thioester, keto group, carbamate (urethane), carbon or ether, each of which groups may be inserted anywhere on the CLM group and PTM group to provide maximum binding of the CLM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the CLM and/or PTM groups.

In certain embodiments, "L" can be linear chains with linear atoms from 4 to 24, the carbon atom in the linear chain can be substituted with oxygen, nitrogen, amide, fluorinated carbon, etc., such as the following:

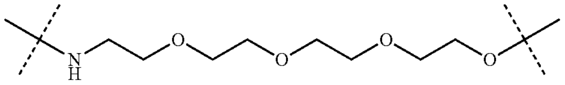
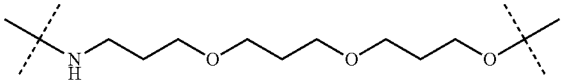
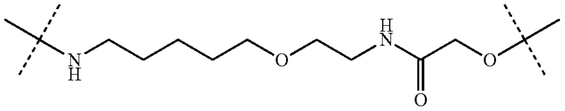
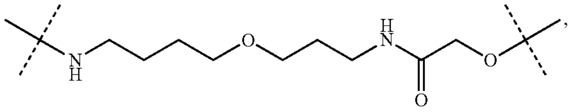
,
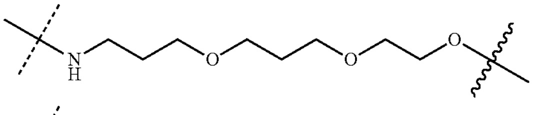
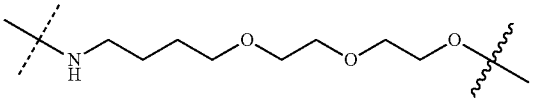
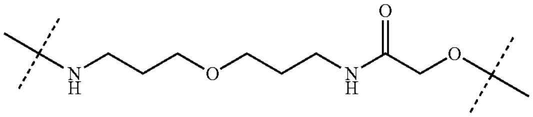
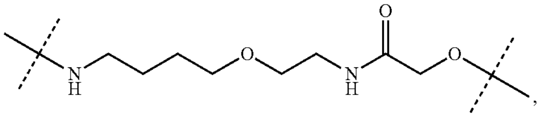
,
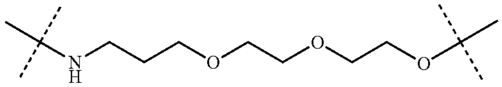
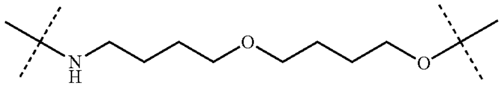
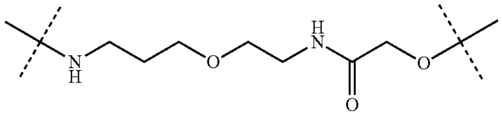
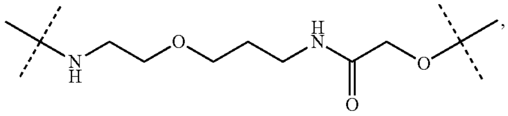
,
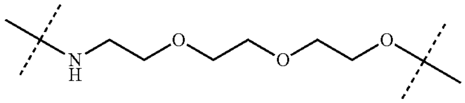
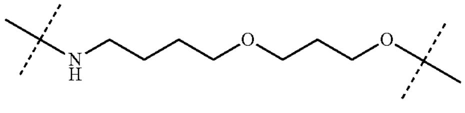

-continued

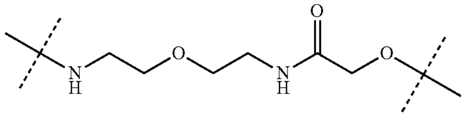
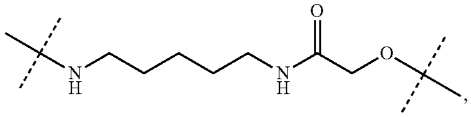
,
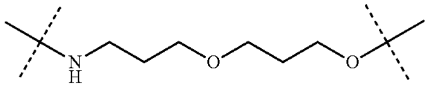
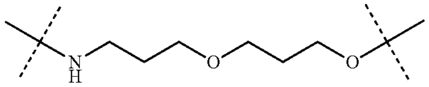
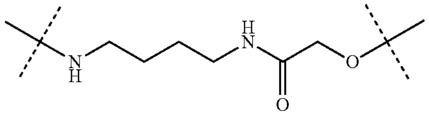
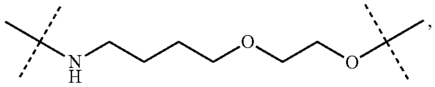
,
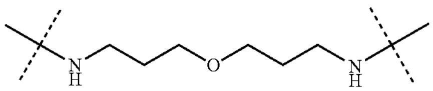
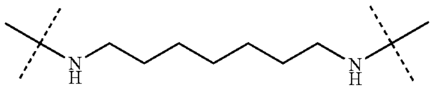
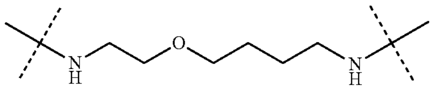
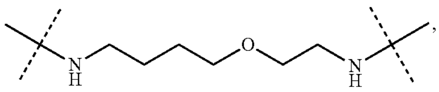
, or
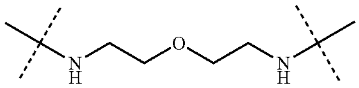
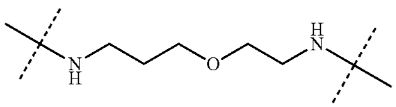
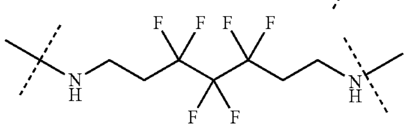
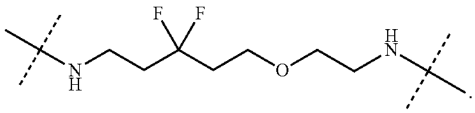
.

In certain embodiments, "L" can be nonlinear chains, and can be aliphatic or aromatic or heteroaromatic cyclic moieties, some examples of "L" include but not be limited to the following:

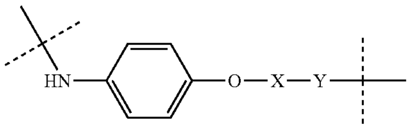

-continued

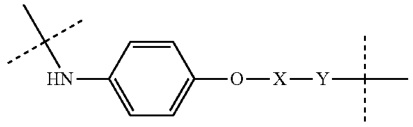

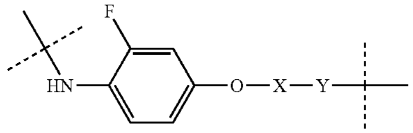

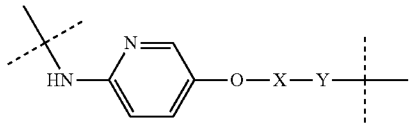

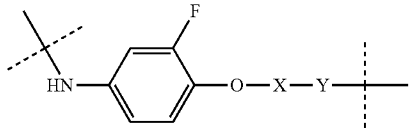

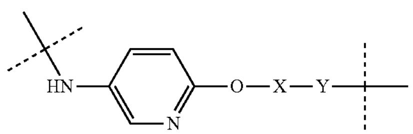

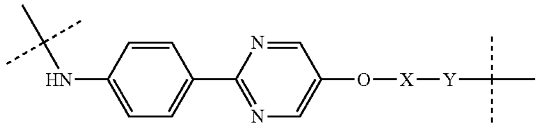

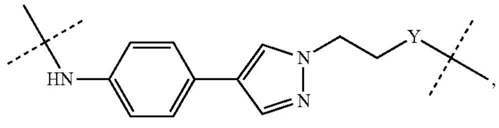

,

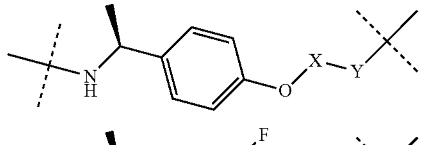

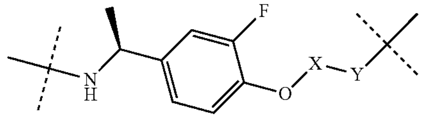

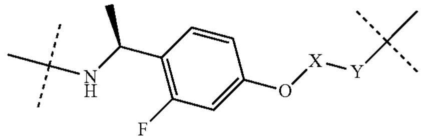

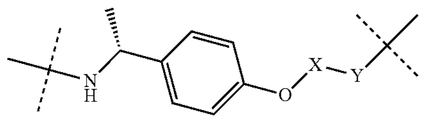

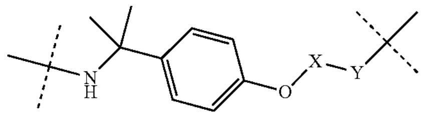

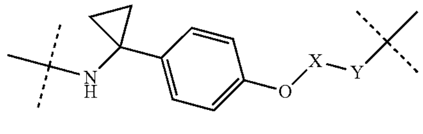

-continued

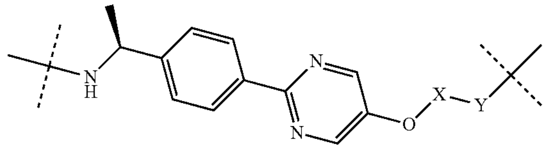

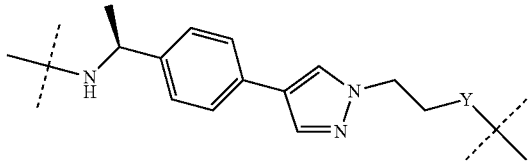

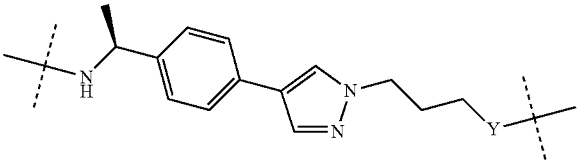

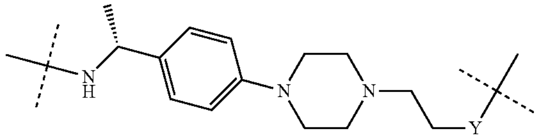

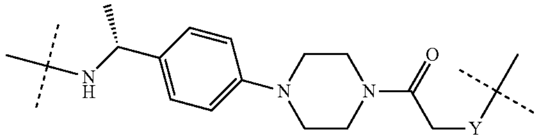

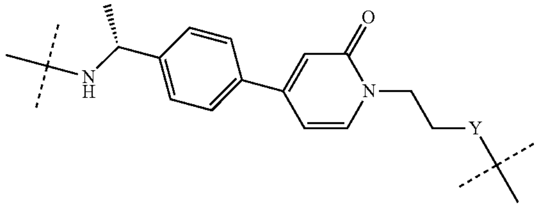

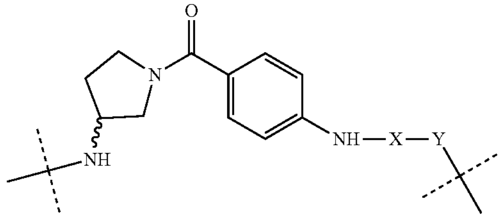

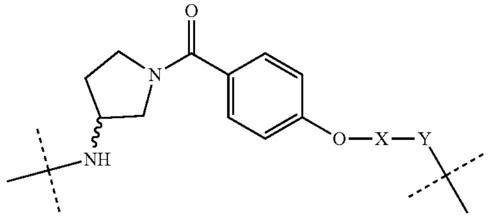

wherein:

"X" in above structures can be linear chain with atoms ranging from 2 to 14, and the mentioned chain can contain heteroatoms such as oxygen; and "Y" in above structures can be O, N, $S(O)_n$ (n=0, 1,2).

Exemplary PTMs

In preferred aspects of the present disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein. In certain aspects, the protein binding moiety is a haloalkane (preferably a $C_1$-$C_{10}$ alkyl group which is substituted with at least one halo group, preferably a halo group at the distal end of the alkyl group, i.e., away from the linker or CLM group), which may covalently bind to a dehalogenase enzyme in a patient or subject or in a diagnostic assay.

PTM groups according to the present disclosure include, for example, include any moiety which binds to a protein specifically (binds to a target protein) and includes the following non-limiting examples of small molecule target protein moieties: Hsp90 inhibitors, kinase inhibitors, androgen receptor inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of these nine types of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by a ubiquitin ligase is a target protein according to the present disclosure. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others.

In still other embodiments, the PTM group is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PT, groups for use in the present disclosure are preferably represented by the chemical structure $—(CH_2)_v$-Halo where v is any integer from 2 to about 12, often about 3 to about 8, more often about 4 to about 6. Halo may be any halogen, but is preferably Cl or Br, more often Cl.

In another embodiment, the present disclosure provides a library of compounds. The library comprises more than one compound wherein each composition has a formula of A-B, wherein A is a ubiquitin pathway protein binding moiety (preferably, an E3 ubiquitin ligase moiety as otherwise disclosed herein) and B is a protein binding member of a molecular library, wherein A is coupled (preferably, through a linker moiety) to B, and wherein the ubiquitin pathway protein binding moiety recognizes an ubiquitin pathway protein, in particular, an E3 ubiquitin ligase, such as cereblon. In a particular embodiment, the library contains a specific cereblon E3 ubiquitin ligase binding moiety bound to random target protein binding elements (e.g., a chemical compound library). As such, the target protein is not determined in advance and the method can be used to determine the activity of a putative protein binding element and its pharmacological value as a target upon degradation by ubiquitin ligase.

The present disclosure may be used to treat a number of disease states and/or conditions, including any disease state and/or condition in which proteins are dysregulated and where a patient would benefit from the degradation of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer (such as prostate cancer) and Kennedy's Disease. In certain additional embodiments, the disease is prostate cancer.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to CLM or ULM groups through linker groups L.

Target proteins which may be bound to the protein target moiety and degraded by the ligase to which the ubiquitin ligase binding moiety is bound include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. In certain embodiments, the target proteins include structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others.

More specifically, a number of drug targets for human therapeutics represent protein targets to which protein target moiety may be bound and incorporated into compounds according to the present disclosure. These include proteins which may be used to restore function in numerous polygenic diseases, including for example B7.1 and B7, TINFR1m, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, Ras1Raf1MEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors (AR), adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase F1k-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

Haloalkane dehalogenase enzymes are another target of specific compounds according to the present disclosure. Compounds according to the present disclosure which contain chloroalkane peptide binding moieties ($C_1$-$C_{12}$ often about $C_2$-$C_{10}$ alkyl halo groups) may be used to inhibit and/or degrade haloalkane dehalogenase enzymes which are used in fusion proteins or related dioagnostic proteins as described in PCT/US2012/063401 filed Dec. 6, 2011 and published as WO 2012/078559 on Jun. 14, 2012, the contents of which is incorporated by reference herein.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of these nine types of small molecule target protein.

Exemplary protein target moieties according to the present disclosure include, haloalkane halogenase inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited hereinbelow are incorporated by reference herein in their entirety.

I. Heat Shock Protein 90 (HSP90) Inhibitors:

HSP90 inhibitors as used herein include, but are not limited to:

1. The HSP90 inhibitors identified in Vallee, et al., "Tricyclic Series of Heat Shock Protein 90 (HSP90) Inhibitors Part I: Discovery of Tricyclic Imidazo[4,5-C]Pyridines as Potent Inhibitors of the HSP90 Molecular Chaperone (2011) *J. Med. Chem.* 54: 7206, including YKB (N-[4-(3H-imidazo [4,5-C]Pyridin-2-yl)-9H-Fluoren-9-yl]-succinamide):

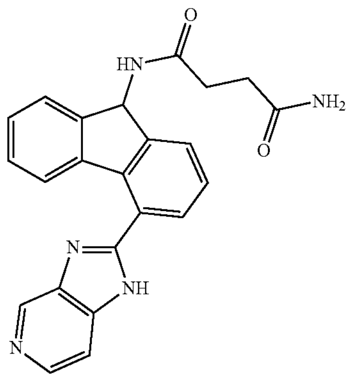 [SMILES: NC(=O)CCC(=O)NC1c2ccccc2-c2c(-c3nc4cnccc4[nH]3)cccc21]

derivatized where a linker group L or a –(L-CLM) group is attached, for example, via the terminal amide group;

2. The HSP90 inhibitor p54 (modified) (8-[(2,4-dimethylphenyl)sulfanyl]-3]pent-4-yn-1-yl-3H-purin-6-amine):

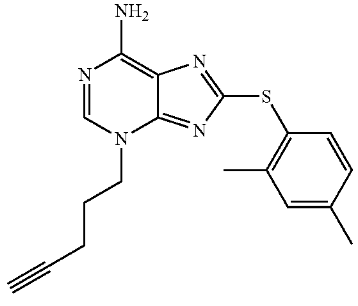 [SMILES: C#CCCCn1cnc(N)c2nc(Sc3ccc(C)cc3C)nc1-2]

derivatized where a linker group L or a -(L-CLM) group is attached, for example, via the terminal acetylene group;

3. The HSP90 inhibitors (modified) identified in Brough, et al., "4,5-Diarylisoxazole HSP90 Chaperone Inhibitors: Potential Therapeutic Agents for the Treatment of Cancer", *J. MED. CHEM.* vol: 51, pag: 196 (2008), including the compound 2GJ (5-[2,4-dihydroxy-5-(1-methylethyl)phenyl]-n-ethyl-4-[4-(morpholin-4-ylmethyl)phenyl]isoxazole-3-carboxamide) having the structure:

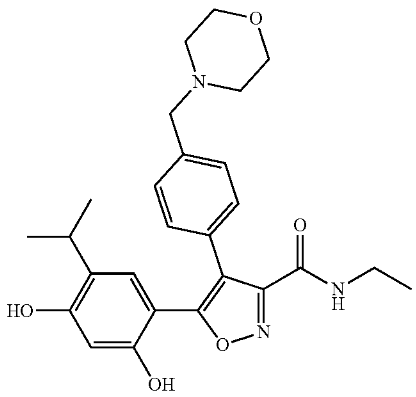 [SMILES: CCNC(=O)c1noc(-c2cc(C(C)C)c(O)cc2O)c1-c1ccc(CN2CCOCC2)cc1]

derivatized, where a linker group L or a –(L-CLM) group is attached, for example, via the amide group (at the amine or at the alkyl group on the amine);

4. The HSP90 inhibitors (modified) identified in Wright, et al., Structure-Activity Relationships in Purine-Based Inhibitor Binding to HSP90 Isoforms, *Chem Biol.* 2004 June; 11(6):775-85, including the HSP90 inhibitor PU3 having the structure:

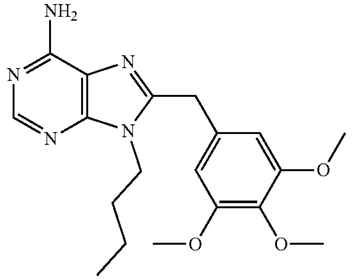 [SMILES: CCCCn1c(Cc2cc(OC)c(OC)c(OC)c2)nc2c(N)ncnc21]

derivatized where a linker group L or -(L-CLM) is attached, for example, via the butyl group; and 5. The HSP90 inhibitor geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] (derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")) (derivatized, where a linker group L or a-(L-CLM) group is attached, for example, via the amide group).

II. Kinase and Phosphatase Inhibitors:

Kinase inhibitors as used herein include, but are not limited to:

1. Erlotinib Derivative Tyrosine Kinase Inhibitor:

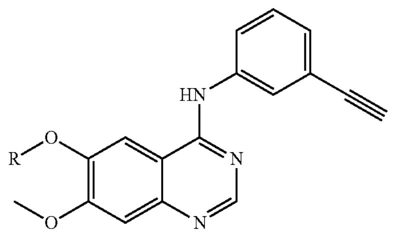

where R is a linker group L or a -(L-CLM) group attached, for example, via the ether group;

2. The kinase inhibitor sunitinib (derivatized):

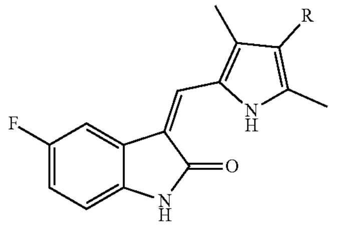

derivatized where R is a linker group L or a –(L-CLM) group attached, for example, to the pyrrole moiety;

3. Kinase Inhibitor sorafenib (derivatized):

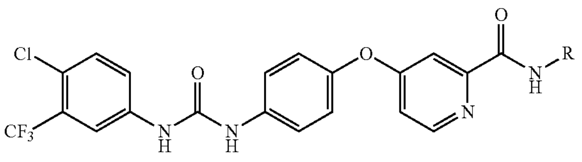

derivatized where R is a linker group L or a -(L-CLM) group attached, for example, to the amide moiety;

4. The kinase inhibitor desatinib (derivatized):

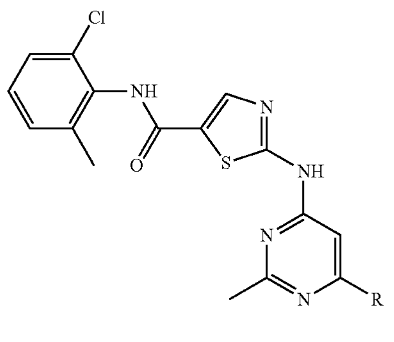

derivatized where R is a linker group L or a –(L-CLM) attached, for example, to the pyrimidine;

5. The kinase inhibitor lapatinib (derivatized):

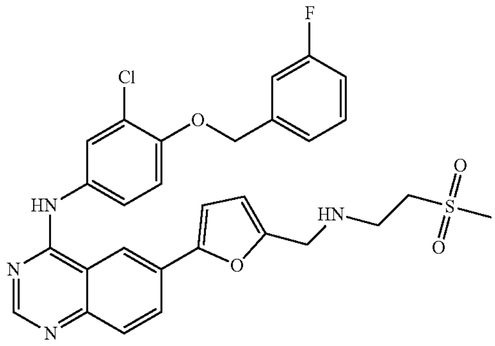 [SMILES: CS(=O)(=O)CCNCc1ccc(-c2ccc3ncnc(Nc4ccc(OCc5cccc(F)c5)c(Cl)c4)c3c2)o1]

derivatized where a linker group L or a –(L-CLM) group is attached, for example, via the terminal methyl of the sulfonyl methyl group;

6. The kinase inhibitor U09-CX-5279 (derivatized):

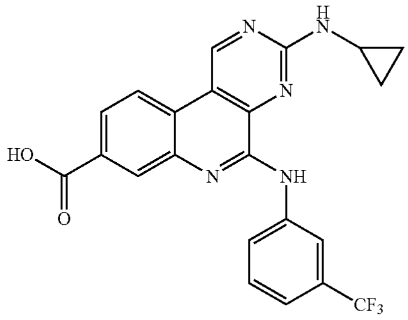 [SMILES: O=C(O)c1ccc2c(c1)nc(Nc1cccc(C(F)(F)F)c1)c1nc(NC3CC3)ncc12]

derivatized where a linker group L or a –(L-CLM) group is attached, for example, via the amine (aniline), carboxylic acid or amine alpha to cyclopropyl group, or cyclopropyl group;

7. The kinase inhibitors identified in Millan, et al., Design and Synthesis of Inhaled P38 Inhibitors for the Treatment of Chronic Obstructive Pulmonary Disease, *J. MED. CHEM.* vol: 54, pag: 7797 (2011), including the kinase inhibitors Y1W and Y1X (Derivatized) having the structures:

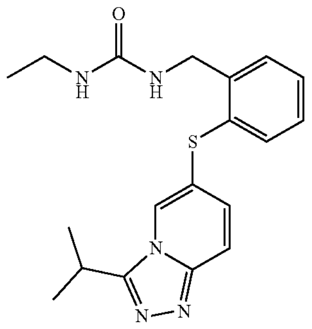 [SMILES: CCNC(=O)NCc1ccccc1Sc1ccc2nnc(C(C)C)n2c1]

YIX(1-ethyl-3-(2-{[3-(1-methylethyl)[1,2,4]triazolo[4,3-a]pyridine-6-yl]sulfanyl}benzyl)urea, derivatized where a linker group L or a-(L-CLM) group is attached, for example, via the $^{i}$propyl group;

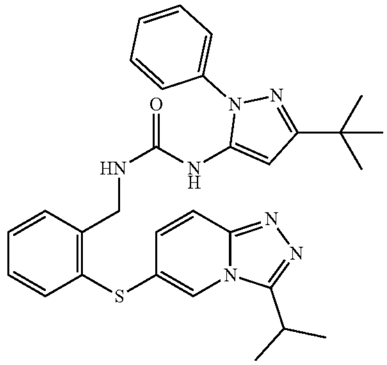 [SMILES: CC(C)c1nnc2ccc(Sc3ccccc3CNC(=O)Nc3cc(C(C)(C)C)nn3-c3ccccc3)cn12]

YIW 1-(3-tert-butyl-1-phenyl-1H-pyrazol-5-yl)-3-(2-{[3-(1-methylethyl)[1,2,4]triazolo[4,3-a]pyridin-6-yl] sulfanyl}benzyl)urea derivatized where a linker group L or a -(L-CLM) group is attached, for example, preferably via either the i-propyl group or the t-butyl group;

8. The kinase inhibitors identified in Schenkel, et al., Discovery of Potent and Highly Selective Thienopyridine Janus Kinase 2 Inhibitors *J. Med. Chem.*, 2011, 54 (24), pp 8440-8450, including the compounds 6TP and 0TP (Derivatized) having the structures:

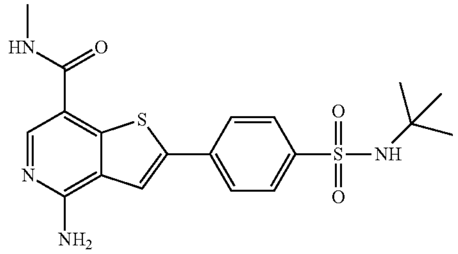 [SMILES: CNC(=O)c1cnc(N)c2cc(-c3ccc(S(=O)(=O)NC(C)(C)C)cc3)sc12]

6TP 4-amino-2-[4-(tert-butylsulfamoyl)phenyl]-N-methylthieno[3,2-c]pyridine-7-carboxamide Thienopyridine 19 derivatized where a linker group L or a -(L-CLM) group is attached, for example, via the terminal methyl group bound to amide moiety;

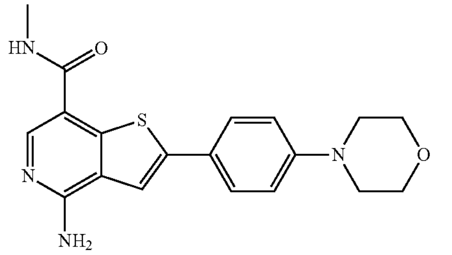 [SMILES: CNC(=O)c1cnc(N)c2cc(-c3ccc(N4CCOCC4)cc3)sc12]

0TP 4-amino-N-methyl-2-[4-(morpholin-4-yl)phenyl]thieno [3,2-c]pyridine-7-carboxamide Thienopyridine 8 derivatized where a linker group L or a –(L-CLM)group is attached, for example, via the terminal methyl group bound to the amide moiety;

9. The kinase inhibitors identified in Van Eis, et al., "2,6-Naphthyridines as potent and selective inhibitors of the novel protein kinase C isozymes", *Biorg. Med. Chem. Lett.* 2011 Dec. 15; 21(24):7367-72, including the kinase inhibitor 07U having the structure:

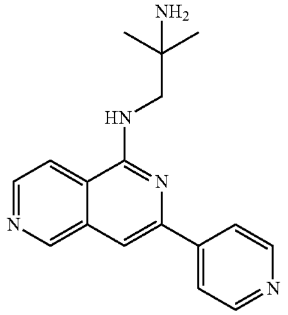 [SMILES: CC(C)(N)CNc1nc(-c2ccncc2)cc2cnccc12]

07U 2-methyl-N~1~-[3-(pyridin-4-yl)-2,6-naphthyridin-1-yl] propane-1,2-diamine derivatized where a linker group L or a –(L-CLM)group is attached, for example, via the secondary amine or terminal amino group;

10. The kinase inhibitors identified in Lountos, et al., "Structural Characterization of Inhibitor Complexes with Checkpoint Kinase 2 (Chk2), a Drug Target for Cancer Therapy", *J. STRUCT. BIOL.* vol: 176, pag: 292 (2011), including the kinase inhibitor YCF having the structure:

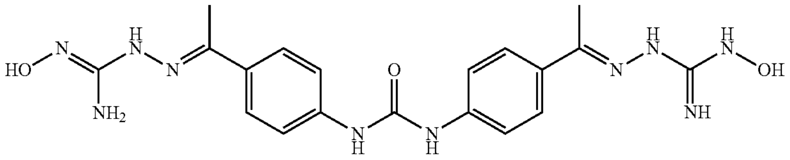 [SMILES: C/C(=N\NC(=N)NO)c1ccc(NC(=O)Nc2ccc(/C(C)=N/N/C(N)=N/O)cc2)cc1]

derivatized where a linker group L or a -(L-CLM) group is attached, for example, via either of the terminal hydroxyl groups;

11. The kinase inhibitors identified in Lountos, et al., "Structural Characterization of Inhibitor Complexes with Checkpoint Kinase 2 (Chk2), a Drug Target for Cancer Therapy", *J. STRUCT. BIOL.* vol: 176, pag: 292 (2011), including the kinase inhibitors XK9 and NXP (derivatized) having the structures:

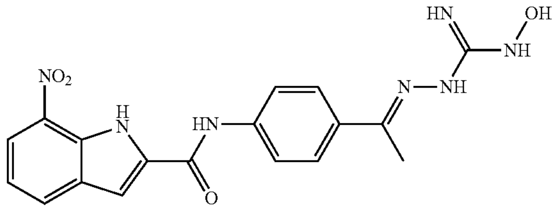 [SMILES: C/C(=N\NC(=N)NO)c1ccc(NC(=O)c2cc3cccc([N+](=O)[O-])c3[nH]2)cc1]

XK9

N-{4-[(1E)-N—(N-hydroxycarbamimidoyl)ethanehydrazonoyl]phenyl}-7-nitro-1H-indole-2-carboxamide;

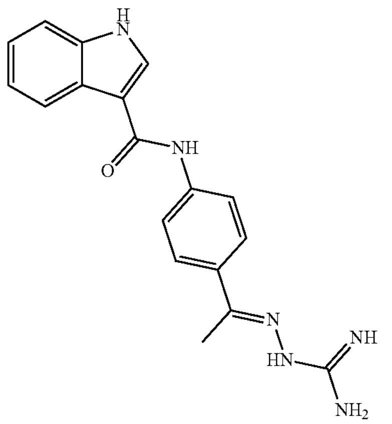 [SMILES: C/C(=N\NC(=N)N)c1ccc(NC(=O)c2c[nH]c3ccccc23)cc1]

NXP

N-{4-[(1E)-N-CARBAMIMIDOYLETHANEHYDRAZONOYL]PHENYL}-1H-INDOLE-3-CARBOXAMIDE derivatized where a linker group L or a -(L-CLM) group is attached, for example, via the terminal hydroxyl group (XK9) or the hydrazone group (NXP);

12. The kinase inhibitor afatinib (derivatized) (N-[4-[(3-chloro-4-fluorophenyl)amino]-7-[[(3S)-tetrahydro-3-furanyl]oxy]-6-quinazolinyl]-4(dimethylamino)-2-butenamide) (Derivatized where a linker group L or a -(L-CLM) group is attached, for example, via the aliphatic amine group);

13. The kinase inhibitor fostamatinib (derivatized) ([6-({5-fluoro-2-[(3,4,5-trimethoxyphenyl)amino]pyrimidin-4-yl}amino)-2,2-dimethyl-3-oxo-2,3-dihydro-4H-pyrido[3,2-b]-1,4-oxazin-4-yl]methyl disodium phosphate hexahydrate) (Derivatized where a linker group L or a -(L-CLM) group is attached, for example, via a methoxy group);

14. The kinase inhibitor gefitinib (derivatized) (N-(3-chloro-4-fluoro-phenyl)-7-methoxy-6-(3-morpholin-4-yl-propoxy)quinazolin-4-amine):

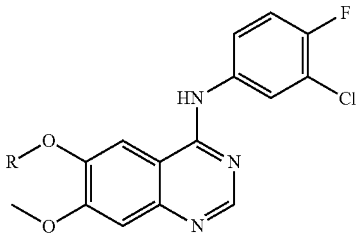

derivatized where a linker group L or a –(L-CLM) group is attached, for example, via a methoxy or ether group;

15. The kinase inhibitor lenvatinib (derivatized) (4-[3-chloro-4-(cyclopropylcarbamoylamino)phenoxy]-7-methoxy-quinoline-6-carboxamide) (derivatized where a linker group L or a -(L-CLM) group is attached, for example, via the cyclopropyl group);

16. The kinase inhibitor vandetanib (derivatized) (N-(4-bromo-2-fluorophenyl)-6-methoxy-7-[(1-methylpiperidin-4-yl)methoxy]quinazolin-4-amine) (derivatized where a linker group L or a -(L-CLM) group is attached, for example, via the methoxy or hydroxyl group);

17. The kinase inhibitor vemurafenib (derivatized) (propane-1-sulfonic acid {3-[5-(4-chlorophenyl)-1H-pyrrolo[2,3-b]pyridine-3-carbonyl]-2,4-difluoro-phenyl}-amide), derivatized where a linker group L or a -(L-CLM) group is attached, for example, via the sulfonyl propyl group;

18. The kinase inhibitor Gleevec (derivatized):

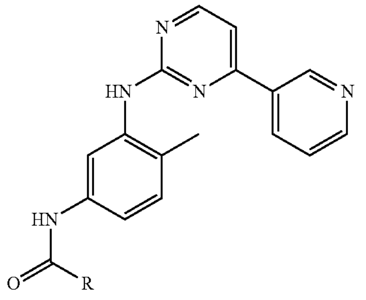

derivatized where R as a linker group L or a-(L-CLM) group is attached, for example, via the amide group or via the aniline amine group;

19. The kinase inhibitor pazopanib (derivatized) (VEGFR3 inhibitor):

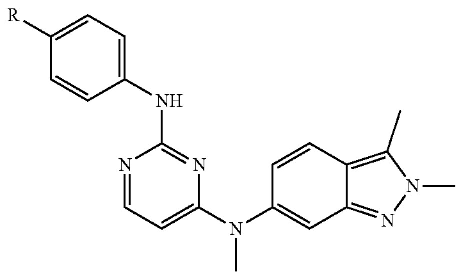

derivatized where R is a linker group L or a –(L-CLM) group attached, for example, to the phenyl moiety or via the aniline amine group;

20. The kinase inhibitor AT-9283 (Derivatized) Aurora Kinase Inhibitor

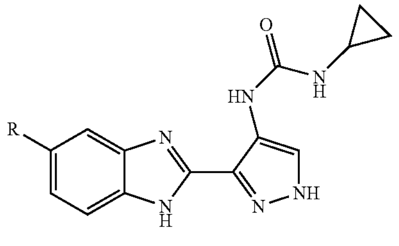

where R is a linker group L or a -(L-CLM) group attached, for example, to the phenyl moiety);

21. The kinase inhibitor TAE684 (derivatized) ALK inhibitor

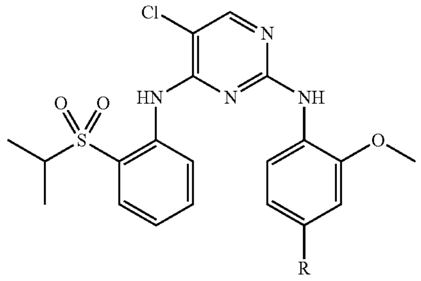

where R is a linker group L or a -(L-CLM) group attached, for example, to the phenyl moiety);

22. The kinase inhibitor nilotanib (derivatized) Abl inhibitor:

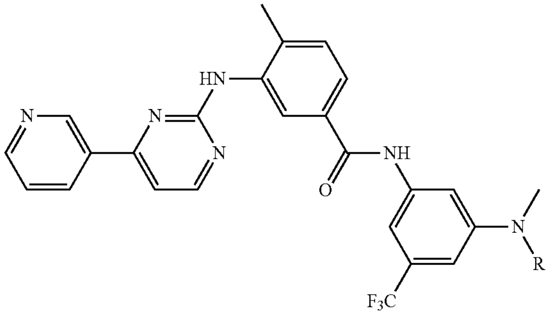

derivatized where R is a linker group L or a -(L-CLM) group attached, for example, to the phenyl moiety or the aniline amine group;

23. Kinase Inhibitor NVP-BSK805 (derivatized) JAK2 Inhibitor

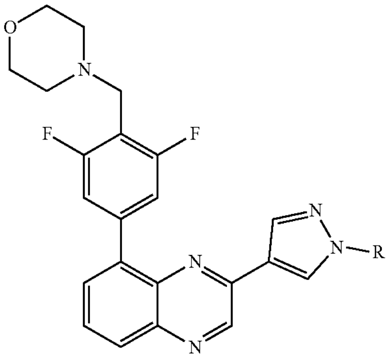

derivatized where R is a linker group L or a –(L-CLM) group attached, for example, to the phenyl moiety or the diazole group;

24. Kinase Inhibitor crizotinib Derivatized Alk Inhibitor

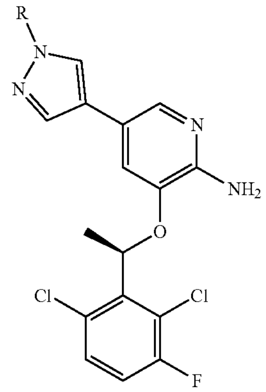

derivatized where R is a linker group L or a -(L-CLM) group attached, for example, to the phenyl moiety or the diazole group;

25. Kinase Inhibitor JNJ FMS (derivatized) Inhibitor

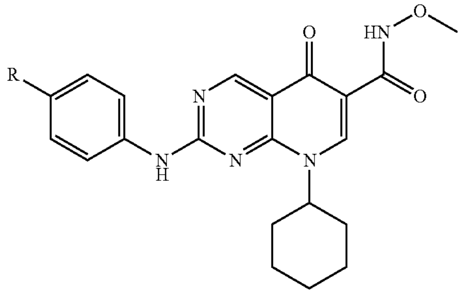

derivatized where R is a linker group L or a -(L-CLM) group attached, for example, to the phenyl moiety;

26. The kinase inhibitor foretinib (derivatized) Met Inhibitor

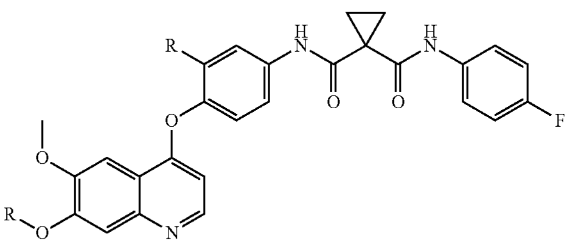

derivatized where R is a linker group L or a -(L-CLM)group attached, for example, to the phenyl moiety or a hydroxyl or ether group on the quinoline moiety;

27. The allosteric Protein Tyrosine Phosphatase Inhibitor PTP1B (derivatized):

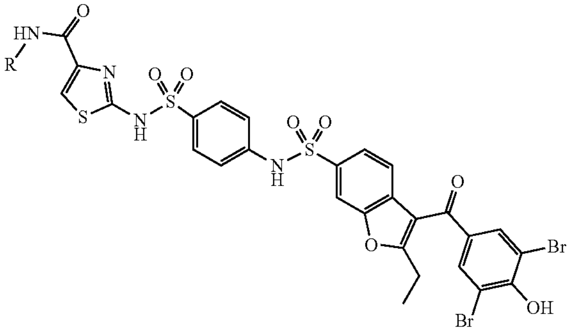

derivatized where a linker group L or a -(L-CLM) group is attached, for example, at R, as indicated;

28. The inhibitor of SHP-2 Domain of Tyrosine Phosphatase (derivatized):

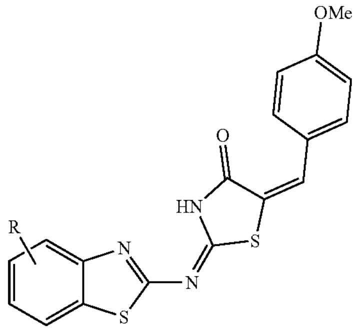

derivatized where a linker group L or a -(L-CLM) group is attached, for example, at R;

29. The inhibitor (derivatized) of BRAF ($BRAF^{V600E}$)/MEK:

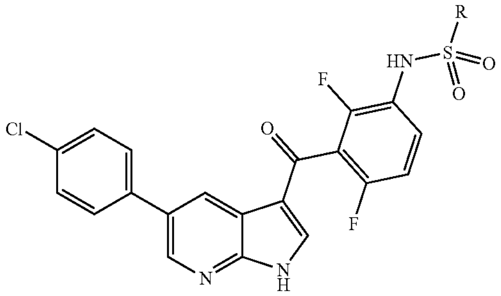

derivatized where a linker group L or a-(L-CLM) group is attached, for example, at R;

30. Inhibitor (derivatized) of Tyrosine Kinase ABL

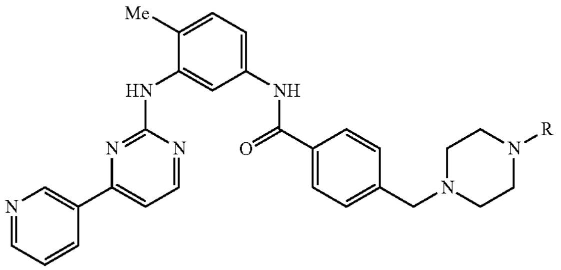

derivatized where a linker group L or a-(L-CLM) group is attached, for example, at R;

31. The kinase inhibitor OSI-027 (derivatized) mTORC1/2 inhibitor

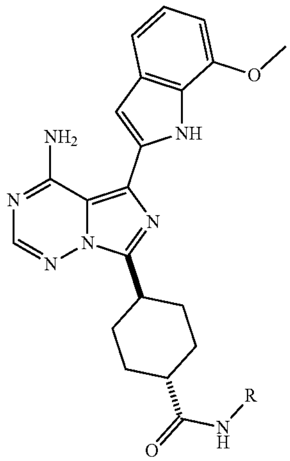

derivatized where a linker group L or a-(L-CLM) group is attached, for example, at R;

32. The kinase inhibitor OSI-930 (derivatized) c-Kit/KDR inhibitor

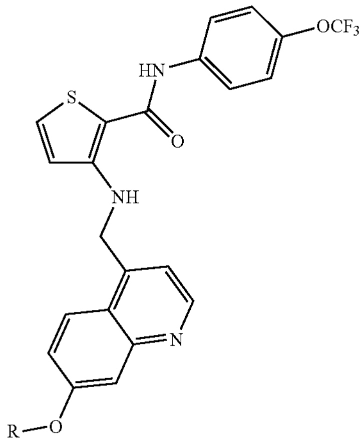

derivatized where a linker group L or a-(L-CLM) group is attached, for example, at R; and 33. The kinase inhibitor OSI-906 (derivatized) IGF1R/IR inhibitor

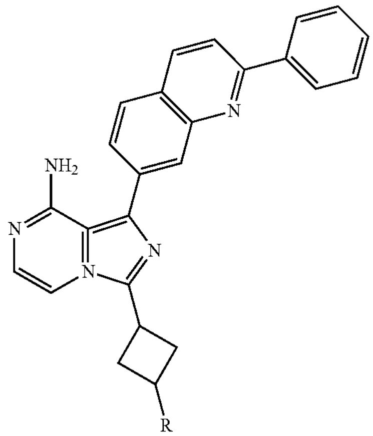

derivatized where a linker group L or a-(L-CLM) group is attached, for example, at R.

Wherein, in any of the embodiments described in sections I-XVII, "R" designates a site for attachment of a linker group L or a -(L-CLM)group on the piperazine moiety.

III. HDM2/MDM2 Inhibitors:

HDM2/MDM2 inhibitors as used herein include, but are not limited to:

1. The HDM2/MDM2 inhibitors identified in Vassilev, et al., In vivo activation of the p53 pathway by small-molecule antagonists of MDM2, *SCIENCE vol:* 303, pag: 844-848 (2004), and Schneekloth, et al., Targeted intracellular protein degradation induced by a small molecule: En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

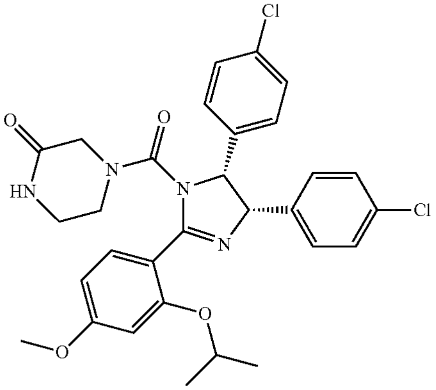 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-CLM)group is attached, for example, at the methoxy group or as a hydroxyl group);

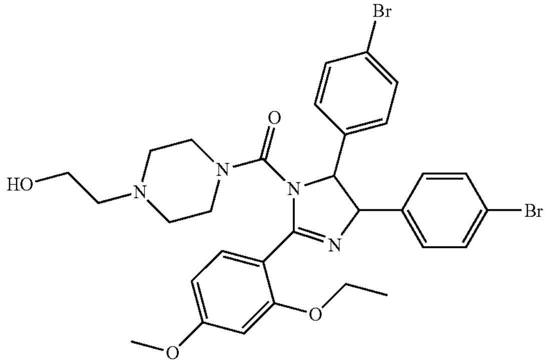 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-CLM) group is attached, for example, at the methoxy group or hydroxyl group);

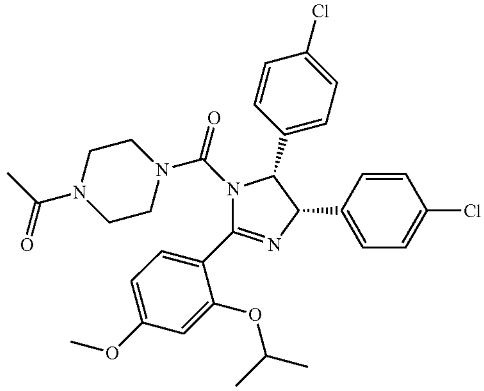 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-CLM) group is attached, for example, via the methoxy group or as a hydroxyl group); and 2. Trans-4-Iodo-4'-Boranyl-Chalcone

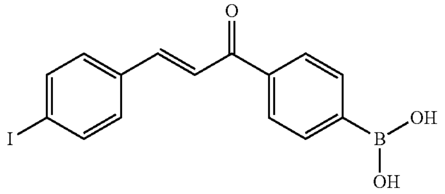 [SMILES: O=C(/C=C/c1ccc(I)cc1)c1ccc(B(O)O)cc1]

(derivatized where a linker group L or a a linker group L or a-(L-CLM) group is attached, for example, via a hydroxy group).

IV. Compounds Targeting Human BET Bromodomain-Containing Proteins:

In certain embodiments, "PTM" can be ligands binding to Bromo- and Extra-terminal (BET) proteins BRD2, BRD3 and BRD4. Compounds targeting Human BET Bromodomain-containing proteins include, but are not limited to the compounds associated with the targets as described below, where "R" or "linker" designates a site for linker group L or a-(L-CLM) group attachment, for example:

1. JQ1, Filippakopoulos et al. Selective inhibition of BET bromodomains. *Nature* (2010):

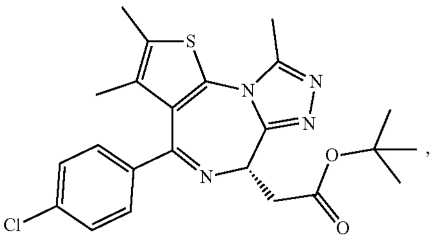
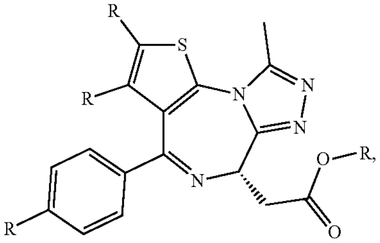
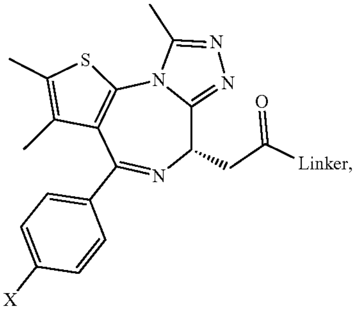
X = Cl, Br, F, H
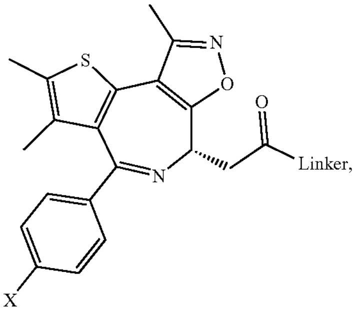
X = Cl, Br, F, H
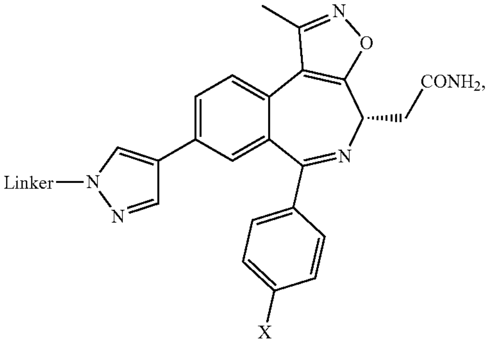
X = Cl, Br, F, H
-continued
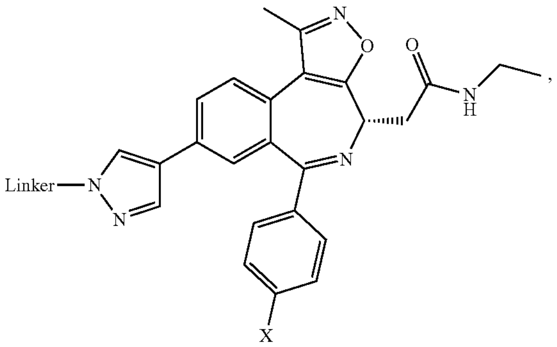
X = Cl, Br, F, H
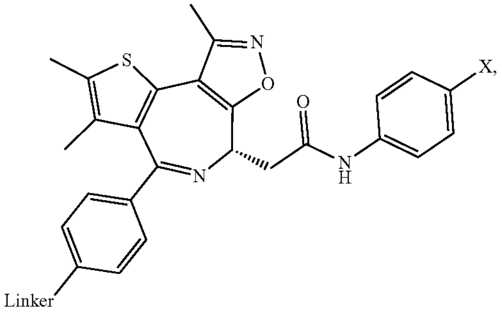
or
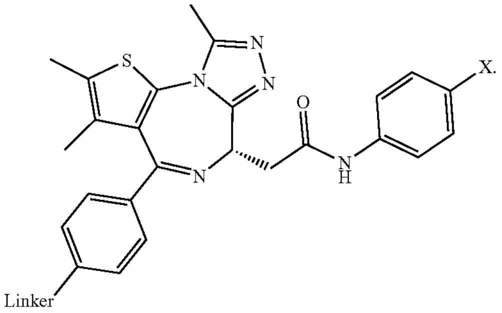
X = H, F
2. I-BET, Nicodeme et al. Supression of Inflammation by a Synthetic Histone Mimic. *Nature* (2010). Chung et al. Discovery and Characterization of Small Molecule Inhibitors of the BET Family Bromodomains. J. Med Chem. (2011):
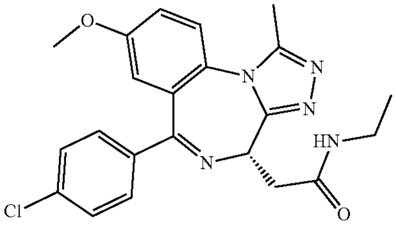

-continued
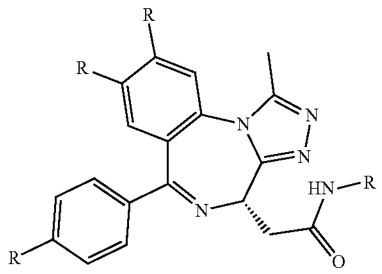
3. Compounds described in Hewings et al. 3,5-Dimethylisoxazoles Act as Acetyl-lysine Bromodomain Ligands. J. Med. Chem. (2011) 54 6761-6770.
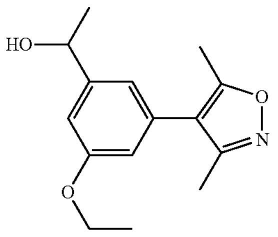
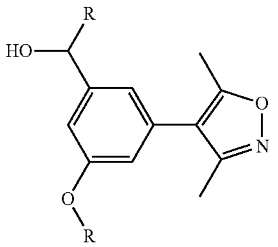
4. I-BET151, Dawson et al. Inhibition of BET Recruitment to Chromatin as an Efective Treatment for MLL-fusion Leukemia. Nature (2011):
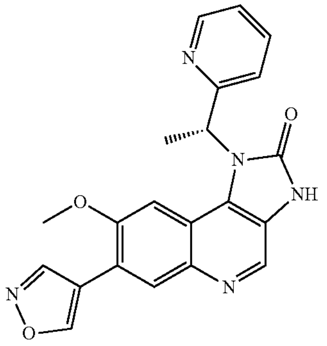
-continued
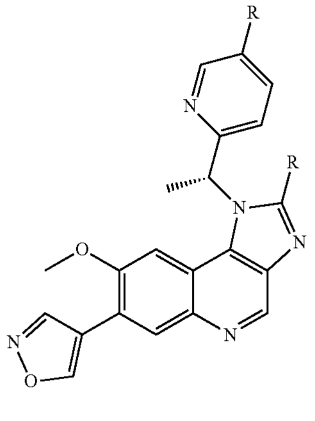
5. Carbazole type (US 2015/0256700)
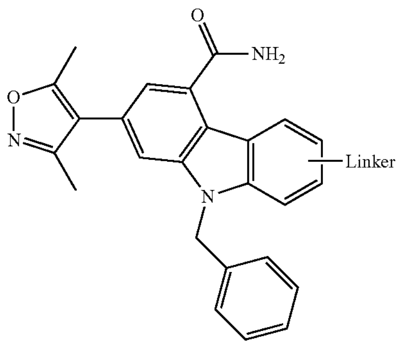
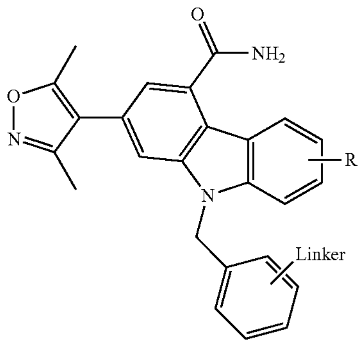
6. Pyrrolopyridone type (US 2015/0148342)
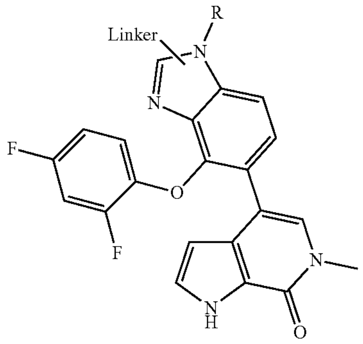

-continued

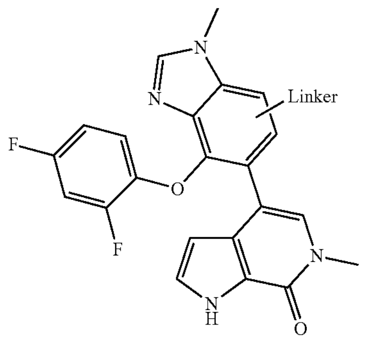

7. Tetrahydroquinoline type (WO 2015/074064)

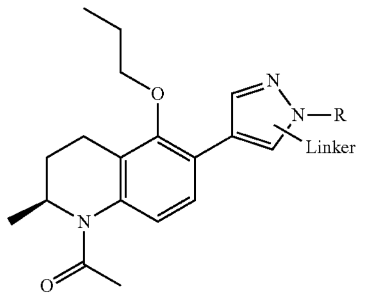

8. Triazolopyrazine type (WO 2015/067770)

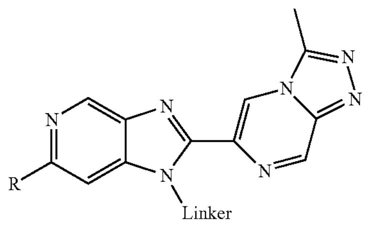

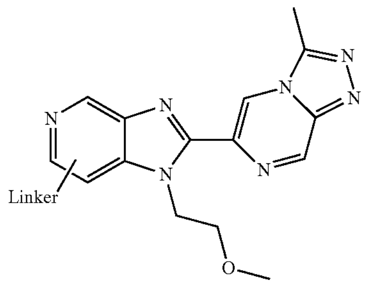

9. Pyridone type (WO 2015/022332)

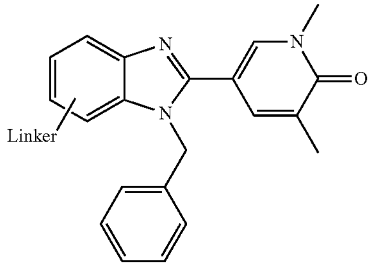

10. Quinazolinone type (WO 2015/015318)

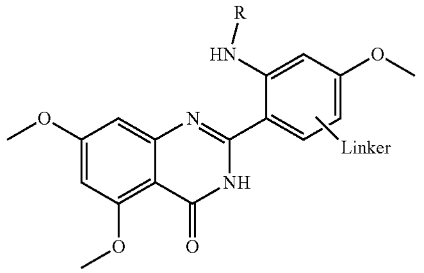

11. Dihydropyridopyrazinone type (WO 2015/011084)

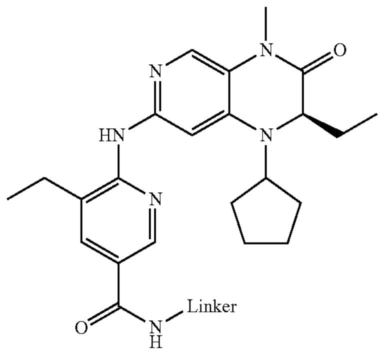

(Where R or L or linker, in each instance, designates a site for attachment, for example, of a linker group L or a -(L-CLM) group).

In any aspect or embodiment described herein, the claimed structure the PTM may be composed of tricyclic diazepine or tricyclic azepine as BET/BRD4 ligand (PTM-a), where the dashed lines indicate the linker connection trajectory and three sites are defined to which linkers may be attached:

PTM-a

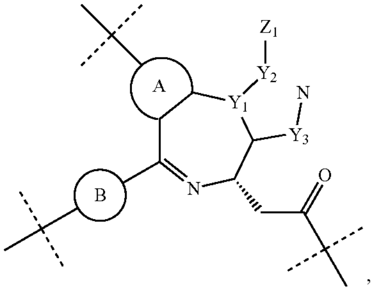

, wherein:

A and B are independently an aromatic ring, a heteroaromatic ring, a 5-membered carbocyclic, a 6-membered carbocyclic, a 5-membered heterocyclic, a 6-membered heterocyclic, a thiophene, a pyrrole, a pyrazole, a pyridine, a pyrimidine, a pyrazine, optionally substituted by alkyl, aloxy, halogen, nitrile or another aromatic or heteroaromatic ring, where A is fused to the central azepine (Y1=C) or diazepine (Y1=N) moiety;

Y1, Y2, and Y3 and Y4 can be carbon, nitrogen or oxygen for to form a fused 5-membered aromatic ring as triazole or isoxazole; and Z1 is methyl, or lower alkyl group.

The fragment of PTM-a as BET/BRD4 ligand is described in the literature (WO 2016/069578; WO2014/001356; WO2016/050821; WO 2015/195863; WO 2014/128111).

In any aspect or embodiment described herein comprising the structure CLM-L-PTM-a, PTM-a can be represented by the following general structures, where dashed line indicates a possible linker connection point. In structure PTM-aa through PTM-ai, the substitution pattern of X and Y can be mono- or bis-substitution.

PTM-aa

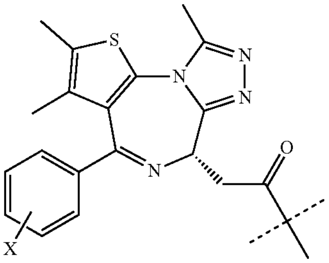

X=Cl, F, Br, H, CN, methyl, acetylene, methoxy

PTM-ab

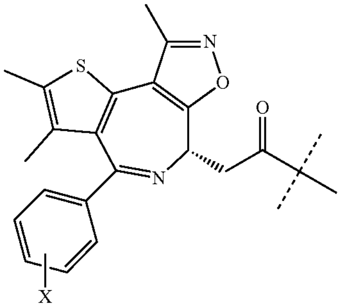

X=Cl, F, Br, H, CN, methyl, acetylene, methoxy

PTM-ac

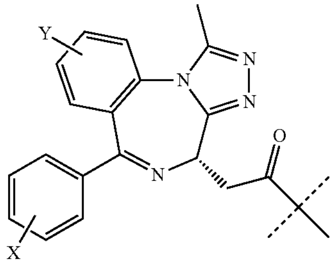

X=Cl, F, Br, H, CN, methyl, methoxy, acetylene

Y: mono- or di-substitution, Y=Me, OMe, N-methylpyrazole/imidazole

PTM-ad

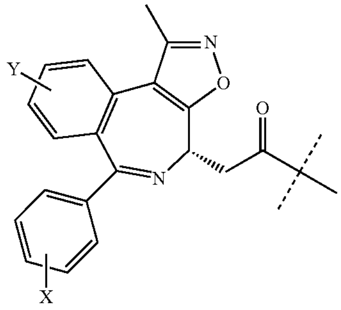

X=Cl, F, Br, H, CN, methyl, methoxy, acetylene

Y: mono- or di-substitution, Y=Me, OMe, N-methylpyrazole/imidazole

PTM-ae

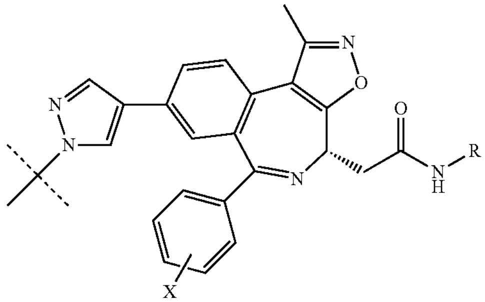

X=Cl, F, Br, H, CN, methyl, methoxy, acetylene

R=lower alkyl, aryl, substituted aryl

PTM-af

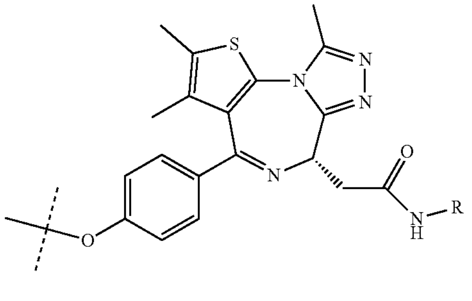

R=lower alkyl, aryl, substituted aryl

PTM-ag

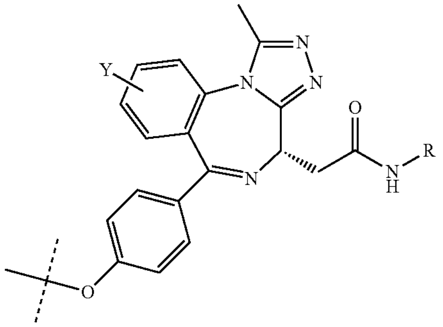

Y: mono- or di-substitution, Y=Me, OMe, N-methylpyrazole/imidazole
R=lower alkyl, aryl, substituted aryl PTM-ah

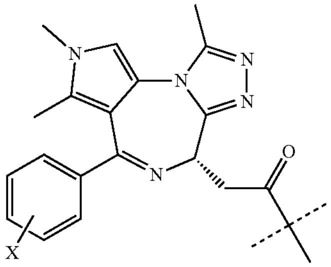

X=Cl, F, Br, H, CN, methyl, acetylene, methoxy

PTM-ai

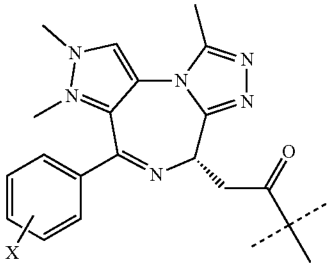

X=Cl, F, Br, H, CN, methyl, acetylene, methoxy

In any aspect or embodiment described herein, the structures of PTM-a as the BET/BRD4 ligand includes, wherein the dashed line indicates the connection point between BET/BRD4 ligand and the linkers:

PTM-a1

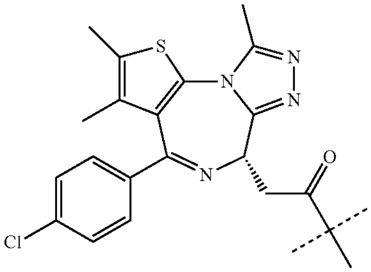

PTM-a2

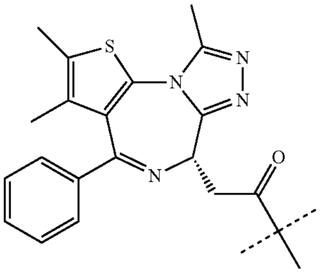

PTM-a3

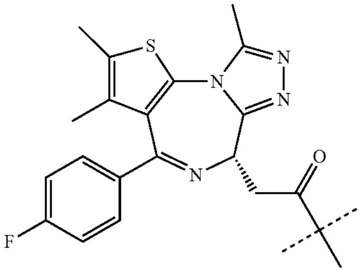

PTM-a4

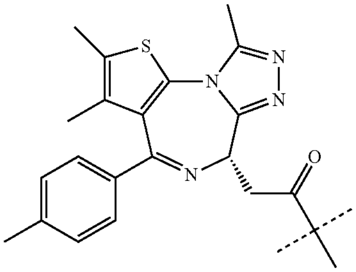

PTM-a5

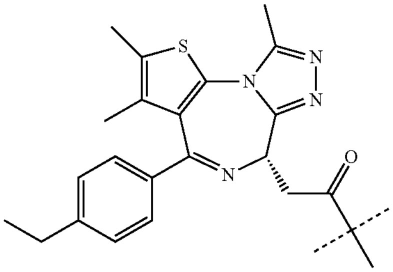

-continued
PTM-a6
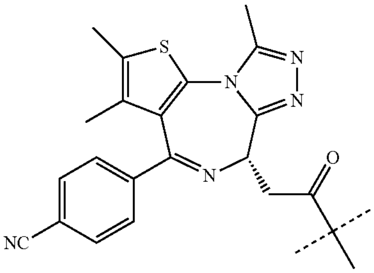
PTM-a7
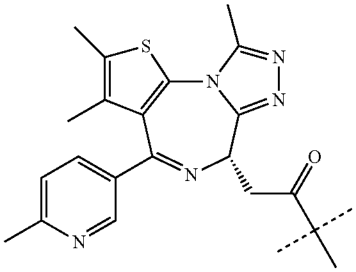
PTM-a8
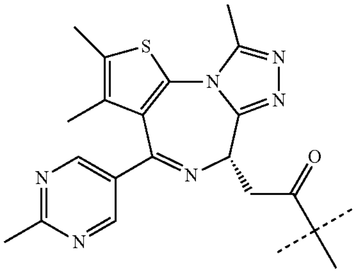
PTM-a9
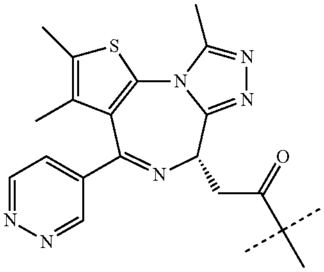
PTM-a10
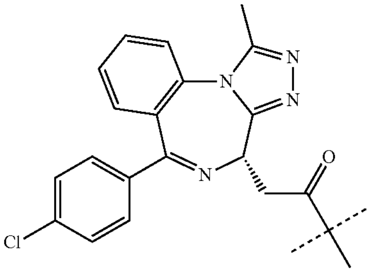
-continued
PTM-a11
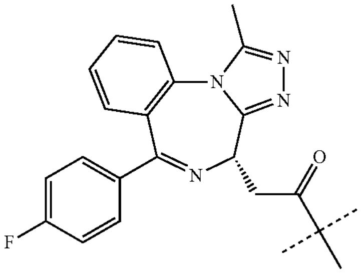
PTM-a12
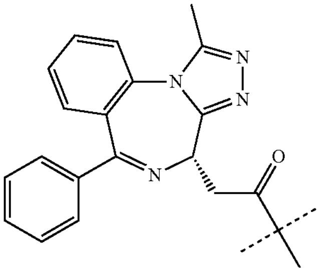
PTM-a13
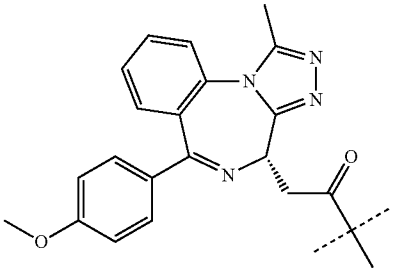
PTM-a14
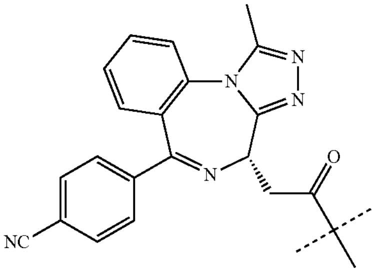
PTM-a15
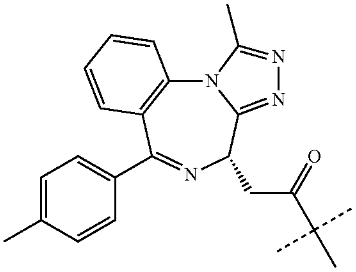

-continued
PTM-a16
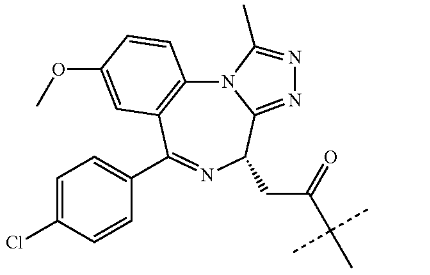
PTM-a17
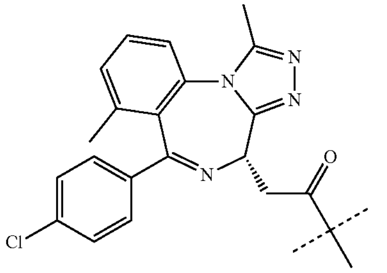
PTM-a18
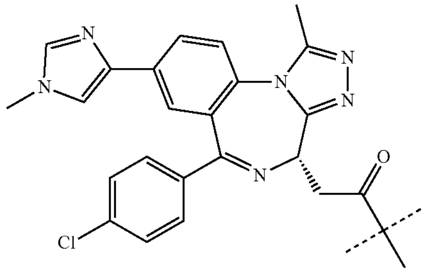
PTM-a19
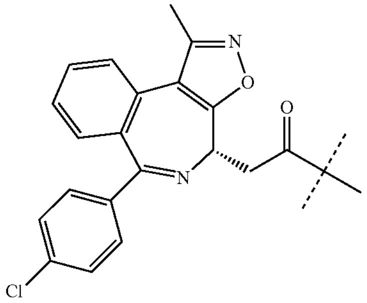
PTM-a20
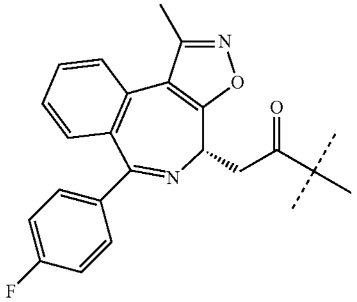
-continued
PTM-a21
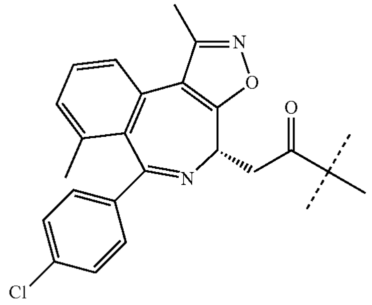
PTM-a22
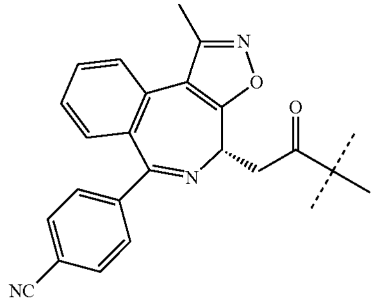
PTM-a23
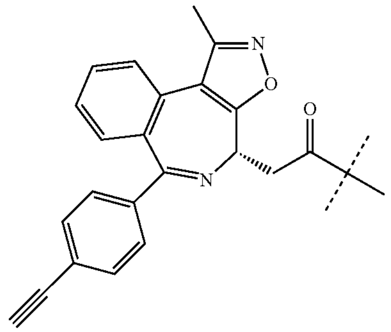
PTM-a24
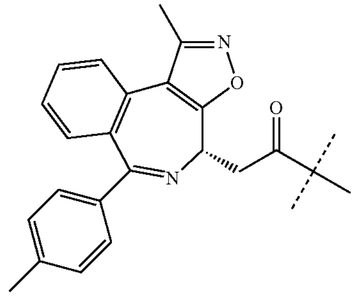
PTM-a25
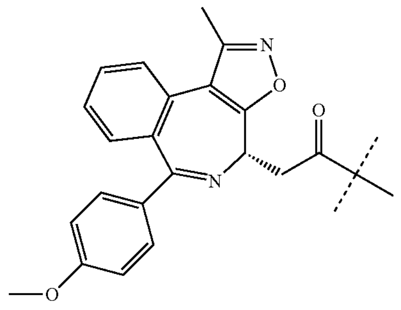

-continued
PTM-a26
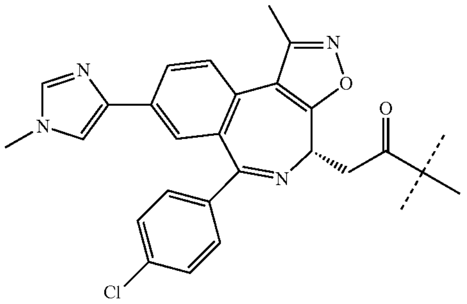
PTM-a27
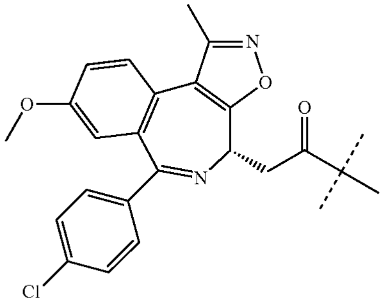
PTM-a28
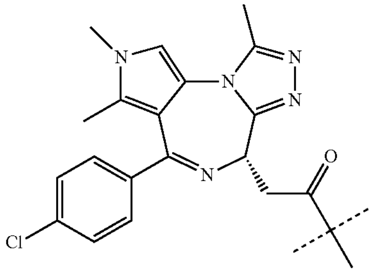
PTM-a29
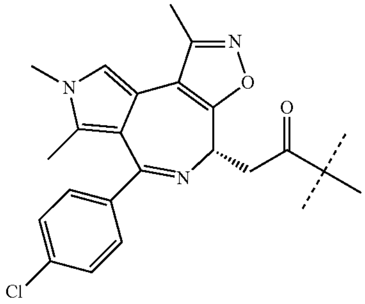
PTM-a30
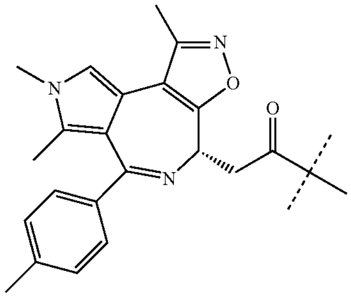
-continued
PTM-a31
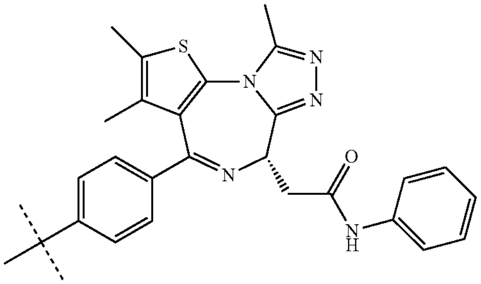
PTM-a32
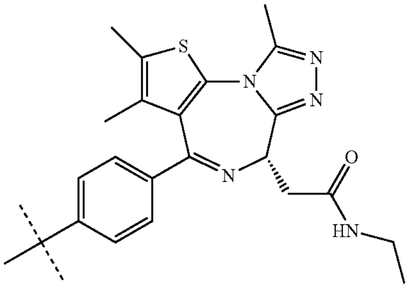
PTM-a33
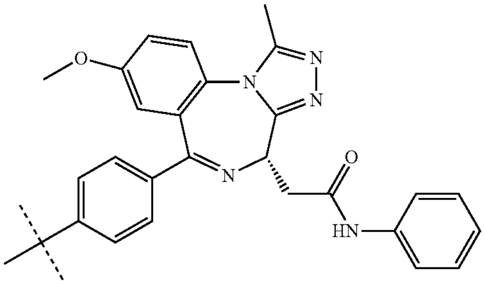
PTM-a34
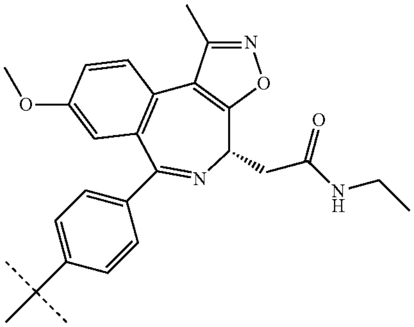
PTM-a35
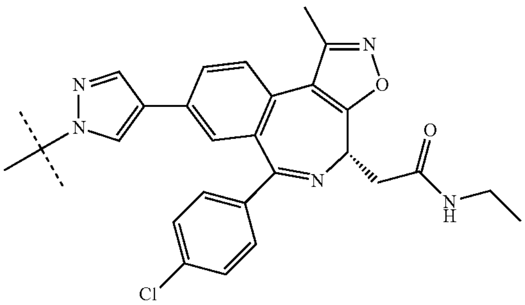

-continued

PTM-a36

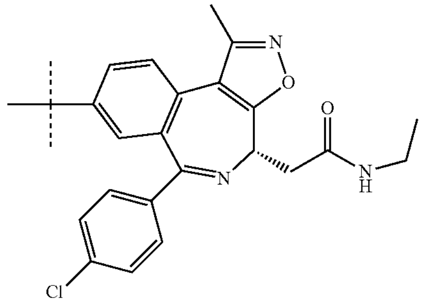

In certain embodiments, the description provides, but not limited to, the following exemplary BET PROTAC (compounds 1 or 2), including salts, prodrugs, polymorphs, analogs, derivatives, and deuterated forms thereof:

-continued

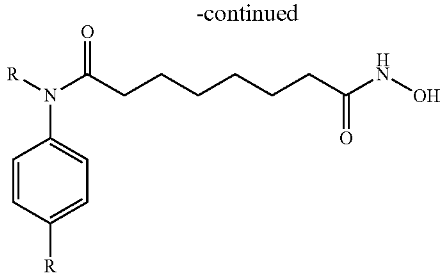

(Derivatized where "R" designates a site for attachment, for example, of a linker group L or a -(L-CLM) group); and 2. Compounds as defined by formula (I) of PCT WO0222577 ("DEACETYLASE INHIBITORS") (Derivatized where a linker group L or a -(L-CLM) group is attached, for example, via the hydroxyl group);

(PROTAC-1)

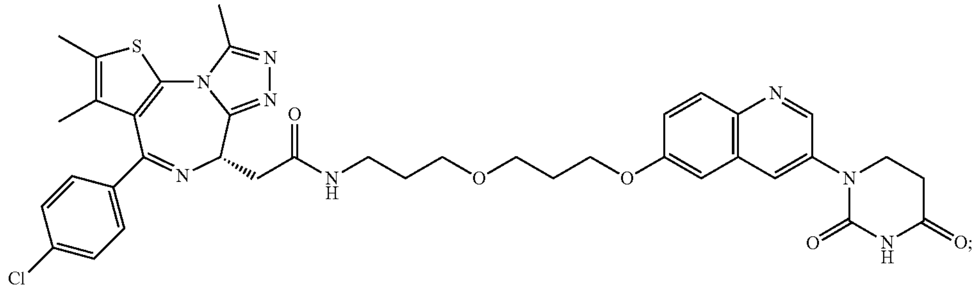

(PROTAC-2)

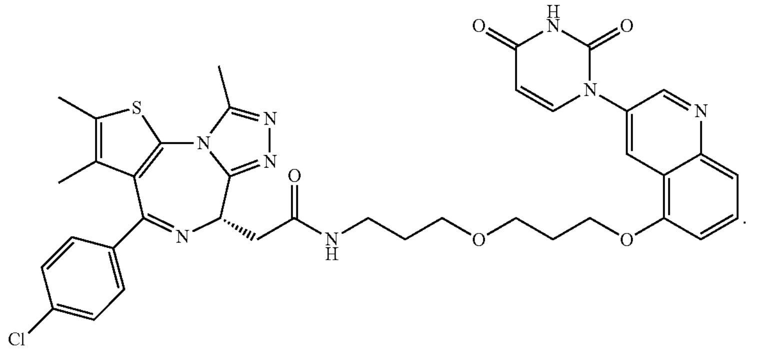

V. HDAC Inhibitors:

HDAC Inhibitors (derivatized) include, but are not limited to:

1. Finnin, M. S. et al. Structures of Histone Deacetylase Homologue Bound to the TSA and SAHA Inhibitors. Nature 40, 188-193 (1999).

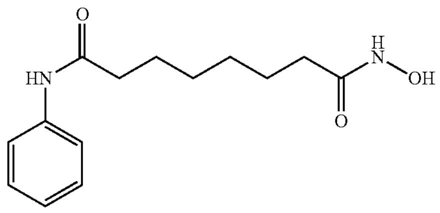

VI. Human Lysine Methyltransferase Inhibitors:

Human Lysine Methyltransferase inhibitors include, but are not limited to:

1. Chang et al. Structural Basis for G9a-Like protein Lysine Methyltransferase Inhibition by BIX-1294. Nat. Struct. Biol. (2009) 16(3) 312.

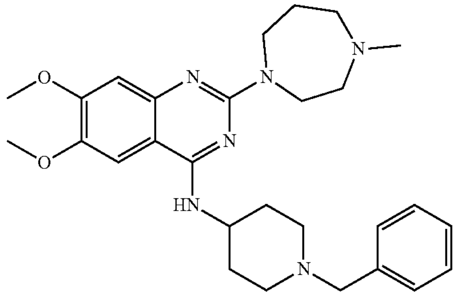

-continued

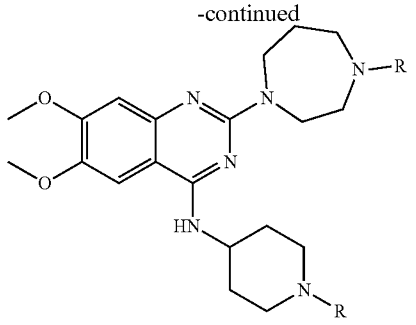

(Derivatized where "R" designates a site for attachment, for example, of a linker group L or a -(L-CLM) group);

2. Liu, F. et al Discovery of a 2,4-Diamino-7-amino-alkoxyquinazoline as a Potent and Selective Inhibitor of Histone Methyltransferase G9a. J. Med. Chem. (2009) 52(24) 7950.

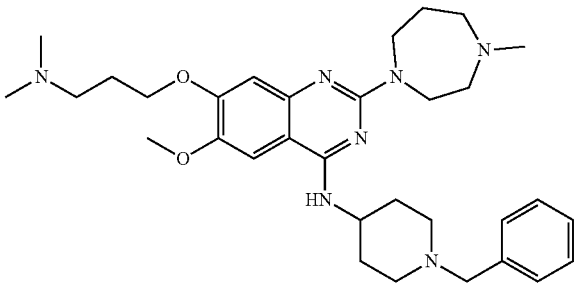

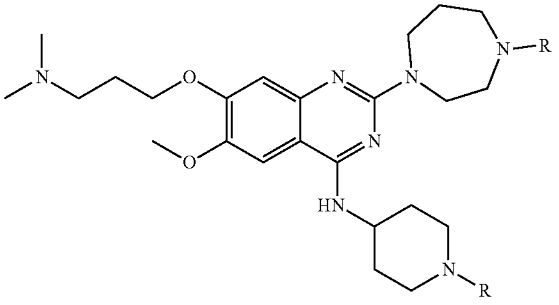

(Derivatized where "R" designates a potential site for attachment, for example, of a linker group L or a -(L-CLM) group);

3. Azacitidine (derivatized) (4-amino-1-β-D-ribofuranosyl-1,3,5-triazin-2(1H)-one) (Derivatized where a linker group L or a -(L-CLM) group is attached, for example, via the hydroxy or amino groups); and 4. Decitabine (derivatized) (4-amino-1-(2-deoxy-b-D-erythro-pentofuranosyl)-1,3,5-triazin-2(1H)-one) (Derivatized where a linker group L or a -(L-CLM) group is attached, for example, via either of the hydroxy groups or at the amino group).

VII. Angiogenesis Inhibitors:

Angiogenesis inhibitors include, but are not limited to:

1. GA-1 (derivatized) and derivatives and analogs thereof, having the structure(s) and binding to linkers as described in Sakamoto, et al., Development of Protacs to target cancer-promoting proteins for ubiquitination and degradation, *Mol Cell Proteomics* 2003 December; 2(12):1350-8;

2. Estradiol (derivatized), which may be bound to a linker group L or a -(L-CLM) group as is generally described in Rodriguez-Gonzalez, et al., Targeting steroid hormone receptors for ubiquitination and degradation in breast and prostate cancer, *Oncogene* (2008) 27, 7201-7211;

3. Estradiol, testosterone (derivatized) and related derivatives, including but not limited to DHT and derivatives and analogs thereof, having the structure(s) and binding to a linker group L or a -(L-CLM) group as generally described in Sakamoto, et al., Development of Protacs to target cancer-promoting proteins for ubiquitination and degradation, *Mol Cell Proteomics* 2003 December; 2(12):1350-8; and 4. Ovalicin, fumagillin (derivatized), and derivatives and analogs thereof, having the structure(s) and binding to a linker group L or a -(L-CLM) group as is generally described in Sakamoto, et al., Protacs: chimeric molecules that target proteins to the Skp 1-Cullin-F box complex for ubiquitination and degradation *Proc Natl Acad Sci USA.* 2001 Jul. 17; 98(15):8554-9 and U.S. Pat. No. 7,208,157.

VIII. Immunosuppressive Compounds:

Immunosuppressive compounds include, but are not limited to:

1. AP21998 (derivatized), having the structure(s) and binding to a linker group L or a -(L-CLM) group as is generally described in Schneekloth, et al., Chemical Genetic Control of Protein Levels: Selective in Vivo Targeted Degradation, *J. AM. CHEM. SOC.* 2004, 126, 3748-3754;
2. Glucocorticoids (e.g., hydrocortisone, prednisone, prednisolone, and methylprednisolone) (Derivatized where a linker group L or a -(L-CLM) group is to bound, e.g. to any of the hydroxyls) and beclometasone dipropionate (Derivatized where a linker group or a -(L-CLM) is bound, e.g. to a proprionate);
3. Methotrexate (Derivatized where a linker group or a -(L-CLM) group can be bound, e.g. to either of the terminal hydroxyls);
4. Ciclosporin (Derivatized where a linker group or a -(L-CLM) group can be bound, e.g. at any of the butyl groups);
5. Tacrolimus (FK-506) and rapamycin (Derivatized where a linker group L or a -(L-CLM) group can be bound, e.g. at one of the methoxy groups); and
6. Actinomycins (Derivatized where a linker group L or a -(L-CLM) group can be bound, e.g. at one of the isopropyl groups).

IX. Compounds targeting the aryl hydrocarbon receptor (AHR):

Compounds targeting the aryl hydrocarbon receptor (AHR) include, but are not limited to:

1. Apigenin (Derivatized in a way which binds to a linker group L or a -(L-CLM) group as is generally illustrated in Lee, et al., Targeted Degradation of the Aryl Hydrocarbon Receptor by the PROTAC Approach: A Useful Chemical Genetic Tool, ChemBioChem Volume 8, Issue 17, pages 2058-2062, Nov. 23, 2007); and
2. SR1 and LGC006 (derivatized such that a linker group L or a -(L-CLM) is bound), as described in Boitano, et al., Aryl Hydrocarbon Receptor Antagonists Promote the Expansion of Human Hematopoietic Stem Cells, Science 10 Sep. 2010: Vol. 329 no. 5997 pp. 1345-1348.

X. Compounds targeting RAF Receptor (Kinase):

PLX4032

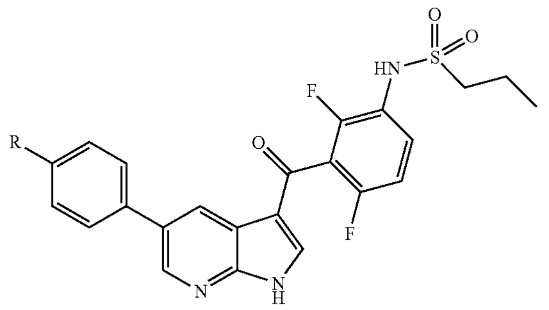

(Derivatized where "R" designates a site for linker group L or -(L-CLM) group attachment, for example).

XI. Compounds Targeting FKBP:

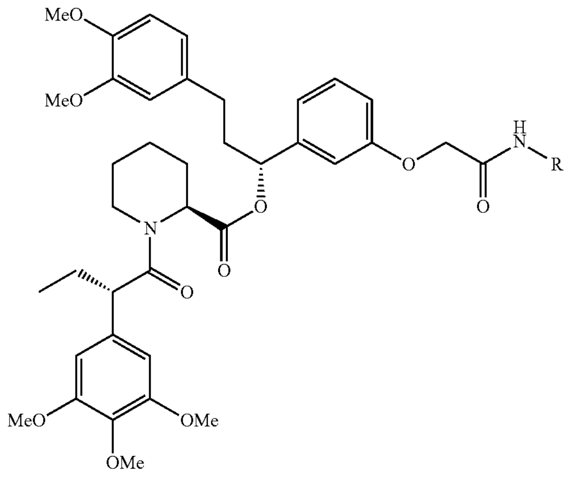

(Derivatized where "R" designates a site for a linker group L or a -(L-CLM) group attachment, for example).

XII. Compounds Targeting Androgen Receptor (AR)

1. RU59063 Ligand (derivatized) of Androgen Rceptor

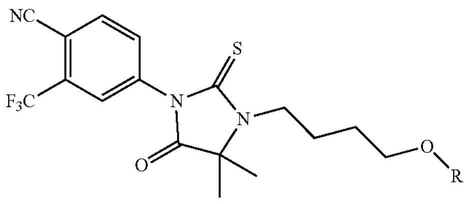

(Derivatized where "R" designates a site for a linker group L or a -(L-CLM) group attachment, for example).

2. SARM Ligand (derivatized) of Androgen Receptor

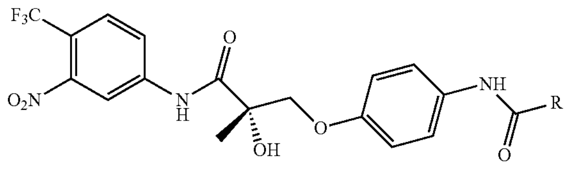

(Derivatized where "R" designates a site for a linker group L or a-(L-CLM) group attachment, for example).

3. Androgen Receptor Ligand DHT (derivatized)

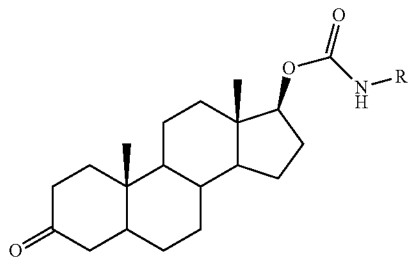

(Derivatized where "R" designates a site for a linker group L or -(L-CLM) group attachment, for example).

4. MDV3100 Ligand (derivatized)

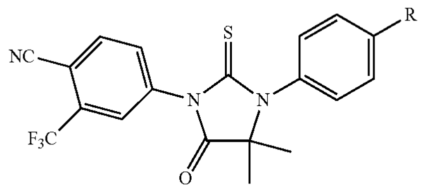

5. ARN-509 Ligand (derivatized)

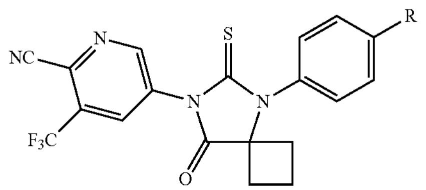

6. Hexahydrobenzisoxazoles

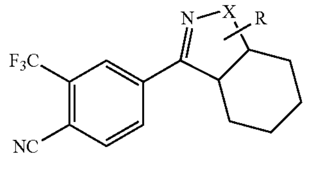

7. Tetramethylcyclobutanes

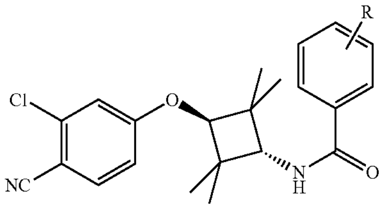

8. In any aspect or embodiment described herein, the PTM is a chemical moiety that binds to the androgen receptor (AR) (ABM). Various androgen receptor binding compounds have been described in literature, including various androgen derivatives such as testosterone, dihydrotestosterone, and metribolone (also known as methyltrienolone or R1881), and non-steroidal compounds such as bicalutamide, enzalutamide, some of which are described above. Those of ordinary skill in the art would appreciate that these androgen receptor binding compounds could be potentially used as an ABM moiety in a PROTAC compound. Such literature includes, but not limited to, G. F. Allan et. al, *Nuclear Receptor Signaling,* 2003, 1, e009; R. H. Bradbury et. al, *Bioorganic & Medicinal Chemistry Letters,* 2011 5442-5445; C. Guo et. al, *Bioorganic & Medicinal Chemistry Letters,* 2012 2572-2578; P. K. Poutiainen et. al, *J. Med. Chem.* 2012, 55, 6316-6327 A. Pepe et. al, *J. Med. Chem.* 2013, 56, 8280-8297; M. E. Jung et al, *J. Med. Chem.* 2010, 53, 2779-2796, which are incorporated by reference herein In any aspect or embodiment described herein, the ABM comprises a structure selected from, but not limited to the structures shown below, wherein a dashed line indicates the attachment point of a linker moiety or a ULM, such as a CLM:

ABM-a

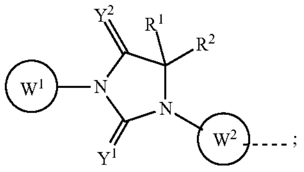

ABM-b

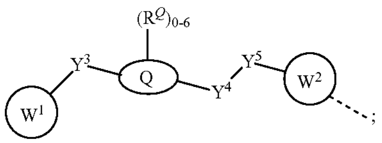

ABM-c

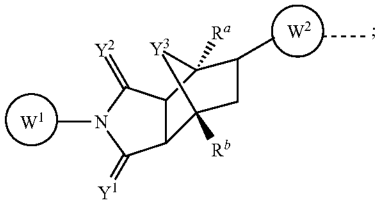

and

ABM-d

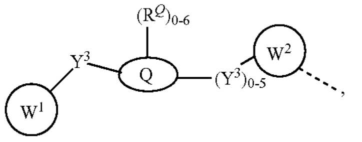

wherein:

$W^1$ is aryl, heteroaryl, bicyclic, or biheterocyclic, each independently substituted by 1 or more H, halo, hydroxyl, nitro, CN, C≡CH, $C_{1-6}$ alkyl (linear, branched, optionally substituted; for example, optionally substituted by 1 or more halo, $C_{1-6}$ alkoxyl), $C_{1-6}$ alkoxyl (linear, branched, optionally substituted; for example, optionally substituted by 1 or more halo), $C_{2-6}$ alkenyl, $C_{2-6}$ alkynyl, or $CF_3$;

$Y^1$, $Y^2$ are each independently $NR^{Y1}$, O, S;

$Y^3$, $Y^4$, $Y^5$ are each independently a bond, O, $NR^{Y2}$, $CR^{Y1}R^{Y2}$, C═O, C═S, SO, $SO_2$, heteroaryl, or aryl;

Q is a 3-6 membered ring with 0-4 heteroatoms, optionally substituted with 0-6 $R^Q$, each $R^Q$, is independently H, $C_{1-6}$ alkyl (linear, branched, optionally substituted; for example, optionally substituted by 1 or more halo, $C_{1-6}$ alkoxyl), halogen, $C_{1-6}$ alkoxy, or 2 $R^Q$ groups taken together with the atom they are attached to, form a 3-8 membered ring system containing 0-2 heteroatoms);

$R^1$, $R^2$, $R^a$, $R^b$, $R^{Y1}$, $R^{Y2}$ are each independently H, $C_{1-6}$ alkyl (linear, branched, optionally substituted; for example, optionally substituted by 1 or more halo, $C_{1-6}$ alkoxyl), halogen, $C_{1-6}$ alkoxy, cyclic, heterocyclic, or $R^1$, $R^2$ together with the atom they are attached to, form a 3-8 membered ring system containing 0-2 heteroatoms);

$W^2$ is a bond, $C_{1-6}$ alkyl, $C_{1-6}$ heteroalkyl, O, aryl, heteroaryl, alicyclic, heterocyclic, biheterocyclic, biaryl, or biheteroaryl, each optionally substituted by 1-10 $R^{W2}$;

each $R^{W2}$ is independently H, halo, $C_{1-6}$ alkyl (linear, branched, optionally substituted; for example, optionally substituted by 1 or more F), —$OR^{W2A}$, $C_{3-6}$ cycloalkyl, $C_{4-6}$ cycloheteroalkyl, $C_{1-6}$ alicyclic (optionally substituted), heterocyclic (optionally substituted), aryl (optionally substituted), or heteroaryl (optionally substituted), bicyclic hereoaryl or aryl, $OC_{1-3}$alkyl (optionally substituted), OH, $NH_2$, $NR^{Y1}R^{Y2}$, CN; and $R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl.

In any aspect or embodiment described herein, the $W^2$ is covalently coupled to one or more ULM or CLM groups, or a linker to which is attached one or more ULM or CLM groups as described herein.

In any aspect or embodiment described herein, $W^1$ is

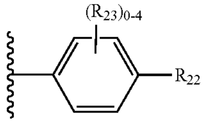

or

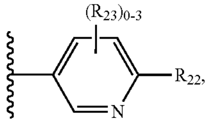

wherein each $R_{22}$ is independently halo, H, optionally substituted alkyl, haloalkyl, cyano, or nitro; and each $R_{23}$ is independently H, halo, $CF_3$, optionally substituted alkyl, alkoxy, haloalkyl, cyano, or nitro.

In any aspect or embodiment described herein, $W^1$ is selected from the group consisting of:

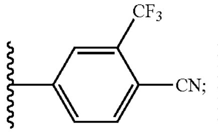

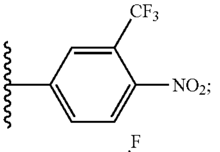

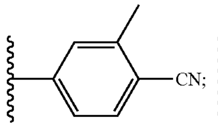

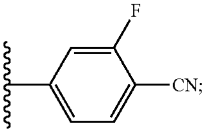

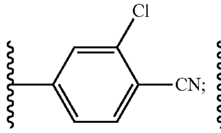

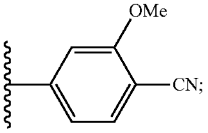

-continued

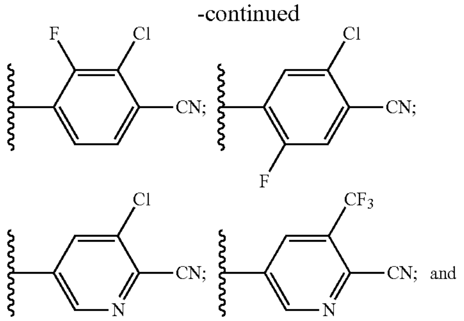

and

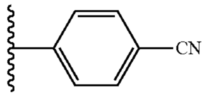

In any aspect or embodiment described herein, the ABM comprises a structure selected from the following structures shown below, where a  indicates tha attachment point of a linker or a ULM:

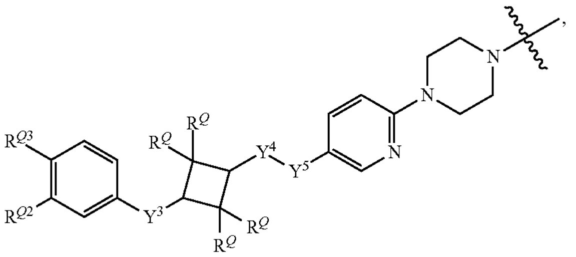

and

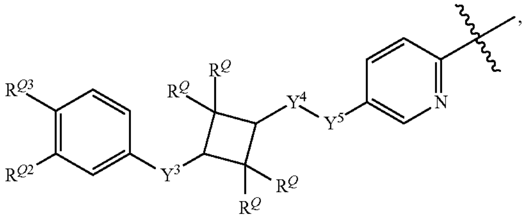

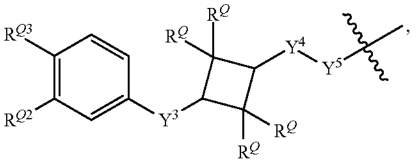

wherein:

$R^{Q2}$ is a H, halogen, $CH_3$ or $CF_3$;

$R^{Q3}$ is H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;

$Y^3$, $Y^4$, $Y^5$ are each independently a bond, O, $NR^{Y2}$, $CR^{Y1}R^{Y2}$, C═O, heteroaryl, or aryl, $R^{Y1}$, $R^2$ are each independently H, or $C_{1-6}$ alkyl (linear, branched, optionally substituted by 1 or more halo, $C_{1-6}$ alkoxyl, cyclic, or heterocyclic); and $R^Q$ each independently is H, $C_1$-$C_6$ alkyl (linear, branched, optionally substituted by 1 or more halo, or $C_{1-6}$ alkoxyl), or two $R^Q$ together with the atom they are attached to, form a 3-8 membered ring system containing 0-2 heteroatoms.

In any aspect or embodiment described herein, each $R^Q$ is independently H or $CH_3$. In another embodiment $R^{Q3}$ is CN.

In any aspect or embodiment described herein, the ABM comprises a structure selected from the following structures shown below, where a  indicates the attachment point of a linker or a ULM:

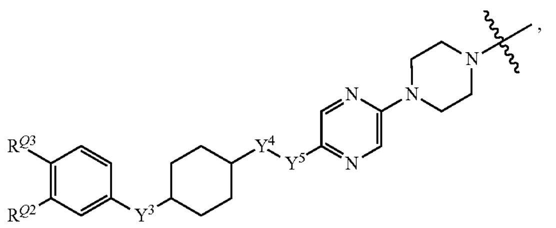

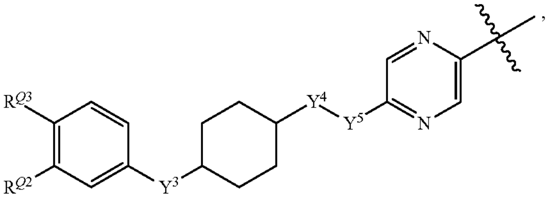

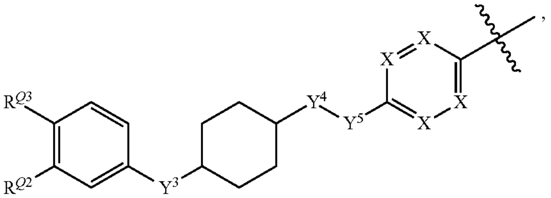

and

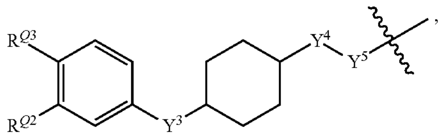

wherein:

$R^{Q2}$ is a H, halogen, CN, $CH_3$ or $CF_3$; and $R^{Q3}$ is H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;

$Y^3$, $Y^4$, $Y^5$ are each independently a bond, O, $NR^{Y2}$, $CR^{Y1}R^{Y2}$, C═O, heteroaryl, or aryl; and $R^{Y1}$, $R^2$ are each independently H or $C_{1-6}$ alkyl (linear, branched, optionally substituted by 1 or more halo, $C_{1-6}$ alkoxyl, cyclic, or heterocyclic); and X is N or C.

In any aspect or embodiment described herein, $R^{Q3}$ is a CN.

In any aspect or embodiment described herein, the ABM comprises a structure shown below, where a dashed line indicates the attachment point of a linker moiety or a ULM or a CLM:

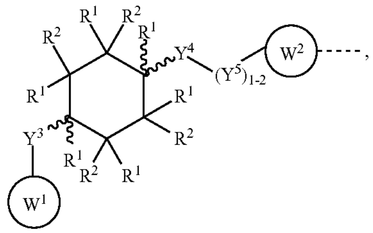

wherein:

$W^1$ is

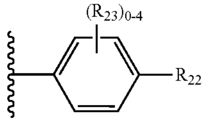
or
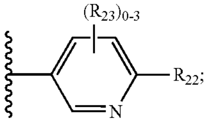

each $R_{22}$ is independently H or —CN;

each $R_{23}$ is independently H, halo, $C_1$-$C_6$ alkyl (linear, branched, optionally substituted), $C_1$-$C_6$ alkoxy, or —$CF_3$;

$Y^3$ is a bond or O;

$Y^4$ is a bond or NH;

$Y^5$ is a bond, C═O, $C_1$-$C_6$ heteroaryl, or $C_1$-$C_6$ aryl;

$R^1$, $R^2$, are each independently H, or $C_1$-$C_6$ alkyl (linear or branched, optionally substituted; for example, optionally substituted by 1 or more halo, or $C_{1-6}$ alkoxyl);

$W^2$ is a bond, $C_{1-6}$ aryl, $C_{1-6}$ heteroaryl, $C_{1-6}$ alicyclic, or $C_{1-6}$ heterocyclic, biheterocyclic, biaryl, or biheteroaryl, each optionally substituted by 1-10 $R^{W2}$; and each $R^{W2}$ is independently H, or halo; and ∿∿ represents a bond that may be stereospecific ((R) or (S)) or non-stereospecific.

In any aspect or embodiment described herein, the $W^2$ is covalently coupled to one or more ULM or CLM groups, or a linker to which is attached one or more ULM or CLM groups as described herein.

In any aspect or embodiment described herein, $W^1$ is selected from the group consisting of:

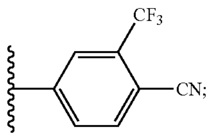
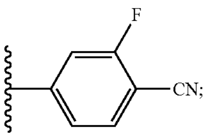
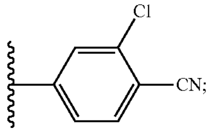
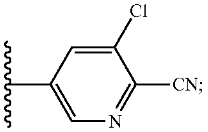
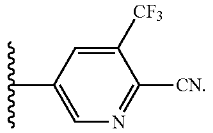

In any aspect or embodiment described herein, $W^2$ is selected from the group consisting of:

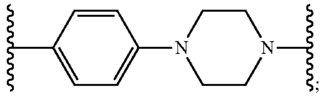
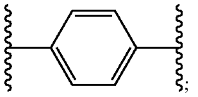
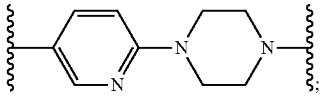
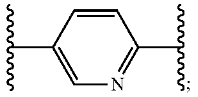
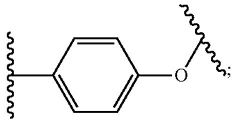
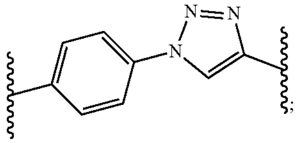
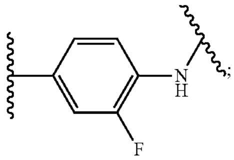
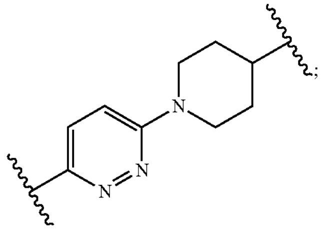
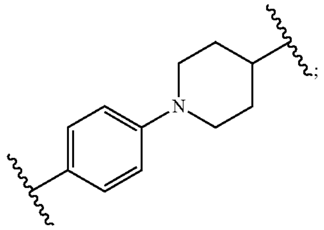
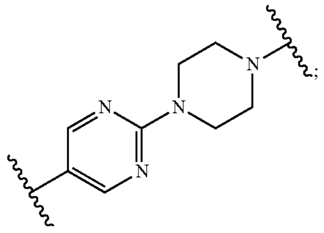
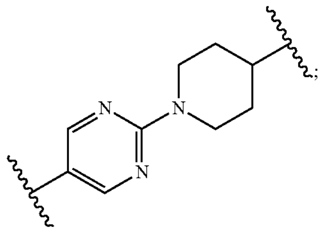

-continued

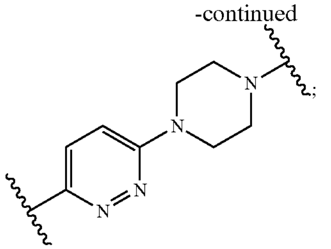

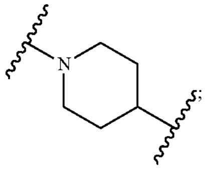

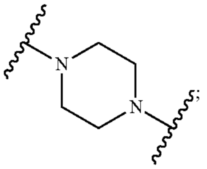

and

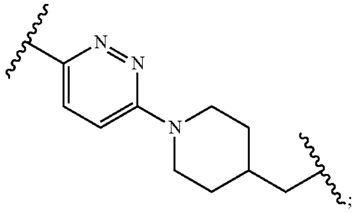

In any aspect or embodiment described herein, the ABM comprises a structure selected from, but not limited to the structures shown below, where a dashed line indicates the attachment point of a linker moiety or a ULM:

ABM-a

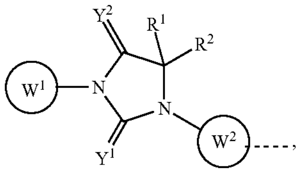

wherein:

$W^1$ is

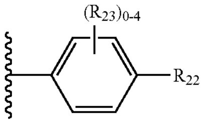

or

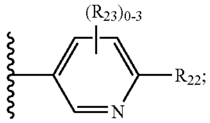

each $R_{22}$ is independently H or —CN;

each $R_{23}$ is independently H, halo, or —$CF_3$;

$Y^1$, $Y^2$ are each independently O or S;

$R^1$, $R^2$, are each independently H or a methyl group;

$W^2$ is a bond, $C_{1-6}$ aryl, or heteroaryl, each optionally substituted by 1, 2 or 3 $R^{W2}$; and each $R^{W2}$ is independently H, halo, $C_{1-6}$ alkyl (optionally substituted by 1 or more F), $OC_{1-3}$alkyl (optionally substituted by 1 or more —F).

In any of the embodiments described herein, the $W^2$ is covalently coupled to one or more ULM or CLM groups, or a linker to which is attached one or more ULM or CLM groups as described herein.

In certain additional embodiments, $W^1$ is selected from the group consisting of:

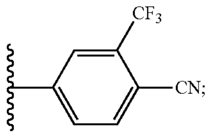

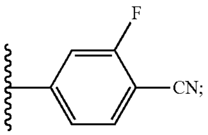

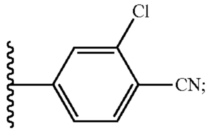

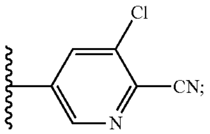

and

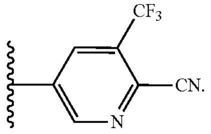

In any aspect or embodiment described herein, $W^2$ is selected from the group consisting of:

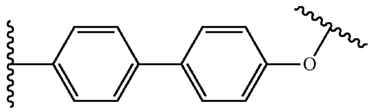

and

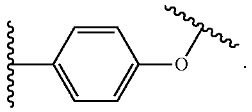

In any aspect or embodiment described herein, ABM is selected from the group consisting of:

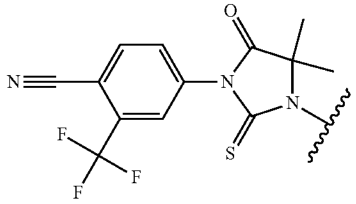

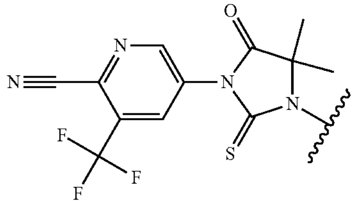

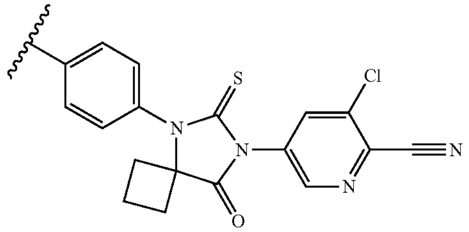

-continued
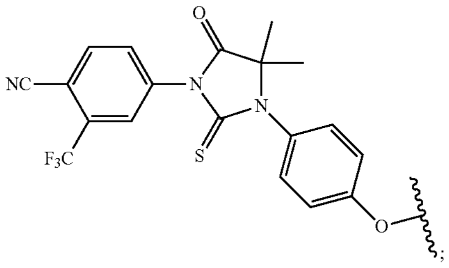
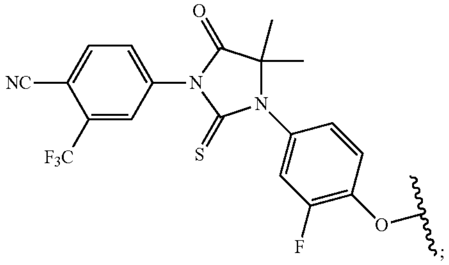
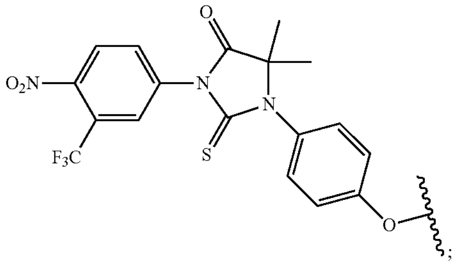
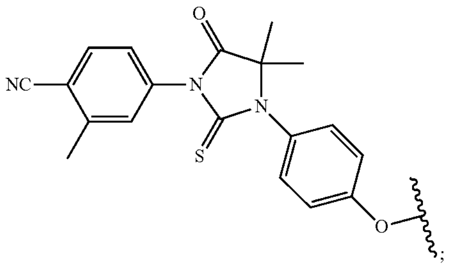
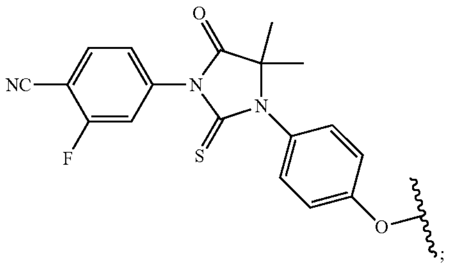
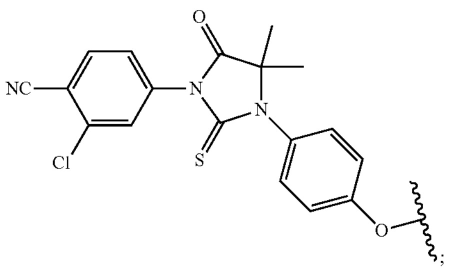
-continued
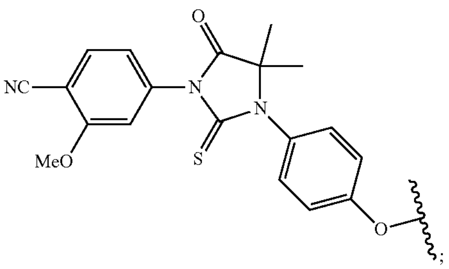
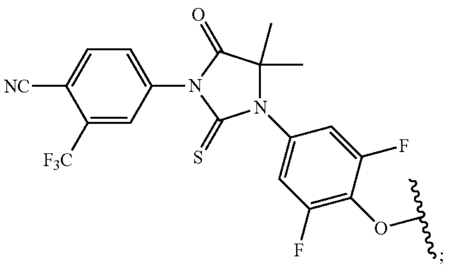
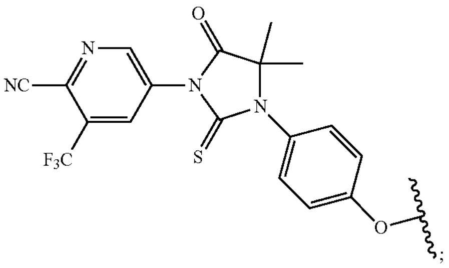
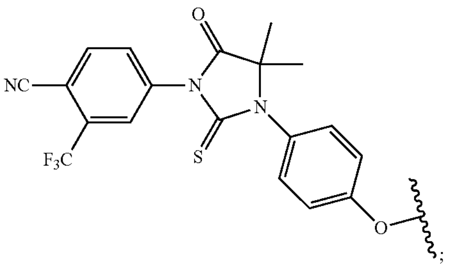
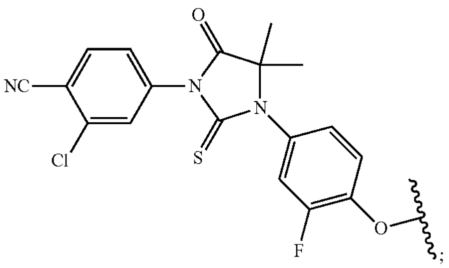
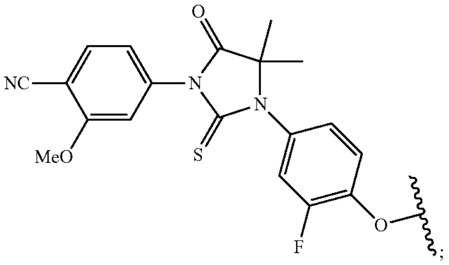

-continued
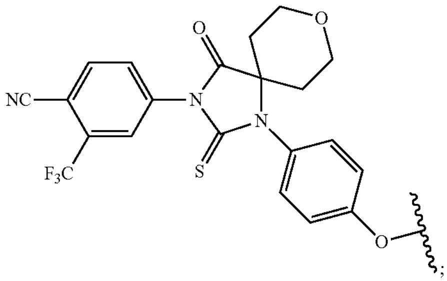
;
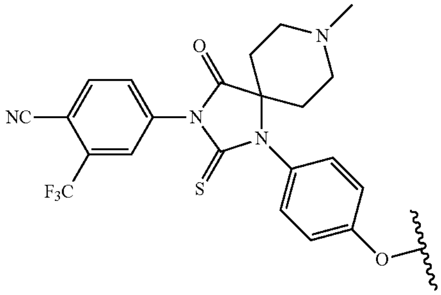
;
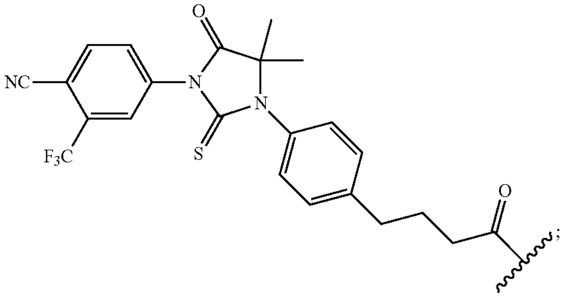
;
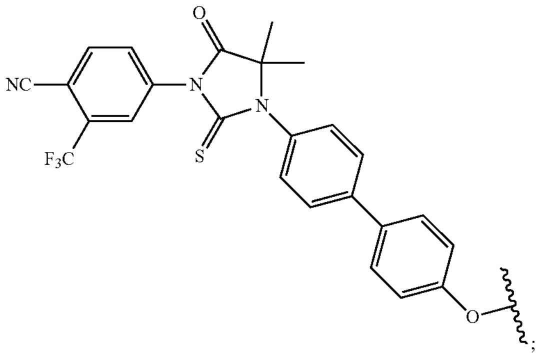
;
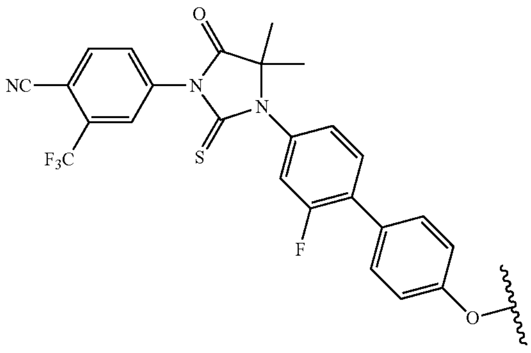
;
-continued
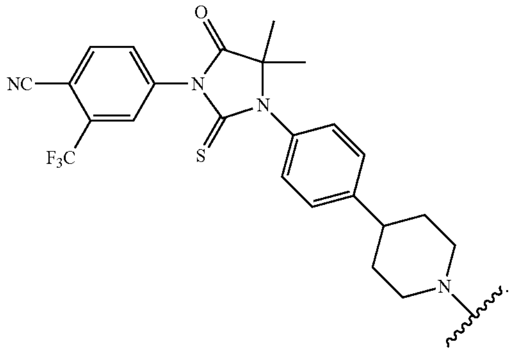
.
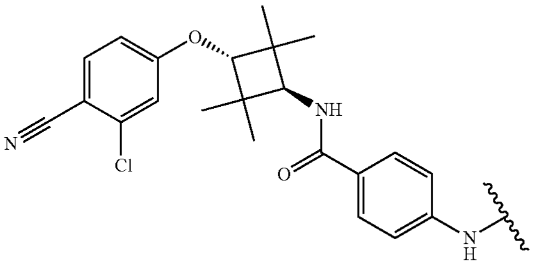
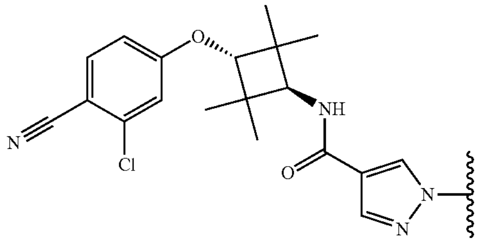
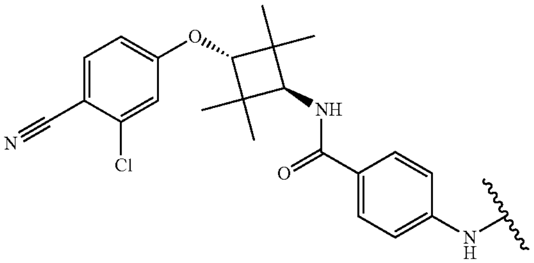
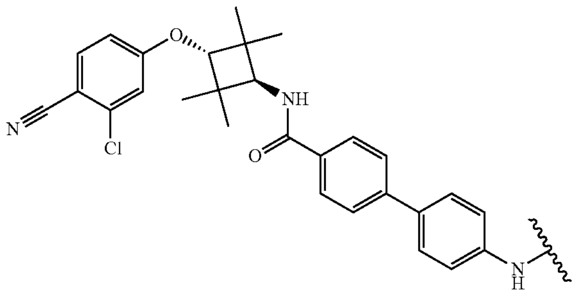
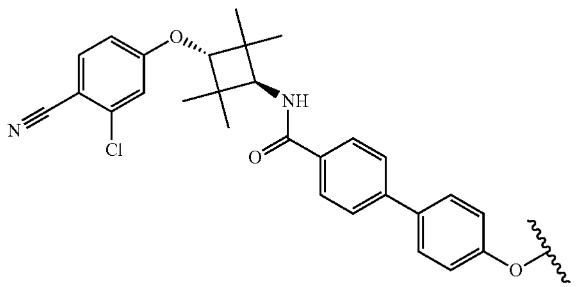

-continued
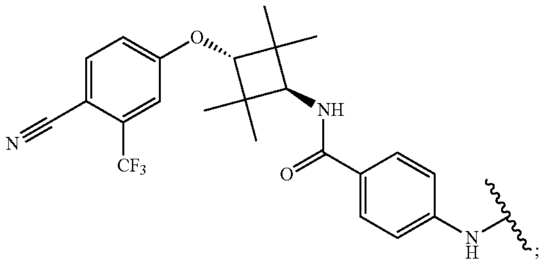
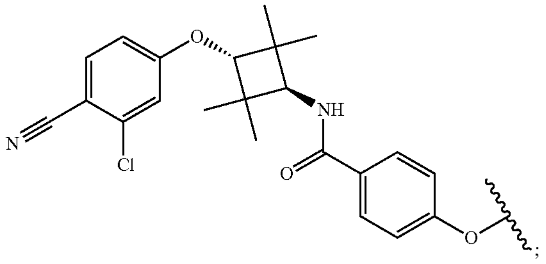
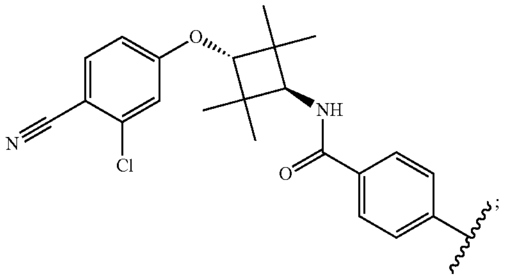
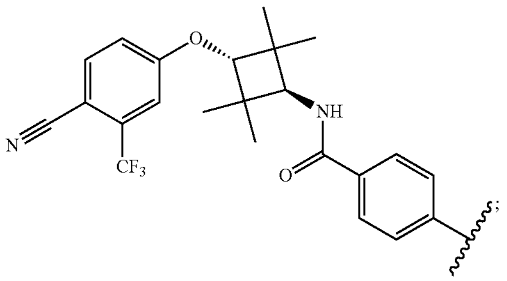
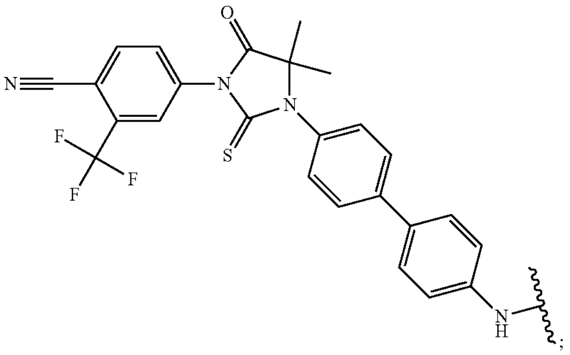
-continued
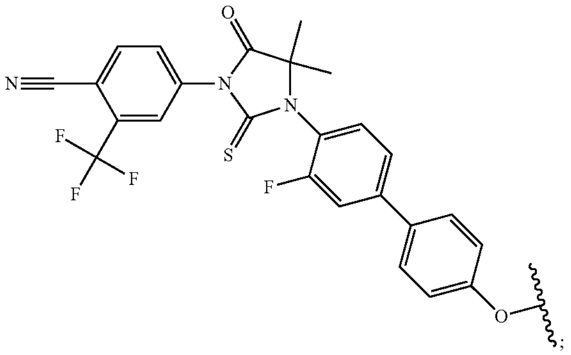
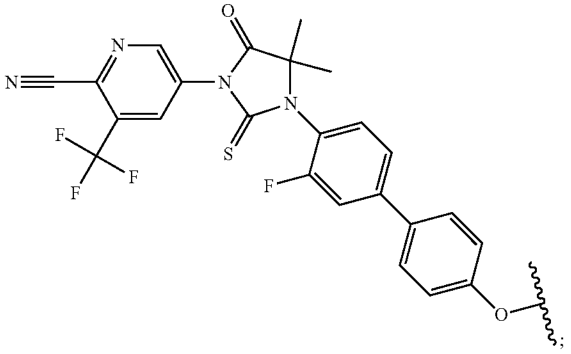
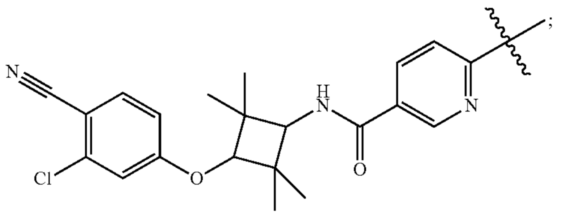
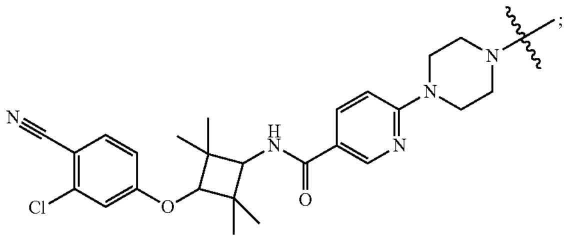
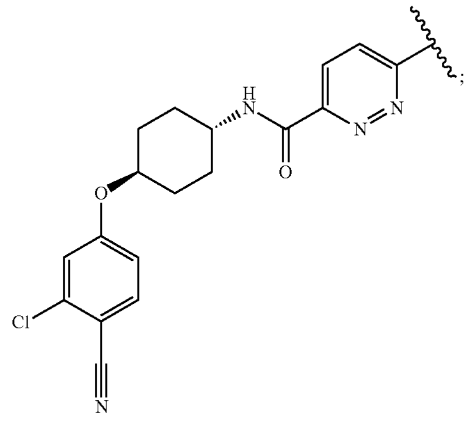

-continued
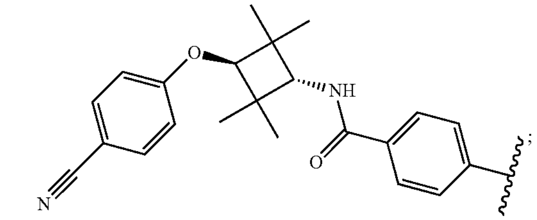
;
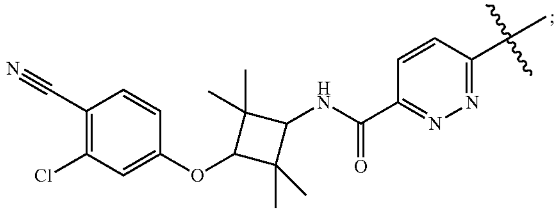
;
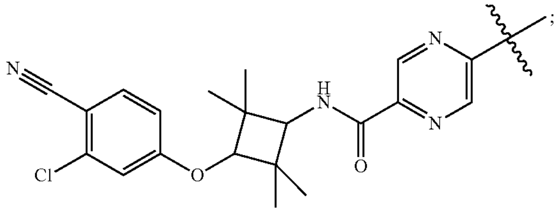
;
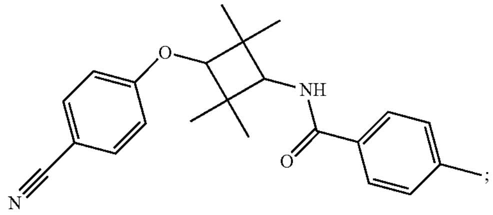
;
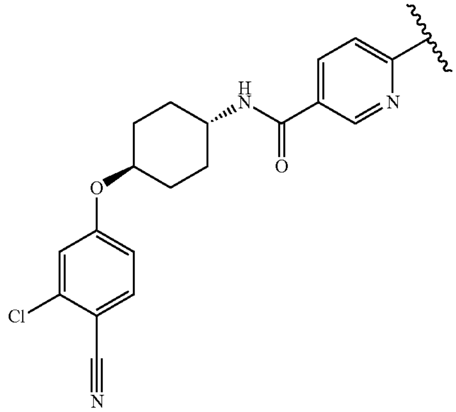
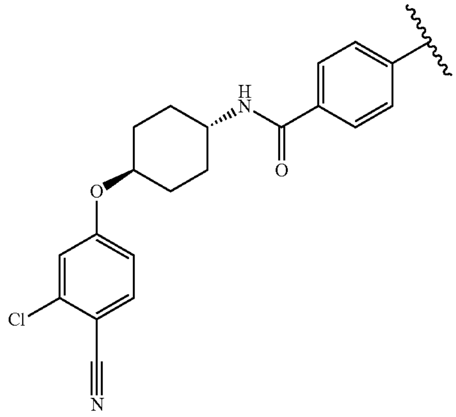
-continued
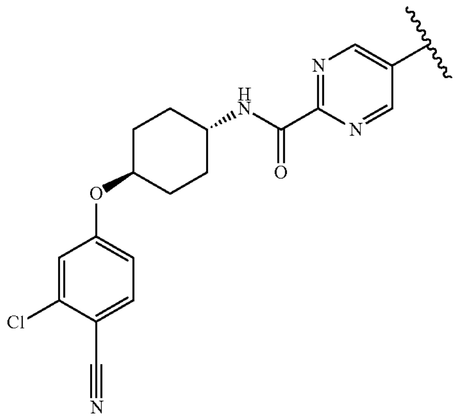
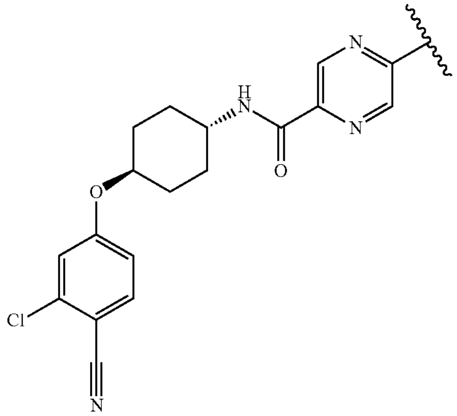
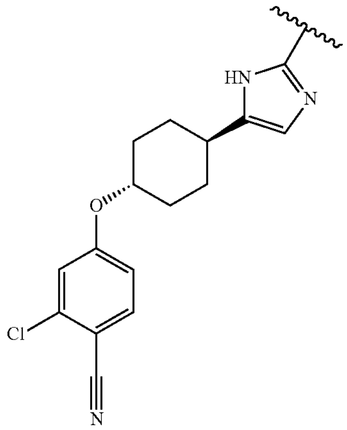
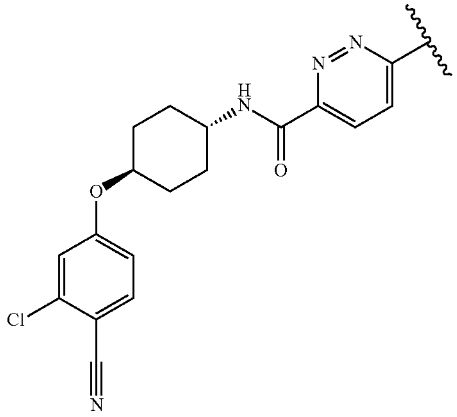

-continued
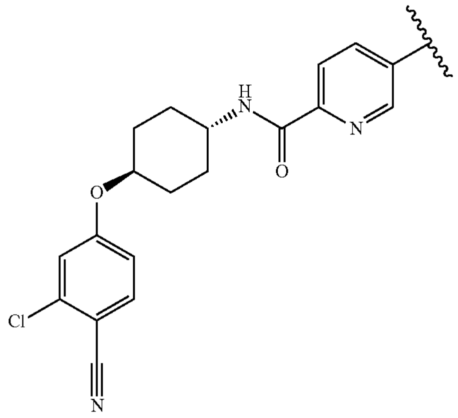
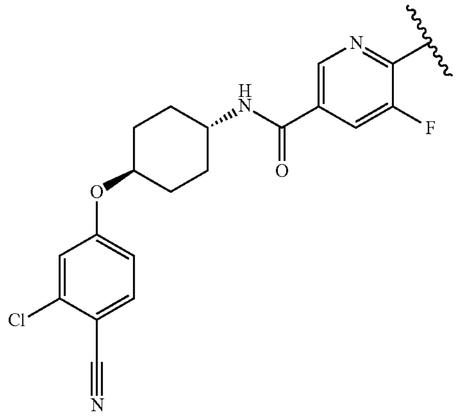
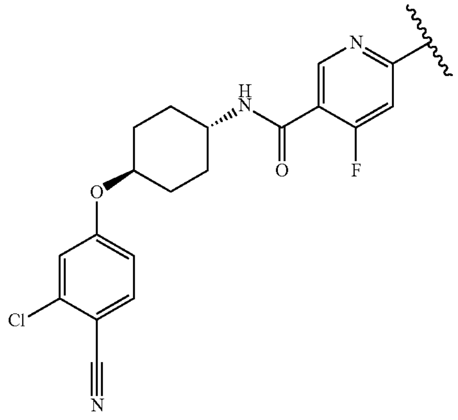
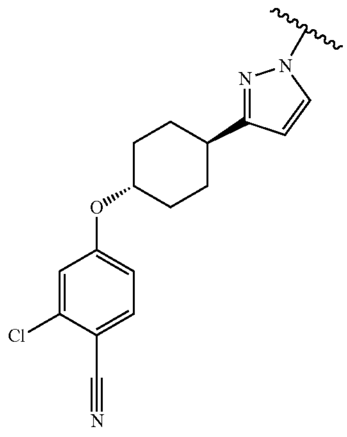
-continued
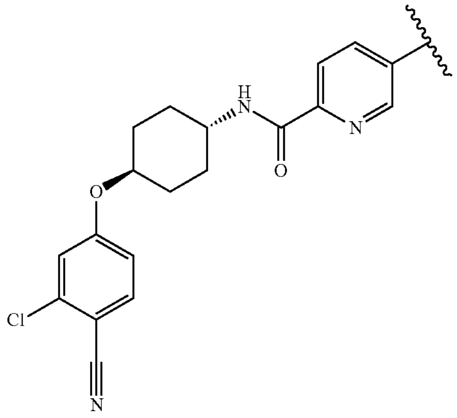
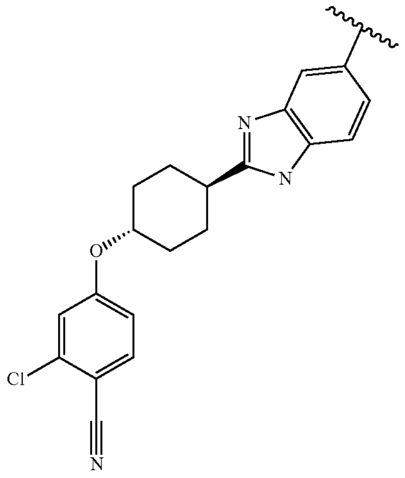
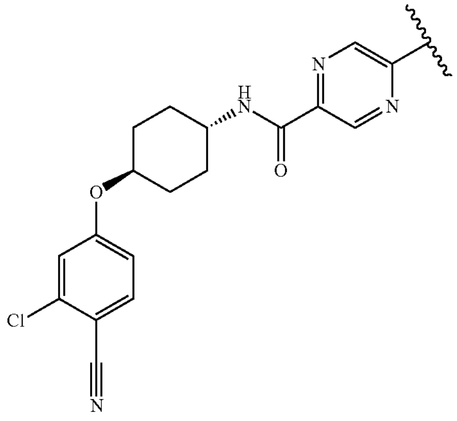
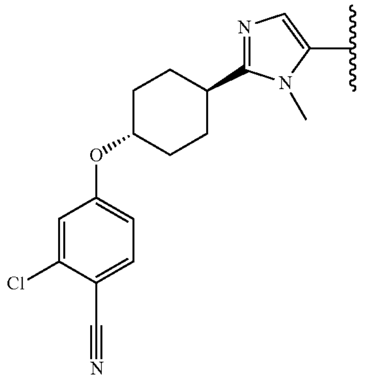

-continued
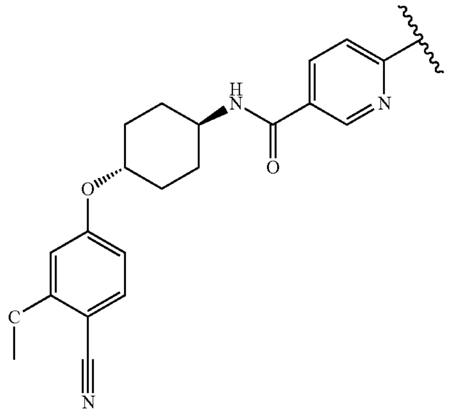
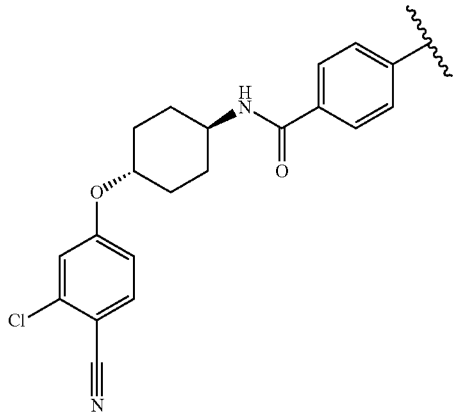
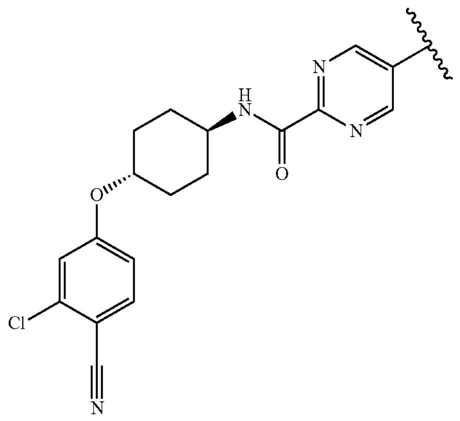
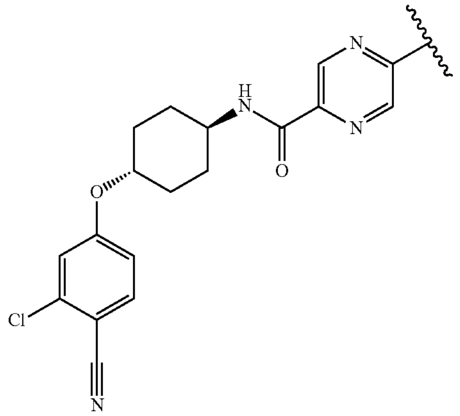
-continued
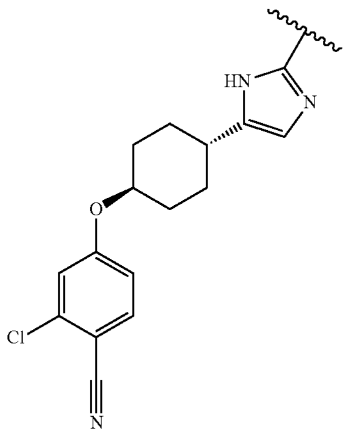
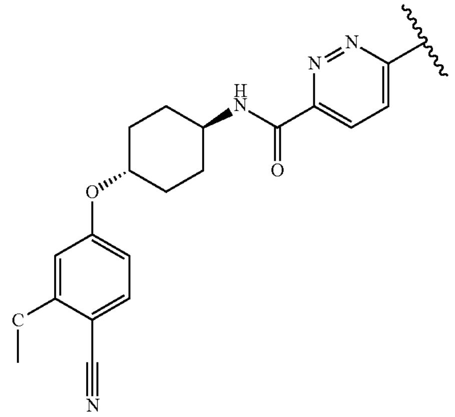
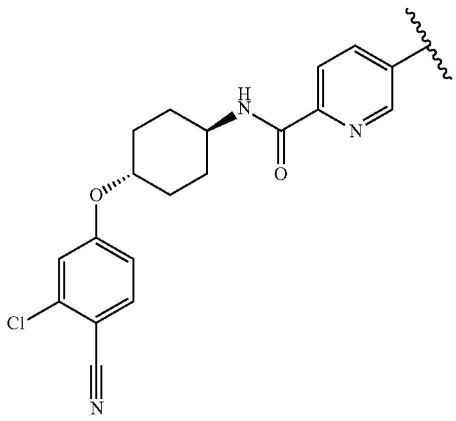
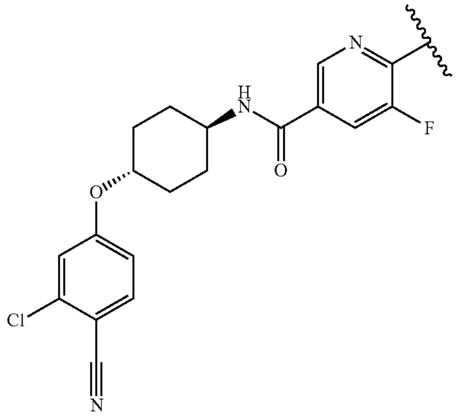

-continued
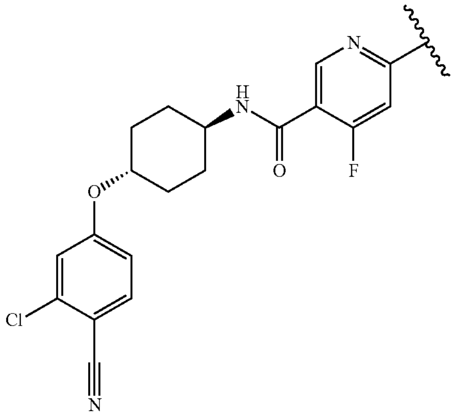
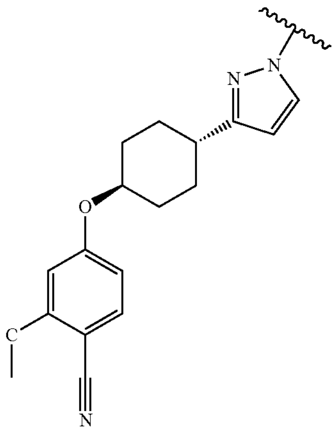
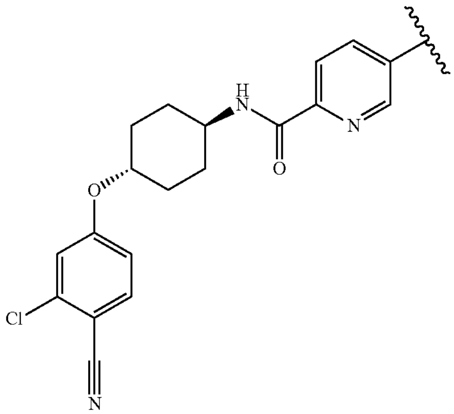
-continued
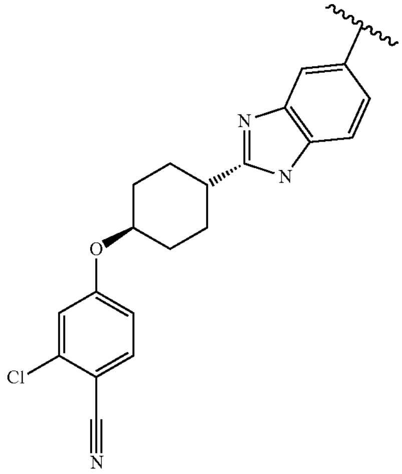
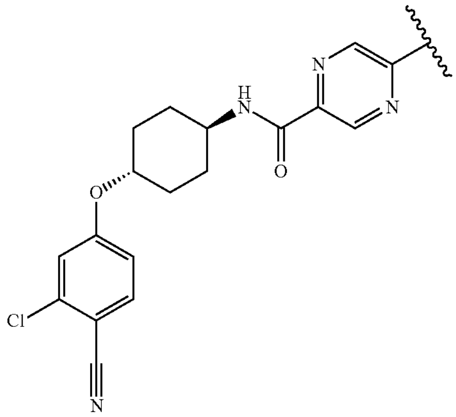
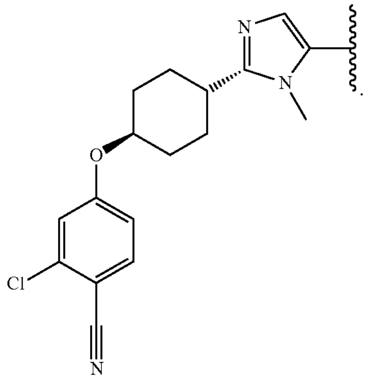
In any aspect or embodiment described herein, the ABM comprises the structure:
ABM-b
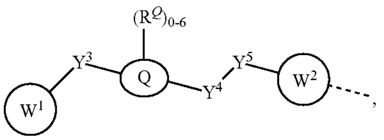
wherein:
$W^1$ is aryl, or heteroaryl, each independently substituted by 1 or more H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;

$Y^3$, $Y^4$, $Y^5$ are each independently a bond, O, $NR^{Y2}$, $CR^{Y1}R^{Y2}$, C═O, C═S, SO, $SO_2$, heteroaryl, or aryl;

Q is a 4 membered alicyclic ring with 0-2 heteroatoms, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{Y1}$, $R^{Y2}$ are each independently H, $C_{1-6}$ alkyl (linear, branched, optionally substituted by 1 or more halo, $C_{1-6}$ alkoxyl);

$W^2$ is a bond, $C_{1-6}$ alkyl, $C_{1-6}$ heteroalkyl, O, $C_{1-6}$ alicyclic, heterocyclic, aryl, biheterocyclic, biaryl, or biheteroaryl, or heteroaryl, each optionally substituted by 1, 2 or 3 $R^{W2}$; and each $R^{W2}$ is independently H, halo, $C_{1-6}$ alkyl (linear, branched, optionally substituted by 1 or more F), $C_{1-6}$ heteroalkyl (linear, branched, optionally substituted), —$OR^{W2A}$ $OC_{1-3}$alkyl (optionally substituted by 1 or more —F), $C_{3-6}$ cycloalkyl, $C_{4-6}$ cycloheteroalkyl (optionally substituted), $C_{1-6}$ alkyl (optionally substituted), $C_{1-6}$ alicyclic (optionally substituted), heterocyclic (optionally substituted), aryl (optionally substituted), heteroaryl (optionally substituted), bicyclic hereoaryl (optionally substituted), bicyclic aryl, OH, $NH_2$, $NR^{Y1}R^{Y2}$, or CN; and $R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl.

In any aspect or embodiment described herein, the description provides an androgen receptor bindingcompound comprising a structure of:

ABM-e

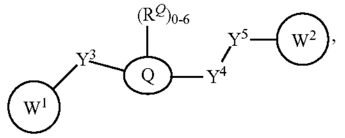

wherein:

$W^1$ is aryl, heteroaryl, bicyclic, or biheterocyclic, each independently substituted by 1 or more H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;

$Y^1$, $Y^2$ are each independently $NR^{Y1}$, O, or S;

$Y^3$, $Y^4$, $Y^5$ are each independently a bond, O, $NR^{Y2}$, $CR^{Y1}R^{Y2}$, C═O, C═S, SO, $SO_2$, heteroaryl, or aryl;

Q is a 3-6 membered alicyclic or aromatic ring with 0-4 heteroatoms, optionally substituted with 0-6 $R^Q$, each $R^Q$, is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^1$, $R^2$, $R^a$, $R^b$, $R^{Y1}$, $R^{Y2}$ are each independently H, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

$W^2$ is a bond, $C_{1-6}$ alkyl, $C_{1-6}$ heteroalkyl, O, $C_{1-6}$ alicyclic, heterocyclic, aryl, biheterocyclic, biaryl, or biheteroaryl, or heteroaryl, each optionally substituted by 1, 2 or 3 $R^{W2}$;

each $R^{W2}$ is independently H, halo, $C_{1-6}$ alkyl (linear, branched, optionally substituted by 1 or more F), $C_{1-6}$ heteroalkyl (linear, branched, optionally substituted), —$OR^{W2A}$, $OC_{1-3}$alkyl (optionally substituted by 1 or more —F), $C_{3-6}$ cycloalkyl, $C_{4-6}$ cycloheteroalkyl, $C_{1-6}$ alkyl (optionally substituted), $C_{1-6}$ alicyclic (optionally substituted), heterocyclic (optionally substituted), aryl (optionally substituted), or heteroaryl (optionally substituted), bicyclic hereoaryl or aryl, OH, $NH_2$, $NR^{Y1}R^{Y2}$, CN; and $R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl.

In any aspect or embodiment described herein, an androgen receptor binding moiety has a structure of:

ABM-e

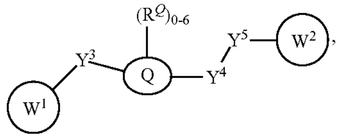

wherein:

$W^1$ is

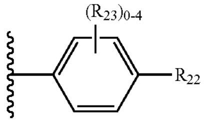

or

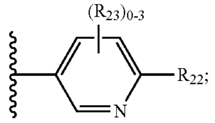

each $R_{22}$ is independently H or —CN;

each R23 is independently H, halo, or —$CF_3$;

$Y^3$ is a bond or O;

Q is a 4 member ring, optionally substituted with 0-4 $R^Q$, each $R^Q$ is independently H or methyl;

Y4 is a bond or NH;

Y5 is a bond, a C═O, or a C═S; and each $W^2$ is independently a bond, C1-6 aryl or heteroaryl, each optionally substituted by 1, 2 or 3 $R^{W2}$, each $R^{W2}$ is independently H, halo, a 6 member alicyclic ring with 1 or 2 heteroatoms or a 5 member aromatic ring with 1 or 2 or 3 heteroatoms.

In any aspect or embodiment described herein, $W^2$ is selected from the group consisting of:

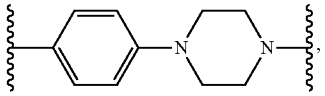,

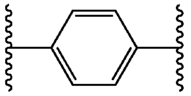

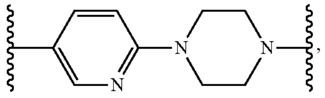,

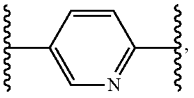,

-continued

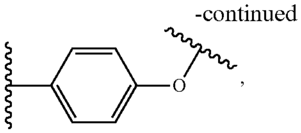

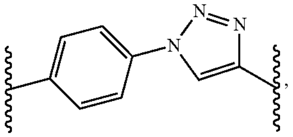

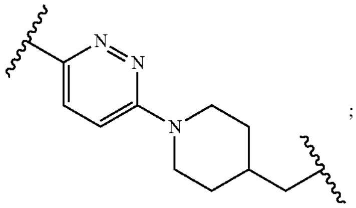

; and

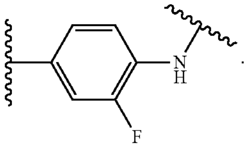

In any aspect or embodiment described herein, the $W^2$ is covalently coupled to one or more ULM or CLM groups, or a linker to which is attached one or more ULM or CLM groups as described herein.

In any aspect or embodiment described herein, $W^1$ is selected from the group consisting of:

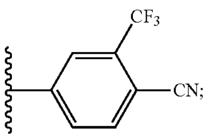

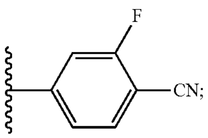

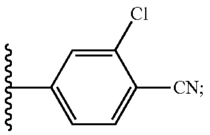

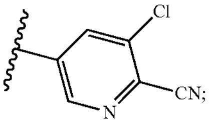

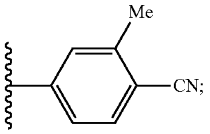

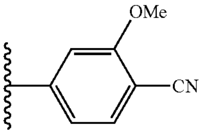

and

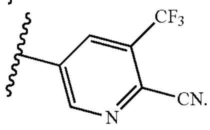

In any aspect or embodiment described herein, an androgen binding moiety has a structure of:

ABM-d

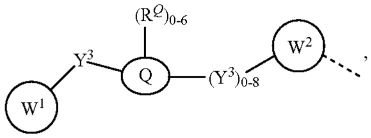

wherein:

$W^1$ is aryl, independently substituted by 1 or more halo, CN;

$Y^3$ are each independently a bond, $NR^{Y2}$, $CR^{Y1}R^{Y2}$, C═O;

Q is a 5 membered aromatic ring with 1 or 2 heteroatoms;

$R^{Y1}$, $R^{Y2}$ are each independently H, $C_{1-6}$ alkyl (linear, branched);

$W^2$ is a bond, aryl, or heteroaryl, each optionally substituted by 1, 2 or 3 $R^{W2}$; and each $R^{W2}$ is independently H, halo, $C_{1-6}$ alkyl (optionally substituted by 1 or more F), $OC_{1-3}$alkyl (optionally substituted by 1 or more —F).

In any aspect or embodiment described herein, the $W^2$ is covalently coupled to one or more ULM or CLM groups, or a linker to which is attached one or more ULM or CLM groups as described herein.

In any aspect or embodiment described herein, $W^1$ is

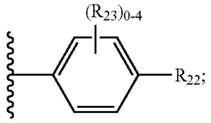

wherein each $R_{22}$ is independently halo or CN; and each $R_{23}$ is independently H or halo.

In any aspect or embodiment described herein, $W^1$ is selected from the group consisting of:

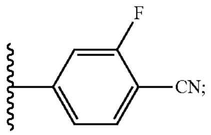

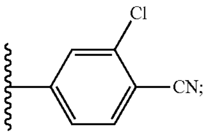

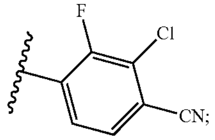

and

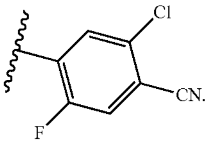

In any aspect or embodiment described herein, Q is

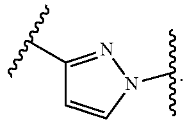 [SMILES: *c1ccn(*)n1]

In any aspect or embodiment described herein, $W^2$ is

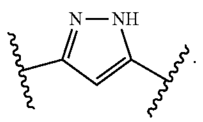 [SMILES: *c1cc(*)[nH]n1]

In any aspect or embodiment described herein, $(Y^3)_{0-5}$ is

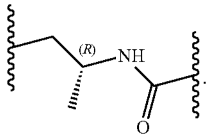

In any aspect or embodiment described herein, the ABM comprises a structure selected from, but not limited to the structures shown below, where a dashed line indicates the attachment point of a linker moiety or a ULM, such as a CLM:

ABM-a

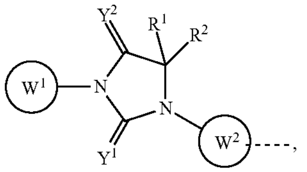

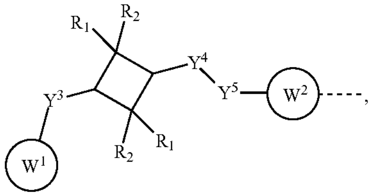

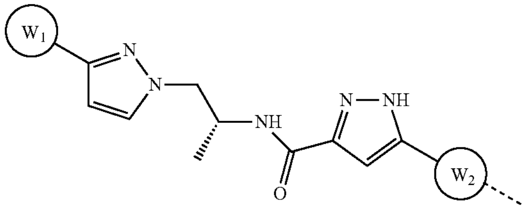

wherein:

$W^1$ is

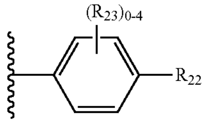

or

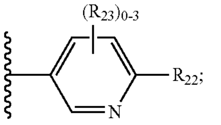

each $R_{22}$ is independently H or —CN;

each $R_{23}$ is independently H, halo, or —$CF_3$;

$Y^1$, $Y^2$ are each independently O or S;

$Y^3$, $Y^4$, $Y^5$ are each independently a bond, O, $NR^{Y2}$, $CR^{Y1}R^{Y2}$, C═O, C═S, SO, or $SO_2$;

$R^1$, $R^2$, are each independently H or a methyl group;

$W^2$ is a bond, $C_{1-6}$ aryl, or heteroaryl, each optionally substituted by 1, 2 or 3 $R^{W2}$; and each $R^{W2}$ is independently H, halo, $C_{1-6}$ alkyl (optionally substituted by 1 or more F), $C_{3-6}$ cycloalkyl, $C_{4-6}$ cycloheteroalkyl, $OC_{1-3}$alkyl (optionally substituted by 1 or more —F).

In any aspect or embodiment described herein, the $W^2$ is covalently coupled to one or more ULM or CLM groups, or a linker to which is attached one or more ULM or CLM groups as described herein.

In any aspect or embodiment described herein, $W^1$ is selected from the group consisting of:

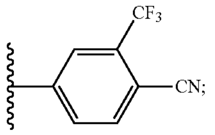

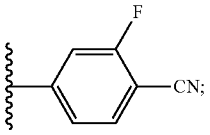

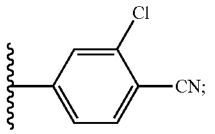

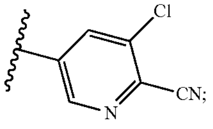

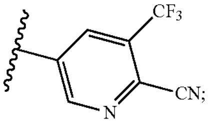

and

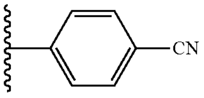

In any aspect or embodiment described herein, W2 is selected from the group consisting of:

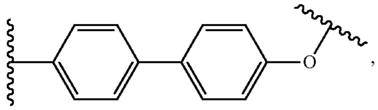

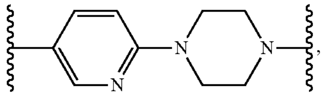

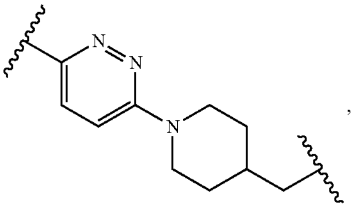

, and

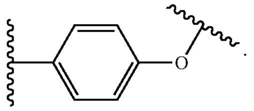

In any aspect or embodiment described herein, the ABM comprises a structure shown below, where a dashed line indicates the attachment point of a linker moiety or a ULM or a CLM:

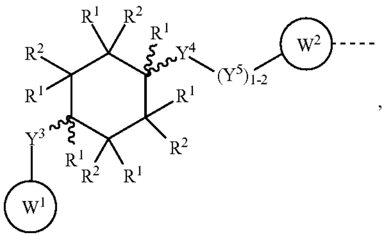

, wherein:

$w^1$ is

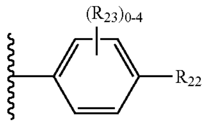
or
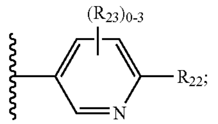

each $R_{22}$ is independently H or —CN;

each $R_{23}$ is independently H, halo, or —$CF_3$;

$Y^3$ is a bond or O;

$Y^4$ is a bond or NH;

$Y^5$ is a bond, C═O, $C_1$-$C_6$ heteroaryl, or $C_1$-$C_6$ aryl;

$R^1$, $R^2$, are each independently H, or $C_1$-$C_6$ alkyl (linear or branched, optionally substituted by 1 or more halo, or $C_{1-6}$ alkoxyl);

$W^2$ is a bond, $C_{1-6}$ aryl, $C_{1-6}$ heteroaryl, $C_{1-6}$ alicyclic, or $C_{1-6}$ heterocyclic, each optionally substituted by 1-10 $R^{W2}$; and each $R^{W2}$ is independently H, or halo; and ∿∿ represents a bond that may be stereospecific ((R) or (S)) or non-stereospecific.

In any of the embodiments described herein, the $W^2$ is covalently coupled to one or more ULM or CLM groups, or a linker to which is attached one or more ULM or CLM groups as described herein.

In certain additional embodiments, $W^1$ is selected from the group consisting of:

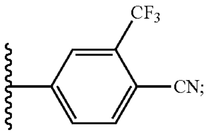
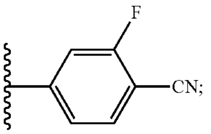
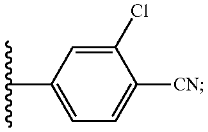
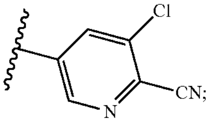
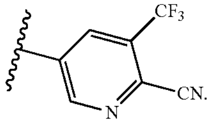

In certain additional embodiments, $W^2$ is selected from the group consisting of:

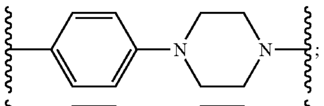
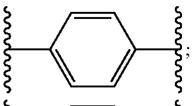
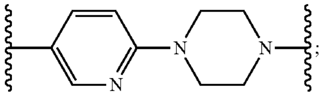
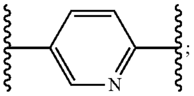
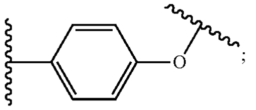
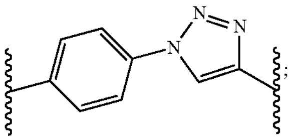

-continued

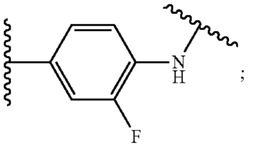
;

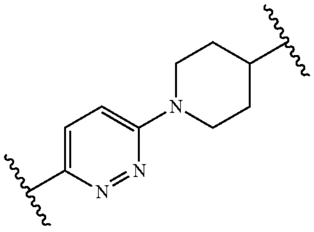
;

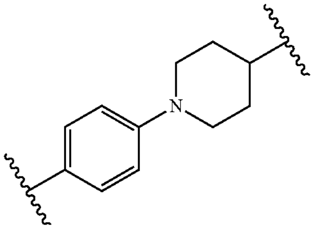
;

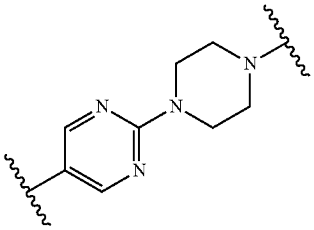
;

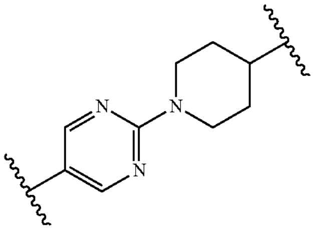
;

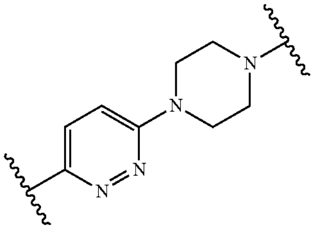
;

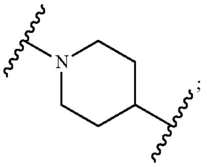
;
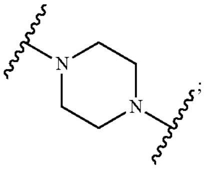
;

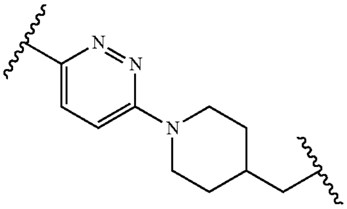
; and

-continued

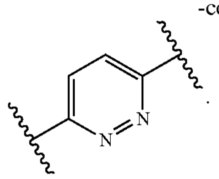

In certain embodiments, the androgen receptor binding compound of ABM is selected from the group consisting of:
trans-2-Chloro-4-[3-amino-2,2,4,4-tetramethylcyclobutoxy] benzonitrile;
cis-2-Chloro-4-[3-amino-2,2,4,4-tetramethylcyclobutoxy] benzonitrile;
trans 6-Amino-N-[3-(3-chloro-4-cyanophenoxy)-2,2,4,4-tetramethylcyclobutyl]pyridazine-3-carboxamide;
trans tert-Butyl N-[3-(3-chloro-4-cyanophenoxy)-2,2,4,4-tetramethylcyclobutyl]carbamate;
trans 4-Amino-N-[3-(3-chloro-4-cyanophenoxy)-2,2,4,4-tetramethylcyclobutyl]benzamide;
trans 5-Amino-N-[3-(3-chloro-4-cyanophenoxy)-2,2,4,4-tetramethylcyclobutyl]pyrazine-2-carboxamide;
trans 2-Amino-N-[3-(3-chloro-4-cyanophenoxy)-2,2,4,4-tetramethylcyclobutyl]pyrimidine-5-carboxamide;
4-Methoxy-N-[(1r,3r)-3-(3-chloro-4-cyanophenoxy)-2,2,4,4-tetramethylcyclobutyl]benzamide;
trans 1-(2-Hydroxyethyl)-N-[3-(3-chloro-4-cyanophenoxy)-2,2,4,4-tetramethylcyclobutyl]-1H-pyrazole-4-carboxamide;
trans 6-Amino-N-[3-(3-chloro-4-cyanophenoxy)-2,2,4,4-tetramethylcyclobutyl]pyridine-3-carboxamide;
trans 4-[(5-Hydroxypentyl)amino]-N-[3-(3-chloro-4-cyanophenoxy)-2,2,4,4-tetramethylcyclobutyl]benzamide; and
trans tert-Butyl 2-({5-[(4-{[3-(3-chloro-4-cyanophenoxy)-2,2,4,4-tetramethylcyclobutyl]carbamoyl}phenyl)aminopentyl}oxy)acetate; and
N-((1r,3r)-3-(4-cyanophenoxy)-2,2,4,4-tetramethylcyclobutyl)-4-methylbenzamide.

In certain embodiments, the description provides, but is not limited to, the following exemplary androgen receptor PROTAC molecules (PROTAC 3 through PROTAC-30), including salts, prodrugs, polymorphs, analogs, derivatives, and deuterated forms thereof:

(PROTAC-3)

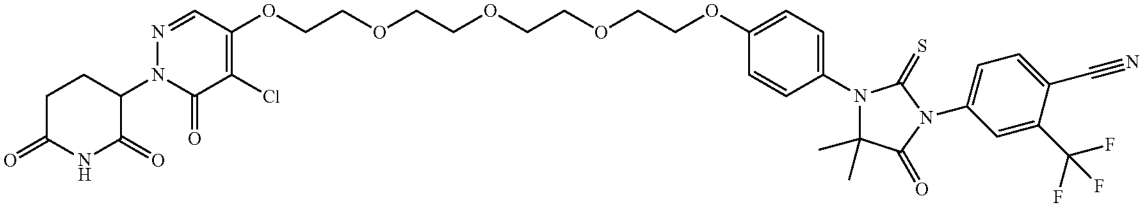

(PROTAC-4)

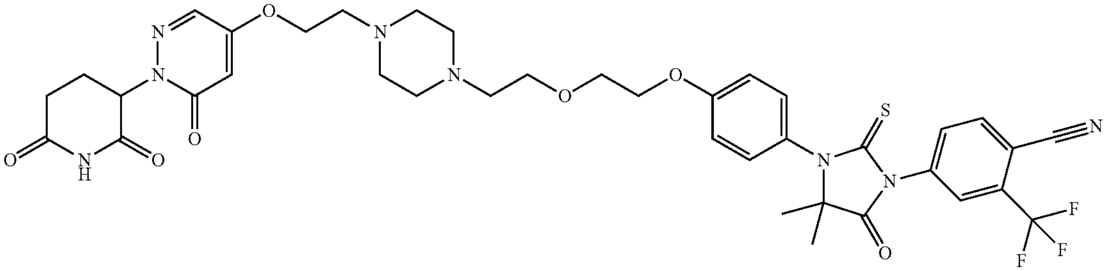

(PROTAC-5)

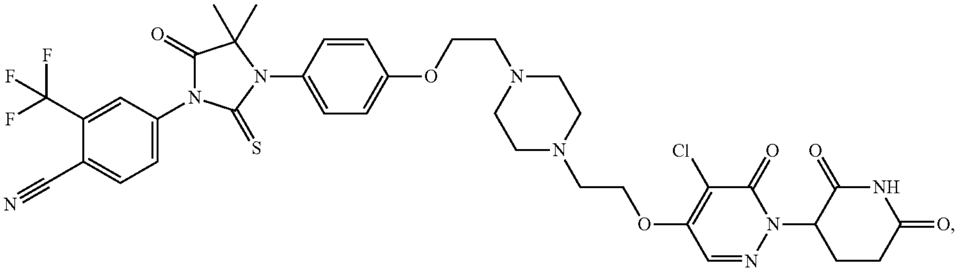

(PROTAC-6)

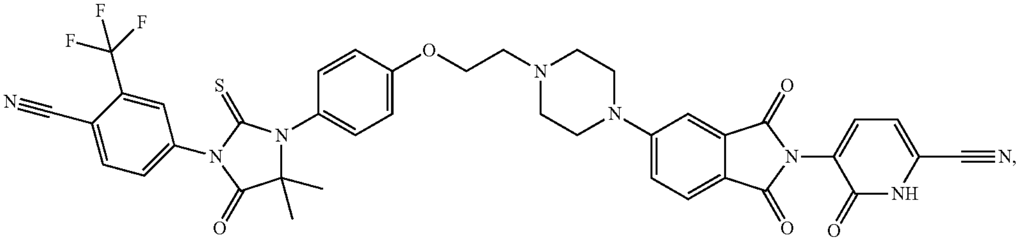

-continued
(PROTAC-7)
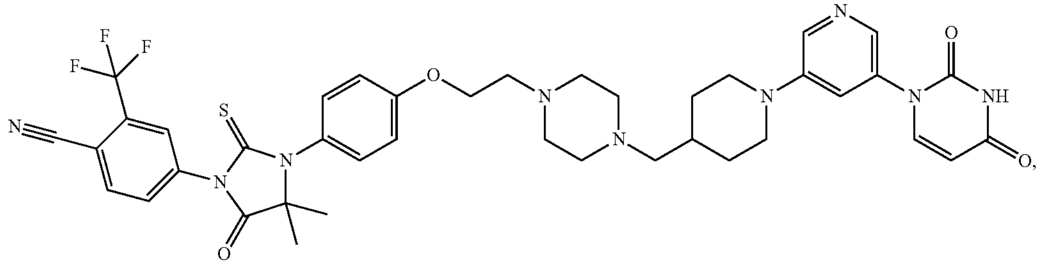
(PROTAC-8)
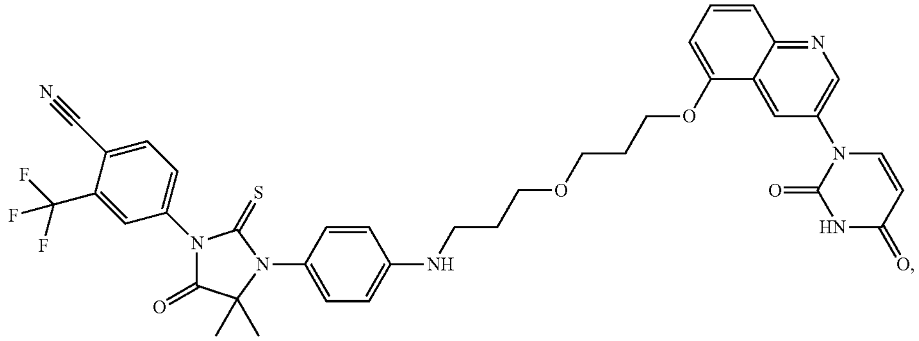
(PROTAC-9)
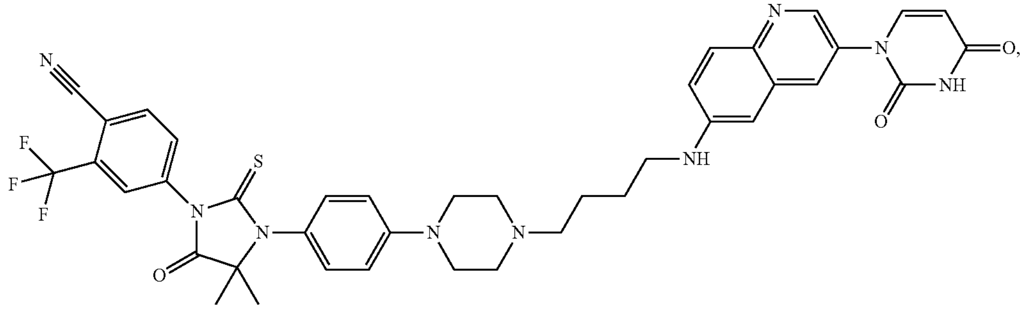
(PROTAC-10)
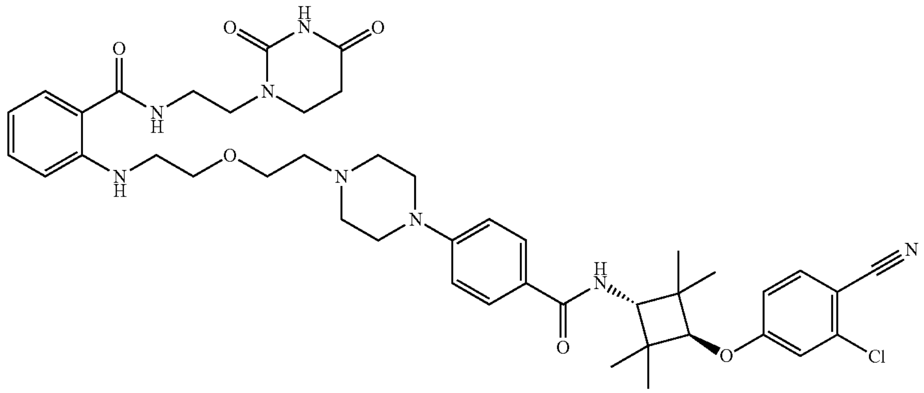

-continued
(PROTAC-11)
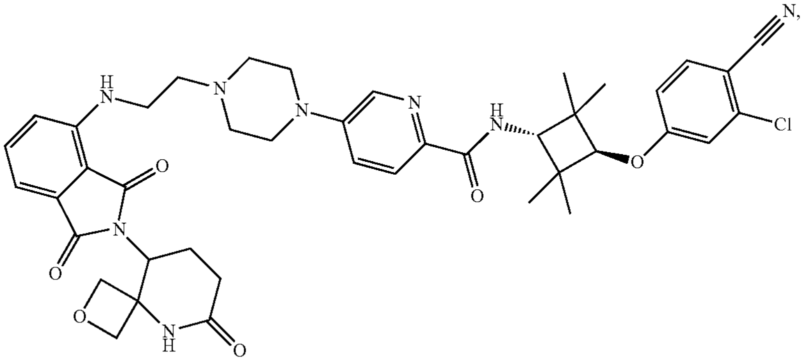
(PROTAC-12)
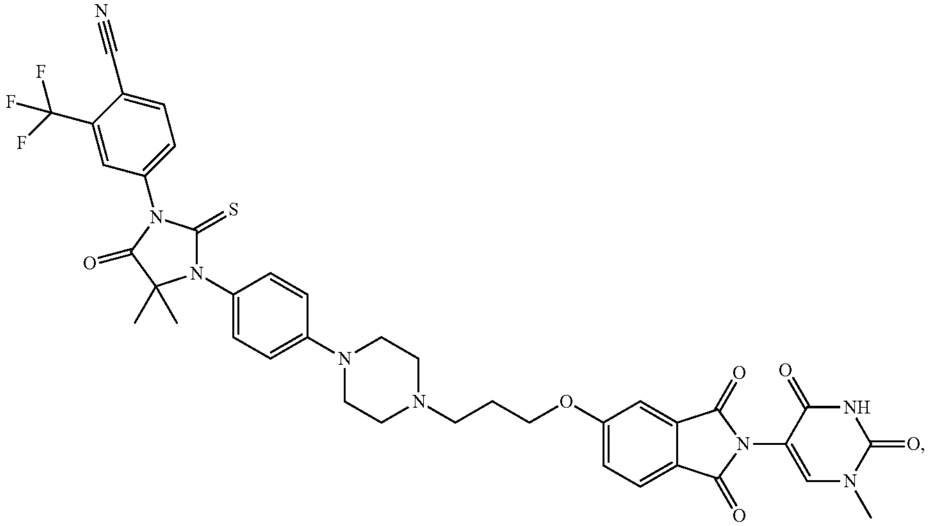
(PROTAC-13)
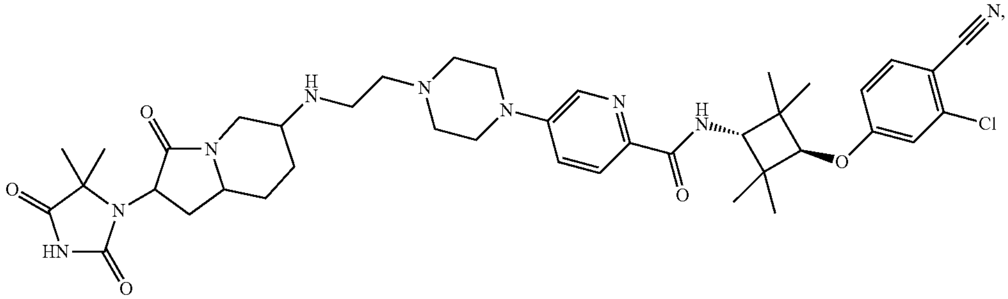
(PROTAC-14)
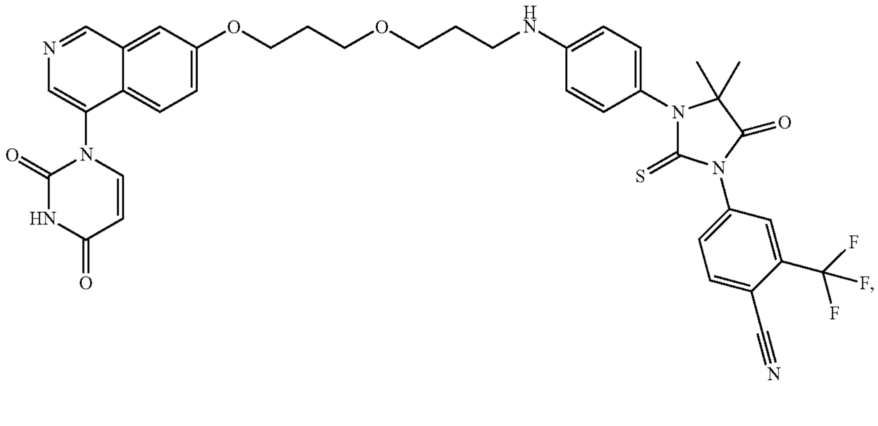

-continued
(PROTAC-15)
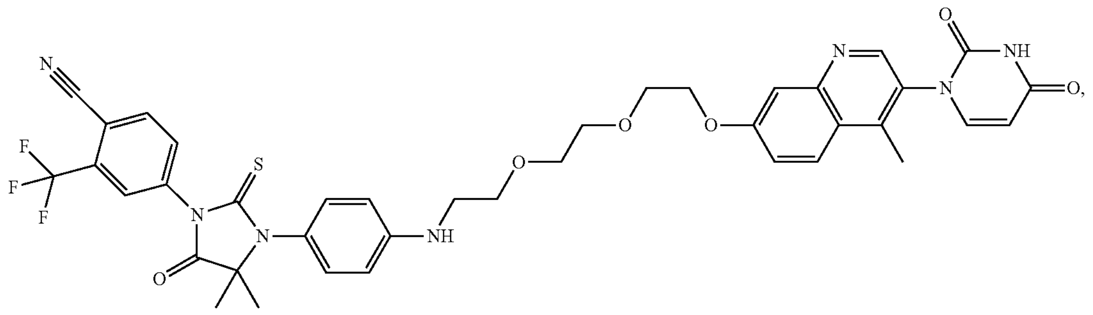
(PROTAC-16)
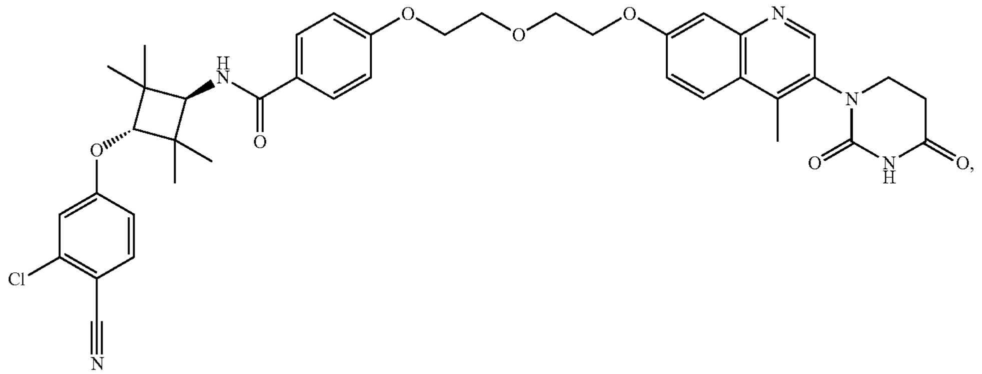
(PROTAC-17)
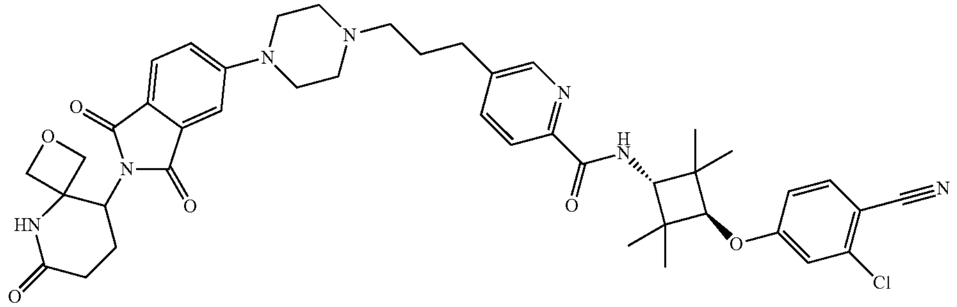
(PROTAC-18)
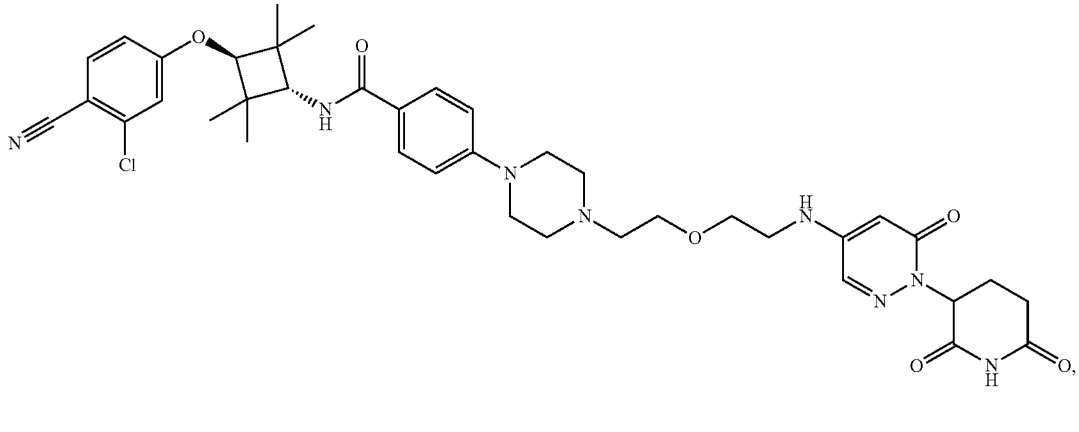

-continued
(PROTAC-19)
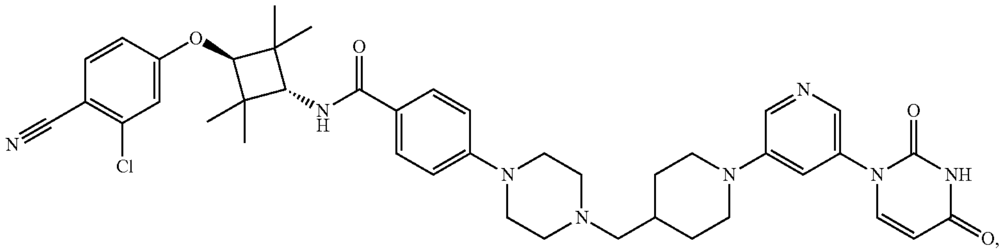
(PROTAC-20)
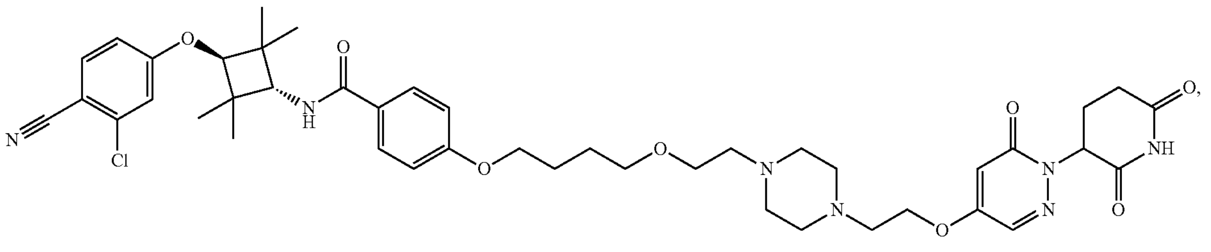
(PROTAC-21)
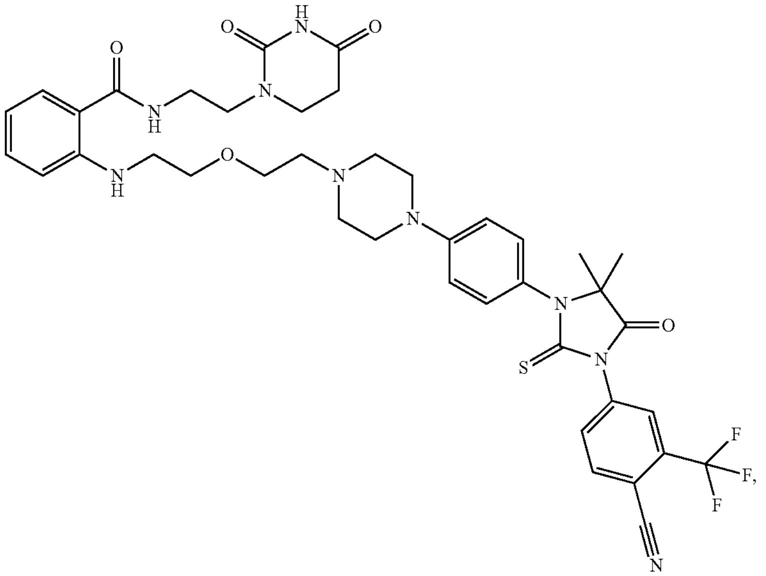
(PROTAC-22)
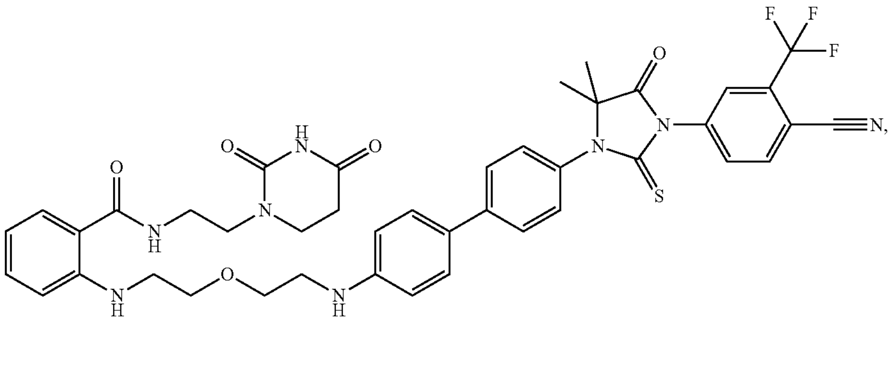

-continued
(PROTAC-23)
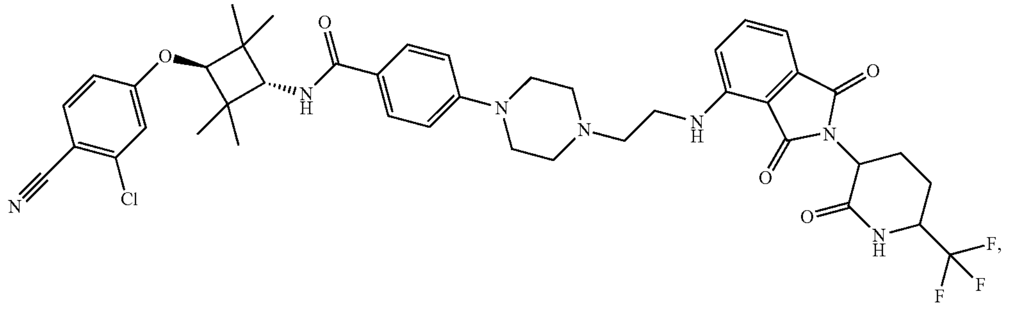
(PROTAC-24)
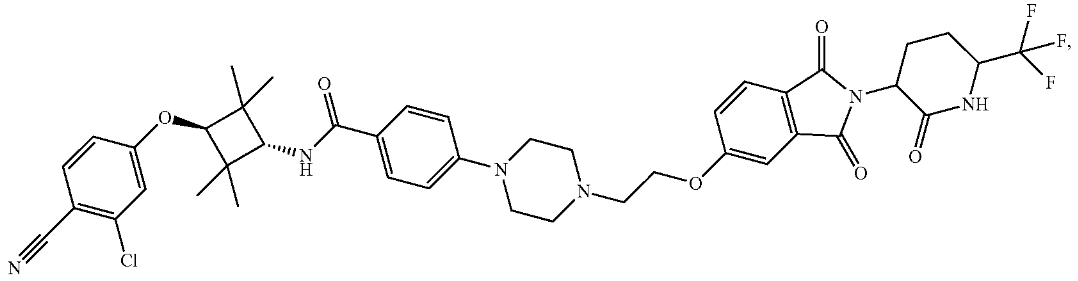
(PROTAC-25)
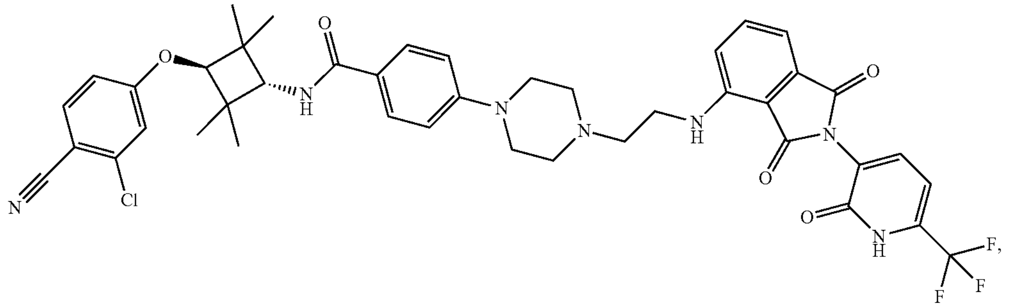
(PROTAC-26)
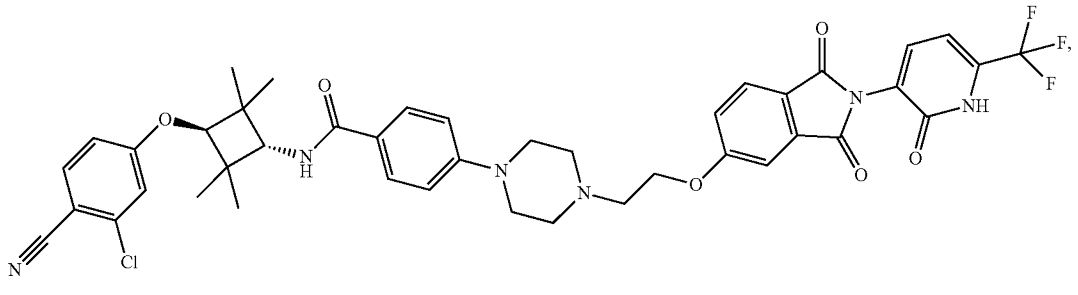

-continued
(PROTAC-27)
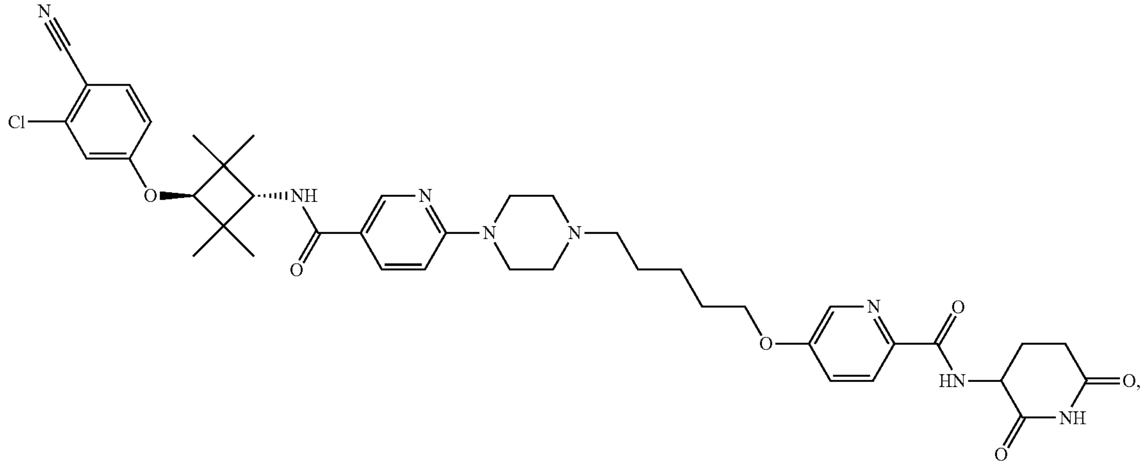
(PROTAC-28)
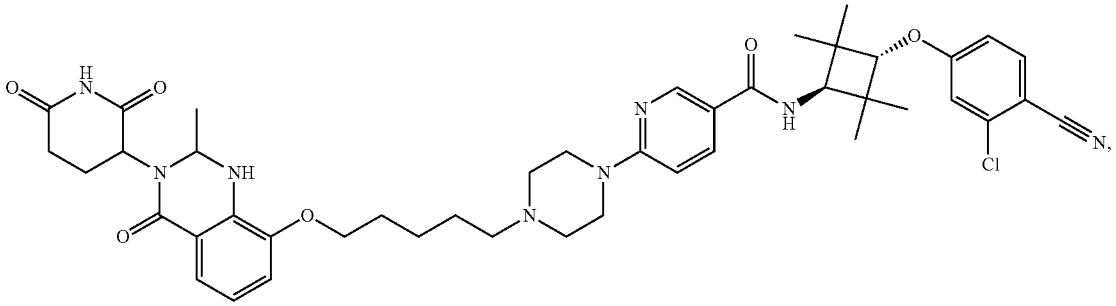
(PROTAC-29)
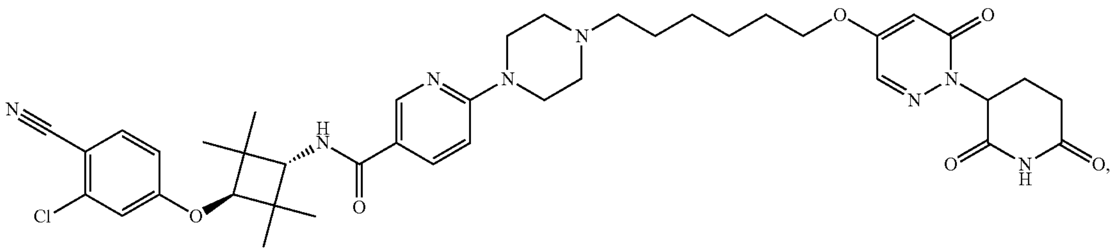
(PROTAC-30)
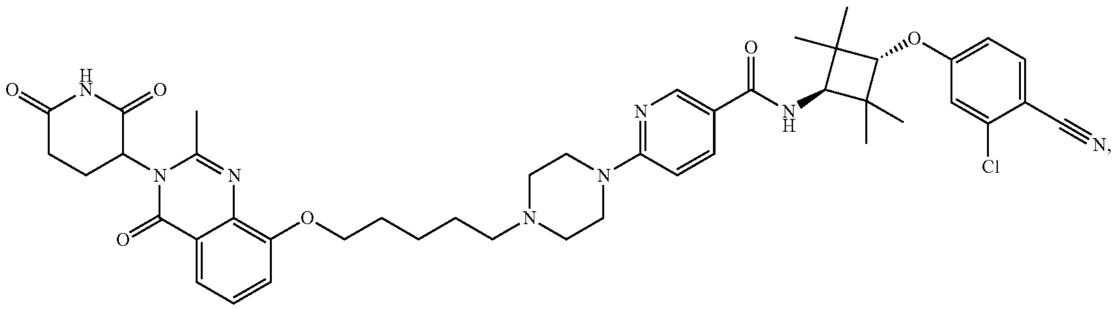

-continued
(PROTAC-31)
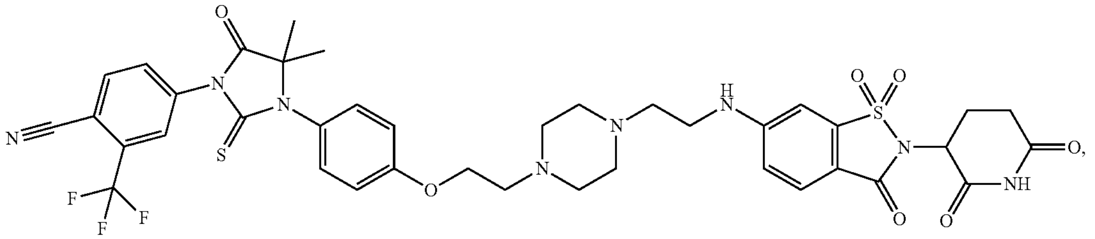
(PROTAC-32)
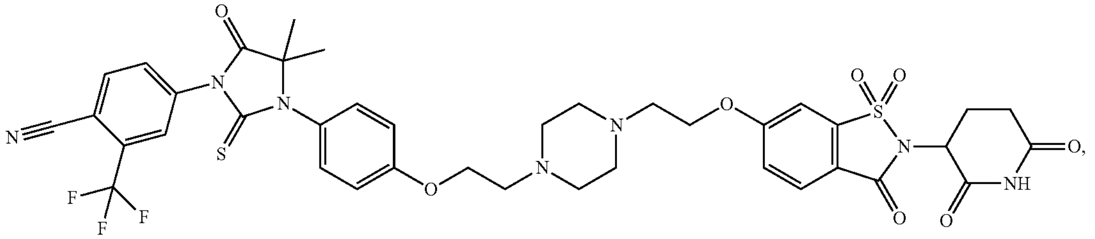
(PROTAC-33)
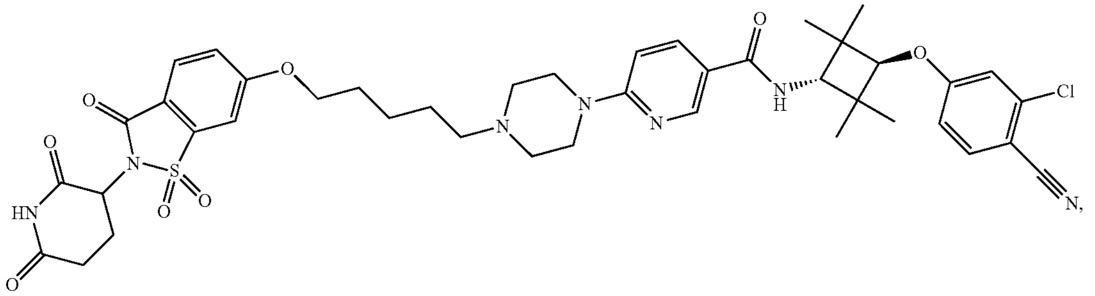
(PROTAC-34)
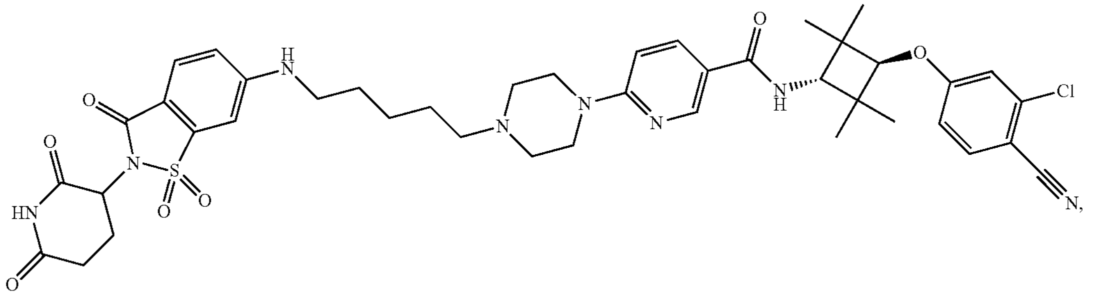
(PROTAC-35)
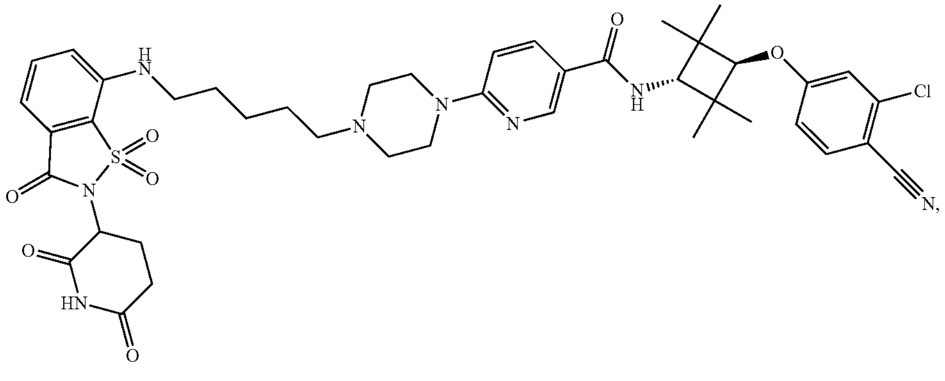

-continued (PROTAC-36)

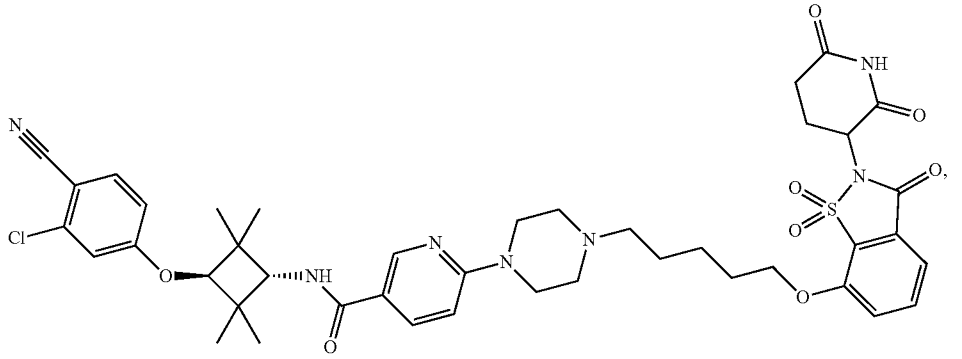

(PROTAC-37)

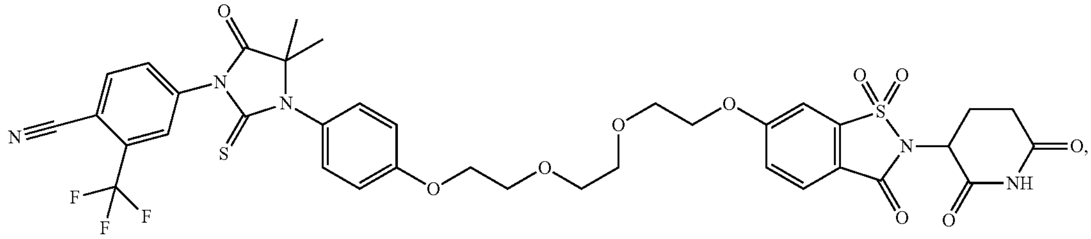

or (PROTAC-38)

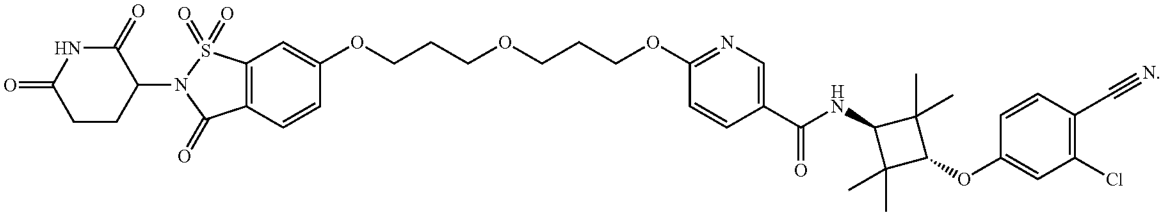

XIII. Compounds Targeting Estrogen Receptor (ER) ICI-182780

1. Estrogen Receptor Ligand

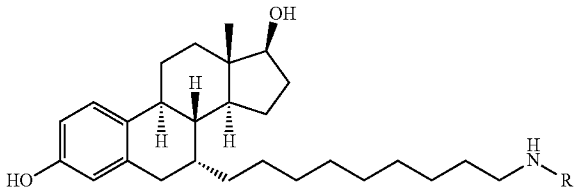

(Derivatized where "R" designates a site for linker group L or -(L-CLM) group attachment).

In any embodiment or aspect described herein, the PTM may be represented by the Formula PTM-I:

PTM-I

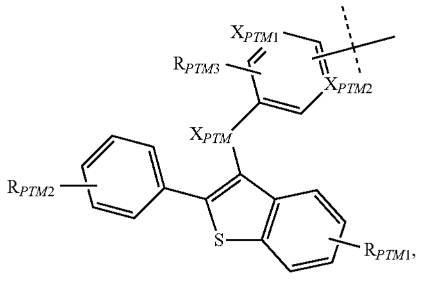

wherein:

$X_{PTM}$ is O or C═O;

each of $X_{PTM1}$ and $X_{PTM2}$ is independently selected from N or CH;

$R_{PTM1}$ is independently selected from OH, O(CO)$R_{PTM}$, O-lower alkyl, wherein $R_{PTM}$ is an alkyl or aryl group in the ester;

at least one $R_{PTM2}$, each independently selected from H, OH, halogen, CN, $CF_3$, $SO_2$-alkyl, O-lower alkyl;

at least one $R_{PTM3}$, each independently selected from H, halogen; and the dashed line indicates the site of attachment of at least one linker, CLM, CLM', PTM, PTM', or a combination thereof.

In any embodiment or aspect described herein, the PTM may be represented by the Formula PTM-I:

PTM-I

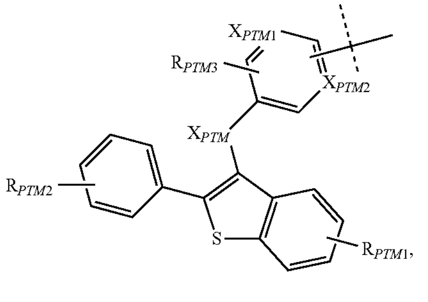

wherein:

$X_{PTM}$ is O or C═O;

each of $X_{PTM1}$ and $X_{PTM2}$ is independently selected from N or CH;

$R_{PTM1}$ is independently selected from OH, O(CO)$R_{PTM}$, O-lower alkyl, wherein $R_{PTM}$ is an alkyl or aryl group in the ester;

each $R_{PTM2}$ is independently selected from H, OH, halogen, CN, $CF_3$, $SO_2$-alkyl, O-lower alkyl;

each $R_{PTM3}$ is independently selected from H, halogen;

the PTM-I comprises as least one $R_{PTM2}$, at least one $R_{PTM3}$, or a combination thereof on the respective rings; and the dashed line indicates the site of attachment of at least one linker, CLM, CLM', PTM, PTM', or a combination thereof.

In any embodiment or aspect described herein, PTM-I has at least one of: two $R_{PTM2}$, two $R_{PTM3}$, or a combination thereof.

In any embodiment or aspect described herein, the PTM may be represented by the Formula PTM-II:

PTM-II

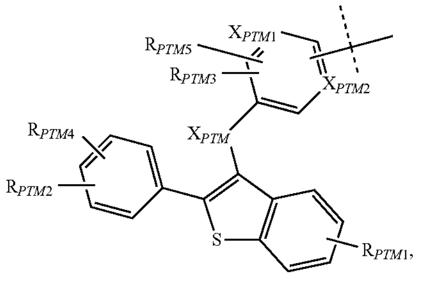

wherein:

$X_{PTM}$ is O or C═O;

each of $X_{PTM1}$ and $X_{PTM2}$ is independently selected from N or CH;

$R^{PTM1}$ is independently selected from OH, O(CO)$R_{PTM}$, O-lower alkyl, wherein $R_{PTM}$ is an alkyl or aryl group in the ester;

$R_{PTM2}$ and $R_{PTM4}$ are independently selected from H, OH, halogen, CN, $CF_3$, $SO_2$-alkyl, O-lower alkyl;

$R_{PTM3}$ and $R_{PTM\ 5}$ are independently selected from H, halogen; and the dashed line indicates the site of attachment of at least one linker, CLM, CLM', PTM, PTM', or a combination thereof.

In aspect or embodiment described herein, O(CO)$R_{PTM}$ functions as a prodrug of the corresponding phenol in Formula PTM-I or PTM-II.

In any embodiment or aspect described herein, the O-lower alkyl of PTM-I or PTM-II an alkyl chain with carbon number 1 to 3.

In aspect or embodiment described herein, the present disclosure provides a compound or PTM of Formula ($I_{PTM}$):

Formula ($I_{PMT}$)

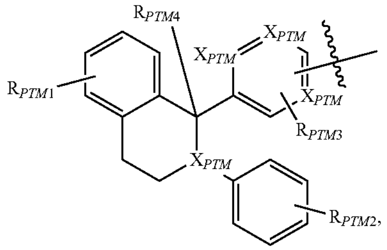

wherein:

each $X_{PTM}$ is independently CH, N;

indicates the site of attachment of at least one linker, CLM, CLM', PTM, PTM', or a combination thereof;

each $R_{PTM}$ is independently OH, halogen, O(CO)$R_{PTM}$, where $R_{PTM}$ is alkyl or cycloalkyl group with 1 to 6 carbons or aryl groups, substitution can be mono-, di- or tri-substituted;

each $R_{PTM2}$ is independently H, halogen, CN, $CF_3$, alkoxy, substitution can be mono- or di-substitution; and each $R_{PTM3}$ is independently H, halogen, substitution can be mono- or di-substitution.

In any aspect or embodiment described herein, the PTM is represented by the Formula ($II_{PTM}$):

Formula ($II_{PMT}$)

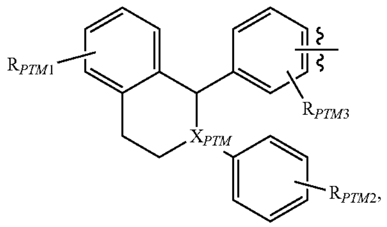

wherein:

$X_{PTM}$ is CH, N;

indicates the site of attachment of at least one linker, CLM, CLM', PTM, PTM', or a combination thereof;

each $R_{PTM1}$ is independently OH, halogen (e.g., F);

each $R_{PTM2}$ is independently H, halogen (e.g., F), $CF_3$, substitution can be mono- or di-substitution; and each $R_{PTM3}$ is independently halogen (e.g. F), substitution can be mono- or di-substitution.

In certain embodiments, at least one of:

$X_{PTM}$ of Formula ($II_{PTM}$) is CH;

$R^{PTM1}$ of Formula ($II_{PTM}$) is OH;

$R_{PTM2}$ of Formula ($II_{PTM}$m) is H;

each $R_{PTM3}$ of Formula ($II_{PTM}$) is independently H or F; or a combination thereof.

XIV. Compounds Targeting Thyroid Hormone Receptor (TR)

1. Thyroid Hormone Receptor Ligand (Derivatized)

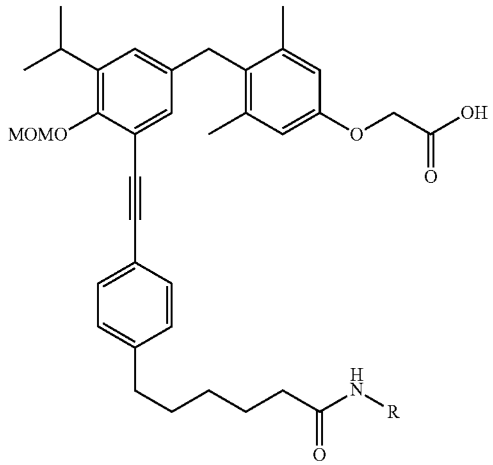

(Derivatized where "R" designates a site for linker group L or -(L-CLM) group attachment and MOMO indicates a methoxymethoxy group).

XV. Compounds Targeting HIV Protease

1. Inhibitor of HIV Protease (Derivatized)

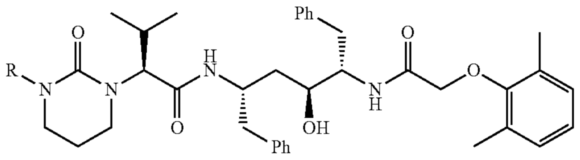

(Derivatized where "R" designates a site for linker group L or -(L-CLM) group attachment). See, *J. Med. Chem.* 2010, 53, 521-538.

2. Inhibitor of HIV Protease

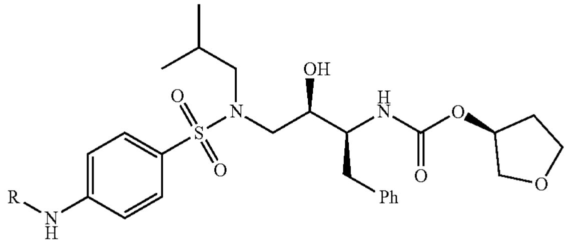

(Derivatized where "R" designates a potential site for linker group L or -(L-CLM) group attachment). See, *J. Med. Chem.* 2010, 53, 521-538.

XVI. Compounds Targeting HIV Integrase

1. Inhibitor of HIV Integrase (Derivatized)

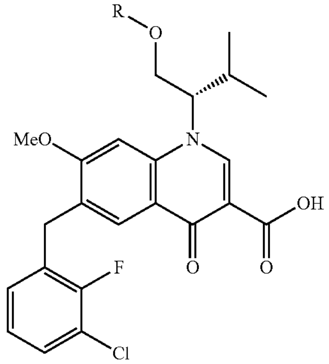

(Derivatized where "R" designates a site for linker group L or -(L-CLM) group attachment). See, *J. Med. Chem.* 2010, 53, 6466.

2. Inhibitor of HIV Integrase (Derivatized)

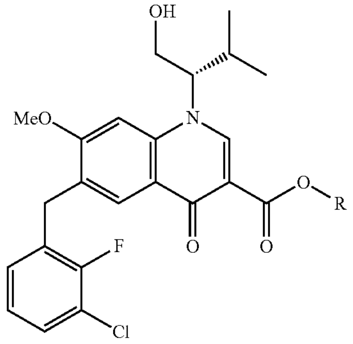

3. Inhibitor of HIV integrase Isetntress (derivatized)

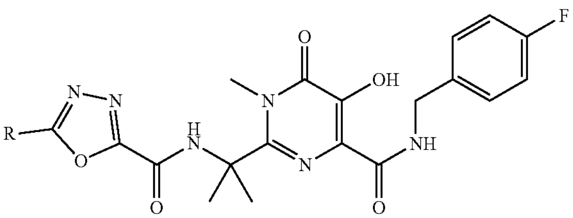

(Derivatized where "R" designates a site for linker group L or -(L-CLM) group attachment). See, *J. Med. Chem.* 2010, 53, 6466.

XVII. Compounds Targeting HCV Protease

1. Inhibitors of HCV Protease (Derivatized)

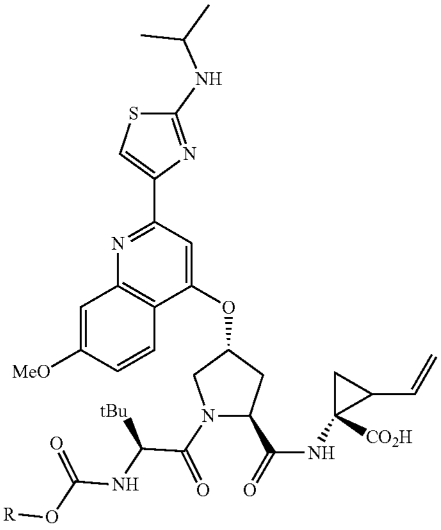

(Derivatized where "R" designates a site for linker group L or -(L-CLM) group attachment).

XVIII. Compounds Targeting Acyl-Protein Thioesterase-1 and -2 (APT1 and APT2)

1. Inhibitor of APT1 and APT2 (Derivatized)

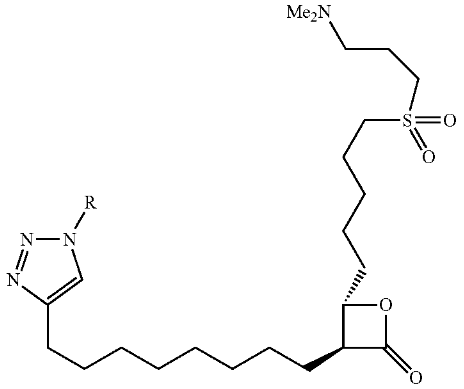

(Derivatized where "R" designates a site for linker group L or -(L-CLM) group attachment). See, *Angew. Chem. Int. Ed.* 2011, 50, 9838 —9842, where L is a linker group as otherwise described herein and said CLM group is as otherwise described herein such that -(L-CLM) binds the CLM group to a PTMgroup as otherwise described herein.

VIV. Compound Targeting Tau Protein

In any aspect or embodiment described herein, the PTM may include a Tau protein binding moieties. For example, the PTM may be represented by Formula I, Formula II, Formula III, Formula IV, Formula V, Formula VI, Formula, VII, Formula, VIII, Formula IX, Formula X, or Formula XI:

I

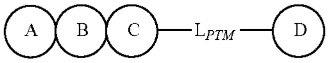

II

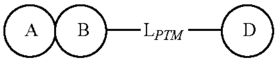

III

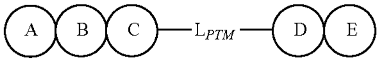

IV

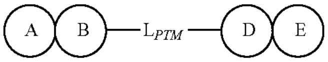

V

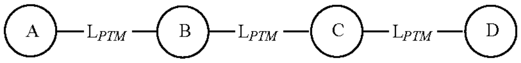

VI

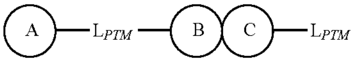

VII

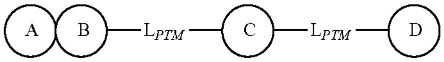

VIII

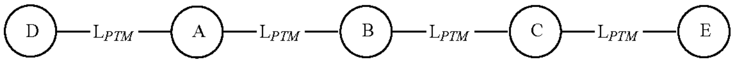

IX

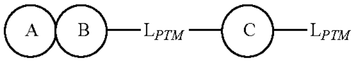

X

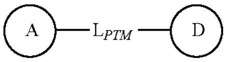

XI

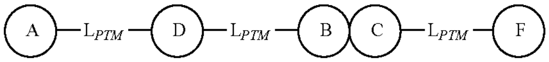, wherein:

A, B, C, D, E, and F are independently selected from an optionally substituted 5- or 6-membered aryl or heteroaryl ring, an optionally substituted 4- to 7-membered cycloalkyl or a heterocycloalkyl, where contact between circles indicates ring fusion; and $L_{PTM}$ is selected from a bond, an alkyl, an alkenyl or an alkynyl, optionally interrupted by one or more rings (i.e., cycloalkyl, heterocycloalkyl, aryl or heteroaryl), or one or more functional groups selected from the groups —O—, —S—, (where $R^1_{PTM}$ is selected from H or alkyl), —N═N—, —S(O)—, —$SO_2$—, —C(O)—, —NHC(O)—, —C(O)NH—, —$NHSO_2$—, —NHC(O)NH—, —NHC(O)O—, or —OC(O)NH—, wherein the said functional group are optionally located at either end of the linker.

In any aspect or embodiment described herein, aryl and heteroaryl rings of A, B, C, D, E, and F of PTM are optionally substituted with 1-3 substituents each independently selected from alkyl, alkenyl, haloalkyl, halogen, hydroxyl, alkoxy, fluoroalkoxy, amino, alkylamino, dialkylamino, acylamino, trifluoromethyl, and cyano, wherein the said alkyl and alkenyl groups are further optionally substituted.

In any aspect or embodiment described herein, the rings of at least one of A, B, C, F, or a combination thereof is selected from optionally substituted 5- or 6-membered aryl or heteroaryl rings;

In any aspect or embodiment described herein, the PTM has the chemical structure of Formula I, wherein:

A, B and C rings are independently 5- or 6-membered fused aryl or heteroaryl rings;

$L_{PTM}$ is selected from a bond or an alkyl, and

D is selected from a 6-membered aryl, heteroaryl or heterocycloalkyl, wherein A, B, C and D are optionally substituted with alkyl, haloalkyl, halogen, hydroxyl, alkoxy, amino, alkylamino, dialkylamino or cyano.

In any aspect or embodiment described herein, The PTM has the chemical structure of Formula I, wherein:

A and C are a phenyl or a 6-membered heteroaryl ring;

B is a 5-membered heteroaryl ring;

$L_{PTM}$ is a bond; and

D is a 6-membered heteroaryl or a 6-membered heterocycloalkyl ring;

wherein each A, B, C and D is optionally independently substituted with alkyl, haloalkyl, halogen, hydroxyl, alkoxy, amino, dialkylamino or cyano, and wherein a nitrogen atom of any of the A, B, C and D rings is not directly connected to a heteroatom or to a carbon atom, to which another heteroatom is directly attached.

In any aspect or embodiment described herein, the PTM has the chemical structure of Formula III or IV, wherein A, B and C are 5- or 6-membered fused aryl or heteroaryl rings, $L_{PTM}$ is selected from a bond or an alkyl, and D and E are 5- or 6-membered fused aryl or heteroaryl rings, wherein A, B, C, D and E are optionally substituted with alkyl, haloalkyl, halogen, hydroxyl, alkoxy, amino, alkylamino, dialkylamino or cyano.

In any aspect or embodiment described herein, the PTM is represented by following chemical structure:

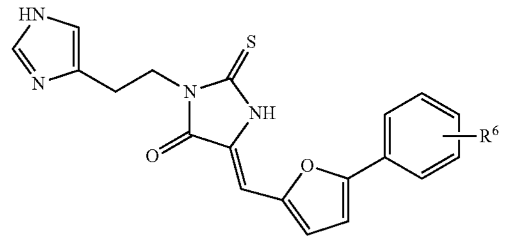

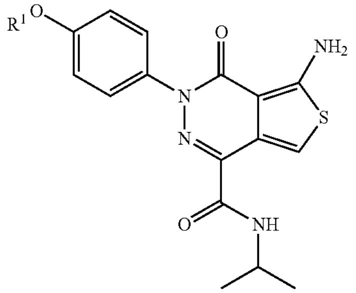

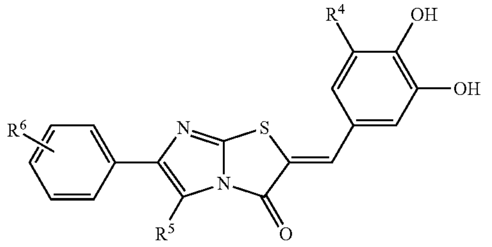

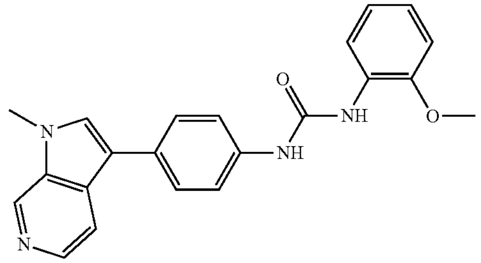

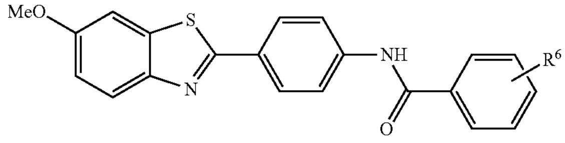

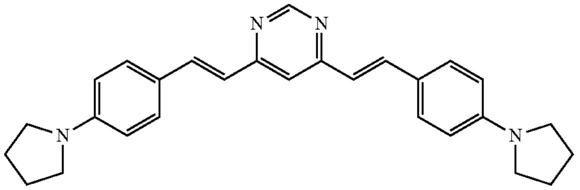

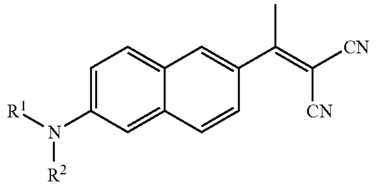

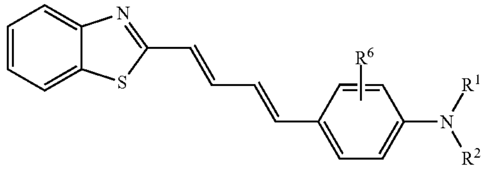

-continued

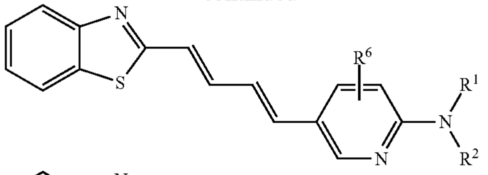

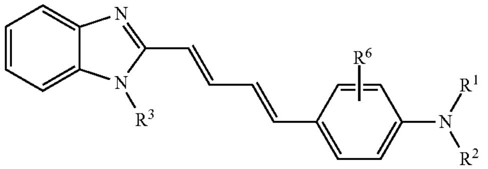

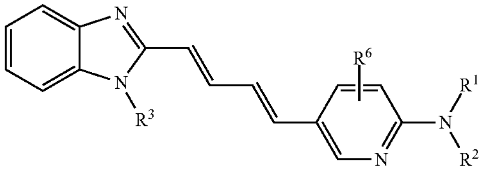

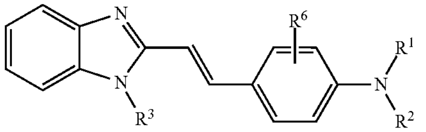

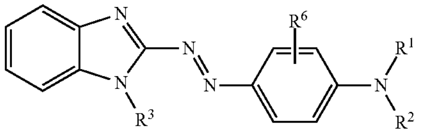

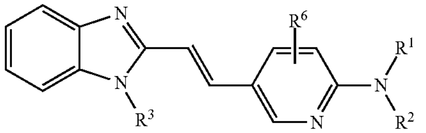

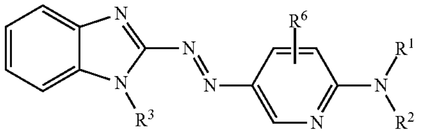

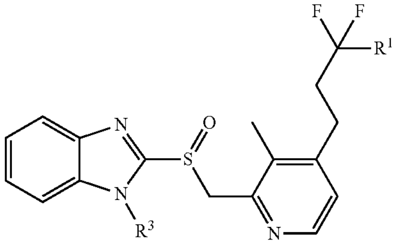

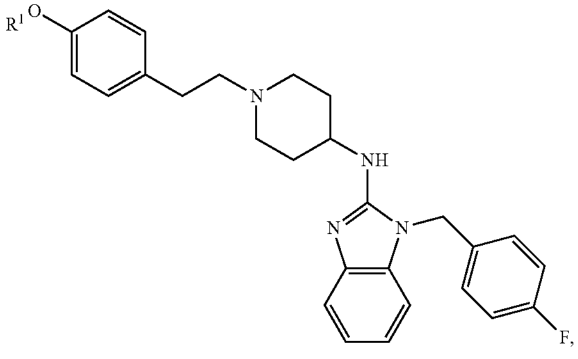

wherein:

R', $R^2$ and $R^3$ are independently selected from H, methyl, ethyl, 2-fluoroethyl and 2,2,2-trifluoroethyl;

$R^4$ and $R^5$ are independently selected from H, methyl, ethyl and halogen; and $R^6$ is 1 to 2 substituents independently selected from H, methyl, ethyl and halogen, wherein the PTM is coupled to a ULM via L.

In any of the aspects or embodiments described herein, the PTM is covalently coupled to one or more ULM (VLM or CLM) groups, or a linker to which is attached one or more ULM (VLM or CLM) groups as described herein.

In any aspect or embodiment described herein, PTM is represented by chemical structure:

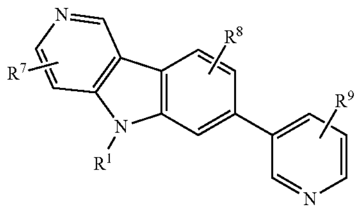

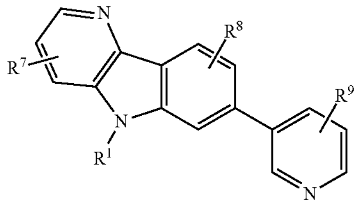

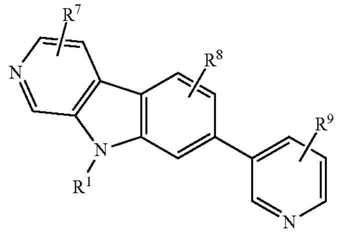

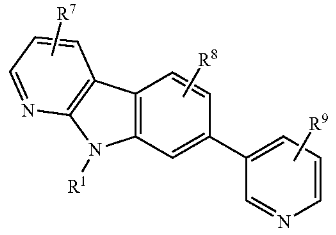

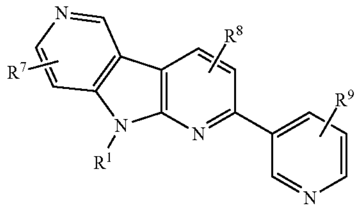

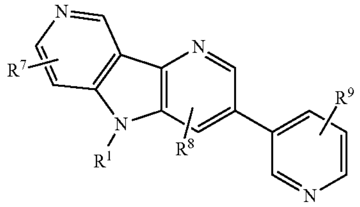

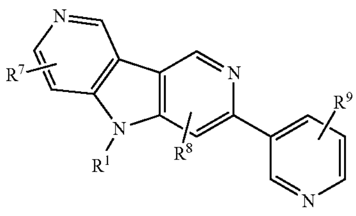
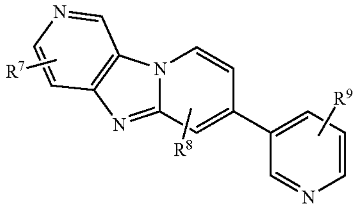
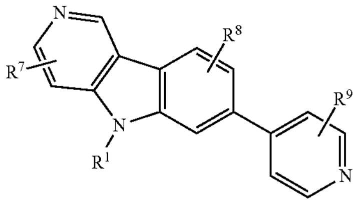
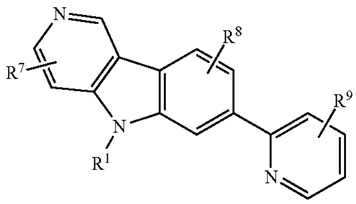
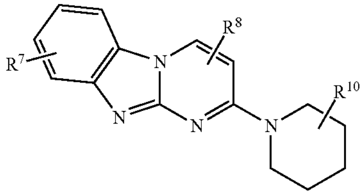
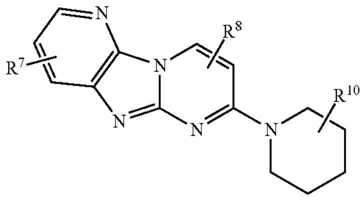
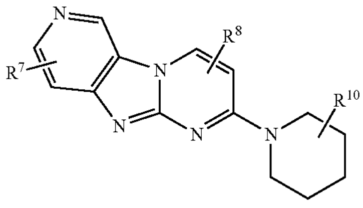
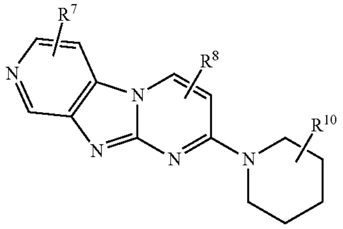
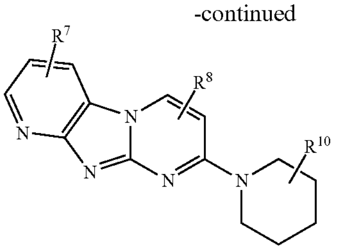
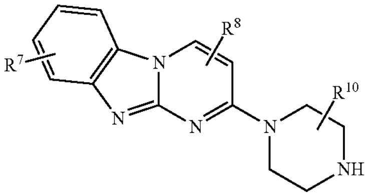
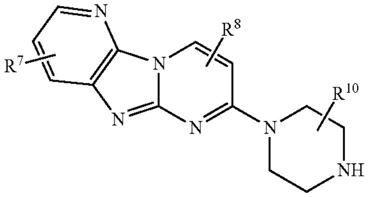
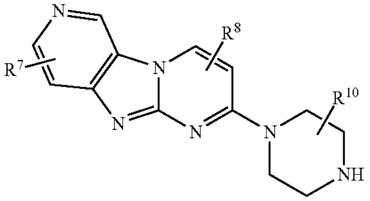
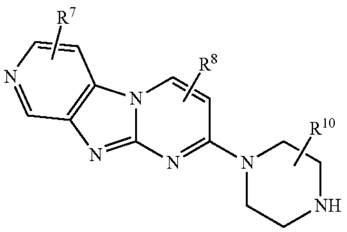
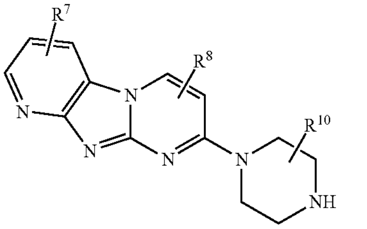
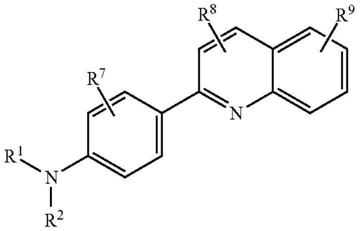
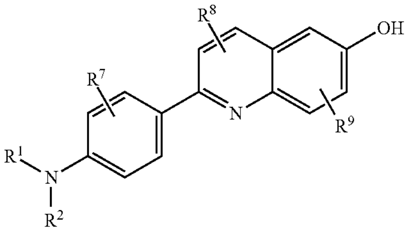

-continued

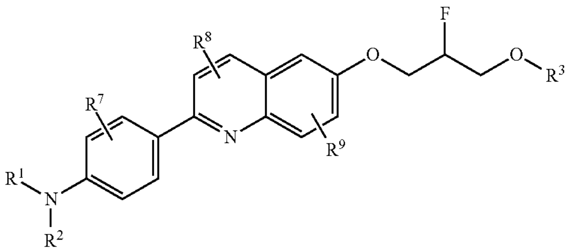

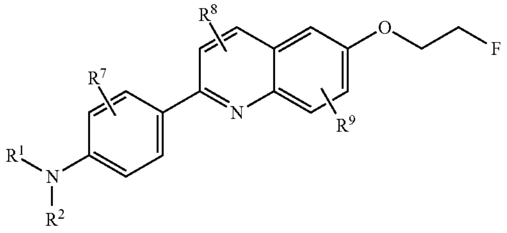

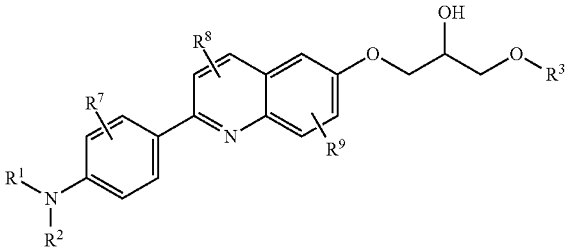

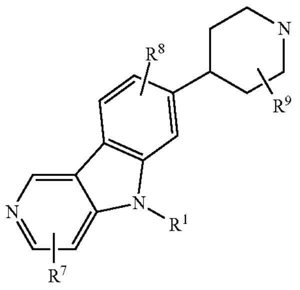

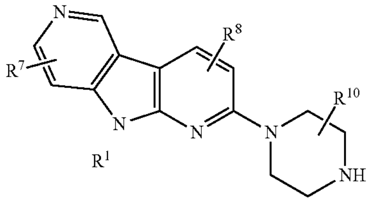

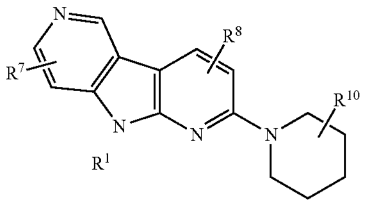

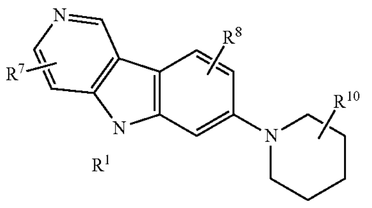

-continued

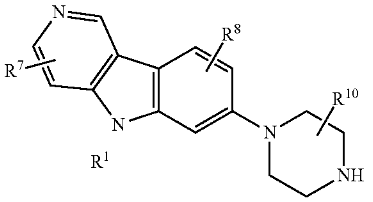

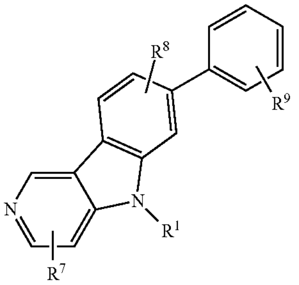

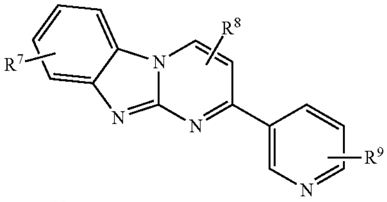

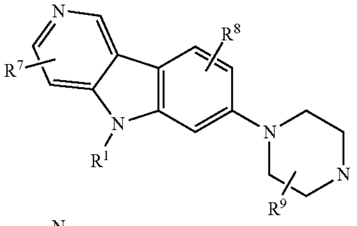

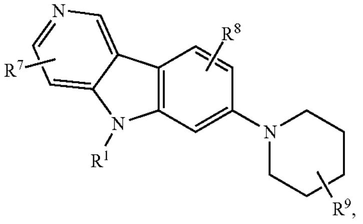

wherein:

R', $R^2$ and $R^3$ are independently selected from H, optionally substituted alkyl, methyl, ethyl, 2-fluoroethyl and 2,2,2-trifluoroethyl; and $R^7$, $R^8$, $R^9$ and $R^{10}$ are 1 to 8 substituents independently selected from H, optionally substituted alkyl, haloalkyl, halogen, hydroxyl, alkoxy, amino, dialkylamino, aceylamino, trifluoromethyl or cyano, and wherein the PTM is coupled to a ULM (VLM or CLM) via L.

In any aspect or embodiment described herein, PTM is represented by chemical

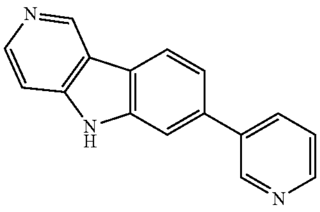

-continued
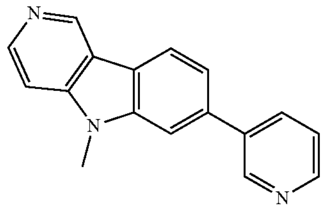
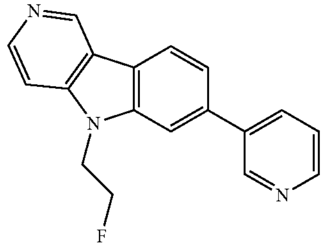
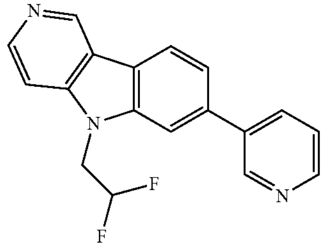
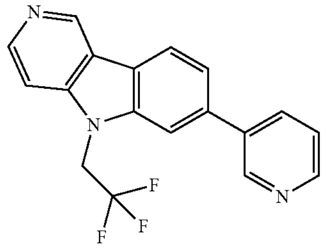
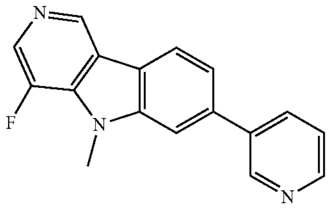
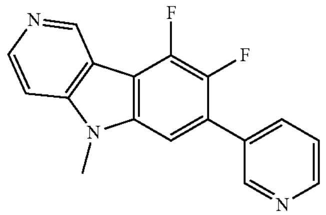
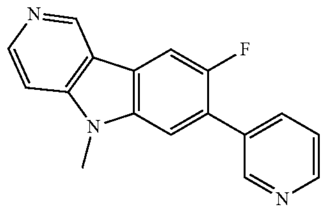
-continued
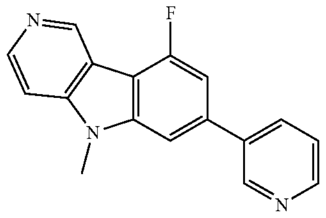
structure:
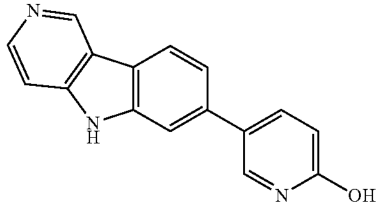
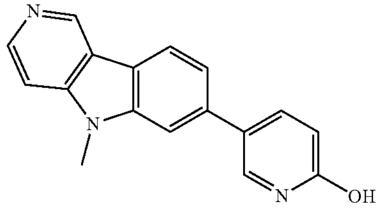
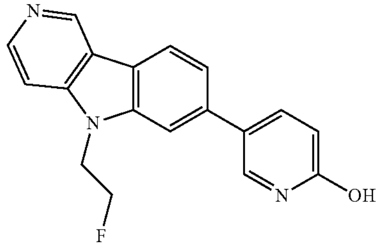
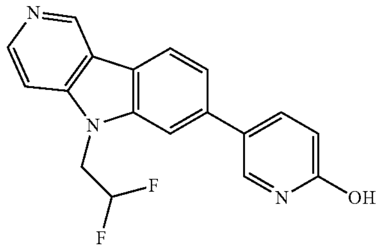
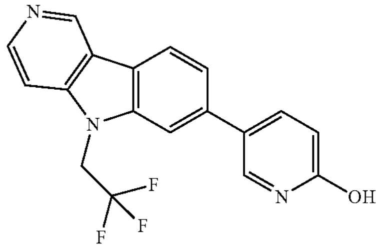
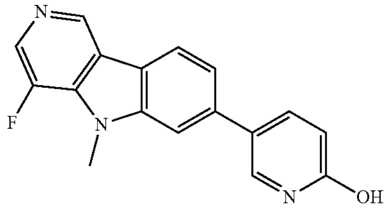

-continued
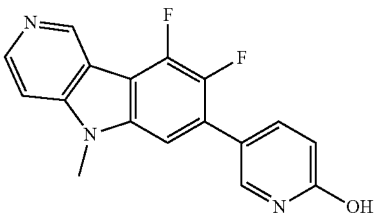
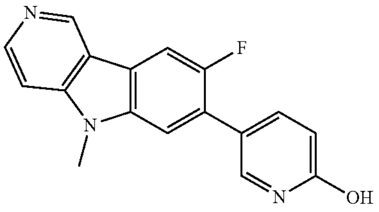
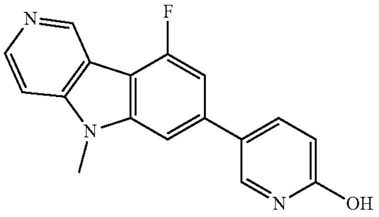
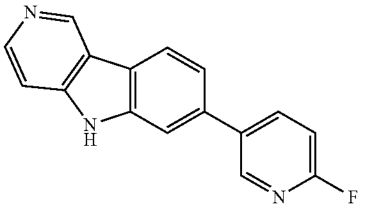
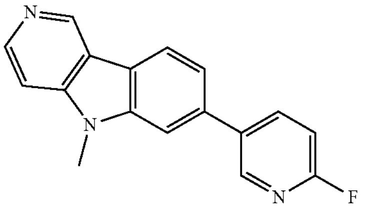
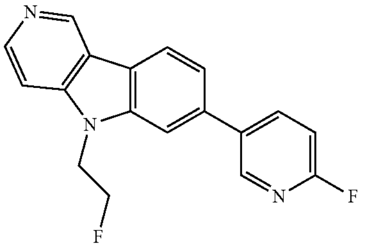
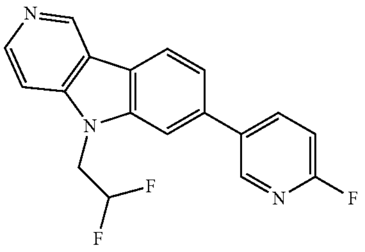
-continued
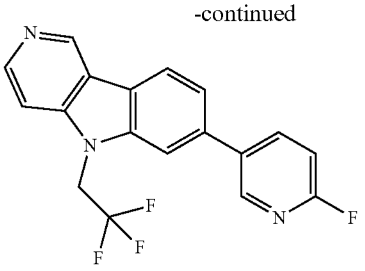
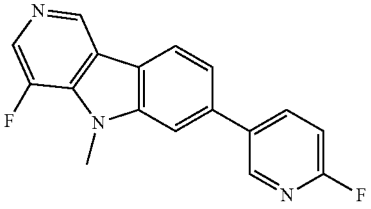
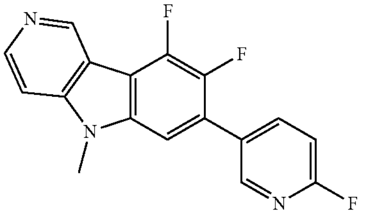
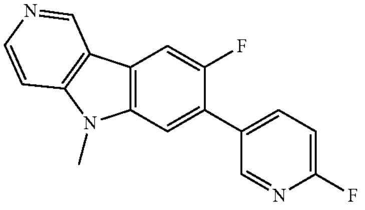
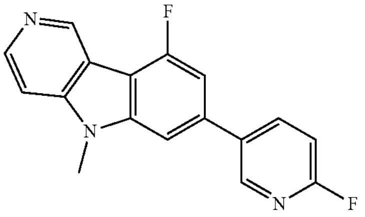
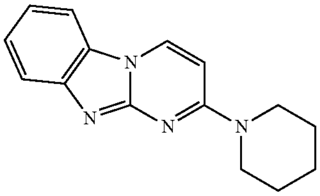
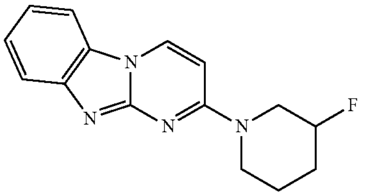
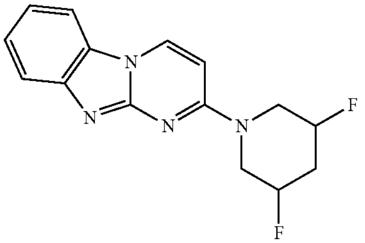

-continued
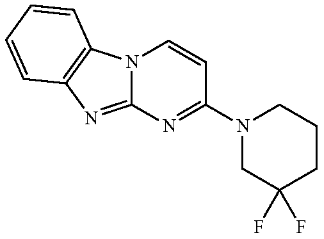
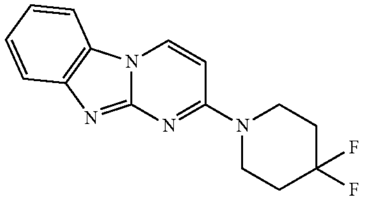
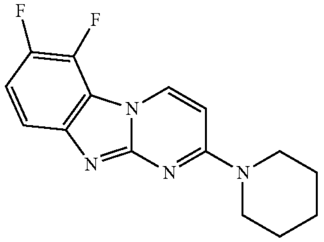
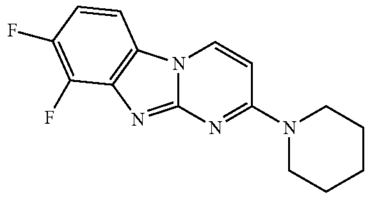
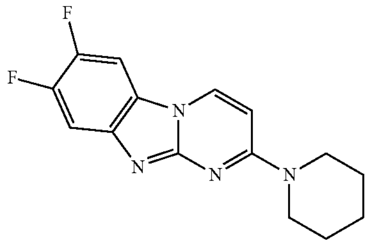
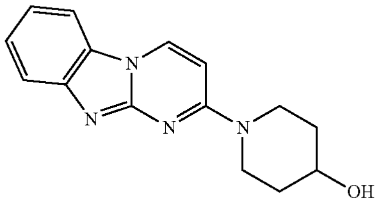
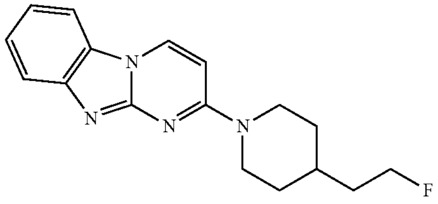
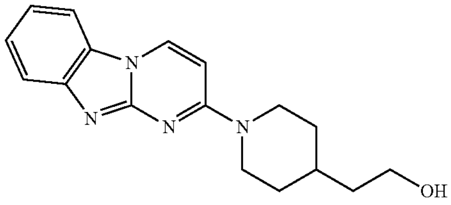
-continued
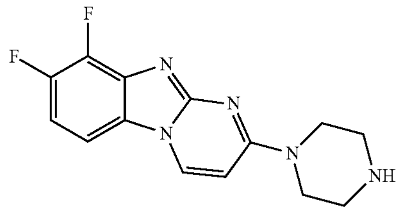
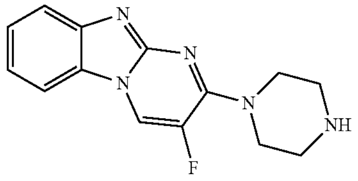
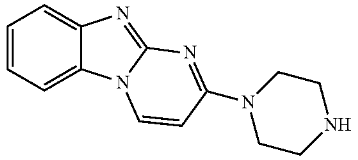
In any aspect or embodiment described herein, the linker attachment point to PTM is as indicated by the dotted line:
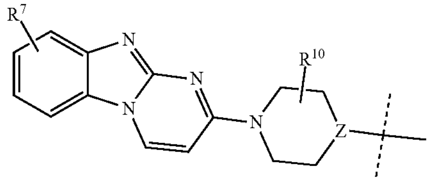
Z = N, CH
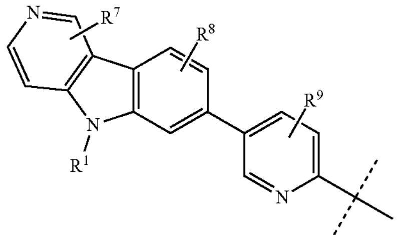
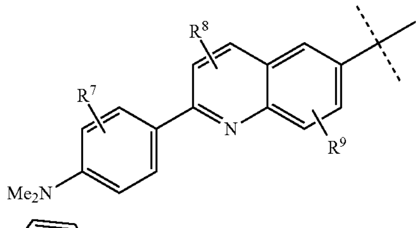
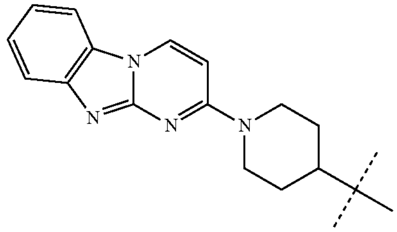

-continued

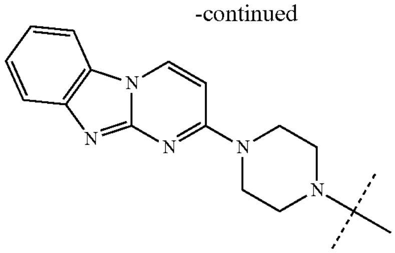

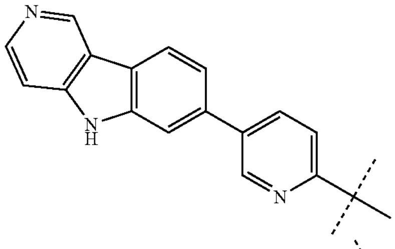

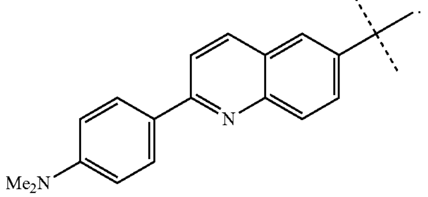

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)] salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosureion may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the invention, one or more compounds according to the present disclosure are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a CLM and a PTM, preferably linked through a linker moiety, as otherwise described herein, wherein the CLM is coupled to the PTM and wherein the CLM recognizes a ubiquitin pathway protein (e.g., an ubiquitin ligase, preferably an E3 ubiquitin ligase such as, e.g., cereblon) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharamaceutically acceptable excipient, carrier, adjuvant, another bioactive agent or combination thereof.

In additional embodiments, the description provides methods for treating or emeliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in that patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term “disease state or condition” is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter’s syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds according to the present disclosure include Alzheimer’s disease, Amyotrophic lateral sclerosis (Lou Gehrig’s disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn’s disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson’s disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present disclosure include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy’s disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley’s Anemia (beta-thalassemia), Copper storage disease (Wilson’s disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George’s syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich’s ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington’s disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Kennedy's syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymilller syndrome, Wolf-Hirschhorn syndrome, Wolff Periodic disease, Weissenbacher-Zweymilller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CIVIL.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocorti sone, fluoxymesterone, flutamide, gleevec, gemcitabine, hydroxyurea, idarubicin, ifosfamide, imatinib, leuprolide, levami sole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-0-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dol as etron, tropi setron, pegfilgrastim, erythropoietin, epoetin alfa, darbepoetin alfa and mixtures thereof.

The term “anti-HIV agent” or “additional anti-HIV agent” includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (-)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI’s (i.e., other than the NNRTI’s according to the present disclosure) may be selected from the group consisting of nevirapine (BI-R6-587), delavirdine (U-90152SIT), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxy carbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697, 661, 342-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/CLMs.

With PTMs and ULMs (e.g. CLMs) in hand one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

Exemplary compounds described in this application can be synthesized by connecting the right hand key fragment prepared according to Schemes 2-30, 2-31,2-40, 2-41, 2-45, and 2-46. The detailed preparation of representative compounds claimed in this application are further described in Schemes 3-10, 3-56, 3-58, and 3-72.

A. Exemplary Cereblon Ligand General Synthetic Schemes

Synthetic schemes 2-30, 2-31, 2-40, 2-41, 2-45, and 2-46 describe the routes used in the preparation of CRBN ligands, as well as CRBN ligands with partial linker moieties connected.

General synthetic scheme 2-30 to prepare intermediate.

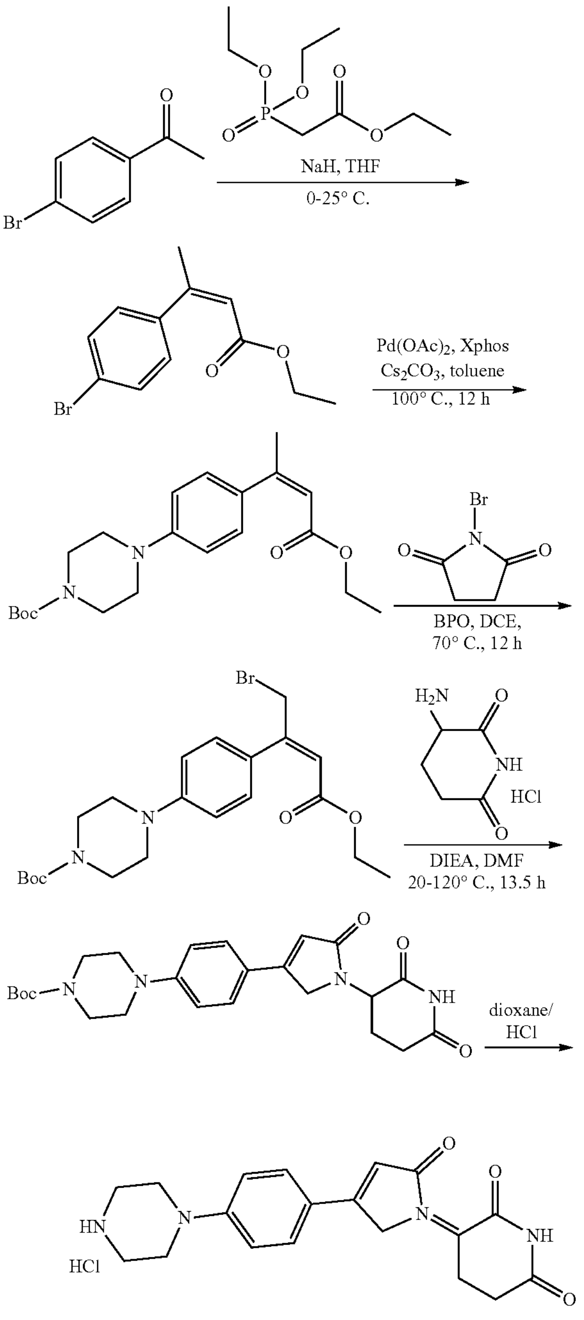

General synthetic scheme 2-31 to prepare intermediate.
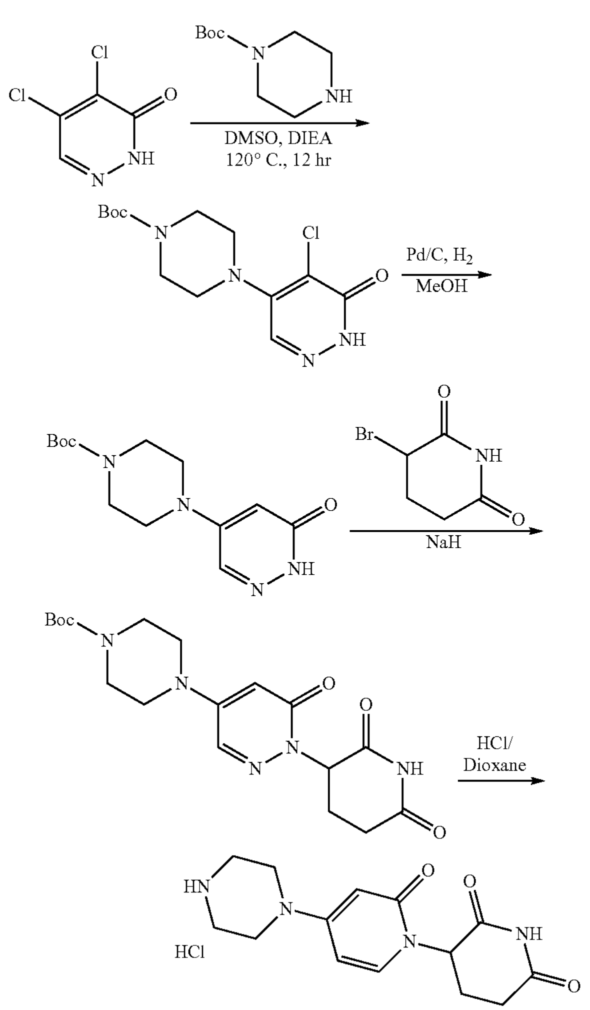
General synthetic scheme 2-40 to prepare intermediate.
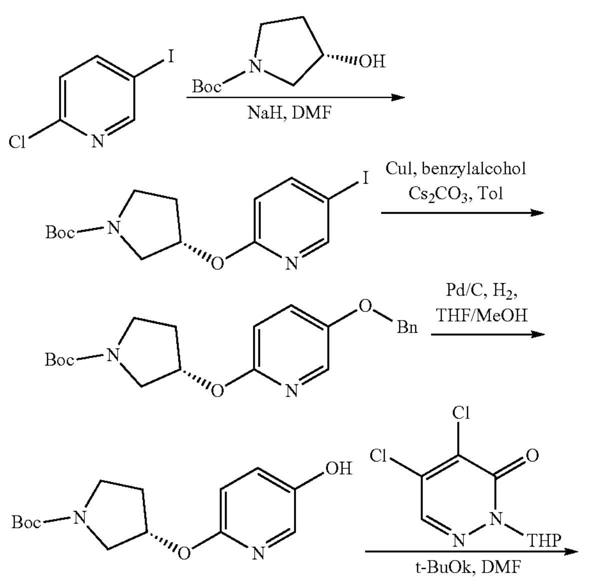
-continued
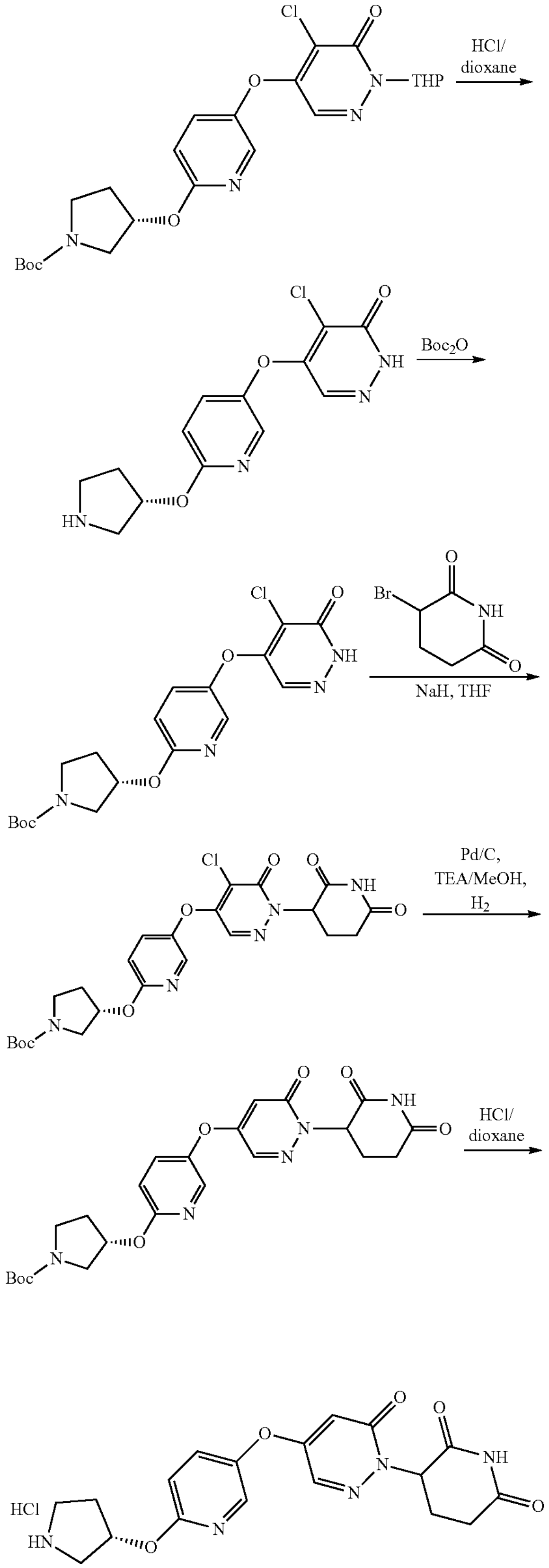

General synthetic scheme 2-41 to prepare intermediate.
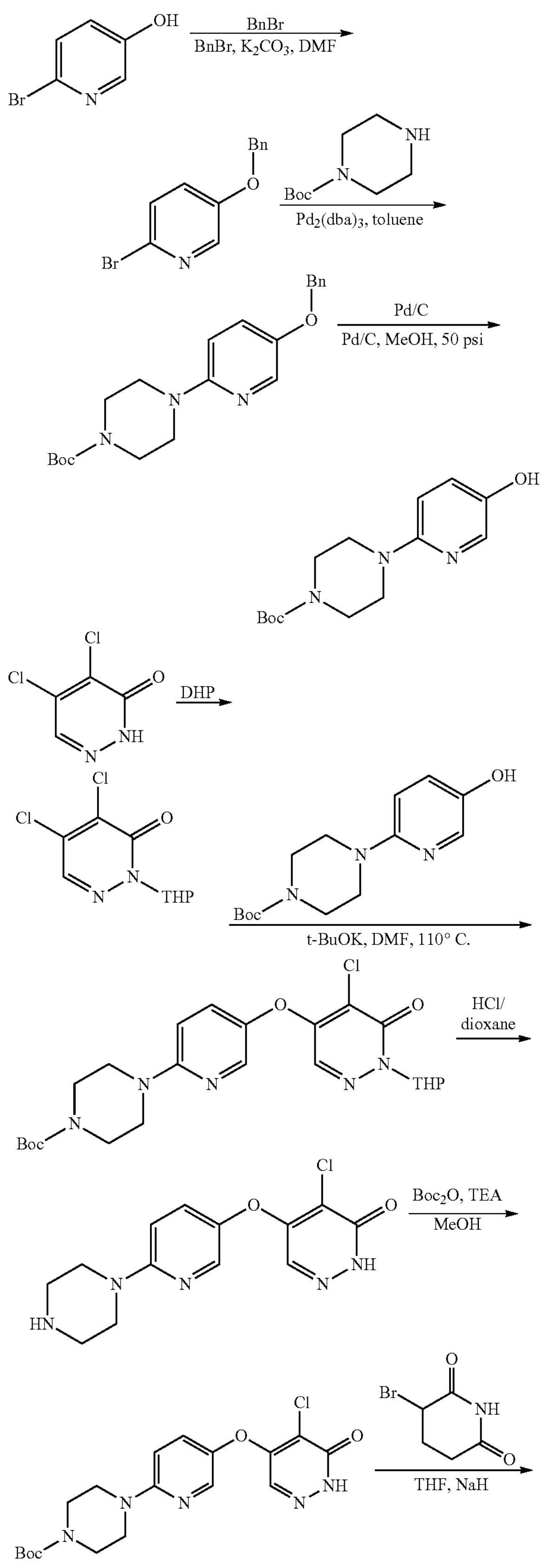
-continued
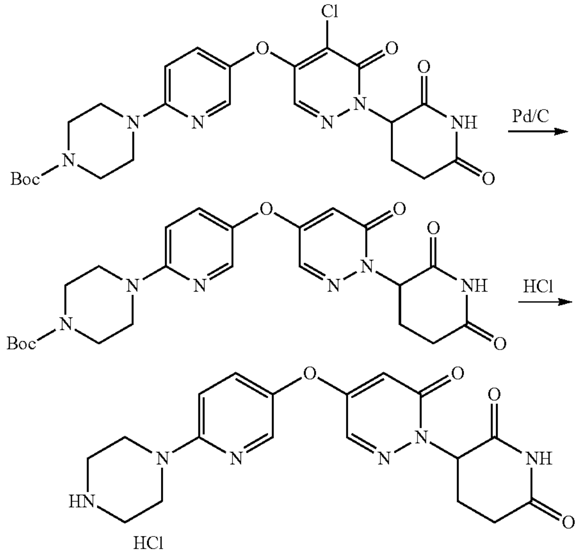
General synthetic scheme 2-45 to prepare intermediate.
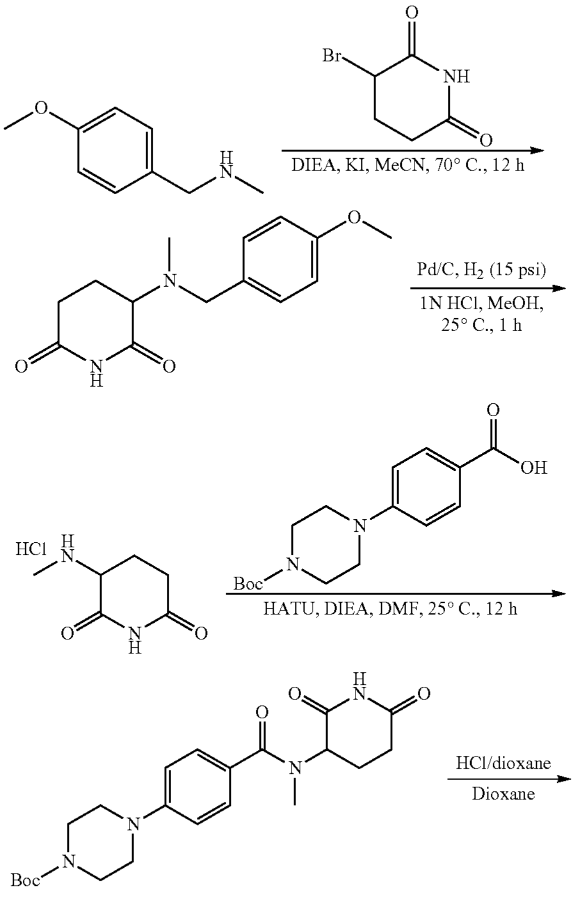

-continued
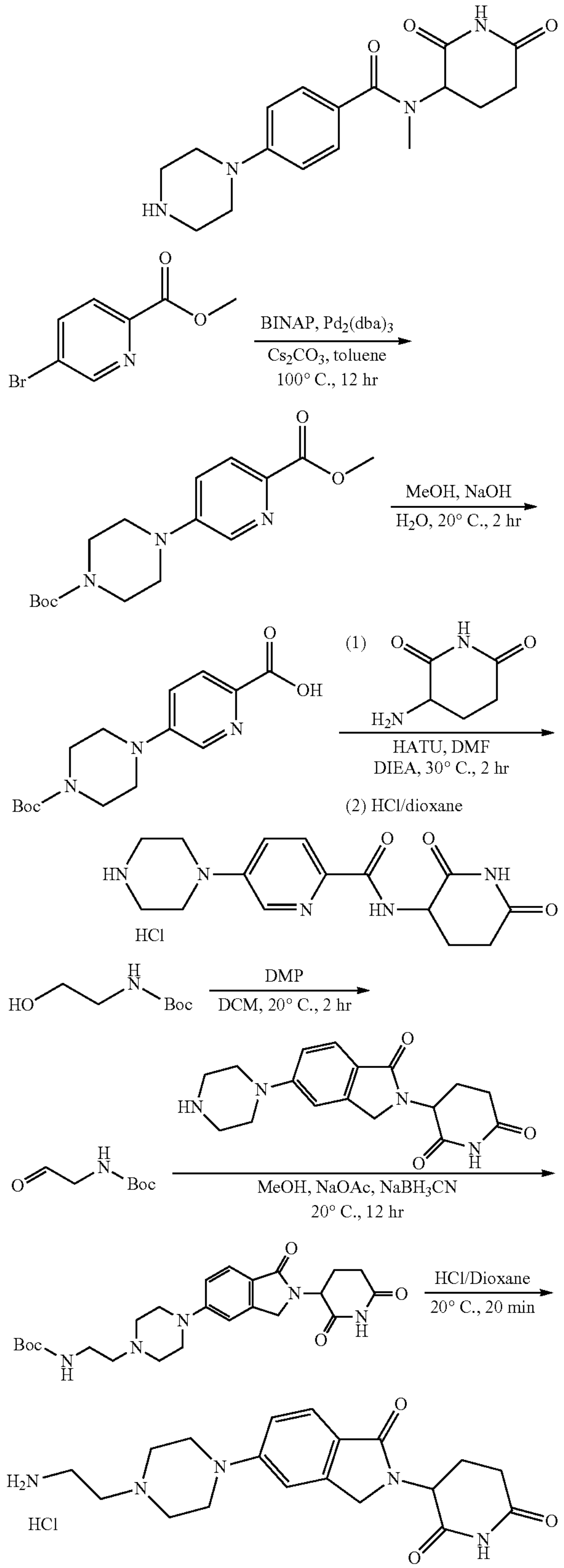
General synthetic scheme 2-46 to prepare intermediate.
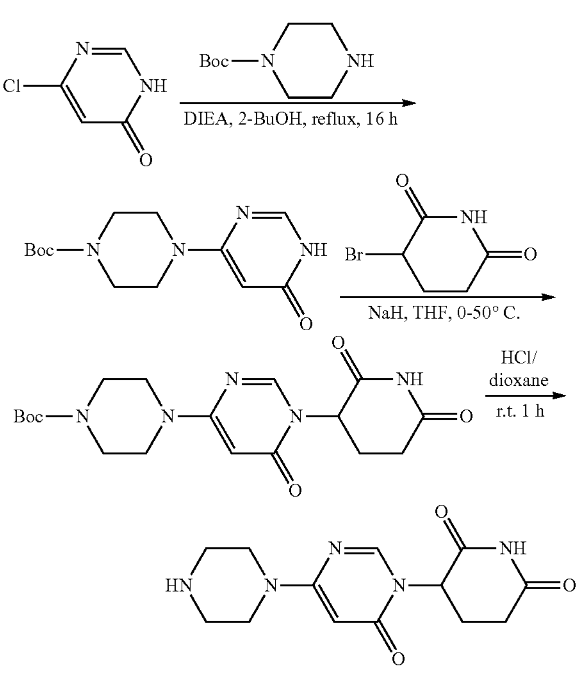
B. Exemplary PROTAC General Synthetic Schemes
Synthetic schemes 3-10, 3-56, 3-58, and 3-72 describe the routes used in the preparation of representative chimeric compounds claimed in this application.
General synthetic scheme 3-10 to prepare claimed compounds.
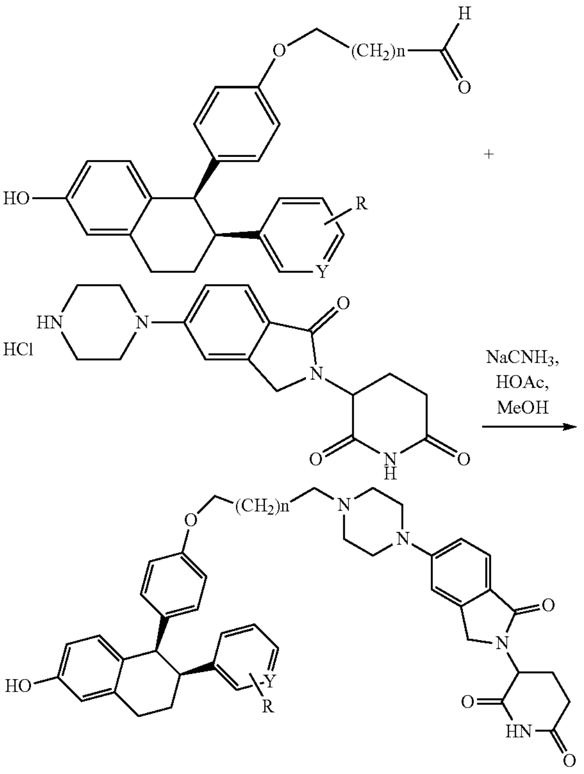
n = 0, 2, 3, 4
R = H, F; Y = CH, N -continued
-continued
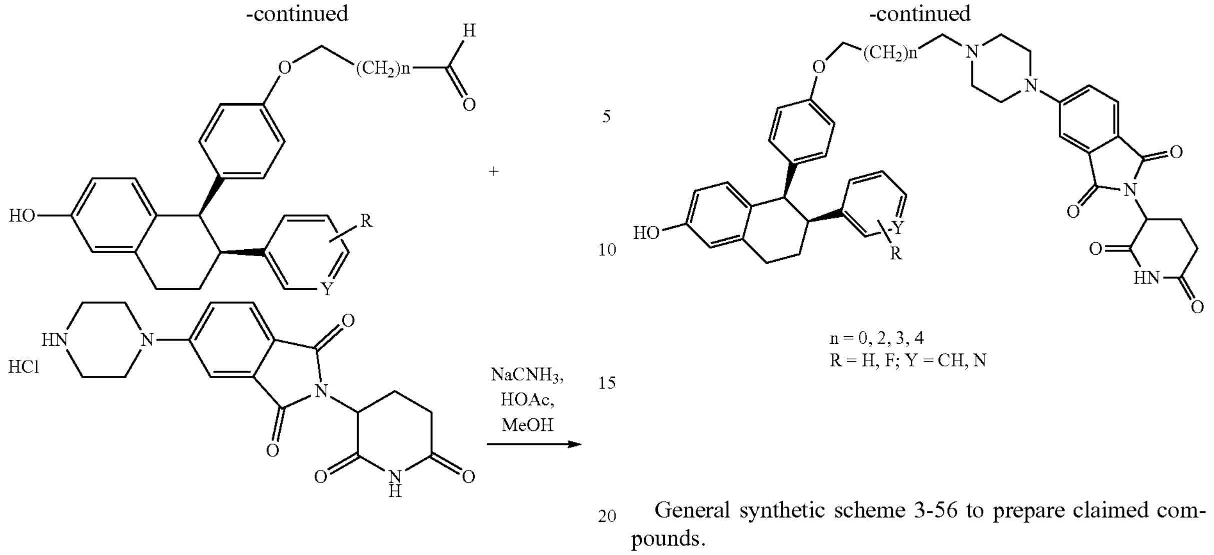
General synthetic scheme 3-56 to prepare claimed compounds.
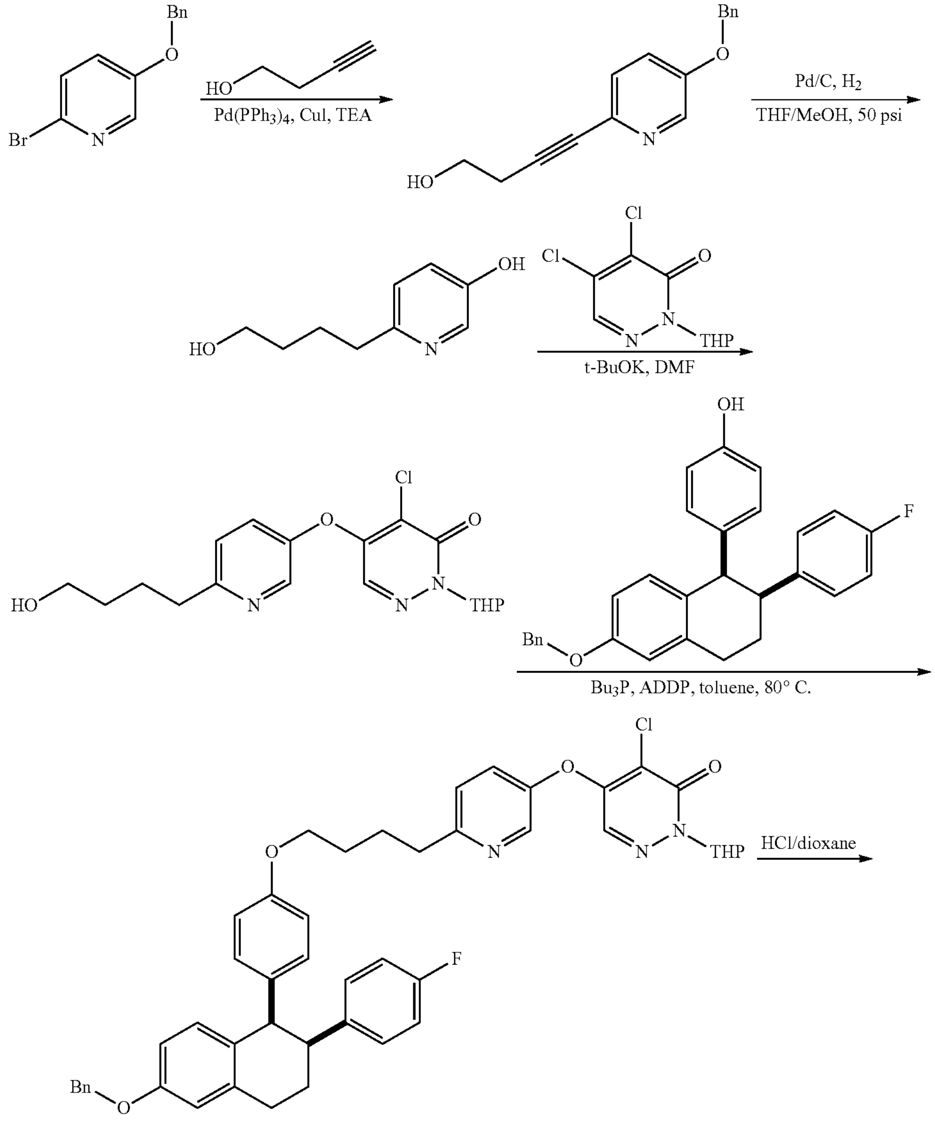

-continued
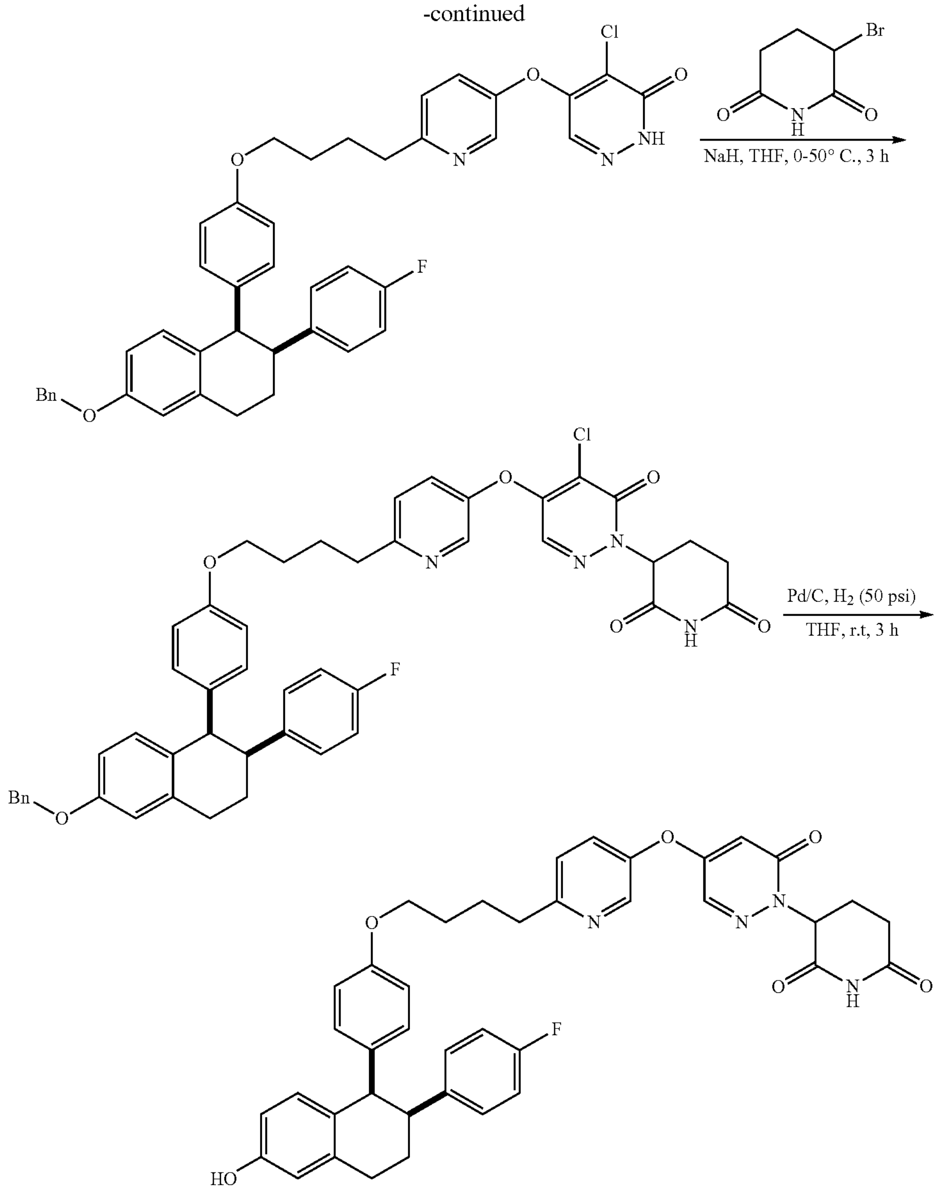
General synthetic scheme 3-58 to prepare claimed compounds.
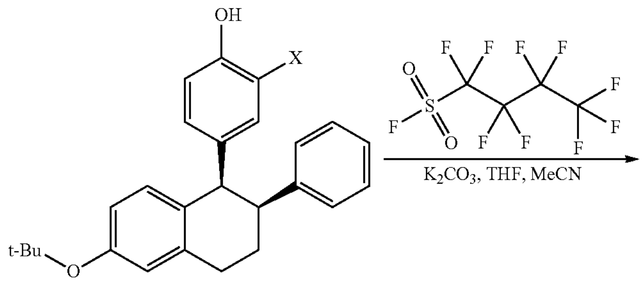

-continued
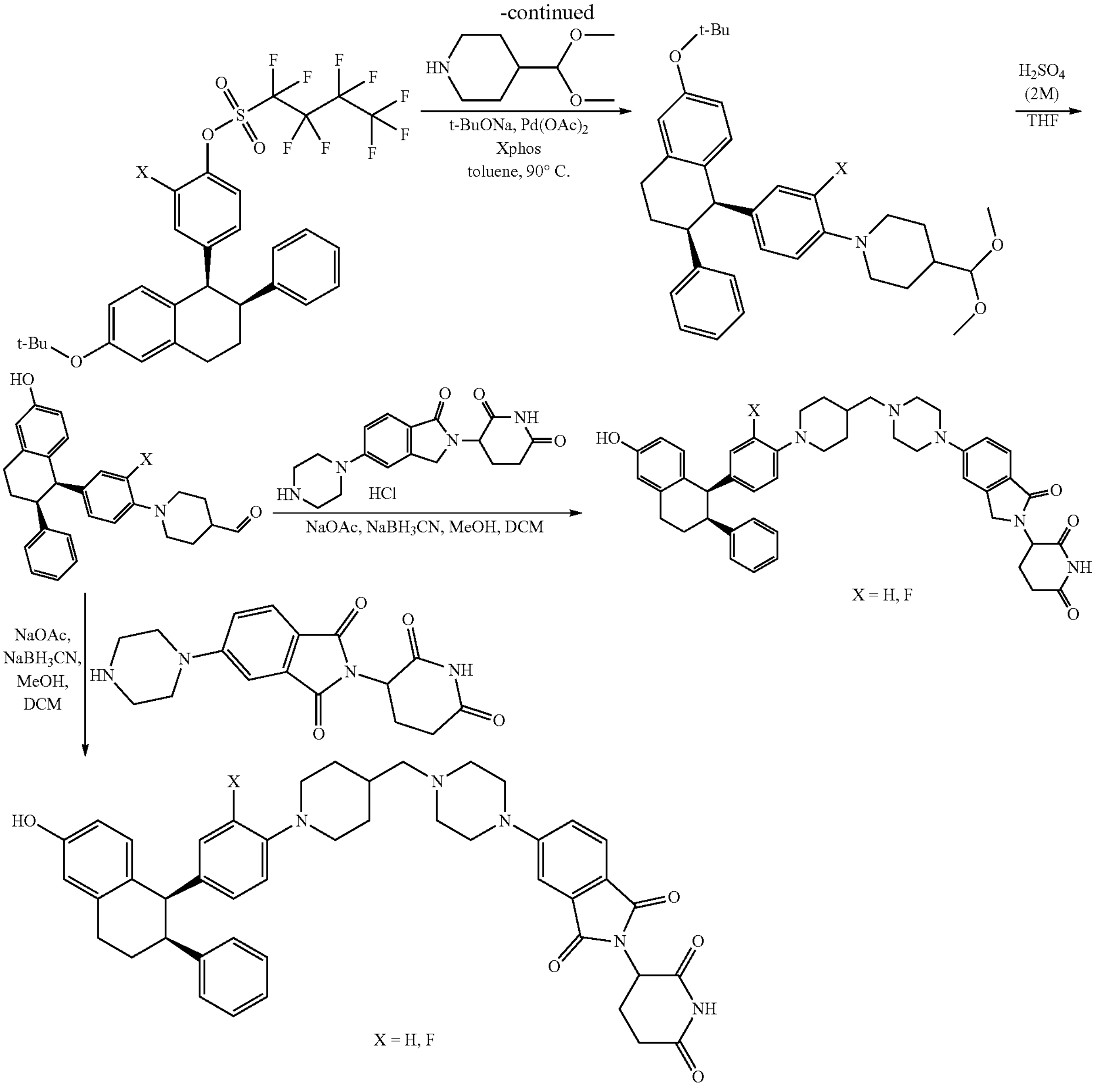
General synthetic scheme 3-72 to prepare claimed compounds.
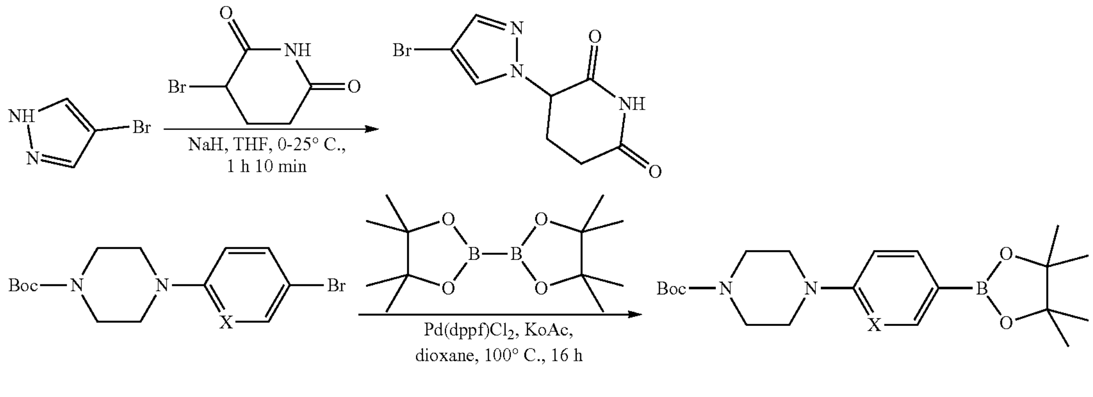

-continued
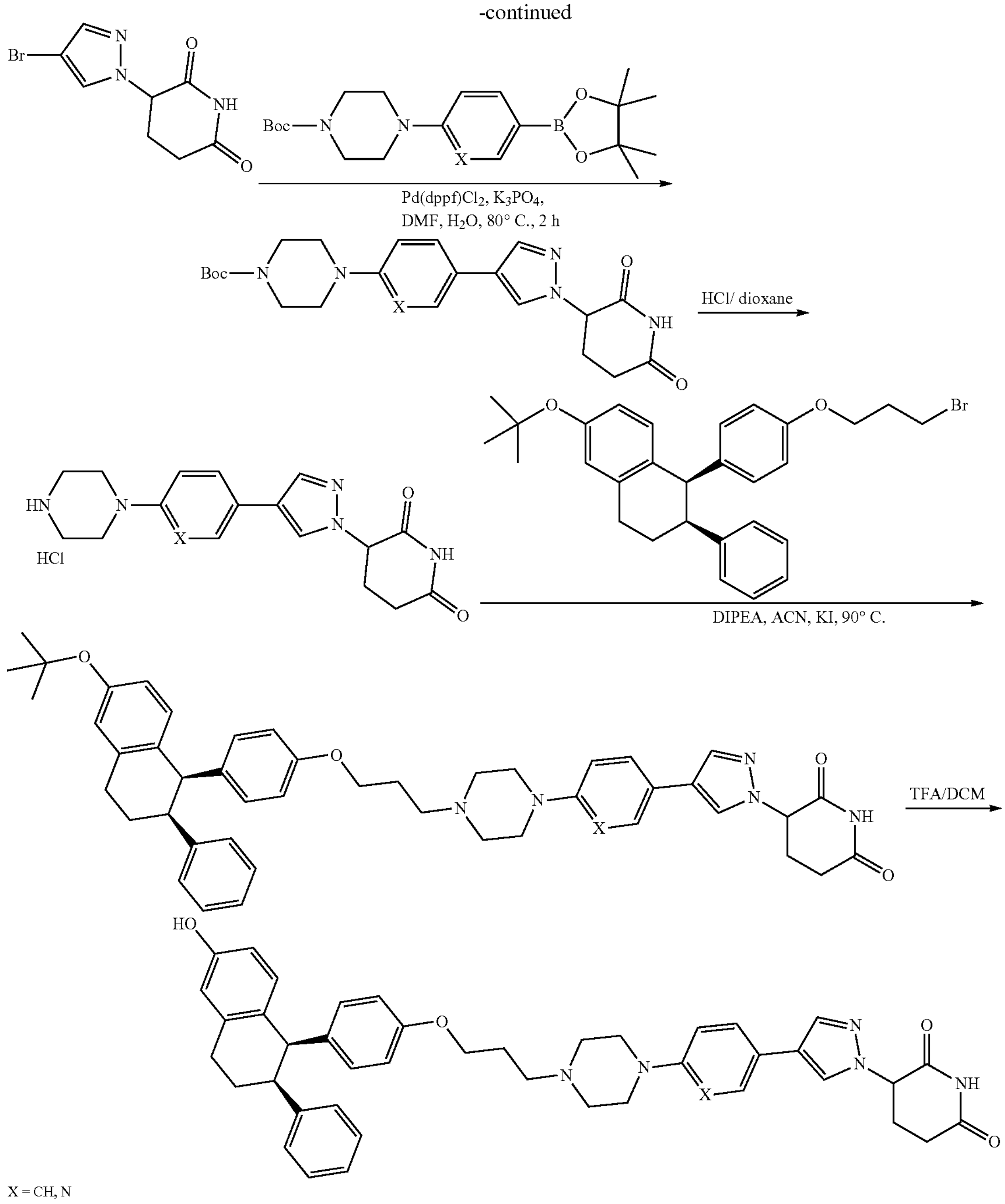
Synthesis of Exemplary PROTAC 1
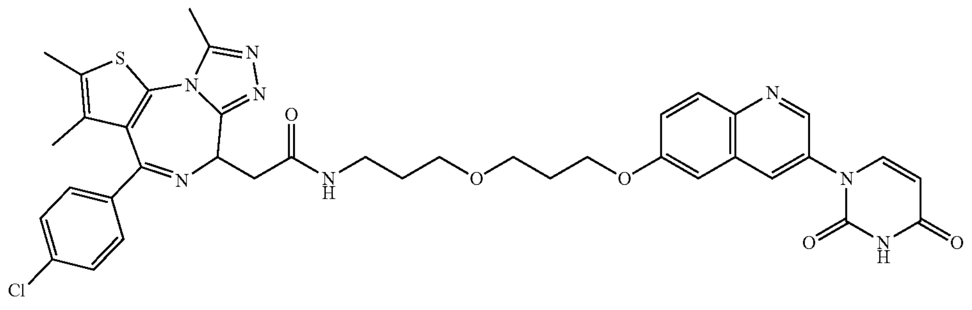 [SMILES: Cc1sc2c(c1C)C(c1ccc(Cl)cc1)=NC(CC(=O)NCCCOCCCOc1ccc3ncc(-n4ccc(=O)[nH]c4=O)cc3c1)c1nnc(C)n1-2]

2-(4-(4-chlorophenyl)-2,3,9-trimethyl-6H-thieno[3, 2-f] [1,2,4]triazolo [4,3-a] [1,4]di azepin-6-yl)-N-(3-(3-((3-(2,4-di oxo-3,4-dihydropyrimi din-1 (2H)-yl)quinolin-6-yl)oxy)propoxy)propyl)acetamide Synthetic Scheme:

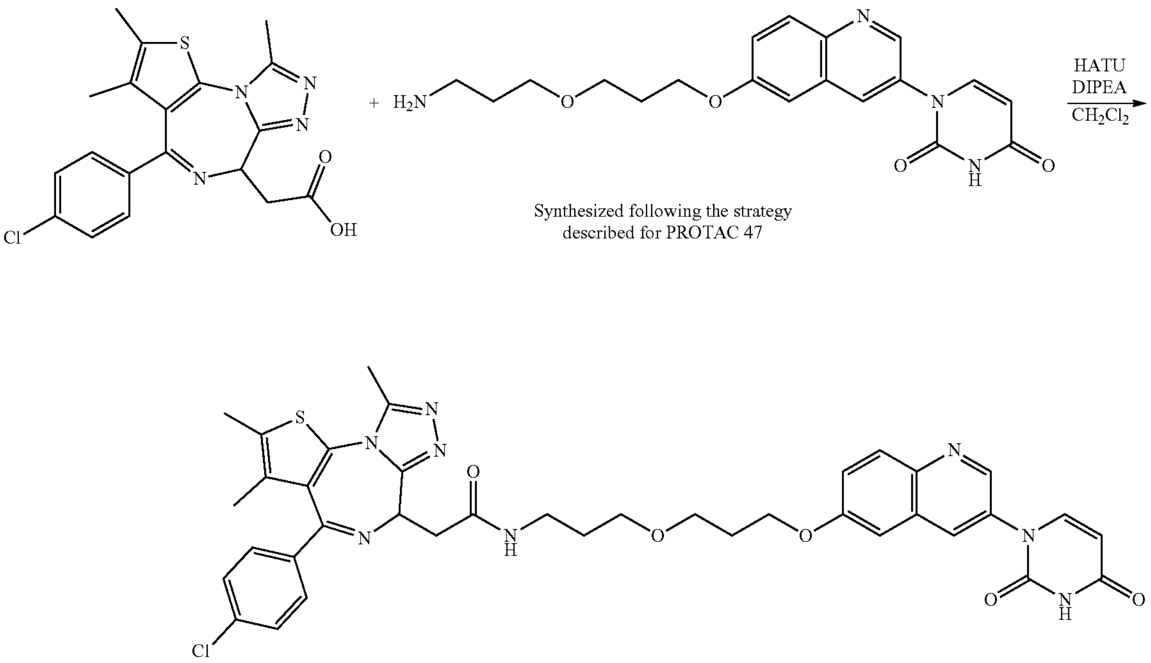

To a solution of (S)-2-(4-(4-chlorophenyl)-2,3,9-trimethyl-6H-thieno[3,2-f] [1,2,4]triazolo[4,3-a][1,4]diazepin-6-yl)acetic acid (20.6 mg, 0.051 mmol) and 1-(5-(3-(3-aminopropoxy)propoxy)quinolin-3-yl)pyrimidine-2,4(1H, 3H)-dione hydrochloride (21.6 mg, 0.053 mmol) in DCM (1 mL) was added diisopropylethylamine (0.022 mL, 0.128 mmol), HATU (20.1 mg, 0.053 mmol) was added and it was stirred at room temperature for 2 hours. The reaction was washed by NaHCO3 solution and the organic layer was separated and dried. The product was purified by column chromatography on silica (10% MeOH/DCM) to give 2-(4-(4-chlorophenyl)-2,3,9-trimethyl-6H-thieno[3,2-f] [1,2,4] triazolo[4,3-a][1,4]diazepin-6-yl)-N-(3-(3-((3-(2,4-dioxo-3, 4-dihydropyrimidin-1(2H)-yl)quinolin-6-yl)oxy)propoxy) propyl)acetamide (25 mg, 65%)

LCMS (m/e+)=753.35 $[M+H]^+$ and m/e+=377.17 $[M+2H]^{2+}$

Synthesis of Exemplary PROTAC 29

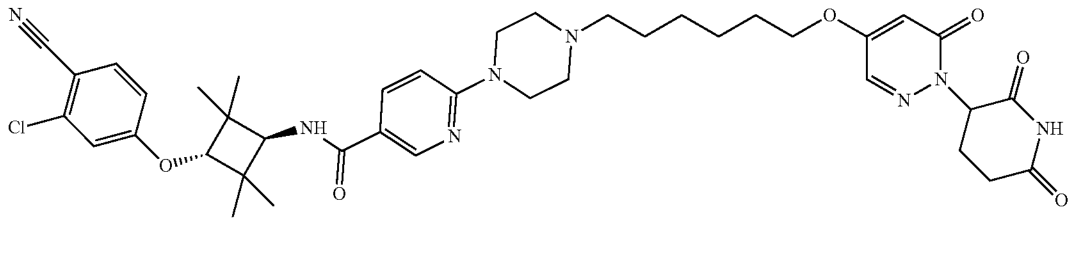 [SMILES: CC1(C)[C@H](NC(=O)c2ccc(N3CCN(CCCCCCOc4cnn(C5CCC(=O)NC5=O)c(=O)c4)CC3)nc2)C(C)(C)[C@H]1Oc1ccc(C#N)c(Cl)c1]

N-((1r,3r)-3-(3-chloro-4-cyanophenoxy)-2,2,4,4-tetramethylcyclobutyl)-6-(4-(6-((1-(2,6-dioxopiperidin-3-yl)-6-oxo-1,6-dihydropyridazin-4-yl)oxy)hexyl)piperazin-1-yl)nicotinamide Synthetic Scheme Part 1-Synthesis of N-((1r,3r)-3-(3-Chloro-4-Cyanophenoxy)-2,2,4,4-tetramethylcyclobutyl)-6-(piperazin-1-yl)nicotinamide

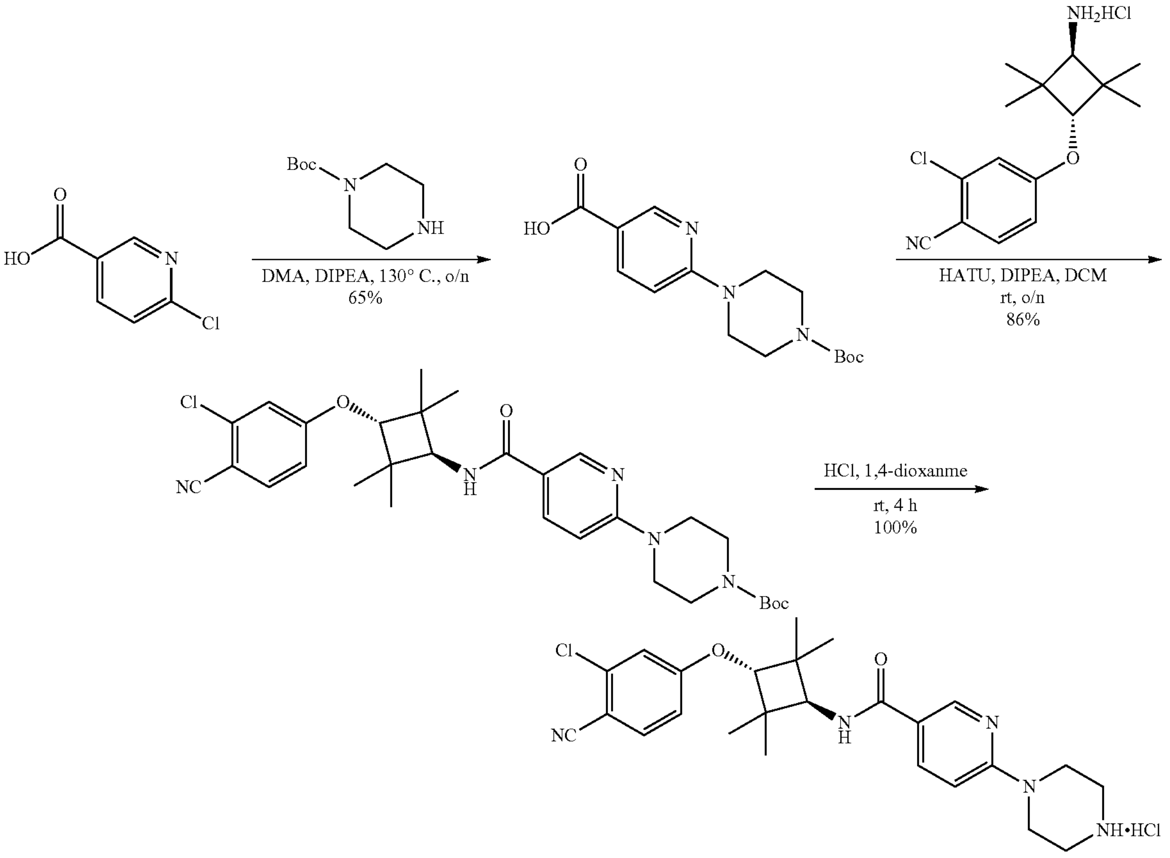

Step 1: Synthesis of 6-(4-(tert-butoxycarbonyl)piperazin-1-yl)nicotinic acid

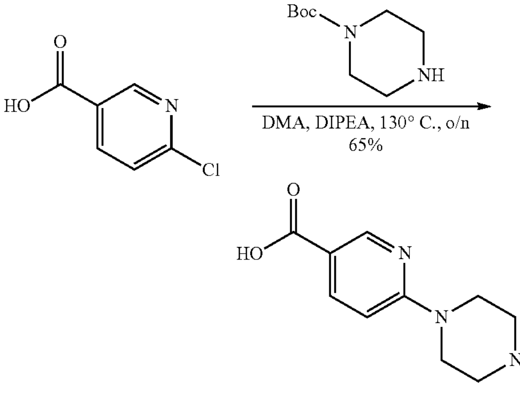

6-Chloronicotinic acid (1.6 g, 10.0 mmol) was dissolved in N,N-dimethylacetamide (15 mL), and tert-butyl piperazine-1-carboxylate (1.9 g, 10.0 mmol) and ethyldiisopropylamine (2.6 g, 20 mmol) were added thereto, followed by stirring at 130° C. overnight. The reaction mixture was concentrated under reduced pressure, and to the obtained residue was added a 1 M aqueous NaOH solution (10 mL), followed by washing with $CHCl_3$ (50 mL). The pH of the aqueous layer was adjusted to around 6 to 7 by the addition of 1 M hydrochloric acid, followed by extraction with $CHCl_3$ (50 mL×3). The organic layer was dried over anhydrous sodium sulfate and the solvent was concentrated under reduced pressure. The obtained residue was purified by silica gel column chromatography ($CH_2Cl_2$/MeOH=10/1) to give 6-(4-(tert-butoxycarbonyl)piperazin-1-yl)nicotinic acid (2.0 g, 65% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity is 83.17%, Rt=1.312 min; MS Calcd.: 307.15; MS Found: 308.2 $[M+H]^+$.

Chemical Formula: $C_{15}H_{21}H_3O_4$, Molecular Weight: 307.34

Step 2: Synthesis of tert-butyl 4-(5-((1r,3r)-3-(3-chloro-4-cyanophenoxy)-2,2,4,4-tetramethylcyclobutylcarbamoyl)pyridin-2-yl)piperazine-1-carboxylate

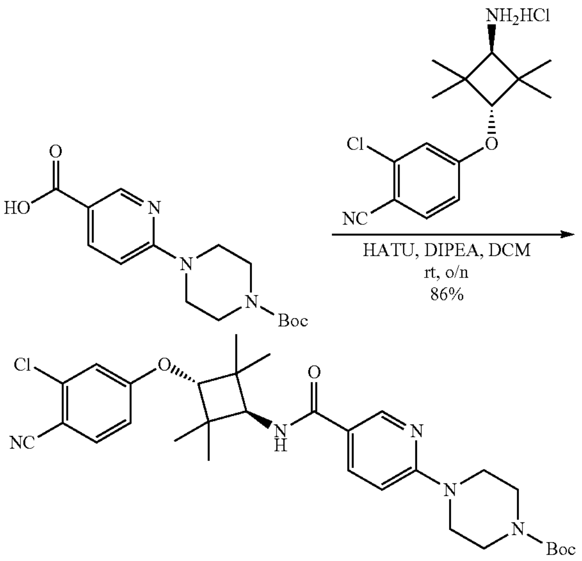

A mixture of 6-(4-(tert-butoxycarbonyl)piperazin-1-yl) nicotinic acid (614 mg, 2.0 mmol), 4-((1r,3r)-3-amino-2,2,4,4-tetramethylcyclobutoxy)-2-chlorobenzonitrile hydrochloride (630 mg, 2.0 mmol), 2-(7-Aza-1H-benzotriazole-1-yl)-1,1,3,3-tetramethyluronium hexafluorophosphate (1.1 g, 3.0 mmol) and ethyldiisopropylamine (516 mg, 4.0 mmol) in dichloromethane (20 mL) was stirred at room temperature overnight. Water (50 mL) was added and extracted with dichloromethane (50 mL×3). Combined organic layers were washed by brine (50 mL×2), dried over anhydrous sodium sulfate. The solvent was concentrated to give the residue, which was purified by column chromatography on silica gel (petroleum ether/ethyl acetate=1/1) to give tert-butyl 4-(5-((1r,3r)-3-(3-chloro-4-cyanophenoxy)-2,2,4,4-tetramethylcyclobutylcarbamoyl)pyridin-2-yl)piperazine-1-carboxylate (977 mg, 86% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity is 88.26%, Rt=2.161 min; MS Calcd.: 567.26; MS Found: 568.3 $[M+H]^+$.

$^1$H NMR (400 MHz, DMSO-$d_6$) δ1.12 (6H, s), 1.22 (6H, s), 1.43 (9H, s), 3.42-3.44 (4H, m), 3.60-3.63 (4H, m), 4.02-4.07 (1H, m), 4.31 (1H, s), 6.88 (1H, d, J=8.8 Hz), 7.00 (1H, dd, J=8.4, 2.4 Hz), 7.21 (1H, d, J=2.4 Hz), 7.65 (1H, d, J=9.2 Hz), 7.91 (1H, d, J=8.8 Hz), 7.99 (1H, dd, J=8.8, 2.4 Hz), 8.64 (1H, d, J=2.4 Hz).

Chemical Formula: $C_{30}H_{38}ClN_5O_4$, Molecular Weight: 568.11

Total H count from HNMR data: 38.

Step 3: Synthesis of N-((1r,3r)-3-(3-chloro-4-cyanophenoxy)-2,2,4,4-tetramethylcyclobutyl)-6-(piperazin-1-yl)nicotinamide hydrochloride

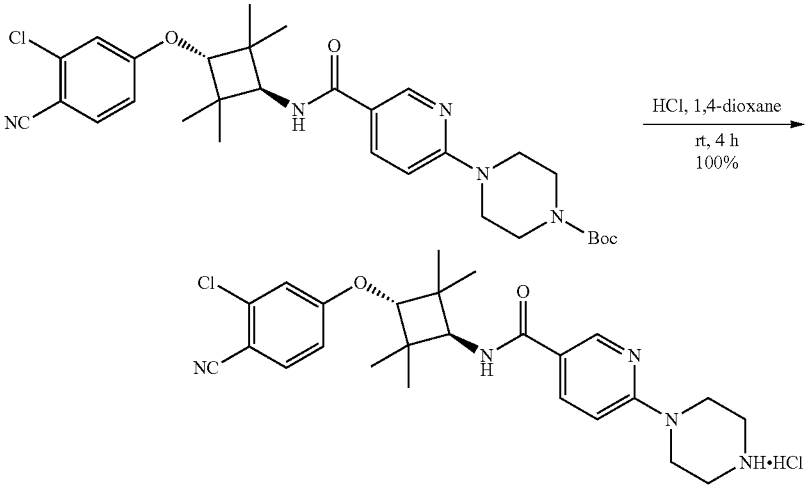

A mixture of tert-butyl 4-(5-((1r,3r)-3-(3-chloro-4-cyanophenoxy)-2,2,4,4-tetramethylcyclobutyl carbamoyl)pyridin-2-yl)piperazine-1-carboxylate (405 mg, 0.7 mmol) in HCl/1,4-dioxane (10 mL) was stirred at room temperature for 4 h. The solvent was removed in vacuum to give N-((1r,3r)-3-(3-chloro-4-cyanophenoxy)-2,2,4,4-tetramethylcyclobutyl)-6-(piperazin-1-yl)nicotinamide hydrochloride (353 mg, 100% yield) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.791 min; MS Calcd.: 467.21; MS Found: 468.3 $[M+H]^+$.

Chemical Formula: $C_{25}H_{31}Cl_2N_5O_2$, Molecular Weight: 504.45

Synthetic Scheme Part 2
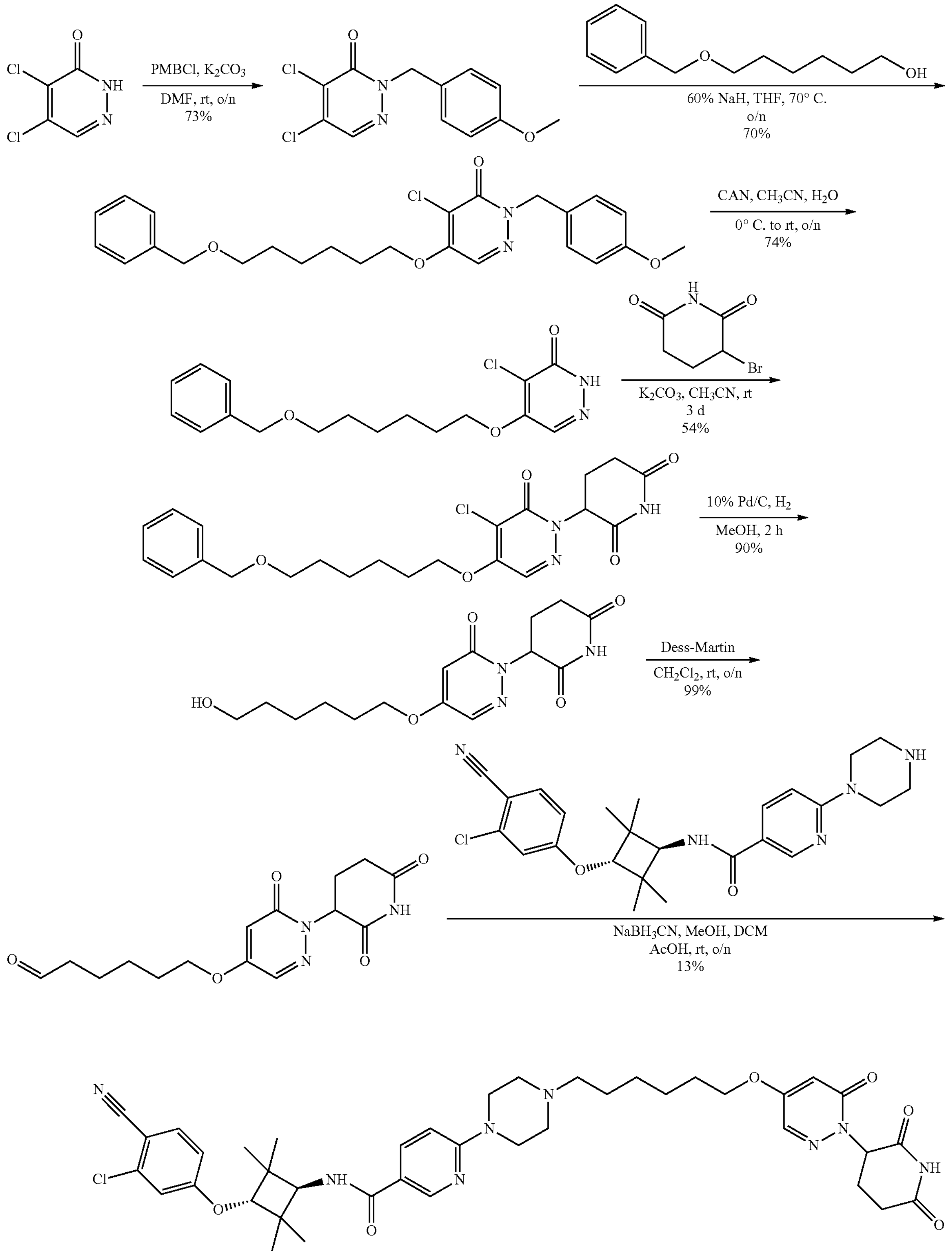

Step 4: Synthesis of 4,5-dichloro-2-(4-methoxybenzyl)pyridazin-3(2H)-one

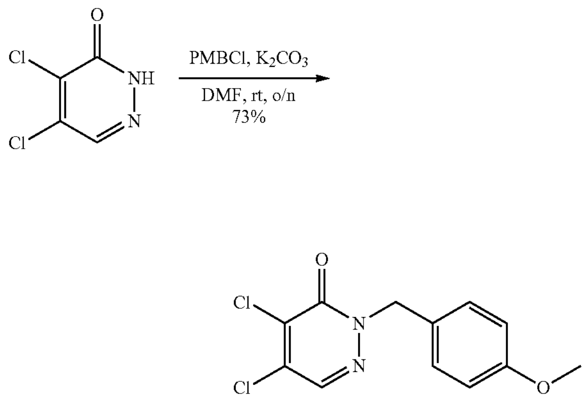

The mixture of 4,5-dichloropyridazin-3(2H)-one (5.0 g, 30.5 mmol), 1-(chloromethyl)-4-methoxybenzene (7.1 g, 45.7 mmol) and potassium carbonate (12.6 g, 91.5 mmol) in N',N'-Dimethylformamide (100 mL) was stirred at room temperature for 12 hours. The mixture was poured into water and extracted with ethyl acetate (100 mL×3). The combined organic phase was concentrated in vacuo and the residue was purified by column chromatography on silica gel (petroleum ether/ethyl acetate=3/1) to give 4,5-dichloro-2-(4-methoxybenzyl)pyridazin-3(2H)-one (6.3 g, 73% yield) as a white solid.

LC-MS (Agilent LCMS 1200-6110, Column: Waters X-Bridge C18 (50 m×4.6 mm×3.5 μm); Column Temperature: 40° C.; Flow Rate: 1.5 mL/min; Mobile Phase: from 95% [water+0.05% TFA] and 5% [$CH_3CN$+0.05% TFA] to 0% [water+0.05% TFA] and 100% [$CH_3CN$+0.05 TFA] in 1.5 min, then under this condition for 0.5 min, finally changed to 95% [water+0.05% TFA] and 5% [$CH_3CN$+0.05% TFA] in 0.1 min and under this condition for 0.1 min). Rt=1.220 min; MS Calcd.: 284.0; MS Found: 285.1 $[M+H]^+$.

Chemical Formula: $C_{12}H_{10}Cl_2N_2O_2$, Molecular Weight: 285.13

Step 5: Synthesis of 5-(6-(benzyloxy)hexyloxy)-4-chloro-2-(4-methoxybenzyl)pyridazin-3(2H)-one

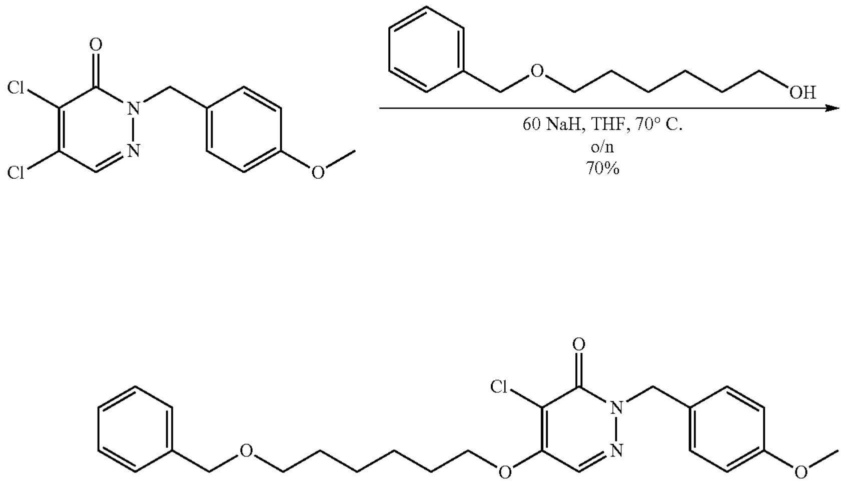

To a solution of 6-(benzyloxy)hexan-1-ol (1.04 g, 50 mmol) in dried THF (100 mL) was added 60% NaH (240 mg, 60 mmol) at 0° C., then it was stirred for 30 minutes, 4,5-dichloro-2-(4-methoxybenzyl)pyridazin-3(2H)-one (1.42 g, 50 mmol) was added, the resulting mixture was refluxed overnight. After cooling to room temperature, the mixture was quenched by aqueous $NH_4Cl$ and then extracted with ethyl acetate (50 mL×2). The combined organic phase was washed with brine (50 mL), dried over $Na_2SO_4$, filtered, concentrated in vacuo and the residue was purified by column chromatography on silica gel (petroleum ether/ethyl acetate=10/1) to give 5-(6-(benzyloxy)hexyloxy)-4-chloro-2-(4-methoxybenzyl)pyridazin-3(2H)-one (1.59 g, 70% yield) as a colorless gel.

$^1H$ NMR (400 MHz, $CDCl_3$) δ 1.40-1.47 (4H, m), 1.59-1.65 (2H, m), 1.69-1.75 (2H, m), 3.46 (2H, t, J=6.4 Hz), 3.78 (3H, s), 4.50 (2H, s), 4.56 (2H, t, J=6.4 Hz), 5.21 (2H, s), 6.85 (2H, d, J=8.4 Hz), 7.26-7.29 (1H, m), 7.33-7.38 (6H, m), 7.69 (1H, s).

Total H count from HNMR data: 29.

Step 6: Synthesis of 5-(6-(benzyloxy)hexyloxy)-4-chloropyridazin-3(2H)-one

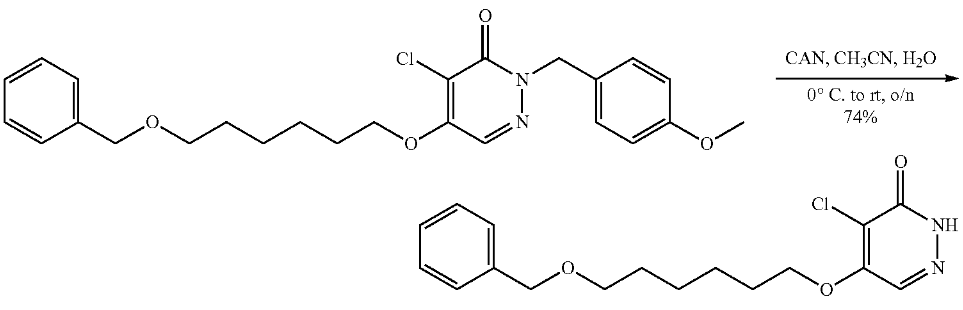

To a solution of 5-(6-(benzyloxy)hexyloxy)-4-chloro-2-(4-methoxybenzyl)pyridazin-3(2H)-one (450 mg, 1 mmol) in $CH_3CN$ (30 mL) at 0° C., was added a solution of CAN (1.37 g, 2.5 mmol) in $H_2O$ (10 mL), and the solution was allowed to warm to room temperature and stirred overnight. At this point the mixture was partitioned between ethyl acetate (30 mL) and half saturated brine (20 mL). The phases were separated, and the aqueous phase was extracted with ethyl acetate (30 mL), then with $CH_2Cl_2$ (30 mL). The combined organic phases were dried ($Na_2SO_4$), filtered, and concentrated in vacuo. The crude product was purified by column chromatography on silica gel (petroleum ether/ethyl acetate=10/1) to afford 5-(6-(benzyloxy)hexyloxy)-4-chloropyridazin-3(2H)-one (250 mg, 74% yield) as a yellow gel.

LC-MS (Agilent LCMS 1200-6110, Column: Waters X-Bridge C18 (50 mm×4.6 mm×3.5 μm); Column Temperature: 40° C.; Flow Rate: 1.5 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.5 min, then under this condition for 0.5 min, finally changed to 95% [water+0.05% TFA] and 5% [$CH_3CN$+0.05% TFA] in 0.1 min and under this condition for 0.1 min). Rt=1.346 min; MS Calcd.: 336.1; MS Found: 337.3 $[M+H]^+$.

Chemical Formula: $C_{17}H_{21}ClN_2O_3$, Molecular Weight: 336.81.

Step 7: Synthesis of 3-(4-(6-(benzyloxy)hexyloxy)-5-chloro-6-oxopyridazin-1(6H)-yl)piperidine-2,6-dione

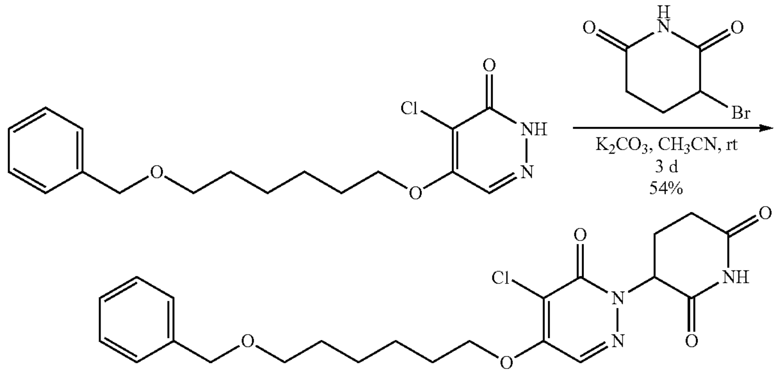

The mixture of 5-(6-(benzyloxy)hexyloxy)-4-chloropyridazin-3(2H)-one (250 mg, 0.74 mmol), 3-bromopiperidine-2,6-dione (143 mg, 0.74 mmol) and potassium carbonate (205 mg, 1.48 mmol) in acetonitrile (40 mL) was stirred at room temperature for 3 days, and then filtrated. The filtrate was concentrated and purified by column chromatography on silica gel (petroleum ether/ethyl acetate=3/2) to give 3-(4-(6-(benzyloxy)hexyloxy)-5-chloro-6-oxopyridazin-1(6H)-yl)piperidine-2,6-dione (180 mg, 54% yield) as a light yellow gel.

$^1H$ NMR (400 MHz, $CDCl_3$) δ 1.40-1.49 (4H, m), 1.61-1.66 (2H, m), 1.72-1.78 (2H, m), 2.20-2.24 (1H, m), 2.65-2.79 (2H, m), 2.86-2.90 (1H, m), 3.47 (2H, t, J=6.4 Hz), 4.50 (2H, s), 4.55-4.61 (2H, m), 5.65 (1H, dd, J=10.8, 5.6 Hz), 7.26-7.34 (5H, m), 7.76 (1H, s), 8.46 (1H, s).

Total H count from HNMR data: 26.

Step 8: Synthesis of 3-(4-(6-hydroxyhexyloxy)-6-oxopyridazin-1(6H)-yl)piperidine-2,6-dione

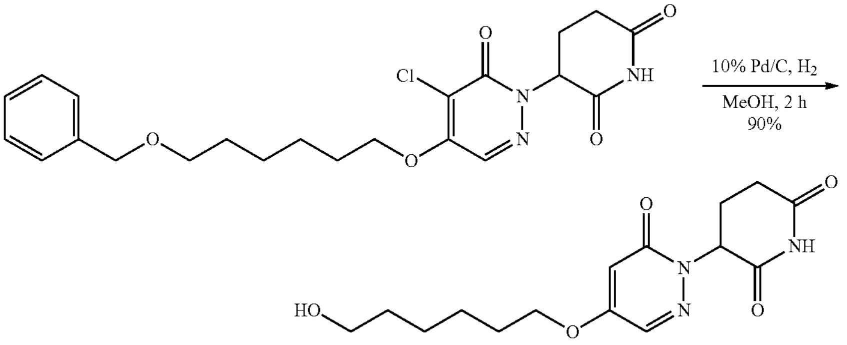

The mixture of 3-(4-(6-(benzyloxy)hexyloxy)-5-chloro-6-oxopyridazin-1(6H)-yl)piperidine-2,6-dione (180 mg, 0.4 mmol) and 10% palladium on activated carbon (100 mg) in MeOH (20 mL) was stirred under 1 atm. hydrogen atmosphere at room temperature for 2 h. It was filtered to remove the solid, the filtrate was concentrated to give 3-(4-(6-hydroxyhexyloxy)-6-oxopyridazin-1(6H)-yl)piperidine-2,6-dione (118 mg, 90% yield) as a light yellow solid.

$^1H$ NMR (400 MHz, DMSO-$d_6$) δ 1.34-1.45 (6H, m), 1.71-1.77 (2H, m), 2.04-2.08 (1H, m), 2.46-2.60 (2H, m), 2.84-2.90 (1H, m), 3.39 (2H, t, J=6.4 Hz), 4.02 (2H, t, J=6.4 Hz), 4.72 (1H, brs), 5.69 (1H, dd, J=12.4, 5.2 Hz), 6.77 (1H, d, J=5.2 Hz), 7.82 (1H, d, J=4.8 Hz), 11.03 (1H, s).

Total H count from HNMR data: 21.

Step 9: Synthesis of 6-(1-(2,6-dioxopiperidin-3-yl)-6-oxo-1,6-dihydropyridazin-4-yloxy)hexanal

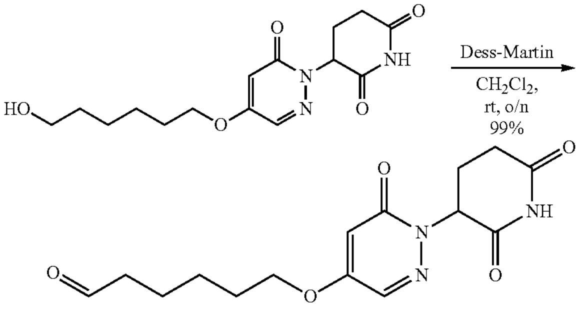

A solution of 3-(4-(6-hydroxyhexyloxy)-6-oxopyridazin-1(6H)-yl)piperidine-2,6-dione (64 mg, 0.2 mmol) in $CH_2Cl_2$ (30 mL) was added Dess-Martin reagent (127 mg, 0.6 mmol), and the mixture was stirred at room temperature overnight. After removal of undissolved solid by suction, the filtrate was concentrated at room temperature to give crude 6-(1-(2,6-dioxopiperidin-3-yl)-6-oxo-1,6-dihydropyridazin-4-yloxy)hexanal (64 mg, 99% yield) as a white semi-solid, it was directly used to the next step without further purification.

LC-MS (Agilent LCMS 1200-6110, Column: Waters X-Bridge C18 (50 mm×4.6 mm×3.5 μm); Column Temperature: 40° C.; Flow Rate: 1.5 mL/min; Mobile Phase: from 95% [water+0.05% TFA] and 5% [$CH_3CN$+0.05% TFA] to 0% [water+0.05% TFA] and 100% [$CH_3CN$+0.05 TFA] in 1.5 min, then under this condition for 0.5 min, finally changed to 95% [water+0.05% TFA] and 5% [$CH_3CN$+0.05% TFA] in 0.1 min and under this condition for 0.1 min). Rt=0.721 min; MS Calcd.: 321.1; MS Found: 322.3 $[M+H]^+$.

Chemical Formula: $C_{15}H_{19}N_3O_5$, Molecular Weight: 321.33.

Step 10: Synthesis of N-((1r,3r)-3-(3-chloro-4-cyanophenoxy)-2,2,4,4-tetramethylcyclobutyl)-6-(4-(6-(1-(2,6-dioxopiperidin-3-yl)-6-oxo-1,6-dihydropyridazin-4-yloxy)hexyl)piperazin-1-yl)nicotinamide

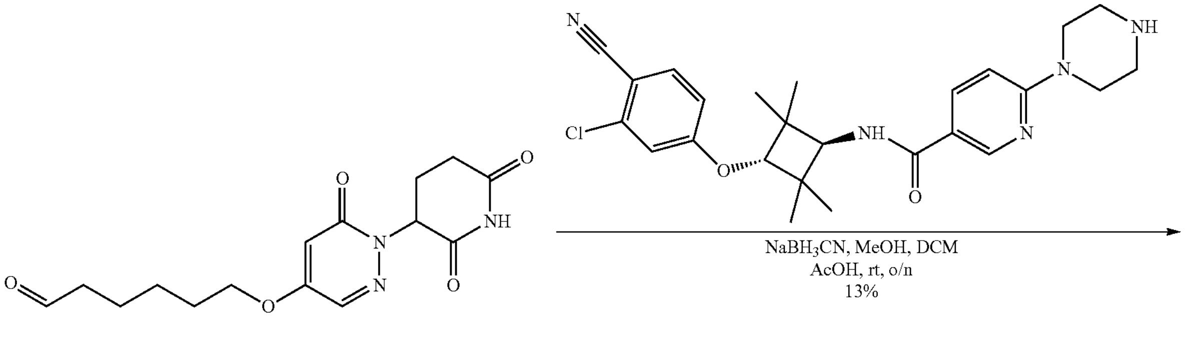

-continued

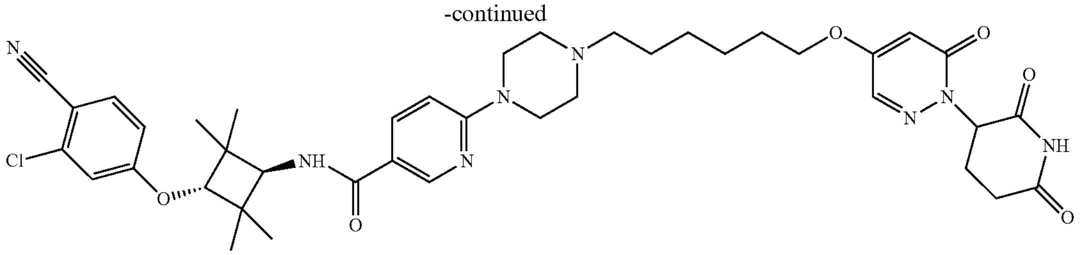

To a solution of N-((1r,3r)-3-(3-chloro-4-cyanophenoxy)-2,2,4,4-tetramethylcyclobutyl)-6-(piperazin-1-yl)nicotinamide hydrochloride (100 mg, 0.2 mmol) in MeOH (5 mL) was added a solution of 6-(1-(2,6-dioxopiperidin-3-yl)-6-oxo-1,6-dihydropyridazin-4-yloxy)hexanal (64 mg, 0.2 mmol) in $CH_2Cl_2$ (5 mL), then $NaBH_3CN$ (40 mg, 0.6 mmol) was added, the resulting mixture was stirred at room temperature overnight. The reaction mixture was concentrated, diluted with water (10 mL) and extracted with $CH_2Cl_2$ (20 mL×2). The organic extract was washed with brine (20 mL), dried over $Na_2SO_4$, filtered, concentrated and purified by Prep-TLC and then Prep-HPLC to give N-((1r,3r)-3-(3-chloro-4-cyanophenoxy)-2,2,4,4-tetramethylcyclobutyl)-6-(4-(6-(1-(2,6-dioxopiperidin-3-yl)-6-oxo-1,6-dihydropyridazin-4-yloxy)hexyl)piperazin-1-yl) nicotinamide (20 mg, 13% yield) as a white solid.

LC-MS (Agilent LCMS 1200-6120, Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min). Purity is 94.07%, Rt=2.741 min; MS Calcd.: 772.4; MS Found: 773.3 $[M+H]^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 93.35%, Rt=9.681 min.

$^1H$ NMR (400 MHz, $CDCl_3$) δ 1.21 (6H, s), 1.25 (6H, s), 1.39-1.44 (2H, m), 1.49-1.62 (4H, m), 1.87-1.93 (2H, m), 2.24-2.28 (1H, m), 2.36-2.43 (2H, m), 2.56 (4H, s), 2.70-2.81 (2H, m), 2.87-2.92 (1H, m), 3.66-3.69 (4H, m), 4.00-4.04 (3H, m), 4.14 (1H, d, J=8.0 Hz), 5.74 (1H, dd, J=11.2, 5.6 Hz), 6.07 (1H, d, J=8.4 Hz), 6.40 (1H, d, J=4.8 Hz), 6.66 (1H, d, J=8.8 Hz), 6.80 (1H, dd, J=8.8, 2.4 Hz), 6.96 (1H, d, J=2.4 Hz), 7.57 (1H, d, J=8.8 Hz), 7.71 (1H, d, J=4.8 Hz), 7.93 (1H, dd, J=8.8, 2.4 Hz), 8.16 (1H, brs), 8.58 (1H, d, J=2.4 Hz).

Chemical Formula: $C_{40}H_{49}ClN_8O_6$, Molecular Weight: 773.32

Total H count from HNMR data: 49.

Synthesis of Exemplary PROTAC 30

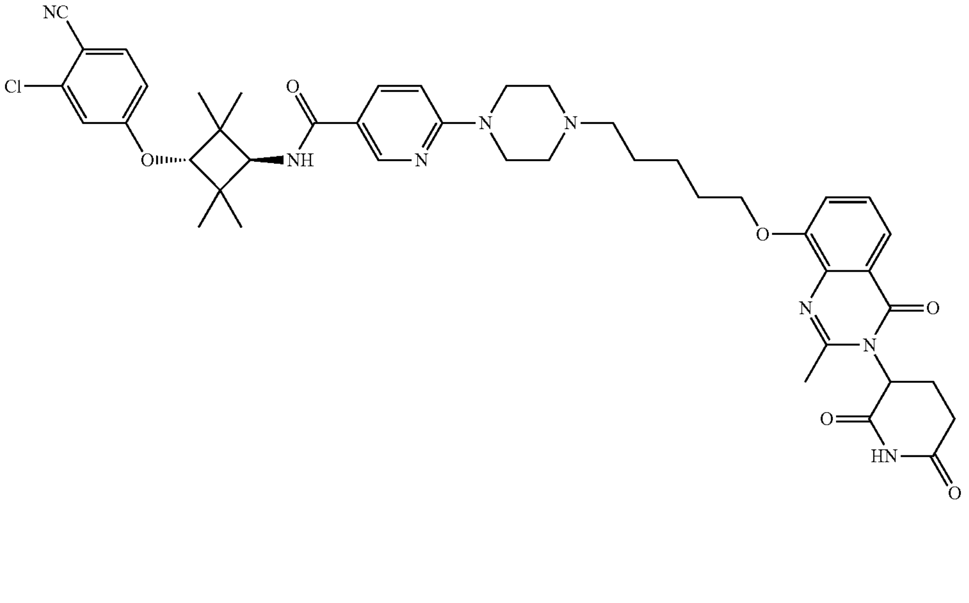 [SMILES: Cc1nc2c(OCCCCCN3CCN(c4ccc(C(=O)N[C@H]5C(C)(C)[C@H](Oc6ccc(C#N)c(Cl)c6)C5(C)C)cn4)CC3)cccc2c(=O)n1C1CCC(=O)NC1=O]

N-((1r, 3 r)-3-(3-chl oro-4-cyanophenoxy)-2,2,4,4-tetramethylcyclobutyl)-6-(4-(5-((3-(2,6-dioxopiperidin-3-yl)-2-methyl-4-oxo-3,4-dihydroquinazolin-8-yl)oxy)pentyl)piperazin-1-yl)nicotinamide
Synthetic Scheme
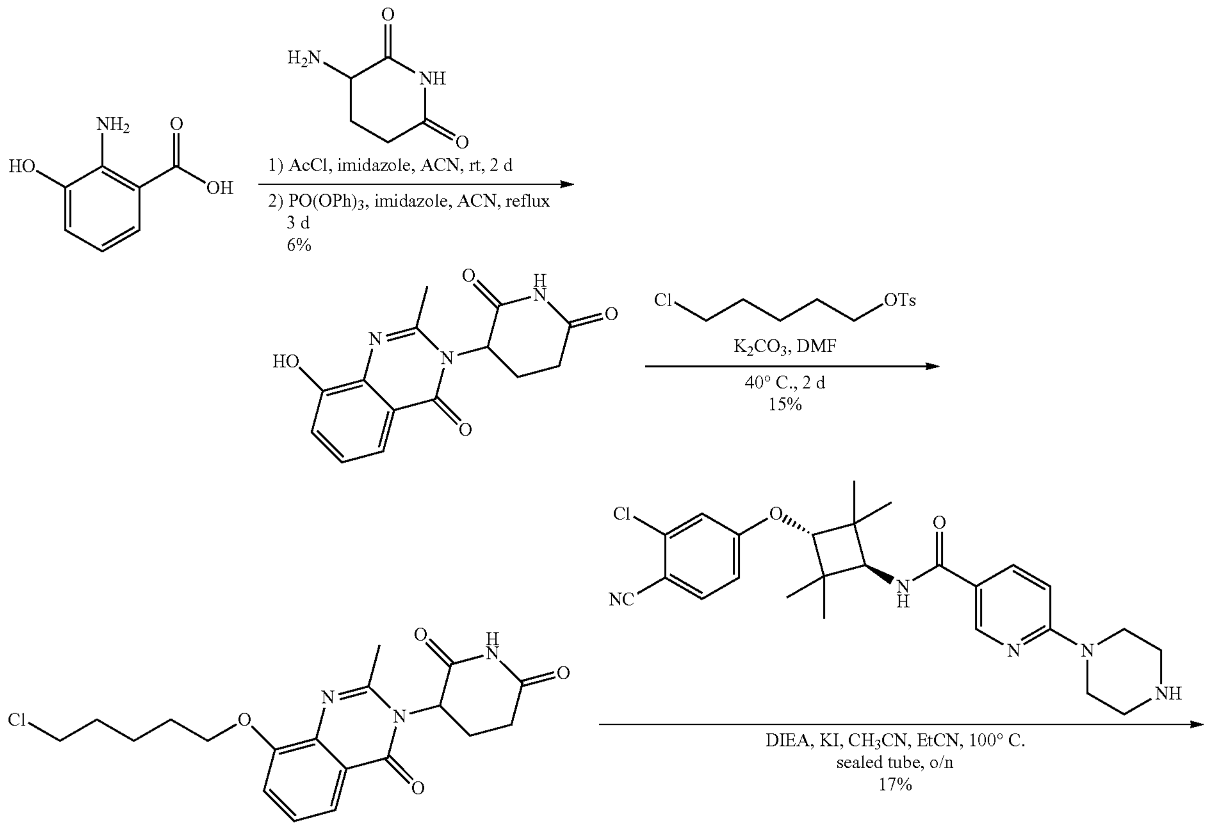
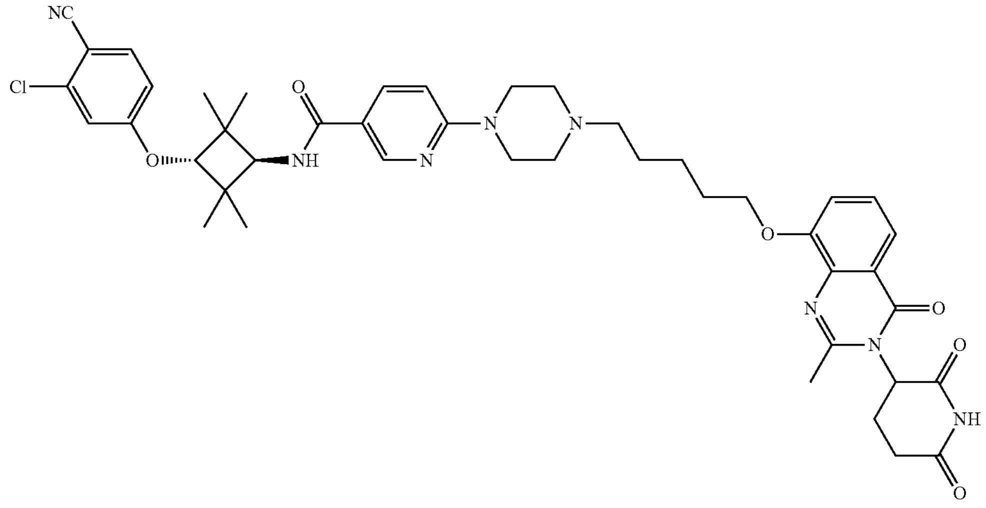

Step 1: Synthesis of 3-(8-hydroxy-2-methyl-4-oxo-quinazolin-3(4H)-yl)piperidine-2,6-dione

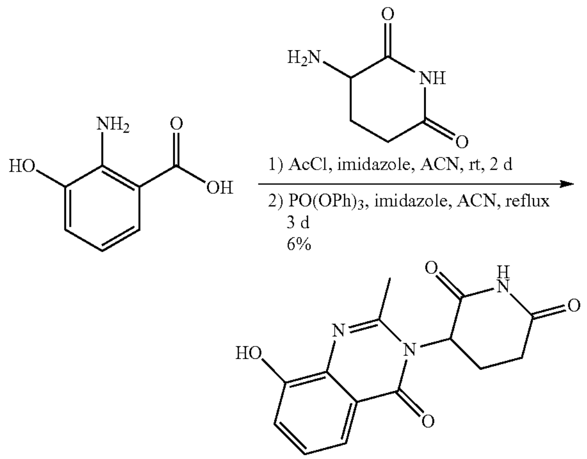

To a stirred mixture of 2-amino-3-hydroxybenzoic acid (2.0 g, 13.1 mmol) and imidazole (2.0 g, 29.4 mmol) in acetonitrile (30 mL), was added acetyl chloride (2.0 mL, 28.7 mmol) at room temperature. The mixture was stirred at room temperature for 2 days. To the mixture, was added 3-amino-piperidine-2,6-dione hydrogen chloride (2.2 g, 13.1 mmol), imidazole (2.0 g, 29.4 mmol) and triphenyl phosphite (4.11 mL, 15.7 mmol) and heated to reflux for 3 days. To the mixture, was added water (60 mL) and conc HCl until pH=1. The solvent was removed in vacuo. To the residue, was added water (50 mL). The aqueous layer was extracted with ethyl acetate (2×50 mL). To the aqueous layer, was added sodium hydrogen carbonate (1.8 g) to pH=7-8, and the mixture was stirred at room temperature to give a suspension. The suspension was filtered and dried to give 3-(8-hydroxy-2-methyl-4-oxo-4H-quinazolin-3-yl)-piperidine-2,6-dione (230 mg, 6% yield) as a gray solid.

$^1$H NMR (400 MHz, DMSO-$d_6$) δ 2.14-2.19 (1H, m), 2.57-2.69 (5H, m), 2.80-2.87 (1H, m), 5.26 (1H, dd, J=11.6, 5.6 Hz), 7.19 (1H, dd, J=8.0, 1.6 Hz), 7.30 (1H, t, J=8.0 Hz), 7.45 (1H, dd, J=8.0, 1.6 Hz), 9.66 (1H, s), 11.03 (1H, s).

Total H count from HNMR data: 13.

Step 2: Synthesis of 3-(8-(5-chloropentyloxy)-2-methyl-4-oxoquinazolin-3(4H)-yl)piperidine-2,6-dione

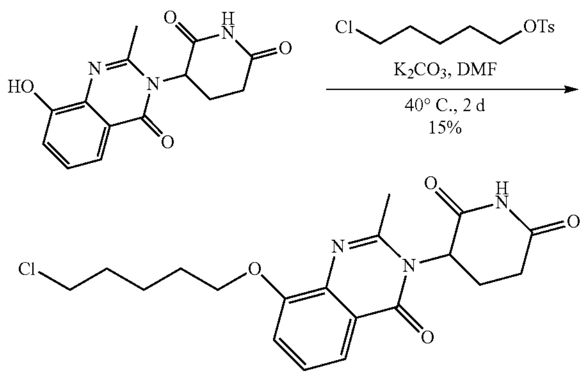

To a solution of 3-(8-hydroxy-2-methyl-4-oxo-4H-quinazolin-3-yl)-piperidine-2,6-dione (91 mg, 0.32 mmol) and 5-chloropentyl 4-methylbenzenesulfonate (88 mg, 0.32 mmol) in DMF (10 mL) was added $K_2CO_3$ (88 mg, 0.64 mmol) at room temperature, then it was heated to 40° C. and stirred for 2 days. The mixture was purified by reverse phase HPLC to give 3-(8-(5-chloropentyloxy)-2-methyl-4-oxoquinazolin-3(4H)-yl)piperidine-2,6-dione (19 mg, 15% yield) as a white solid.

$^1$H NMR (400 MHz, $CDCl_3$) δ 1.65-1.73 (2H, m), 1.87-2.02 (4H, m), 2.13-2.17 (1H, m), 2.66-2.74 (4H, m), 2.89-3.02 (2H, m), 3.60 (2H, t, J=6.4 Hz), 4.19 (2H, t, J=6.4 Hz), 4.77 (1H, dd, J=11.6, 6.4 Hz), 7.21 (1H, d, J=8.0 Hz), 7.38 (1H, t, J=8.0 Hz), 7.76 (1H, d, J=7.2 Hz).

Total H count from HNMR data: 21.

Step 3: Synthesis of N-((1r,3 r)-3-(3-chloro-4-cyanophenoxy)-2,2,4,4-tetramethylcyclobutyl)-6-(4-(5-(3-(2,6-dioxopiperidin-3-yl)-2-methyl-4-oxo-3,4-dihydroquinazolin-8-yl oxy)pentyl)piperazin-1-yl) nicotinamide

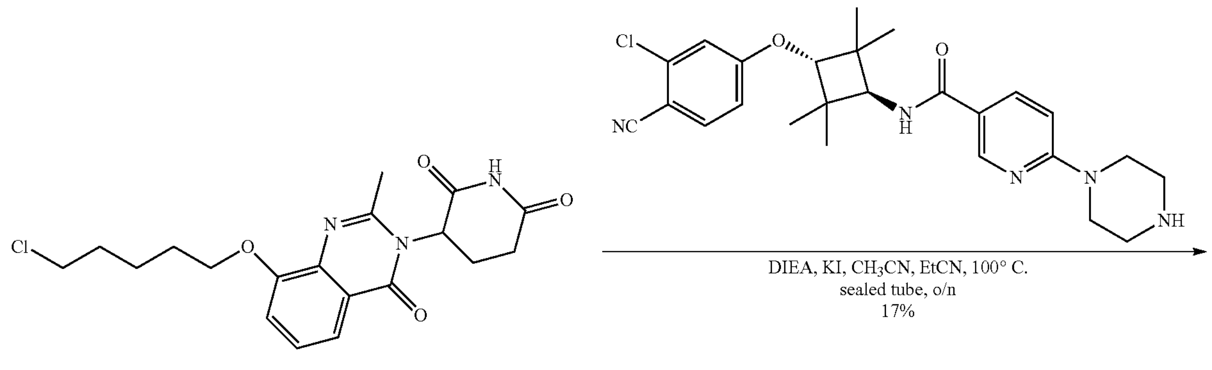

-continued

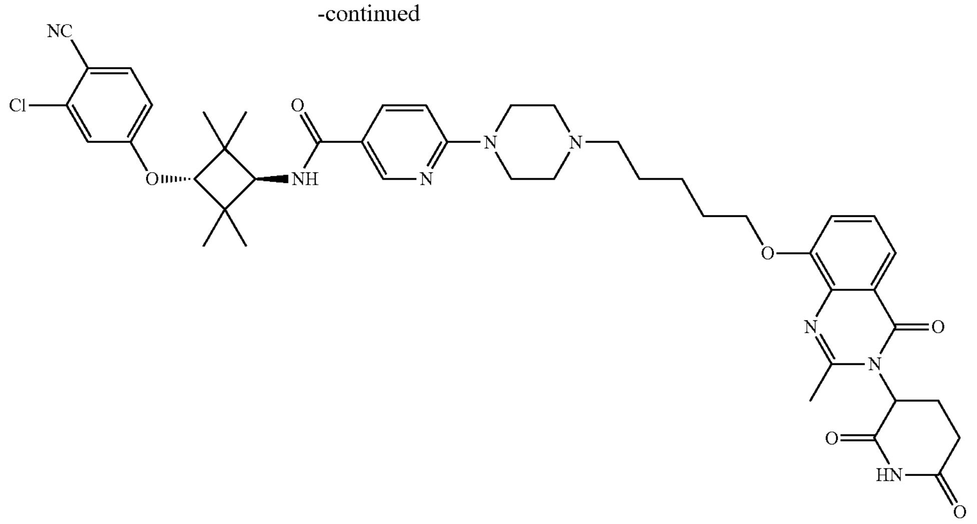

A mixture of 3-(8-(5-chloropentyloxy)-2-methyl-4-oxo-quinazolin-3(4H)-yl)piperidine-2,6-dione (15 mg, 0.038 mmol), DIEA (25 mg, 0.19 mmol), KI (6 mg, 0.038 mmol) and N-((1r,3r)-3-(3-chloro-4-cyanophenoxy)-2,2,4,4-tetramethylcyclobutyl)-6-(piperazin-1-yl)nicotinamide (20 mg, 0.038 mmol) in $CH_3CN$ (10 mL) was stirred at 100° C. overnight. Then it was evaporated, to the residue was added DIEA (25 mg, 0.19 mmol) and EtCN (10 mL), and the solution was stirred at 100° C. overnight. At this point the mixture was diluted with water (10 mL) and extracted by ethyl acetate (20 mL×2). The organic extract was washed with brine (10 mL), dried ($Na_2SO4$), filtered, and concentrated in vacuo. The crude product was purified by prep-HPLC to afford N-((1r,3r)$_3$-(3-chloro-4-cyanophenoxy)-2,2,4,4-tetramethylcyclobutyl)-6-(4-(5-(3-(2,6-dioxopiperidin-3-yl)-2-methyl-4-oxo-3,4-dihydroquinazolin-8-yloxy)pentyl)piperazin-1-yl)nicotinamide (5.5 mg, 17% yield) as a white solid.

LC-MS (Agilent LCMS 1200-6120, Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min). Purity is 93.89%, Rt=1.987 min; MS Calcd.: 822.4; MS Found: 823.4 $[M+H]^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 93.92%, Rt=9.851 min.

$^1$H NMR (400 MHz, $CDCl_3$) δ 1.21 (6H, s), 1.25 (6H, s), 1.59-1.62 (4H, m), 1.90-2.00 (2H, m), 2.14-2.17 (1H, m), 2.70-2.79 (5H, m), 2.86-2.96 (6H, m), 3.15 (1H, dd, J=14.8, 7.2 Hz), 3.88 (4H, s), 4.05 (1H, s), 4.13-4.20 (3H, m), 4.82 (1H, dd, J=11.2, 5.6 Hz), 6.14 (1H, d, J=8.4 Hz), 6.68 (1H, d, J=9.2 Hz), 6.80 (1H, dd, J=8.8, 2.4 Hz), 6.96 (1H, d, J=2.4 Hz), 7.20 (1H, d, J=8.0 Hz), 7.38 (1H, t, J=8.0 Hz), 7.57 (1H, d, J=8.8 Hz), 7.74 (1H, d, J=8.0 Hz), 7.94 (1H, dd, J=8.8, 2.0 Hz), 8.30 (1H, brs), 8.57 (1H, d, J=2.0 Hz).

Chemical Formula: $C_{44}H_{51}ClN_8O_6$, Molecular Weight: 823.38

Total H count from HNMR data: 51.

Synthesis of Exemplary PROTAC 33

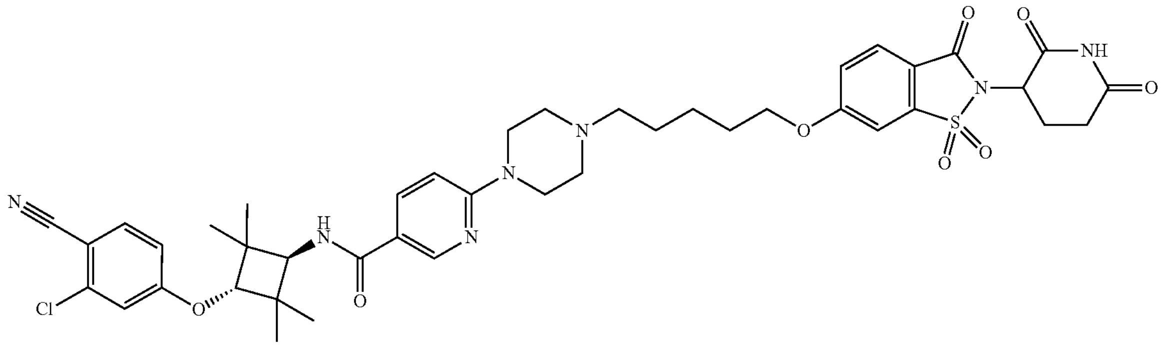 [SMILES: CC1(C)[C@H](NC(=O)c2ccc(N3CCN(CCCCCOc4ccc5c(c4)S(=O)(=O)N(C4CCC(=O)NC4=O)C5=O)CC3)nc2)C(C)(C)[C@H]1Oc1ccc(C#N)c(Cl)c1]

N-((1r,3r)-3-(3-chloro-4-cyanophenoxy)-2,2,4,4-tetramethyl cyclobutyl)-6-(4-(5-((2-(2,6-dioxopiperidin-3-yl)-1,1-dioxido-3-oxo-2,3-dihydrobenzo[d]isothiazol-6-yl)oxy)pentyl)piperazin-1-yl)nicotinamide Synthetic Scheme

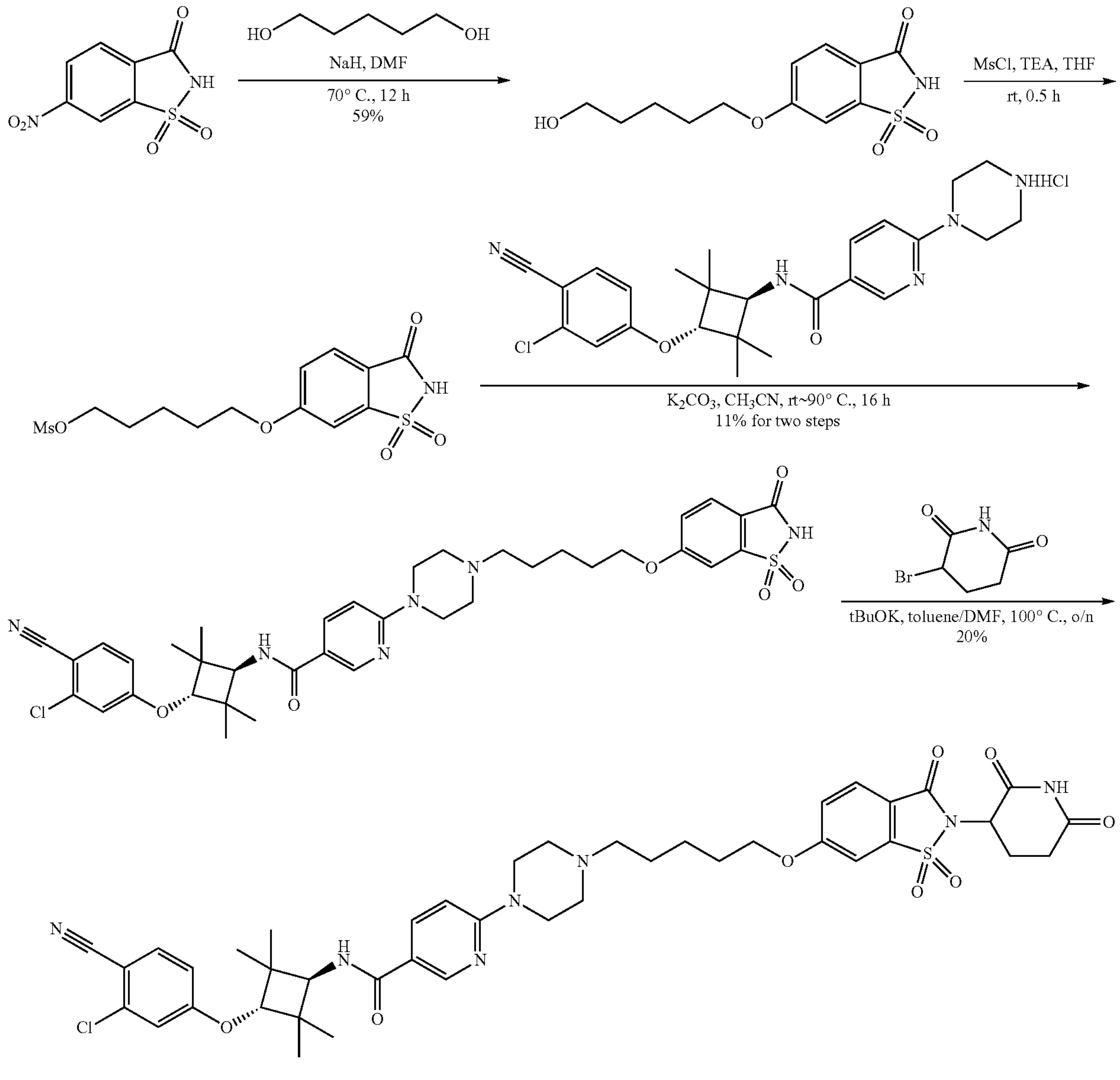

Step 1: Synthesis of 6-((5-hydroxypentyl)oxy)benzo[d]isothiazol-3(2H)-one 1,1-dioxide

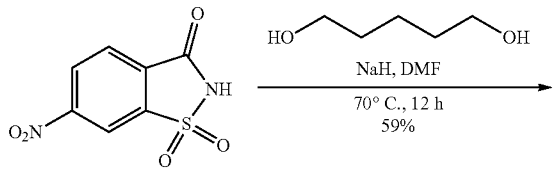

-continued

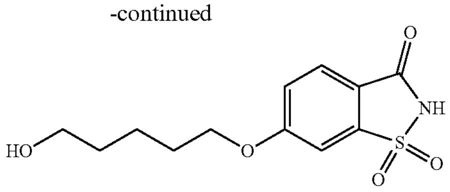

To a solution of pentane-1,5-diol (1.73 g, 16.7 mmol) in N,N-dimethylformamide (15.0 mL) was added sodium hydride (266 mg, 6.66 mmol) under nitrogen. The reaction mixture was stirred at room temperature for 1 h. Then 6-nitrobenzo[d]isothiazol-3(2H)-one 1,1-dioxide (760 mg, 3.33 mmol) was added and stirred at 70° C. for 12 hours. After cooling to room temperature, the solvent was removed in vacuo. The residue was extracted with ethyl acetate (30 mL×3) and water (30 mL). The organic layer was washed with brine (5 mL). The combined organic phases were dried over anhydrous sodium sulfate, filtered, and concentrated in vacuo. The residue was washed by methanol (3 mL) to give 6-((5-hydroxypentyl)oxy)benzo[d]isothiazol-3(2H)-one 1,1-dioxide (560 mg, 59%) as a pale yellow solid.

Agilent LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity is 78.69%, Rt=1.159 min; MS Calcd.: 285.1; MS Found: 284.2 $[M-H]^+$.

Step 2: Synthesis of 5-((1,1-dioxido-3-oxo-2,3-dihydrobenzo[d]isothiazol-6-yl)oxy)pentyl methanesulfonate

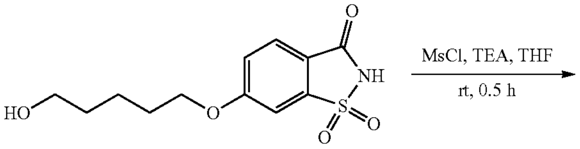

-continued

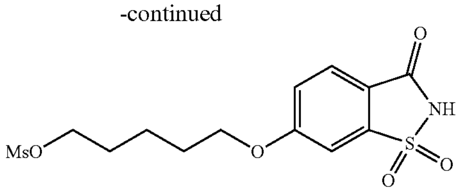

To a solution of 6-((5-hydroxypentyl)oxy)benzo[d]isothiazol-3(2H)-one (120 mg, 0.421 mmol) in tetrahydrofuran (10.0 mL) was added triethylamine (85.1 mg, 0.841 mmol) and methanesulfonyl chloride (38.5 mg, 0.336 mmol) under nitrogen. The resulting reaction mixture was stirred at room temperature for 0.5 hour. The solvent was concentrated in vacuo. The residue was extracted with dichloromethane (10 mL×3) and water (20 mL). The organic phase was dried and concentrated in vacuo to give crude 5-((1,1-dioxido-3-oxo-2,3-dihydrobenzo[d]isothiazol-6-yl)oxy)pentyl methanesulfonate as yellow oil, which was used to the next step without further purification.

Agilent LC-MS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM $NH_4HCO_3$] and 10% [$CH_3CN$] to 5% [water+10 mM $NH_4HCO_3$] and 95% [$CH_3CN$] in 0.5 min, then under this condition for 1.5 min, finally changed to 90% [water+10 mM $NH_4HCO_3$] and 10% [$CH_3CN$] in 0.1 min and under this condition for 0.5 min). Purity is 77.93%, Rt=0.613 min; MS Calcd.: 363.0; MS Found: 362.0 $[M-H]^+$.

Step 3: Synthesis of N-((1r,3r)-3-(3-chloro-4-cyanophenoxy)-2,2,4,4-tetramethylcyclobutyl)-6-(4-(5-((1,1-dioxido-3-oxo-2,3-dihydrobenzo[d]isothiazol-6-yl)oxy)pentyl)piperazin-1-yl)nicotinamide

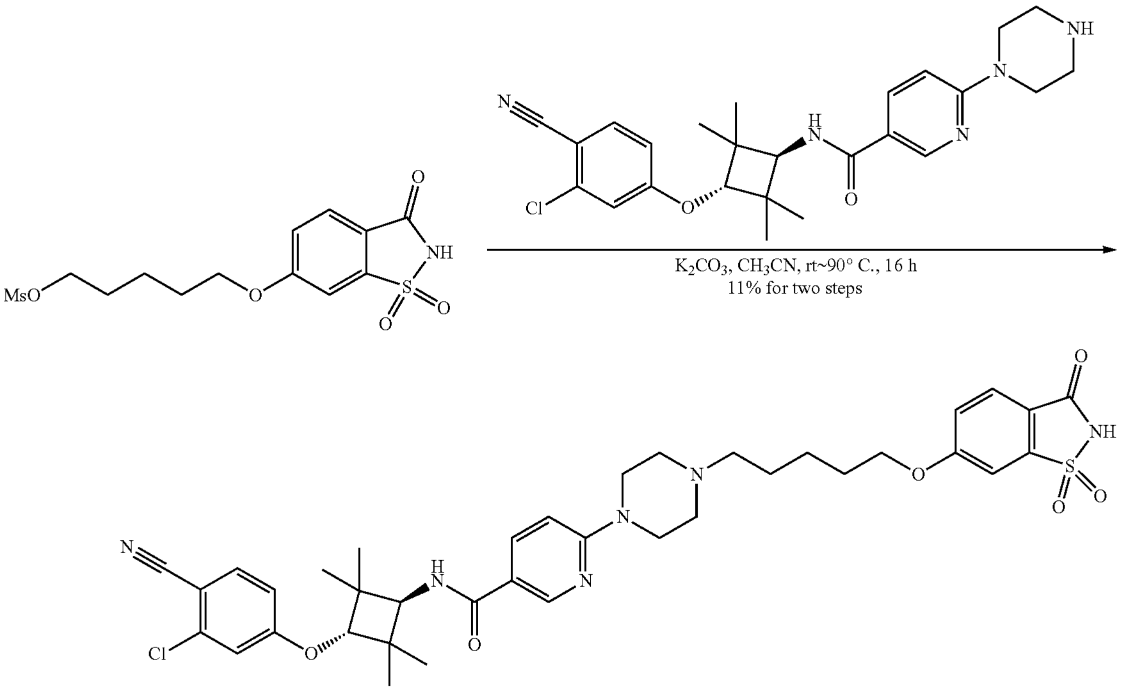

To a solution of 5-((1,1-dioxido-3-oxo-2,3-dihydrobenzo[d]isothiazol-6-yl)oxy)pentyl methanesulfonate (0.421 mmol) in acetonitrile (5 mL) was added potassium carbonate (291 mg, 2.11 mmol) and N-((1r,3r)-3-(3-chloro-4-cyano-phenoxy)-2,2,4,4-tetramethylcyclobutyl)-6-(piperazin-1-yl) nicotinamide hydrochloride (212 mg, 0.421 mmol). The resulting reaction mixture was stirred at 90° C. for 16 hours. The solvent was concentrated in vacuo. The residue was extracted with ethyl acetate (20 mL×3) and water (20 mL). The organic phase was dried and concentrated in vacuo. The residue was purified by prep-HPLC to give N-((1r,3r)-3-(3-chloro-4-cyanophenoxy)-2,2,4,4-tetramethylcyclobutyl)-6-(4-(5-((1,1-dioxido-3-oxo-2,3-dihydrobenzo[d]isothiazol-6-yl)oxy)pentyl)piperazin-1-yl)nicotinamide (34 mg, 11% for two steps) as a pale yellow solid.

Agilent LC-MS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM $NH_4HCO_3$] and 10% [$CH_3CN$] to 5% [water+10 mM $NH_4HCO_3$] and 95% [$CH_3CN$] in 0.5 min, then under this condition for 1.5 min, finally changed to 90% [water+10 mM $NH_4HCO_3$] and 10% [$CH_3CN$] in 0.1 min and under this condition for 0.5 min). Purity is 97.67%, Rt=1.037 min; MS Calcd.: 734.3; MS Found: 735.0 $[M+H]^+$.

Step 4: Synthesis of N-((1r,3r)-3-(3-chloro-4-cyano-phenoxy)-2,2,4,4-tetramethylcyclobutyl)-6-(4-(5-((2-(2,6-dioxopiperidin-3-yl)-1,1-dioxido-3-oxo-2,3-dihydrobenzo[d]isothiazol-6-yl)oxy)pentyl) piperazin-1-yl)nicotinamide

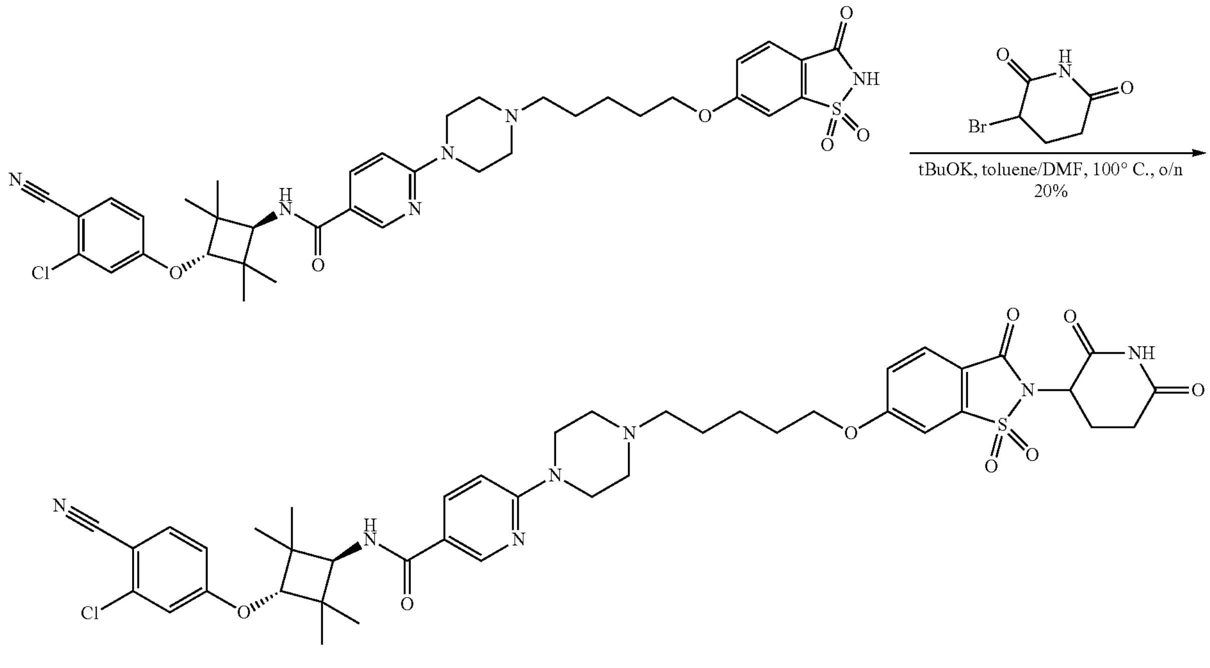

To a solution of N-((1r,3r)-3-(3-chloro-4-cyanophenoxy)-2,2,4,4-tetramethylcyclobutyl)-6-(4-(5-((1,1-dioxido-3-oxo-2,3-dihydrobenzo[d]isothiazol-6-yl)oxy)pentyl)piperazin-1-yl)nicotinamide (30 mg, 0.0408 mmol) in 1,4-dioxane/N,N-dimethylformamide (5 mL/0.5 mL) was added 3-bromopiperidine-2,6-dione (11.8 mg, 0.0612 mmol) and potassium tert-butoxide (9.16 mg, 0.0816 mmol). The reaction mixture was stirred at 100° C. for overnight. After cooling to room temperature, ice-water (2.0 mL) was added, and adjust to PH=2~3 by hydrochloric acid (1N), then extracted with ethyl acetate (20.0 mL×3). The combined organic phase was washed with brine (5.0 mL), dried over anhydrous sodium sulfate, filtered, and concentrated in vacuo. The residue was purified by prep-HPLC and prep-TLC (dichloromethane/methanol=10:1) to give N-((1r,3r)-3-(3-chloro-4-cyanophenoxy)-2,2,4,4-tetramethylcyclobutyl)-6-(4-(5-((2-(2,6-dioxopiperidin-3-yl)-1,1-dioxido-3-oxo-2,3-dihydrobenzo[d]isothiazol-6-yl)oxy)pentyl) piperazin-1-yl)nicotinamide (6.8 mg, 20%) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min.). Purity is 99.03%, Rt=3.087 min; MS Calcd.: 845.3; MS Found: 846.3 $[M+H]^+$.

HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 96.34%, Rt=10.536 min.

$^1$H NMR (400 MHz, DMSO-$d_6$) δ 1.19 (6H, s), 1.22 (6H, s), 1.46-1.55 (4H, m), 1.79-1.80 (2H, m), 2.34-2.40 (3H, m), 2.45 (4H, s), 2.54-2.92 (3H, m), 3.59 (4H, s), 4.06 (1H, d, J=9.2 Hz), 4.20-4.25 (2H, m), 4.30 (1H, s), 5.23-5.28 (0.5H, m), 5.98 (0.5H, t, J=9.2 Hz), 6.87 (1H, d, J=9.2 Hz), 6.99-7.02 (1H, m), 7.21 (1H, d, J=2.0 Hz), 7.35-7.50 (1H, m), 7.63 (1H, d, J=9.2 Hz), 7.81-7.83 (1H, m), 7.90-8.02 (3H, m), 8.62 (1H, d, J=2.0 Hz), 11.19 (1H, t, J=9.6 Hz).

Chemical Formula: $C_{42}H_{48}ClN_7O_3S$, Molecular Weight: 846.39

Total H count from HNMR data: 48.

Synthesis of Exemplary PROTAC 39
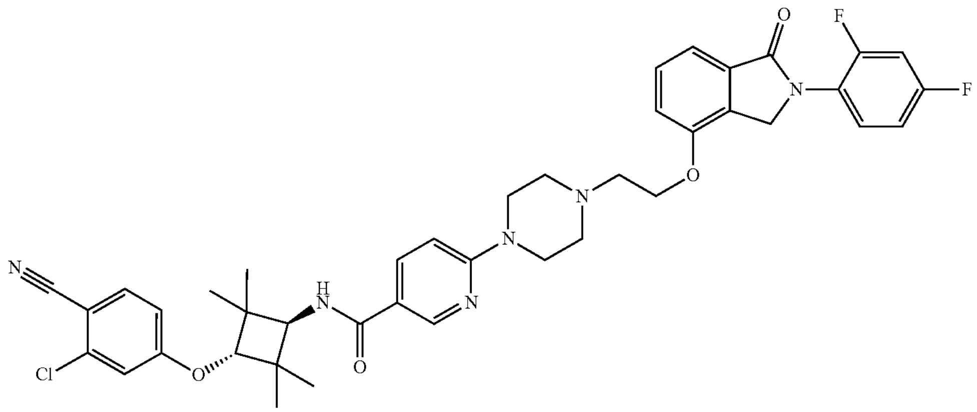 [SMILES: CC1(C)[C@H](NC(=O)c2ccc(N3CCN(CCOc4cccc5c4CN(c4ccc(F)cc4F)C5=O)CC3)nc2)C(C)(C)[C@H]1Oc1ccc(C#N)c(Cl)c1]
N-((1r,3r)-3-(3-chloro-4-cyanophenoxy)-2,2,4,4-tetramethylcyclobutyl)-6-(4-(2-((2-(2,4-difluorophenyl)-1-oxoisoindolin-4-yl)oxy)ethyl)piperazin-1-yl)nicotinamide
Synthetic Scheme:
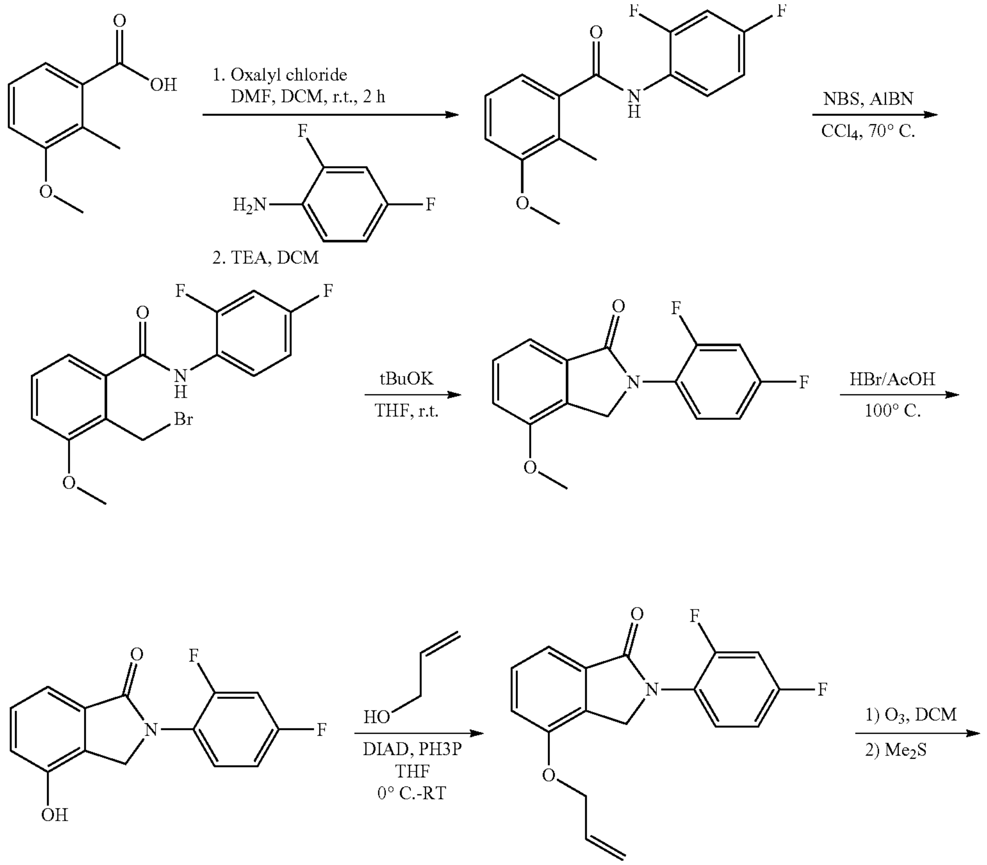

-continued

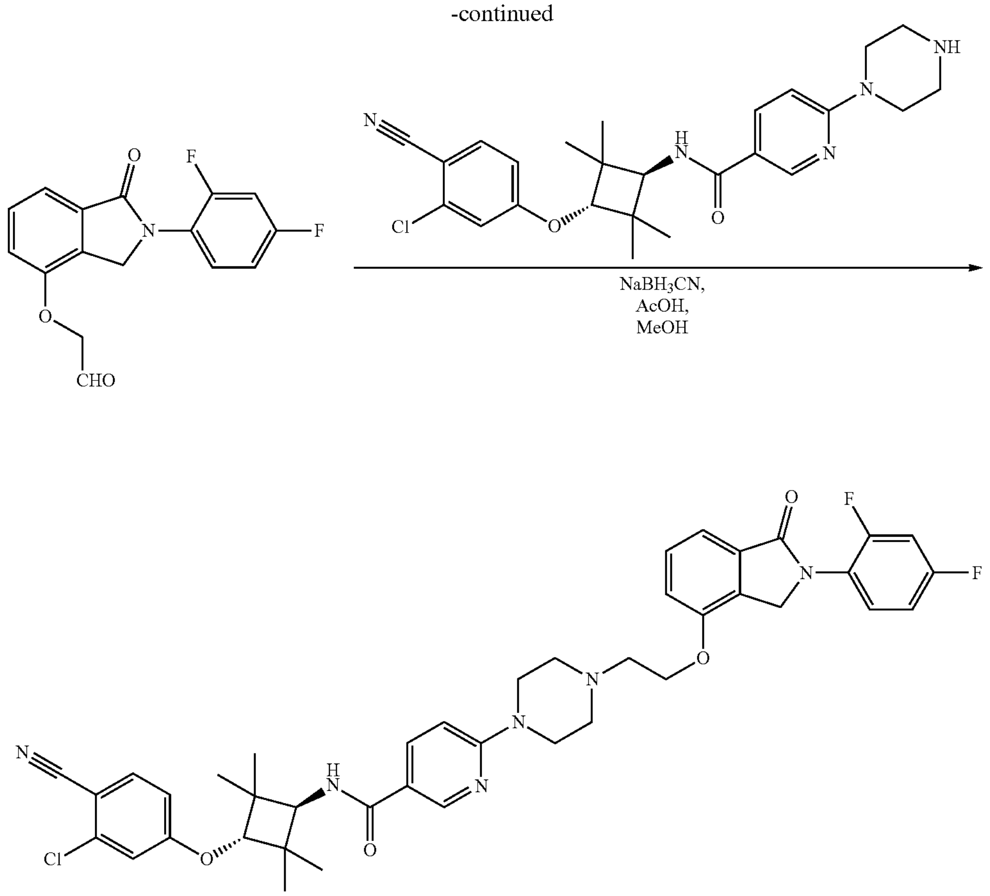

Step 1: Synthesis of N-(2,4-difluorophenyl)-3-methoxy-2-methylbenzamide

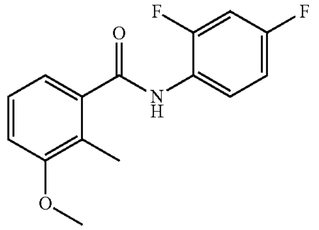 [SMILES: COc1cccc(C(=O)Nc2ccc(F)cc2F)c1C]

A mixture of 3-methoxy-2-methylbenzoic acid (5 g, 30 mmol) and oxalyl chloride (5.6 g, 150 mmol) and N,N-dimethylformamide (0.1 ml) in dichloromethane (20 ml) was stirred at room temperature for 2 hours. TLC showed the reaction was complete. The volatiles were evaporated under reduced pressure to afford 3-methoxy-2-methylbenzoyl chloride (crude) as yellow oil which was used in next step without further purification. A mixture of 3-methoxy-2-methylbenzoyl chloride (crude), 2,4-difluoroaniline (3.8 g, 30 mmol) and triethylamine (12 g, 120 mmol) in dichloromethane (20 ml) was stirred at room temperature for 1 hour. TLC showed the reaction was complete. The reaction mixture was diluted with dichloromethane (20 ml) and washed with brine (20 ml) dried over anhydrous sodium sulfate, and concentrated under reduced pressure to give a crude residue which was purified by silica gel flash chromatography N-(2,4-difluorophenyl)-3-methoxy-2-methylbenzamide (5.8 g, yield 69%) as yellow oil.

Step 2: Synthesis of 2-(bromomethyl)-N-(2,4-difluorophenyl)-3-methoxybenzamide

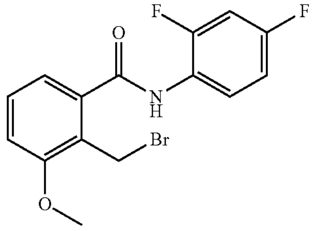 [SMILES: COc1cccc(C(=O)Nc2ccc(F)cc2F)c1CBr]

A mixture of N-(2,4-difluorophenyl)-3-methoxy-2-methylbenzamide (5.8 g, 20.9 mmol), N-Bromosuccinimide (3.9 g, 31.4 mmol) and AIBN (2,2'-Azobis(2-methylpropionitrile)) (342 mg, 2.09 mmol) in carbon tetrachloride (30 ml) was stirred at 70° C. overnight. The volatiles were evaporated under reduced pressure which was purified by silica gel flash column chromatography (eluted with 10-20% ethyl acetate in hexane) to afford 2-(bromomethyl)-N-(2,4-difluorophenyl)-3-methoxybenzamide (5.9 g, yield 80%) as white solid.

LC_MS: ($ES^+$): m/z 356.0, 357.9 $[M+H]^+$. $t_R$=2.907 min.

Step 3: Synthesis of 2-(2,4-difluorophenyl)-4-methoxyisoindolin-1-one

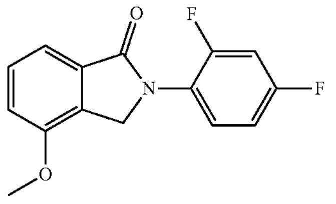 [SMILES: COc1cccc2c1CN(c1ccc(F)cc1F)C2=O]

To a solution of 2-(bromomethyl)-N-(2,4-difluorophenyl)-3-methoxybenzamide (2.0 g, 5.6 mmol) in anhydrous tetrahydrofuran (20 ml) was added potassium tert-butanolate (1M in tetrahydrofuran, 8.4 ml, 8.4 mmol) at 0° C., and the resulting mixture was stirred at 0° C. for 2 hours. TLC showed the reaction was complete. The reaction mixture was partitioned between water (50 ml) and ethyl acetate (50 ml). The organic layer was collected, washed with brine (20 ml×2), dried over anhydrous sodium sulfate, and concentrated under reduced pressure to afford a crude residue which was purified by silica gel flash chromatography (eluted with 20% ethyl acetate in hexane) to afford 2-(2,4-difluorophenyl)-4-methoxyisoindolin-1-one (500 mg, yield 33%) as yellow solid.

Step 4: Synthesis of 2-(2,4-difluorophenyl)-4-hydroxyisoindolin-1-one

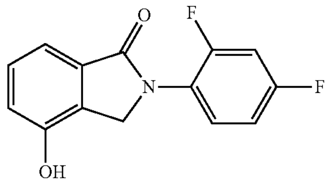 [SMILES: O=C1c2cccc(O)c2CN1c1ccc(F)cc1F]

A mixture of 2-(2,4-difluorophenyl)-4-methoxyisoindolin-1-one (200 mg, 0.727 mmol) in hydrogen bromide in acetic acid solution (33%, 3 ml) was stirred at 100° C. for 2 days. TLC showed the reaction was complete. The volatiles were evaporated under reduced pressure to give a crude residue which was purified by silica gel flash chromatography (eluted with 30%-50 ethyl acetate in hexane) to afford 2-(2,4-difluorophenyl)-4-hydroxyisoindolin-1-one (180 mg, yield 95%) as yellow oil.

LC_MS: (ES+): m/z 262.1 $[M+H]^+$. $t_R$=2.64 min.

Step 5: Synthesis of 4-(allyloxy)-2-(2,4-difluorophenyl)isoindolin-1-one

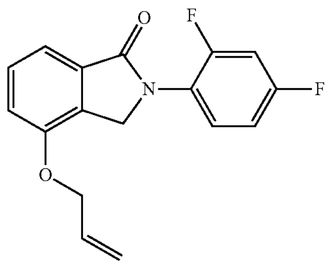 [SMILES: C=CCOc1cccc2c1CN(c1ccc(F)cc1F)C2=O]

To a stirred solution of 2-(2,4-difluorophenyl)-4-hydroxyisoindolin-1-one (180 mg, 0.68 mmol), triphenylphosphine (539 mg, 2.06 mmol) and prop-2-en-1-ol (119 mg, 2.06 mmol) in tetrahydrofuran (5 ml) was added diisopropyl azodicarboxylate (416 mg, 2.06 mmol) in tetrahydrofuran (2 ml) at 0° C., and the reaction mixture was stirred at 0° C. for 30 minutes. TLC showed the reaction was complete. The volatiles were evaporated under reduced pressure to give a crude residue which was purified by silica gel flash chromatography (eluted with 10-20% ethyl acetate in hexane) to afford 4-(allyloxy)-2-(2,4-difluorophenyl)isoindolin-1-one (180 mg, yield 87%) as colorless oil.

LC_MS: (ES+): m/z 302.2 $[M+H]^+$. $t_R$=2.86 min.

Step 6: Synthesis of 2-((2-(2,4-difluorophenyl)-1-oxoisoindolin-4-yl)oxy)acetaldehyde

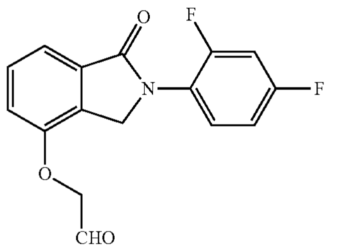 [SMILES: O=CCOc1cccc2c1CN(c1ccc(F)cc1F)C2=O]

An ozone-enrichen steam of oxygen was bubbled through a solution of 4-(allyloxy)-2-(2,4-difluorophenyl)isoindolin-1-one (180 mg, 0.59 mmol) in dichloromethane (20 ml) at −78° C. until the reaction mixture turned dark blue. The solution was purged with oxygen at −78° C. for 20 min to remove the excess ozone. Then to the reaction mixture was added dimethyl sulfide (1.5 ml, 20.4 mmol) at −78° C., the mixture was allowed to warm up to room temperature and stirred overnight. TLC showed the reaction was complete. The reaction mixture was concentrated under reduced pressure to give 2-((2-(2,4-difluorophenyl)-1-oxoisoindolin-4-yl)oxy)acetaldehyde (180 mg, 100%) which was used in next step without further purification.

$^1$H NMR (400 MHz, DMSO-$d_6$): δ 4.68-4.69 (m, 2H), 4.77-4.79 (m, 2H), 6.86-6.93 (m, 4H), 7.33-7.55 (m, 2H), 9.80 (s, 1H).

Chemical Formula: $C_{16}H_{11}F_2NO_3$; Molecular Weight: 303.26;

Total H count from HNMR data: 11;

Step 7: Synthesis of N-((1r,3r)-3-(3-chloro-4-cyano-phenoxy)-2,2,4,4-tetramethylcyclobutyl)-6-(4-(2-((2-(2,4-difluorophenyl)-1-oxoisoindolin-4-yl)oxy)ethyl) piperazin-1-yl)nicotinamide

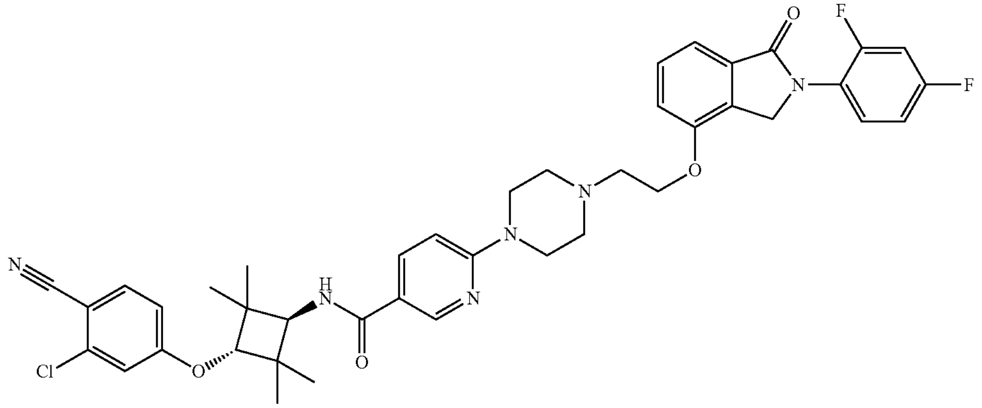 [SMILES: CC1(C)[C@H](NC(=O)c2ccc(N3CCN(CCOc4cccc5c4CN(c4ccc(F)cc4F)C5=O)CC3)nc2)C(C)(C)[C@H]1Oc1ccc(C#N)c(Cl)c1]

To a stirred solution of 242-(2,4-difluorophenyl)-1-oxoi-soindolin-4-yl)oxy)acetaldehyde (160 mg, 0.53 mmol), N-((1r,3r)-3-(3-chloro-4-cyanophenoxy)-2,2,4,4-tetramethylcyclobutyl)-6-(piperazin-1-yl)nicotinamide (300 mg, 0.6 mmol, intermediate in synthesis of exemplary PROTAC 29) and acetic acid (2 drops) in methanol (3 ml) was added sodium cyanoborohydride (150 mg, 2.4 mmol) at room temperature. The reaction mixture was stirred at room temperature overnight. TLC showed the reaction was complete. The reaction mixture was partitioned between ethyl acetate (40 ml) and water (20 ml). The organic layer was collected, washed with brine (20 ml), dried over anhydrous sodium sulfate, and concentrated under reduced pressure to give a crude residue which was purified by prep-TLC (eluted with 10% methanol in dichloromethane) to afford N-((1r,3r)-3-(3-chloro-4-cyanophenoxy)-2,2,4,4-tetramethylcyclobutyl)-6-(4-(2-((2-(2,4-difluorophenyl)-1-oxoisoindolin-4-yl)oxy)ethyl)piperazin-1-yl)nicotinamide (50 mg, yield 12%, 3 steps) as light yellow solid.

$^1$H NMR (400 MHz, $CD_3OD$): δ 1.23 (s, 6H), 1.29 (s, 6H), 2.67-2.82 (m, 4H), 2.92-3.01 (m, 2H), 3.72 (s, 4H), 4.15 (s, 1H), 4.29-4.39 (m, 3H), 4.88 (s, 2H), 6.85-6.87 (m, 2H), 7.10-7.34 (m, 4H), 7.47-7.75 (m, 4H), 7.96-7.98 (m, 1H), 8.61 (s, 1H).

Chemical Formula: $C_{41}H_{41}ClF_2N_6O_4$; Molecular Weight: 755.25;

Total H count from HNMR data: 40;

LC_MS: (ES+): m/z 755.6 $[M+H]^+$. $t_R$=2.534 min.

Synthesis of Exemplary PROTAC 41

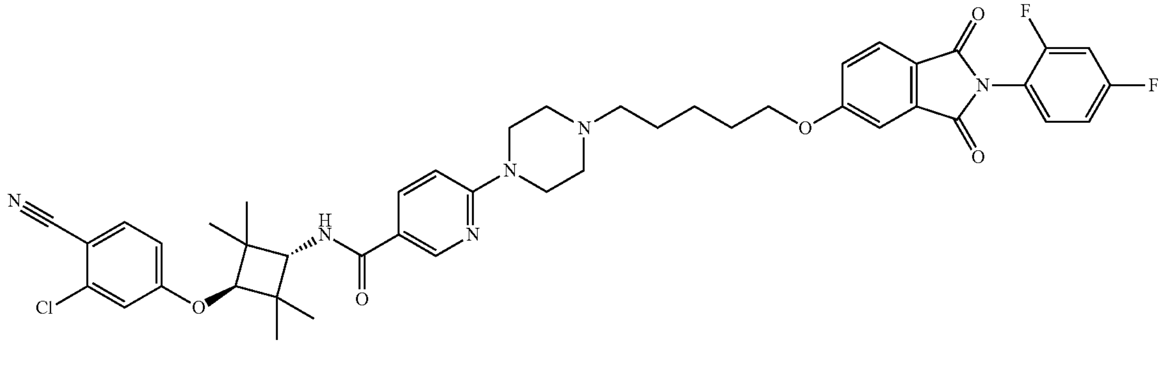 [SMILES: CC1(C)[C@H](NC(=O)c2ccc(N3CCN(CCCCCOc4ccc5c(c4)C(=O)N(c4ccc(F)cc4F)C5=O)CC3)nc2)C(C)(C)[C@H]1Oc1ccc(C#N)c(Cl)c1]

N-((1r,3 r)-3-(3-chl oro-4-cyanophenoxy)-2,2,4,4-tetramethylcyclobutyl)-6-(4-(542-(2,4-difluorophenyl)-1,3-dioxoisoindolin-5-yl)oxy)pentyl)piperazin-1-yl)nicotinamide Synthetic Scheme:

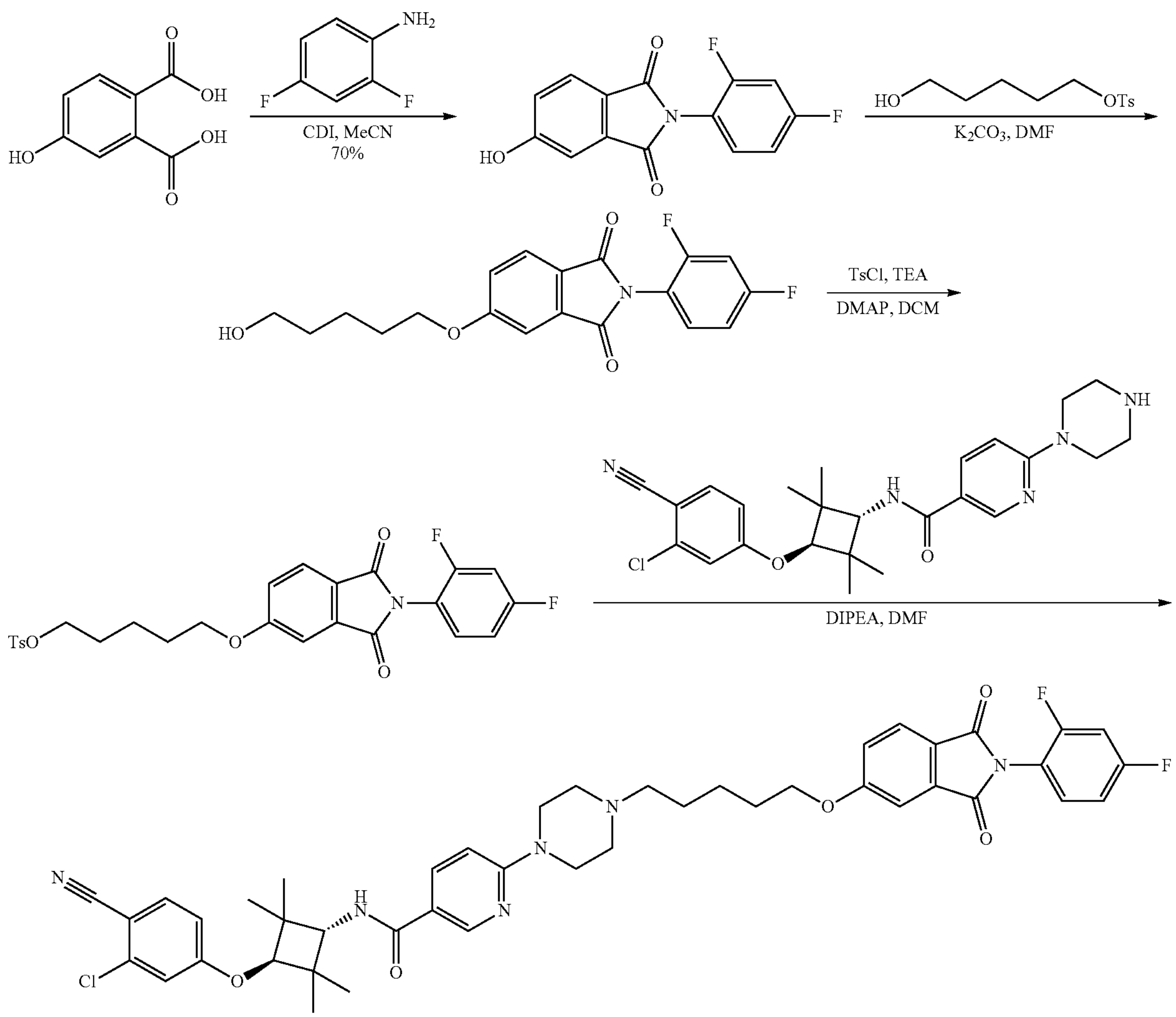

Step 1: Synthesis of 2-(2,4-difluorophenyl)-5-hydroxyisoindoline-1,3-dione

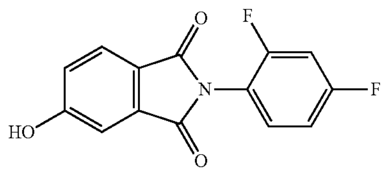 [SMILES: O=C1c2ccc(O)cc2C(=O)N1c1ccc(F)cc1F]

To a solution of 4-hydroxyphthalic acid (2 g, 10.98 mmol) in acetonitrile (50 ml) was added 1,1'-carbonyldiimidazole (3.9 g, 24.16 mmol) in portions at room temperature. After stirring for 30 mins, 2,4-difluoroaniline (1.6 g, 12.08 mmol) was added, and the resulting mixture was stirred at 70° C. for 3 hours. TLC showed the reaction was complete. The reaction mixture was partitioned between ethyl acetate (50 ml) and water (50 ml), the organic layer was washed with brine (50 ml×2) and dried over anhydrous sodium sulfate and concentrated under reduced pressure to give a crude residue which was purified by silica gel flash column chromatography (eluted with 25-35% ethyl acetate in hexane) to afford 2-(2,4-difluorophenyl)-5-hydroxyisoindoline-1,3-dione (2.1 g, yield 70%) as yellow solid.

LC_MS: ($ES^+$): m/z 276.1 $[M+H]^+$. $t_R$=2.462 min.

$^1H$ NMR (400 MHz, DMSO-$d_6$): δ 7.21-7.31 (m, 3H), 7.51-7.56 (m, 1H), 7.60-7.66 (m, 1H), 7.83 (d, J=8.4 Hz, 1H), 11.17 (br, 1H).

Chemical Formula: $C_{14}H_7F_2NO_3$; Molecular Weight: 275.21;

Total H count from HNMR data: 7.

Step 2: Synthesis of 2-(2,4-difluorophenyl)-5((5-hydroxypentypoxy)isoindoline-1,3-dione

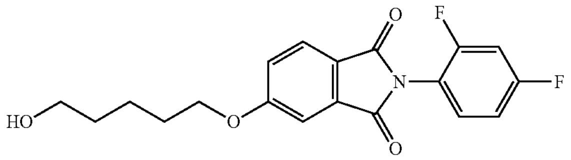 [SMILES: O=C1c2ccc(OCCCCCO)cc2C(=O)N1c1ccc(F)cc1F]

A mixture of 2-(2,4-difluorophenyl)-5-hydroxyisoindoline-1,3-dione (300 mg, 1.09 mmol), 5-hydroxypentyl 4-methylbenzenesulfonate (282 mg, 1.09 mmol) and potassium carbonate (301 mg, 2.18 mmol) in N,N-dimethylformamide (5 ml) was stirred at 50° C. overnight. TLC showed the reaction was complete. The reaction mixture was partitioned between ethyl acetate (30 ml) and water (30 ml), the organic layer was washed with brine (30 ml×2) and dried over anhydrous sodium sulfate and concentrated under reduced pressure to give a crude residue which was purified by silica gel flash column chromatography (eluted with 40-50% ethyl acetate in hexane) to afford 2-(2,4-difluorophenyl)-5-((5-hydroxypentyl)oxy)isoindoline-1,3-dione (217 mg, yield 55%) as white solid.

LC_MS: ($ES^+$): m/z 362.1 $[M+H]^+$. $t_R$=2.658 min.

$^1$H NMR (400 MHz, $CDCl_3$): δ 1.57-1.69 (m, 4H), 1.88-1.91 (m, 2H), 3.70 (t, J=6.2 Hz, 2H), 4.12 (t, J=6.4 Hz, 2H), 6.99-7.05 (m, 2H), 7.22-7.24 (m, 1H), 7.31-7.36 (m, 1H), 7.40-7.41 (m, 1H), 7.85 (d, J=8.4 Hz, 1H).

Chemical Formula: $C_{19}H_{17}F_2NO_4$; Molecular Weight: 361.34;

Total H count from HNMR data: 16.

Step 3: Synthesis of 5-((2-(2,4-difluorophenyl)-1,3-dioxoisoindolin-5-yl)oxy)pentyl 4-methylbenzenesulfonate

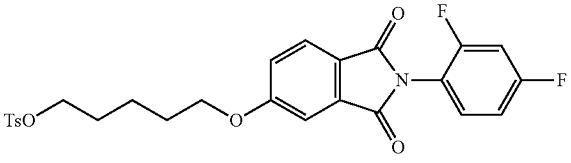 [SMILES: Cc1ccc(S(=O)(=O)OCCCCCOc2ccc3c(c2)C(=O)N(c2ccc(F)cc2F)C3=O)cc1]

To a solution of 2-(2,4-difluorophenyl)-5-((5-hydroxypentyl)oxy)isoindoline-1,3-dione (217 mg, 0.60 mmol), triethylamine (122 mg, 1.20 mmol) and N,N-dimethylpyridin-4-amine (7.3 mg, 0.06 mmol) in dichloromethane (20 ml) was added 4-toluenesulfonyl chloride (171 mg, 0.90 mmol) at 0° C., the reaction mixture was allowed to warm up to room temperature and stirred overnight. TLC showed the reaction was complete. The reaction mixture was diluted with dichloromethane (30 ml), washed with water (50 ml) then brine (50 ml), dried over anhydrous sodium sulfate, and concentrated under reduced pressure to give a crude residue which was purified by silica gel flash chromatography (eluted with 30-50% ethyl acetate in hexane) to afford 5-((2-(2,4-difluorophenyl)-1,3-dioxoisoindolin-5-yl)oxy) pentyl 4-methylbenzenesulfonate (208 mg, yield 67%) as white solid.

LC_MS: ($ES^+$): m/z 516.2 $[M+H]^+$. $t_R$=3.183 min.

$^1$H NMR (400 MHz, DMSO-$d_6$): δ 1.53-1.58 (m, 2H), 1.74-1.85 (m, 4H), 2.45 (s, 3H), 4.05-4.09 (m, 4H), 7.00-7.04 (m, 2H), 7.20-7.22 (m, 1H), 7.31-7.38 (m, 4H), 7.79-7.86 (m, 3H).

Chemical Formula: $C_{26}H_{23}F_2NO_6S$; Molecular Weight: 515.53;

Total H count from HNMR data: 23.

Step 4: Synthesis of N-((1r,3r)-3-(3-chloro-4-cyanophenoxy)-2,2,4,4-tetramethylcyclobutyl)-6-(4-(5-((2-(2,4-difluorophenyl)-1,3-dioxoisoindolin-5-yl)oxy) pentyl)piperazin-1-yl)nicotinamide

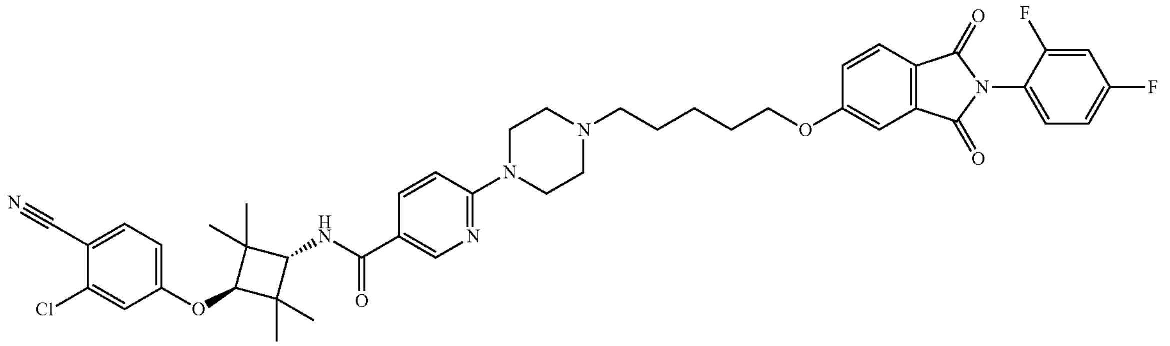 [SMILES: CC1(C)[C@H](NC(=O)c2ccc(N3CCN(CCCCCOc4ccc5c(c4)C(=O)N(c4ccc(F)cc4F)C5=O)CC3)nc2)C(C)(C)[C@H]1Oc1ccc(C#N)c(Cl)c1]

To a stirred solution of 5-((2-(2,4-difluorophenyl)-1,3-dioxoisoindolin-5-yl)oxy)pentyl 4-methylbenzenesulfonate (110 mg, 0.21 mmol), N-ethyl-N-isopropylpropan-2-amine (55 mg, 0.43 mmol) and potassium iodide (3 mg, 0.02 mmol) in N,N-dimethylformamide (2 ml) was added N-((1r, 3r)-3-(3-chloro-4-cyanophenoxy)-2,2,4,4-tetramethylcyclobutyl)-6-(piperazin-1-yl)nicotinamide (100 mg, 0.21 mmol, intermediate in synthesis of exemplary PROTAC 29), and the mixture was stirred at 50° C. overnight under nitrogen. TLC showed the reaction was complete. The reaction mixture was partitioned between ethyl acetate (50 ml) and water (30 ml), the organic layer collected and washed with brine (20 ml×2), dried over anhydrous sodium sulfate and concentrated under reduced pressure to give a crude residue which was purified by silica gel flash column chromatography (eluted with 2-5% methanol in dichloromethane) to afford N-((1r,3r)-3-(3-chloro-4-cyanophenoxy)-2,2,4,4-tetramethylcyclobutyl)-6-(4-(5-((2-(2,4-difluorophenyl)-1,3-dioxoisoindolin-5-yl)oxy)pentyl) piperazin-1-yl)nicotinamide (98.4 mg, yield 57%) as white solid.

LC_MS: ($ES^+$): m/z 811.3 $[M+H]^+$. $t_R$=2.630 min.

$^1H$ NMR (400 MHz, $CD_3OD$): δ 1.12 (s, 6H), 1.22 (s, 6H), 1.48-1.61 (m, 4H), 1.80-1.83 (m, 2H), 2.35-2.44 (m, 6H), 3.59 (br, 4H), 4.06 (d, J=9.2 Hz, 1H), 4.22 (t, J=6.4 Hz, 2H), 4.31 (s, 1H), 6.88-6.90 (m, 1H), 6.99-7.02 (m, 1H), 7.20-7.21 (m, 1H), 7.28-7.32 (m, 1H), 7.40-7.42 (m, 1H), 7.52-7.55 (m, 2H), 7.63-7.65 (m, 2H), 7.89-7.93 (m, 2H), 7.97-7.99 (m, 1H), 8.64 (br, 1H).

Chemical Formula: $C_{44}H_{45}ClF_2N_6O_5$; Molecular Weight: 811.32;

Total H count from HNMR data: 45.

Synthesis of Exemplary PROTAC 42

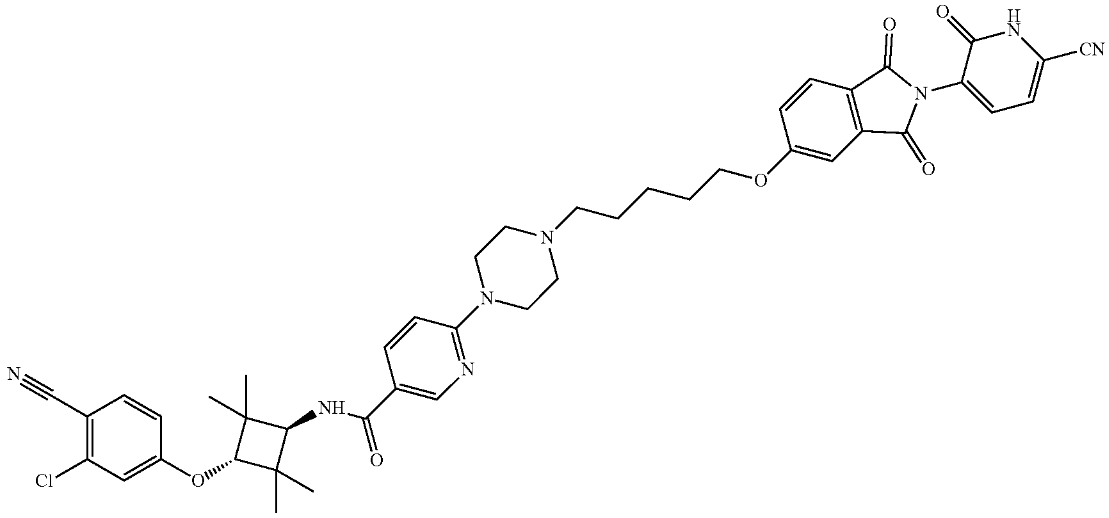 [SMILES: CC1(C)[C@H](NC(=O)c2ccc(N3CCN(CCCCCOc4ccc5c(c4)C(=O)N(c4ccc(C#N)[nH]c4=O)C5=O)CC3)nc2)C(C)(C)[C@H]1Oc1ccc(C#N)c(Cl)c1]

N-((1r,3r)-3-(3-chl oro-4-cyanophenoxy)-2,2,4,4-tetramethylcyclobutyl)-6-(4-(5-((2-(6-cyano-2-oxo-1,2-dihydropyridin-3-yl)-1,3-dioxoisoindolin-5-yl)oxy)pentyl)piperazin-1-yl)nicotinamide Synthetic Scheme

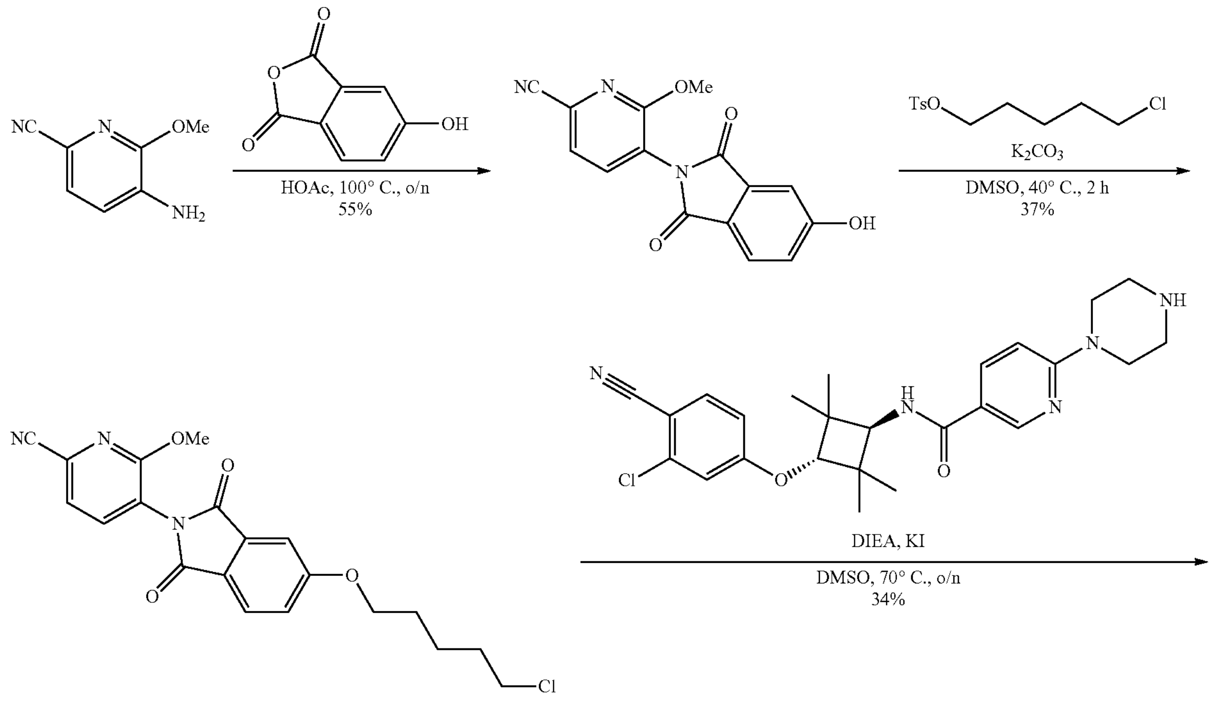

-continued

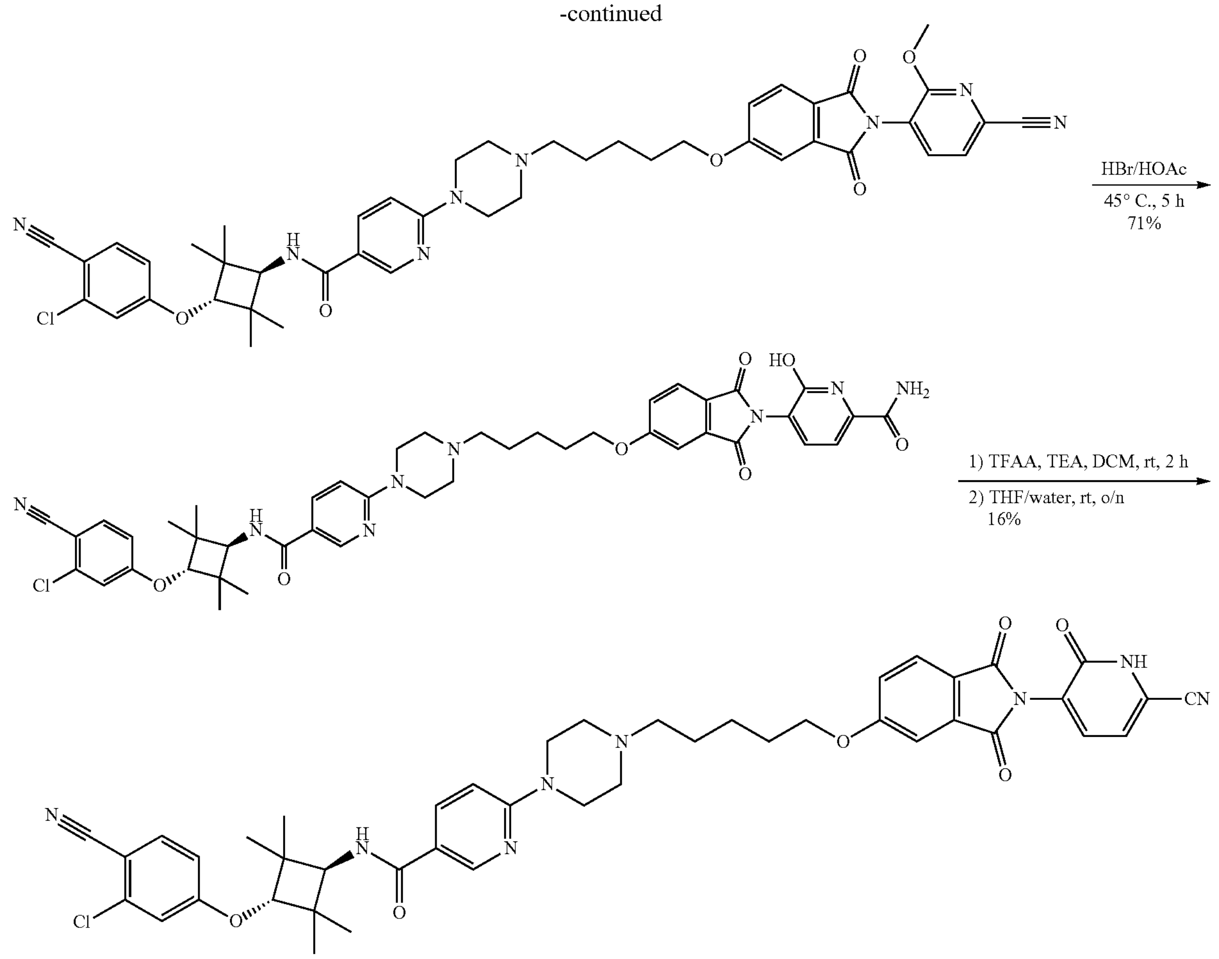

Step 1: Synthesis of 5-(5-hydroxy-1,3-dioxoisoindolin-2-yl)-6-methoxypicolinonitrile

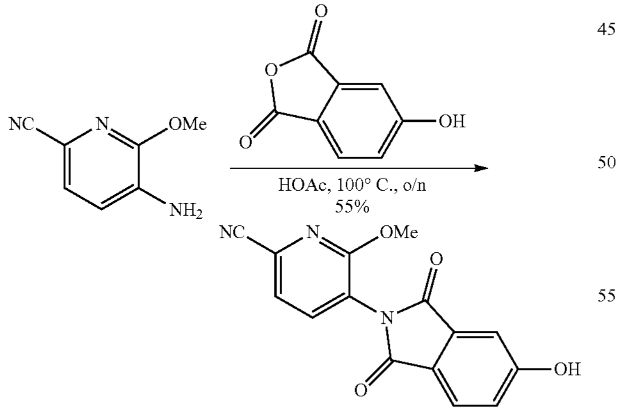

The mixture of 5-amino-6-methoxypicolinonitrile (600 mg, 4.02 mmol) and 5-hydroxyisobenzofuran-1,3-dione (660 mg, 4.02 mmol) in acetic acid glacial (4 mL) was stirred at 100° C. overnight and then cooled down to room temperature. Water (40 mL) was added. The mixture was neutralized with saturated sodium bicarbonate until pH>7. The mixture was extracted with ethyl acetate (20 mL×3). The combined organic layer was washed with brine (10 mL×3), dried over anhydrous sodium sulfate, filtered, and concentrated in vacuo. The residue was washed with ether to give 5-(5-hydroxy-1,3-dioxoisoindolin-2-yl)-6-methoxypicolinonitrile (650 mg, 55%) as a yellow solid.

LC-MS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM $NH_4HCO_3$] and 10% [$CH_3CN$] to 5% [water+10 mM $NH_4HCO_3$] and 95% [$CH_3CN$] in 0.5 min, then under this condition for 1.5 min, finally changed to 90% [water+10 mM $NH_4HCO_3$] and 10% [$CH_3CN$] in 0.1 min and under this condition for 0.5 min). Purity is 69.2%, Rt=0.852 min; MS Calcd.: 295.1; MS Found: 296.0 $[M+H]^+$.

Step 2: Synthesis of 5-(5-(5-chloropentyloxy)-1,3-dioxoisoindolin-2-yl)-6-methoxypicolinonitrile

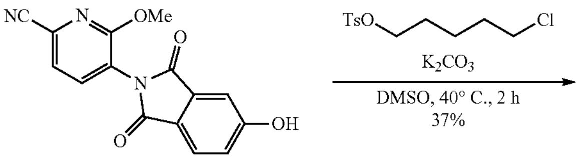

-continued

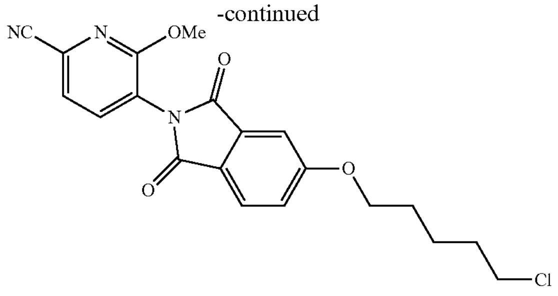

The mixture of 5-(5-hydroxy-1,3-dioxoisoindolin-2-yl)-6-methoxypicolinonitrile (200 mg, 0.68 mmol), potassium carbonate (188 mg, 1.36 mmol) and 5-chloropentyl 4-methylbenzenesulfonate (187 mg, 0.68 mmol) in dimethyl sulfoxide (5 mL) was stirred at 40° C. for 2 hour. The resulting mixture was allowed to cool down to room temperature. Water (20 mL) and ethyl acetate (20 mL) was added. The organic layer was separated, washed with brine (10 mL×2), dried over anhydrous sodium sulfate, filtered, and concentrated in vacuo to give the crude product which was purified by prep-TLC (ethyl acetate/petroleum ether=1:1) to give 5-(5-(5-chloropentyloxy)-1,3-dioxoisoindolin-2-yl)-6-methoxypicolinonitrile (100 mg, 37%) as a yellow solid Step 3: Synthesis of N-((1r,3r)-3-(3-chloro-4-cyanophenoxy)-2,2,4,4-tetramethylcyclobutyl)-6-(4-(5-(2-(6-cyano-2-methoxypyridin-3-yl)-1,3-dioxoisoindolin-5-yloxy)pentyl)piperazin-1-yl)nicotinamide

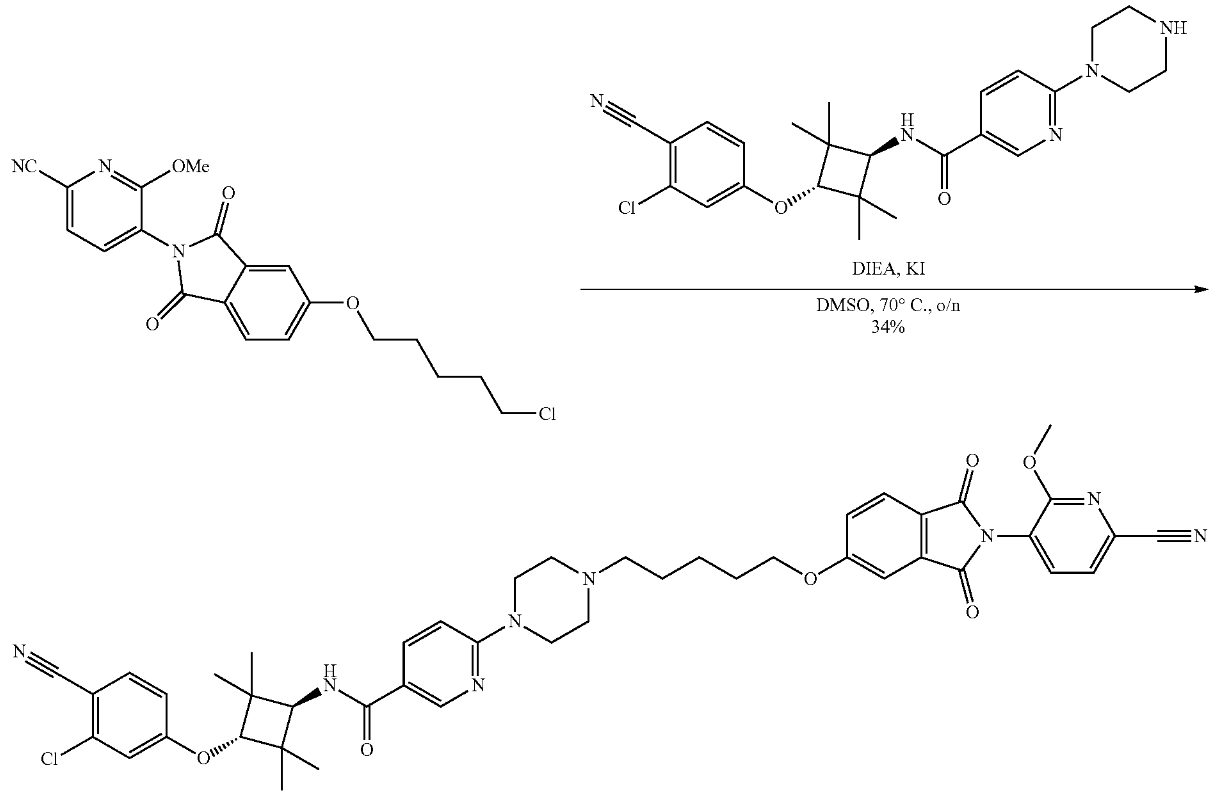

The mixture of methyl 5-(5-(5-chloropentyloxy)-1,3-dioxoisoindolin-2-yl)-6-methoxypicolinonitrile (100 mg, 025 mmol), ethyldiisopropylamine (96.8 mg, 0.75 mmol), potassium iodide (41.5 mg, 0.25 mmol) and N-((1r,3r)-3-(3-chloro-4-cyanophenoxy)-2,2,4,4-tetramethylcyclobutyl)-6-(piperazin-1-yl)nicotinamide (117 mg, 0.25 mmol) in dimethyl sulfoxide (3 mL) was stirred at 70° C. overnight. The resulting mixture was allowed to cool down to room temperature. Water (20 mL) and ethyl acetate (20 mL) was added. The organic layer was separated, washed with brine (50 mL×2), dried over anhydrous sodium sulfate, filtered, and concentrated in vacuo to give the crude product which was purified by prep-TLC (ethyl acetate) to give N-((1r,3r)-3-(3-chloro-4-cyanophenoxy)-2,2,4,4-tetramethylcyclobutyl)-6-(4-(5-(2-(6-cyano-2-methoxypyridin-3-yl)-1,3-dioxoisoindolin-5-yloxy)pentyl)piperazin-1-yl) nicotinamide (53 mg, 34%) as a yellow solid.

Step 4: Synthesis of 5-(5-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-1,3-dioxoisoindolin-2-yl)-6-hydroxypicolinamide

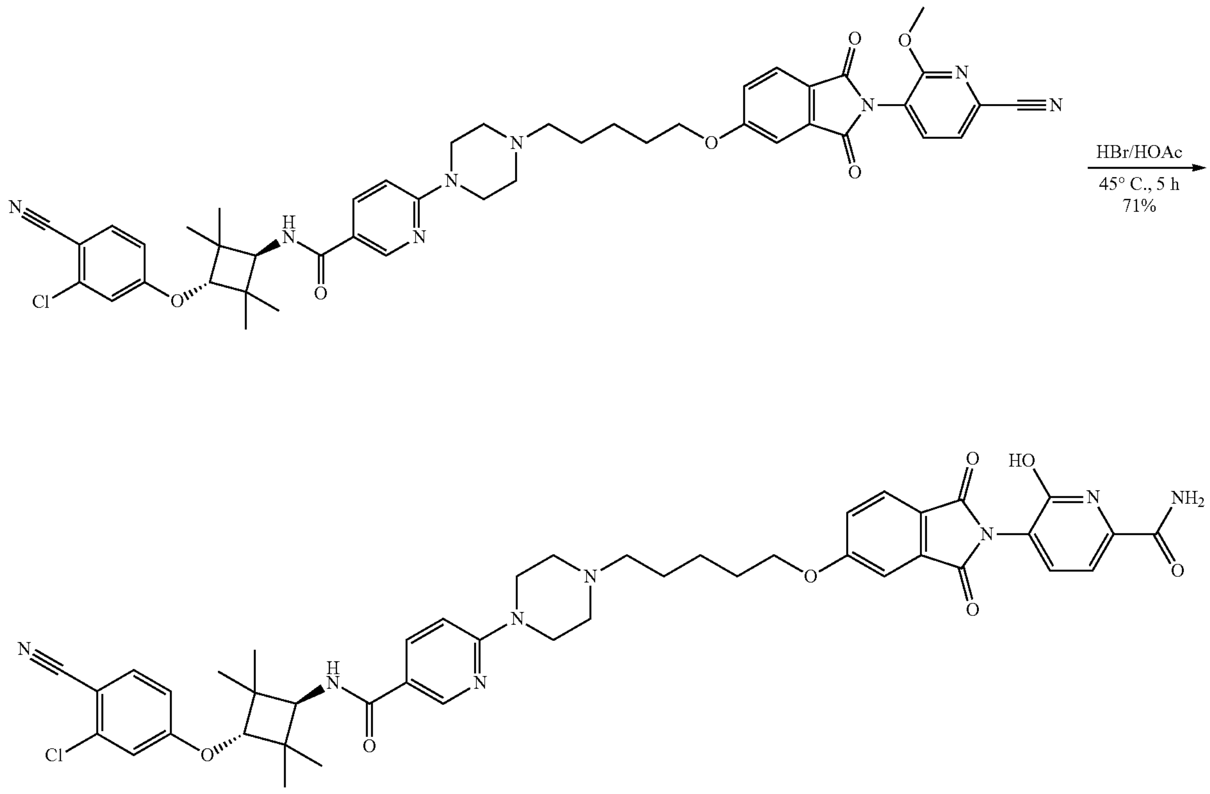

The mixture of N-((1r,3r)-3-(3-chloro-4-cyanophenoxy)-2,2,4,4-tetramethylcyclobutyl)-6-(4-(5-(2-(6-cyano-2-methoxypyridin-3-yl)-1,3-dioxoisoindolin-5-yloxy)pentyl)piperazin-1-yl)nicotinamide (70 mg, 0.084 mmol) in Hydrogen bromide/acetic acid glacial (w/w 48%, 0.5 mL) was stirred at 45° C. for 5 hours. The resulting mixture was allowed to cool down to room temperature. Water (20 mL) was added. The mixture was neutralized with saturated sodium bicarbonate until pH>7 and extracted with ethyl acetate (10 mL×2). The combined organic layers were washed with brine (10 mL×2), dried over anhydrous sodium sulfate, filtered, and concentrated in vacuo to give 5-(5-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-1,3-dioxoisoindolin-2-yl)-6-hydroxypicolinamide (50 mg, 71%) as a white solid.

Step 5: Synthesis of N-((1r,3r)-3-(3-chloro-4-cyanophenoxy)-2,2,4,4-tetramethylcyclobutyl)-6-(4-(5-(2-(6-cyano-2-hydroxypyridin-3-yl)-1,3-dioxoisoindolin-5-yloxy)pentyl)piperazin-1-yl)nicotinamide

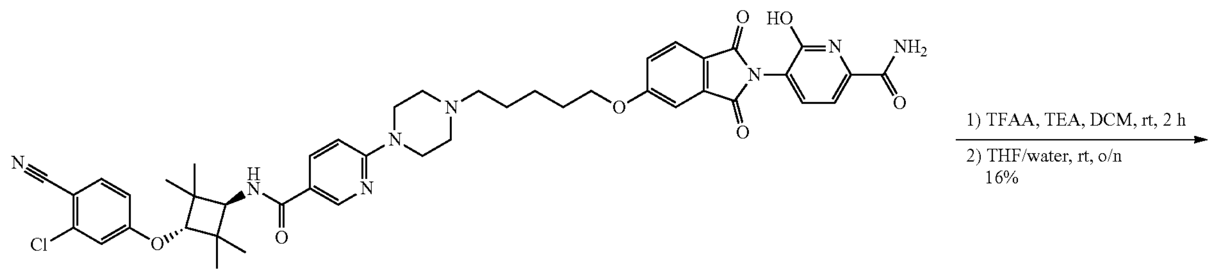

-continued

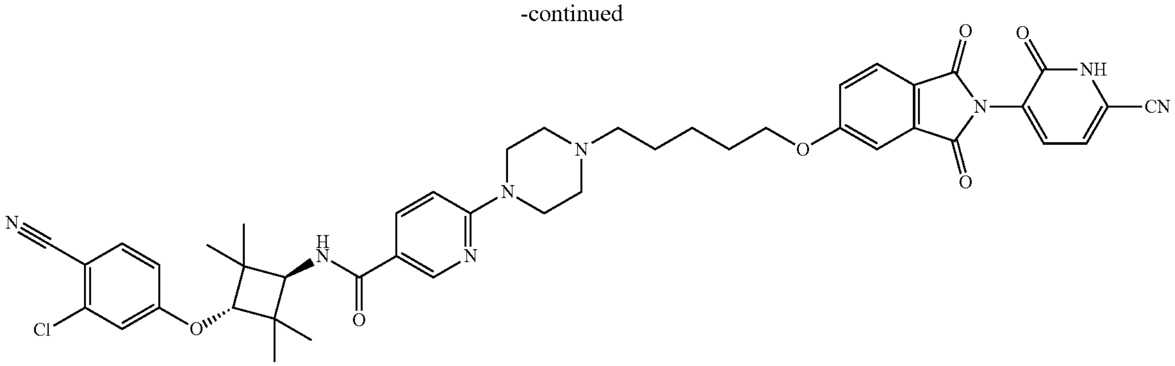

To a solution of 5-(5-(5-(4-(5-((1r,3r)-3-(3-chloro-4-cyanophenoxy)-2,2,4,4-tetramethylcyclobutylcarbamoyl)pyridin-2-yl)piperazin-1-yl)pentyloxy)-1,3-dioxoisoindolin-2-yl)-6-hydroxypicolinamide (45 mg, 0.053 mmol) and triethylamine (21.2 mg, 0.21 mmol) in dichloromethane (4 mL) was added trifluoroacetic anhydride (44.1 mg, 0.21 mmol). The mixture was stirred for 2 hour. The mixture was poured into ice-water (40 mL). Dichloromethane (40 mL) was added. The organic layer was separated, washed with brine (10 mL×2), dried over anhydrous sodium sulfate, filtered, and concentrated in vacuo. The residue was dissolved in tetrahydrofuran (5 mL) and water (5 mL) and stirred overnight. Ethyl acetate (10 mL) was added. The organic layer was separated, washed with brine (10 mL×2), dried over anhydrous sodium sulfate, filtered, and concentrated in vacuo to give crude product which was purified by prep-HPLC to give N-((1r,3r)-3-(3-chloro-4-cyanophenoxy)-2,2,4,4-tetramethylcyclobutyl)-6-(4-(5-(2-(6-cyano-2-hydroxypyridin-3-yl)-1,3-dioxoisoindolin-5-yloxy)pentyl)piperazin-1-yl)nicotinamide (6.8 mg, 16%) as a white solid.

LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.6 min, then under this condition for 1.4 min, finally changed to 95% [water+0.05% TFA] and 5% [$CH_3CN$+0.05% TFA] in 0.05 min and under this condition for 0.7 min). Purity is 99.5%, Rt=1.842 min; MS Calcd.: 816.3; MS Found: no mass responsed.

HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [$CH_3CN$+0.1% TFA] to 0% [water+0.1% TFA] and 100% [$CH_3CN$+0.1% TFA] in 10 min, then under this condition for 5 min, finally changed to 95% [water+0.1% TFA] and 5% [$CH_3CN$+0.1% TFA] in 0.1 min and under this condition for 5 min). Purity is 91.3%, Rt=8.215 min.

$^1H$ NMR (400 MHz, DMSO-$d^6$) δ 1.12 (6H, s), 1.22 (6H, s), 1.42-1.60 (4H, m), 1.77-1.82 (2H, m), 2.36-2.44 (2H, m), 3.30-3.35 (4H, m), 3.58-3.66 (4H, m), 4.06(1H, d, J=9.2 Hz), 4.21 (1H, t, J=6.2 Hz), 4.30 (1H, s), 6.88 (1H, d, J=8.8 Hz), 6.99-7.02 (1H, m), 7.21 (1H, d, J=2.4 Hz), 7.38-7.41 (1H, m), 7.48-7.52 (2H, m), 7.64 (1H, d, J=9.2 Hz), 7.89-7.98 (4H, m), 8.63 (1H, d, J=2.0 Hz).

Chemical Formula: $C_{44}H_{45}ClN_8O_6$; Molecular Weight: 817.33

Total H count from HNMR data: 45

Synthesis of Exemplary PROTAC 43

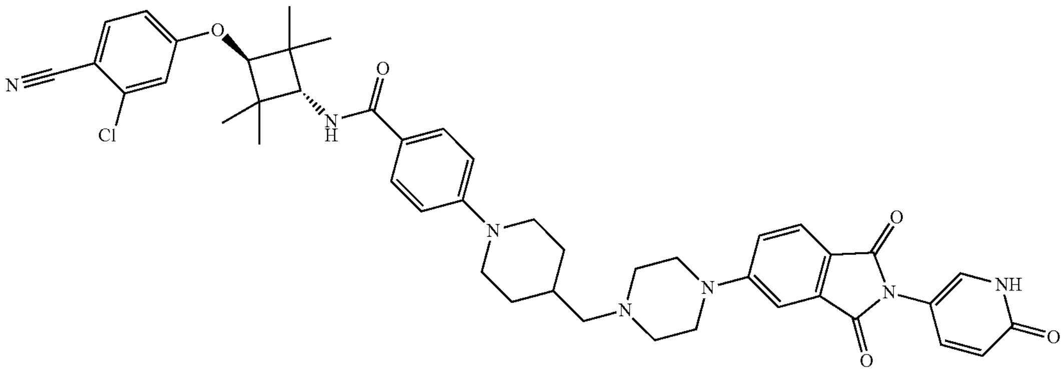 [SMILES: CC1(C)[C@H](NC(=O)c2ccc(N3CCC(CN4CCN(c5ccc6c(c5)C(=O)N(c5ccc(=O)[nH]c5)C6=O)CC4)CC3)cc2)C(C)(C)[C@H]1Oc1ccc(C#N)c(Cl)c1]

N-((1r,3 r)-3-(3-chloro-4-cyanophenoxy)-2,2,4,4-tetramethylcyclobutyl)-4-(4-((4-(1,3-dioxo-2-(6-oxo-1,6-dihydropyridin-3-yl)isoindolin-5-yl)piperazin-1-yl)methyl)piperidin-1-yl)benzamide
Synthetic Scheme
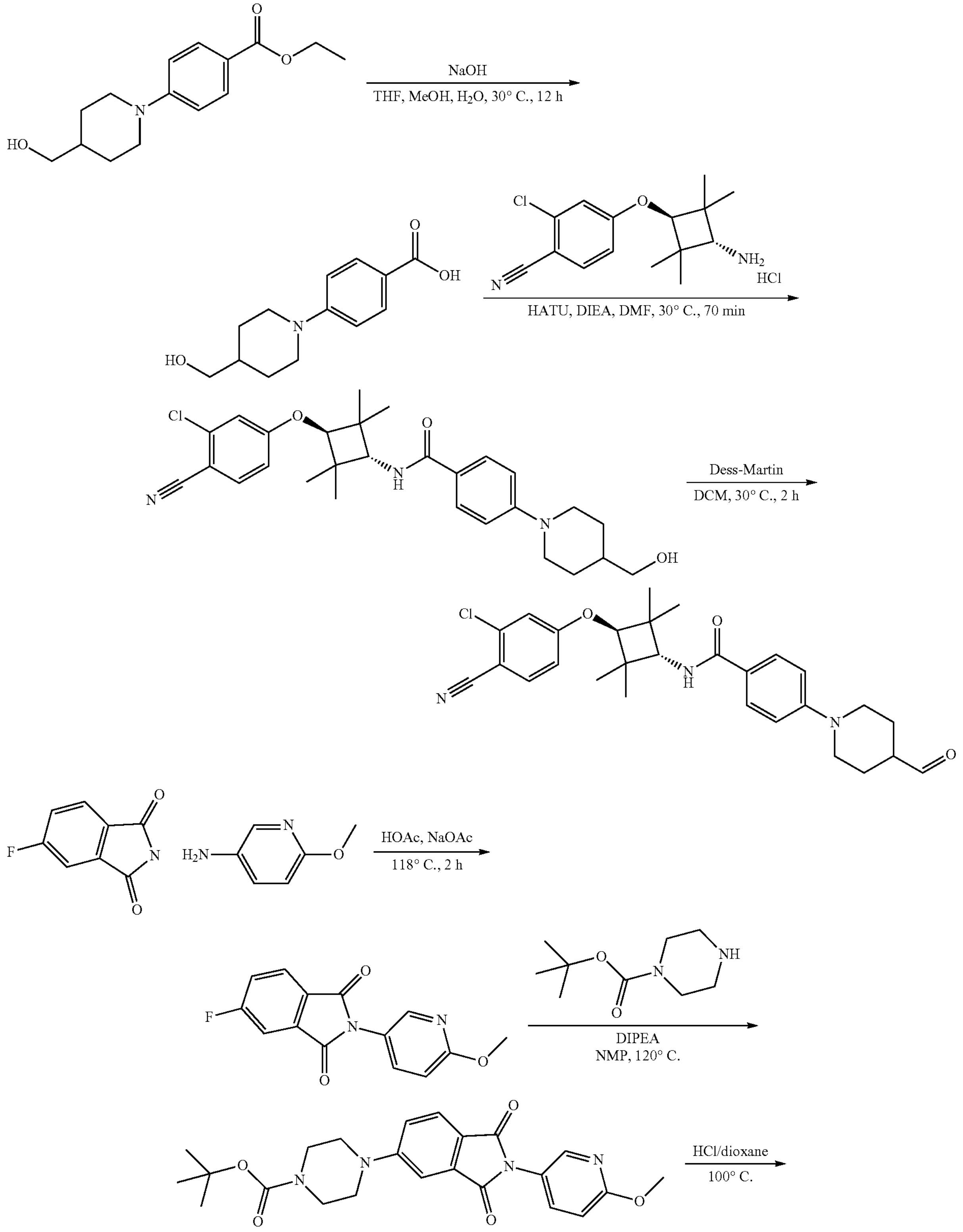

-continued

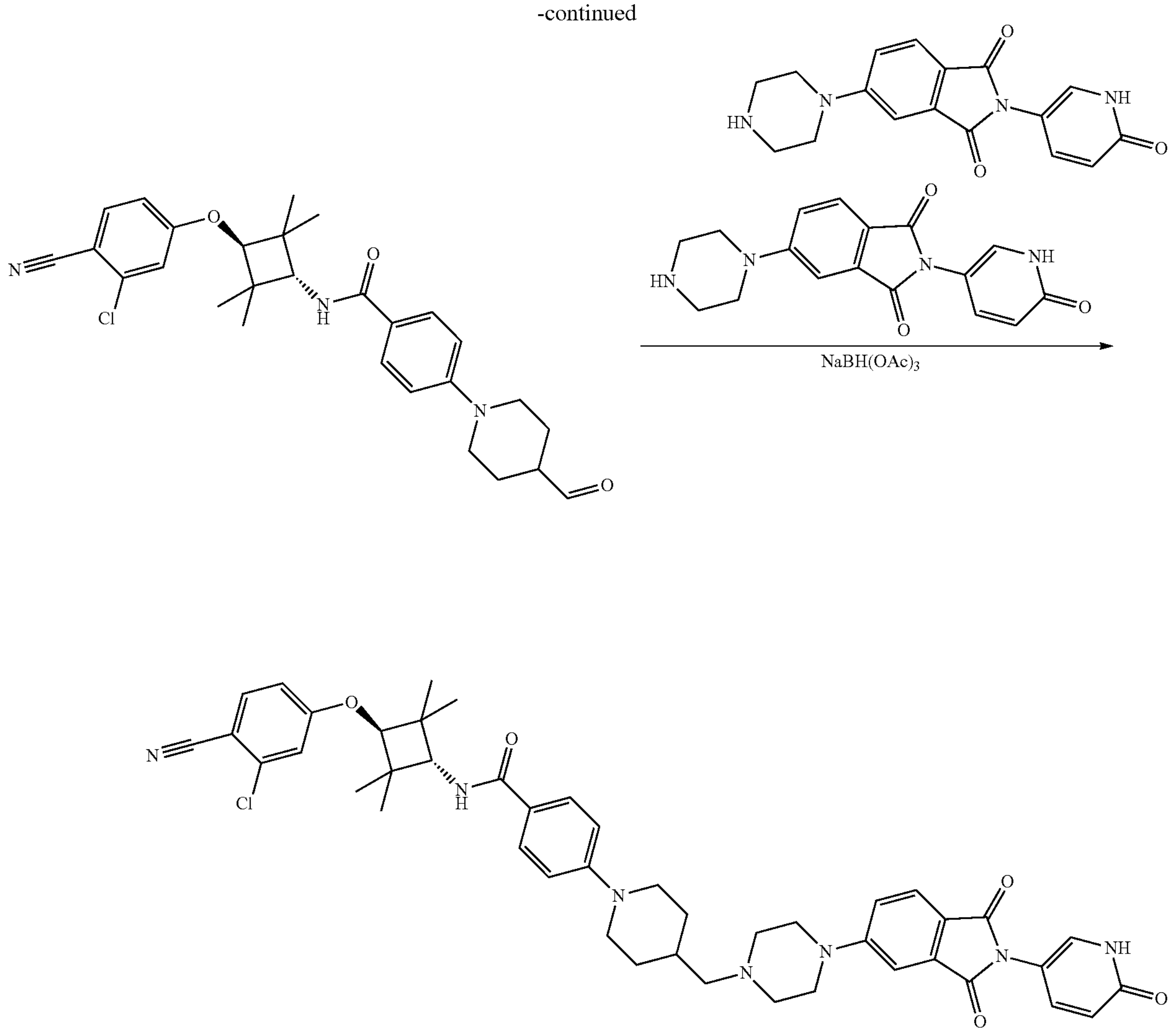

Step 1: Synthesis of 4-[4-(hydroxymethyl)-1-piperidyl]benzoic acid

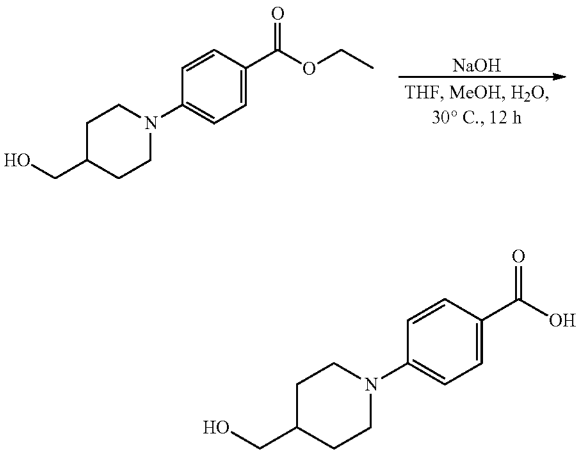

To a solution of ethyl 4-[4-(hydroxymethyl)-1-piperidyl] benzoate (52 g, 197.47 mmol, 1 eq) in tetrahydrofuran (250 mL), methanol (250 mL) and water (250 mL) was added sodium hydroxide (31.6 g, 0.79 mmol, 4 eq). The mixture was stirred at 30° C. for 12 hours. Thin layer chromatography (petroleum ether: ethyl acetate=1:1) showed the reaction was completed. The mixture was adjusted to pH 3-4 with hydrochloric acid (2 M) and filtered. The filter cake was dried in vacuum. The residue was triturated with ethyl acetate (500 mL) to give 4-[4-(hydroxymethyl)-1-piperidyl] benzoic acid (35 g, 148.76 mmol, 75% yield) as a white solid.

$^1$H NMR: (400 MHz, DMSO-$d_6$) δ: 12.19 (s, 1H), 7.74 (d, J=8.8 Hz, 2H), 6.93 (d, J=8.8 Hz, 2H), 4.48 (br t, J=5.2 Hz, 1H), 3.90 (d, J=12.8 Hz, 2H), 3.27 (br t, J=5.2 Hz, 2H), 2.86-2.72 (m, 2H), 1.72 (d, J=12.8 Hz, 2H), 1.66-1.51 (m, 1H), 1.17 (dq, J=4.0, 12.0 Hz, 2H)

Chemical Formula: $C_{13}H_{17}NO_3$, Molecular Weight: 235.28

Total H count from HNMR data: 17.

Step 2: Synthesis of N-[3-(3-chloro-4-cyano-phenoxy)-2,2,4,4-tetramethyl-cyclobutyl]-4-[4-(hydroxymethyl)-1-piperidyl]benzamide

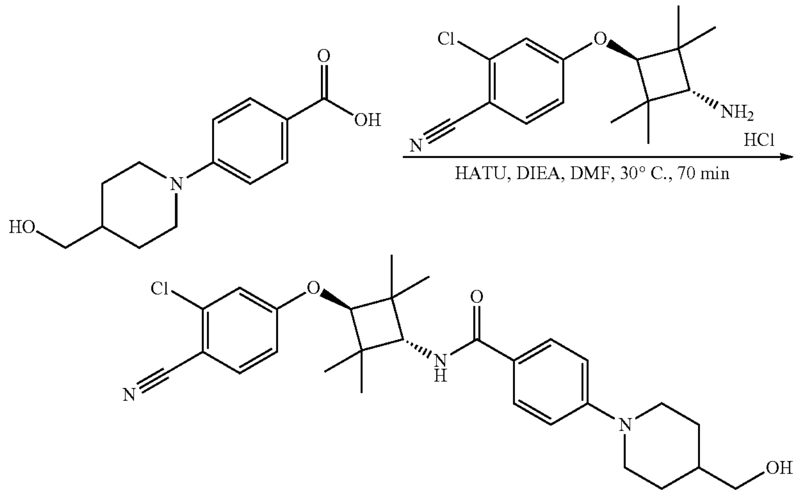

To a solution of 4-[4-(hydroxymethyl)-1-piperidyl]benzoic acid (38 g, 161.51 mmol, 1 eq) and 4-(3-amino-2,2,4,4-tetramethyl-cyclobutoxy)-2-chloro-benzonitrile (50.9 g, 161.51 mmol, 1 eq, hydrochloride) in dimethylformamide (800 mL) was added diisopropylethylamine (83.5 g, 646.04 mmol, 112 mL, 4 eq). The mixture was stirred at 30° C. for 10 min, and then o-(7-azabenzotriazol-1-yl)-n,n,n',n'-tetramethyluronium hexafluorophosphate (64.48 g, 169.59 mmol, 1.05 eq) was added. The mixture was stirred at 30° C. for 1 hour. LCMS showed the reaction was completed and desired MS can be detected. The mixture was poured into water (4 L) and filtered. The filter cake was concentrated and triturated with methanol (500 mL×2) to give N-[3-(3-chloro-4-cyano-phenoxy)-2,2,4,4-tetramethyl-cyclobutyl]-4-[4-(hydroxymethyl)-1-piperidyl]benzamide (72 g, 137.89 mmol, 85% yield, 95% purity) as a white solid.

LCMS: MS (ESI) m/z: 496.1 $[M+1]^+$ $^1$H NMR: (400 MHz, DMSO-$d_6$) δ: 7.90 (d, J=8.8 Hz, 1H), 7.73 (d, J=8.8 Hz, 2H), 7.48 (d, J=9.2 Hz, 1H), 7.20 (d, J=2.4 Hz, 1H), 7.00 (dd, J=2.4, 8.8 Hz, 1H), 6.95 (d, J=8.8 Hz, 2H), 4.48 (t, J=5.2 Hz, 1H), 4.31 (s, 1H), 4.05 (d, J=9.2 Hz, 1H), 3.86 (d, J=12.8 Hz, 2H), 3.27 (t, J=5.6 Hz, 2H), 2.80-2.70 (m, 2H), 1.73 (d, J=11.2 Hz, 2H), 1.63-1.52 (m, 1H), 1.27-1.15 (m, 8H), 1.12 (s, 6H)

Chemical Formula: $C_{28}H_{34}ClN_3O_3$, Molecular Weight: 496.04

Total H count from HNMR data: 34.

Step 3: Synthesis of N-[3-(3-chloro-4-cyano-phenoxy)-2,2,4,4-tetramethyl-cyclobutyl]-4-(4-formyl-1-piperidyl)benzamide

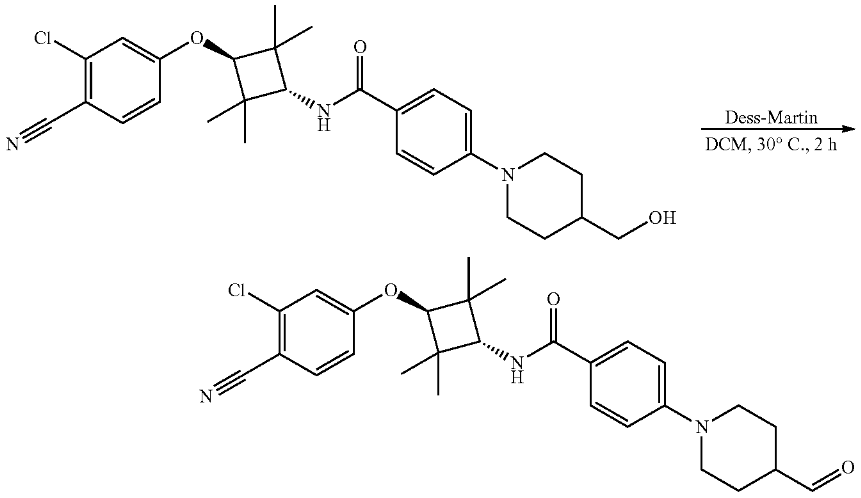

To a solution of N-[3-(3-chloro-4-cyano-phenoxy)-2,2,4,4-tetramethyl-cyclobutyl]-4-[4-(hydroxymethyl)-1-piperidyl]benzamide (65 g, 131.04 mmol, 1 eq) in dichloromethane (700 mL) was added Dess-Martin reagent (76.70 g, 180.83 mmol, 1.38 eq). The mixture was stirred at 30° C. for 2 hours. Thin layer chromatography (dichloromethane: methanol=1:1) showed the reaction was completed. The reaction was adjusted to pH 8-9 with saturated sodium bicarbonate. The mixture was diluted with water (3 L) and extracted with dichloromethane (1.5 L×3). The combined organic phase was washed with saturated brine (1.5 L×2), dried with anhydrous sodium sulfate, filtered and concentrated in vacuum. The residue was purified by silica gel chromatography (dichloromethane: methanol=100:0 to 50:1) to give N-[3-(3-chloro-4-cyano-phenoxy)-2,2,4,4-tetramethyl-cyclobutyl]-4-(4-formyl-1-piperidyl)benzamide (34.6 g, 67.94 mmol, 51% yield, 97% purity) as a white solid.

$^1$H NMR: (400 MHz, DMSO-$d_6$) δ: 9.63 (s, 1H), 7.90 (d, J=8.8 Hz, 1H), 7.74 (d, J=8.8 Hz, 2H), 7.49 (d, J=9.2 Hz, 1H), 7.20 (d, J=2.4 Hz, 1H), 7.03-6.94 (m, 3H), 4.32 (s, 1H), 4.05 (d, J=9.2 Hz, 1H), 3.76 (td, J=3.6, 12.8 Hz, 2H), 3.01-2.92 (m, 2H), 2.62-2.55 (m, 1H), 2.62-2.55 (m, 1H), 1.92 (dd, J=3.6, 12.8 Hz, 2H), 1.62-1.48 (m, 2H), 1.21 (s, 6H), 1.12 (s, 6H)

Chemical Formula: $C_{28}H_{32}ClN_3O_3$, Molecular Weight: 494.02

Total H count from HNMR data: 32.

Step 4: Synthesis of 5-fluoro-2-(6-methoxypyridin-3-yl)isoindoline-1,3-dione

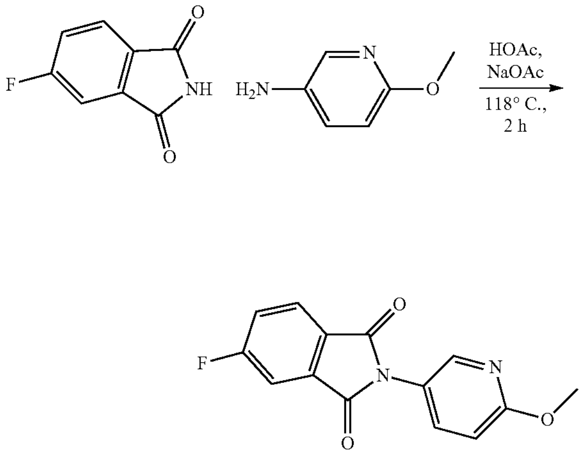

A mixture of 5-fluoro-1,3-dihydro-2-benzofuran-1,3-dione (100.0 mg, 602 μmol), 6-methoxypyridin-3-amine (82.1 mg, 662 μmol), sodium acetate (59.2 mg, 722 μmol), and acetic acid (499 μL, 8.74 mmol) was heated at 118° C. with stirring for 2 hours. The reaction was monitored by LCMS (CF-820-1), which showed a major peak with a mass consistent with the desired product. The reaction was cooled to 90° C. and quenched with water (2 mL). The mixture was allowed to cool to room temperature. The resulting precipitate was filtered and washed with water. The material was dried to give the desired product as a light purple solid, 5-fluoro-2-(6-methoxypyridin-3-yl)-2,3-dihydro-1H-isoindole-1,3-dione (149.1 mg, 547 μmol, 91.4% Yield).

$^1$H NMR (400 MHz, CHLOROFORM-d) δ 8.26 (dd, J=0.49, 2.64 Hz, 1H), 7.98 (dd, J=4.50, 8.22 Hz, 1H), 7.65 (d, J=2.54 Hz, 1H), 7.62-7.64 (m, 1H), 7.48 (dt, J=2.35, 8.51 Hz, 1H), 6.89 (dd, J=0.78, 8.80 Hz, 1H), 4.00 (s, 3H)

LCMS m/e+=273.16 $[M+H]^+$

Step 5: Synthesis of tert-butyl 4-(2-(6-methoxypyridin-3-yl)-1,3-dioxoisoindolin-5-yl)piperazine-1-carboxylate

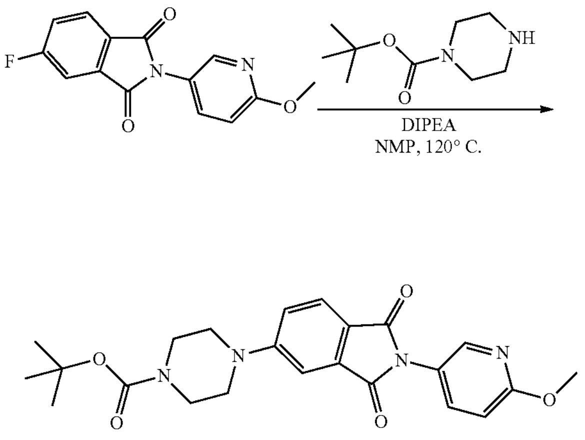

A solution of tert-butyl piperazine-1-carboxylate (34.0 mg, 183 μmol) and 5-fluoro-2-(6-methoxypyridin-3-yl)-2,3-dihydro-1H-isoindole-1,3-dione (50.0 mg, 183 μmol) in methylpyrrolidone (1.0 mL) was charged with N,N-diisopropylethylamine (95.5 μL, 549 μmol). The reaction mixture was heated at 120° C. for 2 hours. The reaction was monitored by LCMS, which showed a major peak with a mass consistent with the desired product and small peak with a mass consistent with the starting material. The reaction was allowed to stir at 120° C. for an additional 16 hours. LCMS showed a major peak with a mass consistent with the desired product. The reaction mixture was quenched with water (2 mL) and extracted with EtOAc (2 mL). The organic layer was washed with brine (1 mL), dried over Na2SO4, filtered, and concentrated under reduced pressure. The crude material was purified by silica gel chromatography on a Teledyne Combiflash ISCO eluting with DCM/MeOH (gradient 100:0 to 95:5). The fraction containing product was concentrated under reduced pressure to yield the desired product as a white solid, tert-butyl 4-[2-(6-methoxypyridin-3-yl)-1,3-dioxo-2,3-dihydro-1H-isoindol-5-yl]piperazine-1-carboxylate (39.6 mg, 90.3 μmol, 49.3% Yield).

LCMS m/e+=439.33 $[M+H]^+$ $^1$H NMR (400 MHz, CHLOROFORM-d) δ 8.25 (d, J=2.15 Hz, 1H), 7.79 (d, J=8.61 Hz, 1H), 7.64 (dd, J=2.74, 8.80 Hz, 1H), 7.35 (d, J=2.35 Hz, 1H), 7.11 (dd, J=2.45, 8.51 Hz, 1H), 6.87 (dd, J=0.59, 8.80 Hz, 1H), 3.98 (s, 3H), 3.60-3.66 (m, 4H), 3.42-3.48 (m, 4H), 1.50 (s, 9H)

Step 6: Synthesis of 2-(6-oxo-1,6-dihydropyridin-3-yl)-5-(piperazin-1-yl)isoindoline-1,3-dione

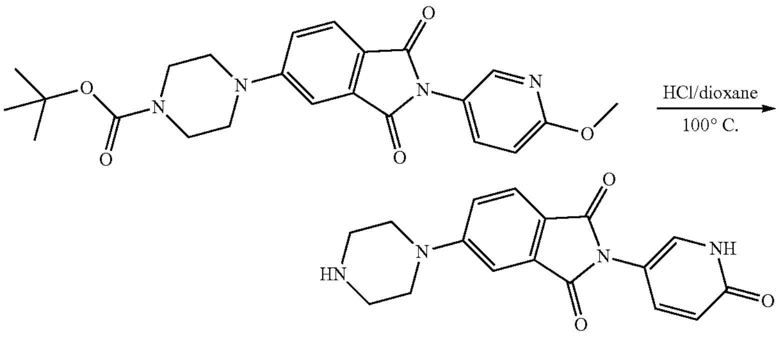

A solution of tert-butyl 4-[2-(6-methoxypyridin-3-yl)-1,3-dioxo-2,3-dihydro-1H-isoindol-5-yl]piperazine-1-carboxylate (39.6 mg, 90.3 μmol) in 4.0 M Hydrochloric acid in 1,4-dioxane (1.0 mL, 4.00 mmol) was stirred at 100° C. for 16 hours. The reaction mixture was concentrated under reduced pressure to yield a white solid, 2-(6-oxo-1,6-dihydropyridin-3-yl)-5-(piperazin-1-yl)-2,3-dihydro-1H-isoindole-1,3-dione hydrochloride (32.5 mg, 90.0 μmol, 100% Yield). The material was used in the next reaction without any further purification.

LCMS m/e+=425.22 $[M+H]^+$

Step 7: Synthesis of N-((1r,3r)-3-(3-chloro-4-cyanophenoxy)-2,2,4,4-tetramethylcyclobutyl)-4-(4-((4-(1,3-dioxo-2-(6-oxo-1,6-dihydropyridin-3-yl)isoindolin-5-yl)piperazin-1-yl)methyl)piperidin-1-yl)benzamide

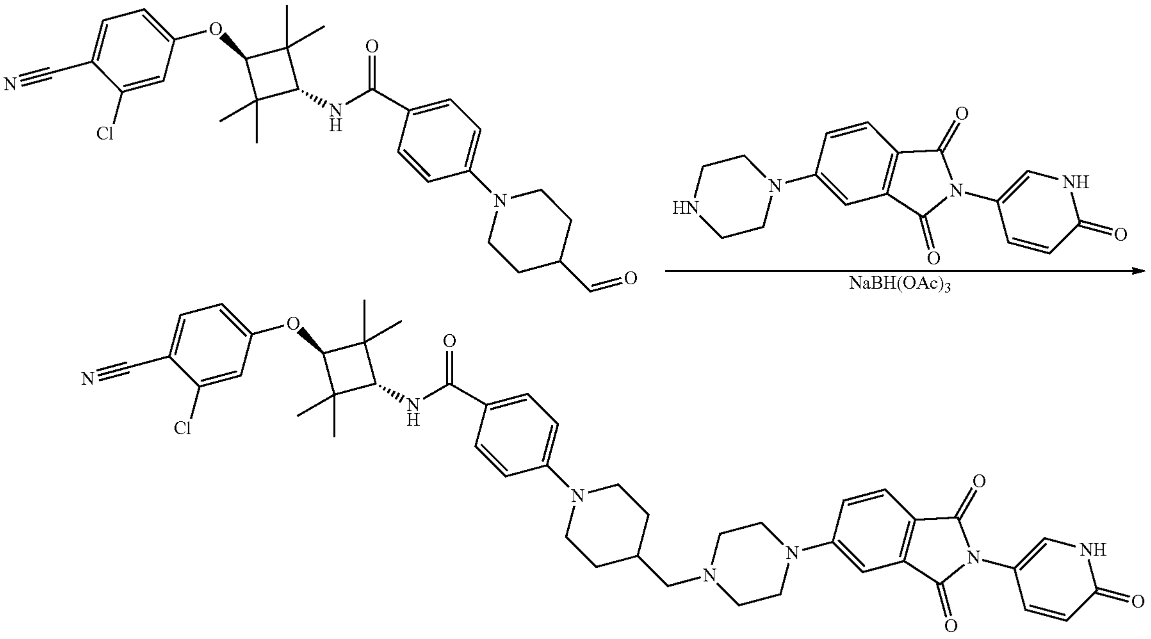

A solution of 4-(4-formylpiperidin-1-yl)-N-[(1r,3r)-3-(3-chloro-4-cyanophenoxy)-2,2,4,4-tetramethylcyclobutyl]benzamide (44.4 mg, 90.0 μmol) and 2-(6-oxo-1,6-dihydropyridin-3-yl)-5-(piperazin-1-yl)-2,3-dihydro-1H-isoindole-1,3-dione hydrochloride (32.5 mg, 90.0 μmol) in ethylene dichloride (1.0 mL) was charged with triethylamine (37.4 μL, 269 μmol) and sodium triacetoxyborohydride (57.0 mg, 269 μmol). The reaction mixture was allowed to stir at room temperature for 5 hours. The reaction mixture was monitored by LCMS, which showed a peak with a mass consistent with the desired product and peaks with masses consistent with the starting materials. The reaction mixture was allowed to stir at room temperature for an additional 16 hours. LMCS showed a major peak with a mass consistent with the desired product. The reaction mixture was quenched with aq. NaHCO3 (1 mL) and extracted with DCM (1 mL). The organic layer was dried over Na2SO4, filtered, and concentrated under reduced pressure. The crude material was purified by silica gel chromatography on a Teledyne Combiflash ISCO eluting with DCM/MeOH (gradient 100:0 to 90:10). The fractions containing product were combined and concentrated under reduced pressure to yield the desired product N-((1r,3r)-3-(3-chloro-4-cyanophenoxy)-2,2,4,4-tetramethylcyclobutyl)-4-(4-((4-(1,3-dioxo-2-(6-oxo-1,6-dihydropyridin-3-yl)isoindolin-5-yl)piperazin-1-yl)methyl)piperidin-1-yl)benzamide as a yellow solid.-mg, (30 mg, 37.3 μmol, 41.5% Yield).

$^1$H NMR (400 MHz, DMSO-$d_6$): δ 7.91 (d, J=8.80 Hz, 1H), 7.72 (t, J=8.41 Hz, 3H), 7.56 (d, J=2.54 Hz, 1H), 7.44-7.53 (m, 2H), 7.38 (d, J=1.96 Hz, 1H), 7.28 (dd, J=2.05, 8.71 Hz, 1H), 7.21 (d, J=2.35 Hz, 1H), 7.00 (dd, J=2.35, 8.80 Hz, 1H), 6.96 (d, J=9.00 Hz, 2H), 6.41 (d, J=9.78 Hz, 1H), 4.32 (s, 1H), 4.05 (d, J=9.00 Hz, 1H), 3.86 (d, J=12.52 Hz, 2H), 3.45 (br. s., 4H), 2.79 (t, J=11.74 Hz, 2H), 2.21 (d, J=6.46 Hz, 2H), 1.81 (d, J=11.15 Hz, 3H), 1.21 (s, 6H), 1.12 (s, 6H)

LCMS m/e+=802.57 [M+

Synthesis of Exemplary PROTAC 46

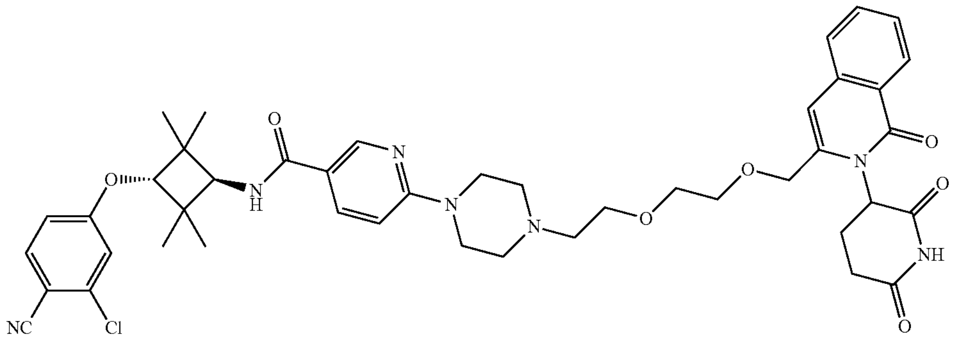 [SMILES: CC1(C)[C@H](NC(=O)c2ccc(N3CCN(CCOCCOCc4cc5ccccc5c(=O)n4C4CCC(=O)NC4=O)CC3)nc2)C(C)(C)[C@H]1Oc1ccc(C#N)c(Cl)c1]

N-((1r,3 r)-3-(3-chloro-4-cyanophenoxy)-2,2,4,4-tetramethylcyclobutyl)-6-(4-(2-(2-((2-(2,6-dioxopiperidin-3-yl)-1-oxo-1,2-dihydroisoquinolin-3-yl)methoxy)ethoxy)ethyl)piperazin-1-yl)nicotinamide Synthetic Scheme:

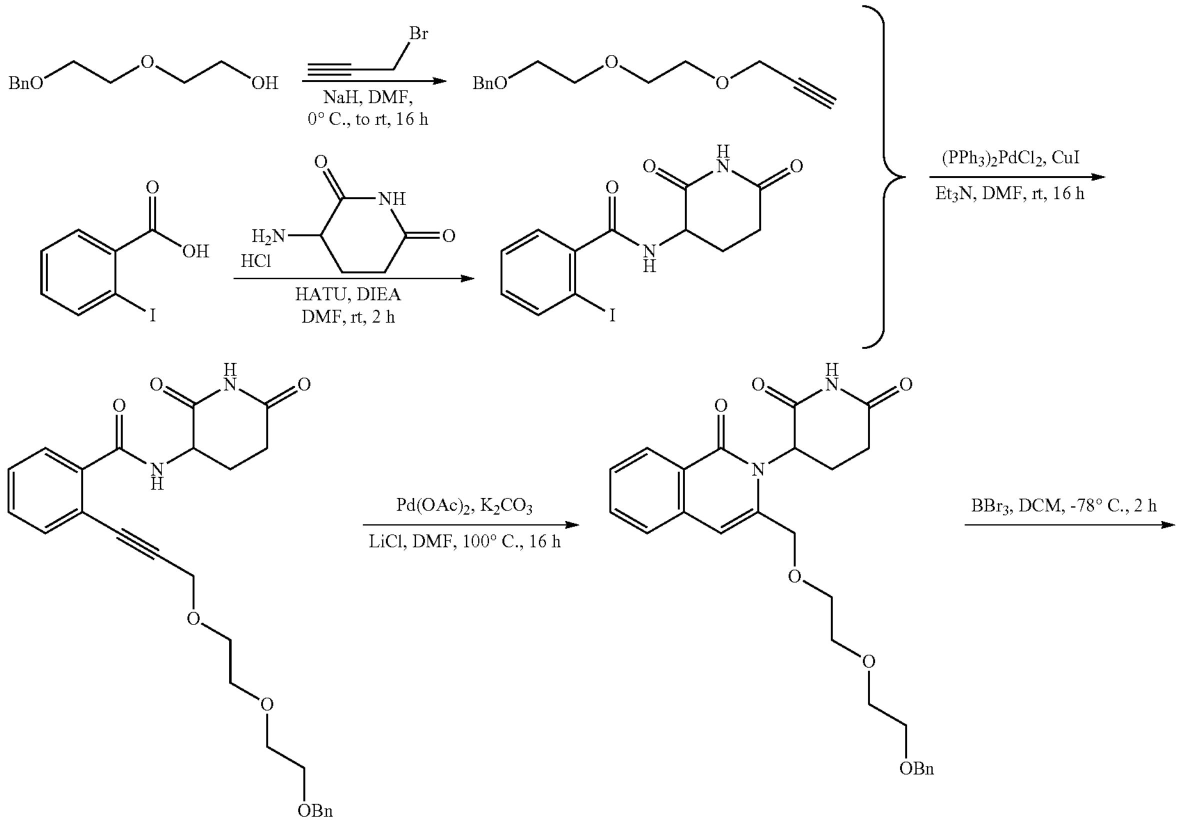

-continued

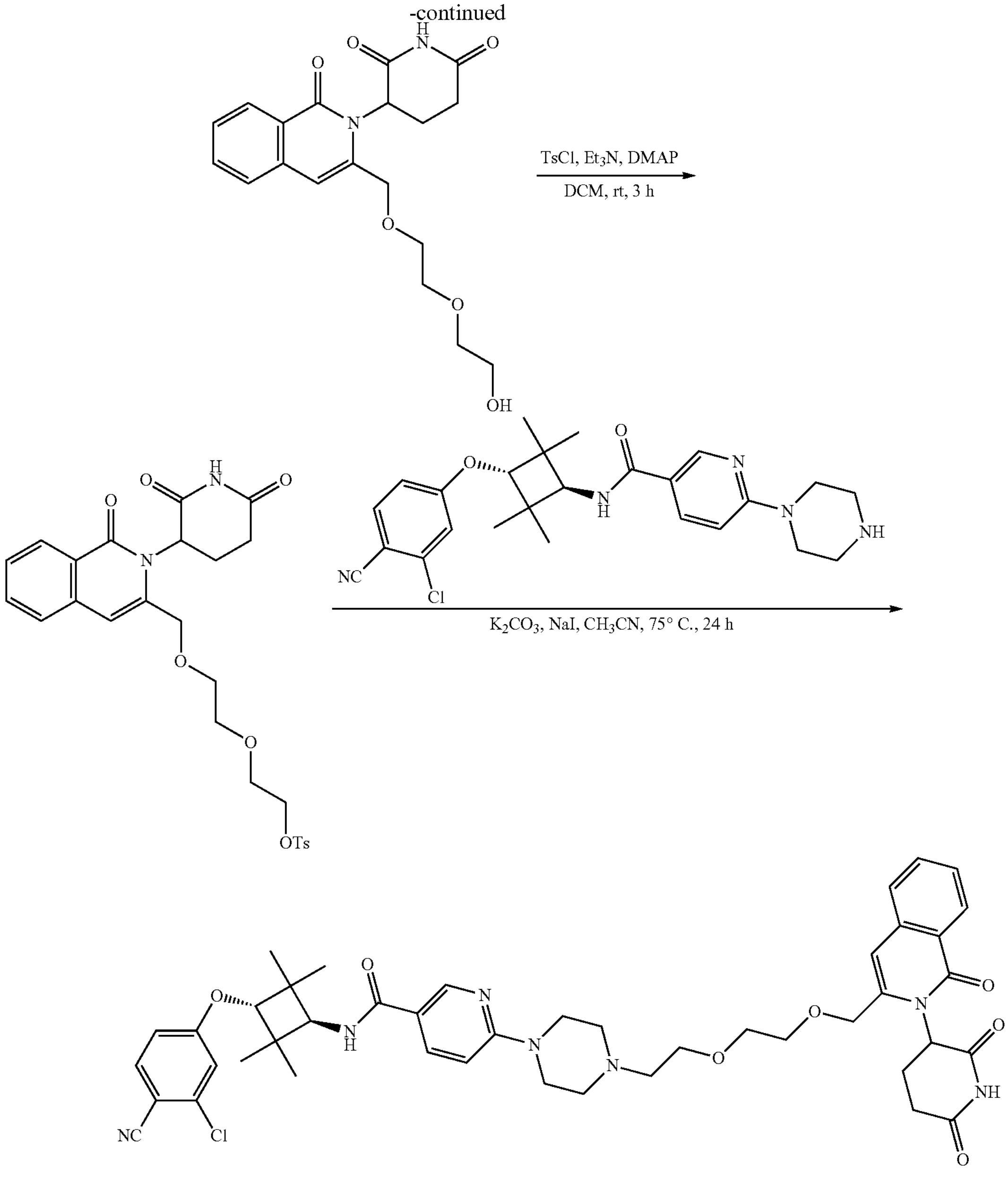

Step 1: Synthesis of N-(2,6-dioxopiperidin-3-yl)-2-iodobenzamide

Into a 100-mL round-bottom flask, was placed 2-iodobenzoic acid (5.0 g, 20.16 mmol, 1.00 equiv), N,N-dimethylformamide (40 mL), HATU (7.66 g, 20.15 mmol, 1.00 equiv), DIEA (7.80 g, 60.35 mmol, 3.00 equiv), after stirred 10 minutes, 3-aminopiperidine-2,6-dione (3.30 g, 25.76 mmol, 1.00 equiv) was added. The resulting solution was stirred for 2 hours at room temperature. The reaction was then quenched by the addition of 500 mL of water/ice. The solids were collected by filtration. The resulting mixture was concentrated under vacuum. This resulted in 6.48 g (90%) of N-(2,6-dioxopiperidin-3-yl)-2-iodobenzamide as a off-white solid.

LC-MS ($ES^+$): m/z 358.85 [$MH^+$], $t_R$=0.56 min, (1.90 minute run).

Step 2: Synthesis of ([2-[2-(prop-2-yn-1-yloxy) ethoxy]ethoxy]methyl)benzene

Into a 250-mL 3-necked round-bottom flask purged and maintained with an inert atmosphere of nitrogen, was placed 2-[2-(benzyloxy)ethoxy]ethan-1-ol (10.0 g, 50.96 mmol, 1.00 equiv), N,N-dimethylformamide (100 mL). This was followed by the addition of sodium hydride (2.4 g, 100.00 mmol, 1.20 equiv) in several batches at 0° C., after stirred 30 minutes. To this was added a solution of 3-bromoprop-1-yne (7.285 g, 61.24 mmol, 1.20 equiv) in N,N-dimethylformamide (30 mL) dropwise with stirring at 0° C. The resulting solution was stirred overnight at room temperature. The reaction was then quenched by the addition of 300 mL of water/ice. The resulting solution was extracted with ethyl acetate (300 mL) and the organic layers combined. The resulting mixture was washed with brine (300 mL). The mixture was dried over anhydrous sodium sulfate. The residue was applied onto a silica gel column with ethyl acetate/petroleum ether (1/4). This resulted in 9.5 g (80%) of ([2-[2-(prop-2-yn-1-yloxy)ethoxy]ethoxy]methyl)benzene as light yellow oil.

LC-MS ($ES^+$): m/z 234.95 [$MH^+$], $t_R$=1.15 min, (2.00 minute run).

Step 3: Synthesis of 2-(3-(2-(2-(benzyloxy)ethoxy)ethoxy)prop-1-ynyl)-N-(2,6-dioxopiperidin-3-yl)benzamide Into a 25-mL round-bottom flask purged and maintained with an inert atmosphere of nitrogen, was placed N-(2,6-dioxopiperidin-3-yl)-2-iodobenzamide (1.5 g, 4.1 mmol, 1.00 equiv), N,N-dimethylformamide (20 mL), $(PPh_3)_2PdCl_2$ (293 mg, 0.41 mmol, 0.1 equiv), CuI (79 mg, 0.41 mmol, 0.1 equiv), triethylamine (1.69 g, 16 mmol, 4.00 equiv), (2-[2-(prop-2-yn-1-yloxy)ethoxy]ethoxymethyl)benzene (1.17 g, 5.0 mmol, 1.20 equiv). The resulting solution was stirred overnight at room temperature. The resulting solution was extracted with ethyl acetate (300 mL) and the organic layers combined. The resulting mixture was washed with brine (300 mL). The mixture was dried over anhydrous sodium sulfate. The residue was applied onto a silica gel column with ethyl acetate/petroleum ether (7/3). This resulted in 1.74 g of 2-(3-(2-(2-(benzyloxy)ethoxy)ethoxy)prop-1-ynyl)-N-(2,6-dioxopiperidin-3-yl)benzamide as light yellow oil.

LC-MS ($ES^+$): m/z 465.10 [$MH^+$], $t_R$=0.79 min, (1.90 minute run).

Step 4: Synthesis of 3-[3-([2-[2-(benzyloxy)ethoxy]ethoxy]methyl)-1-oxo-1,2-dihydroisoquinolin-2-yl]piperidine-2,6-dione Into a 25-mL round-bottom flask purged and maintained with an inert atmosphere of nitrogen, was placed a solution of 2-(3-[2-[2-(benzyloxy)ethoxy]ethoxy]prop-1-yn-1-yl)-N-(2,6-dioxopiperidin-3-yl)benzamide (1.0 g, 2.15 mmol, 1.00 equiv) in N,N-dimethylformamide (10 mL), $Pd(OAc)_2$ (24.0 mg, 0.11 mmol, 0.05 equiv), LiCl (90.0 mg, 2.14 mmol, 1.00 equiv), potassium carbonate (594.0 mg, 4.30 mmol, 2.00 equiv). The resulting solution was stirred overnight at 100° C. in an oil bath. The solids were filtered out. The residue was applied onto a silica gel column with ethyl acetate/petroleum ether (7/3). This resulted in 465.0 mg (47%) of 3-[3-([2-[2-(benzyloxy)ethoxy]ethoxy]methyl)-1-oxo-1,2-dihydroisoquinolin-2-yl]piperidine-2,6-dione as light yellow oil.

LC-MS ($ES^+$): m/z 465.10 [$MH^+$], $t_R$=0.74 min, (1.90 minute run).

Step 5: Synthesis of 3-(3-[[2-(2-hydroxyethoxy)ethoxy]methyl]-1-oxo-1,2-dihydroisoquinolin-2-yl)piperidine-2,6-dione Into a 100-mL 3-necked round-bottom flask purged and maintained with an inert atmosphere of nitrogen, was placed 3-[3-([2-[2-(benzyloxy)ethoxy]ethoxy]methyl)-1-oxo-1,2-dihydroisoquinolin-2-yl]piperidine-2,6-dione (420.0 mg, 0.90 mmol, 1.00 equiv), dichloromethane (10 mL). This was followed by the addition of $BBr_3$ (1M in DCM) (3.61 mL, 4.00 equiv) dropwise with stirring at −78° C. The resulting solution was stirred for 1 hat −78° C. in a liquid nitrogen bath. The reaction was then quenched by the addition of 20 mL of sodium bicarbonate at −78° C. The resulting solution was extracted with dichloromethane (100 mL) and the organic layers combined and dried over anhydrous sodium sulfate. The residue was applied onto a silica gel column with dichloromethane/methanol (10/1). This resulted in 212.0 mg (63%) of 3-(3-[[2-(2-hydroxyethoxy)ethoxy]methyl]-1-oxo-1,2-dihydroisoquinolin-2-yl)piperidine-2,6-dione as light yellow oil.

LC-MS ($ES^+$): m/z 374.95 [$MH^+$], $t_R$=0.41 min, (1.90 minute run).

Step 6: Synthesis of 2-(2-[[2-(2,6-dioxopiperidin-3-yl)-1-oxo-1,2-dihydroisoquinolin-3-yl]methoxy]ethoxy)ethyl 4-methylbenzene-1-sulfonate Into a 50-mL round-bottom flask, was placed 3-(3-[[2-(2-hydroxyethoxy)ethoxy]methyl]-1-oxo-1,2-dihydroisoquinolin-2-yl)piperidine-2,6-dione (212.0 mg, 0.57 mmol, 1.00 equiv), dichloromethane (10.0 mL), TsCl (215.4 mg, 1.13 mmol, 2.00 equiv), triethylamine (171.0 mg, 1.69 mmol, 3.00 equiv), 4-dimethylaminopyridine (6.98 mg, 0.06 mmol, 0.10 equiv). The resulting solution was stirred for 3 hours at room temperature. The resulting solution was extracted with dichloromethane (100 mL) and the organic layers combined. The resulting mixture was washed with brine (100 mL). The mixture was dried over anhydrous sodium sulfate. The residue was applied onto a silica gel column with ethyl acetate/petroleum ether (4/1). This resulted in 238.0 mg (80%) of 2-(2-[[2-(2,6-dioxopiperidin yl)-1-oxo-1,2-dihydroisoquinolin-3-yl]methoxy]ethoxy)ethyl 4-methylbenzene-1-sulfonate as light yellow oil.

LC-MS ($ES^+$): m/z 529.10 [$MH^+$], $t_R$=0.76 min, (1.90 minute run).

Step 7: Synthesis of 6-[4-[2-(2-[[2-(2,6-dioxopiperidin-3-yl)-1-oxo-1,2-dihydroisoquinolin-3-yl]methoxy]ethoxy)ethyl]piperazin-1-yl]-N-[(1r,3r)-3-(3-chloro-4-cyanophenoxy)-2,2,4,4-tetramethylcyclobutyl]pyridine-3-carboxamide Into a 20-mL microwave tube purged and maintained with an inert atmosphere of nitrogen, was placed 6-(piperazin-1-yl)-N-[(1r,3r)-3-(3-chloro-4-cyanophenoxy)-2,2,4,4-tetramethylcyclobutyl]pyridine-3-carboxamide (65.0 mg, 0.14 mmol, 1.00 equiv), acetonitrile (5.0 mL), potassium carbonate (71.3 mg, 0.52 mmol, 4.00 equiv), 2-(2-[[2-(2,6-dioxopiperidin-3-yl)-1-oxo-1,2-dihydroisoquinolin-3-yl]methoxy]ethoxy)ethyl 4-methylbenzene-1-sulfonate (68.0 mg, 0.13 mmol, 1.00 equiv), NaI (19.38 mg, 0.13 mmol, 1.00 equiv). The resulting solution was stirred for 24 hours at 75° C. in an oil bath. The solids were filtered out. The resulting mixture was concentrated under vacuum. Then purified by Prep-HPLC-Column:)(Bridge Shield RP18 OBD Column, 5 um, 19*150 mm; Mobile Phase A:water (10 mmol/L $NH_4HCO_3$), Mobile Phase B: acetonitrile; Flow rate: 20 mL/min; Gradient: 61% B to 70% B in 8 min; 254 nm; Rt: 6.7 min This resulted in 50.0 mg (47%) of 6-[4-[2-(2-[[2-(2,6-dioxopiperidin-3-yl)-1-oxo-1,2-dihydroisoquinolin-3-yl]methoxy]ethoxy)ethyl]piperazin-1-yl]-N-[(1r,3r)-3-(3-chloro-4-cyanophenoxy)-2,2,4,4-tetramethylcyclobutyl]pyridine-3-carboxamide as a white solid.

$^1$H NMR (400 MHz, $CDCl_3$): δ 8.81 (s, 1H), 8.58-8.57 (d, J=2.4 Hz, 1H), 8.23-8.21 (d, J=7.6 Hz, 1H), 7.92-7.89 (m, 1H), 7.57-7.48 (m, 2H), 7.38-7.34 (m, 1H), 7.26-7.21 (m, 1H), 6.97-6.96 (d, J=2.0 Hz, 1H), 6.81-6.78 (m, 1H), 6.61-6.59 (d, J=9.2 Hz, 1H), 6.25 (s, 1H), 6.11-6.09 (d, J=8.0 Hz, 1H), 4.82-4.79 (m, 1H), 4.32-4.29 (m, 2H), 4.26-4.23 (m, 1H), 4.15-4.13 (m, 1H), 4.04 (s, 1H), 3.76-3.67 (m, 10H), 2.95-2.90 (m, 1H), 2.70-2.62 (m, 7H), 2.23-2.19 (m, 2H), 1.25 (s, 6H), 1.21 (s, 6H);

LC-MS ($ES^+$): m/z 824.75/826.75 [$MH^+$], $t_R$=2.43 min, (4.80 minute run).

Chemical formula: $C_{44}H_{50}ClN_7O_7$ [823.35/825.35]

Total H count from HNMR data: 50

Synthesis of Exemplary PROTAC 47
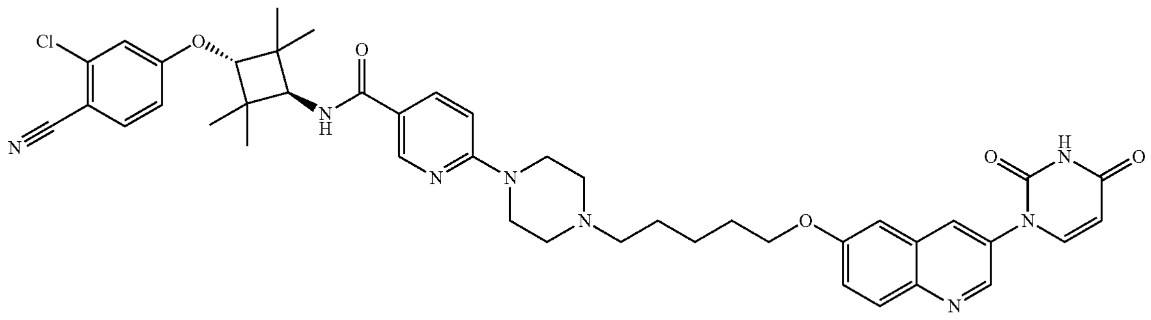 [SMILES: CC1(C)[C@H](NC(=O)c2ccc(N3CCN(CCCCCOc4ccc5ncc(-n6ccc(=O)[nH]c6=O)cc5c4)CC3)nc2)C(C)(C)[C@H]1Oc1ccc(C#N)c(Cl)c1]
N-((1r,3r)-3-(3-chloro-4-cyanophenoxy)-2,2,4,4-tetramethylcyclobutyl)-6-(4-(5-((3-(2,4-dioxo-3,4-dihydropyrimidin-1(2H)-yl)quinolin-6-yl)oxy)pentyl)piperazin-1-yl)nicotinamide
Synthetic Scheme
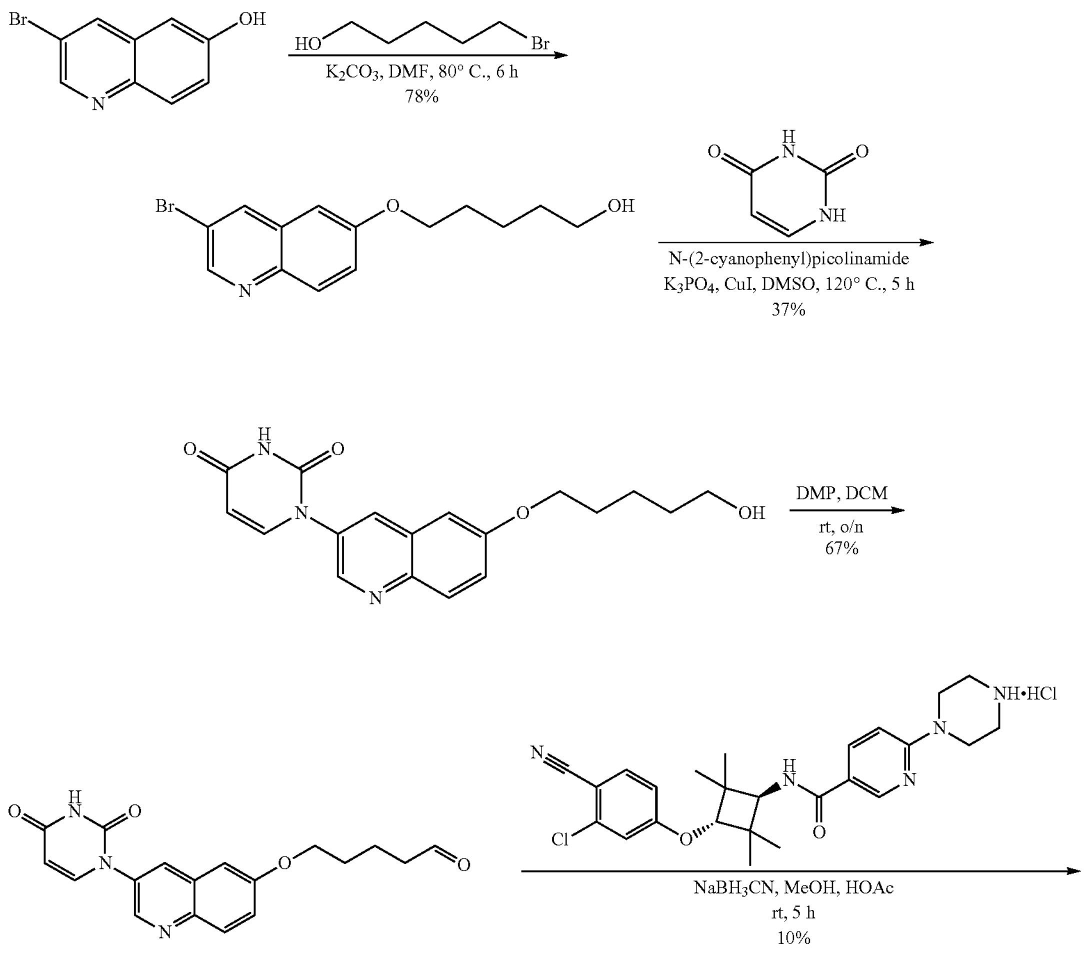

-continued

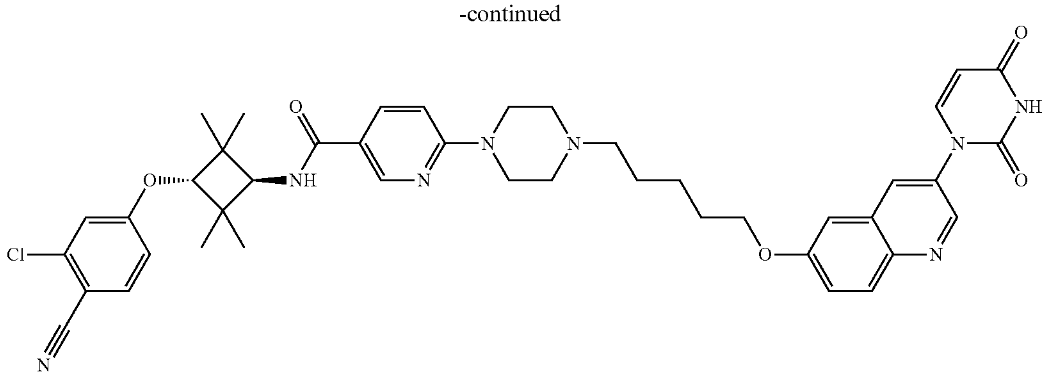

Step 1: Synthesis of methyl 5-(3-bromoquinolin-6-yloxy)pentan-1-ol

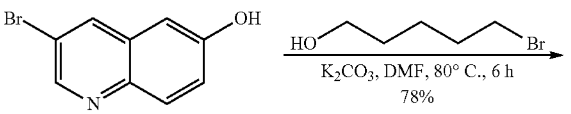

-continued

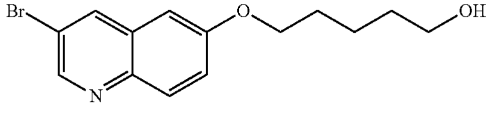

A mixture of 3-bromoquinolin-6-ol (700 mg, 3.1 mmol), 5-bromopentan-1-ol (518 mg, 3.1 mmol) and potassium carbonate (856 mg, 6.2 mmol) in N,N-dimethylformamide (5 mL) was heated at 80° C. for 6 hours. The reaction mixture was cooled to room temperature. Water (10 mL) was added and extracted with ethyl acetate (20 mL×3). The combined organic layers were washed with water (20 mL×2) and brine (20 mL), dried over anhydrous sodium sulfate. The solvent was concentrated to give the residue, which was purified by column chromatography on silica gel (petroleum ether/ethyl acetate=1/1) to give 5-(3-bromoquinolin-6-yloxy)pentan-1-ol (750 mg, 78% yield) as a yellow solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity is 91.43%, Rt=1.767 min; MS Calcd.: 309.04; MS Found: 310.0 $[M+H]^+$.

Step 2: Synthesis of 1-(6-(5-hydroxypentyloxy)quinolin-3-yl)pyrimidine-2,4(1H,3H)-dione

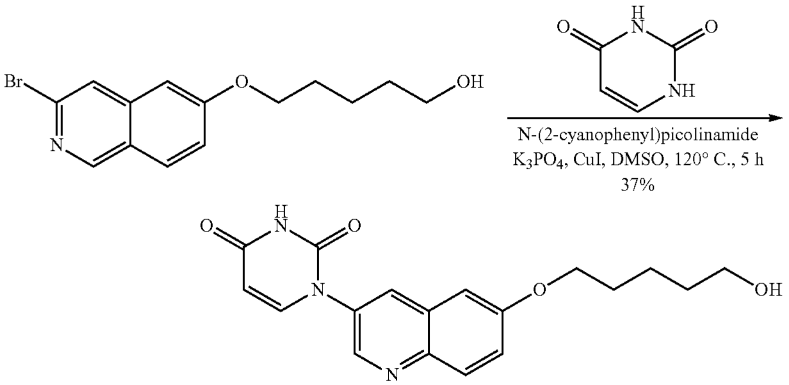

A solution of 5-(3-bromoquinolin-6-yloxy)pentan-1-ol (496 mg, 1.6 mmol), pyrimidine-2,4(1H,3H)-dione (538 mg, 4.8 mmol), potassium phosphate (1.0 g, 4.8 mmol), cuprous iodide (304 mg, 1.6 mmol), N-(2-cyanophenyl)picolinamide (357 mg, 1.6 mmol) in dimethyl sulfoxide (10 mL) was heated at 120° C. for 5 hours under argon atmosphere. The reaction mixture was cooled to room temperature. Water (10 mL) was added, extracted with ethyl acetate (20 mL×2). Combined organic layers were washed with brine (10 mL×2), dried over anhydrous sodium sulfate. The solvent was removed and the residue was purified by column chromatography on silica gel (methanol/dichloromethane=1/20) to give 1-(6-(5-hydroxypentyloxy)quinolin-3-yl)pyrimidine-2,4(1H,3H)-dione (200 mg, 37% yield) as an off-white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.325 min; MS Calcd.: 341.14; MS Found: 342.2 [M+H]$^+$.

Step 3: Synthesis of 5-(3-(2,4-dioxo-3,4-dihydropyrimidin-1(2H)-yl)quinolin-6-yloxy)pentanal

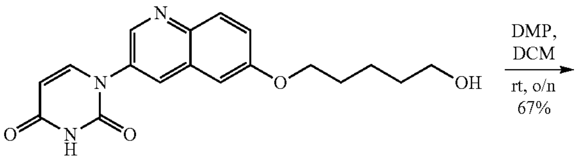

-continued

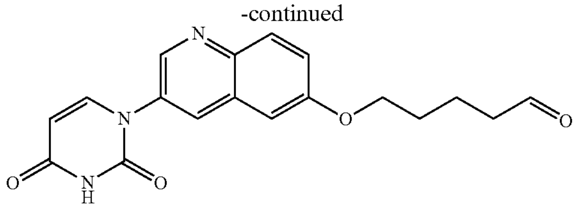

A mixture of 1-(6-(5-hydroxypentyloxy)quinolin-3-yl)pyrimidine-2,4(1H,3H)-dione (150 mg, 0.4 mmol) and Dess-Martin periodinane (559 mg, 1.3 mmol) in dichloromethane (15 mL) was stirred at room temperature overnight. The reaction mixture was filtered and the filtered cake was washed with dichloromethane (10 mL×2). The filtrate was concentrated and the residue was purified by Prep-TLC (dichloromethane/methanol=5/1) to give 5-(3-(2,4-dioxo-3,4-dihydropyrimidin-1(2H)-yl)quinolin-6-yloxy)pentanal (100 mg, 67% yield) as a yellow solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.396 min; MS Calcd.: 339.12; MS Found: 340.2 [M+H]$^+$.

Step 4: Synthesis of N-((1r,3r)-3-(3-chloro-4-cyanophenoxy)-2,2,4,4-tetramethylcyclobutyl)-6-(4-(5-(3-(2,4-dioxo-3,4-dihydropyrimidin-1(2H)-yl)quinolin-6-yloxy)pentyl)piperazin-1-yl)nicotinamide

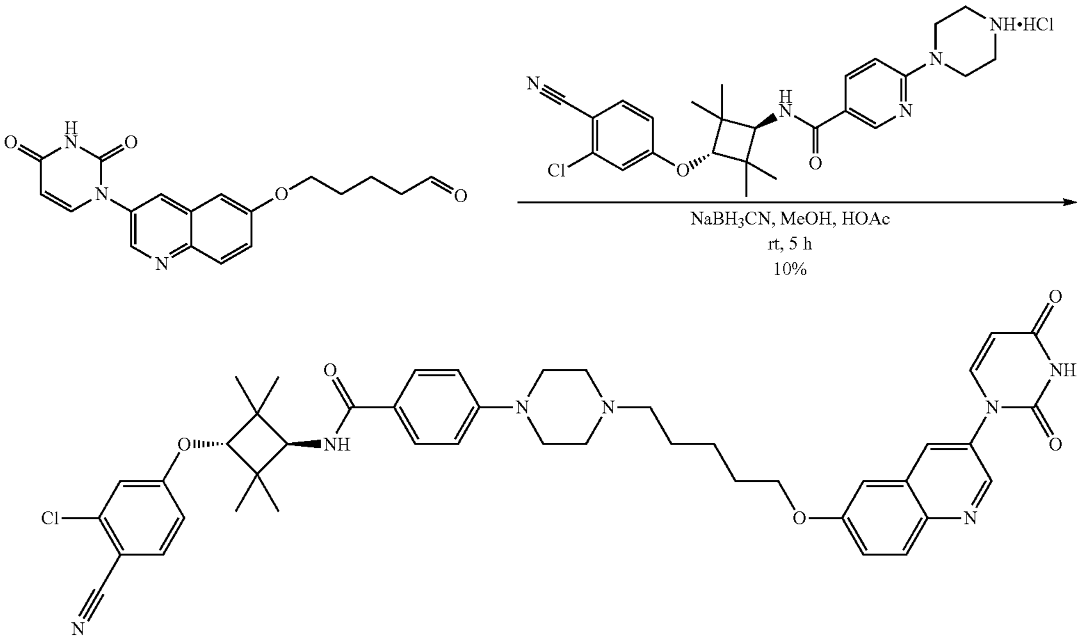

A mixture of 5-(3-(2,4-dioxo-3,4-dihydropyrimidin-1(2H)-yl)quinolin-6-yloxy)pentanal (100 mg, 0.29 mmol), N-((1r,3r)-3-(3-chloro-4-cyanophenoxy)-2,2,4,4-tetramethylcyclobutyl)-6-(piperazin-1-yl)nicotinamide hydrochloride (149 mg, 0.29 mmol), sodium cyanoborohydride (36 mg, 0.58 mmol) in methanol (5 mL) and acetic acid glacial (0.5 mL) was stirred at room temperature overnight. Water (10 mL) was added and extracted with dichloromethane (20 mL×3). Combined organic layers were washed with brine (10 mL×2), dried over anhydrous sodium sulfate. The solvent was concentrated to give the residue, which was purified by Prep-HPLC to give N-((1r,3r)-3-(3-chloro-4-cyanophenoxy)-2,2,4,4-tetramethylcyclobutyl)-6-(4-(5-(3-(2,4-dioxo-3,4-dihydropyrimidin-1(2H)-yl)quinolin yloxy)pentyl)piperazin-1-yl)nicotinamide (23 mg, 10% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min). Purity is 94.84%, Rt=2.864 min; MS Calcd.: 790.34; MS Found: 791.30 [M+H]$^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 95.31%, Rt=9.913 min.

$^1$H NMR (400 MHz, $CDCl_3$) δ 1.21 (6H, s), 1.25 (6H, s), 1.58-1.66 (4H, m), 1.90-1.94 (2H, m), 2.43-2.47 (2H, m), 2.56-2.58 (4H, m), 3.67-3.70 (4H, m), 4.04 (1H, s), 4.09-4.15 (3H, m), 5.93 (1H, d, J=8.0 Hz), 6.07 (1H, d, J=8.0 Hz), 6.66 (1H, d, J=9.2 Hz), 6.80 (1H, dd, J=8.8, 2.4 Hz), 6.96 (1H, d, J=2.4 Hz), 7.09 (1H, d, J=2.8 Hz), 7.41-7.46 (2H, m), 7.57 (1H, d, J=8.8 Hz), 7.93 (1H, dd, J=9.2, 2.4 Hz), 8.05-8.07 (2H, m), 8.58 (1H, d, J=2.4 Hz), 8.73 (1H, d, J=2.4 Hz).

Chemical Formula: $C_{43}H_{47}ClN_8O_5$, Molecular Weight: 791.34

Total H count from HNMR data: 46.

Synthesis of Exemplary PROTAC 48

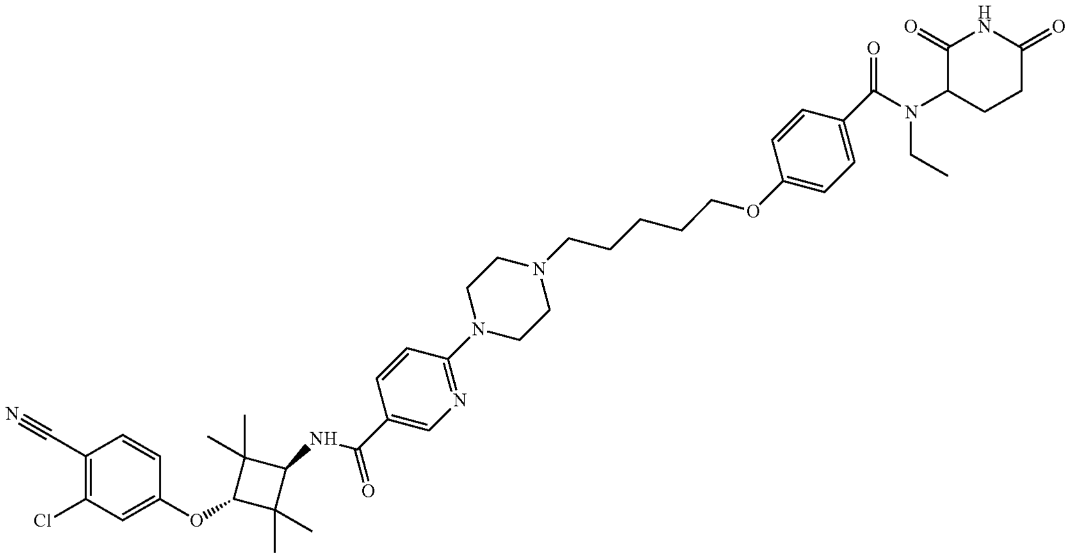 [SMILES: CCN(C(=O)c1ccc(OCCCCCN2CCN(c3ccc(C(=O)N[C@H]4C(C)(C)[C@H](Oc5ccc(C#N)c(Cl)c5)C4(C)C)cn3)CC2)cc1)C1CCC(=O)NC1=O]

rac-N-((1r,3r)-3-(3-chloro-4-cyanophenoxy)-2,2,4,4-tetramethylcyclobutyl)-6-(4-(5-(4-((2,6-dioxopiperidin-3-yl)(ethyl)carbamoyl)phenoxy)pentyl)piperazin-1-yl)nicotinamide Synthetic Scheme

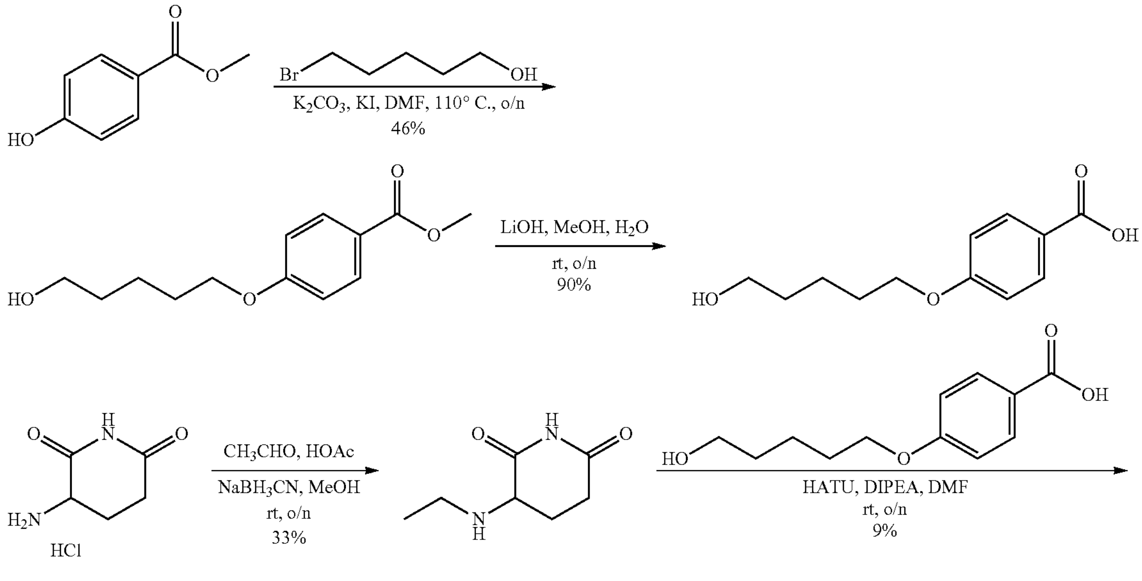

-continued

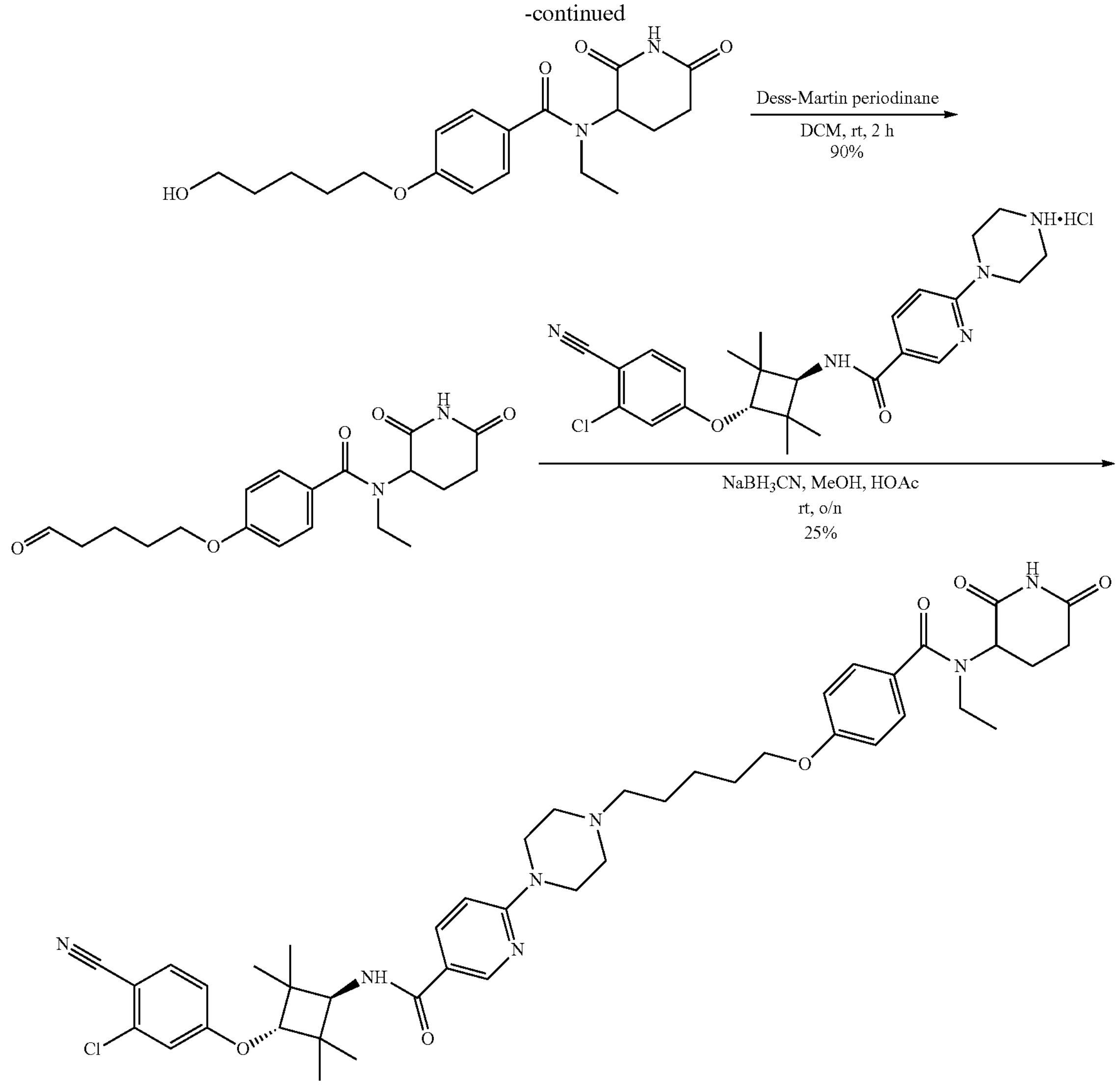

Step 1: Synthesis of methyl 4-(5-hydroxypentyloxy)benzoate

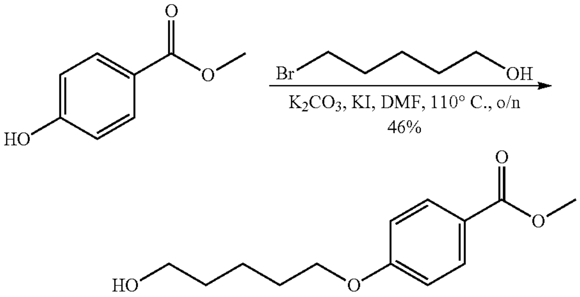

A mixture of methyl 4-hydroxybenzoate (3.0 g, 20 mmol), 5-bromopentan-1-ol (3.3 g, 20 mmol), potassium carbonate (5.5 g, 40 mmol) and potassium iodide (0.3 g, 2 mmol) in N,N-dimethylformamide (20 mL) was heated at 110° C. overnight. The reaction mixture was cooled to room temperature. Water (50 mL) was added. Extracted with ethyl acetate (50 mL×3) and combined organic layers were washed with water (30 mL×2) and brine (30 mL×2), dried over anhydrous sodium sulfate. The solvent was concentrated to give the residue, which was purified by column chromatography on silica gel (petroleum ether/ethyl acetate=10/1) to give methyl 4-(5-hydroxypentyloxy)benzoate (2.2 g, 46% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity is 98.48%, Rt=1.637 min; MS Calcd.: 238.1; MS Found: 239.2 $[M+H]^+$.

Step 2: Synthesis of 4-(5-hydroxypentyloxy)benzoic acid

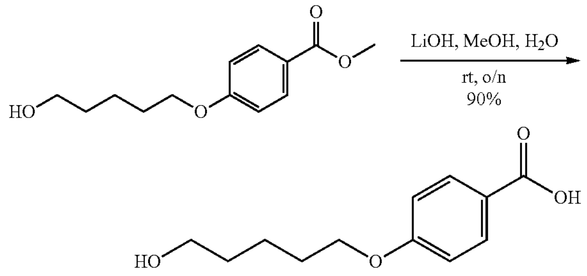

A mixture of methyl 4-(5-hydroxypentyloxy)benzoate (2.2 g, 9.2 mmol), lithium hydroxide (1.6 g, 36.9 mmol) in methanol (10 mL) and water (1 mL) was stirred at room temperature overnight. The solvent was removed in vacuum and water (5 mL) was added. It was extracted with ethyl acetate and the water phase was adjust pH=5-6 with 1N aqueous hydrochloride. Filtered and the solid was collected, which was dried in vacuum to afford 4-(5-hydroxypentyloxy)benzoic acid (1.9 g, 90% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.073 min; MS Calcd.: 224.1; MS Found: 225.3 $[M+H]^+$.

Step 3: Synthesis of 3-(ethylamino)piperidine-2,6-dione

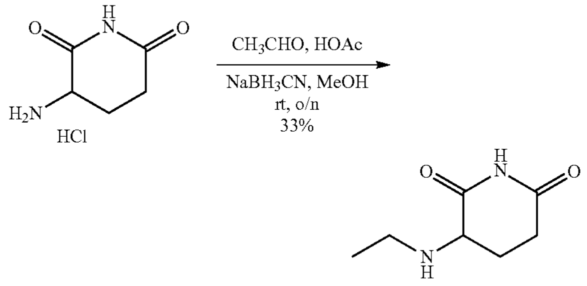

A mixture of 3-aminopiperidine-2,6-dione hydrochloride (3.8 g, 23 mmol), acetaldehyde (1.0 g, 23 mmol), sodium cyanoborohydride (4.3 g, 69 mmol) in methanol (30 mL) and acetic acid glacial (0.5 mL) was stirred at room temperature overnight. Water (10 mL) was added and extracted with dichloromethane (50 mL×3). Combined organic layers were washed by brine (30 mL×2), dried over anhydrous sodium sulfate. The solvent was concentrated to give the residue, which was purified by column chromatography on silica gel (dichloromethane/methanol=10/1) to give 3-(ethylamino)piperidine-2,6-dione (3.0 g, 33% yield) as a yellow oil.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=0.737 min; MS Calcd.: 156.1; MS Found: 157.2 $[M+H]^+$.

Step 4: Synthesis of N-(2,6-dioxopiperidin-3-yl)-N-ethyl-4-(5-hydroxypentyloxy)benzamide

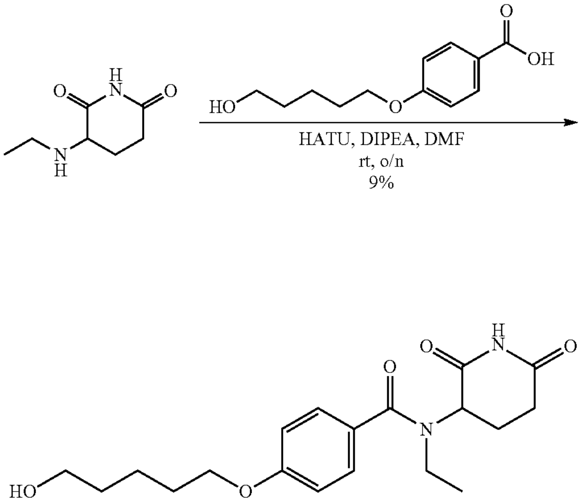

A mixture of 3-(ethylamino)piperidine-2,6-dione (500 mg, 3.2 mmol), 4-(5-hydroxypentyloxy)benzoic acid (3.3 g, 20 mmol), ethyldiisopropylamine (826 mg, 6.4 mmol) and 2-(7-Aza-1H-benzotriazole-1-yl)-1,1,3,3-tetramethyluronium hexafluorophosphate (1.8 g, 4.8 mmol) in N,N-dimethylformamide (5 mL) was stirred at room temperature overnight. Water (10 mL) was added. Extracted with ethyl acetate (20 mL×3) and combined organic layers were washed with water (20 mL×2) and brine (20 mL×2), dried over anhydrous sodium sulfate. The solvent was concentrated to give the residue, which was purified by column chromatography on silica gel (dichloromethane/methanol=10/1) to give N-(2,6-dioxopiperidin-3-yl)-N-ethyl-4-(5-hydroxypentyloxy)benzamide (108 mg, 9% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.377 min; MS Calcd.: 362.2; MS Found: 363.2 $[M+H]^+$.

Step 5: Synthesis of N-(2,6-dioxopiperidin-3-yl)-N-ethyl-4-(5-oxopentyloxy)benzamide

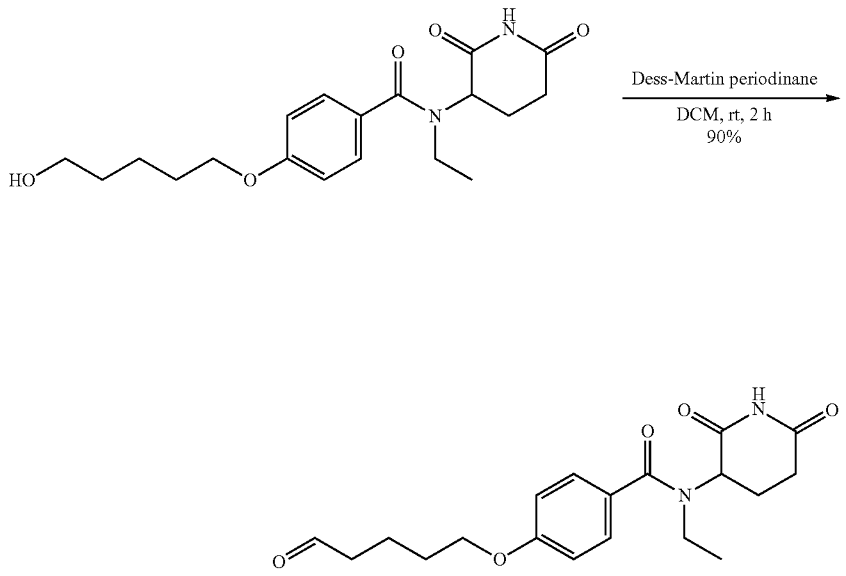

A mixture of N-(2,6-dioxopiperidin-3-yl)-N-ethyl-4-(5-hydroxypentyloxy)benzamide (108 mg, 0.3 mmol) and Dess-Martin periodinane (254 mg, 0.6 mmol) in dichloromethane (10 mL) was stirred at room temperature for 2 hours. The reaction mixture was filtered and the cake was washed by dichloromethane (10 mL×2). The filtrate was concentrated and the residue was purified by prep-TLC (dichloromethane/methanol=5/1) to give N-(2,6-dioxopiperidin-3-yl)-N-ethyl-4-(5-oxopentyloxy)benzamide (97 mg, 90% yield) as a yellow solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.465 min; MS Calcd.: 360.2; MS Found: 361.2 $[M+H]^+$.

Step 6: Synthesis of N-((1r,3r)-3-(3-chloro-4-cyano-phenoxy)-2,2,4,4-tetramethylcyclobutyl)-6-(4-(5-(4-((2,6-dioxopiperidin-3-yl)(ethyl)carbamoyl)phenoxy)pentyl)piperazin-1-yl)nicotinamide

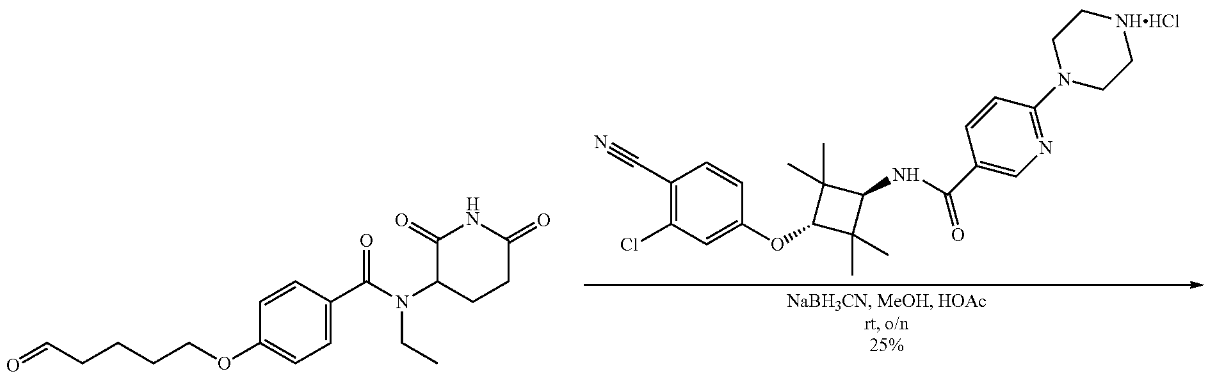

-continued

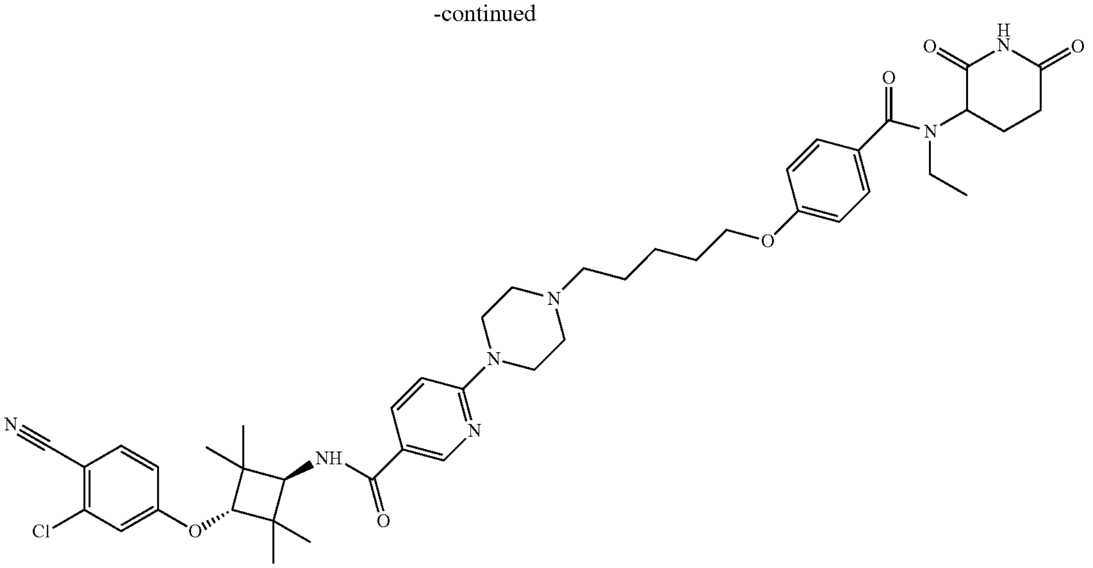

A mixture of N-(2,6-dioxopiperidin-3-yl)-N-ethyl-4-(5-oxopentyloxy)benzamide (97 mg, 0.27 mmol), N-((1r,3r)-3-(3-chloro-4-cyanophenoxy)-2,2,4,4-tetramethylcyclobutyl)-6-(piperazin-1-yl)nicotinamide hydrochloride (136 mg, 0.27 mmol), sodium cyanoborohydride (34 mg, 0.54 mmol) in methanol (5 mL) and acetic acid glacial (0.5 mL) was stirred at room temperature overnight. Water (10 mL) was added and extracted with dichloromethane (20 mL×3). Combined organic layers were washed by brine (10 mL×2), dried over anhydrous sodium sulfate. The solvent was concentrated to give the residue, which was purified by prep-HPLC to give N-((1r,3r)-3-(3-chloro-4-cyanophenoxy)-2,2,4,4-tetramethylcyclobutyl)-6-(4-(5-(4-((2,6-dioxopiperidin-3-yl)(ethyl)carbamoyl)phenoxy)pentyl)piperazin-1-yl)nicotinamide (55 mg, 25% yield) as an off-white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min). Purity is 98.20%, Rt=2.918 min; MS Calcd.: 811.38; MS Found: 812.30 $[M+H]^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 99.92%, Rt=10.259 min.

$^1H$ NMR (400 MHz, DMSO-$d_6$) δ 1.10-1.13 (9H, m), 1.21 (6H, s), 1.44-1.53 (4H, m), 1.74-1.77 (2H, m), 1.99-2.08 (1H, m), 2.31-2.34 (3H, m), 2.42-2.45 (5H, m), 2.67-2.68 (1H, m), 3.29-3.34 (3H, m), 3.58-3.59 (4H, m), 4.00-4.07 (3H, m), 4.30 (1H, s), 6.86 (1H, d, J=8.8 Hz), 6.98-7.02 (3H, m), 7.22 (1H, d, J=2.4 Hz), 7.31 (2H, d, J=8.0 Hz), 7.63 (1H, d, J=9.2 Hz), 7.91 (1H, d, J=8.8 Hz), 7.95 (1H, dd, J=8.8, 2.4 Hz), 8.62 (1H, d, J=2.0 Hz), 10.78 (1H, s).

Chemical Formula: $C_{44}H_{54}ClN_7O_6$, Molecular Weight: 812.40

Total H count from HNMR data: 54.

Synthesis of Exemplary PROTAC 50

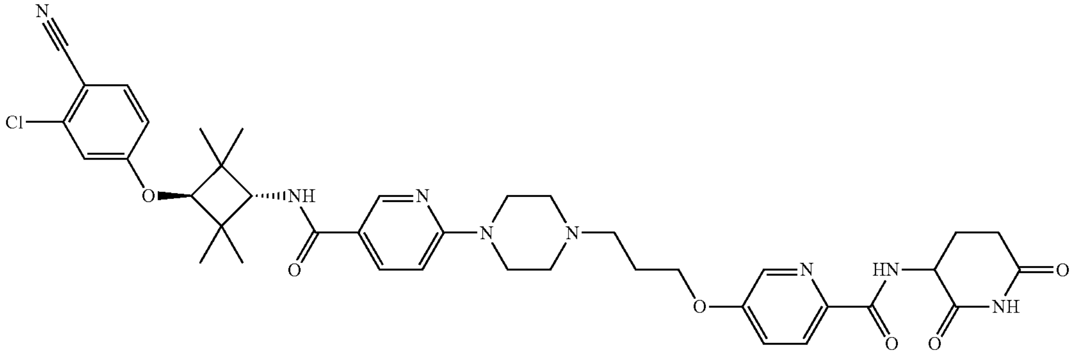 [SMILES: CC1(C)[C@H](NC(=O)c2ccc(N3CCN(CCCOc4ccc(C(=O)NC5CCC(=O)NC5=O)nc4)CC3)nc2)C(C)(C)[C@H]1Oc1ccc(C#N)c(Cl)c1]

5-(3-(4-(5-(((1r,3r)-3-(3-chloro-4-cyanophenoxy)-2,2,4,4-tetramethylcyclobutyl)carbamoyl)pyridin-2-yl)piperazin-1-yl)propoxy)-N-(2,6-dioxopiperidin-3-yl)picolinamide
Synthetic Scheme
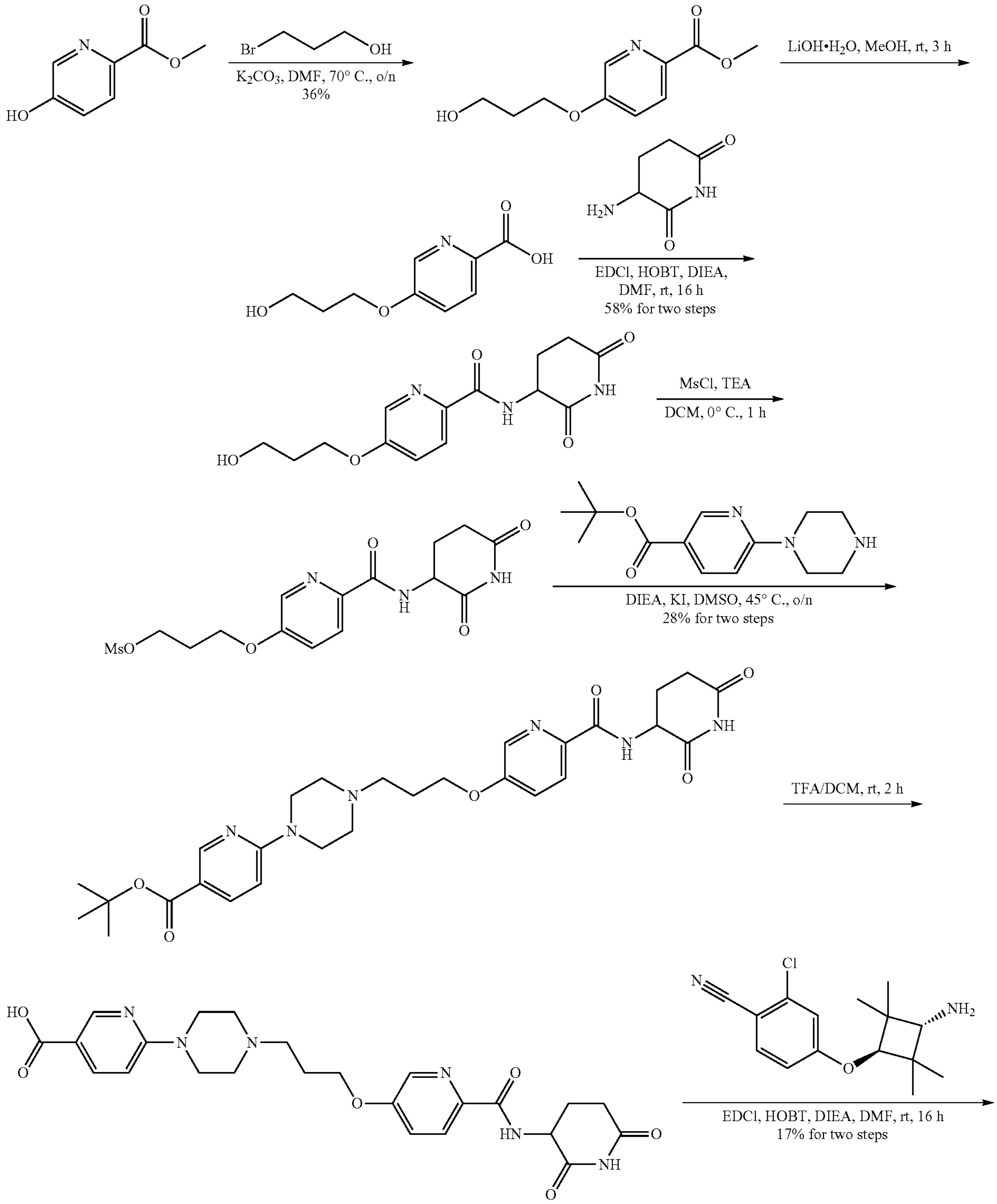

-continued

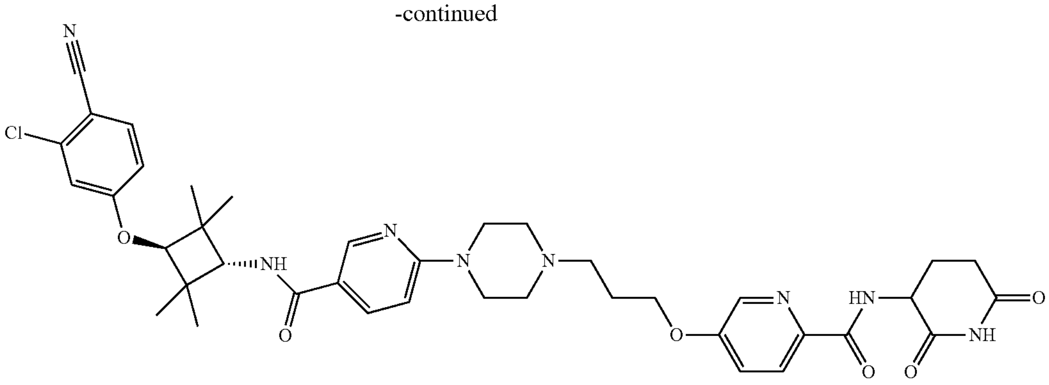

Step 1: Synthesis of methyl 5-(3-hydroxypropoxy)picolinate

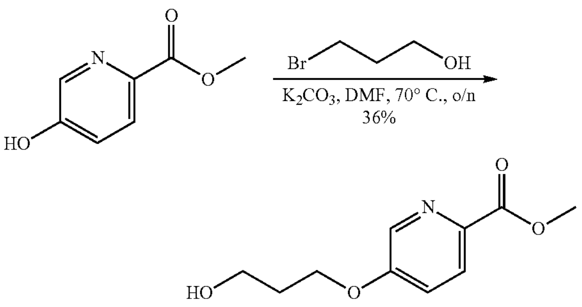

To a solution of methyl 5-hydroxypicolinate (5.0 g, 32.6 mmol) in N,N-dimethylformamide (60.0 mL) was added 3-bromopropan-1-ol (5.45 g, 39.2 mmol), potassium carbonate (9.03 g, 65.3 mmol). The reaction mixture was stirred at 70° C. overnight. The solvent was removed in vacuo. The residue was purified by silica gel chromatography (dichloromethane/methanol=20:1) to give methyl 5-(3-hydroxypropoxy)picolinate (2.5 g, 36%) as a pale yellow solid.

$^1$H NMR (400 MHz, DMSO-$d_6$) δ 1.90 (2H, t, J=6.0 Hz), 3.57 (2H, q, J=5.9 Hz), 3.84 (3H, s), 4.20 (2H, t, J=6.4 Hz), 4.62 (1H, t, J=5.2 Hz), 7.52 (1H, dd, J=8.8 Hz, 2.8 Hz), 8.04 (1H, d, J=8.8 Hz), 8.37 (1H, d, J=2.8 Hz).

Chemical Formula: $C_{10}H_{13}NO_4$, Molecular Weight: 211.21

Total H count from HNMR data: 13.

Step 2: Synthesis of 5-(3-hydroxypropoxy)picolinic acid

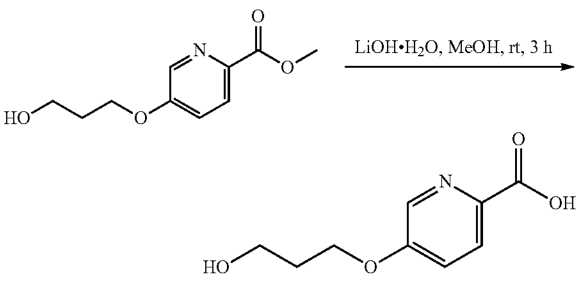

To a solution of methyl 5-(3-hydroxypropoxy)picolinate (2.5 g, 11.8 mmol) in methanol (50 mL) was added lithium hydroxide (1.49 g, 35.5 mmol). The mixture was stirred at room temperature for 3 hours. The solvent was removed and added aq. hydrochloric acid (0.5 M) adjust to PH=2-3. The water was removed in vacuo and the residue was washed with dichloromethane/methanol (10:1), filtered and concentrated in vacuo to give crude 5-(3-hydroxypropoxy)picolinic acid as a pale yellow solid, which was used for the next step without further purification.

Step 3: Synthesis of N-(2,6-dioxopiperidin-3-yl)-5-(3-hydroxypropoxy)picolinamide

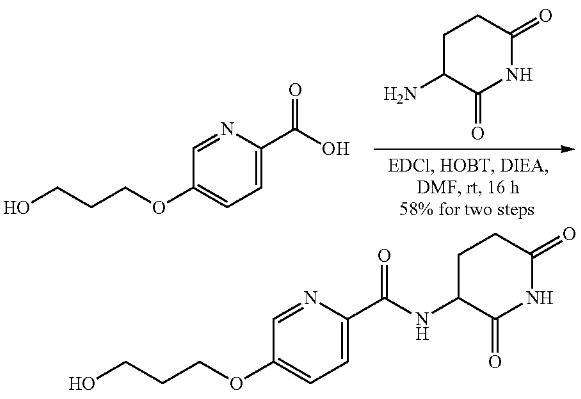

5-(3-hydroxypropoxy)picolinic acid (crude, 11.8 mmol), 1-(3-dimethylaminopropyl)-3-ethylcarbodiimide hydrochloride (EDCI) (3.39 g, 17.7 mmol), 1-hydroxybenzotriazole hydrate (HOBt) (2.40 g, 17.7 mmol) and ethyldiisopropylamine (4.58 g, 35.4 mmol) in N, N-dimethylformamide (DMF) (30 mL) was stirred for 30 minutes, and then 3-aminopiperidine-2,6-dione (2.14 g, 13.0 mmol) was added. The mixture was stirred at room temperature overnight and water (100 mL) was added. The aqueous layer was extracted by ethyl acetate (100 mL×3). The combined organic layer was washed by brine (20 mL×4), dried over anhydrous sodium sulfate, filtered, and concentrated in vacuo. The residue was purified by silica gel (dichloromethane/methanol=20:1) to give N-(2,6-dioxopiperidin-3-yl)-5-(3-hydroxypropoxy)picolinamide (2.1 g, 58% for two steps) as a pale yellow solid.

Step 4: Synthesis of 3-(6-(2,6-dioxopiperidin-3-ylcarbamoyl)pyridin-3-yloxy)propyl methane-sulfonate

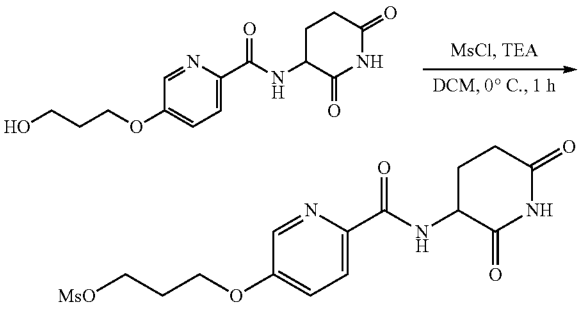

To a solution of N-(2,6-dioxopiperidin-3-yl)-5-(3-hydroxypropoxy)picolinamide (500 mg, 1.63 mmol) in dichloromethane (50.0 mL) was added triethylamine (329 mg, 3.25 mmol) and methanesulfonyl chloride (224 mg, 1.95 mmol) under nitrogen. The resulting reaction mixture was stirred at 0° C. for 1 hour. Then water (20.0 mL) was added and extracted with dichloromethane (20 mL×3), washed by brine, dried and concentrated in vacuo to give crude 3-(6-(2,6-dioxopiperidin-3-ylcarbamoyl)pyridin-3-yloxy)propyl methanesulfonate as pale yellow oil, which was used for the next step without further purification.

Step 5: Synthesis of tert-butyl 6-chloronicotinate

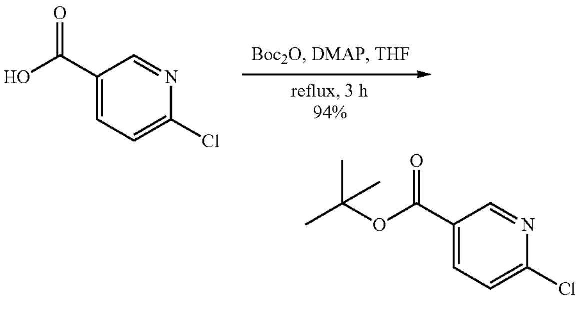

A solution of 6-chloronicotinic acid (31.6 g, 200 mmol) and 4-dimethylaminopyridine (2.4 g, 20 mmol) in THF (250 mL) was refluxed for 3 hours. Then di-tert-butyl dicarbonate (65.0 g, 300 mmol) was added dropwise. After addition, the reaction mixture was refluxed for 3 hours. Upon reaction completion, the reaction mixture was cooled to room temperature. The solvent was removed and the residue was purified by column chromatography on silica gel (ethyl acetate/petroleum ether=0~1/10) to give tert-butyl 6-chloronicotinate (40 g, 94% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity is 100%, Rt=1.984 min; MS Calcd.: 213.06; MS Found: 214.2 $[M+H]^+$.

$^1H$ NMR (400 MHz, DMSO-$d_6$) δ 1.56 (9H, s), 7.67 (1H, d, J=8.4 Hz), 8.26 (1H, dd, J=8.0, 2.4 Hz), 8.86 (1H, d, J=2.4 Hz).

Chemical Formula: $C_{10}H_{12}ClNO_2$, Molecular Weight: 213.66

Total H count from HNMR data: 12.

Step 6: Synthesis of tert-butyl 6-(piperazin-1-yl)nicotinate

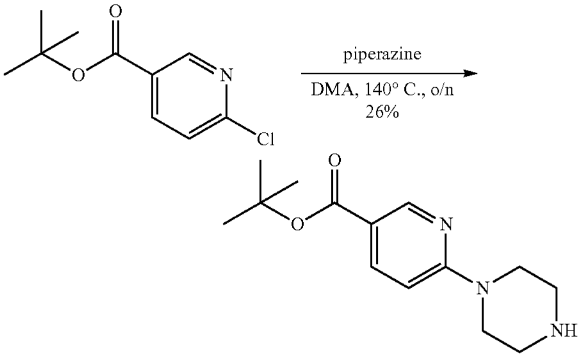

A mixture of tert-butyl 6-chloronicotinate (20.0 g, 94 mmol) and piperazine (8.9 g, 103 mmol) in N,N-dimethylacetamide (100 mL) was stirred at 140° C. overnight. The reaction mixture was cooled to room temperature and saturated aqueous potassium carbonate solution (200 mL) was added portionwise. The mixture was filtered and the filtrate was extracted with ethyl acetate (600 mL×2). The combined organic layers were washed with water (600 mL×4) and brine (600 mL), dried over anhydrous sodium sulfate. The solvent was concentrated under reduced pressure and the residue was purified by column chromatography on silica gel (dichloride/methanol=10/1) to give tert-butyl 6-(piperazin-1-yl)nicotinate (6.5 g, 26% yield) as a yellow solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min). Purity is 100%, Rt=2.068 min; MS Calcd.: 263.16; MS Found: 264.3 $[M+H]^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 97.11%, Rt=7.311 min.

$^1H$ NMR (400 MHz, DMSO-$d_6$) δ 1.51 (9H, s), 2.75 (4H, t, J=4.8 Hz), 3.30 (1H, brs), 3.54 (4H, t, J=4.8 Hz), 6.80 (1H, d, J=9.2 Hz), 7.86 (1H, dd, J=8.8, 2.4 Hz), 8.57 (1H, d, J=2.4 Hz).

Chemical Formula: $C_{14}H_{21}N_3O_2$, Molecular Weight: 263.34

Total H count from HNMR data: 21.

Step 7: Synthesis of tert-butyl 6-(4-(3-(6-(2,6-dioxopiperidin-3-ylcarbamoyl)pyridin-3-yloxy)propyl) piperazin-1-yl)nicotinate

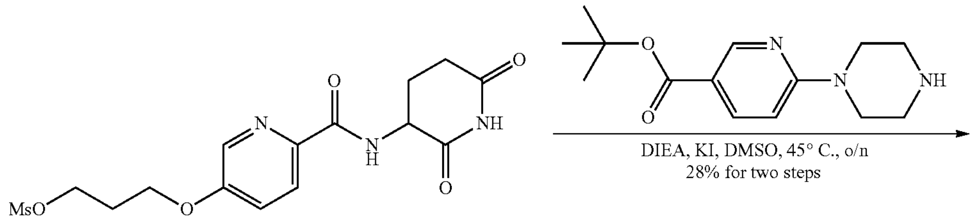

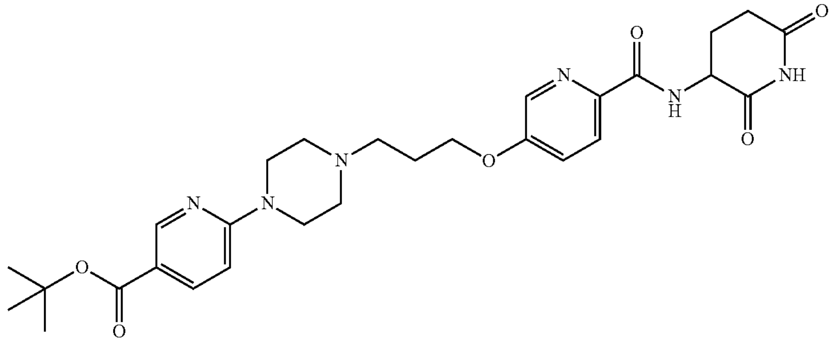

To a solution of 3-(6-(2,6-dioxopiperidin-3-ylcarbamoyl) pyridin-3-yloxy)propyl methanesulfonate (crude, 1.63 mmol) in dimethyl sulfoxide (5.0 mL) was added tert-butyl 6-(piperazin-1-yl)nicotinate (472 mg, 1.79 mmol), ethyldiisopropylamine (632 mg, 4.89 mmol) and potassium iodide (27.1 mg, 0.163 mmol). The reaction mixture was stirred at 45° C. overnight. Then water (20 mL) was added and extracted with ethyl acetate (20 mL×3), washed with brine (5 mL×4). The combined organic phases were dried over anhydrous sodium sulfate, filtered, and concentrated in vacuo. The residue was purified by prep-TLC (dichloromethane/methanol=10:1) to give tert-butyl 6-(4-(3-(6-(2,6-dioxopiperidin-3-ylcarbamoyl)pyridin-3-yloxy)propyl) piperazin-1-yl)nicotinate (250 mg, 28% for two steps) as a pale yellow solid.

$^1$H NMR (400 MHz, $CDCl_3$) δ 1.57 (9H, s), 1.70-1.72 (2H, m), 1.99-2.08 (2H, m), 2.54-2.64 (6H, m), 2.79-2.85 (2H, m), 3.69 (4H, t, J=4.8 Hz), 4.17 (2H, t, J=6.4 Hz), 4.76-4.82 (1H, m), 6.58 (1H, d, J=9.2 Hz), 7.31 (1H, dd, J=8.8 Hz, 3.2 Hz), 7.98 (1H, dd, J=8.8 Hz, 2.4 Hz), 8.13 (1H, d, J=8.8 Hz), 8.16 (1H, brs), 8.25 (1H, d, J=2.8 Hz), 8.51 (1H, d, J=6.8 Hz), 8.76 (1H, d, J=2.0 Hz).

Chemical Formula: $C_{28}H_{36}N_6O_6$, Molecular Weight: 552.62

Total H count from HNMR data: 36.

Step 8: Synthesis of 6-(4-(3-(6-(2,6-dioxopiperidin-3-ylcarbamoyl)pyridin-3-yloxy)propyl)piperazin-1-yl)nicotinic acid

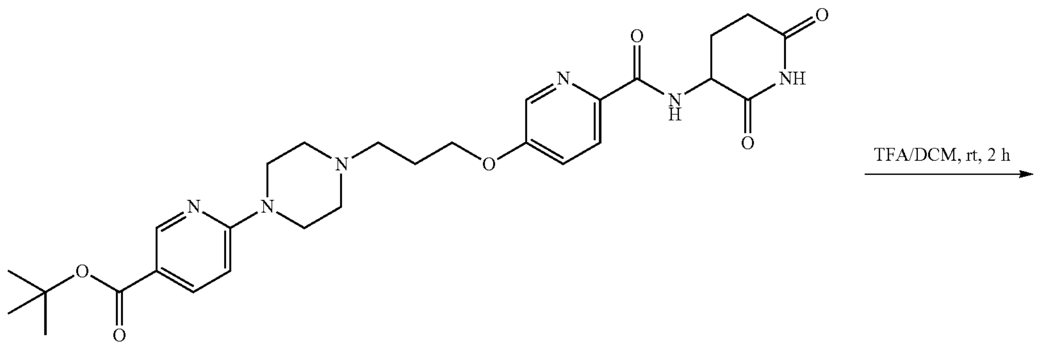

-continued

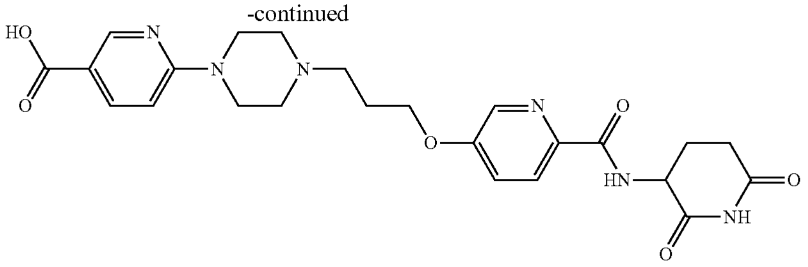

To a solution of tert-butyl 6-(4-(3-(6-(2,6-dioxopiperidin-3-ylcarbamoyl)pyridin-3-yloxy)propyl)piperazin-1-yl)nicotinate (250 mg, 0.452 mmol) in dichloromethane (3.0 mL) was added trifluoroacetic acid (1 mL). The reaction mixture was stirred at room temperature for 2 hours. Then solvent was removed in vacuo to give 6-(4-(3-(6-(2,6-dioxopiperidin-3-ylcarbamoyl)pyridin-3-yloxy)propyl)piperazin-1-yl) nicotinic acid (crude) as pale yellow oil, which was used for the next step without further purification.

Step 9: Synthesis of 5-(3-(4-(5-((1r,3r)-3-(3-chloro-4-cyanophenoxy)-2,2,4,4-tetramethylcyclobutylcarbamoyl)pyridin-2-yl)piperazin-1-yl)propoxy)-N-(2,6-dioxopiperidin-3-yl)picolinamide

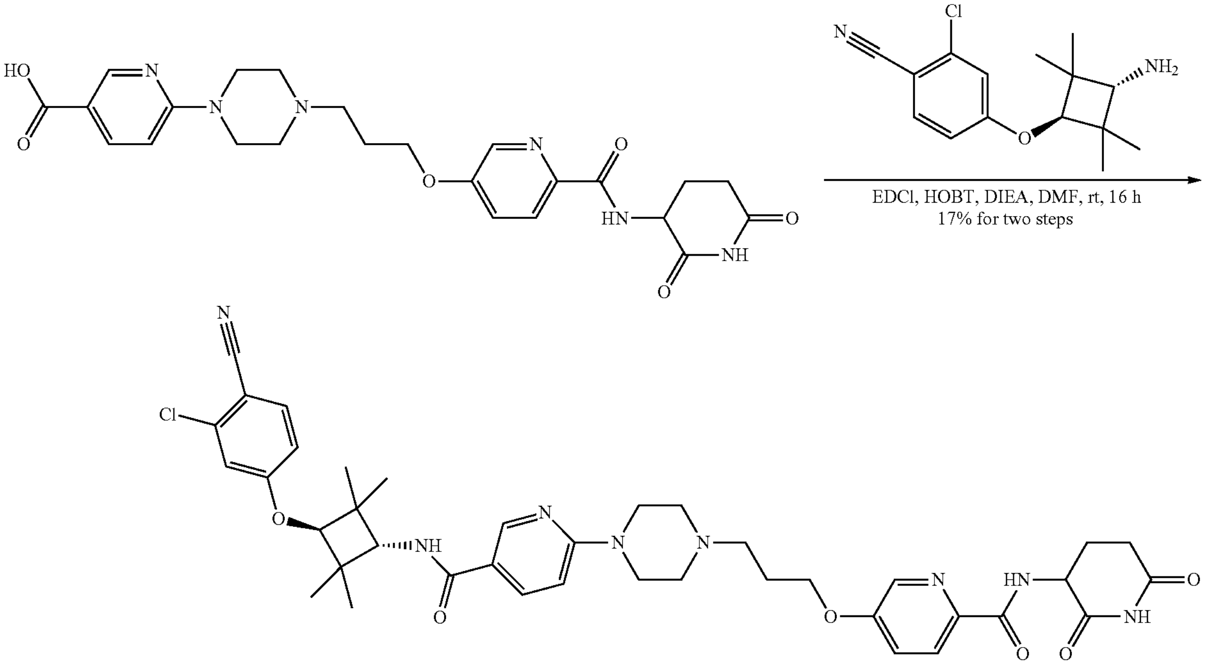

To a solution of 6-(4-(3-(6-(2,6-dioxopiperidin-3-ylcarbamoyl)pyridin-3-yloxy)propyl)piperazin-1-yl)nicotinic acid (crude, 0.452 mmol), 1-(3-dimethylaminopropyl)-3-ethylcarbodiimide hydrochloride (EDCI) (130 mg, 0.678 mmol), 1-hydroxybenzotriazole hydrate (HOBt) (91.9 mg, 0.678 mmol) and ethyldiisopropylamine (175 mg, 1.36 mmol) in N N-dimethylformamide (DMF) (15 mL) was stirred for 30 minutes, and then 4-((1r,3r)-3-amino-2,2,4,4-tetramethylcyclobutoxy)-2-chlorobenzonitrile (139 mg, 0.497 mmol) was added. The mixture was stirred at room temperature overnight and water (20 mL) was added. The aqueous layer was extracted by ethyl acetate (20 mL×3). The combined organic layer was washed by brine (5 mL×4), dried over anhydrous sodium sulfate, filtered, and concentrated in vacuo. The residue was purified by prep-TLC (dichloromethane/methanol=10:1) and prep-HPLC to give 5-(3-(4-(5-((1r,3r)-3-(3-chloro-4-cyanophenoxy)-2,2,4,4-tetramethylcyclobutylcarbamoyl)pyridin-2-yl)piperazin-1-yl) propoxy)-N-(2,6-dioxopiperidin-3-yl)picolinamide (57.7 mg, 17% for two steps) as a white solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min.). Purity is 94.69%, Rt=2.803 min; MS Calcd.: 756.3; MS Found: 757.3 $[M+H]^+$.

HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95%

[water+10 mM $NH_4HCO_3$] and 5% [$CH_3CN$] in 0.1 min and under this condition for 5 min). Purity is 85.08%, Rt=9.741 min.

$^1$H NMR (400 MHz, DMSO-$d_6$) δ 1.12 (6H, s), 1.22 (6H, s), 1.94-2.01 (3H, m), 2.18-2.22 (1H, m), 2.49-2.50 (6H, m), 2.75-2.83 (1H, m), 2.99 (1H, d, J=4.8 Hz), 3.61 (4H, s), 4.06 (1H, d, J=9.2 Hz), 4.19-4.23 (2H, m), 4.31 (1H, s), 4.74-4.80 (1H, m), 6.88 (1H, d, J=9.2 Hz), 7.01 (1H, dd, J=8.8 Hz, 2.4 Hz), 7.21 (1H, d, J=2.4 Hz), 7.58 (1H, dd, J=8.8 Hz, 2.4 Hz), 7.63 (1H, d, J=9.2 Hz), 7.90 (1H, d, J=8.4 Hz), 7.96 (1H, dd, J=8.8 Hz, 2.4 Hz), 8.02 (1H, d, J=8.8 Hz), 8.34 (1H, d, J=2.8 Hz), 8.63 (1H, d, J=2.4 Hz), 8.89 (1H, d, J=8.4 Hz), 10.87 (1H, s).

Chemical Formula: $C_{39}H_{45}ClN_8O_6$, Molecular Weight: 757.28

Total H count from HNMR data: 45.

Synthesis of exemplary PROTAC 53

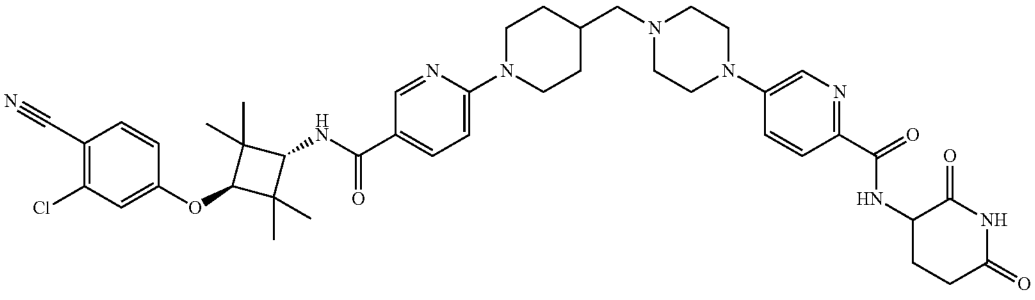 [SMILES: CC1(C)[C@H](NC(=O)c2ccc(N3CCC(CN4CCN(c5ccc(C(=O)NC6CCC(=O)NC6=O)nc5)CC4)CC3)nc2)C(C)(C)[C@H]1Oc1ccc(C#N)c(Cl)c1]

5-(4-((1-(5-(((1r,3r)-3-(3-chloro-4-cyanophenoxy)-2,2,4,4-tetramethylcyclobutyl)carbamoyl)pyridin-2-yl)piperidin-4-yl)methyl)piperazin-1-yl)-N-(2,6-dioxopiperidin-3-yl)picolinamide Synthetic Scheme:

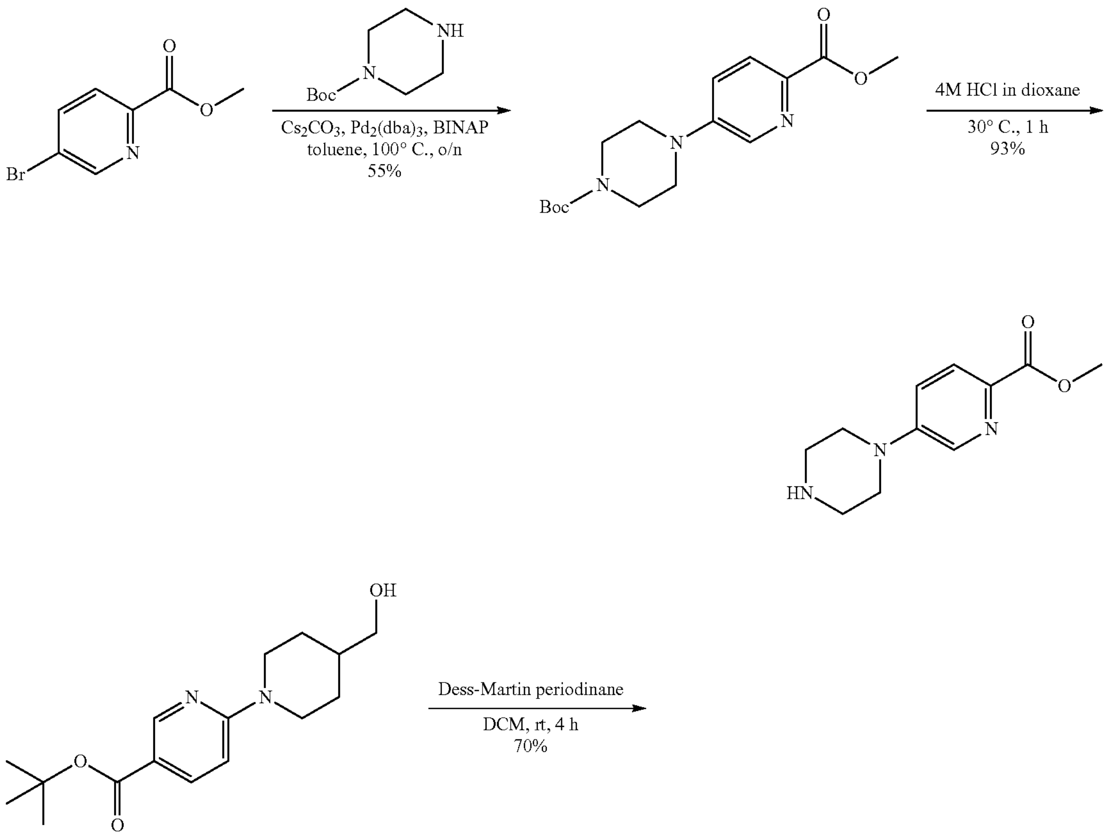

-continued
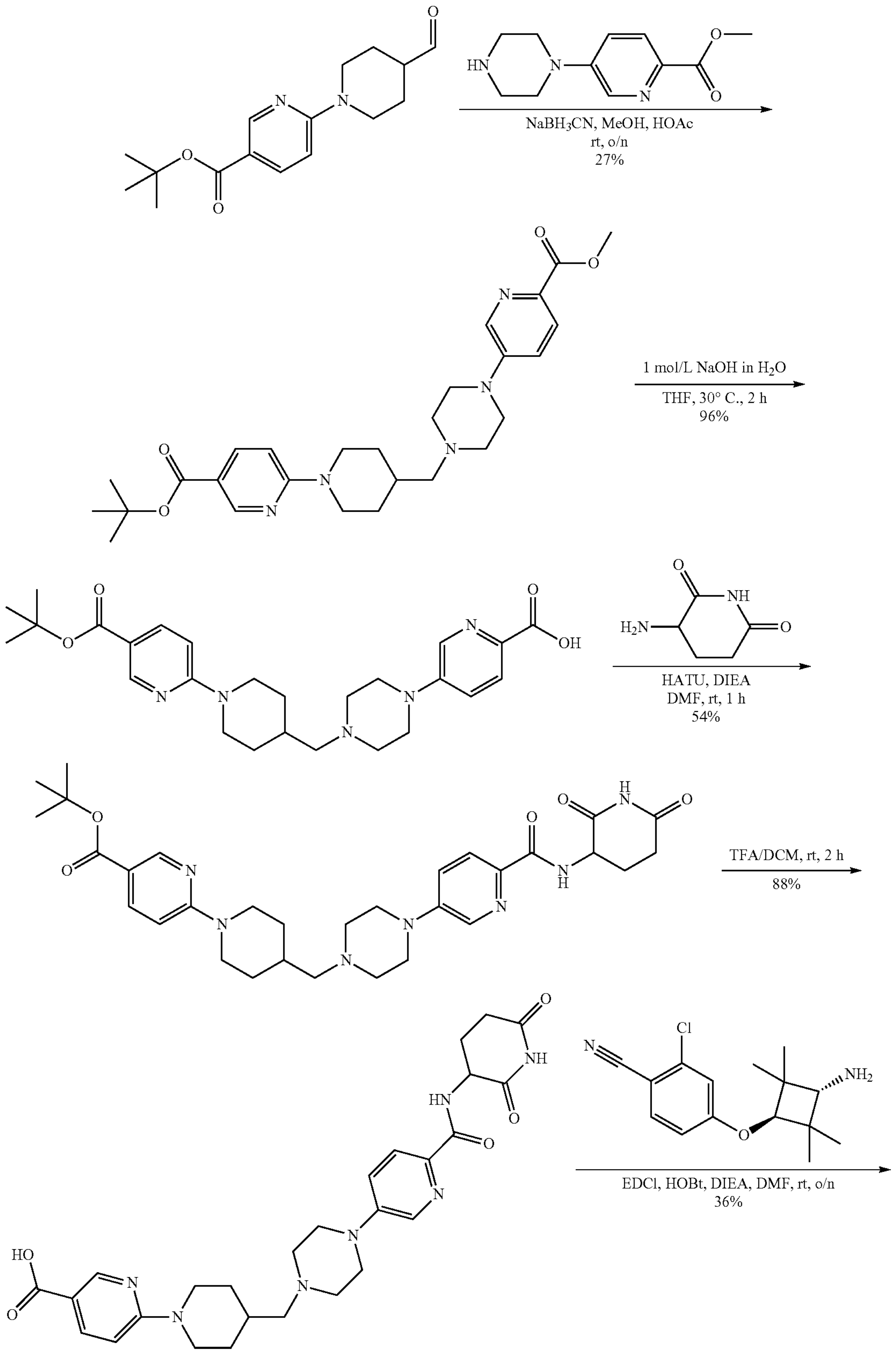

-continued

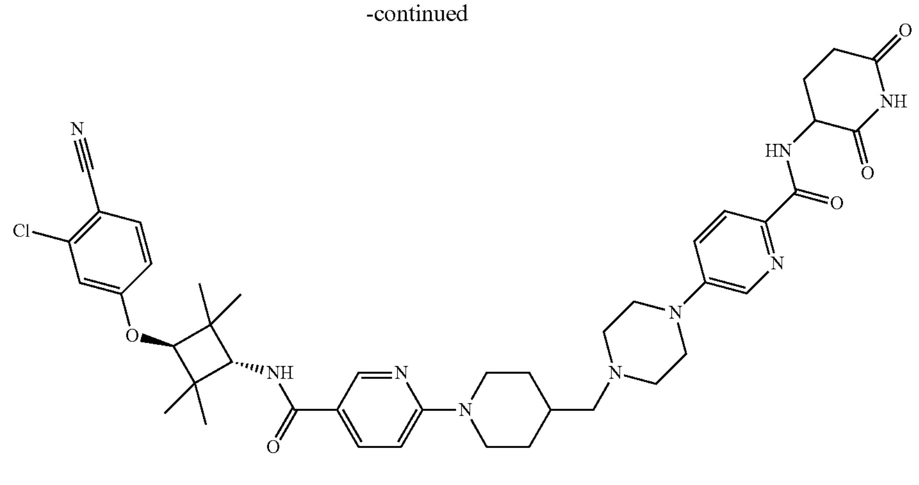

Step 1: Synthesis of tert-butyl 4-(6-(methoxycarbonyl)pyridin-3-yl)piperazine-1-carboxylate

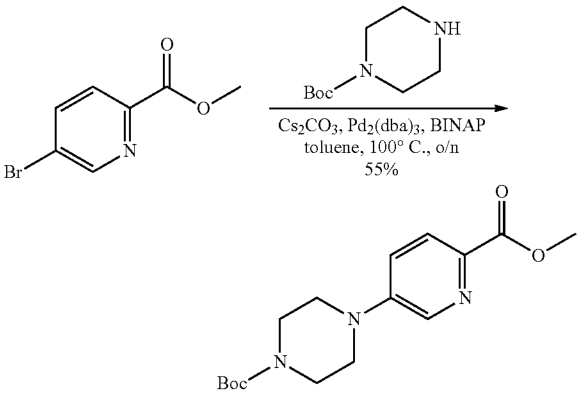

To a solution of methyl 5-bromopicolinate (14.8 g, 68.5 mmol) and tert-butyl piperazine-1-carboxylate (15.3 g, 82.2 mmol) in toluene (150 mL) was added cesium carbonate (55.8 g, 171.3 mmol), tris(dibenzylideneacetone)dipalladium(0) (3.15 g, 3.44 mmol) and (+/−)-2,2'-Bis(diphenylphosphino)-1,1'-binaphthyl (4.62 g, 7.42 mmol), then it was stirred at 100° C. under nitrogen overnight. After cooling, it was quenched by water (100 mL) and extracted with ethyl acetate (100 mL×3). The combined organic layers were washed by brine (200 mL), dried over anhydrous sodium sulfate, filtered and concentrated in vacuo. The residue was purified by column chromatography on silica gel (petroleum ether/ethyl acetate=5/1) to give tert-butyl 4-(6-(methoxycarbonyl)pyridin-3-yl)piperazine-1-carboxylate (12.0 g, 55% yield) as a brown solid.

LC-MS: (Agilent LCMS 1200-6120, Column: Waters X-Bridge C18 (30 mm×4.6 mm×3.5 μm); Column Temperature: 40° C.; Flow Rate: 2.0 mL/min; Mobile Phase: from 90% [water+10 mM $NH_4HCO_3$] and 10% [$CH_3CN$] to 5% [water+10 mM $NH_4HCO_3$] and 95% [$CH_3CN$] in 1.0 min, then under this condition for 1.0 min). Purity is 82.48%, Rt=0.991 min; MS Calcd.: 321.17; MS Found: 322.2 $[M+H]^+$.

Chemical Formula: $C_{16}H_{23}N_3O_4$, Molecular Weight: 321.37.

Step 2: Synthesis of methyl 5-(piperazin-1-yl)picolinate

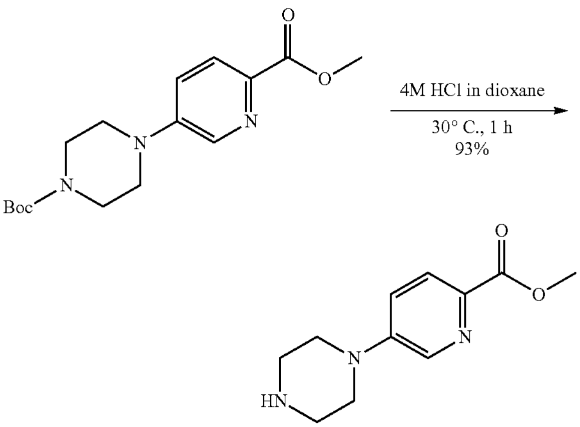

A mixture of tert-butyl 4-(6-(methoxycarbonyl)pyridin-3-yl)piperazine-1-carboxylate (12.0 g, 37.4 mmol) in a solution of HCl gas in 1,4-dioxane (100 mL, 4.0 M) was stirred at 30° C. for 1 h. The reaction mixture was concentrated in vacuo to give methyl 5-(piperazin-1-yl)picolinate (7.6 g, 93% yield) as a brown solid.

Chemical Formula: $C_{11}H_{15}N_3O_2$, Molecular Weight: 221.26.

Step 3: Synthesis of tert-butyl 6-(4-formylpiperidin-1-yl)nicotinate

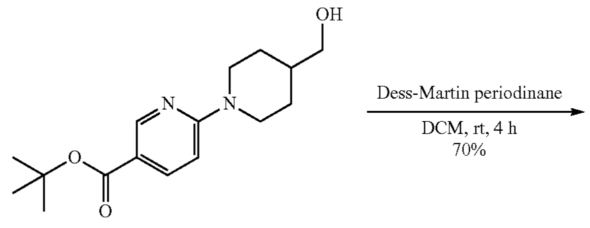

-continued

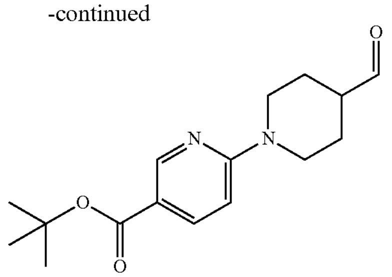

A mixture of tert-butyl 6-(4-(hydroxymethyl)piperidin-1-yl)nicotinate (5.0 g, 17.1 mmol) and Dess-Martin periodinane (21.8 g, 51.4 mmol) in DCM (200 mL) was stirred at room temperature for 4 hours. The mixture was filtered and the filtrate was concentrated in vacuo give tert-butyl 6-(4-formylpiperidin-1-yl)nicotinate (3.5 g, 70% yield) as yellow gel.

Chemical Formula: $C_{16}H_{22}N_2O_3$, Molecular Weight: 290.36

Step 4: Synthesis of methyl 5-(4-((1-(5-(tert-butoxycarbonyl)pyridin-2-yl)piperidin-4-yl)methyl)piperazin-1-yl)picolinate

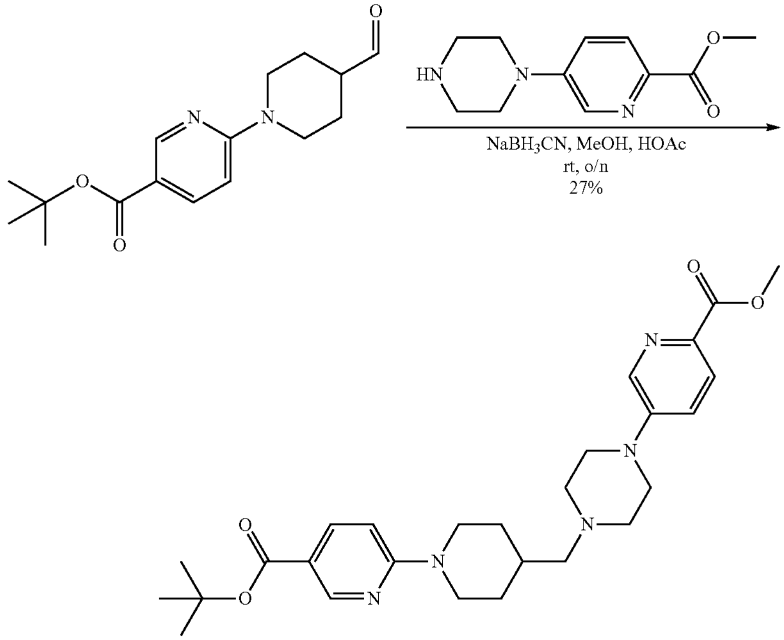

To a solution of tert-butyl 6-(4-formylpiperidin-1-yl)nicotinate (3.5 g, 12.1 mmol) and methyl 5-(piperazin-1-yl)picolinate (2.67 g, 12.1 mmol) in MeOH (50 mL) was added $NaBH_3CN$ (1.52 g, 18.0 mmol) and AcOH (2 mL), then it was stirred at room temperature overnight. It was diluted with water (50 mL), extracted with DCM (50 mL×3). The combined organic layers were washed by brine (50 mL), dried over anhydrous sodium sulfate, filtered and concentrated in vacuo. The residue was purified by column chromatography on silica gel (DCM/MeOH=20/1) to give methyl 5-(4-((1-(5-(tert-butoxycarbonyl)pyridin-2-yl)piperidin-4-yl)methyl)piperazin-1-yl)picolinate (1.6 g, 27% yield) as a brown solid.

LC-MS: (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.987 min; MS Calcd.: 495.28 MS Found: 496.3 $[M+H]^+$.

Chemical Formula: $C_{27}H_{37}N_5O_4$, Molecular Weight: 495.61.

-

Step 5: Synthesis of 5-(4-((1-(5-(tert-butoxycarbonyl)pyridin-2-yl)piperidin-4-yl)methyl)piperazin-1-yl)picolinic acid

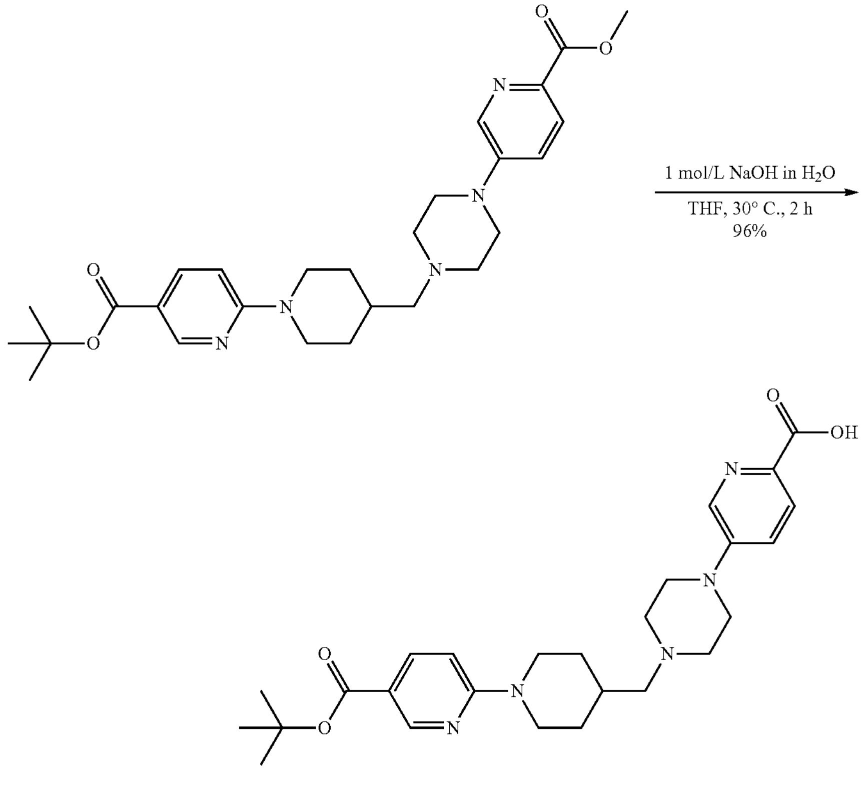

To a solution of methyl 5-(4-((1-(5-(tert-butoxycarbonyl)pyridin-2-yl)piperidin-4-yl)methyl)piperazin-1-yl)picolinate (1.6 g, 2.35 mmol) in THF (60 mL) was added 1 mol/L aqueous NaOH (30 mL), then it was stirred at 30° C. for 2 hours. It was quenched with water (100 mL) and extracted with DCM (50 mL×3). The combined organic layers were washed by brine (100 mL), dried over anhydrous sodium sulfate, filtered and concentrated in vacuo to give 5-(4-((1-(5-(tert-butoxycarbonyl)pyridin-2-yl)piperidin-4-yl)methyl)piperazin-1-yl)picolinic acid (1.5 g, 96% yield) as a brown solid.

LC-MS: (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.557 min; MS Calcd.: 481.27, MS Found: 482.3 $[M+H]^+$.

Chemical Formula: $C_{26}H_{35}N_5O_4$, Molecular Weight: 481.59.

Step 6: Synthesis of tert-butyl 6-(4-((4-(6-(2,6-dioxopiperidin-3-ylcarbamoyl)pyridin-3-yl)piperazin-1-yl)methyl)piperidin-1-yl)nicotinate

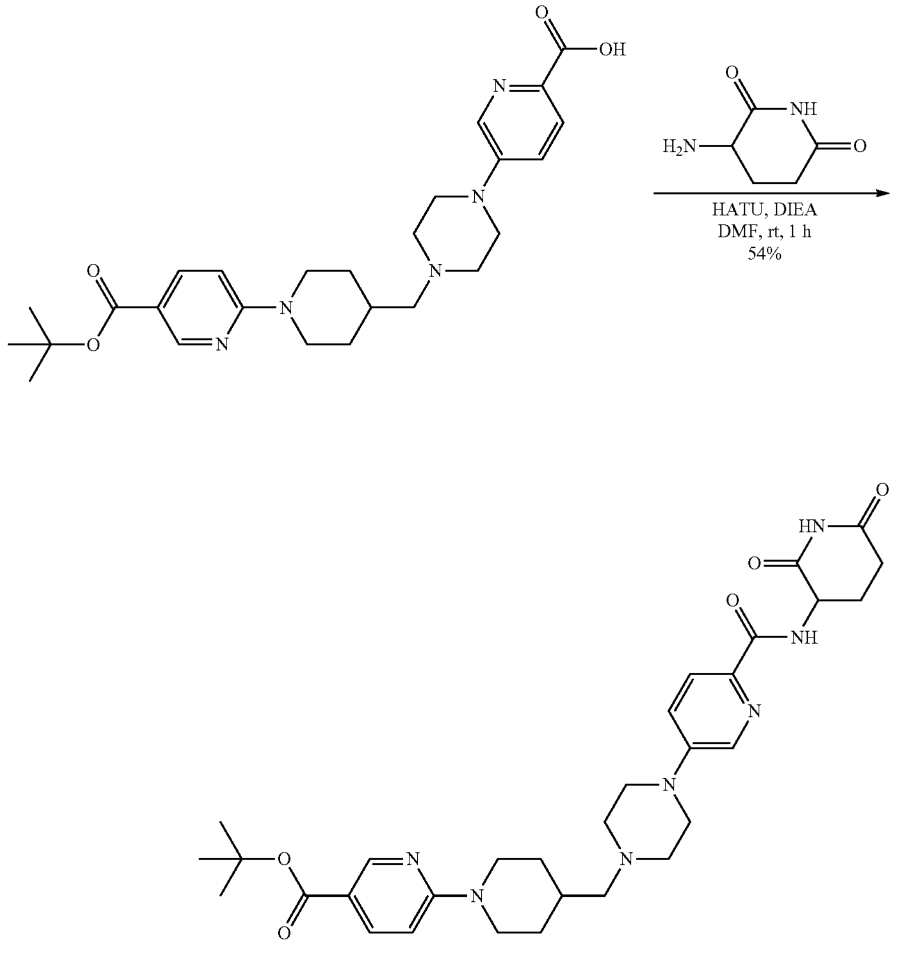

A mixture of 5-(4-((1-(5-(tert-butoxycarbonyl)pyridin-2-yl)piperidin yl)methyl)piperazin-1-yl)picolinic acid (1.5 g, 3.1 mmol), 3-aminopiperidine-2,6-dione (0.56 g, 3.4 mmol), HATU (1.77 g, 4.65 mmol) and DIEA (0.8 g, 6.2 mmol) in DMF (50 mL) was stirred at room temperature for 1 hour. The mixture was poured into water (30 mL) and extracted with DCM (30 mL×3). The combined organic phase was concentrated and the residue was purified by Prep-HPLC to give tert-butyl 6-(4-((4-(6-(2,6-dioxopiperidin-3-ylcarbamoyl)pyridin yl)piperazin-1-yl)methyl)piperidin-1-yl)nicotinate (1.0 g, 54% yield) as a white solid.

LC-MS: (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.879 min; MS Calcd.: 591.32; MS Found: 592.3 $[M+H]^+$.

Chemical Formula: $C_{31}H_{41}N_7O_5$, Molecular Weight: 591.70.-

Step 7: Synthesis of 6-(4-((4-(6-(2,6-dioxopiperidin-3-ylcarbamoyl)pyridin-3-yl)piperazin-1-yl)methyl)piperidin-1-yl)nicotinic acid

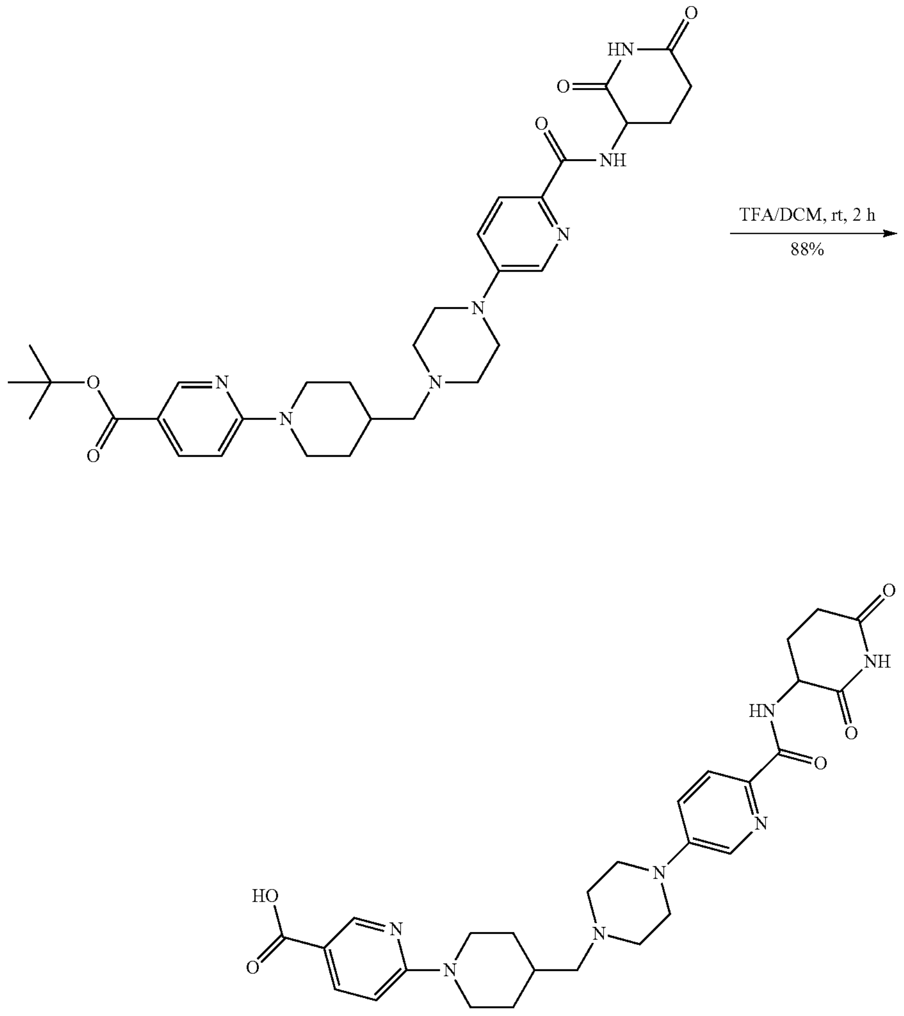

To a solution of tert-butyl 6-(4-((4-(6-(2,6-dioxopiperidin-3-ylcarbamoyl)pyridin-3-yl)piperazin-1-yl)methyl)piperidin-1-yl)nicotinate (500 mg, 0.85 mmol) in DCM (10 mL) was added TFA (5 mL), then it was stirred at room temperature for 2 hours. The reaction mixture was concentrated in vacuo to give 6-(4-((4-(6-(2,6-dioxopiperidin-3-ylcarbamoyl)pyridin-3-yl)piperazin-1-yl)methyl)piperidin-1-yl)nicotinic acid (400 mg, 88% yield) as a white solid.

LC-MS: (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Rt=1.215 min; MS Calcd.: 535.25; MS Found: 536.3 $[M+H]^+$.

Chemical Formula: $C_{27}H_{33}N_7O_5$, Molecular Weight: 535.59.

Step 8: Synthesis of 5-(4-((1-(5-((1r,3r)-3-(3-chloro-4-cyanophenoxy)-2,2,4,4-tetramethylcyclobutylcarbamoyl)pyridin-2-yl)piperidin-4-yl)methyl)piperazin-1-yl)-N-(2,6-dioxopiperidin-3-yl)picolinamide

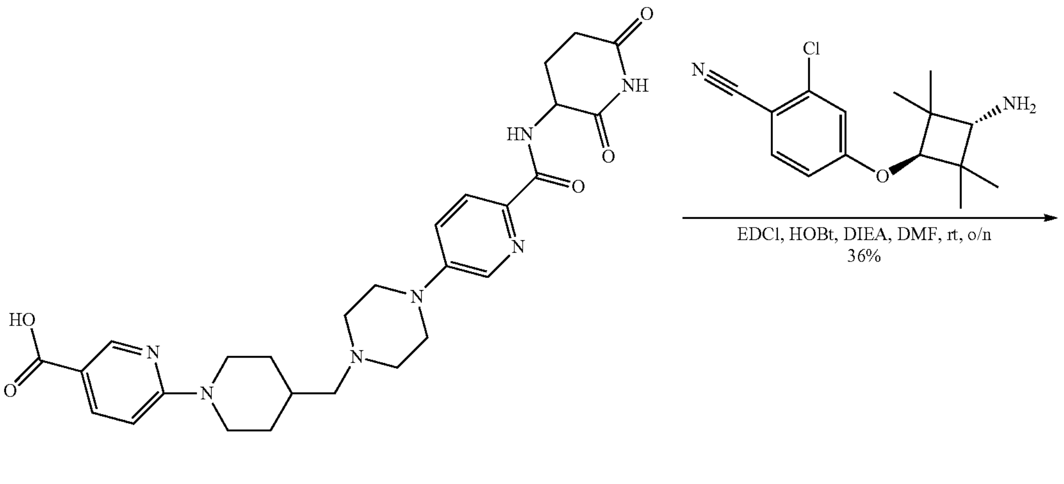

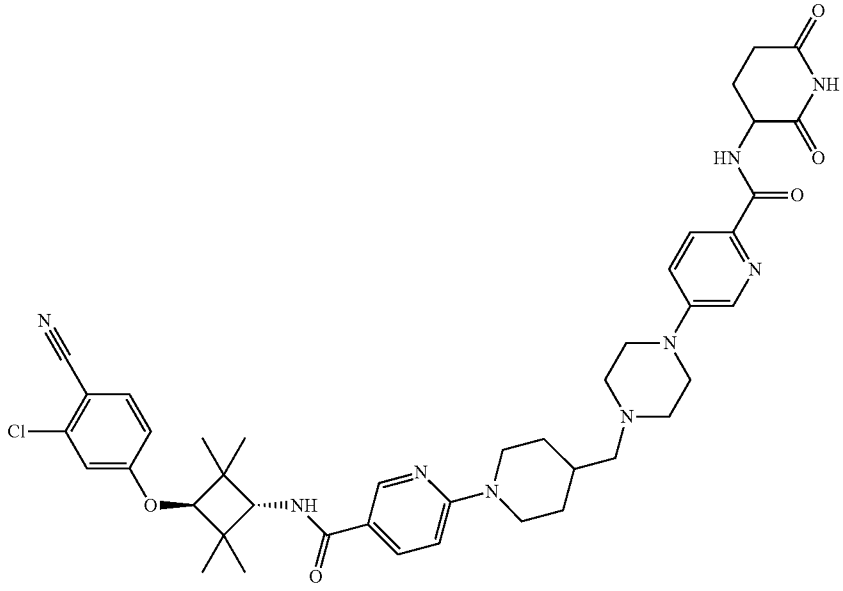

A mixture of 6-(4-((4-(6-(2,6-dioxopiperidin-3-ylcarbamoyl)pyridin-3-yl)piperazin-1-yl)methyl)piperidin-1-yl)nicotinic acid (400 mg, 0.75 mmol), 4-((1r,3r)-3-amino-2,2,4,4-tetramethylcyclobutoxy)-2-chlorobenzonitrile (207.7 mg, 0.75 mmol), EDCI (158.4 mg, 0.825 mmol), HOBt (153 mg, 1.125 mmol) and DIEA (290.25 mg, 2.25 mmol) in DMF (10 mL) were stirred at room temperature overnight. Then the reaction mixture was quenched by water (20 mL) and extracted by DCM (20 mL×3). The combined organic layers were washed by brine (30 mL), dried over anhydrous sodium sulfate, filtered and concentrated in vacuo. The residue was purified by Prep-HPLC to give 5-(4-((1-(5-((1r,3r)-3-(3-chloro-4-cyanophenoxy)-2,2,4,4-tetramethylcyclobutylcarbamoyl)pyridin-2-yl)piperidin-4-yl)methyl)piperazin-1-yl)-N-(2,6-dioxopiperidin-3-yl)picolinamide (215 mg, 36% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min). Purity is 90.80%, Rt=3.023 min; MS Calcd.: 795.36; MS Found: 796.3 $[M+H]^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 90.34%, Rt=10.276 min.

$^1$H NMR (400 MHz, $CDCl_3$) δ 0.76-0.81 (1H, m), 1.15-1.21 (16H, m), 1.80-2.23 (5H, m), 2.53-2.59 (4H, m), 2.71-2.78 (2H, m), 2.85-2.91 (2H, m), 3.29 (3H, brs), 3.97 (1H, s), 4.07 (1H, d, J=8 Hz), 4.38 (2H, d, J=12.8 Hz), 4.69-4.75 (1H, m), 5.98 (1H, d, J=8.4 Hz), 6.60 (1H, d, J=8.8 Hz), 6.73 (1H, dd, J=8.8, 2.4 Hz), 6.89 (1H, d, J=2.4 Hz), 7.14-7.17 (1H, m), 7.50 (1H, d, J=8.8 Hz), 7.84 (1H, dd, J=8.8, 2.4 Hz), 7.92 (1H, s), 7.97 (1H, d, J=8.8 Hz), 8.15 (1H, d, J=2.4 Hz), 8.38 (1H, d, J=6.8 Hz), 8.50 (1H, d, J=2.4 Hz).

Chemical Formula: $C_{42}H_{50}ClN_9O_5$, Molecular Weight: 796.36.

Total H count from HNMR data: 50.

-continued

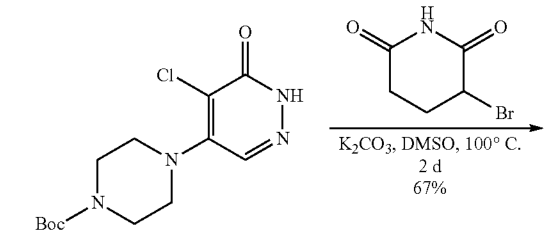

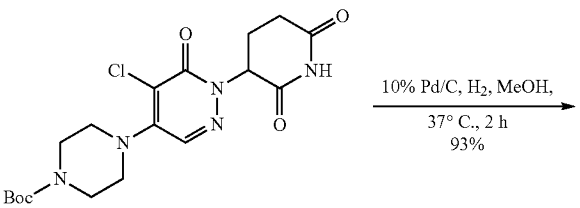

Synthesis of Exemplary PROTAC 61

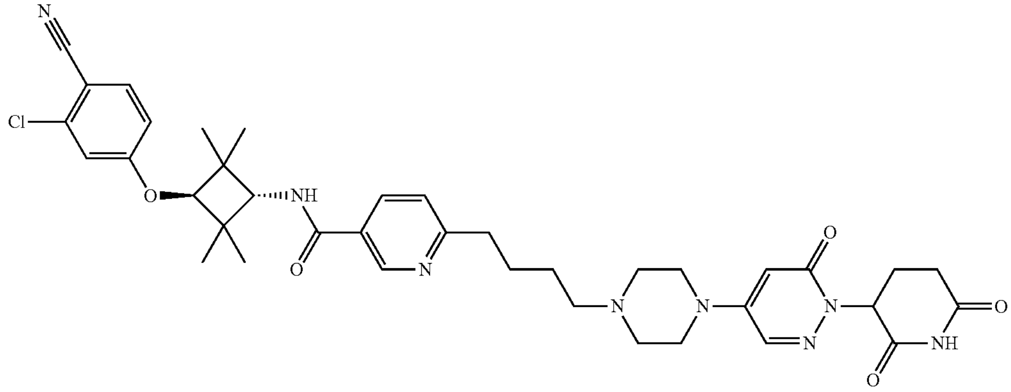 [SMILES: CC1(C)[C@H](NC(=O)c2ccc(CCCCN3CCN(c4cnn(C5CCC(=O)NC5=O)c(=O)c4)CC3)nc2)C(C)(C)[C@H]1Oc1ccc(C#N)c(Cl)c1]

N-((1r,3r)-3-(3-chloro-4-cyanophenoxy)-2,2,4,4-tetramethylcyclobutyl)-6-(4-(4-(1-(2,6-dioxopiperidin-3-yl)-6-oxo-1,6-dihydropyridazin-4-yl)piperazin-1-yl)butyl)nicotinamide Synthetic Scheme Part 1

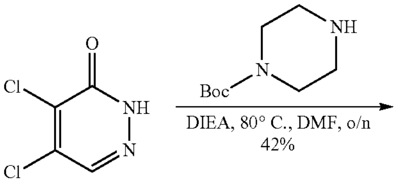

-continued

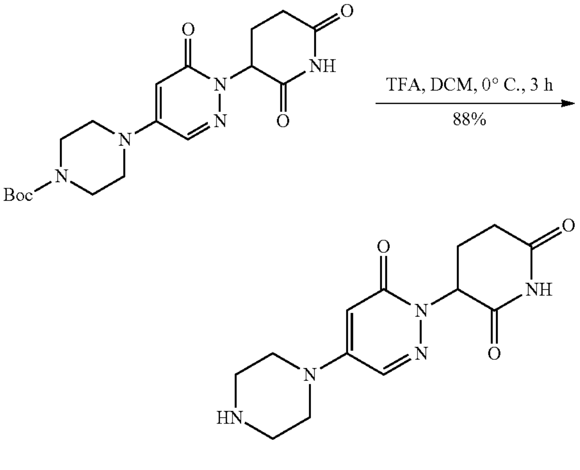

Synthetic Scheme Part 2
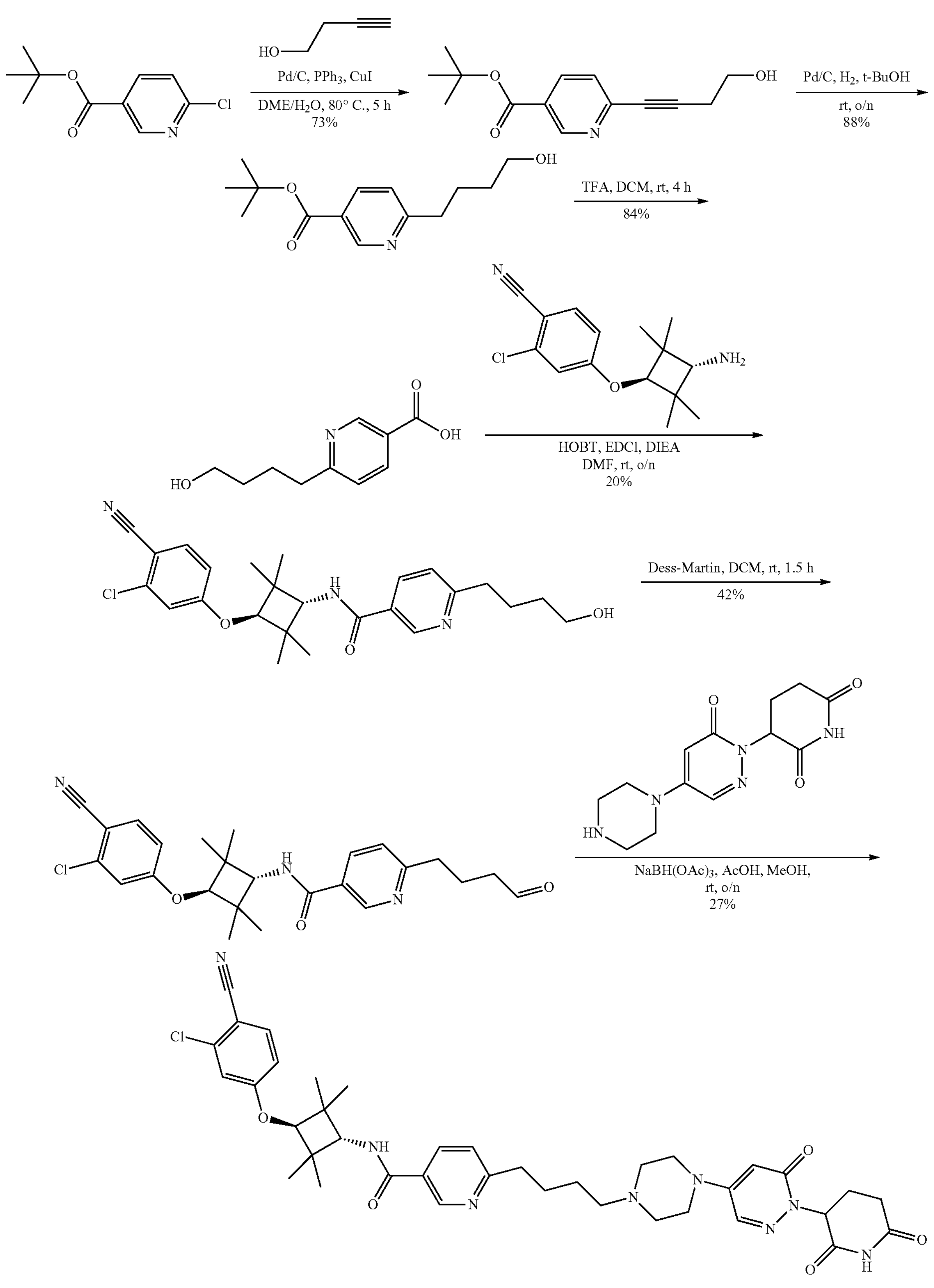

Step 1: Synthesis of tert-butyl 6-(4-hydroxybut-1-ynyl)nicotinate

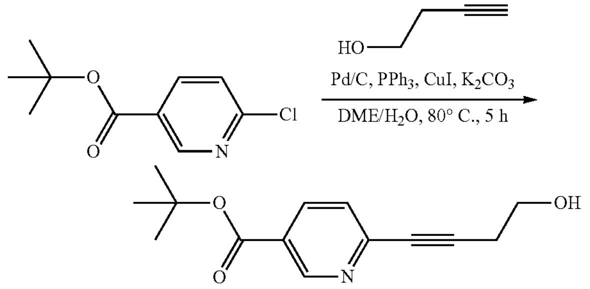

tert-butyl 6-chloronicotinate (2.0 g, 9.39 mmol) is dissolved in dimethoxyethane (50 ml) and added in succession with water (30 mL), potassium carbonate (5.18 g, 37.6 mmol), copper(I) iodide (0.1 g, 0.5 mmol), triphenylphosphine (0.26 g, 1 mmol) and 10 percent (w/w) palladium on carbon (0.3 g). The reaction mixture is stirred for 30 minutes at room temperature, then added with 2-methyl-3-butyn-2-ol (5 ml, 50 mmol), heated at 80° C. for 5 hours, then cooled, filtered through Celite, diluted with water (150 mL) and extracted with ethyl acetate (100 mL×2). The organic phase is washed with water, dried over sodium sulfate, filtered and concentrated evaporated in vacuo. The resulting reaction crude is purified by column and flash chromatography on silica gel to give tert-butyl 6-(4-hydroxybut-1-ynyl)nicotinate (1.7 g, 73%) as colorless oil.

Step 2: Synthesis of tert-butyl 6-(4-hydroxybutyl)nicotinate

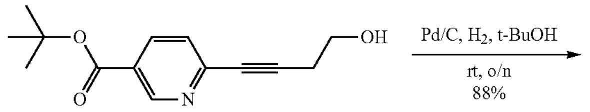

-continued

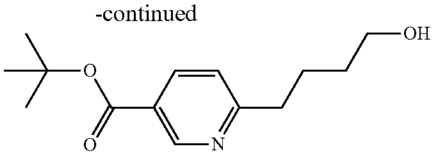

A solution of tert-butyl 6-(4-hydroxybut-1-ynyl)nicotinate (500 mg, 2.0 mmol), Pd/C (50 mg) in tert-butanol (10 mL) was stirred at room temperature overnight under an atmosphere of hydrogen(g). The mixture was filtered through a pad of celite to remove the palladium. The solvent was evaporated in vocuo to give tert-butyl 6-(4-hydroxybutyl)nicotinate (450 mg, 88% yield) as a yellow oil. The residue was used to next step without further purification.

Step 3: Synthesis of 6-(4-hydroxybutyl)nicotinic acid

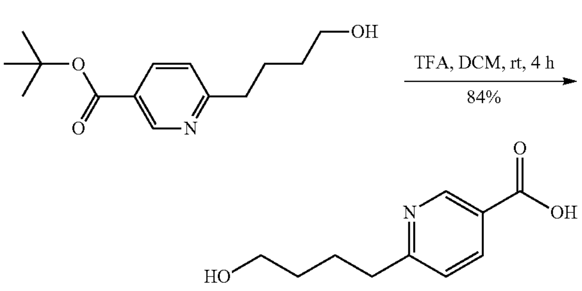

To a solution of 6-(4-hydroxybutyl)nicotinate (200 mg, 0.79 mmol) in dichloromethane (5 mL) was added TFA (5 mL), then it was stirred at room temperature for 2 hours. It was concentrated in vacuo to give crude 6-(4-hydroxybutyl) nicotinic acid (130 mg, 84% yield) as yellow oil, which was directly used to the next step without further purification.

Step 4: Synthesis of N-((1r,3r)-3-(3-chloro-4-cyanophenoxy)-2,2,4,4-tetramethylcyclobutyl)-6-(4-hydroxybutyl)nicotinamide

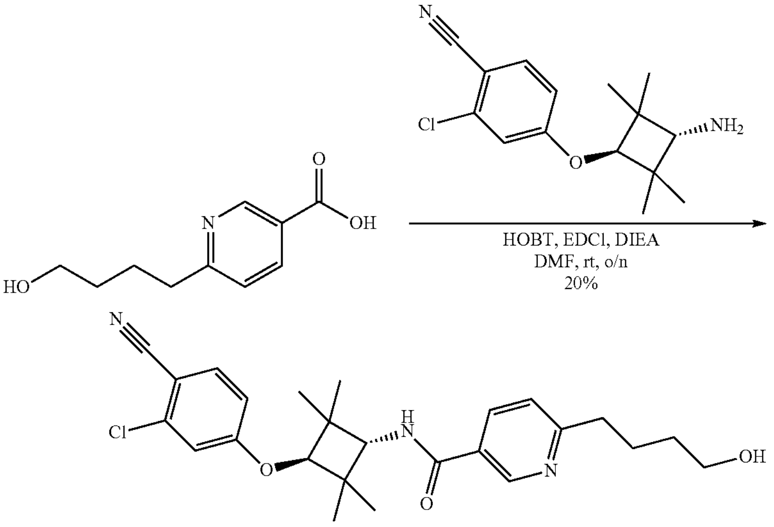

To a solution of 6-(4-hydroxybutyl)nicotinic acid (570 mg, crude, 2.9 mmol), 4-((1r,3r)-3-amino-2,2,4,4-tetramethylcyclobutoxy)-2-chlorobenzonitrile (400 mg, 1.4 mmol), EDCI (472 mg, 2.4 mmol) and HOBt (332 mg, 2.4 mmol) in DMF (10 mL) was added DIEA (800 mg, 6.2 mmol), then it was stirred at room temperature for two days. It was diluted by water (20 ml) and extracted by ethyl acetate (20 mL×2). The organic extract was washed by water (40 mL×3) and brine (40 mL), dried over anhydrous $Na_2SO_4$, filtered and concentrated in vacuo. The residue was purified by Prep-TLC to give N-((1r,3r)-3-(3-chloro-4-cyanophenoxy)-2,2,4,4-tetramethylcyclobutyl)-6-(4-hydroxybutyl)nicotinamide (262 mg, 20% yield) as pale yellow solid.

LCMS (Agilent LCMS 1200-6120, Column: Waters X-Bridge C18 (50 mm×6 mm×5 μm); Column Temperature: 40° C.; Flow Rate: 2.0 mL/min; Mobile Phase: from 90% [(total 10 mM $AcONH_4$) water/$CH_3CN$=900/100 (v/v)] and 10% [(total 10 mM $AcONH_4$) water/$CH_3CN$=100/900 (v/v)] to 10% [(total 10 mM $AcONH_4$) water/$CH_3CN$=900/100 (v/v)] and 90% [(total 10 mM $AcONH_4$) water/$CH_3CN$=100/900 (v/v)] in 1.6 min, then under this condition for 2.4 min, finally changed to 90% [(total 10 mM $AcONH_4$) water/$CH_3CN$=900/100 (v/v)] and 10% [(total 10 mM $AcONH_4$) water/$CH_3CN$=100/900 (v/v)] in 0.1 min and under this condition for 0.7 min). Rt=1.832 min; MS Calcd.: 455.98 MS Found: 456.2$[M+H]_+$.

Chemical Formula: $C_{25}H_{30}ClN_3O_3$, Molecular Weight: 455.98

Step 5: Synthesis of N-((1r,3r)-3-(3-chloro-4-cyanophenoxy)-2,2,4,4-tetramethylcyclobutyl)-6-(4-oxobutyl)nicotinamide

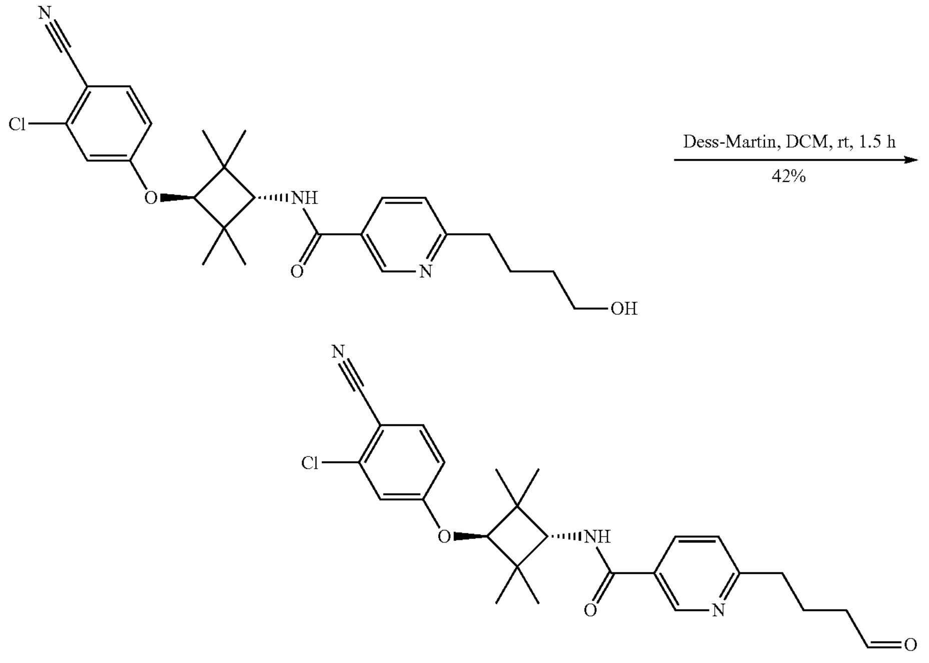

A mixture of N-(2,6-dioxopiperidin-3-yl)-5-(5-hydroxypentyloxy) picolinamide (240 mg, 0.53 mmol) and Dess-Martin periodinane (269 mg, 0.64 mmol) in dichloromethane (10 mL) was stirred at room temperature 1.5 hours. The reaction mixture was filtered, and the filter cake was washed by dichloromethane (10 mL×3). The filtrate was concentrated and purified by Prep-TLC (DCM/MeOH=100/5) to give N-((1r,3r)-3-(3-chloro-4-cyanophenoxy)-2,2,4,4-tetramethylcyclobutyl)-6-(4-oxobutyl)nicotinamide (100 mg, 42% yield) as a yellow solid.

LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM $AcONH_4$) water/$CH_3CN$=900/100 (v/v)] and 10% [(total 10 mM $AcONH_4$) water/$CH_3CN$=100/900 (v/v)] to 10% [(total 10 mM $AcONH_4$) water/$CH_3CN$=900/100 (v/v)] and 90% [(total 10 mM $AcONH_4$) water/$CH_3CN$=100/900 (v/v)] in 1.6 min, then under this condition for 2.4 min, finally changed to 90% [(total 10 mM $AcONH_4$) water/$CH_3CN$=900/100 (v/v)] and 10% [(total 10 mM $AcONH_4$) water/$CH_3CN$=100/900 (v/v)] in 0.1 min and under this condition for 0.7 min). Purity is 52.80, Rt=1.977 min; MS Calcd.:453.96; MS Found: 454.2 $[M+H]^+$.

Step 6: Synthesis of tert-butyl 4-(5-chloro-6-oxo-1,6-dihydropyridazin-4-yl)piperazine-1-carboxylate

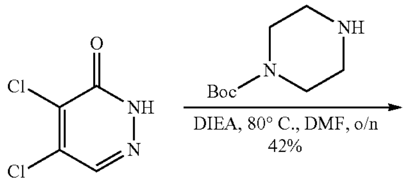

-continued

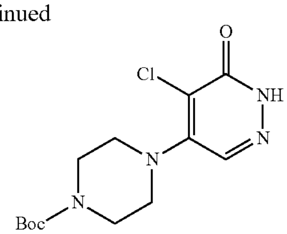

To a solution of 4,5-dichloropyridazin-3(2H)-one (10 g, 60.6 mmol), in N,N-dimethylformamide (40 mL) was added tert-butyl piperazine-1-carboxylate (22.5 g, 121.2 mmol) and DIEA (25 g, 182 mmol). The mixture was stirred at 80° C. overnight. After cooling to room temperature, the misture was filtered, and the residue was washed with ethyl acetate (100 mL×3) and DCM(100 mL×3) to give compound tert-butyl 4-(5-chloro-6-oxo-1,6-dihydropyridazin-4-yl)piperazine-1-carboxylate (8 g, 42% yield) as pale yellow solid.

LCMS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM $NH_4HCO_3$] and 10% [$CH_3CN$] to 5% [water+10 mM $NH_4HCO_3$] and 95% [$CH_3CN$] in 0.5 min, then under this condition for 1.5 min, finally changed to 90% [water+10 mM $NH_4HCO_3$] and 10% [$CH_3CN$] in 0.1 min and under this condition for 0.5 min.) Purity is 87.88%. Rt=0.903 min; MS Calcd.:314.77 MS Found: 315.2 $[M+H]^+$.

Chemical Formula: $C_{13}H_{19}ClN_4O_3$, Molecular Weight: 314.77

Step 7: Synthesis of tert-butyl 4-(5-chloro-1-(2,6-dioxopiperidin-3-yl)-6-oxo-1,6-dihydropyridazin-4-yl)piperazine-1-carboxylate

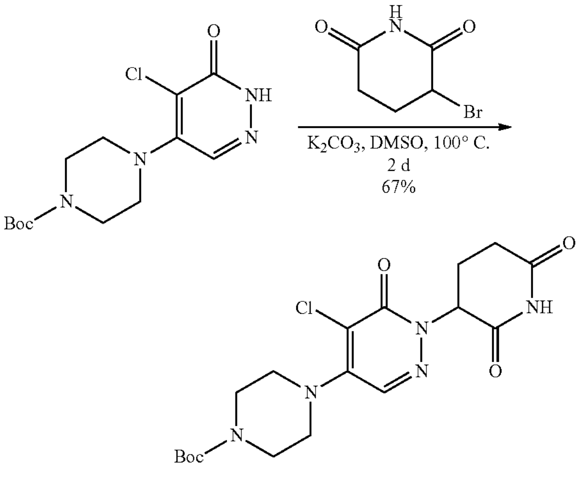

To a solution of 1-bromo-4-(5-bromopentyloxy)benzene (4 g, 12.7 mmol) in DMSO (20 mL) was added 3-bromopiperidine-2,6-dione (4.8 mg, 25.4 mmol) and potassium carbonate (5.3 g, 38.1 mmol). The mixture was stirred at 40° C. for two days. After cooling to room temperature, the misture was filtered, and the residue was washed with ethyl acetate (20 mL×3) and DCM(20 mL×3). The combined organic phases were dried over anhydrous sodium sulfate and concentrated in vacuo and purified by column chromatography on silica gel (petroether/ethyl acetate=1:4) to give tert-butyl 4-(5-chloro-1-(2,6-dioxopiperidin-3-yl)-6-oxo-1,6-dihydropyridazin-4-yl)piperazine-1-carboxylate (3.7 g, 67% yield) as pale yellow solid.

Step 8: Synthesis of tert-butyl 4-(1-(2,6-dioxopiperidin-3-yl)-6-oxo-1,6-dihydropyridazin-4-yl)piperazine-1-carboxylate

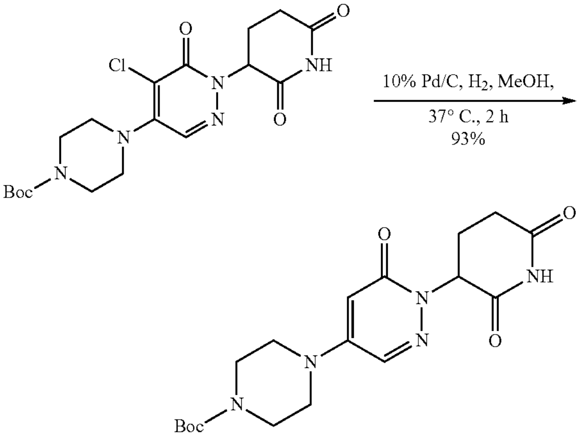

A mixture of tert-butyl 4-(5-chloro-1-(2,6-dioxopiperidin-3-yl)-6-oxo-1,6-dihydropyridazin-4-yl)piperazine-1-carboxylate (300 mg, 0.7 mmol) and 10% palladium on activated carbon (90 mg) in MeOH (30 mL) was stirred under 1 atm hydrogen atmosphere at 37° C. overnight. It was filtered to remove the solid, the filtrate was concentrated in vacuo to give 3-(4-(3-hydroxypropoxy)-6-oxopyridazin-1(6H)-yl)piperidine-2,6-dione (190 mg, 93% yield) as a yellow solid.

LC-MS (Agilent LCMS 1200-6120, Column: Waters X-Bridge C18 (30 mm×6 mm×5 μm); Column Temperature: 40° C.; Flow Rate: 2.0 mL/min; Mobile Phase: from 90% [water+10 mM $NH_4HCO_3$] and 10% [$CH_3CN$] to 5% [water+10 mM $NH_4HCO_3$] and 95% [$CH_3CN$] in 0.5 min, then under this condition for 1.5 min, finally changed to 90% [water+10 mM $NH_4HCO_3$] and 10% [$CH_3CN$] in 0.1 min and under this condition for 0.5 min.). Purity is 77.70%. Rt=0.873 min; MS Calcd.: 391.42. MS Found: 392.2 $[M+H]^+$.

Chemical Formula: $C_{18}H_{25}N_5O_5$, Molecular Weight: 391.42

Step 9: Synthesis of 3-(6-oxo-4-(piperazin-1-yl)pyridazin-1(6H)-yl)piperidine-2,6-dione

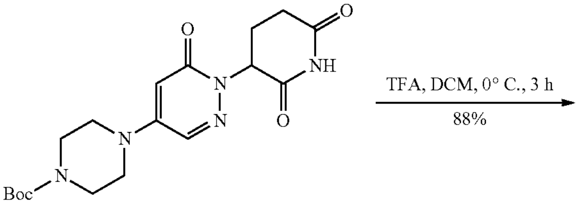

-continued

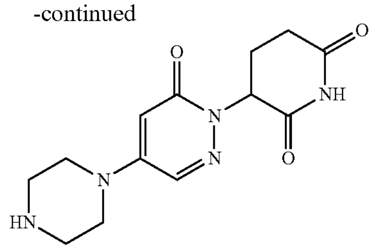

To a solution of 3-(4-(3-hydroxypropoxy)-6-oxopyridazin-1(6H)-yl)piperidine-2,6-dione (50 mg, 0.10 mmol) in DCM (3 mL) and trifluoroacetic acid (3 mL) was stirred at rt for 3 h. Then the solvent was directly removed to give 3-(6-oxo-4-(piperazin-1-yl)pyridazin-1(6H)-yl)piperidine-2,6-dione(124 mg, crude, 88% yield) which was directly used to the next step without further purification.

Step 10: Synthesis of N-((1r,3r)-3-(3-chloro-4-cyanophenoxy)-2,2,4,4-tetramethylcyclobutyl)-6-(4-(4-(1-(2,6-dioxopiperidin-3-yl)-6-oxo-1,6-dihydropyridazin-4-yl)piperazin-1-yl)butyl)nicotinamide during 6 hours at room temperature. The resulting mixture was stirred at room temperature for another 1 hour. The reaction mixture was concentrated, diluted with brine (15 mL) and extracted with $CH_2Cl_2$/MeOH (10/1, 20 mL×2). The organic was dried over $Na_2SO_4$, filtered, concentrated and purified by Prep-HPLC to give N-((1r,3r)-3-(3-chloro-4-cyanophenoxy)-2,2,4,4-tetramethylcyclobutyl)-6-(4-(4-(1-(2,6-dioxopiperidin-3-yl)-6-oxo-1,6-dihydropyridazin-4-yl)piperazin-1-yl)butyl)nicotinamide (56 mg, 27% yield) as a pale yellow solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min.). Purity is 99.06%, Rt=2.650 min; MS Calcd.: 728.3; MS Found: 729.4 $[M+H]^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95%

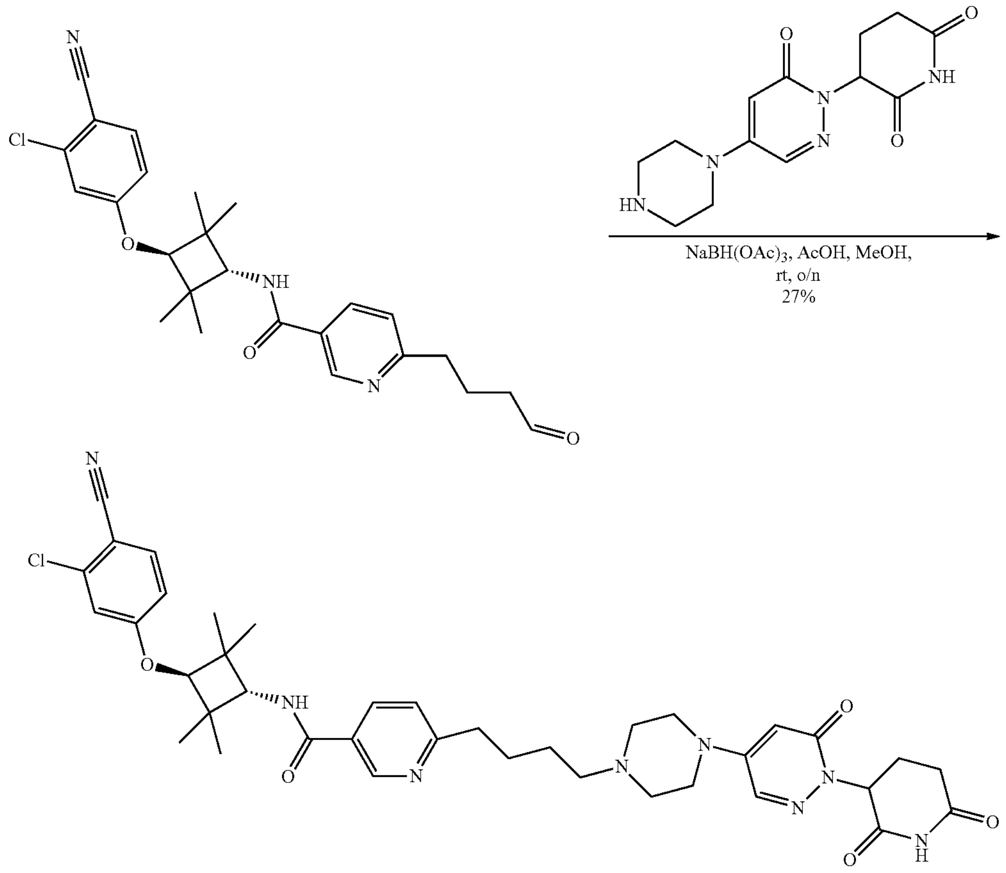

To a solution of 3-(6-oxo-4-(piperazin-1-yl)pyridazin-1(6H)-yl)piperidine-2,6-dione (100 mg, 0.34 mmol), N-((1r,3r)-3-(3-chloro-4-cyanophenoxy)-2,2,4,4-tetramethylcyclobutyl)-6-(4-oxobutyl)nicotinamide (130 mg, 0.29 mmol) in MeOH (6 mL) was added acetic acid(3 drops), then $NaBH_3CN$ (23 mg, 0.35 mmol) was added in 7 portions

[water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 96.51%, Rt=9.185 min.

$^1H$ NMR (400 MHz, $CDCl_3$) δ 1.16 (7H, s), 1.21 (7H, s), 1.71-1.75 (2H, m), 2.13-2.16 (1H, m), 2.34-2.37 (2H, m), 2.45-2.47 (4H, m), 2.55-2.71 (2H, m), 2.77-2.84 (3H, m), 3.25-3.28 (4H, m), 3.99 (1H, s), 4.09 (1H, d, J=8.4 Hz), 5.63-5.68 (1H, m), 5.82 (1H, d, J=2.8 Hz), 6.11 (1H, d, J=8.0 Hz), 6.74 (1H, dd, J=8.8, 2.4 Hz), 6.90 (1H, d, J=2.0 Hz), 7.21 (1H, s), 7.50 (1H, d, J=8.8 Hz), 7.64 (1H, d, J=3.2 Hz), 7.91 (1H, brs), 7.96 (1H, dd, J=8.0, 2.0 Hz), 8.83 (1H, d, J=1.6 Hz).

Chemical Formula: $C_{38}H_{45}ClN_8O_5$, Molecular Weight: 729.27

Total H count from HNMR data: 45.

Synthesis of Exemplary PROTAC 70

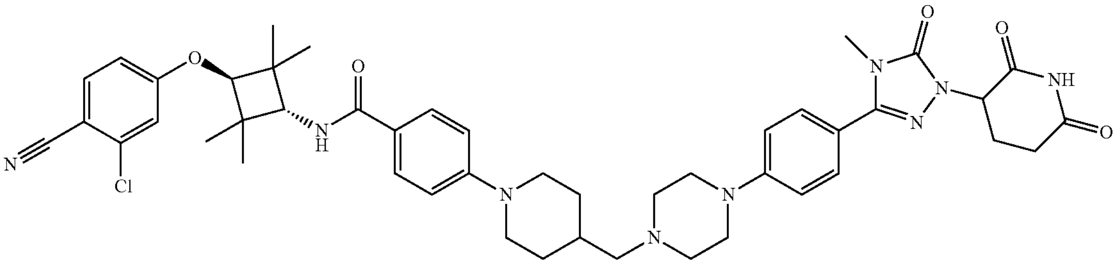 [SMILES: Cn1c(-c2ccc(N3CCN(CC4CCN(c5ccc(C(=O)N[C@H]6C(C)(C)[C@H](Oc7ccc(C#N)c(Cl)c7)C6(C)C)cc5)CC4)CC3)cc2)nn(C2CCC(=O)NC2=O)c1=O]

N-((1r,3r)-3-(3-chloro-4-cyanophenoxy)-2,2,4,4-tetramethyl cyclobutyl)-4-(4-((4-(4-(1-(2,6-dioxopiperidin-3-yl)-4-methyl-5-oxo-4,5-dihydro-1H-1,2,4-triazol-3-yl)phenyl)piperazin-1-yl)methyl)piperidin-1-yl)benzamide Synthetic Scheme

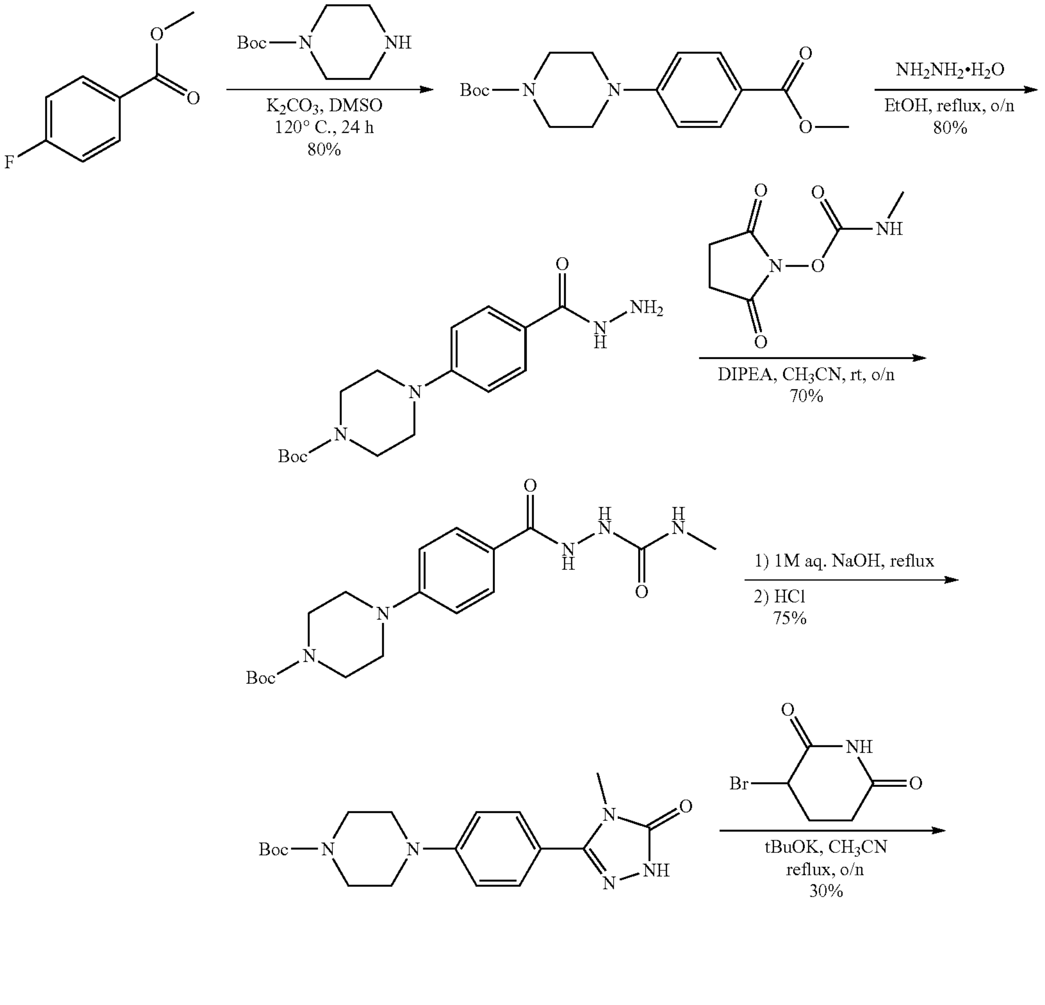

-continued
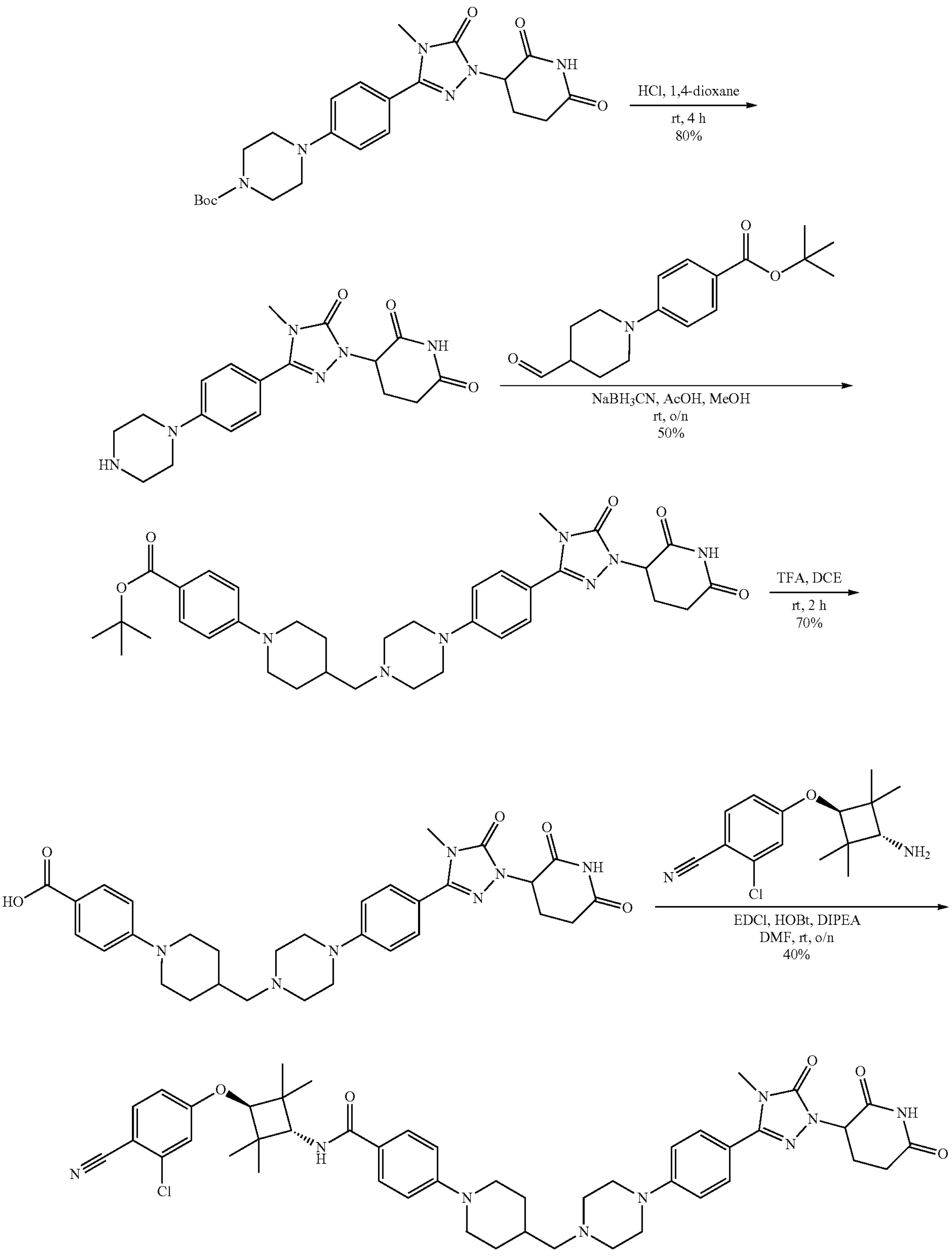

Step 1: Synthesis of tert-butyl 4-(4-(methoxycarbonyl)phenyl)piperazine-1-carboxylate

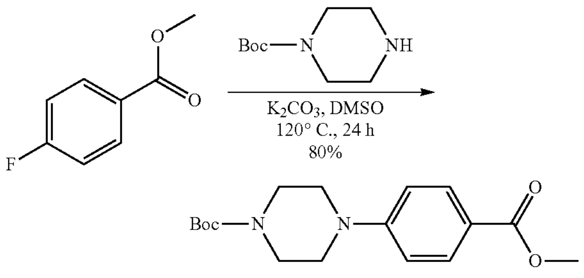

The mixture of methyl 4-fluorobenzoate (3.1 g, 20.0 mmol) tert-butyl piperazine-1-carboxylate (3.7 g, 20.0 mmol) and potassium carbonate (2.7 g, 40.0 mmol) in dimethyl sulfoxide (30 mL) was heaed at 120° C. for 24 hours. The mixture was poured into water (100 mL) and extracted with ethyl acetate (50 mL×3). The combined organic phase was concentrated in vacuo to give tert-butyl 4-(4-(methoxycarbonyl)phenyl)piperazine-1-carboxylate (5.1 g, 80% yield) as a white solid.

Chemical Formula: $C_{17}H_{24}NO_2$, Molecular Weight: 320.38

Step 2: Synthesis of tert-butyl 4-(4-(hydrazinecarbonyl)phenyl)piperazine-1-carboxylate

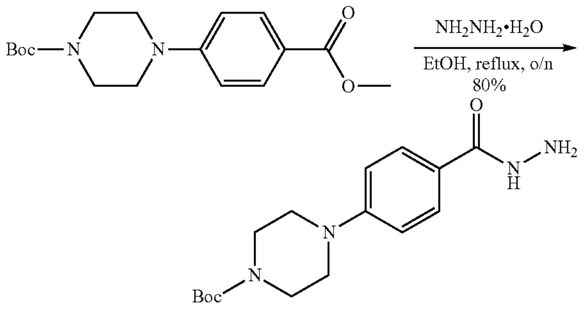

The mixture of tert-butyl 4-(4-(methoxycarbonyl)phenyl) piperazine-1-carboxylate (3.2 g, 10.0 mmol) and hydrazine hydrate (1.0 g, 20.0 mmol) in ethanol (30 mL) was refluxed overnight. The mixture was concentrated to give tert-butyl 4-(4-(hydrazinecarbonyl)phenyl)piperazine-1-carboxylate (2.6 g, 80% yield) as a white solid used directly.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min.) Purity is 78.9%, Rt=1.609 min. MS Calcd.: 320.1; MS Found: 321.3 $[M+H]^+$.

Chemical Formula: $C_{16}H_{24}N_4O_3$, Molecular Weight: 320.39

Step 3: Synthesis of tert-butyl 4-(4-(2-(methylcarbamoyl)hydrazinecarbonyl) phenyl)piperazine-1-carboxylate

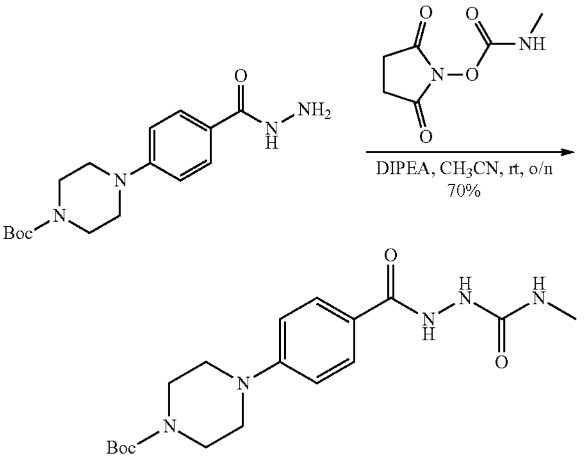

A mixture of tert-butyl 4-(4-(hydrazinecarbonyl)phenyl) piperazine-1-carboxylate (2.0 g, 6.3 mmol) and 2,5-dioxopyrrolidin-1-yl methylcarbamate (1.1 g, 6.3 mmol) in acetonitrile (30 mL) was stirred at room temperature overnight. The mixture was poured into water (30 mL) and filtered to give tert-butyl 4-(4-(2-(methylcarbamoyl)hydrazinecarbonyl)phenyl)piperazine-1-carboxylate (1.7 g, 70%) as a white solid.

Chemical Formula: $C_{18}H_{27}N_5O_4$, Molecular Weight: 377.44

Step 4: Synthesis of tert-butyl 4-(4-(4-methyl-5-oxo-4,5-dihydro-1H-1,2,4-triazol-3-yl)phenyl)piperazine-1-carboxylate

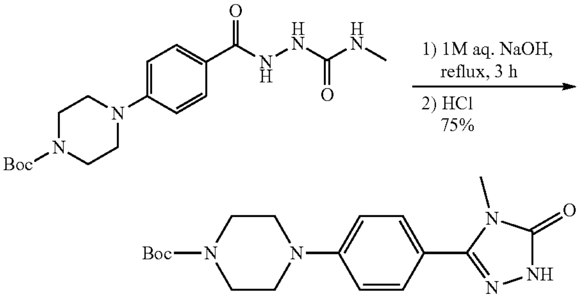

The mixture of tert-butyl 4-(4-(2-(methylcarbamoyl)hydrazinecarbonyl)phenyl)piperazine-1-carboxylate (1.7 g, 4.5 mmol) and sodium hydroxide (360 mg, 9.0 mmol) in water (15 mL) was refluxed for 3 hours. The mixture was cooled to room temperature and the pH value of the mixture was adjusted to 5-6 by hydrochloride acid (1.0 N). The mixture was extracted with dichloromethane (30 mL×3) and the combined organic phase was concentrated in vacuo to give tert-butyl 4-(4-(4-methyl-5-oxo-4,5-dihydro-1H-1,2,4-triazol-3-yl)phenyl)piperazine-1-carboxylate (1.2 g, 75% yield) as a white solid.

Chemical Formula: $C_{18}H_{25}N_5O_3$, Molecular Weight: 359.42

Step 5: Synthesis of tert-butyl 4-(4-(1-(2,6-dioxopiperidin-3-yl)-4-methyl-5-oxo-4,5-dihydro-1H-1,2,4-triazol-3-yl)phenyl)piperazine-1-carboxylate

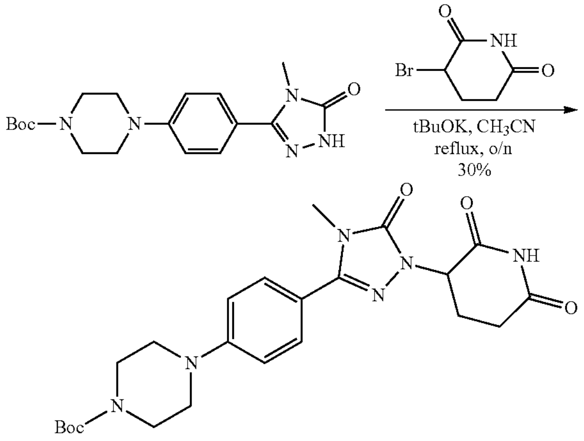

The mixture of tert-butyl 4-(4-(4-methyl-5-oxo-4,5-dihydro-1H-1,2,4-triazol-3-yl)phenyl)piperazine-1-carboxylate (1.2 g, 3.3 mmol), 3-bromopiperidine-2,6-dione (1.3 g, 6.6 mmol) and potassium tert-butoxide (1.1 g, 9.9 mmol) in acetonitrile (20 mL) was refluxed overnight. The mixture was poured into saturated ammonium chloride solution (30 mL) and extracted with dichloromethane (30 mL×3). The combined organic phase was concentrated in vacuo and the residue was purified by Prep-HPLC to give tert-butyl 4-(4-(1-(2,6-dioxopiperidin-3-yl)-4-methyl-5-oxo-4,5-dihydro-1H-1,2,4-triazol-3-yl)phenyl)piperazine-1-carboxylate (465 mg, 30% yield) as a white solid.

Chemical Formula: $C_{23}H_{30}N_6O_5$, Molecular Weight: 470.52

Step 6: Synthesis of 3-(4-methyl-5-oxo-3-(4-(piperazin-1-yl)phenyl)-4,5-dihydro-1H-1,2,4-triazol-1-yl)piperidine-2,6-dione

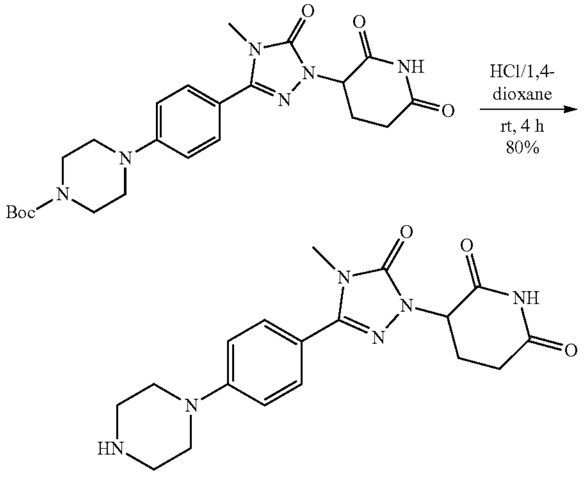

A solution of tert-butyl 4-(4-(1-(2,6-dioxopiperidin-3-yl)-4-methyl-5-oxo-4,5-dihydro-1H-1,2,4-triazol-3-yl)phenyl)piperazine-1-carboxylate (465 mg, 0.99 mmol) in dry hydrochloride/1,4-dioxane(20 mL, 4.0 N.) was stirred at room temperature for 4 h. The mixture was concentrated in vacuo to give 3-(4-methyl-5-oxo-3-(4-(piperazin-1-yl)phenyl)-4,5-dihydro-1H-1,2,4-triazol-1-yl)piperidine-2,6-dione (293 mg, 80% yield) as a white solid.

Chemical Formula: $C_{18}H_{22}N_6O_3$, Molecular Weight: 370.41

Step 7: Synthesis of tert-butyl 4-(4-(hydroxymethyl)piperidin-1-yl)benzoate

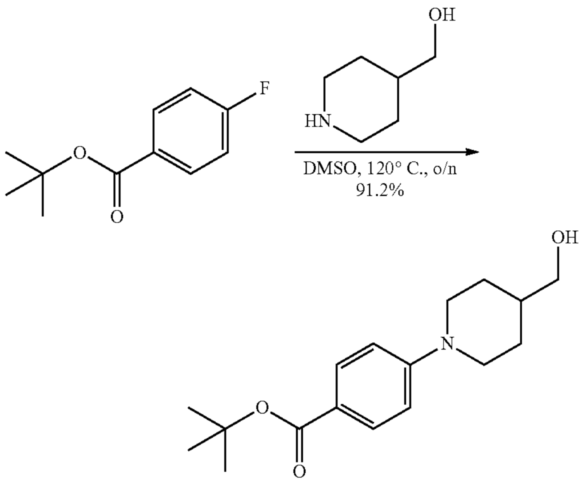

To a solution of tert-butyl 4-fluorobenzoate (23 g, 0.12 mmol) in DMSO (100 mL) was added piperidin-4-ylmethanol (40.5 g, 0.35 mmol). The mixture was heated to 120° C. overnight under nitrogen. After cooling to room temperature, water (50 mL) was added to the reaction mixture, and extracted with ethyl acetate (20 mL×3). The organic layer was washed with brine (15 mL×3). The combined organic phases were dried over anhydrous sodium sulfate and concentrated in vacuo, and purified by CC (PE/EA=10:1) to give compound tert-butyl 4-(4-(hydroxymethyl)piperidin-1-yl)benzoate (31 g, 91.2%) as a white solid.

LCMS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 90% [(total 10 mM $AcONH_4$) water/$CH_3CN$=900/100 (v/v)] and 10% [(total 10 mM $AcONH_4$) water/$CH_3CN$=100/900 (v/v)] to 10% [(total 10 mM $AcONH_4$) water/$CH_3CN$=900/100 (v/v)] and 90% [(total 10 mM $AcONH_4$) water/$CH_3CN$=100/900 (v/v)] in 1.6 min, then under this condition for 2.4 min, finally changed to 90% [(total 10 mM $AcONH_4$) water/$CH_3CN$=900/100 (v/v)] and 10% [(total 10 mM $AcONH_4$) water/$CH_3CN$=100/900 (v/v)] in 0.1 min and under this condition for 0.7 min). Purity is 99.57%, Rt=2.035 min.; MS Calcd.: 291.2; MS Found: 292.2 [M+H]+.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 93.27%, Rt=9.542 min.

$^1$H NMR (400 MHz, $CDCl_3$) δ 1.29-1.40 (2H, m), 1.49 (1H, d, J=5.4 Hz), 1.57 (9H, s), 1.70-1.75 (1H, m), 1.82 (2H, d, J=12.8 Hz), 2.80-2.87 (2H, m), 3.53 (2H, t, J=5.8 Hz), 3.87-3.90 (2H, m), 6.85 (2H, d, J=9.2 Hz), 7.84 (2H, d, J=9.2 Hz).

Chemical Formula: $C_{17}H_{25}NO_3$, Molecular Weight: 291.39

Total H count from HNMR data: 25.

Step 8: Synthesis of tert-butyl 4-(4-formylpiperidin-1-yl)benzoate

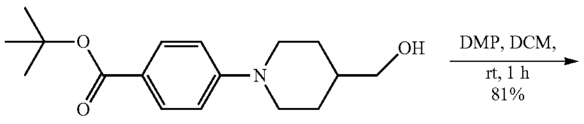

-continued

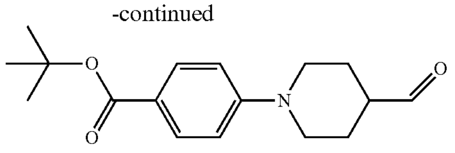

To a solution of tert-butyl 4-(4-(hydroxymethyl)piperidin-1-yl)benzoate (300 mg, 1.03 mmol) in dichloromethane (20 mL) was added Dess-Martin periodinane (1.31 g, 3.09 mmol) slowly at 0° C. The reaction mixture was stirred at room temperature for 1 hour. Then filtered, and concentrated in vacuo to give compound tert-butyl 4-(4-formylpiperidin-1-yl)benzoate (240 mg, 81%) as a pale yellow solid.

Step 9: Synthesis of tert-butyl 4-(4-((4-(4-(1-(2,6-dioxopiperidin-3-yl)-4-methyl-5-oxo-4,5-dihydro-1H-1,2,4-triazol-3-yl)phenyl)piperazin-1-yl)methyl)piperidin-1-yl)benzoate

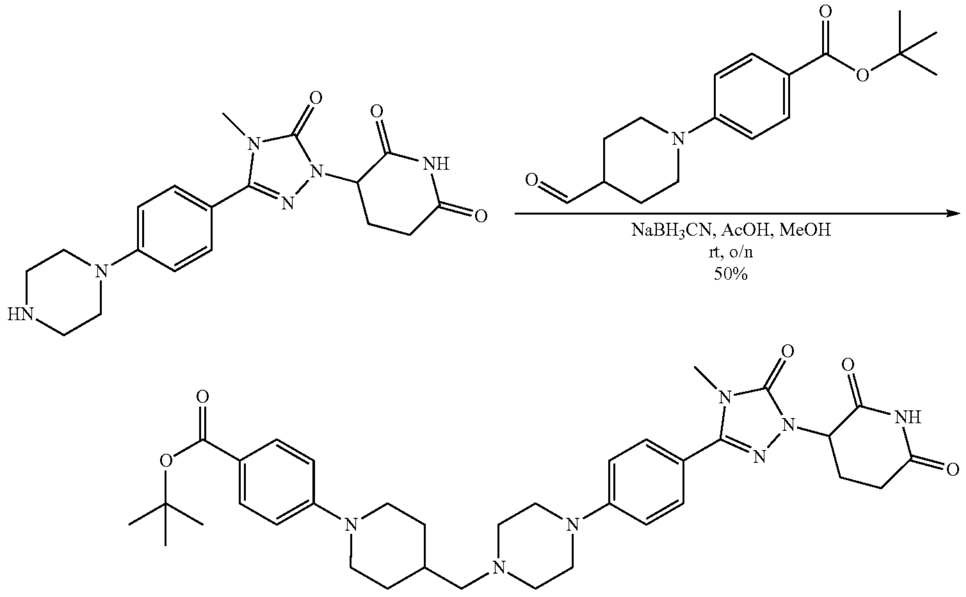

The mixture of 3-(4-methyl-5-oxo-3-(4-(piperazin-1-yl)phenyl)-4,5-dihydro-1H-1,2,4-triazol-1-yl)piperidine-2,6-dione (200 mg, 0.54 mmol), tert-butyl 4-(4-formylpiperidin-1-yl)benzoate (156 mg, 0.54 mmol), sodium cyanoborohydride (100 mg, 1.6 mmol) and acetic acid (0.5 mL) in methanol (10 mL) was stirring at room temperature overnight. The mixture was poured into water (20 mL) and extracted with dichloromethane (20 mL×3). The combined organic phase was purified by column chromatography on silica gel (dichloromethane/methanol=20/1) to give tert-butyl 4-(4-((4-(4-(1-(2,6-dioxopiperidin-3-yl)-4-methyl-5-oxo-4,5-dihydro-1H-1,2,4-triazol-3-yl)phenyl)piperazin-1-yl)methyl)piperidin-1-yl)benzoate (173 mg, 50% yield) as a brown solid.

Chemical Formula: $C_{35}H_{45}N_7O_5$, Molecular Weight: 643.78

Step 10: Synthesis of 4-(4-((4-(4-(1-(2,6-dioxopiperidin-3-yl)-4-methyl-5-oxo-4,5-dihydro-1H-1,2,4-triazol-3-yl)phenyl)piperazin-1-yl)methyl)piperidin-1-yl)benzoic acid

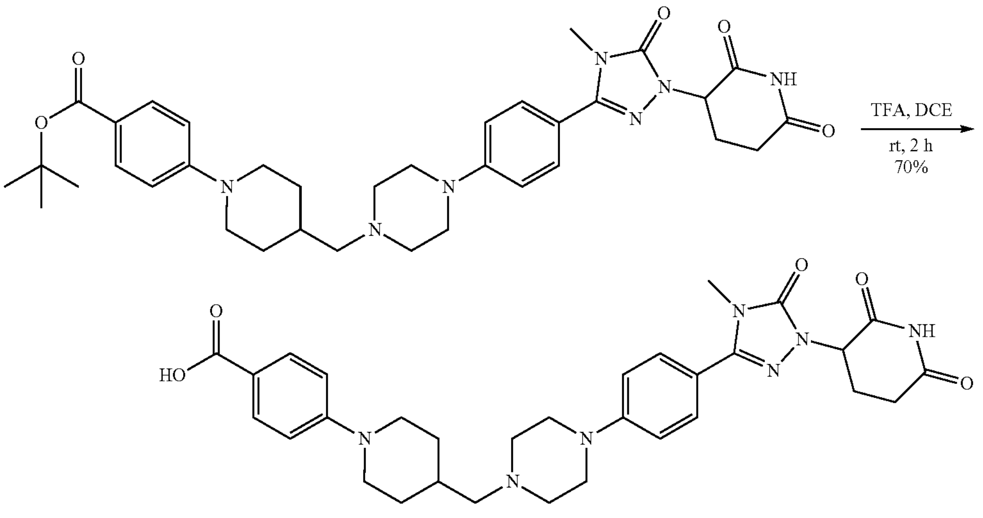

The mixture of tert-butyl 4-(4-((4-(4-(1-(2,6-dioxopiperidin-3-yl)-4-methyl-5-oxo-4,5-dihydro-1H-1,2,4-triazol-3-yl)phenyl)piperazin-1-yl)methyl)piperidin-1-yl)benzoate (150 mg, 0.23 mmol) and trifluoroacetic acid (265 mg, 2.3 mmol) in 1,2-dichloroethane (10 mL) was stirred for 2 h. The mixture was concentrated in vacuo to give 4-(4-((4-(4-(1-(2,6-dioxopiperidin-3-yl)-4-methyl-5-oxo-4,5-dihydro-1H-1,2,4-triazol-3-yl)phenyl)piperazin-1-yl)methyl)piperidin-1-yl)benzoic acid (95 mg, 70% yield) as a brown solid, which was directly used to next step without further purification.

Chemical Formula: $C_{31}H_{37}N_7O_5$, Molecular Weight: 587.67

Step 11: Synthesis of N-((1r,3r)-3-(3-chloro-4-cyanophenoxy)-2,2,4,4-tetramethylcyclobutyl)-4-(4-((4-(4-(1-(2,6-dioxopiperidin-3-yl)-4-methyl-5-oxo-4,5-dihydro-1H-1,2,4-triazol-3-yl)phenyl)piperazin-1-yl)methyl)piperidin-1-yl)benzamide

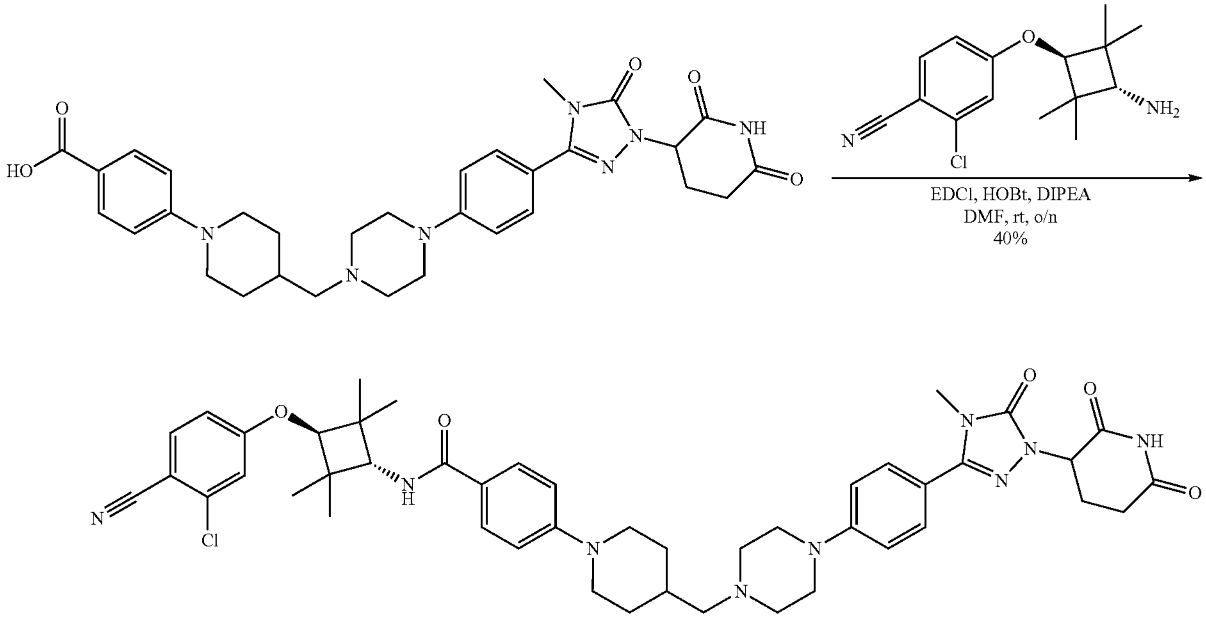 [SMILES: Cn1c(-c2ccc(N3CCN(CC4CCN(c5ccc(C(=O)O)cc5)CC4)CC3)cc2)nn(C2CCC(=O)NC2=O)c1=O ; CC1(C)[C@H](N)C(C)(C)[C@H]1Oc1ccc(C#N)c(Cl)c1 ; "EDCl, HOBt, DIPEADMF, rt, o/n40%" ; Cn1c(-c2ccc(N3CCN(CC4CCN(c5ccc(C(=O)N[C@H]6C(C)(C)[C@H](Oc7ccc(C#N)c(Cl)c7)C6(C)C)cc5)CC4)CC3)cc2)nn(C2CCC(=O)NC2=O)c1=O]

The mixture of 4-(4-((4-(4-(1-(2,6-dioxopiperidin-3-yl)-4-methyl-5-oxo-4,5-dihydro-1H-1,2,4-triazol-3-yl)phenyl)piperazin-1-yl)methyl)piperidin-1-yl)benzoic acid (95 mg, 0.16 mmol), 4-((1r,3r)-3-amino-2,2,4,4-tetramethylcyclobutoxy)-2-chlorobenzonitrile (45 mg, 0.16 mmol), 2-(7-azabenzotriazol-1-yl)-N,N,N',N'-tetramethyluronium hexafluorophosphate (91 mg, 0.24 mmol) and ethyldiisopropylamine (62 mg, 0.48 mmol) in N,N-dimethylformamide (5 mL) was stirring at room temperature overnight. The mixture was poured into water (10 mL) and extracted with dichloromethane (10 mL×3). The combined organic phase was concentrated in vacuo and the residue was purified by Prep-HPLC to give N-((1r,3r)-3-(3-chloro-4-cyanophenoxy)-2,2,4,4-tetramethylcyclobutyl)-4-(4-((4-(4-(1-(2,6-dioxopiperidin-3-yl)-4-methyl-5-oxo-4,5-dihydro-1H-1,2,4-triazol-3-yl)phenyl)piperazin-1-yl)methyl)piperidin-1-yl)benzamide (54 mg, 40% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min). Purity is 99.4%, Rt=3.160 min; MS Calcd.: 847.3; MS Found: 848.4 $[M+H]^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 94.0%, Rt=10.750 min.

$^1H$ NMR (400 MHz, DMSO-$d_6$) δ 1.12 (7H, brs), 1.21 (8H, brs), 1.79-1.82 (3H, m), 2.08-2.12 (1H, m), 2.20-2.22 (2H, m), 2.41-2.45 (3H, m), 2.59-2.63 (1H, m), 2.76-2.87 (3H, m), 3.26-3.27 (5H, m), 3.30 (3H, s), 3.84-3.87 (2H, m), 4.04-4.06 (1H, m), 4.32 (1H, s), 5.18 (1H, dd, J=5.6, 12.8 Hz), 6.94-7.05 (5H, m), 7.20 (1H, d, J=2.4 Hz), 7.47-7.53 (3H, m), 7.73 (1H, d, J=8.8 Hz), 7.90 (1H, d, J=8.8 Hz), 11.0 (1H, s).

Chemical Formula: $C_{46}H_{54}ClN_9O_5$, Molecular Weight: 848.43

Total H count from HNMR data: 54

Synthesis of Exemplary PROTAC 79

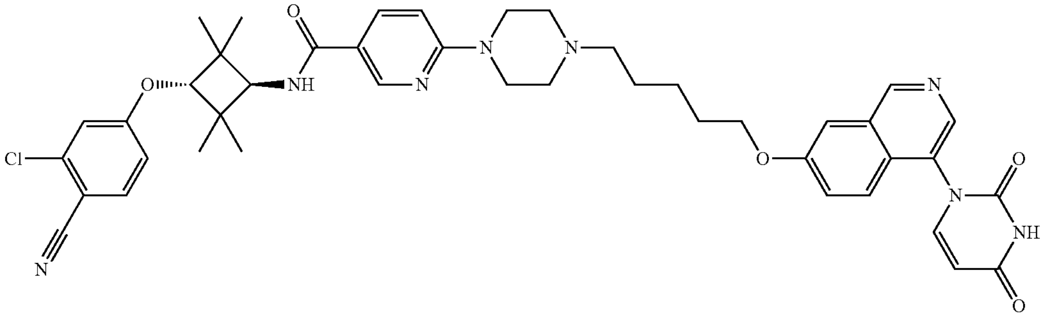 [SMILES: CC1(C)[C@H](NC(=O)c2ccc(N3CCN(CCCCCOc4ccc5c(-n6ccc(=O)[nH]c6=O)cncc5c4)CC3)nc2)C(C)(C)[C@H]1Oc1ccc(C#N)c(Cl)c1]

N-((1r,3 r)-3-(3-chloro-4-cyanophenoxy)-2,2,4,4-tetramethylcyclobutyl)-6-(4-(5-((4-(2,4-dioxo-3,4-dihydropyrimidin-1(2H)-yl)isoquinolin-7-yl)oxy)pentyl)piperazin-1-yl)nicotinamide Synthetic Scheme

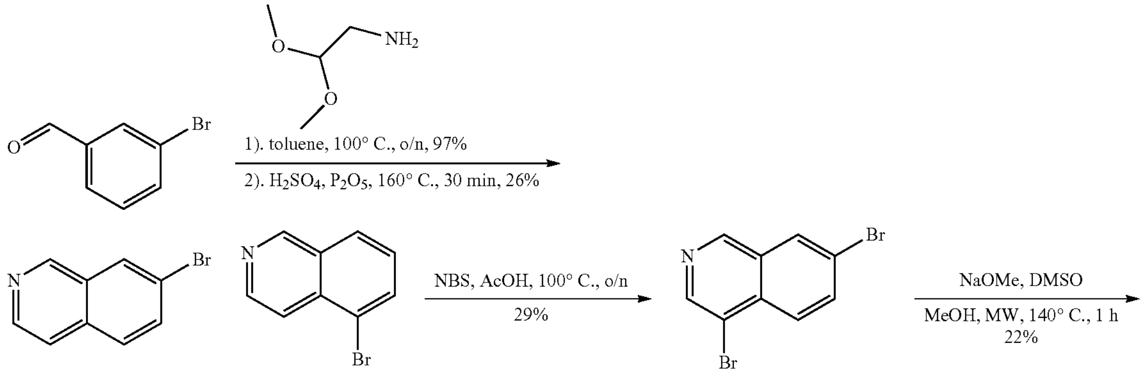

-continued
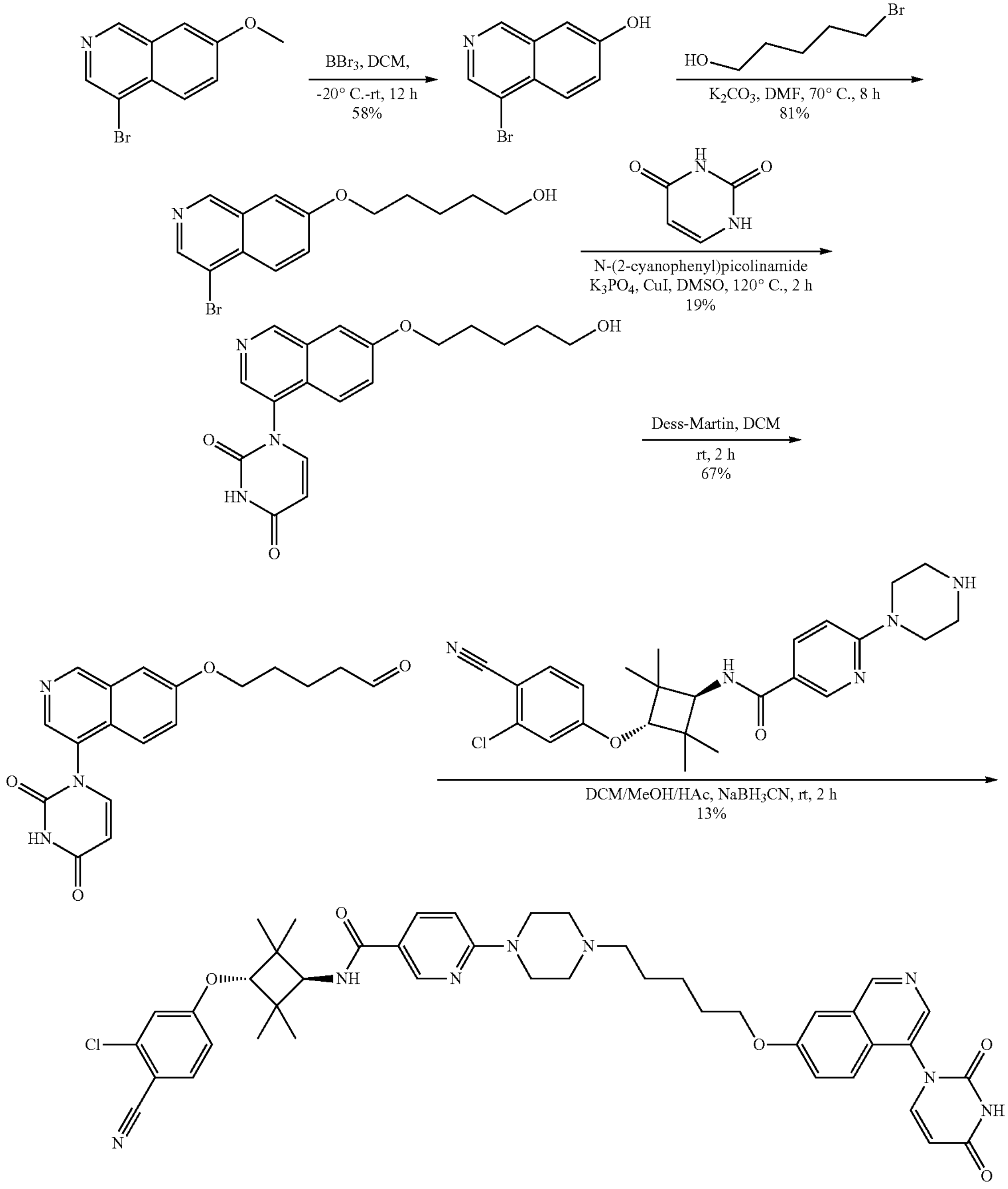
Step 1: Synthesis of 7-bromoisoquinoline
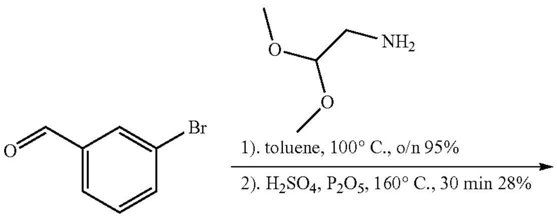
-continued
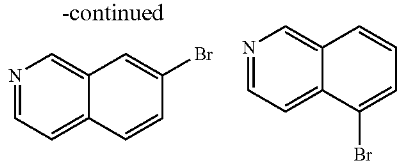
To a solution of 3-bromobenzaldehyde (50.0 g, 0.27 mol) in toluene (250 mL) was added aminoacetaldehyde dimethyl acetal (31.1 g, 0.30 mol) was stirred at room temperature for few minutes, then heated at 100° C. overnight. The reaction solvent was evaporated to afford 3-bromobenzalaminoacetal (70 g, 95%) as yellow oil which was directly used to next step without further purification.

To a solution of phosphorus pentoxide (140 g, 2v) in concentrated sulphuric acid (70 mL, 1v) stirred at room temperature for few minutes, then stirred at 0° C., 3-bromobenzalaminoacetal (70 g, 0.26 mol) was added slowly to the mixture prepared above. Then the mixture was heated to 160° C. for 30 minutes. After cooling to room temperature, the reaction mixture was carefully poured into ice water (100 mL) while vigorously stirred, then filtered, the pH was further increased to 9 using saturated sodium hydroxide and extracted with dichloromethane (100 mL×3), the combined organic phases were dried over anhydrous sodium sulfate, filtered, and concentrated in vacuo, and purified by silica gel (petroleum ether/ethyl acetate=6:1) to give mixture of 7-bromoisoquinoline and 5-bromoisoquinoline (15.0 g, 28%) as a yellow solid.

Step 2: Synthesis of 4,7-dibromoisoquinoline

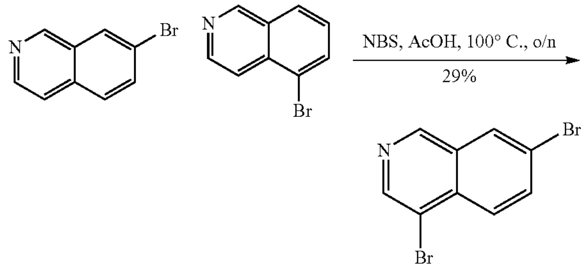

To a solution of a mixture of 7-bromoisoquinoline and 5-bromoisoquinoline (15.0 g, 0.072 mol) in acetic acid (30 mL) was added N-bromosuccinimide (19.3 g, 0.11 mol). The mixture was heated to 100° C. overnight under nitrogen. After cooling to room temperature, water (10 mL) was added to the reaction mixture and neutralized by saturated sodium hydroxide then extracted with ethyl acetate (10 mL×3). The combined organic phases were dried over anhydrous sodium sulfate and concentrated in vacuo, and purified by silica gel (petroleum ether/ethyl acetate=15:1) to give compound 4,7-dibromoisoquinoline (6.0 g, 29%) as a yellow solid.

$^1$H NMR (400 MHz, $CDCl_3$) δ 7.87-7.90 (1H, m), 8.05 (1H, d, J=8.8 Hz), 8.15 (1H, m), 8.75 (1H, s), 9.01 (1H, s).

Chemical Formula: $C_9H_5Br_2N$, Molecular Weight: 286.95

Total H count from HNMR data: 5.

Step 3: Synthesis of 4-bromo-7-methoxyisoquinoline

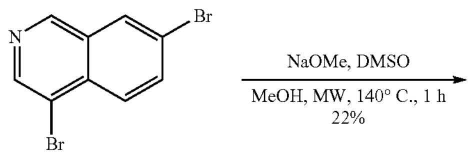

-continued

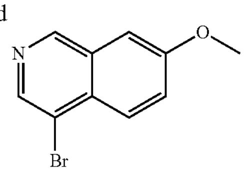

To a solution of 4,7-dibromoisoquinoline (1.0 g, 3.5 mmol) in dimethyl sulfoxide/methanol (4:3) (10 mL) was added sodium methanolate (0.3 g, 5.6 mmol). The mixture was heated in a microwave reactor at 140° C. for 1 hour. Water (5 mL) was added to the mixture and extracted with ethyl acetate (5 mL×3). The combined organic layer was washed with brine (5 mL×2), dried over anhydrous sodium sulfate, filtered and concentrated in vacuo and purified by silica gel (petroleum ether/ethyl acetate=10:1) to give 4-bromo-7-methoxyisoquinoline (180 mg, 22%) as a yellow solid.

$^1$H NMR (400 MHz, DMSO-$d^6$) δ 3.95 (3H, s), 7.57-7.60 (1H, m), 7.63 (1H, d, J=2.4 Hz), 7.99 (1H, d, J=8.8 Hz), 8.59 (1H, s), 9.21 (1H, s).

Chemical Formula: $C_{10}H_8BrNO$, Molecular Weight: 238.08

Total H count from HNMR data: 8.

Step 4: Synthesis of 4-bromoisoquinolin-7-ol

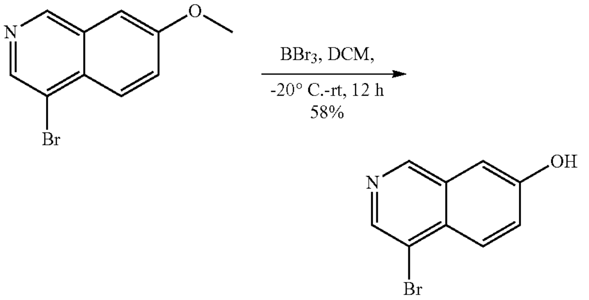

To a solution of 4-bromo-7-methoxyisoquinoline (110 mg, 0.46 mmol) in dichloromethane (2 mL) was added $BBr_3$ (1.0M) in dichloromethane (4.6 mL, 4.6 mmol) at −20° C., then stirred at room temperature for 12 hours. The reaction mixture was poured in cold water and neutralized with saturated sodium bicarbonate, then extracted with dichloromethane (5 mL×3). The combined organic layer was dried over anhydrous sodium sulfate, filtered and concentrated in vacuo and purified by prep-TLC (petroether/ethyl acetate=3:1) to give 4-bromoisoquinolin-7-ol (60 mg, 58%) as light oil.

LC-MS (Agilent LCMS 1200-6120, Column: Waters X-Bridge C18 (30 mm×4.6 mm×3.5 μm); Column Temperature: 40° C.; Flow Rate: 1.5 mL/min; Mobile Phase: from 90% [water+10 mM $NH_4HCO_3$] and 10% [$CH_3CN$] to 5% [water+10 mM $NH_4HCO_3$] and 95% [$CH_3CN$] in 0.5 min, then under this condition for 1.5 min, finally changed to 90% [water+10 mM $NH_4HCO_3$] and 10% [$CH_3CN$] in 0.1 min and under this condition for 0.5 min). Purity is 90.50%, Rt=1.078 min; MS Calcd.: 223.7; MS Found: 224.7 $[M+H]^+$.

Step 5: Synthesis of 5-(4-bromoisoquinolin-7-yloxy)pentan-1-ol

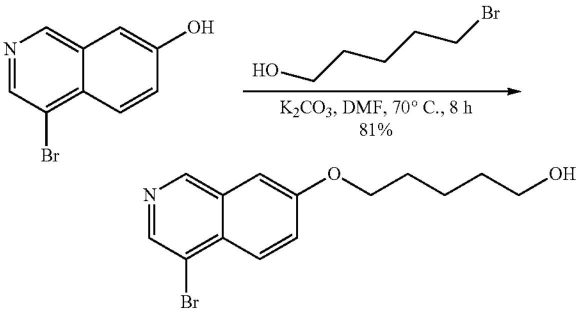

To a solution of compound 4-bromoisoquinolin-7-ol (0.90 g, 4.02 mmol) in DMF (10 mL) was added 5-bromopentan-1-ol (0.66 g, 4.02 mmol) and potassium carbonate (0.74 g, 8.04 mmol), then stirred at 70° C. for 8 hours. The reaction mixture was poured in cold water and extracted with dichloromethane/methanol (10 mL×3). The combined organic layer was dried over anhydrous sodium sulfate, filtered and concentrated in vacuo and purified by prep-TLC (dichloromethane/methanol=15:1) to give 5-(4-bromoisoquinolin-7-yloxy)pentan-1-ol (1.0 g, 81%) as a yellow solid.

$^1$H NMR (400 MHz, DMSO-d$^6$) δ 1.49-1.51 (4H, m), 1.82 (2H, t, J=6.8 Hz), 3.43-3.44 (2H, m), 4.16 (2H, t, J=6.4 Hz), 4.41 (1H, t, J=5.2 Hz), 7.58-7.64 (2H, m), 8.00 (1H, d, J=9.2 Hz), 8.59 (1H, s), 9.19(1H, s).

Chemical Formula: $C_{14}H_{16}BrNO_2$, Molecular Weight: 310.19

Total H count from HNMR data: 16.

Step 6: Synthesis of 1-(7-(5-hydroxypentyloxy)isoquinolin-4-yl)pyrimidine-2,4(1H,3H)-dione

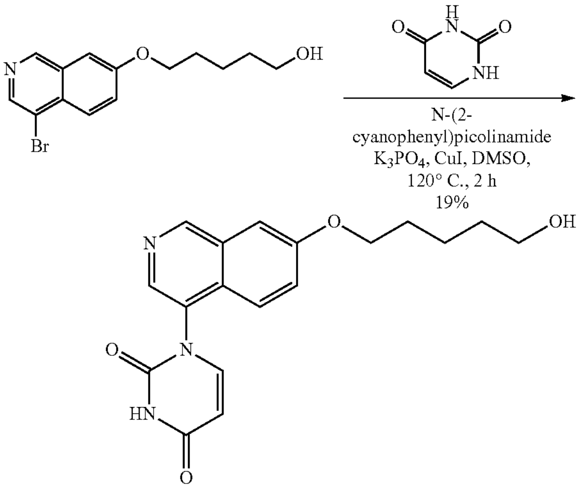

A solution of 5-(4-bromoisoquinolin-7-yloxy)pentan-1-ol (100 mg, 0.32 mmol), pyrimidine-2,4(1H,3H)-dione (48 mg, 0.38 mmol), $K_3PO_4$ (200 mg, 0.96 mmol), CuI (30 mg, 0.16 mmol), N-(2-cyanophenyl)picolinamide (22 mg, 0.16 mmol) in DMSO (6 mL) was heated at 120° C. for 2 hours under argon atmosphere. The reaction mixture was cooled to room temperature poured in cold water and extracted with dichloromethane/methanol (10 mL×3). The combined organic layer was dried over anhydrous sodium sulfate, filtered and concentrated in vacuo and purified by prep-TLC (dichloromethane/methanol=12:1) to give 1-(7-(5-hydroxypentyloxy)isoquinolin-4-yl)pyrimidine-2,4(1H,3H)-dione (21 mg, 19%) as a yellow solid.

$^1$H NMR (400 MHz, DMSO-d$^6$) δ 1.49-1.51 (4H, m), 1.80-1.83 (2H, m), 3.42-3.44 (2H, m), 4.16 (2H, t, J=6.4 Hz), 4.41 (1H, t, J=5.2 Hz), 5.75-5.78 (1H, m), 7.50 (1H, dd, J=9.2, 2.8 Hz), 7.69-7.77 (3H, m), 8.44 (1H, s), 9.31 (1H, s), 11.61 (1H, s).

Chemical Formula: $C_{18}H_{19}N_3O_4$, Molecular Weight: 341.36

Total H count from HNMR data: 19.

Step 7: Synthesis of 5-(4-(2,4-dioxo-3,4-dihydropyrimidin-1(2H)-yl)isoquinolin-7-yloxy)pentanal

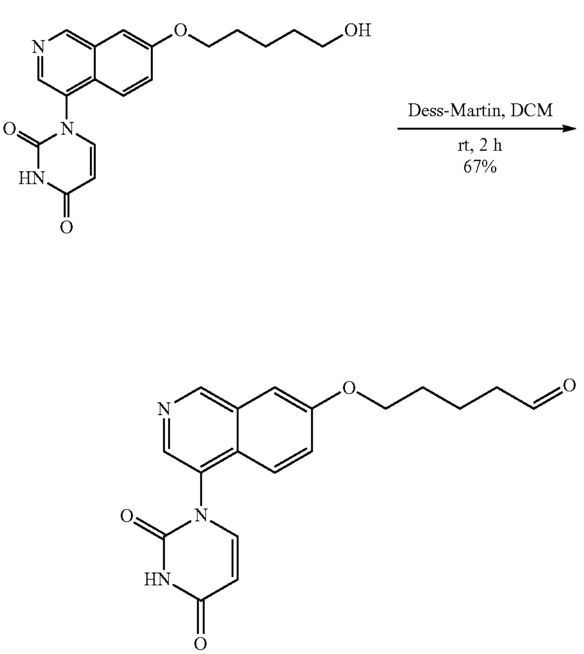

To a solution of 1-(7-(5-hydroxypentyloxy)isoquinolin-4-yl)pyrimidine-2,4(1H,3H)-dione (30 mg, 0.088 mmol) in dichloromethane (10 mL) was added Dess-Martin periodinane (112 mg, 0.26 mmol). The mixture was stirred at room temperature for 2 hours. The mixture was added to water (10.0 mL) and extracted with dichloromethane (10.0 mL×2). The combined organic layer was washed with brine (20 mL), dried over anhydrous sodium sulfate, filtered and concentrated in vacuo and purified by prep-TLC (dichloromethane/methanol=12:1) to give 5-(4-(2,4-dioxo-3,4-dihydropyrimidin-1(2H)-yl)isoquinolin-7-yloxy)pentanal (20 mg, 67%) as a yellow solid.

Step 8: Synthesis of N-((1r,3r)-3-(3-chloro-4-cyanophenoxy)-2,2,4,4-tetramethylcyclobutyl)-6-(4-(5-(4-(2,4-dioxo-3,4-dihydropyrimidin-1(2H)-yl)isoquinolin-7-yloxy)pentyl)piperazin-1-yl)nicotinamide

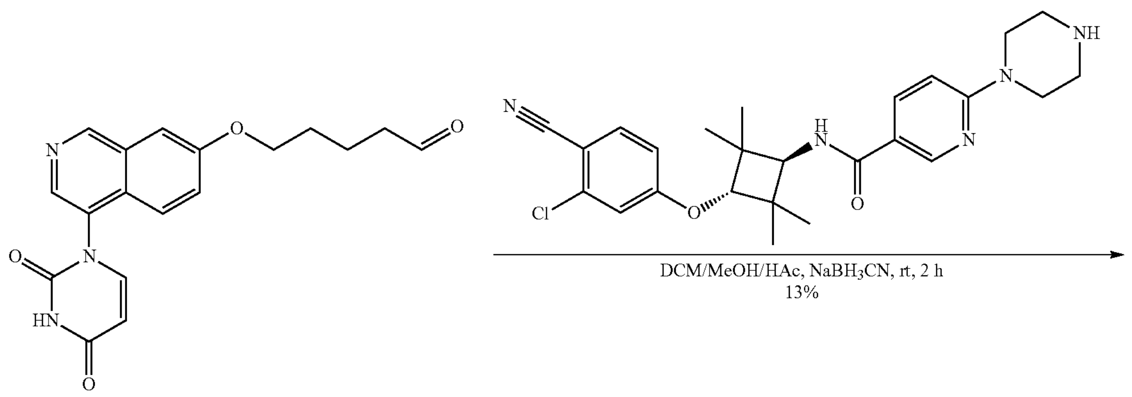

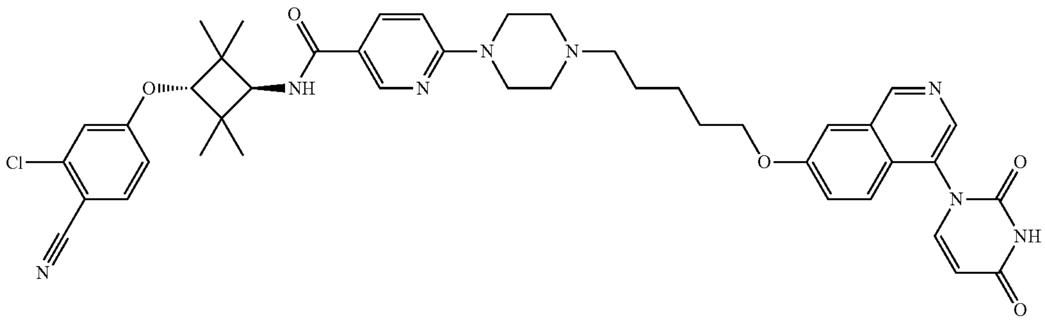

To a solution of 5-(4-(2,4-dioxo-3,4-dihydropyrimidin-1(2H)-yl)isoquinolin yloxy)pentanal (20 mg, 0.058 mmol) in dry methanol/1,2-dichloroethane/HOAc (5 mL/3 mL/0.1 mL) was added N-((1r,3r)-3-(3-chloro-4-cyanophenoxy)-2,2,4,4-tetramethylcyclobutyl) (piperazin-1-yl)nicotinamide (27 mg, 0.058 mmol). The mixture was left to stir for 30 minutes under N2 gas. Then sodium cyanoborohydride (7 mg, 0.116 mmol) was added and the reaction mixture was left to stir overnight. The solvent was removed and the residue partitioned between dichloromethane and water, washed with brine, dried over anhydrous sodium sulfate, filtered, and concentrated in vacuo to give crude product. The residue was purified by prep-HPLC to give compound N-((1r,3r)-3-(3-chloro-4-cyanophenoxy)-2,2,4,4-tetramethylcyclobutyl)-6-(4-(5-(4-(2,4-dioxo-3,4-dihydropyrimidin-1(2H)-yl)isoquinolin-7-yloxy)pentyl)piperazin-1-yl)nicotinamide (6.0 mg, 13%) as a yellow solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min). Purity is 93.61%, Rt=2.885 min.; MS Calcd.: 790.3; MS Found: 791.3 $[M+H]^+$.

HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 92.34%, Rt=9.952 min.

$^1H$ NMR (400 MHz, DMSO-$d_6$) δ 1.12 (6H, s), 1.21 (6H, s), 1.49-1.57 (4H, m), 1.83-1.86 (2H, m), 2.31-2.40 (5H, m), 2.67-2.68 (1H, m), 3.58-3.60 (4H, m), 4.05(1H, d, J=9.2 Hz), 4.17-4.20 (2H, m), 4.30 (1H, s), 5.76(1H, d, J=8.4 Hz), 6.86(1H, d, J=8.8 Hz), 6.99-7.02 (1H, m), 7.21 (1H, d, J=2.0 Hz), 7.50-7.52 (1H, m), 7.63 (1H, d, J=9.6 Hz), 7.70-7.76 (3H, m), 7.90-7.97 (2H, m), 8.44 (1H, s), 8.62 (1H, d, J=1.6 Hz), 9.31 (1H, s).

Chemical Formula: $C_{43}H_{47}ClN_8O_5$, Molecular Weight: 791.34

Total H count from HNMR data: 47.

Synthesis of Exemplary PROTAC 80
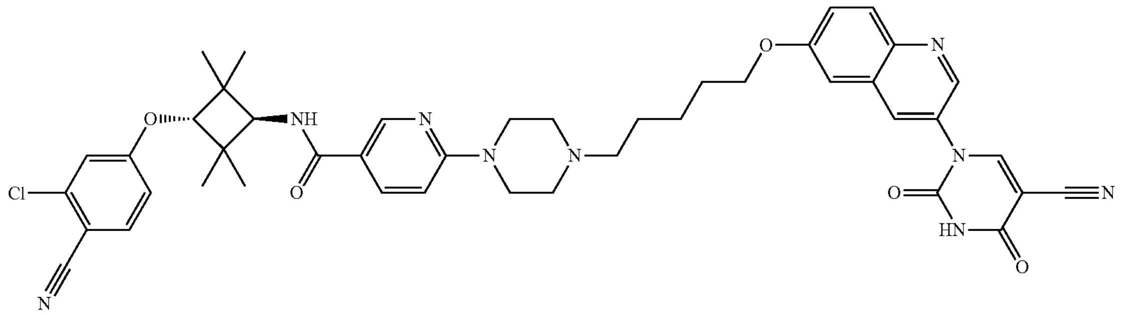 [SMILES: CC1(C)[C@H](NC(=O)c2ccc(N3CCN(CCCCCOc4ccc5ncc(-n6cc(C#N)c(=O)[nH]c6=O)cc5c4)CC3)nc2)C(C)(C)[C@H]1Oc1ccc(C#N)c(Cl)c1]
N-((1r,3r)-3-(3-chloro-4-cyanophenoxy)-2,2,4,4-tetramethylcyclobutyl)-6-(4-(5-((3-(5-cyano-2,4-dioxo-3,4-dihydropyrimidin-1(2H)-yl)quinolin-6-yl)oxy)pentyl)piperazin-1-yl)nicotinamide
Synthetic Scheme
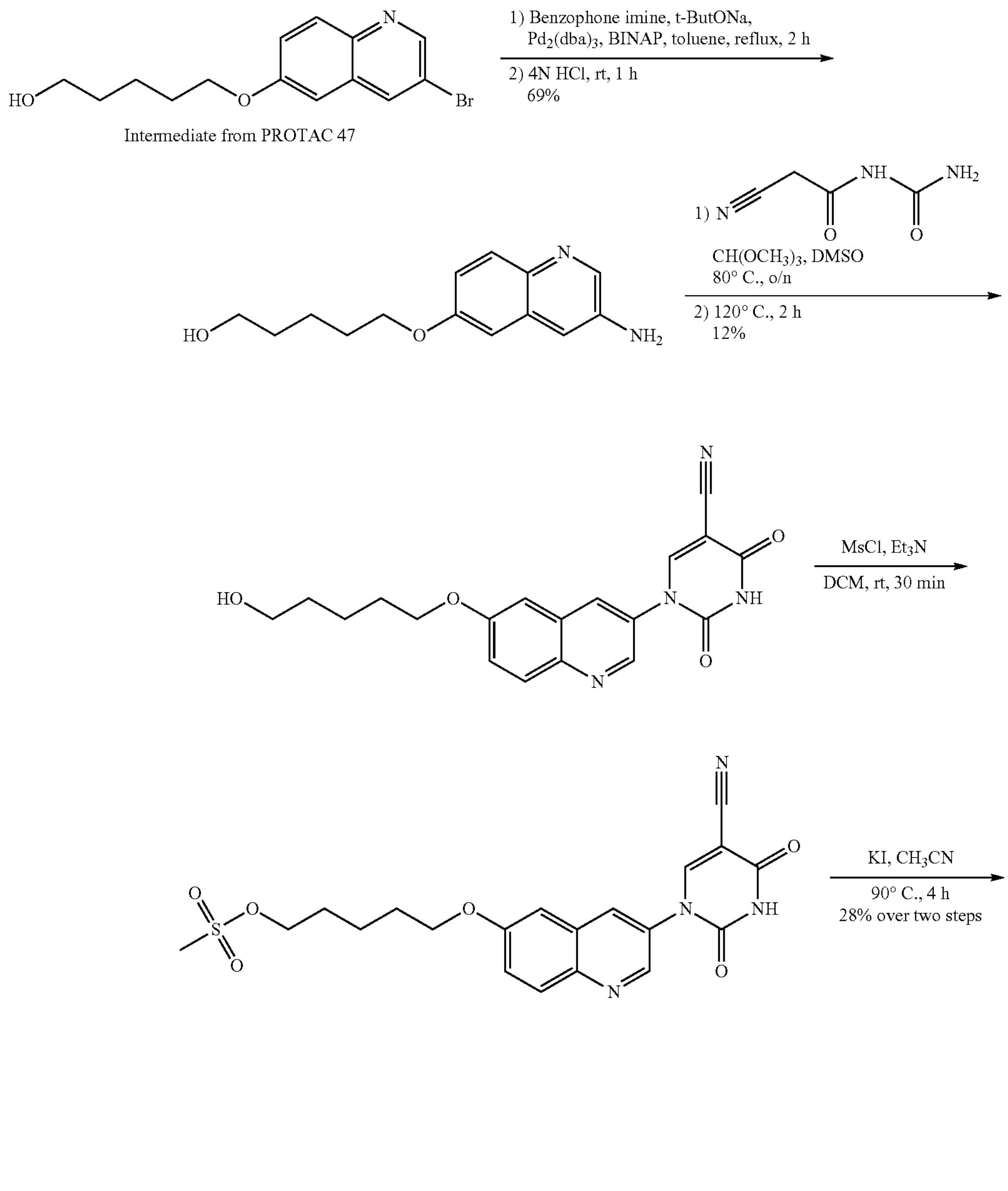

-continued

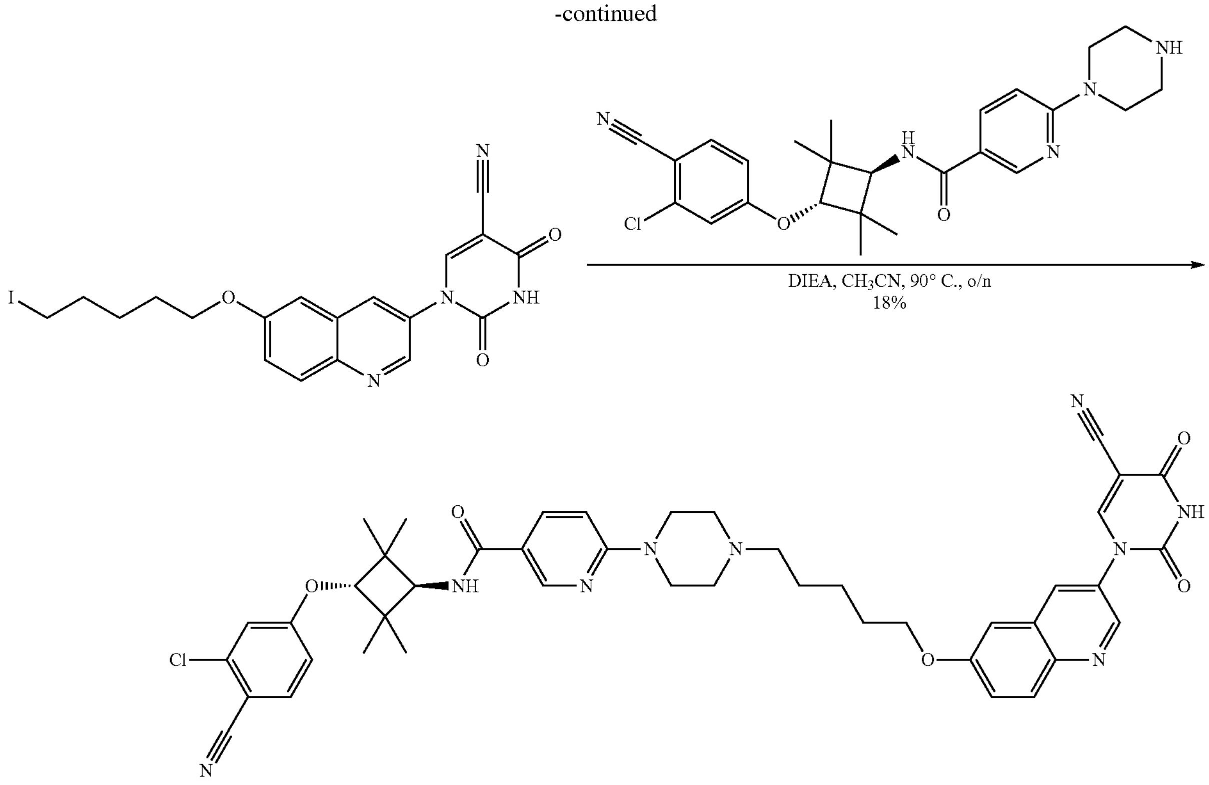

Step 1: Synthesis of 5-(3-aminoquinolin-6-yloxy)pentan-1-ol

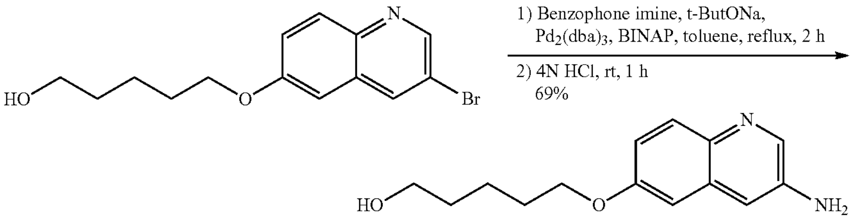

To a solution of 5-(3-bromoquinolin-6-yloxy)pentan-1-ol (1.1 g, 3.6 mmol), benzophenone imine (684 mg, 3.8 mmol) and sodium tert-butoxide (691 mg, 7.2 mmol) in toluene (20 mL) was added (+/−)-2,2'-bis(diphenylphosphino)-1,1'-binaphthyl (448 mg, 0.7 mmol) and tris(dibenzylideneacetone)dipalladium (207 mg, 0.36 mmol) under nitrogen atmosphere, and the mixture was refluxed for 2 hours. When it was cooled to room temperature, water (20 mL) was added. The resulted mixture was extracted by ethyl acetate (10 mL×3), washed by brine (20 mL×3), dried over anhydrous sodium sulfate and filtered. Then 4N HCl (5 mL) was added to the filtrate, the mixture was stirred for an hour. The layers were separated and the organic layer was extracted by water (10 mL×3). Then the combined water phase was adjusted to pH=9 with sat. $NaHCO_3$, extracted by ethyl acetate (10 mL×3), dried over anhydrous $Na_2SO_4$, filtered and concentrated. The residue was purified by column chromatography on silica gel (dichloromethane/methanol=8/1) to give 5-(3-aminoquinolin-6-yloxy)pentan-1-ol (600 mg, 69% yield) as a white solid.

LCMS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min.) Purity is 97.35%, Rt=1.361 min. MS Calcd.: 246.14; MS Found: 247.3 $[M+H]^+$.

$^1H$ NMR (400 MHz, DMSO-$d_6$) δ 1.45-1.49 (4H, m), 1.76 (2H, t, J=6.8 Hz), 3.42 (2H, dd, J=11.2, 6.0 Hz), 4.03 (2H, t, J=6.4 Hz), 4.40 (1H, t, J=5.2 Hz), 5.60 (2H, s), 6.93 (1H, dd, J=8.8, 2.4 Hz), 6.97 (1H, d, J=2.4 Hz), 7.02 (1H, d, J=2.4 Hz), 7.62 (1H, d, J=8.8 Hz), 8.23 (1H, d, J=2.8 Hz).

Chemical Formula: $C_{14}H_{18}N_2O_2$, Molecular Weight: 246.30.

Total H count from HNMR data: 18.

Step 2: Synthesis of 1-(6-(5-hydroxypentyloxy)quinolin-3-yl)-2,4-dioxo-1,2,3,4-tetrahydropyrimidine-5-carbonitrile

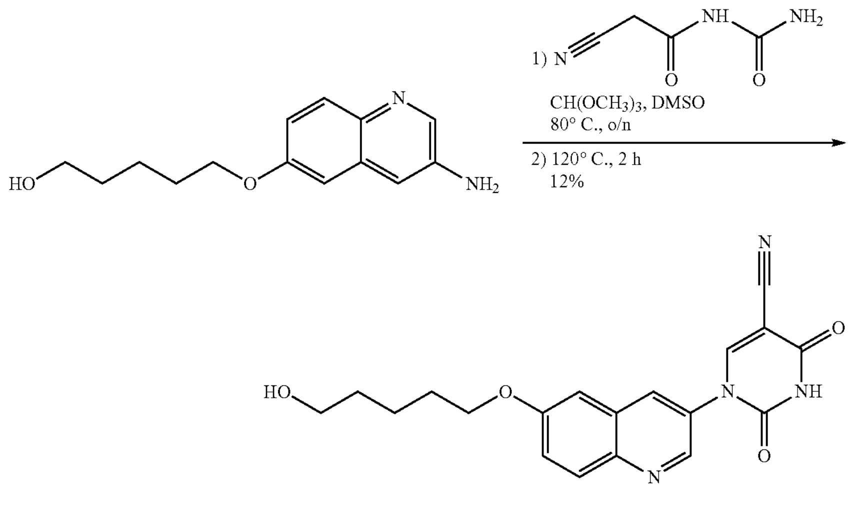

The solution of 5-(3-aminoquinolin-6-yloxy)pentan-1-ol (600 mg, 2.44 mmol), N-carbamoyl-2-cyanoacetamide (1.2 g, 9.76 mmol) and trimethoxymethane (1.0 g, 9.76 mmol) in dimethyl sulfoxide (10 mL) was stirred at 80° C. overnight, and the reaction mixture continued to stir at 120° C. for 2 hours. When it was cooled to room temperature, water (30 mL) was added to the mixture and a white solid resulted. The resulted mixture was filtered and the solid was purified by Prep-HPLC to give 1-(6-(5-hydroxypentyloxy)quinolin-3-yl)-2,4-dioxo-1,2,3,4-tetrahydropyrimidine-5-carbonitrile (110 mg, 12% yield) as a white solid.

$^1$H NMR (400 MHz, DMSO-$d_6$) δ 1.49-1.51 (4H, m), 1.81 (2H, t, J=6.4 Hz), 3.43 (2H, d, J=5.2 Hz), 4.13 (2H, t, J=6.4 Hz), 4.41 (1H, t, J=5.2 Hz), 7.44 (1H, d, J=2.4 Hz), 7.49 (1H, dd, J=9.2, 2.8 Hz), 7.99 (1H, d, J=9.2 Hz), 8.36 (1H, d, J=2.4 Hz), 8.77 (1H, d, J=2.4 Hz), 8.95 (1H, s), 12.31 (1H, brs).

Chemical Formula: $C_{19}H_{18}N_4O_4$, Molecular Weight: 366.37.

Total H count from HNMR data: 18.

Step 3: Synthesis of 5-(3-(5-cyano-2,4-dioxo-3,4-dihydropyrimidin-1(2H)-yl)quinolin-6-yloxy)pentyl methanesulfonate

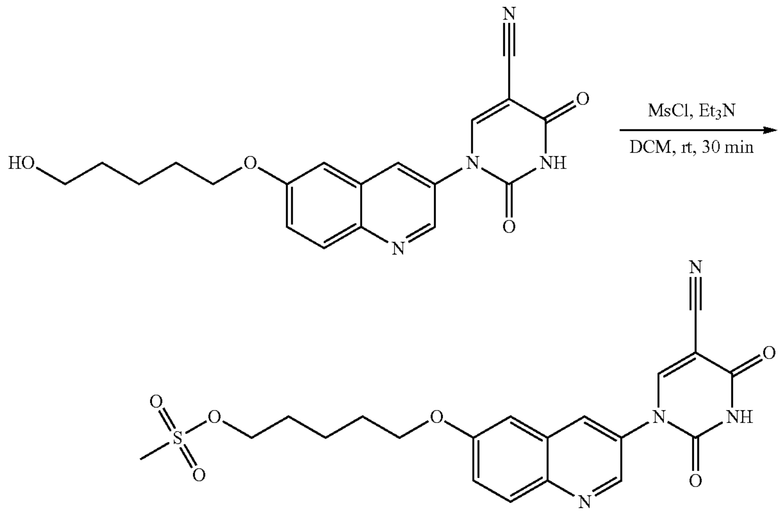

To a solution of 1-(6-(5-hydroxypentyloxy)quinolin-3-yl)-2,4-dioxo-1,2,3,4-tetrahydropyrimidine-5-carbonitrile (110 mg, 0.30 mmol) and triethylamine (98 mg, 0.90 mmol) in dichloromethane (4 mL) was added methanesulfonyl chloride (51 mg, 0.45 mmol) at 0° C., and the mixture was stirred at room temperature for 30 minutes. Then water (5 mL) was added to the mixture, and the resulted mixture was extracted by dichloromethane (5 mL×3), washed by brine (5 mL×3), dried over anhydrous $Na_2SO_4$, filtered and concentrated. The crude product (150 mg) was directly used to the next step without further purification.

Step 4: Synthesis of 1-(6-(5-iodopentyloxy)quinolin-3-yl)-2,4-dioxo-1,2,3,4-tetrahydropyrimidine-5-carbonitrile

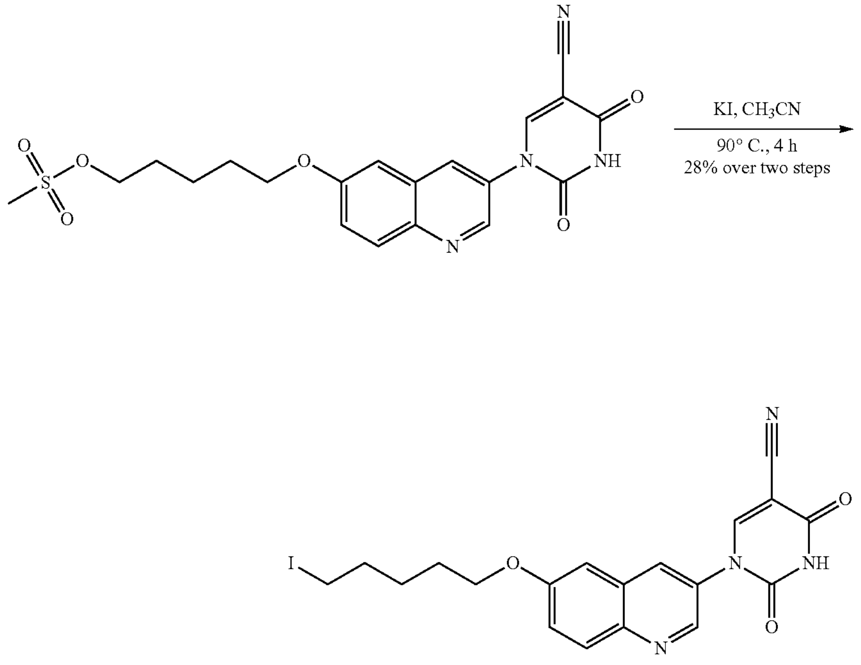

To a solution of 5-(3-(5-cyano-2,4-dioxo-3,4-dihydropyrimidin-1(2H)-yl)quinolin-6-yloxy)pentyl methanesulfonate (150 mg) in acetonitrile (3 mL) was added potassium iodide (50 mg, 0.3 mmol), and the mixture was stirred at 90° C. for 4 hours. When it was cooled to room temperature, water (5 mL) was added to the mixture, and the resulted mixture was extracted by dichloromethane (5 mL×3), washed by brine (5 mL×3), dried over anhydrous Na2SO4, filtered and concentrated. The residue was purified by Prep-TLC (dichloromethane/methanol=10/1) to give the desired product (40 mg, 28% yield over two steps).

LCMS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 90% [(total 10 mM $AcONH_4$) water/$CH_3CN$=900/100 (v/v)] and 10% [(total 10 mM $AcONH_4$) water/$CH_3CN$=100/900 (v/v)] to 10% [(total 10 mM $AcONH_4$) water/$CH_3CN$=900/100 (v/v)] and 90% [(total 10 mM $AcONH_4$) water/$CH_3CN$=100/900 (v/v)] in 1.6 min, then under this condition for 2.4 min, finally changed to 90% [(total 10 mM $AcONH_4$) water/$CH_3CN$=900/100 (v/v)] and 10% [(total 10 mM $AcONH_4$) water/$CH_3CN$=100/900 (v/v)] in 0.1 min and under this condition for 0.7 min.) Purity is 66.97%, Rt=2.066 min. MS Calcd.: 476.03; MS Found: 477.0 $[M+H]^+$.

Step 5: Synthesis of N-((1r,3r)-3-(3-chloro-4-cyanophenoxy)-2,2,4,4-tetramethylcyclobutyl)-6-(4-(5-(3-(5-cyano-2,4-dioxo-3,4-dihydropyrimidin-1(2H)-yl)quinolin-6-yloxy)pentyl)piperazin-1-yl)nicotinamide

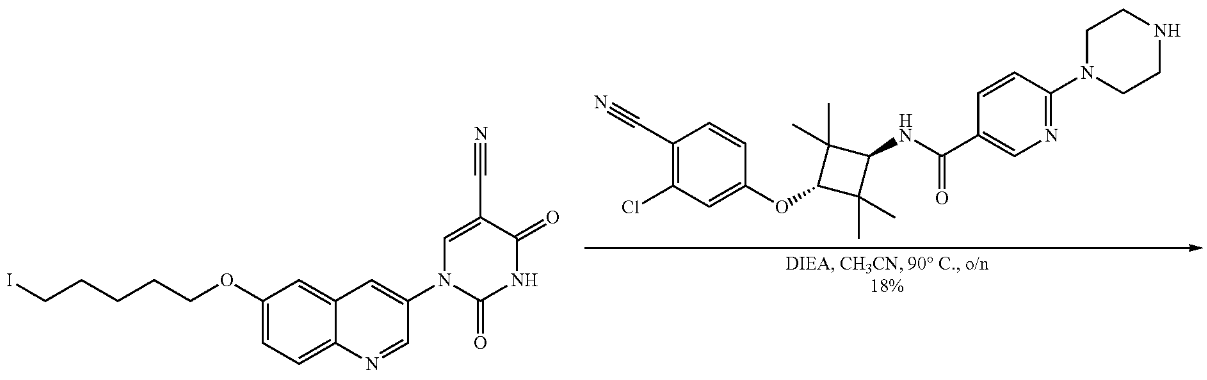

-continued

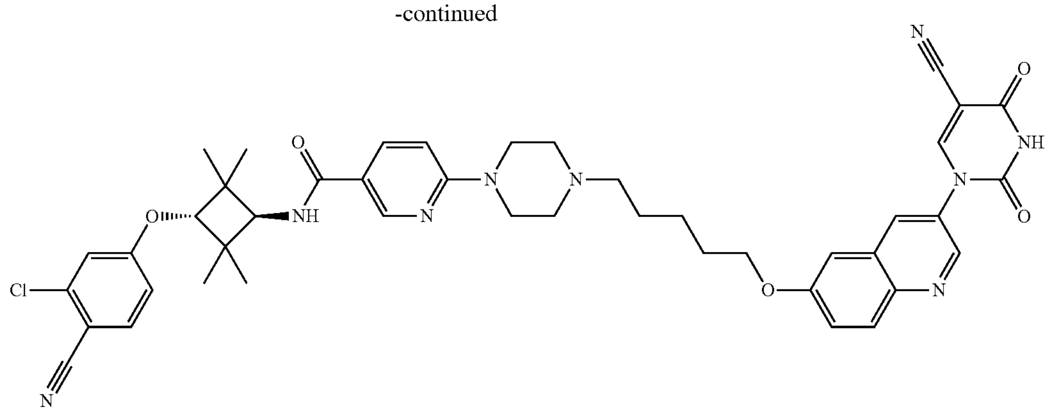

A solution of 1-(6-(5-iodopentyloxy)quinolin-3-yl)-2,4-dioxo-1,2,3,4-tetrahydropyrimidine-5-carbonitrile (40 mg, 0.08 mmol), N-((1r,3r)-3-(3-chloro-4-cyanophenoxy)-2,2,4,4-tetramethylcyclobutyl)-6-(piperazin-1-yl)nicotinamide (39 mg, 0.08 mmol), and ethyldiisopropylamine (30 mg, 0.25 mmol) in acetonitrile (2 mL) was stirred at 90° C. overnight. When it was cooled to room temperature, water (5 mL) was added and the mixture was extracted by ethyl acetate (2 mL×3), washed by brine (5 mL×3), dried over anhydrous $Na_2SO_4$, filtered, and concentrated. The residue was purified by Prep-HPLC to give N-((1r,3r)-3-(3-chloro-4-cyanophenoxy)-2,2,4,4-tetramethylcyclobutyl)-6-(4-(5-(3-(5-cyano-2,4-dioxo-3,4-dihydropyrimidin-1(2H)-yl)quinolin-6-yloxy)pentyl)piperazin-1-yl)nicotinamide (12 mg, 18% yield) as a white solid.

LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min.) Purity is 94.03%, Rt=2.703 min; MS Calcd.: 815.33; MS Found: 816.3 $[M+H]^+$.

HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min.) Purity is 96.02%, Rt=9.232 min.

$^1H$ NMR (400 MHz, DMSO-$d_6$) δ 1.11 (6H, s), 1.21 (6H, s), 1.50-1.57 (4H, m), 1.81-1.86 (2H, m), 2.33-2.37 (2H, m), 2.45-2.50 (4H, m), 3.59 (4H, s), 4.05 (1H, d, J=9.2 Hz), 4.15 (2H, t, J=6.4 Hz), 4.30 (1H, s), 6.86 (1H, d, J=9.2 Hz), 7.00 (1H, dd, J=8.8, 2.0 Hz), 7.21 (1H, d, J=2.4 Hz), 7.45 (1H, d, J=2.4 Hz), 7.50 (1H, dd, J=5.2, 2.4 Hz), 7.63 (1H, d, J=9.2 Hz), 7.91 (1H, d, J=8.8 Hz), 7.95 (1H, dd, J=8.8, 2.0 Hz), 8.00 (1H, d, J=9.2 Hz), 8.37 (1H, d, J=2.0 Hz), 8.62 (1H, d, J=2.0 Hz), 8.78 (1H, d, J=2.4 Hz), 8.96 (1H, s), 12.28 (1H, brs).

Chemical Formula: $C_{44}H_{46}ClN_9O_5$, Molecular Weight: 816.35.

Total H count from HNMR data: 46.

Synthesis of Exemplary PROTAC 81

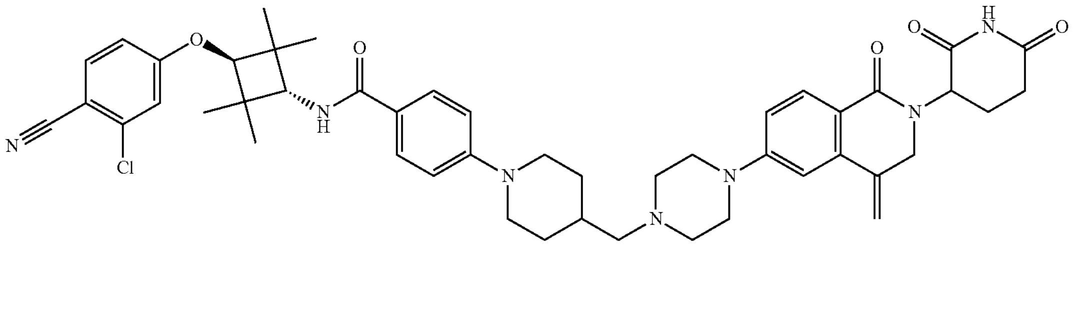 [SMILES: C=C1CN(C2CCC(=O)NC2=O)C(=O)c2ccc(N3CCN(CC4CCN(c5ccc(C(=O)N[C@H]6C(C)(C)[C@H](Oc7ccc(C#N)c(Cl)c7)C6(C)C)cc5)CC4)CC3)cc21]

N-((1r,3r)-3-(3-chloro-4-cyanophenoxy)-2,2,4,4-tetramethylcyclobutyl)-4-(4-((4-(2-(2,6-dioxopiperidin-3-yl)-4-methylene-1-oxo-1,2,3,4-tetrahydroisoquinolin-6-yl)piperazin-1-yl)methyl)piperidin-1-yl)benzamide
Reaction Scheme:
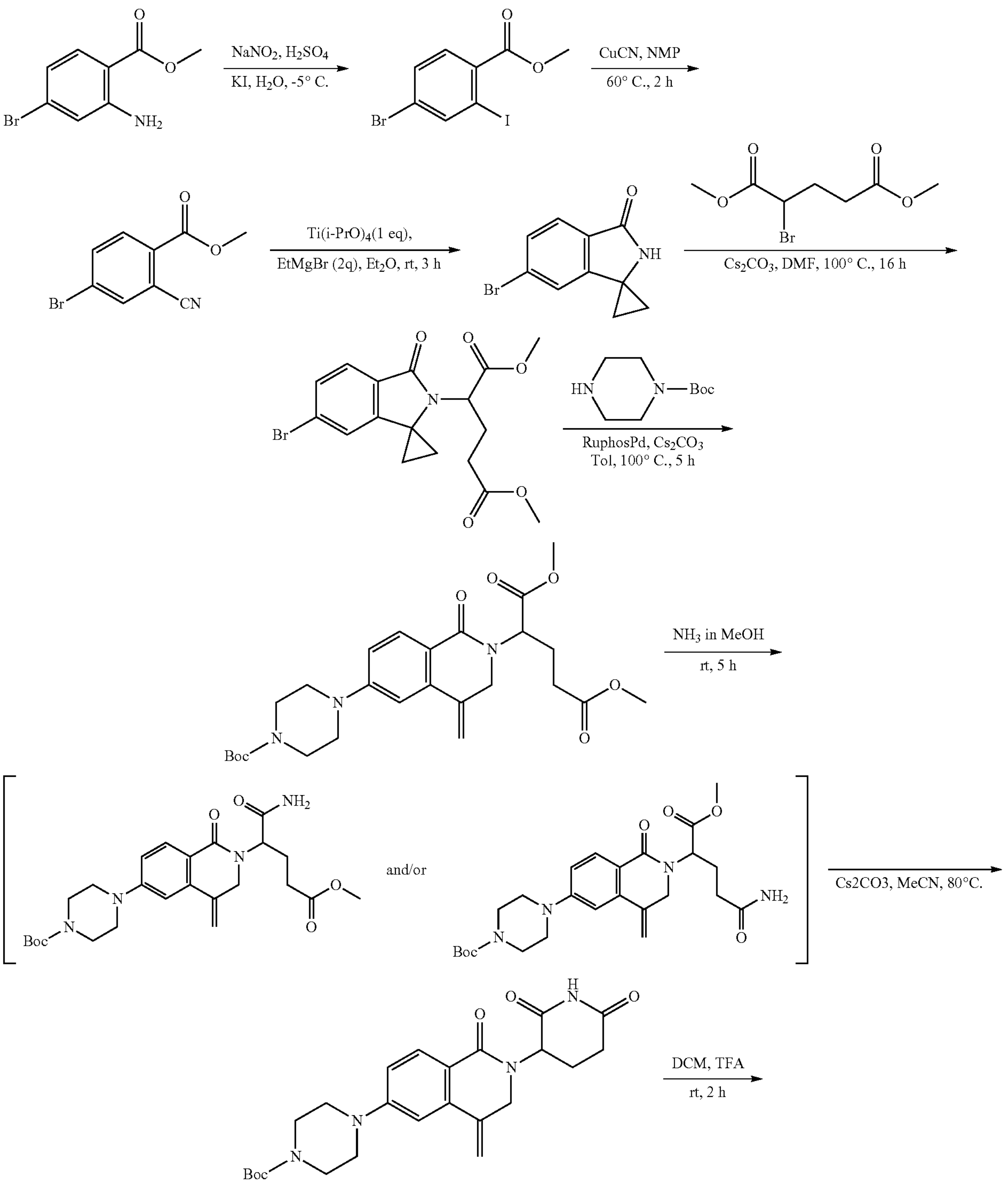

-continued

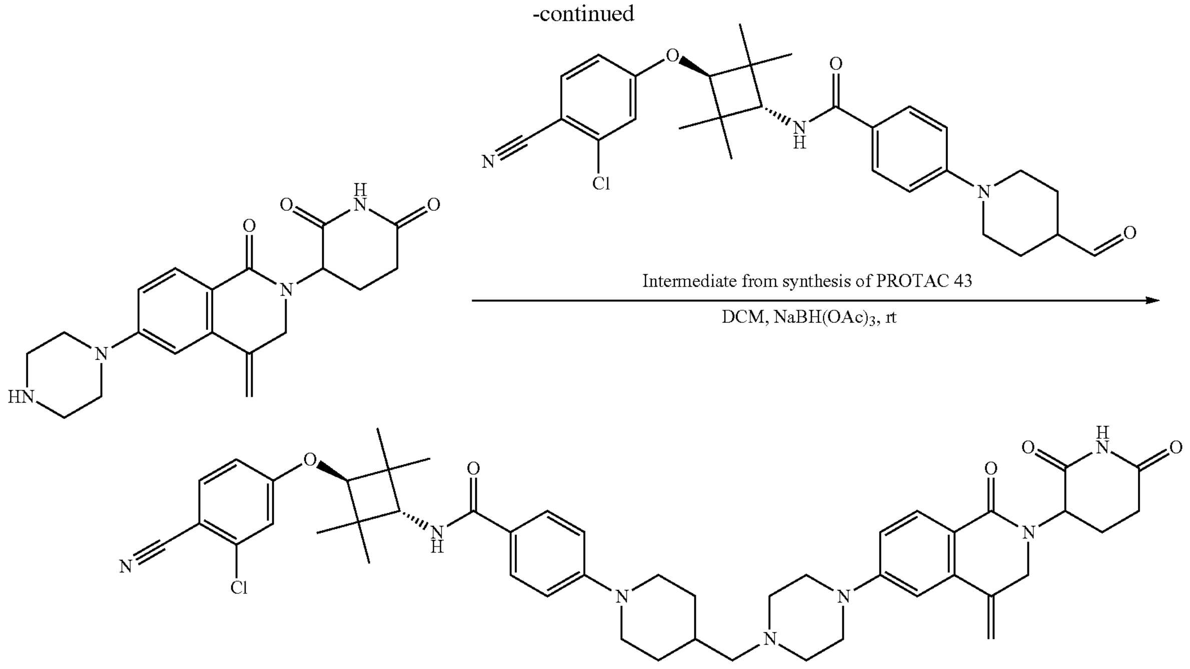

Step 1: Synthesis of methyl 4-bromo-2-iodobenzoate

Into a 1000-mL 3-necked round-bottom flask, was placed methyl 2-amino-4-bromobenzoate (5.0 g, 21.73 mmol, 1.00 equiv), a solution of sulfuric acid (20%) (20 mL) in water (100 mL). This was followed by the addition of a solution of $NaNO_2$ (1.8 g, 26.09 mmol, 1.20 equiv) in water (20 mL) dropwise with stirring at 0° C., after stirred 1 hour at 0° C. To this was added a solution of iodopotassium (7.21 g, 43.43 mmol, 2.00 equiv) in water (30 mL) dropwise with stirring at 0° C. The resulting solution was stirred for 1 hour at 0° C. in a water/ice bath. The reaction was then quenched by the addition of 200 mL of water/ice. The resulting solution was extracted with ethyl acetate (100 mL×3) and the organic layers combined. The resulting mixture was washed with brine (100 mL×1). The residue was applied onto a silica gel column with ethyl acetate/petroleum ether (1/5). This resulted in 5.97 g (81%) of methyl 4-bromo-2-iodobenzoate as light yellow oil.

Step 2: Synthesis of methyl 4-bromo-2-cyanobenzoate

Into a 250-mL round-bottom flask, was placed methyl 4-bromo-2-iodobenzoate (5.8 g, 17.01 mmol, 1.00 equiv), NMP (60 mL), CuCN (1.82 g, 20.45 mmol, 1.20 equiv). The resulting solution was stirred for 2 hours at 60° C. in an oil bath. The resulting solution was extracted with ethyl acetate (50 mL×2) and the organic layers combined. The resulting mixture was washed with FeSO4 (aq.) (50 mL×2). The mixture was dried over anhydrous sodium sulfate. The residue was applied onto a silica gel column with ethyl acetate/petroleum ether (1/3). This resulted in 3.68 g (90%) of methyl 4-bromo-2-cyanobenzoate as a white solid.

Step 3: Synthesis of 6'-bromospiro[cyclopropane-1,1'-isoindolin]-3'-one

Into a 100-mL 3-necked round-bottom flask purged and maintained with an inert atmosphere of nitrogen, was placed methyl 4-bromo-2-cyanobenzoate (2.0 g, 8.33 mmol, 1.00 equiv), ether (40 mL), 2-(propan-2-yloxy)propane propan-2-ol propan-2-yltitanium dihydrate (2.75 mL, 1.10 equiv). This was followed by the addition of EtMgBr (3M) (5.5 mL, 2.00 equiv) dropwise with stirring at 0° C. The resulting solution was stirred for 3 hour at room temperature. The reaction was then quenched by the addition of 20 mL of hydrogen chloride (1M). The resulting solution was extracted with ethyl acetate (50 mL×2) and the organic layers combined and dried over anhydrous sodium sulfate. The residue was applied onto a silica gel column with ethyl acetate/petroleum ether (7/3). This resulted in 409 mg (21%) of 6'-bromospiro[cyclopropane-1,1'-isoindolin]-3'-one as a yellow solid.

LC-MS ($ES^+$): m/z 238.00, 240.00 [$MH^+$], $t_R$=0.79 min, (1.90 minute run).

Step 4: Synthesis of dimethyl 2-(6'-bromo-3'-oxospiro[cyclopropane-1,1'-isoindolin]-2'-yl)pentanedioate Into a 100-mL round-bottom flask, was placed 6'-bromospiro[cyclopropane-1,1'-isoindolin]-3'-one (895.0 mg, 3.76 mmol, 1.00 equiv), N,N-dimethylformamide (15.0 mL), $Cs_2CO_3$ (2.44 g, 7.49 mmol, 2.00 equiv), 1,5-dimethyl 2-bromopentanedioate (2.69 g, 11.25 mmol, 3.00 equiv). The resulting solution was stirred overnight at 100° C. in an oil bath. The resulting solution was extracted with ethyl acetate (50 mL×2) and the organic layers combined. The resulting mixture was washed with brine (50 mL×2). The mixture was dried over anhydrous sodium sulfate. The residue was applied onto a silica gel column with ethyl acetate/petroleum ether (3/7). This resulted in 740.0 mg (50%) of dimethyl 2-(6'-bromo-3'-oxospiro[cyclopropane-1,1'-isoindolin]-2'-yl)pentanedioate as light yellow oil.

LC-MS ($ES^+$): m/z 395.85, 397.85 $t_R$=1.01 min, (1.90 minute run).

Step 5: Synthesis of dimethyl 2-(6-(4-(tert-butoxycarbonyl)piperazin-1-yl)-4-methylene-1-oxo-3,4-dihydroisoquinolin-2(1H)-yl)pentanedioate Into a 20-mL round-bottom flask purged and maintained with an inert atmosphere of nitrogen, was placed dimethyl 2-(6'-bromo-3'-oxospiro[cyclopropane-1,1'-isoindolin]-2'-yl)pentanedioate (740.0 mg, 1.87 mmol, 1.00 equiv), toluene (10 mL), tert-butyl piperazine-1-carboxylate (418.0 mg, 2.24 mmol, 1.20 equiv), $Cs_2CO_3$ (1.217 g, 3.74 mmol, 2.00 equiv), RuphosPd (140.5 mg, 0.17 mmol, 0.10 equiv). The resulting solution was stirred for 8 hours at 100° C. in an oil bath. The residue was applied onto a silica gel column with ethyl acetate/petroleum ether (1/1). This resulted in 303.0 mg (32%) of dimethyl 2-(6-(4-(tert-butoxycarbonyl)piperazin-1-yl)-4-methylene-1-oxo-3,4-dihydroisoquinolin-2(1H)-yl)pentanedioate as light yellow oil.

LC-MS ($ES^+$): m/z 502.20 [$MH^+$], $t_R$=0.96 min, (1.90 minute run).

Step 6: Synthesis of tert-butyl 4-[2-(1-carbamoyl-4-methoxy-4-oxobutyl)-4-methylidene-1-oxo-1,2,3,4-tetrahydroisoquinolin-6-yl]piperazine-1-carboxylate Into a 100 mL round-bottom flask, was placed 1,5-dimethyl 2-(6-[4-[(tert-butoxy)carbonyl]piperazin-1-yl]-4-methylidene-1-oxo-1,2,3,4-tetrahydroisoquinolin-2-yl)pentanedioate (400 mg, 0.80 mmol, 1 equiv), MeOH (50 mL), $NH_3$. The resulting solution was stirred for 5 hours at room temperature. The residue was applied onto a silica gel column with dichloromethane/methanol (20:1). This resulted in 100 mg (25.77%) of tert-butyl 4-[2-(1-carbamoyl-4-methoxy-4-oxobutyl)-4-methylidene-1-oxo-1,2,3,4-tetrahydroisoquinolin-6-yl]piperazine-1-carboxylate (and/or it's regioisomere as shown in the scheme above) as a yellow solid.

Step 7: Synthesis of tert-butyl 4-[2-(2,6-dioxopiperidin-3-yl)-4-methylidene-1-oxo-1,2,3,4-tetrahydroisoquinolin-6-yl]piperazine-1-carboxylate Into a 50 mL round-bottom flask, was placed tert-butyl 4-[2-(1-carbamoyl-4-methoxy-4-oxobutyl)-4-methylidene-1-oxo-1,2,3,4-tetrahydroisoquinolin-6-yl]piperazine-1-carboxylate (188 mg, 0.39 mmol, 1 equiv), acetonitrile (20 mL), $Cs_2CO_3$ (629.5 mg, 1.93 mmol, 5 equiv). The resulting solution was stirred for 3 hours at 80° C. in an oil bath. The solids were filtered out. The residue was applied onto a silica gel column with dichloromethane/methanol (20:1). The collected fractions were combined and concentrated under vacuum. This resulted in 100 mg (56.94%) of tert-butyl 4-[2-(2,6-dioxopiperidin-3-yl)-4-methylidene-1-oxo-1,2,3,4-tetrahydroisoquinolin-6-yl]piperazine-1-carboxylate as a yellow solid.

Step 8: Synthesis of 3-[4-methylidene-1-oxo-6-(piperazin-1-yl)-1,2,3,4-tetrahydroisoquinolin-2-yl]piperidine-2,6-dione (Trifluoroacetate salt)

Into a 50 mL round-bottom flask, was placed tert-butyl 4-[2-(2,6-dioxopiperidin-3-yl)-4-methylidene-1-oxo-1,2,3,4-tetrahydroisoquinolin-6-yl]piperazine-1-carboxylate (120 mg, 0.26 mmol, 1 equiv), dichloromethane (20 mL), TFA (1.5 mL). The resulting solution was stirred for 2 hours at room temperature. The resulting mixture was concentrated under vacuum. This resulted in 93 mg (77.86%) of 3-[4-methylidene-1-oxo-6-(piperazin-1-yl)-1,2,3,4-tetrahydroisoquinolin-2-yl]piperidine-2,6-dione (TFA salt) as a yellow solid.

Step 9: Synthesis of N-((1r,3r)-3-(3-chloro-4-cyanophenoxy)-2,2,4,4-tetramethylcyclobutyl)-4-(4-((4-(2-(2,6-dioxopiperidin-3-yl)-4-methylene-1-oxo-1,2,3,4-tetrahydroisoquinolin-6-yl)piperazin-1-yl)methyl)piperidin-1-yl)benzamide Into a 50 mL round-bottom flask, was placed 4-(4-formylpiperidin-1-yl)-N-[(1r,3r)-3-(3-chloro-4-cyanophenoxy)-2,2,4,4-tetramethylcyclobutyl]benzamide (83 mg, 0.17 mmol, 1 equiv), dichloromethane (20 mL), 3-[4-methylidene-1-oxo-6-(piperazin-1-yl)-1,2,3,4-tetrahydroisoquinolin-2-yl]piperidine-2,6-dione (TFA salt) (91.2 mg, 0.20 mmol, 1.2 equiv), $NaBH(OAc)_3$ (106.8 mg, 0.50 mmol, 3 equiv). The resulting solution was stirred for 1 overnight at room temperature. The reaction was then quenched by the addition of water. The resulting solution was extracted with dichloromethane The resulting mixture was washed with brine. The mixture was dried over anhydrous sodium sulfate. The crude product was purified by Prep-HPLC with the following conditions: Column, X Bridge Prep C18 OBD Column, 19 150 mm 5 um; mobile phase, water (10 mmol/L $NH_4HCO_3$) and acetonitrile (58.0% acetonitrile up to 78.0% in 8 min); Detector, UV 254 nm. The product was obtained and concentrated under vacuum, and lyophiliation. This resulted in 80.3 mg (57.42%) of N-((1r,3r)-3-(3-chloro-4-cyanophenoxy)-2,2,4,4-tetramethylcyclobutyl)-4-(4-((4-(2-(2,6-dioxopiperidin-3-yl)-4-methylene-1-oxo-1,2,3,4-tetrahydroisoquinolin-6-yl)piperazin-1-yl)methyl)piperidin yl)benzamide as a white solid.

$^1H$ NMR (400 MHz, DMSO) δ 10.88(s, 1H), 7.91-7.89 (m, 1H), 7.78-7.72(m, 3H), 7.50-7.47 (d, J=9.2 Hz, 1H), 7.21 (s, 1H), 7.09-6.94(m, 5H), 5.75 (s, 1H), 5.29 (s, 1H), 5.15-4.95(m, 1H), 4.32(s, 1H), 4.21-4.04 (m, 3H), 3.87-3.84 (m, 2H), 3.32-3.30 (m, 7H), 2.84-2.76 (m, 3H), 2.65-2.56 (m, 1H), 2.48-2.37 (m, 1H), 2.22-2.18 (m, 2H), 1.90-1.79 (m, 4H), 1.40-1.16 (m, 9H), 1.16-1.09 (m, 6H);

LC-MS ($ES^+$): m/z 832.35[$MH^+$], $t_R$=1.53 min, (3.00 minute run).

Chemical formula: $C_{47}H_{54}ClN_7O_5$ [831.39]

Total H count from HNMR data: 54

Synthesis of Exemplary PROTAC 82

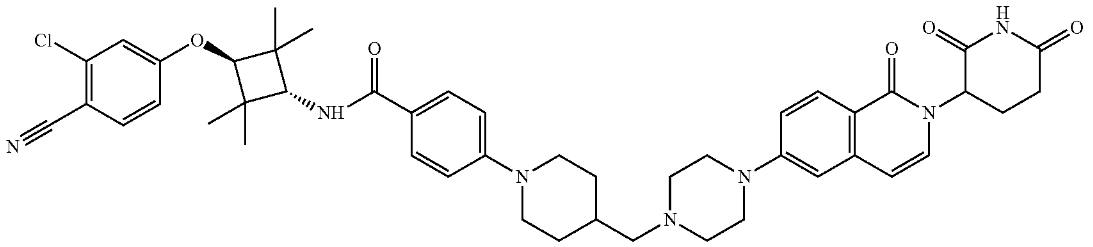 [SMILES: CC1(C)[C@H](NC(=O)c2ccc(N3CCC(CN4CCN(c5ccc6c(=O)n(C7CCC(=O)NC7=O)ccc6c5)CC4)CC3)cc2)C(C)(C)[C@H]1Oc1ccc(C#N)c(Cl)c1]

N-((1r,3r)-3-(3-chloro-4-cyanophenoxy)-2,2,4,4-tetramethylcyclobutyl)-4-(4-((4-(2-(2,6-dioxopiperidin-3-yl)-1-oxo-1,2-dihydroisoquinolin-6-yl)piperazin-1-yl)methyl)piperidin-1-yl)benzamide
Synthetic Scheme
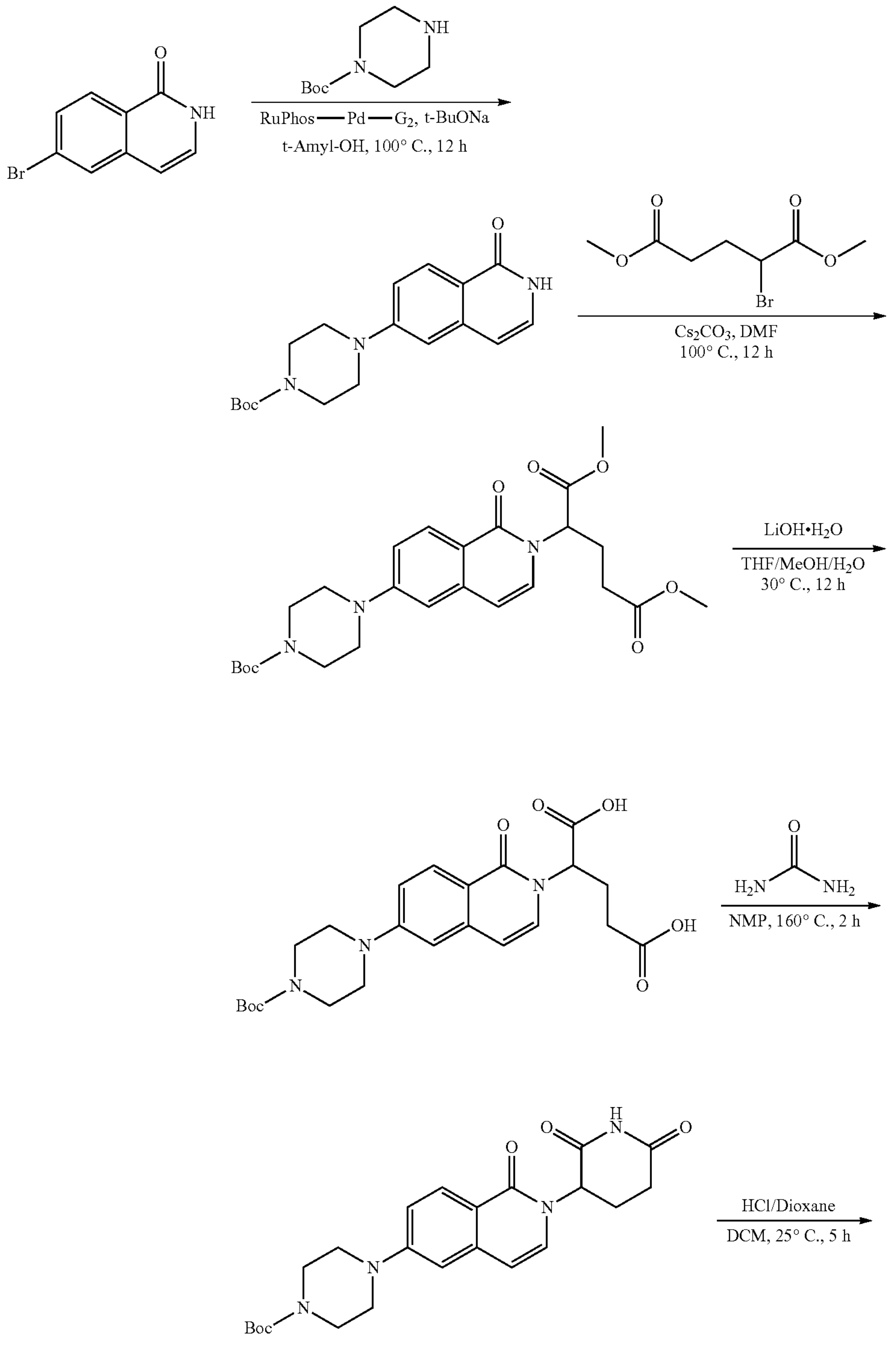

-continued

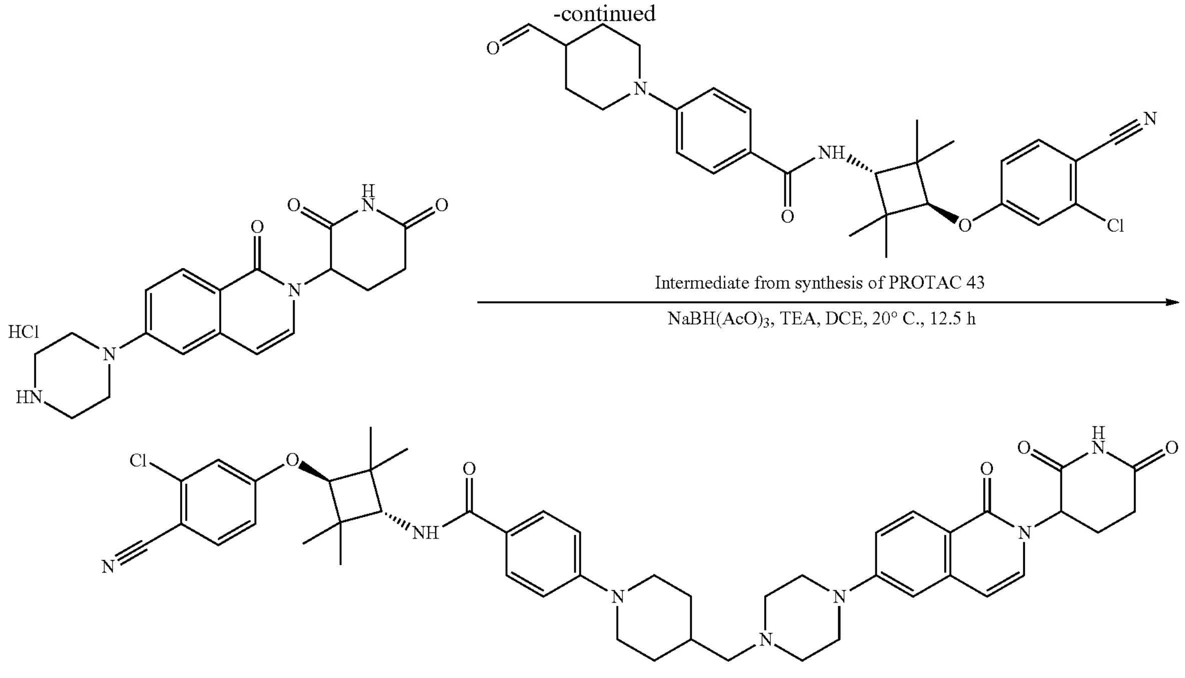

Step 1: Synthesis of tert-butyl 4-(1-oxo-2H-isoquinolin-6-yl)piperazine-1-carboxylate

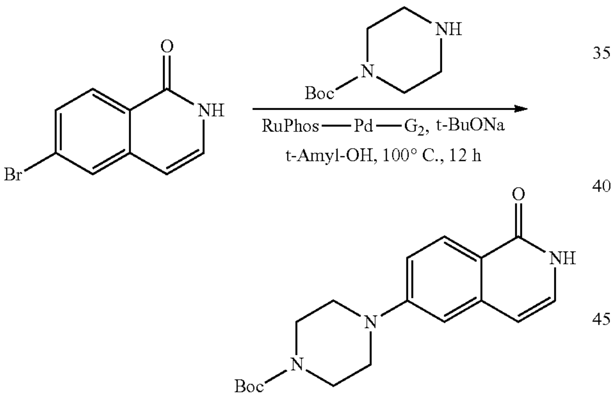

A mixture of 6-bromo-2H-isoquinolin-1-one (2 g, 8.93 mmol, 1 eq), tert-butyl piperazine-1-carboxylate (2.49 g, 13.39 mmol, 1.5 eq), sodium tert-butoxide (2 M, 13.4 mL, 3 eq) and [2-(2-aminophenyl)phenyl]-chloro-palladium; dicyclohexyl-[2-(2,6-diisopropoxyphenyl)phenyl]phosphane (693 mg, 0.89 mmol, 0.1 eq) in tert-amyl alcohol (30 mL) was degassed and purged with nitrogen for 3 times, and then the mixture was stirred at 100° C. for 12 hours under nitrogen atmosphere. LCMS showed the reaction was completed and desired MS can be detected. The reaction mixture was diluted with water (100 mL) and extracted with ethyl acetate (50 mL×3). The combined organic phase was washed with saturated brine (50 mL×2), dried with anhydrous sodium sulfate, filtered and concentrated in vacuum. The residue was purified by silica gel chromatography (petroleum ether: ethyl acetate=20:1 to 3:1) to give tert-butyl 4-(1-oxo-2H-isoquinolin-6-yl)piperazine-1-carboxylate (2.3 g, 6.98 mmol, 78% yield) as a white solid LCMS: MS (ESI) m/z: 330.1 $[M+1]^+$ $^1H$ NMR: (400 MHz, $CDCl_3$) δ: 10.73 (s, 1H), 8.27 (d, J=8.8 Hz, 1H), 7.13-7.05 (m, 2H), 6.81 (d, J=2.4 Hz, 1H), 6.42 (d, J=7.2 Hz, 1H), 3.65-3.59 (m, 4H), 3.39-3.34 (m, 4H), 1.50 (s, 9H)

Chemical Formula: $C_{18}H_{23}N_2O_3$, Molecular Weight: 329.39

Total H count from HNMR data: 23.

Step 2: Synthesis of dimethyl 2-[6-(4-tert-butoxycarbonylpiperazin-1-yl)-1-oxo-2-isoquinolyl]pentanedioate

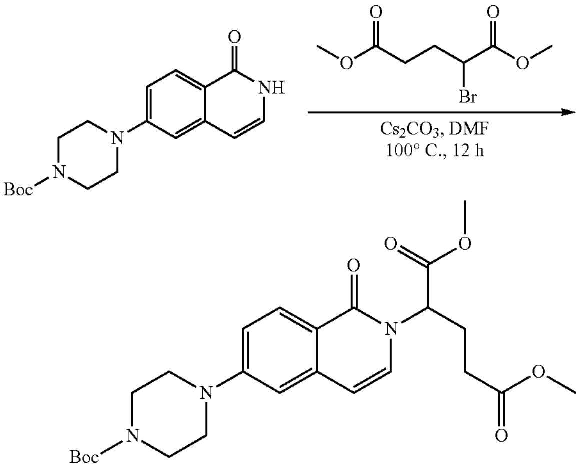

To a solution of tert-butyl 4-(1-oxo-2H-isoquinolin-6-yl) piperazine-1-carboxylate (800 mg, 2.43 mmol, 1 eq) in dimethylformamide (16 mL) was added cesium carbonate (2.37 g, 7.29 mmol, 3 eq) and dimethyl 2-bromopentanedioate (696 mg, 2.91 mmol, 1.2 eq). The mixture was stirred at 100° C. for 12 hours. LCMS showed the reaction was completed and desired MS can be detected. The reaction mixture was adjusted to pH 4-5 with hydrochloric acid (1 M). The reaction was diluted with water (60 mL) and extracted with ethyl acetate (30 mL×3). The combined organic phase was washed with saturated brine (30 mL×2), dried with anhydrous sodium sulfate, filtered and concentrated in vacuum to give the crude product dimethyl 2-[6-(4-tert-butoxycarbonylpiperazin-1-yl)-1-oxo-2-isoquinolyl] pentanedioate (700 mg, crude) as a light yellow oil was used into the next step without further purification.

LCMS: MS (ESI) m/z: 474.1 [M+1]$^+$.

Chemical Formula: $C_{25}H_{33}N_3O_7$, Molecular Weight: 487.55

Step 3: Synthesis of 2-[6-(4-tert-butoxycarbonylpiperazin-1-yl)-1-oxo-2-isoquinolyl]pentanedioic acid

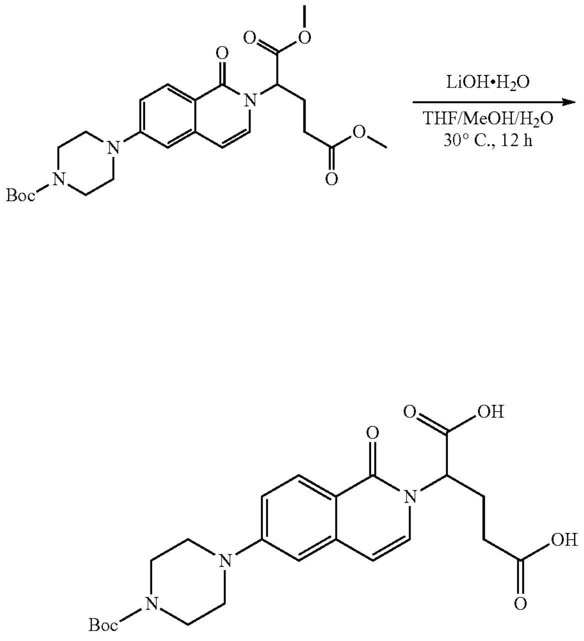

To a solution of dimethyl 2-[6-(4-tert-butoxycarbonylpiperazin-1-yl)-1-oxo-2-isoquinolyl]pentanedioate (800 mg, 1.64 mmol, 1 eq) in tetrahydrofuran(5 mL), methanol (5 mL) and water (5 mL) was added lithium hydroxide monohydrate (413 mg, 9.85 mmol, 6 eq). The mixture was stirred at 30° C. for 12 hours. LCMS showed the reaction was completed and desired MS can be detected. The reaction was adjusted to pH 4~5 with hydrochloric acid (1 M) and diluted with water (25 mL). The reaction was extracted with ethyl acetate (15 mL×3). The combined organic phase was dried with anhydrous sodium sulfate, filtered and concentrated in vacuum to give the crude product 2-[6-(4-tert-butoxycarbonylpiperazin-1-yl)-1-oxo-2-isoquinolyl]pentanedioic acid (800 mg, crude) as a yellow solid was used into the next step without further purification.

LCMS: MS (ESI) m/z: 460.1 [M+1]$^+$

Chemical Formula: $C_{23}H_{29}N_3O_7$, Molecular Weight: 459.49

Step 4: Synthesis of tert-butyl 4-[2-(2,6-dioxo-3-piperidyl)-1-oxo-6-isoquinolyl]piperazine-1-carboxylate

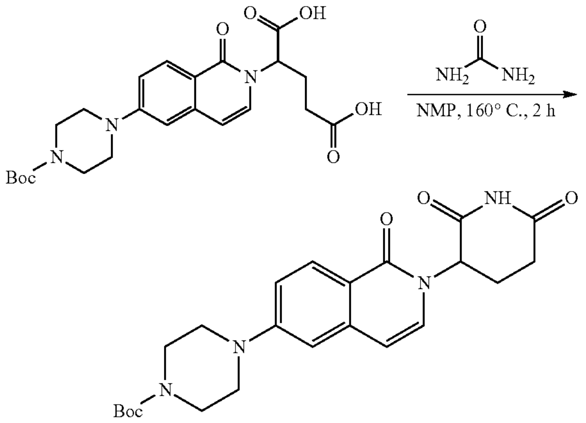

To a solution of 2-[6-(4-tert-butoxycarbonylpiperazin-1-yl)-1-oxo-2-isoquinolyl]pentanedioic acid (800 mg, 1.74 mmol, 1 eq) in N-methyl-2-pyrrolidone (10 mL) was added urea (522 mg, 8.71 mmol, 5 eq). The mixture was stirred at 160° C. for 2 hours. LCMS showed the reaction was completed and desired MS can be detected. The reaction mixture was diluted with water (50 mL) and extracted with ethyl acetate (25 mL×3). The combined organic phase was washed with saturated brine (30 mL×2), dried with anhydrous sodium sulfate, filtered and concentrated in vacuum. The residue was purified by Semi-preparative reverse phase HPLC (column: Phenomenex Synergi Max-RP 250*50 mm*10 um; mobile phase: [water(0.225%FA)-ACN]; B%: 30ACN%-60ACN%, 30 min; 50%min). Tert-butyl 4-[2-(2,6-dioxo-3-piperidyl)-1-oxo-6-isoquinolyl]piperazine-1-carboxylate (100 mg, 0.22 mmol, 13% yield) was obtained as a white solid.

LCMS: MS (ESI) m/z: 441.1 [M+1]$^+$

Chemical Formula: $C_{23}H_{28}N_4O_5$, Molecular Weight: 440.49

Step 5: Synthesis of 3-(1-oxo-6-piperazin-1-yl-2-isoquinolyl)piperidine-2,6-dione

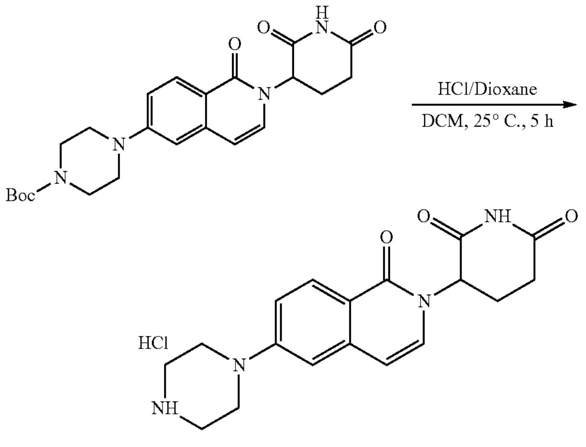

To a solution of tert-butyl 4-[2-(2,6-dioxo-3-piperidyl)-1-oxo-6-isoquinolyl]piperazine-1-carboxylate (100 mg, 0.22 mmol, 1 eq) in dichloromethane (3 mL) was added 4 M hydrochloric acid in dioxane (3 mL, 52.86 eq). The mixture was stirred at 25° C. for 4 hours. LCMS showed 14% of the starting material was remained and the reaction was stirred another 1 hour. Thin layer chromatography (dichloromethane: methanol=10:1) showed the reaction was completed. The reaction mixture was concentrated under reduced pressure to remove dichloromethane and dioxane, hydrochloric acid to give the crude prodcut 3-(1-oxo-6-piperazin-1-yl-2-isoquinolyl)piperidine-2,6-dione (85 mg, crude, hydrochloride) as a light yellow solid.

LCMS: MS (ESI) m/z: 341.0 $[M+1]^+$.

Chemical Formula: $C_{18}H_{20}N_4O_3$, Molecular Weight: 340.38

Step 6: Synthesis of N-[3-(3-chloro-4-cyano-phenoxy)-2,2,4,4-tetramethyl-cyclobutyl]-4-[4-[[4-[2-(2,6-dioxo-3-piperidyl)-1-oxo-6-isoquinolyl]piperazin-1-yl]methyl]-1-piperidyl]benzamide

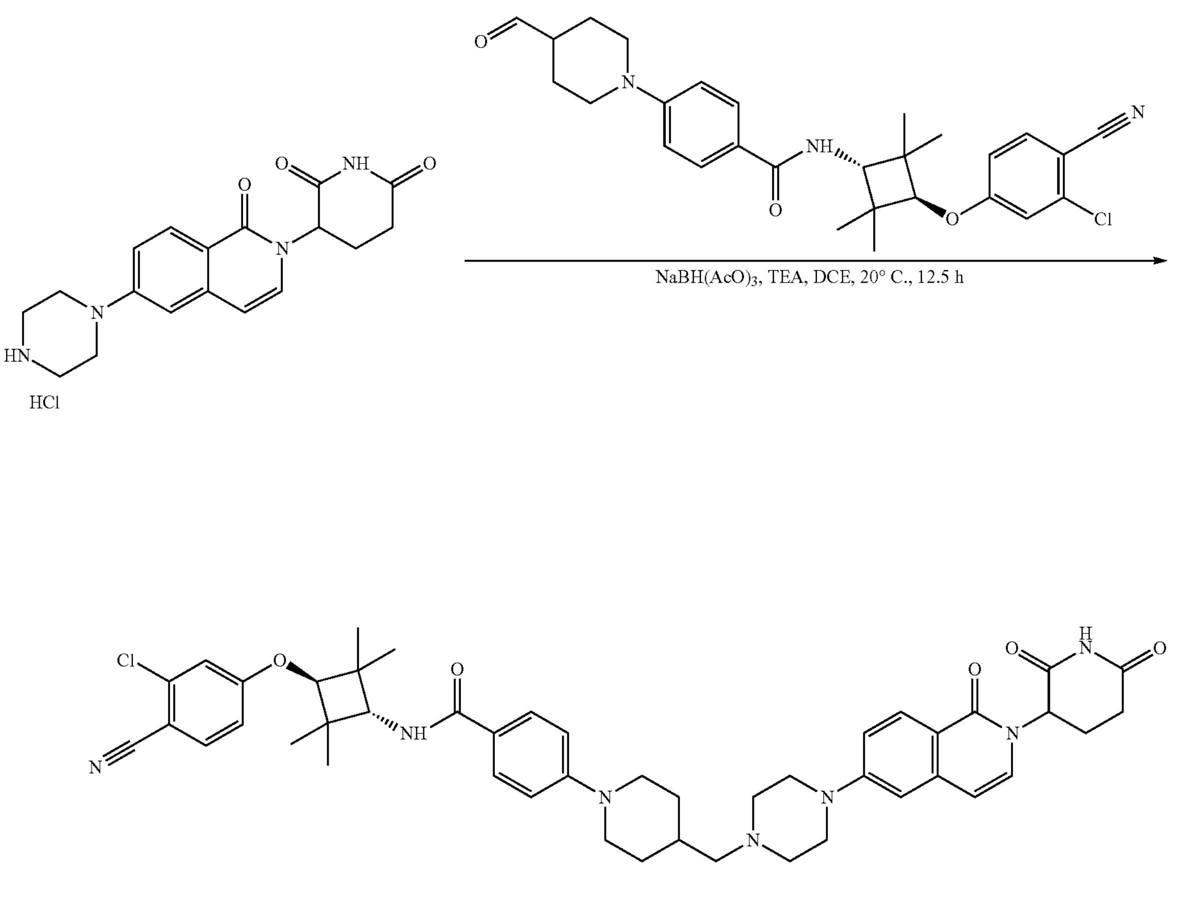

To a solution of 3-(1-oxo-6-piperazin-1-yl-2-isoquinolyl)piperidine-2,6-dione (85 mg, 0.22 mmol, 1 eq, hydrochloride) in 1,2-dichloroethane (4 mL) was added triethylamine (0.9 mmol, 0.12 mL, 4 eq) and N-[3-(3-chloro-4-cyano-phenoxy)-2,2,4,4-tetramethyl-cyclobutyl]-4-(4-formyl-1-piperidyl)benzamide (111 mg, 0.22 mmol, 1 eq). The mixture was stirred at 20° C. for 0.5 hour. Sodium triacetoxyborohydride (95 mg, 0.45 mmol, 2 eq) was added and the mixture was stirred at 20° C. for 12 hours. LCMS showed the reaction was completed and desired MS can be detected. The reaction mixture was concentrated under reduced pressure to remove 1,2-dichloroethane. The residue was dissolved into dimethylformamide (3 mL) and filtered. The filter was purified by Semi-preparative reverse phase HPLC (column: Phenomenex Synergi C18 150*25*10 um; mobile phase: [water(0.05%HCl)-ACN]; B%: 23%-53%, 10 min) N-[3-(3-chloro-4-cyano-phenoxy)-2,2,4,4-tetramethyl-cyclobutyl]-4-[4-[[4-[2-(2,6-dioxo-3-piperidyl)-1-oxo-6-isoquinolyl]piperazin-1-yl]methyl]-1-piperidyl]benzamide (50.9 mg, 0.05 mmol, 25% yield, 95.8% purity, hydrochloride) as a white solid.

LCMS: MS (ESI) m/z: 818.4 $[M+1]^+$.

$^1$H NMR: (400 MHz, DMSO-$d_6$) δ: 11.07-10.90 (m, 1H), 10.57 (s, 1H), 8.10-8.01 (m, 1H), 7.91 (d, J=8.8 Hz, 1H), 7.80 (d, J=8.8 Hz, 2H), 7.58 (br d, J=9.2 Hz, 1H), 7.33 (d, J=7.6 Hz, 1H), 7.29-7.23 (m, 1H), 7.21 (d, J=2.4 Hz, 1H), 7.16-7.05 (m, 3H), 7.01 (dd, J=2.4, 8.8 Hz, 1H), 6.56-6.37 (m, 1H), 6.56-6.37 (m, 1H), 4.34 (s, 1H), 4.06 (d, J=9.2 Hz, 3H), 3.87 (br d, J=12.8 Hz, 2H), 3.68-3.60 (m, 1H), 3.22-3.08 (m, 4H), 3.00-2.76 (m, 3H), 2.65-2.55 (m, 1H), 2.54-2.52 (m, 2H), 2.47-2.43 (m, 1H), 2.23-2.11 (m, 1H), 2.05-1.90 (m, 3H), 1.55-1.30 (m, 2H), 1.23 (s, 6H), 1.14 (s, 6H)

Chemical Formula: $C_{46}H_{52}ClN_7O_5$, Molecular Weight: 818.40

Total H count from HNMR data: 53.

Synthesis of Exemplary PROTAC 89

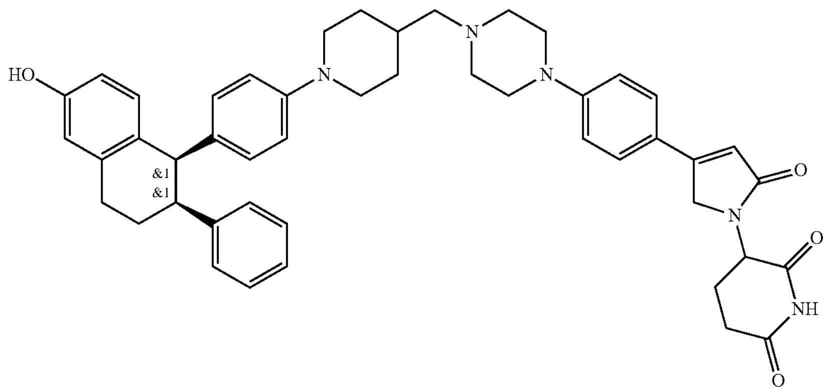 [SMILES: O=C1CCC(N2CC(c3ccc(N4CCN(CC5CCN(c6ccc([C@@H]7c8ccc(O)cc8CC[C@@H]7c7ccccc7)cc6)CC5)CC4)cc3)=CC2=O)C(=O)N1]

3-[3-[4-[4-[[1-[4-[(1R,2S)-6-hydroxy-2-phenyl-tetralin-1-yl]phenyl]-4-piperidyl]methyl]piperazin-1-yl]phenyl]-5-oxo-2H-pyrrol-1-yl]piperidine-2,6-dione Step 1: Preparation of 6-tert-butoxytetralin-1-one

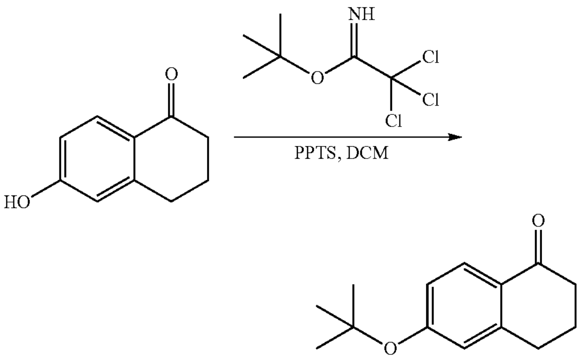

To a stirred solution of 6-hydroxytetralin-1-one (50 g, 308.29 mmol, 1 eq) in anhydrous dichloromethane (2000 mL) at 0° C. was added tert-butyl 2,2,2-trichloroethanimidate (67.36 g, 308.29 mmol, 55 mL, 1 eq) and pyridinium para-toluenesulfonate (7.75 g, 30.83 mmol, 0.1 eq). The reaction mixture was stirred at 10° C. for 3 hours. Additional portion of tert-butyl 2,2,2-trichloroethanimidate (67.36 g, 308.29 mmol, 55 mL, 1 eq) and pyridinium para-toluenesulfonate (7.75 g, 30.83 mmol, 0.1 eq) was added and the reaction mixture was stirred at 10° C. for 15 hours. This process was repeated three times. Thin layer chromatography (petroleum ether: ethyl acetate=3:1, $R_f$=0.8) showed the most of reactant was still remained, the reaction mixture was stirred at 10° C. for 72 hours. The reaction mixture was quenched by addition a solution of sodium hydrogen carbonate (1500 mL) at 15° C., and then extracted with dichloromethane (300 mL×3). The combined organic layers were washed with brine (300 mL×2), dried over anhydrous sodium sulfate, filtered and concentrated under reduced pressure. The residue was purified by silica gel chromatography (petroleum ether: ethyl acetate=100:1 to 50:1) to get 6-tert-butoxytetralin-1-one (21 g, 96.20 mmol, 31% yield) as a yellow oil. $^1$H NMR (400 MHz, $CDCl_3$) δ 7.97 (d, J=8.8 Hz, 1H), 6.91 (dd, J=2.4, 8.8 Hz, 1H), 6.82 (d, J=2.0 Hz, 1H), 2.93-3.90 (t, J=6.0 Hz, 2H), 2.63-2.60 (m, t, J=6.0 Hz, 2H), 2.13 (m, 2H), 1.43 (s, 9H)

Step 2: Preparation of (6-tert-butoxy-3,4-dihydronaphthalen-1-yl)trifluoromethanesulfonate

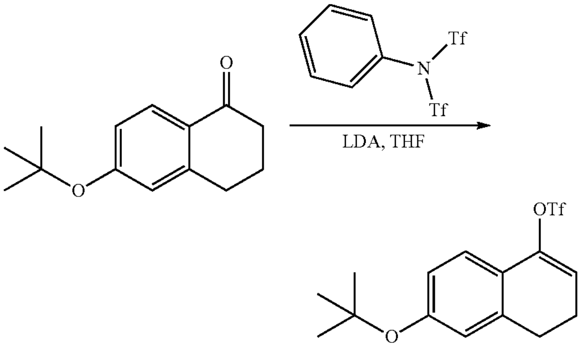

To a solution of 6-tert-butoxytetralin-1-one (40 g, 183.24 mmol, 1 eq) in tetrahydrofuran (500 mL) was added lithium diiso-propylamide (2 M, 137 mL, 1.5 eq) at −70° C. The mixture was stirred at −70° C. for 1 hour, then 1,1,1-trifluoro-N-phenyl-N-(trifluoromethylsulfonyl) methanesulfonamide (72.01 g, 201.56 mmol, 1.1 eq) in tetrahydrofuran (200 mL) was added dropwise to the mixture. The reaction mixture was stirred at 20° C. for 2 hours. Thin layer chromatography (petroleum ether: ethyl acetate=5:1) showed the reaction was completed. Saturated ammonium chloride (300 mL) was added to the mixture, the organic phase was separated. Ethyl acetate (500 mL×3) was added to the mixture, the resulting mixture was washed with brine (1000 mL×2). The combined organic phase was dried over sodium sulfate, filtered and concentrated in vacuum. The residue was purified by silica gel chromatography (petroleum ether: ethyl acetate=1:0 to 50:1) to give (6-tert-butoxy-3,4-dihydronaphthalen-1-yl) trifluoromethanesulfonate (52 g, 144.64 mmol, 78% yield, 97% purity) as a yellow oil. LC-MS (ESI) m/z: 294.9 [M+1−56]$^+$. $^1$H-NMR (400 MHz, $CDCl_3$) δ: 7.30 (d, J=6.4 Hz, 1H), 6.91 (d, J=8.4 Hz, 1H), 6.84 (s, 1H), 5.95 (s, 1H), 2.93-2.78 (m, 2H), 2.59-2.46 (m, 2H), 1.42 (s, 9H).

Step 3: Preparation of 4-(6-tert-butoxy-3,4-dihydronaphthalen-1-yl)phenol

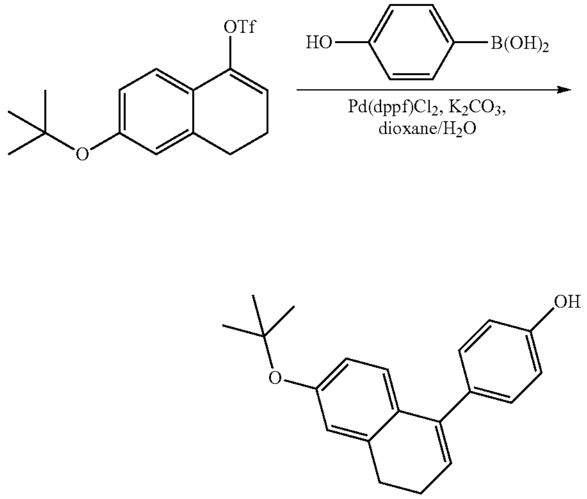

To a solution of (6-tert-butoxy-3,4-dihydronaphthalen-1-yl) trifluoromethanesulfonate (52 g, 148.42 mmol, 1 eq), (4-hydroxyphenyl)boronic acid (24.57 g, 178.11 mmol, 1.2 eq) in dioxane (800 mL) and water (150 mL) was added potassium carbonate (41.03 g, 296.84 mmol, 2 eq) and (1,1'-Bis(diphenylphosphino)ferrocene)palladium(II) dichloride (10.86 g, 14.84 mmol, 0.1 eq) under nitrogen. The reaction mixture was stirred at 100° C. for 10 hours. Thin layer chromatography (petroleum ether: ethyl acetate=5:1) showed the reaction was completed. The residue was diluted with water (500 mL) and extracted with ethyl acetate (500 mL×2). The combined organic layers were washed with brine (1000 mL×2), dried with anhydrous sodium sulfate, filtered and concentrated in vacuum. The residue was purified by silica gel chromatography (petroleum ether:tetrahydrofuran=50:1 to 20:1) to give 4-(6-tert-butoxy-3,4-dihydronaphthalen-1-yl)phenol (43 g, 131.46 mmol, 88% yield, 90% purity) as a yellow oil. LCMS (ESI) m/z: 239.1 $[M+1-56]^+$; $^1$H-NMR (400 MHz, $CDCl_3$) δ 7.23 (d, J=7.6 Hz, 2H), 6.91 (d, J=8.0 Hz, 1H), 6.87-6.79 (m, 3H), 6.73 (d, J=8.4 Hz, 1H), 5.95 (s, 1H), 4.83-4.75 (m, 1H), 2.87-2.73 (m, 2H), 2.44-2.31 (m, 2H), 1.37 (s, 9H)

Step 4: Preparation of 4-(2-bromo-6-tert-butoxy-3,4-dihydronaphthalen-1-yl)phenol

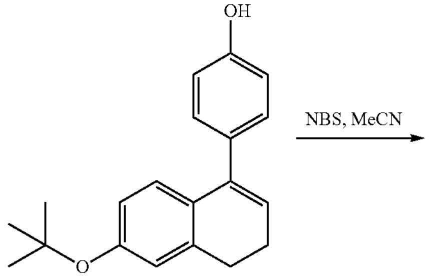

-continued

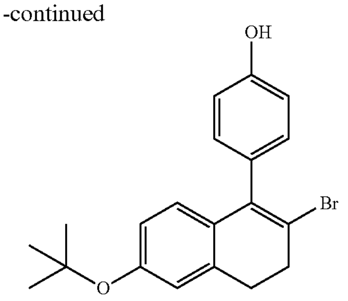

To a solution of 4-(6-tert-butoxy-3,4-dihydronaphthalen-1-yl)phenol (1 g, 3.06 mmol, 1 eq) in acetonitrile (20 mL) was added N-bromosuccinimide (489 mg, 2.75 mmol, 0.9 eq) in three portions. The reaction mixture was stirred at 20° C. for 1.5 hours. LC-MS showed the reaction was completed. The residue was diluted with water (20 mL) and extracted with ethyl acetate (20 mL×2). The combined organic layers were washed with brine (20 mL×2), dried with anhydrous sodium sulfate, filtered and concentrated in vacuum. The residue was purified by silica gel chromatography (petroleum ether: ethyl acetate=1:0 to 20:1) to give 4-(2-bromo-6-tert-butoxy-3,4-dihydronaphthalen-1-yl)phenol (1 g, 2.46 mmol, 80% yield, 91% purity) as a yellow oil. LC-MS (ESI) m/z: 316.9 $[M+1-56]^+$; $^1$H NMR (400 MHz, $CDCl_3$) δ 7.12 (d, J=8.4 Hz, 2H), 6.90 (d, J=8.0 Hz, 2H), 6.77 (s, 1H), 6.69-6.62 (m, 1H), 6.60-6.53 (m, 1H), 4.86 (s, 1H), 2.96 (s, 4H), 1.35 (s, 9H).

Step 5: Preparation of 4-(6-tert-butoxy-2-phenyl-3,4-dihydronaphthalen-1-yl)phenol

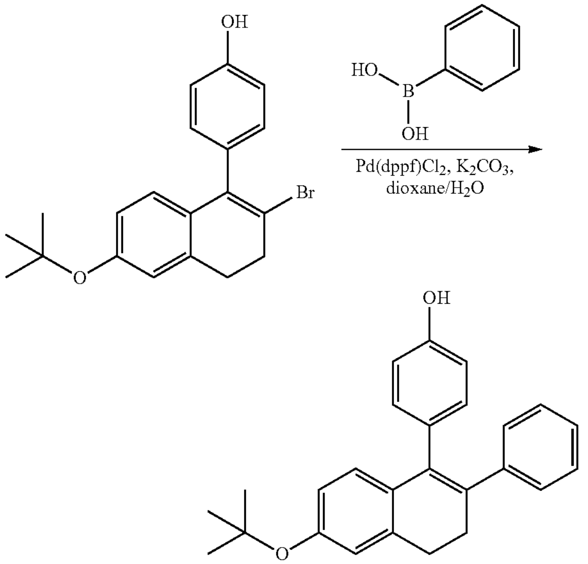

To a solution of 4-(2-bromo-6-tert-butoxy-3,4-dihydronaphthalen-1-yl)phenol (1 g, 2.46 mmol, 1 eq), phenylboronic acid (314 mg, 2.58 mmol, 1.05 eq) in dioxane (10 mL) and water (2 mL) was added potassium carbonate (678 mg, 4.91 mmol, 2 eq) and (1,1'-bis(diphenylphosphino)ferrocene)palladium(II) dichloride (179 mg, 0.24 mmol, 0.1 eq) under nitrogen. The reaction mixture was stirred at 100° C. for 12 hours. LC-MS showed the reaction was completed.

The residue was diluted with water (20 mL) and extracted with ethyl acetate (20 mL×2). The combined organic layers were washed with brine (20 mL×3), dried with anhydrous sodium sulfate, filtered and concentrated in vacuum. The residue was purified by silica gel chromatography (petroleum ether:ethyl acetate=1:0 to 10:1) to get 4-(6-tert-butoxy phenyl-3,4-dihydronaphthalen-1-yl)phenol (930 mg, 2.35 mmol, 95% yield, 93% purity) as a orange oil. LCMS (ESI) m/z: 314.1 [M+1−56]$^+$; $^1$H NMR (400 MHz, $CDCl_3$) δ 7.16-7.09 (m, 2H), 7.08-6.99 (m, 3H), 6.97-6.89 (m, 2H), 6.86-6.82 (m, 1H), 6.74-6.66 (m, 4H), 4.70 (s, 1H), 2.99-2.89 (m, 2H), 2.84-2.75 (m, 2H), 1.37 (s, 9H)

Step 6: Preparation of 4-(6-tert-butoxy-2-phenyl-tetralin-1-yl)phenol

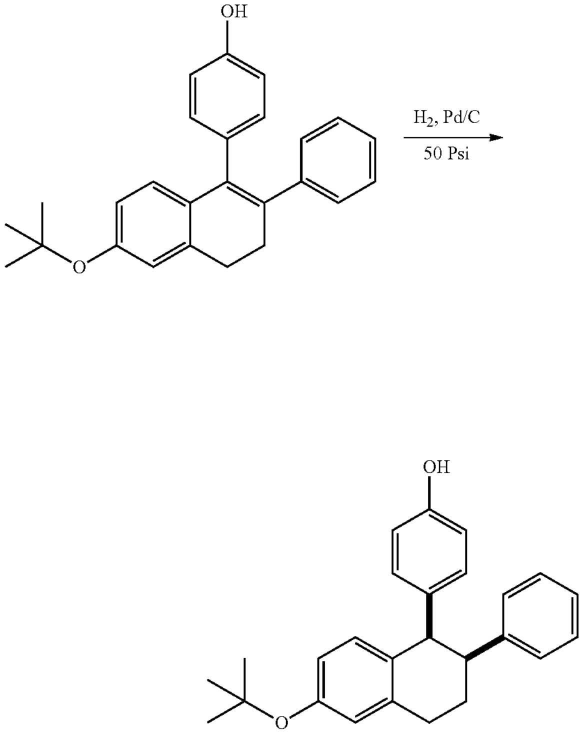

To a solution of 4-(6-tert-butoxy-2-phenyl-3,4-dihydronaphthalen-1-yl)phenol (930 mg, 2.35 mmol, 1 eq) in tetrahydrofuran (20 mL) and methanol (4 mL) was added palladium on activated carbon catalyst (100 mg, 10% purity) under nitrogen. The suspension was degassed under vacuum and purged with hydrogen three times. The mixture was stirred under hydrogen (50 psi) at 30° C. for 36 hours. LC-MS showed the reaction was completed. The reaction mixture was filtered and the solution was concentrated. The resulting material was directly used into the next step without further purification to afford cis-4-(6-tert-butoxy-2-phenyl-tetralin-1-yl)phenol (870 mg, 2.14 mmol, 91% yield, 91% purity) as a white solid. LC-MS (ESI) m/z: 317.0 [M+1−56]$^+$; $^1$H-NMR (400 MHz, $CDCl_3$) δ 7.22-7.12 (m, 3H), 6.89-6.78 (m, 4H), 6.74 (dd, J=2.0, 8.4 Hz, 1H), 6.45 (d, J=8.4 Hz, 2H), 6.27 (d, J=8.4 Hz, 2H), 4.51 (s, 1H), 4.25 (d, J=4.8 Hz, 1H), 3.38 (dd, J=3.2, 12.8 Hz, 1H), 3.08-2.99 (m, 2H), 2.27-2.08 (m, 1H), 1.87-1.76 (m, 1H), 1.37 (s, 9H)

Step 7: Preparation of WX-ARV-HD-012-E1, 4-[(1S,2R)-6-tert-butoxy-2-phenyl-tetralin-1-yl]phenol

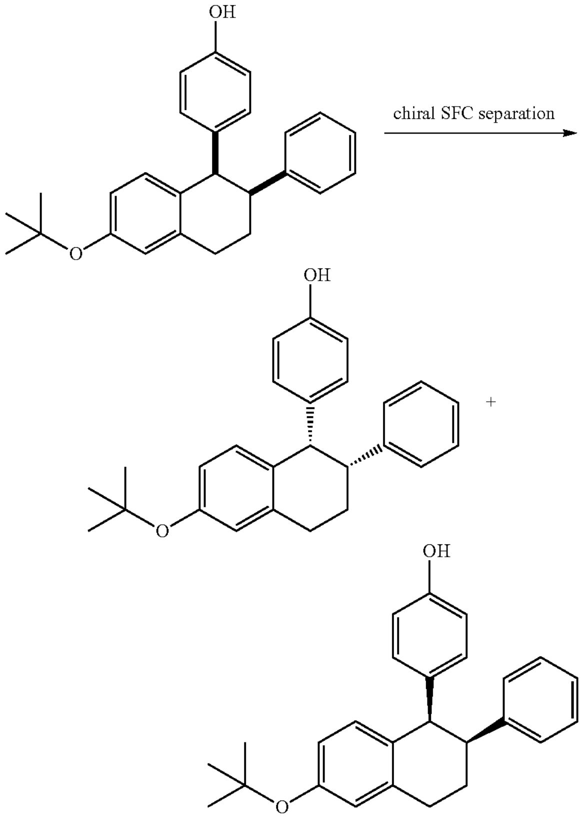

4-(6-tert-butoxy-2-phenyl-tetralin-1-yl)phenol (870 mg, 2.13 mmol, 1 eq) was subjected to supercritical fluid chromatography for chiral separation (column: AD, 250 mm×30 mm, 5 um; mobile phase: 0.1% ammonium hydroxide in methanol, 20%-20%, 4.2 min for each run) to get 4-[(1S, 2R)-6-tert-butoxy-2-phenyl-tetralin-1-yl]phenol (420 mg, 1.04 mmol, 97% yield, 92% purity) as the first fraction and 4-[(1R, 2S)-6-tert-butoxy-2-phenyl-tetralin-1-yl]phenol (420 mg, 1.04 mmol, 97% yield, 92% purity) as a second fraction. Fraction 1: [□]$_D$=+336.9 (C=0.50 g/100 mL in ethyl acetate), LC-MS (ESI) m/z: 395.1 [M+23]$^+$; $^1$H NMR (400 MHz, DMSO-$d_6$) δ 9.02 (s, 1H), 7.20-7.07 (m, 3H), 6.87-6.79 (m, 3H), 6.79-6.72 (m, 1H), 6.71-6.64 (m, 1H), 6.36 (d, J=8.4 Hz, 2H), 6.15 (d, J=8.4 Hz, 2H), 4.19 (d, J=4.8 Hz, 1H), 3.31-3.26 (m, 1H), 3.09-2.89 (m, 2H), 2.17-2.04 (m, 1H), 1.79-1.65 (m, 1H), 1.29 (s, 9H).

Fraction 2: [α]$_D$=−334.1 (C=0.50 g/100 mL in ethyl acetate), LC-MS (ESI) m/z: 395.2 [M+23]$^+$; $^1$H-NMR (400 MHz, DMSO-$d_6$) δ: 9.02 (s, 1H), 7.21-7.06 (m, 3H), 6.88-6.78 (m, 3H), 6.78-6.72 (m, 1H), 6.71-6.64 (m, 1H), 6.36 (d, J=8.4 Hz, 2H), 6.15 (d, J=8.4 Hz, 2H), 4.19 (d, J=4.8 Hz, 1H), 3.30-3.27 (m, 1H), 3.08-2.90 (m, 2H), 2.16-2.04 (m, 1H), 1.79-1.65 (m, 1H), 1.29 (s, 9H).

Step 8: Preparation of 4-(6-benzyloxy-2-phenyl-3,4-dihydronaphthalen-1-yl)phenyl] 1,1,2,2,3,3,4,4,4-nonafluorobutane-1-sulfonate

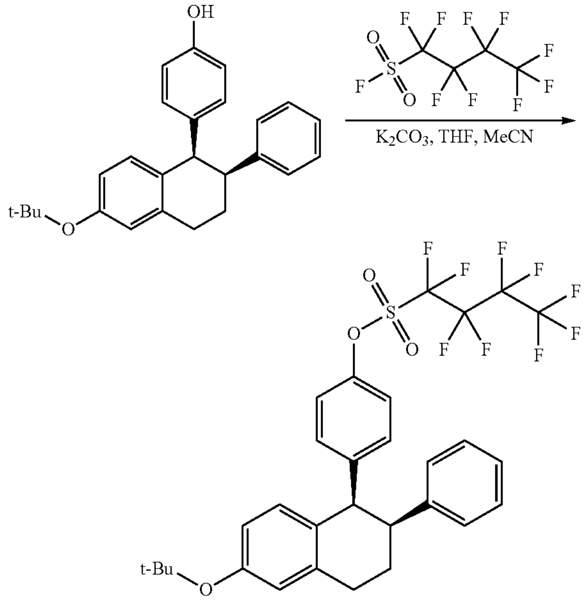

To a solution of 4-[(1R,2S)-6-tert-butoxy-2-phenyl-tetralin-1-yl]phenol (1 g, 2.68 mmol, 1 eq) and 1,1,2,2,3,3,4,4,4-nonafluorobutane-1-sulfonyl fluoride (811 mg, 2.68 mmol, 1 eq) in tetrahydrofuran (5 mL) and acetonitrile (5 mL) was added potassium carbonate (557 mg, 4.03 mmol, 1.5 eq). The reaction mixture was stirred at 25° C. for 16 hours. TLC (petroleum ether:ethyl acetate=10: 1) indicated the starting material was consumed completely and one new spot formed. The reaction mixture was concentrated under reduced pressure. The residue was purified by silica gel chromatography (petroleum ether:ethyl acetate=1:0 to 50:1). The desired compound [4-[(1R,2S)-6-tert-butoxy-2-phenyl-tetralin-1-yl]phenyl]1,1,2,2,3,3,4,4,4-nonafluorobutane-1-sulfonate (1.6 g, 2.44 mmol, 91% yield) was obtained as a colorless oil. $^1$H NMR (400 MHz, $CDCl_3$) δ 7.21-7.11 (m, 3H), 6.94-6.86 (m, 3H), 6.84-6.73 (m, 4H), 6.46 (d, J=8.8 Hz, 2H), 4.33 (d, J=5.2 Hz, 1H), 3.50-3.40 (m, 1H), 3.16-2.95 (m, 2H), 2.20-2.02 (m, 1H), 1.91-1.79 (m, 1H), 1.38 (s, 9H)

Step 9: Preparation of 1-[4-(6-benzyloxy-2-phenyl-3, 4-dihydronaphthalen-1-yl) phenyl]-4-(dimethoxymethyl)piperidine

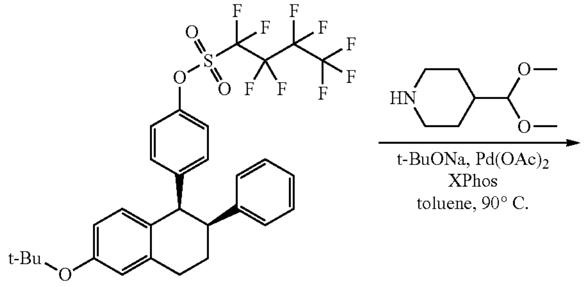

-continued

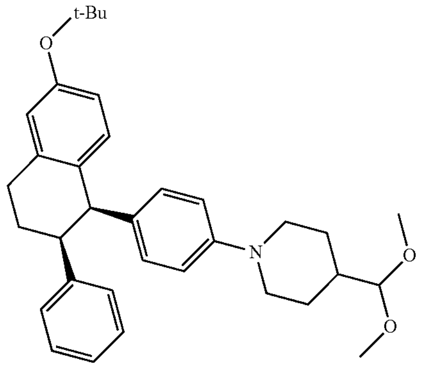

A mixture of [4-[(1R,2S)-6-tert-butoxy-2-phenyl-tetralin-1-yl]phenyl] 1,1,2,2,3,3,4,4,4-nonafluorobutane-1-sulfonate (1.6 g, 2.44 mmol, 1 eq), 4-(dimethoxymethyl)piperidine (584 mg, 3.67 mmol, 1.5 eq), sodium tert-butoxide (705 mg, 7.33 mmol, 3 eq), palladium acetate (82 mg, 0.37 mmol, 0.15 eq) and dicyclohexylphosphino-2',4',6'-triisopropylbiphenyl (233 mg, 0.49 mmol, 0.2 eq) in toluene (30 mL) was degassed and purged with nitrogen 3 times, and then the mixture was stirred at 90° C. for 16 hours under nitrogen atmosphere. LC-MS showed one main peak with desired MS was detected. TLC (petroleum ether: ethyl acetate=10:1) indicated the starting material was consumed completely and one new spot formed. The mixture was cooled, diluted with ethyl acetate (50 mL), filtered on a plug of celite, the filter cake was washed with ethyl acetate (30 mL). The filtrate was concentrated. The residue was purified by silica gel chromatography (petroleum ether: ethyl acetate=100:1 to 10:1). The desired compound 1-[4-[(1R,2S)-6-tert-butoxy-2-phenyl-tetralin-1-yl]phenyl]-4-(dimethoxymethyl) piperidine (1.1 g, 2.14 mmol, 87% yield) was obtained as a white solid. LCMS (ESI) m/z: 514.3 [M+1]$^+$; $^1$H NMR (400 MHz, $CDCl_3$) δ 7.21-7.11 (m, 3H), 6.88-6.78 (m, 4H), 6.73 (dd, J=2.4, 8.0 Hz, 1H), 6.57 (d, J=8.4 Hz, 2H), 6.27 (d, J=8.8 Hz, 2H), 4.23 (d, J=4.8 Hz, 1H), 4.06 (d, J=7.2 Hz, 1H), 3.63-3.52 (m, 2H), 3.41-3.30 (m, 7H), 3.13-2.96 (m, 2H), 2.54 (d, J=2.0, 12.0 Hz, 2H), 2.28-2.10 (m, 1H), 1.85-1.63 (m, 4H), 1.49-1.31 (m, 11H).

Step 10: Preparation of 1-[4-[4-(dimethoxymethyl)-1-piperidyl] phenyl]-2-phenyl-tetralin-6-ol

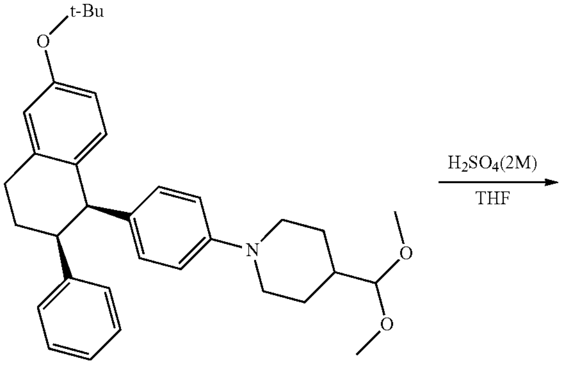

-continued

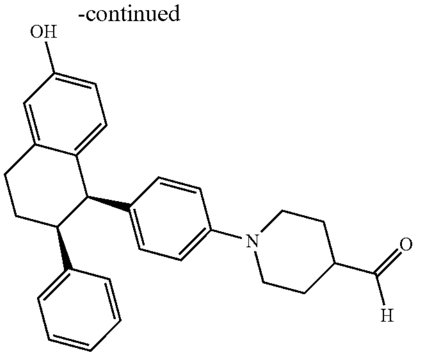

To a solution of 1-[4-[(1R,2S)-6-tert-butoxy-2-phenyl-tetralin-1-yl]phenyl]-4-(dimethoxymethyl)piperidine (1.1 g, 2.14 mmol, 1 eq) in tetrahydrofuran (45 mL) was added sulfuric acid (2 M, 43 mL, 40 eq). The reaction mixture was stirred at 70° C. for 1 hour. Thin-Layer Chromatography (petroleum ether: ethyl acetate=3:1) indicated the starting material was consumed completely and one new spot formed. The reaction mixture was quenched by addition saturated sodium bicarbonate solution to pH=7-8, and extracted with ethyl acetate (20 mL×2). The combined organic layers were washed with brine (20 mL), dried over sodium sulfate, filtered and concentrated under reduced pressure. The residue was used into next step without further purification. The desired compound 1-[4-[(1R,2S)-6-hydroxy-2-phenyl-tetralin-1-yl]phenyl]piperidine-4-carbaldehyde (900 mg, 2.14 mmol, 99% yield, 97% purity) was obtained as light yellow solid. LCMS MS (ESI) m/z: 412.1 $[M+1]^+$ Step 11: Preparation of ethyl (Z)-3-(4-bromophenyl)but-2-enoate

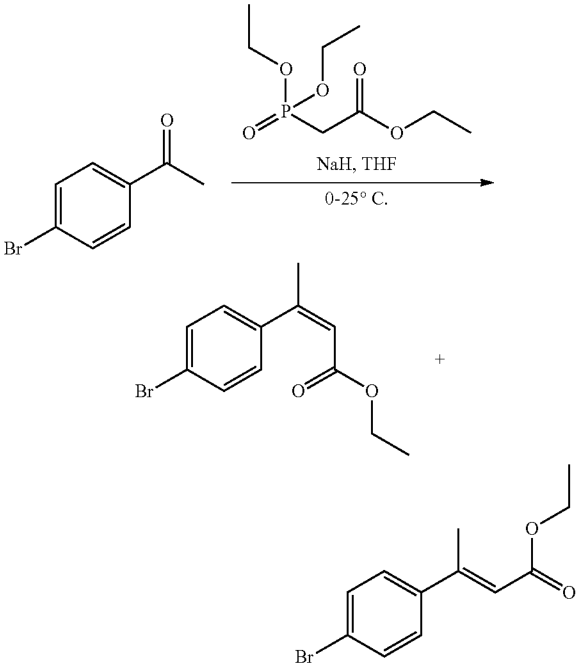

To a suspension of sodium hydride (2.41 g, 60.29 mmol, 60% purity, 1.2 eq) in tetrahydrofuran (100 mL) cooled to 0° C. was slowly added ethyl 2-diethoxyphosphorylacetate (13.52 g, 60.29 mmol, 12 mL, 1.2 eq) and the reaction mixture was stirred at 25° C. for 1 hour. A solution of 1-(4-bromophenyl)ethanone (10 g, 50.24 mmol, 1 eq) in tetrahydrofuran (100 mL) was added dropwise and the mixture was stirred at 25° C. for 12 hours. To this mixture was added saturated aqueous ammonium chloride (50 mL). The mixture was extracted with ethyl acetate (100 mL×3). The organic layer was dried over anhydrous sodium sulfate and concentrated. The residue was purified with prep-HPLC (acetonitrile:water=50:1 to 5:1). Ethyl (Z)-3-(4-bromophenyl)but-2-enoate (6.6 g, 24.52 mmol, 48.9% yield) was obtained as a yellow oil and ethyl (E)-3-(4-bromophenyl) but-2-enoate (2.6 g, 9.66 mmol, 19.3% yield) was also obtained as a yellow oil. LC/MS (ESI) m/z: 270.0 $[M+1]^+$; $^1H$ NMR (400 MHz, $CDCl_3$) δ 7.48 (d, J=8.4 Hz, 2H), 7.09 (d, J=8.4 Hz, 2H), 5.93 (s, 1H), 4.02 (q, J=7.2 Hz, 2H), 2.16 (s, 3H), 1.13 (t, J=7.2 Hz, 3H); $^1H$ NMR (400 MHz, $CDCl_3$) δ 7.58 (d, J=8.4 Hz, 2H), 7.48 (d, J=8.8 Hz, 2H), 6.05 (s, 1H), 4.02 (q, J=14.4 Hz, 2H), 2.52 (s, 3H), 1.13 (q, J=14.4 Hz, 3H).

Step 12: Preparation of tert-butyl 4-[4-[(Z)-3-ethoxy-1-methyl-3-oxo-prop-1-enyl]phenyl]piperazine-1-carboxylate

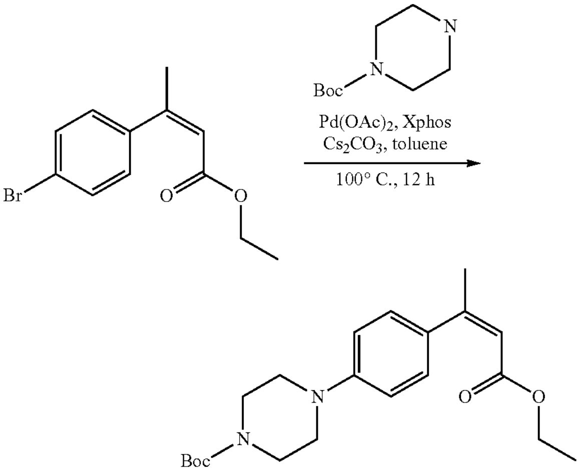

A mixture of ethyl (Z)-3-(4-bromophenyl)but-2-enoate (2.0 g, 7.43 mmol, 1 eq), tert-butyl piperazine-1-carboxylate (2.08 g, 11.15 mmol, 1.5 eq), cesium carbonate (4.84 g, 14.86 mmol, 2 eq), palladium acetate (334 mg, 1.49 mmol, 0.2 eq) and XPhos (708 mg, 1.49 mmol, 0.2 eq) in toluene (30 mL) was degassed and purged with nitrogen three times. The mixture was stirred at 100° C. for 12 hours under nitrogen atmosphere. The resulting mixture were filtered and concentrated under reduced pressure. The residue was washed with saturated brine (30 mL×2) and extracted with ethyl acetate (30 mL×2). The combined organic layers were dried over anhydrous sodium sulfate, filtered and concentrated under reduced pressure. The residue was purified by semi-preparative reverse phase HPLC (column: Phenomenex Synergi Max-RP 250×50 mm, 10 um; mobile phase: [water(0.225% formic acid)-acetonitrile]; B%: 50% acetonitrile-80% acetonitrile, 30 min). Tert-butyl 4-[4-[(Z)-3-ethoxy-1-methyl-3-oxo-prop-1-enyl]phenyl]piperazine-1-carboxylate (2.24 g, 5.83 mmol, 78% yield, 97% purity) was obtained as a white solid. LC/MS (ESI) m/z: 375.1 $[M]^+$.

Step 13: Preparation of tert-butyl 4-[4-[(E)-1-(bromomethyl)-3-ethoxy-3-oxo-prop-1-enyl]phenyl] piperazine-1-carboxylate

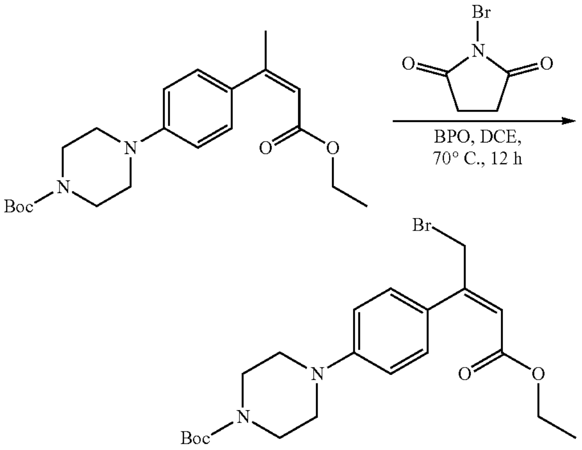

To a solution of tert-butyl 4-[4-[(Z)-3-ethoxy-1-methyl-3-oxo-prop-1-enyl]phenyl] piperazine-1-carboxylate (1.0 g, 2.60 mmol, 1 eq) and 1-bromopyrrolidine-2,5-dione (462.93 mg, 2.60 mmol, 1 eq) in dichloroethane (10 mL) was added benzoyl peroxide(189 mg, 0.78 mmol, 0.3 eq). The mixture was degassed and purged with nitrogen 3 times. The mixture was stirred at 70° C. for 12 hours under nitrogen atmosphere. LC-MS showed ~24% of desired compound was detected. The reaction mixture was washed with saturated aqueous brine (25 mL×2) and extracted with dichloromethane (40 mL×2). The combined organic layers were dried over anhydrous sodium sulfate, filtered and concentrated under reduced pressure. The residue was purified by silica gel chromatography (petroleum ether/ethyl acetate=50/1 to 25:1). Tert-butyl 4-[4-[(E)-1-(bromomethyl)-3-ethoxy-3-oxo-prop-1-enyl]phenyl]piperazine-1-carboxylate (0.3 g, 0.43 mmol, 16% yield, 65% purity) was obtained as a yellow oil. LC/MS (ESI) m/z: 453.0 $[M+1]^+$.

Step 14: Preparation of tert-butyl 4-[4-[1-(2,6-dioxo-3-piperidyl)-5-oxo-2H-pyrrol-3-yl]phenyl]piperazine-1-carboxylate

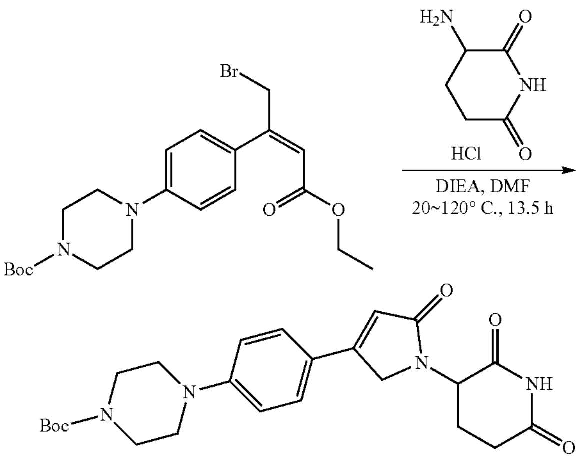

To a mixture of 3-aminopiperidine-2,6-dione (84.95 mg, 0.52 mmol, 1.2 eq, HCl salt) in dimethyl formamide (3 mL) was added N,N-diisopropylethylamine (556 mg, 4.30 mmol, 0.7 mL, 10 eq). The mixture was stirred at 20° C. for 1 hour. Then tert-butyl 4-[4-[(E)-1-(bromomethyl)-3-ethoxy-3-oxo-prop-1-enyl]phenyl]piperazine-1-carboxylate (0.3 g, 0.43 mmol, 1 eq) was added to the reaction and the mixture was stirred at 50° C. for 0.5 hour. The resulting mixture was further heated up to 120° C. and stirred for 12 hours. LC-MS showed desired compound was detected. The reaction mixture was cooled, diluted with ethyl acetate, washed with saturated aqueous brine (25 mL×2) and extracted with ethyl acetate (30 mL×2). The combined organic layers were dried over anhydrous sodium sulfate, filtered and concentrated under reduced pressure. The residue was purified by triturated with methyl tert-butyl ether (15 mL). The product tert-butyl 4-[4-[1-(2,6-dioxo-3-piperidyl)-5-oxo-2H-pyrrol-3-yl]phenyl]piperazine-1-carboxylate (175 mg, 0.23 mmol, 52% yield, 58% purity) was obtained as a brown solid. LC/MS (ESI) m/z: 455.1 $[M+1]^+$.

Step 15: Preparation of 3-[5-oxo-3-(4-piperazin-1-ylphenyl)-2H-pyrrol-1-yl]piperidine-2,6-dione

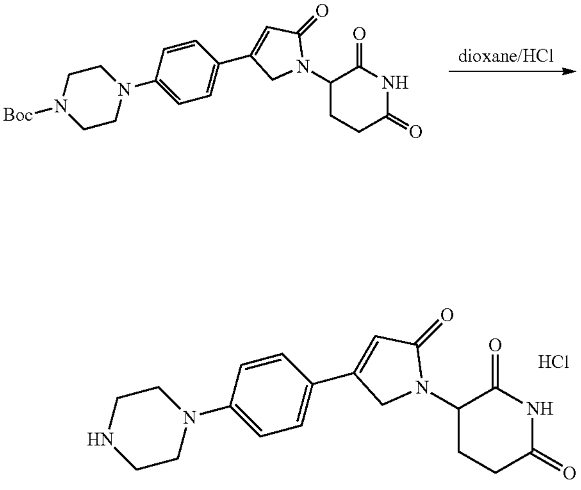

To a solution of tert-butyl 4-[4-[1-(2,6-dioxo-3-piperidyl)-5-oxo-2H-pyrrol-3-yl]phenyl]piperazine-1-carboxylate (175 mg, 0.22 mmol, 1 eq) was added HCl in dioxane (4 M, 5 mL). The mixture was stirred at 20° C. for 1 hour. The reaction mixture was concentrated under vacuum to give a residue. 3-[5-Oxo-3-(4-piperazin-1-ylphenyl)-2H-pyrrol-1-yl]piperidine-2,6-dione (260 mg, crude, HCl salt) was obtained as a brown solid. LC/MS (ESI) m/z: 355.1 $[M+1]^+$.

Step 16: Preparation of 3-[3-[4-[4-[[1-[4-[(1R,2S)-6-hydroxy-2-phenyl-tetralin-1-yl]phenyl]-4-piperidyl]methyl]piperazin-1-yl]phenyl]-5-oxo-2H-pyrrol-1-yl]piperidine-2,6-dione (exemplary PROTAC 89)

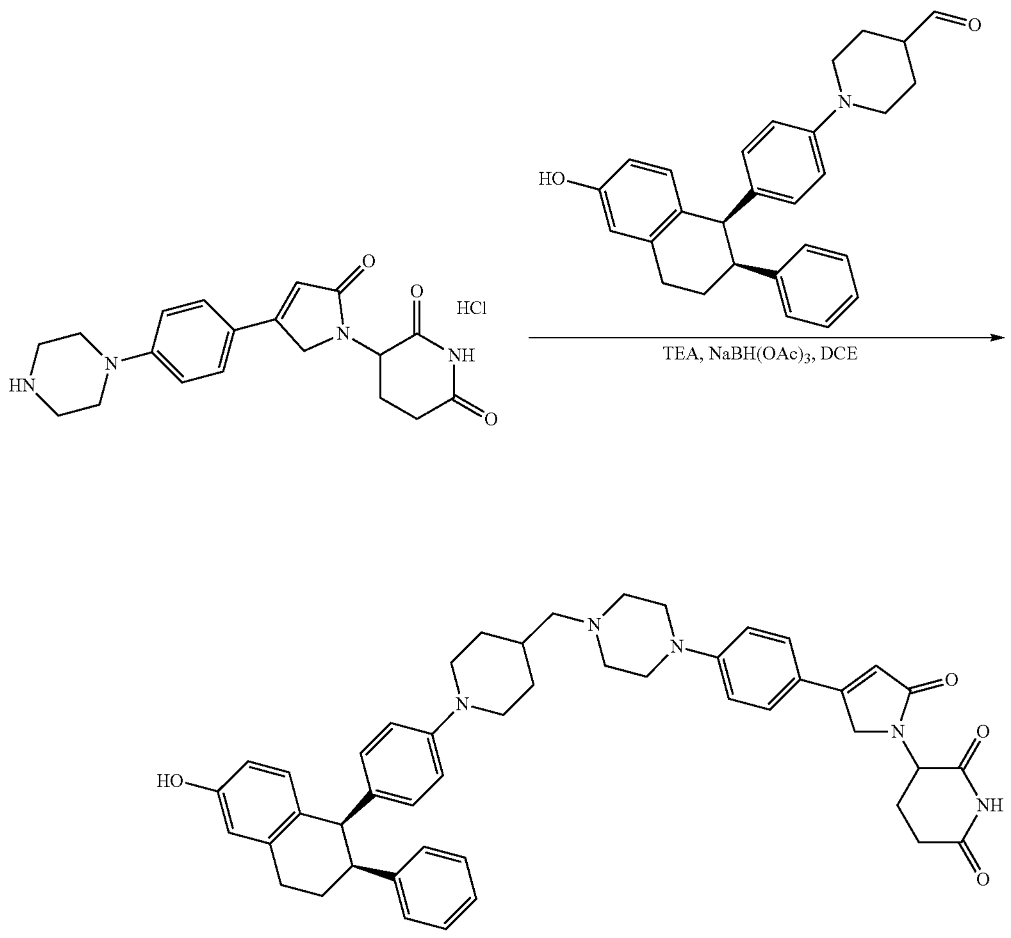

To a solution of 3-[5-oxo-3-(4-piperazin-1-ylphenyl)-2H-pyrrol-1-yl]piperidine-2,6-dione (260 mg, 0.66 mmol, 1 eq, HCl salt) in dichloroethane (3 mL) was added triethylamine (202 mg, 2.00 mmol, 0.3 mL, 3 eq) and 1-[4-[(1R, 2S)-6-hydroxy-2-phenyl-tetralin-1-yl]phenyl]piperidine-4-carbaldehyde (109 mg, 0.26 mmol, 0.4 eq). The mixture was stirred at 25° C. for 15 minutes, and then sodium borohydride acetate (282 mg, 1.33 mmol, 2 eq) was added. The mixture was stirred at 25° C. for another 11.5 hours. LC-MS showed ~74% of desired compound was detected. The reaction mixture was diluted with dichloromethane, washed with saturated brine (20 mL×2) and extracted with dichloromethane (30 mL×2). The combined organic layers were dried over anhydrous sodium sulfate, filtered and concentrated under reduced pressure to give a residue. The residue was purified by prep-HPLC (column: Phenomenex Synergi C18 150×25 mm, 10 um; mobile phase: [water (0.225% formic acid)-acetonitrile]; B%: 22%-43% in 10 min). The product 3-[3-[4-[4-[[1-[4-[(1R, 2S)-6-hydroxy-2-phenyl-tetralin-1-yl]phenyl]-4-piperidyl]methyl]piperazin-1-yl]phenyl]-5-oxo-2H-pyrrol-1-yl]piperidine-2,6-dione (38.7 mg, 0.04 mmol, 7% yield, 95% purity, formate salt) was obtained as a brown solid.

LC/MS (ESI) m/z: 750.3 $[M+1]^+$;

$^1$H-NMR (400 MHz, DMSO-$d_6$) δ 10.95 (s, 1H), 8.19 (s, 1H), 7.50 (d, J=8.8 Hz, 2H), 7.21-7.06 (m, 3H), 6.96 (d, J=8.8 Hz, 2H), 6.83 (d, J=6.4 Hz, 2H), 6.64 (d, J=8.4 Hz, 1H), 6.59 (d, J=2.4 Hz, 1H), 6.53 (d, J=8.8 Hz, 2H), 6.47 (dd, J=2.4, 8.4 Hz, 1H), 6.40 (s, 1H), 6.19 (d, J=8.8 Hz, 2H), 4.91 (dd, J=5.2, 13.2 Hz, 1H), 4.45-4.33 (m, 1H), 4.29-4.19 (m, 1H), 4.12 (d, J=4.8 Hz, 1H), 3.52 (s, 1H), 3.49-3.48 (m, 1H), 3.30 (s, 2H), 3.24 (s, 3H), 3.04-2.79 (m, 3H), 2.60 (s, 1H), 2.52 (d, J=2.0 Hz, 2H), 2.47 (b s, 4H), 2.32-2.23 (m, 1H), 2.18 (d, J=6.8 Hz, 2H), 2.13-2.03 (m, 1H), 1.99-1.88 (m, 1H), 1.80-1.59 (m, 4H), 1.22-1.06 (m, 2H).

Synthesis of Exemplary PROTAC 102

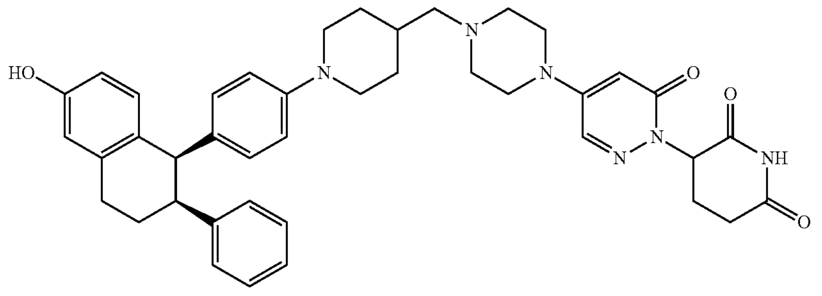 [SMILES: O=C1CCC(n2ncc(N3CCN(CC4CCN(c5ccc([C@@H]6c7ccc(O)cc7CC[C@@H]6c6ccccc6)cc5)CC4)CC3)cc2=O)C(=O)N1]

3-[4-[4-[[1-[4-[(1R, 2 S)-6-hydroxy-2-phenyl-tetralin-1-yl]phenyl]-4-piperidyl]methyl]piperazin-1-yl]-6-oxo-pyridazin-1-yl]piperidine-2,6-dione Step 1: Preparation of tert-butyl 4-(5-chloro-6-oxo-1H-pyridazin-4-yl) piperazine-1-carboxylate

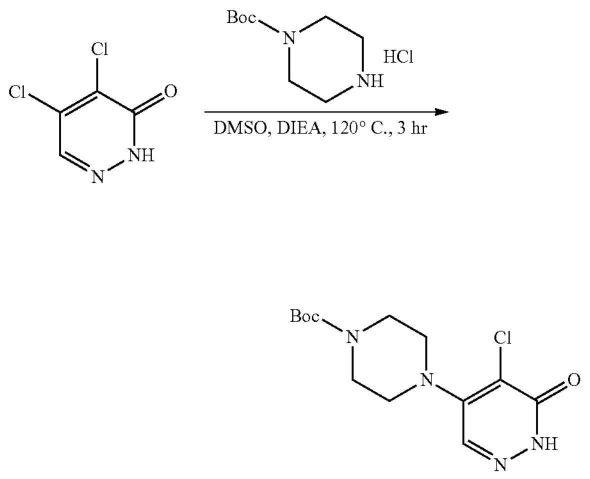

To a solution of 4,5-dichloro-1H-pyridazin-6-one (5 g, 30.31 mmol, 1 eq) in dimethylsulfoxide (100 mL) was added diisopropylethylamin (11.75 g, 90.92 mmol, 3 eq) and tert-butyl piperazine-1-carboxylate hydrochloride (6.75 g, 30.31 mmol, 1 eq). The mixture was stirred at 120° C. for 3 hours. The resulting mixture was cooled to room temperature, filtered and quenched by addition of water (500 mL), then extracted with ethyl acetate (100 mL×3). The combined organic phase was washed with brine (100 mL), dried over anhydrous sodium sulfate, filtered and concentrated under reduce pressure. The residue was purified by silica gel chromatography (dichloromethane:methyl alcohol=200:1 to 100:1). Tert-butyl 4-(5-chloro-6-oxo-1H-pyridazin-4-yl)piperazine-1-carboxylate (8.18 g, 24.95 mmol, 82% yield, 96% purity) was obtained as a yellow solid. LC/MS (ESI) m/z: 315.1 $[M+1]^+$; $^1H$ NMR (400 MHz, $CDCl_3$) δ 11.95 (s, 1H), 7.66 (s, 1H), 3.64-3.57 (m, 4H), 3.44-3.36 (m, 4H), 1.49 (s, 9H).

Step 2: Preparation of tert-butyl 4-(6-oxo-1H-pyridazin-4-yl) piperazine-1-carboxylate

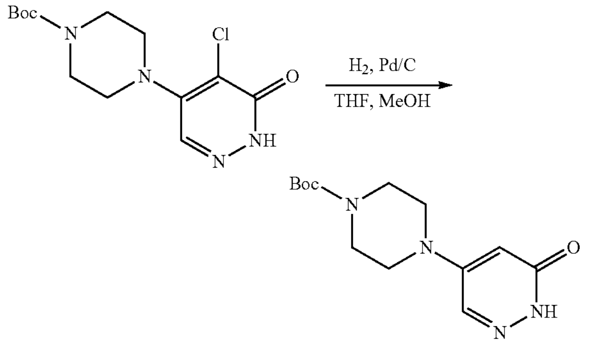

To a solution of tert-butyl 4-(5-chloro-6-oxo-1H-pyridazin-4-yl)piperazine-1-carboxylate (1 g, 3.18 mmol, 1 eq) in tetrahydrofuran (1 mL) and methanol (9 mL) was added palladium/active carbon catalyst (200 mg, 10% purity) under nitrogen. The suspension was degassed under vacuum and purged with hydrogen several times. The mixture was stirred under hydrogen (45 psi) at 25° C. for 0.5 hour. The reaction was basified with triethylamine, and then filtered and the filtrate was concentrated. The residue was used for next step without further purification. Tert-butyl 4-(6-oxo-1H-pyridazin-4-yl) piperazine-1-carboxylate (1 g, crude) was obtained as a white solid. LC/MS (ESI) m/z: 281.1 $[M+1]^+$; $^1H$ NMR (400 MHz, DMSO) δ 12.22 (br s, 1H), 10.38-10.03 (m, 1H), 7.91 (d, J=2.8 Hz, 1H), 3.46-3.37 (m, 4H), 3.04 (br d, J=7.2 Hz, 4H), 1.41 (s, 9H).

Step 3: Preparation of tert-butyl 4-[1-(2,6-dioxo-3-piperidyl)-6-oxo-pyridazin-4-yl]piperazine-1-carboxylate

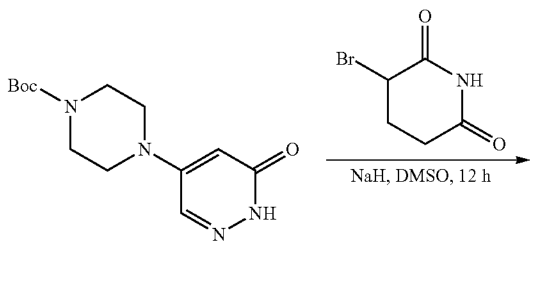

-continued

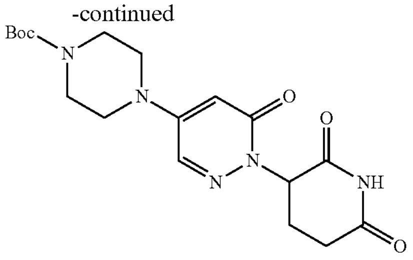

To a solution of tert-butyl 4-(6-oxo-1H-pyridazin-4-yl) piperazine-1-carboxylate (950 mg, 3.39 mmol, 1 eq) in dimethylsulfoxide (15 mL) was added sodium hydride (271 mg, 6.78 mmol, 60% purity, 2 eq) at 25° C. followed by the addition of 3-bromopiperidine-2,6-dione (650 mg, 3.39 mmol, 1 eq). The mixture was stirred at 25° C. for 12 hours. The resulting mixture was filtered and quenched by addition of water (200 mL), and extracted with ethyl acetate (50 mL×3). The combined organic phase was washed with brine (50 mL×3), dried over anhydrous sodium sulfate, filtered and concentrated under reduce pressure. The residue was purified by semi-preparative reverse phase HPLC (column: Phenomenex luna C18 250×50 mm, 10 um; mobile phase: [water(0.225% formic acid)-ACN]; B%: 16%-46% in 30 min). Tert-butyl 4-[1-(2,6-dioxo-3-piperidyl)-6-oxo-pyridazin-4-yl]piperazine-1-carboxylate (190 mg, 0.48 mmol, 14% yield) was obtained as a white solid. LC/MS (ESI) m/z: 392.1 $[M+1]^+$; $^1H$ NMR (400 MHz, DMSO) δ 8.02 (s, 1H), 7.72 (d, J=2.8 Hz, 1H), 5.74 (dd, J=5.3, 11.6 Hz, 1H), 3.62-3.53 (m, 4H), 3.34 (s, 4H), 2.95-2.83 (m, 1H), 2.82-2.58 (m, 2H), 2.27-2.17 (m, 1H), 1.49 (s, 9H).

Step 4: Preparation of 3-(6-oxo-4-piperazin-1-yl-pyridazin-1-yl) piperidine-2,6-dione

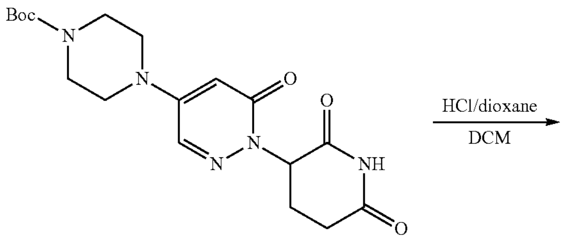

-continued

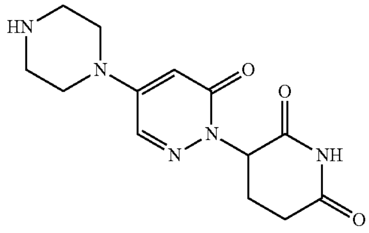

To a solution of tert-butyl 4-[1-(2,6-dioxo-3-piperidyl)-6-oxo-pyridazin-4-yl]piperazine-1-carboxylate (190 mg, 0.48 mmol, 1 eq) in dichloromethane (2 mL) was added hydrochloride in dioxane (4 M, 10 mL, 78 eq). The mixture was stirred at 25° C. for 0.5 hour. The resulting mixture was concentrated under reduced pressure to remove dioxane. The crude product was used into the next step without further purification. Compound 3-(6-oxo-4-piperazin-1-yl-pyridazin-1-yl) piperidine-2,6-dione (120 mg, 0.36 mmol, 75% yield, hydrochloride) was obtained as a light yellow solid. LC/MS (ESI) m/z: 292.0 $[M+1]^+$.

Step 5: Preparation of 3-[4-[4-[[1-[4-[(1R,2S)-6-hydroxy-2-phenyl-tetralin-1-yl]phenyl]-4-piperidyl]methyl]piperazin-1-yl]-6-oxo-pyridazin-1-yl]piperidine-2,6-dione (exemplary PROTAC 102)

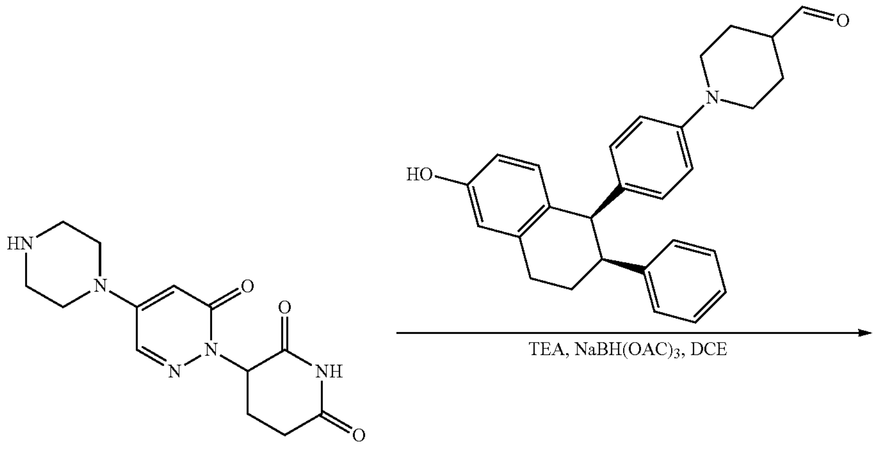

-continued

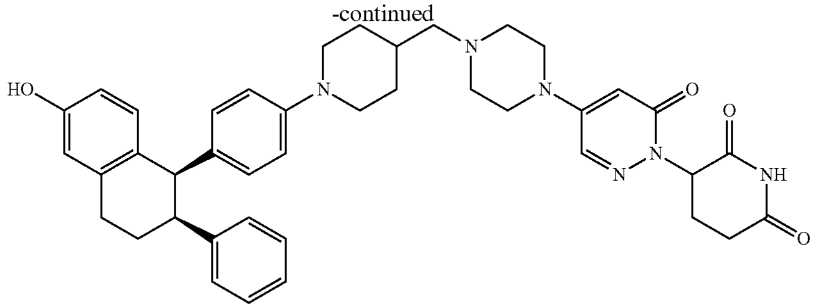

To a solution of 3-(6-oxo-4-piperazin-1-yl-pyridazin-1-yl)piperidine-2,6-dione (57 mg, 0.17 mmol, 1.2 eq, hydrochloride salt) and 1-[4-[(1R, 2S)-6-hydroxy-2-phenyl-tetralin-1-yl]phenyl]piperidine-4-carbaldehyde (60 mg, 0.14 mmol, 1 eq, see step 10, synthesis of exemplary PROTAC 89) in 1,2-dichloroethane (3 mL) was added triethylamine (30 mg, 0.29 mmol, 2 eq) and the mixture was stirred at 25° C. for 0.5 hour. Then sodium triacetoxyborohydride (93 mg, 0.43 mmol, 3 eq) was added. The mixture was further stirred at 25° C. for 0.5 hour. The reaction mixture was concentrated under reduced pressure to remove 1,2-dichloroethane. The residue was purified by prep-HPLC (column: Luna C18 150×25 mm, 5 um; mobile phase: [water(0.225% formic acid)-ACN]; B%: 18%-38% in 7.8 min). Compound 3-[4-[4-[[1-[4-[(1R, 2S)-6-hydroxy-2-phenyl-tetralin-1-yl]phenyl]-4-piperidyl]methyl]piperazin-1-yl]-6-oxo-pyridazin-1-yl]piperidine-2,6-dione (33 mg, 0.04 mmol, 30% yield, 99% purity, formate salt) was obtained as a white solid. LC/MS (ESI) m/z: 687.3 $[M+1]^+$; $^1$H-NMR (400 MHz, DMSO-$d_6$) δ10.96 (s, 1H), 8.22 (s, 1H), 8.04 (d, J=2.4 Hz, 1H), 7.18-7.10 (m, 3H), 6.83 (d, J=6.4 Hz, 2H), 6.64 (d, J=8.4 Hz, 1H), 6.59 (d, J=2.4 Hz, 1H), 6.52 (d, J=8.8 Hz, 2H), 6.47 (dd, J=2.4, 8.4 Hz, 1H), 6.19 (d, J=8.8 Hz, 2H), 5.84 (d, J=2.8 Hz, 1H), 5.58 (dd, 12.4 Hz, 1H), 4.12 (d, J=4.4 Hz, 1H), 3.27 (s, 4H), 3.02-2.79 (m, 3H), 2.57 (d, J=4.0 Hz, 1H), 2.52 (d, J=2.0 Hz, 4H), 2.46 (s, 1H), 2.42 (d, J=4.8 Hz, 5H), 2.20-2.06 (m, 3H), 2.02-1.93 (m, 1H), 1.73 (d, J=14.0 Hz, 3H), 1.61 (s, 1H), 1.19-1.07 (m, 2H).

Synthesis of Exemplary PROTAC 106

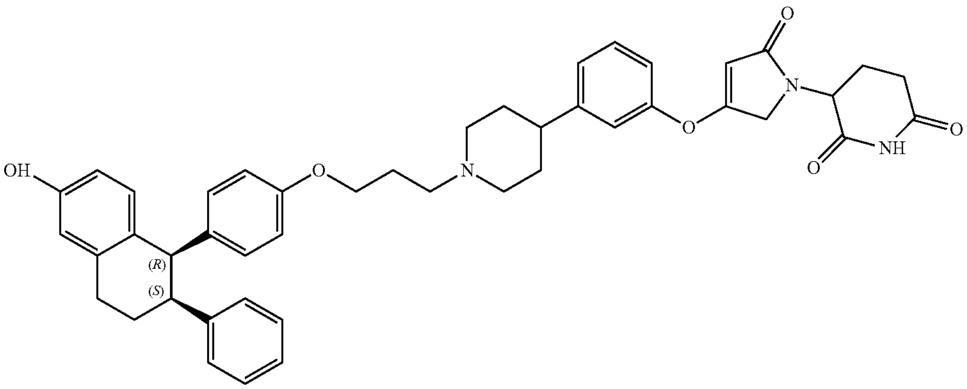

3-(4-(3-(1-(3-(4-((1R,2 S)-6-hydroxy-2-phenyl-1,2,3,4-tetrahydronaphthalen-1-yl)phenoxy)propyl)piperidin-4-yl)phenoxy)-2-oxo-2,5-dihydro-1H-pyrrol-1-yl)piperidine-2,6-dione Synthetic Scheme Part 1:

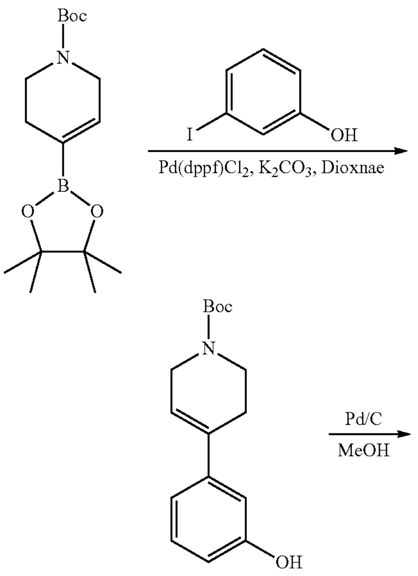

-continued

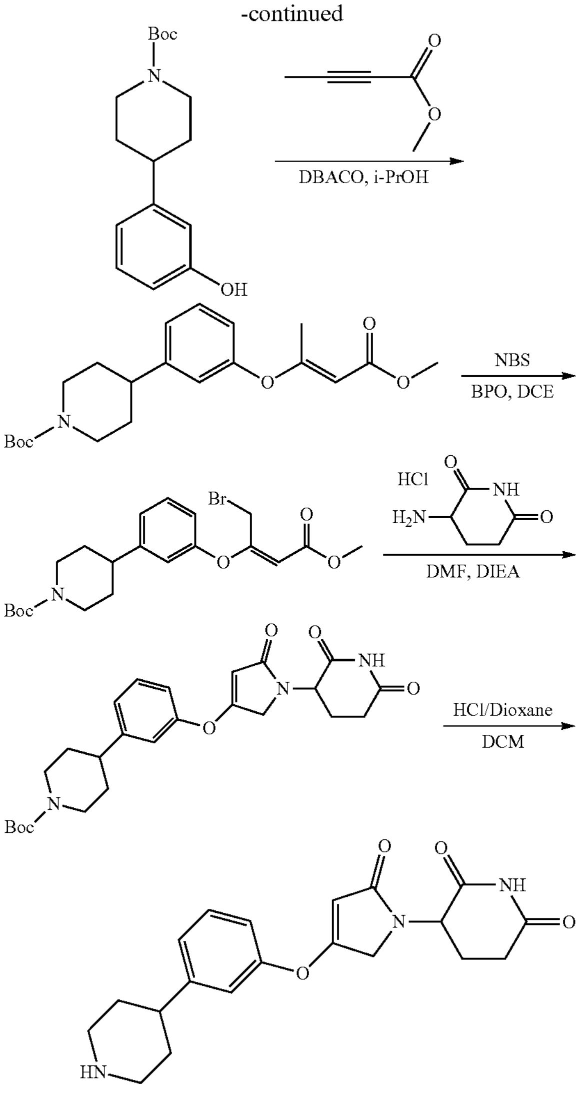

Step 1: Preparation of tert-butyl 4-(3-hydroxyphenyl)-3,6-dihydro-2H-pyridine-1-carboxylate

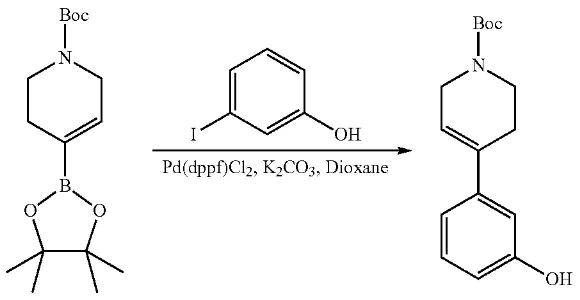

To a mixture of tert-butyl 4-(4,4,5,5-tetramethyl-1,3,2-dioxaborolan-2-yl)-3,6-dihydro-2H-pyridine-1-carboxylate (7.00 g, 22.64 mmol, 1.00 eq) and 3-iodophenol (4.98 g, 22.64 mmol, 1.00 eq) in dioxane (100 mL) and water (10 mL) was added potassium carbonate (6.26 g, 45.28 mmol, 2.00 eq) and cyclopentyl(diphenyl)phosphane; dichloropalladium; iron (1.66 g, 2.26 mmol, 0.10 eq) under nitrogen. The mixture stirred at 90° C. for 4 hours under nitrogen. LC-MS showed the starting material was consumed completely and one main peak with desired MS was detected. The reaction mixture was poured into water (500 mL) and filtered, the filtrated diluted with ethyl acetate (200 mL) and extracted with ethyl acetate (300 mL*3), the combined organice phase washed with saturation brine (150 mL), dried over anhydrous sodium sulfate, filtered and concentrated under reduce pressure. The residue was purified by silica gel column chromatography (Petroleum ether/Ethyl acetate=10/1 to 8/1). Tert-butyl 4-(3-hydroxyphenyl)-3,6-dihydro-2H-pyridine-1-carboxylate (4.00 g, 14.53 mmol, 64% yield) was obtained as a white solid LCMS: MS (ESI) m/z: 298.1 $[M+23]^+$ Chemical Formula: $C_{16}H_{21}NO_3$, Molecular Weight: 275.34

Step 2: Preparation of tert-butyl 4-(3-hydroxyphenyl)piperidine-1-carboxylate

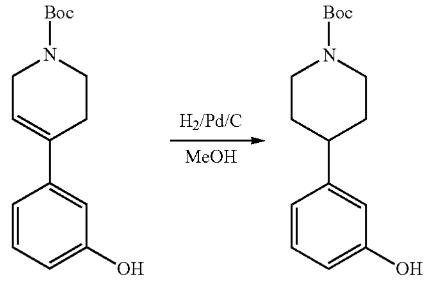 [SMILES: "MeOH" ; CC(C)(C)OC(=O)N1CC=C(c2cccc(O)c2)CC1 ; "H2/Pd/C" ; CC(C)(C)OC(=O)N1CCC(c2cccc(O)c2)CC1]

To a solution of tert-butyl 4-(3-hydroxyphenyl)-3,6-dihydro-2H-pyridine-1-carboxylate (4.00 g, 14.53 mmol, 1.00 eq) in methanol (4 mL) was added palladium on activated carbon catalyst (1.00 g, 10% purity) under nitrogen. The suspension was degassed under vacuum and purged with hydrogen several times. The mixture was stirred under hydrogen (40 psi) at 30° C. for 4 hours. LC-MS showed that the starting material was consumed completely and one main peak with desired MS was detected. The reaction mixture was filtered and concentrated under reduce pressure. The residue was used for next step without further purification. Crude tert-butyl 4-(3-hydroxyphenyl)piperidine-1-carboxylate (4.00 g, crude) as an off-white solid was obtained LCMS: MS (ESI) m/z: 300 $[M+23]^+$ Chemical Formula: $C_{16}H_{23}NO_3$, Molecular Weight: 277.36

Step 3: Preparation of tert-butyl 4-[3-[(E)-3-methoxy-1-methyl-3-oxo-prop-1-enoxy]phenyl]piperidine-1-carboxylate

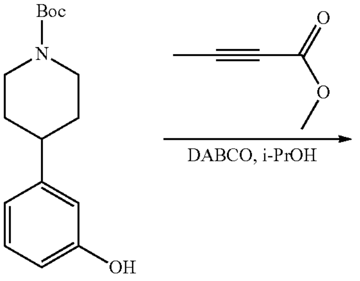

-continued

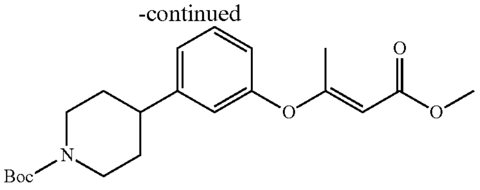

To a solution of tert-butyl 4-(3-hydroxyphenyl)piperidine-1-carboxylate (2.00 g, 7.21 mmol, 1.00 eq) and methyl but-2-ynoate (1.06 g, 10.82 mmol, 1.50 eq) in isopropanol (20 mL) was added 1,4-diazabicyclo[2.2.2]octane (808 mg, 7.21 mmol, 1.00 eq). The mixture was stirred at 15° C. for 12 hours. LC-MS showed that the starting material was consumed completely and one main peak with desired MS was detected. The reaction mixture was quenched by water 20 mL at 15° C., and extracted with ethyl acetate (20 mL×3). The combined organic layers were washed with saturation brine (20 mL×2), dried over anhydrous sodium sulfate, filtered and concentrated under reduced pressure. The residue was purified by silica gel column chromatography (petroleum ether:ethyl acetate=20:1 to 10:1). Tert-butyl 4-[3-[(E)-3-methoxy-1-methyl-3-oxo-prop-1-enoxy]phenyl]piperidine-1-carboxylate (1.72 g, 4.58 mmol, 63% yield) was obtained as a white solid.

LCMS: MS (ESI) m/z: 398.1 $[M+23]^+$

Chemical Formula: $C_{21}H_{29}NO_5$, Molecular Weight: 375.46

Step 4: Preparation of tert-butyl (E)-4-(3-((1-bromo-4-methoxy-4-oxobut-2-en-2-yl)oxy)phenyl) piperidine-1-carboxylate

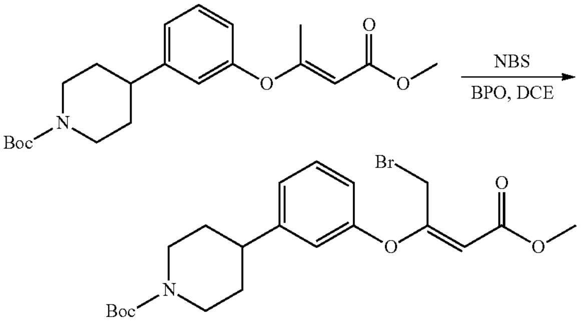

To a mixture of tert-butyl4-[3-[(E)-3-methoxy-1-methyl-3-oxo-prop-1-enoxy]phenyl]piperi dine-1-carboxylate (1.2 g, 3.20 mmol, 1.00 eq) in dichloroethane (50 mL) was added a solution of N-bromosuccinimide (853 mg, 4.79 mmol, 1.5 eq) and benzoyl peroxide (232 mg, 0.96 mmol, 0.3 eq). The mixture stirred at 70° C. for 12 hours. LC-MS showed that the starting material was consumed completely and one main peak with desired MS was detected. The mixture was quenched by addition of water (200 mL), diluted with ethyl acetate (20 mL) and extracted with ethyl acetate (30 mL×3), the combined organic phase washed with saturation brine (30 mL), dried over anhydrous sodium sulfate, filtered and concentrated under reduce pressure. The residue was purified by silica gel column chromatography (petroleum ether:ethyl acetate=100:1-40:1). Tert-butyl4-[3-[(E)-1-(bromomethyl)-3-methoxy-3-oxo-prop-1-enoxy]phenyl]piperidine-1-carboxylate (960 mg, crude) was obtained as a yellow oil.

LCMS: MS (ESI) m/z: 477.9 $[M+23]^+$

Chemical Formula: $C_{21}H_{28}BrNO_5$, Molecular Weight: 454.35

Step 5: Preparation of tert-butyl 4-[3-[[1-(2,6-dioxo-3-piperidyl)-5-oxo-2H-pyrrol-3-yl]oxy]phenyl] piperidine-1-carboxylate

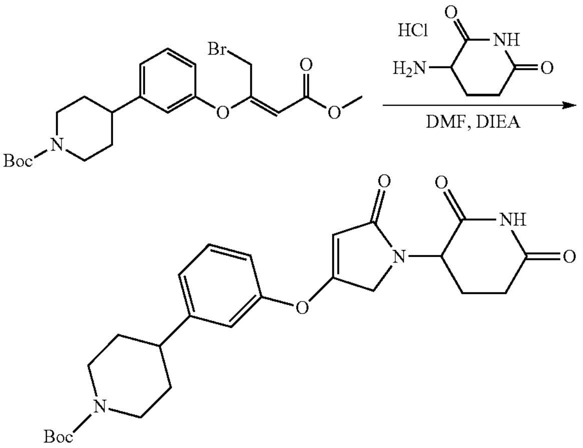

To a mixure of 3-aminopiperidine-2,6-dione (1.56 g, 9.46 mmol, 5 eq, hydrochloride) in dimethylformamide (20 mL) was added diisopropylethylamine (2.45 g, 18.93 mmol, 10 eq). The mixture stirred at 14° C. for 1 hr. The tert-butyl 4-[3-[(E)-1-(bromomethyl)-3-methoxy-3-oxo-prop-1-enoxy]phenyl]piperidine-1-carboxylate (860 mg, 1.89 mmol, 1 eq) was added to the reaction. And then the mixture stirred at 50° C. for 0.5 hour. Then the mixture was heated up to 100° C. for 12 hours. LC-MS showed that the starting material bromide was consumed completely and one main peak with desired MS was detected. The mixture was quenched by addition of water (200 mL), diluted with ethyl acetate (50 mL) and extracted with ethyl acetate (50 mL×3), the combined organic phase washed with saturation brine (50 mL×3), dried over anhydrous sodium sulfate, filtered and concentrated under reduce pressure. The residue was purified by triturated with methyl tert-butyl ether (30 mL). Tert-butyl 4-[3-[[1-(2,6-dioxo-3-piperidyl)-5-oxo-2H-pyrrol-3-yl]oxy]phenyl]piperidine-1-carboxylate (376 mg, 0.80 mmol, 42% yield) as a brown solid was obtained LCMS: MS (ESI) m/z: 492.2 $[M+23]^+$ Chemical Formula: $C_{25}H_{31}N_3O_6$, Molecular Weight: 469.53

Step 6: Preparation of 3-[5-oxo-3-[3-(4-piperidyl) phenoxy]-2H-pyrrol-1-yl]piperidine-2,6-dione

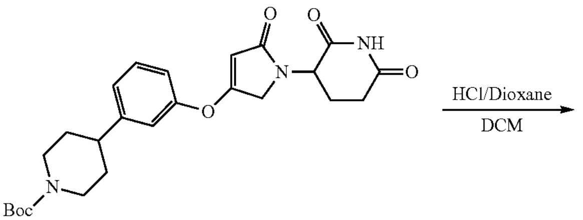

-continued

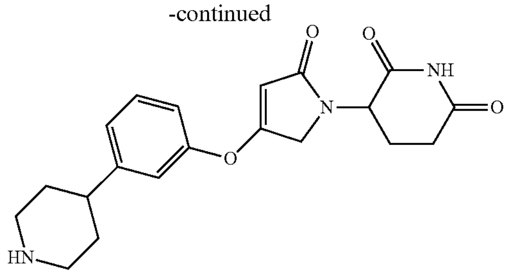

To a mixture of tert-butyl 4-[3-[[1-(2,6-dioxo-3-piperidyl)-5-oxo-2H-pyrrol-3-yl]oxy]phenyl]piperidine-1-carboxylate (420 mg, 0.89 mmol, 1 eq) in dichloromethane (10 mL) was added hydrogen chloride/dioxane (4 M, 4 mL, 20 eq). The mixture stirred at 14° C. for 0.5 hour. LC-MS showed that the starting material was consumed completely and one main peak with desired MS was detected. The reaction was concentrated under reduce pressure. The residue was used for next step without further purification. Crude 3-[5-oxo-3-[3-(4-piperidyl)phenoxy]-2H-pyrrol-1-yl]piperidine-2,6-dione (400 mg, crude, hydrochloride) as a brown solid was obtained LCMS: MS (ESI) m/z: 370 $[M+1]^+$ Chemical Formula: $C_{20}H_{23}N_3O_4$, Molecular Weight: 369.41

Synthetic Scheme Part 2

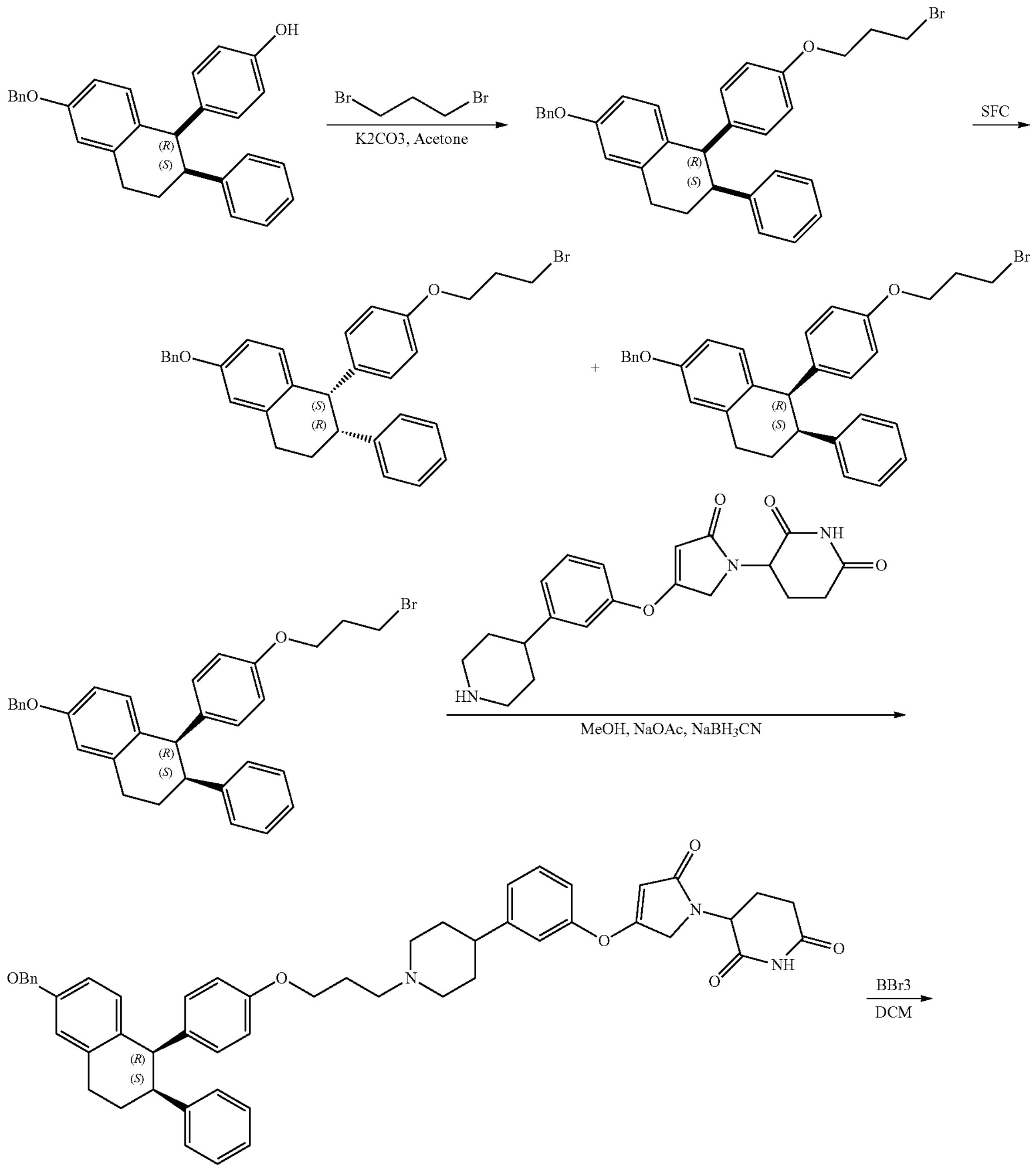

-continued

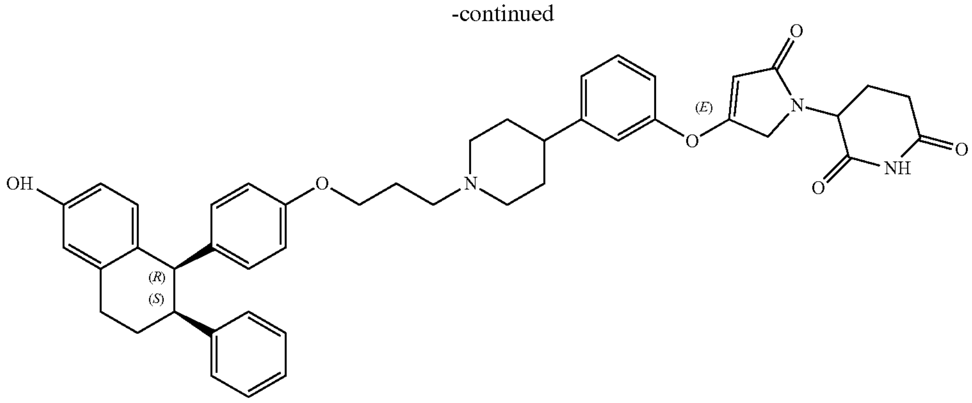

Step 7: Preparation of (cis)-6-benzyloxy-1-[4-(3-bromopropoxy)phenyl]-2-phenyl-tetralin

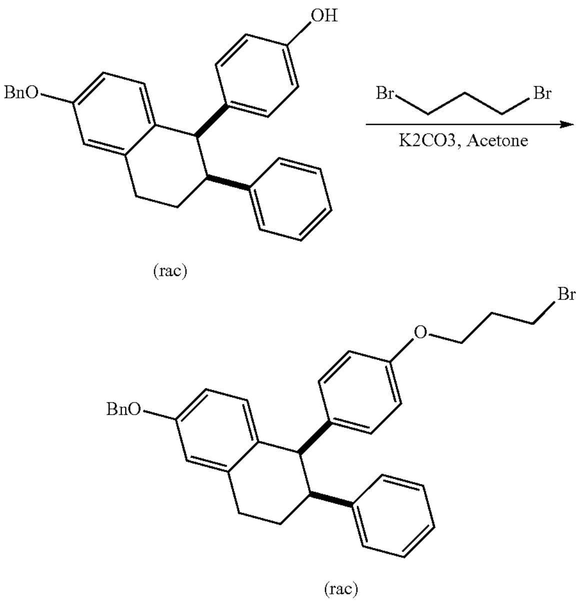

To a solution of 4-[(1R,2S)-6-benzyloxy-2-phenyl-tetralin-1-yl]phenol (1.00 g, 2.46 mmol, 1.00 eq) in acetone (20 mL) was added potassium carbonate (1.02 g, 7.38 mmol, 3.00 eq) and 1,3-dibromopropane (2.48 g, 12.30 mmol, 1.3 mL, 5.00 eq). The mixture was stirred at 70° C. for 12 hours. LC-MS showed the starting material was consumed completely and one main peak with desired MS was detected. The reaction mixture was quenched by addition water (40 mL) at 15° C., and extracted with ethyl acetate (20 mL×3). The combined organic layers were washed with ethyl acetate (20 mL×2), dried over anhydrous sodium sulfate, filtered and concentrated under reduced pressure. The residue was purified by prep-HPLC (column: Phenomenex Synergi Max-RP 250*50 mm*10 um; mobile phase: [water (0.225%FA)-ACN]; B%: 70%-100%,30; 52%min). (cis)-6-benzyloxy-1-[4-(3-bromopropoxy)phenyl]-2-phenyl-tetralin (850 mg, 1.61 mmol, 65% yield, 99% purity) was obtained as a white solid.

LCMS: MS (ESI) m/z: 527.2 $[M+1]^+$

Chemical Formula: $C_{32}H_{31}BrO_2$, Molecular Weight: 527.49

Step 8: Preparation of (1S,2R)-6-benzyloxy-1-[4-(3-bromopropoxy)phenyl]-2-phenyl-tetralin and (1R, 2S)-6-benzyloxy-1-[4-(3-bromopropoxy)phenyl]-2-phenyl-tetralin

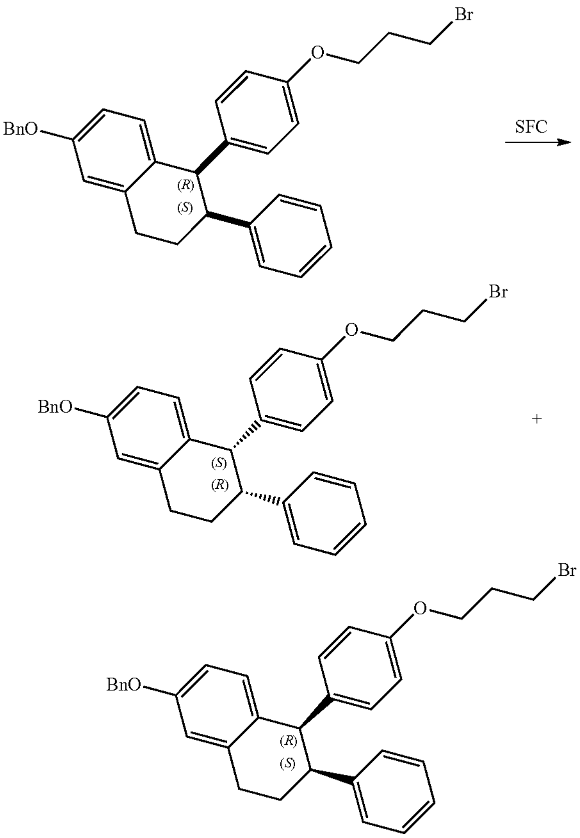

The enantiomers of (cis) 6-benzyloxy-1-[4-(3-bromopropoxy)phenyl]-2-phenyl-tetralin (850 mg, 1.61 mmol, 1.00 eq) were separated using Supercritical Fluid Chromatography. The residue was separated by Supercritical Fluid Chromatography (column: OJ(250 mm*30 mm,10 um); mobile phase: [0.1%NH3H2O MEOH]; B%:60%-60%,20.9 min; 300minmin) Flow rate: 2 mL/min Wavelength: 220 nm.

(1S,2R)-6-benzyloxy-1-[4-(3-bromopropoxy)phenyl]-2-phenyl-tetralin (350 mg, 0.65 mmol, 81% yield, 97% purity) was obtained as a white solid.

(1R,2S)-6-benzyloxy-1-[4-(3-bromopropoxy)phenyl]-2-phenyl-tetralin (350 mg, 0.66 mmol, 82% yield, 99% purity) was obtained as a white solid.

Chemical Formula: $C_{32}H_{31}BrO_2$, Molecular Weight: 527.49

Step 9: Preparation of 3-[3-[3-[1-[3-[4-[(1R,2S)-6-benzyloxy-2-phenyl-tetralin-1-yl]phenoxy]propyl]-4-piperidyl]phenoxy]-5-oxo-2H-pyrrol-1-yl]piperidine-2,6-dione

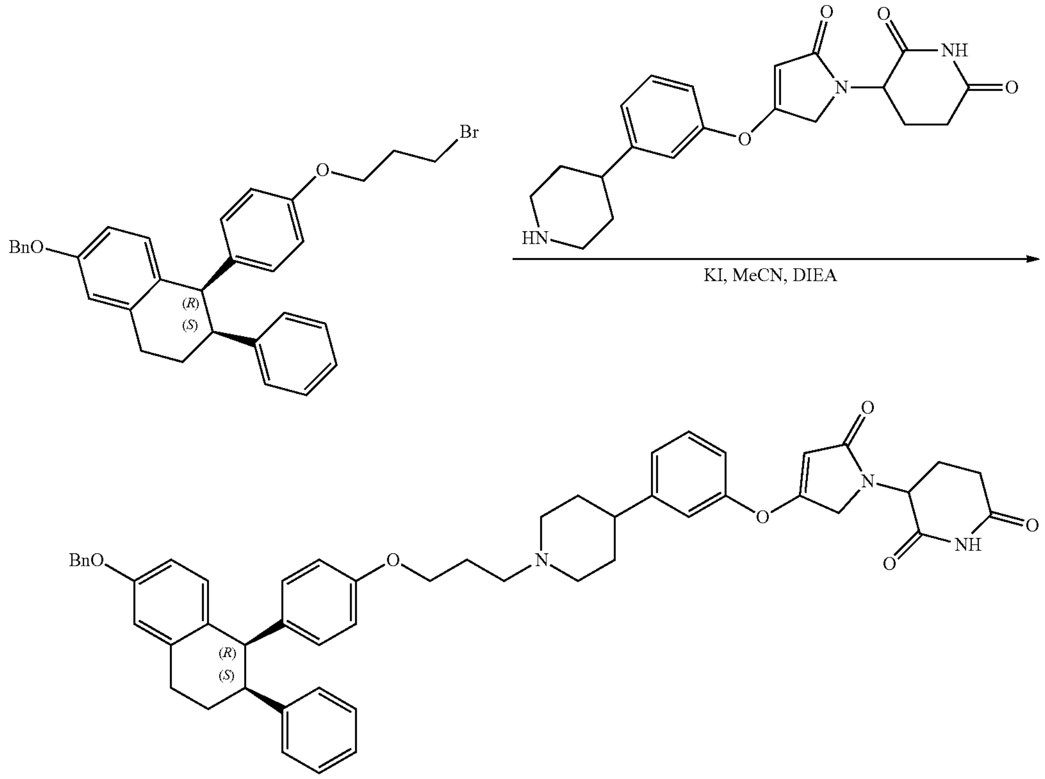

To a mixture of (1R,2S)-6-benzyloxy-1-[4-(3-bromopropoxy)phenyl]-2-phenyl-tetralin (164 mg, 0.31 mmol, 1.1 eq) and 3-[5-oxo-3-[3-(4-piperidyl)phenoxy]-2H-pyrrol-1-yl]piperidine-2,6-dione (115 mg, 0.28 mmol, 1 eq, hydrochloride) in acetonitrile (5 mL) was added diisopropylethylamine (110 mg, 0.85 mmol, 3 eq) and potassium iodide (47 mg, 0.28 mmol, 1 eq). The mixture stirred at 100° C. for 1.5 hours. LC-MS showed that the amine starting material was consumed completely and one main peak with desired MS was detected. The mixture was quenched by addition water (100 mL), diluted with ethyl acetate (15 mL), extracted with ethyl acetate (20 mL×4), the combined organic phase washed with saturation brine (20 mL), dried over anhydrous sodium sulfate, filtered and concentrated under reduce pressure. The residue was purified by prep-TLC (dichloromethane:methanol=10:1). 3-[3-[3-[1-[3-[4-[(1R,2S)-6-benzyloxy-2-phenyl-tetralin-1-yl]phenoxy]propyl]-4-piperidyl]phenoxy]-5-oxo-2H-pyrrol-1-yl]piperidine-2,6-dione (100 mg, 0.12 mmol, 43% yield) as a brown solid was obtained.

LCMS: MS (ESI) m/z: 816.4 $[M+1]^+$

Chemical Formula: $C_{52}H_{53}N_3O_6$, Molecular Weight: 815.99

Step 10: Preparation of 3-[3-[3-[1-[3-[4-[(1R,2S)-6-hydroxy-2-phenyl-tetralin-1-yl]phenoxy]propyl]-4-piperidyl]phenoxy]-5-oxo-2H-1-pyrrol-1-yl]piperidine-2,6-dione

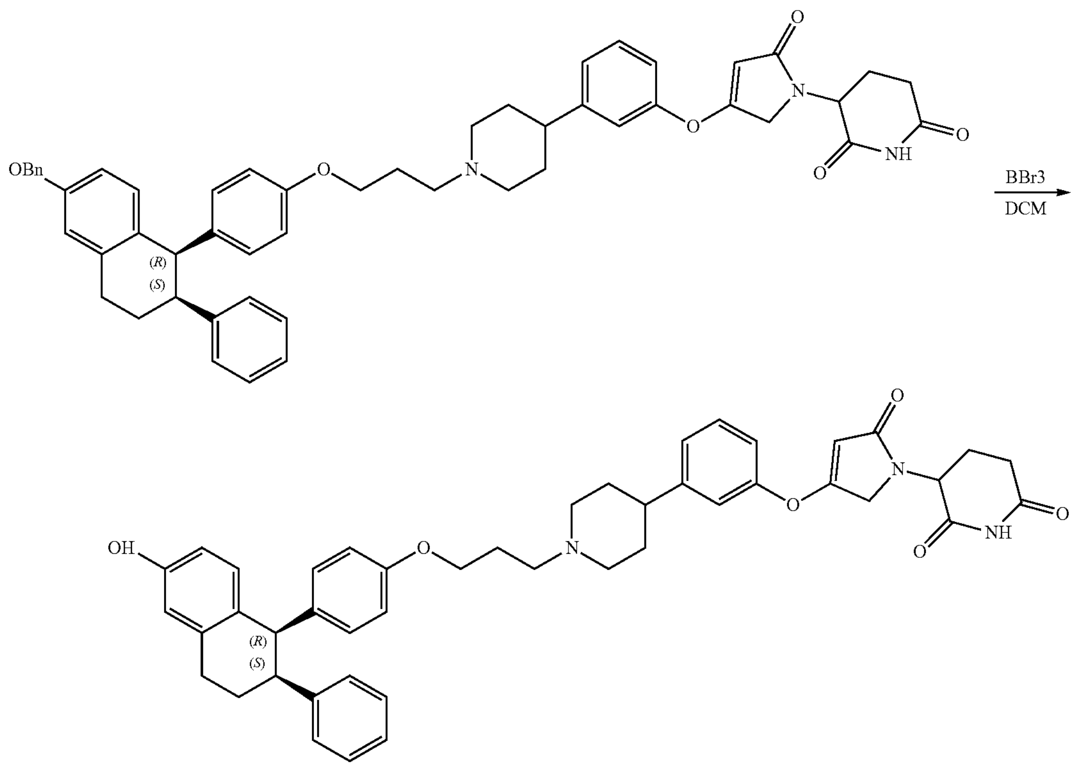

To a mixture of 3-[3-[3-[1-[3-[4-[(1R,2S)-6-benzyloxy-2-phenyl-tetralin-1-yl]phenoxy]propyl]-4-piperidyl]phenoxy]-5-oxo-2H-pyrrol-1-yl]piperidine-2,6-dione (100 mg, 0.12 mmol, 1 eq) in dichloromethane (5 mL) was added boron tribromide (92 mg, 0.37 mmol, 3 eq) at −68° C. The mixture stirred at −68° C. for 30 minutes. LC-MS showed the starting material was consumed completely and one main peak with desired MS was detected. The residue was diluted with water (20 mL) and extracted with ethyl acetate (20 mL×2). The combined organic layers were washed with saturated brines (20 mL×3), dried with anhydrous sodium sulfate, filtered and concentrated in vacuum. The residue was purified by prep-HPLC (column: Boston Green ODS 150*30 5u; mobile phase: [water(0.225%FA)-ACN]; B%: 34%-55%,10 min). 3-[3-[3-[1-[3-[4-[(1R,2S)-6-hydroxy-2-phenyl-tetralin-1-yl]phenoxy]propyl]-4-piperidyl]phenoxy]-5-oxo-2H-pyrrol-1-yl]piperidine-2,6-dione (16 mg, 0.02 mmol, 16% yield, 97% purity, formate) was obtained as a white solid LCMS: MS (ESI) m/z: 726.3 $[M+1]^+$ $^1H$ NMR: (400 MHz, DMSO-$d_6$)

δ=10.92 (s, 1H), 9.48-8.87 (m, 1H), 8.21 (s, 1H), 7.41-7.34 (m, 1H), 7.23-7.06 (m, 6H), 6.82 (d, J=6.8 Hz, 2H), 6.66-6.57 (m, 2H), 6.55-6.44 (m, 3H), 6.25 (d, J=8.8 Hz, 2H), 4.91-4.82 (m, 2H), 4.18-3.97 (m, 3H), 3.84 (t, J=6.4 Hz, 2H), 3.30-3.27 (m, 2H), 3.02-2.82 (m, 5H), 2.55-2.52 (m, 3H), 2.39 (t, J=6.9 Hz, 2H), 2.26 (dd, J=4.8, 13.6 Hz, 1H), 2.11-1.58 (m, 11H)

Chemical Formula: $C_{45}H_{47}N_3O_6$, Molecular Weight: 725.87

Synthesis of Exemplary PROTAC 107
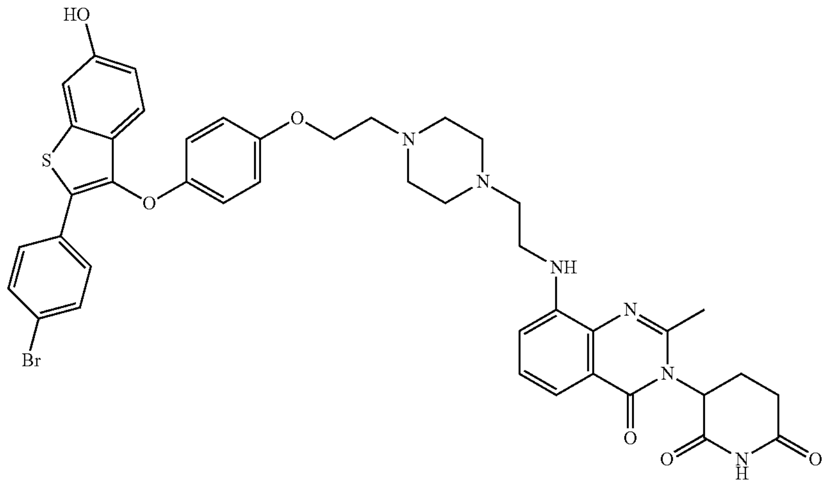 [SMILES: Cc1nc2c(NCCN3CCN(CCOc4ccc(Oc5c(-c6ccc(Br)cc6)sc6cc(O)ccc56)cc4)CC3)cccc2c(=O)n1C1CCC(=O)NC1=O]
3-(8-((2-(4-(2-(4-(2-(4-bromophenyl)-6-hydroxy-benzo[b]thiophen-3-yl)oxy)phenoxy)ethyl)piperazin-1-yl)ethyl)amino)-2-methyl-4-oxoquinazolin-3(4H)-yl)piperidine-2,6-dione
Synthetic Scheme part 1:
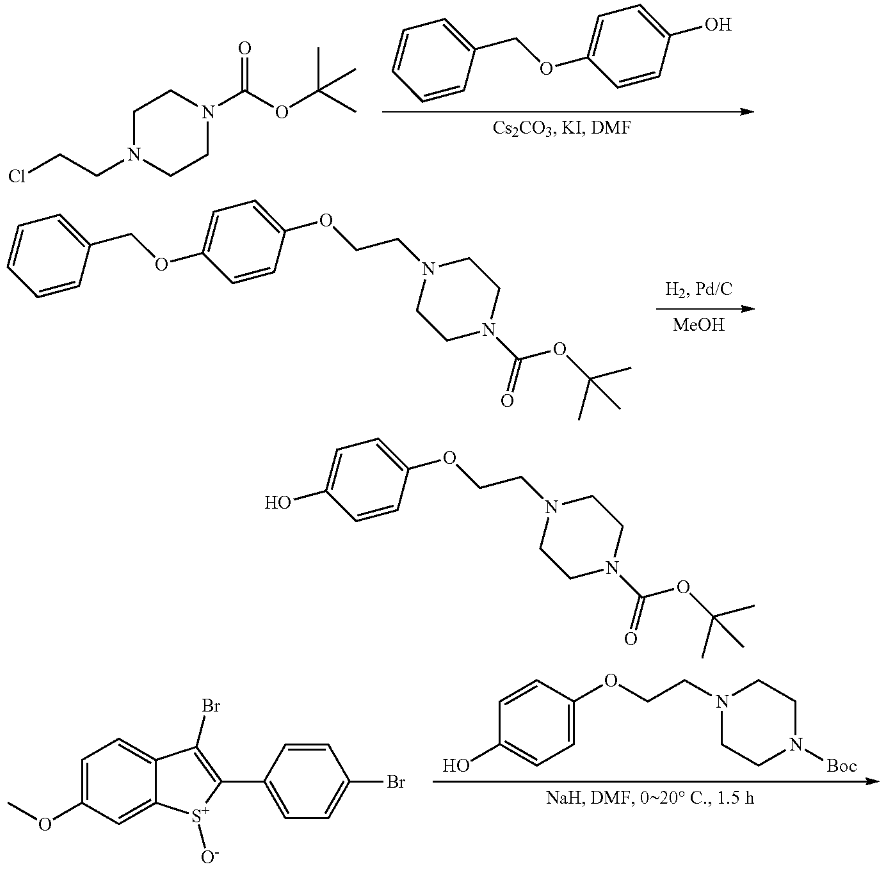

-continued
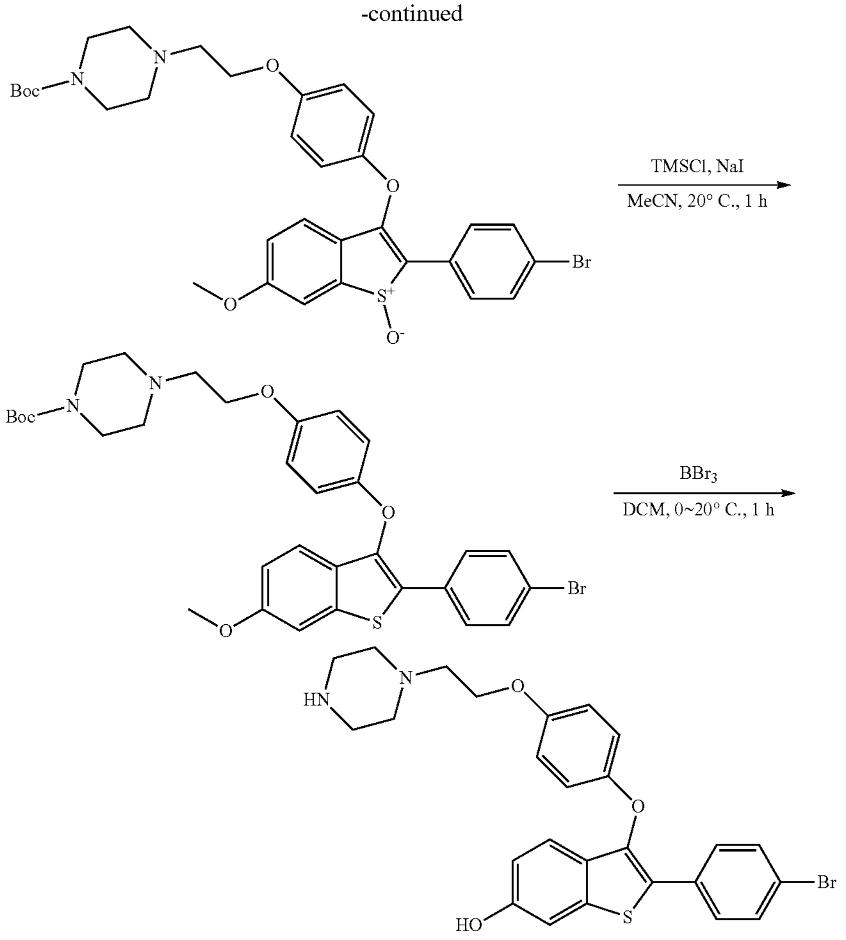
Synthetic Scheme part 2:
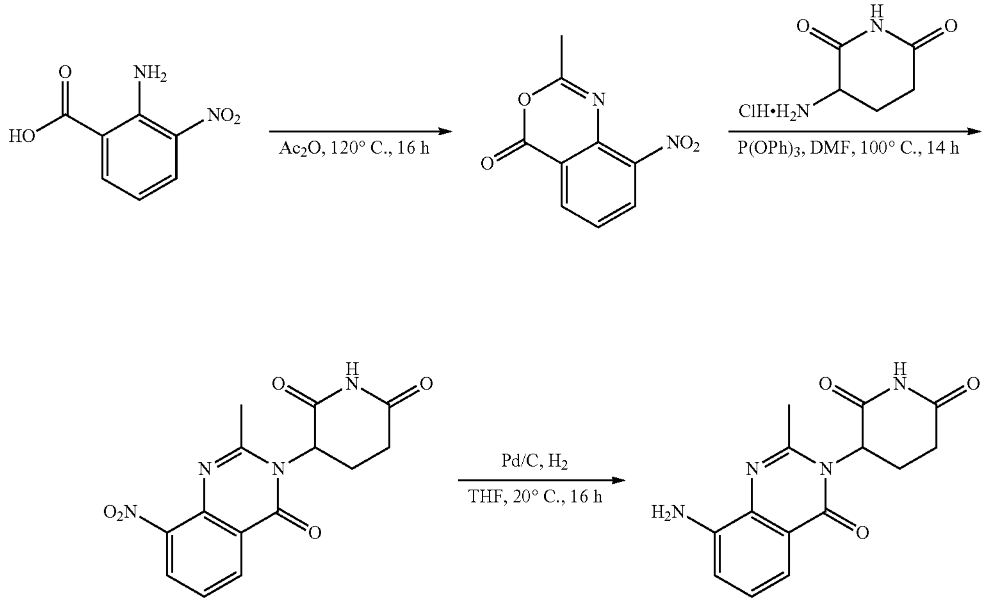

-continued
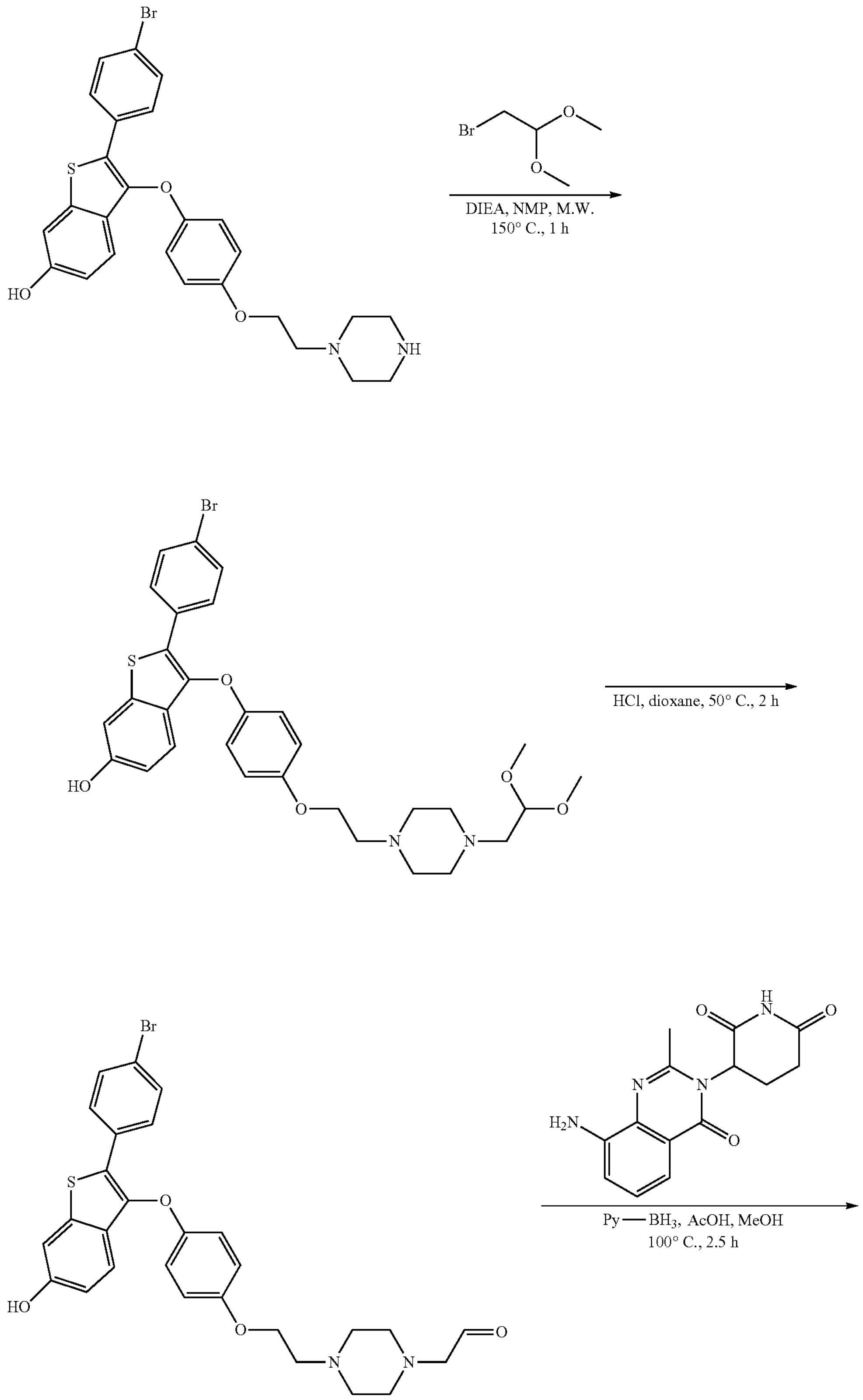

-continued

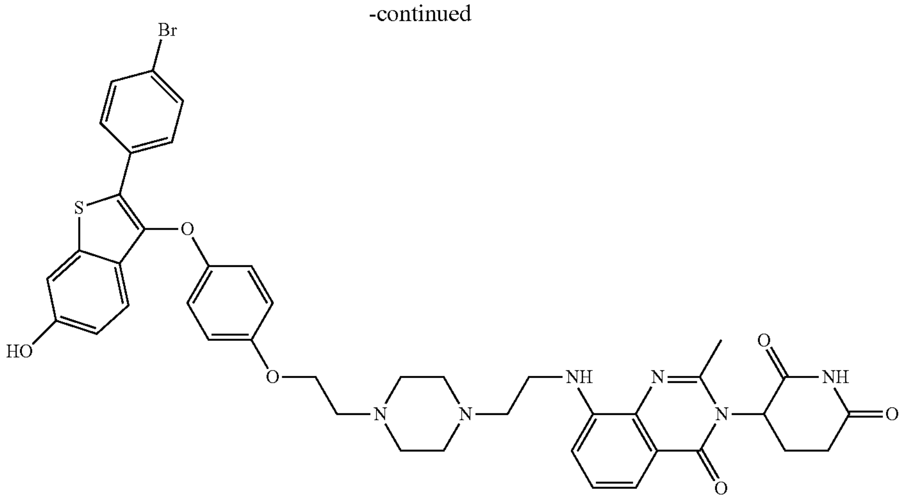

Step 1: Synthesis of tert-butyl4-[2-(4-benzyloxyphenoxy)ethyl]piperazine-1-carboxylate

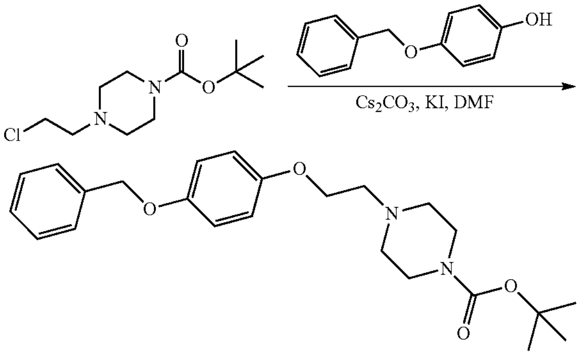

To a solution of tert-butyl 4-(2-chloroethyl)piperazine-1-carboxylate (1.00 g, 4.02 mmol, 1.00 eq), 4-benzyloxyphenol (965 mg, 4.82 mmol, 1.20 eq) in N,N-dimethylformamide (20 mL) was added cesium carbonate (1.57 g, 4.82 mmol, 1.20 eq) and potassium iodide (66 mg, 0.4 mmol, 0.10 eq) under nitrogen. The reaction was stirred at 80° C. for 10 hours. TLC (Petroleum ether/Ethyl acetate=3/1) and LCMS showed most of the starting material was consumed. Water (100 mL) was added to the mixture, the resulting mixture was extracted with Ethyl acetate (50 mL×3). The combined organic phase was washed with brine (80 mL), dried over sodium sulfate, filtered and concentrated in vacuum. The residue was purified by silica gel chromatography (Petroleum ether/Ethyl acetate=50/1 to 3/1). tert-butyl 4-[2-(4-benzyloxyphenoxy)ethyl]piperazine-1-carboxylate (1.4 g, 3.39 mmol, 84% yield) was obtained as a colorless oil.

Chemical Formula: $C_{24}H_{32}N_2O_4$, Molecular Weight: 412.5

Total H count from HNMR data: 32

$^1$H NMR: (400 MHz, CHLOROFORM-d)

δ: 7.46-7.29 (m, 5H), 6.95-6.88 (m, 2H), 6.88-6.81 (m, 2H), 5.02 (s, 2H), 4.07 (t, J=5.8 Hz, 2H), 3.51-3.42 (m, 4H), 2.80 (t, J=5.8 Hz, 2H), 2.56-2.48 (m, 4H), 1.47 (s, 9H)

Step 2: Synthesis of tert-butyl 4-[2-(4-hydroxyphenoxy)ethyl]piperazine-1-carboxylate

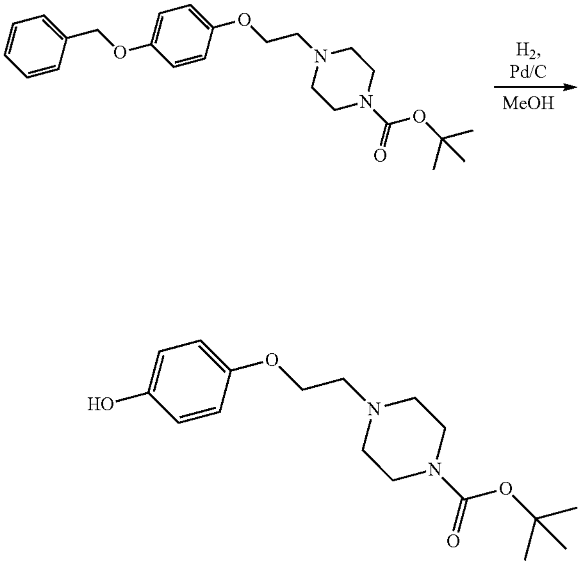

To a solution of tert-butyl 4-[2-(4-benzyloxyphenoxy)ethyl]piperazine-1-carboxylate (1.40 g, 3.39 mmol, 1.00 eq) in methanol (20 mL) was added palladium on carbon (200 mg, 10% purity) under nitrogen. The suspension was degassed under vacuum and purged with hydrogen several times. The mixture was stirred under hydrogen (50 psi) at 20° C. for 4 hours. TLC (Petroleum ether/Ethyl acetate=1/1) showed most of the starting material was consumed. The reaction mixture was filtered and the filter was concentrated in vacuum. Tert-butyl 4-[2-(4-hydroxyphenoxy)ethyl]piperazine-1-carboxylate (1 g, 3.07 mmol, 90% yield, 99% purity) was obtained as a light yellow solid.

Chemical Formula: C17H26N2O4, Molecular Weight: 322.4

Total H count from HNMR data: 26

$^1$H NMR: (400 MHz, CHLOROFORM-d)

δ: 6.74 (s, 4H), 4.04 (t, J=5.6 Hz, 2H), 3.54-3.38 (m, 5H), 2.79 (t, J=5.6 Hz, 2H), 2.53 (s, 4H), 1.46 (s, 9H)

Step 3: Synthesis of tert-butyl 4-(2-(4-(2-(4-bromophenyl)-6-methoxy-1-oxidobenzo[b]thiophen-3-yl)oxy)phenoxy)ethyl)piperazine-1-carboxylate

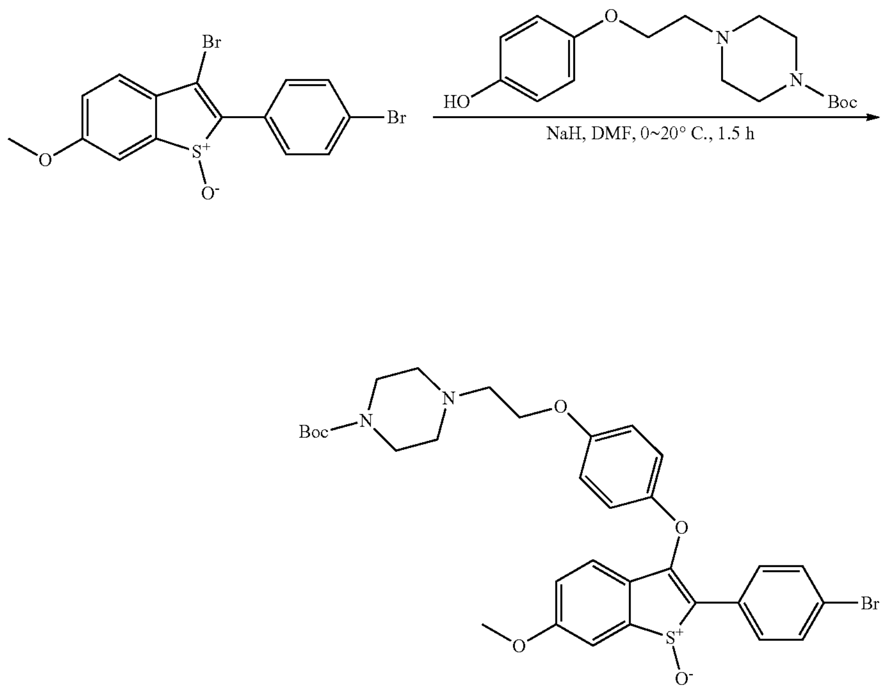

To a solution of tert-butyl 4-[2-(4-hydroxyphenoxy)ethyl]piperazine-1-carboxylate (234 mg, 0.72 mmol, 1.00 eq) in N,N-dimethylformamide (5 mL) was added NaH (29 mg, 0.72 mmol, 60% mineral oil, 1.00 eq) at 0° C. The mixture was stirred at 20° C. for 0.5 hour. 3-bromo-2-(4-bromophenyl)-6-methoxy-1-oxido-benzothiophen-1-ium (300 mg, 0.72 mmol, 1.00 eq) was added, and then the mixture was stirred at 20° C. for 1 hour. LCMS showed the reaction was completed and desired MS can be detected. The reaction mixture was quenched with water (10 mL) and extracted with ethyl acetate (10 mL×3). The combined organic phase was washed with saturated brine (10 mL×2), dried with anhydrous sodium sulfate, filtered and concentrated in vacuum to afford tert-butyl 4-[2-[4-[2-(4-bromophenyl)-6-methoxy-1-oxido-benzothiophen-1-ium-3-yl]oxyphenoxy]ethyl]piperazine-1-carboxylate (430 mg, 0.66 mmol, 90% yield) as a yellow solid, which was directly used for next step without further purification.

LCMS: MS (ESI) m/z: 657.0 $[M+1]^+$ $^1H$ NMR: (400 MHz, $CDCl_3$)

δ: 7.65 (d, J=8.4 Hz, 2H), 7.52-7.46 (m, 3H), 7.05-6.89 (m, 4H), 6.81 (d, J=8.4 Hz, 2H), 4.05 (t, J=5.6 Hz, 2H), 3.89 (s, 3H), 3.50-3.42 (m, 4H), 2.81 (t, J=5.6 Hz, 2H), 2.52 (s, 4H), 1.47 (s, 9H)

Chemical Formula: $C_{32}H_{35}BrN_2O_6S$, Molecular Weight: 655.60

Total H count from HNMR data: 35.

Step 4: Synthesis of tert-butyl 4-(2-(4-((2-(4-bromophenyl)-6-methoxybenzo[b]thiophen-3-yl)oxy)phenoxy)ethyl)piperazine-1-carboxylate

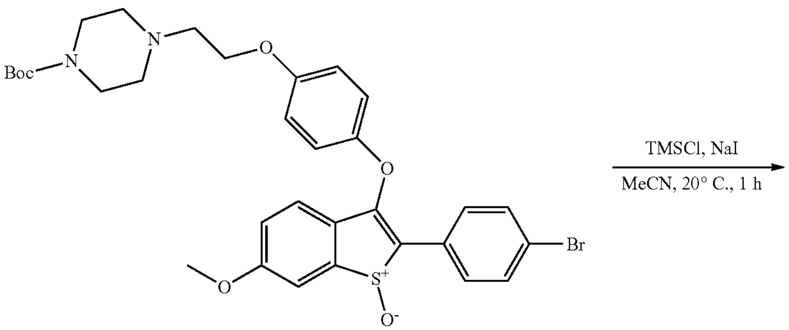

-continued

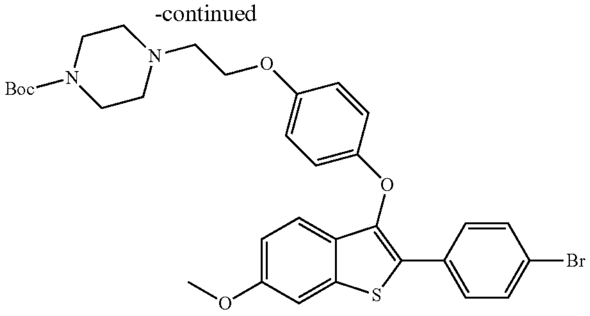

To a solution of tert-butyl 4-[2-[4-[2-(4-bromophenyl)-6-methoxy-1-oxido-benzothiophen-1-ium-3-yl]oxyphenoxy]ethyl]piperazine-1-carboxylate (370 mg, 0.56 mmol, 1.00 eq) in acetonitrile (6 mL) was added sodium iodide (254 mg, 1.69 mmol, 3.00 eq) and trimethylchlorosilane (123 mg, 1.13 mmol, 2.00 eq). The mixture was stirred at 20° C. for 1 hour. LCMS showed the reaction was completed and desired MS can be detected. The reaction mixture was quenched with saturated sodium sulfite (2 mL), diluted with water (15 mL) and extracted with ethyl acetate (10 mL×2). The combined organic phase was washed with saturated brine (10 mL×2), dried with anhydrous sodium sulfate, filtered and concentrated in vacuum to give the crude product tert-butyl 4-[2-[4-[2-(4-bromophenyl)-6-methoxy-benzothiophen-3-yl]oxyphenoxy]ethyl]piperazine-1-carboxylate (350 mg, crude) as a yellow oil, which was directly used for next step without further purification.

LCMS: MS (ESI) m/z: 639.0 $[M+1]^+$.

Chemical Formula: $C_{32}H_{35}BrN_2O_5S$, Molecular Weight: 639.60

Step 5: Synthesis of 2-(4-bromophenyl)-3-(4-(2-(piperazin-1-yl)ethoxy)phenoxy)benzo[b]thiophen-6-ol

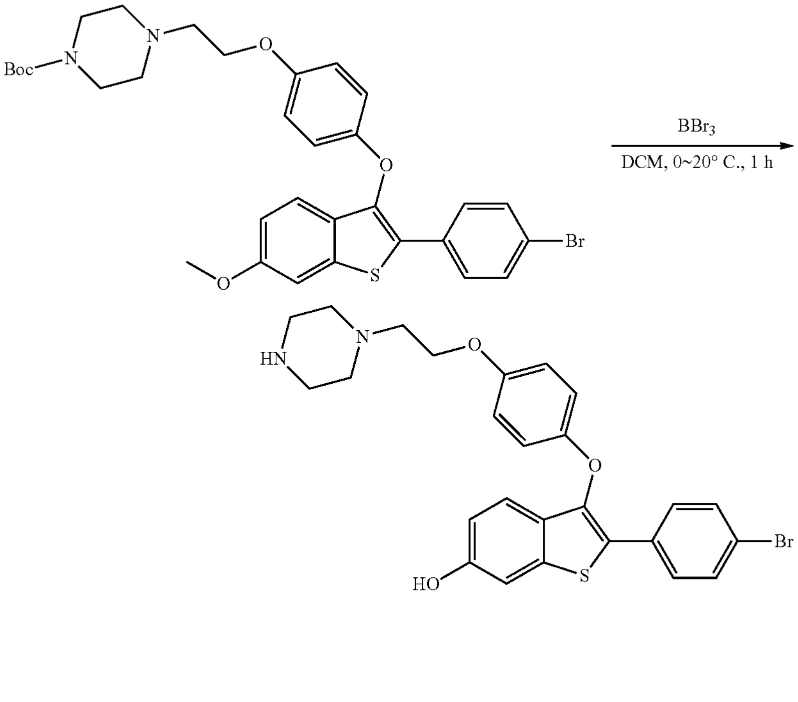

To a solution of tert-butyl 4-[2-[4-[2-(4-bromophenyl)-6-methoxy-benzothiophen-3-yl]oxyphenoxy]ethyl]piperazine-1-carboxylate (350 mg, 0.55 mmol, 1.00 eq) in dichloromethane (6 mL) was added boron tribromide (410 mg, 1.64 mmol, 0.16 mL, 3.00 eq) at 0° C. The mixture was stirred at 20° C. for 1 hour. LCMS showed the reaction was completed and desired MS can be detected. The reaction mixture was quenched with saturated sodium bicarbonate (5 mL) at 0° C., and diluted with water (10 mL) and extracted with dichloromethane (10 mL×3). The combined organic phase was washed with saturated brine (5 mL×2), dried with anhydrous sodium sulfate, filtered and concentrated in vacuum to give 2-(4-bromophenyl)-3-[4-(2-piperazin-1-ylethoxy)phenoxy]benzothiophen-6-ol (250 mg, crude) as a yellow solid, which was directly used for next step without further purification.

LCMS: MS (ESI) m/z: 527.0 $[M+1]^+$.

$^1H$ NMR: (400 MHz, DMSO-$d_6$)

δ: 7.65-7.56 (m, 4H), 7.31 (d, J=2.0 Hz, 1H), 7.14 (d, J=8.4 Hz, 1H), 6.86 (s, 4H), 6.83 (dd, J=2.0, 8.4 Hz, 1H), 5.75 (s, 1H), 3.97 (t, J=5.6 Hz, 2H), 2.78-2.66 (m, 4H), 2.61 (t, J=5.6 Hz, 2H), 2.40 (s, 4H), 2.45-2.34 (m, 1H)

Chemical Formula: $C_{26}H_{25}BrN_2O_3S$, Molecular Weight: 525.46

Total H count from HNMR data: 25.

Step 6: Synthesis of 2-methyl-8-nitro-4H-benzo [d] [1,3]oxazin-4-one

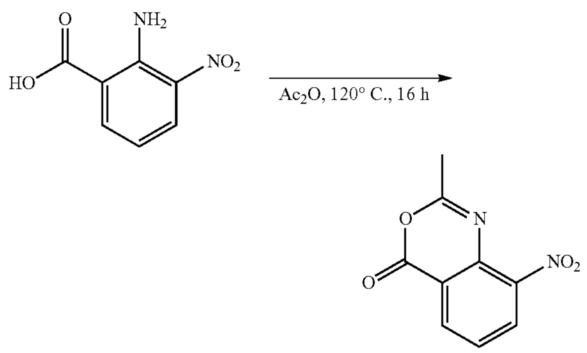

A mixture of 2-amino-3-nitro-benzoic acid (2 g, 10.98 mmol, 1.00 eq) in acetic anhydride (10 mL) was stirred at 120° C. for additional 16 hours. TLC (Petroleum ether:Ethyl acetate) indicated a new spot was formed. The reaction mixture was concentrated to remove the solvent. The residue was triturated with petroleum ether: ethyl acetate=2:1 (30 mL), then filtrated. The filtrate cake was obtained as the desired product 2-methyl-8-nitro-3,1-benzoxazin-4-one (600 mg, 2.91 mmol, 26%yield).

$^1$H NMR: (400 MHz, DMSO-$d_6$)

δ: 8.42-8.31 (m, 2H), 7.72 (t, J=8.0 Hz, 1H), 3.42 (s, 3H).

Chemical Formula: $C_9H_6N_2O_4$, Molecular Weight: 206.15

Total H count from HNMR data: 6.

Step 7: Synthesis of 3-(2-methyl-8-nitro-4-oxoquinazolin-3(4H)-yl)piperidine-2,6-dione

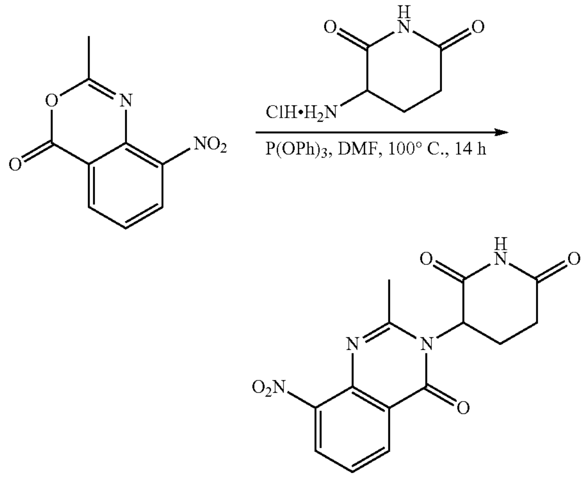

To a solution of 2-methyl-8-nitro-3,1-benzoxazin-4-one (1 g, 4.85 mmol, 1.00 eq) and 3-aminopiperidine-2,6-dione (956 mg, 5.82 mmol, 1.20 eq, hydrochloride) in N,N-dimethylformamide (15 mL) was added triphenyl phosphite (2.26 g, 7.27 mmol, 1.9 mL, 1.50 eq). The mixture was stirred at 100° C. for 14 hours. LCMS showed the reaction was completed and desired MS can be detected. The reaction mixture was diluted with water (40 mL) extracted with ethyl acetate (30 mL×2). The combined organic phase was washed with brine (30 mL×3), dried with anhydrous sodium sulfate, filtered and concentrated in vacuum to give the crude product 3-(2-methyl-8-nitro-4-oxo-quinazolin-3-yl)piperidine-2,6-dione (450 mg, crude) was used into the next step without further purification.

LCMS: MS (ESI) m/z: 316.9 $[M+1]^1$.

Chemical Formula: $C_{14}H_{12}N_4O_5$, Molecular Weight: 316.27

Step 8: Synthesis of 3-(8-amino-2-methyl-4-oxoquinazolin-3(4H)-yl)piperidine-2,6-dione

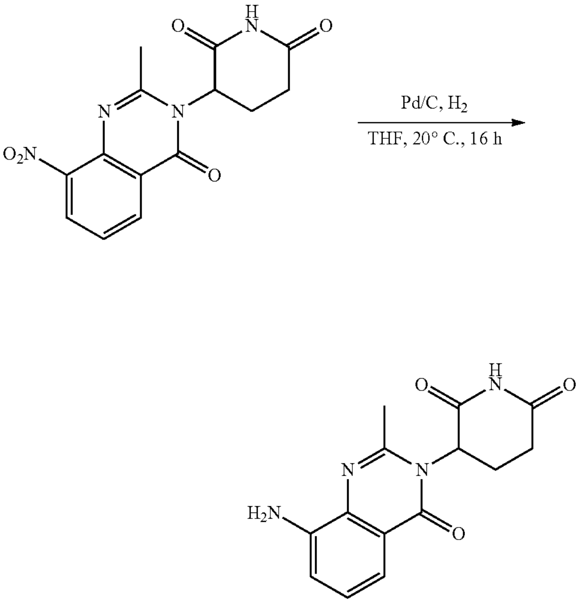 [SMILES: Cc1nc2c([N+](=O)[O-])cccc2c(=O)n1C1CCC(=O)NC1=O ; "Pd/C, H2" ; "THF, 20° C., 16 h" ; Cc1nc2c(N)cccc2c(=O)n1C1CCC(=O)NC1=O]

To a solution of 3-(2-methyl-8-nitro-4-oxo-quinazolin-3-yl)piperidine-2,6-dione (450 mg, 1.42 mmol, 1.00 eq) in tetrahydrofuran (50 mL) was added Palladium/C catalyst (100 mg, 0.14 mmol, 10% purity) under nitrogen atmosphere. The suspension was degassed and purged with hydrogen for 3 times. The mixture was stirred under hydrogen (15 Psi) at 20° C. for 16 hours. LCMS showed the reaction was completed and desired MS can be detected. The reaction mixture was filtered and the filter was concentrated to give the crude product 3-(8-amino-2-methyl-4-oxo-quinazolin-3-yl)piperidine-2,6-dione (380 mg, 1.33 mmol, 94% yield) was used into the next step without further purification.

LCMS: MS (ESI) m/z: 287.1 $[M+1]^+$.

$^1$H NMR: (400 MHz, DMSO-$d_6$)

δ: 11.01 (s, 1H), 7.20-7.10 (m, 2H), 6.97 (dd, J=2.0, 7.2 Hz, 1H), 5.67 (s, 2H), 5.27-5.18 (m, 1H), 2.91-2.79 (m, 1H), 2.70-2.58 (m, 5H), 2.21-2.10 (m, 1H)

Chemical Formula: $C_{14}H_{14}N_4O_3$, Molecular Weight: 286.29

Total H count from HNMR data: 14.

Step 9: Synthesis of 2-(4-bromophenyl)-3-(4-(2-(4-(2,2-dimethoxyethyl)piperazin-1-yl)ethoxy)phenoxy)benzo[b]thiophen-6-ol

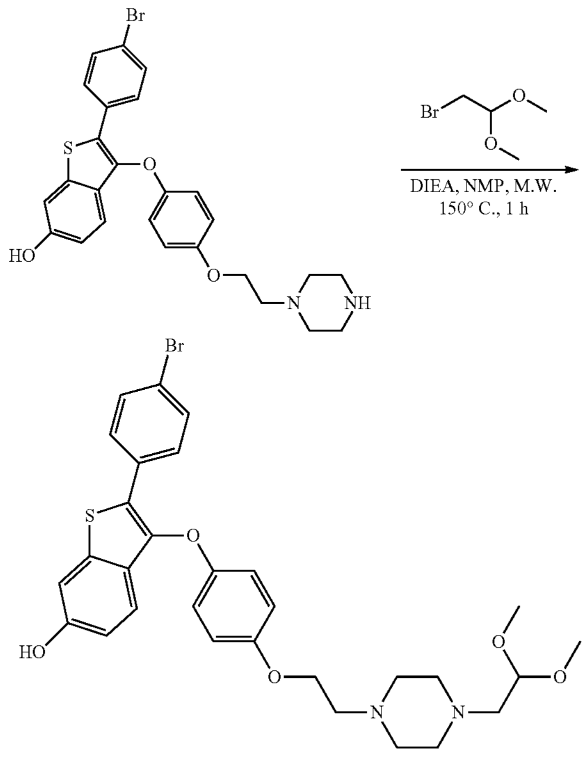

2-(4-bromophenyl)-3-[4-(2-piperazin-1-ylethoxy)phenoxy]benzothiophen-6-ol (250 mg, 0.33 mmol, 1.00 eq, hydrobromide), diisopropylethylamine (213 mg, 1.65 mmol, 0.3 mL, 5.00 eq) and 2-bromo-1,1-dimethoxy-ethane (112 mg, 0.66 mmol, 0.1 mL, 2.00 eq) were taken up into a microwave tube in N-methyl-2-pyrrolidone (3.00 mL). The sealed tube was heated at 150° C. for 1 hour under microwave. TLC (dichloromethane: methanol=10:1, $R_f$=0.52) the reaction was completed and a new spot formed. The reaction mixture was diluted with water (10 mL) and extracted with ethyl acetate (5 mL×3). The combined organic phase was washed with saturated brine (5 mL×2), dried with anhydrous sodium sulfate, filtered and concentrated in vacuum. The residue was purified by prep-TLC (dichloromethane: methanol=10:1) to give 2-(4-bromophenyl)-3-[4-[2-[4-(2,2-dimethoxyethyl)piperazin-1-yl]ethoxy]phenoxy]benzothiophen-6-ol (120 mg, 0.2 mmol, 59% yield) as a yellow solid.

LCMS: MS (ESI) m/z: 615.0 $[M+1]^+$.

Chemical Formula: $C_{30}H_{33}BrN_2O_5S$, Molecular Weight: 613.56

Step 10: Synthesis of 2-(4-(2-(4-((2-(4-bromophenyl)-6-hydroxybenzo[b] thiophen-3-yl)oxy)phenoxy)ethyl)piperazin-1-yl)acetaldehyde

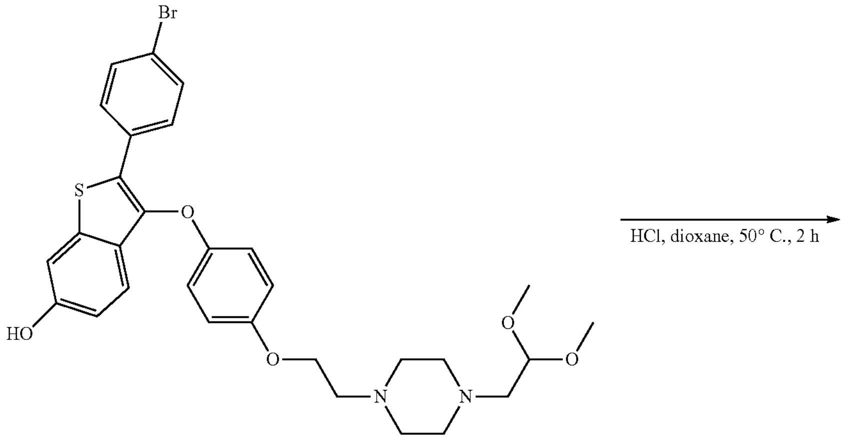

-continued

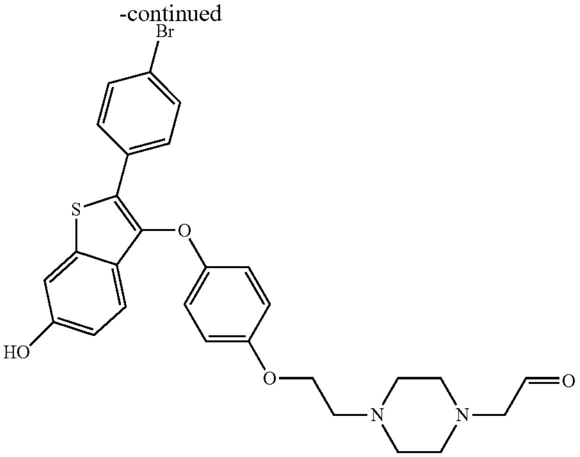

To a solution of 2-(4-bromophenyl)-3-[4-[2-[4-(2,2-dimethoxyethyl)piperazin-1-yl]ethoxy]phenoxy]benzothiophen-6-ol (120 mg, 0.20 mmol, 1.00 eq) in dioxane (2 mL) was added hydrochloric acid (2 M, 2 mL, 20.45 eq). The mixture was stirred at 50° C. for 2 hours. LCMS showed the reaction was completed and desired MS can be detected. The reaction mixture was concentrated under reduced pressure to remove dioxane and water to give the crude product 2-[4-[2-[4-[2-(4-bromophenyl)-6-hydroxy-benzothiophen-3-yl]oxyphenoxy]ethyl]piperazin-1-yl]acetaldehyde (100 mg, crude) was used into the next step without further purification.

LCMS: MS (ESI) m/z: 585.0 $[M+18]^+$.

Chemical Formula: $C_{28}H_{27}BrN_2O_4S$, Molecular Weight: 567.49

Step 11: Synthesis of 3-(8-((2-(4-(2-(4-((2-(4-bromophenyl)-6-hydroxybenzo[b]thiophen-3-yl)oxy)phenoxy)ethyl)piperazin-1-yl)ethyl)amino)-2-methyl-4-oxoquinazolin-3(4H)-yl)piperidine-2,6-dione

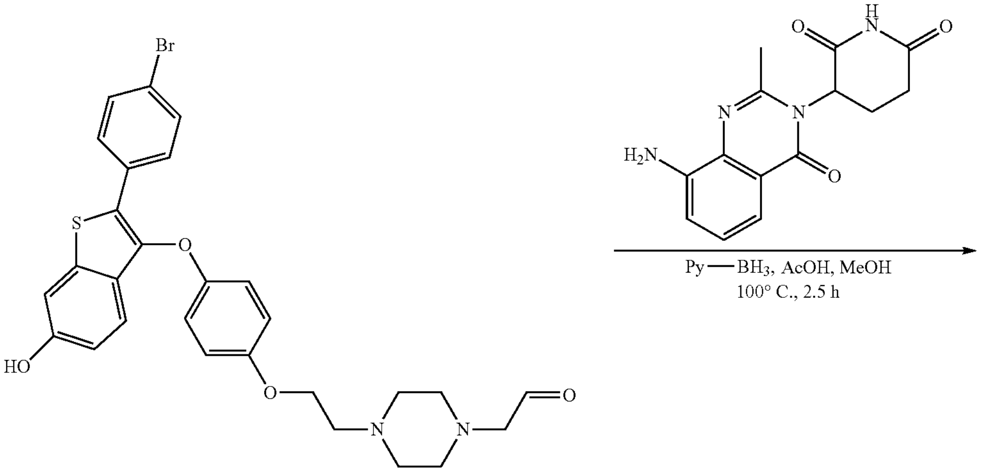

-continued

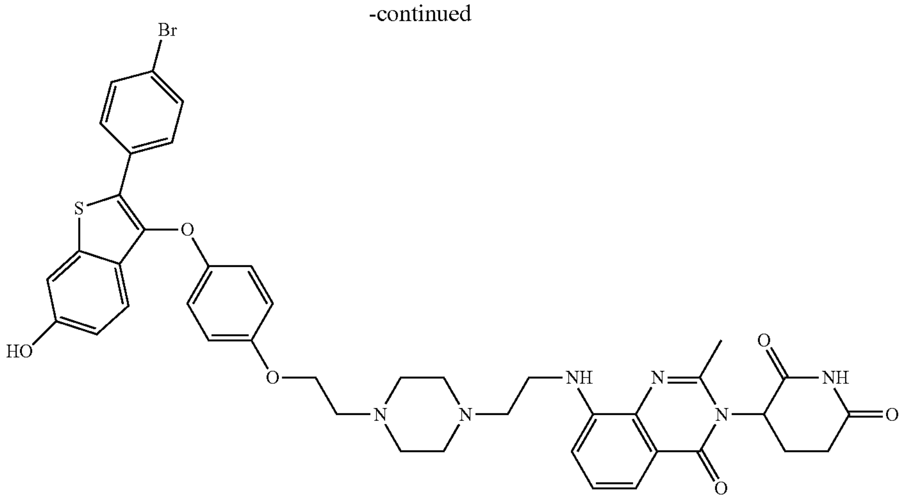

To a solution of 2-[4-[2-[4-[2-(4-bromophenyl)-6-hydroxy-benzothiophen-3-yl]oxyphenoxy]ethyl]piperazin-1-yl]acetaldehyde (1000 mg, 0.18 mmol, 1.00 eq) in methanol (2 mL) was added acetic acid (0.2 mL) and 3-(8-amino-2-methyl-4-oxo-quinazolin-3-yl) piperidine-2,6-dione (50 mg, 0.18 mmol, 1.00 eq). The mixture was stirred at 20° C. for 0.5 hour. Borane; 2-methylpyridine (38 mg, 0.35 mmol, 2.00 eq) was added, then the mixture was stirred at 20° C. for 2 hours. LCMS showed the reaction was completed and desired MS can be detected. The reaction mixture was purified by prep-HPLC (column: Boston Green ODS 150*30 5u; mobile phase: [water (0.225%FA)-ACN]; B%: 25%-55%, 10 min). Then the collected fraction was concentrated to remove most of acetonitrile and hydrochloric acid (1 M, 2 mL) was added. The solution was lyophilized to 3-[8-[2-[4-[2-[4-[2-(4-bromophenyl)-6-hydroxy-benzothiophen-3-yl]oxyphenoxy]ethyl]piperazin-1-yl]ethylamino]-2-methyl-4-oxo-quinazolin-3-yl]piperidine-2,6-dione (10 mg, 0.01 mmol, 7% yield, hydrochloride) as a yellow solid.

LCMS: MS (ESI) m/z: 839.0 $[M+1]^+$.

$^1H$ NMR: (400 MHz, DMSO-$d_6$)

δ6: 11.01 (s, 1H), 10.04 (s, 1H), 7.62 (s, 4H), 7.33 (d, J=2.0 Hz, 1H), 7.31-7.23 (m, 1H), 7.21-7.11 (m, 2H), 7.01 (br d, J=8.0 Hz, 1H), 6.92 (q, J=8.8 Hz, 4H), 6.85 (dd, J=2.0, 8.8 Hz, 1H), 5.25 (dd, J=5.2, 13.2 Hz, 1H), 4.29 (s, 2H), 3.68-3.45 (m, 14H), 2.87-2.79 (m, 1H), 2.69-2.61 (m, 5H), 2.19-2.10 (m, 1H)

Chemical Formula: $C_{42}H_{41}BrN_6O_6S$, Molecular Weight: 837.78

Total H count from HNMR data: 40.

Synthesis of Exemplary PROTAC 108

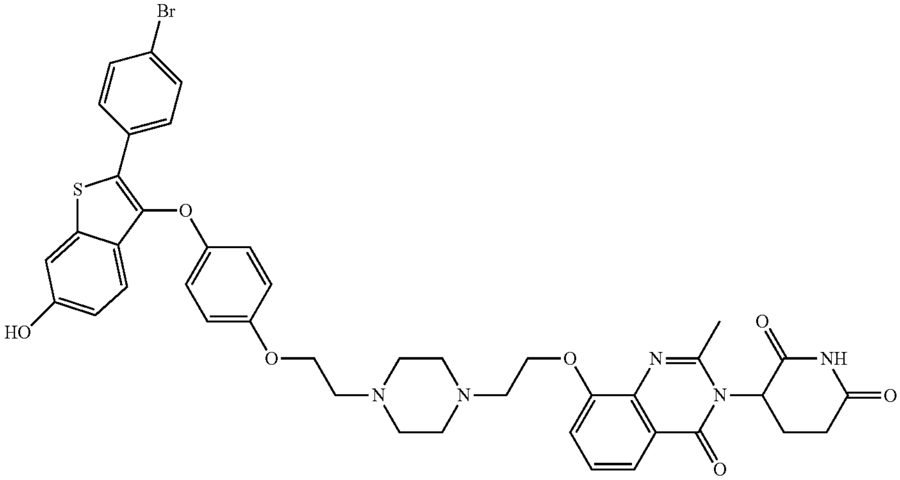 [SMILES: Cc1nc2c(OCCN3CCN(CCOc4ccc(Oc5c(-c6ccc(Br)cc6)sc6cc(O)ccc56)cc4)CC3)cccc2c(=O)n1C1CCC(=O)NC1=O]

3-(8-(2-(4-(2-(4-((2-(4-bromophenyl)-6-hydroxy-benzo[b]thiophen-3-yl)oxy)phenoxy)ethyl)piperazin-1-yl)ethoxy)-2-methyl-4-oxoquinazolin-3(4H)-yl) piperidine-2,6-dione
Synthetic Scheme:
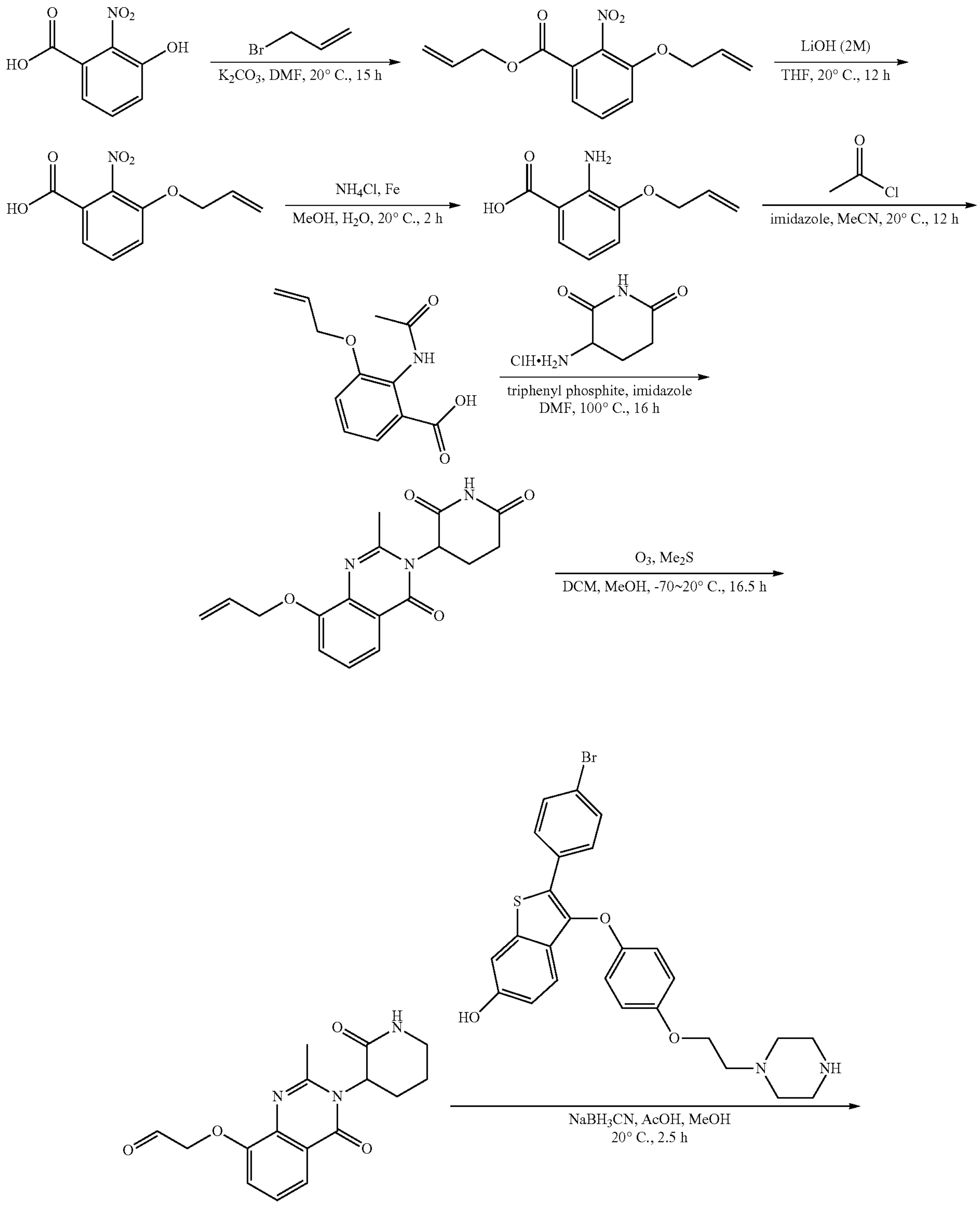

-continued

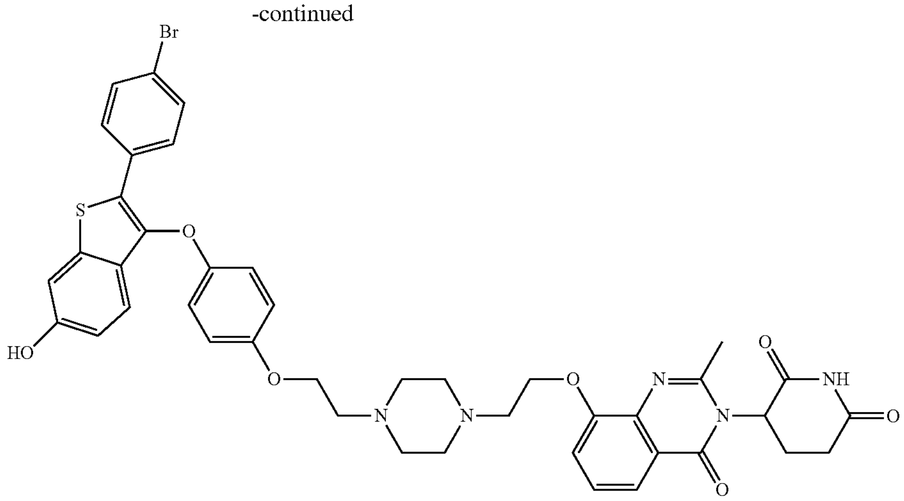

Step 1: Synthesis of allyl 3-(allyloxy)-2-nitrobenzoate

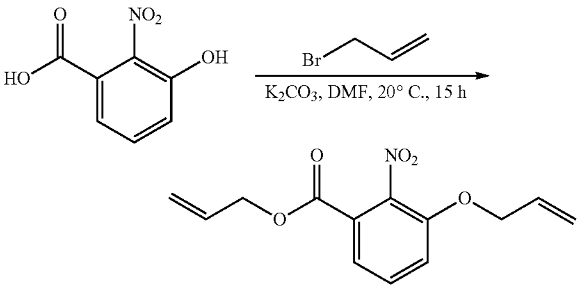

To a solution of 3-hydroxy-2-nitro-benzoic acid (1 g, 5.46 mmol, 1.00 eq) in N,N-dimethylformamide (15 mL) was added potassium carbonate (3 g, 21.84 mmol, 4.00 eq) and 3-bromoprop-1-ene (2.64 g, 21.84 mmol, 4.00 eq). The mixture was stirred at 20° C. for 15 hours. LCMS showed the reaction was completed and desired MS can be detected. The residue was diluted with water (100 mL) and extracted with ethyl acetate (30 mL×3). The combined organic phase was washed with brine (30 mL×2), dried with anhydrous sodium sulfate, filtered and concentrated in vacuum to give allyl 3-allyloxy-2-nitro-benzoate (1.30 g, crude) as a yellow oil.

LCMS: MS (ESI) m/z: 286.0 $[M+23]^+$.

Chemical Formula: $C_{13}H_{13}NO_5$, Molecular Weight: 263.25

Step 2: Synthesis of 3-(allyloxy)-2-nitrobenzoic acid

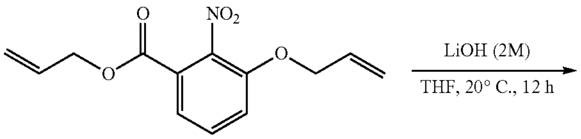

-continued

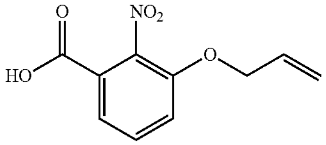

To a solution of allyl 3-allyloxy-2-nitro-benzoate (1.44 g, 5.47 mmol, 1.00 eq) in tetrahydrofuran (40 mL) was added lithium hydroxide monohydrate (2 M, 11 mL, 4.00 eq). The mixture was stirred at 20° C. for 12 hours. LCMS showed the reaction was completed and desired MS can be detected. The reaction mixture was adjusted to pH=(4~5) by hydrochloric acid (2 M, 10 mL) and diluted with water (50 mL) and extracted with ethyl acetate (30 mL×3). The combined organic phase was washed with saturated brine (40 mL×2), dried with anhydrous sodium sulfate, filtered and concentrated in vacuum to give 3-allyloxy-2-nitro-benzoic acid (1.20 g, crude) was used into the next step without further purification.

LCMS: MS (ESI) m/z: 246.0 $[M+23]^+$.

$^1H$ NMR: (400 MHz, $CDCl_3$)

δ: 7.70 (d, J=8.0 Hz, 1H), 7.52 (t, J=8.0 Hz, 1H), 7.32 (d, J=8.0 Hz, 1H), 6.07-5.93 (m, 1H), 5.47-5.29 (m, 2H), 4.70 (d, J=5.2 Hz, 2H)

Chemical Formula: $C_{10}H_9NO_5$, Molecular Weight: 223.18

Total H count from HNMR data: 8.

Step 3: Synthesis of 3-(allyloxy)-2-aminobenzoic acid

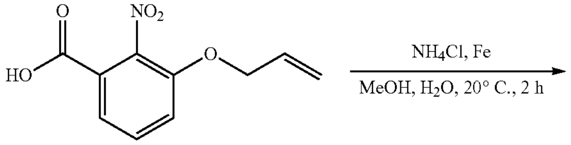

-continued

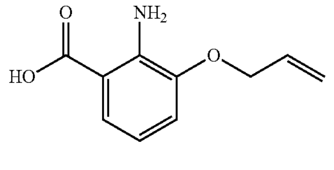

To a solution of 3-allyloxy-2-nitro-benzoic acid (1.2 g, 5.38 mmol, 1.00 eq) in methanol (20 mL) and water (5 mL) was slowly added iron (1.2 g, 21.52 mmol, 4.00 eq), ammonium chloride (1.44 g, 26.90 mmol, 5.00 eq) at 20° C. The mixture was stirred at 80° C. for 2 hours. LCMS showed the reaction was completed and desired MS can be detected. The reaction mixture was filtered and the filtrate was concentrated to give 3-allyloxy-2-amino-benzoic acid (850 mg, crude) used in the next step without further purification.

LCMS: MS (ESI) m/z: 194.1 $[M+1]^+$.

$^1H$ NMR: (400 MHz, $CDCl_3$)

δ: 7.54 (s, 1H), 6.99-6.44 (m, 2H), 6.07 (s, 2H), 5.39 (s, 2H), 4.59 (s, 3H), 4.76-4.40 (m, 1H)

Chemical Formula: $C_{10}H_{11}NO_3$, Molecular Weight: 193.20

Total H count from HNMR data: 11.

Step 4: Synthesis of 2-acetamido-3-(allyloxy)benzoic acid

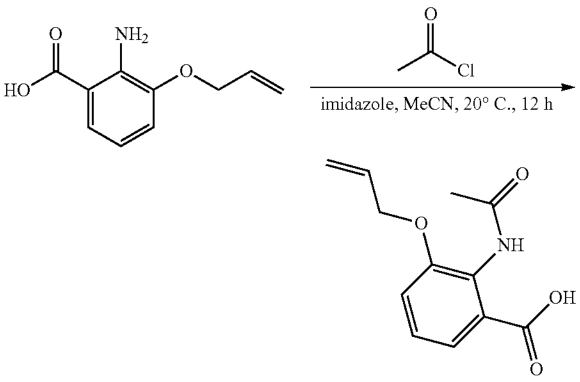

To a solution of 3-allyloxy-2-amino-benzoic acid (800 mg, 4.14 mmol, 1.00 eq) in acetonitrile (10 mL) was added imidazole (282 mg, 4.14 mmol, 1.00 eq) and acetyl chloride (650 mg, 8.28 mmol, 2.00 eq). The mixture was stirred at 20° C. for 12 hours. LCMS showed the reaction was completed and desired MS can be detected. The reaction was diluted with water (30 mL) and extracted with ethyl acetate (15 mL×3). The combined organic phase was washed with saturated brine (20 mL×2), dried with anhydrous sodium sulfate, filtered and concentrated in vacuum to give 2-acetamido-3-allyloxy-benzoic acid (900 mg, crude) as a yellow solid, which was directly used for next step without further purification.

LCMS: MS (ESI) m/z: 236.1 $[M+1]^+$.

Chemical Formula: $C_{12}H_{13}NO_4$, Molecular Weight: 235.24

Step 5: Synthesis of 3-(8-(allyloxy)-2-methyl-4-oxoquinazolin-3(4H)-yl)piperidine-2,6-dione

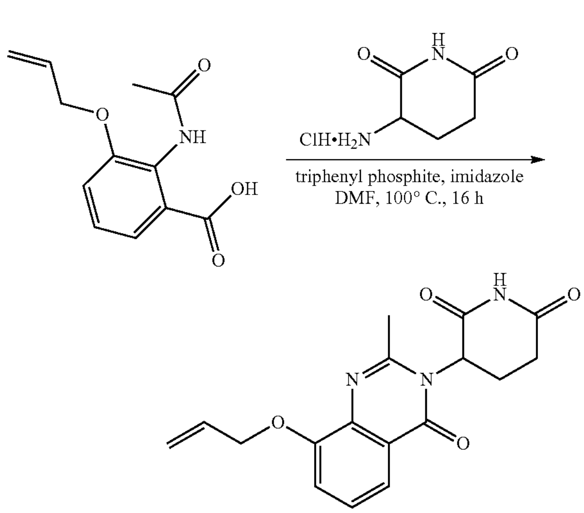

To a solution of 2-acetamido-3-allyloxy-benzoic acid (800 mg, 3.40 mmol, 1.00 eq) and 3-aminopiperidine-2,6-dione (672 mg, 4.08 mmol, 1.20 eq, hydrochloride) in N,N-dimethylformamide (15 mL) was added triphenyl phosphite (1.58 g, 5.10 mmol, 1.50 eq) and imidazole (232 mg, 92.60 mmol, 27.23 eq). The mixture was stirred at 100° C. for 16 hours. LCMS showed the reaction was completed and desired MS can be detected. The reaction mixture was diluted with water (40 mL) and extracted with ethyl acetate (20 mL×2). The combined organic phase was washed with saturated brine (20 mL×2), dried with anhydrous sodium sulfate, filtered and concentrated in vacuum. The residue was purified by silica gel column chromatography (dichloromethane: methanol=100:1 to 20:1) to give 3-(8-allyloxy-2-methyl-4-oxo-quinazolin-3-yl)piperidine-2,6-dione (420 mg, 1.28 mmol, 38% yield) as a light yellow solid.

LCMS: MS (ESI) m/z: 328.2 $[M+1]^+$.

$^1H$ NMR: (400 MHz, DMSO-$d_6$)

δ: 11.03 (s, 1H), 7.58 (dd, J=1.6, 7.6 Hz, 1H), 7.43-7.32 (m, 2H), 6.17-6.01 (m, 1H), 5.45 (dd, J=1.6, 17.2 Hz, 1H), 5.34-5.25 (m, 2H), 4.74 (d, J=4.8 Hz, 2H), 2.88-2.79 (m, 1H), 2.70-2.55 (m, 5H), 2.20-2.12 (m, 1H)

Chemical Formula: $C_{17}H_{17}N_3O_4$, Molecular Weight: 327.33

Total H count from HNMR data: 17.

Step 6: Synthesis of 2-((3-(2,6-dioxopiperidin-3-yl)-2-methyl-4-oxo-3,4-dihydroquinazolin-8-yl)oxy) acetaldehyde

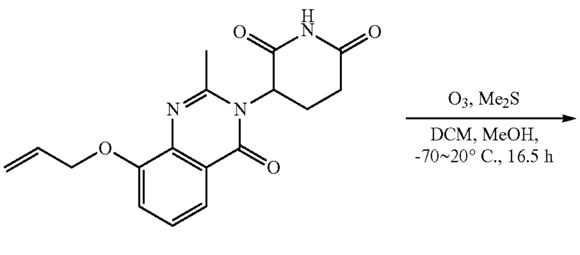

-continued

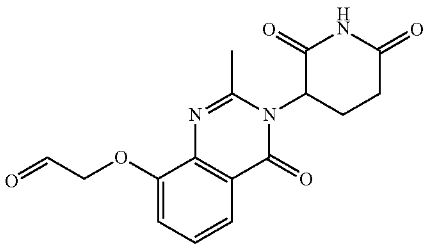

Ozone was bubbled into a solution of 3-(8-allyloxy-2-methyl-4-oxo-quinazolin-3-yl)piperidine-2,6-dione (200 mg, 0.61 mmol, 1.00 eq) in dichloromethane (8 mL) and methanol (2 mL) at −70° C. for 30 minutes. After excess ozone was purged by nitrogen, and dimethylsulfide (380 mg, 6.11 mmol, 10.00 eq) was added at −70° C. The mixture was stirred at 20° C. for 16 hours. LCMS showed the reaction was completed and desired MS can be detected. The reaction mixture was concentrated under reduced pressure to remove methanol, dichloromethane and dimethylsulfide to give the 2-[3-(2,6-dioxo-3-piperidyl)-2-methyl-4-oxo-quinazolin-8-yl]oxyacetaldehyde (220 mg, crude) as a brown solid.

LCMS: MS (ESI) m/z: 362.0 $[M+23]^+$.

Chemical Formula: $C_{16}H_{15}N_3O_5$, Molecular Weight: 329.31

Step 7: Synthesis of 3-(8-(2-(4-(2-(4-((2-(4-bromophenyl)-6-hydroxybenzo[b]thiophen-3-yl)oxy)phenoxy)ethyl)piperazin-1-yl)ethoxy)-2-m ethyl-4-oxo-quinazolin-3(4H)-yl)piperidine-2,6-dione

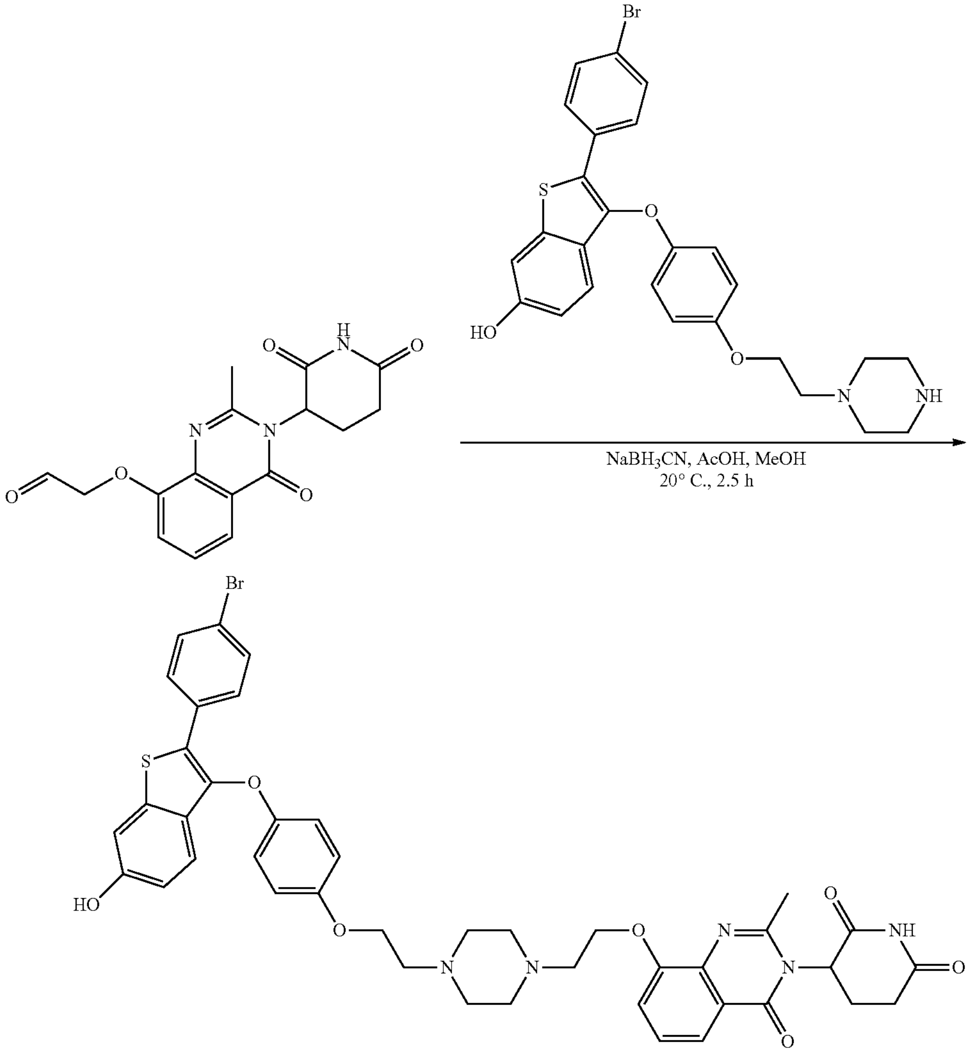

To a solution of 2-[3-(2,6-dioxo-3-piperidyl)-2-methyl-4-oxo-quinazolin yl]oxyacetaldehyde (120 mg, 0.36 mmol, 1.00 eq) in methanol (4 mL) was added 2-(4-bromophenyl)-3-[4-(2-piperazin-1-ylethoxy)phenoxy]benzothiophen-6-ol (110 mg, 0.18 mmol, 0.50 eq, hydrobromide, ntermediate from synthesis of exemplary PROTAC 107, see above) and acetic acid (44 mg,0.72 mmol, 2.00 eq). The mixture was stirred at 20° C. for 0.5 hour. Sodium cyanoborohydride (44 mg, 0.73 mmol, 2.00 eq) was added at 20° C., and then the mixture was stirred at 20° C. for 2 hours. LCMS showed the reaction was completed and desired MS can be detected. The reaction mixture concentrated under reduced pressure to remove methanol. The residue was purified by prep-HPLC (column: Phenomenex Synergi C18 150*30 mm*4 um; mobile phase: [water (0.225%FA)-ACN]; B%: 25%-55%, 12 min). Then the collected fraction was concentrated to remove most of acetonitrile and hydrochloric acid (1 M, 2 mL) was added. The solution was lyophilized to give 3-[8-[2-[4-[2-[4-[2-(4-bromophenyl)-6-hydroxy-benzothiophen-3-yl]oxyphenoxy]ethyl]piperazin-1-yl]ethoxy]-2-methyl-4-oxo-quinazolin-3-yl]piperidine-2,6-dione (18 mg, 0.02 mmol, 5% yield, 91% purity, hydrochloride) as a white solid.

LCMS: MS (ESI) m/z: 840.2 $[M+1]^+$.

$^1H$ NMR: (400 MHz, DMSO-$d_6$)

δ: 11.06 (s, 1H), 9.99 (s, 1H), 7.66 (d, J=7.2 Hz, 1H), 7.63 (s, 4H), 7.54-7.42 (m, 1H), 7.52-7.42 (m, 1H), 7.33 (d, J=2.0 Hz, 1H), 7.15 (d, J=8.8 Hz, 1H), 6.97-6.91 (m, 4H), 6.84 (dd, J=2.0, 8.8 Hz, 1H), 5.28 (dd, J=5.2, 13.2 Hz, 1H), 4.54 (s, 2H), 4.27 (s, 4H), 3.56-3.49 (m, 10H), 2.82-2.80 (m, 1H), 2.65-2.59 (m, 5H), 2.21-2.14 (m, 1H)

Chemical Formula: $C_{42}H_{40}BrN_5O_7S$, Molecular Weight: 838.77

Total H count from HNMR data: 40.

Synthesis of Exemplary PROTAC 112

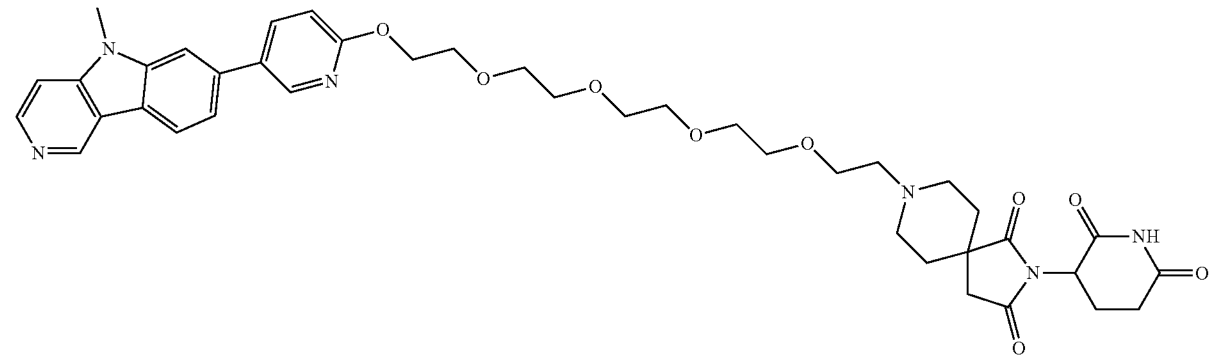 [SMILES: Cn1c2ccncc2c2ccc(-c3ccc(OCCOCCOCCOCCOCCN4CCC5(CC4)CC(=O)N(C4CCC(=O)NC4=O)C5=O)nc3)cc21]

2-(2,6-dioxopiperidin-3-yl)-8-(14-((5-(5-methyl-5H-pyrido[4,3-b]indol-7-yl)pyridin-2-yl)oxy)-3,6,9,12-tetraoxatetradecyl)-2,8-diazaspiro[4.5]decane-1,3-dione Reaction Scheme:

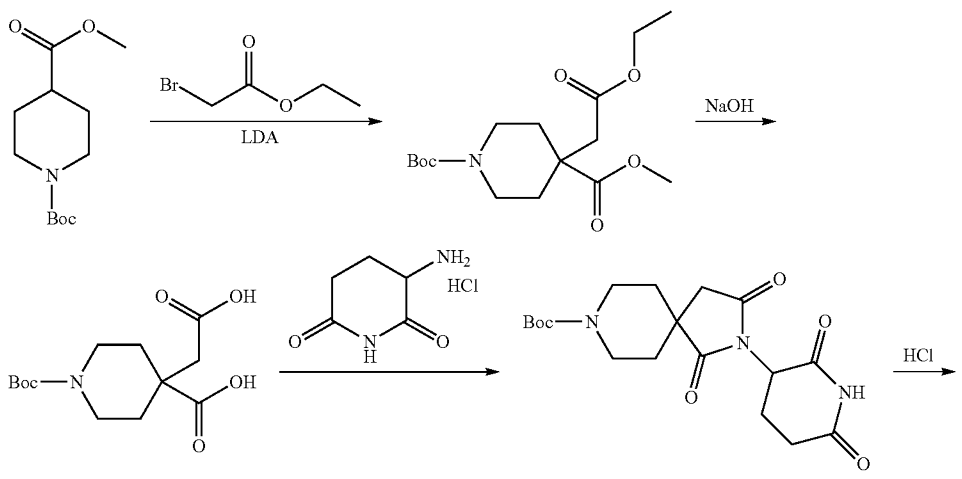

-continued
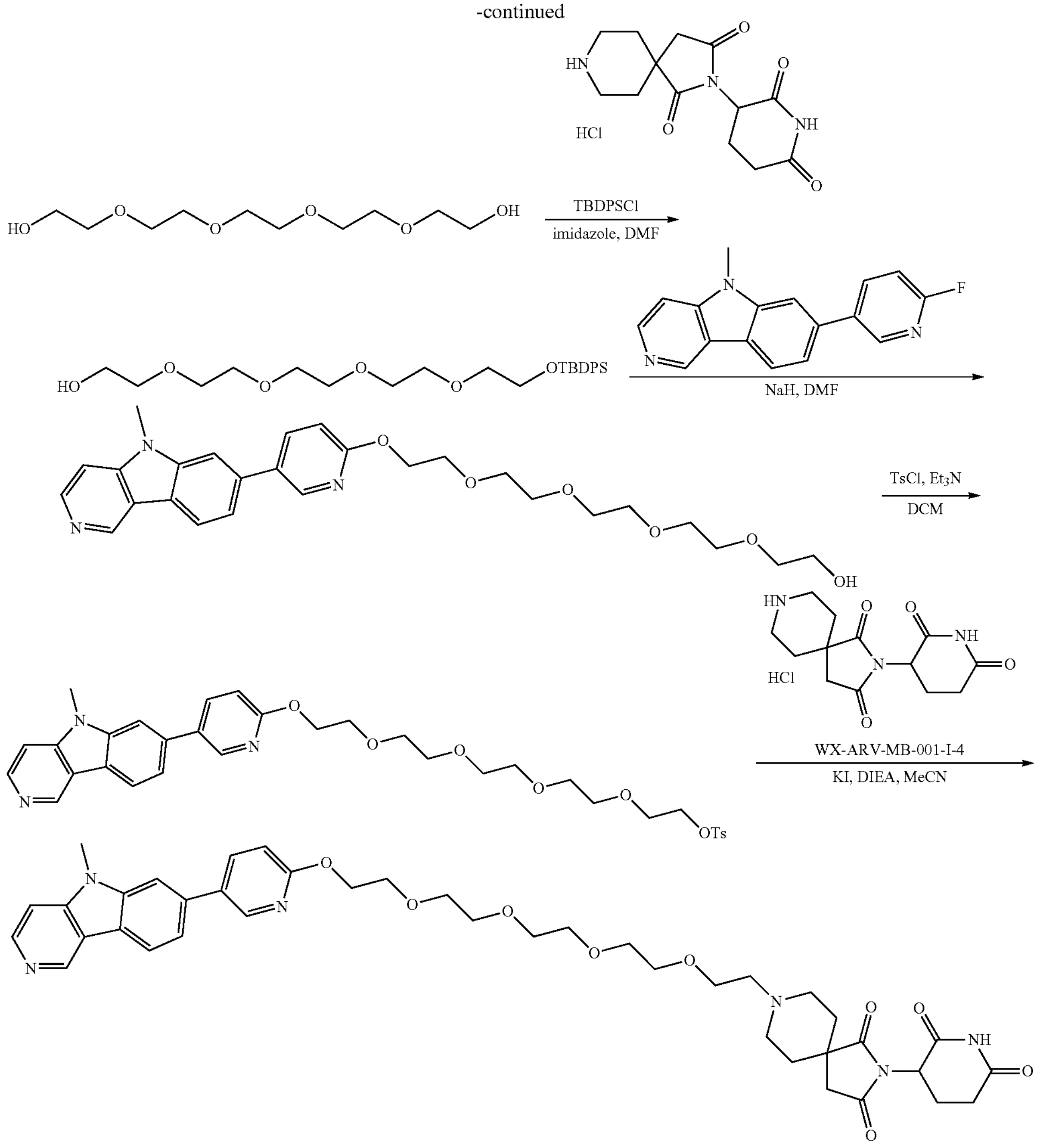
Step 1:-Preparation of 1-tert-butyl 4-methyl 4-(2-ethoxy-2-oxoethyl)-piperidine-1,4-dicarboxylate
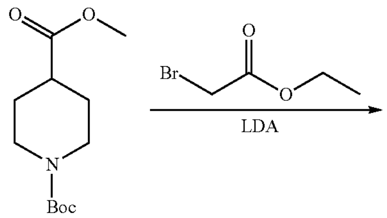
-continued
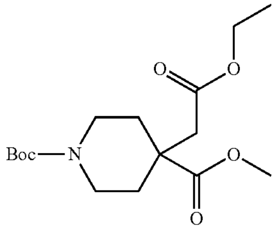
To a solution of ethyl 2-bromoacetate (8.65 g, 51.80 mmol, 5.7 mL, 1 eq) in tetrahydrofuran (1000 mL) was added lithium diiso-propylamide (2 M, 39 mL, 1.5 eq) at −78° C. The mixture was stirred at −78° C. for 1 hour. Then O1-tert-butyl O4-methyl piperidine-1,4-dicarboxylate (20 g, 82.2 mmol, 1.59 eq) was added and the mixture was stirred at this temperature for 1 h. After this, the mixture was stirred at 15° C. for another 24 hours. Thin-Layer Chromatography (petroleum ether: ethyl acetate=5:1) indicated 50% of Reactant 1 was remained, and one major new spot ($R_f$=0.46) with lower polarity was detected. The reaction mixture was quenched by addition of aqueous ammonium chloride 500 mL, and then extracted with ethyl acetate 1500 mL (500 mL×3). The combined organic layers were washed with brine 1500 mL (500 mL×3), dried over sodium sulfate, filtered and concentrated under reduced pressure. The residue was purified by flash silica gel chromatography. O1-tert-butyl O4-methyl 4-(2-ethoxy-2-oxo-ethyl) piperidine-1, 4-dicarboxylate (3.8 g, 11.5 mmol, 22% yield) was obtained as a brown oil.

$^1$H NMR: (400 MHz, $CDCl_3$) δ 4.07-3.95 (m, 2H), 3.73-3.50 (m, 5H), 3.06 (br s, 2H), 2.50 (br s, 2H), 1.99 (d, J=13.6 Hz, 2H), 1.47-1.38 (m, 2H), 1.38-1.33 (m, 9H), 1.21-1.10 (m, 3H).

Chemical Formula: $C_{16}H_{27}NO_6$, Molecular Weight: 329.39

2. Step: Preparation of 1-(tert-butoxycarbonyl)-4-(carboxymethyl) piperidine-4-carboxylic acid

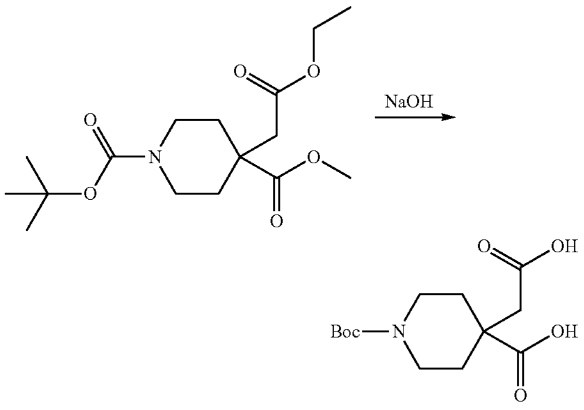

To a solution of O1-tert-butyl O4-methyl 4-(2-ethoxy-2-oxo-ethyl) piperidine-1, 4-dicarboxylate (3.8 g, 11.50 mmol, 1 eq) in tetrahydrofuran (20 mL), water (15 mL) was added sodium hydroxide (2.3 g, 57.7 mmol, 5 eq) and methanol (10 mL). The mixture was stirred at 25° C. for 36 h. High performance liquid chromatography-mass spectrometry showed Reactant 1 was consumed completely. The reaction mixture was diluted with water 20 mL and concentrated under reduced pressure to remove tetrahydrofuran and methanol. The water layer was washed with petroleum ether (30 mL×2), then acided by hydrochloric acid solution to pH-5, extracted with ethyl acetate (30 mL×3). The combined organic layers were washed with brine 60 mL, dried over sodium sulfate, filtered and concentrated under reduced pressure. 1-tert-butoxycarbonyl-4-(carboxymethyl) piperidine-4-carboxylic acid (2.9 g, 10 mmol, 87% yield) was obtained as a brown solid.

LCMS: MS (ESI) m/z: 286.

$^1$H NMR: (400 MHz, $CDCl_3$) δ 3.69 (br s, 2H), 3.36-3.23 (m, 2H), 2.72 (s, 2H), 2.19-2.12 (m, 2H), 1.56 (br t, J=9.7 Hz, 1H), 1.48 (s, 10H)

Chemical Formula: $C_{13}H_{21}NO_6$, Molecular Weight: 287.31

3. Step: Preparation of tert-butyl 2-(2, 6-dioxopiperidin-3-yl)-1,3-dioxo-2,8-diazaspiro[4.5]decane-8-carboxylate

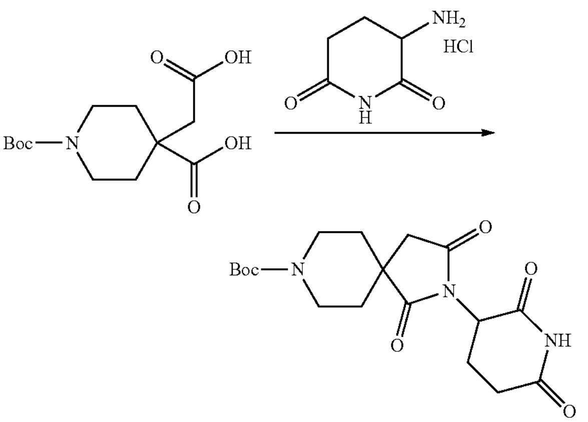

A mixture of 1-tert-butoxycarbonyl-4-(carboxymethyl) piperidine-4-carboxylic acid (1.9 g, 6.61 mmol, 1 eq) and acetic anhydride (21.80 g, 213.54 mmol, 20 mL, 32.29 eq) was degassed and purged with nitrogen for 3 times, and then the mixture was stirred at 120° C. for 0.5 houe under nitrogen atmosphere. The reaction mixture was concentrated under reduced pressure to remove acetic anhydride. The residue was diluted with pyridine (20 mL) and added 3-aminopiperidine-2,6-dione (1.31 g, 7.94 mmol, 1.2 eq, hydrochloride). The mixture was stirred at 140° C. under nitrogen atmosphere for 12 h. High performance liquid chromatography-mass spectrometry showed Reactant 1 was consumed completely and one main peak with desired mass was detected. The reaction mixture was concentrated under reduced pressure. The residue was washed with water (10 mL×3) to give the product. Tert-butyl 2-(2, 6-dioxo-3-piperidyl)-1, 3-dioxo-2, 8-diazaspiro [4.5]decane-8-carboxylate (1.2 g, 3.2 mmol, 47% yield) was obtained as a grey solid.

LCMS: MS (ESI) m/z: 402 $[M+23]^+$ $^1$H NMR: (400 MHz, $CDCl_3$) δ 7.91 (s, 1H), 4.74 (dd, J=5.3, 12.3 Hz, 1H), 3.94 s, 2H), 2.97 (t, J=11.7 Hz, 2H), 2.80 (d, J=15.4 Hz, 1H), 2.75-2.55 (m, 4H), 2.00-1.88 (m, 3H), 1.50 (s, 2H), 1.40 (s, 9H)

Chemical Formula: $C_{18}H_{25}N_3O_6$, Molecular Weight: 379.41

4. Step: Preparation of 2-(2, 6-dioxopiperidin-3-yl)-2, 8-diazaspiro [4.5]decane-1, 3-dione

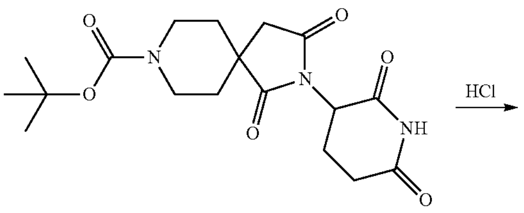

-continued

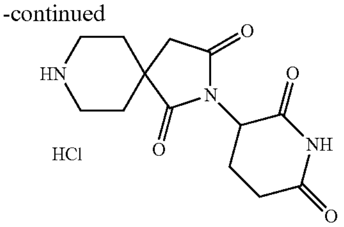

To a solution of tert-butyl 2-(2, 6-dioxo-3-piperidyl)-1, 3-dioxo-2, 8-diazaspiro [4.5]decane-8-carboxylate (1.2 g, 3.16 mmol, 1 eq) in dioxane (15 mL) was added hydrochloric acid solution (4 M in dioaxne, 20 mL, 25.3 eq). The mixture was stirred at 15° C. for 3 hour. The reaction mixture was concentrated under reduced pressure. 2-(2,6-dioxo-3-piperidyl)-2,8-diazaspiro[4.5]decane-1,3-dione (1.2 g, hydrochloride) was obtained as a grey solid.

$^1$H NMR: (400 MHz, DMSO-$d_6$) δ 11.08 (s, 1H), 8.93 (s, 1H), 8.64 (s, 1H), 4.95 (dd, J=5.4, 12.8 Hz, 1H), 3.29 (s, 2H), 3.07-2.93 (m, 2H), 2.92-2.87 (m, 2H), 2.86-2.78 (m, 1H), 2.58 (s, 1H), 2.47-2.36 (m, 1H), 2.09-1.87 (m, 3H), 1.80 (d, J=14.1 Hz, 2H)

Chemical Formula: $C_{13}H_{17}N_3O_4$, Molecular Weight: 279.29

5. Step: Preparation of 2-[2-[2-[2-[2-[tert-butyl(diphenyl)silyl]oxyethoxy]ethoxy]ethoxy]ethoxy]ethanol

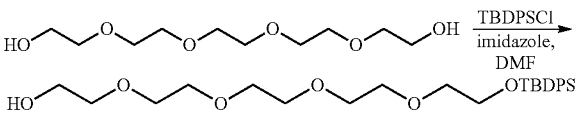

To a solution of 2-[2-[2-[2-(2-hydroxyethoxy)ethoxy]ethoxy]ethoxy]ethanol (2 g, 8.40 mmol, 1 eq) in dichloromethane (20 mL) was added imidazole (1.92 g, 12.6 mmol, 1.9 mL, 1.5 eq) and tert-butyl-chloro-diphenyl-silane (2.42 g, 8.8 mmol, 2.3 mL, 1.05 eq). The mixture was stirred at 15° C. for 3 hours. Thin-Layer Chromatography (Ethyl Acetate) indicated 10% of Reactant 1 was remained, and one major new spot ($R_f$=0.32) with lower polarity was detected. High performance liquid chromatography-mass spectrometry showed desired MS was detected. The reaction mixture was concentrated under reduced pressure. The residue was purified by silica gel chromatography (petroleum ether/ethyl acetate=1/1 to 0:1). 2-[2-[2-[2-[2-[tert-butyl(diphenyl)silyl]oxyethoxy]ethoxy]ethoxy]ethoxy]ethanol (1.77 g, 3.7 mmol, 44% yield) was obtained as a colorless oil.

LCMS: MS (ESI) m/z: 494 [M+18]$^+$

HNMR: (400 MHz, $CDCl_3$) δ 7.75-7.66 (m, 4H), 7.48-7.36 (m, 6H), 3.83 (t, J=5.4 Hz, 2H), 3.77-3.58 (m, 18H), 2.51 (s, 1H), 1.07 (s, 9H)

Chemical Formula: $C_{26}H_{40}O_6Si$, Molecular Weight: 476.68

6. Step: Preparation of 2-[2-[2-[2-[2-[[5-(5-methylpyrido[4,3-b]indol-7-yl)-2-pyridyl]oxy]ethoxy]ethoxy]ethoxy]ethoxy]ethanol

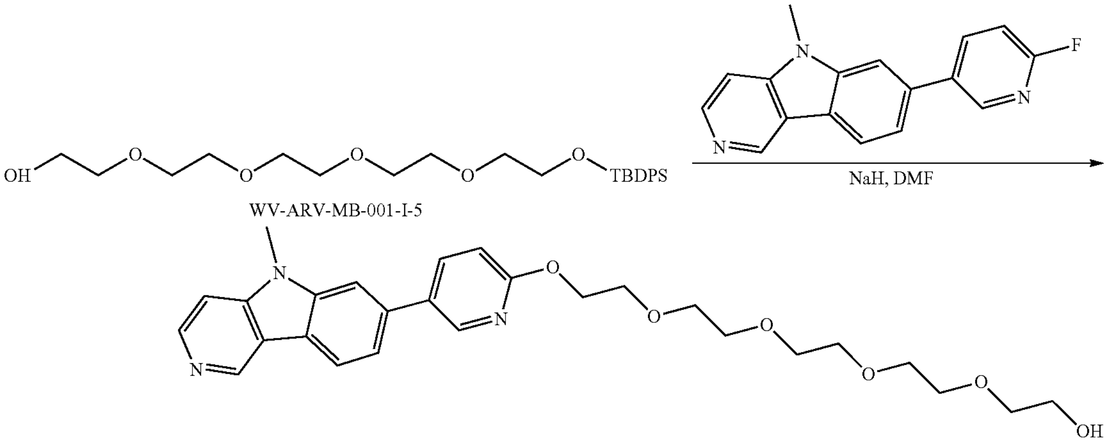

WV-ARV-MB-001-I-5

WV-ARV-MB-001-I-6

To a solution of 2-[2-[2-[2-[2-[tert-butyl (diphenyl) silyl]oxyethoxy]ethoxy]ethoxy]ethoxy]ethanol (258 mg, 0.54 mmol, 1.5 eq) in N,N-dimethylformamide (5 mL) was added sodium hydride (29 mg, 0.72 mmol, 60% purity in mineral oil, 2 eq) at 0° C. The mixture was stirred at 15° C. for 1 hour. Then 7-(6-fluoro-3-pyridyl)-5-methyl-pyrido [4, 3-b] indole (0.1 g, 361 umol, 1 eq) was added. The mixture was stirred at 15° C. for 12 hours. High performance liquid chromatography-mass spectrometry showed Reactant 1 was consumed completely and one main peak with desired MS was detected. The reaction mixture was quenched by the addition od water (15 mL) at 0° C., and then extracted with ethyl acetate 45 mL (15 mL*3). The combined organic layers were dried over sodium sulfate, filtered and concentrated under reduced pressure to give a residue. The residue was purified by column chromatography (dichloromethane: methanol=20:1, $R_f$=0.21). 2-[2-[2-[2-[2-[[5-(5-methylpyrido[4,3-b]indol-7-yl)-2-pyridyl]oxy]ethoxy]ethoxy]ethoxy]ethoxy]ethanol (0.09 g, 0.14 mmol, 39% yield, 78% purity) was obtained as brown oil.

LCMS: MS (ESI) m/z: 496.0 [M+1]$^+$

HNMR: (400 MHz, $CDCl_3$) δ 9.27 (s, 1H), 8.51 (s, 1H), 8.41 (d, J=2.2 Hz, 1H), 8.15 (d, J=8.2 Hz, 1H), 7.88-7.82 (m, 1H), 7.53 (s, 1H), 7.48 (dd, J=1.3, 8.1 Hz, 1H), 7.38-7.33 (m, 1H), 6.87 (d, J=8.7 Hz, 1H), 4.51-4.47 (m, 2H), 3.89 (s, 3H), 3.85-3.82 (m, 2H), 3.70-3.63 (m, 12H)

Chemical Formula: $C_{27}H_{33}N_3O_6$, Molecular Weight: 495.57

7. Step: Preparation of 2-[2-[2-[2-[2-[[5-(5-methylpyrido[4,3-b]indol-7-yl)-2-pyridyl]oxy]ethoxy]ethoxy]ethoxy]ethoxy]ethyl 4-methylbenzenesulfonate

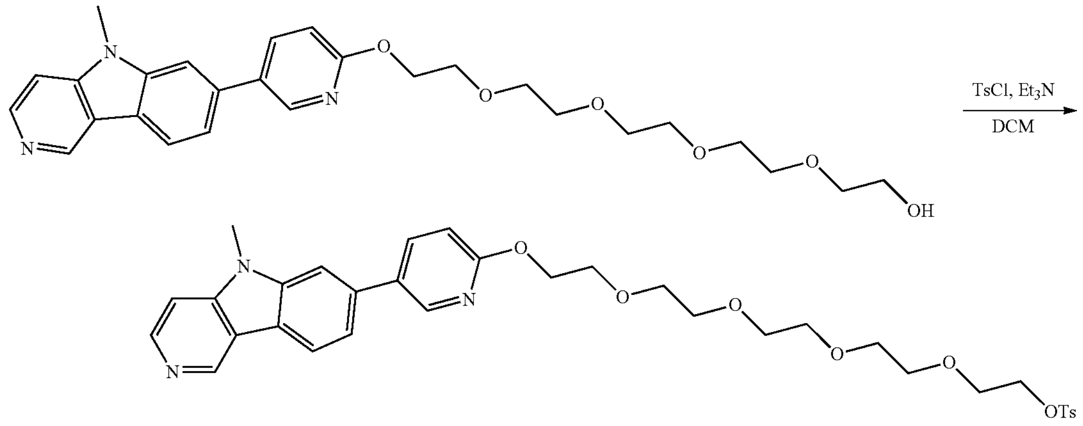

To a solution of 2-[2-[2-[2-[2-[[5-(5-methylpyrido[4, 3-b]indol-7-yl)-2-pyridyl]oxy]ethoxy]ethoxy]ethoxy]ethoxy]ethanol (90 mg, 0.18 mmol, 1 eq) in dichloromethane (5 mL) was added triethylamine (37 mg, 0.36 mmol, 2 eq), then p-toluensulfonyl chloride (139 mg, 0.73 mmol, 4 eq) was added. The mixture was stirred at 15° C. for 12 hours. LCMS showed Reactant 1 was consumed completely and one main peak with desired mass was detected. The reaction mixture was concentrated under reduced pressure. The residue was purified by prep-Thin-Layer Chromatography (dichloromethane: methanol=10:1, the product $R_f$=0.27). 2-[2-[2-[2-[2-[[5-(5-methylpyrido[4,3-b]indol-7-yl)-2-pyridyl]oxy]ethoxy]ethoxy]ethoxy]ethoxy]ethyl 4-methylbenzenesulfonate (0.05 g, 0.07 mmol, 36% yield, 86% purity) was obtained as a yellow oil.

LCMS: MS (ESI) m/z: 650[M+1]$^+$

Chemical Formula: $C_{34}H_{39}N_3O_8S$, Molecular Weight: 649.75

8. Step: Preparation of 2-(2,6-dioxopiperidin-3-yl)-8-(14-((5-(5-methyl-5H-pyrido[4,3-b]indol-7-yl)pyridin-2-yl)oxy)-3,6,9,12-tetraoxatetradecyl)-2,8-diazaspiro[4.5]decane-1,3-dione

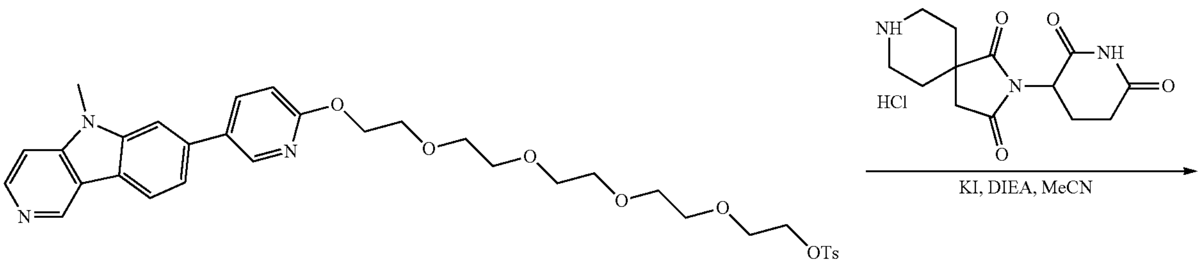

-continued

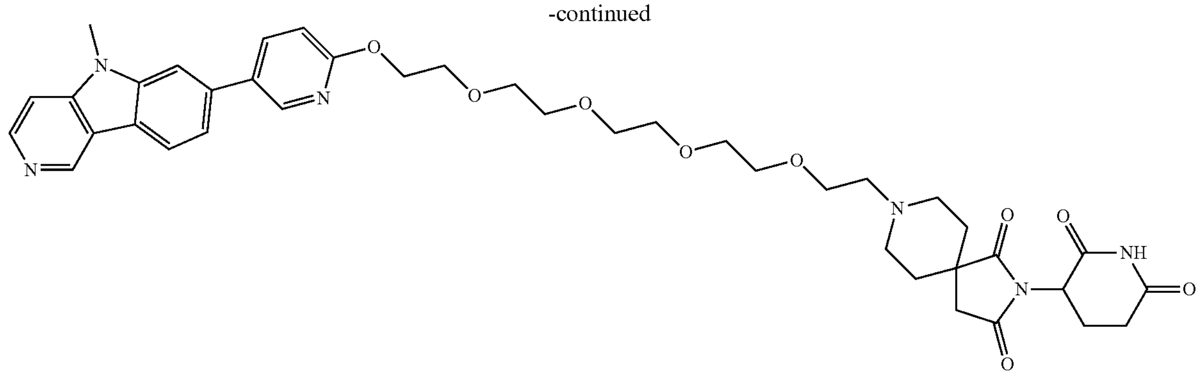

A mixture of 2-[2-[2-[2-[2-[[5-(5-methylpyrido[4, 3-b]indol-7-yl)-2-pyridyl]oxy]ethoxy]ethoxy]ethoxy]ethoxy]ethyl4-methylbenzenesulfonate (50 mg, 0.07 mmol, 1 eq), 2-(2, 6-dioxo-3-piperidyl)-2, 8-diazaspiro[4.5]decane-1,3-dione (32 mg, 0.10 mmol, 1.33 eq, hydrochloride), potassium iodide (19 mg, 0.12 mmol, 1.5 eq), N,N-diisopropylethylamine (30 mg, 0.23 mmol, 3 eq) in acetonitrile (5 mL) was degassed and purged with nitrogen for 3 times, and then the mixture was stirred at 100° C. for 12 hours under nitrogen atmosphere. LCMS showed Reactant 1 was consumed completely and one main peak with desired MS was detected. The reaction mixture was concentrated under reduced pressure. The residue was purified by semi-preparative reverse phase HPLC (column: Phenomenex Synergi C18 150*25*10 um; mobile phase: [water (0.05%HCl)-ACN]; B%: 0%-30%, 10 min). The purity of residue was 90%. The residue was purified by semi-preparative reverse phase HPLC (column: Phenomenex Synergi C18 150*30 mm*4 um; mobile phase: [water(0.225%FA)-ACN]; B%: 0%-26%,10.5 min; FlowRate(ml/min): 25). 2-(2,6-dioxo-3-piperidyl)-8-[2-[2-[2-[2-[2-[[5-(5-methylpyrido[4,3-b]indol-7-yl)-2-pyridyl]oxy]ethoxy]ethoxy]ethoxy]ethoxy]ethyl]-2,8-diazaspiro[4.5]decane-1,3-dione (12.9 mg, 0.01 mmol, 20% yield, 99% purity, bis formate salt) was obtained as a yellow solid.

LCMS: MS (ESI) m/z: 757.3 $[M+1]^+$

HNMR: (400 MHz, DMSO-$d_6$) δ: 11.03 (s, 1H), 9.36 (s, 1H), 8.65 (d, J=2.4 Hz, 1H), 8.50 (d, J=6.4 Hz, 1H), 8.33 (d, J=8.0 Hz, 1H), 8.23-8.19 (m, 3H), 7.99 (s, 1H), 7.63-7.62 (m, 2H), 6.98 (d, J=8.8 Hz, 1H), 4.90 (dd, J=5.2, 13.2 Hz, 1H), 4.45 (t, J=4.8 Hz, 2H), 3.96 (s, 3H), 3.79 (t, J=4.8 Hz, 2H), 3.61-3.54 (m, 6H), 3.51-3.47 (m, 7H), 2.84-2.76 (m, 3H), 2.67-2.66 (m, 2H), 2.54-2.53 (m, 1H), 2.47-2.33 (m, 4H), 2.03 (t, J=10.4 Hz, 2H), 1.87-1.75 (m, 3H), 1.52-1.49 (m, 2H).

Chemical Formula: $C_{40}H_{48}N_6O_9$, Molecular Weight: 756.84

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present invention, but should not be seen as limiting the present invention in any way.

Exemplary Embodiments of the Present Disclosure

The present disclosure encompasses the following specific embodiments. These following embodiments may include all of the features recited in a proceeding embodiment, as specified. Where applicable, the following embodiments may also include the features recited in any proceeding embodiment inclusively or in the alternative One aspect discloses a bifunctional compound having the chemical structure: CLM-L-PTM, or a pharmaceutically acceptable salt, enantiomer, stereoisomer, solvate, polymorph or prodrug thereof, wherein: the PTM is a small molecule comprising a protein targeting moiety; the L is a bond or a chemical linking moiety covalently coupling the CLM and the PTM; and the CLM is a small molecule cereblon E3 ubiquitin ligase binding moiety that binds or targets an cereblon E3 ubiquitin ligase and has a chemical structure selected from the group consisting of:

(a)

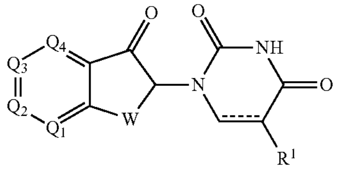

(b)

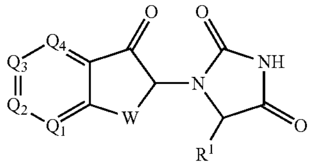

(c)

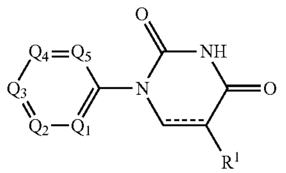

(d)

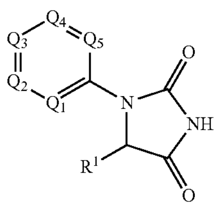

-continued
(e)
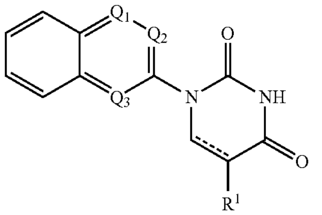
(f)
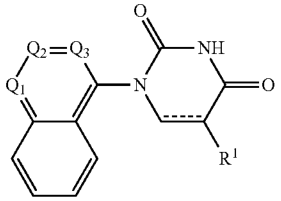
(g)
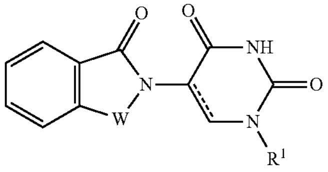
(h)
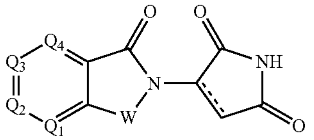
(i)
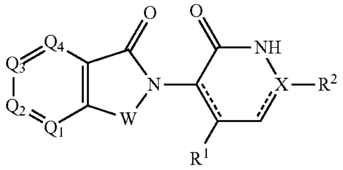
(j)
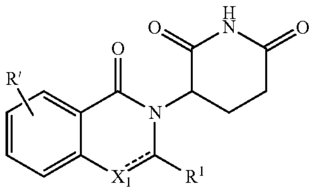
(k)
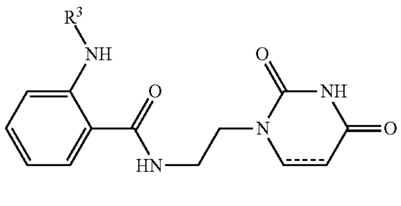
(l)
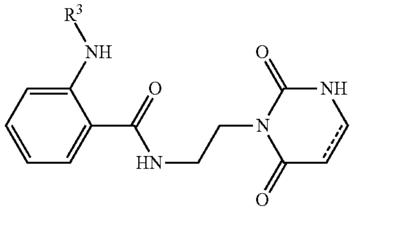
-continued
(m)
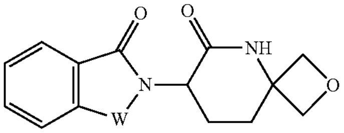
(n)
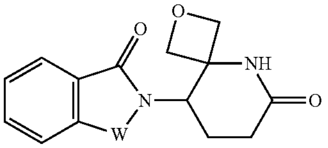
(o)
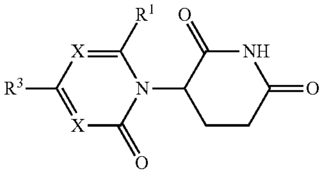
(p)
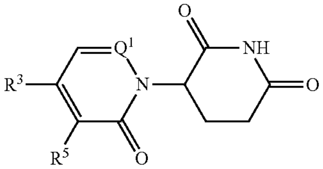
(q)
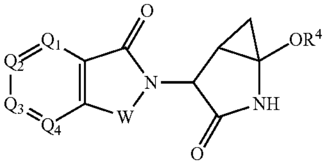
(r)
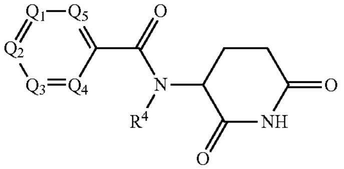
(s)
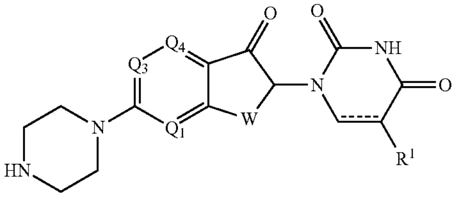
(t)
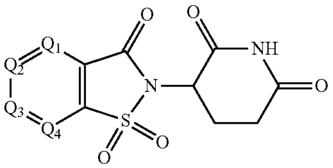
(ba)
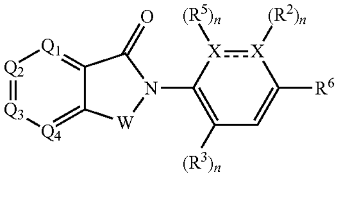

-continued (bc)

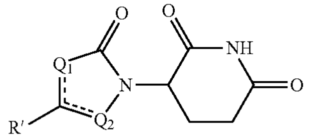

(bb)

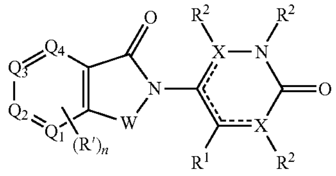

(bd)

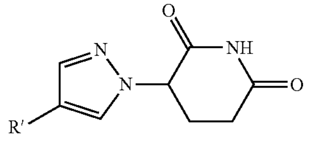

(be)

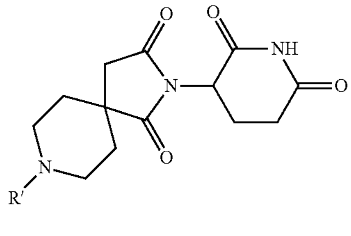

(bf)

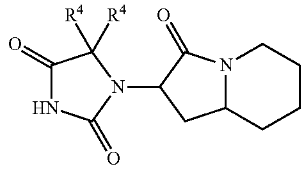

(bg)

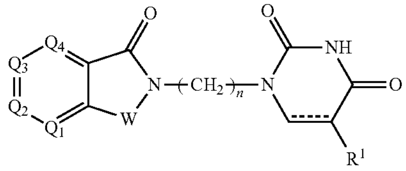

(bh)

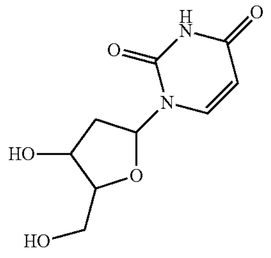

(bi)

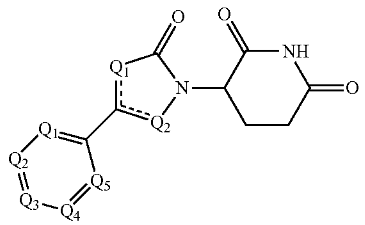

-continued (j')

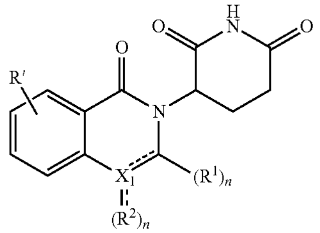

(p')

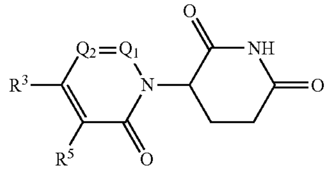

(h')

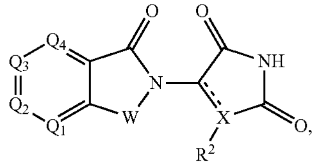

wherein:

W is independently selected from $CH_2$, CHR, C═O, $SO_2$, NH, and N-alkyl;

$Q_1$, $Q_2$, $Q_3$, $Q_4$, $Q_5$ are each independently represent a carbon C or N substituted with a group independently selected from R', N or N-oxide;

$R^1$ is selected from absent, H, OH, CN, C1-C3 alkyl, C═O;

$R^2$ is selected from the group absent, H, OH, CN, C1-C3 alkyl, $CHF_2$, $CF_3$, CHO, C(═O)$NH_2$;

$R^3$ is selected from absent, H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), substituted alkoxy (e.g., substituted C1-C6 or C1-C3 alkoxyl);

$R^4$ is selected from H, alkyl, substituted alkyl;

$R^5$ and $R^6$ are each independently H, halogen, C(═O)R', CN, OH, $CF_3$;

X is C, CH, C═O, or N;

$X_1$ is C═O, N, CH, or $CH_2$;

R' is selected from H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, C(═O)$OR^2$, optionally substituted phenyl;

n is 0-4;

and ⫽ is a single or double bond.

In any aspect or embodiment described herein, the CLM is linked to the PTM, the chemical linker group (L), or a combination thereof via W, X, $R^1$, $R^2$, $R^3$, $R^4$, R', $Q_1$, $Q_2$, $Q_3$, $Q_4$, and $Q_5$.

In any aspect or embodiment described herein, the PTM is a moiety that binds Brd4, Tau Protein, Estrogen Receptor (ER) or Androgen Receptor (AR).

In any aspect or embodiment described herein, the compound further comprises a second E3 ubiquitin ligase binding moiety coupled through a linker group.

In any aspect or embodiment described herein, the second E3 ubiquitin ligase binding moiety binds or targets an E3 ubiquitin ligase selected from the group consisting of Von Hippel-Lindau (VLM), cereblon (CLM), mouse double-minute homolog2 (MLM), and inhibitors of apoptosis proteins (ILM).
In any aspect or embodiment described herein, the CLM is represented by a chemical structure selected from the group consisting of:
(v)
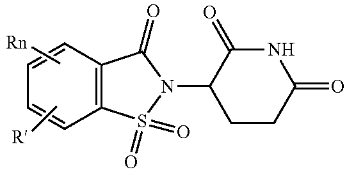
(w)
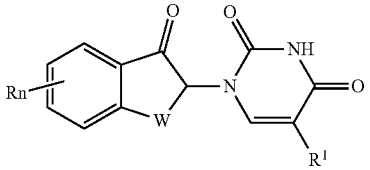
(x)
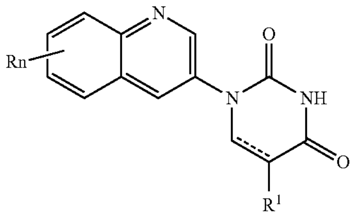
(y)
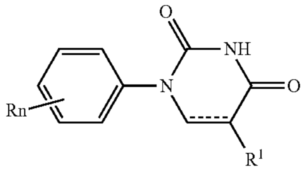
(z)
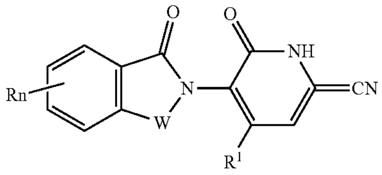
(aa)
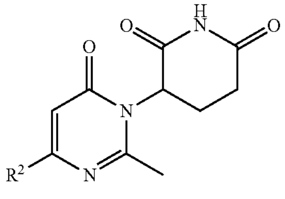
(ab)
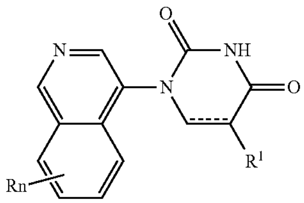
-continued
(ac)
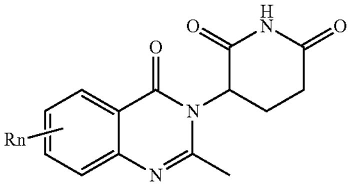
(ad)
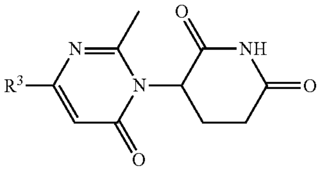
(ae)
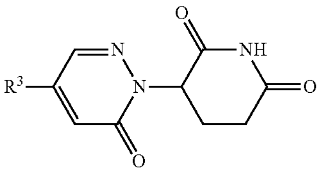
(af)
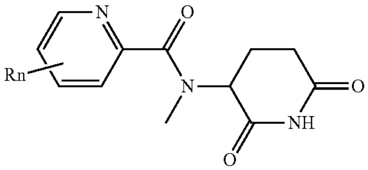
(ag)
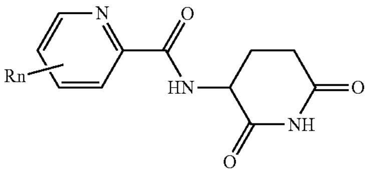
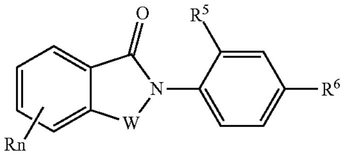
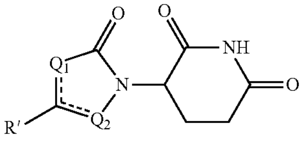
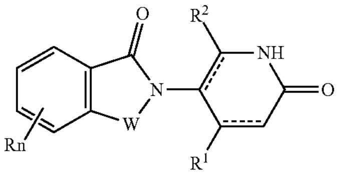
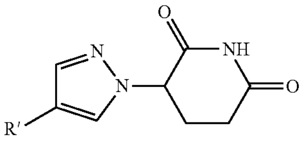

-continued

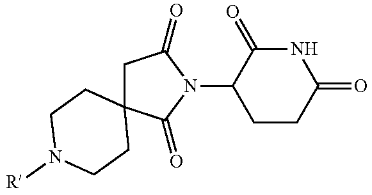

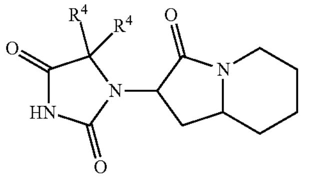

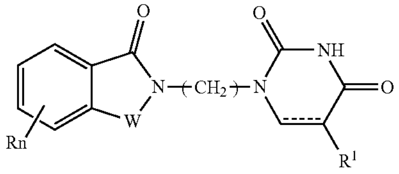

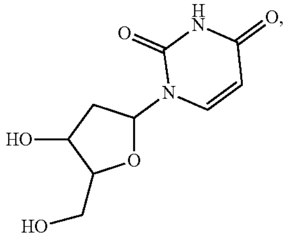

wherein:

W is independently selected from the group $CH_2$, CHR, C═O, $SO_2$, NH, and N-alkyl;

$R^1$ is selected from the group absent, H, CH, CN, C1-C3 alkyl;

$R^2$ is H or a C1-C3 alkyl;

$R^3$ is selected from H, alkyl, substituted alkyl, alkoxy, substituted alkoxy;

$R^4$ is methyl or ethyl;

$R^5$ is H or halo;

$R^6$ is H or halo;

R is H or halogen;

R' is H or an attachment point for a PTM, a PTM', a chemical linker group (L), a ULM, a CLM, a CLM', Q1 and Q2 are each independently C or N substituted with a group independently selected from H or C1-C3 alkyl;

--- is a single or double bond; and

Rn comprises a functional group or an ato.

In any aspect or embodiment described herein, the CLM is represented by a chemical structure selected by:

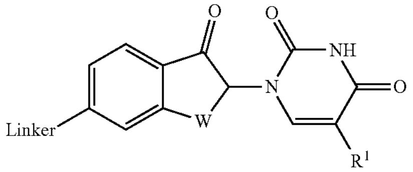

-continued

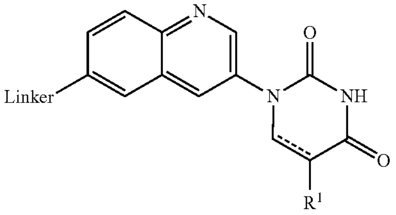

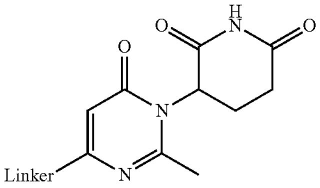

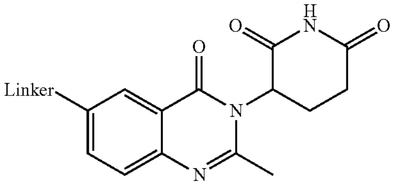

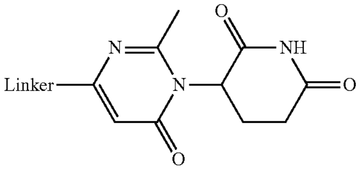

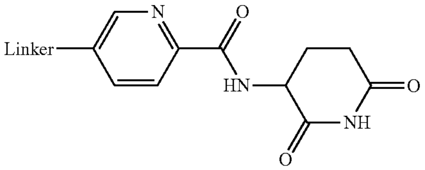

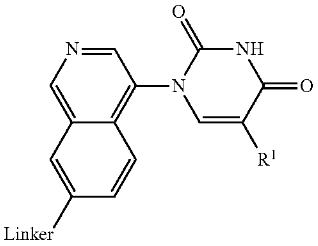

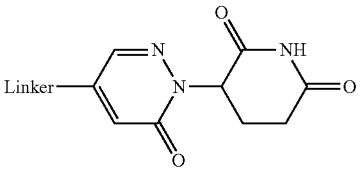

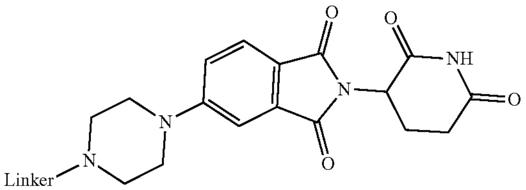

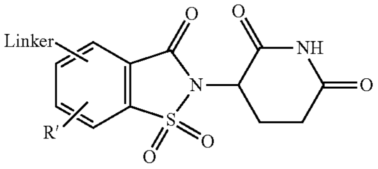

-continued
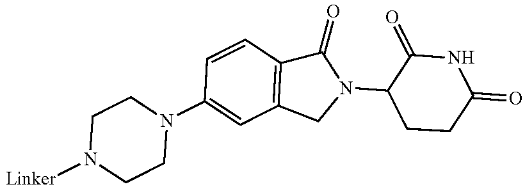
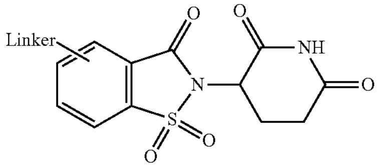
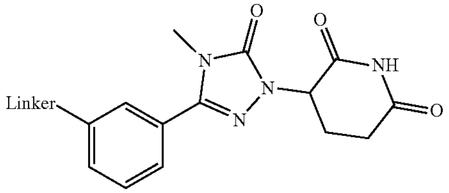
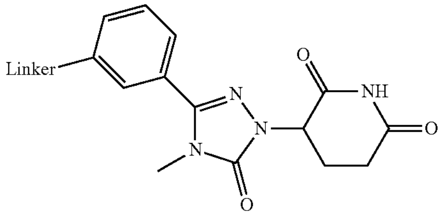
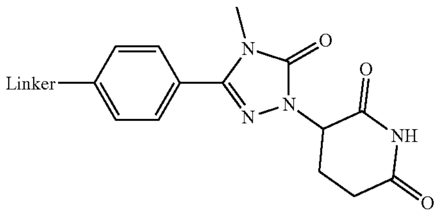
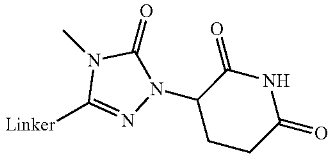
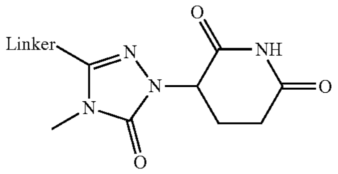
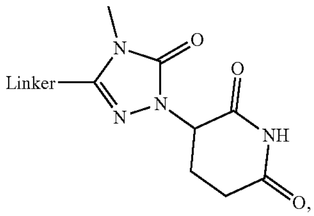
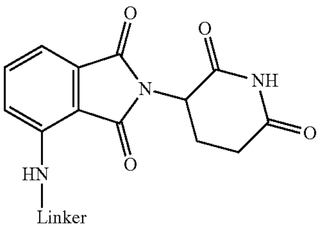
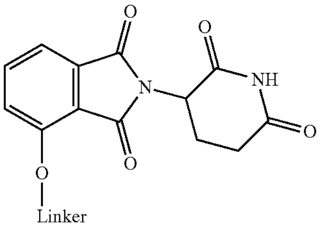
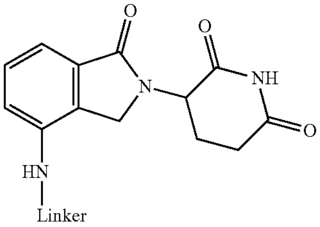
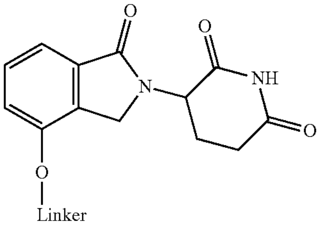
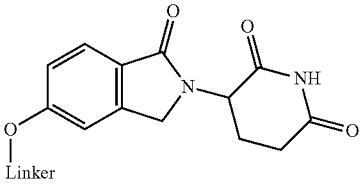
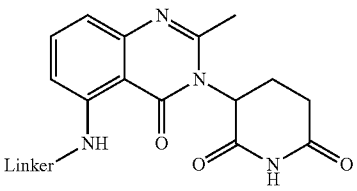
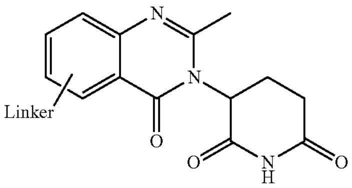
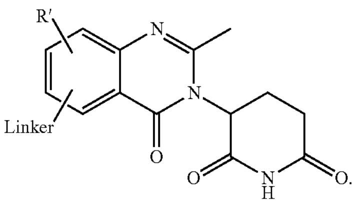
wherein R' is a halogen.
In any aspect or embodiment described herein, the CLM is represented by a chemical structure selected by:

In any aspect or embodiment described herein, the linker (L) comprises a chemical structural unit represented by the formula:

$-(A^L)q-$ wherein:

$(A^L)_q$ is a group which is connected to a CLM or PTM moiety; and q is an integer greater than or equal to 1;

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{L3}C({=}NCN)NR^{L4}$, $NR^{L3}C({=}NCN)$, $NR^{L3}C({=}CNO_2)NR^{L4}$, $C_{3-11}$cycloalkyl optionally substituted with 0-6 $R^{L1}$ and/or $R_{L2}$ groups, $C_{3-11}$heteocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH═CH($C_{1-8}$alkyl), C($C_{1-8}$alkyl)═CH($C_{1-8}$alkyl), C($C_{1-8}$alkyl)═C($C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)SO_2N(C_{1-8}alkyl)_2$, NH $SO_2NH(C_{1-8}alkyl)$, NH $SO_2N(C_{1-8}alkyl)_2$, NH $SO_2NH_2$.

In any aspect or embodiment described herein, the L is selected from the group consisting of:

—N(R)—$(CH2)_m$—$O(CH2)_n$—$O(CH2)_o$—$O(CH2)_p$—$O(CH2)_q$—$O(CH2)_r$-OCH2-,

—O—$(CH2)_m$—$O(CH2)_n$—$O(CH2)_o$—$O(CH2)_p$—$O(CH2)_q$—$O(CH2)_r$-OCH2-,

—O—$(CH2)_m$—$O(CH2)_n$—$O(CH2)_o$—$O(CH2)_p$—$O(CH2)_q$—$O(CH2)_r$—O—;

—N(R)—$(CH2)_m$—$O(CH2)_n$—$O(CH2)_o$—$O(CH2)_p$—$O(CH2)_q$—$O(CH2)_r$—O—;

—$(CH2)_m$—$O(CH2)_n$—$O(CH2)_o$—$O(CH2)_p$—$O(CH2)_q$—$O(CH2)_r$—O—;

—$(CH2)_m$—$O(CH2)_n$—$O(CH2)_o$—$O(CH2)_p$—$(CH2)_q$—$O(CH2)_r$-OCH2-;

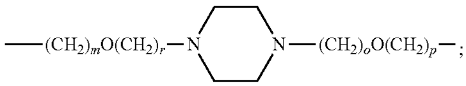

;

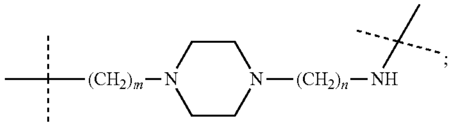

;

-continued

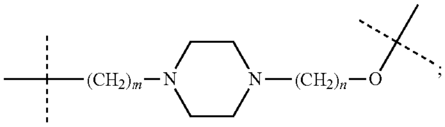

;

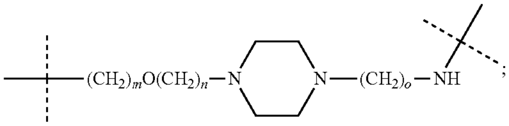

;

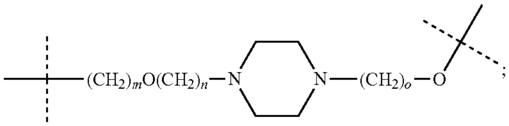

;

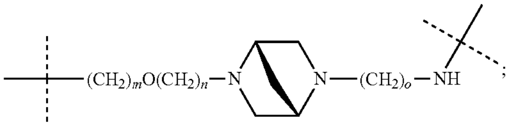

;

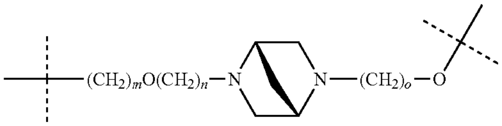

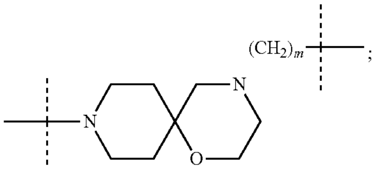

;

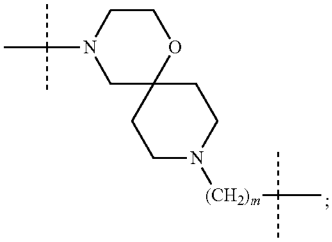

;

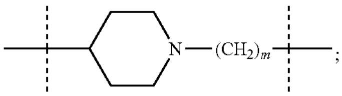

;

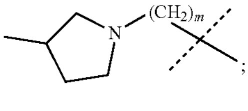

;

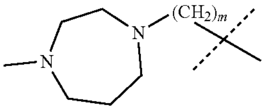

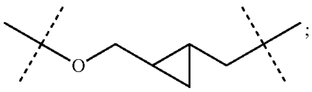

;

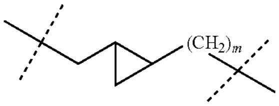

;

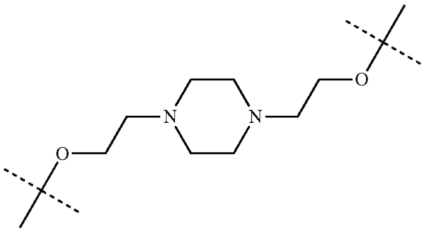

;

-continued
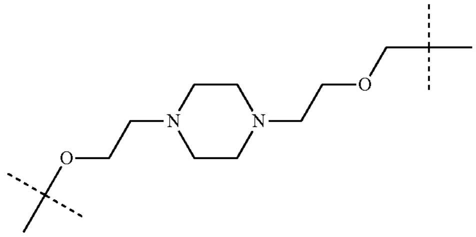
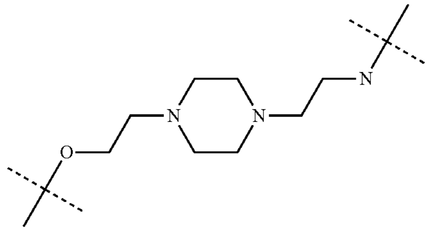
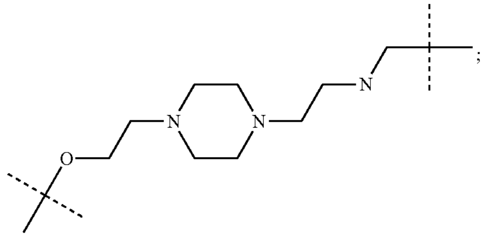
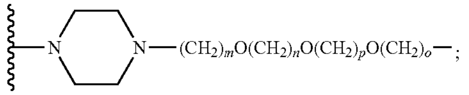
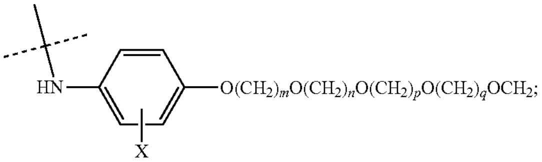
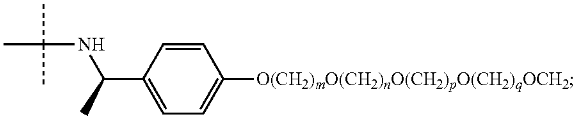
-continued
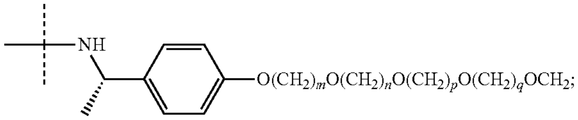
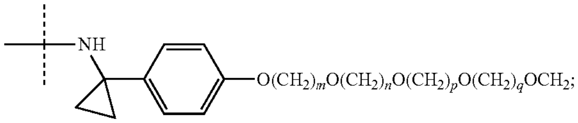
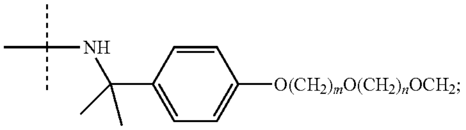
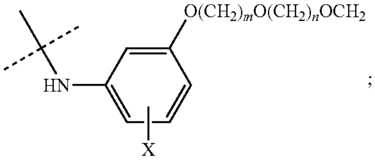
; and
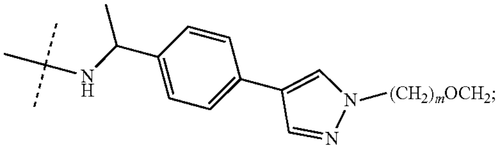
wherein
m, n, o, p, q, and r of the linker are independently 0, 1, 2, 3, 4, 5, 6, 7, 8, 9, 10, 11, 12, 13, 14, 15, 16, 17, 18, 19, 20;
when the number is zero, there is no N—O or O—O bond
R of the linker is H, methyl and ethyl;
X of the linker is H and F
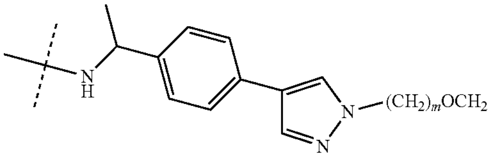
where m of the linker can be 2, 3, 4, 5
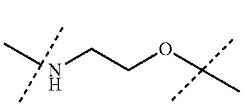
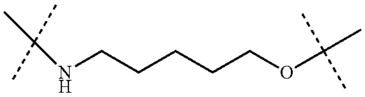
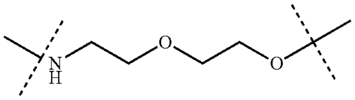
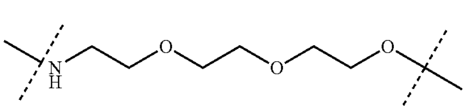
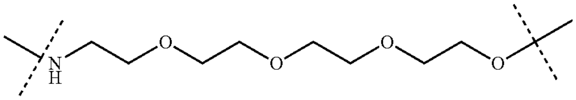
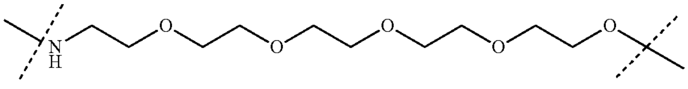
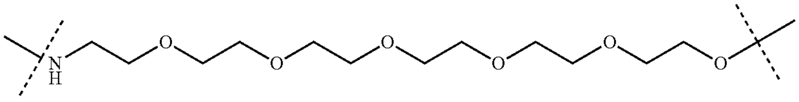
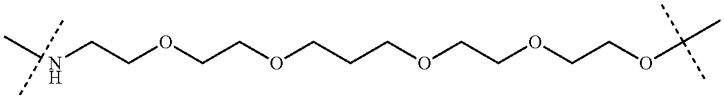

-continued
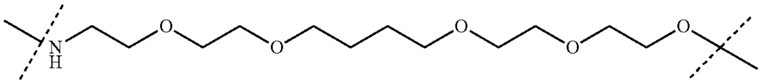
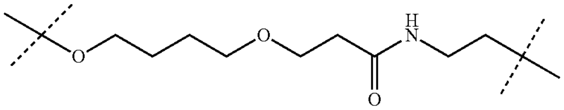
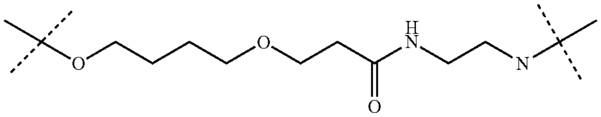 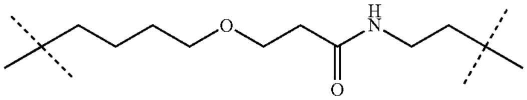
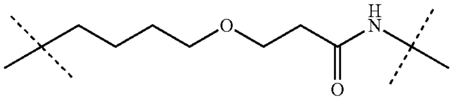 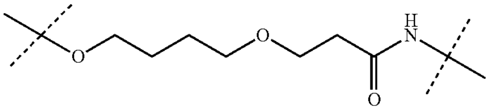
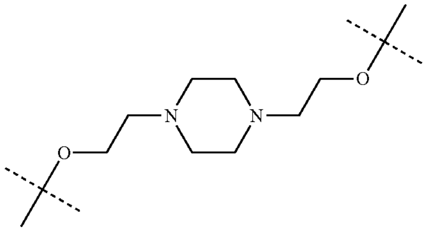 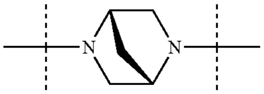 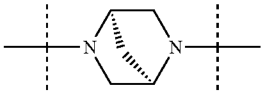
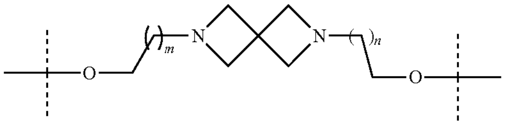 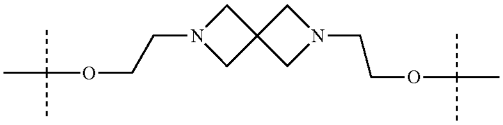
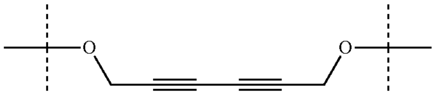 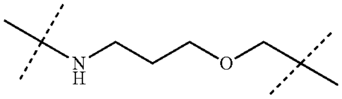
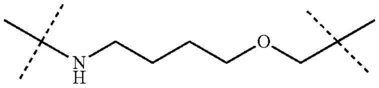 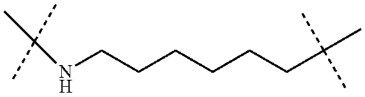
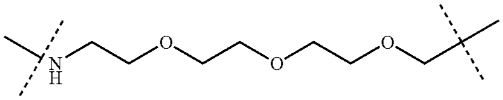 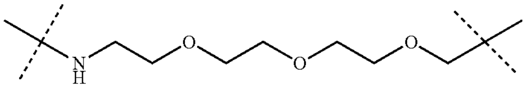
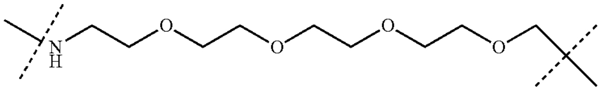 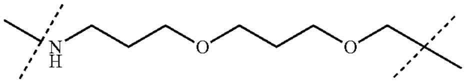
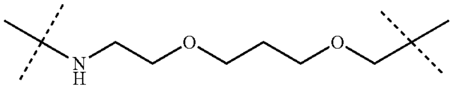 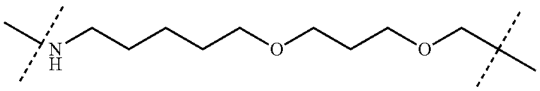
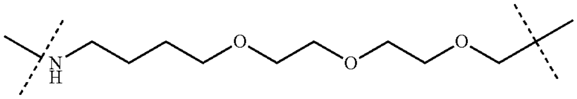 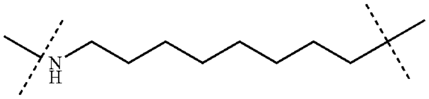
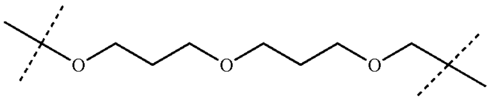 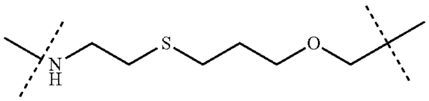
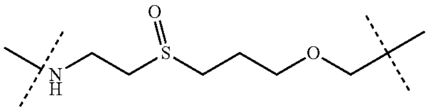 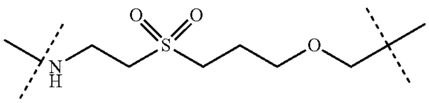
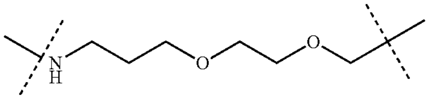 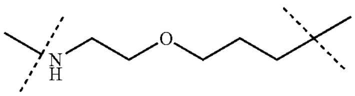

-continued
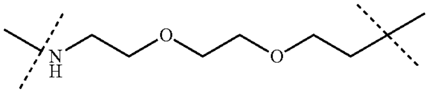
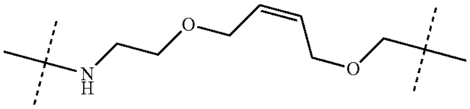
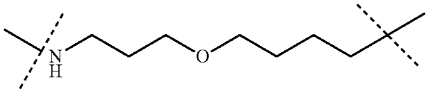
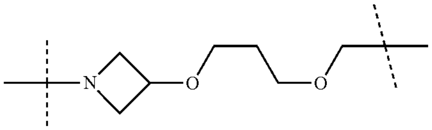
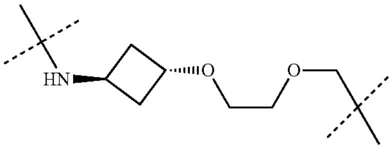
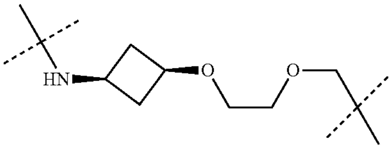
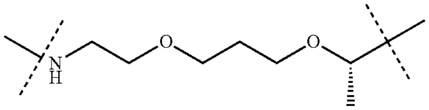
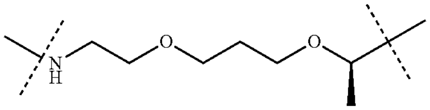
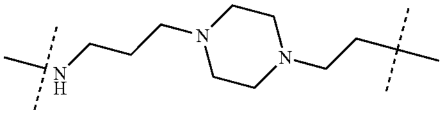
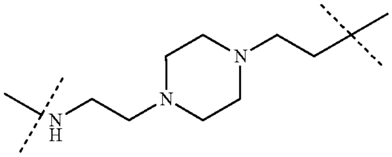
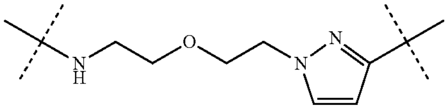
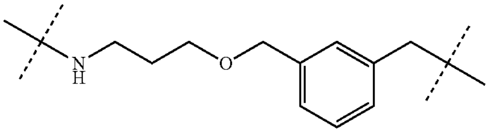
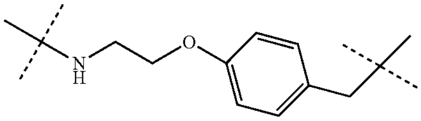
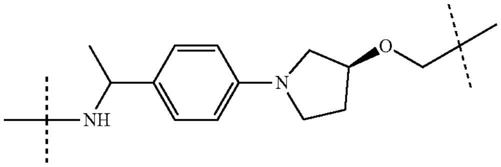
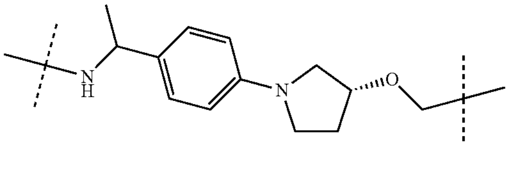
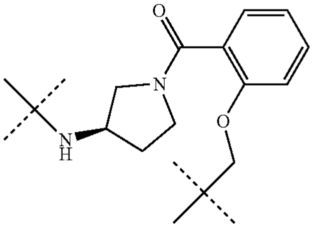
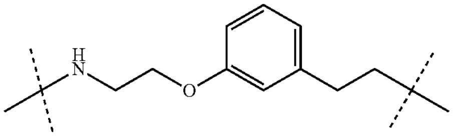
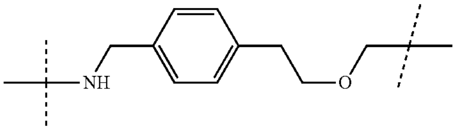
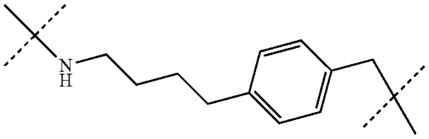
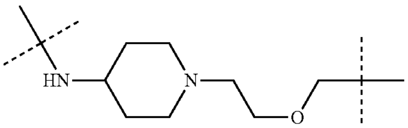
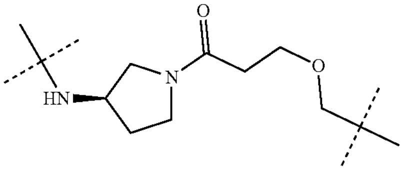
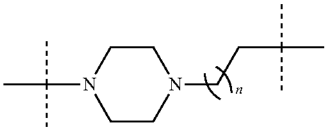

-continued
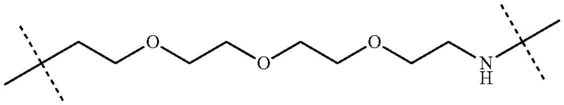
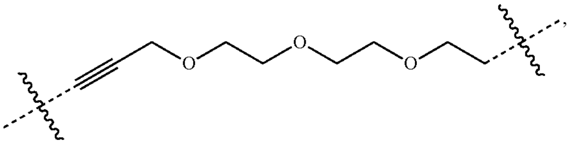,
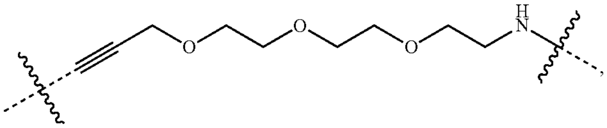,
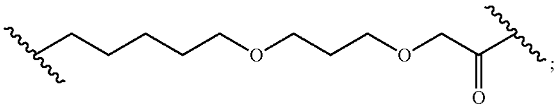;
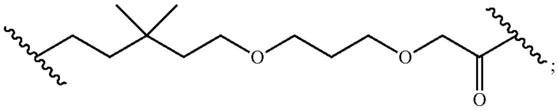;
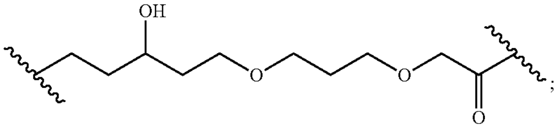;
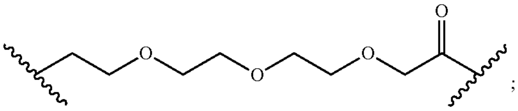;
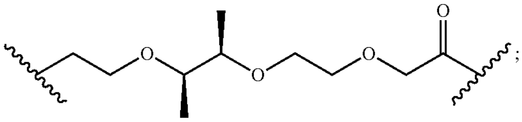;
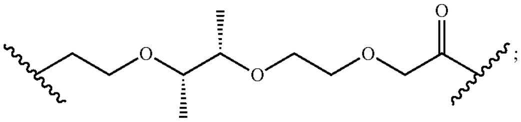;
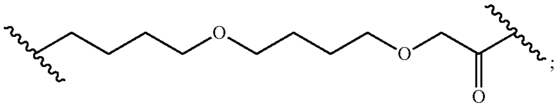;
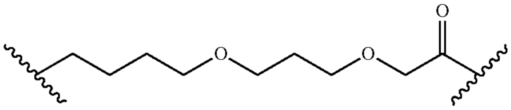;
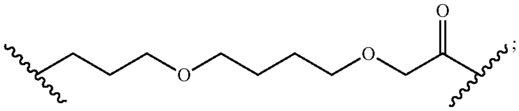;
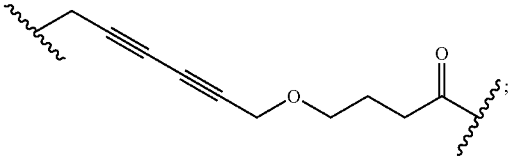;
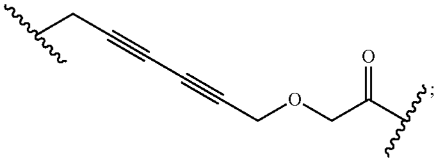;
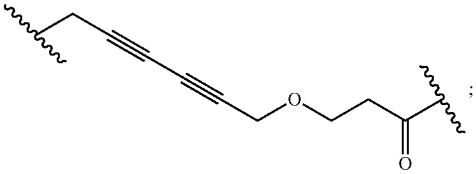;
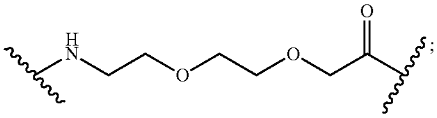;
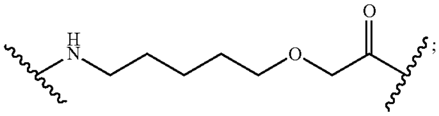;
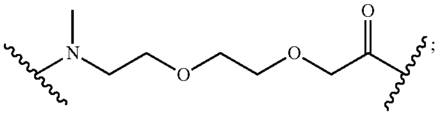;
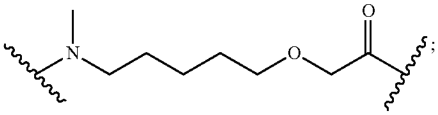;
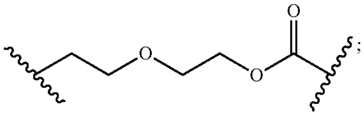;
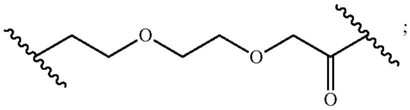;
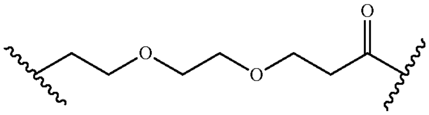;
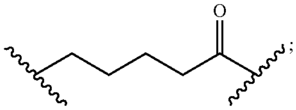;
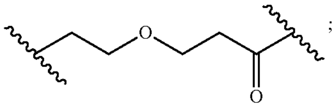;
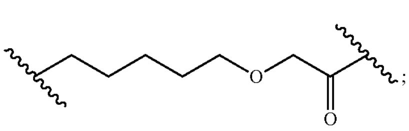;
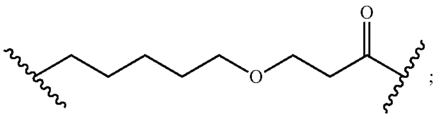;

-continued
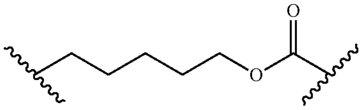;
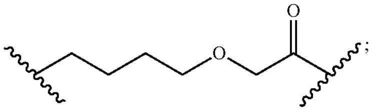;
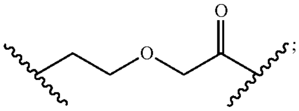;
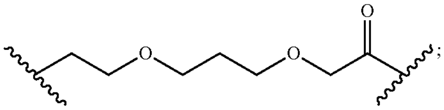;
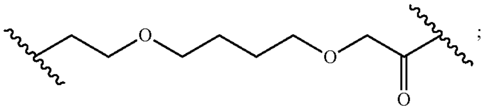;
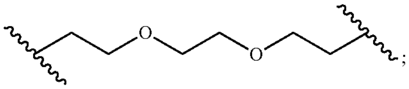;
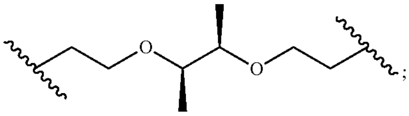;
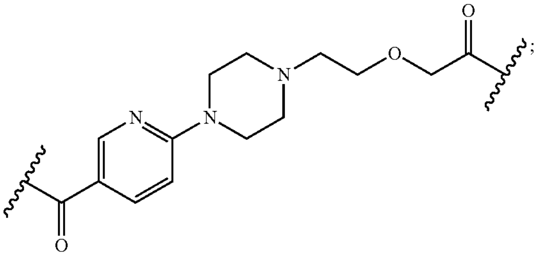;
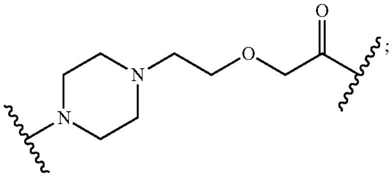;
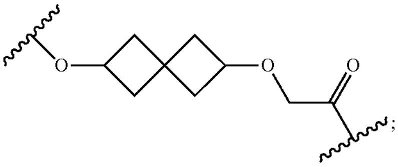;
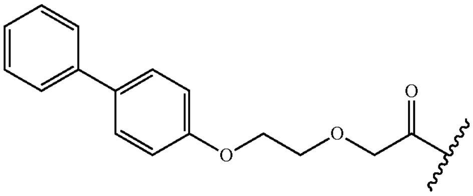;
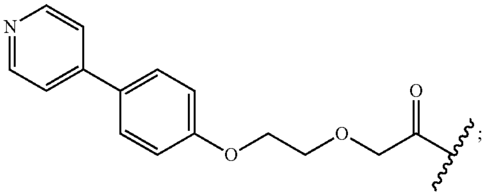;
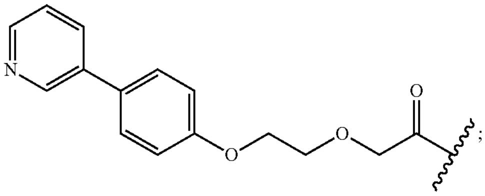;
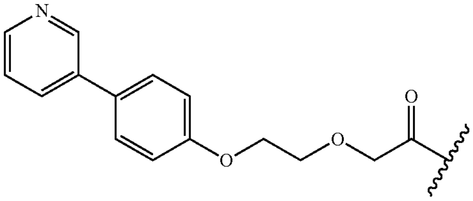;
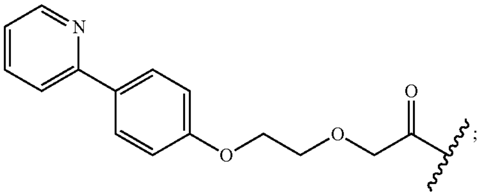;
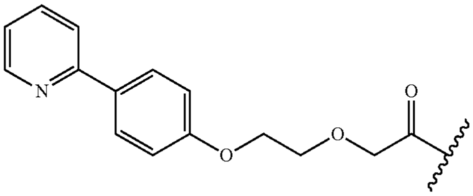;
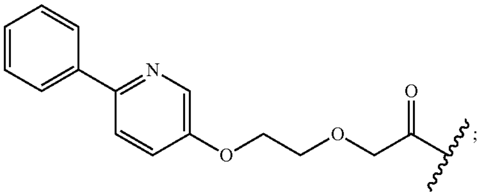;
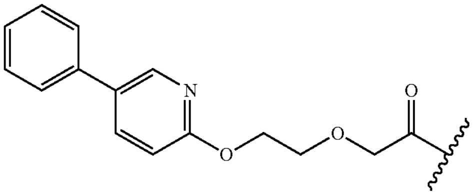;
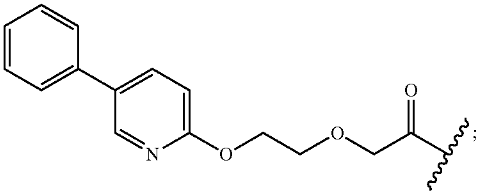;

-continued
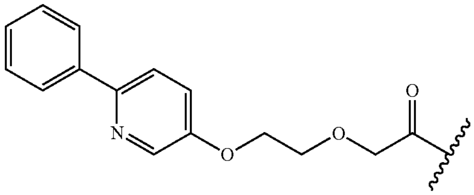
;
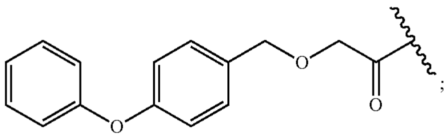
;
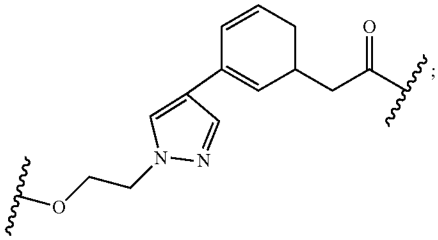
;
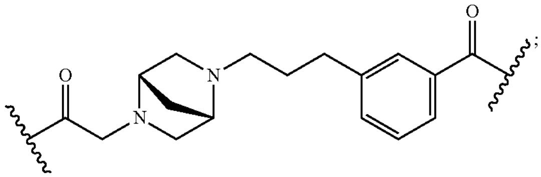
;
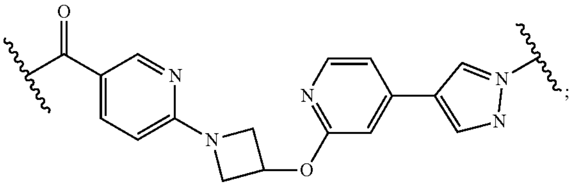
;
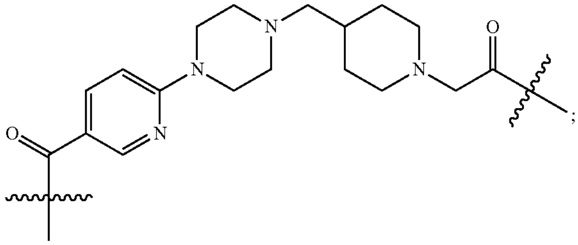
;
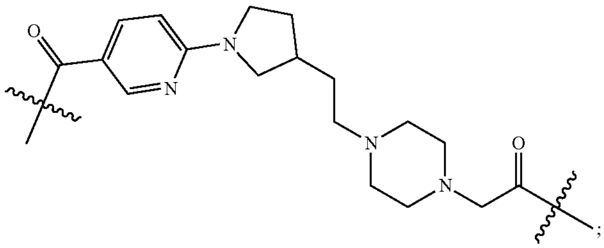
;
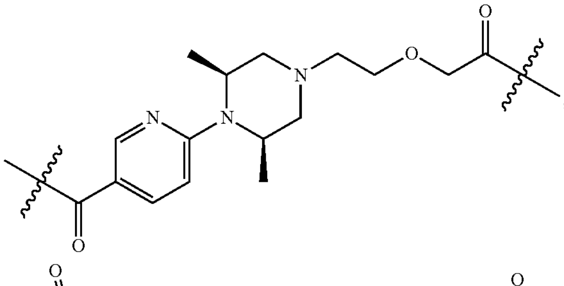
;
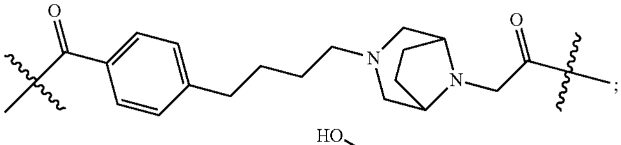
;
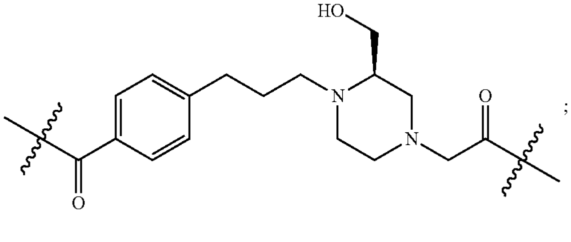
;
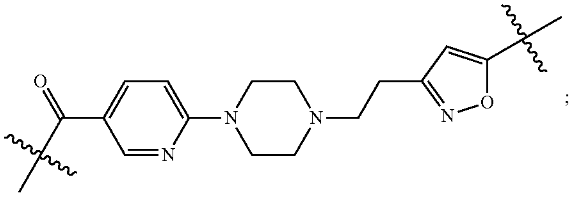
;

-continued
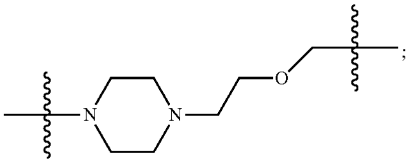
;
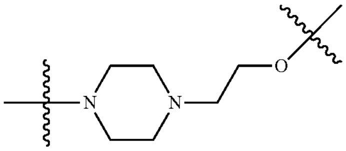
;
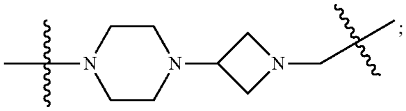
;
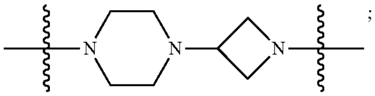
;
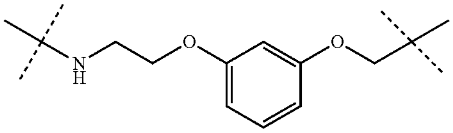
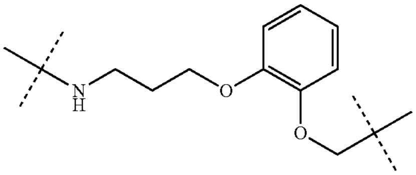
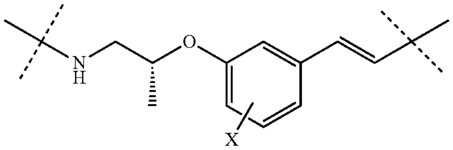
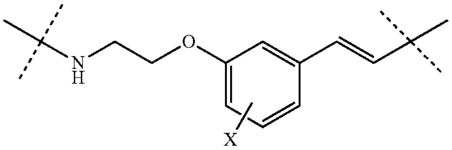
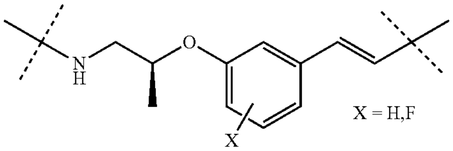
X = H,F
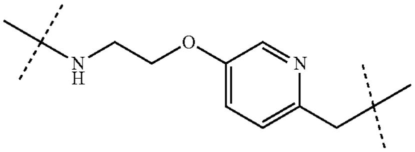
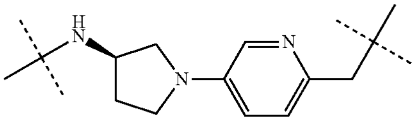
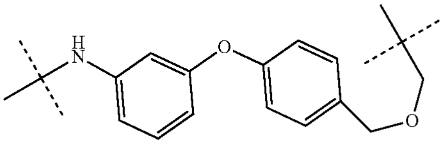
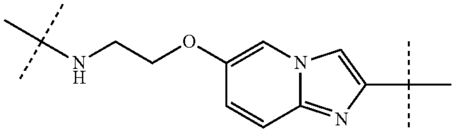
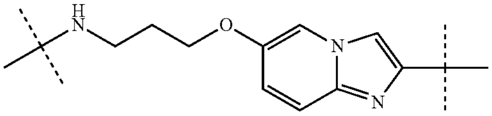
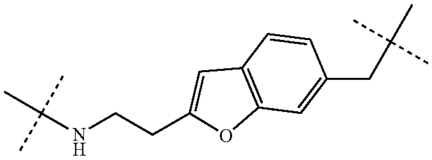
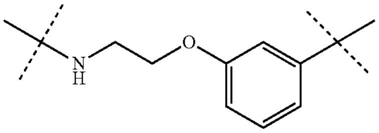
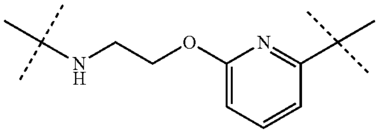
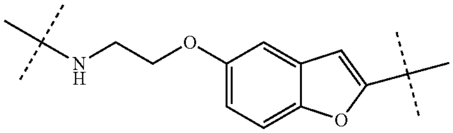
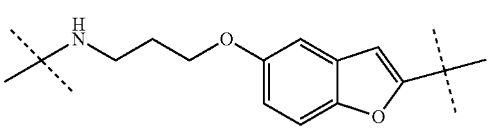
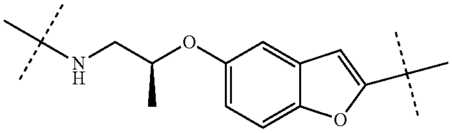
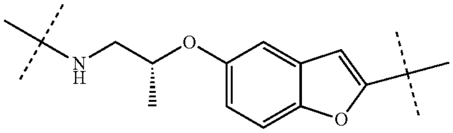
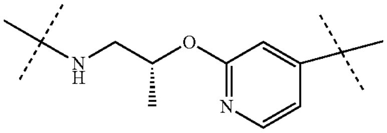

-continued
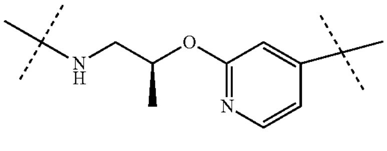
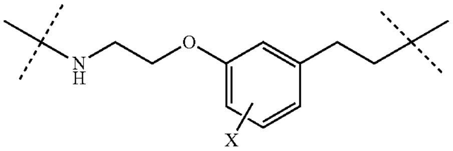
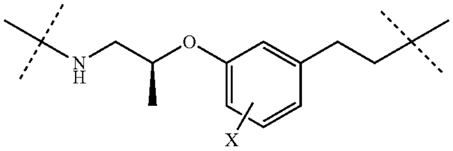
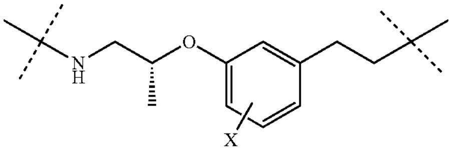
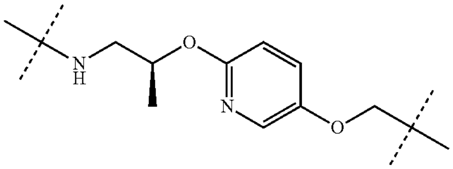
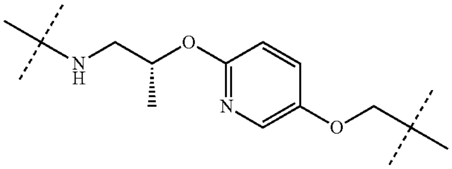
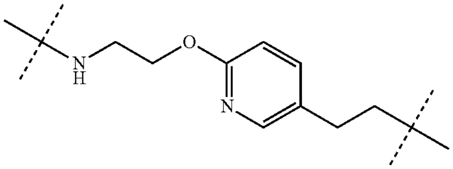
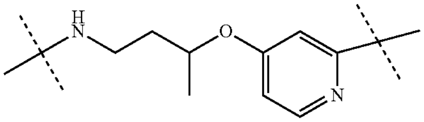
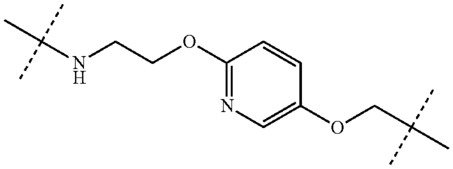
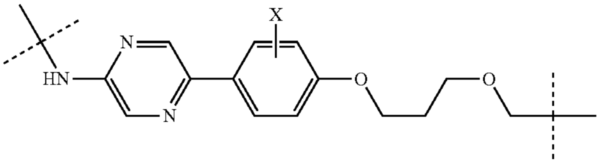
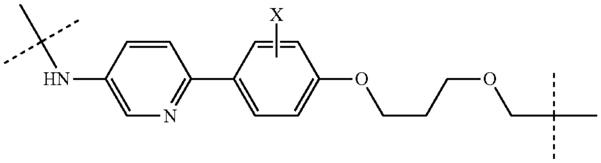
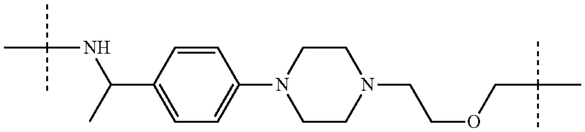
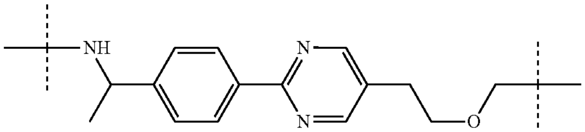
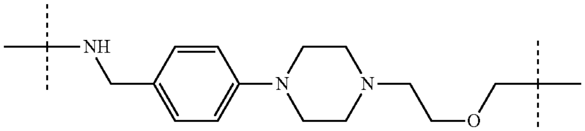
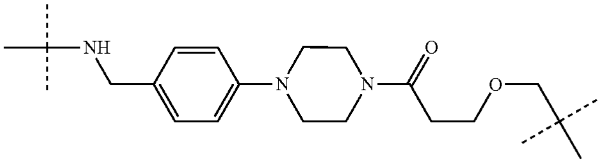
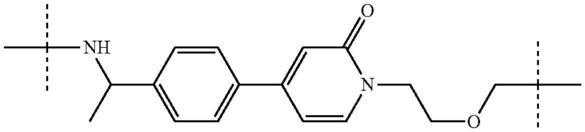

-continued
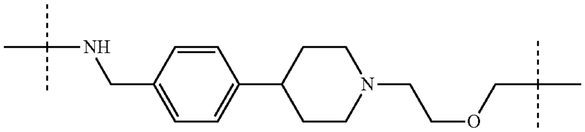
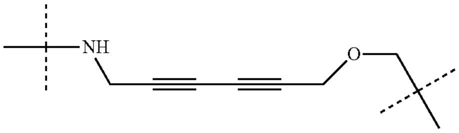
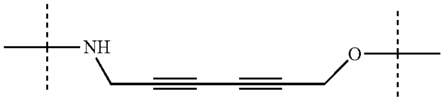
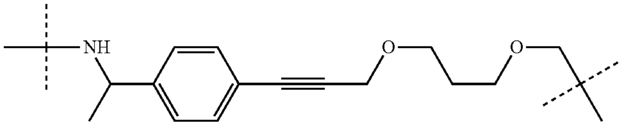
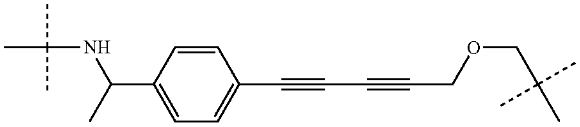
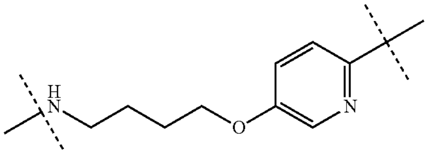
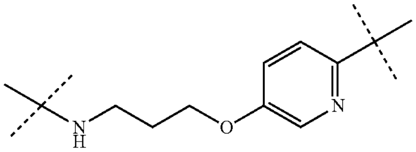
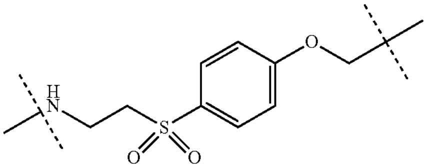
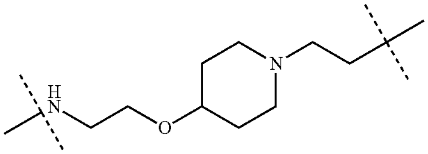
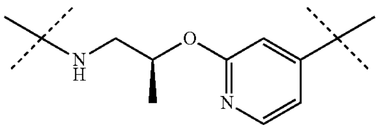
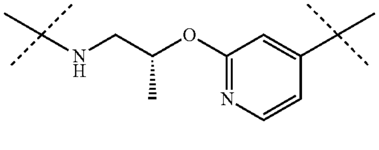
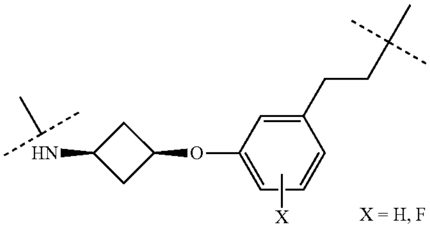
X = H, F
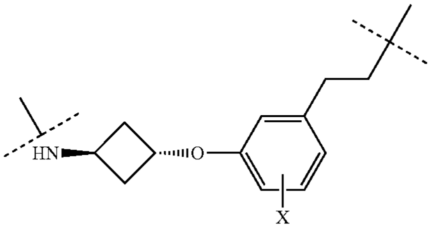
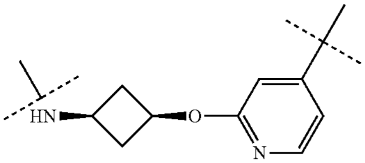
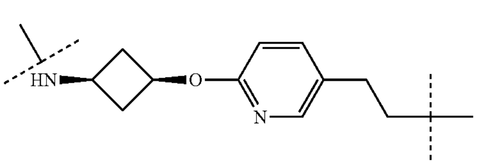
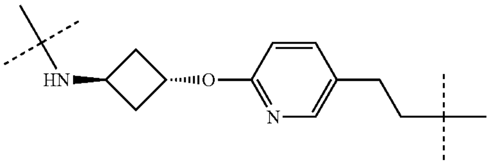
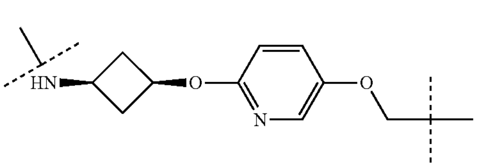
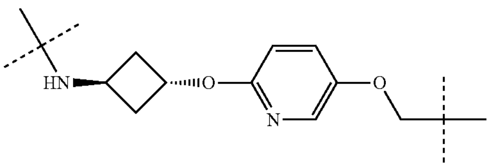
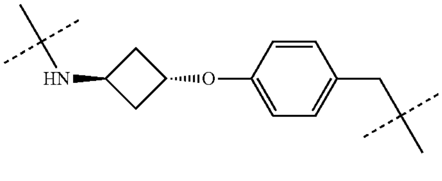
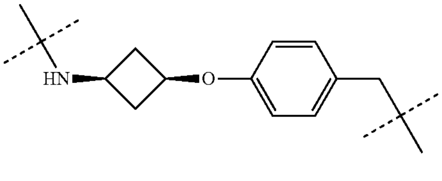

-continued
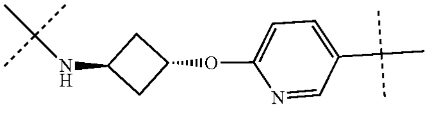
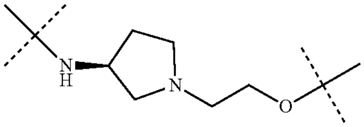
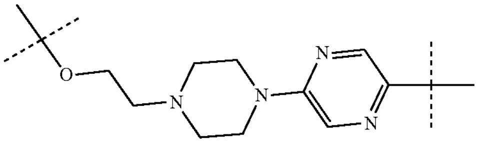
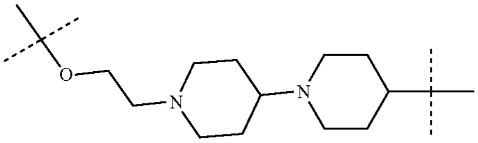
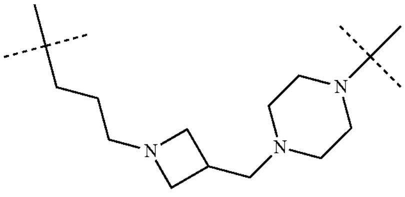
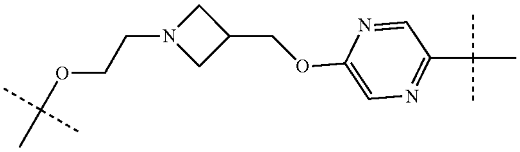
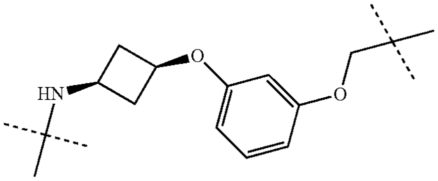
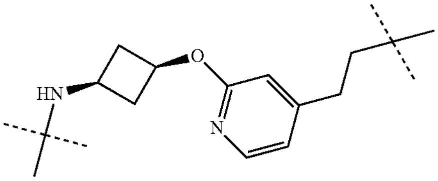
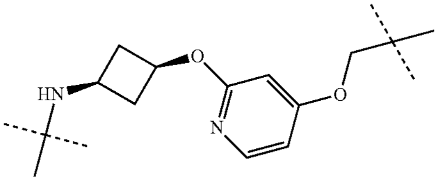
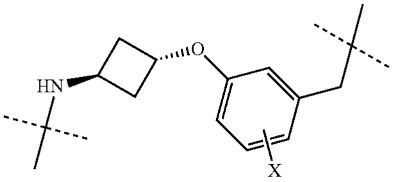
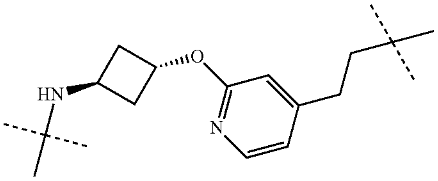
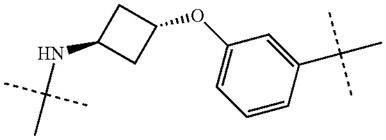
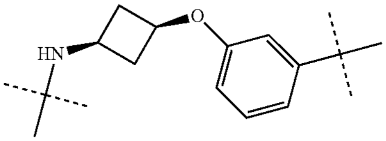
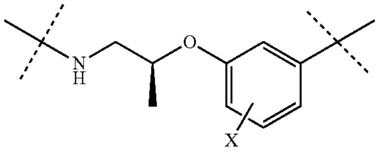
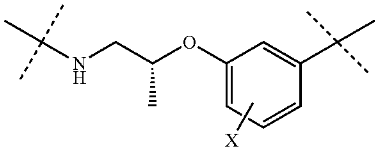
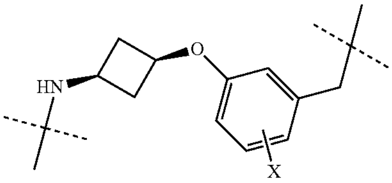
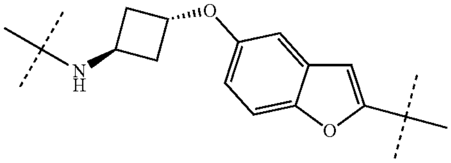
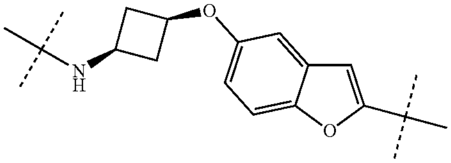
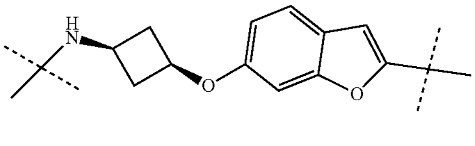
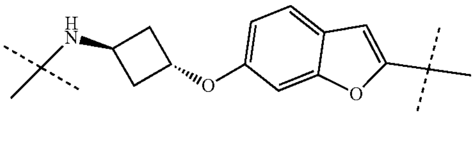

-continued
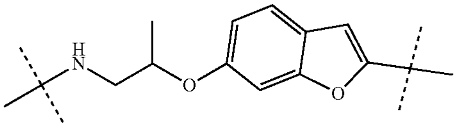
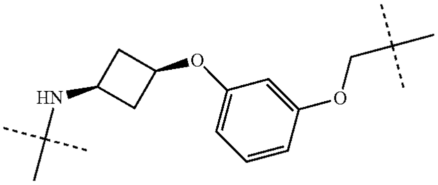
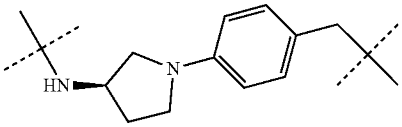
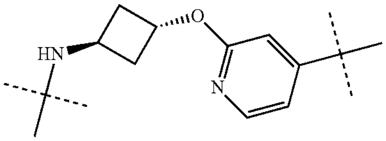
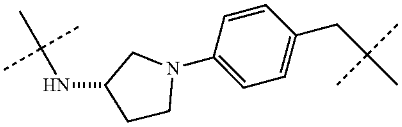
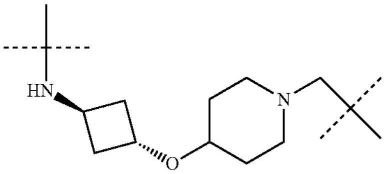
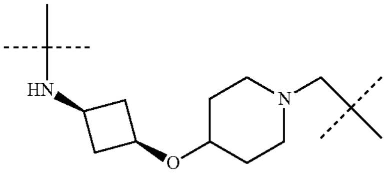
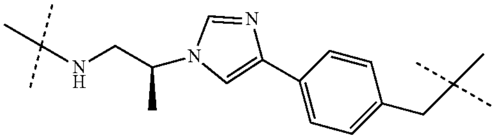
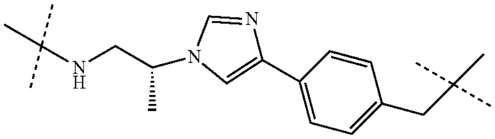
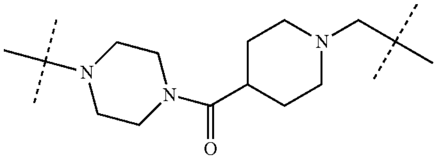
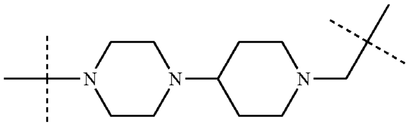
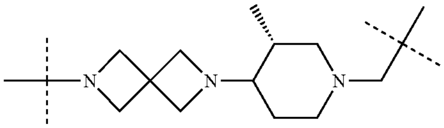
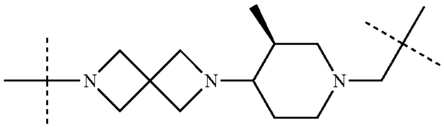
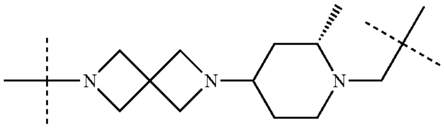
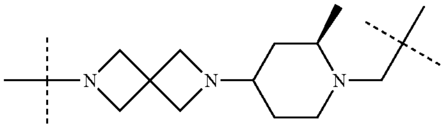
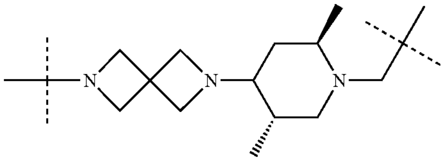
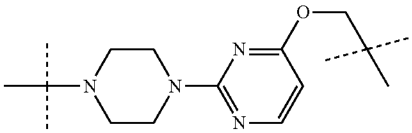
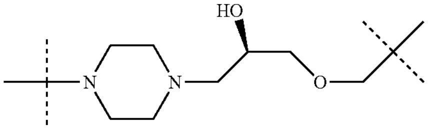
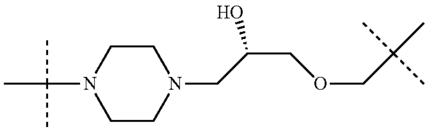
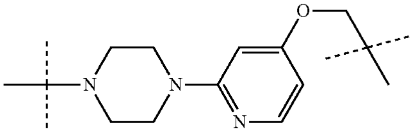
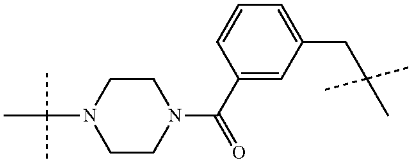
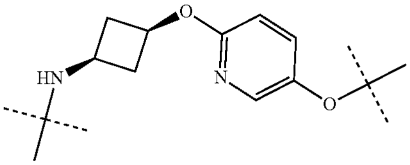

-continued
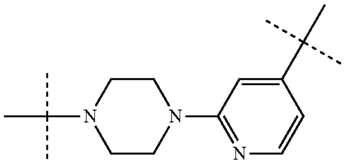 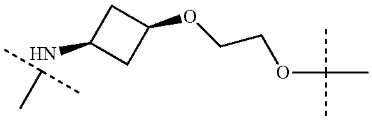
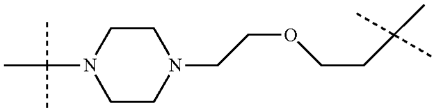 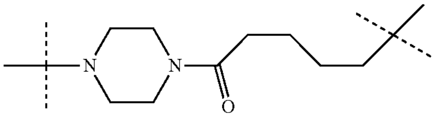
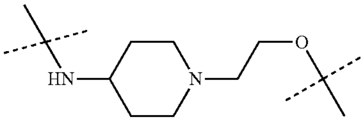 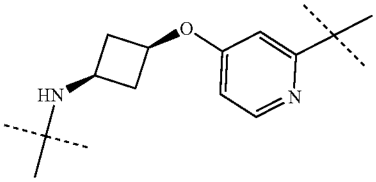 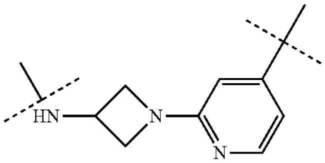
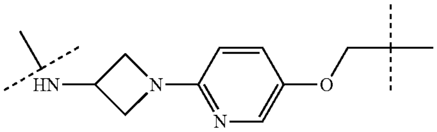 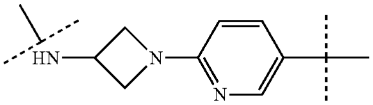
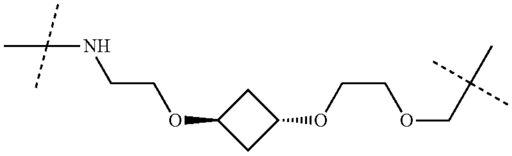 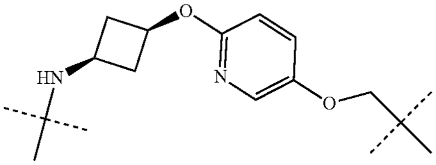
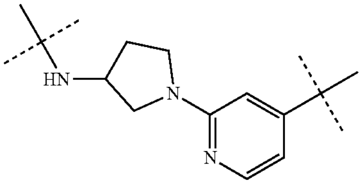 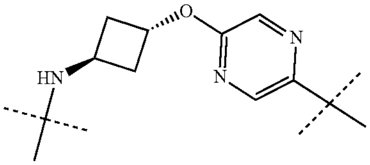 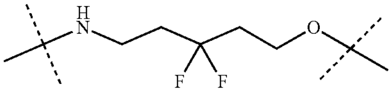
where n and m of the linker can be 0, 1, 2, 3, 4, 5, 6, 7, 8, 9, 10, 11, 12, 13, 14, 15, 16, 17, 18, 19, 20.
In any aspect or embodiment described herein, the L is selected from the group consisting of:
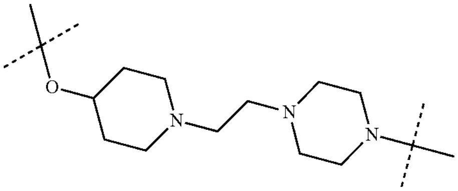 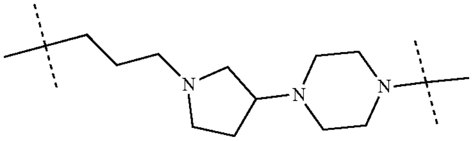
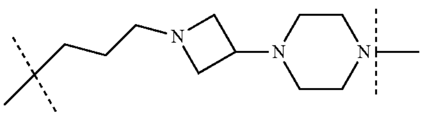 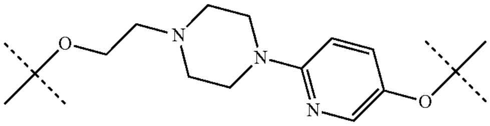
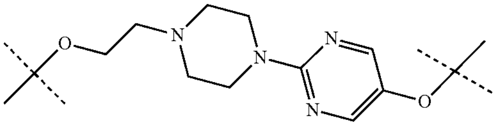 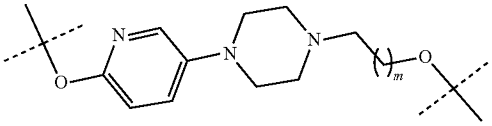
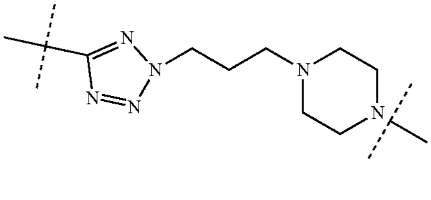 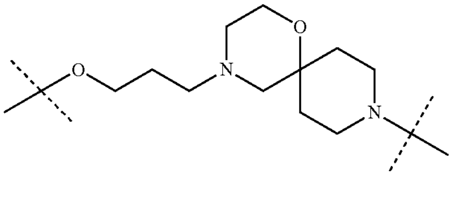

-continued
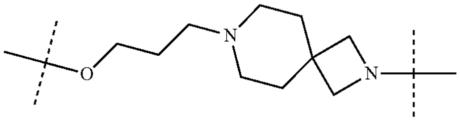
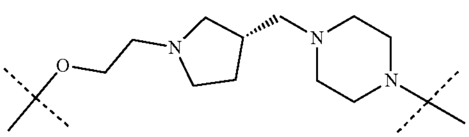
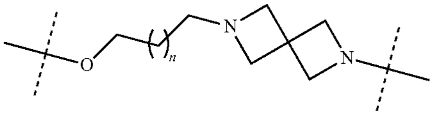
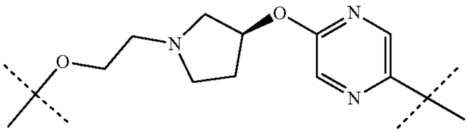
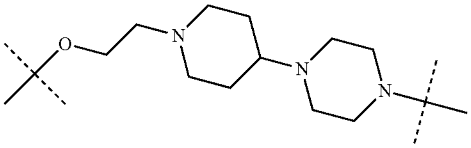
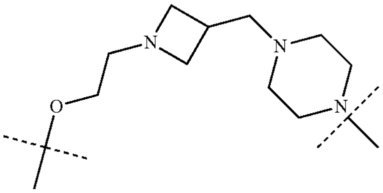
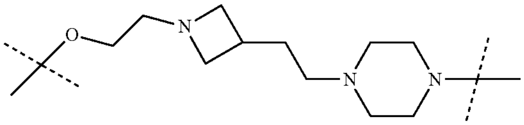
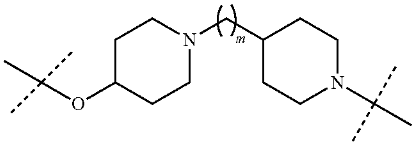
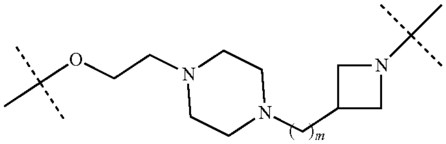
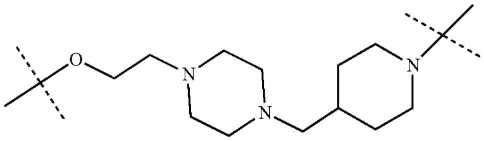
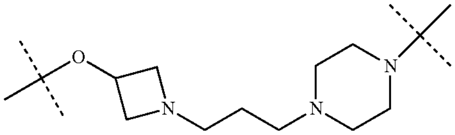
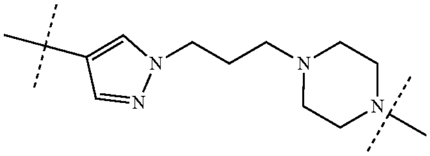
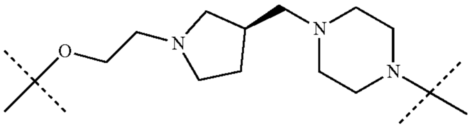
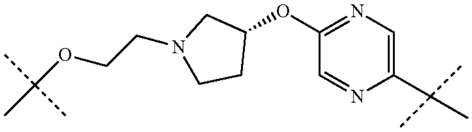
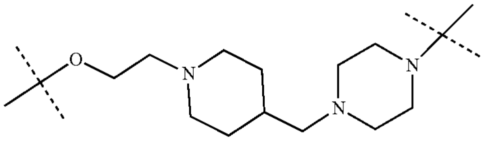
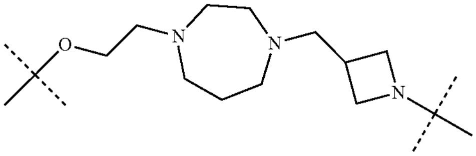
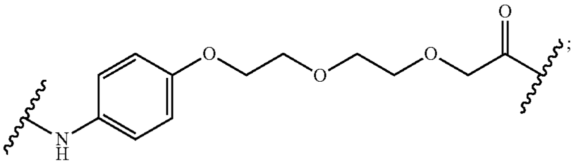;
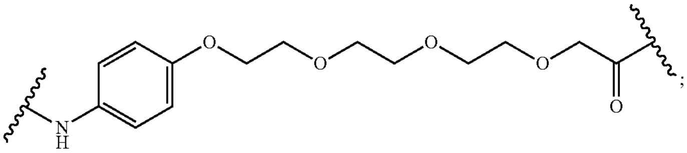;
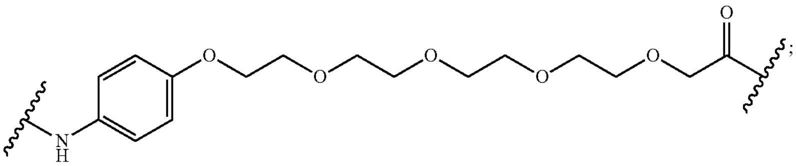;

-continued
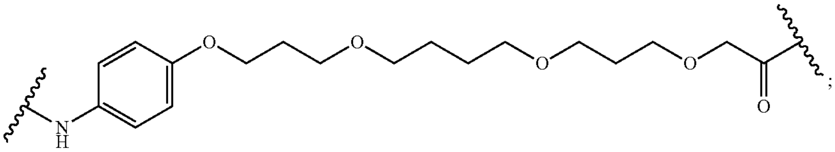
;
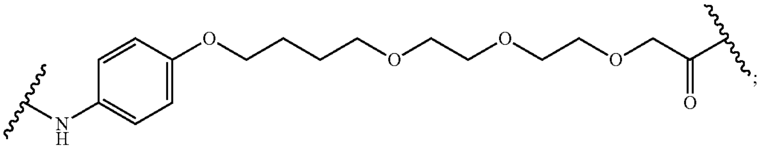
;
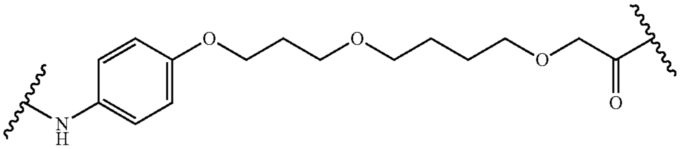
;
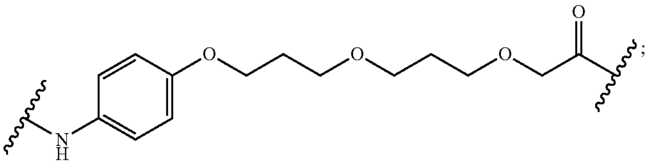
;
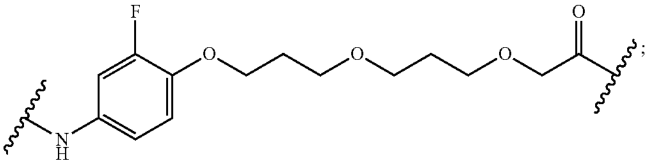
;
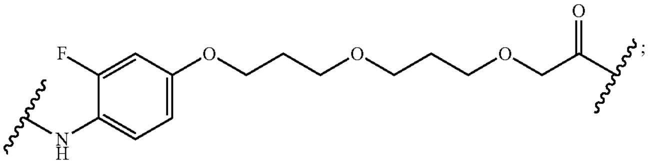
;
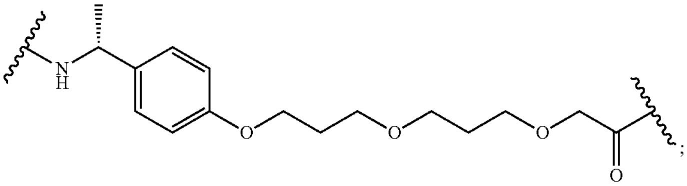
;
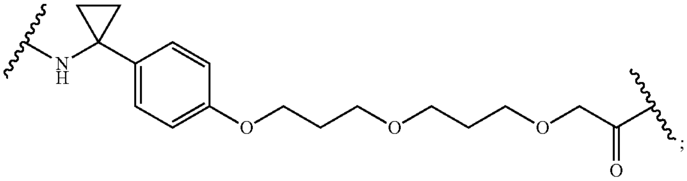
;
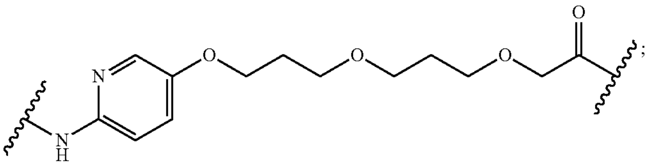
;
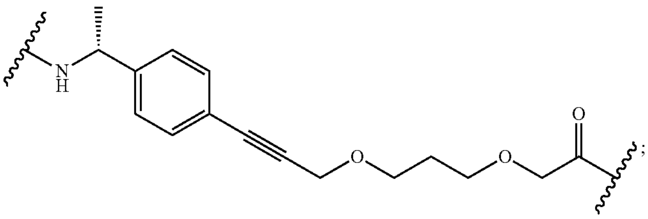
;

-continued
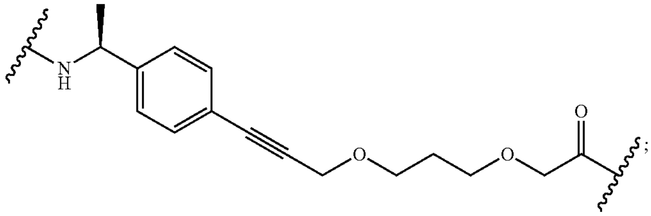;
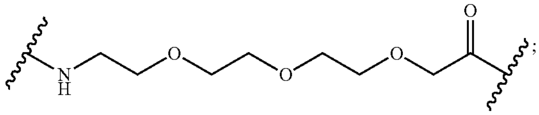;
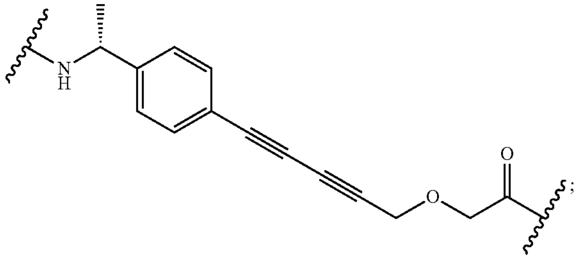; 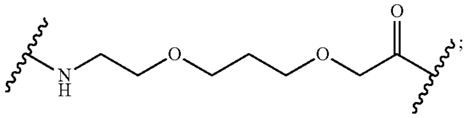;
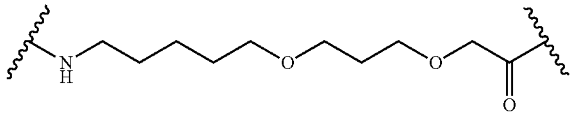;
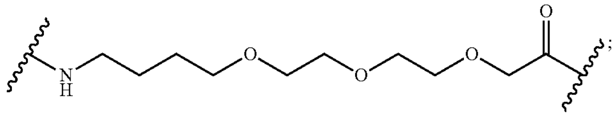; 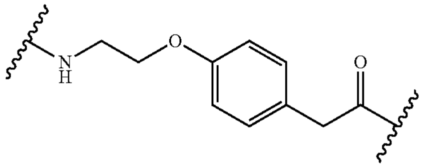;
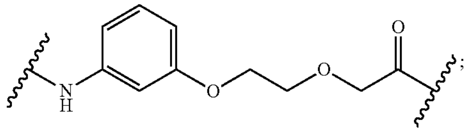; 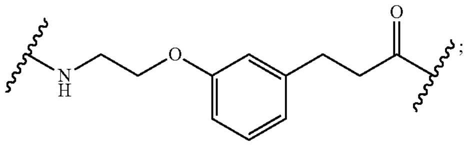;
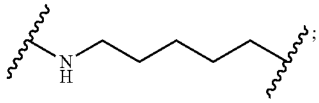; 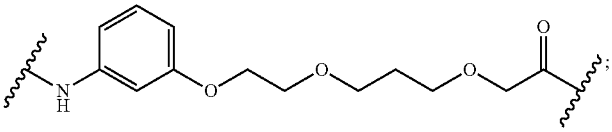;
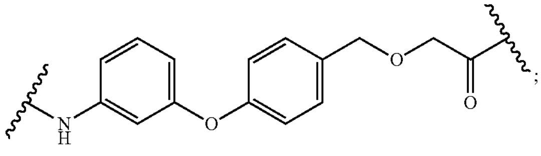; 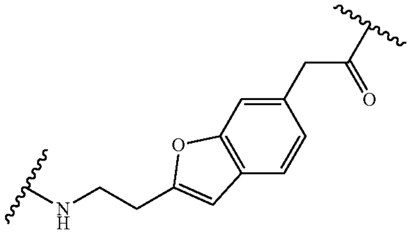;
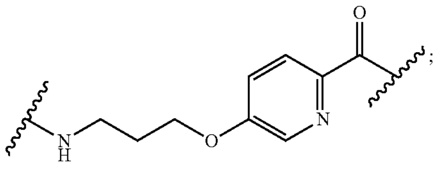; 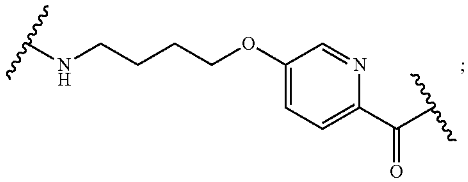;

-continued
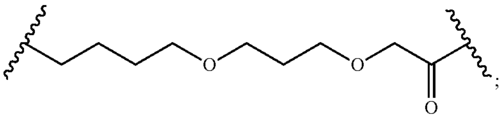;
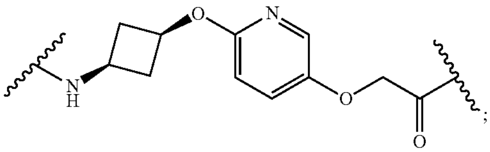;
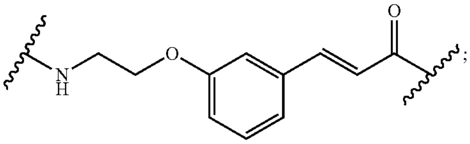;
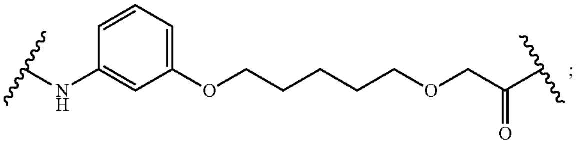;
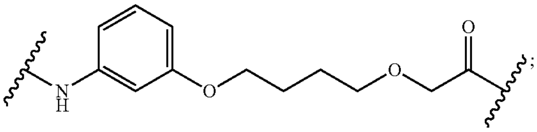;
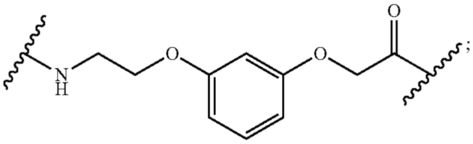;
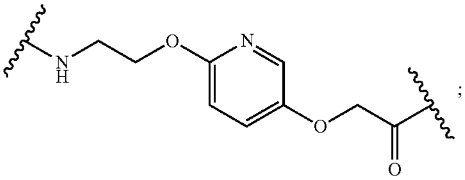;
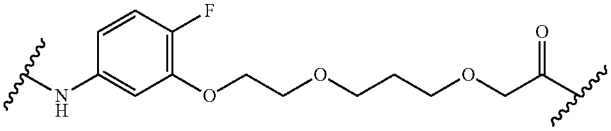;
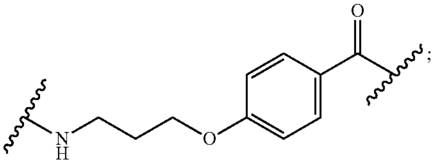;
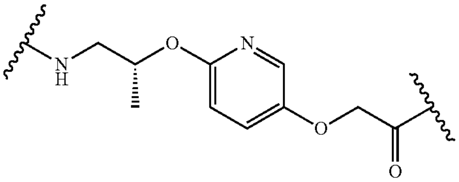;
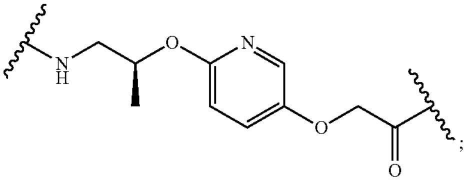;
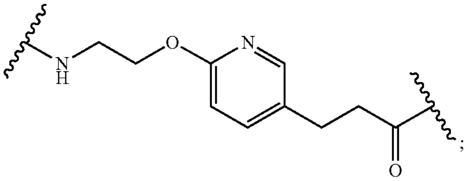;
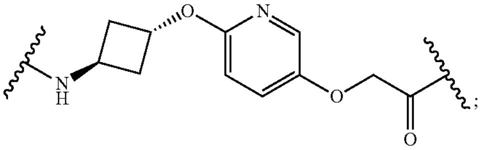;
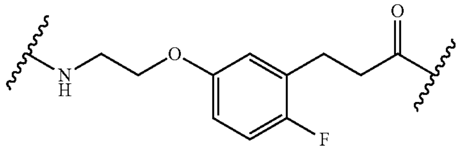;
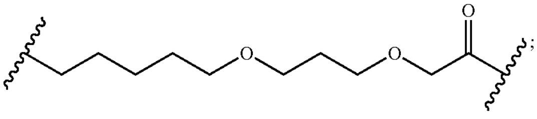;
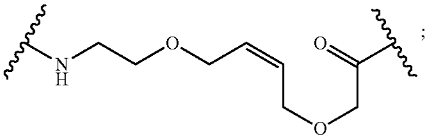;
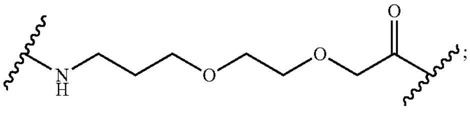;
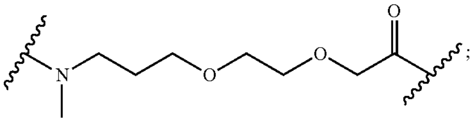;
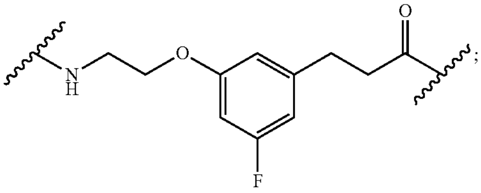;
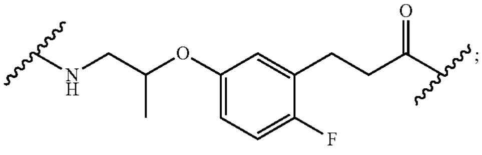;

-continued
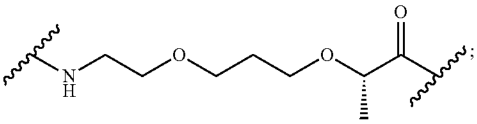;
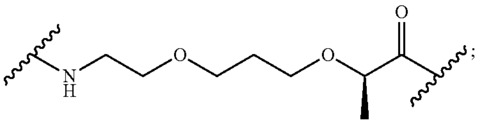;
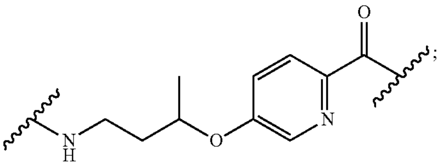;
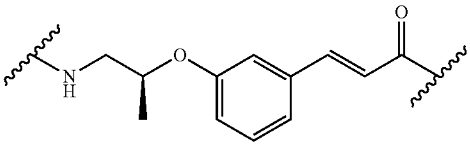;
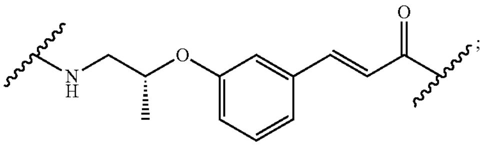;
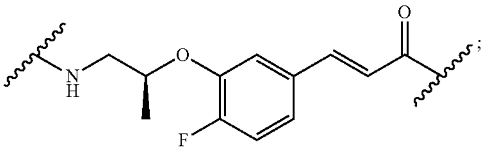;
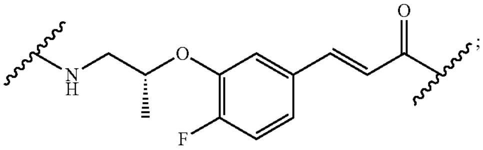;
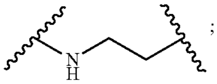;
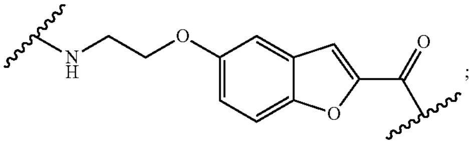;
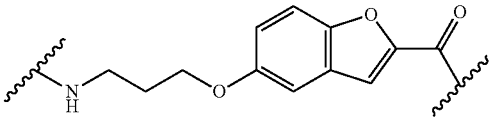;
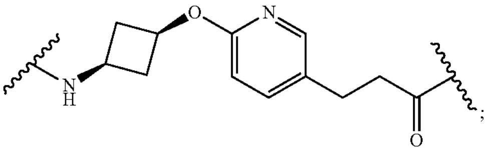;
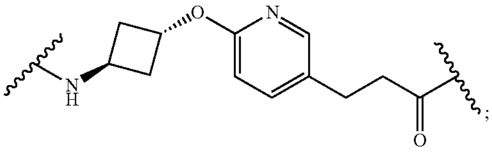;
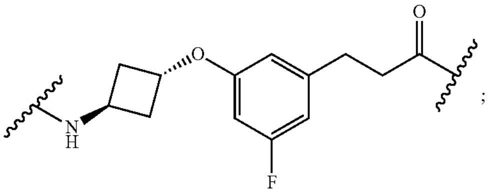;
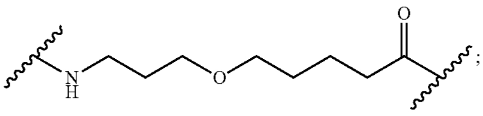;
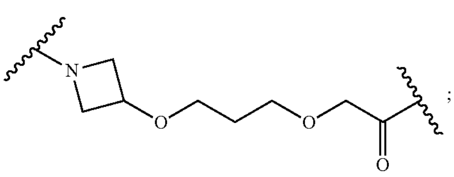;
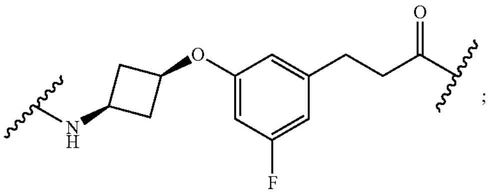;
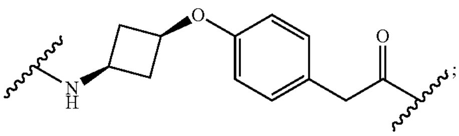;
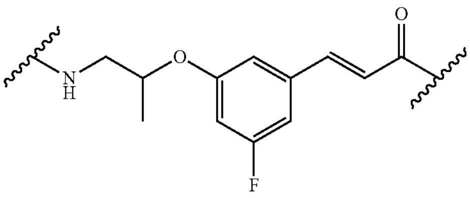;
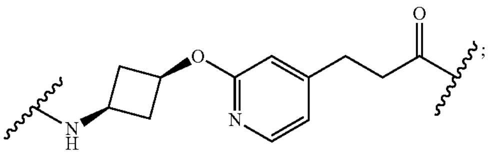;
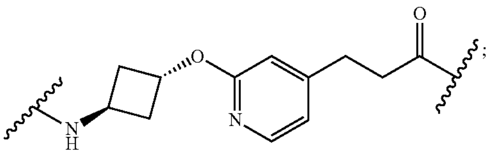;

-continued
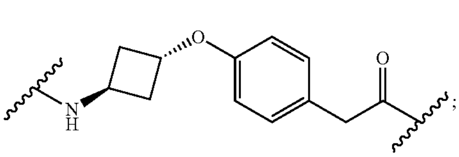;
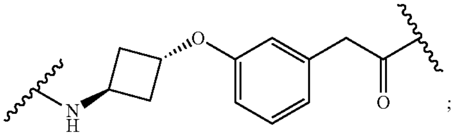;
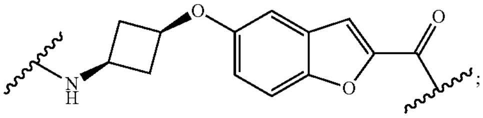;
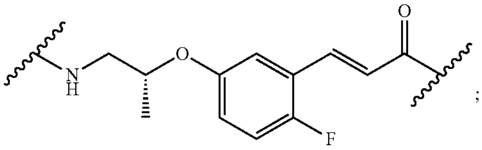;
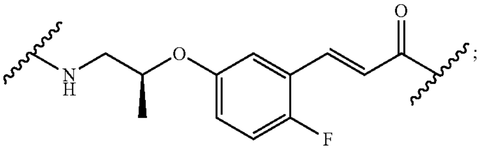;
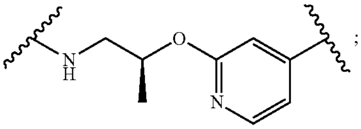;
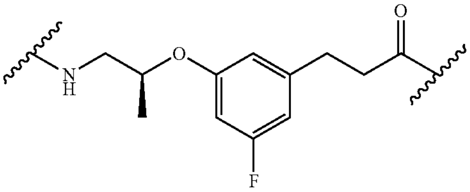;
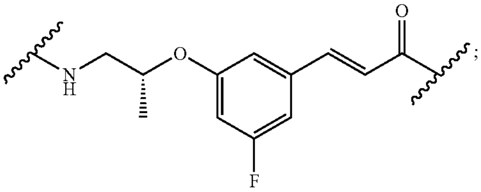;
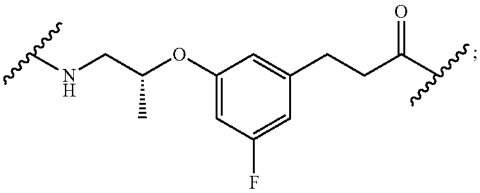;
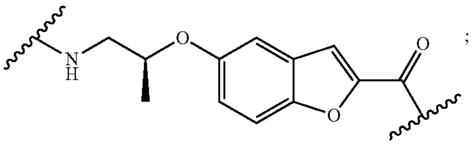;
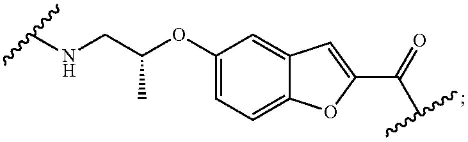;
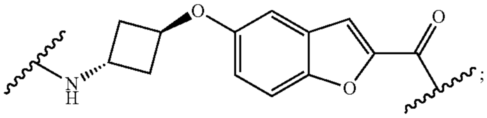;
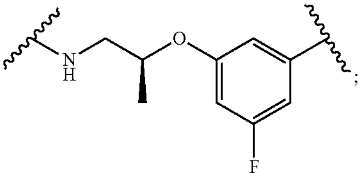;
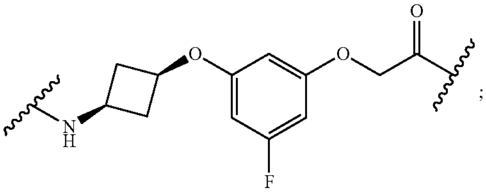;
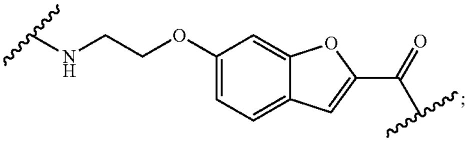;
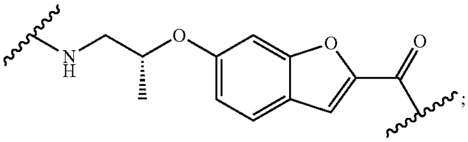;
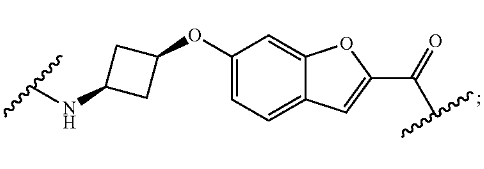;
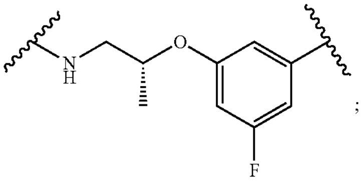;
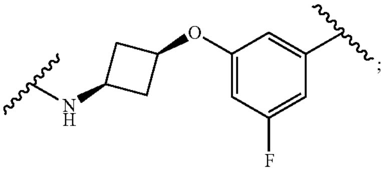;
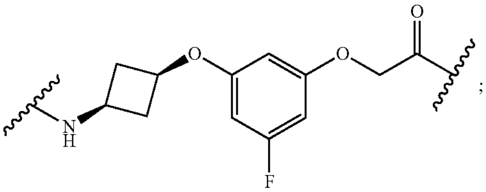;

-continued
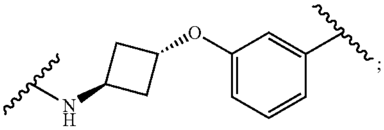
;
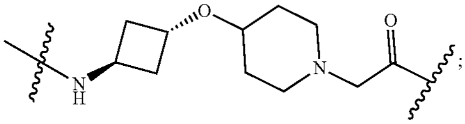
;
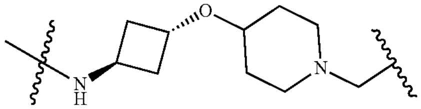
and
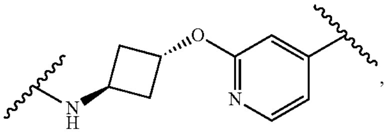
,
wherein each m and n is independently selected from 0, 1, 2, 3, 4, 5, 6, 7, 8, 9, 10, 11, 12, 13, 14, 15, 16, 17, 18, 19, 20.
In any aspect or embodiment described herein, the linker (L) is selected from the group consisting of:
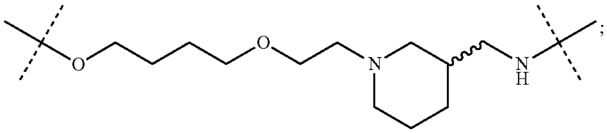
;
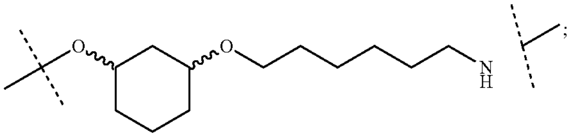
;
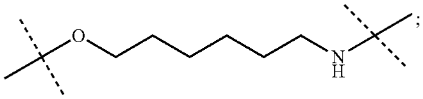
;
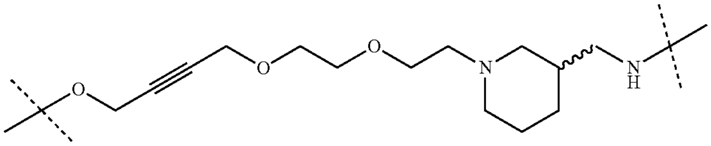
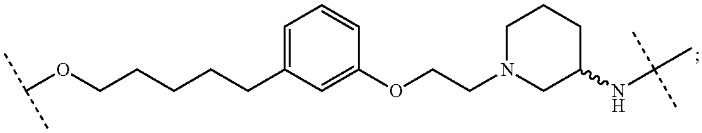
;
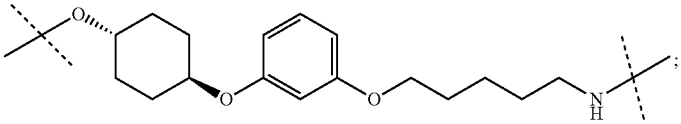
;
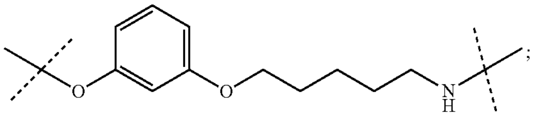
;
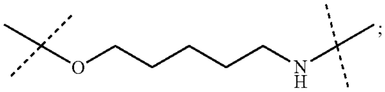
;
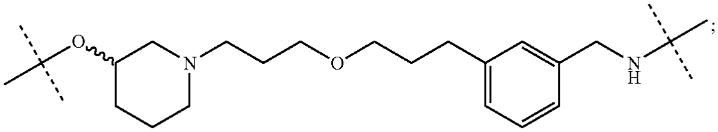
;
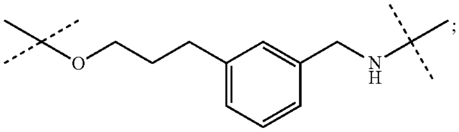
;
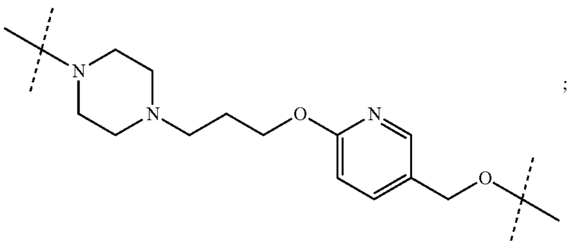
;

-continued
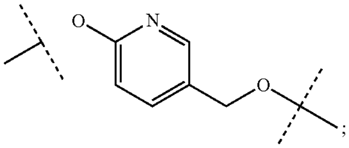
;
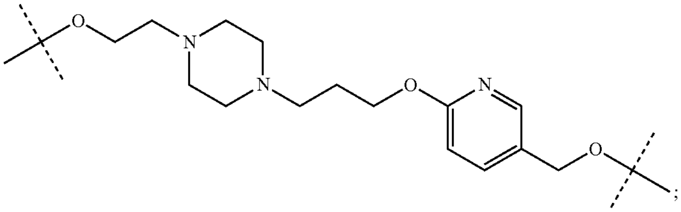
;
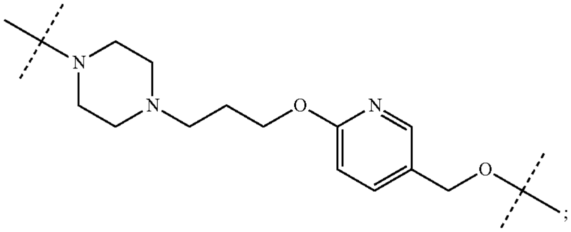
;
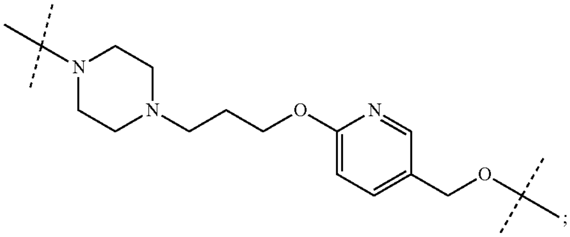
;
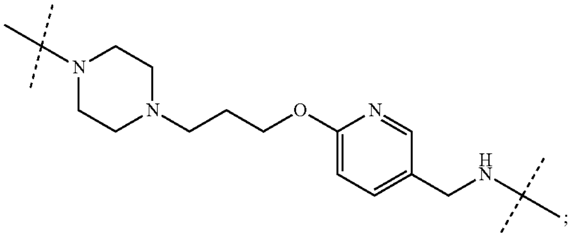
;
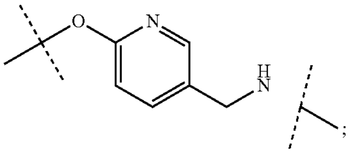
;
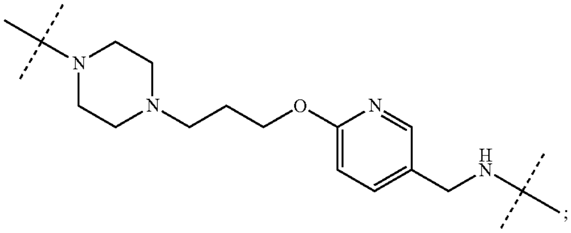
;
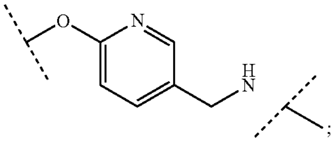
;
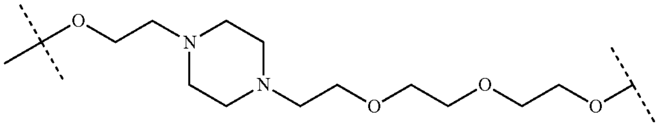
;
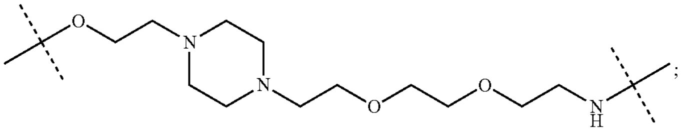
;
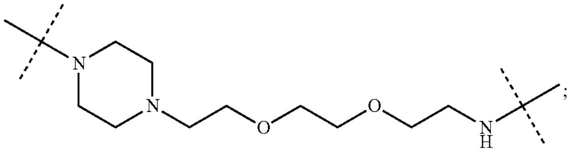
;
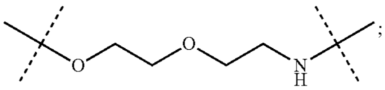
;
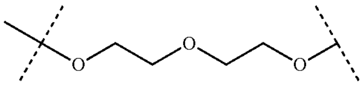
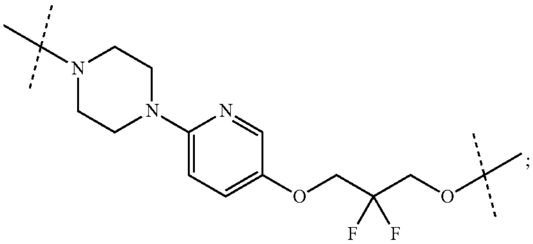
;

-continued
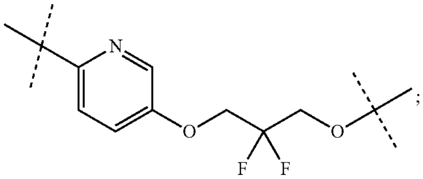 ; 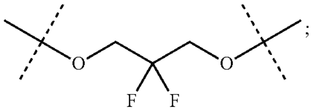 ;
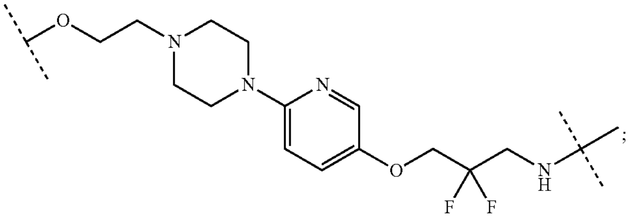 ;
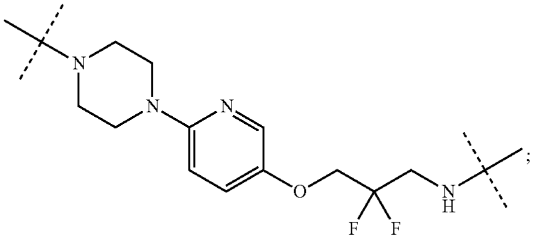 ; 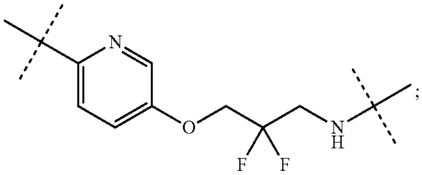 ;
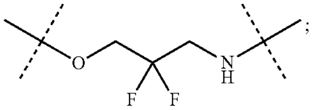 ; 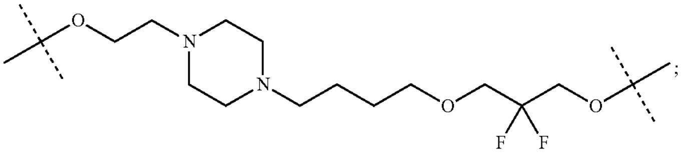 ;
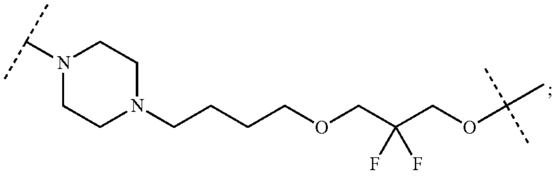 ; 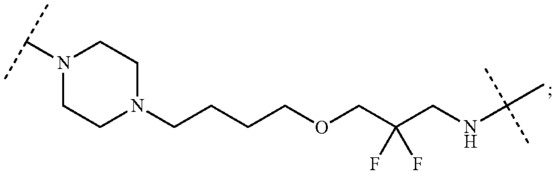 ;
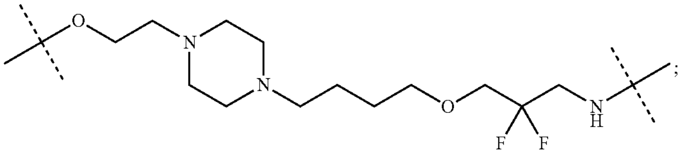 ;
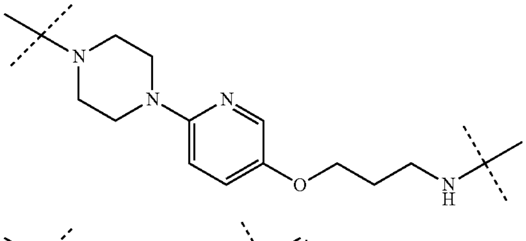 ; 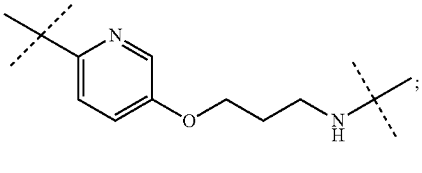 ;
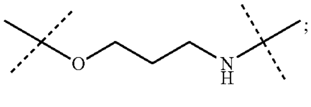 ; 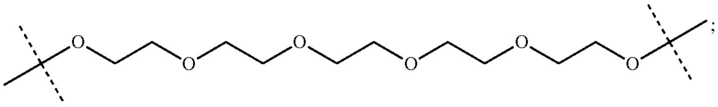 ;
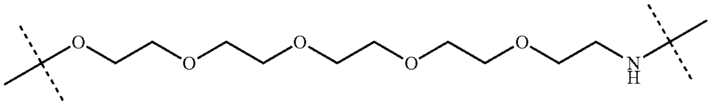
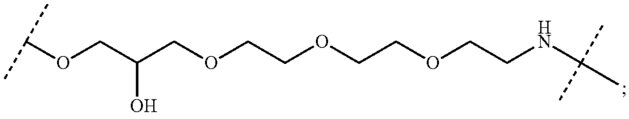 ;

-continued
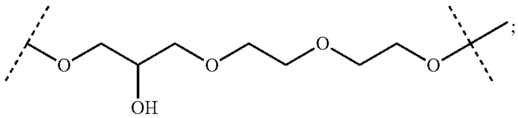;
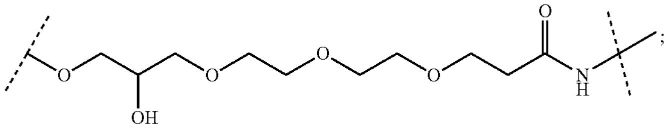;
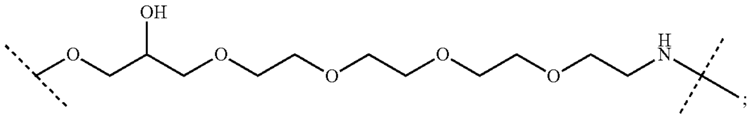;
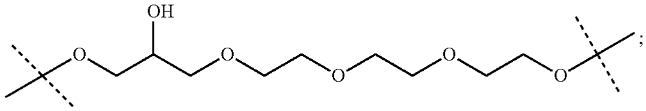;
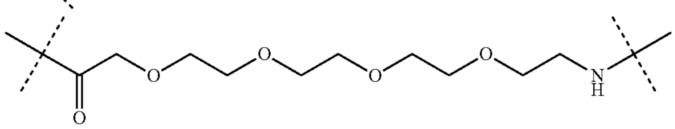;
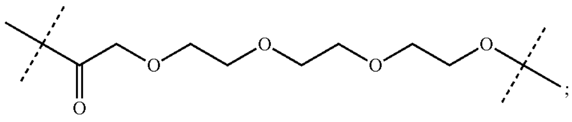;
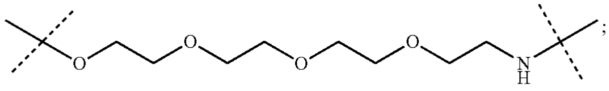;
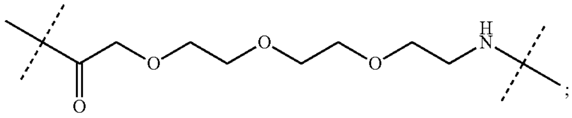; 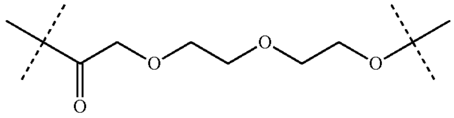;
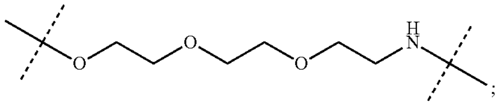;
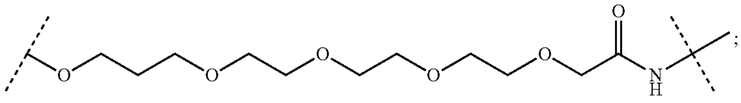;
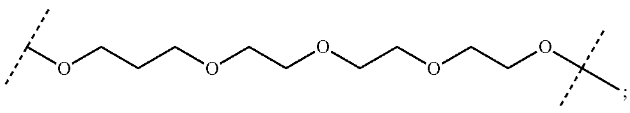; 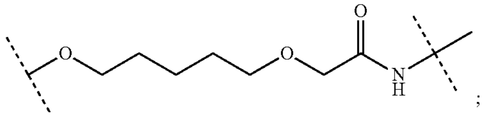;
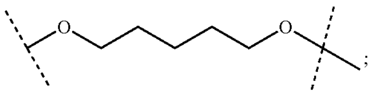; 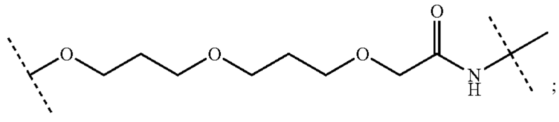;
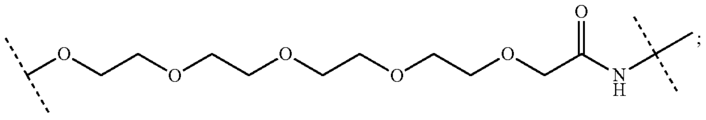;
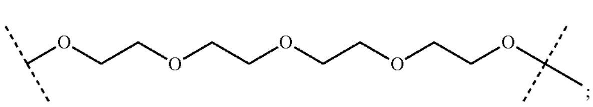; 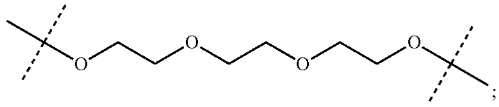;
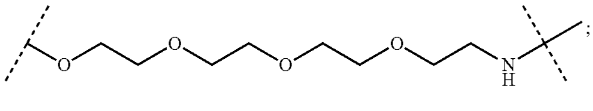; 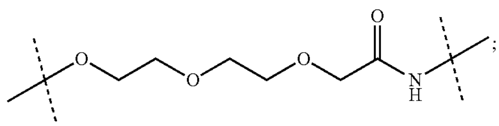;

-continued
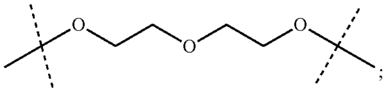
;
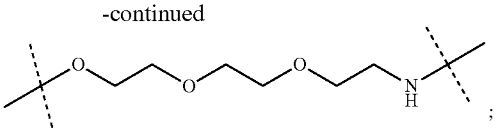
;
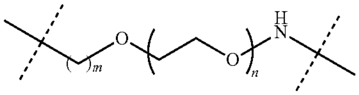
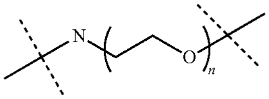
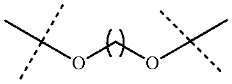
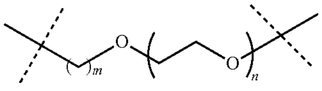
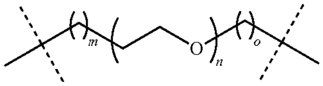
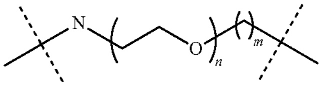
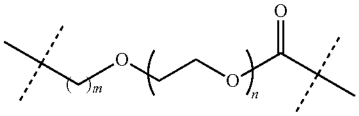
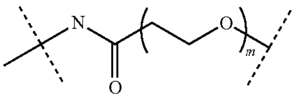
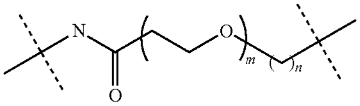
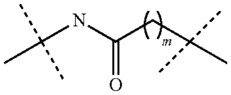
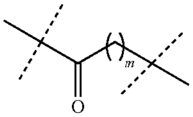
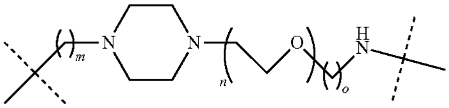
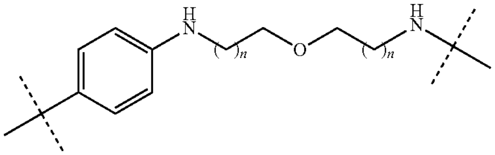
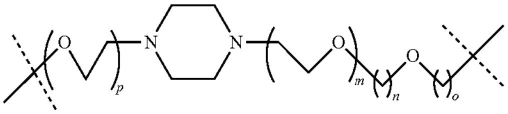
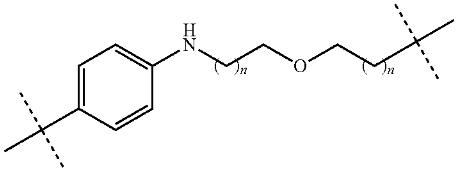
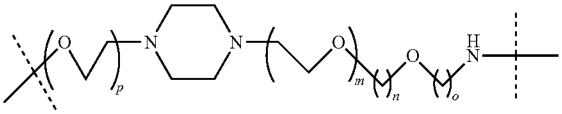
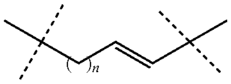
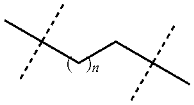
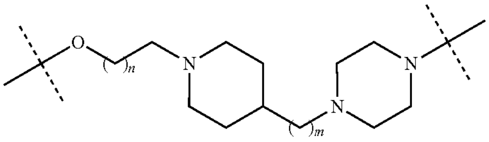
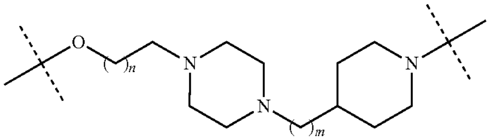
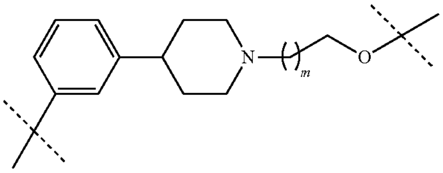
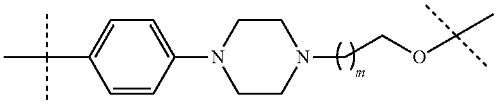
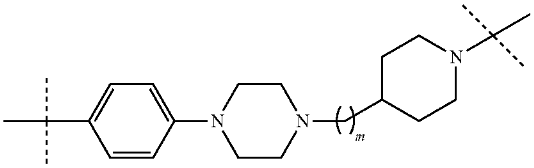
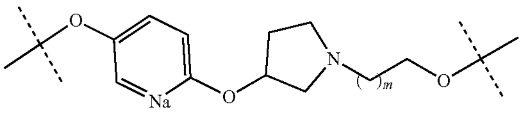
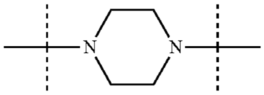
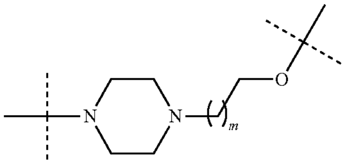
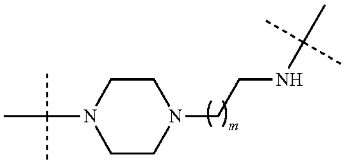
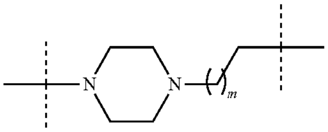
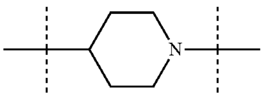

-continued
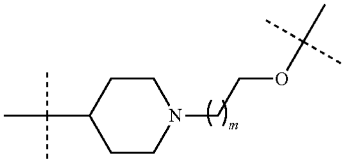
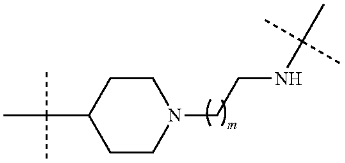
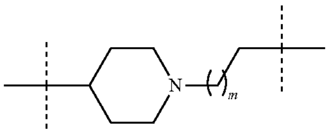
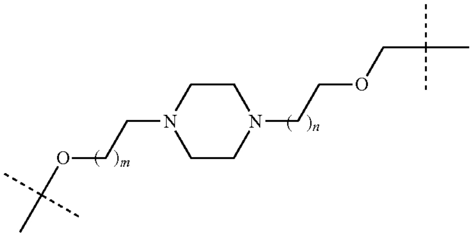
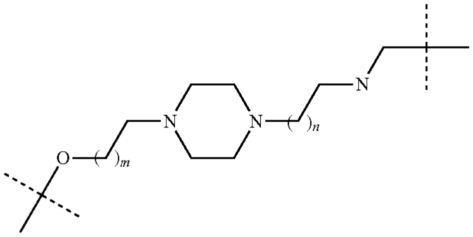
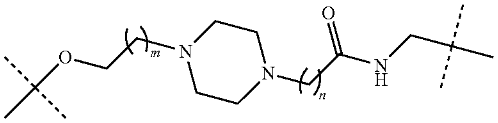
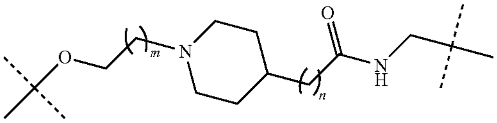
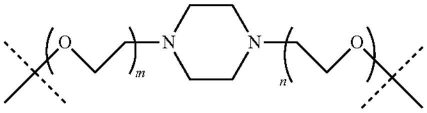
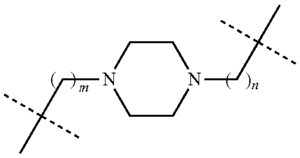
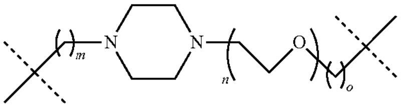
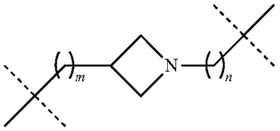
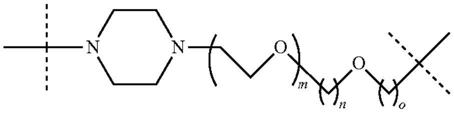
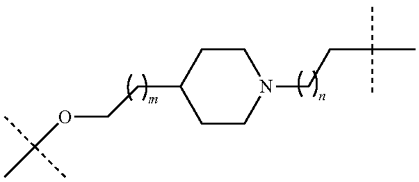
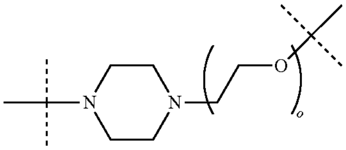
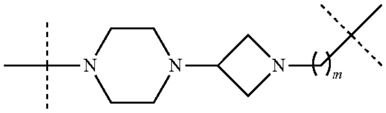
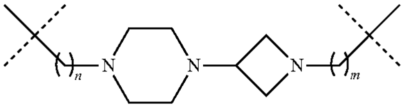
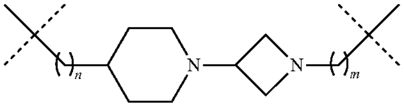
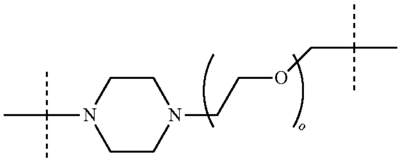
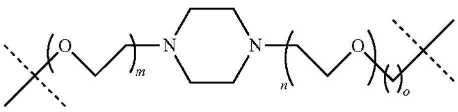
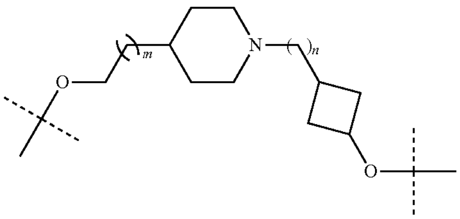
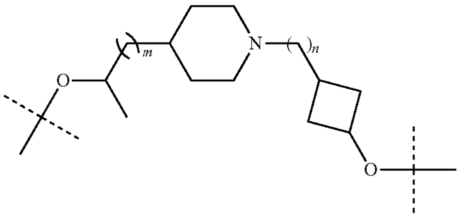
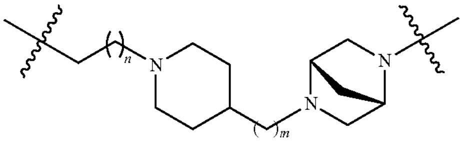

-continued
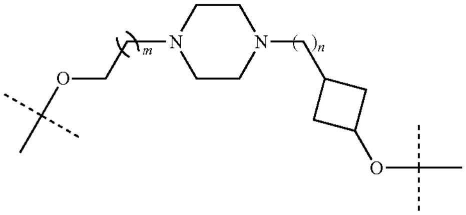
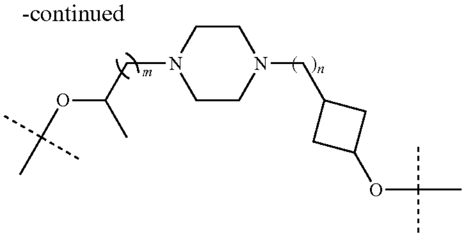
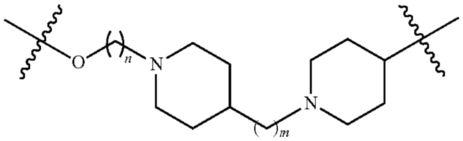
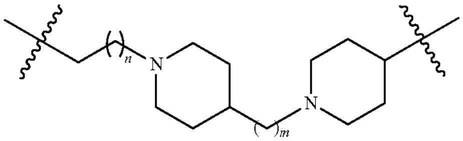
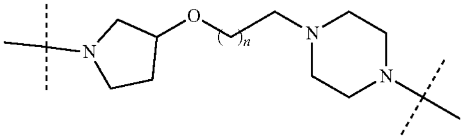
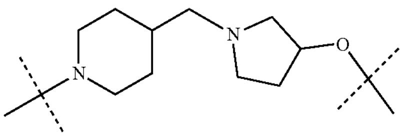
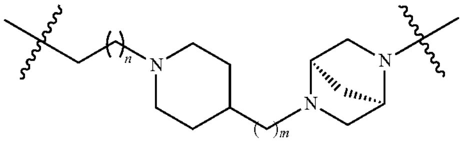
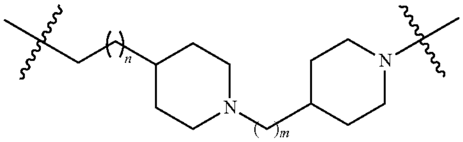
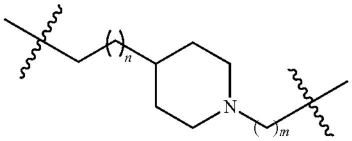
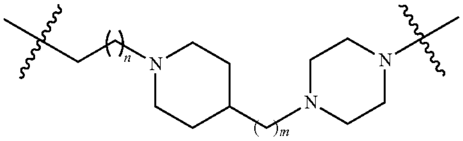
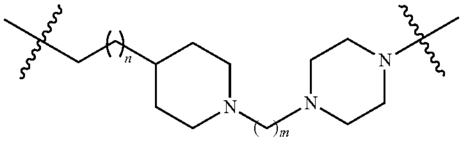
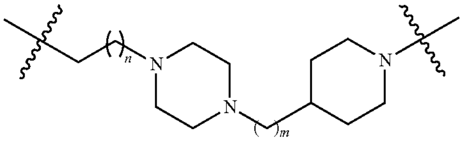
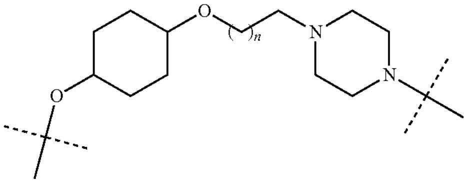
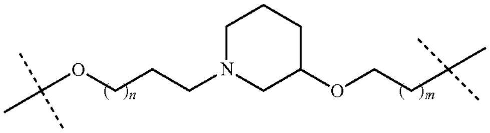
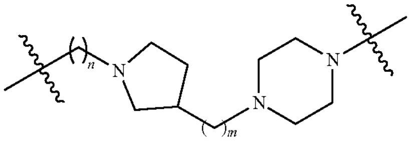
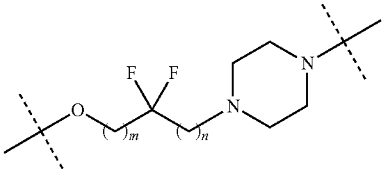
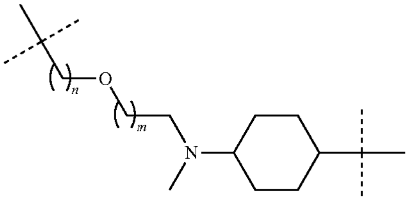
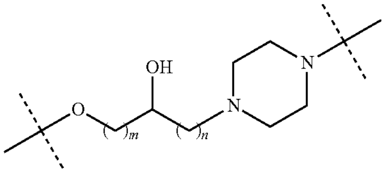
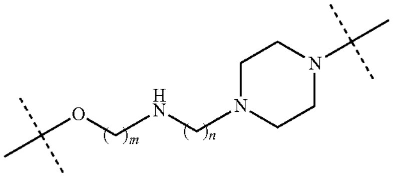
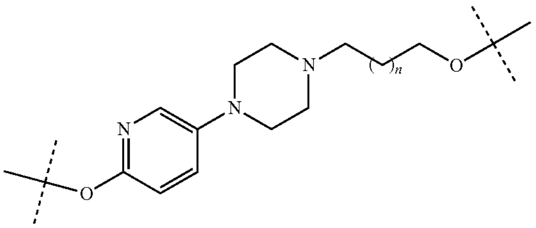

-continued
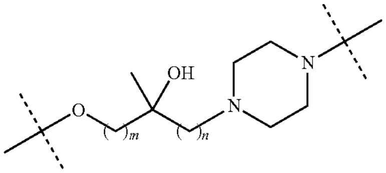
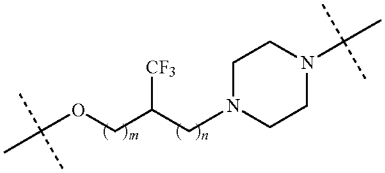
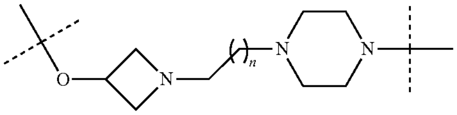
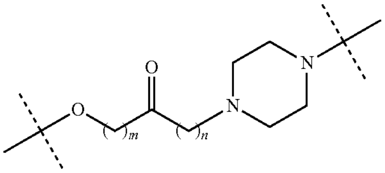
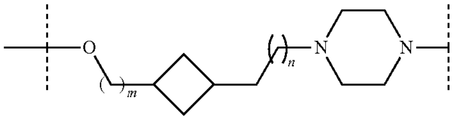
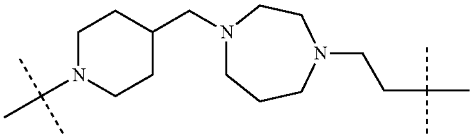
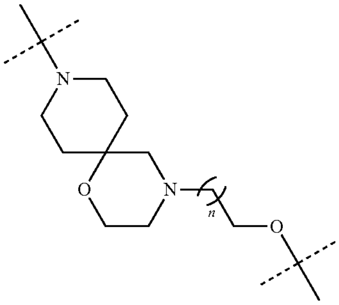
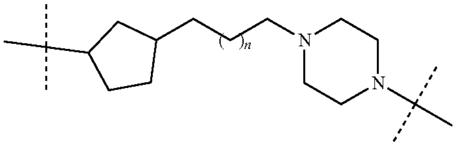
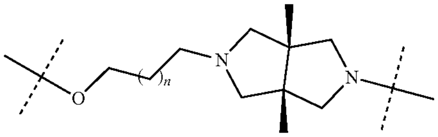
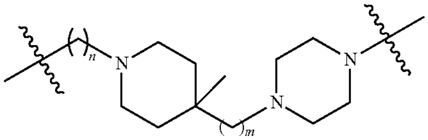
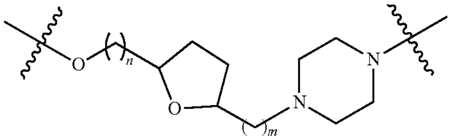
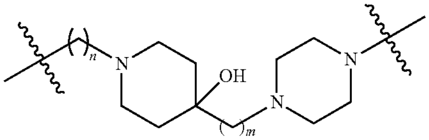
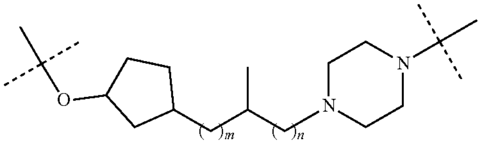
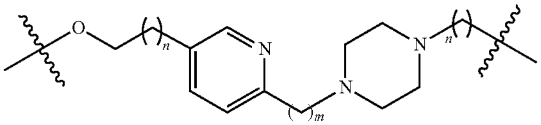
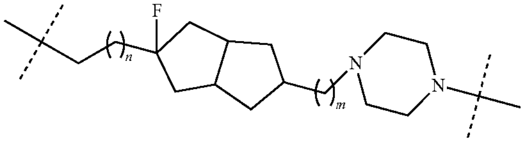
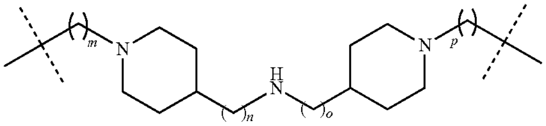
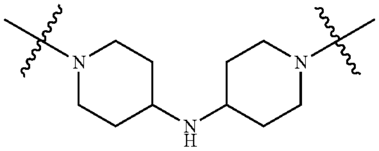
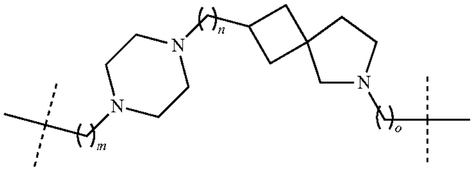
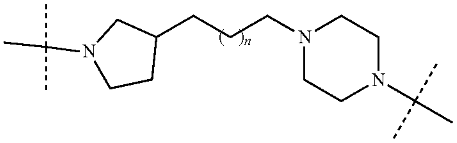
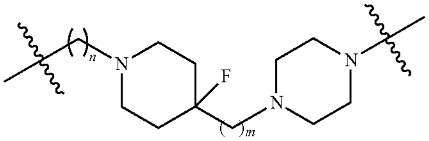

-continued
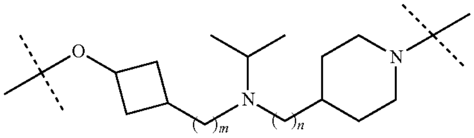
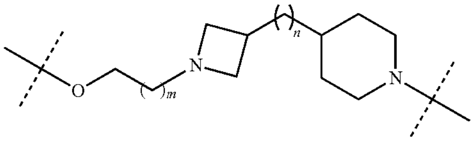
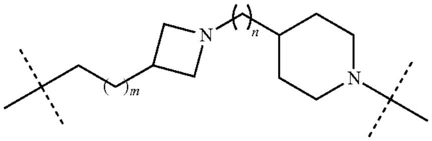
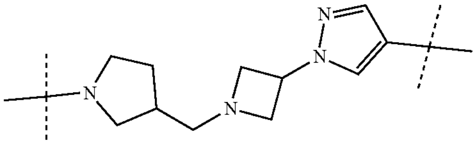
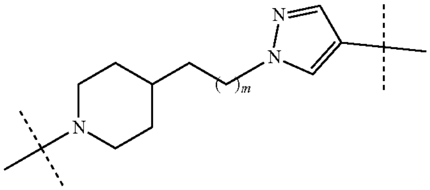
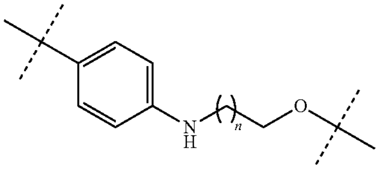
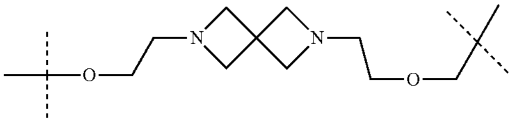
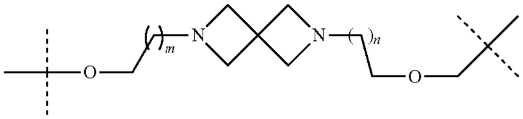
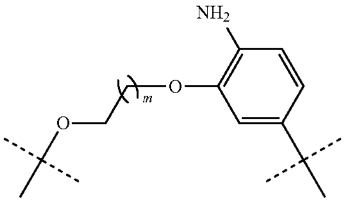
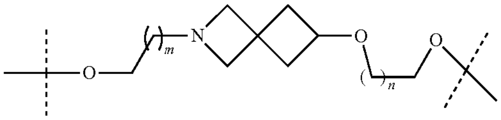
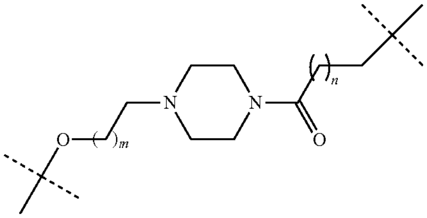
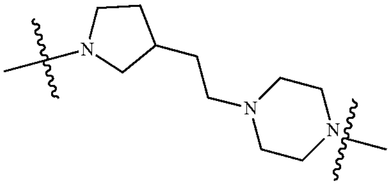
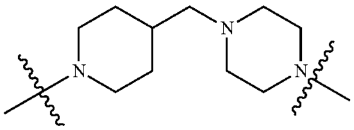
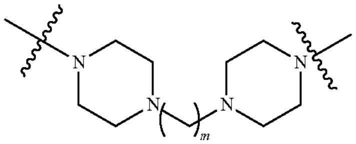
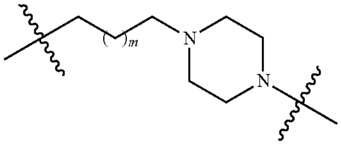
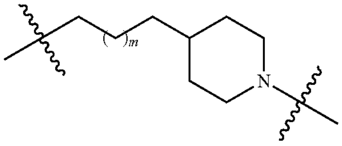
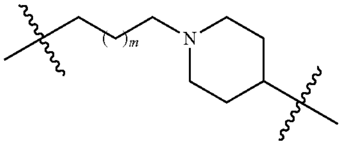
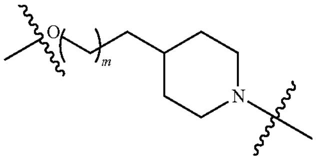
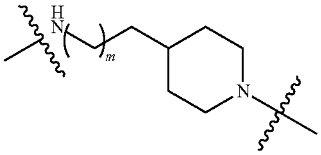
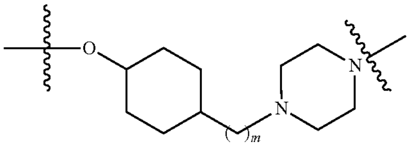
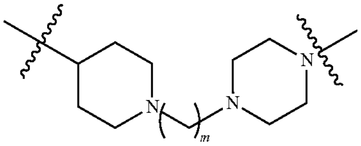
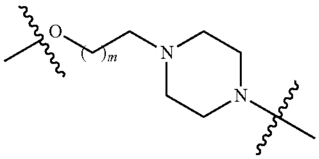
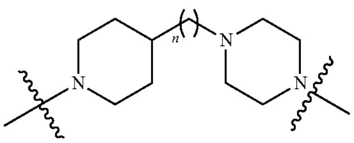
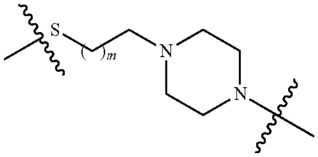

-continued
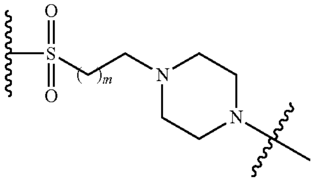
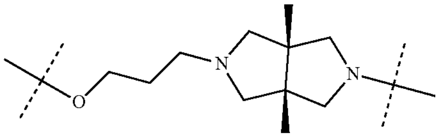
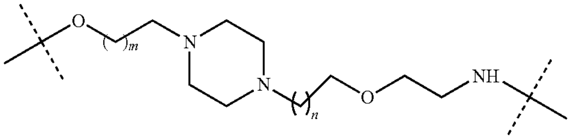
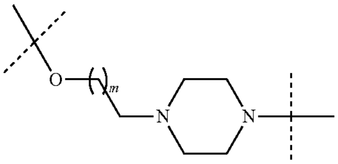
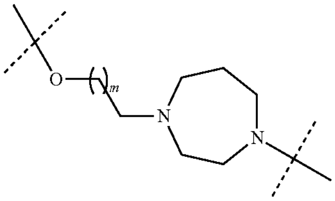
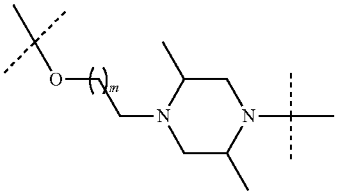
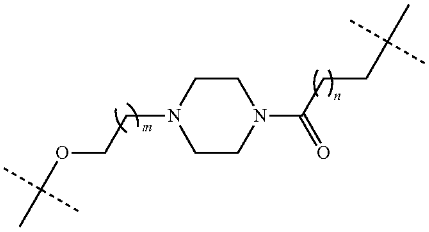
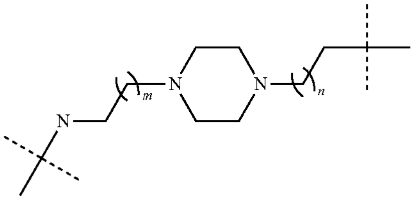
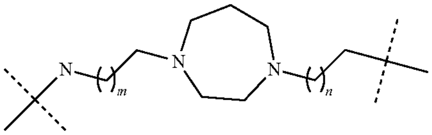
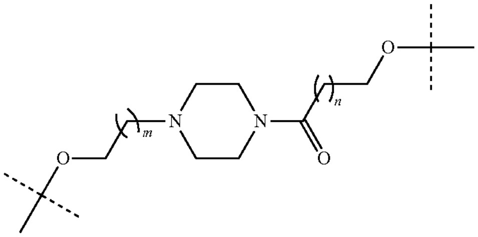
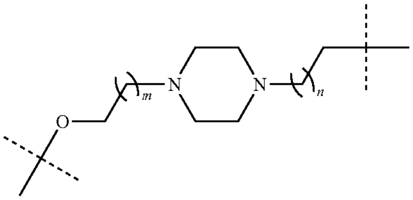
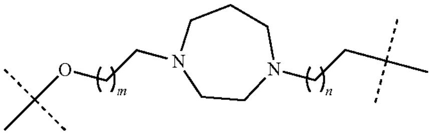
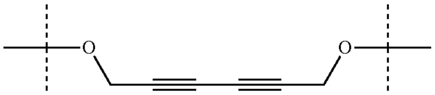
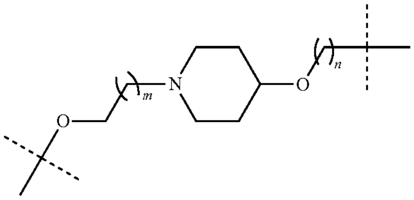
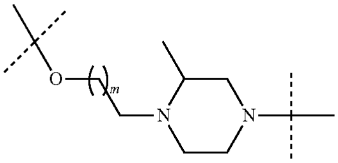
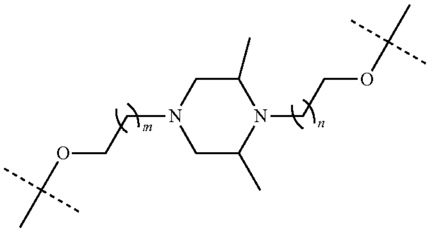
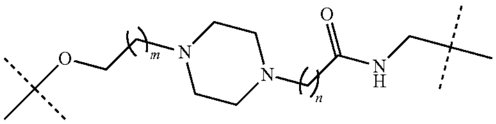

-continued
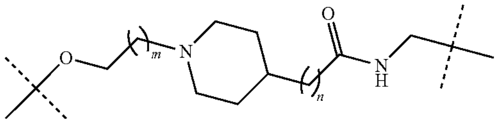
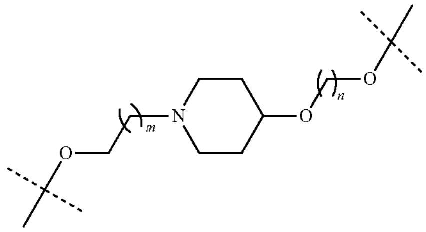
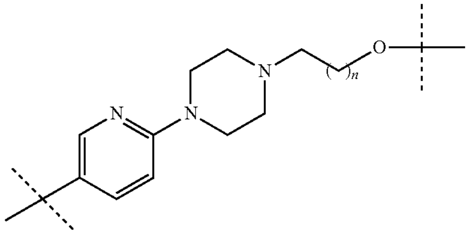
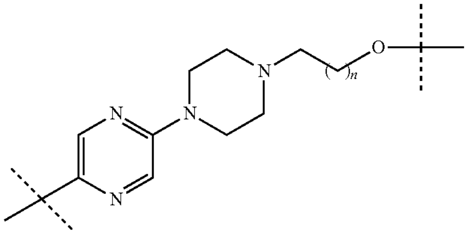
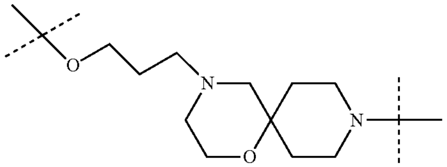
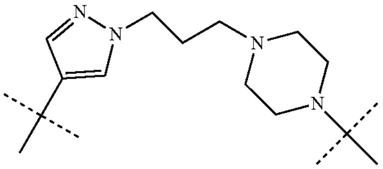
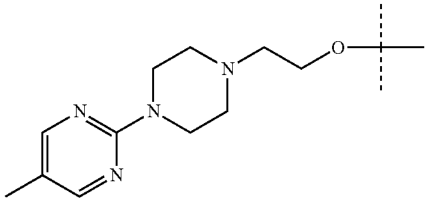
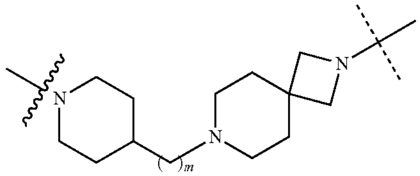
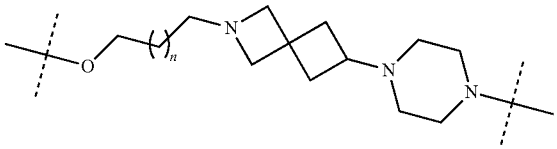
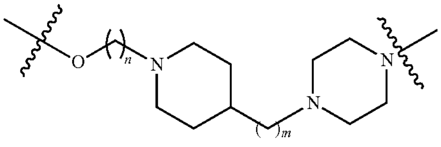
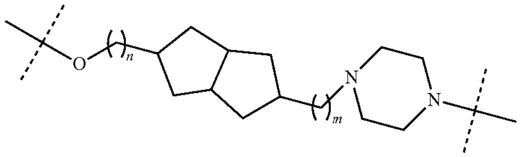
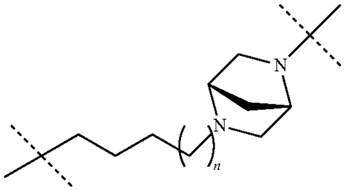
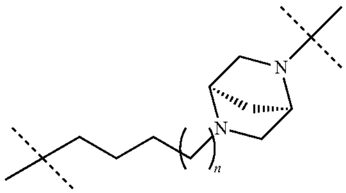
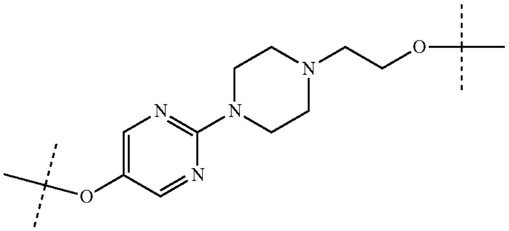
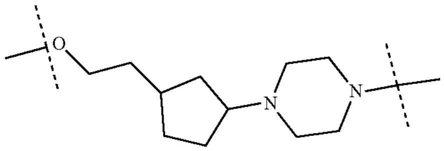
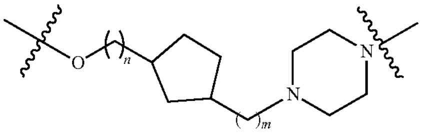
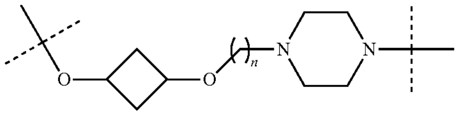
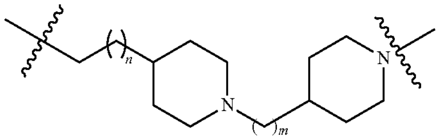

-continued
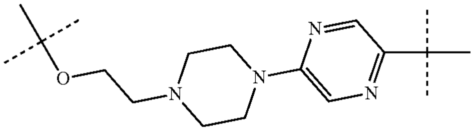
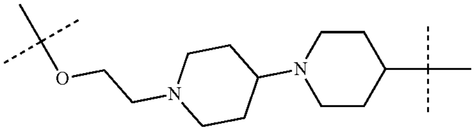
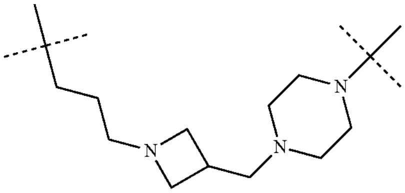
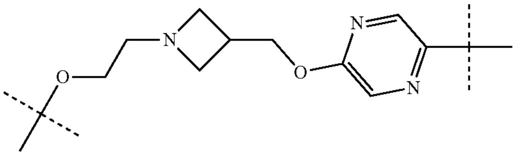
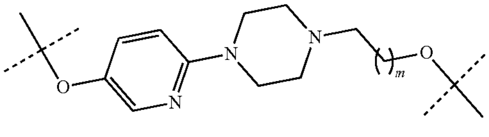
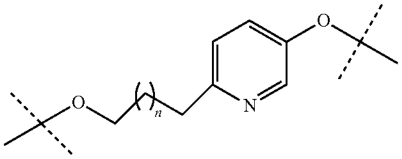
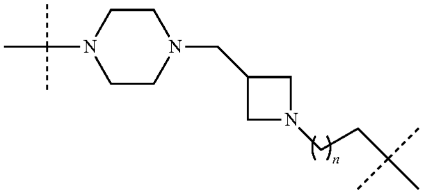
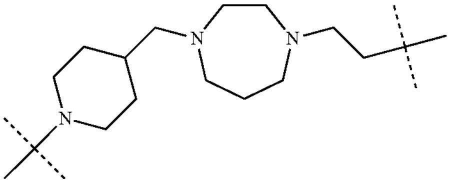
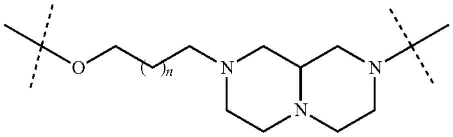
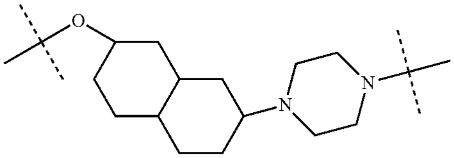
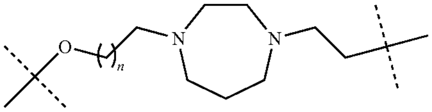
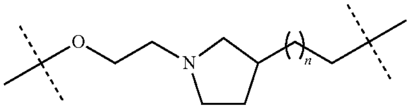
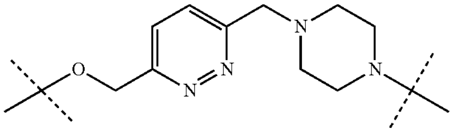
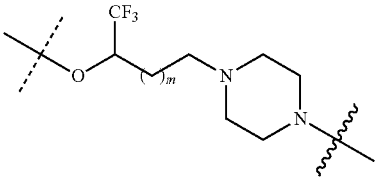
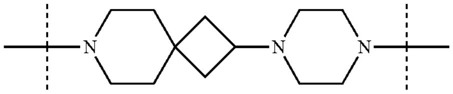
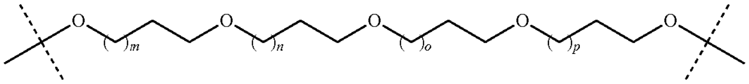
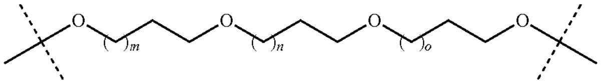
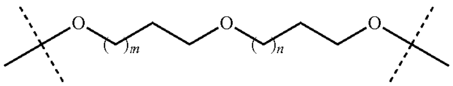
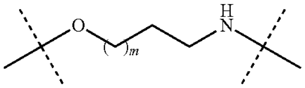
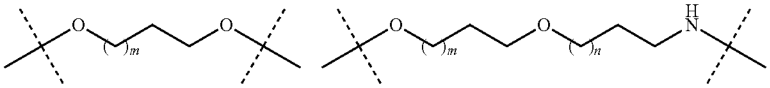
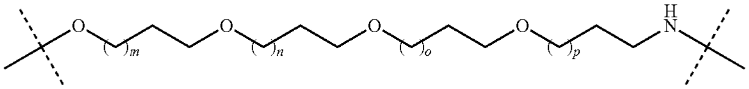

-continued
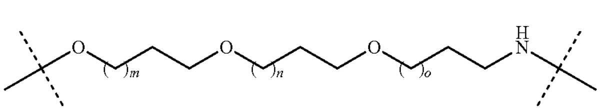
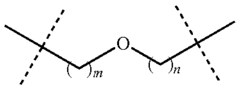
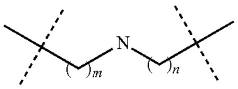
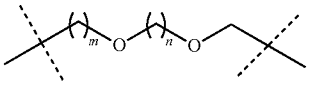
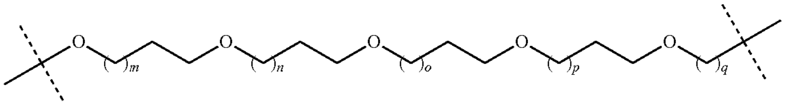
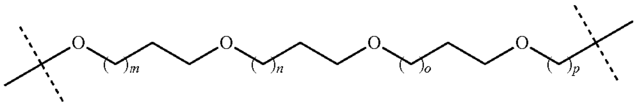
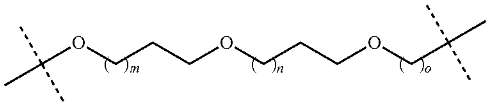
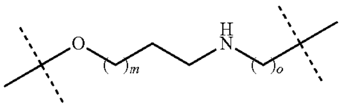
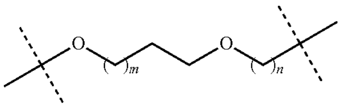
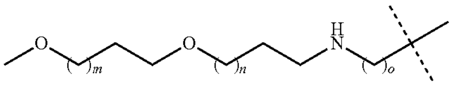
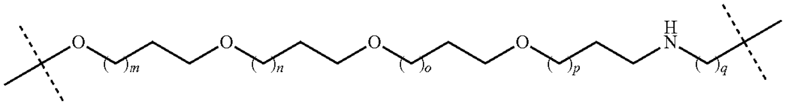
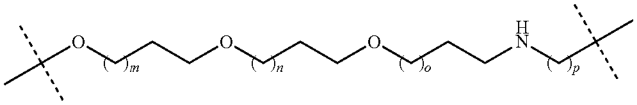
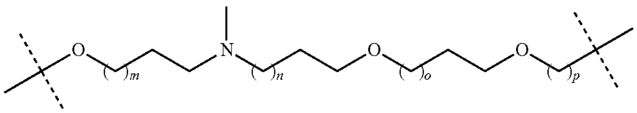
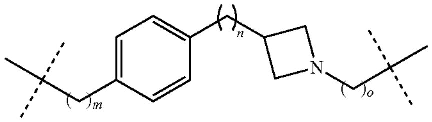
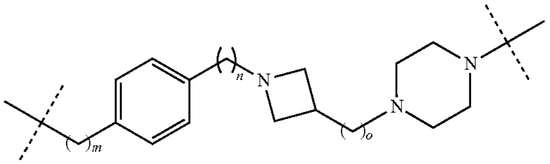
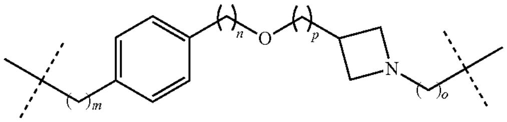
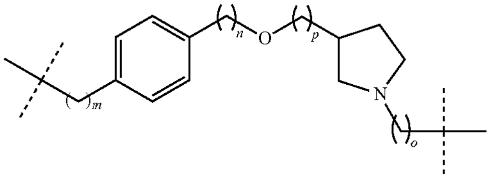
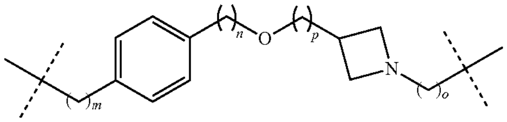
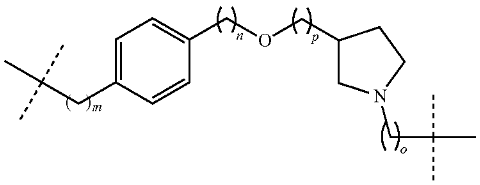
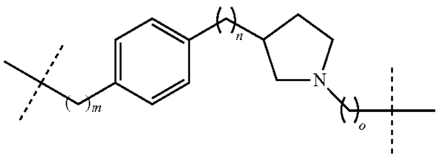
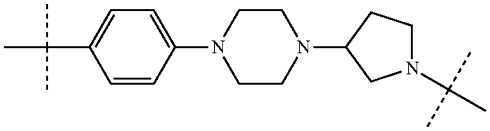
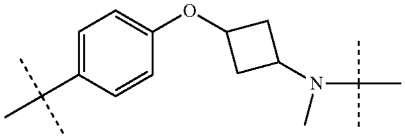
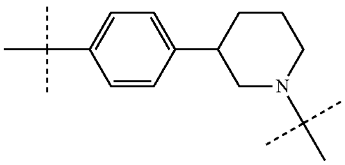
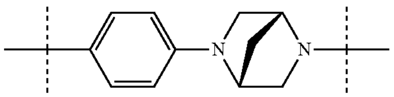

-continued
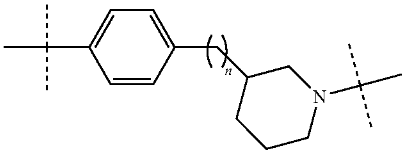
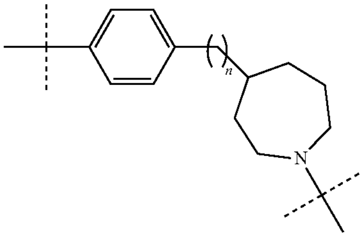
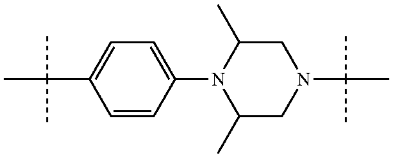
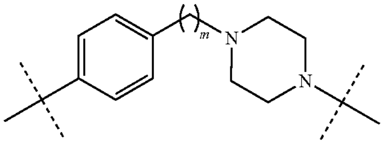
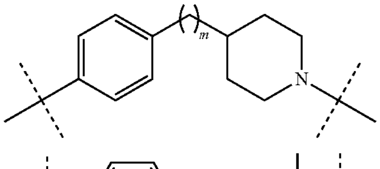
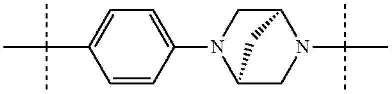
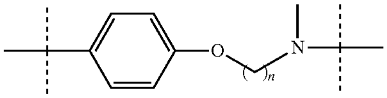
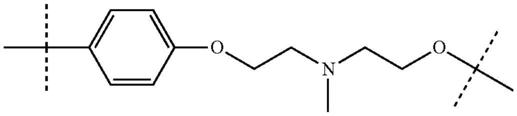
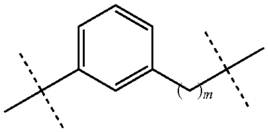
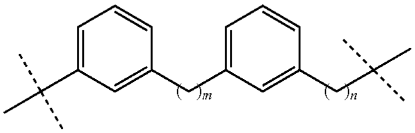
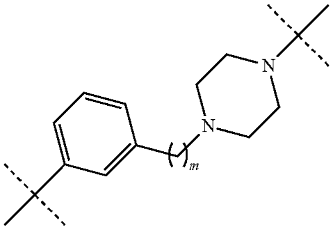
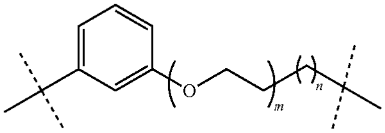
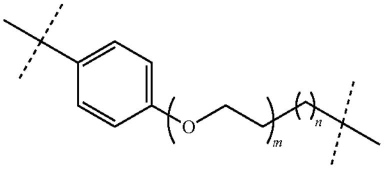
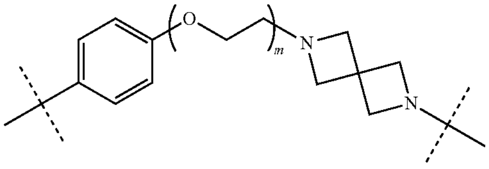
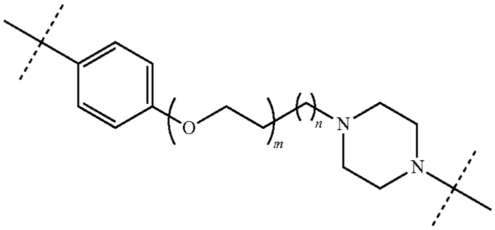
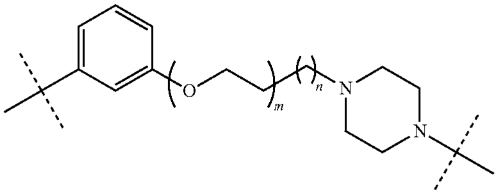
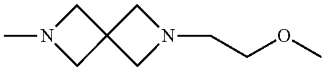
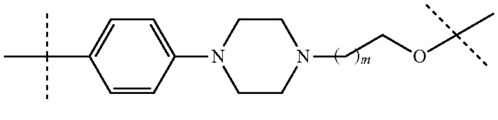
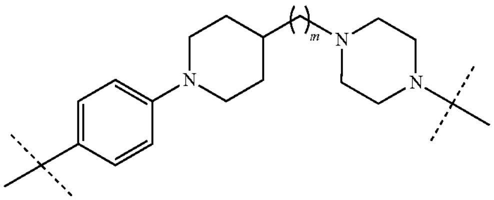

-continued
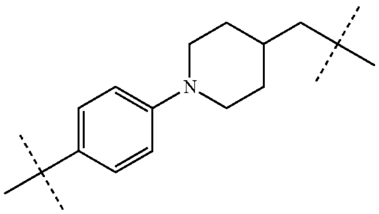
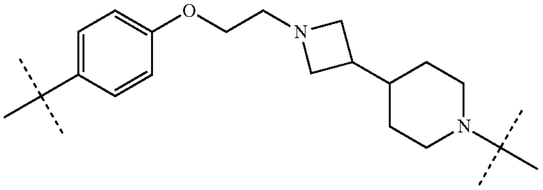
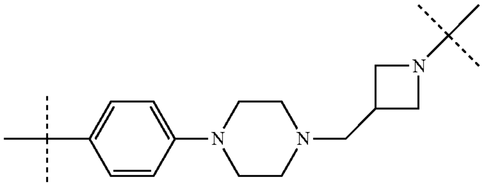
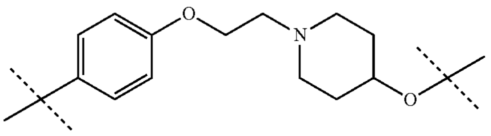
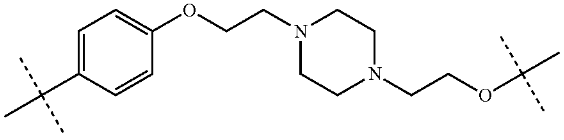
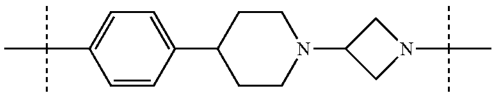
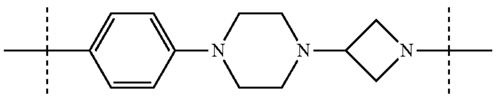
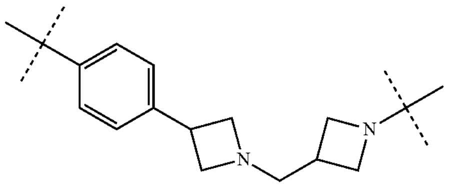
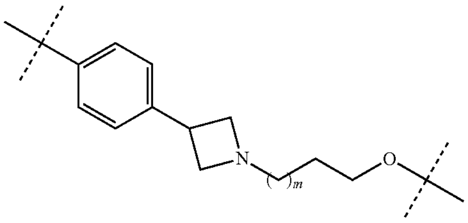
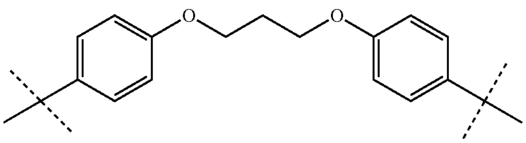
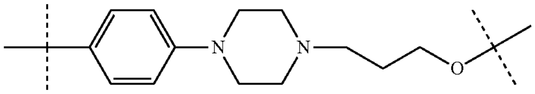
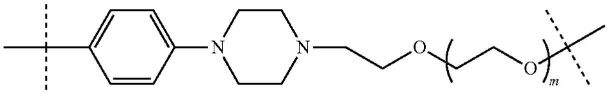
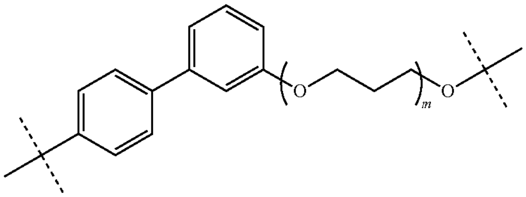
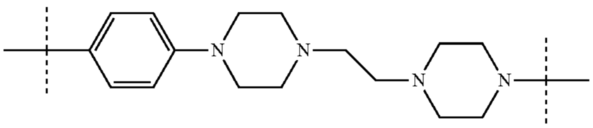
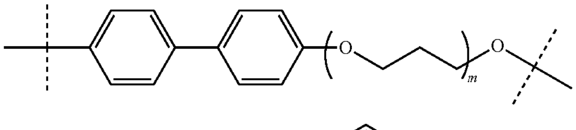
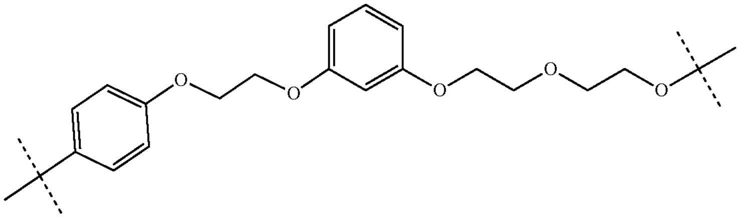
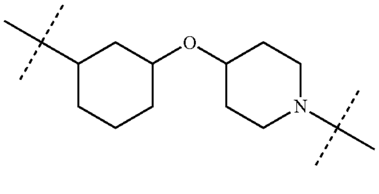

-continued
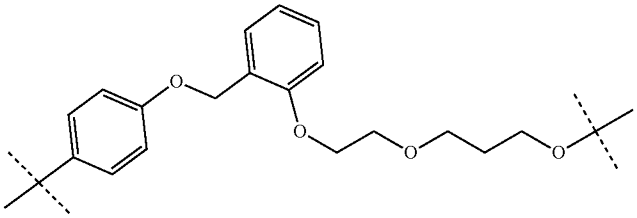
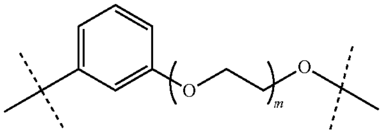
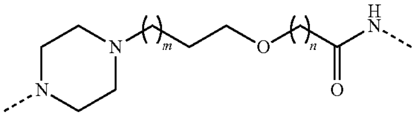
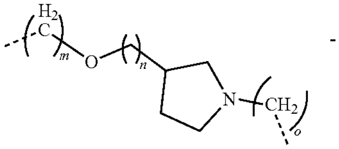
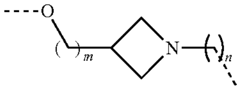
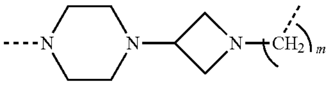
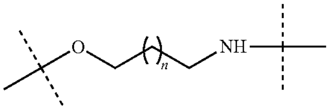
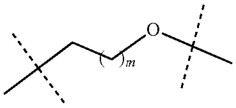
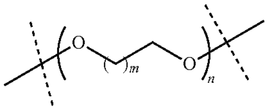
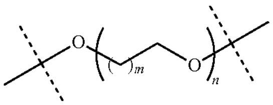
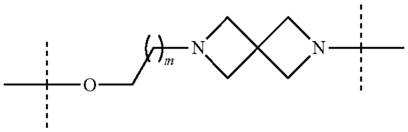
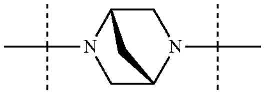
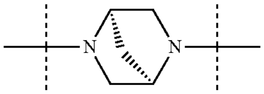
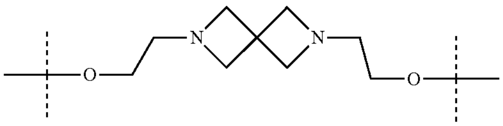
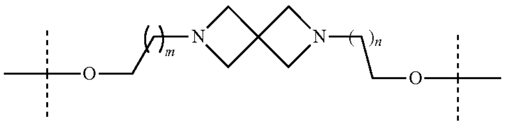
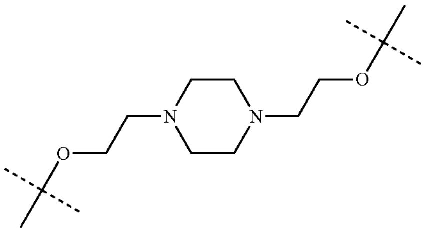
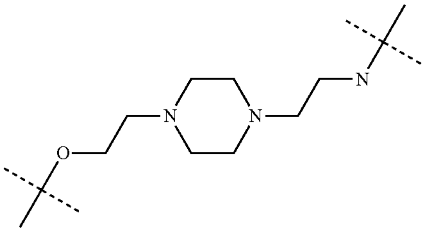
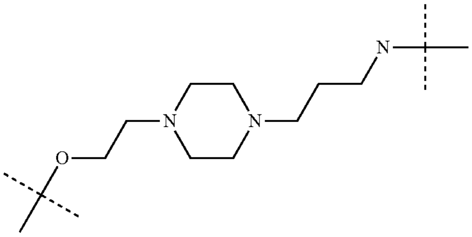
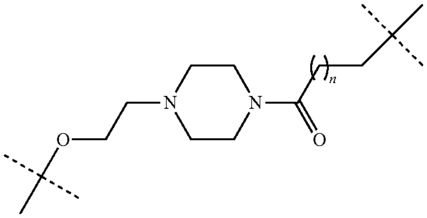
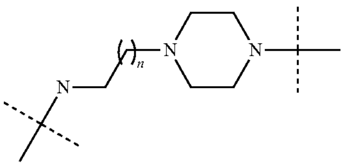
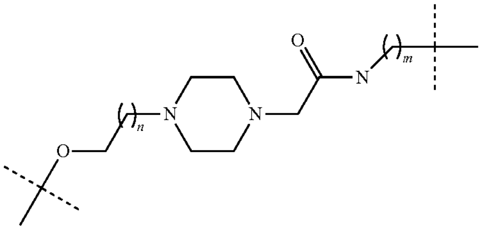
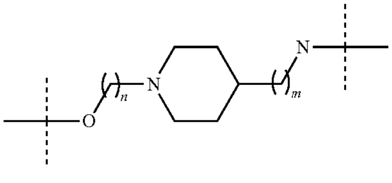

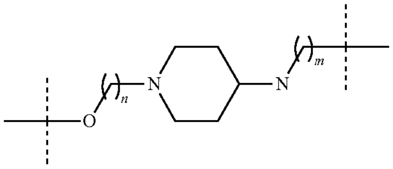
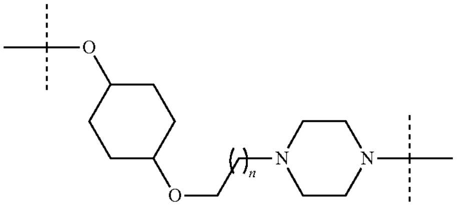
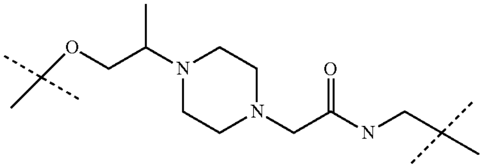
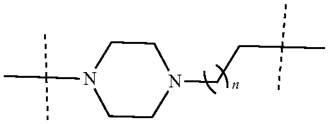
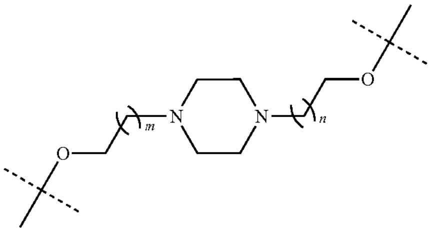
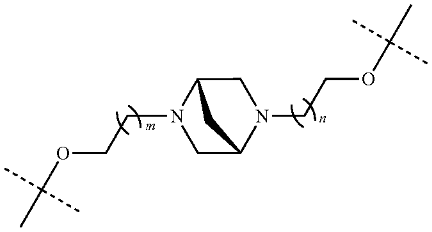
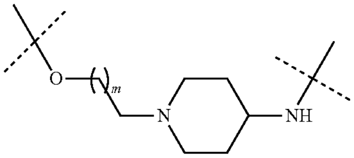
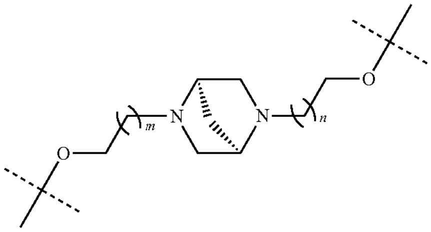
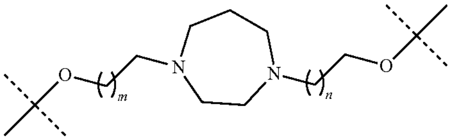
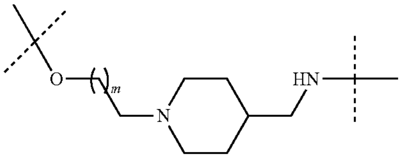
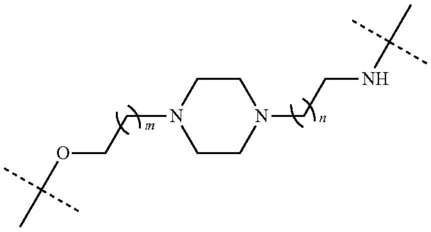
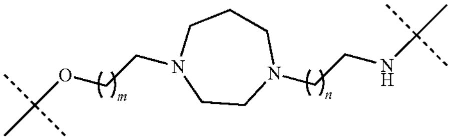
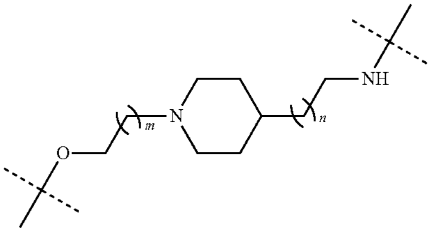
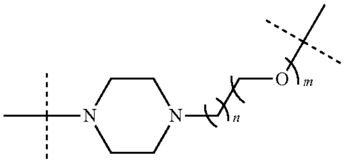
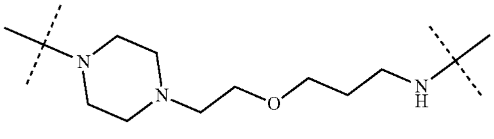
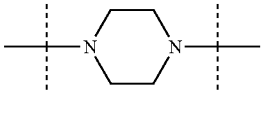
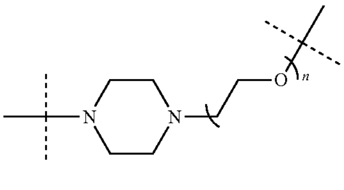

-continued
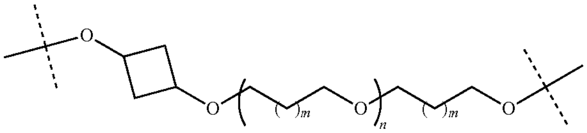
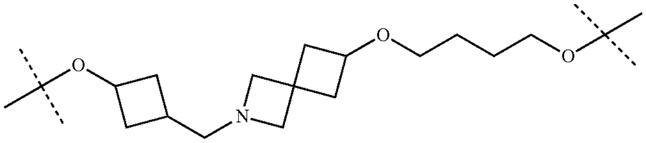
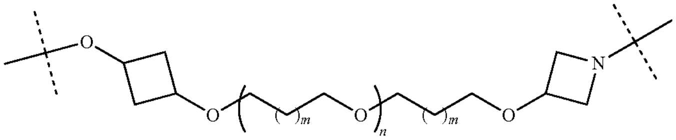
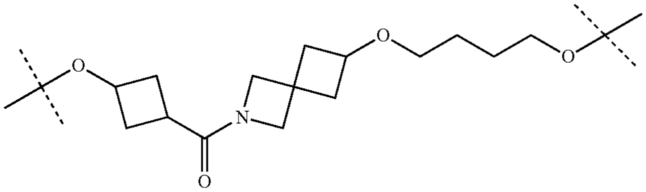
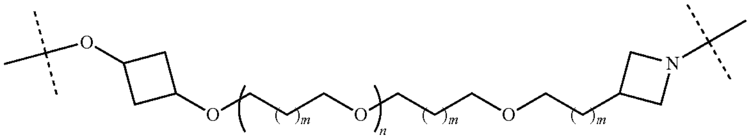
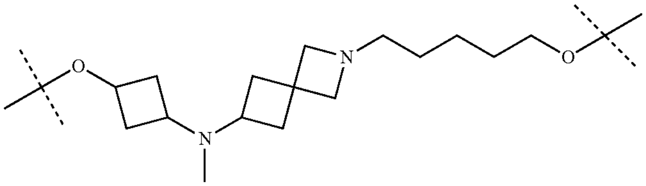
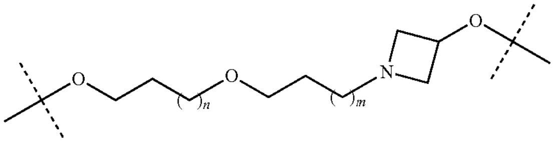
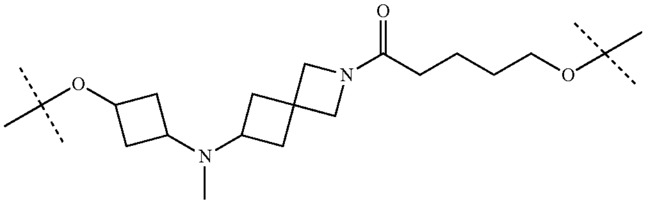
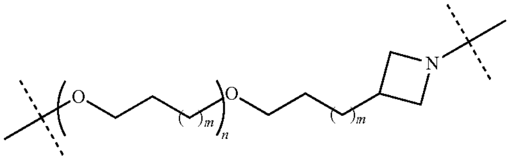
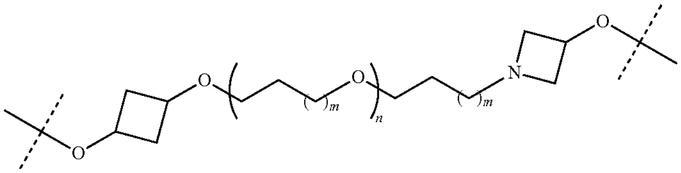

-continued
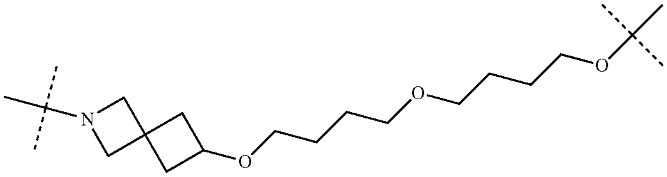
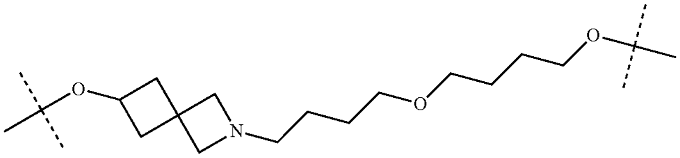
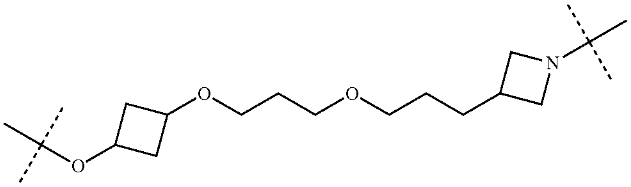
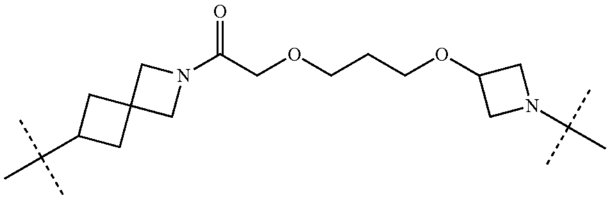
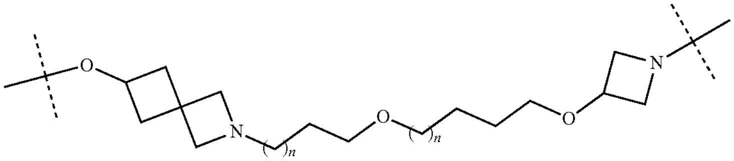
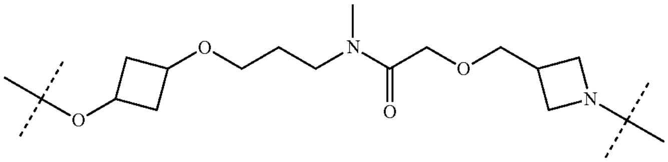
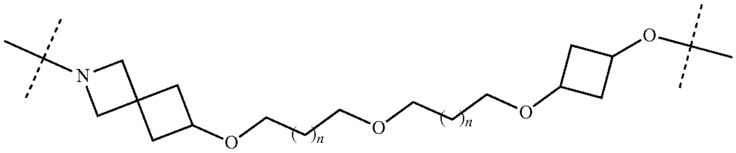
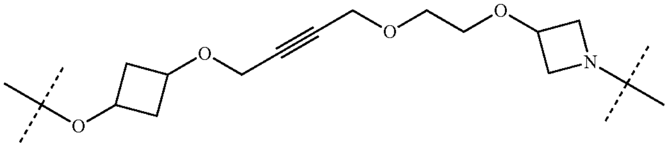
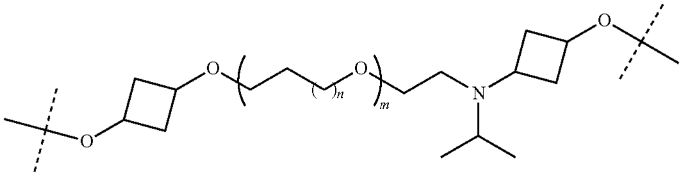
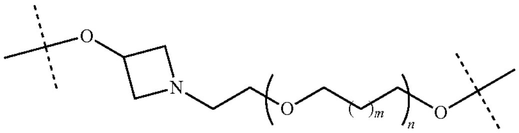

-continued
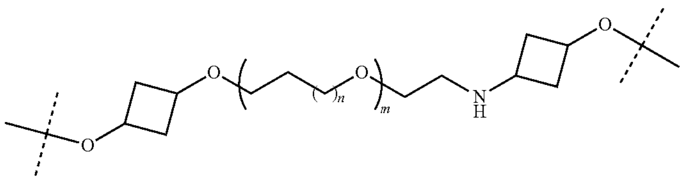
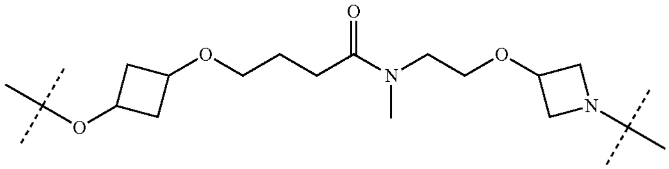
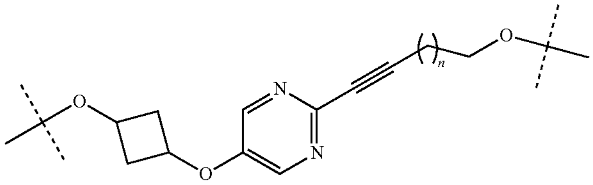
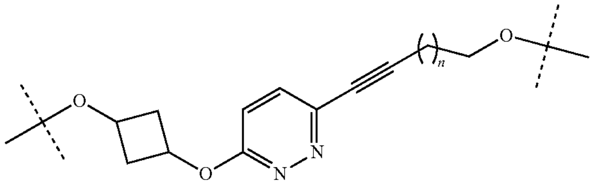
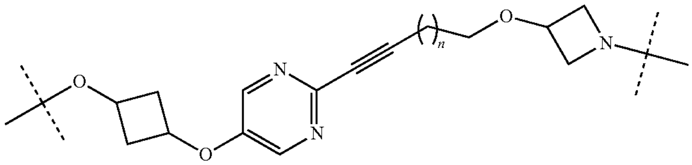
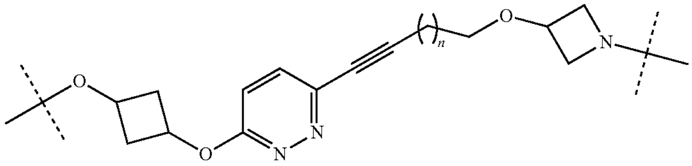
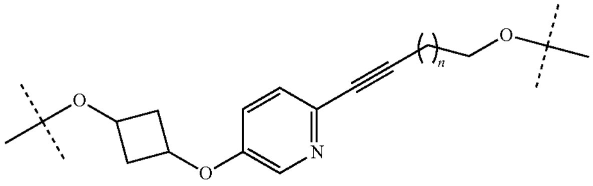
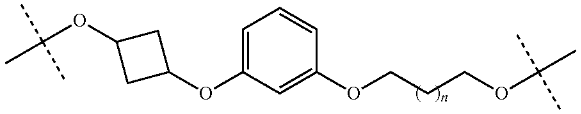
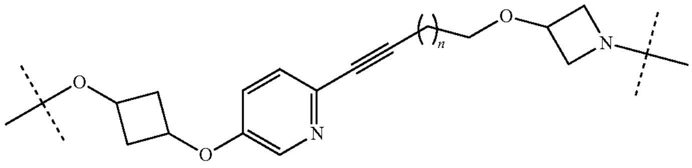
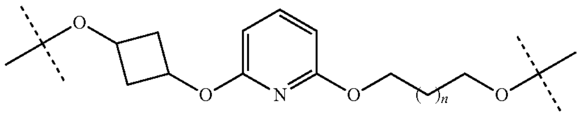

-continued
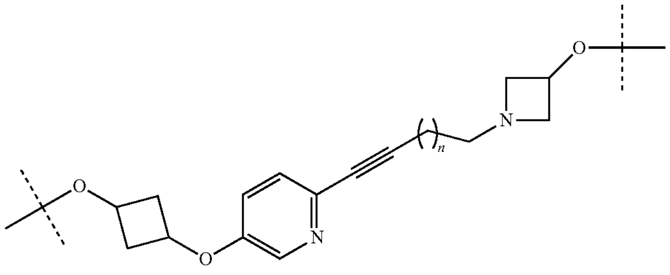
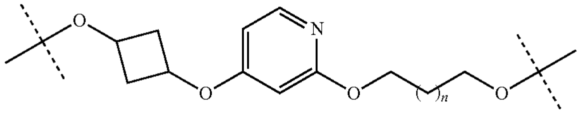
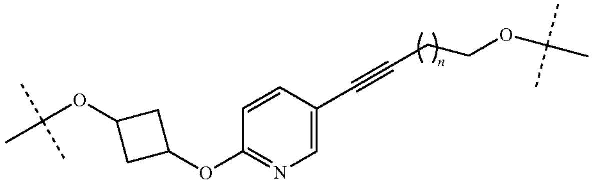
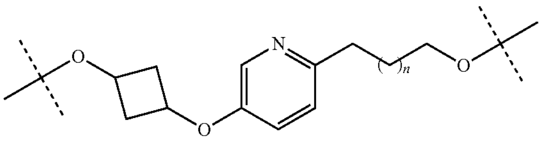
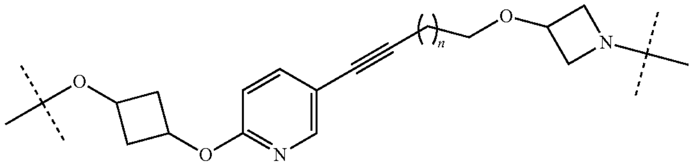
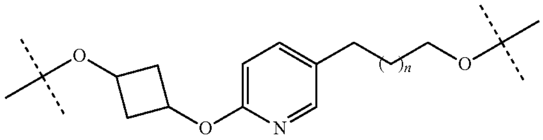
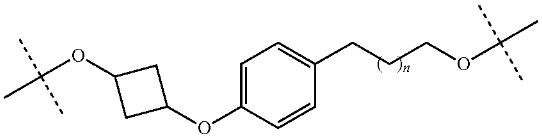
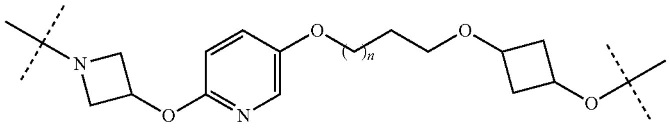
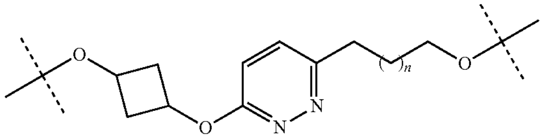
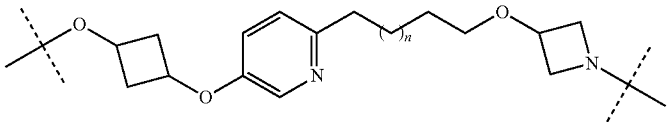
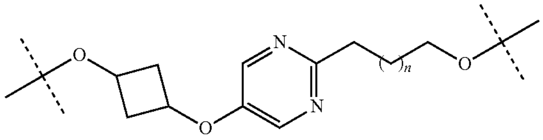
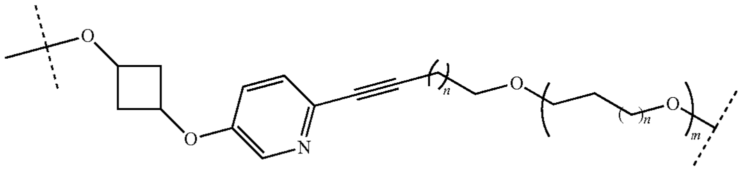

-continued
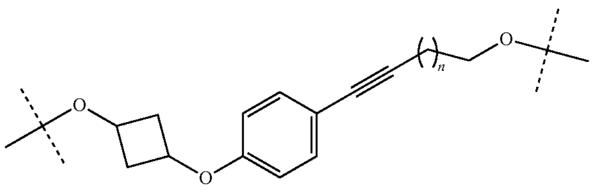
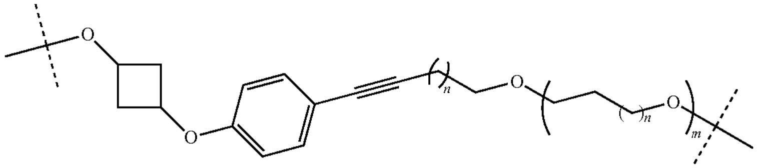
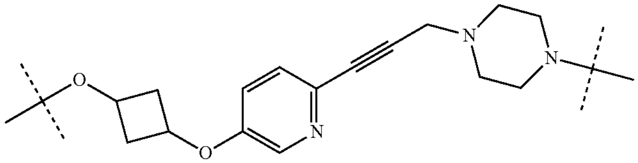
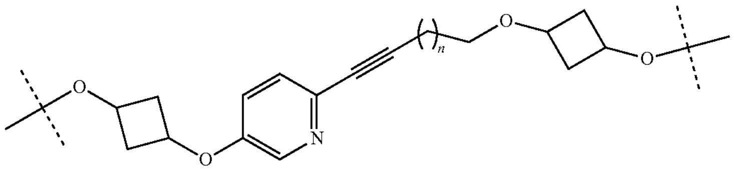
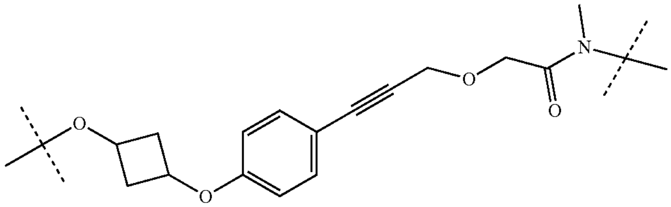
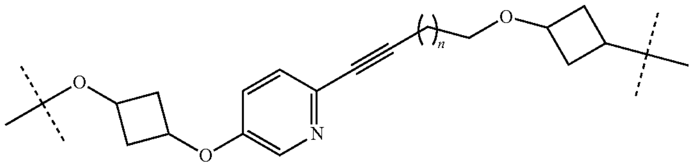
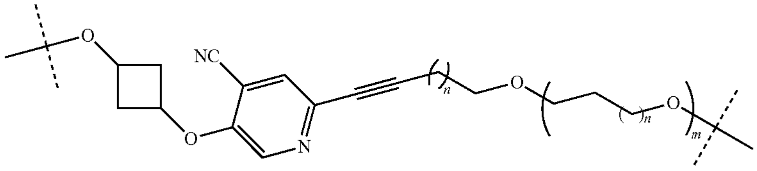
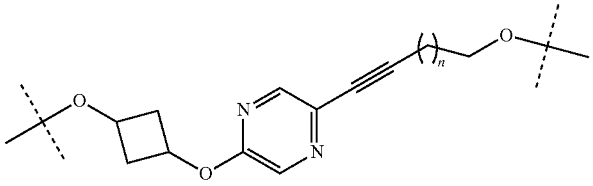
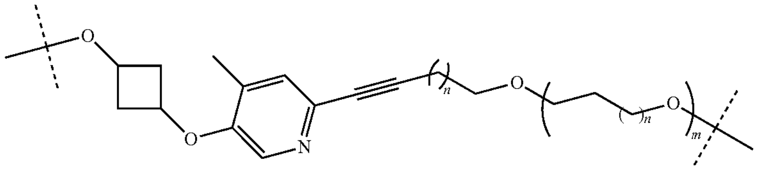

-continued
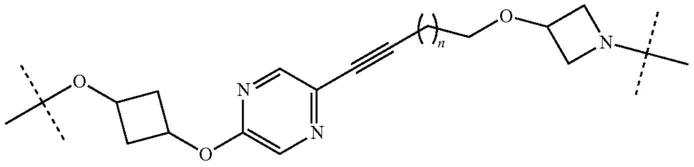
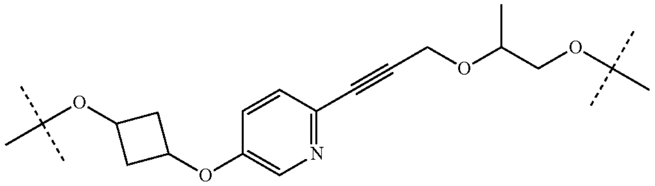
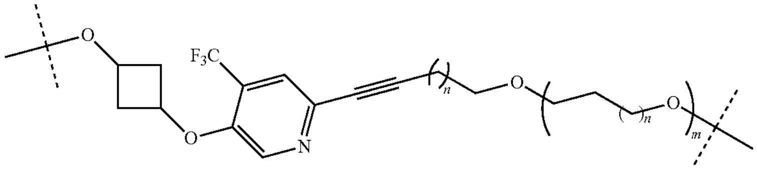
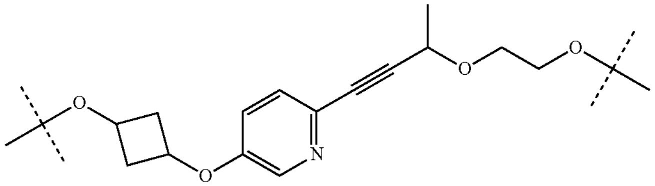
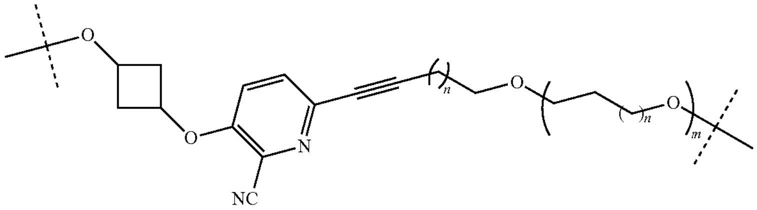
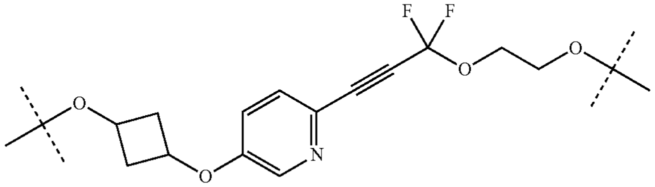
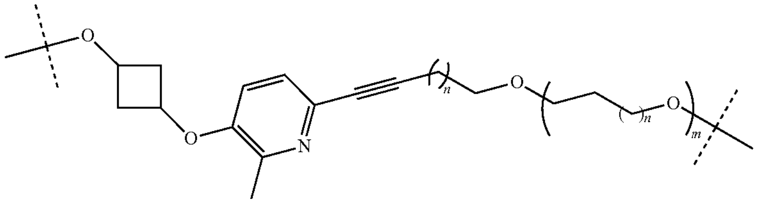
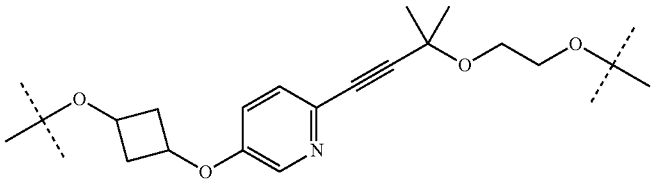
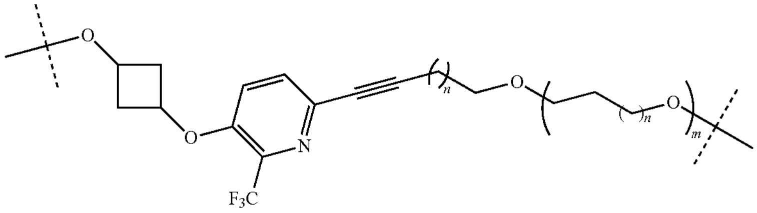

-continued
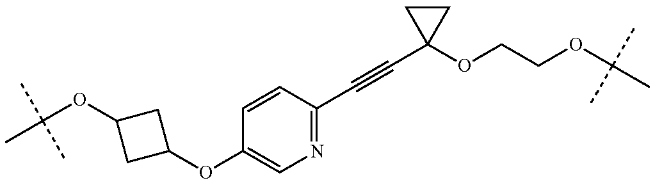
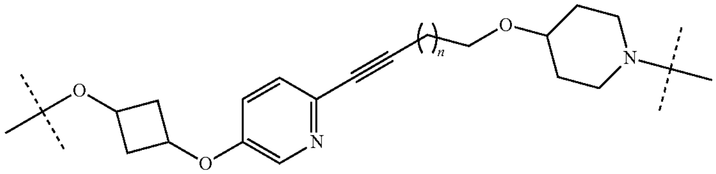
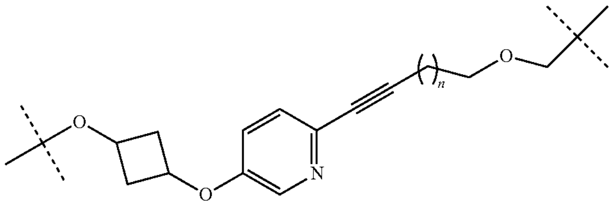
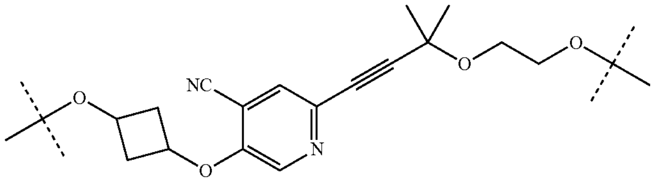
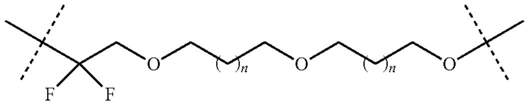
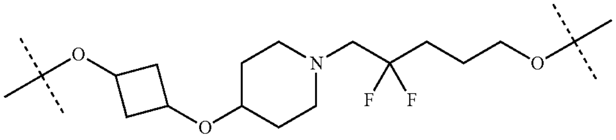
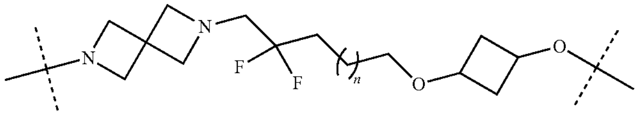
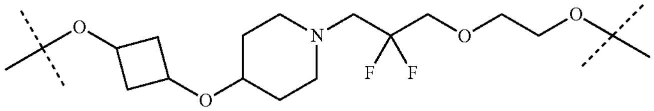
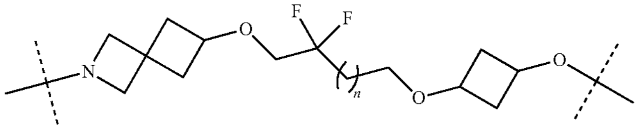
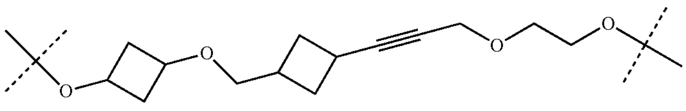
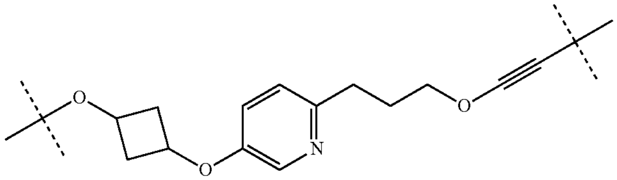
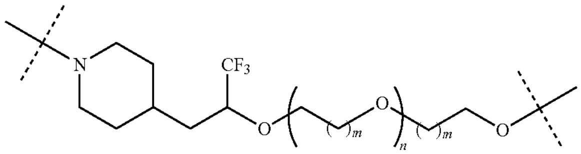

-continued
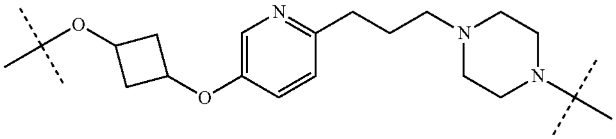
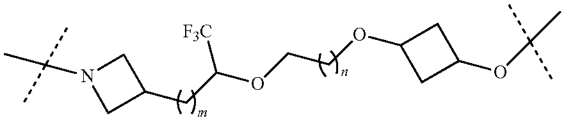
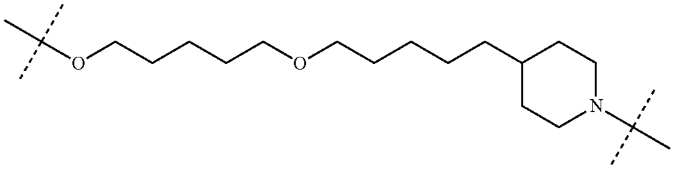
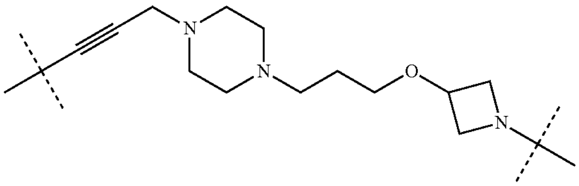
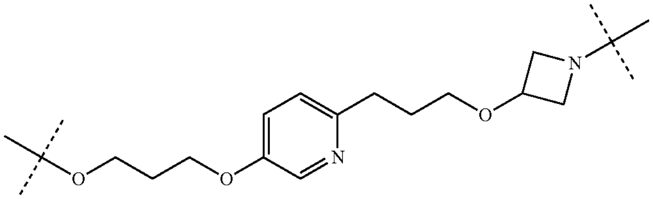
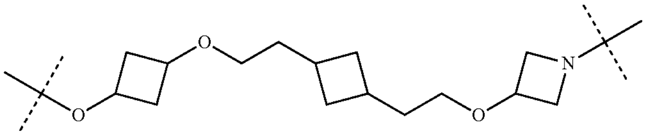
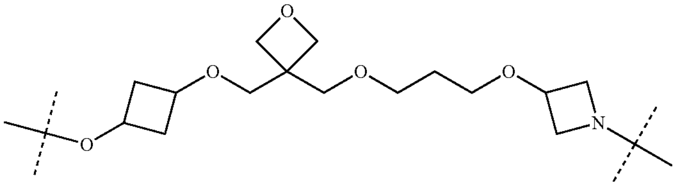
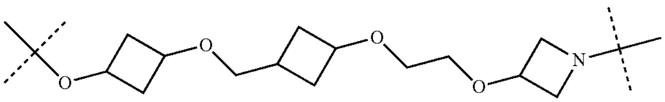
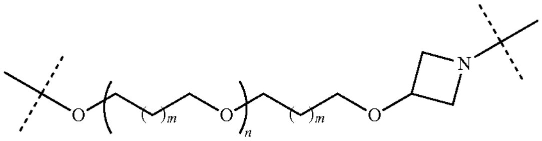
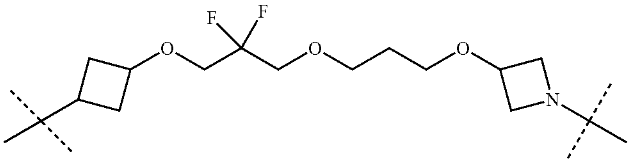
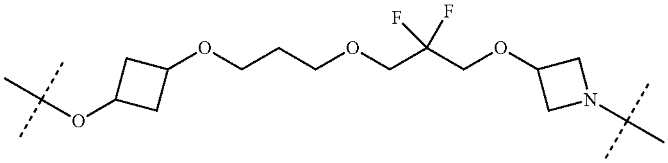

-continued
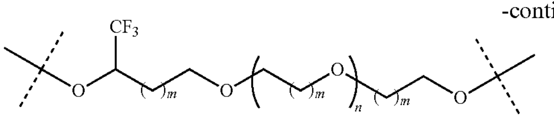
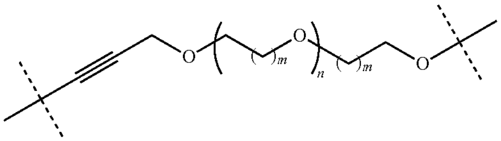
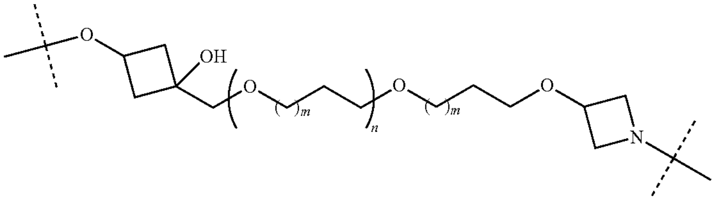
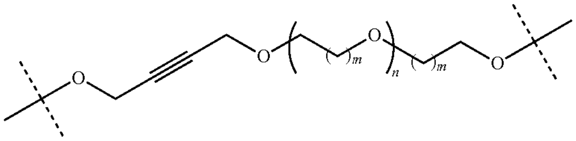
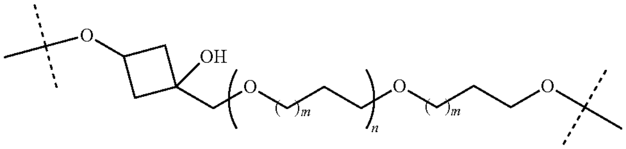
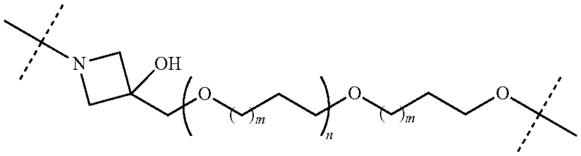
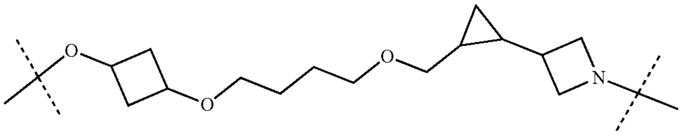
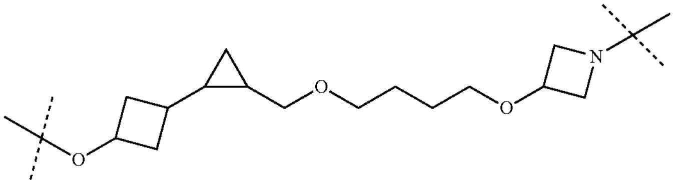
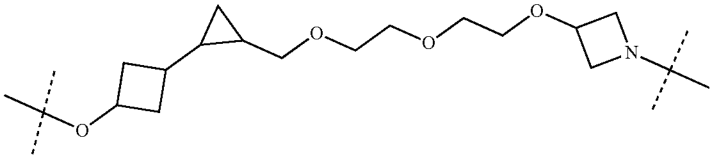
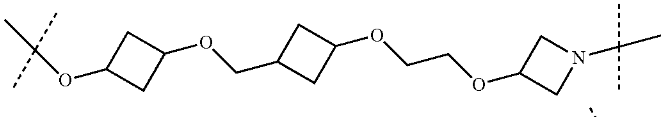
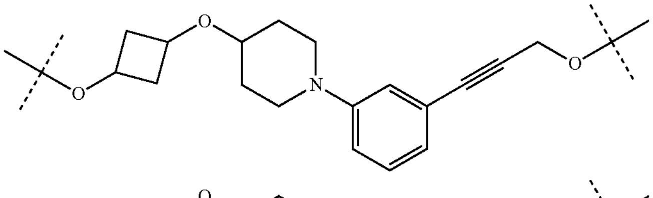
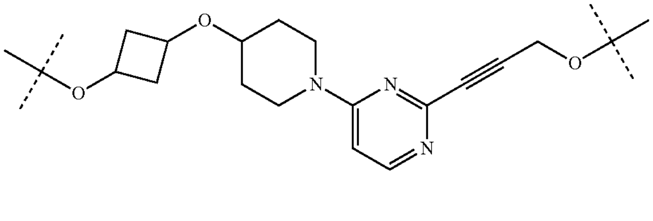

-continued
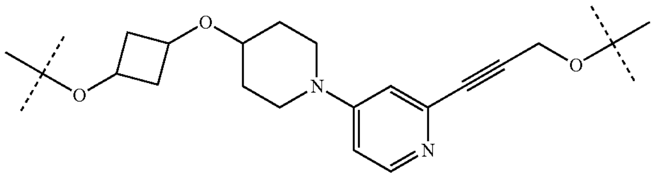
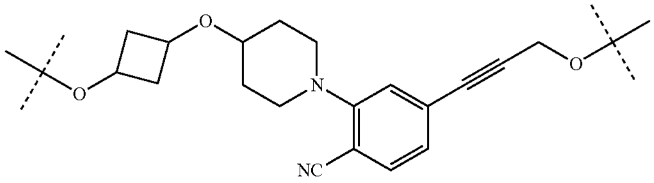
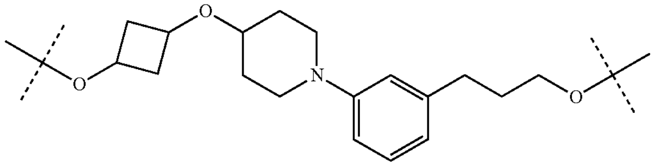
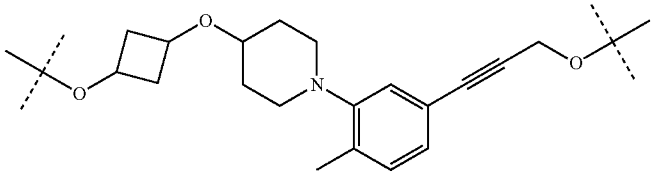
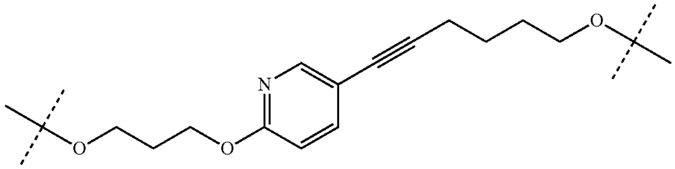
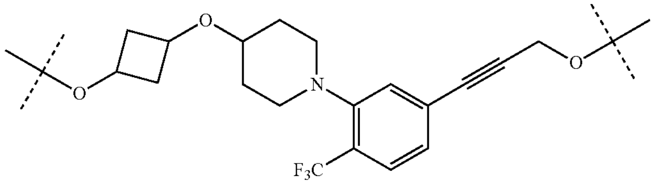
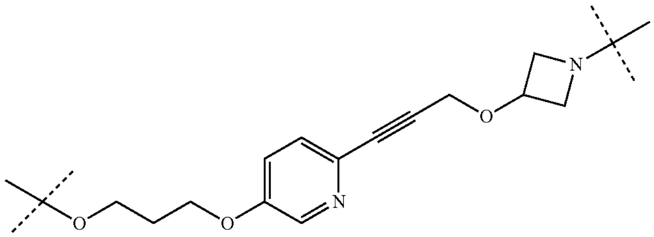
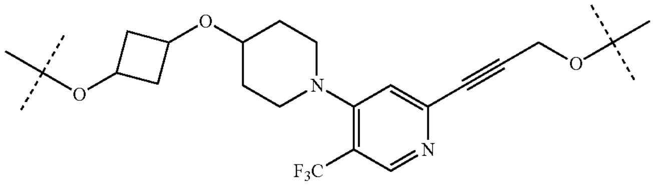
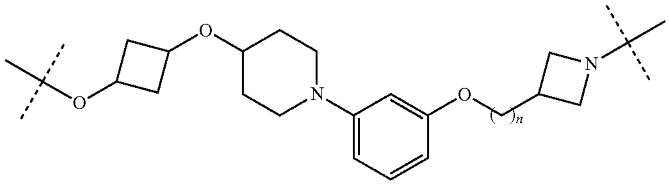

-continued
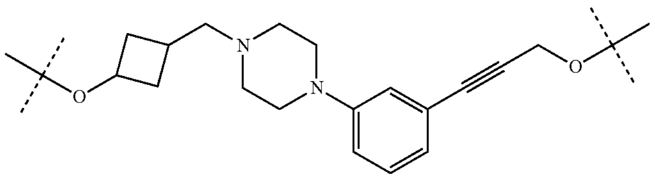
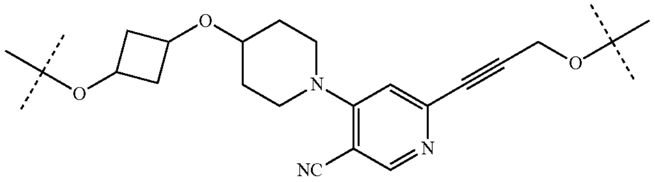
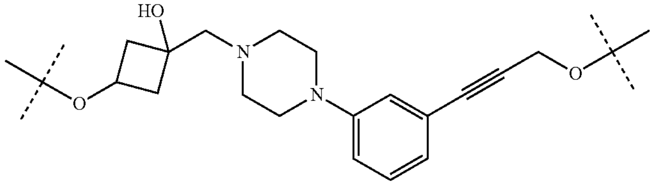
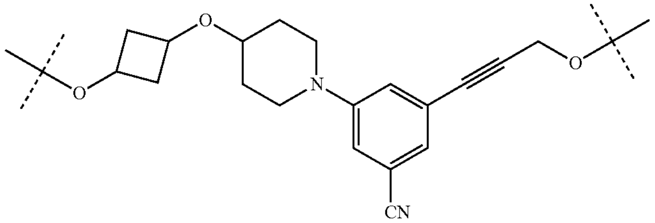
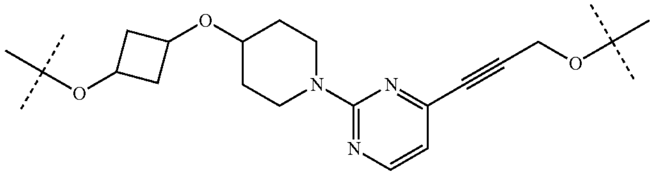
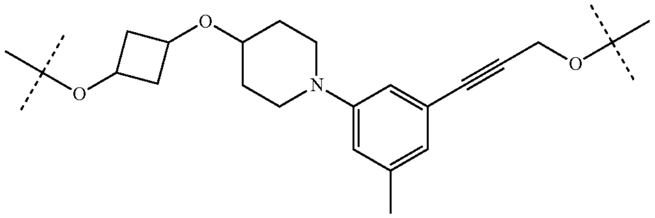
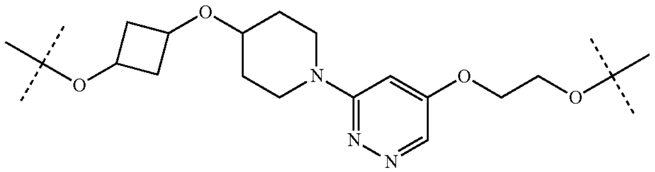
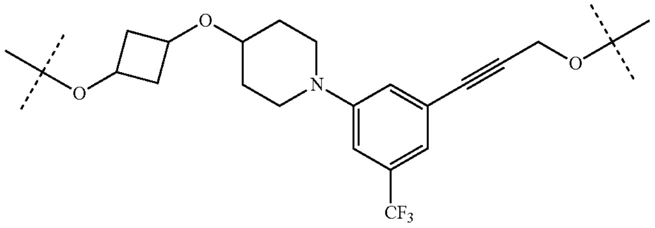
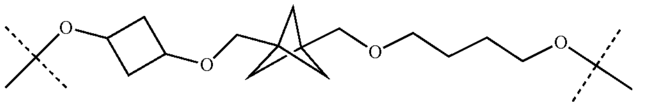

-continued
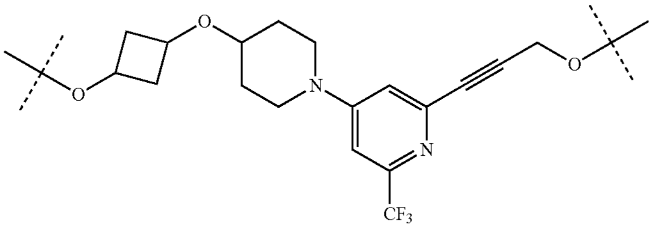
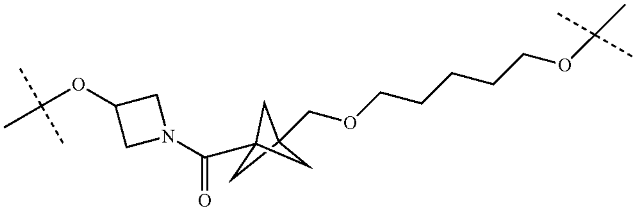
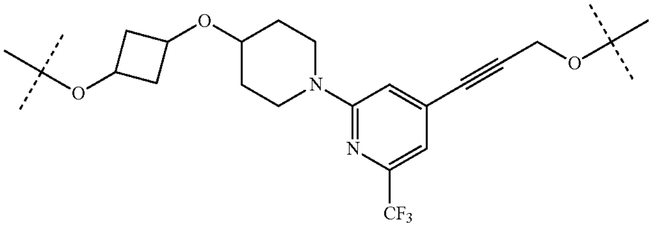
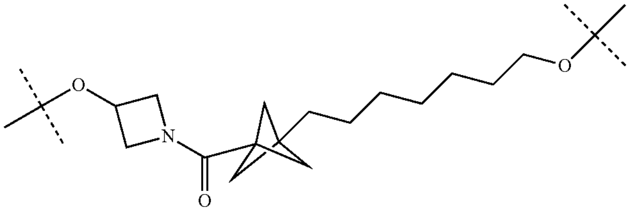
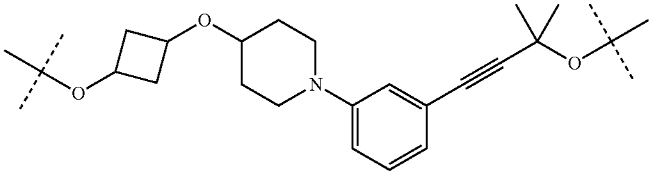
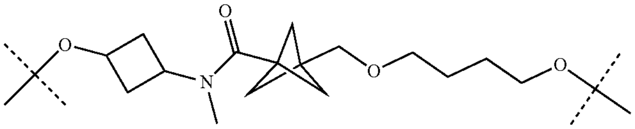
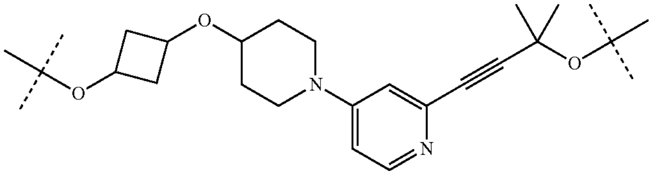
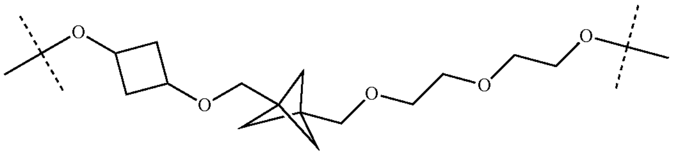
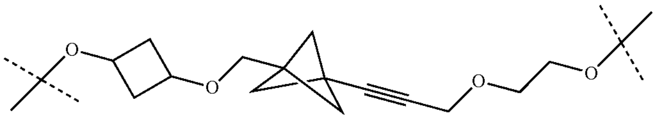

-continued
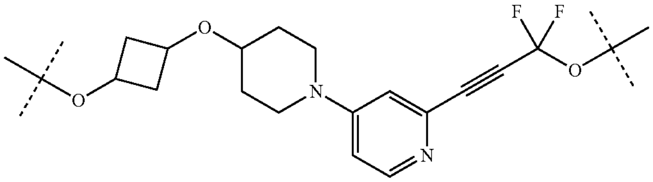
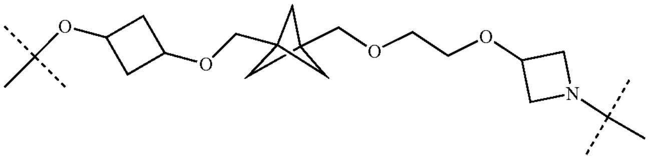
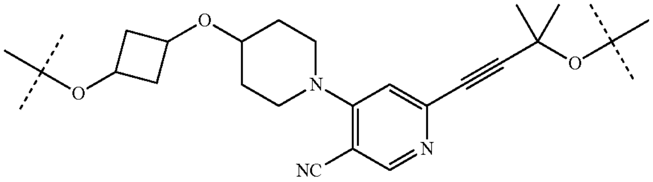
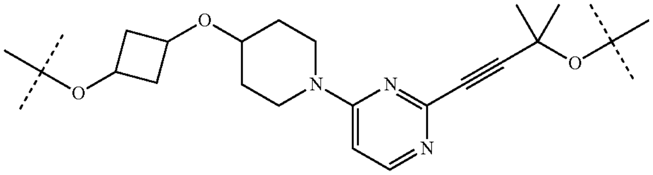
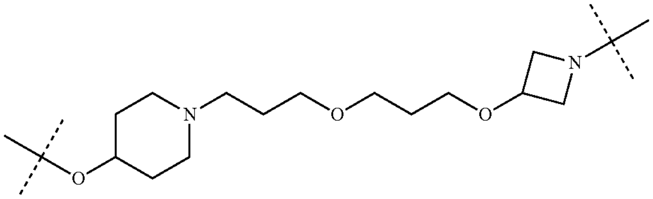
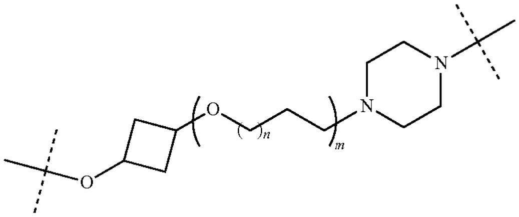
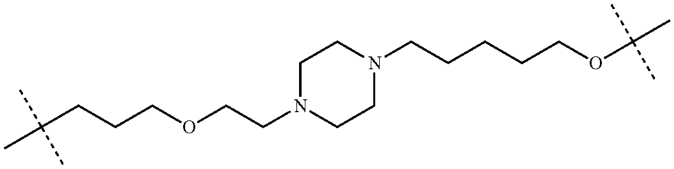
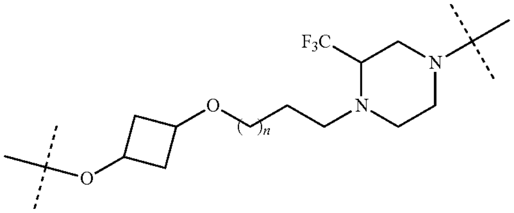
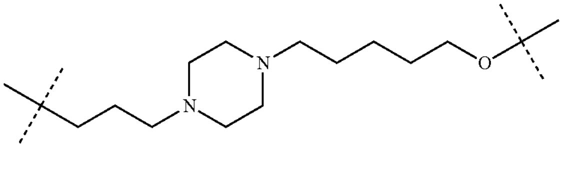
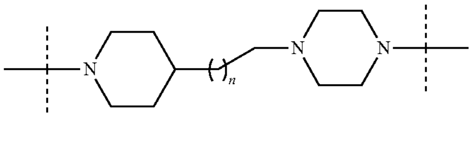
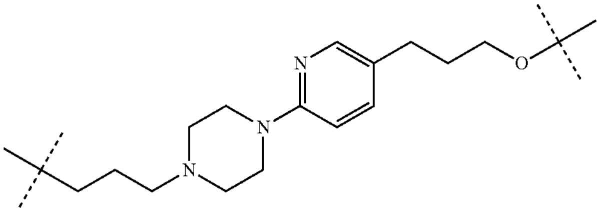

-continued
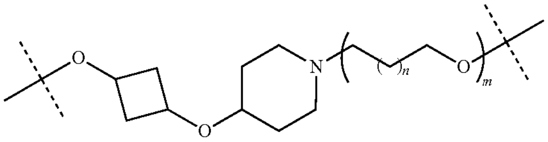
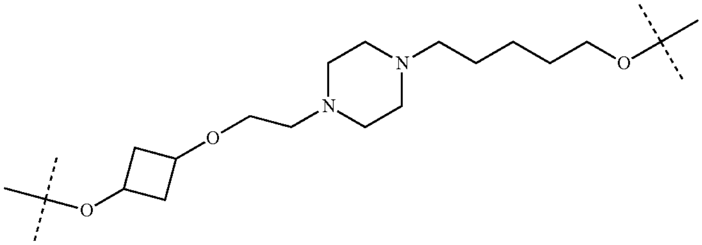
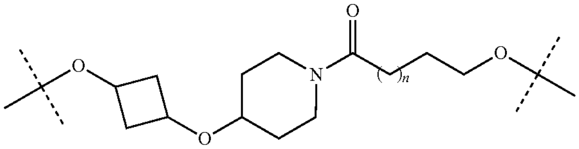
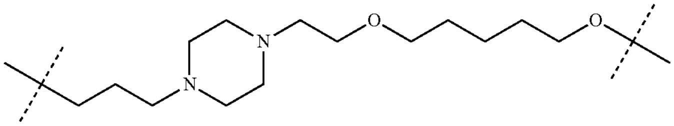
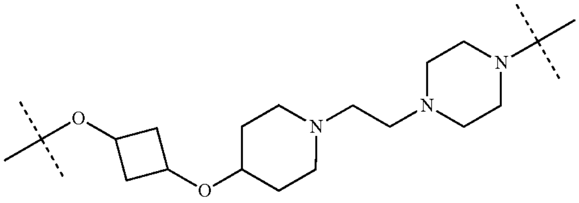
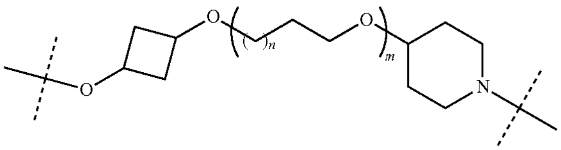
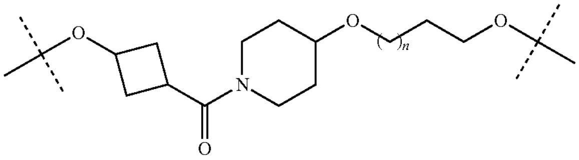
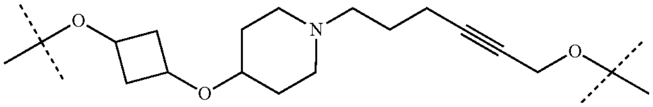
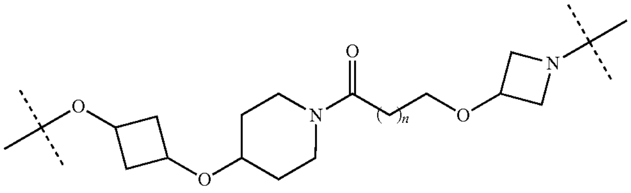
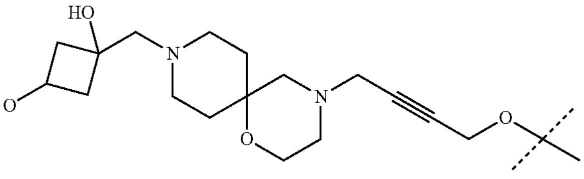
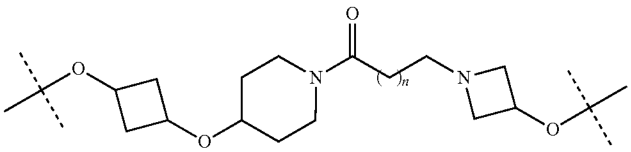

-continued
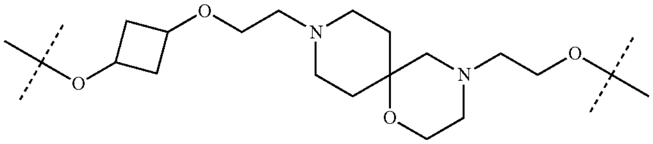
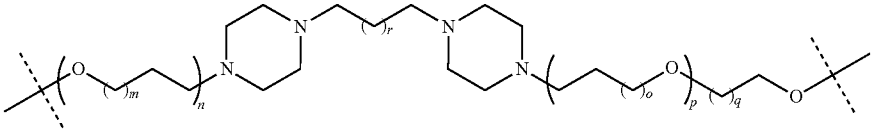
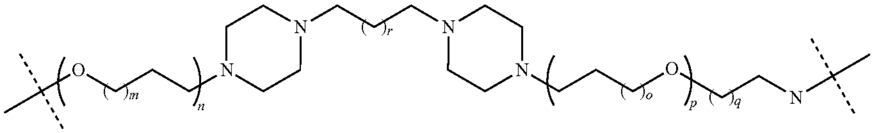
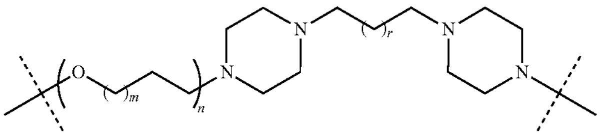
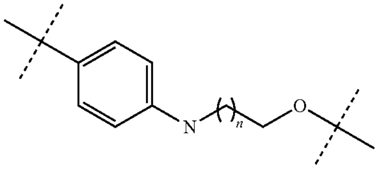
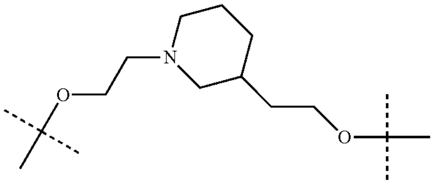
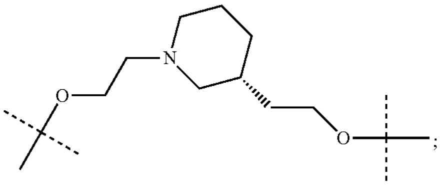
;
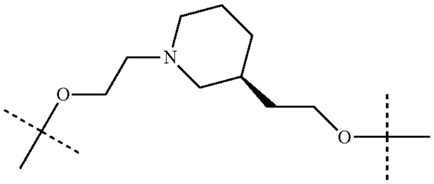
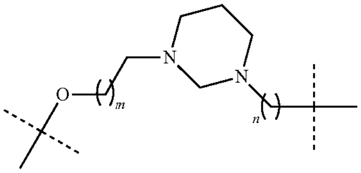
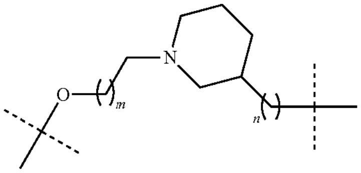
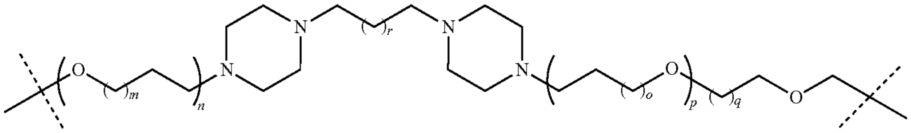
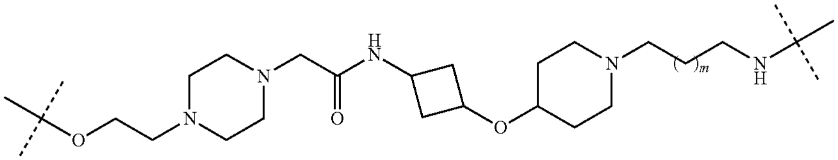
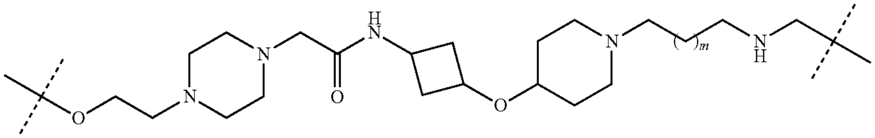
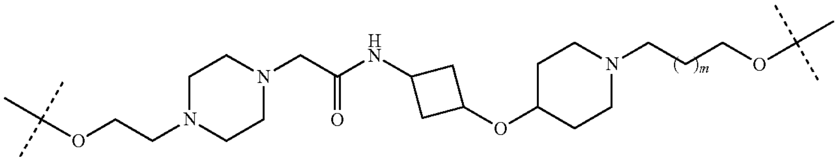

-continued
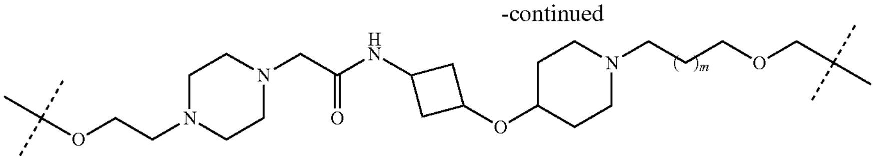
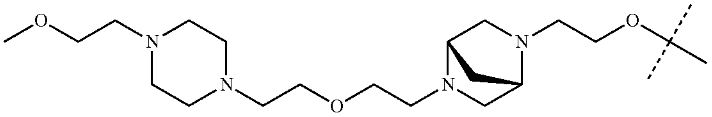
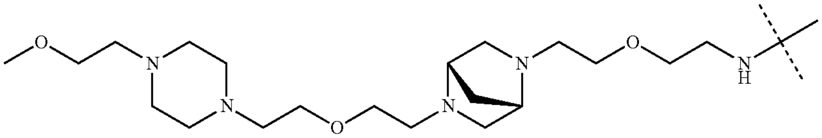
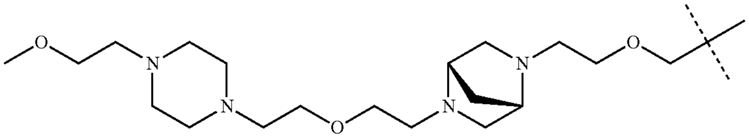
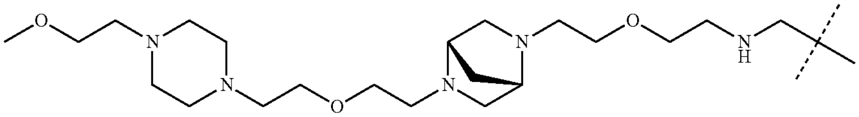
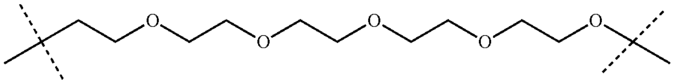
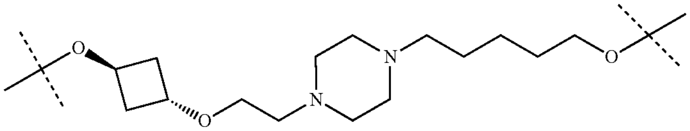
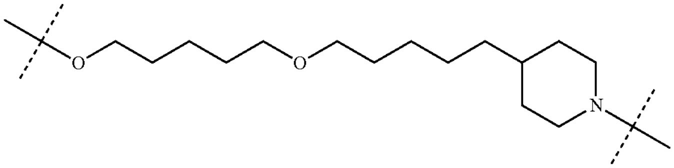
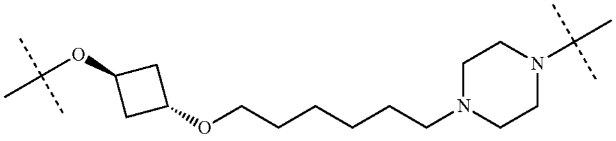
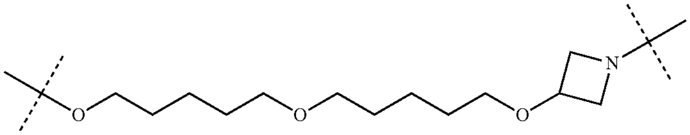
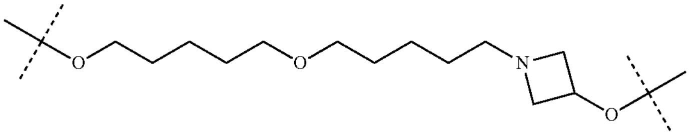
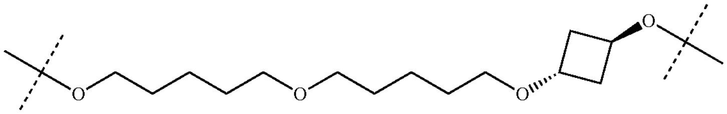
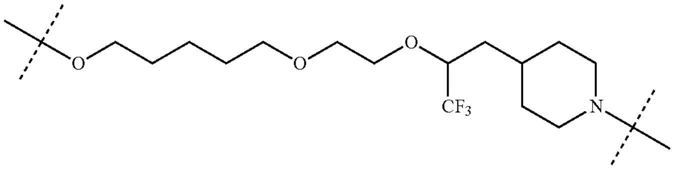

-continued
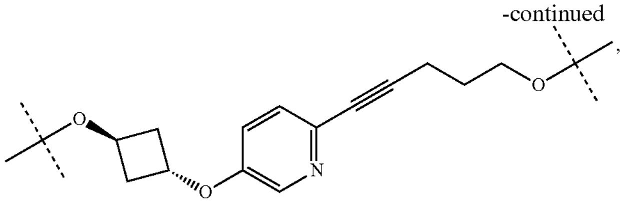
wherein each m, n, o, p, q, and r is independently 0, 1, 2, 3, 4, 5, 6, 7, 8, 9, 10, 11, 12, 13, 14, 15, 16, 17, 18, 19, or 20.
In any aspect or embodiment described herien, the linker (L) is selected from the group consisting of:
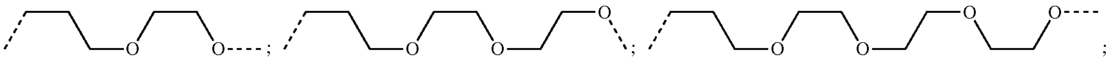
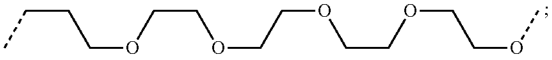
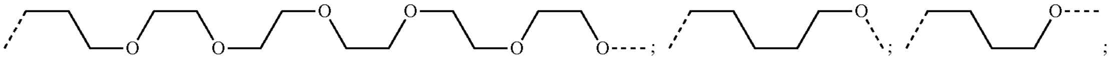
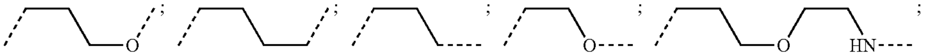
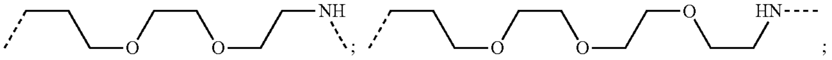
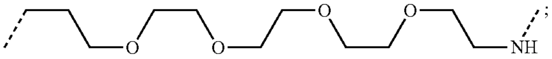
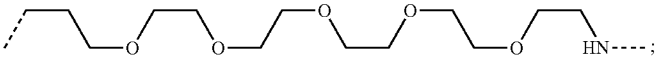
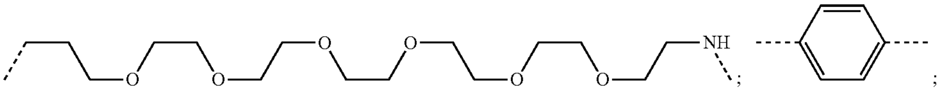
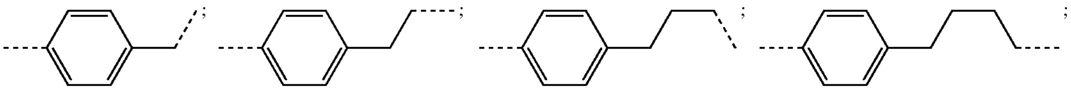
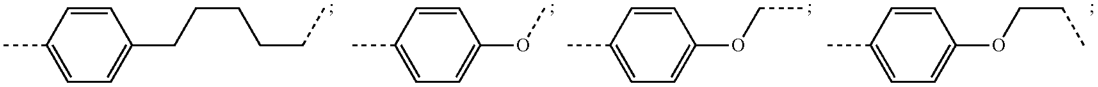
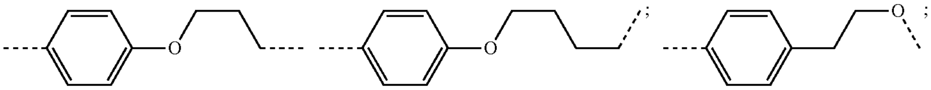
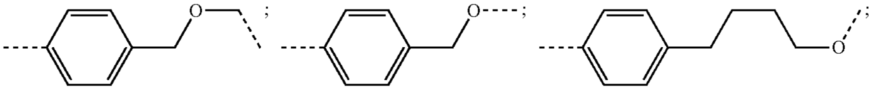
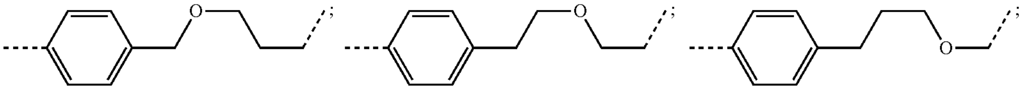
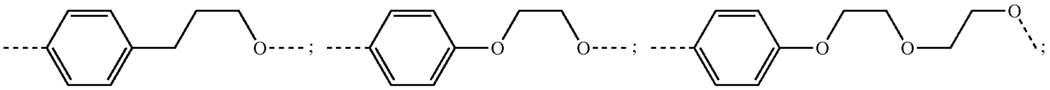
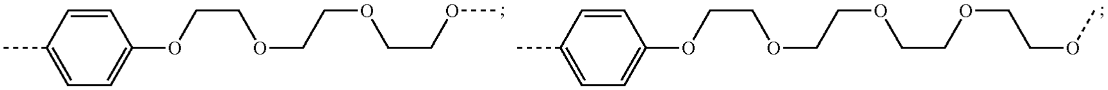
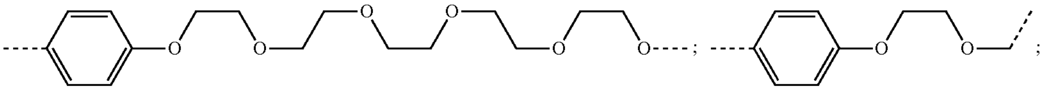
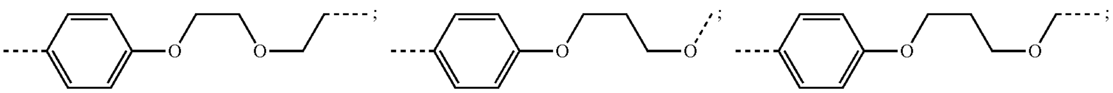
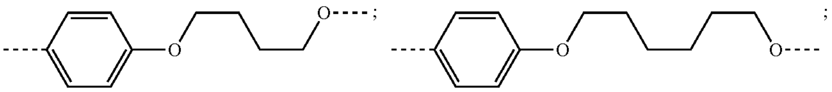

-continued
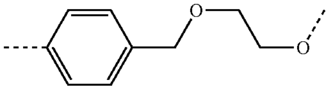;
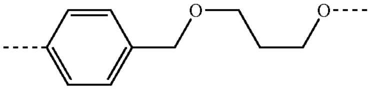;
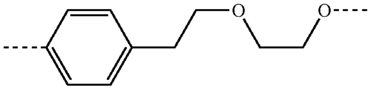;
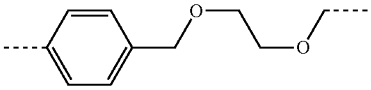;
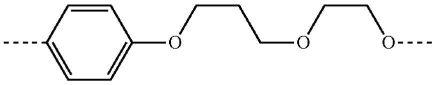;
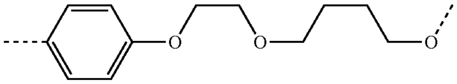;
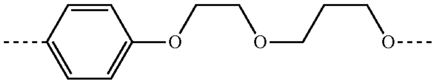;
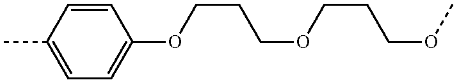;
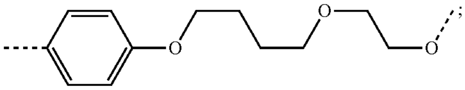;
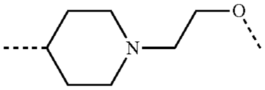;
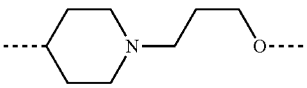;
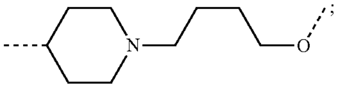;
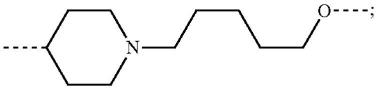;
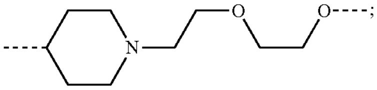;
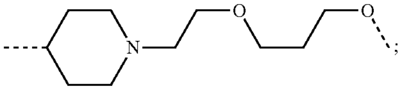;
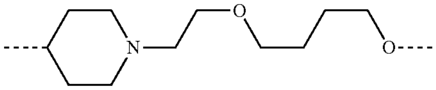;
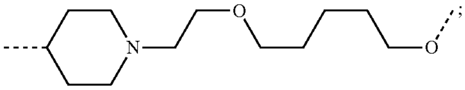;
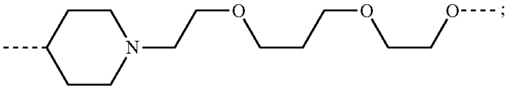;
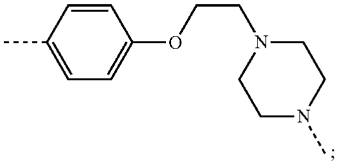;
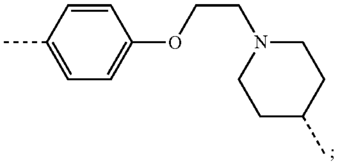;
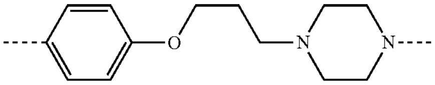;
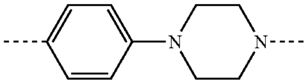;
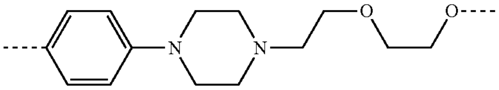;
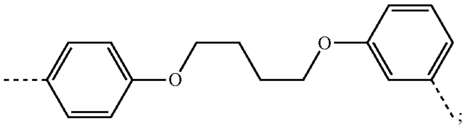;
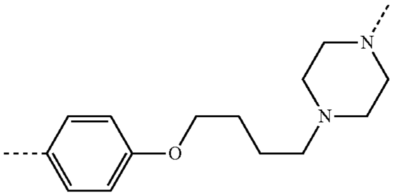;
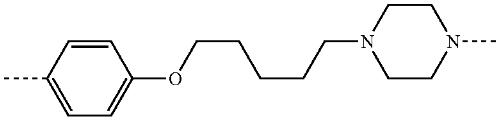;
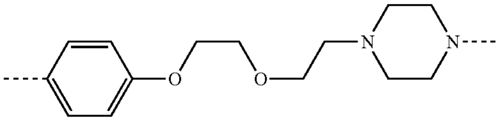;
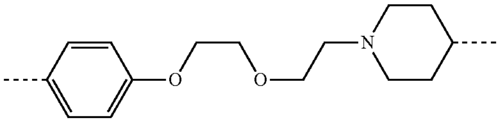;
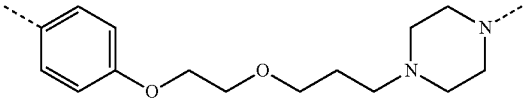;
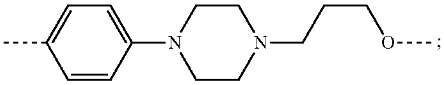;
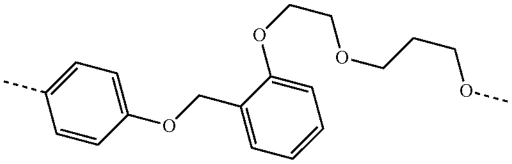;
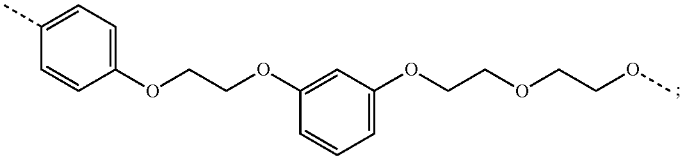;

-continued
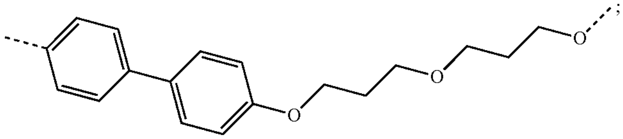 ;
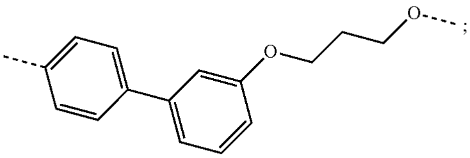 ;
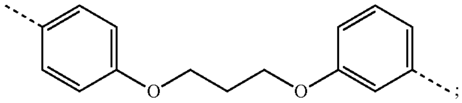 ;
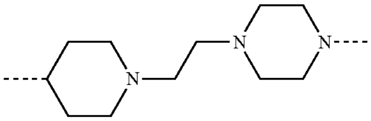 ;
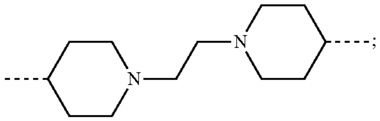 ;
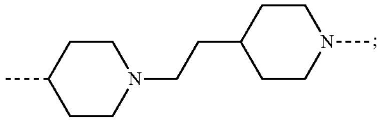 ;
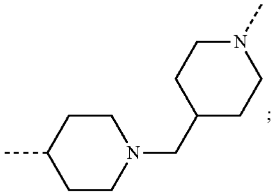 ;
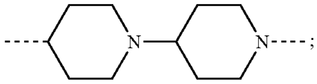 ;
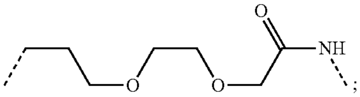 ;
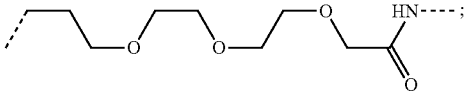 ;
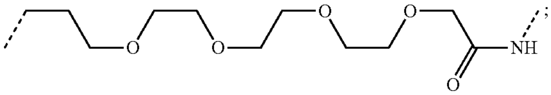 ;
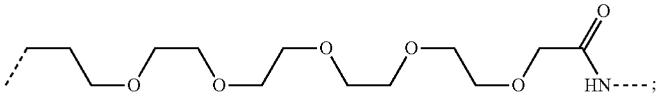 ;
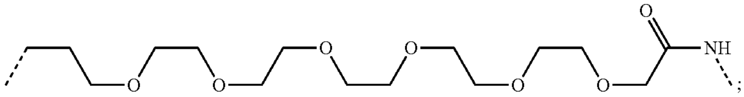 ;
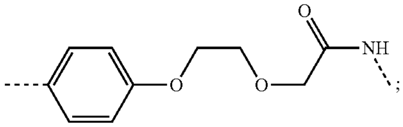 ;
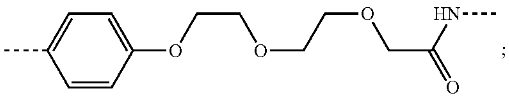 ;
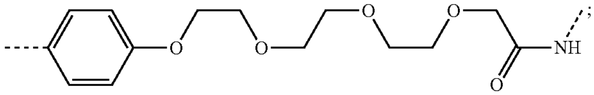 ;
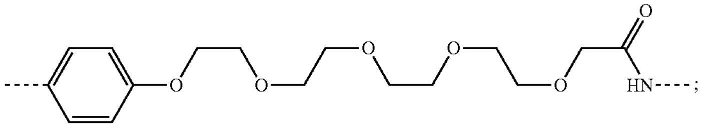 ;
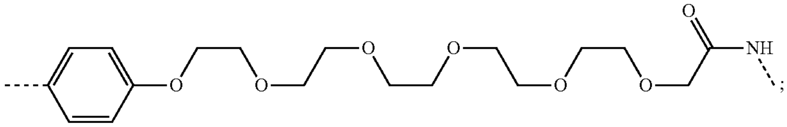 ;
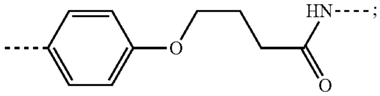 ;
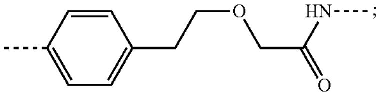 ;
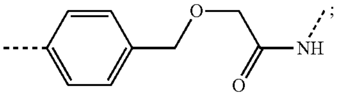 ;
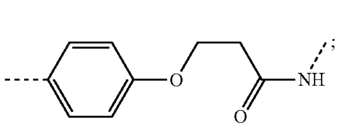 ;
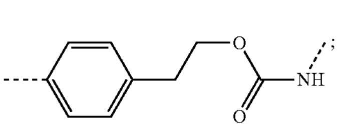 ;
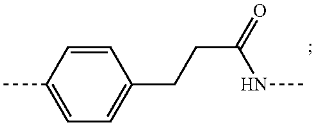 ;
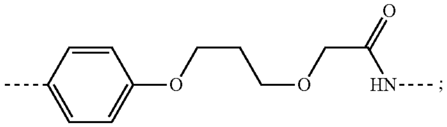 ;

-continued
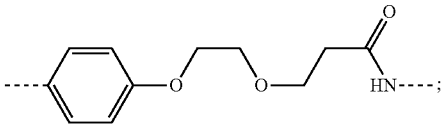 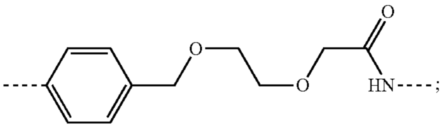
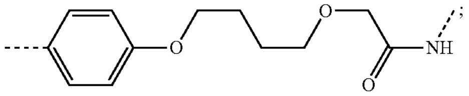 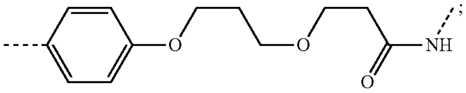
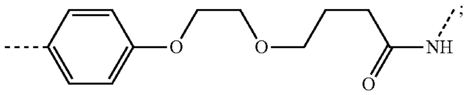 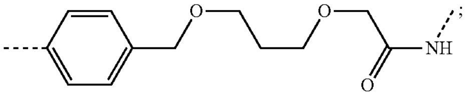
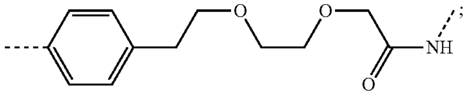 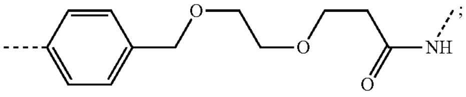
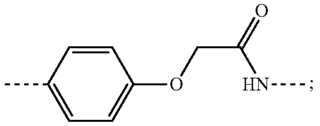
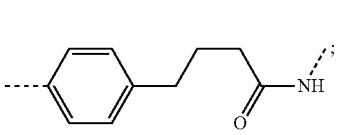 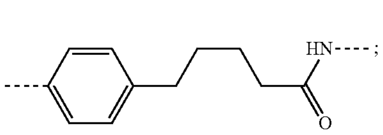 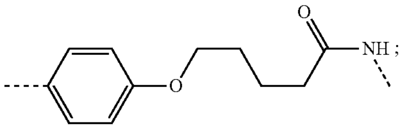
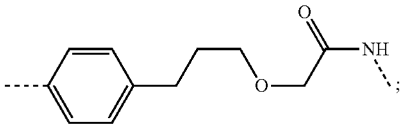 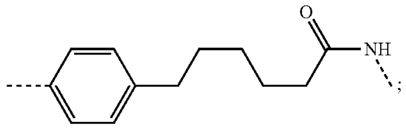
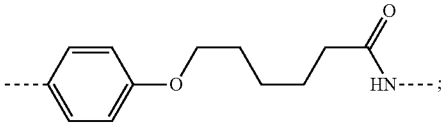 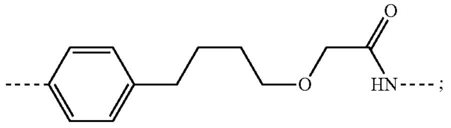
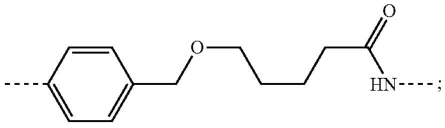 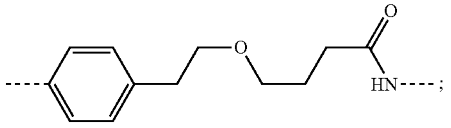
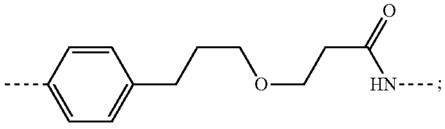 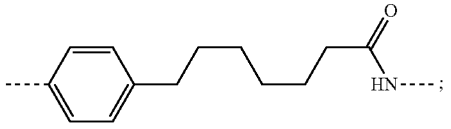
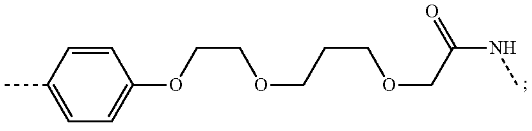 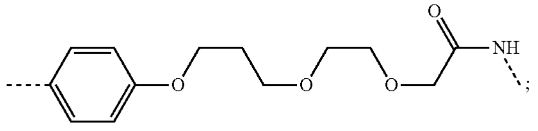
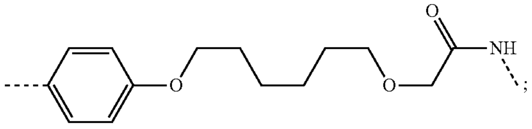 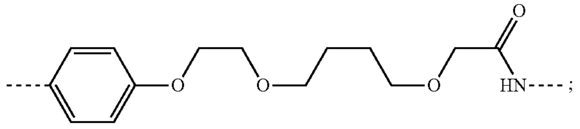
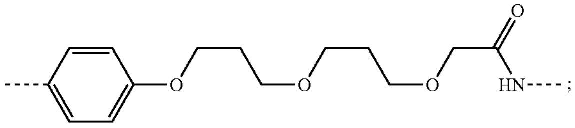 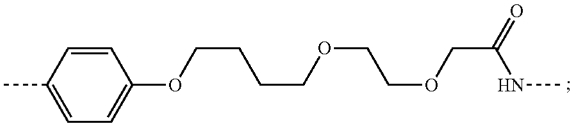
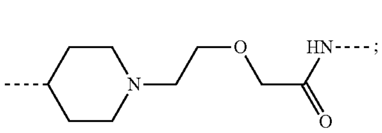 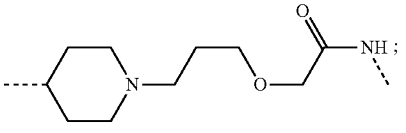

-continued
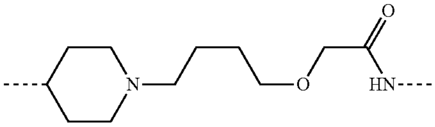 ; 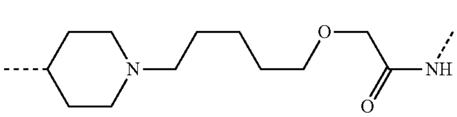 ;
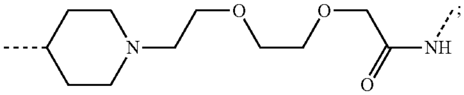 ; 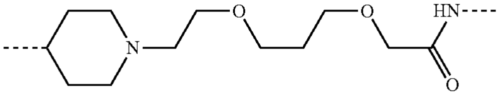 ;
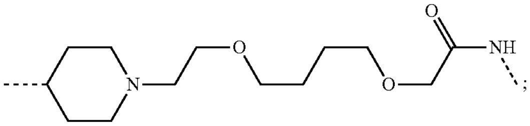 ; 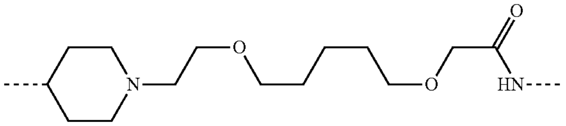 ;
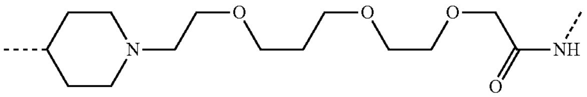 ; 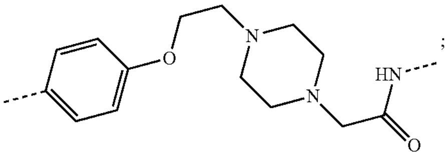 ;
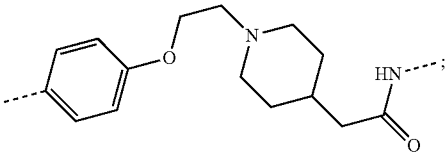 ;
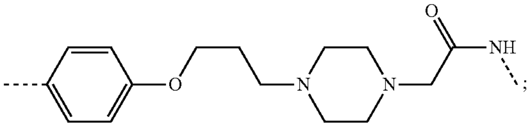 ; 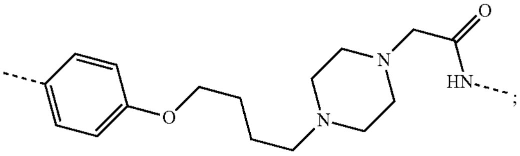 ;
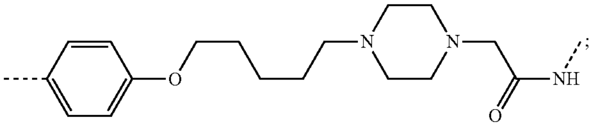 ;
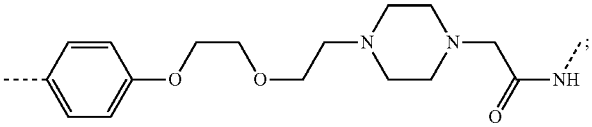 ;
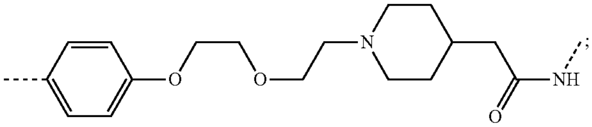 ; 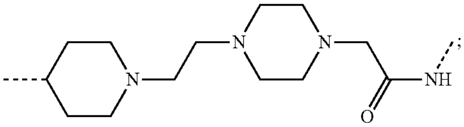 ;
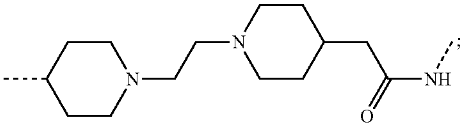 ; 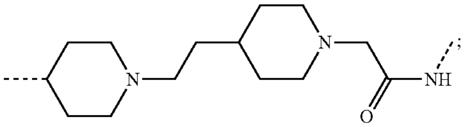 ;
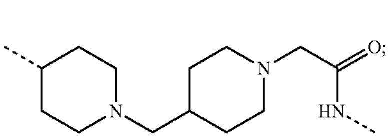 ; 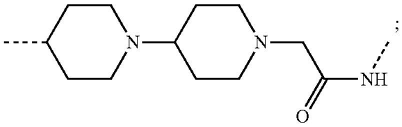 ; 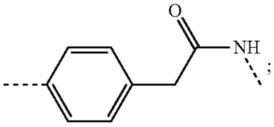 ;
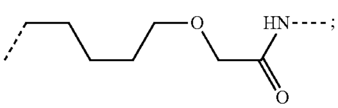 ; 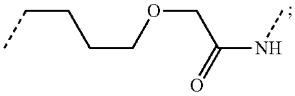 ; 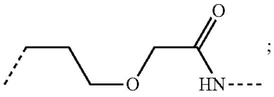 ;
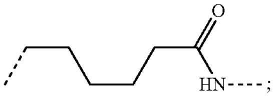 ; 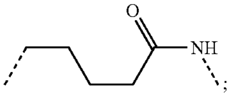 ; 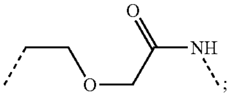 ;

-continued
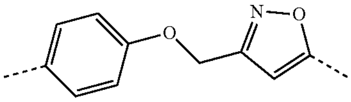;
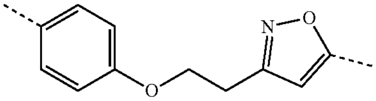;
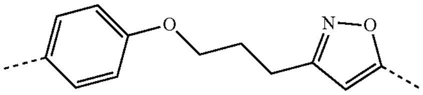;
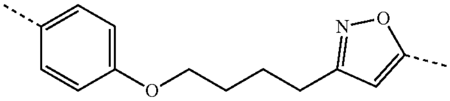;
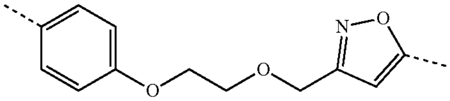;
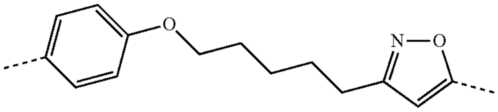;
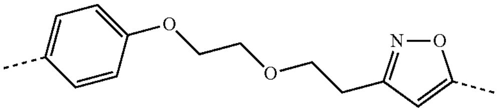;
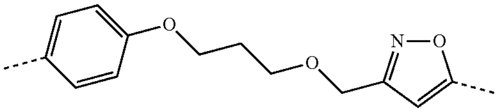;
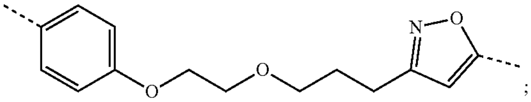;
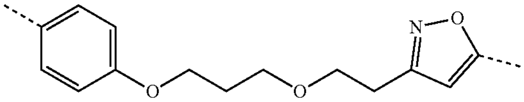;
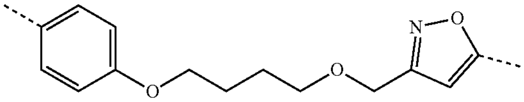;
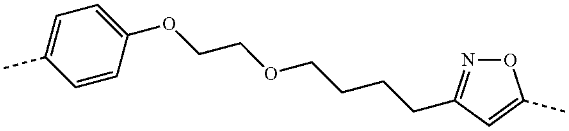;
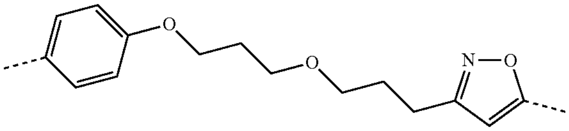;
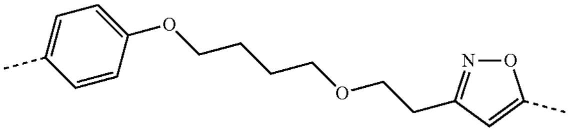;
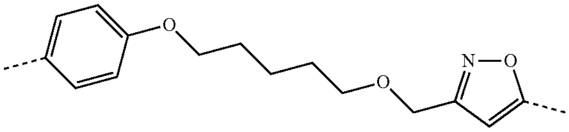;
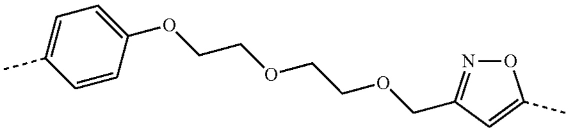;
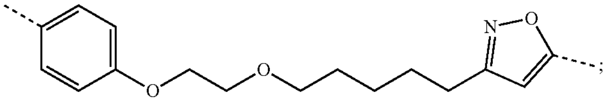;
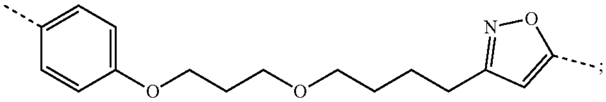;
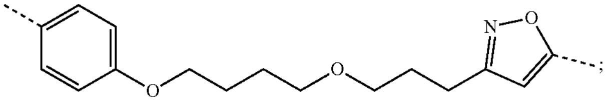;
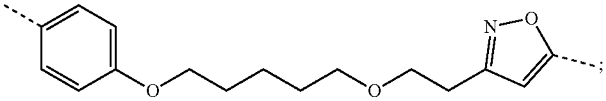;

-continued
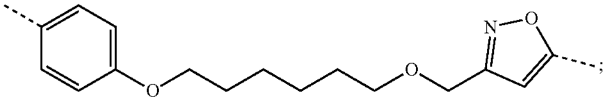;
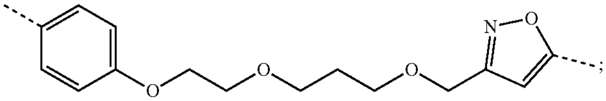;
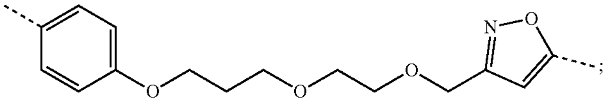;
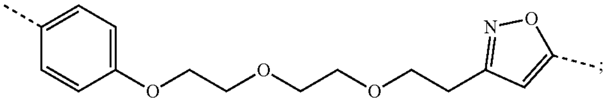;
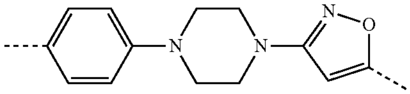
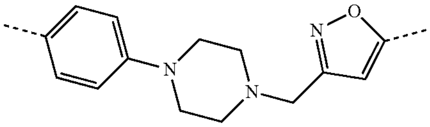;
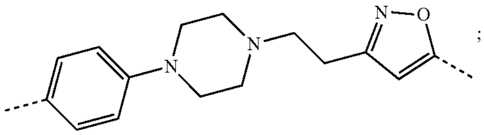;
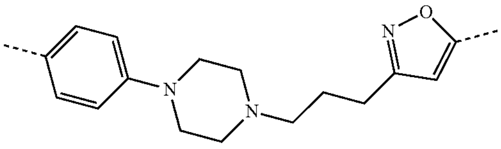;
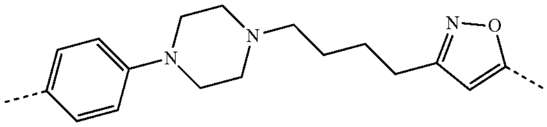;
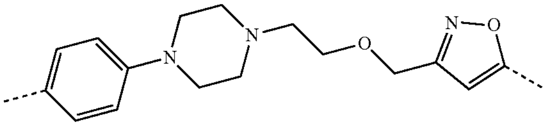;
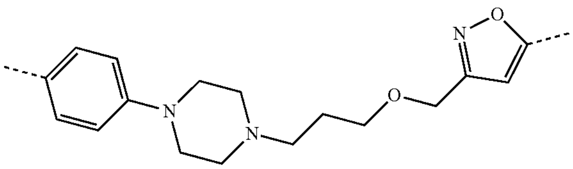;
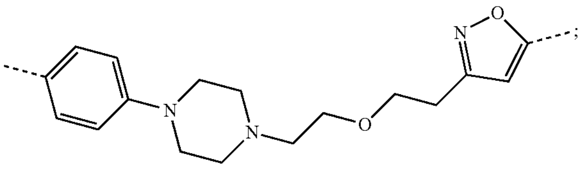;
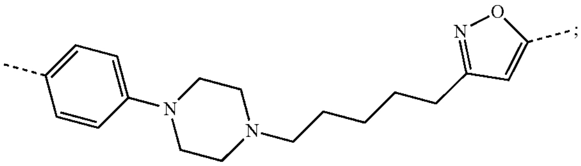;
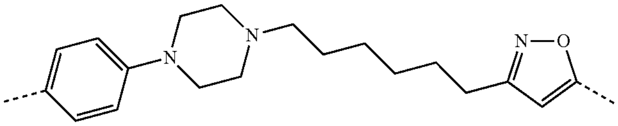;
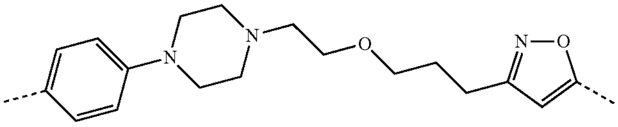;
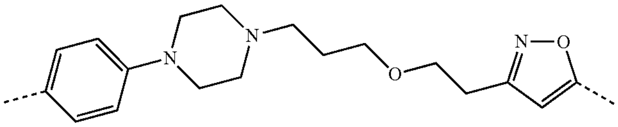;
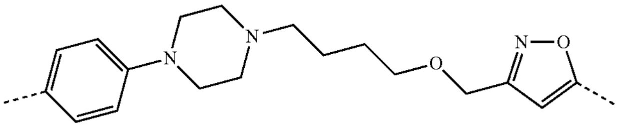;

-continued
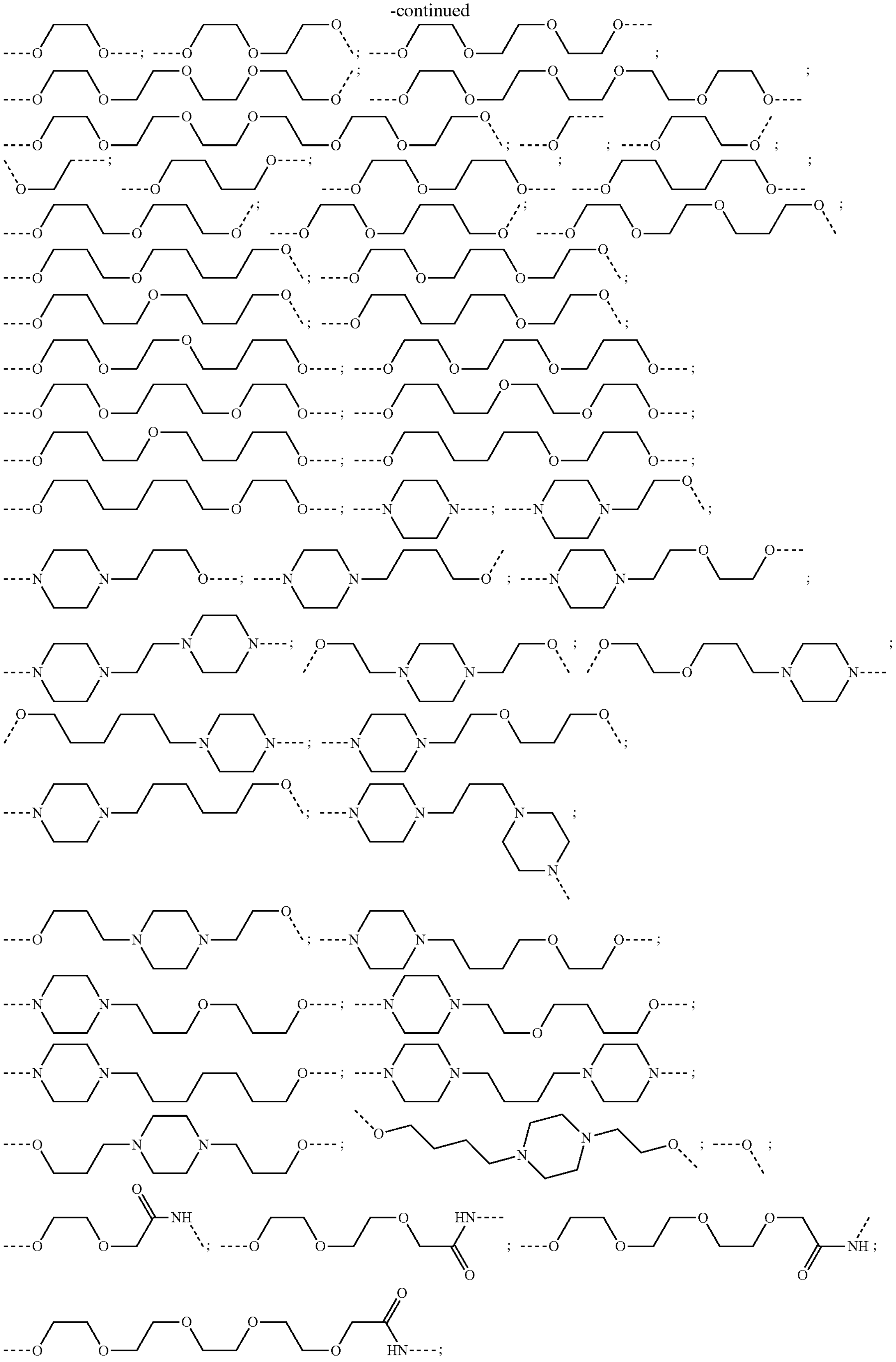

-continued
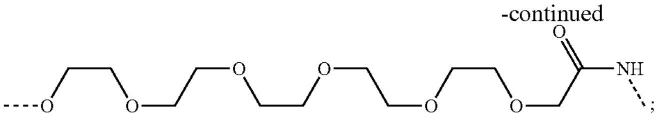 ;
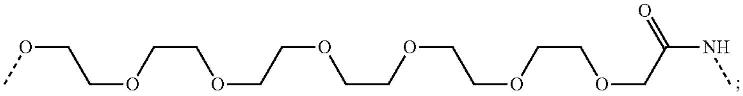 ; 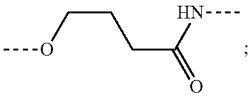 ;
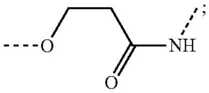 ; 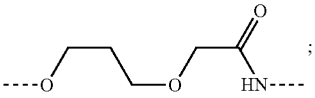 ; 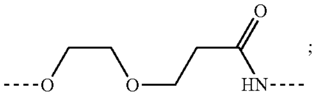 ;
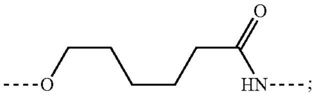 ; 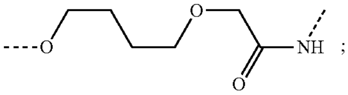 ; 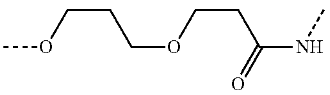 ;
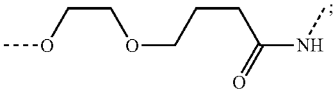 ; 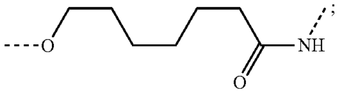 ; 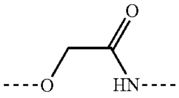 ;
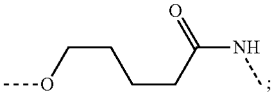 ; 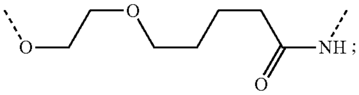 ; 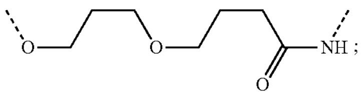 ;
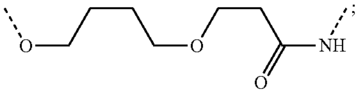 ; 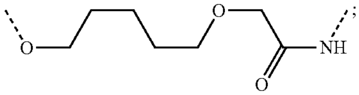 ;
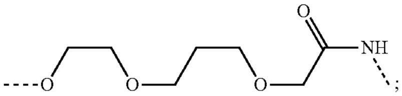 ; 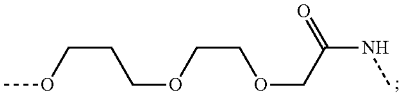 ;
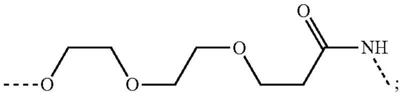 ; 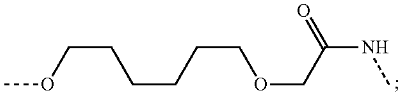 ;
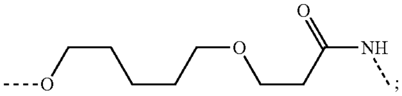 ; 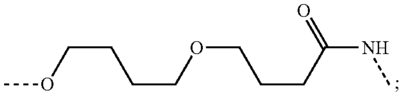 ;
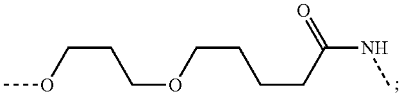 ; 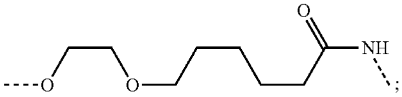 ;
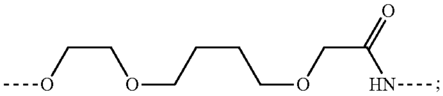 ; 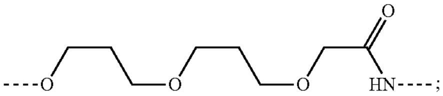 ;
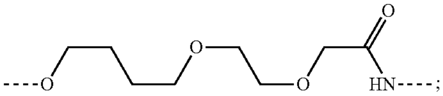 ; 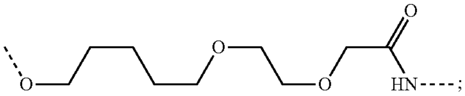 ;
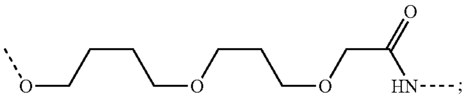 ; 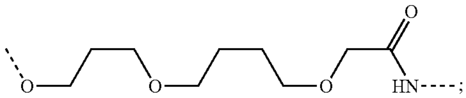 ;
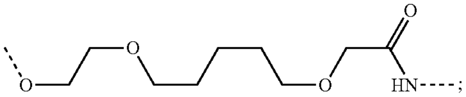 ; 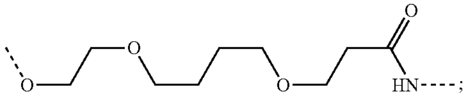 ;
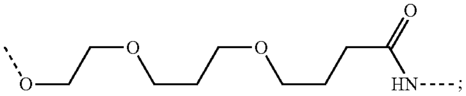 ; 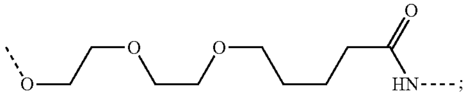 ;

-continued
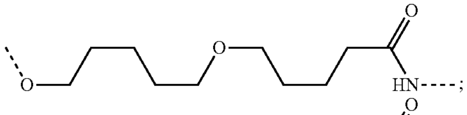;
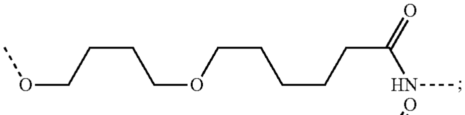;
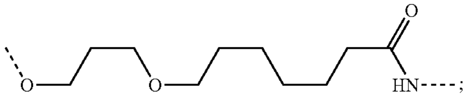;
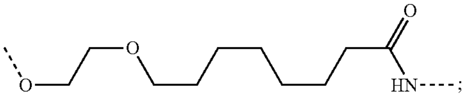;
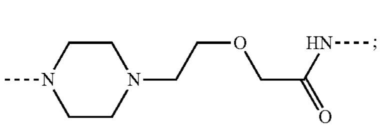;
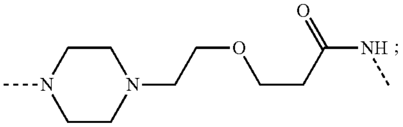;
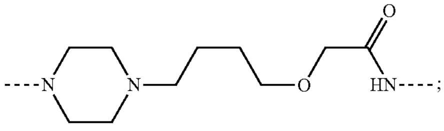;
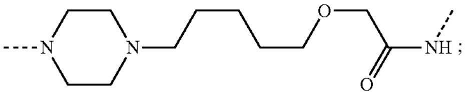;
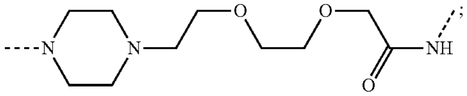;
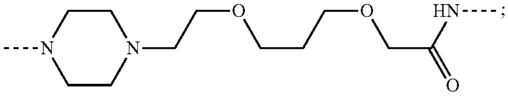;
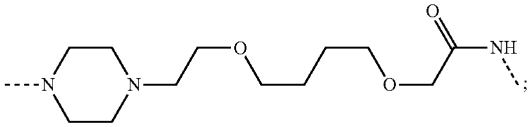;
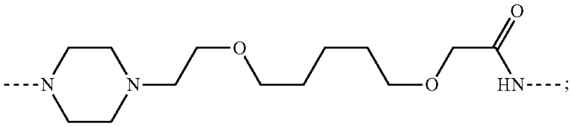;
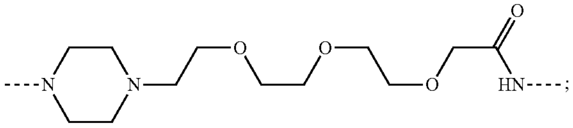;
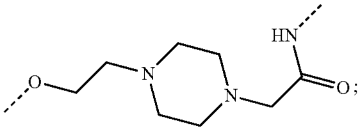;
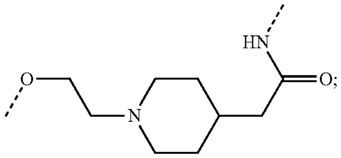;
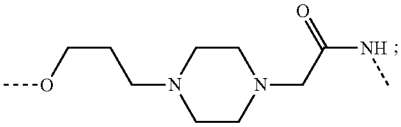;
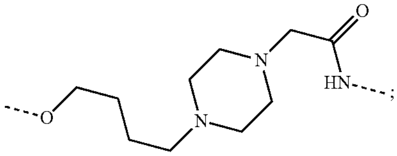;
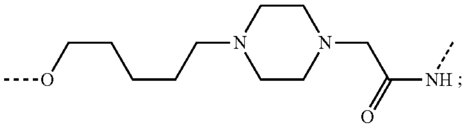;
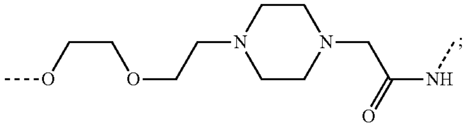;
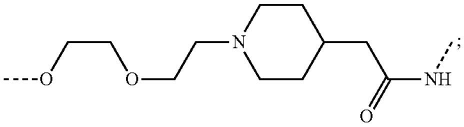;
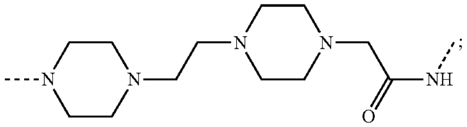;
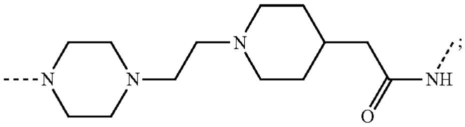;
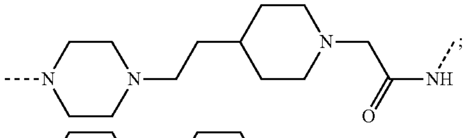;
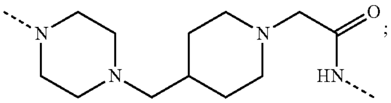;
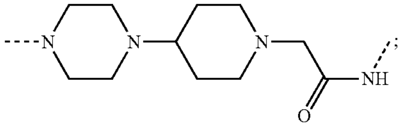;
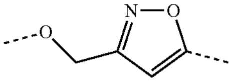;
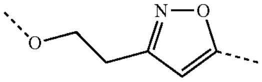;
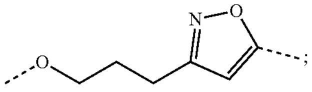;
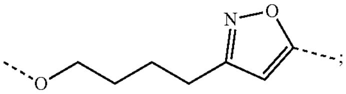;
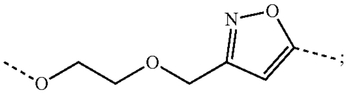;

-continued
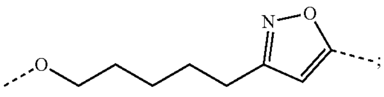; 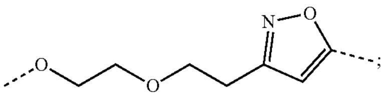;
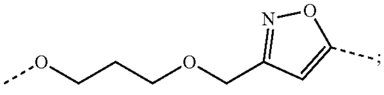; 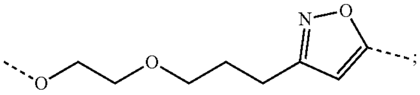;
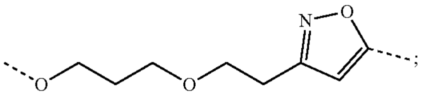; 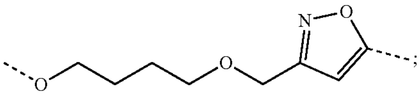;
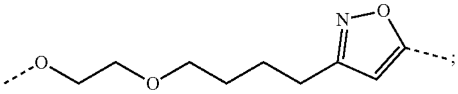; 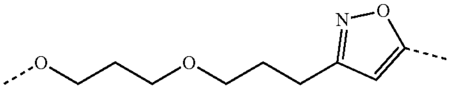;
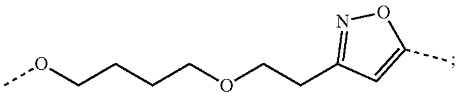; 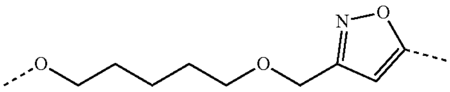;
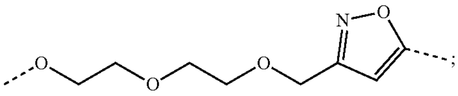; 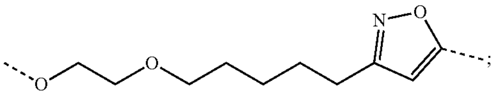;
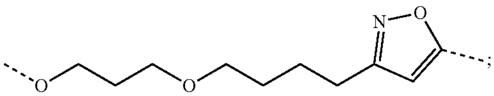; 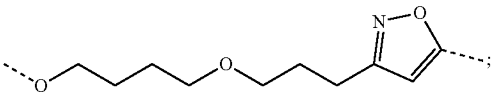;
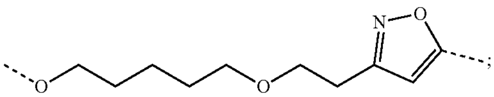; 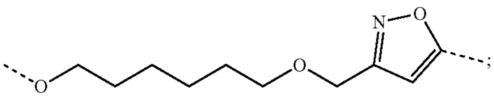;
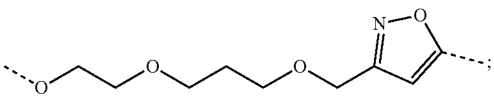; 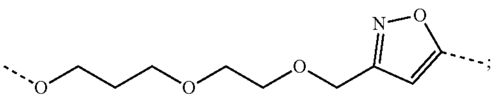;
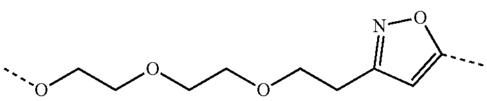; 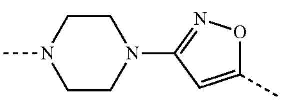; 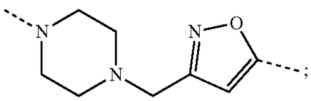;
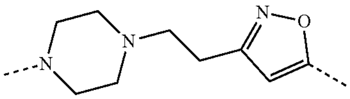; 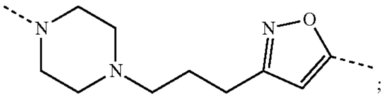;
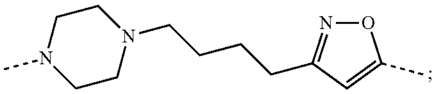; 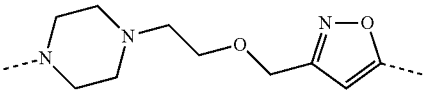;
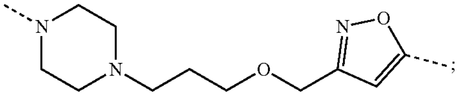; 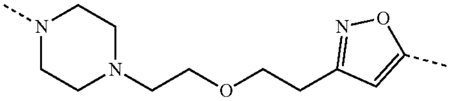;
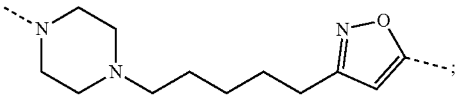; 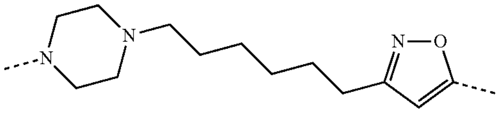;
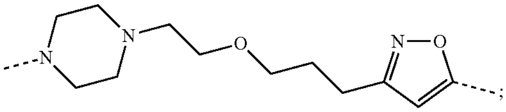; 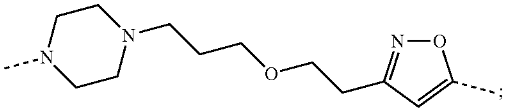;
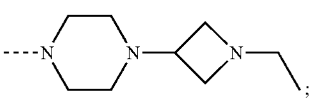; and 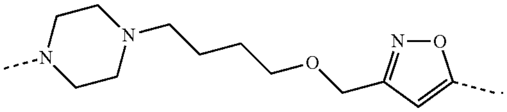.

In any aspect or embodiment described herein, the linker (L) is selected from:
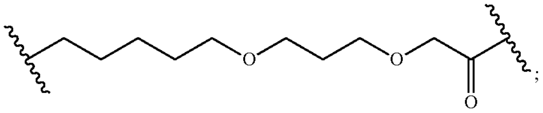
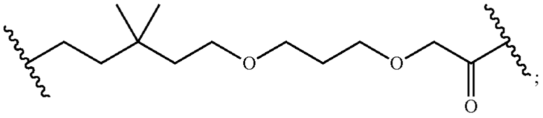
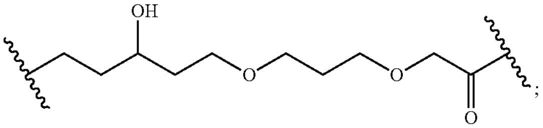
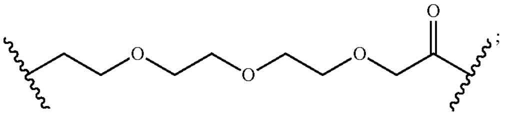
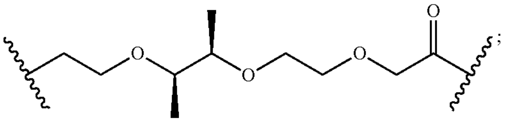
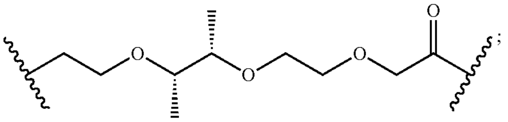
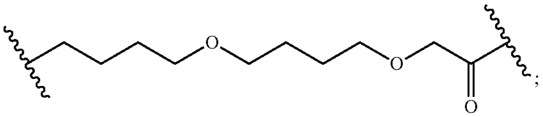
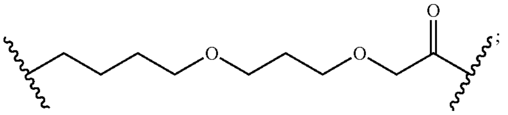
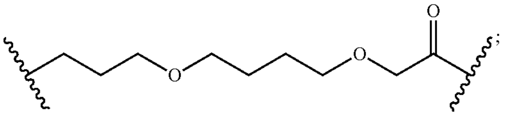
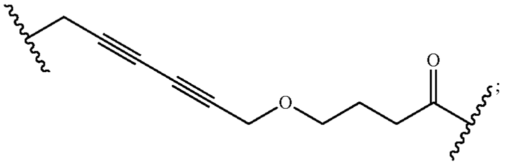
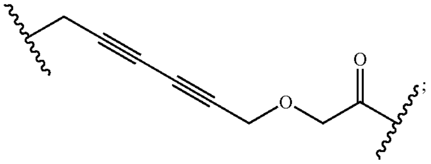
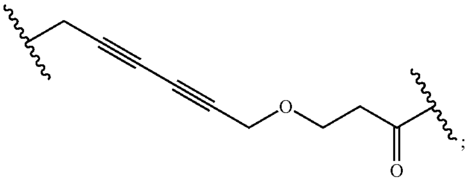
-continued
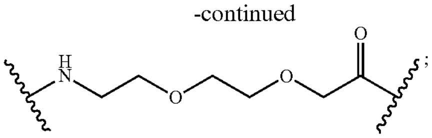
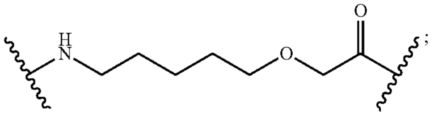
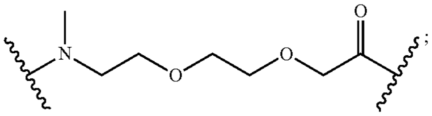
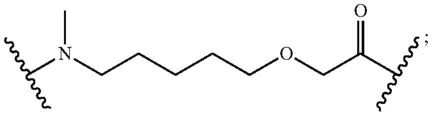
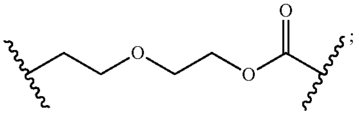
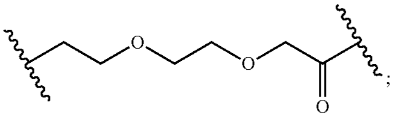
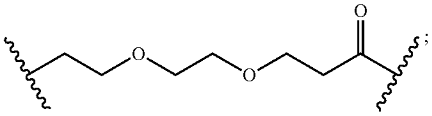
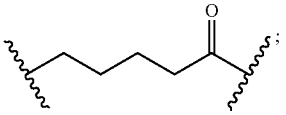
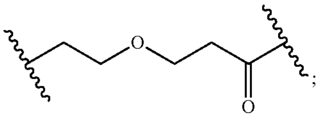
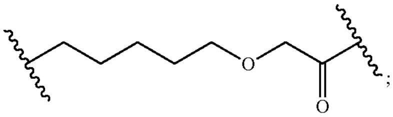
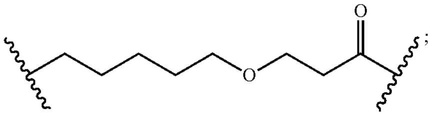
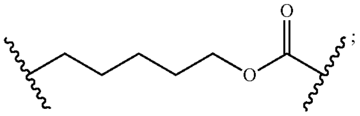
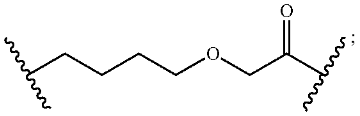
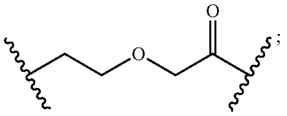
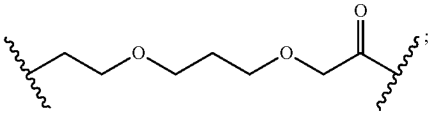

-continued
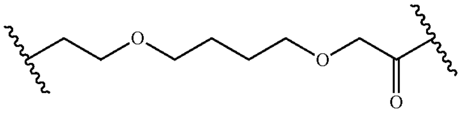
;
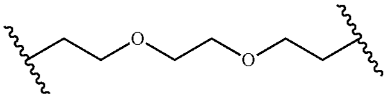
;
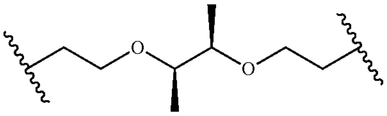
;
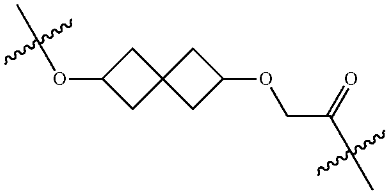
;
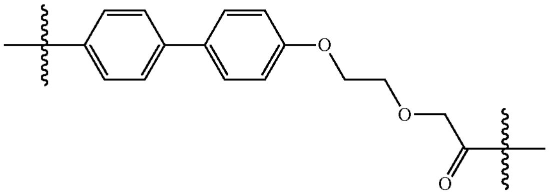
;
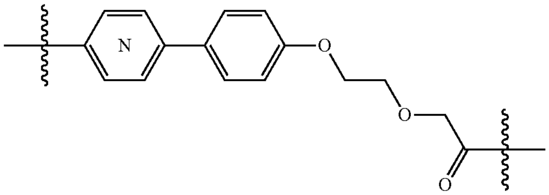
;
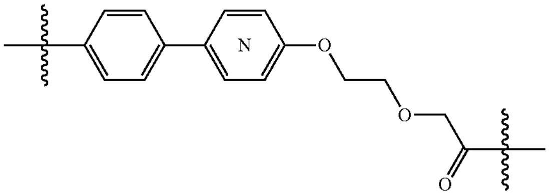
;
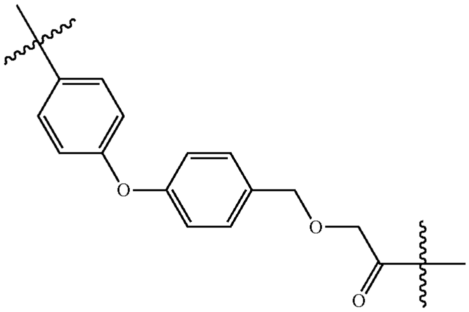
;
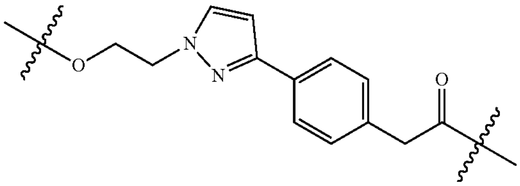
;
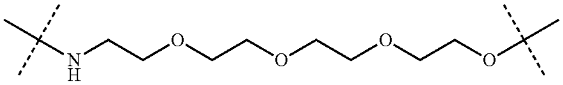
-continued
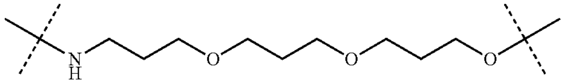
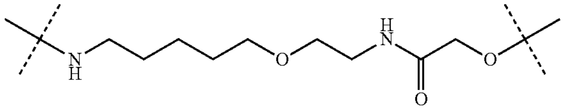
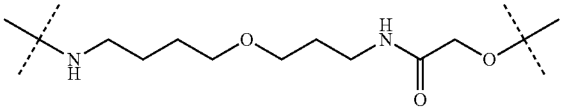
,
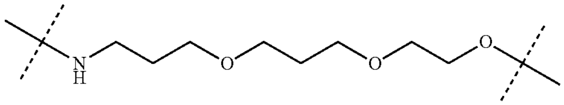
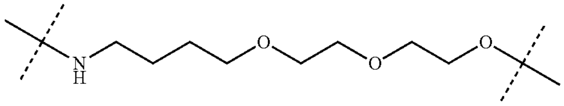
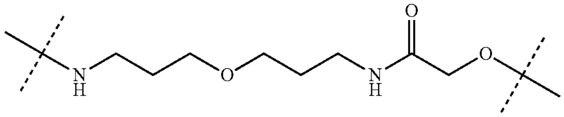
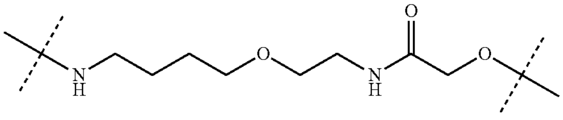
,
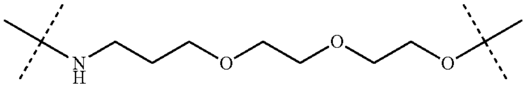
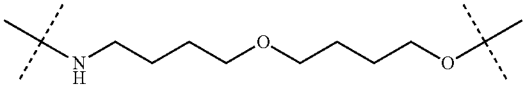
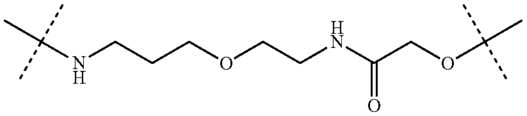
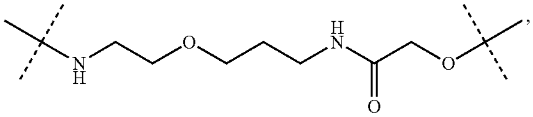
,
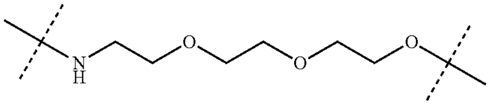
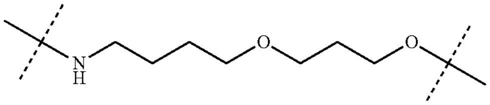
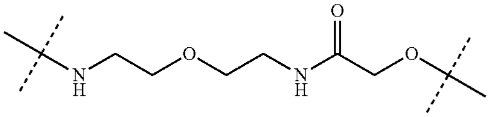
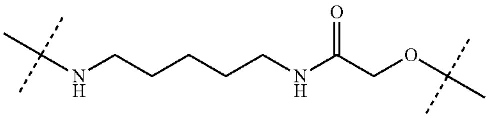
,
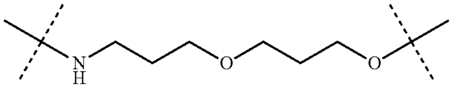

-continued
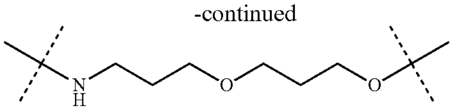
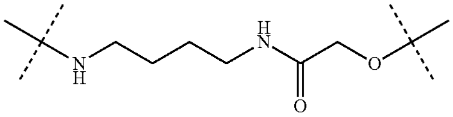
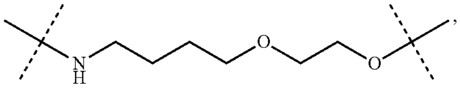
,
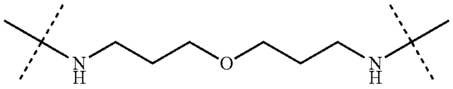
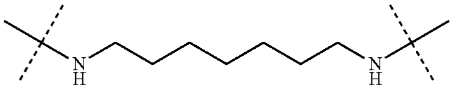
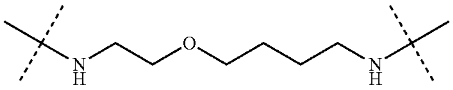
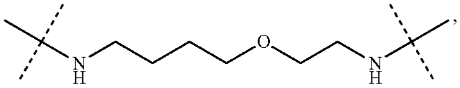
,
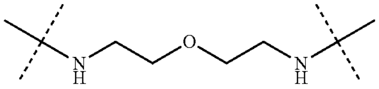
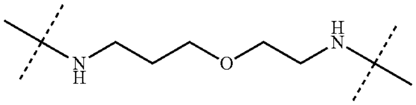
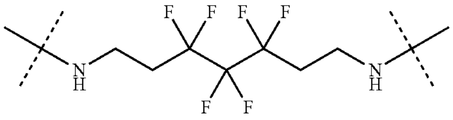
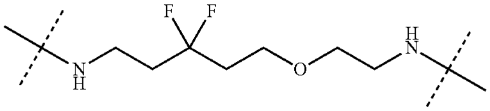
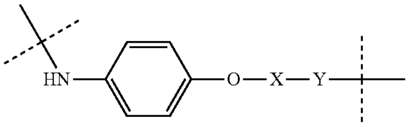
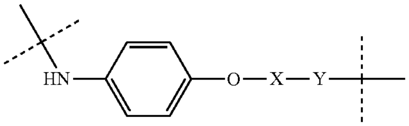
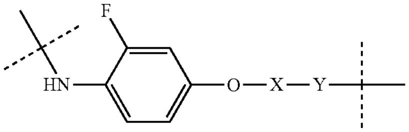
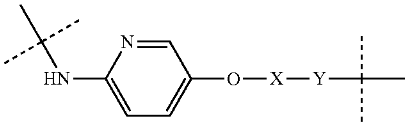
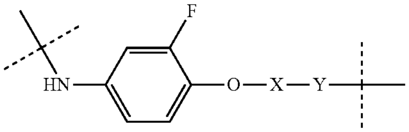
-continued
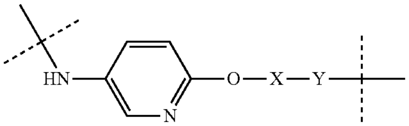
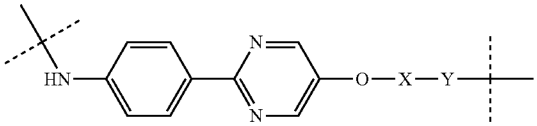
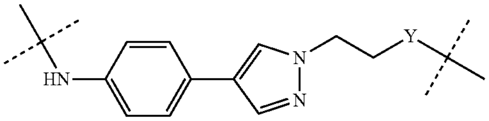
,
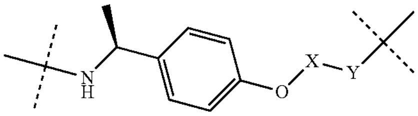
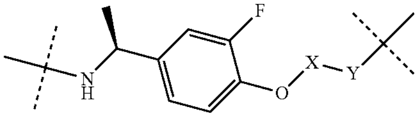
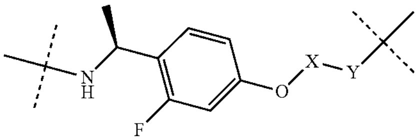
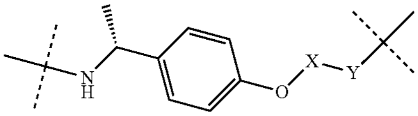
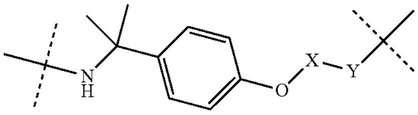
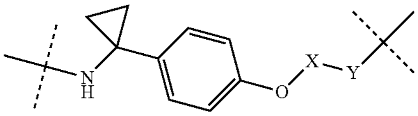
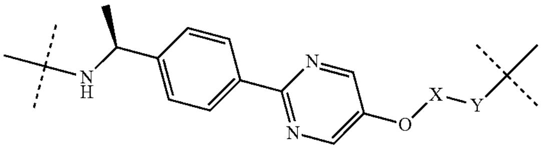
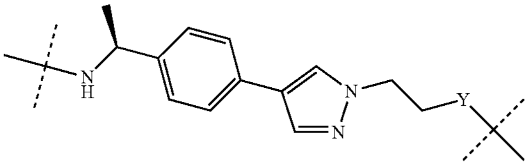
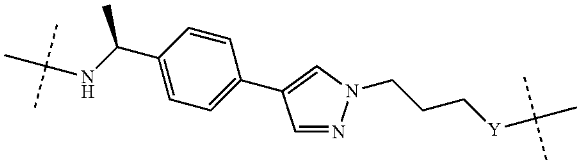
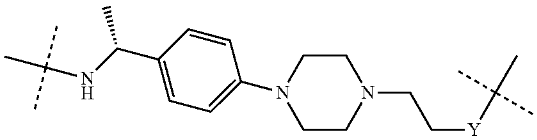

-continued

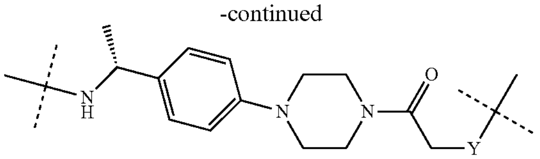

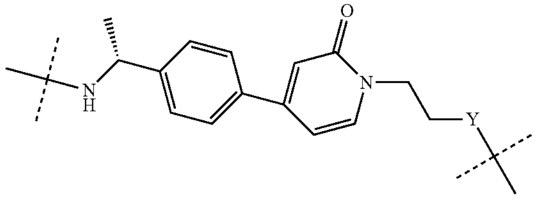

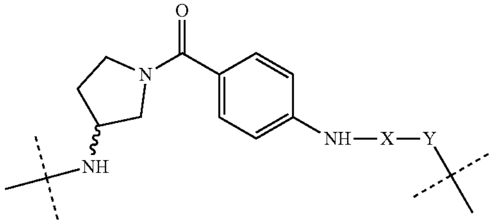

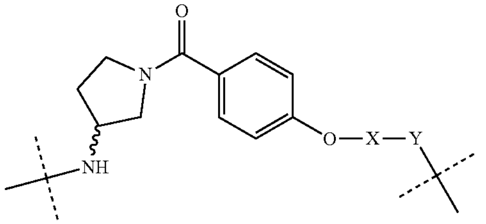

wherein:

"X" in above structures can be linear chain with atoms ranging from 2 to 14, and the mentioned chain can contain heteroatoms such as oxygen; and "Y" in above structures can be O, N, $S(O)_n$ (n=0, 1, 2).

In any aspect or embodiment described herein, the linker (L) comprises a structure selected from:

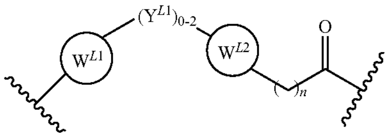

or

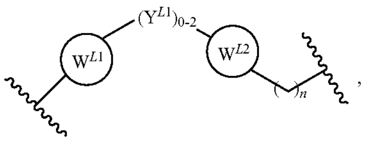

wherein:

$W^{L1}$ and $W^{L2}$ are each independently a 4-8 membered ring with 0-4 heteroatoms, optionally substituted with $R^Q$, each $R^Q$ is independently a H, halo, OH, CN, $CF_3$, $C_1$-$C_6$ alkyl (linear, branched, optionally substituted), $C_1$-$C_6$ alkoxy (linear, branched, optionally substituted), or 2 $R^Q$ groups taken together with the atom they are attached to, form a 4-8 membered ring system containing 0-4 heteroatoms;

$Y^{L1}$ is each independently a bond, $C_1$-$C_6$ alkyl (linear, branched, optionally substituted) and optionally one or more C atoms are replaced with O; or $C_1$-$C_6$ alkoxy (linear, branched, optionally substituted);

n is 0-10; and a dashed line indicates the attachment point to the PTM or CLM moieties.

In any aspect or embodiment described herein, the linker (L) comprises a structure selected from:

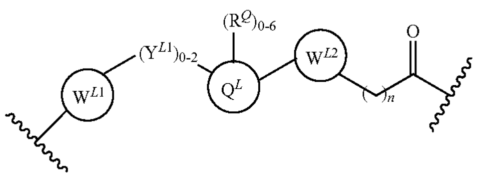

or

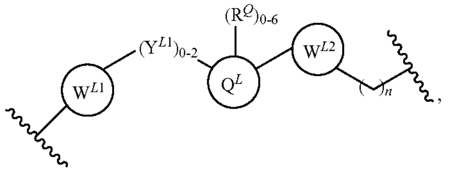

wherein:

$W^{L1}$ and $W^{L2}$ are each independently aryl, heteroaryl, cyclic, heterocyclic, $C_{1-6}$ alkyl, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C═O, C═S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or CLM moieties.

In any aspect or embodiment described herein, the linker (L) is a polyethylenoxy group optionally substituted with aryl or phenyl comprising from 1 to 10 ethylene glycol units.

In any aspect or embodiment described herein, the compound comprises multiple ULMs, multiple CLMs, multiple PTMs, multiple linkers or any combinations thereof.

In any aspect or embodiment described herein, the PTM has a chemical structure including at least one of (A), (B), (C), (D), (E), or a combination thereof:

(A) an estrogen receptor binding moiety (EBM) comprising PTM-I or PTM-II:

PTM-I

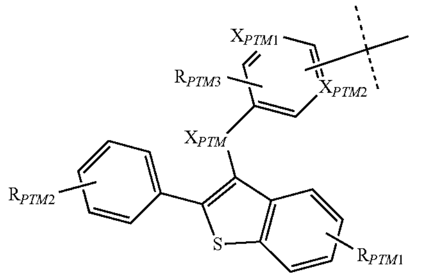

and

PTM-II

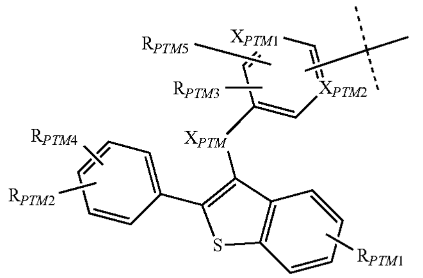

, wherein:

$X_{PTM}$ is O or C═O;

each of $X_{PTM1}$ and $X_{PTM2}$ is independently selected from N or CH;

$R^{PTM1}$ is independently selected from OH, O(CO)$R_{PTM}$, O-lower alkyl, wherein $R_{PTM}$ is an alkyl or aryl group in the ester;

$R_{PTM2}$ and $R_{PTM4}$ are independently selected from H, OH, halogen, CN, $CF_3$, $SO_2$-alkyl, O-lower alkyl;

$R_{PTM3}$ and $R_{PTM5}$ are independently selected from H, halogen;

PTM2 and at least one $R_{PTM3}$ on each respective rings; and the

indicates the site of attachment of at least one of the linker, the CLM, a CLM', or a combination thereof;

(B) an estrogen receptor protein targeting moiety represented by the chemical structure:

Formula ($I_{PTM}$)

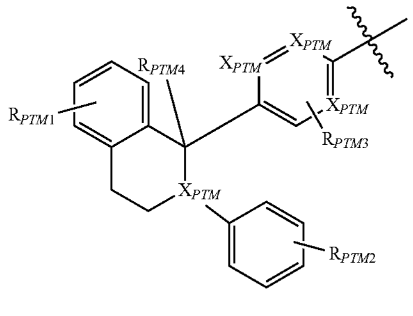

or

-continued

Formula ($II_{PTM}$)

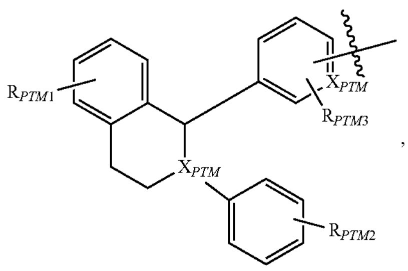

, wherein:

each $X_{PTM}$ is independently CH, N;

 indicates the site of attachment of at least one of the linker, the CLM, a CLM', or a combination thereof;

each $R_{PTM1}$ is independently OH, halogen, alkoxy, methoxy, ethoxy, O(CO)$R_{PTM}$, wherein the substitution can be a mono-, di- or tri-substitution and the $R_{PTM}$ is alkyl or cycloalkyl group with 1 to 6 carbons or aryl groups;

each $R_{PTM2}$ is independently H, halogen, CN, $CF_3$, liner or branched alkyl, alkoxy, methoxy, ethoxy, wherein the substitution can be mono- or di-substitution;

each $R_{PTM3}$ is independently H, halogen, wherein the substitution can be mono- or di-substitution; and $R_{PTM4}$ is a H, alkyl, methyl, ethyl.

(C) an androgen receptor (AR) binding moiety (ABM) comprises a structure selected from the group consisting of:

ABM-a

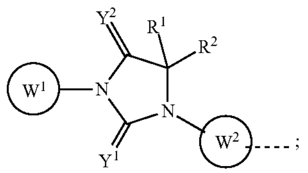

ABM-b

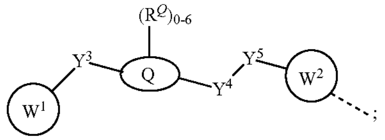

ABM-c

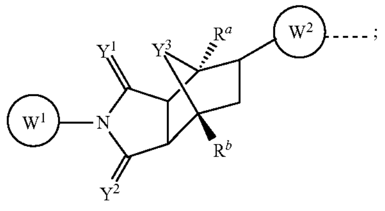

and

ABM-d

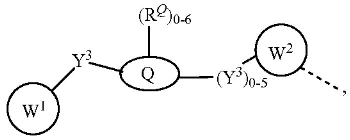

wherein:

$W^1$ is aryl, heteroaryl, bicyclic, or biheterocyclic, each independently substituted by 1 or more H, halo, hydroxyl, nitro, CN, C≡CH, $C_{1-6}$ alkyl (linear, branched, optionally substituted; for example, optionally substituted by 1 or more halo, $C_{1-6}$ alkoxyl), $C_{1-6}$ alkoxyl (linear, branched, optionally substituted; for example, optionally substituted by 1 or more halo), $C_{2-6}$ alkenyl, $C_{2-6}$ alkynyl, or $CF_3$;

$Y^1$, $Y^2$ are each independently $NR^{Y1}$, O, S, SO2, heteroaryl, or aryl;

$Y^3$, $Y^4$, $Y^5$ are each independently a bond, O, $NR^{Y2}$, $CR^{Y1}R^{Y2}$, C═O, C═S, SO, $SO_2$, heteroaryl, or aryl;

Q is a 3-6 membered ring with 0-4 heteroatoms, optionally substituted with 0-6 $R^Q$, each $R^Q$, is independently H, $C_{1-6}$ alkyl (linear, branched, optionally substituted, for example, optionally substituted by 1 or more halo, $C_{1-6}$ alkoxyl), halogen, $C_{1-6}$ alkoxy, or 2 $R^Q$ groups taken together with the atom they are attached to, form a 3-8 membered ring system containing 0-2 heteroatoms);

$R^1$, $R^2$, $R^a$, $R^b$, $R^{Y1}$, $R^{Y2}$ are each independently H, $C_{1-6}$ alkyl (linear, branched, optionally substituted; for example, optionally substituted by 1 or more halo, $C_{1-6}$ alkoxyl), halogen, $C_{1-6}$ alkoxy, cyclic, heterocyclic or $R^1$, $R^2$ together with the atom they are attached to, form a 3-8 membered ring system containing 0-2 heteroatoms);

$W^2$ is a bond, $C_{1-6}$ alkyl, $C_{1-6}$ heteroalkyl, O, aryl, heteroaryl, alicyclic, heterocyclic, biheterocyclic, biaryl, or biheteroaryl, each optionally substituted by 1-10 $R^{W2}$;

each $R^{W2}$ is independently H, halo, $C_{1-6}$ alkyl (linear or branched optionally substituted; for example, optionally substituted by 1 or more F), —$OR^{W2A}$, $C_{3-6}$ cycloalkyl, $C_{4-6}$ cycloheteroalkyl, $C_{1-6}$ alkyl (optionally substituted), heterocyclic (optionally substituted), aryl (optionally substituted), or heteroaryl (optionally substituted), bicyclic hereoaryl or aryl, $OC_{1-3}$alkyl (optionally substituted; for example, optionally substituted by 1 or more —F), OH, $NH_2$, $NR^{Y1}R^{Y2}$, CN;

$R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl; and the dashed line indicates the site of attachment of at least one of the linker, the CLM, a CLM', or a combination thereof;

(D) a Tau proteion targeting moiety that is represented by at least one of Formula I-XI:

I

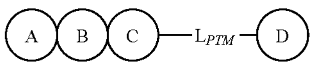

II

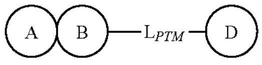

III

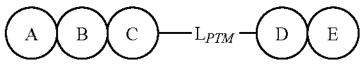

IV

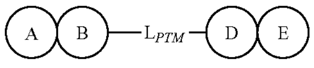

V

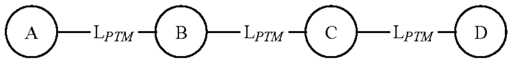

-continued

VI

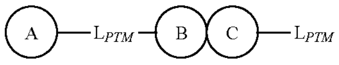

VII

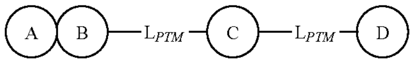

VIII

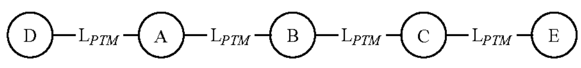

IX

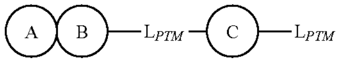

X

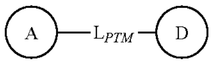

XI

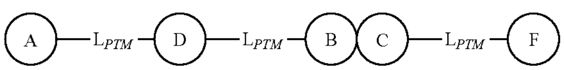, wherein:

A, B, C, D, E, and F are independently selected from an optionally substituted 5- or 6-membered aryl or heteroaryl ring, an optionally substituted 4- to 7-membered cycloalkyl or a heterocycloalkyl, where contact between circles indicates ring fusion;

$L_{PTM}$ is selected from a bond, an alkyl, an alkenyl or an alkynyl, optionally interrupted by one or more rings (i.e., cycloalkyl, heterocycloalkyl, aryl or heteroaryl), or one or more functional groups selected from the groups —O—, —S—, —$NR^1_{PTM}$—, —N═N—, —S(O)—, —$SO_2$—, —C(O)—, —NHC(O)—, —C(O)NH—, —$NHSO_2$—, —NHC(O)NH—, —NHC(O)O—, or —OC(O)NH—, wherein the said functional group is optionally located at either end of the linker; and $R^1_{PTM}$ is selected from H or alkyl.

(E) a tricyclic diazepine or azepine BET/BRD4 binding ligand comprising a group according to the chemical structure PTM-a:

PTM-a

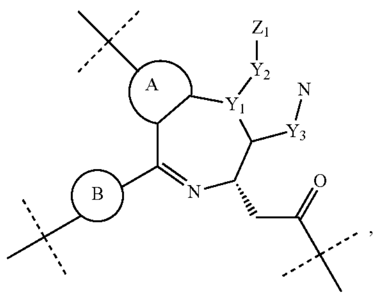, wherein:

$Y_1$, $Y_2$ and $Y_3$ are independently selected from the group of carbon, nitrogen or oxygen and together with the atoms to form an aromatic fused ring.

A and B are independently selected from the group of a 5-membered aromatic ring, a 6-membered aromatic ring, a heteroaromatic ring, a carbocyclic, a thiophene a pyrrole ring, a pyridine, a pyrimidine, a pyrazine, a pyrazole ring each optionally substituted with alkyl, alkoxy, halogen, an aromatic and a heteroaromatic ring; wherein ring A is fused to the central azepine (Y1=C) or diazepine (Y1=N) moiety; and Z1 is selected from the group of methyl or analkyl group, and wherein the dashed line indicates the site of attachment of at least one of the linker, the CLM, a CLM', or a combination thereof.

In any aspect or embodiment described herein, in the Tau protein targeting moiety, at least one of:

at least one of A, B, C, F, or a combination thereof is selected from optionally substituted 5- or 6-membered aryl or heteroaryl rings;

aryl and heteroaryl rings of A, B, C, D and E of PTM are optionally substituted with 1-8 sub stituents each independently selected from alkyl, alkenyl, haloalkyl, halogen, hydroxyl, alkoxy, fluoroalkoxy, amino, alkylamino, dialkylamino, acylamino, trifluoromethyl and cyano, wherein the said alkyl and alkenyl groups are further optionally substituted; or a combination thereof.

In any aspect or embodiment described herein, the PTM is Formula I and:

A, B and C rings are independently 5- or 6-membered fused aryl or heteroaryl rings;

$L_{PTM}$ is selected from a bond or an alkyl; and

D is selected from a 6-membered aryl, heteroaryl or heterocycloalkyl, wherein A, B, C and D are optionally substituted with alkyl, haloalkyl, halogen, hydroxyl, alkoxy, amino, alkylamino, dialkylamino, trifluoromethyl or cyano.

In any aspect or embodiment described herein, the PTM is Formula I and:

A and C are a phenyl or a 6-membered heteroaryl ring;

B is a 5-membered heteroaryl ring;

$L_{PTM}$ is a bond; and

D is a 6-membered heteroaryl or a 6-membered heterocycloalkyl ring, wherein each A, B, C and D is optionally independently substituted with alkyl, haloalkyl, halogen, hydroxyl, alkoxy, amino, dialkylamino, trifluoromethyl, or cyano, and wherein a nitrogen atom of any of the A, B, C and D rings is not directly connected to a heteroatom or to a carbon atom, to which another heteroatom is directly attached.

In any aspect or embodiment described herein, the PTM is Formula III or IV and:

A, B and C are 5- or 6-membered fused aryl or heteroaryl rings;

$L_{PTM}$ is selected from a bond or an alkyl; and

D and E are 5- or 6-membered fused aryl or heteroaryl rings;

wherein A, B, C, D and E are optionally substituted with alkyl, haloalkyl, halogen, hydroxyl, alkoxy, amino, alkylamino, dialkylamino, trifluoromethyl, or cyano.

In any aspect or embodiment described herein, the PTM has a structure selected from the group consisting of:

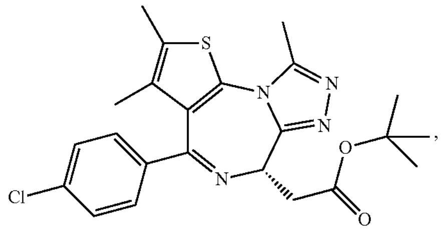

-continued

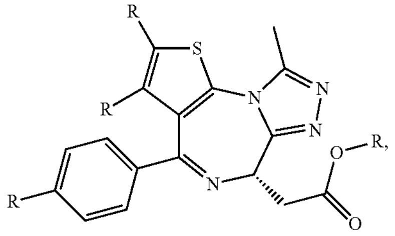

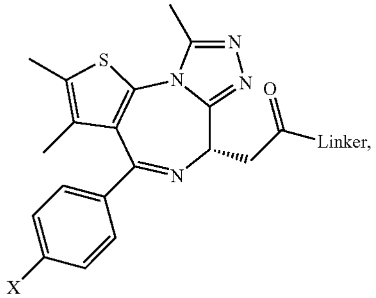

X = Cl, Br, F, H

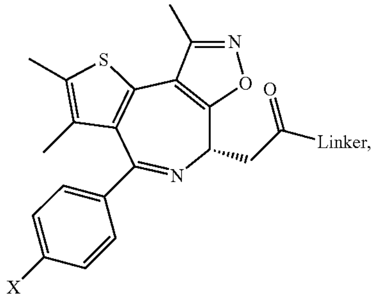

X = Cl, Br, F, H

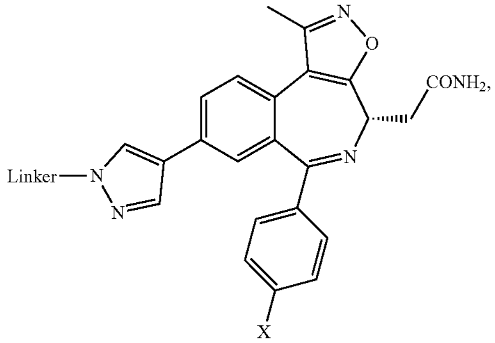

X = Cl, Br, F, H

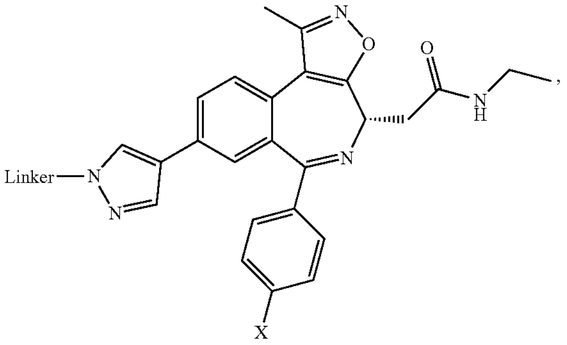

X = Cl, Br, F, H

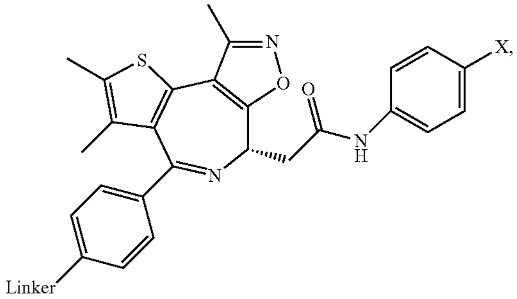
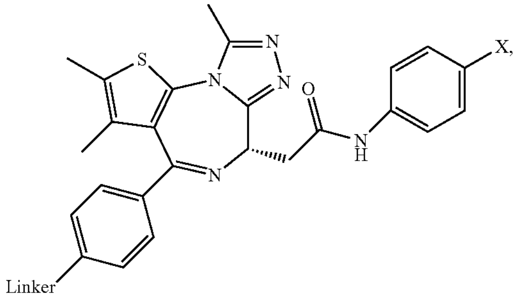
X = H, F
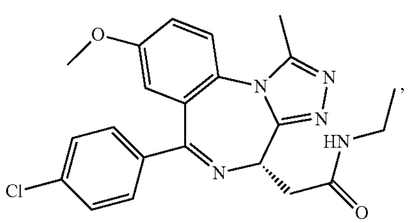
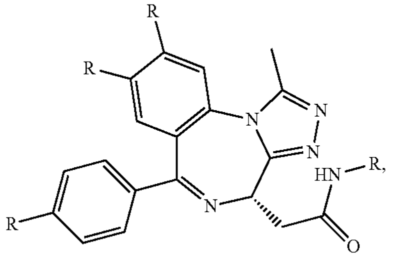
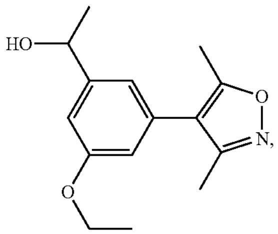
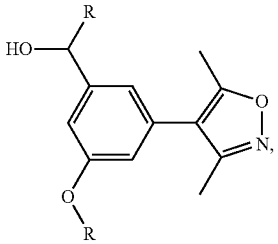
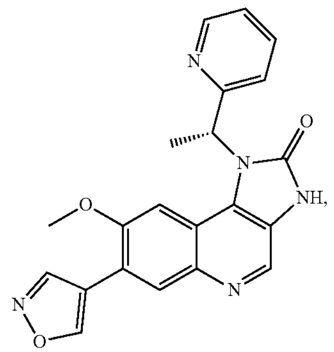
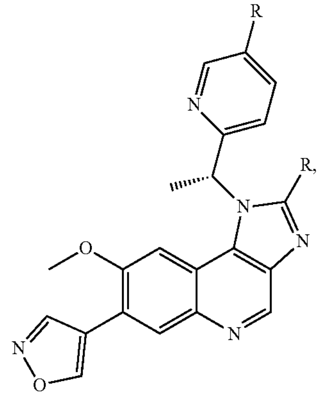
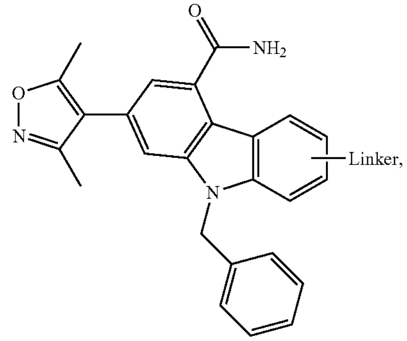
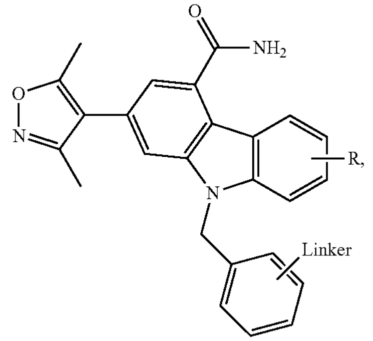

-continued

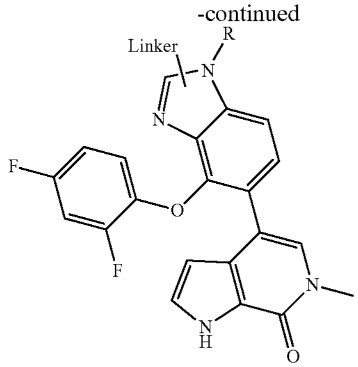
,
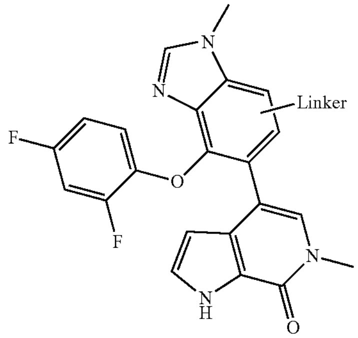
,
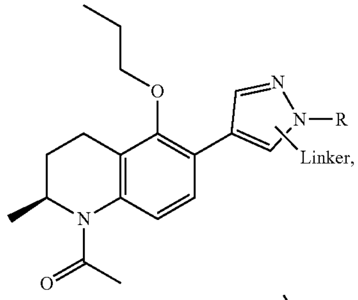
,
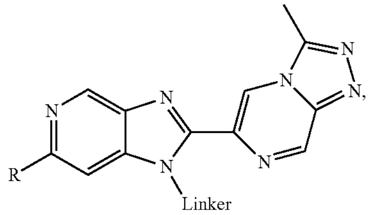
,
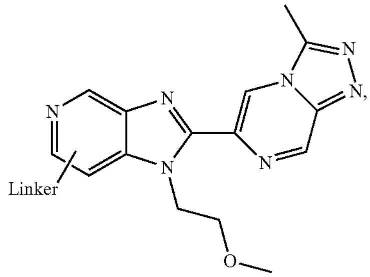
,
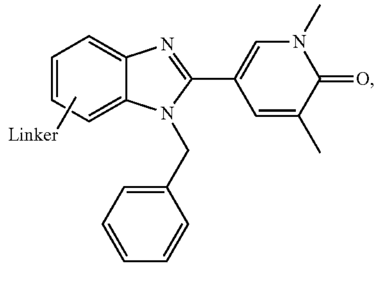
,
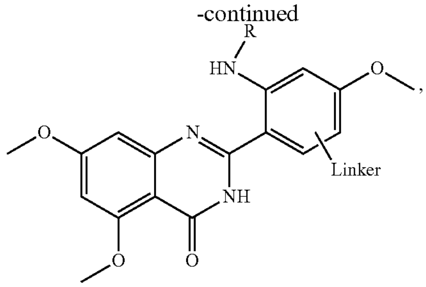
,
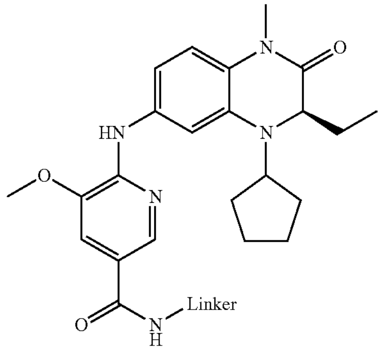
; and
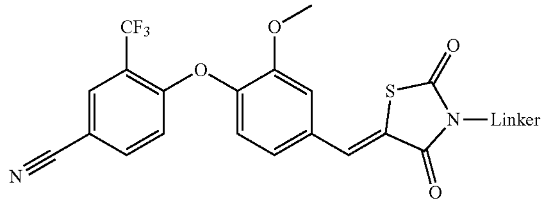

wherein R or Linker is a bond or a chemical linker moiety coupling the CLM to the PTM, including pharmaceutically acceptable salt forms thereof.

In any aspect or embodiment described herein, the compound is selected from the group consisting of PRO TAC-1 through PRO TAC-112.

In any aspect or embodiment described herein, the compound is selected from the group consisting of:

4-{3-[4-({1-[5-chloro-1-(2,6-dioxopiperidin-3-yl)-6-oxo-1,6-dihydropyridazin-4-yl]-1,4,7,10-tetraoxadodecan-12-yl}oxy)phenyl]-4,4-dimethyl-5-oxo-2-sulfanylideneimidazolidin-1-yl}-2-(trifluoromethyl)benzonitrile;

4-{3-[4-(2-{2-[4-(2-[1-(2,6-dioxopiperidin-3-yl)-6-oxo-1,6-dihydropyridazin yl]oxylethyl)piperazin-1-yl]ethoxy}ethoxy)phenyl]-4,4-dimethyl-5-oxo-2-sulfanylideneimidazolidin-1-yl}-2-(trifluoromethyl) benzonitrile;

4-[3-(4-{2-[4-(2-{[5-chloro-1-(2,6-dioxopiperidin-3-yl)-6-oxo-1,6-dihydropyridazin-4-yl]oxy}ethyl)piperazin-1-yl]ethoxy}phenyl)-4,4-dimethyl-5-oxo-2-sulfanylideneimidazolidin-1-yl]-2-(trifluoromethyl)benzonitrile;

6-{4-[5-({6-[(2,6-dioxopiperidin-3-yl)carbamoyl]pyridin-3-yl}oxy)pentyl]piperazin-1-yl}-N-[(1r,3r)-3-(3-chloro-4-cyanophenoxy)-2,2,4,4-tetramethylcyclobutyl]pyridine-3-carboxamide;

6-[4-(5-{[3-(2,6-dioxopiperidin-3-yl)-2-methyl-4-oxo-1,2,3,4-tetrahydroquinazolin-8-yl]oxy}pentyl)piperazin-1-yl]-N-[(1r,3 r)-3-(3-chloro-4-cyanophenoxy)-2,2,4,4-tetramethylcyclobutyl]pyridine-3-carboxamide;

6-[4-(6-{[1-(2,6-dioxopiperidin-3-yl)-6-oxo-1,6-dihydropyridazin-4-yl]oxy}hexyl)piperazin-1-yl]-N-[(1r,3r)-3-(3-chloro-4-cyanophenoxy)-2,2,4,4-tetramethylcyclobutyl]pyridine-3-carboxamide;

6-[4-(5-{[3-(2,6-dioxopiperidin-3-yl)-2-methyl-4-oxo-3,4-dihydroquinazolin-8-yl]oxy}pentyl)piperazin-1-yl]-N-[(1r,3r)-3-(3-chloro-4-cyanophenoxy)-2,2,4,4-tetramethylcyclobutyl]pyridine-3-carboxamide;

5-(5-{4-[2-(4-{3-[4-cyano-3-(trifluoromethyl)phenyl]-5,5-dimethyl-4-oxo-2-sulfanylideneimidazolidin-1-yl}phenoxy)ethyl]piperazin-1-yl}-1,3-dioxo-2,3-dihydro-1H-isoindol-2-yl)-6-oxo-1,6-dihydropyridine-2-carbonitrile;

4-[3-(4-{2-[4-({1-[5-(2,4-dioxo-1,2,3,4-tetrahydropyrimidin-1-yl)pyridin-3-yl]piperidin-4-yl}methyl)piperazin-1-yl]ethoxy}phenyl)-4,4-dimethyl-5-oxo-2-sulfanylideneimidazolidin-1-yl]-2-(trifluoromethyl)benzonitrile;

4-[3-(4-{[3-(3-{[3-(2,4-dioxo-1,2,3,4-tetrahydropyrimidin-1-yl)quinolin-5-yl]oxy}propoxy)propyl]amino}phenyl)-4,4-dimethyl-5-oxo-2-sulfanylideneimidazolidin-1-yl]-2-(trifluoromethyl)benzonitrile;

4-[3-(4-{[3-(3-{[3-(2,4-dioxo-1,2,3,4-tetrahydropyrimidin-1-yl)quinolin-5-yl]oxy}propoxy)propyl]amino}phenyl)-4,4-dimethyl-5-oxo-2-sulfanylideneimidazolidin-1-yl]-2-(trifluoromethyl)benzonitrile;

4-[4-(2-{2-[(2-{[2-(2,4-dioxo-1,3-diazinan-1-yl)ethyl]carbamoyl}phenyl)amino]ethoxy}ethyl)piperazin-1-yl]-N-[(1r,3r)-3-(3-chloro-4-cyanophenoxy)-2,2,4,4-tetramethylcyclobutyl]benzamide;

5-(4-{2-[(1,3-dioxo-2-{6-oxo-2-oxa-5-azaspiro[3.5]nonan-9-yl}-2,3-dihydro-1H-isoindol-4-yl)amino]ethyl}piperazin-1-yl)-N-[1r,3r)-3-(3-chloro-4-cyanophenoxy)-2,2,4,4-tetramethylcyclobutyl]pyridine-2-carboxamide;

4-(4,4-dimethyl-3-{4-[4-(3-{[2-(1-methyl-2,4-dioxo-1,2,3,4-tetrahydropyrimidin-5-yl)-1,3-dioxo-2,3-dihydro-1H-isoindol-5-yl]oxy}propyl)piperazin-1-yl]phenyl}-5-oxo-2-sulfanylideneimidazolidin-1-yl)-2-(trifluoromethyl)benzonitrile;

5-[4-(2-{[2-(5,5-dimethyl-2,4-dioxoimidazolidin-1-yl)-3-oxo-octahydroindolizin-6-yl]amino}ethyl)piperazin-1-yl]-N-[(1r,3 r)-3-(3-chloro-4-cyanophenoxy)-2,2,4,4-tetramethylcyclobutyl]pyri dine-2-carboxamide;

4-[3-(4-{[3-(3-{[4-(2,4-dioxo-1,2,3,4-tetrahydropyrimidin-1-yl)isoquinolin-7-yl]oxy}propoxy)propyl]amino}phenyl)-4,4-dimethyl-5-oxo-2-sulfanylideneimidazolidin-1-yl]-2-(trifluoromethyl)benzonitrile;

4-[3-(4-{1-[3-(2,4-dioxo-1,2,3,4-tetrahydropyrimi din-1-yl)-4-methylquinolin-7-yl]-1,4,7-trioxa-10-azadecan-10-yl}phenyl)-4,4-dimethyl-5-oxo-2-sulfanylideneimidazolidin-1-yl]-2-(trifluoromethyl)b enzonitrile;

4-[2-(2-{[3-(2,4-dioxo-1,3-diazinan-1-yl)-4-methylquinolin-7-yl]oxy}ethoxy)ethoxy]-N-[(1r,3r)-3-(3-chloro-4-cyanophenoxy)-2,2,4,4-tetramethylcyclobutyl]benzamide;

5-{3-[4-(1,3-dioxo-2-{6-oxo-2-oxa-5-azaspiro[3.5]nonan-9-yl}-2,3-dihydro-1H-isoindol-5-yl)piperazin-1-yl]propyl}-N-[(1r,3 r)-3-(3-chloro-4-cyanophenoxy)-2,2,4,4-tetramethylcyclobutyl]pyri dine-2-carboxamide;

4-{4-[2-(2-{[1-(2,6-dioxopiperidin-3-yl)-6-oxo-1,6-dihydropyridazin-4-yl]amino}ethoxy)ethyl]piperazin-1-yl}-N-[(1r,3r)-3-(3-chloro-4-cyanophenoxy)-2,2,4,4-tetramethylcyclobutyl]benzamide;

4-[4-({1-[5-(2,4-dioxo-1,2,3,4-tetrahydropyrimidin-1-yl)pyridin-3-yl]piperidin-4-yl}methyl)piperazin-1-yl]-N-[(1r,3r)-3-(3-chloro-4-cyanophenoxy)-2,2,4,4-tetramethylcyclobutyl]benzamide;

4-(4-{2-[4-(2-{[1-(2,6-dioxopiperidin-3-yl)-6-oxo-1,6-dihydropyridazin-4-yl]oxy}ethyl)piperazin-1-yl]ethoxy}butoxy)-N-[(1r,3r)-3-(3-chloro-4-cyanophenoxy)-2,2,4,4-tetramethylcyclobutyl]benzamide;

2-[(2-{2-[4-(4-{3-[4-cyano-3-(trifluoromethyl)phenyl]-5,5-dimethyl-4-oxo-2-sulfanylideneimidazolidin-1-yl}phenyl)piperazin-1-yl]ethoxy}ethyl)amino]-N-[2-(2,4-dioxo-1,3-diazinan-1-yl)ethyl]benzamide;

2-{[2-(2-{[4-(4-{3-[4-cyano-3-(trifluoromethyl)phenyl]-5,5-dimethyl-4-oxo-2-sulfanylideneimidazolidin-1-yl}phenyl)phenyl]amino}ethoxy)ethyl]amino}-N-[2-(2,4-dioxo-1,3-diazinan-1-yl)ethyl]benzamide;

4-{4-[2-({1,3-dioxo-2-[2-oxo-6-(trifluoromethyl)piperidin-3-yl]-2,3-dihydro-1H-isoindol-4-yl}amino)ethyl]piperazin-1-yl}-N- [(1r,3r)-3-(3-chloro-4-cyanophenoxy)-2,2,4,4-tetramethylcyclobutyl]benzamide;

4-{4-[2-({1,3-dioxo-2-[2-oxo-6-(trifluoromethyl)piperidin-3-yl]-2,3-dihydro-1H-isoindol-5-yl}oxy)ethyl]piperazin-1-yl}-N-[(1r,3r)-3-(3-chloro-4-cyanophenoxy)-2,2,4,4-tetramethylcyclobutyl]benzamide;

4-{4-[2-({1,3-di oxo-2-[2-oxo-6-(trifluoromethyl)-1,2-dihydropyridin-3-yl]-2,3-dihydro-1H-isoindol-4-yl}amino)ethyl]piperazin-1-yl}-N-[(1r,3r)-3-(3-chloro-4-cyanophenoxy)-2,2,4,4-tetramethyl cyclobutyl]benzamide;

4-{4-[2-({1,3-di oxo-2-[2-oxo-6-(trifluoromethyl)-1,2-dihydropyridin-3-yl]-2,3-dihydro-1H-isoindol-5-yl}oxy)ethyl]piperazin-1-yl}-N-[(1r,3 r)-3-(3-chloro-4-cyanophenoxy)-2,2,4,4-tetramethylcyclobutyl]benzamide;

4-[3-(4-{2-[4-(2-{[2-(2,6-dioxopiperidin-3-yl)-1,1,3-tri oxo-2,3-dihydro-1λ$^6$,2-benzothiazol-6-yl]amino}ethyl)piperazin-1-yl]ethoxy}phenyl)-4,4-dimethyl-5-oxo-2-sulfanylideneimidazolidin-1-yl]-2-(trifluoromethyl)benzonitrile;

4-[3-(4-{2-[4-(2-{[2-(2,6-dioxopiperidin-3-yl)-1,1,3-trioxo-2,3-dihydro-1λ$^6$,2-benzothiazol-6-yl]oxy}ethyl)piperazin-1-yl]ethoxy}phenyl)-4,4-dimethyl-5-oxo-2-sulfanylideneimidazolidin-1-yl]-2-(trifluoromethyl)benzonitrile;

6-[4-(5-{[2-(2,6-dioxopiperidin-3-yl)-1,1,3-tri oxo-2,3-dihydro-1λ$^6$,2-benzothiazol-6-yl]oxy}pentyl)piperazin-1-yl]-N-[(1r,3 r)-3-(3-chloro-4-cyanophenoxy)-2,2,4,4-tetramethylcyclobutyl]pyridine-3-carboxamide;

6-[4-(5-{[2-(2,6-dioxopiperidin-3-yl)-1,1,3-trioxo-2,3-dihydro-1λ$^6$,2-benzothiazol-6-yl]amino}pentyl)piperazin-1-yl]-N-[(1r,3 r)-3-(3-chloro-4-cyanophenoxy)-2,2,4,4-tetramethylcyclobutyl]pyridine-3-carboxamide;

6-[4-(5-{[2-(2,6-dioxopiperidin-3-yl)-1,1,3-trioxo-2,3-dihydro-1λ$^6$,2-benzothiazol-7-yl]amino}pentyl)piperazin-1-yl]-N-[(1r,3 r)-3-(3-chloro-4-cyanophenoxy)-2,2,4,4-tetramethylcyclobutyl]pyri dine-3-carboxamide;

6-[4-(5-{[2-(2,6-dioxopiperidin-3-yl)-1,1,3-trioxo-2,3-dihydro-1λ$^6$,2-benzothiazol-7-yl]oxy}pentyl)piperazin-1-yl]-N-[(1r,3 r)-3-(3-chloro-4-cyanophenoxy)-2,2,4,4-tetramethylcyclobutyl]pyridine-3-carboxamide;

4-[3-(4-{2-[2-(2-{[2-(2,6-dioxopiperidin-3-yl)-1,1,3-trioxo-2,3-dihydro-1λ$^6$,2-benzothiazol-6-yl]oxy}ethoxy)ethoxy]ethoxy}phenyl)-4,4-dimethyl-5-oxo-2-sulfanylideneimidazolidin-1-yl]-2-(trifluoromethyl)benzonitrile; and 6-[3-(3-{[2-(2,6-dioxopiperidin-3-yl)-1,1,3-trioxo-2,3-dihydro-1λ$^6$, 2-benzothiazol-6-yl]oxy}propoxy)propoxy]-N-[(1r,3 r)-3-(3-chloro-4-cyanophenoxy)-2,2,4,4-tetramethylcyclobutyl]pyridine-3-carboxamide, including pharmaceutically acceptable salt forms thereof.

Another aspect discloses a composition comprising an effective amount of a bifunctional compound of the present disclosure, and a pharmaceutically acceptable carrier.

In any aspect or embodiment described herein, the composition further comprises at least one of additional bioactive agent or another bifunctional compound of the present disclosure.

In any aspect or embodiment described herein, the additional bioactive agent is anti-cancer agent, an anti-neurodegenerative agent, an antimicrobial agent, an antiviral agent, an anti-HIV agent, or an antifungal agent.

A further aspect disclosuses a composition comprising an effective amount of at least one compound of the present disclosure and a pharmaceutically acceptable carrier, additive, and/or excipient for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with the accumulation and/or aggregation of the target protein.

In any aspect or embodiment described herein, the disease or disorder is selected from the group consisting of asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

In any aspect or embodiment described herein, the disease or disorder is selected from the group consisting of Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

In any aspect or embodiment described herein, the disease or disorder is selected from the group consisting of aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Kennedy's syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymuller syndrome and Xeroderma pigmentosum.

In any aspect or embodiment described herein, wherein the composition further comprising an additional bioactive agent.

In any aspect or embodiment described herein, the additional bioactive agent is at least one of an anti-cancer agent, an anti-neurodegenerative agent, an antimicrobial agent, an antiviral agent, an anti-HIV agent, an antifungal agent, or a combination thereof.

In any aspect or embodiment described herein, the anti-cancer agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6, Azgly 10](pyro-Glu-His-Trp-Ser-Tyr-D-Ser(Bu t)-Leu-Arg-Pro-Azgly-$NH_2$ acetate [$C_{59}H_{84}N_{18}Oi_4$—$(C_2H_4O_2)$x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevac, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

Another aspect discloses a method for inducing degradation of a target protein in a cell comprising administering an effective amount of a compound of the present disclosure to the cell, wherein the compound effectuates degradation of the target protein.

A yet further aspect discloses a composition comprising an effective amount of a compound of the present disclosure for use in a method for treating cancer, said method comprising administering the composition to a patient in need thereof, wherein the composition is effectuates for the treatment or alleviation of at least one symptom of cancer in the patient.

In any aspect or embodiment described herein, the cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; multiple myeloma, sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

In any of the aspects or embodiments described herein, the L comprises nonlinear chains, aliphatic or aromatic or heteroaromatic cyclic moieties.

In any of the aspects or embodiments described herein, the L is selected from the group consisting of:

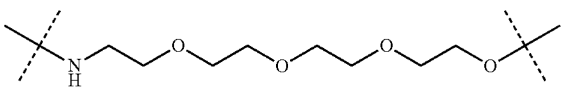

-continued

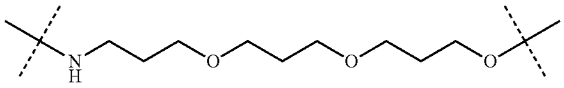

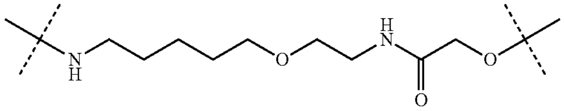

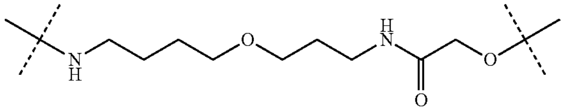

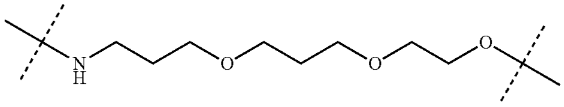

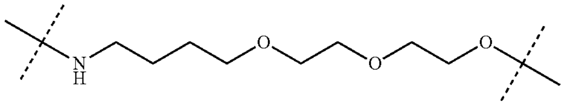

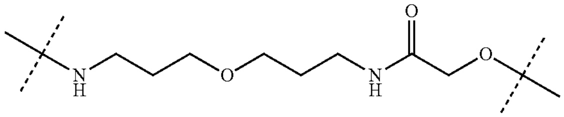

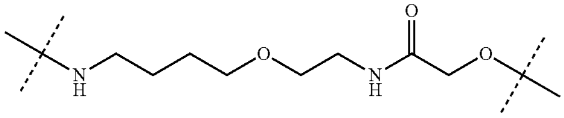

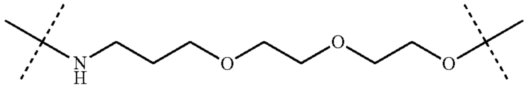

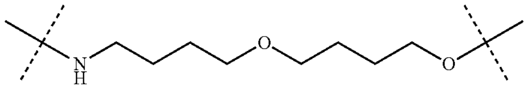

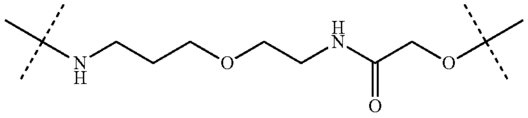

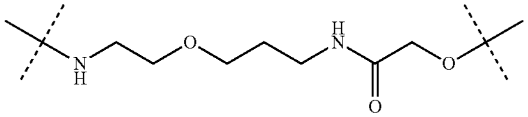

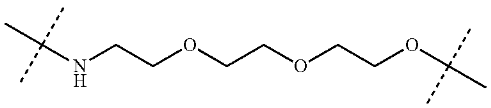

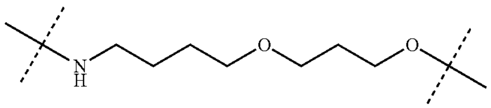

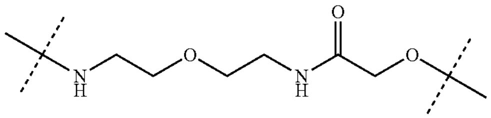

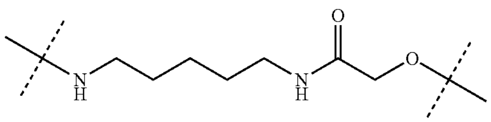

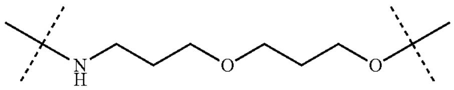

-continued
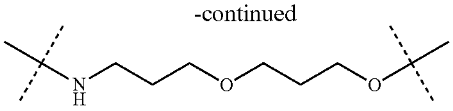
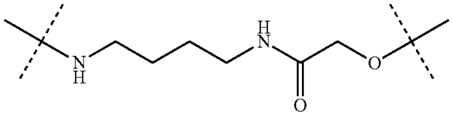
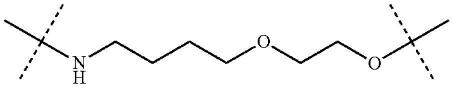
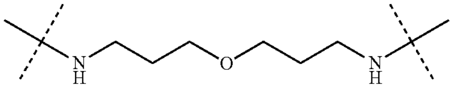
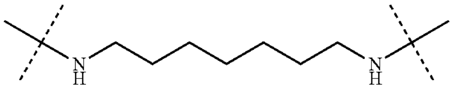
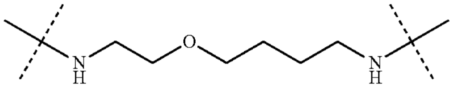
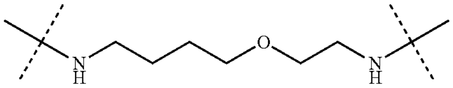
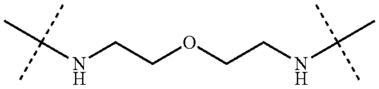
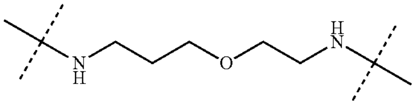
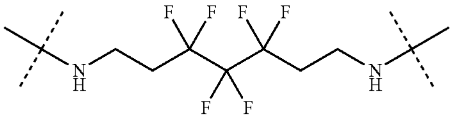
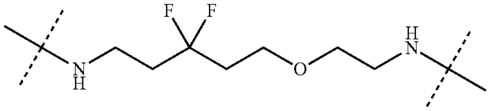
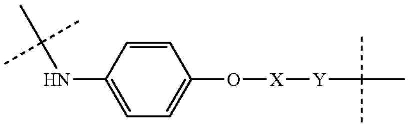
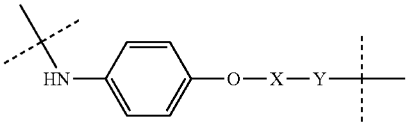
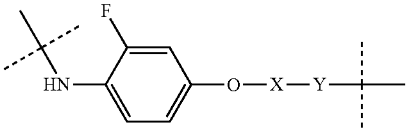
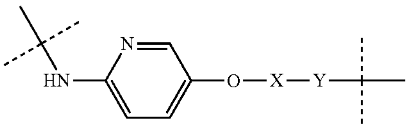
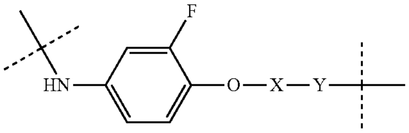
-continued
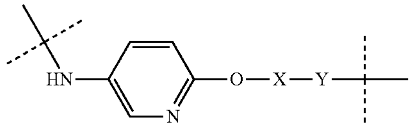
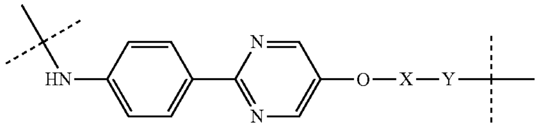
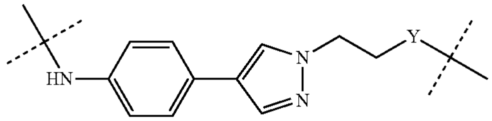
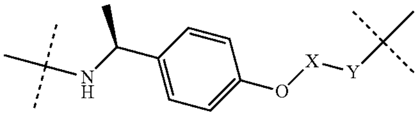
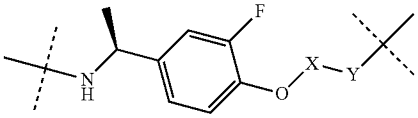
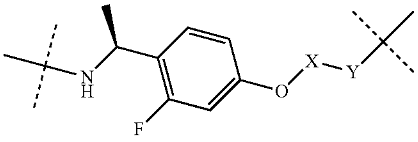
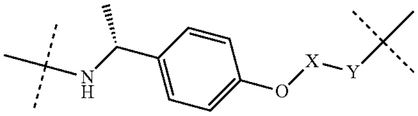
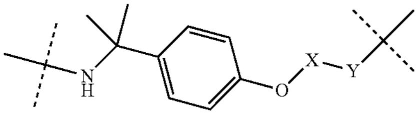
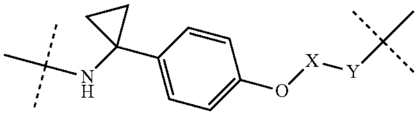
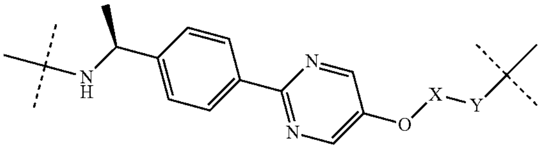
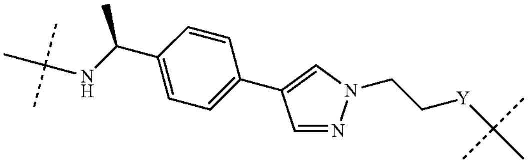
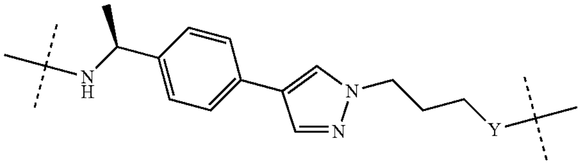
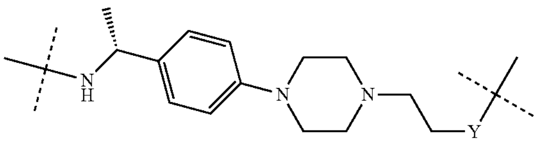

-continued

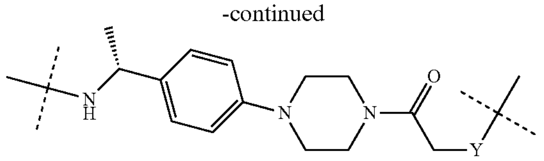

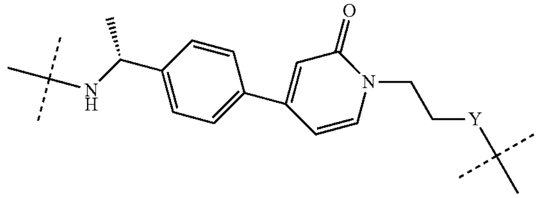

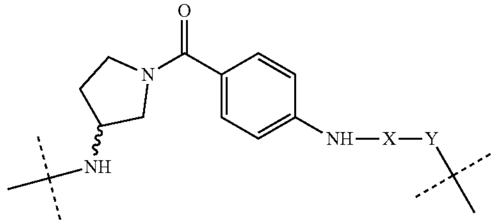

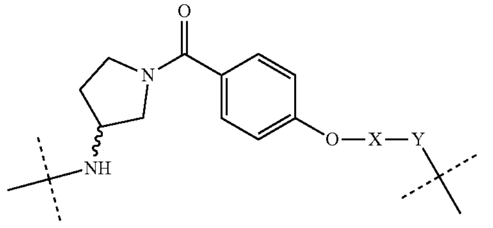

wherein:

"X" is a linear chain with atoms ranging from 2 to 14 optionally substituted to contain heteroatoms; and "Y" is independently slected from the group consisting of O, N, $S(O)_n$ (n=0, 1, 2).

EXAMPLES

Abbreviations

ACN: acetonitrile
ADDP: 1,1'-(azodicarbonyl)dipiperidine
BAST: N,N-bis(2-methoxyethyl)aminosulfur trifluoride
BPO: benzoyl peroxide
Cbz: Carbonylbezyloxy
DAST: diethylaminosulfur trifluoride
DBE: 1,2-dibromoethane
DCM: dichloromethane
DEAD: diethyl azodicarboxylate
DIAD: diisopropyl azodicarboxylate
DIBAL: disiobutylaluminium hydride
DIEA or DIPEA: diisopropylethylamine
DMA: N,N-dimethylacetamide
DMF: N,N-dimethylformamide
DMP: Dess-Martin periodinane
EA: ethyl acetate
EDCI: 1-ethyl-3-(3-dimethylaminopropyl)carbodiimide
HBTU: N,N,N'N'-tetramethyl-O-(1H-benzotriazol-1-yl) uronium hexafluorophosphate
HMDS: bis9trimethylsilyl)amine
HMPA: hexamethylphosphoramide
LDA: lithium diisopropylamide
MCPBA: meta-chloroperoxybenzoic acid
MsCl: methanesulfonyl chloride
M.W: microwave
NBS: N-bromosuccinimide
NMP: N-methylpyrrolidone
PCC: pyridinium chlorochromate
Pd-118 or Pd(dtpf)$Cl_2$: 1,1'-bis(di-tert-butylphosphino) ferrocene dichloropalladium
Pd(dppf)$Cl_2$: 1,1'-bis(diphenylphosphino)ferrocene dichloropalladium
$Pd(dba)_2$: bis(dibenzylideneacetone)palladium
$Pd_2(dba)_3$: Tris(dibenzylideneacetone)dipalladium
PPTS: pyridium p-tolunesulfonate
PTSA: p-toluenesulfonic acid
RuPhos-Pd-G3: XPhos-Pd-G3: [(2-dicyclohexylphosphino-2',6'-diisopropoxy-1,1'-biphenyl)-2-(2'-amino-1,1'-biphenyl)]palladium(II) methanesulfonate
RuPhos-Pd-G2: Chloro[(2-dicyclohexylphosphino-2',6'-diisopropoxy-1,1'-biphenyl)-2-(2'-amino-1,1'-biphenyl)]palladium(II)
SFC: supercritical fluid chromatography
t-BuXPhos-Pd-G3: [(2-di-tert-butylphosphino-2',4',6'-triisopropyl-1,1'-biphenyl)-2-(2'-amino-1,1'-biphenyl)] palladium(II) methanesulfonate
TEA: trimethylamine
TFA: trifluoroacetic acid
TLC: thin layer chromatography
TMP: 2,2,6,6-tetramethylpiperidine
TEMPO: 2,2,6,6-tetramethylpiperidine-N-oxide
TosCl or TsCl: p-toluenesulfonyl chloride
TsOH: p-toluenesulfonic acid
XantPhos: 4,5-bis(diphenylphosphino)-9,9-dimethylxanthene
XPhos: 2-dicyclohexylphosphino-2'4'6'-triisopropylbiphenyl
XPhos-Pd-G3: [(2-dicyclohexylphosphino-2',4',6'-triisopropyl-1,1'-biphenyl)-2-(2'-amino-1,1'-biphenyl)]palladium(II) methanesulfonate
12354-85-7: bis(pentamethylcyclopentadienylrhodium dichloride)

A. Cloning, expression and purification of human CRBN and DDB1. The procedure is standard to one versed in the art, as typified by the description in Lopez-Girona et al. (Cereblon is a direct protein target for immunomodulatory and antiproliferative activities of lenalidomide and pomalidomide, A Lopez-Girona, D Mendy, T Ito, K Miller, A K Gandhi, J Kang, S Karasawa, G Carmel, P Jackson, M Abbasian, A Mahmoudi, B Cathers, E Rychak, S Gaidarova, R Chen, P H Schafer, H Handa, T 0 Daniel, J F Evans and R Chopra, Leukemia 26: 2326-2335, 2012).

The cDNAs for the CRBN and DDB1 genes can be amplified by PCR using Pfusion (NEB) as the polymerase.

CRBN can be cloned into pBV-ZZ-HT-LIC, pBV-GST-LIC, pMA-HT-LIC, and DDB1 into pBV-notag-LIC, using ligation-independent cloning 26. For cloning into the mammalian vector pMA-HT-LIC, the CRBN-Flag-Reverse oligo adds a C-terminal FLAG tag for immunodetection. The DDB1-Rev adds a StrepTag 27. A ZZ-tag 28 is necessary to achieve high expression of soluble CRBN; without it, the His-CRBN expressed at low level, while a GST-CRBN results in aggregated protein. Recombinant baculovirus of ZZ-His-CRBN and DDB1-StrepTag (ST) are generated and amplified using Bac-to-Bac baculovirus expression system from Invitrogen in Sf9 insect cells. ZZ-His-CRBN and DDB1-ST are co-expressed in High Five (Tni) insect in 10L wave bags at 27° C. using un-supplemented ESF921 media from Expression Systems. Cells are harvested 48 hours post infection by centrifugation and paste re-suspended in PBS plus5× Protease Inhibitor cocktail (Roche, Indianapolis, Ind.).

All subsequent protein purification steps are carried out at 4° C. Frozen cells are thawed, resuspended in 5 volumes of lysis buffer (50 mM Tris HCl pH 8.0, 0.5 M NaCl, 10% glycerol, 2 mM DTT) plus 20 mM imidazole and protease inhibitors, lysed and centrifuged to yield a clear supernatant. The CRBN-DDB1 is purified on a ÄKTA-xpress system (GE Healthcare) using a Nickel-Sepharose and S200 Sephacryl chromatography. The complex is then further purified using anion exchange chromatography on an 8 ml MonoQ column and a second pass on a S-200 gel filtration. CRBN-DDB1 is identified by SDS-PAGE and the CRBN-DDB1 containing fractions were pooled and stored at −70° C.

2. Fluorescence Thermal Melt Assay to Measure Binding of Compounds to Recombinant CRBN The assay is standard to one versed in the art, as typified by the description in Lopez-Girona et al. (Cereblon is a direct protein target for immunomodulatory and antiproliferative activities of lenalidomide and pomalidomide, A Lopez-Girona, D Mendy, T Ito, K Miller, A K Gandhi, J Kang, S Karasawa, G Carmel, P Jackson, M Abbasian, A Mahmoudi, B Cathers, E Rychak, S Gaidarova, R Chen, P H Schafer, H Handa, T O Daniel, J F Evans and R Chopra, Leukemia 26: 2326-2335, 2012).

Thermal stabilities of CRBN-DDB1 in the presence or absence of test compounds are done in the presence of Sypro Orange in a microplate format according to Pantoliano et al. (Pantoliano M W, Petrella E C, Kwasnoski J D, Lobanov V S, Myslik J, Graf E et al. High-density miniaturized thermal shift assays as a general strategy for drug discovery. J Biomol Screen 2001; 6: 429-440.) Two mg of protein in 20 ml of assay buffer (25 mM Tris HCl, pH 8.0, 150 mM NaCl, 2 uM Sypro Orange) are subjected to stepwise increase of temperature from 20 to 70° C. and the fluorescence read at every 1° C. on an ABIPrism 7900HT (Applied Biosystems, Carlsbad, CA, USA). Compounds are dissolved in DMSO (1% final in assay) and tested in quadruplicate at a concentration range between 30 nM to 1000 uM; controls contained 1% DMSO only.

3. LCMS Method

The analysis is conducted on a Poroshell 120 EC C18 column (50 mm×3.0 mm internal diameter 2.7 μm packing diameter) at 45° C.

The solvents employed are:

A=0.1% v/v solution of formic acid in water.

B=0.1% v/v solution of formic acid in acetonitrile.

The gradient employed are as follows:

| Time (minutes) | Flow Rate (mL/min) | % A | % B |
|---|---|---|---|
| 0 | 1 | 95 | 5 |
| 0.5 | 1 | 95 | 5 |
| 3.0 | 1 | 1 | 99 |
| 3.75 | 1 | 1 | 99 |
| 4.0 | 1 | 95 | 5 |

The UV detection is an averaged signal from wavelength of 210 nm to 350 nm and mass spectra are recorded on a mass spectrometer using positive mode electrospray ionization.

The following illustrates the mobile phases and gradients used when compounds undergo purification by preparative HPLC.

4. Preparative HPLC (Formic Acid Modifier)

The HPLC analysis is conducted on an X Bridge RP18 OBD column (150 mm×19 mm internal diameter, 5 μm packing diameter) at ambient temperature.

The solvents employed are:

A=0.1% v/v solution of formic acid in water.

B=acetonitrile.

5. Preparative HPLC (Ammonium Bicarbonate Modifier)

The HPLC analysis is conducted on an X Bridge RP18 OBD column (150 mm×19 mm internal diameter, 5 μm packing diameter) at ambient temperature.

The solvents employed are:

A=10 mM ammonium bicarbonate in water.

B=acetonitrile.

For each of the preparative purifications, irrespective of the modifier used, the gradient employed is dependent upon the retention time of the particular compound undergoing purification as recorded in the analytical LCMS. The flow rate is 20 mL/min.

The UV detection is a signal from wavelength of 254 nm or 220 nm.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

B. Synthesis

The synthetic details for the examples included below are representative of the general procedures that inform on the synthesis of the broader example set.

1. N-(3-(5-bromo-2-chloropyrimidin-4-ylamino) propyl)-N-methylcyclobutane carboxamide

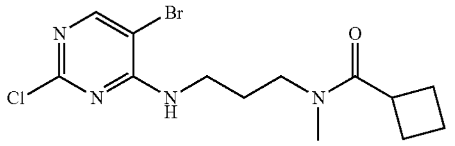 [SMILES: CN(CCCNc1nc(Cl)ncc1Br)C(=O)C1CCC1]

Step 1: tert-butyl N-{3-[(5-bromo-2-chloropyrimidin-4-yl)amino]propyl}-N-methylcarbamate

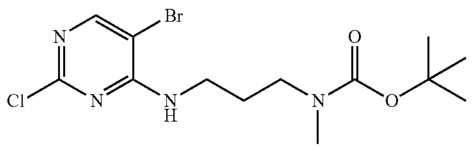 [SMILES: CN(CCCNc1nc(Cl)ncc1Br)C(=O)OC(C)(C)C]

A mixture of tert-butyl N-(3-aminopropyl)-N-methylcarbamate (826 mg, 4.40 mmol) and 5-bromo-2,4-dichloropyrimidine (400 mg, 1.76 mmol) in MeOH (10 mL) was stirred at rt for 1 h. The reaction mixture was then concetrated in vacuo, and the residue was purfied using a Teledyne ISCO Chromatography [0→35% EtOAc/Heptanes] to afford tert-butyl N-{3-[(5-bromo-2-chloropyrimidin-4-yl)amino]propyl}-N-methylcarbamate (615 mg, 92% yield). LC-MS ($ES^+$): m/z=381.05/383.05 [$MH^+$], $t_R$=2.55 min.

Step 2: {3-[(5-bromo-2-chloropyrimidin-4-yl)amino]propyl}(methyl)amine

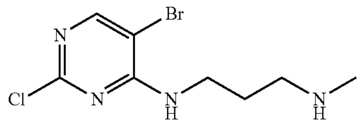

To a solution of tert-butyl N-{3-[(5-bromo-2-chloropyrimidin-4-yl)amino]propyl}-N-methylcarbamate (615 mg, 1.62 mmoL) in DCM (5 mL) was added trifluoroacetic acid (0.54 mL, 6.5 mmol) at it After the mixture was stirred for 1 h, it was concetrated in vacuo. The residue was purified using a Teledyne ISCO Chromatography [0→15% methanol in DCM] to afford {3-[(5-bromo-2-chloropyrimidin-4-yl)amino]propyl}(methyl)amine (371 mg, 82% yield). LC-MS ($ES^+$): m/z=280.99/282.99 [$MH^+$], $t_R$=1.13 min.

Step 3: N-{3-[(5-bromo-2-chloropyrimidin-4-yl)amino]propyl}-N-methylcyclobutanecarboxamide

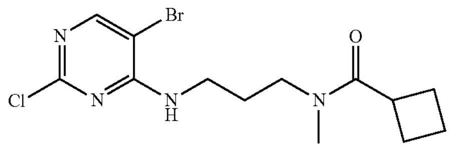 [SMILES: CN(CCCNc1nc(Cl)ncc1Br)C(=O)C1CCC1]

To a solution of {3-[(5-bromo-2-chloropyrimidin-4-yl)amino]propyl}(methyl)amine (371 mg, 1.33 mmol) and cyclobutanecarbonyl chloride (188 mg, 1.60 mmol) in DCM (10 mL) at rt was added triethyl amine (0.41 mL, 2.92 mmol). The reaction mixture was left to stir at rt for 16 h, then concetrated in vacuo. The residue was purified using a Teledyne ISCO Chromatography [0→100% EtOAc/Heptanes] to afford N-{3-[(5-bromo-2-chloropyrimidin-4-yl)amino]propyl}-N-methylcyclobutane carboxamide (268 mg, 56%). LC-MS ($ES^+$): m/z=363.04/365.04 [$MH^+$], $t_R$=2.18 min.

2. (S)-2-(4-(4-chlorophenyl)-2,3,9-trimethyl-6H-thieno [3,2-f][1,2,4]triazolo[4,3-a][1,4]diazepin-6-yl)acetic acid

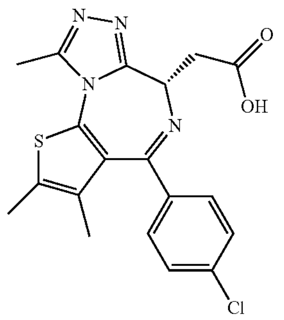 [SMILES: Cc1sc2c(c1C)C(c1ccc(Cl)cc1)=N[C@@H](CC(=O)O)c1nnc(C)n1-2]

The title compound was prepared according to the procedures described in WO2011/143660

3. (Z)-4-(4-((2,4-dioxothiazolidin-5-ylidene)methyl)-2-methoxyphenoxy)-3-(trifluoromethyl)benzonitrile

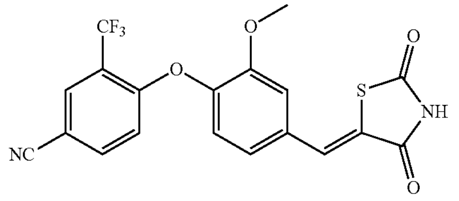 [SMILES: COc1cc(/C=C2\SC(=O)NC2=O)ccc1Oc1ccc(C#N)cc1C(F)(F)F]

The title compound was prepared according to the procedures described in Patch, R. J. et al *J. Med. Chem.* 2011, 54, 788-808.

4. 4-[3-(4-hydroxyphenyl)-4,4-dimethyl-5-oxo-2-sulfanylideneimidazolidin-1-yl]-2-(trifluoromethyl)benzonitrile

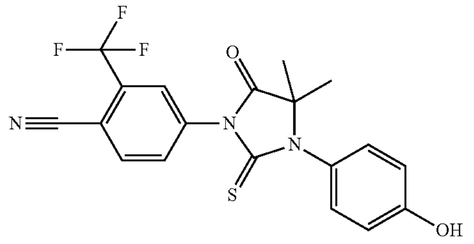 [SMILES: CC1(C)C(=O)N(c2ccc(C#N)c(C(F)(F)F)c2)C(=S)N1c1ccc(O)cc1]

The title compound was prepared according to the procedures described in Jung, M. E. et al *J. Med. Chem.* 2010, 53, 2779-2796.

5. 2-chloro-4-(trans-3-amino-2,2,4,4-tetramethylcyclobutoxy)benzonitrile hydrogen chloride salt

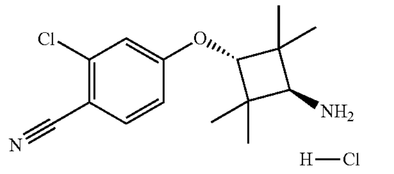

The title compound was prepared according to the procedures described in Guo, C. et al *J. Med. Chem.* 2011, 54, 7693-7704.

C. Protein Degradation Bioassays

The following bioassays evaluate the level of protein degradation observed in various cell types using representative compounds disclosed herein.

In each bioassay, cells were treated with varying amounts of compounds encompassed by the present disclosure. The degradation of the following proteins may be evaluated:

TANK-binding kinase 1 (TBK1), estrogen receptor α (ERα), bromodomain-containing protein 4 (BRD4), androgen receptor (AR), c-Myc, and tau protein.

1. ERE Luciferase Assay for Compounds in Table 2

T47D-1(Bluc cells (ATCC® ECRL 2 65, T47D human breast cancer cells stably transfected with estrogen responsive element/promoter/luciferase reporter gene) were seeded into 96-well white opaque plates in IR: PM growth medium supplemented with 10% fetal bovine serum (FBS) and allowed to adhere overnight in a 37° C. humidified incubator. The following day, cells were treated with PROTACs in a 12-point concentration curve (top final concentration of 300 nM with subsequent concentrations being 3-fold less with 2 μM being the lowest concentration in the assay). Each PROTAC was tested independently in two experiments on 96-well plates. After 24 hours, media was removed and lysis buffer was added to the wells. Following lysis, Bright-Glo™ Luciferase Assay Substrate (Promega, Madison WI) was added and the luciferase activity was measured using a Cytation 3 plate reader (BioTek™, Winooski, VT). Each compound was assayed in duplicate and the activity was calculated as 1050 using GraphPad Prism software (San Diego, CA).

2. Estrogen Receptor-Alpha (ERα) Degradation Assay in MCF-7 Cells Using Western Blot Method for Table 5

The exemplary novel ERα degraders were assessed for their activity in degrading ERα in MCF-7 cells via western blot. The assay was carried out in the presence of 10% FBS or high percentage of human or mouse serum. Protocols of the western blot assay are described below.

MCF7 cells were grown in DMEM/F12 with 10% FBS and seeded at 24,000 cells per well in 100 μl into 96-well clear tissue culture plates. The following day, the cells were treated with PROTACs in a 7-point concentration curve with 100 nM being the top concentration and serial dilutions to make the other concentrations (30 nM, 10 nM. 3 nM, 1 nM, and 0.3 nM). At all concentrations, 0.01% DMSO is the final concentration in the well. The following day, the plates are aspirated, washed with 50 μl of cold PBS. The cells are lysed with 50 μl/well 4° C. Cell Lysis Buffer (Catalog #9803; Cell Signaling Technology, Danvers, MA) (20 mM Tris-HCL (pH 7.5), 150 mM NaCl, 1 mM $Na_2EDTA$, 1 mM EGTA, 1% Triton, 2.5 mM sodium pyrophosphate, 1 mM B-glycerophosphate, 1 mM sodium vanadate, 1 μg/ml leupeptin). Lysates were clarified at 16,000× g for 10 minutes, and 2 μg of protein was subjected to SDS-PAGE analysis and followed by immunoblotting according to standard protocols. The antibodies used were ERα (Cell Signaling, Technologies Catalog #8644), and Tubulin (Sigma Catalog #T9026; St. Louis, MO). Detection reagents were Clarity Western ECL substrate (Bio-Rad Catalog 4170-5060; Hercules, CA).

Alternatively, MCF7 cells were grown in DMEM/F12 with 10% FBS and seeded at 24,000 cells per well in 500 μl in 24-well clear tissue culture plates. The following day, the cells were treated with PROTACs in a 5-point concentration curve (100 nM, 33 nM, 11 nM, 3.7 nM, and 1.2 nM) in the presence of 0.01% DMSO. After 72 hours, the wells are aspirated and washed with 500 μl of PBS. The cells are lysed with 100 μl/well 4° C. Cell Lysis Buffer (Catalog #9803; Cell Signaling Technology, Danvers, MA) (20 mM Tris-HCL (pH 7.5), 150 mM NaCl, 1 mM $Na_2EDTA$, 1 mM EGTA, 1% Triton, 2.5 mM sodium pyrophosphate, 1 mM B-glycerophosphate, 1 mM sodium vanadate, 1 ug/ml leupeptin). Lysates were clarified at 16,000× g for 10 minutes, and 2 μg of protein was subjected to SDS-PAGE analysis and followed by immunoblotting according to standard protocols. The antibodies used were ERα (Cell Signaling Technologies Catalog #8644), and Tubulin (Sigma Catalog #T9026; St. Louis, MO). Detection reagents were Clarity Western ECL substrate (Bio-Rad Catalog 4170-5060; Hercules, CA).

3. Estrogen receptor-alpha (ERα) degradation assay using In-Cell Western™ Assay for Table 5

Degradation of ERα by claimed compounds were determined in MCF7 cells using an In-Cell Western™ assay. Briefly, MCF7 cells were plated in 96-well plates (2000 cells per well in 100 μl media) and incubated at 37° C. under an atmosphere of 5% $CO_2$ in a humidified incubator overnight. One-hundred (100) μl of media containing test compound (at 2× concentration) was added to the appropriate wells to provide 11 serially decreasing concentrations (top final concentration, 1 μM then 3-fold less for the next 10 concentrations); a vehicle control (DMSO) was also added for each compound. For each experiment, all compounds were assayed in duplicate plates. Cells were then incubated for 3 or 5 days in the above-mentioned environment. The assay was terminated by removal of media, a single wash with ice-cold PBS and the addition of 50 $_{1}$1.1 paraformaldehyde (PFA: 4% in PBS). After 15 minutes in PFA at room temperature, the cells were permeabilized in Tris-phosphate-buffered saline with Tween (0.1%) (TBST) supplemented with Triton X-100 (0.5%) for 15 minutes. Cells were then blocked in BSA (TBST with BSA, 3%) for one hour. Primary antibodies for the detection of ERα (rabbit monoclonal, 1:1000, Cell Signaling Technology Catalog #8644) and tubulin (mouse monoclonal, 1:5000, Sigma Catalog #T6074) in TBST with BSA (3%) were added. The cells were incubated overnight at 4° C. The cells were then washed thrice with TBST at room temperature and then incubated with anti-rabbit and anti-mouse fluorescently-labelled secondary antibodies (IRDye®; LI-COR; Lincoln, NE) in LI-COR blocking buffer (Catalog #927-50000) for one hour at room temperature. Following 3 washes with TBST, the buffer was removed and the plates were read on an Odyssey® infrared imaging system (LI-COR®; Lincoln, NE) at 700 nm and 800 nm. Using commercial software (ImageStudio™; LI-COR, Lincoln, NE), the staining intensity for ERα and tubulin in each well was quantified and exported for analysis. For each data point, ERα intensity was normalized to tubulin intensity and for each compound all normalized intensity values were normalized to the vehicle control. $DC_{50}$ and $D_{max}$ values were determined following a 4-parameter $IC_{50}$ curve fit using ACAS dose response module (McNeil & Co Inc.).

4. BRD4 Western Protocol

VCaP cells were purchased from ATCC and cultured in Dulbecco's Modified Eagle's Medium (ATCC), supplemented with 10% FBS (ATCC) and Penicillin/Streptomycin (Life Technologies). DMSO control and compound treatments (0.003 μM, 0.01 μM, 0.03 μM and 0.1 μM) were performed in 12-well plates for 16 h. Cells were harvested, and lysed in RIPA buffer (50 mM Tris pH8, 150 mM NaCl, 1% Tx-100, 0.1% SDS, 0.5% sodium deoxycholate) supplemented with protease and phosphatase inhibitors. Lysates were clarified at 16,000 g for 10 minutes, and protein concentration was determined. Equal amount of protein (20 μg) was subjected to SDS-PAGE analysis and followed by immunoblotting according to standard protocols. The antibodies used were BRD4 (Cell Signaling #13440), and Actin (Sigma #5441). Detection reagents were Clarity Western ECL substrate (Bio-rad #170-5060).

5. AR ELISA Assay Protocol

Compounds were evaluated in this assay in LNCaP and/or VCaP cells utilizing similar protocols. The protocols used with VCaP cells are described below. The androgen receptor ELISA assay was performed using PathScan AR Sandwich ELISA (Cell Signaling Catalog #12850) according to the following assay steps:

VCaP cells were seeded at 40,000 cells/well at a volume of 100 μL/well in VCaP assay medium [Phenol red free RPMI (Gibco Cat #11835-030); 5% Charcoal Stripped (Dextran treated) FBS (Omega Scientific, Cat #FB-04); 1% penstrep (Life Technologies, Gibco Cat #: 10378-016)] in Corning 3904 plates. The cells were incubated for a minimum of 3 days. Cells were dosed with PROTACs diluted in 0.01% DMSO and the drug treatment was allowed for 5 hours.

AR ELISA (Cell Signaling) was performed as follows. 1× Cell Signaling Cell lysis buffer was made (Catalogue #9803; comes with the kit). Media from the treated wells is aspirated, and 100 μL 1× cell lysis buffer/well is added. The cells were placed on a shaker for 10 minutes at 4° C. Twenty microliters of lysate was transferred to 100 μl of Diluent in ELISA plate (0.15 μg/ml −0.075 μg/ml). The lysate-diluent mixture was shaken for 30 minutes at 37° C. Allow mouse AR antibody, anti-mouse antibody, TMB, and STOP solution to come to room temperature. The 1× ELISA buffer included in kit was made and loaded in the reservoir.. Media from the plates was discarded, the ELISA plate tapped hard on paper towel, and washed 4×200 μl ELISA wash buffer using a plate washer.

One-hundred (100) μL/well of mouse AR detection Ab was added; the plates were covered and shaken at 37° C. for 1 hour; media was discarded from the plates, the plates were tapped on a paper towel, washed 4× with 200 μL ELISA wash buffer with a plate washer.

One-hundred (100) μL/well of anti-mouse-HRP conjugated Ab (comes with the kit) was added; the plates were covered and shaken at 37° C. for 30 minutes; the TMB reagent was allowed to come to room temperature; the media was discard from the plate, the plates were tapped on paper towl, washed 4× with 200 μL of ELISA wash buffer; the plates were tapped the plates on paper towl. One-hundred (100) μL of TMB was added and the plates shaken for 2 minutes—while watching for color development. One-hundred (100) μL Stop solution was added when light blue color developed. Plates were shaken and read at 450 nM.

Progression of prostate cancer in patients treated with anti-androgen therapy usually involves one of several mechanisms of enhanced Androgen Receptor (AR) signaling, including increased intratumoral androgen synthesis, increased AR expression and AR mutations. PROTACs (PROteolysis TArgeting Chimera), which use bi-functional molecules that simultaneously bind a target of choice and an E3 ligase, cause ubiquitination via induced proximity and degradation of the targeted, pathological protein. As opposed to traditional target inhibition, which is a competitive process, degradation is a progressive process. As such, it is less susceptible to increases in endogenous ligand, target expression, or mutations in the target. Thus, this technology appears to be ideal for addressing the mechanisms of AR resistance in patients with prostate cancer. Data was analyzed and plotted using GraphPad Prism software.

6. BRD4 Human c-Myc ELISA Assay Protocol

22RV-1 cells were seeded at 30,000 cells/well at a volume of 75 μL/well in RPMI with 10% FBS media in 96-well plates and grown overnight at 37° C. Cells were dosed with compounds at 4× concentration diluted in 0.4% DMSO; compounds were serially diluted 1:3 for 8-point dose curve. Twenty-five (25) ul of the compounds was added to cells for a final concentration starting at 300 nM-0.3 nM or 1 uM-1 nM in 0.1% DMSO and incubated for 18 hours. Media was aspirated, cells were washed 1× with PBS and aspirated. Cells were lysed in 50 ul RIPA buffer (50 mM Tris pH8, 150 mM NaCl, 1% Tx-100, 0.1% SDS, 0.5% sodium deoxycholate) supplemented with protease and phosphatase inhibitors. Plates were incubated on ice for 15 minutes then centrifuged at 4° C. for 10 minutes at 4000 rpm. Fifty (50) ul of cleared lysate from a 96-well assay plate was added into 96-well c-myc ELISA plate (Novex, Life Technologies Catalog #KH02041). c-myc standard was reconstituted with standard diluent buffer; standard curve range of 333 pg/ml-0 pg/ml was prepared, diluted 1:2 for 8-point dose curve. The rest of the assay was performed following the protocol from the c-myc ELISA kit. Data was analyzed and plotted using GraphPad Prism software. Compounds described in the present disclosure were assayed and c-myc suppression potency are listed in Table 4.

7. BRD4 Immunoblotting

22Rv 1 and VCaP cell lines were purchased from ATCC. BRD2 ( #5848), BRD4 ( #13440), PARP ( #9532), c-Myc ( #5605) antibodies were purchased from cell signaling. BRD3 (sc-81202) antibody was purchased from Santa Cruz Biotech. Antibodies used for immunohistochemistry were c-MYC (abcam #ab32072) and BRD4 (Bethyl Laboratories #a301-985a50). Actin and Tubulin antibodies were purchased from Sigma.

Cells were lysed in RIPA buffer (Thermo Fisher Cat #89900) supplemented with protease inhibitors (Pierce™ Protease Inhibitor Tablets, EDTA-free Cat #88266). Lysates were centrifuged at 16,000×g and supernatants were used for SDS-PAGE. Western blotting was carried out following standard protocols.

8. BRD4 Cell Proliferation Assay

22RV-1 cells were seeded at 5,000 cells/well at a volume of 75 μL/well in RPMI+10% FBS media in 96-well plates and grown overnight at 37° C. Cells were dosed with compounds at four concentrations diluted in 0.4% DMSO; compounds were serially diluted 1:3 for 10-point dose curve. Twenty-twenty (25) ul of compounds was added to cells for a final concentration starting at 300 nM-0.3 nM in 0.1% DMSO and incubated for 72 hours. In a separate plate, 100 ul of 5,000 cells/well were plated in 8 wells, 100 ul of CellTiter-Glo (CellTiter-Glo® Luminescent Cell Viability Assay, Promega #G7573) was added and incubated for 30 minutes, then read on luminometer to assess initial signal for cell growth. After 72 hours, 100 ul of CellTiter-Glo® was added and incubated for 30 minutes, then read on luminometer. Data was analyzed and plotted using GraphPad Prism software.

9. BRD4 Apoptosis Assay

22RV-1 cells were seeded at 5,000 cells/well at a volume of 75 μL/well in RPMI+10% FBS media in 96-well plates and grown overnight at 37° C. Cells were dosed with compounds at 4× concentrations diluted in 0.4% DMSO; compounds were serially diluted 1:3 for 8-point dose curve. Twenty-five (25) ul of compounds was added to cells for a final concentration starting at 300 nM-0.3 nM in 0.1% DMSO and incubated for 48 hours. After 48 hours, 100 ul of Caspase-Glo® 3/7 (Promega Caspase-Glo® 3/7 Assay #G8093 was added and incubated for 30 minutes, then read on luminometer. Data was analyzed and plotted using GraphPad Prism software.

10. Tau Protein In Vitro Degradation Assay

To determine effect of PROTACs on tau protein degradation SK—N—SH cells were seeded in a 24-well tissue culture-treated plate for at least 18-hours prior to compound addition. Tau PROTACs were evaluated for tau degradation by lysing the cells in RIPA buffer with protease inhibitors following a 72-hour incubation with tau PROTACs. Cell lysates were run on standard SDS-PAGE gels, and tau levels were detected by Western blotting using Tau-13 antibody from Abcam (Cambridge, UK) that binds to all forms of human tau. The data was shown in Tables 6.

Small molecule inhibitors have been the cornerstone of oncology drug development and generally work by inhibiting enzyme activity (such as kinase inhibitors) or by interfering protein-protein interactions (such as BRD4 inhibitors). Given the reversible binding of most small molecule inhibitors, large systemic drug concentrations are often required to ensure sufficient functional inhibition. Additionally, achieving and maintaining a high systemic drug level that is required for in vivo efficacy has proven challenging for many targets.

BRD4, a member of the bromodomain and extraterminal domain (BET) family, is a protein characterized by two bromodomains (BD domain) at the N-terminus and an extraterminal domain (ET domain) at the C-terminus. The two BD domains recognize and interact with acetylated-lysine residues at the N-terminal tail of histone protein. The ET domain is considered to serve a scaffolding function in recruiting diverse transcriptional regulators, but has not yet been fully characterized. BRD4 has been shown to be located at super-enhancer regions, which often reside upstream of important oncogenes, such as c-MYC, Bcl-xL and BCL-6, and play a key role in regulating their expressions. Based on its role in regulating gene expression by recruiting relevant transcription modulators to specific genomic loci, BRD4 is a candidate drug target for treating and/or preventing a number of human cancers, such as midline carcinoma, acute myeloid leukemia (AML), multiple myeloma (MM), Burkitt lymphoma (BL), and prostate cancer.

Several small molecule BET bromodomain inhibitors have been developed, such as $JQ_1$, iBET, and OTX15, which have shown therapeutic potential in certain preclinical models of various cancers, including BL. Almost all BL cases contain c-myc gene translocation that places it under control of a super-enhancer located upstream of IgH, thus driving an abnormally high level of c-MYC expression, tumor development and maintenance. Preclinical studies with BRD4 inhibitors demonstrate their ability to suppress c-MYC and proliferation in BL cell lines; however, the $IC_{50}$ values of these inhibitors is often in the range of 100 nM to 1 μM.

Materials and Methods

The details of the experimental design and procedures are provided below:

Inhibitors $JQ_1$, OTX-15, and pomalidomide were synthesized according to methods published.

1. $K_D$ Determination

The surface plasmon resonance (SPR) experiments were conducted on a Biacore3000 (GE Healthcare). Myc-tagged cereblon was immobilized on a carboxymethylated dextran surface (CM5) amine coupled to anti-Myc antibody to recognize the Myc tag. His-tagged cereblon protein was immobilized on a carboxymethylated dextran surface with nitriloacetic acid (NTA), taking advantage of NTA/$Ni^{2+}$ chelation. The prepared surface was allowed to equilibrate over three hours in running buffer (10 mM HEPES buffer @ pH 7.4, 150 mM NaCl, 0.005% P20, 2% DMSO).

All compounds were prepared in 100% DMSO stock plates with a top concentration of 5 mM in a 3× serial dilution. Compounds were transferred from the stock plate to the assay plate and diluted into running buffer containing no DMSO. All compounds were run as a six-concentration series with a final assay top concentration of 100 μM.

Data analysis was performed in Scrubber 2 (BioLogic software, Campbell, Australia). Blanks were subtracted and data was corrected for DMSO against a standard DMSO curve. All reported KD values represent an average of at least N=2 and were obtained by fitting to a minimum of five concentrations using a 1:1 fitting algorithm. The data is shown in Table 1 below, wherein "a" is a $K_D$ of <1 μM, "b" represents a $K_D$ of 1 μM to 10 μM, "c" represents a $K_D$ of >10 μM to 100 μM and "d" represents a $K_D$ of >100 μM or no response.

TABLE 1

Suface Plasmon Resonance Data for Examplary CLMs

| Example Number | Chemical Structure | $K_D$ Binding to immobilized CRBN protein in SPR assay |
|---|---|---|
| Control-1 (Pomalidomide) | 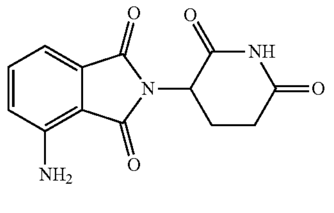 [SMILES: Nc1cccc2c1C(=O)N(C1CCC(=O)NC1=O)C2=O] | a |

TABLE 1-continued
| Example Number | Chemical Structure | $K_D$ Binding to immobilized CRBN protein in SPR assay |
|---|---|---|
| Suface Plasmon Resonance Data for Examplary CLMs | | |
| Control-2 (Lenalidomide) | 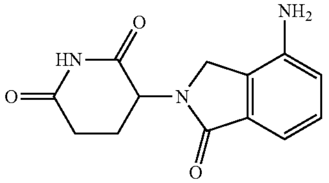 [SMILES: Nc1cccc2c1CN(C1CCC(=O)NC1=O)C2=O] | a |
| 1 | 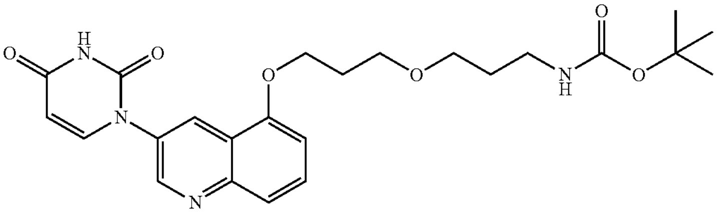 [SMILES: CC(C)(C)OC(=O)NCCCOCCCOc1cccc2ncc(-n3ccc(=O)[nH]c3=O)cc12] | b |
| 2 | 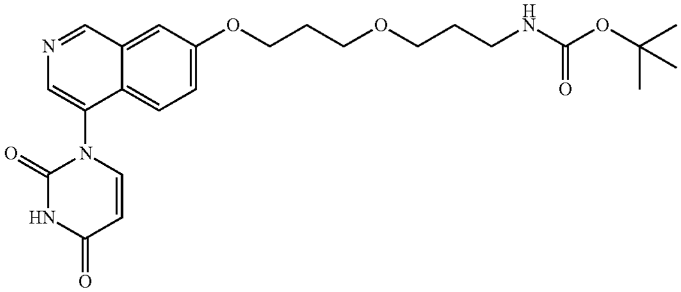 [SMILES: CC(C)(C)OC(=O)NCCCOCCCOc1ccc2c(-n3ccc(=O)[nH]c3=O)cncc2c1] | b |
| 3 | 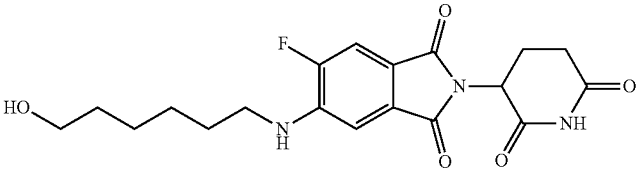 [SMILES: O=C1CCC(N2C(=O)c3cc(F)c(NCCCCCCO)cc3C2=O)C(=O)N1] | c |
| 4 | 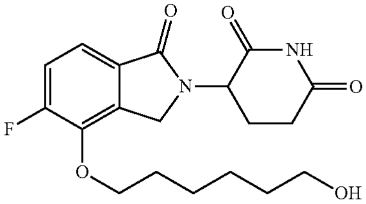 [SMILES: O=C1CCC(N2Cc3c(ccc(F)c3OCCCCCCO)C2=O)C(=O)N1] | c |
| 5 | 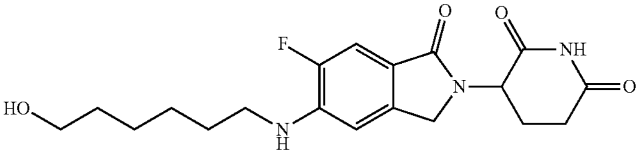 [SMILES: O=C1CCC(N2Cc3cc(NCCCCCCO)c(F)cc3C2=O)C(=O)N1] | c |
| 6 | 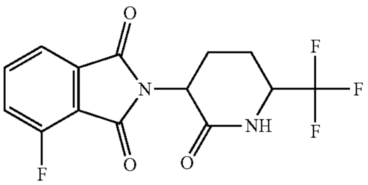 [SMILES: O=C1NC(C(F)(F)F)CCC1N1C(=O)c2cccc(F)c2C1=O] | d |

TABLE 1-continued
Suface Plasmon Resonance Data for Examplary CLMs
| Example Number | Chemical Structure | $K_D$ Binding to immobilized CRBN protein in SPR assay |
|---|---|---|
| 7 | 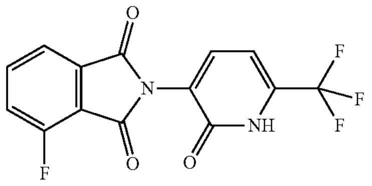 [SMILES: O=C1c2cccc(F)c2C(=O)N1c1ccc(C(F)(F)F)[nH]c1=O] | d |
| 8 | 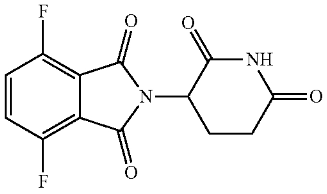 [SMILES: O=C1CCC(N2C(=O)c3c(F)ccc(F)c3C2=O)C(=O)N1] | d |
| 9 | 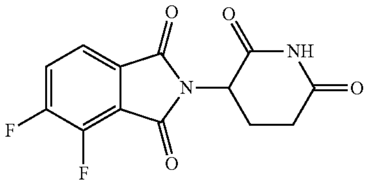 [SMILES: O=C1CCC(N2C(=O)c3ccc(F)c(F)c3C2=O)C(=O)N1] | b |
| 10 | 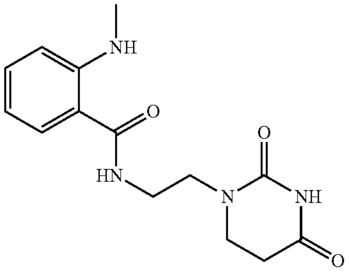 [SMILES: CNc1ccccc1C(=O)NCCN1CCC(=O)NC1=O] | d |
| 11 | 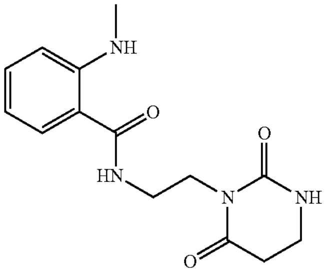 [SMILES: CNc1ccccc1C(=O)NCCN1C(=O)CCNC1=O] | d |
| 12 | 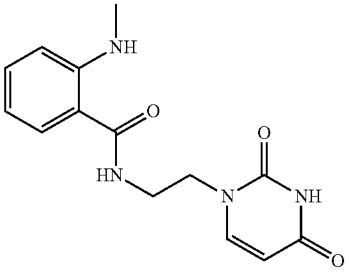 [SMILES: CNc1ccccc1C(=O)NCCn1ccc(=O)[nH]c1=O] | d |

TABLE 1-continued
| Example Number | Chemical Structure | $K_D$ Binding to immobilized CRBN protein in SPR assay |
|---|---|---|
| 13 | 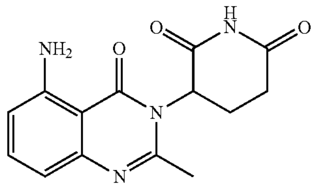 [SMILES: Cc1nc2cccc(N)c2c(=O)n1C1CCC(=O)NC1=O] | d |
| 14 | 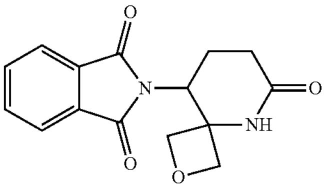 [SMILES: O=C1CCC(N2C(=O)c3ccccc3C2=O)C2(COC2)N1] | d |
| 15 | 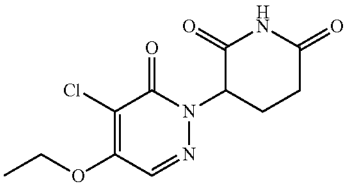 [SMILES: CCOc1cnn(C2CCC(=O)NC2=O)c(=O)c1Cl] | d |
| 16 | 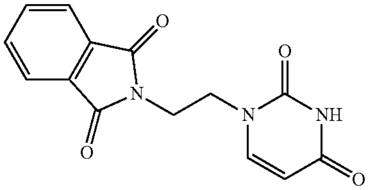 [SMILES: O=C1c2ccccc2C(=O)N1CCn1ccc(=O)[nH]c1=O] | d |
| 17 | 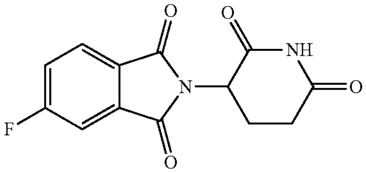 [SMILES: O=C1CCC(N2C(=O)c3ccc(F)cc3C2=O)C(=O)N1] | d |
| 18 | 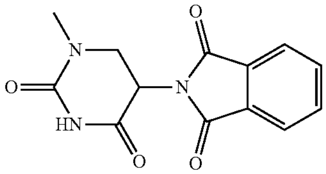 [SMILES: CN1CC(N2C(=O)c3ccccc3C2=O)C(=O)NC1=O] | d |
| 19 | 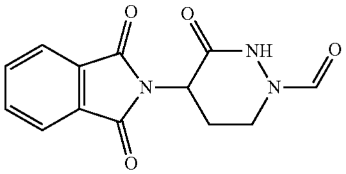 [SMILES: O=CN1CCC(N2C(=O)c3ccccc3C2=O)C(=O)N1] | d |
| 20 | 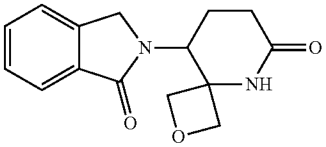 [SMILES: O=C1CCC(N2Cc3ccccc3C2=O)C2(COC2)N1] | d |
Suface Plasmon Resonance Data for Examplary CLMs TABLE 1-continued
| Suface Plasmon Resonance Data for Examplary CLMs | | |
|---|---|---|
| Example Number | Chemical Structure | $K_D$ Binding to immobilized CRBN protein in SPR assay |
| 21 | 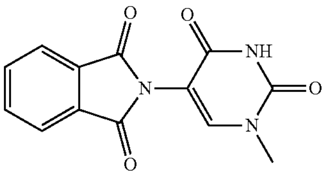 [SMILES: Cn1cc(N2C(=O)c3ccccc3C2=O)c(=O)[nH]c1=O] | d |
| 22 | 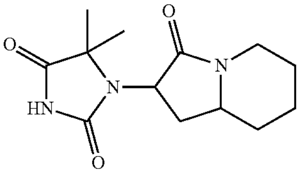 [SMILES: CC1(C)C(=O)NC(=O)N1C1CC2CCCCN2C1=O] | d |
| 23 | 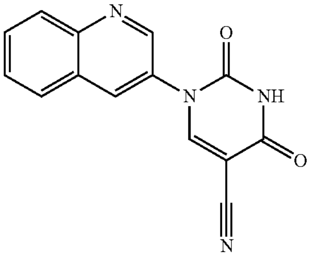 [SMILES: N#Cc1cn(-c2cnc3ccccc3c2)c(=O)[nH]c1=O] | c |
| 24 | 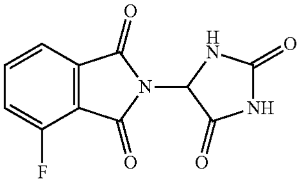 [SMILES: O=C1NC(=O)C(N2C(=O)c3cccc(F)c3C2=O)N1] | d |
| 25 | 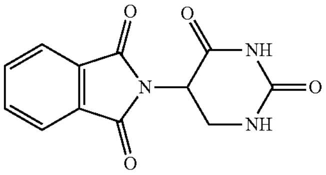 [SMILES: O=C1NCC(N2C(=O)c3ccccc3C2=O)C(=O)N1] | d |
| 26 | 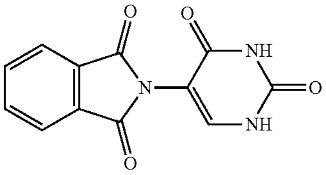 [SMILES: O=C1c2ccccc2C(=O)N1c1c[nH]c(=O)[nH]c1=O] | d |

TABLE 1-continued
Suface Plasmon Resonance Data for Examplary CLMs
| Example Number | Chemical Structure | $K_D$ Binding to immobilized CRBN protein in SPR assay |
|---|---|---|
| 27 | 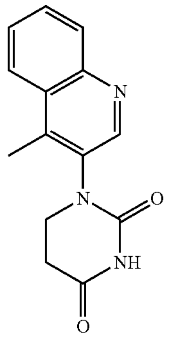 [SMILES: Cc1c(N2CCC(=O)NC2=O)cnc2ccccc12] | d |
| 28 | 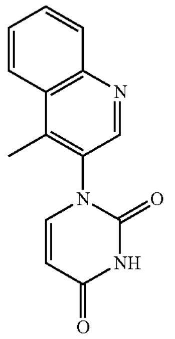 [SMILES: Cc1c(-n2ccc(=O)[nH]c2=O)cnc2ccccc12] | c |
| 29 | 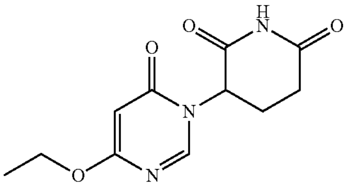 [SMILES: CCOc1cc(=O)n(C2CCC(=O)NC2=O)cn1] | c |
| 30 | 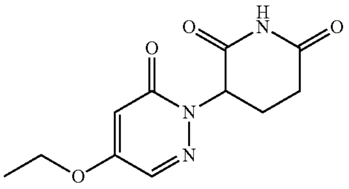 [SMILES: CCOc1cnn(C2CCC(=O)NC2=O)c(=O)c1] | b |
| 31 | 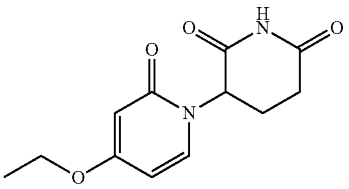 [SMILES: CCOc1ccn(C2CCC(=O)NC2=O)c(=O)c1] | d |

TABLE 1-continued
| Example Number | Chemical Structure | $K_D$ Binding to immobilized CRBN protein in SPR assay |
|---|---|---|
| | Suface Plasmon Resonance Data for Examplary CLMs | |
| 32 | 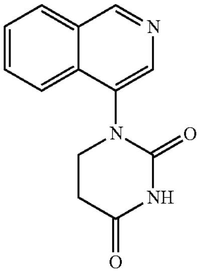 [SMILES: O=C1CCN(c2cncc3ccccc23)C(=O)N1] | b |
| 33 | 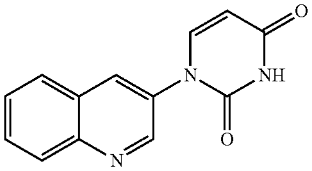 [SMILES: O=c1ccn(-c2cnc3ccccc3c2)c(=O)[nH]1] | d |
| 34 | 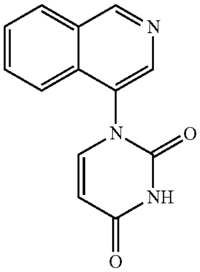 [SMILES: O=c1ccn(-c2cncc3ccccc23)c(=O)[nH]1] | c |
| 35 | 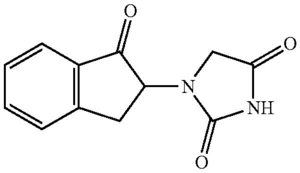 [SMILES: O=C1CN(C2Cc3ccccc3C2=O)C(=O)N1] | d |
| 36 | 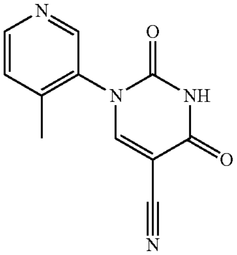 [SMILES: Cc1ccncc1-n1cc(C#N)c(=O)[nH]c1=O] | d |
| 37 | 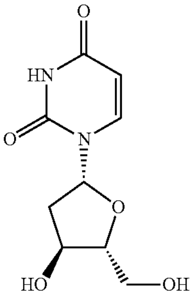 [SMILES: O=c1ccn([C@H]2C[C@H](O)[C@@H](CO)O2)c(=O)[nH]1] | d |

TABLE 1-continued
Suface Plasmon Resonance Data for Examplary CLMs
| Example Number | Chemical Structure | $K_D$ Binding to immobilized CRBN protein in SPR assay |
|---|---|---|
| 38 | 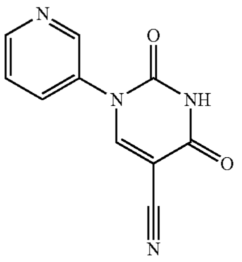 [SMILES: N#Cc1cn(-c2cccnc2)c(=O)[nH]c1=O] | d |
| 39 | 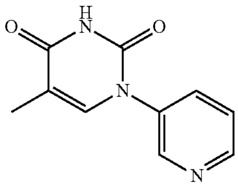 | d |
| 40 | 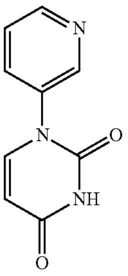 [SMILES: O=c1ccn(-c2cccnc2)c(=O)[nH]1] | c |
| 41 | 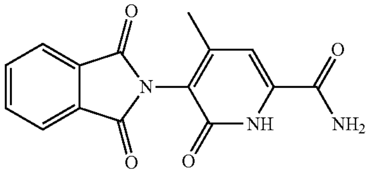 [SMILES: Cc1cc(C(N)=O)[nH]c(=O)c1N1C(=O)c2ccccc2C1=O] | d |
| 42 | 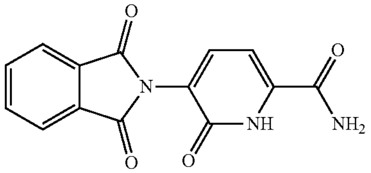 [SMILES: NC(=O)c1ccc(N2C(=O)c3ccccc3C2=O)c(=O)[nH]1] | d |
| 43 | 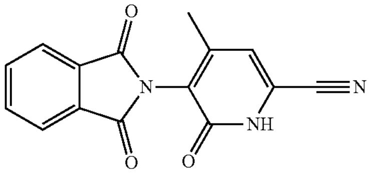 [SMILES: Cc1cc(C#N)[nH]c(=O)c1N1C(=O)c2ccccc2C1=O] | c |

TABLE 1-continued

| Suface Plasmon Resonance Data for Examplary CLMs | | |
|---|---|---|
| Example Number | Chemical Structure | $K_D$ Binding to immobilized CRBN protein in SPR assay |
| 44 | 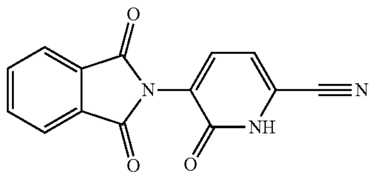 [SMILES: N#Cc1ccc(N2C(=O)c3ccccc3C2=O)c(=O)[nH]1] | c |

2. Cells and Reagents

NAMALWA, Ramos, CA-46 and DAUDI cells were purchased from ATCC and maintained as instructed. Antibodies against BRD4 ( #E2A7X), c-MYC ( #D84C$_{12}$), PARP ( #46D11) were purchased from Cell Signaling Technology. Actin ( #A5441) antibody was purchased from SigmaAldrich. Secondary antibodies ( #7074, #7076) were purchased from Cell Signaling Technology. MG132 ( #M7449) was purchased from SigmaAldrich. Carfizomib ( #S2853) was purchased from Selleck.

2. Western Blot Analysis

Cultured cells are collected in lysis buffer containing 40 mM HEPES (pH 7.4), 140 mM NaCl, 2.5 mM EDTA, 1% NP-40, 0.1% SDS and protease inhibitor cocktail. After 10 minutes of centrifugation (14000 rpm), supernatant is collected for protein concentration determination by BCA method and subjected for immunoblotting by standard protocol. Western blot results are visualized using Bio-Rad Clarity ECL Western Blotting Substrate on Bio-Rad ChemiDoc™ MP imaging system.

3. RT-PCR

RNA extraction is performed with Aurum™ Total RNA Mini Kit ( #732-6820) from Bio-Rad. First-strand cDNA from total RNA is synthesized with High-Capacity cDNA Reverse Transcription Kit ( #4368813) from Life Technologies according to manufacturer's instruction. Quantitative PCR is performed using Bio-rad SsoAdvanced™ Universal SYBR® Green Supermix ( #172-5271).

4. Proliferation Assay

To assess the effect of the inhibitors on proliferation, cells (50,000/1000 are seeded in 96-well tissue culture plates followed by addition of compound at the indicated concentration. After 72 hours, 100 μL per well of reconstituted CellTiter-Glo (CTG) reagent ( #G7572 from Promega) is added and read on Cytation 3 imaging reader from BioTek. Relative cell growth is determined by comparing assay readings of treated cells with control DMSO treated cells.

TABLE 2

| Exemplary PROTACs of the present disclosure | | | |
|---|---|---|---|
| PROTAC-# | Chemical Structure | Name | Synthesis |
| PROTAC-27 | 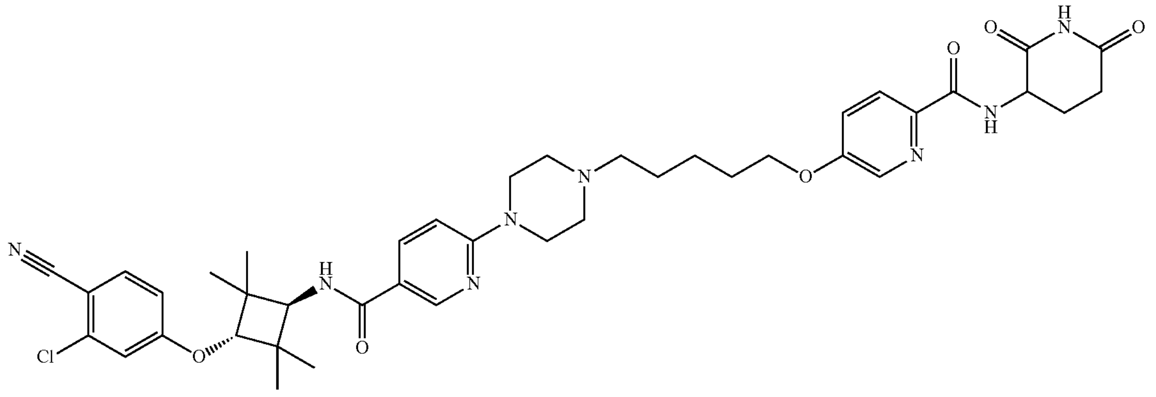 [SMILES: CC1(C)[C@H](NC(=O)c2ccc(N3CCN(CCCCCOc4ccc(C(=O)NC5CCC(=O)NC5=O)nc4)CC3)nc2)C(C)(C)[C@H]1Oc1ccc(C#N)c(Cl)c1] | rac-5-((5-(4-(5-(((1r,3r)-3-(3-chloro-4-cyanophenoxy)-2,2,4,4-tetramethylcyclobutyl) carbamoyl)pyridin-2-yl) piperazin-1-yl)pentyl)oxy)-N-(2,6-dioxopiperidin-3-yl)picolinamide | Following route described for PROTAC 50 |
| PROTAC-28 | 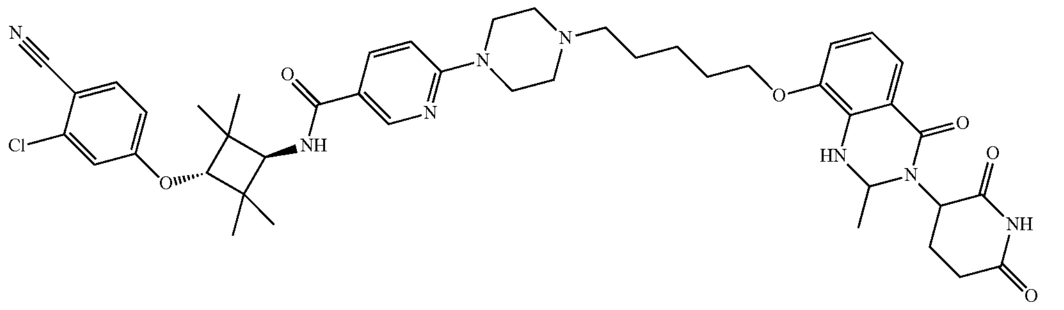 [SMILES: CC1Nc2c(OCCCCCN3CCN(c4ccc(C(=O)N[C@H]5C(C)(C)[C@H](Oc6ccc(C#N)c(Cl)c6)C5(C)C)cn4)CC3)cccc2C(=O)N1C1CCC(=O)NC1=O] | rac-N-((1r,3r)-3-(3-chloro-4-cyanophenoxy)-2,2,4,4-tetramethylcyclobutyl)-6-(4-(5-((3-(2,6-dioxopiperidin-3-yl)-2-methyl-4-oxo-1,2,3,4-tetrahydroquinazolin-8-yl)oxy)pentyl)piperazin-1-yl)nicotinamide | Byproduct from synthesis of PROTAC-30 |
| PROTAC-29 | 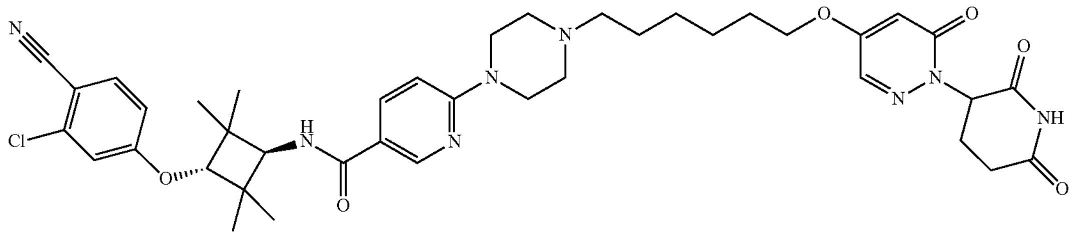 [SMILES: CC1(C)[C@H](NC(=O)c2ccc(N3CCN(CCCCCCOc4cnn(C5CCC(=O)NC5=O)c(=O)c4)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(6-((1-(2,6-dioxopiperidin-3-yl)-6-oxo-1,6-dihydropyridazin-4-yl)oxy)hexyl)piperazin-1-yl)nicotinamide | Described in detail |

TABLE 2-continued

| Exemplary PROTACs of the present disclosure | | | |
|---|---|---|---|
| PROTAC-# | Chemical Structure | Name | Synthesis |
| PROTAC-30 | 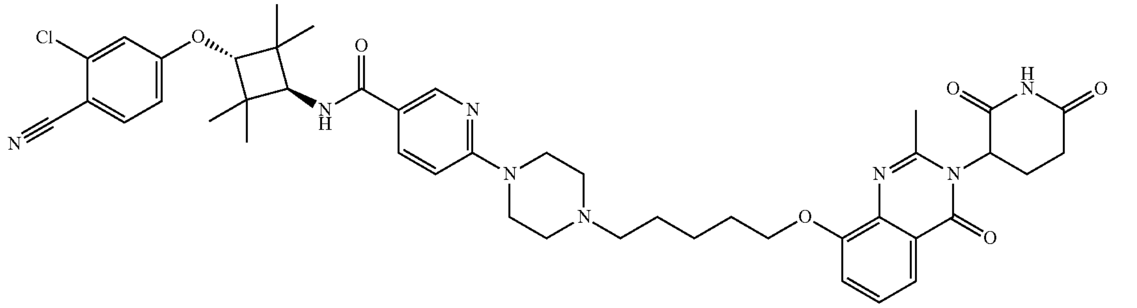 [SMILES: Cc1nc2c(OCCCCCN3CCN(c4ccc(C(=O)N[C@H]5C(C)(C)[C@H](Oc6ccc(C#N)c(Cl)c6)C5(C)C)cn4)CC3)cccc2c(=O)n1C1CCC(=O)NC1=O] | rac-N-((1r,3r)-3-(3-chloro-4-cyanophenoxy)-2,2,4,4-tetramethylcyclobutyl)-6-(4-(5-((3-(2,6-dioxopiperidin-3-yl)-2-methyl-4-oxo-3,4-dihydroquinazolin-8-yl)oxy)pentyl)piperazin-1-yl)nicotinamide | Described in detail |
| PROTAC-33 | 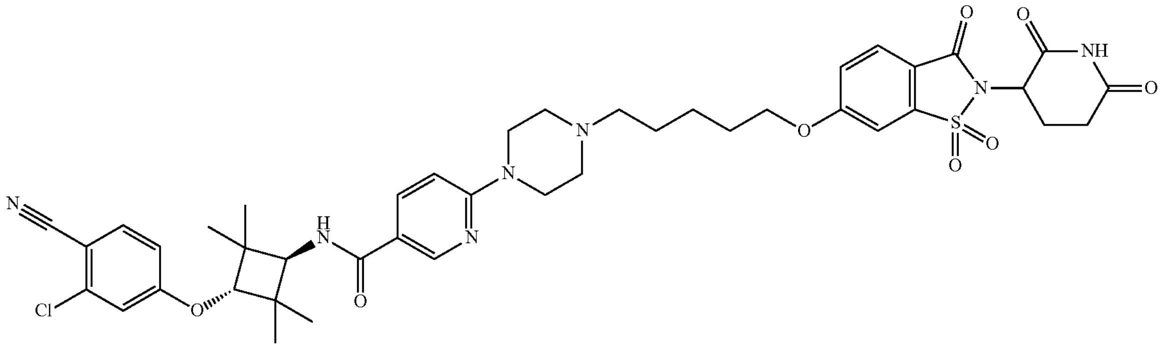 [SMILES: CC1(C)[C@H](NC(=O)c2ccc(N3CCN(CCCCCOc4ccc5c(c4)S(=O)(=O)N(C4CCC(=O)NC4=O)C5=O)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(5-((2-(2,6-dioxopiperidin-3-yl)-1,1-dioxido-3-oxo-2,3-dihydrobenzo[d]isothiazol-6-yl)oxy)pentyl)piperazin-1-yl)nicotinamide | Described in detail |

TABLE 2-continued

| Exemplary PROTACs of the present disclosure | | | |
|---|---|---|---|
| PROTAC-# | Chemical Structure | Name | Synthesis |
| PROTAC-39 | 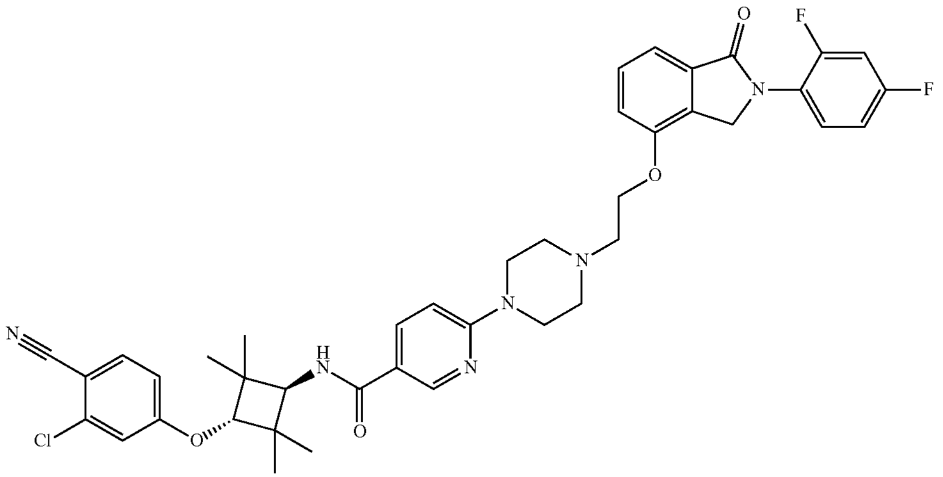 [SMILES: CC1(C)[C@H](NC(=O)c2ccc(N3CCN(CCOc4cccc5c4CN(c4ccc(F)cc4F)C5=O)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(2-((2-(2,4-difluorophenyl)-1-oxoisoindolin-4-yl)oxy)ethyl)piperazin-1-yl)nicotinamide | Described in detail |
| PROTAC-40 | 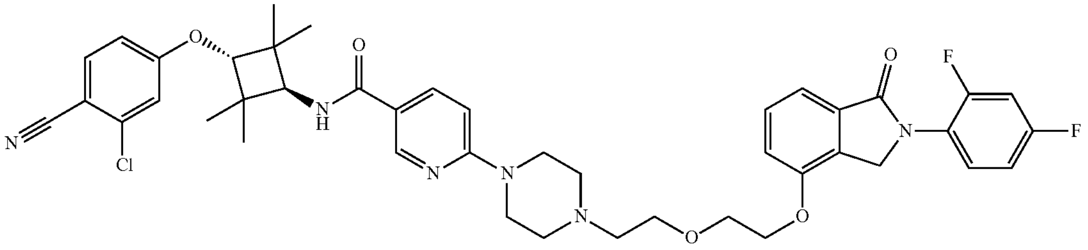 [SMILES: CC1(C)[C@H](NC(=O)c2ccc(N3CCN(CCOCCOc4cccc5c4CN(c4ccc(F)cc4F)C5=O)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(2-(2-((2-(2,4-difluoro-phenyl)-1-oxoisoindolin-4-yl)oxy)ethoxy)ethyl)piperazin-1-yl)nicotinamide | Following route described for PROTAC 40 |

TABLE 2-continued

Exemplary PROTACs of the present disclosure

| PROTAC-# | Chemical Structure | Name | Synthesis |
| --- | --- | --- | --- |
| PROTAC-41 | 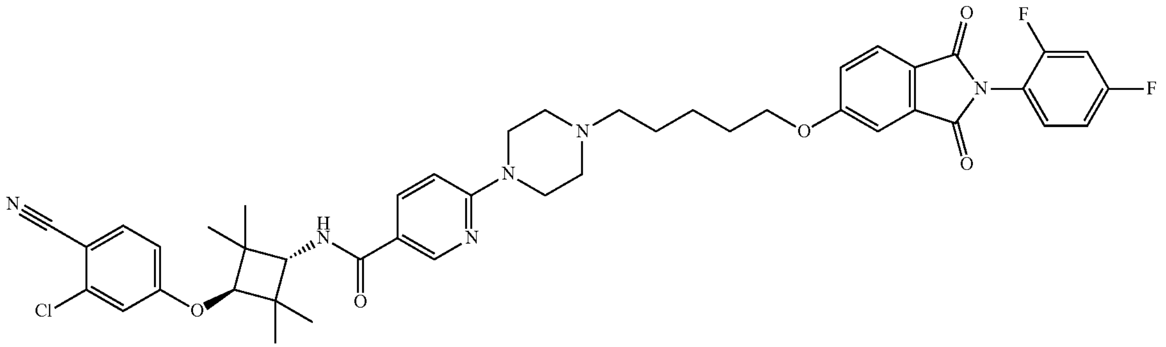 [SMILES: CC1(C)[C@H](NC(=O)c2ccc(N3CCN(CCCCCOc4ccc5c(c4)C(=O)N(c4ccc(F)cc4F)C5=O)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(5-((2-(2,4-difluorophenyl)-1,3-dioxoisoindolin-5-yl)oxy)pentyl)piperazin-1-yl)nicotinamide | Described in detail |
| PROTAC-42 | 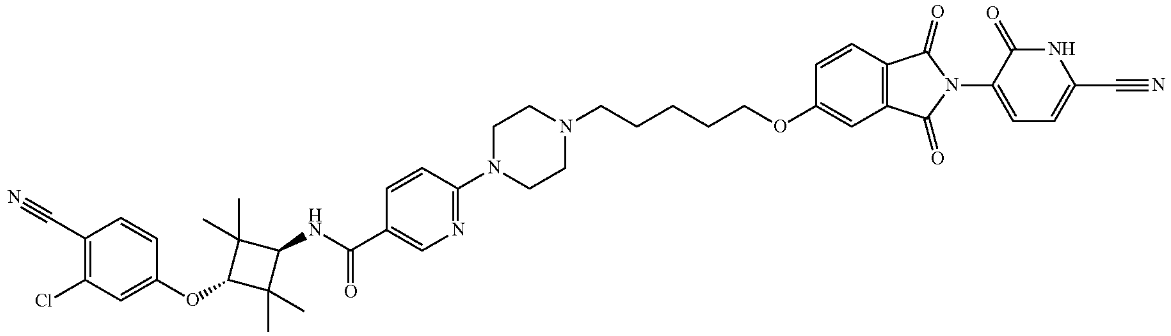 [SMILES: CC1(C)[C@H](NC(=O)c2ccc(N3CCN(CCCCCOc4ccc5c(c4)C(=O)N(c4ccc(C#N)[nH]c4=O)C5=O)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(5-((2-(6-cyano-2-oxo-1,2-dihydropyridin-3-yl)-1,3-dioxoisoindolin-5-yl)oxy)pentyl)piperazin-1-yl)nicotinamide | Described in detail |
| PROTAC-43 | 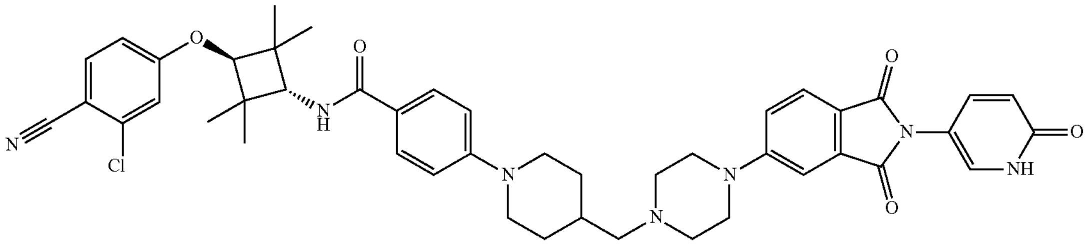 [SMILES: CC1(C)[C@H](NC(=O)c2ccc(N3CCC(CN4CCN(c5ccc6c(c5)C(=O)N(c5ccc(=O)[nH]c5)C6=O)CC4)CC3)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-(4-((4-(1,3-dioxo-2-(6-oxo-1,6-dihydropyridin-3-yl)isoindolin-5-yl)piperazin-1-yl)methyl)piperidin-1-yl)benzamide | Described in detail |

TABLE 2-continued

Exemplary PROTACs of the present disclosure

| PROTAC-# | Chemical Structure | Name | Synthesis |
| --- | --- | --- | --- |
| PROTAC-44 | 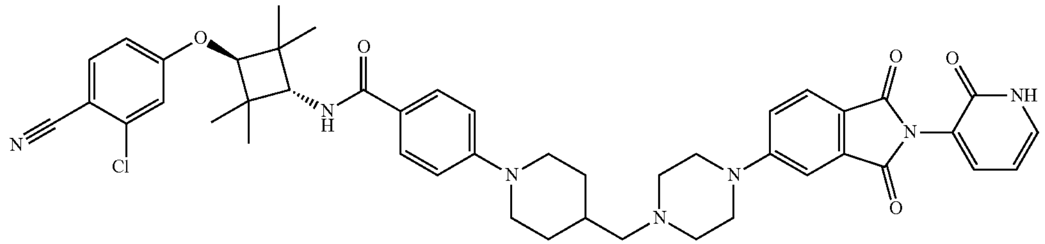 [SMILES: CC1(C)[C@H](NC(=O)c2ccc(N3CCC(CN4CCN(c5ccc6c(c5)C(=O)N(c5ccc[nH]c5=O)C6=O)CC4)CC3)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-(4-((4-(1,3-dioxo-2-(2-oxo-1,2-dihydropyridin-3-yl)isoindolin-5-yl)piperazin-1-yl)methyl)piperidin-1-yl)benzamide | Following route described for PROTAC 43 |
| PROTAC-45 | 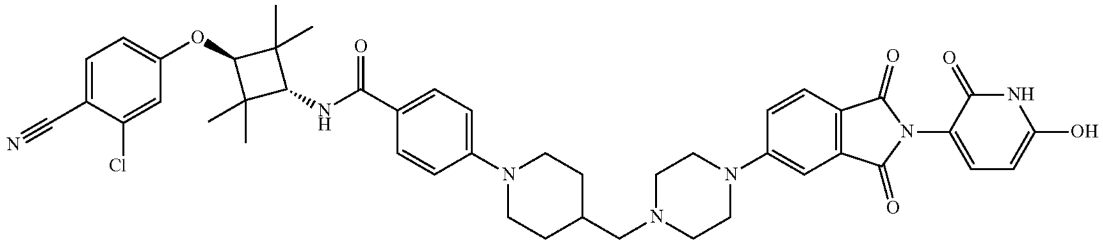 [SMILES: CC1(C)[C@H](NC(=O)c2ccc(N3CCC(CN4CCN(c5ccc6c(c5)C(=O)N(c5ccc(O)[nH]c5=O)C6=O)CC4)CC3)cc2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-4-(4-((4-(2-(6-hydroxy-2-oxo-1,2-dihydropyridin-3-yl)-1,3-dioxoisoindolin-5-yl)piperazin-1-yl)methyl)piperidin-1-yl)benzamide | Following route described for PROTAC 43 (using HBr/HOAc for demethylation step) |
| PROTAC-46 | 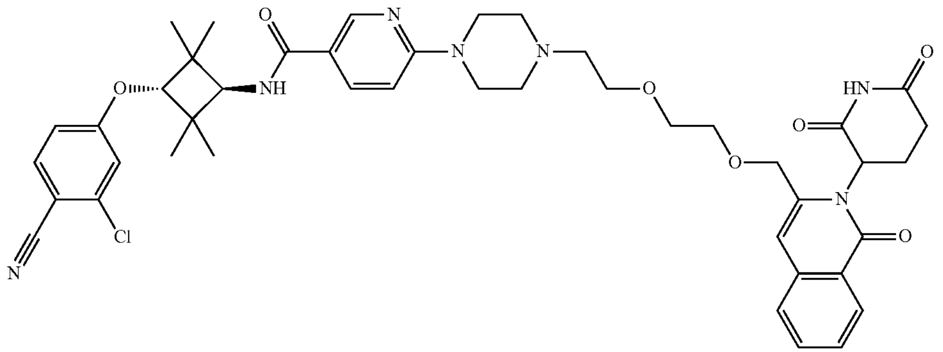 [SMILES: CC1(C)[C@H](NC(=O)c2ccc(N3CCN(CCOCCOCc4cc5ccccc5c(=O)n4C4CCC(=O)NC4=O)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(2-(2-((2-(2,6-dioxo-piperidin-3-yl)-1-oxo-1,2-dihydroisoquinolin-3-yl)methoxy)ethoxy)ethyl) piperazin-1-yl)nicotinamide | Described in detail |

TABLE 2-continued

| Exemplary PROTACs of the present disclosure | | | |
|---|---|---|---|
| PROTAC-# | Chemical Structure | Name | Synthesis |
| PROTAC-47 | 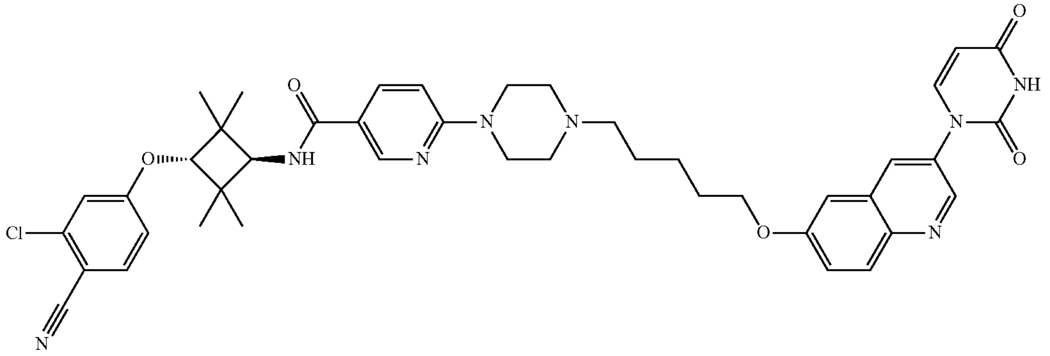 [SMILES: CC1(C)[C@H](NC(=O)c2ccc(N3CCN(CCCCCOc4ccc5ncc(-n6ccc(=O)[nH]c6=O)cc5c4)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(5-((3-(2,4-dioxo-3,4-dihydropyrimidin-1(2H)-yl)quinolin-6-yl)oxy)pentyl)piperazin-1-yl)nicotinamide | Described in detail |
| PROTAC-48 | 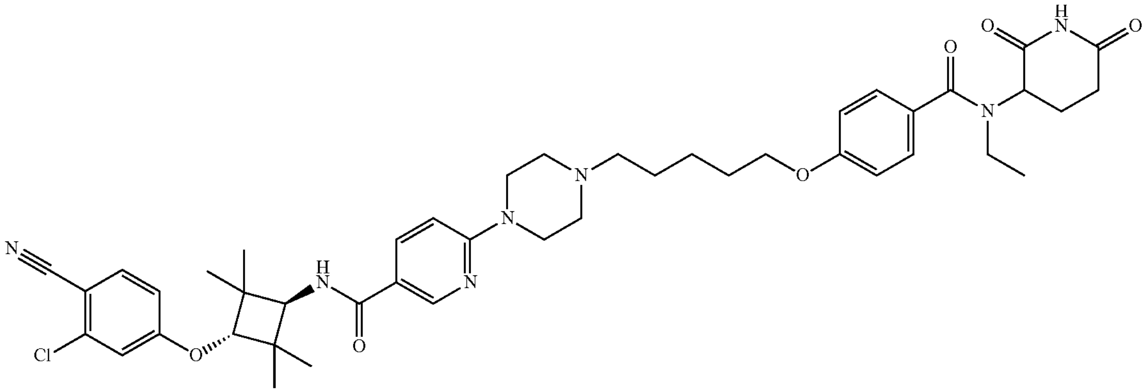 [SMILES: CCN(C(=O)c1ccc(OCCCCCN2CCN(c3ccc(C(=O)N[C@H]4C(C)(C)[C@H](Oc5ccc(C#N)c(Cl)c5)C4(C)C)cn3)CC2)cc1)C1CCC(=O)NC1=O] | rac-N-((1r,3r)-3-(3-chloro-4-cyanophenoxy)-2,2,4,4-tetramethylcyclobutyl)-6-(4-(5-(4-((2,6-dioxopiperidin-3-yl)(ethyl)carbamoyl)phenoxy)pentyl)piperazin-1-yl)nicotinamide | Described in detail |

TABLE 2-continued

| Exemplary PROTACs of the present disclosure | | | |
|---|---|---|---|
| PROTAC-# | Chemical Structure | Name | Synthesis |
| PROTAC-49 | 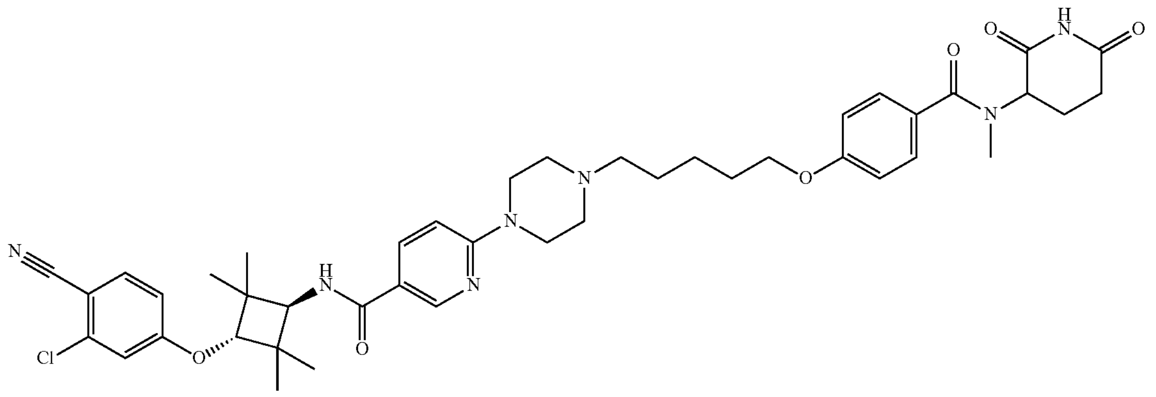 [SMILES: CN(C(=O)c1ccc(OCCCCCN2CCN(c3ccc(C(=O)N[C@H]4C(C)(C)[C@H](Oc5ccc(C#N)c(Cl)c5)C4(C)C)cn3)CC2)cc1)C1CCC(=O)NC1=O] | rac-N-((1r,3r)-3-(3-chloro-4-cyanophenoxy)-2,2,4,4-tetramethylcyclobutyl)-6-(4-(5-(4-((2,6-dioxopiperidin-3-yl)(methyl)carbamoyl) phenoxy)pentyl)piperazin-1-yl)nicotinamide | Following route described for PROTAC 48 |
| PROTAC-50 | 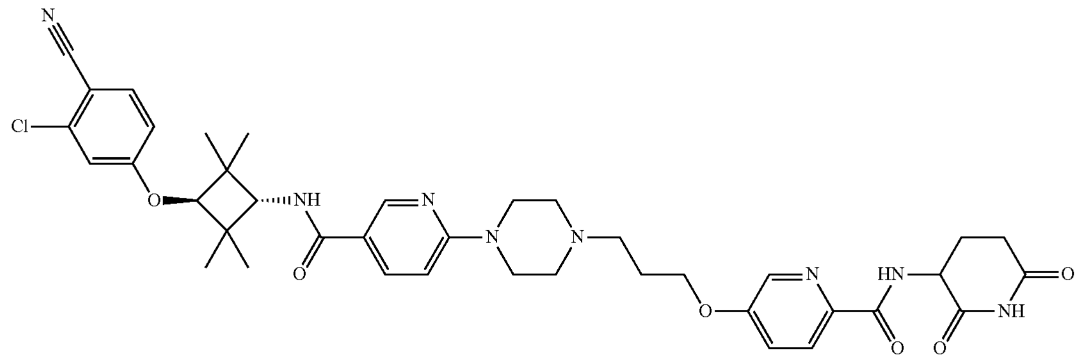 [SMILES: CC1(C)[C@H](NC(=O)c2ccc(N3CCN(CCCOc4ccc(C(=O)NC5CCC(=O)NC5=O)nc4)CC3)nc2)C(C)(C)[C@H]1Oc1ccc(C#N)c(Cl)c1] | rac-5-(3-(4-(5-(((1r,3r)-3-(3-chloro-4-cyanophenoxy)-2,2,4,4-tetramethylcyclobutyl)carbamoyl)pyridin-2-yl)piperazin-1-yl)propoxy)-N-(2,6-dioxopiperidin-3-yl)picolinamide | Described in detail |
| PROTAC-51 | 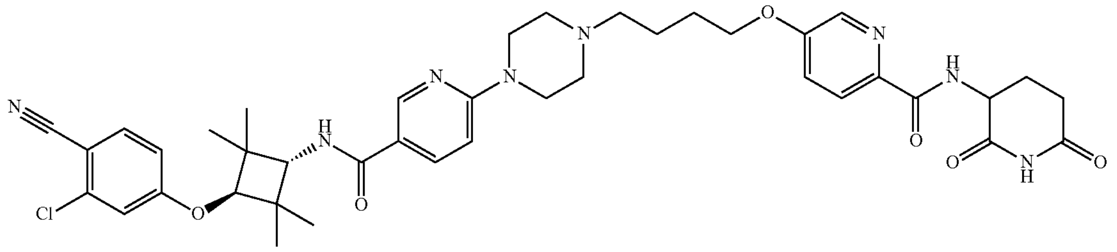 [SMILES: CC1(C)[C@H](NC(=O)c2ccc(N3CCN(CCCCOc4ccc(C(=O)NC5CCC(=O)NC5=O)nc4)CC3)nc2)C(C)(C)[C@H]1Oc1ccc(C#N)c(Cl)c1] | rac-5-(4-(4-(5-(((1r,3r)-3-(3-chloro-4-cyanophenoxy)-2,2,4,4-tetramethylcyclobutyl)carbamoyl)pyridin-2-yl)piperazin-1-yl)butoxy)-N-(2,6-dioxopiperidin-3-yl)picolinamide | Following route described for PROTAC 50 |

TABLE 2-continued

| Exemplary PROTACs of the present disclosure | | | |
|---|---|---|---|
| PROTAC-# | Chemical Structure | Name | Synthesis |
| PROTAC-52 | 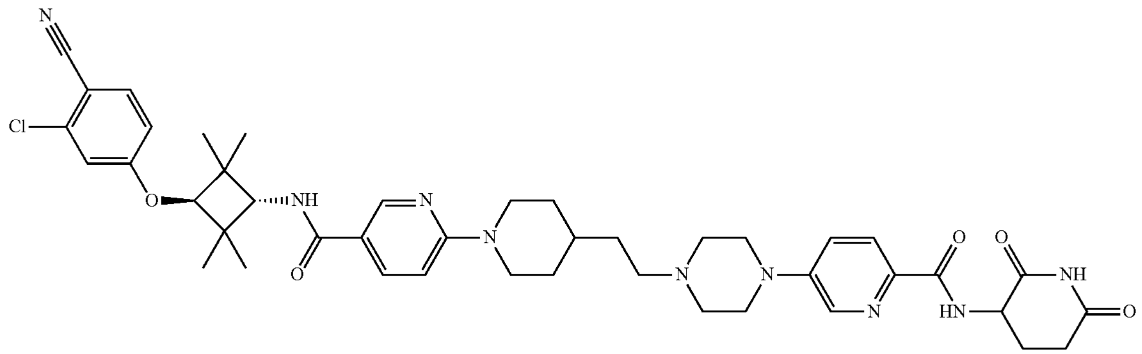 [SMILES: CC1(C)[C@H](NC(=O)c2ccc(N3CCC(CCN4CCN(c5ccc(C(=O)NC6CCC(=O)NC6=O)nc5)CC4)CC3)nc2)C(C)(C)[C@H]1Oc1ccc(C#N)c(Cl)c1] | rac-5-(4-(2-(1-(5-(((1r,3r)-3-(3-chloro-4-cyano-phenoxy)-2,2,4,4-tetramethylcyclobutyl)carbamoyl)pyridin-2-yl)piperidin-4-yl)ethyl)piperazin-1-yl)-N-(2,6-dioxopiperidin-3-yl)picolinamide | Following route described for PROTAC 53 |
| PROTAC-53 | 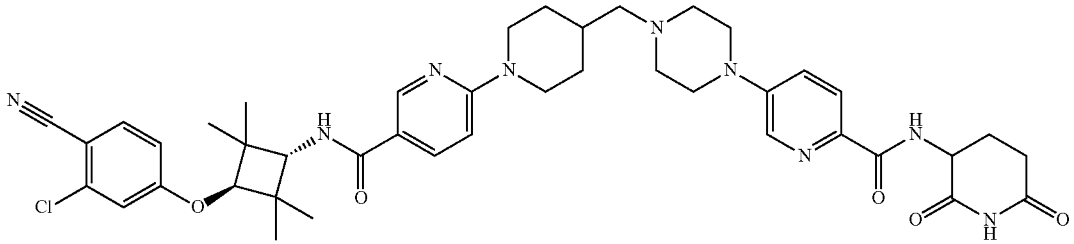 [SMILES: CC1(C)[C@H](NC(=O)c2ccc(N3CCC(CN4CCN(c5ccc(C(=O)NC6CCC(=O)NC6=O)nc5)CC4)CC3)nc2)C(C)(C)[C@H]1Oc1ccc(C#N)c(Cl)c1] | rac-5-(4-((1-(5-(((1r,3r)-3-(3-chloro-4-cyanophenoxy)-2,2,4,4-tetramethylcyclo-butyl)carbamoyl)pyridin-2-yl)piperidin-4-yl)methyl)piperazin-1-yl)-N-(2,6-dioxopiperidin-3-yl)picolinamide | Described in detail |
| PROTAC-54 | 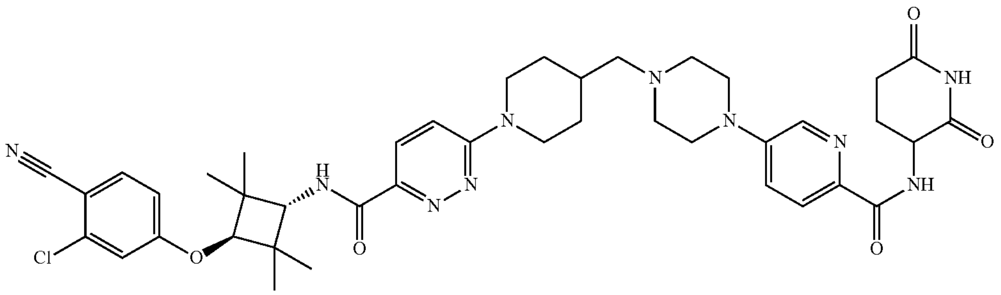 [SMILES: CC1(C)[C@H](NC(=O)c2ccc(N3CCC(CN4CCN(c5ccc(C(=O)NC6CCC(=O)NC6=O)nc5)CC4)CC3)nn2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-((4-(6-((2,6-dioxopiperidin-3-yl)carbamoyl)pyridin-3-yl)piperazin-1-yl)methyl)piperidin-1-yl)pyridazine-3-carboxamide | Following route described for PROTAC 53 |

TABLE 2-continued

| Exemplary PROTACs of the present disclosure | | | |
|---|---|---|---|
| PROTAC-# | Chemical Structure | Name | Synthesis |
| PROTAC-55 | 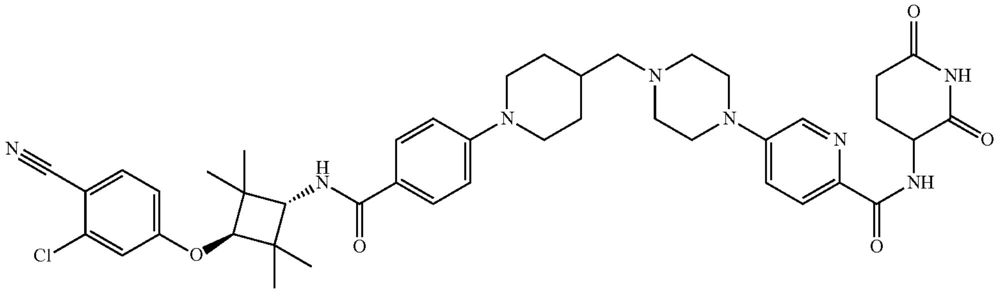 [SMILES: CC1(C)[C@H](NC(=O)c2ccc(N3CCC(CN4CCN(c5ccc(C(=O)NC6CCC(=O)NC6=O)nc5)CC4)CC3)cc2)C(C)(C)[C@H]1Oc1ccc(C#N)c(Cl)c1] | rac-5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-N-(2,6-dioxopiperidin-3-yl)picolinamide | Following route described for PROTAC 53 |
| PROTAC-56 | 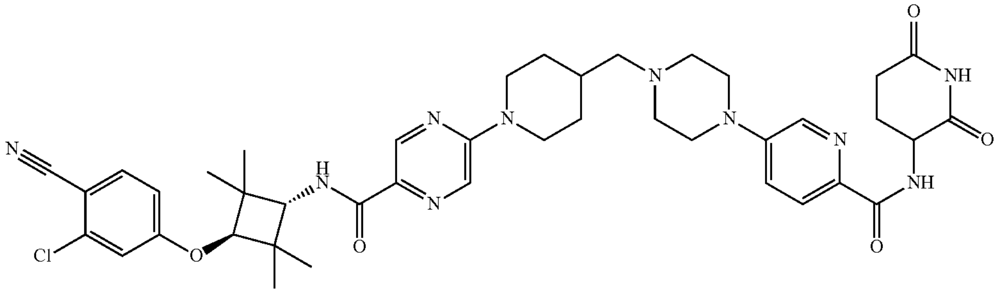 [SMILES: CC1(C)[C@H](NC(=O)c2cnc(N3CCC(CN4CCN(c5ccc(C(=O)NC6CCC(=O)NC6=O)nc5)CC4)CC3)cn2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-5-(4-((4-(6-((2,6-dioxopiperidin-3-yl)carbamoyl)pyridin-3-yl)piperazin-1-yl)methyl)piperidin-1-yl)pyrazine-2-carboxamide | Following route described for PROTAC 53 |
| PROTAC-57 | 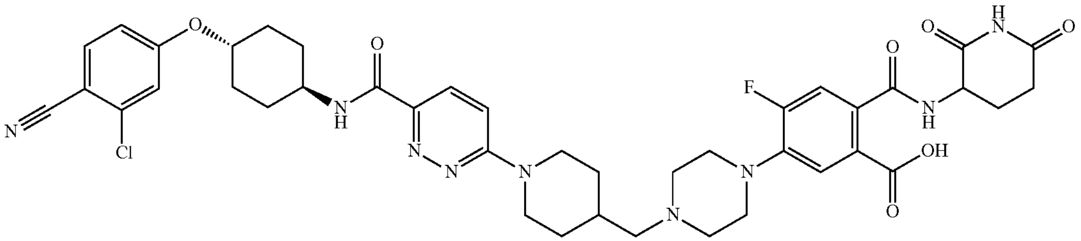 [SMILES: N#Cc1ccc(O[C@H]2CC[C@H](NC(=O)c3ccc(N4CCC(CN5CCN(c6cc(C(=O)O)c(C(=O)NC7CCC(=O)NC7=O)cc6F)CC5)CC4)nn3)CC2)cc1Cl] | 5-(4-((1-(6-(((1r,4r)-4-(3-chloro-4-cyanophenoxy)cyclohexyl)carbamoyl)pyridazin-3-yl)piperidin-4-yl)methyl)piperazin-1-yl)-2-((2,6-dioxopiperidin-3-yl)carbamoyl)-4-fluorobenzoic acid | Following route described for PROTAC 53 |

TABLE 2-continued

| Exemplary PROTACs of the present disclosure | | | |
|---|---|---|---|
| PROTAC-# | Chemical Structure | Name | Synthesis |
| PROTAC-58 | 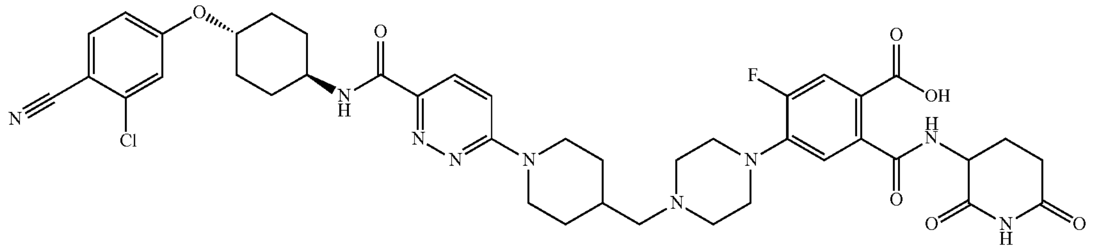 [SMILES: N#Cc1ccc(O[C@H]2CC[C@H](NC(=O)c3ccc(N4CCC(CN5CCN(c6cc(C(=O)NC7CCC(=O)NC7=O)c(C(=O)O)cc6F)CC5)CC4)nn3)CC2)cc1Cl] | 4-(4-((1-(6-(((1r,4r)-4-(3-chloro-4-cyanophenoxy)cyclohexyl)carbamoyl)pyridazin-3-yl)piperidin-4-yl)methyl)piperazin-1-yl)-2-((2,6-dioxopiperidin-3-yl)carbamoyl)-5-fluorobenzoic acid | Following route described for PROTAC 53 |
| PROTAC-59 | 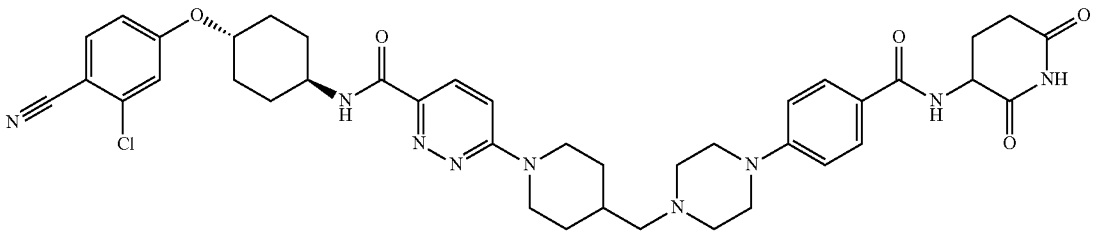 [SMILES: N#Cc1ccc(O[C@H]2CC[C@H](NC(=O)c3ccc(N4CCC(CN5CCN(c6ccc(C(=O)NC7CCC(=O)NC7=O)cc6)CC5)CC4)nn3)CC2)cc1Cl] | N-((1r,4r)-4-(3-chloro-4-cyanophenoxy)cyclohexyl)-6-(4-((4-(4-((2,6-dioxopiperidin-3-yl)carbamoyl)phenyl)piperazin-1-yl)methyl)piperidin-1-yl)pyridazine-3-carboxamide | Following route described for PROTAC 53 |
| PROTAC-60 | 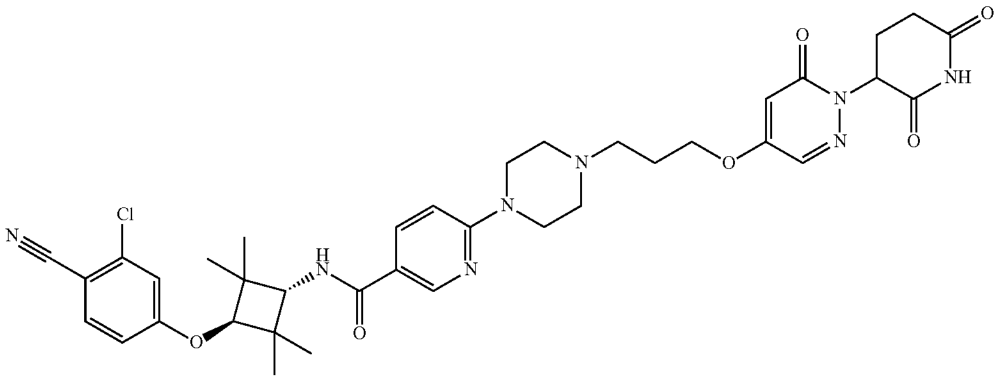 [SMILES: CC1(C)[C@H](NC(=O)c2ccc(N3CCN(CCCOc4cnn(C5CCC(=O)NC5=O)c(=O)c4)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(3-((1-(2,6-dioxopiperidin-3-yl)-6-oxo-1,6-dihydropyridazin-4-yl)oxy)propyl)piperazin-1-yl)nicotinamide | Following route described for PROTAC 29 |

TABLE 2-continued

| Exemplary PROTACs of the present disclosure | | | |
|---|---|---|---|
| PROTAC-# | Chemical Structure | Name | Synthesis |
| PROTAC-61 | 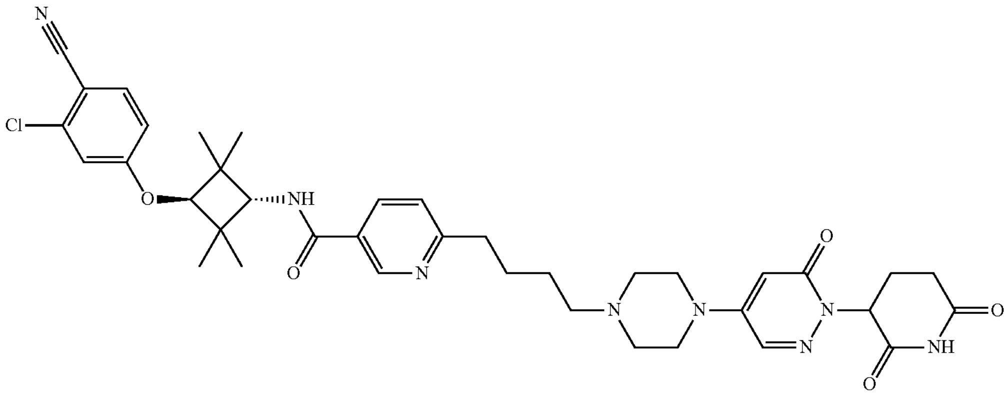 [SMILES: CC1(C)[C@H](NC(=O)c2ccc(CCCCN3CCN(c4cnn(C5CCC(=O)NC5=O)c(=O)c4)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(4-(1-(2,6-dioxopiperidin-3-yl)-6-oxo-1,6-dihydropyridazin-4-yl)piperazin-1-yl)butyl)nicotinamide | Described in detail |
| PROTAC-62 | 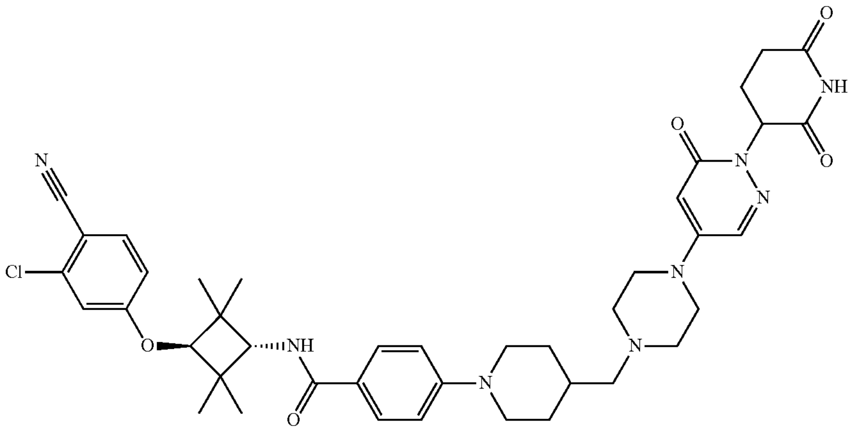 [SMILES: CC1(C)[C@H](NC(=O)c2ccc(N3CCC(CN4CCN(c5cnn(C6CCC(=O)NC6=O)c(=O)c5)CC4)CC3)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-(4-((4-(1-(2,6-dioxopiperidin-3-yl)-6-oxo-1,6-dihydropyridazin-4-yl)piperazin-1-yl)methyl)piperidin-1-yl)benzamide | Following route described for PROTAC 61 |

TABLE 2-continued

| Exemplary PROTACs of the present disclosure | | | |
|---|---|---|---|
| PROTAC-# | Chemical Structure | Name | Synthesis |
| PROTAC-63 | 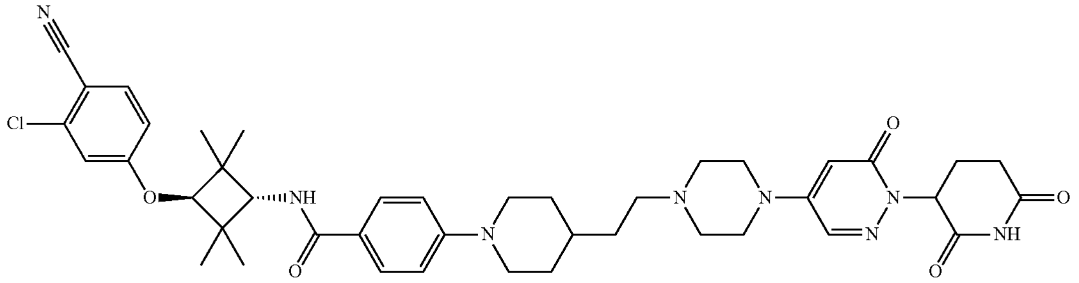 [SMILES: CC1(C)[C@H](NC(=O)c2ccc(N3CCC(CCN4CCN(c5cnn(C6CCC(=O)NC6=O)c(=O)c5)CC4)CC3)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-(4-(2-(4-(1-(2,6-dioxopiperidin-3-yl)-6-oxo-1,6-dihydropyridazin-4-yl)piperazin-1-yl)ethyl)piperidin-1-yl)benzamide | Following route described for PROTAC 61 |
| PROTAC-66 | 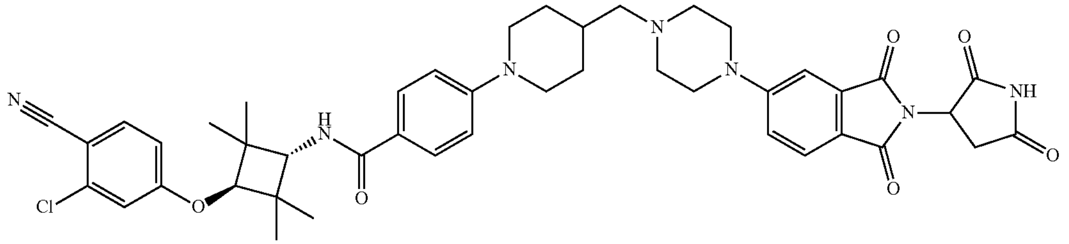 [SMILES: CC1(C)[C@H](NC(=O)c2ccc(N3CCC(CN4CCN(c5ccc6c(c5)C(=O)N(C5CC(=O)NC5=O)C6=O)CC4)CC3)cc2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-4-(4-((4-(2-(2,5-dioxopyrrolidin-3-yl)-1,3-dioxoisoindolin-5-yl)piperazin-1-yl)methyl)piperidin-1-yl)benzamide | Following route described for PROTAC 43, using 3-amino-pyrrolidine-2,5-dione as starting material |
| PROTAC-67 | 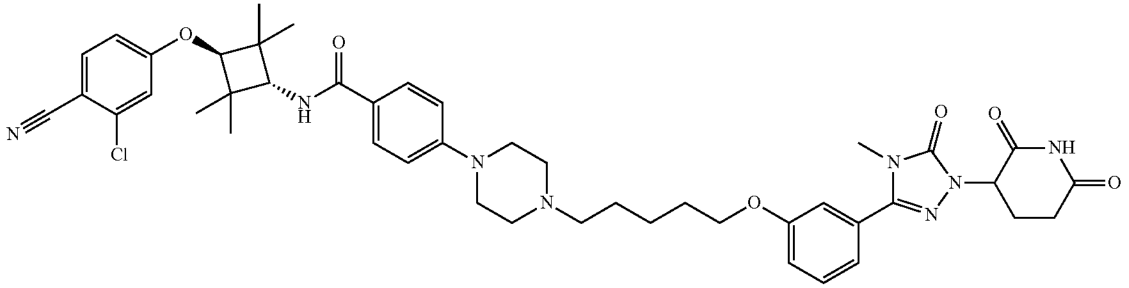 [SMILES: Cn1c(-c2cccc(OCCCCCN3CCN(c4ccc(C(=O)N[C@H]5C(C)(C)[C@H](Oc6ccc(C#N)c(Cl)c6)C5(C)C)cc4)CC3)c2)nn(C2CCC(=O)NC2=O)c1=O] | rac-N-((1r,3r)-3-(3-chloro-4-cyanophenoxy)-2,2,4,4-tetramethylcyclobutyl)-4-(4-(5-(3-(1-(2,6-dioxopiperidin-3-yl)-4-methyl-5-oxo-4,5-dihydro-1H-1,2,4-triazol-3-yl)phenoxy)pentyl)piperazin-1-yl)benzamide | Following route described for PROTAC 70 |

TABLE 2-continued

| Exemplary PROTACs of the present disclosure | | | |
|---|---|---|---|
| PROTAC-# | Chemical Structure | Name | Synthesis |
| PROTAC-68 | 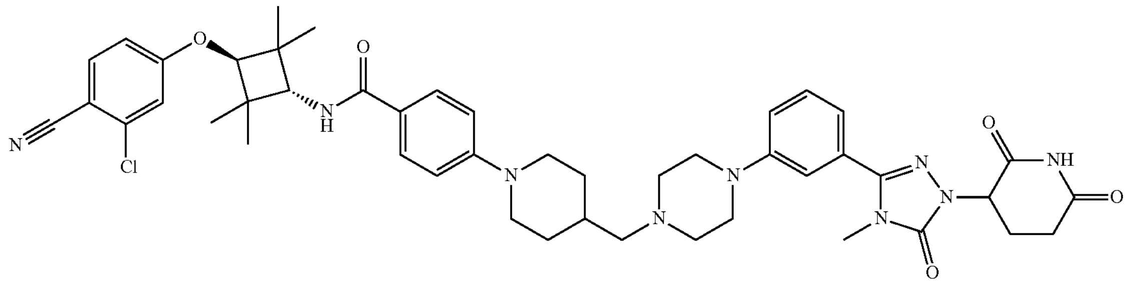 [SMILES: Cn1c(-c2cccc(N3CCN(CC4CCN(c5ccc(C(=O)N[C@H]6C(C)(C)[C@H](Oc7ccc(C#N)c(Cl)c7)C6(C)C)cc5)CC4)CC3)c2)nn(C2CCC(=O)NC2=O)c1=O] | rac-N-((1r,3r)-3-(3-chloro-4-cyanophenoxy)-2,2,4,4-tetramethylcyclobutyl)-4-(4-((4-(3-(1-(2,6-dioxo-piperidin-3-yl)-4-methyl-5-oxo-4,5-dihydro-1H-1,2,4-triazol-3-yl)phenyl)piperazin-1-yl)methyl)piperidin-1-yl)benzamide | Following route described for PROTAC 70 |
| PROTAC-69 | 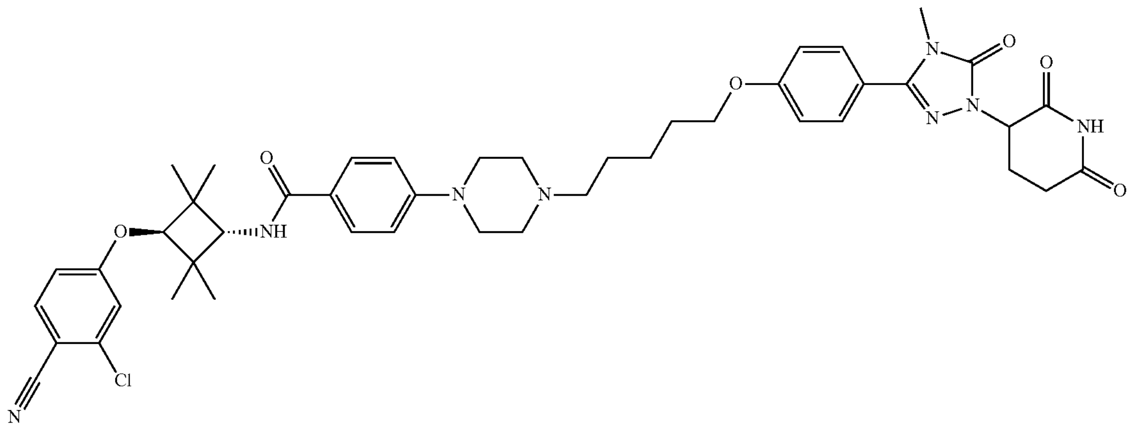 [SMILES: Cn1c(-c2ccc(OCCCCCN3CCN(c4ccc(C(=O)N[C@H]5C(C)(C)[C@H](Oc6ccc(C#N)c(Cl)c6)C5(C)C)cc4)CC3)cc2)nn(C2CCC(=O)NC2=O)c1=O] | rac-N-((1r,3r)-3-(3-chloro-4-cyanophenoxy)-2,2,4,4-tetramethylcyclobutyl)-4-(4-(5-(4-(1-(2,6-dioxo-piperidin-3-yl)-4-methyl-5-oxo-4,5-dihydro-1H-1,2,4-triazol-3-yl)phenoxy)pentyl)piperazin-1-yl)benzamide | Following route described for PROTAC 70 |
| PROTAC-70 | 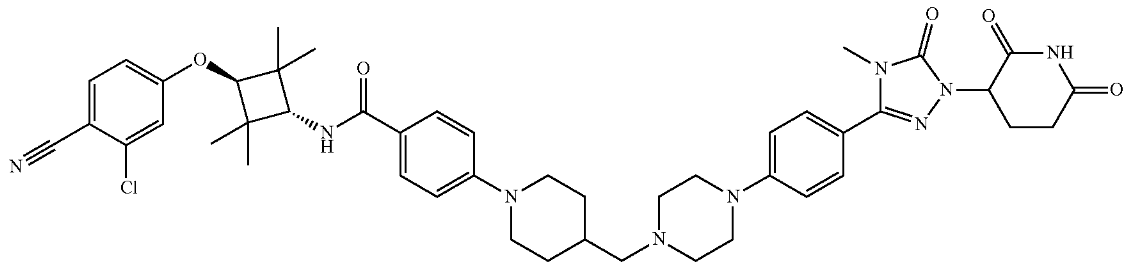 [SMILES: Cn1c(-c2ccc(N3CCN(CC4CCN(c5ccc(C(=O)N[C@H]6C(C)(C)[C@H](Oc7ccc(C#N)c(Cl)c7)C6(C)C)cc5)CC4)CC3)cc2)nn(C2CCC(=O)NC2=O)c1=O] | rac-N-((1r,3r)-3-(3-chloro-4-cyanophenoxy)-2,2,4,4-tetramethylcyclobutyl)-4-(4-((4-(4-(1-(2,6-dioxo-piperidin-3-yl)-4-methyl-5-oxo-4,5-dihydro-1H-1,2,4-triazol-3-yl)phenyl)piperazin-1-yl)methyl)piperidin-1-yl)benzamide | Described in detail |

TABLE 2-continued

| Exemplary PROTACs of the present disclosure | | | |
|---|---|---|---|
| PROTAC-# | Chemical Structure | Name | Synthesis |
| PROTAC-75 | 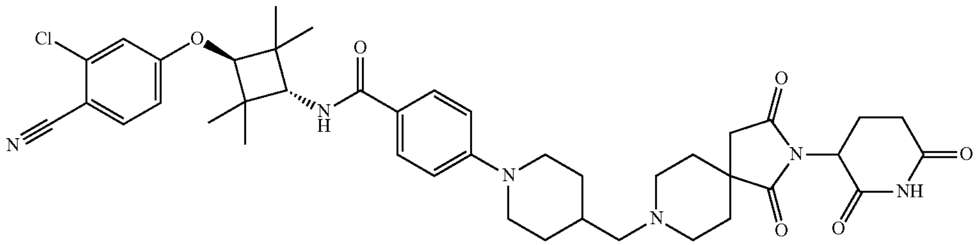 [SMILES: CC1(C)[C@H](NC(=O)c2ccc(N3CCC(CN4CCC5(CC4)CC(=O)N(C4CCC(=O)NC4=O)C5=O)CC3)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-(4-((2-(2,6-dioxopiperidin-3-yl)-1,3-dioxo-2,8-diazaspiro[4.5]decan-8-yl)methyl)piperidin-1-yl)benzamide | Following route described for PROTAC 53 and 112 |
| PROTAC-76 | 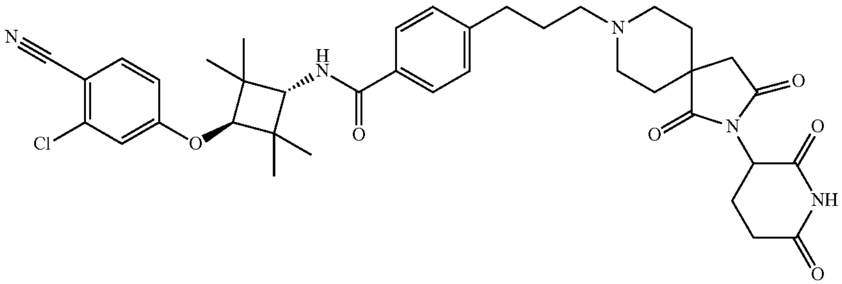 [SMILES: CC1(C)[C@H](NC(=O)c2ccc(CCCN3CCC4(CC3)CC(=O)N(C3CCC(=O)NC3=O)C4=O)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-(3-(2-(2,6-dioxopiperidin-3-yl)-1,3-dioxo-2,8-diazaspiro[4.5]decan-8-yl)propyl)benzamide | Following route described for PROTAC 61 and 112 |
| PROTAC-77 | 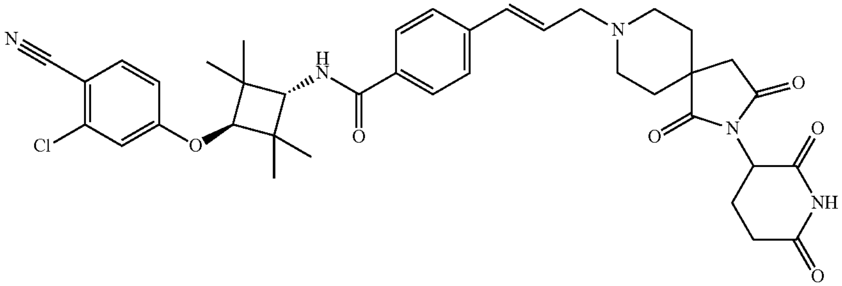 [SMILES: CC1(C)[C@H](NC(=O)c2ccc(/C=C/CN3CCC4(CC3)CC(=O)N(C3CCC(=O)NC3=O)C4=O)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-((E)-3-(2-(2,6-dioxo-piperidin-3-yl)-1,3-dioxo-2,8-diazaspiro[4.5]decan-8-yl)prop-1-en-1-yl)benzamide | Following route described for PROTAC 61 and 112 |

TABLE 2-continued

| Exemplary PROTACs of the present disclosure | | | |
|---|---|---|---|
| PROTAC-# | Chemical Structure | Name | Synthesis |
| PROTAC-78 | 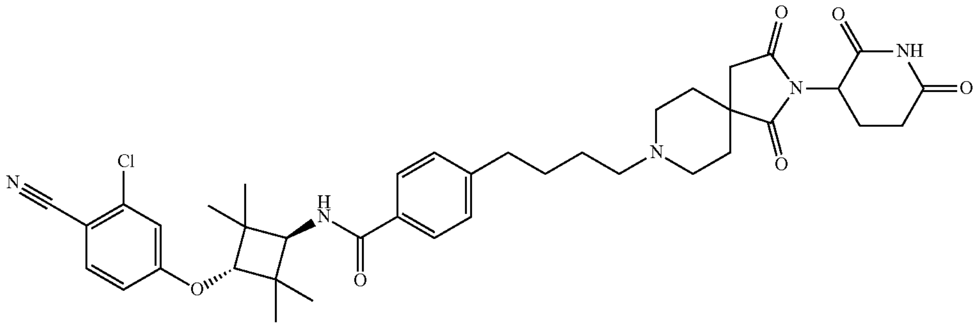 [SMILES: CC1(C)[C@H](NC(=O)c2ccc(CCCCN3CCC4(CC3)CC(=O)N(C3CCC(=O)NC3=O)C4=O)cc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-4-(4-(2-(2,6-dioxopiperidin-3-yl)-1,3-dioxo-2,8-diazaspiro[4.5]decan-8-yl)butyl)benzamide | Following route described for PROTAC 61 and 112 |
| PROTAC-79 | 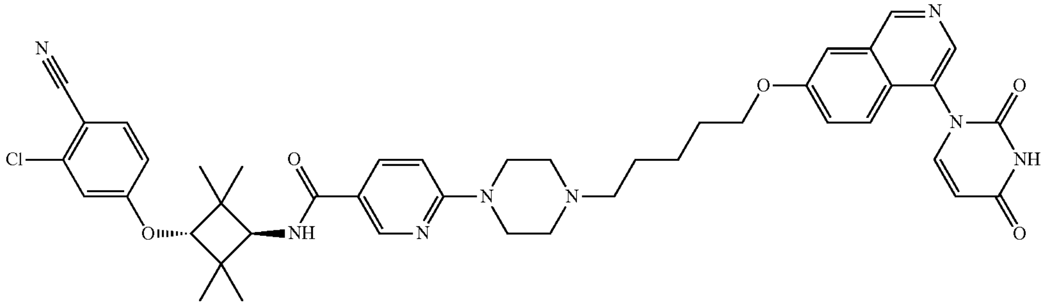 [SMILES: CC1(C)[C@H](NC(=O)c2ccc(N3CCN(CCCCCOc4ccc5c(-n6ccc(=O)[nH]c6=O)cncc5c4)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(5-((4-(2,4-dioxo-3,4-dihydropyrimidin-1(2H)-yl)isoquinolin-7-yl)oxy)pentyl)piperazin-1-yl)nicotinamide | Described in detail |

TABLE 2-continued

| Exemplary PROTACs of the present disclosure | | | |
|---|---|---|---|
| PROTAC-# | Chemical Structure | Name | Synthesis |
| PROTAC-80 | 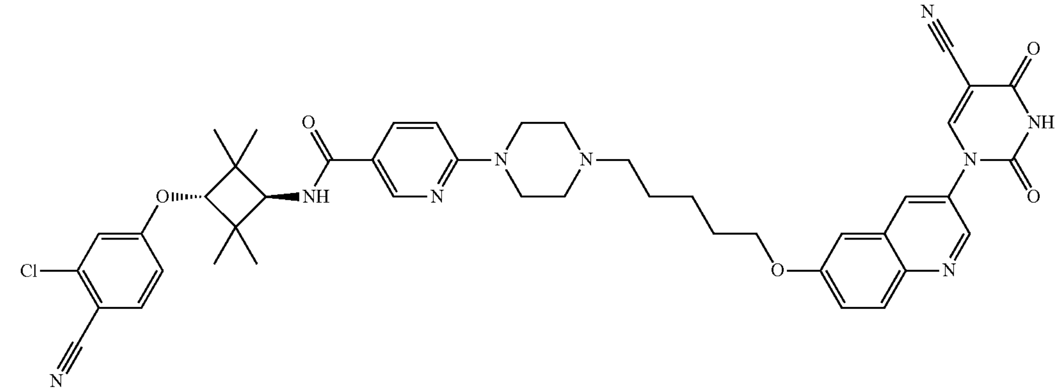 [SMILES: CC1(C)[C@H](NC(=O)c2ccc(N3CCN(CCCCCOc4ccc5ncc(-n6cc(C#N)c(=O)[nH]c6=O)cc5c4)CC3)nc2)C(C)(C)[C@H]1Oc1ccc(C#N)c(Cl)c1] | rac-N-((1r,3r)-3-(3-chloro-4-cyanophenoxy)-2,2,4,4-tetramethylcyclobutyl)-6-(4-(5-((3-(5-cyano-2,4-dioxo-3,4-dihydropyrimidin-1(2H)-yl)quinolin-6-yl)oxy)pentyl)piperazin-1-yl)nicotinamide | Described in detail |
| PROTAC-81 | 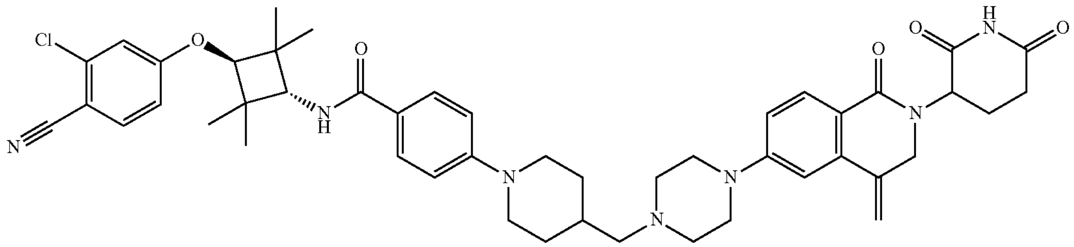 [SMILES: C=C1CN(C2CCC(=O)NC2=O)C(=O)c2ccc(N3CCN(CC4CCN(c5ccc(C(=O)N[C@H]6C(C)(C)[C@H](Oc7ccc(C#N)c(Cl)c7)C6(C)C)cc5)CC4)CC3)cc21] | rac-N-((1r,3r)-3-(3-chloro-4-cyanophenoxy)-2,2,4,4-tetramethylcyclobutyl)-4-(4-((4-(2-(2,6-dioxopiperidin-3-yl)-4-methylene-1-oxo-1,2,3,4-tetrahydroisoquinolin-6-yl)piperazin-1-yl)methyl)piperidin-1-yl)benzamide | Described in detail |
| PROTAC-82 | 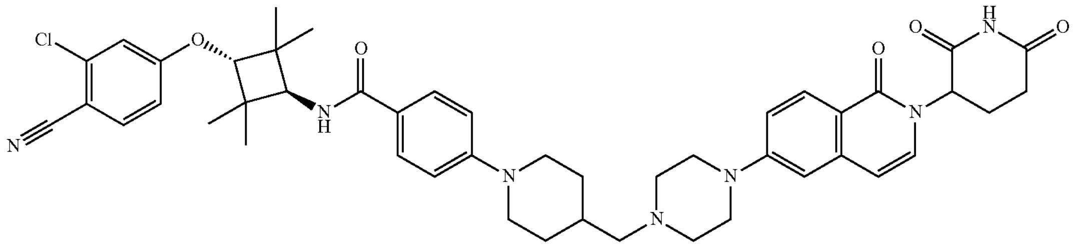 [SMILES: CC1(C)[C@H](NC(=O)c2ccc(N3CCC(CN4CCN(c5ccc6c(=O)n(C7CCC(=O)NC7=O)ccc6c5)CC4)CC3)cc2)C(C)(C)[C@H]1Oc1ccc(C#N)c(Cl)c1] | N-((1r,3r)-3-(3-chloro-4-cyanophenoxy)-2,2,4,4-tetramethylcyclobutyl)-4-(4-((4-(2-(2,6-dioxopiperidin-3-yl)-1-oxo-1,2-dihydroisoquinolin-6-yl)piperazin-1-yl)methyl)piperidin-1-yl)benzamide | Described in detail |

TABLE 2-continued

| Exemplary PROTACs of the present disclosure | | | |
|---|---|---|---|
| PROTAC-# | Chemical Structure | Name | Synthesis |
| PROTAC-1 | 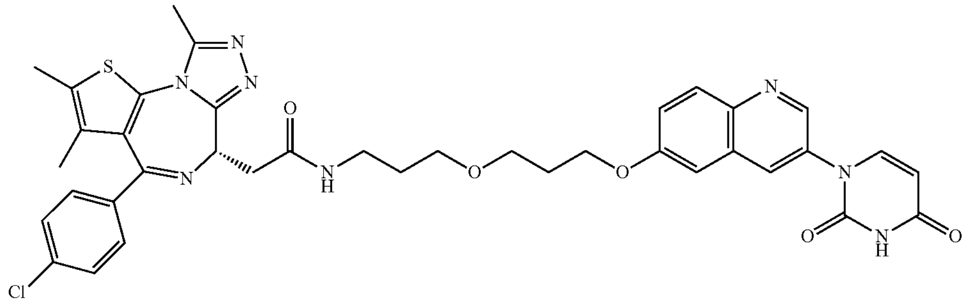 [SMILES: Cc1sc2c(c1C)C(c1ccc(Cl)cc1)=N[C@@H](CC(=O)NCCCOCCCOc1ccc3ncc(-n4ccc(=O)[nH]c4=O)cc3c1)c1nnc(C)n1-2] | rac-(R)-2-(4-(4-chloro-phenyl)-2,3,9-trimethyl-6H-thieno[3,2-f][1,2,4]triazolo[4,3-a][1,4]diazepin-6-yl)-N-(3-(3-((3-(2,4-dioxo-3,4-dihydropyrimidin-1(2H)-yl)quinolin-6-yl)oxy)propoxy)propyl)acetamide | Described in detail |
| PROTAC-89 | 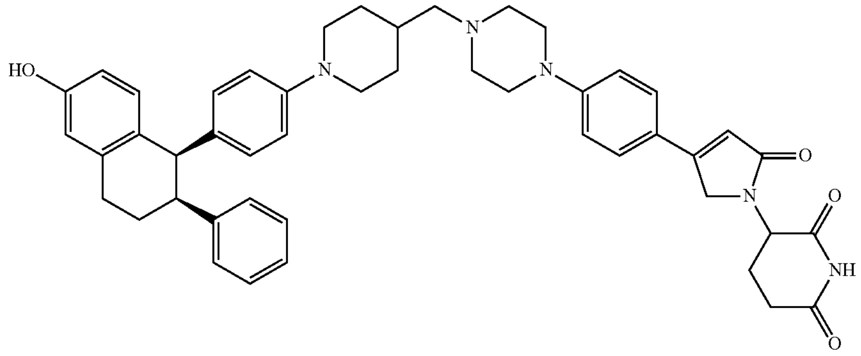 [SMILES: O=C1CCC(N2CC(c3ccc(N4CCN(CC5CCN(c6ccc([C@@H]7c8ccc(O)cc8CC[C@@H]7c7ccccc7)cc6)CC5)CC4)cc3)=CC2=O)C(=O)N1] | rac-3-(4-(4-(4-((1-(4-((1R,2S)-6-hydroxy-2-phenyl-1,2,3,4-tetrahydronaphthalen-1-yl)phenyl)piperidin-4-yl)methyl)piperazin-1-yl)phenyl)-2-oxo-2,5-dihydro-1H-pyrrol-1-yl)piperidine-2,6-dione | Described in detail; see also Scheme 2-30, 3-58 |
| PROTAC-90 | 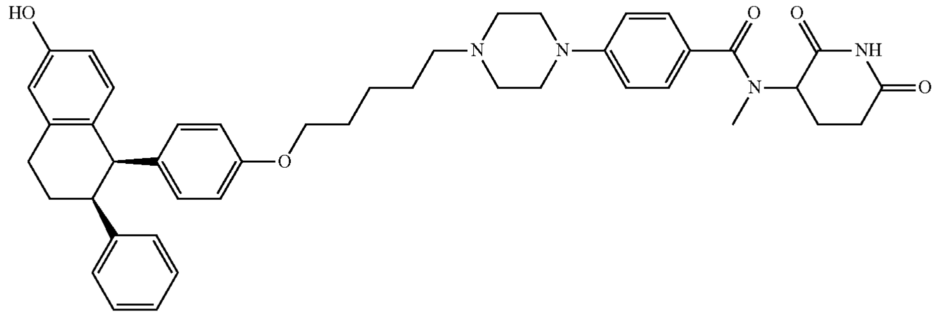 [SMILES: CN(C(=O)c1ccc(N2CCN(CCCCCOc3ccc([C@@H]4c5ccc(O)cc5CC[C@@H]4c4ccccc4)cc3)CC2)cc1)C1CCC(=O)NC1=O] | rac-N-(2,6-dioxopiperidin-3-yl)-4-(4-(5-(4-((1R,2S)-6-hydroxy-2-phenyl-1,2,3,4-tetrahydronaphthalen-1-yl)phenoxy)pentyl)piperazin-1-yl)-N-methylbenzamide | Scheme 2-45, 3-10 |

TABLE 2-continued

| Exemplary PROTACs of the present disclosure | | | |
|---|---|---|---|
| PROTAC-# | Chemical Structure | Name | Synthesis |
| PROTAC-91 | 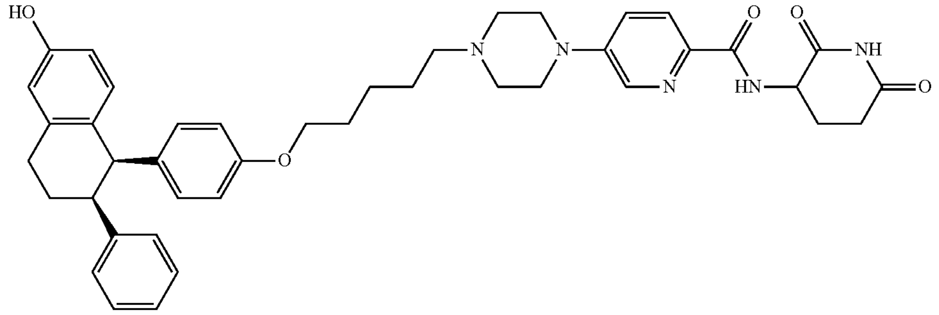 [SMILES: O=C1CCC(NC(=O)c2ccc(N3CCN(CCCCCOc4ccc([C@@H]5c6ccc(O)cc6CC[C@@H]5c5ccccc5)cc4)CC3)cn2)C(=O)N1] | rac-N-(2,6-dioxopiperidin-3-yl)-5-(4-(5-(4-((1R,2S)-6-hydroxy-2-phenyl-1,2,3,4-tetrahydronaphthalen-1-yl)phenoxy)pentyl)piperazin-1-yl)picolinamide | Scheme 2-45, 3-10 |
| PROTAC-92 | 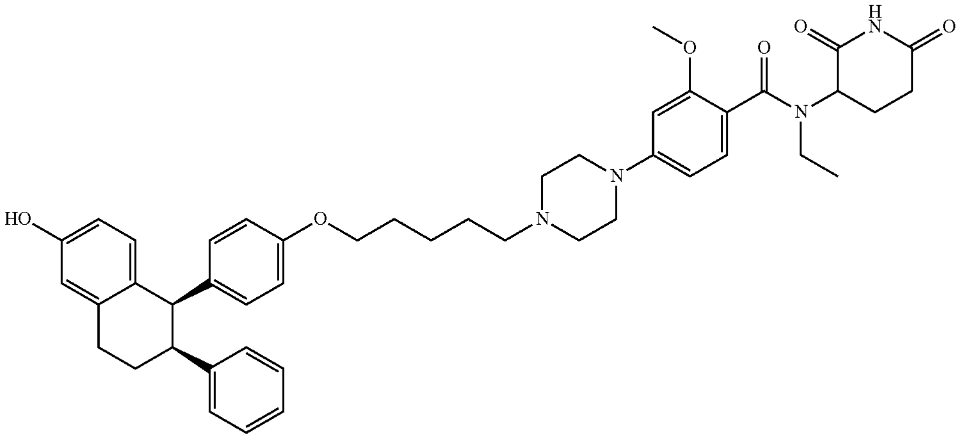 [SMILES: CCN(C(=O)c1ccc(N2CCN(CCCCCOc3ccc([C@@H]4c5ccc(O)cc5CC[C@@H]4c4ccccc4)cc3)CC2)cc1OC)C1CCC(=O)NC1=O] | rac-N-(2,6-dioxopiperidin-3-yl)-N-ethyl-4-(4-(5-(4-((1R,2S)-6-hydroxy-2-phenyl-1,2,3,4-tetrahydronaphthalen-1-yl)phenoxy)pentyl)piperazin-1-yl)-2-methoxybenzamide | Scheme 2-45, 3-10 |

TABLE 2-continued

| Exemplary PROTACs of the present disclosure | | | |
|---|---|---|---|
| PROTAC-# | Chemical Structure | Name | Synthesis |
| PROTAC-93 | 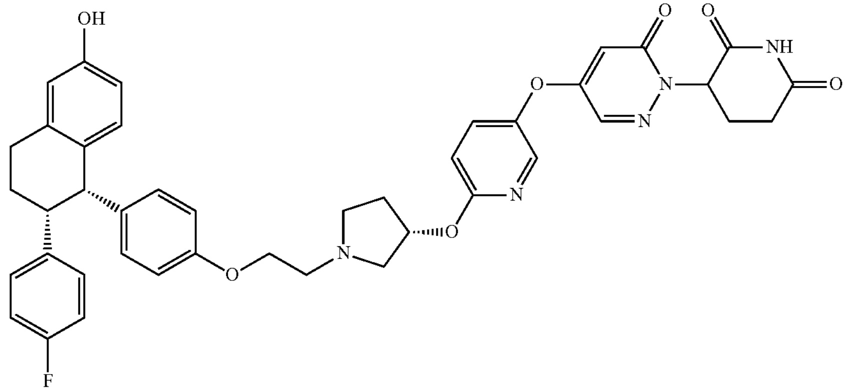 [SMILES: O=C1CCC(n2ncc(Oc3ccc(O[C@H]4CCN(CCOc5ccc([C@H]6c7ccc(O)cc7CC[C@H]6c6ccc(F)cc6)cc5)C4)nc3)cc2=O)C(=O)N1] | rac-3-(4-((6-(((R)-1-(2-(4-((1R,2S)-2-(4-fluorophenyl)-6-hydroxy-1,2,3,4-tetrahydronaphthalen-1-yl)phenoxy)ethyl)pyrrolidin-3-yl)oxy)pyridin-3-yl)oxy)-6-oxopyridazin-1(6H)-yl)piperidine-2,6-dione | Scheme 2-40, 3-10 |
| PROTAC-94 | 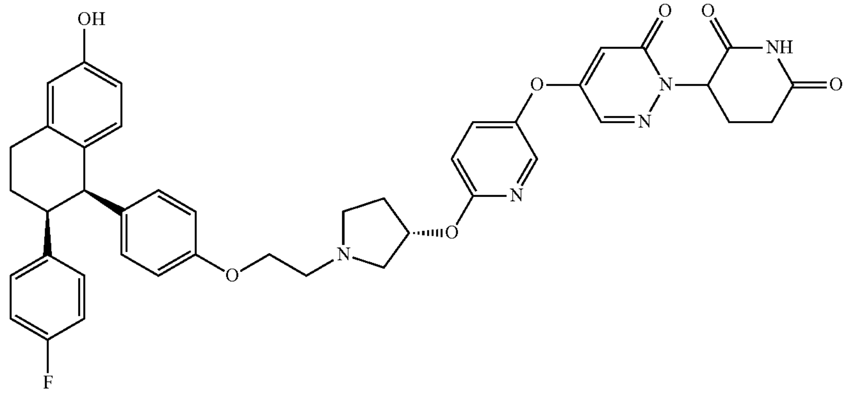 [SMILES: O=C1CCC(n2ncc(Oc3ccc(O[C@H]4CCN(CCOc5ccc([C@@H]6c7ccc(O)cc7CC[C@@H]6c6ccc(F)cc6)cc5)C4)nc3)cc2=O)C(=O)N1] | rac-3-(4-((6-(((R)-1-(2-(4-((1S,2R)-2-(4-fluorophenyl)-6-hydroxy-1,2,3,4-tetrahydronaphthalen-1-yl)phenoxy)ethyl)pyrrolidin-3-yl)oxy)pyridin-3-yl)oxy)-6-oxopyridazin-1(6H)-yl)piperidine-2,6-dione | Scheme 2-40, 3-10 |

TABLE 2-continued

| Exemplary PROTACs of the present disclosure | | | |
|---|---|---|---|
| PROTAC-# | Chemical Structure | Name | Synthesis |
| PROTAC-95 | 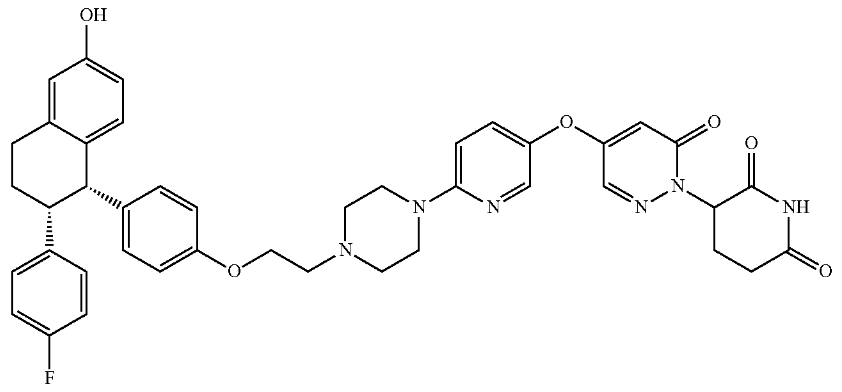 [SMILES: O=C1CCC(n2ncc(Oc3ccc(N4CCN(CCOc5ccc([C@H]6c7ccc(O)cc7CC[C@H]6c6ccc(F)cc6)cc5)CC4)nc3)cc2=O)C(=O)N1] | rac-3-(4-((6-(4-(2-(4-((1R,2S)-2-(4-fluorophenyl)-6-hydroxy-1,2,3,4-tetrahydronaphthalen-1-yl)phenoxy)ethyl)piperazin-1-yl)pyridin-3-yl)oxy)-6-oxopyridazin-1(6H)-yl)piperidine-2,6-dione | Scheme 2-41, 3-10 |
| PROTAC-96 | 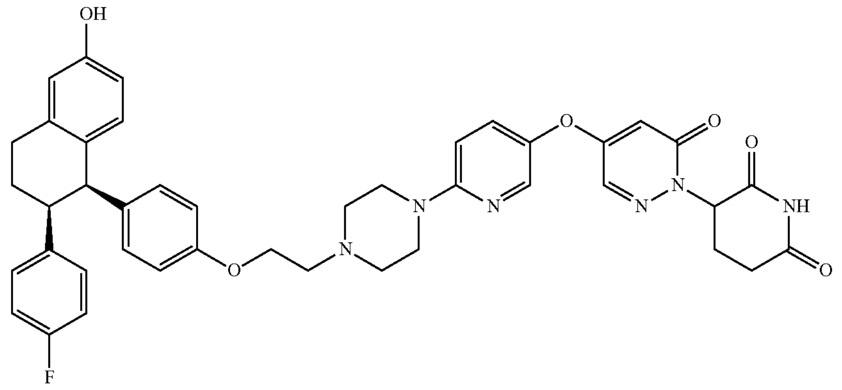 [SMILES: O=C1CCC(n2ncc(Oc3ccc(N4CCN(CCOc5ccc([C@@H]6c7ccc(O)cc7CC[C@@H]6c6ccc(F)cc6)cc5)CC4)nc3)cc2=O)C(=O)N1] | rac-3-(4-((6-(4-(2-(4-((1R,2S)-2-(4-fluoro-phenyl)-6-hydroxy-1,2,3,4-tetrahydro-naphthalen-1-yl)phenoxy)ethyl)piperazin-1-yl)pyridin-3-yl)oxy)-6-oxopyridazin-1(6H)-yl)piperidine-2,6-dione | Scheme 2-41, 3-10 |

TABLE 2-continued

| Exemplary PROTACs of the present disclosure | | | |
|---|---|---|---|
| PROTAC-# | Chemical Structure | Name | Synthesis |
| PROTAC-97 | 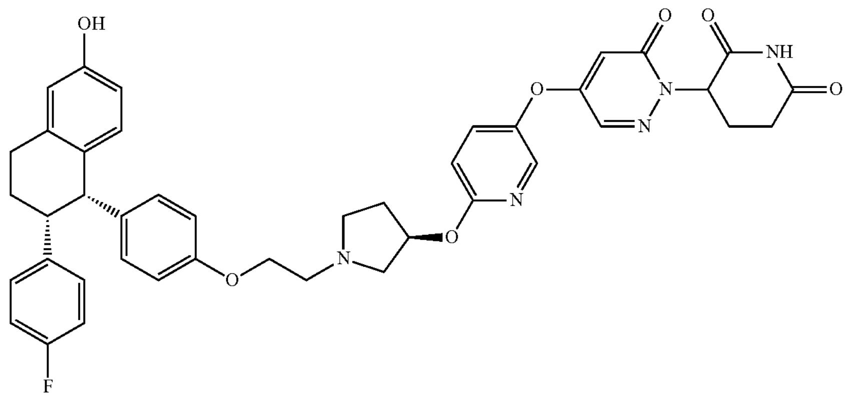 [SMILES: O=C1CCC(n2ncc(Oc3ccc(O[C@@H]4CCN(CCOc5ccc([C@H]6c7ccc(O)cc7CC[C@H]6c6ccc(F)cc6)cc5)C4)nc3)cc2=O)C(=O)N1] | rac-3-(4-((6-(((R)-1-(2-(4-((1S,2R)-2-(4-fluorophenyl)-6-hydroxy-1,2,3,4-tetrahydronaphthalen-1-yl)phenoxy)ethyl) pyrrolidin-3-yl)oxy) pyridin-3-yl)oxy)-6-oxopyridazin-1(6H)-yl)piperidine-2,6-dione | Scheme 2-40, 3-10 |
| PROTAC-98 | 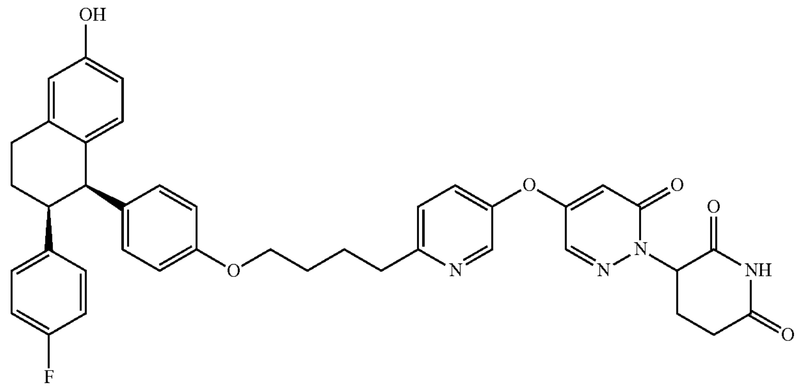 [SMILES: O=C1CCC(n2ncc(Oc3ccc(CCCCOc4ccc([C@@H]5c6ccc(O)cc6CC[C@@H]5c5ccc(F)cc5)cc4)nc3)cc2=O)C(=O)N1] | rac-3-(4-((6-(4-(4-((1R,2S)-2-(4-fluorophenyl)-6-hydroxy-1,2,3,4-tetrahydro-naphthalen-1-yl)phenoxy) butyl)pyridin-3-yl) oxy)-6-oxopyridazin-1(6H)-yl)piperidine-2,6-dione | Scheme 3-56 |

TABLE 2-continued

| Exemplary PROTACs of the present disclosure | | | |
|---|---|---|---|
| PROTAC-# | Chemical Structure | Name | Synthesis |
| PROTAC-99 | 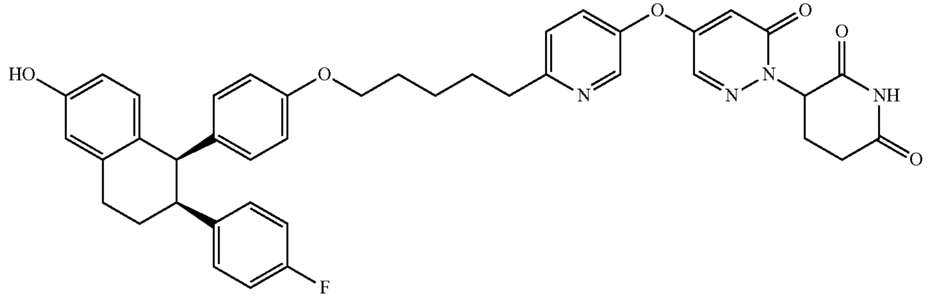 [SMILES: O=C1CCC(n2ncc(Oc3ccc(CCCCCOc4ccc([C@@H]5c6ccc(O)cc6CC[C@@H]5c5ccc(F)cc5)cc4)nc3)cc2=O)C(=O)N1] | rac-3-(4-((6-(5-(4-((1R,2S)-2-(4-fluorophenyl)-6-hydroxy-1,2,3,4-tetrahydro-naphthalen-1-yl) phenoxy)pentyl)pyridin-3-yl)oxy)-6-oxopyridazin-1(6H)-yl)piperidine-2,6-dione | Scheme 3-56 |
| PROTAC-100 | 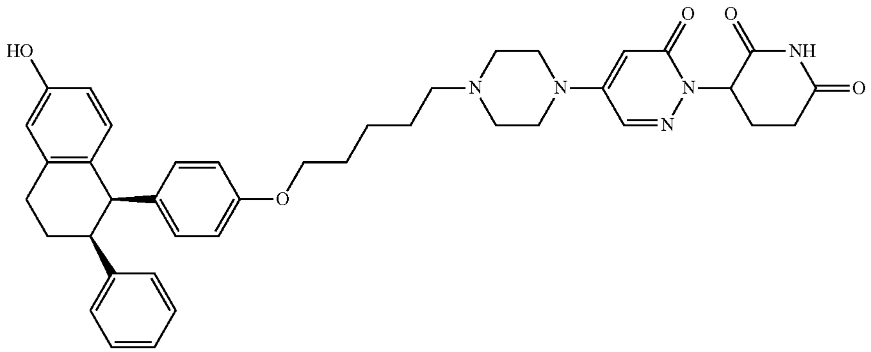 [SMILES: O=C1CCC(n2ncc(N3CCN(CCCCCOc4ccc([C@@H]5c6ccc(O)cc6CC[C@@H]5c5ccccc5)cc4)CC3)cc2=O)C(=O)N1] | rac-3-(4-(4-(5-(4-((1R,2S)-6-hydroxy-2-phenyl-1,2,3,4-tetrahydronaphthalen-1-yl)phenoxy)pentyl) piperazin-1-yl)-6-oxopyridazin-1(6H)-yl)piperidine-2,6-dione | Scheme 2-31, 3-10 |
| PROTAC-101 | 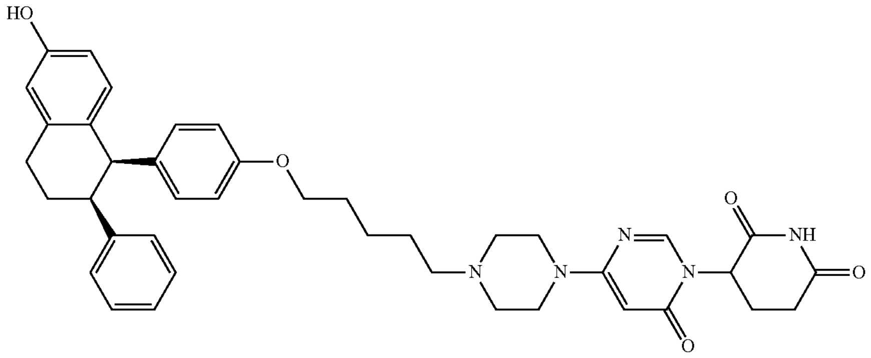 [SMILES: O=C1CCC(n2cnc(N3CCN(CCCCCOc4ccc([C@@H]5c6ccc(O)cc6CC[C@@H]5c5ccccc5)cc4)CC3)cc2=O)C(=O)N1] | rac-3-(4-(4-(5-(4-((1R,2S)-6-hydroxy-2-phenyl-1,2,3,4-tetrahydronaphthalen-1-yl)phenoxy)pentyl) piperazin-1-yl)-6-oxopyrimidin-1(6H)-yl)piperidine-2,6-dione | Scheme 2-46, 3-10 |

TABLE 2-continued

| Exemplary PROTACs of the present disclosure | | | |
|---|---|---|---|
| PROTAC-# | Chemical Structure | Name | Synthesis |
| PROTAC-102 | 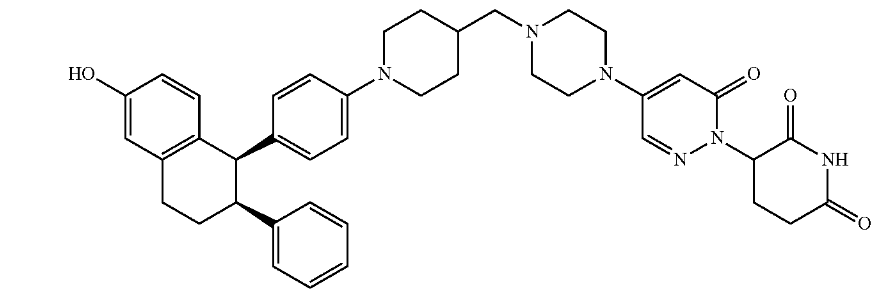 [SMILES: O=C1CCC(n2ncc(N3CCN(CC4CCN(c5ccc([C@@H]6c7ccc(O)cc7CC[C@@H]6c6ccccc6)cc5)CC4)CC3)cc2=O)C(=O)N1] | 3-(4-(4-((1-(4-((1R,2S)-6-hydroxy-2-phenyl-1,2,3,4-tetrahydronaphthalen-1-yl)phenyl)piperidin-4-yl)methyl)piperazin-1-yl)-6-oxopyridazin-1(6H)-yl)piperidine-2,6-dione | Described in detail; see also Scheme 2-31, 3-58 |
| PROTAC-103 | 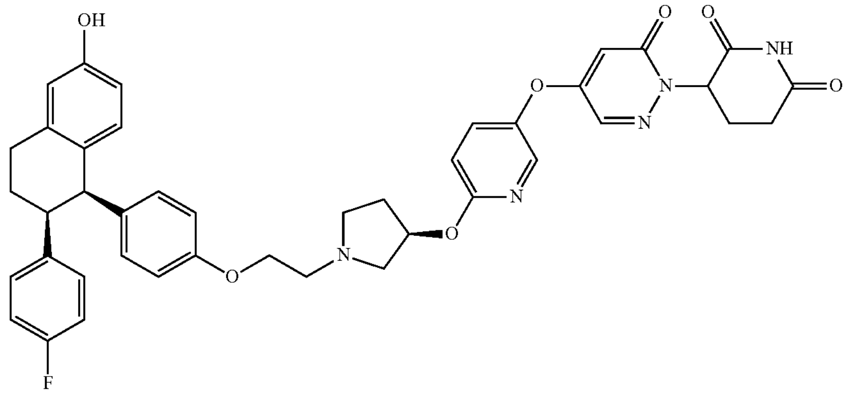 [SMILES: O=C1CCC(n2ncc(Oc3ccc(O[C@@H]4CCN(CCOc5ccc([C@@H]6c7ccc(O)cc7CC[C@@H]6c6ccc(F)cc6)cc5)C4)nc3)cc2=O)C(=O)N1] | 3-(4-((6-(((R)-1-(2-(4-((1R,2S)-2-(4-fluorophenyl)-6-hydroxy-1,2,3,4-tetrahydronaphthalen-1-yl)phenoxy)ethyl) pyrrolidin-3-yl)oxy) pyridin-3-yl)oxy)-6-oxopyridazin-1(6H)-yl)piperidine-2,6-dione | Scheme 2-40, 3-10 |
| PROTAC-104 | 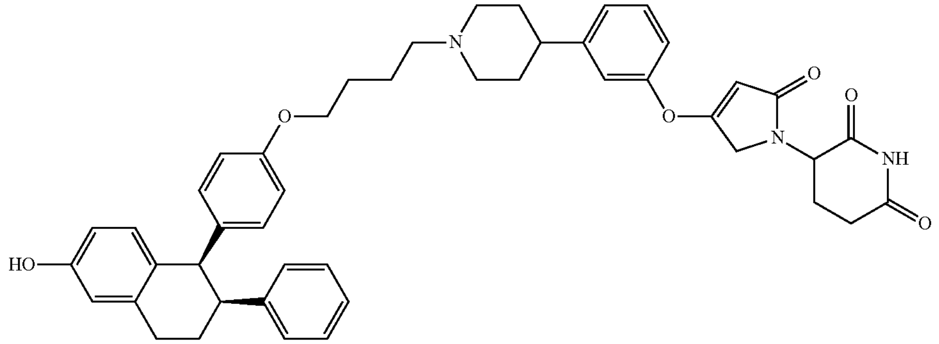 [SMILES: O=C1CCC(N2CC(Oc3cccc(C4CCN(CCCCOc5ccc([C@@H]6c7ccc(O)cc7CC[C@@H]6c6ccccc6)cc5)CC4)c3)=CC2=O)C(=O)N1] | rac-3-(4-(3-(1-(4-(4-((1R,2S)-6-hydroxy-2-phenyl-1,2,3,4-tetrahydronaphthalen-1-yl)phenoxy)butyl) piperidin-4-yl)phenoxy)-2-oxo-2,5-dihydro-1H-pyrrol-1-yl)piperidine-2,6-dione | Following route described for PROTAC 106 |

TABLE 2-continued

| Exemplary PROTACs of the present disclosure | | | |
|---|---|---|---|
| PROTAC-# | Chemical Structure | Name | Synthesis |
| PROTAC-105 | 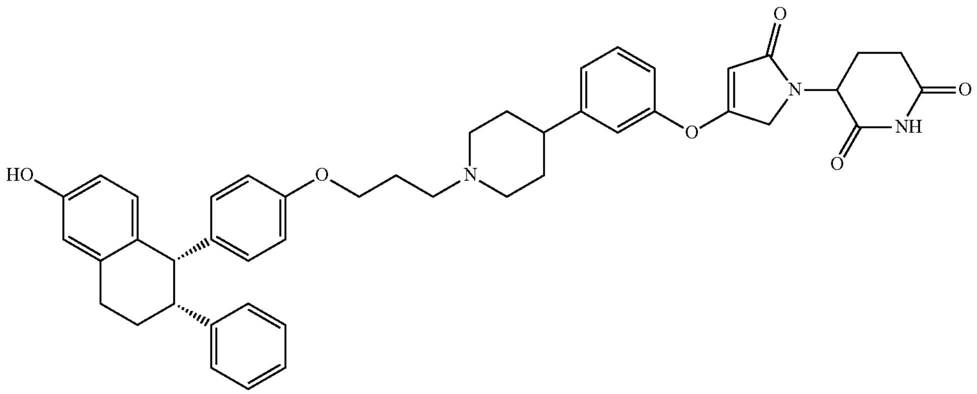 [SMILES: O=C1CCC(N2CC(Oc3cccc(C4CCN(CCCOc5ccc([C@H]6c7ccc(O)cc7CC[C@H]6c6ccccc6)cc5)CC4)c3)=CC2=O)C(=O)N1] | rac-3-(4-(3-(1-(3-(4-((1R,2S)-6-hydroxy-2-phenyl-1,2,3,4-tetrahydronaphthalen-1-yl)phenoxy)propyl) piperidin-4-yl)phenoxy)-2-oxo-2,5-dihydro-1H-pyrrol-1-yl)piperidine-2,6-dione | Following route described for PROTAC 106 |
| PROTAC-106 | 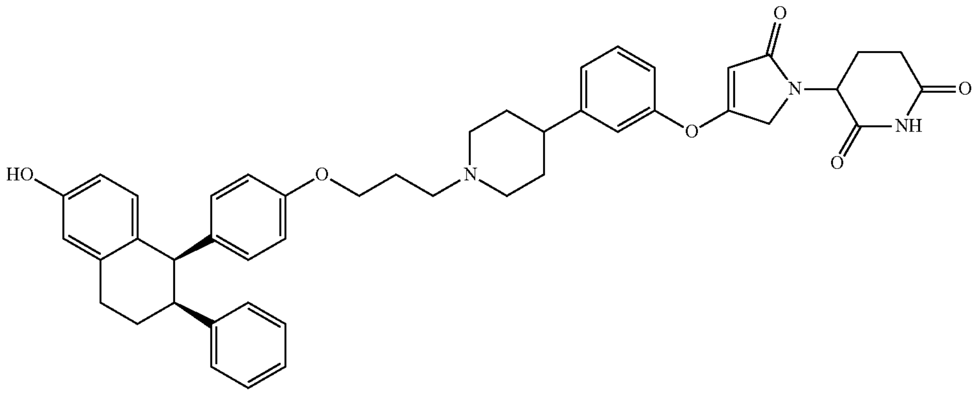 [SMILES: O=C1CCC(N2CC(Oc3cccc(C4CCN(CCCOc5ccc([C@@H]6c7ccc(O)cc7CC[C@@H]6c6ccccc6)cc5)CC4)c3)=CC2=O)C(=O)N1] | rac-3-(4-(3-(1-(3-(4-((1R,2S)-6-hydroxy-2-phenyl-1,2,3,4-tetrahydronaphthalen-1-yl)phenoxy)propyl) piperidin-4-yl)phenoxy)-2-oxo-2,5-dihydro-1H-pyrrol-1-yl)piperidine-2,6-dione | Described in detail |

TABLE 2-continued

Exemplary PROTACs of the present disclosure

| PROTAC-# | Chemical Structure | Name | Synthesis |
|---|---|---|---|
| PROTAC-107 | 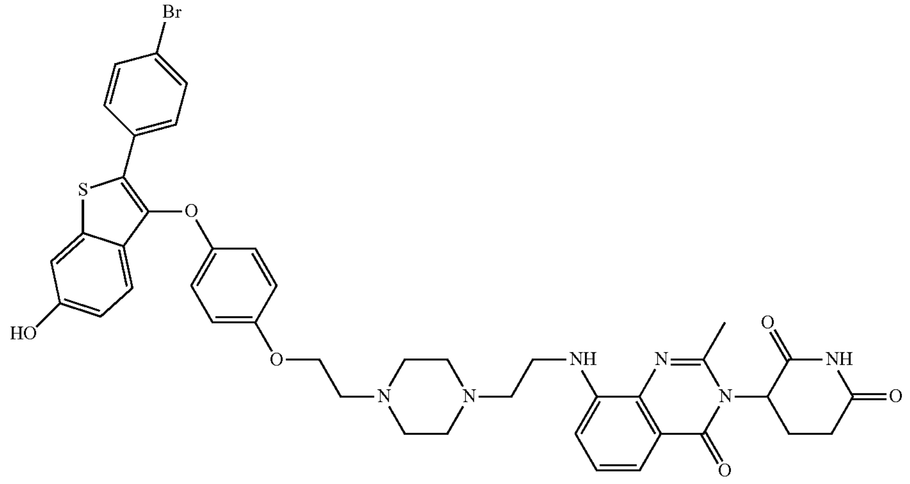 [SMILES: Cc1nc2c(NCCN3CCN(CCOc4ccc(Oc5c(-c6ccc(Br)cc6)sc6cc(O)ccc56)cc4)CC3)cccc2c(=O)n1C1CCC(=O)NC1=O] | 3-(8-((2-(4-(2-(4-((2-(4-bromophenyl)-6-hydroxybenzo[b]thiophen-3-yl)oxy)phenoxy)ethyl)piperazin-1-yl)ethyl)amino)-2-methyl-4-oxoquinazolin-3(4H)-yl)piperidine-2,6-dione | Described in detail |
| PROTAC-108 | 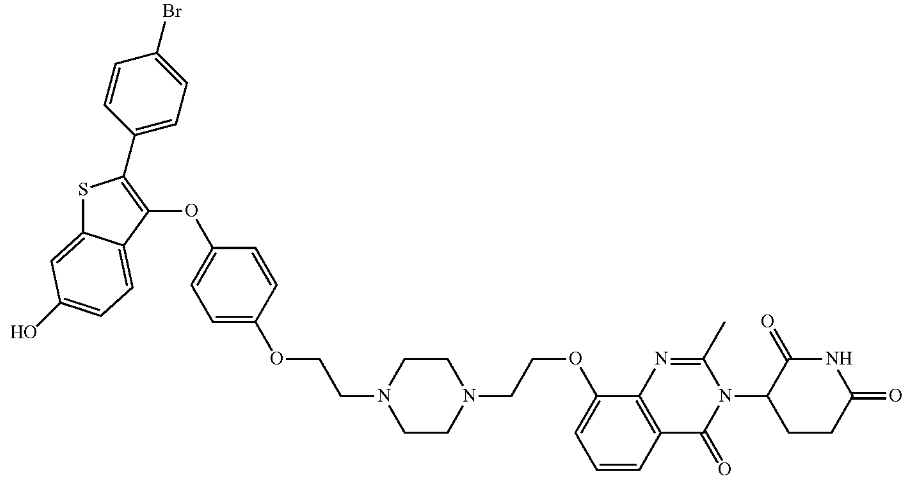 [SMILES: Cc1nc2c(OCCN3CCN(CCOc4ccc(Oc5c(-c6ccc(Br)cc6)sc6cc(O)ccc56)cc4)CC3)cccc2c(=O)n1C1CCC(=O)NC1=O] | 3-(8-(2-(4-(2-(4-((2-(4-bromophenyl)-6-hydroxybenzo[b]thiophen-3-yl)oxy)phenoxy)ethyl)piperazin-1-yl)ethoxy)-2-methyl-4-oxoquinazolin-3(4H)-yl)piperidine-2,6-dione | Described in detail |

TABLE 2-continued

| Exemplary PROTACs of the present disclosure | | | |
|---|---|---|---|
| PROTAC-# | Chemical Structure | Name | Synthesis |
| PROTAC-109 | 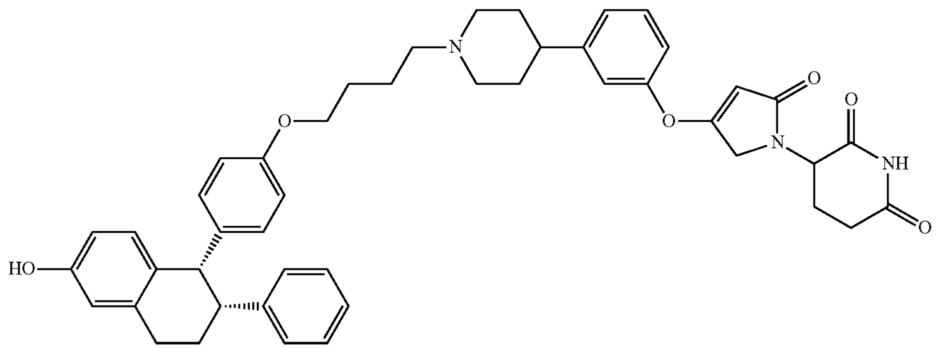 [SMILES: O=C1CCC(N2CC(Oc3cccc(C4CCN(CCCCOc5ccc([C@H]6c7ccc(O)cc7CC[C@H]6c6ccccc6)cc5)CC4)c3)=CC2=O)C(=O)N1] | rac-3-(4-(3-(1-(4-(4-((1R,2S)-6-hydroxy-2-phenyl-1,2,3,4-tetrahydronaphthalen-1-yl)phenoxy)butyl) piperidin-4-yl)phenoxy)-2-oxo-2,5-dihydro-1H-pyrrol-1-yl)piperidine-2,6-dione | Following route described for PROTAC 106 |
| PROTAC-110 | 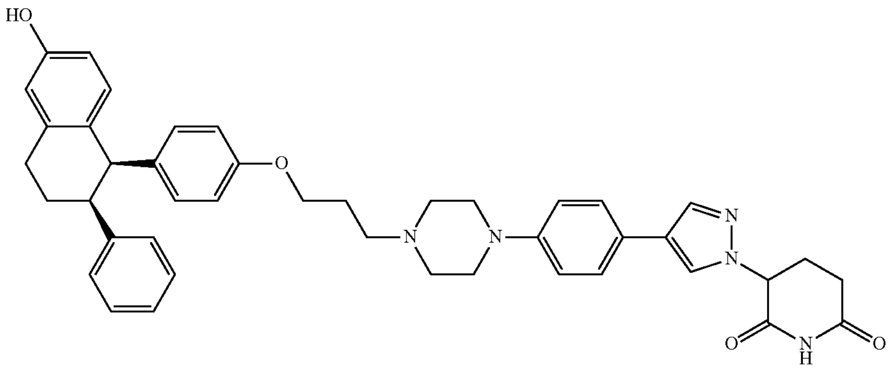 [SMILES: O=C1CCC(n2cc(-c3ccc(N4CCN(CCCOc5ccc([C@@H]6c7ccc(O)cc7CC[C@@H]6c6ccccc6)cc5)CC4)cc3)cn2)C(=O)N1] | rac-3-(4-(4-(4-(3-(4-((1R,2S)-6-hydroxy-2-phenyl-1,2,3,4-tetrahydronaphthalen-1-yl)phenoxy)propyl) piperazin-1-yl)phenyl)-1H-pyrazol-1-yl) piperidine-2,6-dione | Scheme 3-72 |

TABLE 2-continued

| Exemplary PROTACs of the present disclosure | | | |
|---|---|---|---|
| PROTAC-# | Chemical Structure | Name | Synthesis |
| PROTAC-111 | 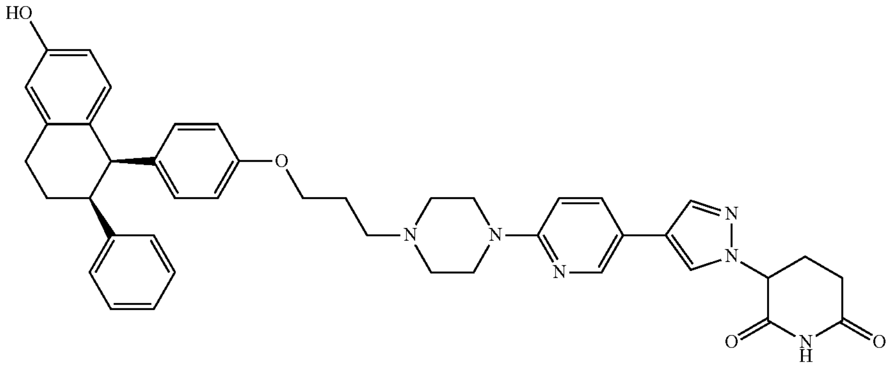 [SMILES: O=C1CCC(n2cc(-c3ccc(N4CCN(CCCOc5ccc([C@@H]6c7ccc(O)cc7CC[C@@H]6c6ccccc6)cc5)CC4)nc3)cn2)C(=O)N1] | rac-3-(4-(6-(4-(3-(4-((1R,2S)-6-hydroxy-2-phenyl-1,2,3,4-tetrahydronaphthalen-1-yl)phenoxy)propyl)piperazin-1-yl)pyridin-3-yl)-1H-pyrazol-1-yl)piperidine-2,6-dione | Scheme 3-72 |
| PROTAC-112 | 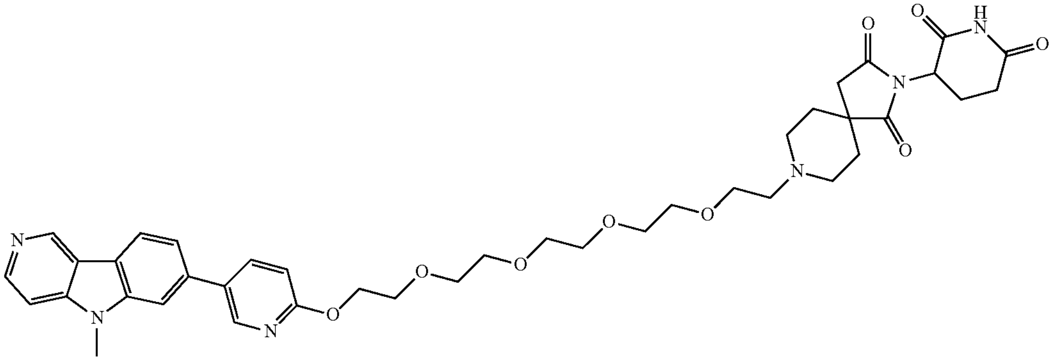 [SMILES: Cn1c2ccncc2c2ccc(-c3ccc(OCCOCCOCCOCCOCCN4CCC5(CC4)CC(=O)N(C4CCC(=O)NC4=O)C5=O)nc3)cc21] | 2-(2,6-dioxopiperidin-3-yl)-8-(14-((5-(5-methyl-5H-pyrido[4,3-b]indol-7-yl)pyridin-2-yl)oxy)-3,6,9,12-tetraoxatetradecyl)-2,8-diazaspiro[4.5]decane-1,3-dione | Synthesis described in detail |

TABLE 3

Characteristics of exemplary androgen receptor PROTACs

| PROTAC-# | AR DC50 (nM)* | AR Dmax %** | MS signal 1 m/e+ $[M + H]^+$ | NMR |
|---|---|---|---|---|
| PROTAC-27 | B | B | 785.06 | $^1$H NMR (400 MHz, $d^6$-DMSO) δ 1.11 (6H, s), 1.21 (6H, s), 1.46-1.54 (4H, m), 1.77-1.81 (2H, m), 1.96-2.00 (1H, m), 2.14-2.25 (1H, m), 2.33 (2H, t, J = 6.8), 2.44 (5H, s), 2.75-2.83 (1H, m), 3.59 (1H, s), 4.03 (1H, d, J = 6.0 Hz), 4.15 (2H, t, J = 6.8), 4.30 (1H, s), 4.73-4.80 (1H, m), 6.86 (1H, d, J = 9.2 Hz), 7.00 (1H, dd, J = 2.4, 8.8 Hz), 7.21 (1H, d, J = 2.4 Hz), 7.56 (1H, dd, J = 2.8, 5.6 Hz,), 7.63 (1H, d, J = 9.2 Hz), 7.91 (1H, d, J = 8.8 Hz), 7.95 (1H, dd, J = 2.4, 6.8 Hz,), 8.01 (1H, d, J = 8.8 Hz), 8.33 (1H, d, J = 2.8 Hz), 8.62 (1H, d, J = 2.4 Hz), 8.89 (1H, d, J = 6.8 Hz), 10.87 (1H, brs). |
| PROTAC-28 | D | C | 825.36 | |
| PROTAC-29 | A | B | 773.33 | $^1$H NMR (400 MHz, $CDCl_3$) δ 1.21 (6H, s), 1.25 (6H, s), 1.39-1.44 (2H, m), 1.49-1.62 (4H, m), 1.87-1.93 (2H, m), 2.24-2.28 (1H, m), 2.36-2.43 (2H, m), 2.56 (4H, s), 2.70-2.81 (2H, m), 2.87-2.92 (1H, m), 3.66-3.69 (4H, m), 4.00-4.04 (3H, m), 4.14 (1H, d, J = 8.0 Hz), 5.74 (1H, dd, J = 11.2, 5.6 Hz), 6.07 (1H, d, J = 8.4 Hz), 6.40 (1H, d, J = 4.8 Hz), 6.66 (1H, d, J = 8.8 Hz), 6.80 (1H, dd, J = 8.8, 2.4 Hz), 6.96 (1H, d, J = 2.4 Hz), 7.57 (1H, d, J = 8.8 Hz), 7.71 (1H, d, J = 4.8 Hz), 7.93 (1H, dd, J = 8.8, 2.4 Hz), 8.16 (1H, brs), 8.58 (1H, d, J = 2.4 Hz), |
| PROTAC-30 | D | C | 823.34 | $^1$H NMR (400 MHz, $CDCl_3$) δ 1.21 (6H, s), 1.25 (6H, s), 1.59-1.62 (4H, m), 1.90-2.00 (2H, m), 2.14-2.17 (1H, m), 2.70-2.79 (5H, m), 2.86-2.96 (6H, m), 3.15 (1H, dd, J = 14.8, 7.2 Hz), 3.88 (4H, s), 4.05 (1H, s), 4.13-4.20 (3H, m), 4.82 (1H, dd, J = 11.2, 5.6 Hz), 6.14 (1H, d, J = 8.4 Hz), 6.68 (1H, d, J = 9.2 Hz), 6.80 (1H, dd, J = 8.8, 2.4 Hz), 6.96 (1H, d, J = 2.4 Hz), 7.20 (1H, d, J = 8.0 Hz), 7.38 (1H, t, J = 8.0 Hz), 7.57 (1H, d, J = 8.8 Hz), 7.74 (1H, d, J = 8.0 Hz), 7.94 (1H, dd, J = 8.8, 2.0 Hz), 8.30 (1H, brs), 8.57 (1H, d, J = 2.0 Hz). |
| PROTAC-33 | B | B | 846.18 | $^1$H NMR (400 MHz, DMSO-$d_6$) δ 1.19 (6H, s), 1.22 (6H, s), 1.46-1.55 (4H, m), 1.79-1.80 (2H, m), 2.34-2.40 (3H, m), 2.45 (4H, s), 2.54-2.92 (3H, m), 3.59 (4H, s), 4.06 (1H, d, J = 9.2 Hz), 4.20-4.25 (2H, m), 4.30 (1H, s), 5.23-5.28 (0.5H, m), 5.98 (0.5H, t, J = 9.2 Hz), 6.87 (1H, d, J = 9.2 Hz), 6.99-7.02 (1H, m), 7.21 (1H, d, J = 2.0 Hz), 7.35-7.50 (1H, m), 7.63 (1H, d, J = 9.2 Hz), 7.81-7.83 (1H, m), 7.90-8.02 (3H, m), 8.62 (1H, d, J = 2.0 Hz), 11.19 (1H, t, J = 9.6 Hz). |
| PROTAC-39 | D | 0C | 755.23 | $^1$H NMR (400 MHz, $CD_3OD$): δ 1.23 (s, 6H), 1.29 (s, 6H), 2.67-2.82 (m, 4H), 2.92-3.01 (m, 2H), 3.72 (s, 4H), 4.15 (s, 1H), 4.29-4.39 (m, 3H), 4.88 (s, 2H), 6.85-6.87 (m, 2H), 7.10-7.34 (m, 4H), 7.47-7.75 (m, 4H), 7.96-7.98 (m, 1H), 8.61 (s, 1H). |
| PROTAC-40 | D | C | 799.3 | $^1$H NMR (400 MHz, $CD_3OD$): δ 1.21 (s, 6H), 1.27 (s, 6H), 2.68-2.73 (m, 6H), 3.61 (br, 4H), 3.75-3.76 (m, 2H), 3.87-.89 (m, 2H), 4.12 (s, 1H), 4.27 (s, 1H), 4.33-4.34 (m, 2H), 6.74 (d, J = 9.2 Hz, 1H), 6.95-6.98 (m, 1H), 7.06-7.16 (m, 3H), 7.29 (d, J = 8.2 Hz, 1H), 7.43 (d, J = 7.2 Hz, 1H), 7.51-7.75 (m, 3H), 7.71 (d, J = 8.8 Hz, 1H), 7.92 (d, J = 8.8 Hz, 1H), 8.55 (s, 1H). |
| PROTAC-41 | D | C | 811.23 | $^1$H NMR (400 MHz, $CD_3OD$): δ 1.12 (s, 6H), 1.22 (s, 6H), 1.48-1.61 (m, 4H), 1.80-1.83 (m, 2H), 2.35-2.44 (m, 6H), 3.59 (br, 4H), 4.06 (d, J = 9.2 Hz, 1H), 4.22 (t, J = 6.4 Hz, 2H), 4.31 (s, 1H), 6.88-6.90 (m, 1H), 6.99-7.02 (m, 1H), 7.20-7.21 (m, 1H), 7.28-7.32 (m, 1H), 7.40-7.42 (m, 1H), 7.52-7.55 (m, 2H), 7.63-7.65 (m, 2H), 7.89-7.93 (m, 2H), 7.97-7.99 (m, 1H), 8.64 (br, 1H). |
| PROTAC-42 | 0C | C | 817.2 | $^1$H NMR (400 MHz, DMSO-$d^6$) δ 1.12 (6H, s), 1.22 (6H, s), 1.42-1.60 (4H, m), 1.77-1.82 (2H, m), 2.36-2.44 (2H, m), 3.30-3.35 (4H, m), 3.58-3.66 (4H, m), 4.06 (1H, d, J = 9.2 Hz), 4.21 (1H, t, J = 6.2 Hz), 4.30 (1H, s), 6.88 (1H, d, J = 8.8 Hz), 6.99-7.02 (1H, m), 7.21 (1H, d, J = 2.4 Hz), 7.38-7.41 (1H, m), 7.48-7.52 (2H, m), 7.64 (1H, d, J = 9.2 Hz), 7.89-7.98 (4H, m), 8.63 (1H, d, J = 2.0 Hz). |
| PROTAC-43 | D | C | 802.57 | $^1$H NMR (400 MHz, DMSO-d6): δ 7.91 (d, J = 8.80 Hz, 1H), 7.72 (t, J = 8.41 Hz, 3H), 7.56 (d, J = 2.54 Hz, 1H), 7.44-7.53 (m, 2H), 7.38 (d, J = 1.96 Hz, 1H), 7.28 (dd, J = 2.05, 8.71 Hz, 1H), 7.21 (d, J = 2.35 Hz, 1H), 7.00 (dd, J = 2.35, 8.80 Hz, 1H), 6.96 (d, J = 9.00 Hz, 2H), 6.41 (d, J = 9.78 Hz, 1H), 4.32 (s, 1H), 4.05 (d, J = 9.00 Hz, 1H), 3.86 (d, J = 12.52 Hz, 2H), 3.45 (br. s., 4H), 2.79 (t, J = 11.74 Hz, 2H), 2.21 (d, J = 6.46 Hz, 2H), 1.81 (d, J = 11.15 Hz, 3H), 1.21 (s, 6H), 1.12 (s, 6H) |

TABLE 3-continued

Characteristics of exemplary androgen receptor PROTACs

| PROTAC-# | AR DC50 (nM)* | AR Dmax %** | MS signal 1 m/e+ $[M + H]^+$ | NMR |
|---|---|---|---|---|
| PROTAC-44 | D | C | 802.57 | $^1$H NMR (400 MHz, CHLOROFORM-d) δ 7.76 (d, J = 8.41 Hz, 1H), 7.69 (d, J = 9.00 Hz, 2H), 7.58 (d, J = 8.80 Hz, 1H), 7.51-7.55 (m, 1H), 7.40 (dd, J = 1.96, 6.65 Hz, 1H), 7.36 (d, J = 2.15 Hz, 1H), 7.10 (dd, J = 2.05, 8.71 Hz, 1H), 6.97 (d, J = 2.35 Hz, 1H), 6.94 (d, J = 9.00 Hz, 2H), 6.82 (dd, J = 2.45, 8.71 Hz, 1H), 6.37 (t, J = 6.85 Hz, 1H), 6.12 (d, J = 8.02 Hz, 1H), 4.16 (d, J = 8.22 Hz, 1H), 4.05 (s, 1H), 3.83-3.91 (m, 2H), 3.40-3.50 (m, 4H), 2.85 (t, J = 11.44 Hz, 2H), 2.55-2.66 (m, 4H), 2.30 (d, J = 7.04 Hz, 2H), 1.92 (d, J = 12.91 Hz, 2H), 1.27 (s, 6H), 1.23 (s, 6H) |
| PROTAC-45 | D | C | 818.56 | |
| PROTAC-46 | D | C | 823.96 | $^1$H NMR (400 MHz, $CDCl_3$): δ 8.81 (s, 1H), 8.58-8.57 (d, J = 2.4 Hz, 1H), 8.23-8.21 (d, J = 7.6 Hz, 1H), 7.92-7.89 (m, 1H), 7.57-7.48 (m, 2H), 7.38-7.34 (m, 1H), 7.26-7.21 (m, 1H), 6.97-6.96 (d, J = 2.0 Hz, 1H), 6.81-6.78 (m, 1H), 6.61-6.59 (d, J = 9.2 Hz, 1H), 6.25 (s, 1H), 6.11-6.09 (d, J = 8.0 Hz, 1H), 4.82-4.79 (m, 1H), 4.32-4.29 (m, 2H), 4.26-4.23 (m, 1H), 4.15-4.13 (m, 1H), 4.04 (s, 1H), 3.76-3.67 (m, 10H), 2.95-2.90 (m, 1H), 2.70-2.62 (m, 7H), 2.23-2.19 (m, 2H), 1.25 (s, 6H), 1.21 (s, 6H); |
| PROTAC-47 | B | C | 791.3 | $^1$H NMR (400 MHz, $CDCl_3$) δ 1.21 (6H, s), 1.25 (6H, s), 1.58-1.66 (4H, m), 1.90-1.94 (2H, m), 2.43-2.47 (2H, m), 2.56-2.58 (4H, m), 3.67-3.70 (4H, m), 4.04 (1H, s), 4.09-4.15 (3H, m), 5.93 (1H, d, J = 8.0 Hz), 6.07 (1H, d, J = 8.0 Hz), 6.66 (1H, d, J = 9.2 Hz), 6.80 (1H, dd, J = 8.8, 2.4 Hz), 6.96 (1H, d, J = 2.4 Hz), 7.09 (1H, d, J = 2.8 Hz), 7.41-7.46 (2H, m), 7.57 (1H, d, J = 8.8 Hz), 7.93 (1H, dd, J = 9.2, 2.4 Hz), 8.05-8.07 (2H, m), 8.58 (1H, d, J = 2.4 Hz), 8.73 (1H, d, J = 2.4 Hz). |
| PROTAC-48 | D | C | 812.15 | $^1$H NMR (400 MHz, DMSO-$d_6$) δ 1.10-1.13 (9H, m), 1.21 (6H, s), 1.44-1.53 (4H, m), 1.74-1.77 (2H, m), 1.99-2.08 (1H, m), 2.31-2.34 (3H, m), 2.42-2.45 (5H, m), 2.67-2.68 (1H, m), 3.29-3.34 (3H, m), 3.58-3.59 (4H, m), 4.00-4.07 (3H, m), 4.30 (1H, s), 6.86 (1H, d, J = 8.8 Hz), 6.98-7.02 (3H, m), 7.22 (1H, d, J = 2.4 Hz), 7.31 (2H, d, J = 8.0 Hz), 7.63 (1H, d, J = 9.2 Hz), 7.91 (1H, d, J = 8.8 Hz), 7.95 (1H, dd, J = 8.8, 2.4 Hz), 8.62 (1H, d, J = 2.0 Hz), 10.78 (1H, s). |
| PROTAC-49 | D | C | 798.33 | $^1$H NMR (400 MHz, DMSO-$d_6$) δ 1.12 (6H, s), 1.21-1.26 (8H, m), 1.45-1.53 (4H, m), 1.74-1.76 (2H, m), 1.96-1.98 (1H, m), 2.33-2.44 (7H, m), 2.78-2.87 (4H, m), 3.58-3.59 (4H, m), 4.01-4.07 (3H, m), 4.30 (1H, s), 6.87 (1H, d, J = 9.2 Hz), 6.98-7.02 (3H, m), 7.21 (1H, d, J = 2.8 Hz), 7.41 (2H, d, J = 8.0 Hz), 7.63 (1H, d, J = 9.2 Hz), 7.91 (1H, d, J = 8.8 Hz), 7.96 (1H, dd, J = 8.8, 2.4 Hz), 8.62 (1H, d, J = 2.0 Hz), 10.89 (1H, s). |
| PROTAC-50 | A | B | 757.54 | $^1$H NMR (400 MHz, DMSO-$d_6$) δ 1.12 (6H, s), 1.22 (6H, s), 1.94-2.01 (3H, m), 2.18-2.22 (1H, m), 2.49-2.50 (6H, m), 2.75-2.83 (1H, m), 2.99 (1H, d, J = 4.8 Hz), 3.61 (4H, s), 4.06 (1H, d, J = 9.2 Hz), 4.19-4.23 (2H, m), 4.31 (1H, s), 4.74-4.80 (1H, m) 6.88 (1H, d, J = 9.2 Hz), 7.01 (1H, dd, J = 8.8 Hz, 2.4 Hz), 7.21 (1H, d, J = 2.4 Hz), 7.58 (1H, dd, J = 8.8 Hz, 2.4 Hz), 7.63 (1H, d, J = 9.2 Hz), 7.90 (1H, d, J = 8.4 Hz), 7.96 (1H, dd, J = 8.8 Hz, 2.4 Hz), 8.02 (1H, d, J = 8.8 Hz), 8.34 (1H, d, J = 2.8 Hz), 8.63 (1H, d, J = 2.4 Hz), 8.89 (1H, d, J = 8.4 Hz), 10.87 (1H, s). |
| PROTAC-51 | A | C | 771.55 | $^1$H NMR (400 MHz, DMSO-$d_6$) δ 1.12 (6H, s), 1.21 (6H, s), 1.62-1.66 (2H, m), 1.79-1.83 (2H, m), 1.97-2.01 (1H, m), 2.18-2.22 (1H, m), 2.37-2.41 (2H, m), 2.46-2.50 (5H, m), 2.77-2.80 (1H, m), 3.60 (4H, s), 4.05 (1H, d, J = 9.2 Hz), 4.18 (2H, t, J = 6.0 Hz), 4.30 (1H, s), 4.74-4.79 (1H, m), 6.87 (1H, d, J = 9.2 Hz), 7.01 (1H, dd, J = 2.4 Hz, 8.8 Hz), 7.21 (1H, d, J = 2.4 Hz), 7.57 (1H, dd, J = 2.8 Hz, 8.8 Hz), 7.64 (1H, d, J = 9.2 Hz), 7.91 (1H, d, J = 8.8 Hz), 7.96 (1H, dd, J = 2.4 Hz, 8.8 Hz), 8.02 (1H, d, J = 8.8 Hz), 8.34 (1H, d, J = 2.8 Hz), 8.62 (1H, d, J = 2.4 Hz), 8.90 (1H, d, J = 8.8 Hz), 10.88 (1H, s). |
| PROTAC-52 | A | B | 810.61 | $^1$H NMR (400 MHz, DMSO-$d_6$) δ 1.12 (6H, s), 1.22 (6H, s), 1.42-1.43 (2H, m), 1.61-1.63 (1H, m), 1.75-1.78 (2H, m), 1.96-2.01 (1H, m), 2.14-2.22 (1H, m), 2.33-2.40 (3H, m), 2.45-2.49 (5H, m), 2.51-2.55 (5H, m), 2.85-2.91 (3H, m), 4.05 (1H, d, J = 9.6 Hz), 4.30 (1H, s), 4.41 (2H, d, J = 13.2 Hz), 4.72-4.76 (1H, m), 6.85 (1H, d, J = 8.8 Hz), 7.01 (1H, dd, J = 8.8, 2.4 |

TABLE 3-continued

Characteristics of exemplary androgen receptor PROTACs

| PROTAC-# | AR DC50 (nM)* | AR Dmax %** | MS signal 1 m/e+ [M + H]+ | NMR |
|---|---|---|---|---|
| | | | | Hz), 7.21 (1H, d, J = 2.4 Hz), 7.42 (1H, dd, J = 8.8, 2.4 Hz), 7.60 (1H, d, J = 9.2 Hz), 7.85-7.94 (3H, m), 8.32 (1H, d, J = 2.8 Hz), 8.61 (1H, d, J = 2.0 Hz), 8.74 (1H, d, J = 8.4 Hz), 10.86 (1H, s). |
| PROTAC-53 | A | A | 796.59 | $^1$H NMR (400 MHz, $CDCl_3$) δ 0.76-0.81 (1H, m), 1.15-1.21 (16H, m), 1.80-2.23 (5H, m), 2.53-2.59 (4H, m), 2.71-2.78 (2H, m), 2.85-2.91 (2H, m), 3.29 (3H, brs), 3.97 (1H, s), 4.07 (1H, d, J = 8 Hz), 4.38 (2H, d, J = 12.8 Hz), 4.69-4.75 (1H, m), 5.98 (1H, d, J = 8.4 Hz), 6.60 (1H, d, J = 8.8 Hz), 6.73 (1H, dd, J = 8.8, 2.4 Hz), 6.89 (1H, d, J = 2.4 Hz), 7.14-7.17 (1H, m), 7.50 (1H, d, J = 8.8 Hz), 7.84 (1H, dd, J = 8.8, 2.4 Hz), 7.92 (1H, s), 7.97 (1H, d, J = 8.8 Hz), 8.15 (1H, d, J = 2.4 Hz), 8.38 (1H, d, J = 6.8 Hz), 8.50 (1H, d, J = 2.4 Hz). |
| PROTAC-54 | B | B | 797.59 | $^1$H NMR (400 MHz, DMSO-$d_6$) δ 1.07-1.23 (14H, m), 1.84-2.03 (4H, m), 2.16-2.23 (3H, m), 2.51-2.60 (5H, m), 2.75-2.80 (1H, m), 3.02-3.08 (2H, m), 3.36 (4H, s), 4.01 (1H, d, J = 9.2 Hz), 4.46-4.52 (3H, m), 4.72-4.78 (1H, m), 7.03 (1H, dd, J = 8.8, 2.4 Hz), 7.25 (1H, d, J = 2.0 Hz), 7.36-7.44 (2H, m), 7.81-7.92 (3H, m), 8.24 (1H, d, J = 9.2 Hz), 8.33 (1H, d, J = 1.6 Hz), 8.73 (1H, d, J = 8.4 Hz), 10.85 (1H, s). |
| PROTAC-55 | A | B | 795.59 | $^1$H NMR (400 MHz, DMSO-$d_6$) δ 1.13 (6H, s), 1.15-1.22 (8H, m), 1.80-1.83 (3H, m), 1.99-2.03 (1H, m), 2.16-2.23 (3H, m), 2.50-2.51 (5H, m), 2.76-2.82 (3H, m), 3.36 (4H, s), 3.86 (2H, d, J = 12.4 Hz), 4.05 (1H, d, J = 9.2 Hz), 4.32 (1H, s), 4.71-4.78 (1H, m), 6.95-7.02 (3H, m), 7.21 (1H, d, J = 2.0 Hz), 7.42 (1H, dd, J = 8.8, 2.4 Hz), 7.49 (1H, d, J = 9.2 Hz), 7.74 (2H, d, J = 8.8 Hz), 7.86-7.92 (2H, m), 8.32 (1H, d, J = 2.4 Hz), 8.73 (1H, d, J = 8.4 Hz), 10.85 (1H, s). |
| PROTAC-56 | B | B | 797.58 | $^1$H NMR (400 MHz, DMSO-$d_6$) δ 1.13 (6H, s), 1.19 (6H, s), 1.83-1.86 (2H, m), 1.90-2.02 (2H, m), 2.16-2.23 (3H, m), 2.48-2.51 (6H, m), 2.76-2.82 (1H, m), 2.99-3.05 (3H, m), 3.35 (4H, s), 3.96 (1H, d, J = 9.2 Hz), 4.43 (1H, s), 4.47-4.50 (2H, m), 4.71-4.78 (1H, m), 7.03 (1H, dd, J = 2.4 Hz, 8.8 Hz), 7.25 (1H, d, J = 2.4 Hz), 7.42 (1H, dd, J = 2.8 Hz, 8.8 Hz), 7.80-7.91 (3H, m), 8.33 (2H, d, J = 4.8 Hz), 8.60 (1H, d, J = 1.2 Hz), 8.72 (1H, d, J = 8.0 Hz), 10.85 (1H, s). |
| PROTAC-57 | B | A | 830.53 | |
| PROTAC-58 | 0C | B | 830.53 | |
| PROTAC-59 | A | A | 768.53 | |
| PROTAC-60 | D | C | 731.51 | $^1$H NMR (400 MHz, DMSO-$d_6$) δ 1.12 (6H, s), 1.22 (6H, s), 1.92-2.08 (3H, m), 2.41-2.50 (7H, m), 2.55-2.60 (1H, m), 2.83-2.91 (1H, m), 3.61 (4H, s), 4.05-4.13 (3H, m), 4.30 (1H, s), 5.65 (1H, dd, J = 12.4, 5.2 Hz), 6.36 (1H, d, J = 2.8 Hz), 6.87 (1H, d, J = 9.2 Hz), 7.00 (1H, dd, J = 8.8, 2.4 Hz), 7.21 (1H, d, J = 2.4 Hz), 7.63 (1H, d, J = 9.2 Hz), 7.82 (1H, d, J = 2.8 Hz), 7.91 (1H, d, J = 8.8 Hz), 7.96 (1H, dd, J = 8.8, 2.8 Hz), 8.63 (1H, d, J = 2.4 Hz), 11.03 (1H, s). |
| PROTAC-61 | A | B | 729.53 | $^1$H NMR (400 MHz, $CDCl_3$) δ 1.16 (7H, s), 1.21 (7H, s), 1.71-1.75 (2H, m), 2.13-2.16 (1H, m), 2.34-2.37 (2H, m), 2.45-2.47 (4H, m), 2.55-2.71 (2H, m), 2.77-2.84 (3H, m), 3.25-3.28 (4H, m) 3.99 (1H, s), 4.09 (1H, d, J = 8.4 Hz), 5.63-5.68 (1H, m), 5.82 (1H, d, J = 2.8 Hz), 6.11 (1H, d, J = 8.0 Hz), 6.74 (1H, dd, J = 8.8, 2.4 Hz), 6.90 (1H, d, J = 2.0 Hz), 7.21 (1H, s), 7.50 (1H, d, J = 8.8 Hz), 7.64 (1H, d, J = 3.2 Hz), 7.91 (1H, brs), 7.96 (1H, dd, J = 8.0, 2.0 Hz), 8.83 (1H, d, J = 1.6 Hz). |
| PROTAC-62 | A | B | 769.57 | $^1$H NMR (400 MHz, DMSO-$d_6$) δ 1.12 (6H, s), 1.22 (6H, s), 1.78-1.81 (3H, m), 1.97-2.01 (1H, m), 2.19-2.21 (2H, m), 2.44 (6H, brs), 2.75-2.81 (3H, m), 3.35 (6H, brs), 3.85 (2H, d, J = 11.2 Hz), 4.05 (1H, d, J = 9.2 Hz), 4.32 (1H, s), 5.57-5.61 (1H, m), 5.87 (1H, d, J = 2.8 Hz), 6.95-7.02 (3H, m), 7.21 (1H, d, J = 2.4 Hz), 7.50 (1H, d, J = 9.2 Hz), 7.73 (2H, d, J = 8.8 Hz), 7.91 (1H, d, J = 8.8 Hz), 8.06 (1H, d, J = 2.4 Hz), 10.98 (1H, s). |
| PROTAC-63 | A | A | 783.59 | $^1$H NMR (400 MHz, DMSO-$d_6$) δ 1.12 (6H, s), 1.22-1.26 (8H, m), 1.39-1.44 (3H, m), 1.74-1.77 (2H, m), 1.98-2.00 (1H, m), 2.33-2.45 (8H, m), 2.72-2.85 (3H, m), 3.32-3.34 (4H, m), 3.83-3.86 (2H, m), 4.05 (1H, d, J = 8.8 Hz), 4.32 (1H, s), 5.58-5.61 |

TABLE 3-continued

Characteristics of exemplary androgen receptor PROTACs

| PROTAC-# | AR DC50 (nM)* | AR Dmax %** | MS signal 1 m/e+ [M + H]$^+$ | NMR |
|---|---|---|---|---|
| | | | | (1H, m), 5.85-5.86 (1H, m), 6.95 (2H, d, J = 9.2 Hz), 7.00 (1H, dd, J = 9.2, 2.4 Hz), 7.21 (1H, d, J = 2.4 Hz), 7.50 (1H, d, J = 8.8 Hz), 7.73 (2H, d, J = 8.8 Hz), 7.91 (1H, d, J = 8.8 Hz), 8.05 (1H, d, J = 2.8 Hz), 10.97 (1H, s). |
| PROTAC-66 | D | C | 806.57 | |
| PROTAC-67 | B | C | 837.61 | $^1$H NMR (400 MHz, DMSO-$d_6$) δ 1.13 (6H, s), 1.22 (6H, s), 1.46-1.54 (4H, m), 1.75-1.79 (2H, m), 2.07-2.17 (1H, m), 2.33-2.41 (3H, m), 2.60-2.70 (1H, m), 2.85-2.94 (1H, m), 3.22-3.28 (4H, m), 3.30-3.36 (7H, m), 4.03-4.07 (3H, m), 4.33 (1H, s), 5.21-5.25 (1H, m), 6.95-7.02 (3H, m), 7.12-7.14 (1H, m), 7.20-7.26 (3H, m), 7.45 (1H, t, J = 8.0 Hz), 7.52 (1H, d, J = 9.2 Hz), 7.75 (2H, d, J = 8.8 Hz), 7.91 (1H, d, J = 8.8 Hz), 11.1 (1H, s). |
| PROTAC-68 | A | A | 848.62 | $^1$H NMR (400 MHz, D6-DMSO): δ 1.13 (s, 6H), 1.18-1.27 (m, 2H), 1.22 (s, 6H), 1.76-1.83 (m, 3H), 2.07-2.15 (m, 1H), 2.18-2.25 (m, 2H), 2.42-2.50 (m, 4H), 2.50-2.56 (m, 3H), 2.59-2.67 (m, 1H), 2.75-2.82 (m, 2H), 2.84-2.93 (m, 1H), 3.16-3.26 (m, 4H), 3.29 (s, 1H), 3.86 (d, J = 12.4 Hz, 2H), 4.05 (d, J = 9.2 Hz, 1H), 4.32 (s, 1H), 5.19-5.24 (m, 1H), 6.96 (d, J = 8.8 Hz, 2H), 7.00 (dd, J = 2.4, 8.8 Hz, 1H), 7.05 (d, J = 7.6 Hz, 1H), 7.11-7.14 (m, 2H), 7.21 (d, J = 2.4 Hz, 1H), 7.37 (t, J = 8.0 Hz, 1H), 7.47 (d, J = 9.2 Hz, 1H), 7.74 (d, J = 8.8 Hz, 2H), 7.90 (d, J = 8.8 Hz, 1H), 11.04 (s, 1H),. |
| PROTAC-69 | A | B | 837.61 | $^1$H NMR (400 MHz, DMSO-$d_6$) δ 1.13 (6H, s), 1.22 (6H, s), 1.37-1.59 (4H, m), 1.74-1.81 (2H, m), 2.09-2.13 (1H, m), 2.31-2.38 (3H, m), 2.59-2.67 (1H, m), 2.80-2.93 (1H, m), 3.22-3.27 (4H, m), 3.30 (3H, m), 3.30-3.34 (4H, m), 4.02-4.08 (3H, m), 4.32 (1H, s), 5.18-5.22 (1H, m), 6.95-7.02 (3H, m), 7.06-7.10 (2H, m), 7.21 (1H, d, J = 2.4 Hz), 7.51 (1H, d, J = 9.2 Hz), 7.60-7.64 (2H, m), 7.75 (2H, d, J = 8.8 Hz), 7.91 (1H, d, J = 8.8 Hz), 11.03 (1H, s). |
| PROTAC-70 | A | A | 848.62 | $^1$H NMR (400 MHz, DMSO-$d_6$) δ 1.12 (7H, brs), 1.21 (8H, brs), 1.79-1.82 (3H, m), 2.08-2.12 (1H, m), 2.20-2.22 (2H, m), 2.41-2.45 (3H, m), 2.59-2.63 (1H, m), 2.76-2.87 (3H, m), 3.26-3.27 (5H, m), 3.30 (3H, s), 3.84-3.87 (2H, m), 4.04-4.06 (1H, m), 4.32 (1H, s), 5.18 (1H, dd, J = 5.6, 12.8 Hz), 6.94-7.05 (5H, m), 7.20 (1H, d, J = 2.4 Hz), 7.47-7.53 (3H, m), 7.73 (1H, d, J = 8.8 Hz), 7.90 (1H, d, J = 8.8 Hz), 11.0 (1H, s). |
| PROTAC-75 | D | 6C | 757.55 | |
| PROTAC-76 | D | C | 702.5 | $^1$H NMR (400 MHz, METHANOL-$d_4$) δ 7.74 (dd, J = 8.51, 12.03 Hz, 3H), 7.35 (d, J = 8.22 Hz, 2H), 7.13 (d, J = 2.54 Hz, 1H), 6.99 (dd, J = 2.45, 8.71 Hz, 1H), 4.95 (dd, J = 5.48, 12.72 Hz, 1H), 4.29 (s, 1H), 4.16 (s, 1H), 2.96 (d, J = 11.93 Hz, 2H), 2.66-2.82 (m, 6H), 2.61 (dd, J = 4.40, 13.40 Hz, 1H), 2.41-2.48 (m, 2H), 2.14-2.24 (m, 2H), 1.98-2.11 (m, 3H), 1.85-1.94 (m, 2H), 1.68 (d, J = 12.91 Hz, 2H), 1.29 (s, 6H), 1.23 (s, 6H) |
| PROTAC-77 | D | C | 700.48 | $^1$H NMR (400 MHz, METHANOL-$d_4$) δ 7.81 (d, J = 8.41 Hz, 2H), 7.73 (d, J = 8.61 Hz, 1H), 7.57 (d, J = 8.41 Hz, 2H), 7.13 (d, J = 2.54 Hz, 1H), 6.99 (dd, J = 2.45, 8.71 Hz, 1H), 6.77 (d, J = 15.85 Hz, 1H), 6.40-6.50 (m, 1H), 4.97 (dd, J = 5.58, 12.62 Hz, 1H), 4.30 (s, 1H), 4.17 (s, 1H), 3.45 (d, J = 6.26 Hz, 2H), 3.12-3.22 (m, 2H), 2.56-2.86 (m, 6H), 2.52 (br. s., 1H), 2.09-2.21 (m, 2H), 1.98-2.05 (m, 1H), 1.80 (d, J = 13.50 Hz, 2H), 1.29 (s, 6H), 1.24 (s, 6H) |
| PROTAC-78 | D | C | 716.52 | $^1$H NMR (400 MHz, METHANOL-$d_4$) δ 7.74 (dd, J = 8.51, 11.25 Hz, 3H), 7.33 (d, J = 8.22 Hz, 2H), 7.13 (d, J = 2.35 Hz, 1H), 6.99 (dd, J = 2.35, 8.80 Hz, 1H), 4.95 (dd, J = 5.48, 12.72 Hz, 1H), 4.29 (s, 1H), 4.16 (s, 1H), 2.99 (d, J = 11.54 Hz, 2H), 2.67-2.86 (m, 6H), 2.61 (dd, J = 4.21, 13.21 Hz, 1H), 2.46-2.54 (m, 2H), 2.25 (t, J = 11.25 Hz, 2H), 1.97-2.12 (m, 3H), 1.65-1.75 (m, 4H), 1.55-1.64 (m, 2H), 1.29 (s, 6H), 1.23 (s, 6H) |
| PROTAC-79 | B | C | 791.23 | $^1$H NMR (400 MHz, DMSO-$d_6$) δ 1.12 (6H, s), 1.21 (6H, s), 1.49-1.57 (4H, m), 1.83-1.86 (2H, m), 2.31-2.40 (5H, m), 2.67-2.68 (1H, m), 3.58-3.60 (4H, m), 4.05 (1H, d, J = 9.2 Hz), 4.17-4.20 (2H, m), 4.30 (1H, s), 5.76 (1H, d, J = 8.4 Hz), 6.86 (1H, d, J = 8.8 Hz), 6.99-7.02 (1H, m), 7.21 (1H, d, J = 2.0 Hz), 7.50-7.52 (1H, m), 7.63 (1H, d, J = 9.6 Hz), 7.70-7.76 (3H, m), 7.90-7.97 (2H, m), 8.44 (1H, s), 8.62 (1H, d, J = 1.6 Hz), 9.31 (1H, s). |

TABLE 3-continued

Characteristics of exemplary androgen receptor PROTACs

| PROTAC-# | AR DC50 (nM)* | AR Dmax %** | MS signal 1 m/e+ [M + H]$^+$ | NMR |
|---|---|---|---|---|
| PROTAC-80 | D | C | 816.23 | $^1$H NMR (400 MHz, DMSO-$d_6$) δ 1.11 (6H, s), 1.21 (6H, s), 1.50-1.57 (4H, m), 1.81-1.86 (2H, m), 2.33-2.37 (2H, m), 2.45-2.50 (4H, m), 3.59 (4H, s), 4.05 (1H, d, J = 9.2 Hz), 4.15 (2H, t, J = 6.4 Hz), 4.30 (1H, s), 6.86 (1H, d, J = 9.2 Hz), 7.00 (1H, dd, J = 8.8, 2.0 Hz), 7.21 (1H, d, J = 2.4 Hz), 7.45 (1H, d, J = 2.4 Hz), 7.50 (1H, dd, J = 5.2, 2.4 Hz), 7.63 (1H, d, J = 9.2 Hz), 7.91 (1H, d, J = 8.8 Hz), 7.95 (1H, dd, J = 8.8, 2.0 Hz), 8.00 (1H, d, J = 9.2 Hz), 8.37 (1H, d, J = 2.0 Hz), 8.62 (1H, d, J = 2.0 Hz), 8.78 (1H, d, J = 2.4 Hz), 8.96 (1H, s), 12.28 (1H, brs). |
| PROTAC-81 | A | A | 832.62 | $^1$H NMR (400 MHz, DMSO) δ 10.88 (s, 1H), 7.91-7.89 (m, 1H), 7.78-7.72 (m, 3H), 7.50-7.47 (d, J = 9.2 Hz, 1H), 7.21 (s, 1H), 7.09-6.94 (m, 5H), 5.75 (s, 1H), 5.29 (s, 1H), 5.15-4.95 (m, 1H), 4.32 (s, 1H), 4.21-4.04 (m, 3H), 3.87-3.84 (m, 2H), 3.32-3.30 (m, 7H), 2.84-2.76 (m, 3H), 2.65-2.56 (m, 1H), 2.48-2.37 (m, 1H), 2.22-2.18 (m, 2H), 1.90-1.79 (m, 4H), 1.40-1.16 (m, 9H), 1.16-1.09 (m, 6H); |
| PROTAC-82 | A | A | 818.59 | $^1$H NMR: (400 MHz, DMSO-$d_6$) δ: 11.07-10.90 (m, 1H), 10.57 (s, 1H), 8.10-8.01 (m, 1H), 7.91 (d, J = 8.8 Hz, 1H), 7.80 (d, J = 8.8 Hz, 2H), 7.58 (br d, J = 9.2 Hz, 1H), 7.33 (d, J = 7.6 Hz, 1H), 7.29-7.23 (m, 1H), 7.21 (d, J = 2.4 Hz, 1H), 7.16-7.05 (m, 3H), 7.01 (dd, J = 2.4, 8.8 Hz, 1H), 6.56-6.37 (m, 1H), 6.56-6.37 (m, 1H), 4.34 (s, 1H), 4.06 (d, J = 9.2 Hz, 3H), 3.87 (br d, J = 12.8 Hz, 2H), 3.68-3.60 (m, 1H), 3.22-3.08 (m, 4H), 3.00-2.76 (m, 3H), 2.65-2.55 (m, 1H), 2.54-2.52 (m, 2H), 2.47-2.43 (m, 1H), 2.23-2.11 (m, 1H), 2.05-1.90 (m, 3H), 1.55-1.30 (m, 2H), 1.23 (s, 6H), 1.14 (s, 6H) |

*DC50 (nM) and IC50 (nM):
A < 1
1 <= B < 10
10 <= C < 100
D >= 100
**Dmax (% degraded)
A > 75
50 < B <= 75
C <= 50

TABLE 4

Characteristic of exemplary BDR4 PROTACs

| PROTAC-# | $IC_{50}$ Myc (nM)* | $I_{Max}$ Myc (%)** | MS signal 1 m/e+ [M + H]$^+$ | NMR |
|---|---|---|---|---|
| PROTAC-1 | >1D | 40C | 753.35 | |

*DC50 (nM) and IC50 (nM):
A < 1
1 <= B < 10
10 <= C < 100
D >= 100
**Dmax (% degraded)
A > 75
50 < B <= 75
C <= 50

TABLE 5

| Characteristics of exemplary estrogen receptor PROTACs | | | | | |
|---|---|---|---|---|---|
| PROTAC-#* | ER Target Engagement $IC_{50}$ (nM)* | ER degradation $DC_{50}$ (nM)*+ | ER Degradation $D_{max}$ (%)** | MS signal 1 m/e+ $[M + H]^+$ | NMR |
| PROTAC-89 | B | B | 8A | 750.6 | $^1H$ NMR: (400 MHz, DMSO-$d_6$) δ: 10.95 (s, 1H), 8.19 (s, 1H), 7.50 (d, J = 8.8 Hz, 2H), 7.21-7.06 (m, 3H), 6.96 (d, J = 8.8 Hz, 2H), 6.83 (d, J = 6.4 Hz, 2H), 6.64 (d, J = 8.4 Hz, 1H), 6.59 (d, J = 2.4 Hz, 1H), 6.53 (d, J = 8.8 Hz, 2H), 6.47 (dd, J = 2.4, 8.4 Hz, 1H), 6.40 (s, 1H), 6.19 (d, J = 8.8 Hz, 2H), 4.91 (dd, J = 5.2, 13.2 Hz, 1H), 4.45-4.33 (m, 1H), 4.29-4.19 (m, 1H), 4.12 (d, J = 4.8 Hz, 1H), 3.52 (s, 1H), 3.49-3.48 (m, 1H), 3.30 (s, 2H), 3.24 (s, 3H), 3.04-2.79 (m, 3H), 2.60 (s, 1H), 2.52 (d, J = 2.0 Hz, 2H), 2.47 (b s, 4H), 2.32-2.23 (m, 1H), 2.18 (d, J = 6.8 Hz, 2H), 2.13-2.03 (m, 1H), 1.99-1.88 (m, 1H), 1.80-1.59 (m, 4H), 1.22-1.06 (m, 2H). |
| PROTAC-90 | B | B | A | 715.58 | $^1H$ NMR: (400 MHz, DMSO-$d_6$) δ = 10.86 (s, 1H), 9.13 (s, 1H), 8.13 (s, 1H), 7.42-7.21 (m, 2H), 7.18-7.07 (m, 3H), 6.97 (d, J = 7.5 Hz, 2H), 6.82 (d, J = 6.4 Hz, 2H), 6.69-6.57 (m, 2H), 6.56-6.44 (m, 3H), 6.26 (d, J = 8.4 Hz, 2H), 5.13-4.56 (m, 1H), 4.17 (d, J = 5.2 Hz, 1H), 3.81 (t, J = 6.4 Hz, 2H), 3.53-3.38 (m, 7H), 3.05-2.70 (m, 9H), 2.55 (d, J = 12.0 Hz, 2H), 2.43-2.35 (m, 1H), 2.18-1.92 (m, 2H), 1.77-1.61 (m, 3H), 1.55 (s, 2H), 1.44-1.31 (m, 2H) |
| PROTAC-91 | B | B | A | 702.56 | $^1H$ NMR: (400 MHz, DMSO-$d_6$) δ = 10.85 (s, 1H), 8.73 (d, J = 8.4 Hz, 1H), 8.30 (d, J = 2.8 Hz, 1H), 8.20 (s, 1H), 7.85 (d, J = 8.8 Hz, 1H), 7.40 (dd, J = 2.8, 8.8 Hz, 1H), 7.19-7.08 (m, 3H), 6.82 (d, J = 6.8 Hz, 2H), 6.64 (d, J = 7.6 Hz, 2H), 6.60 (s, 2H), 6.55-6.46 (m, 3H), 6.25 (d, J = 8.8 Hz, 2H), 4.79-4.65 (m, 1H), 4.17 (d, J = 4.8 Hz, 1H), 3.81 (t, J = 6.4 Hz, 2H), 3.03-2.88 (m, 2H), 2.87-2.72 (m, 1H), 2.70-2.59 (m, 1H), 2.55-2.52 (m, 4H), 2.46-2.27 (m, 4H), 2.24-1.96 (m, 4H), 1.77-1.58 (m, 3H), 1.54-1.42 (m, 2H), 1.39 (d, J = 6.4 Hz, 2H) |
| PROTAC-92 | | D | C | 759.62 | $^1H$ NMR: (400 MHz, DMSO-$d_6$) δ = 10.69 (s, 1H), 9.10 (s, 1H), 8.12 (s, 1H), 7.18-7.04 (m, 3H), 6.90 (d, J = 8.4 Hz, 1H), 6.80 (d, J = 6.8 Hz, 2H), 6.65-6.56 (m, 2H), 6.54-6.42 (m, 5H), 6.23 (d, J = 8.8 Hz, 2H), 4.26 (s, 1H), 4.15 (d, J = 4.8 Hz, 1H), 4.38-4.06 (m, 1H), 3.86-3.68 (m, 5H), 3.23-3.04 (m, 6H), 3.00-2.87 (m, 2H), 2.72 (s, 1H), 2.50 (s, 5H), 2.31 (d, J = 1.6 Hz, 2H), 2.15-1.85 (m, 2H), 1.73-1.58 (m, 3H), 1.53-1.42 (m, 1H), 1.36 (d, J = 6.8 Hz, 2H), 1.07 (br s, 1H), 0.97 (t, J = 6.8 Hz, 2H) |
| PROTAC-93 | C | | C | 746.5 | $^1H$ NMR: (400 MHz, DMSO-d6) δ: 11.06 (s, 1H), 10.93-10.63 (m, 1H), 8.21 (d, J = 2.0 Hz, 1H), 8.14 (d, J = 2.8 Hz, 1H), 7.85-7.76 (m, 1H), 7.04-6.94 (m, 3H), 6.90-6.81 (m, 2H), 6.69-6.58 (m, 4H), 6.50-6.48 (m, 1H), 6.33 (d, J = 8.4 Hz, 2H), 5.87 (d, J = 2.8 Hz, 1H), 5.70-5.65 (m, 1H), 5.61-5.45 (m, 1H), 4.30-4.16 (m, 3H), 3.74 (d, J = 18.1 Hz, 2H), 3.65-3.56 (m, 3H), 3.40-3.22 (m, 1H), 3.05-2.82 (m, 3H), 2.65-2.54 (m, 4H), 2.33-1.90 (m, 4H), 1.71 (d, J = 7.3 Hz, 1H). |
| PROTAC-94 | A | | C | 746.5 | $^1H$ NMR: (400 MHz, DMSO-$d_6$) δ: 11.28-10.91 (m, 2H), 8.21 (d, J = 2.9 Hz, 1H), 8.14 (d, J = 2.7 Hz, 1H), 7.82-7.80 (m, 1H), 7.05-6.94 (m, 3H), 6.89-6.78 (m, 2H), 6.68-6.58 (m, 4H), 6.51-6.49 (m, 1H), 6.33 (d, J = 8.6 Hz, 2H), 5.87 (s, 1H), 5.69-6.57 (m, 1H), 5.61-5.45 (m, 1H), 4.30-4.14 (m, 3H), 3.62-3.49 (m, 3H), 3.45-3.27 (m, 3H), 3.07-2.80 (m, 3H), 2.63-2.54 (m, |

TABLE 5-continued

| Characteristics of exemplary estrogen receptor PROTACs | | | | | |
|---|---|---|---|---|---|
| PROTAC-#* | ER Target Engagement $IC_{50}$ (nM)* | ER degradation $DC_{50}$ (nM)*+ | ER Degradation $D_{max}$ (%)** | MS signal 1 m/e+ $[M + H]^+$ | NMR |
| | | | | | 4H), 2.28-1.94 (m, 4H), 1.70 (d, J = 6.6 Hz, 1H). |
| PROTAC-95 | D | | C | 745.52 | $^1$H NMR: (400 MHz, DMSO) δ 11.05 (s, 1H), 9.19 (br s, 1H), 8.22 (s, 1H), 8.09 (t, J = 2.6 Hz, 2H), 7.56 (dd, J = 2.9, 9.2 Hz, 1H), 7.03-6.91 (m, 3H), 6.85 (dd, J = 5.8, 8.5 Hz, 2H), 6.68-6.55 (m, 4H), 6.49 (dd, J = 2.5, 8.3 Hz, 1H), 6.29 (d, J = 8.7 Hz, 2H), 5.81 (d, J = 2.8 Hz, 1H), 5.67 (br dd, J = 5.2, 12.2 Hz, 1H), 4.17 (br d, J = 4.9 Hz, 1H), 3.98 (br t, J = 5.6 Hz, 2H), 3.57 (s, 1H), 3.49 (br s, 3H), 3.33 (br dd, J = 3.2, 12.7 Hz, 1H), 3.17-2.80 (m, 4H), 2.70-2.68 (m, 2H), 2.64-2.61 (m, 1H), 2.58-2.52 (m, 4H), 2.19-1.94 (m, 2H), 1.70 (br d, J = 7.0 Hz, 1H). |
| PROTAC-96 | A | | C | 745.52 | $^1$H NMR: (400 MHz, DMSO) δ 11.05 (s, 1H), 9.19 (br s, 1H), 8.22 (s, 1H), 8.09 (t, J = 2.6 Hz, 2H), 7.56 (dd, J = 2.9, 9.2 Hz, 1H), 7.03-6.91 (m, 3H), 6.85 (dd, J = 5.8, 8.5 Hz, 2H), 6.68-6.55 (m, 4H), 6.49 (dd, J = 2.5, 8.3 Hz, 1H), 6.29 (d, J = 8.7 Hz, 2H), 5.81 (d, J = 2.8 Hz, 1H), 5.67 (br dd, J = 5.2, 12.2 Hz, 1H), 4.17 (br d, J = 4.9 Hz, 1H), 3.98 (br t, J = 5.6 Hz, 2H), 3.57 (s, 1H), 3.49 (br s, 3H), 3.33 (br dd, J = 3.2, 12.7 Hz, 1H), 3.17-2.80 (m, 4H), 2.70-2.68 (m, 2H), 2.64-2.61 (m, 1H), 2.58-2.52 (m, 4H), 2.19-1.94 (m, 2H), 1.70 (br d, J = 7.0 Hz, 1H). |
| PROTAC-97 | C | | C | 746.5 | $^1$H NMR: (400 MHz, DMSO-$d_6$) δ: 11.06 (s, 1H), 10.95-10.67 (m, 1H), 9.18 (s, 1H), 8.20 (d, J = 2.9 Hz, 1H), 8.14 (d, J = 2.8 Hz, 1H), 7.80 (dd, J = 2.8, 8.9 Hz, 1H), 7.03-6.92 (m, 3H), 6.85 (dd, J = 5.7, 8.4 Hz, 2H), 6.66-6.60 (m, 4H), 6.49 (dd, J = 2.2, 8.3 Hz, 1H), 6.32 (d, J = 8.7 Hz, 2H), 5.86 (d, J = 2.8 Hz, 1H), 5.68 (dd, J = 5.0, 12.2 Hz, 1H), 5.60-5.46 (m, 1H), 4.28-4.14 (m, 3H), 4.11-3.98 (m, 1H), 3.81-3.67 (m, 2H), 3.65-3.55 (m, 3H), 3.38-3.21 (m, 1H), 2.97-2.91 (m, 3H), 2.67-2.61 (m, 2H), 2.57-2.5 (m, 1H), 2.33-2.06 (m, 3H), 1.71-1.69 (m, 1H) |
| PROTAC-98 | B | | C | 689.47 | $^1$H NMR: (400 MHz, DMSO-d6) δ 11.06 (s, 1H), 9.23 (s, 1H), 8.47 (d, J = 2.2 Hz, 1H), 8.14 (d, J = 2.4 Hz, 1H), 7.72 (dd, J = 2.4, 8.6 Hz, 1H), 7.42 (d, J = 8.4 Hz, 1H), 6.98 (t, J = 8.8 Hz, 2H), 6.88-6.78 (m, 2H), 6.67-6.60 (m, 2H), 6.56 (d, J = 8.2 Hz, 2H), 6.49 (d, J = 8.2 Hz, 1H), 6.28 (d, J = 8.2 Hz, 2H), 5.88 (d, J = 2.5 Hz, 1H), 5.69 (dd, J = 4.6, 12.0 Hz, 1H), 4.16 (br d, J = 4.6 Hz, 1H), 3.86 (br t, J = 5.8 Hz, 2H), 3.32-3.26 (m, 1H), 3.05-2.87 (m, 3H), 2.82 (br t, J = 7.6 Hz, 2H), 2.62 (br s, 1H), 2.46-2.39 (m, 1H), 2.06 (br d, J = 5.6 Hz, 2H), 1.80 (br d, J = 7.0 Hz, 2H), 1.70 (br d, J = 6.4 Hz, 3H) |
| PROTAC-99 | C | | C | 703.49 | $^1$H NMR: (400 MHz, DMSO-d6) δ 11.07 (s, 1H), 9.18 (s, 1H), 8.51-8.38 (m, 1H), 8.14 (d, J = 2.8 Hz, 1H), 7.71 (dd, J = 2.8, 8.4 Hz, 1H), 7.41 (d, J = 8.4 Hz, 1H), 7.01-6.92 (m, 2H), 6.88-6.76 (m, 2H), 6.67-6.59 (m, 2H), 6.55 (d, J = 8.7 Hz, 2H), 6.49 (br d, J = 8.3 Hz, 1H), 6.27 (br d, J = 8.4 Hz, 2H), 5.86 (d, J = 2.6 Hz, 1H), 5.69 (br dd, J = 5.2, 12.4 Hz, 1H), 4.16 (d, J = 4.6 Hz, 1H), 3.82 (br t, J = 6.3 Hz, 2H), 2.99-2.85 (m, 3H), 2.78 (t, J = 7.6 Hz, 2H), 2.59 (d, J = 17.4 Hz, 1H), 2.47-2.40 (m, 1H), 2.08-2.00 (m, 2H), 1.78-1.65 (m, 5H), 1.42 (d, J = 6.4 Hz, 2H) |
| PROTAC-100 | B | B | B | 676.54 | $^1$H NMR: (400 MHz, DMSO-$d_6$) δ = 10.95 (s, 1H), 9.12 (s, 1H), 8.13 (s, 1H), 8.02 (d, J = 2.8 Hz, 1H), 7.18-7.08 (m, 3H), 6.81 (d, |

TABLE 5-continued

| Characteristics of exemplary estrogen receptor PROTACs | | | | | |
|---|---|---|---|---|---|
| PROTAC-#* | ER Target Engagement $IC_{50}$ (nM)* | ER degradation $DC_{50}$ (nM)*+ | ER Degradation $D_{max}$ (%)** | MS signal 1 m/e+ $[M + H]^+$ | NMR |
| | | | | | J = 6.4 Hz, 2H), 6.66-6.58 (m, 2H), 6.57-6.42 (m, 4H), 6.28-6.22 (m, 2H), 5.83 (d, J = 2.4 Hz, 1H), 5.57 (m, 1H), 4.16 (d, J = 4.8 Hz, 1H), 3.79 (t, J = 6.4 Hz, 2H), 3.02-2.77 (m, 4H), 2.59-2.50 (m, 5H), 2.44-2.39 (m, 4H), 2.33-2.26 (m, 2H), 2.14-1.96 (m, 2H), 1.74-1.61 (m, 3H), 1.50-1.31 (m, 4H) |
| PROTAC-101 | B | B | B | 676.54 | $^1$H NMR: (400 MHz, DMSO) δ 10.93 (s, 1H) 9.13 (br s, 1H) 8.22 (d, J = 3.51 Hz, 2H) 7.09-7.19 (m, 3H) 6.83 (br d, J = 6.53 Hz, 2H) 6.65 (d, J = 8.68 Hz, 1H) 6.61 (s, 1H) 6.46-6.57 (m, 3H) 6.26 (d, J = 8.66 Hz, 2H) 6.16 (s, 1H) 5.87-5.94 (m, 1H) 4.18 (d, J = 4.77 Hz, 1H) 3.81 (br t, J = 6.40 Hz, 2H) 3.56 (br s, 3H) 3.30 (br s, 1H) 2.76-3.03 (m, 3H) 2.56-2.58 (m, 1H) 2.58 (br d, J = 17.69 Hz, 1H) 2.35-2.41 (m, 1H) 2.29 (br t, J = 7.03 Hz, 4H) 1.99-2.21 (m, 3H) 1.56-1.77 (m, 3H) 1.43-1.54 (m, 2H) 1.38 (br d, J = 7.15 Hz, 2H) |
| PROTAC-102 | B | B | A | 687.55 | $^1$H NMR: (400 MHz, DMSO-$d_6$) δ: 10.96 (s, 1H), 8.22 (s, 1H), 8.04 (d, J = 2.4 Hz, 1H), 7.18-7.10 (m, 3H), 6.83 (d, J = 6.4 Hz, 2H), 6.64 (d, J = 8.4 Hz, 1H), 6.59 (d, J = 2.4 Hz, 1H), 6.52 (d, J = 8.8 Hz, 2H), 6.47 (dd, J = 2.4, 8.4 Hz, 1H), 6.19 (d, J = 8.8 Hz, 2H), 5.84 (d, J = 2.8 Hz, 1H), 5.58 (dd, J = 5.2, 12.4 Hz, 1H), 4.12 (d, J = 4.4 Hz, 1H), 3.27 (s, 4H), 3.02-2.79 (m, 3H), 2.57 (d, J = 4.0 Hz, 1H), 2.52 (d, J = 2.0 Hz, 4H), 2.46 (s, 1H), 2.42 (d, J = 4.8 Hz, 5H), 2.20-2.06 (m, 3H), 2.02-1.93 (m, 1H), 1.73 (d, J = 14.0 Hz, 3H), 1.61 (s, 1H), 1.19-1.07 (m, 2H) |
| PROTAC-103 | A | | C | 746.5 | $^1$H NMR: (400 MHz, DMSO-d6) δ: 11.33-10.84 (m, 2H), 8.20 (t, J = 2.9 Hz, 1H), 8.13 (d, J = 2.8 Hz, 1H), 7.79 (d, J = 2.9, 8.3 Hz, 1H), 7.03-6.92 (m, 3H), 6.85 (dd, J = 5.7, 8.3 Hz, 2H), 6.68-6.58 (m, 4H), 6.49 (dd, J = 2.1, 8.3 Hz, 1H), 6.32 (d, J = 8.6 Hz, 2H), 5.86 (d, J = 2.0 Hz, 1H), 5.72-5.62 (m, 1H), 5.60-5.46 (m, 1H), 4.26-4.12 (m, 3H), 4.10-3.99 (m, 1H), 3.63-3.51 (m, 1H), 3.46-3.21 (m, 4H), 3.06-2.80 (m, 3H), 2.61 (d, J = 3.2 Hz, 3H), 2.61-2.60 (m, 1H), 2.60-2.50 (m, 1H), 2.18-1.96 (m, 2H), 1.69 (d, J = 7.7 Hz, 1H) |
| PROTAC-104 | 6B | D | C | 740.58 | 1H NMR: (400 MHz, DMSO-d6) δ: 10.93 (s, 1H), 8.28 (s, 1H), 7.41 (t, J = 8.1 Hz, 1H), 7.24-7.08 (m, 6H), 6.83 (d, J = 7.2 Hz, 2H), 6.67-6.60 (m, 2H), 6.56-6.45 (m, 3H), 6.27 (d, J = 8.4 Hz, 2H), 4.94-4.85 (m, 2H), 4.20-4.00 (m, 3H), 3.84 (d, J = 5.6 Hz, 2H), 3.37-3.23 (m, 2H), 2.96 (d, J = 8.0 Hz, 5H), 2.58 (s, 1H), 2.38-2.22 (m, 4H), 2.15-1.86 (m, 4H), 1.80-1.53 (m, 9H) |
| PROTAC-105 | B | D | C | 726.56 | $^1$H NMR: (400 MHz, DMSO-$d_6$) δ = 10.93 (s, 1H), 9.17 (s, 1H), 8.24 (s, 1H), 7.43-7.36 (m, 1H), 7.24-7.07 (m, 6H), 6.83 (d, J = 6.4 Hz, 2H), 6.68-6.59 (m, 2H), 6.56-6.45 (m, 3H), 6.27 (d, J = 8.4 Hz, 2H), 4.94-4.84 (m, 2H), 4.20-3.99 (m, 3H), 3.86 (t, J = 6.4 Hz, 2H), 3.30 (s, 2H), 3.04-2.84 (m, 5H), 2.59-2.53 (m, 3H), 2.41 (t, J = 7.2 Hz, 2H), 2.28 (dd, J = 4.8, 13.6 Hz, 1H), 2.13-1.60 (m, 11H) |
| PROTAC-106 | A | B | C | 726.56 | $^1$H NMR: (400 MHz, DMSO-$d_6$) δ = 10.92 (s, 1H), 9.48-8.87 (m, 1H), 8.21 (s, 1H), 7.41-7.34 (m, 1H), 7.23-7.06 (m, 6H), 6.82 (d, J = 6.8 Hz, 2H), 6.66-6.57 (m, 2H), 6.55-6.44 (m, 3H), 6.25 (d, J = 8.8 Hz, 2H), 4.91-4.82 (m, 2H), 4.18-3.97 (m, 3H), 3.84 (t, J = 6.4 Hz, 2H), 3.30-3.27 (m, 2H), |

TABLE 5-continued

| Characteristics of exemplary estrogen receptor PROTACs | | | | | |
|---|---|---|---|---|---|
| PROTAC-#* | ER Target Engagement $IC_{50}$ (nM)* | ER degradation $DC_{50}$ (nM)*+ | ER Degradation $D_{max}$ (%)** | MS signal 1 m/e+ $[M + H]^+$ | NMR |
| | | | | | 3.02-2.82 (m, 5H), 2.55-2.52 (m, 3H), 2.39 (t, J = 6.9 Hz, 2H), 2.26 (dd, J = 4.8, 13.6 Hz, 1H), 2.11-1.58 (m, 11H) |
| PROTAC-107 | C | D | C | 837.14 | 1H NMR: (400 MHz, DMSO-d6) δ: 11.01 (s, 1H), 10.04 (s, 1H), 7.62 (s, 4H), 7.33 (d, J = 2.0 Hz, 1H), 7.31-7.23 (m, 1H), 7.21-7.11 (m, 2H), 7.01 (br d, J = 8.0 Hz, 1H), 6.92 (q, J = 8.8 Hz, 4H), 6.85 (dd, J = 2.0, 8.8 Hz, 1H), 5.25 (dd, J = 5.2, 13.2 Hz, 1H), 4.29 (s, 2H), 3.68-3.45 (m, 14H), 2.87-2.79 (m, 1H), 2.69-2.61 (m, 5H), 2.19-2.10 (m, 1H) |
| PROTAC-108 | B | D | C | 838.12 | 1H NMR: (400 MHz, DMSO-d6) δ: 11.06 (s, 1H), 9.99 (s, 1H), 7.66 (d, J = 7.2 Hz, 1H), 7.63 (s, 4H), 7.54-7.42 (m, 1H), 7.52-7.42 (m, 1H), 7.33 (d, J = 2.0 Hz, 1H), 7.15 (d, J = 8.8 Hz, 1H), 6.97-6.91 (m, 4H), 6.84 (dd, J = 2.0, 8.8 Hz, 1H), 5.28 (dd, J = 5.2, 13.2 Hz, 1H), 4.54 (s, 2H), 4.27 (s, 4H), 3.56-3.49 (m, 10H), 2.82-2.80 (m, 1H), 2.65-2.59 (m, 5H), 2.21-2.14 (m, 1H) |
| PROTAC-109 | D | D | C | 740.58 | 1H NMR: (400 MHz, DMSO-d6) δ: 10.90 (s, 1H), 8.23 (s, 1H), 7.40-7.33 (m, 1H), 7.20-7.05 (m, 6H), 6.80 (d, J = 6.8 Hz, 2H), 6.64-6.55 (m, 2H), 6.53-6.43 (m, 3H), 6.23 (d, J = 8.4 Hz, 2H), 4.91-4.80 (m, 2H), 4.17-3.97 (m, 3H), 3.83-3.77 (m, 2H), 3.25 (d, J = 3.6 Hz, 1H), 3.01-2.79 (m, 5H), 2.55-2.50 (m, 3H), 2.39-2.23 (m, 4H), 2.11-1.85 (m, 4H), 1.75-1.51 (m, 8H) |
| PROTAC-110 | A | A | B | 696.54 | $^1$H NMR: (400 MHz, DMSO-d6) δ: 11.08 (s, 1H), 9.13 (br s, 1H), 8.14 (s, 1H), 8.09 (s, 1H), 7.82 (s, 1H), 7.42 (d, J = 8.7 Hz, 2H), 7.20-7.08 (m, 3H), 6.93 (d, J = 8.9 Hz, 2H), 6.83 (br d, J = 6.7 Hz, 2H), 6.68-6.58 (m, 2H), 6.54 (d, J = 8.7 Hz, 2H), 6.48 (dd, J = 2.4, 8.3 Hz, 1H), 6.26 (d, J = 8.5 Hz, 2H), 5.35 (dd, J = 5.1, 11.9 Hz, 1H), 4.18 (d, J = 5.3 Hz, 1H), 3.87 (br t, J = 6.3 Hz, 2H), 3.30-3.21 (m, 4H), 3.13 (br s, 4H), 3.04-2.76 (m, 3H), 2.66-2.55 (m, 2H), 2.45 (br s, 3H), 2.30-2.19 (m, 1H), 2.17-2.02 (m, 1H), 1.90-1.77 (m, 2H), 1.76-1.66 (m, 1H) |
| PROTAC-111 | A | | C | 697.54 | $^1$H NMR: (400 MHz, DMSO-d6) δ: 11.08 (br s, 1H), 9.40-8.74 (m, 1H), 8.37 (d, J = 2.0 Hz, 1H), 8.21 (br s, 1H), 8.14 (s, 1H), 7.86 (s, 1H), 7.73 (dd, J = 2.1, 8.8 Hz, 1H), 7.20-7.07 (m, 3H), 6.88-6.77 (m, 3H), 6.68-6.58 (m, 2H), 6.57-6.45 (m, 3H), 6.26 (br d, J = 8.4 Hz, 2H), 5.37 (br dd, J = 5.0, 11.9 Hz, 1H), 4.17 (br d, J = 4.8 Hz, 1H), 3.87 (br t, J = 6.1 Hz, 2H), 3.48-3.46 (m, 4H), 3.32-3.30 (m, 4H), 3.00-2.74 (m, 5H), 2.33-2.19 (m, 4H), 2.16-2.01 (m, 1H), 1.90-1.79 (m, 2H), 1.70 (br d, J = 7.2 Hz, 1H) |

+Exemplary PROTACS 93-97, 103, 107, and 108 were assessed in MCF7 cells with a 3 day incubation; exemplary PROTACs 89-91, 98-102, 110, and 111 were assessed in MCF7 cells with a 5 day incubation; and exemplary PROTACs 92, 104-106, and 109 were assessed in T47D with a 5 day incubation.

*DC50 (nM) and IC50 (nM):

A < 1

1 <= B < 10

10 <= C < 100

D >= 100

**Dmax (% degraded)

A > 75

50 < B <= 75

C <= 50

TABLE 6

| Characteristics of an exemplary Tau PROTAC | | | |
|---|---|---|---|
| PROTAC-# | Tau degradation % DMax** | MS signal 1 m/e+ $[M + H]^+$ | NMR |
| PROTAC-112 | C | 757.57 | HNMR: (400 MHz, DMSO-d6) δ: 11.03 (s, 1H), 9.36 (s, 1H), 8.65 (d, J = 2.4 Hz, 1H), 8.50 (d, J = 6.4 Hz, 1H), 8.33 (d, J = 8.0 Hz, 1H), 8.23-8.19 (m, 3H), 7.99 (s, 1H), 7.63-7.62 (m, 2H), 6.98 (d, J = 8.8 Hz, 1H), 4.90 (dd, J = 5.2, 13.2 Hz, 1H), 4.45 (t, J = 4.8 Hz, 2H), 3.96 (s, 3H), 3.79 (t, J = 4.8 Hz, 2H), 3.61-3.54 (m, 6H), 3.51-3.47 (m, 7H), 2.84-2.76 (m, 3H), 2.67-2.66 (m, 2H), 2.54-2.53 (m, 1H), 2.47-2.33 (m, 4H), 2.03 (t, J = 10.4 Hz, 2H), 1.87-1.75 (m, 3H), 1.52-1.49 (m, 2H). |

**Dmax (% degraded)
A > 75
50 < B <= 75
C <= 50

5. Industrial Applicability

A novel bifunctional molecule, which contains a BRD4 or an androgen receptor recruiting moiety and an E3 Ligase Cereblon recruiting moiety, through PROTAC technology is described. The bifunctional molecules of the present disclosure actively degrades BRD4, leading to significant and persistent downstream MYC suppression and robust cellular proliferation suppression and apoptosis induction. PROTAC mediated protein degradation provides a promising strategy in targeting the “undruggable” pathological proteins by traditional approaches.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A compound having the chemical structure:

CLM-L-PTM, or a pharmaceutically acceptable salt thereof, wherein the L is a chemical linking moiety covalently linking the CLM and the PTM, and wherein:

the PTM is

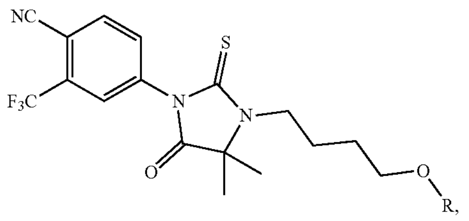

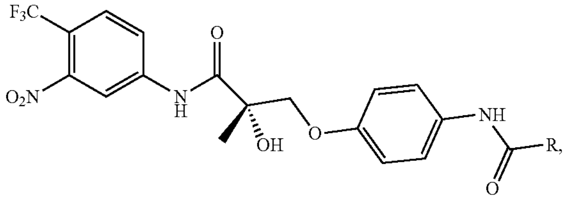

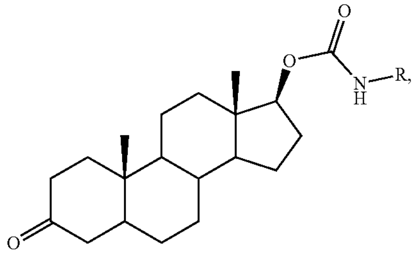

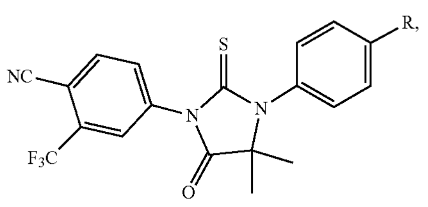

or

-continued

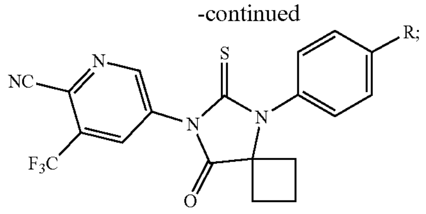

wherein R designates the site of attachment to L; and the CLM is selected from the group consisting of:

(r)

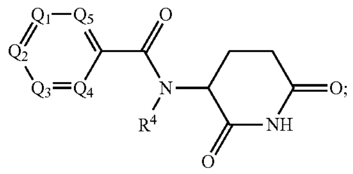

(p)

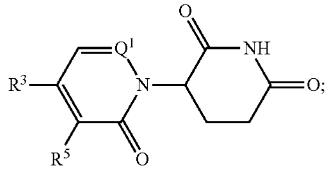

and (ae)

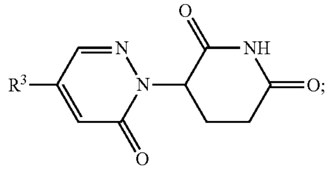

wherein $R^3$ is H, $C_1$-$C_3$ alkyl, or $C_1$-$C_3$ alkoxyl;

$R^4$ is H or $C_1$-$C_3$ alkyl;

$R^5$ is H or $C_1$-$C_3$ alkyl;

$Q_1$, $Q_2$, $Q_3$, and $Q_4$ are each independently a carbon substituted with a R';

R' is H, halogen, $C_1$-$C_3$ alkyl, or $C_1$-$C_3$ alkoxyl; and $Q_5$ is N; wherein the CLM is covalently joined to L via $R^3$, $R^4$, $R^5$, R', $Q_1$, $Q_2$, $Q_3$, or $Q_4$.

2. The compound of claim 1, or a pharmaceutically acceptable salt thereof, wherein the linker (L) is:

$-(A^L)q-$ wherein:

q is an integer greater than or equal to 1;

each $A^L$ is independently selected from the group consisting of a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $C_{3-11}$cycloalkyl substituted with 0-6 $R^{L1}$ groups, $C_{3-11}$heterocyclyl substituted with 0-6 $R^{L1}$ groups, aryl substituted with 0-6 $R^{L1}$ groups, and heteroaryl substituted with 0-6 $R^{L1}$ groups; and $R^{L1}$, $R^{L2}$, $R^{L3}$, and $R^{L4}$ are, independently, selected from H, halogen, $C_{1-8}$alkyl, $OC_{1-8}$alkyl, $NHC_{1-8}$alkyl, N($C_{1-8}$alkyl)$_2$, OH, $NH_2$, $CO_2H$, CN, $CF_3$, $CHF_2$, and $CH_2F$.

3. The compound of claim 1, or a pharmaceutically acceptable salt thereof, wherein the linker (L) is a polyethylenoxy group optionally substituted with aryl or phenyl comprising from 1 to 10 ethylene glycol units.

4. A compound, wherein the compound is

| PROTAC # | Chemical Structure | Name |
|---|---|---|
| PROTAC-89 | 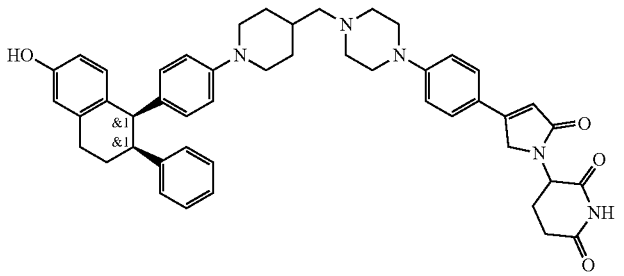 [SMILES: O=C1CCC(N2CC(c3ccc(N4CCN(CC5CCN(c6ccc([C@@H]7c8ccc(O)cc8CC[C@@H]7c7ccccc7)cc6)CC5)CC4)cc3)=CC2=O)C(=O)N1] | rac-3-(4-(4-(4-((1-(4-((1R,2S)-6-hydroxy-2-phenyl-1,2,3,4-tetrahydronaphthalen-1-yl)phenyl)piperidin-4-yl)methyl)piperazin-1-yl)phenyl)-2-oxo-2,5-yl)piperidine-2,6-dione |
| PROTAC-90 | 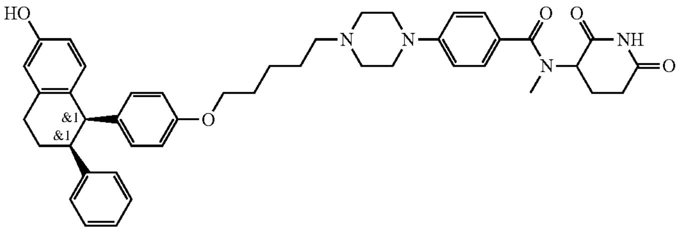 [SMILES: CN(C(=O)c1ccc(N2CCN(CCCCCOc3ccc([C@@H]4c5ccc(O)cc5CC[C@@H]4c4ccccc4)cc3)CC2)cc1)C1CCC(=O)NC1=O] | rac-N-(2,6-dioxopiperidin-3-yl)-4-(4-(5-(4-((1R,2S)-6-hydroxy-2-phenyl-1,2,3,4-tetrahydronaphthalen-1-yl)phenoxy)pentyl)piperazin-1-yl)-N-methylbenzamide |

-continued

| PROTAC # | Chemical Structure | Name |
| --- | --- | --- |
| PROTAC-91 | 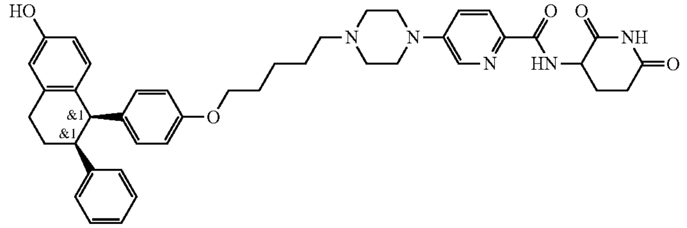 [SMILES: O=C1CCC(NC(=O)c2ccc(N3CCN(CCCCCOc4ccc([C@@H]5c6ccc(O)cc6CC[C@@H]5c5ccccc5)cc4)CC3)cn2)C(=O)N1] | rac-N-(2,6-dioxopiperidin-3-yl)-5-(4-(5-(4-((1R,2S)-6-hydroxy-2-phenyl-1,2,3,4-tetrahydronaphthalen-1-yl)phenoxy)pentyl)piperazin-1-yl)picolinamide |
| PROTAC-92 | 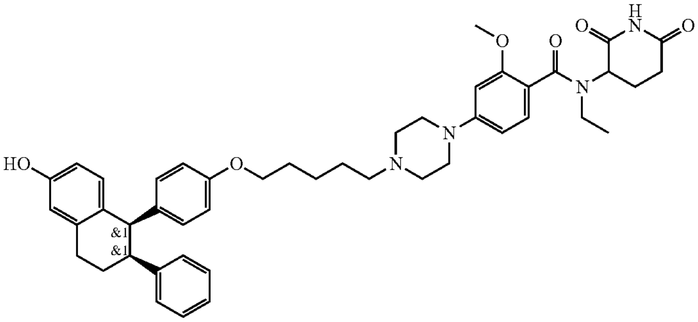 [SMILES: CCN(C(=O)c1ccc(N2CCN(CCCCCOc3ccc([C@@H]4c5ccc(O)cc5CC[C@@H]4c4ccccc4)cc3)CC2)cc1OC)C1CCC(=O)NC1=O] | rac-N-(2,6-dioxopiperidin-3-yl)-N-ethyl-4-(4-(5-(4-((1R,2S)-6-hydroxy-2-phenyl-1,2,3,4-tetrahydronaphthalen-1-yl)phenoxy)pentyl)piperazin-1-yl)-2-methoxybenzamide |
| PROTAC-93 | 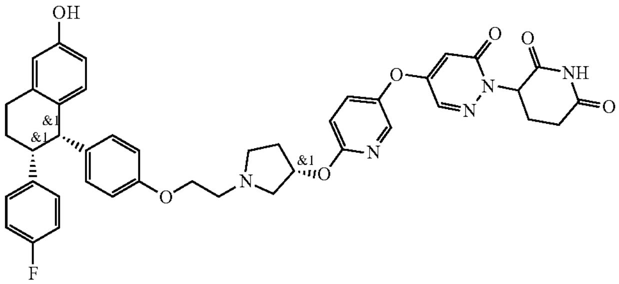 [SMILES: O=C1CCC(n2ncc(Oc3ccc(O[C@H]4CCN(CCOc5ccc([C@H]6c7ccc(O)cc7CC[C@H]6c6ccc(F)cc6)cc5)C4)nc3)cc2=O)C(=O)N1] | rac-3-(4-((6-(((R)-1-(2-(4-((1R,2S)-2-(4-fluorophenyl)-6-hydroxy-1,2,3,4-tetrahydronaphthalen-1-yl)phenoxy)ethyl)pyrrolidin-3-yl)oxy)pyridin-3-yl)oxy)-6-oxopyridazin-1(6H)-yl)piperidine-2,6-dione |
| PROTAC-94 | 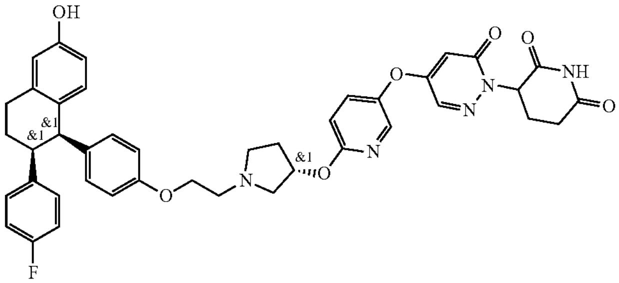 [SMILES: O=C1CCC(n2ncc(Oc3ccc(O[C@H]4CCN(CCOc5ccc([C@@H]6c7ccc(O)cc7CC[C@@H]6c6ccc(F)cc6)cc5)C4)nc3)cc2=O)C(=O)N1] | rac-3-(4-((6-(((R)-1-(2-(4-((1S,2R)-2-(4-fluorophenyl)-6-hydroxy-1,2,3,4-tetrahydronaphthalen-1-yl)phenoxy)ethyl)pyrrolidin-3-yl)oxy)pyridin-3-yl)oxy)-6-oxopyridazin-1(6H)-yl)piperidine-2,6-dione |
| PROTAC-95 | 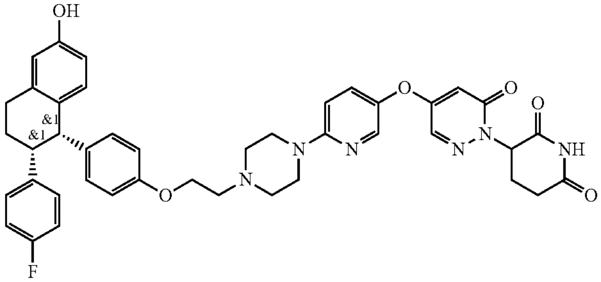 [SMILES: O=C1CCC(n2ncc(Oc3ccc(N4CCN(CCOc5ccc([C@H]6c7ccc(O)cc7CC[C@H]6c6ccc(F)cc6)cc5)CC4)nc3)cc2=O)C(=O)N1] | rac-3-(4-((6-(4-(2-(4-((1R,2S)-2-(4-fluorophenyl)-6-hydroxy-1,2,3,4-tetrahydronaphthalen-1-yl)phenoxy)ethyl)piperazin-1-yl)pyridin-3-yl)oxy)-6-oxopyridazin-1(6H)-yl)piperidine-2,6-dione |

-continued

| PROTAC # | Chemical Structure | Name |
|---|---|---|
| PROTAC-96 | 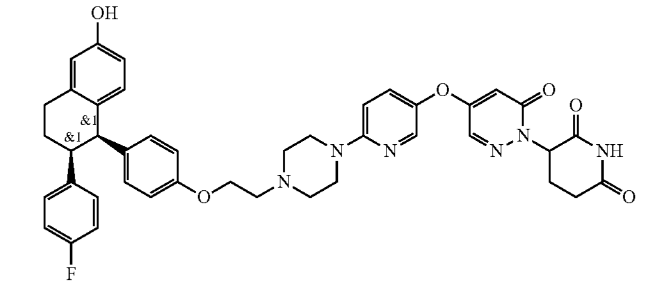 [SMILES: O=C1CCC(n2ncc(Oc3ccc(N4CCN(CCOc5ccc([C@@H]6c7ccc(O)cc7CC[C@@H]6c6ccc(F)cc6)cc5)CC4)nc3)cc2=O)C(=O)N1] | rac-3-(4-((6-(4-(2-(4-((1R,2S)-2-(4-fluorophenyl)-6-hydroxy-1,2,3,4-tetrahydronaphthalen-1-yl)phenoxy)ethyl)piperazin-1-yl)pyridin-3-yl)oxy)-6-oxopyridazin-1(6H)-yl)piperidine-2,6-dione |
| PROTAC-97 | 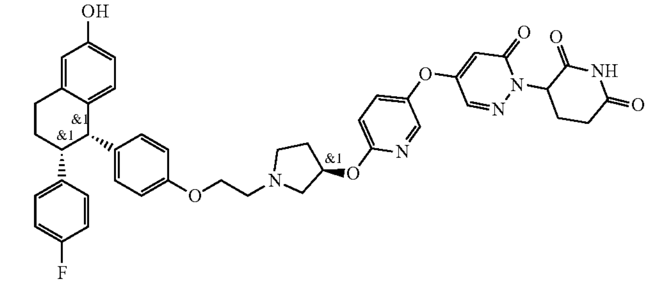 [SMILES: O=C1CCC(n2ncc(Oc3ccc(O[C@@H]4CCN(CCOc5ccc([C@H]6c7ccc(O)cc7CC[C@H]6c6ccc(F)cc6)cc5)C4)nc3)cc2=O)C(=O)N1] | rac-3-(4-((6-(((R)-1-(2-(4-((1S,2R)-2-(4-fluorophenyl)-6-hydroxy-1,2,3,4-tetrahydronaphthalen-1-yl)phenoxy)ethyl)pyrrolidin-3-yl)oxy)pyridin-3-yl)oxy)-6-oxopyridazin-1(6H)-yl)piperidine-2,6-dione |
| PROTAC-98 | 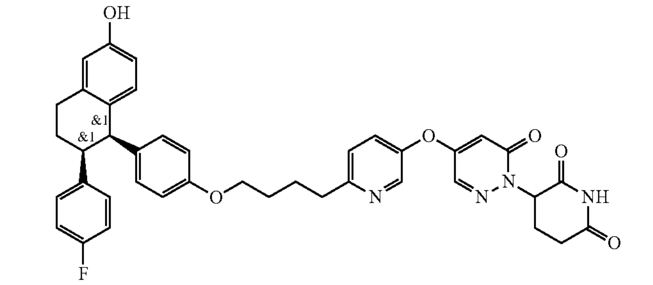 [SMILES: O=C1CCC(n2ncc(Oc3ccc(CCCCOc4ccc([C@@H]5c6ccc(O)cc6CC[C@@H]5c5ccc(F)cc5)cc4)nc3)cc2=O)C(=O)N1] | rac-3-(4-((6-(4-(4-((1R,2S)-2-(4-fluorophenyl)-6-hydroxy-1,2,3,4-tetrahydronaphthalen-1-yl)phenoxy)butyl)pyridin-3-yl)oxy)-6-oxopyridazin-1(6H)-yl)piperidine-2,6-dione |
| PROTAC-99 | 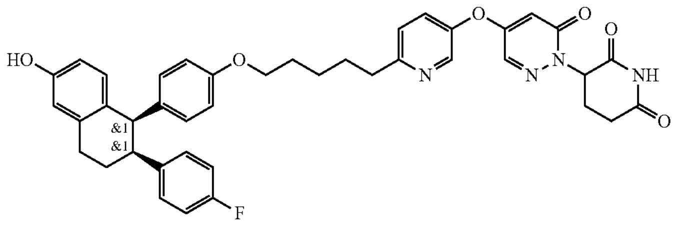 [SMILES: O=C1CCC(n2ncc(Oc3ccc(CCCCCOc4ccc([C@@H]5c6ccc(O)cc6CC[C@@H]5c5ccc(F)cc5)cc4)nc3)cc2=O)C(=O)N1] | rac-3-(4-((6-(5-(4-((1R,2S)-2-(4-fluorophenyl)-6-hydroxy-1,2,3,4-tetrahydronaphthalen-1-yl)phenoxy)pentyl)pyridin-3-yl)oxy)-6-oxopyridazin-1(6H)-yl)piperidine-2,6-dione |
| PROTAC-100 | 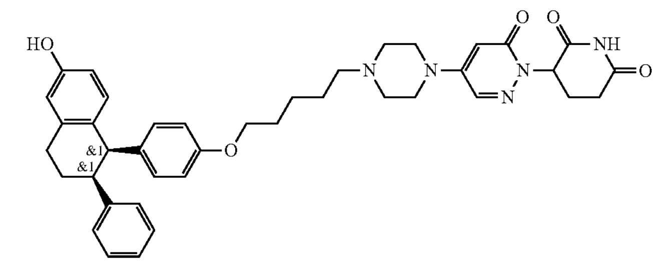 [SMILES: O=C1CCC(n2ncc(N3CCN(CCCCCOc4ccc([C@@H]5c6ccc(O)cc6CC[C@@H]5c5ccccc5)cc4)CC3)cc2=O)C(=O)N1] | rac-3-(4-(4-(5-(4-((1R,2S)-6-hydroxy-2-phenyl-1,2,3,4-tetrahydronaphthalen-1-yl)phenoxy)pentyl)piperazin-1-yl)-6-oxopyridazin-1(6H)-yl)piperidine-2,6-dione |

-continued

| PROTAC # | Chemical Structure | Name |
|---|---|---|
| PROTAC-101 | 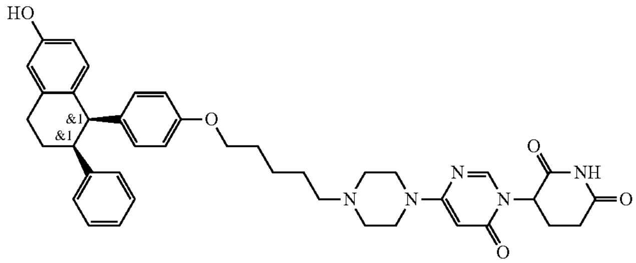 [SMILES: O=C1CCC(n2cnc(N3CCN(CCCCCOc4ccc([C@@H]5c6ccc(O)cc6CC[C@@H]5c5ccccc5)cc4)CC3)cc2=O)C(=O)N1] | rac-3-(4-(4-(5-(4-((1R,2S)-6-hydroxy-2-phenyl-1,2,3,4-tetrahydronaphthalen-1-yl)phenoxy)pentyl)piperazin-1-yl)-6-oxopyrimidin-1(6H)-yl)piperidine-2,6-dione |
| PROTAC-102 | 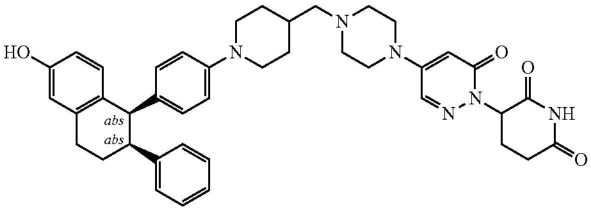 [SMILES: O=C1CCC(n2ncc(N3CCN(CC4CCN(c5ccc([C@@H]6c7ccc(O)cc7CC[C@@H]6c6ccccc6)cc5)CC4)CC3)cc2=O)C(=O)N1] | 3-(4-(4-((1-(4-((1R,2S)-6-hydroxy-2-phenyl-1,2,3,4-tetrahydronaphthalen-1-yl)phenyl)piperidin-4-yl)methyl)piperazin-1-yl)-6-oxopyridazin-1(6H)-yl)piperidine-2,6-dione |
| PROTAC-103 | 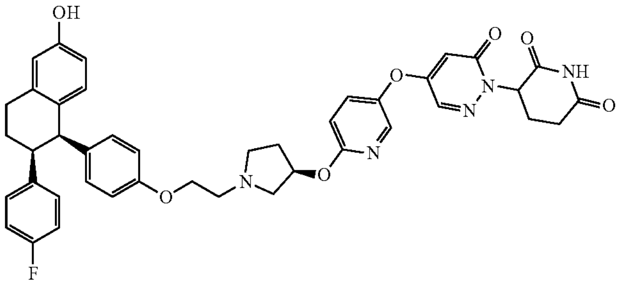 [SMILES: O=C1CCC(n2ncc(Oc3ccc(O[C@@H]4CCN(CCOc5ccc([C@@H]6c7ccc(O)cc7CC[C@@H]6c6ccc(F)cc6)cc5)C4)nc3)cc2=O)C(=O)N1] | 3-(4-((6-(((R)-1-(2-(4-((1R,2S)-2-(4-fluorophenyl)-6-hydroxy-1,2,3,4-tetrahydronaphthalen-1-yl)phenoxy)ethyl)pyrrolidin-3-yl)oxy)pyridin-3-yl)oxy)-6-oxopyridazin-1(6H)-yl)piperidine-2,6-dione |
| PROTAC-104 | 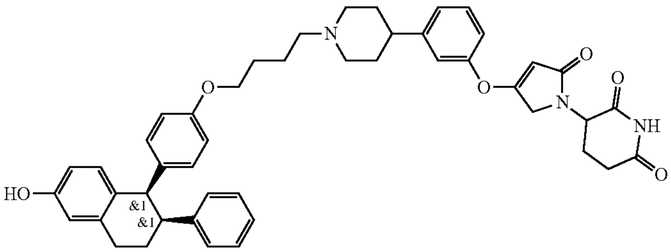 [SMILES: O=C1CCC(N2CC(Oc3cccc(C4CCN(CCCCOc5ccc([C@@H]6c7ccc(O)cc7CC[C@@H]6c6ccccc6)cc5)CC4)c3)=CC2=O)C(=O)N1] | rac-3-(4-(3-(1-(4-(4-((1R,2S)-6-hydroxy-2-phenyl-1,2,3,4-tetrahydronaphthalen-1-yl)phenoxy)butyl)piperidin-4-yl)phenoxy)-2-oxo-2,5-dihydro-1H-pyrrol-1-yl)piperidine-2,6-dione |
| PROTAC-105 | 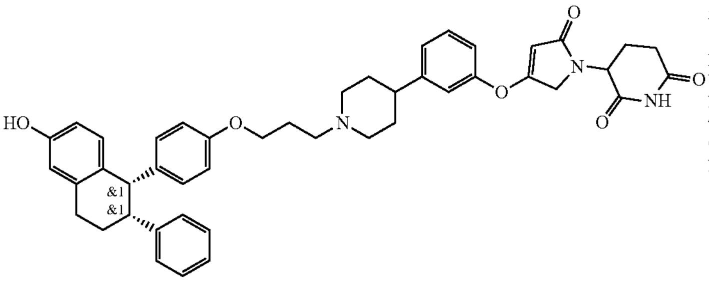 [SMILES: O=C1CCC(N2CC(Oc3cccc(C4CCN(CCCOc5ccc([C@H]6c7ccc(O)cc7CC[C@H]6c6ccccc6)cc5)CC4)c3)=CC2=O)C(=O)N1] | rac-3-(4-(3-(1-(3-(4-((1R,2S)-6-hydroxy-2-phenyl-1,2,3,4-tetrahydronaphthalen-1-yl)phenoxy)propyl)piperidin-4-yl)phenoxy)-2-oxo-2,5-dihydro-1H-pyrrol-1-yl)piperidine-2,6-dione |

-continued

| PROTAC # | Chemical Structure | Name |
| --- | --- | --- |
| PROTAC-106 | 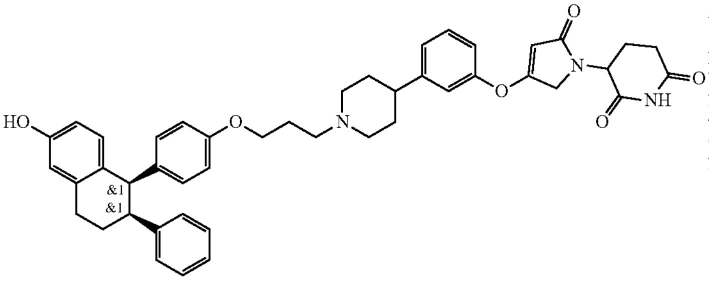 [SMILES: O=C1CCC(N2CC(Oc3cccc(C4CCN(CCCOc5ccc([C@@H]6c7ccc(O)cc7CC[C@@H]6c6ccccc6)cc5)CC4)c3)=CC2=O)C(=O)N1] | rac-3-(4-(3-(1-(3-(4-((1R,2S)-6-hydroxy-2-phenyl-1,2,3,4-tetrahydronaphthalen-1-yl)phenoxy)propyl)piperidin-4-yl)phenoxy)-2-oxo-2,5-dihydro-1H-pyrrol-1-yl)piperidine-2,6-dione |
| PROTAC-109 | 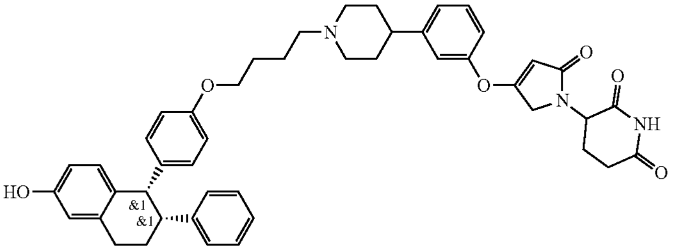 [SMILES: O=C1CCC(N2CC(Oc3cccc(C4CCN(CCCCOc5ccc([C@H]6c7ccc(O)cc7CC[C@H]6c6ccccc6)cc5)CC4)c3)=CC2=O)C(=O)N1] | rac-3-(4-(3-(1-(4-(4-((1R,2S)-6-hydroxy-2-phenyl-1,2,3,4-tetrahydronaphthalen-1-yl)phenoxy)butyl)piperidin-4-yl)phenoxy)-2-oxo-2,5-dihydro-1H-pyrrol-1-yl)piperidine-2,6-dione |
| PROTAC-110 | 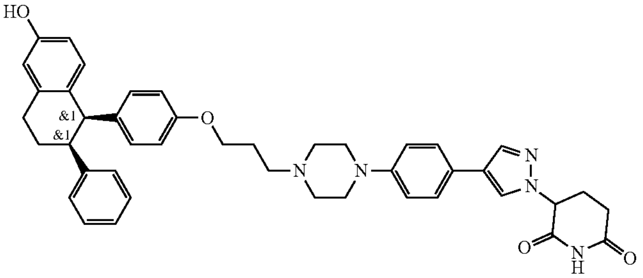 [SMILES: O=C1CCC(n2cc(-c3ccc(N4CCN(CCCOc5ccc([C@@H]6c7ccc(O)cc7CC[C@@H]6c6ccccc6)cc5)CC4)cc3)cn2)C(=O)N1] | rac-3-(4-(4-(4-(3-(4-((1R,2S)-6-hydroxy-2-phenyl-1,2,3,4-tetrahydronaphthalen-1-yl)phenoxy)propyl)piperazin-1-yl)phenyl)-1H-pyrazol-1-yl)piperidine-2,6-dione |
| | or | |
| PROTAC-111 | 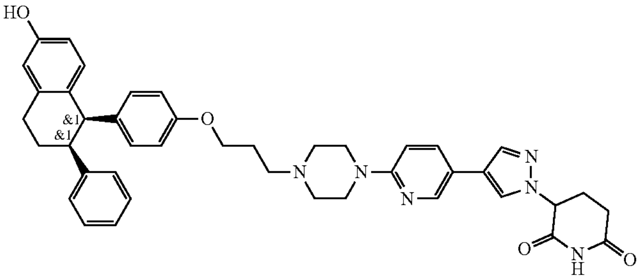 [SMILES: O=C1CCC(n2cc(-c3ccc(N4CCN(CCCOc5ccc([C@@H]6c7ccc(O)cc7CC[C@@H]6c6ccccc6)cc5)CC4)nc3)cn2)C(=O)N1] | rac-3-(4-(6-(4-(3-(4-((1R,2S)-6-hydroxy-2-phenyl-1,2,3,4-tetrahydronaphthalen-1-yl)phenoxy)propyl)piperazin-1-yl)pyridin-3-yl)-1H-pyrazol-1-yl)piperidine-2,6-dione |

or a pharmaceutically acceptable salt thereof.

5. A pharmaceutical composition comprising a compound of claim 1, or a pharmaceutically acceptable salt thereof, and a pharmaceutically acceptable carrier.

6. A compound having the chemical structure:

CLM-L-PTM, or a pharmaceutically acceptable salt thereof, wherein the L is a chemical linking moiety covalently linking the CLM and the PTM, and wherein:

the PTM is:

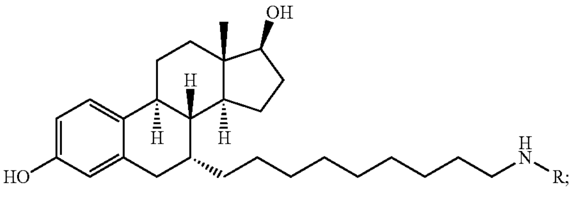

wherein R designates the site of attachment to L; and the CLM is selected from the group consisting of:

(r)

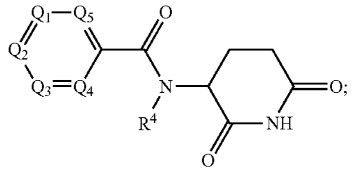

(p)

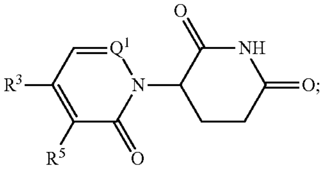

and (ae)

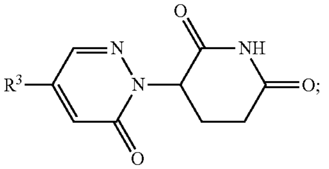

wherein $R^3$ is H, $C_1$-$C_3$ alkyl, or $C_1$-$C_3$ alkoxyl;

$R^4$ is H or $C_1$-$C_3$ alkyl;

$R^5$ is H or $C_1$-$C_3$ alkyl;

$Q_1$, $Q_2$, $Q_3$ and $Q_4$ each independently represent a carbon substituted with R';

R' is H, halogen, $C_1$-$C_3$ alkyl, or $C_1$-$C_3$ alkoxyl; and $Q_5$ is N; wherein the CLM is covalently joined to L via $R^3$, $R^4$, $R^5$, R' $Q_1$, $Q_2$, $Q_3$, or $Q_4$.

7. A pharmaceutical composition comprising a compound of claim 6, or a pharmaceutically acceptable salt thereof, and a pharmaceutically acceptable carrier.

8. A pharmaceutical composition comprising a compound of claim 4, or a pharmaceutically acceptable salt thereof, and a pharmaceutically acceptable carrier.

9. The compound of claim 1, or a pharmaceutically acceptable salt thereof, wherein the L is selected from the group consisting of:

$N(R)—(CH2)_m—O(CH2)_n—O(CH2)_p—O\ (CH2)_p—O\ (CH2)_q—O(CH2)_r—OCH_2—$, $O—(CH2)_m—O(CH2)_n—O(CH2)_o—O(CH2)_p—O\ (CH2)_q—O\ (CH2)_r—OCH_2—$, $—O—(CH2)_m—O(CH2)_n—O\ (CH2)_o—O(CH2)_p—O\ (CH2)_q—O(CH2)_r—O—$;

$—N(R)—(CH2)_m—O(CH2)_n—O(CH2)_o—O(CH2)_p—O\ (CH2)_q—O(CH2)_r—O—$;

$—(CH2)_m—O(CH2)_n—O(CH2)_o—O(CH2)_p—O\ (CH2)_q—O(CH2)_r—O—$;

$—(CH2)_m—O(CH2)_n—O(CH2)_o—O(CH2)_p—O\ (CH2)_q—O(CH2)_r—OCH_2—$;

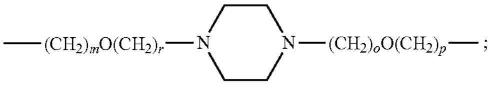

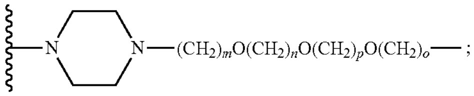

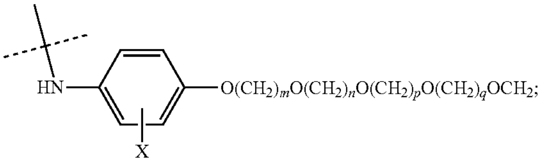

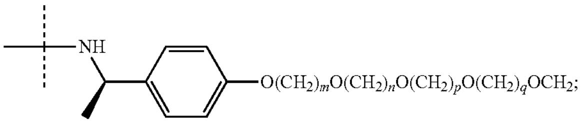

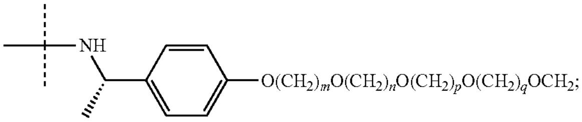

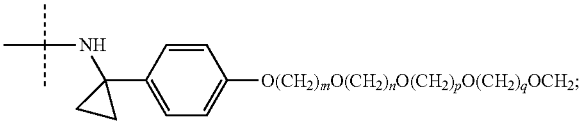

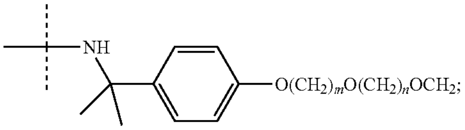

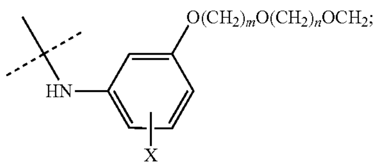

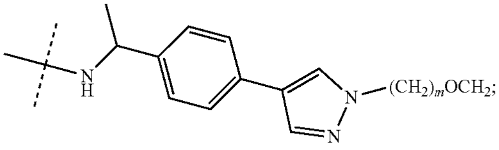

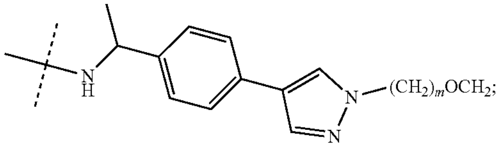

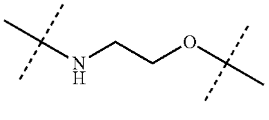

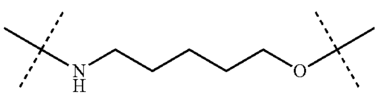

-continued
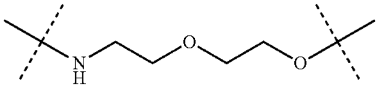
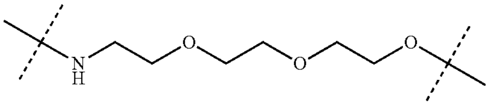
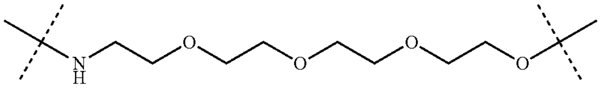
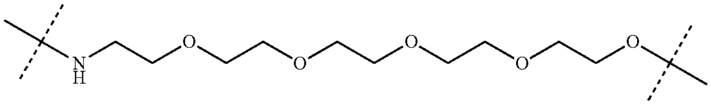
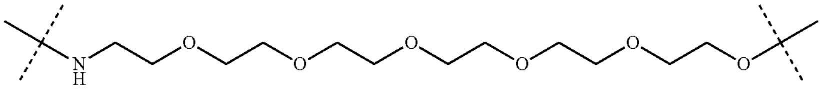
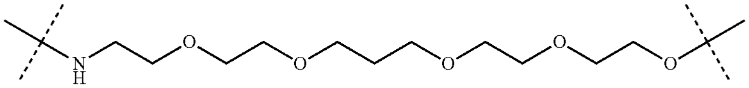
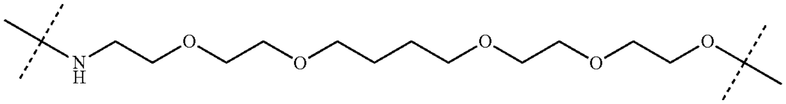
;
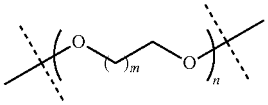
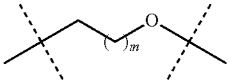
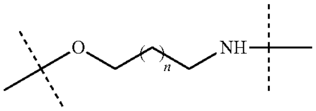
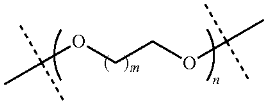
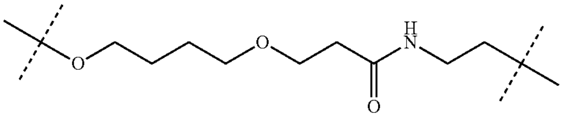
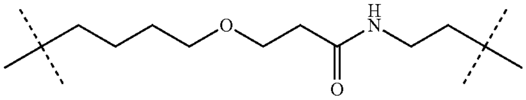
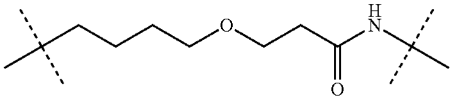
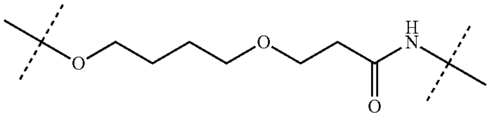
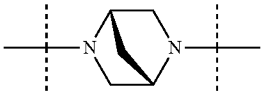
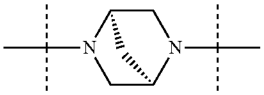
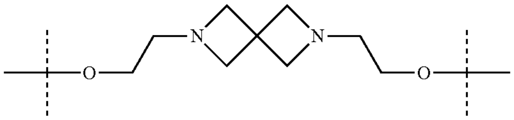
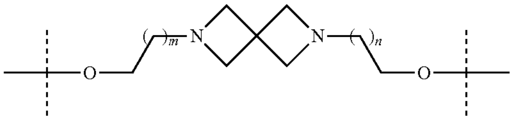
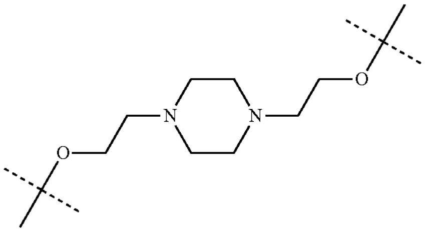
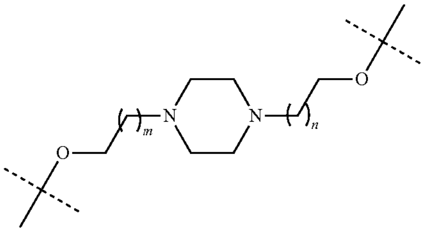
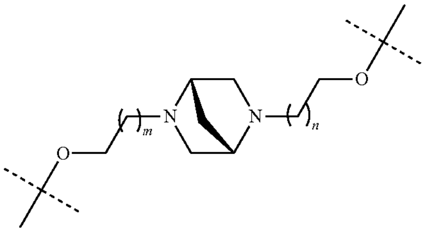
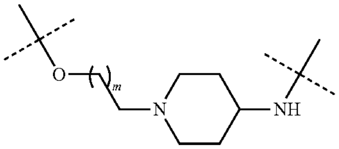

-continued
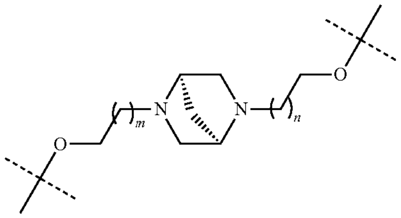
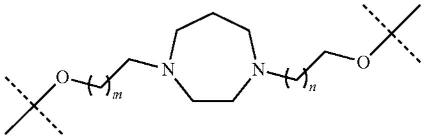
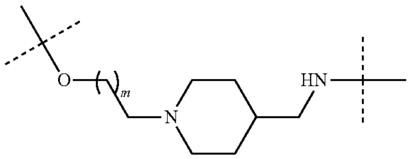
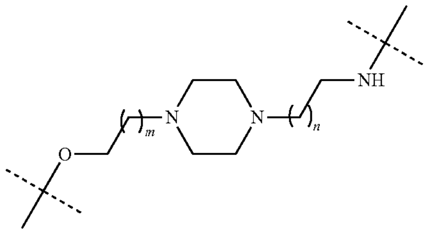
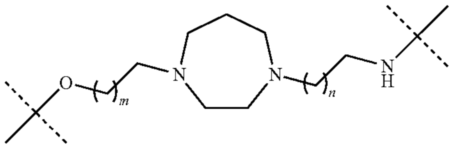
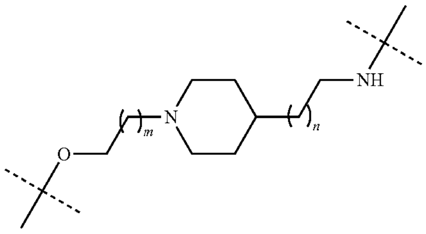
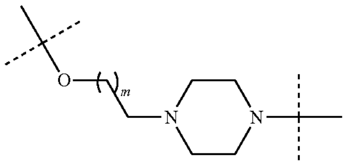
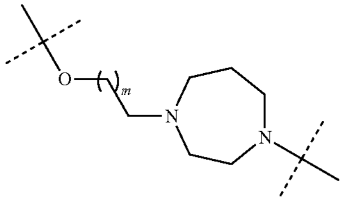
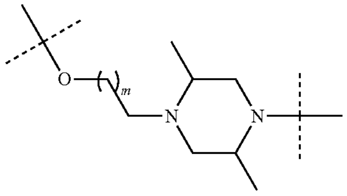
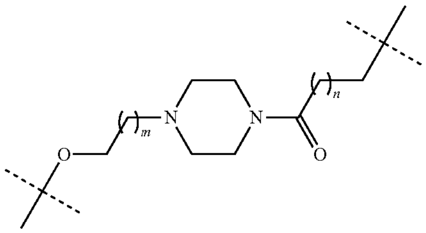
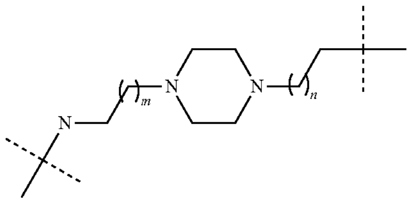
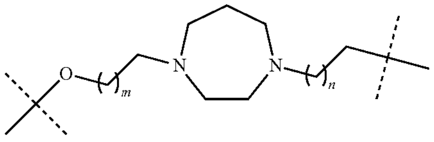
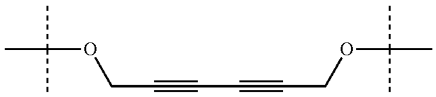
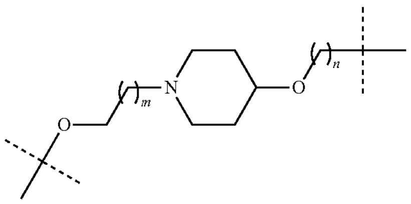
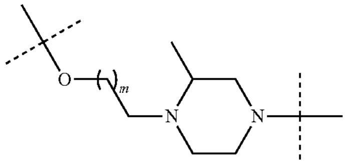
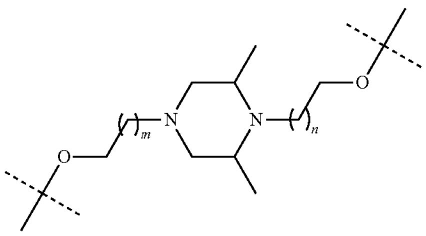
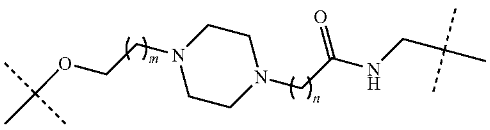

-continued
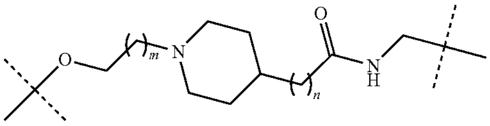
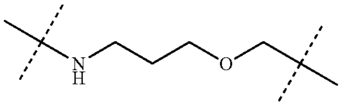
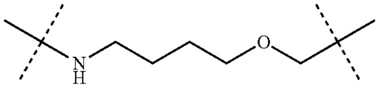
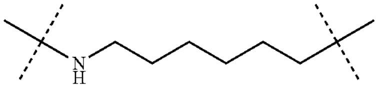
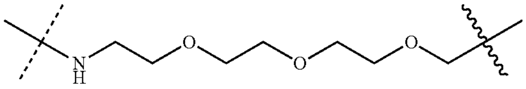
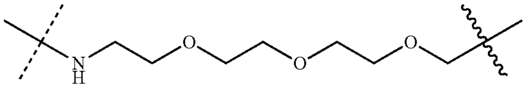
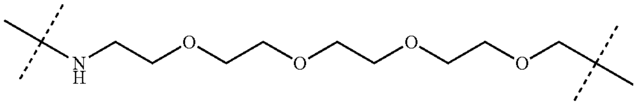
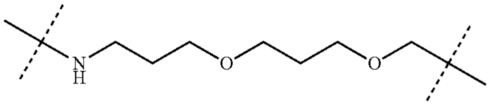
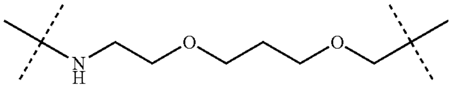
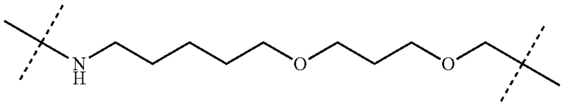
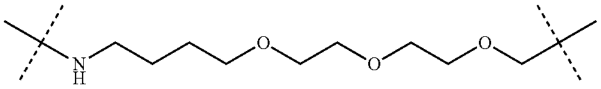
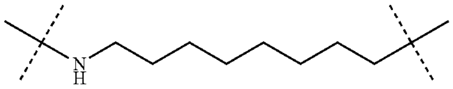
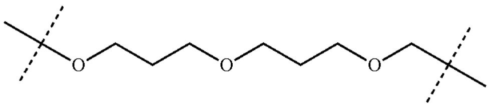
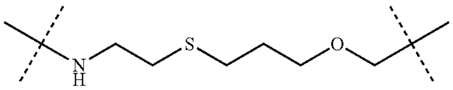
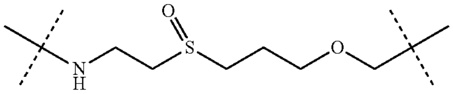
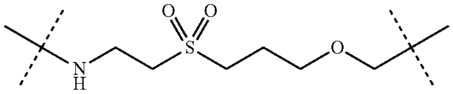
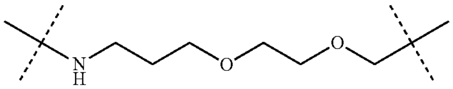
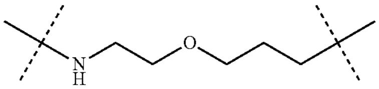
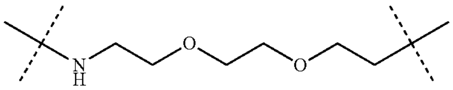
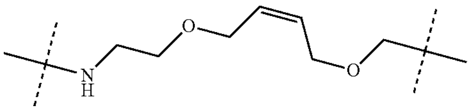
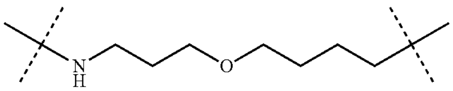
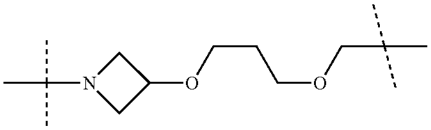
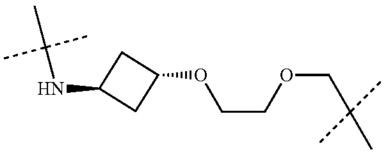
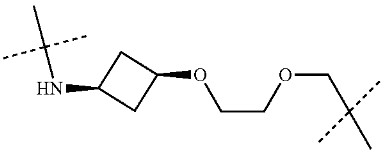
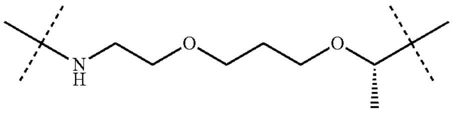
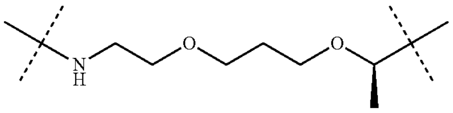
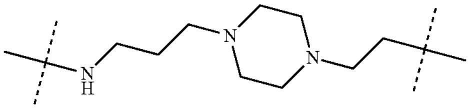
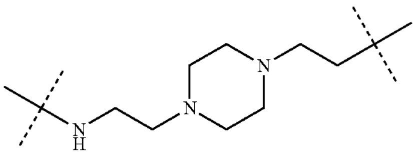

-continued
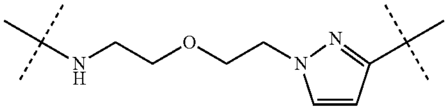
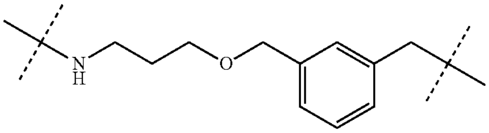
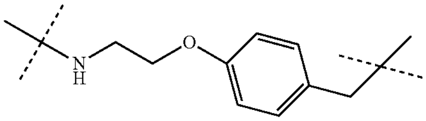
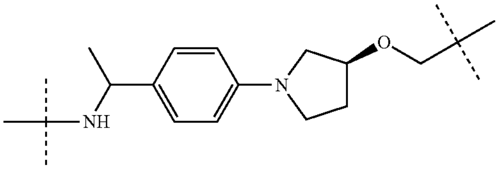
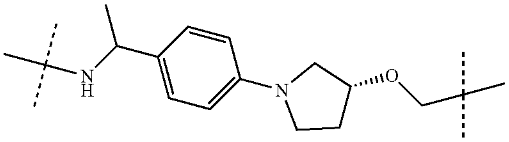
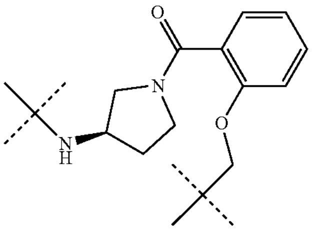
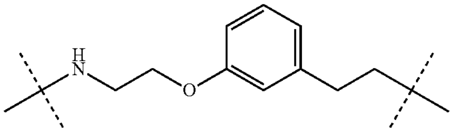
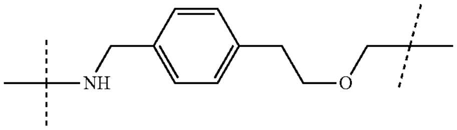
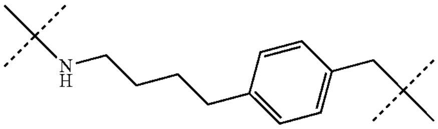
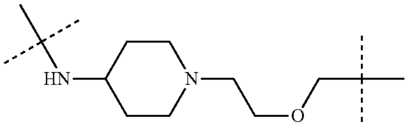
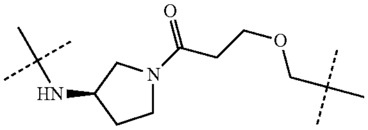
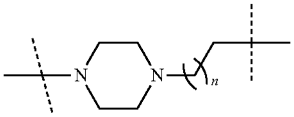
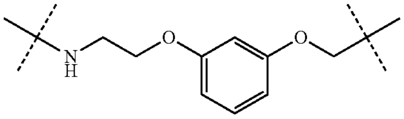
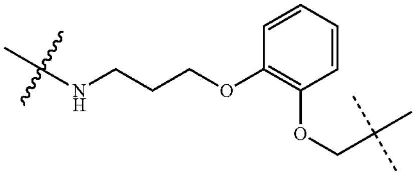
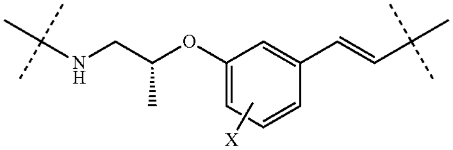
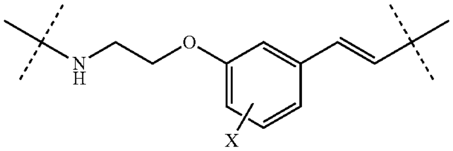
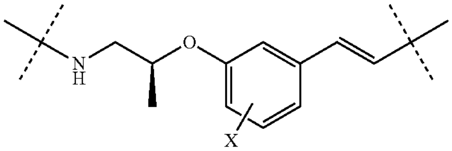
X = H, F
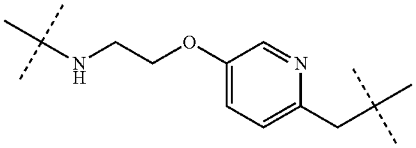
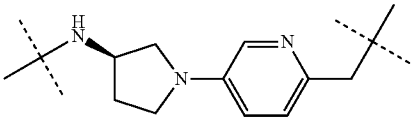
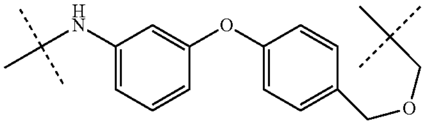
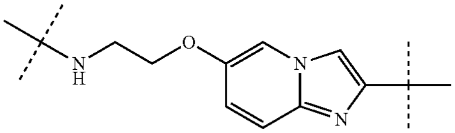

-continued
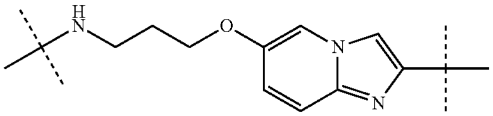
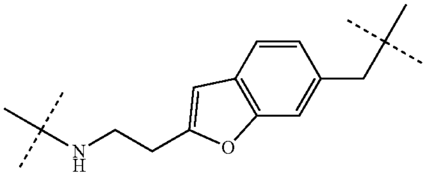
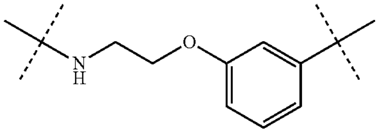
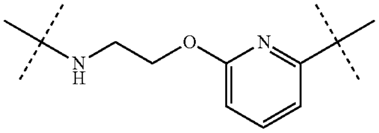
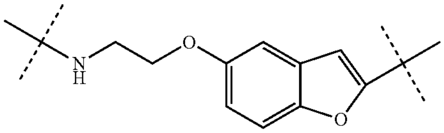
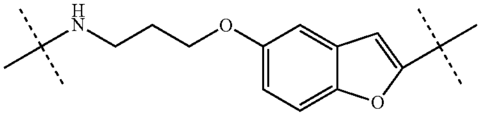
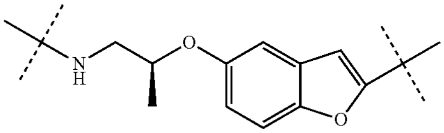
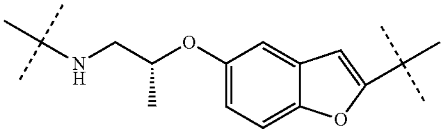
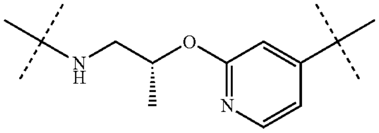
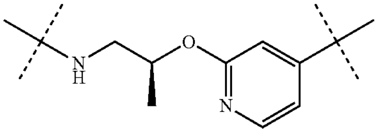
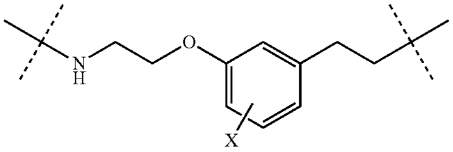
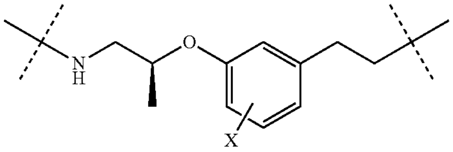
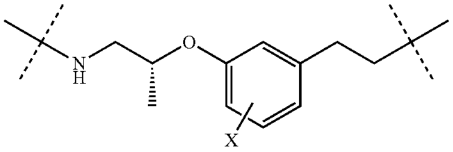
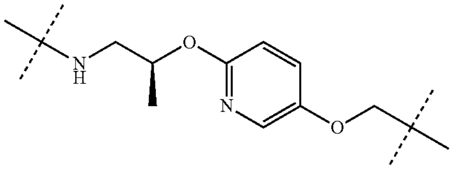
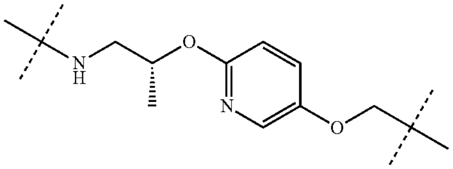
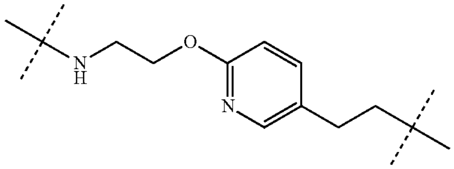
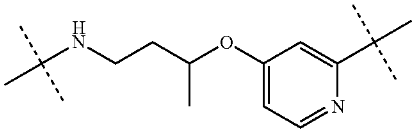
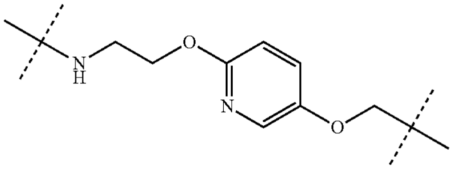
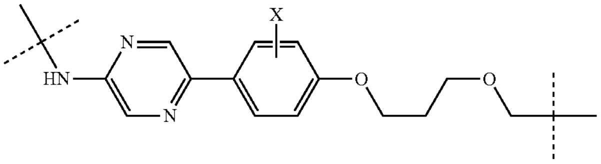
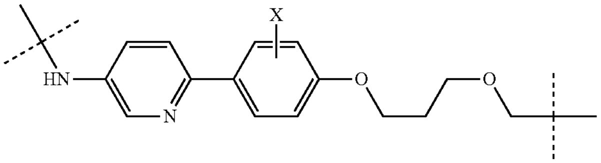

-continued
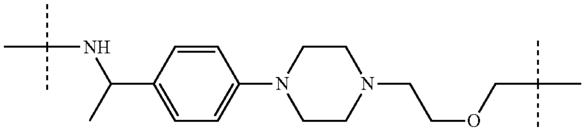
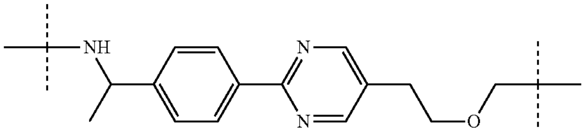
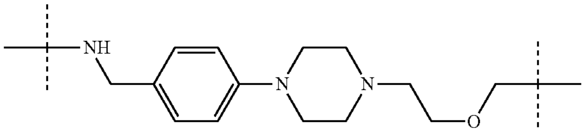
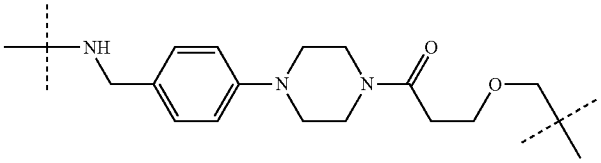
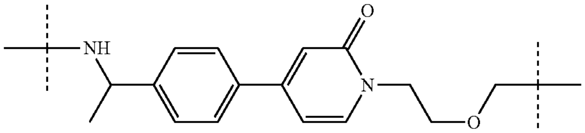
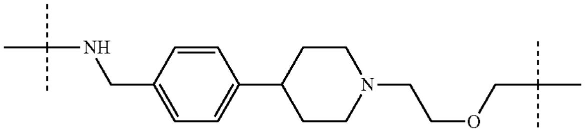
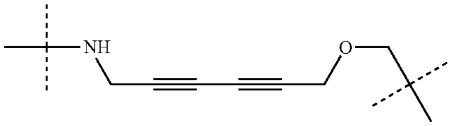
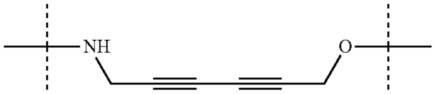
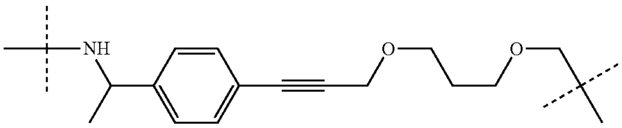
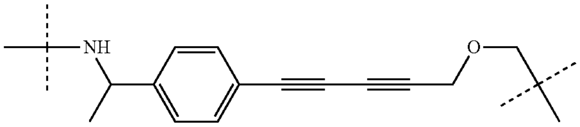
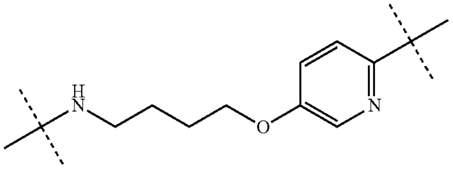
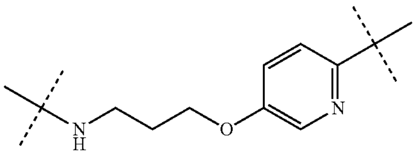
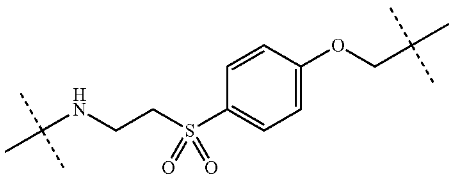
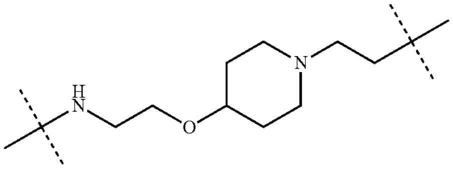
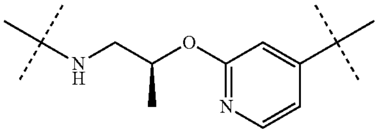
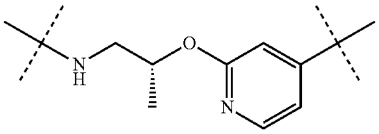
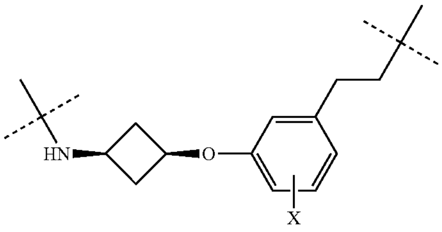

-continued
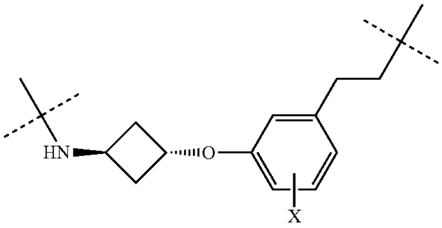
X = H, F
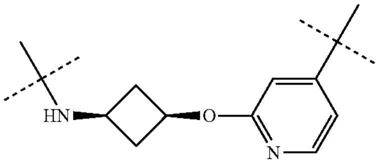
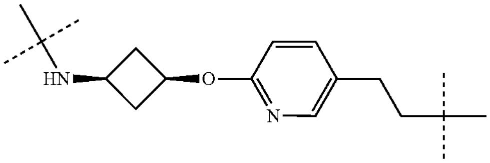
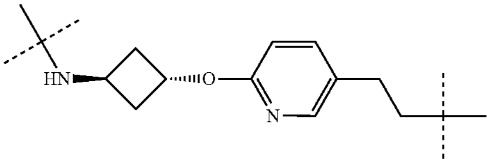
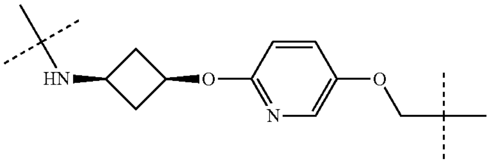
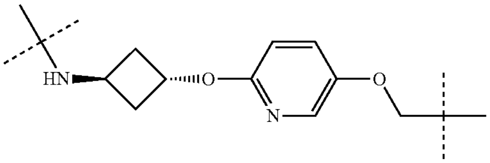
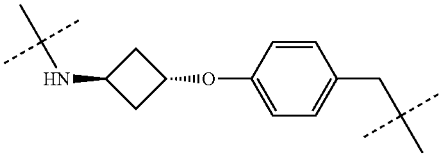
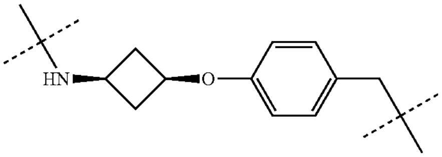
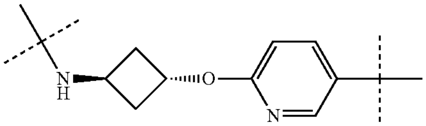
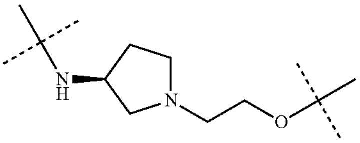
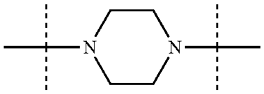
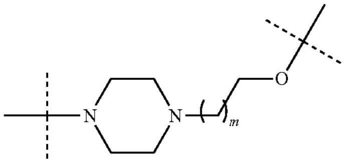
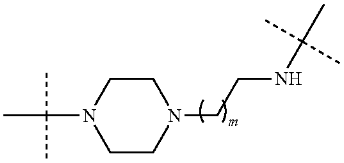
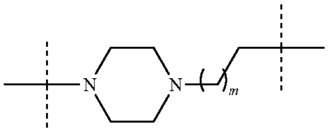
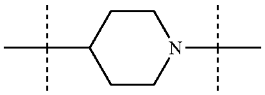
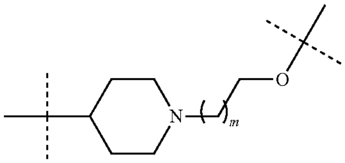
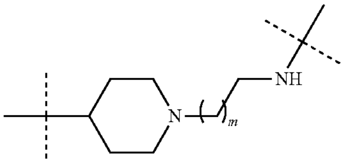
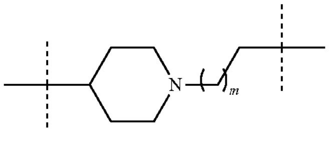
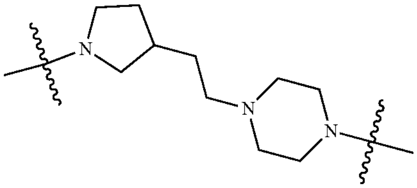
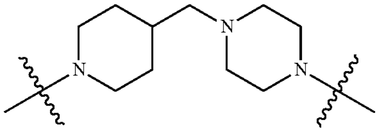
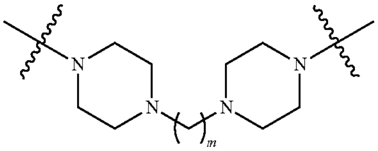
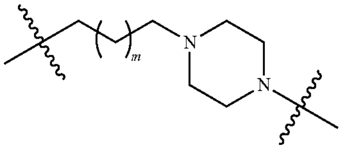
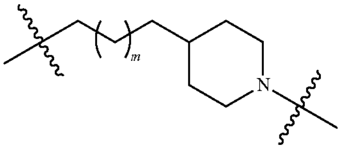
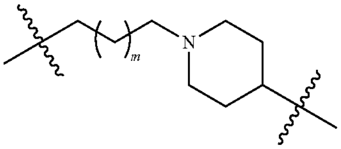

-continued
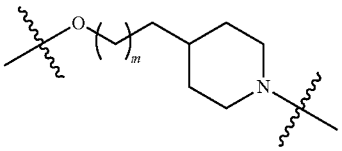
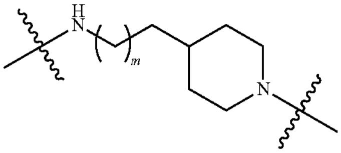
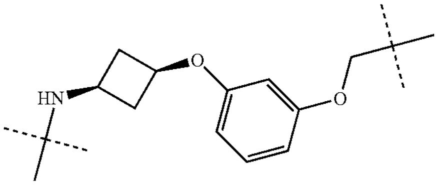
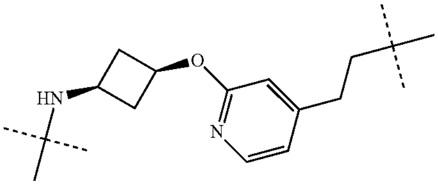
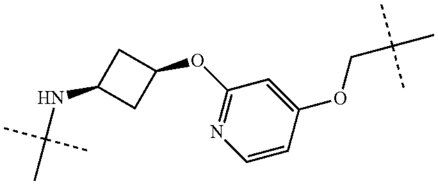
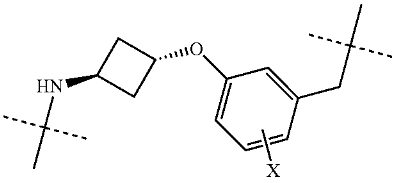
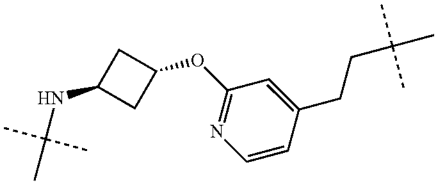
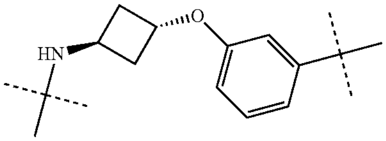
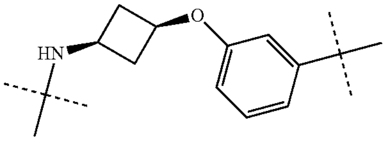
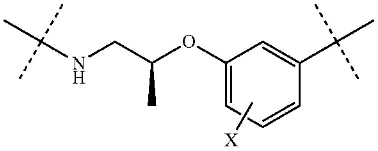
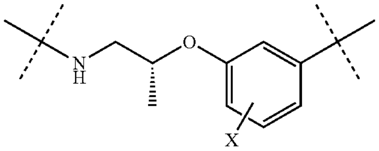
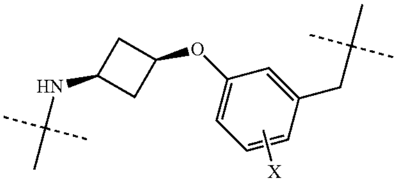
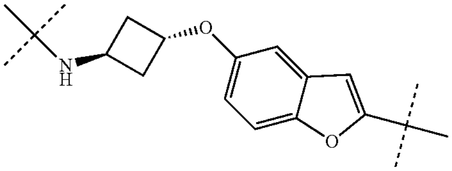
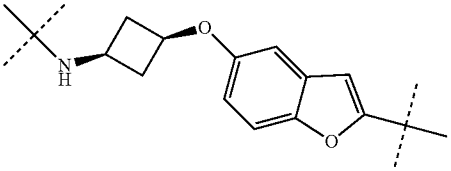
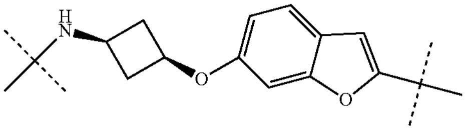
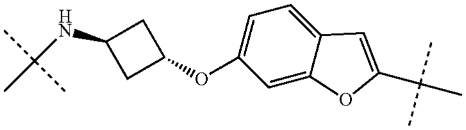
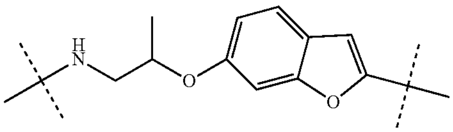
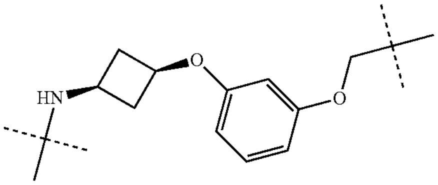
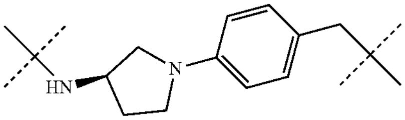
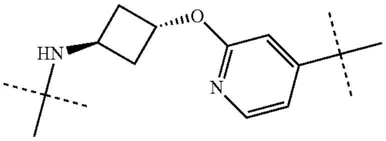

-continued
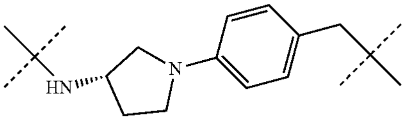
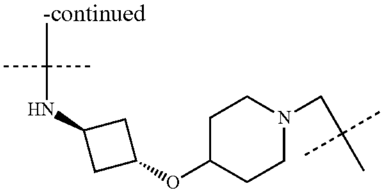
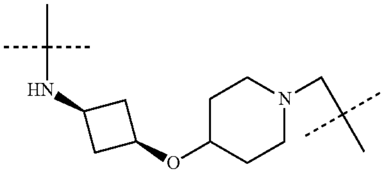
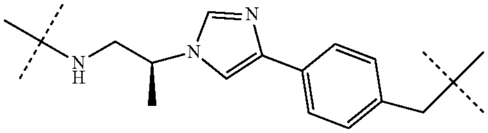
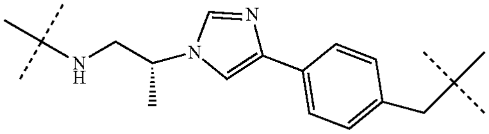
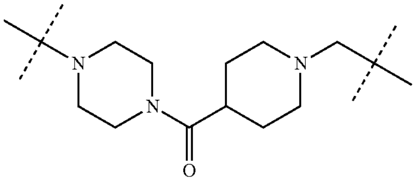
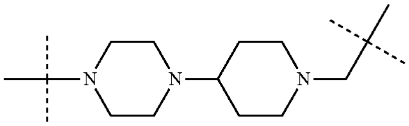
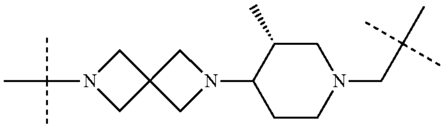
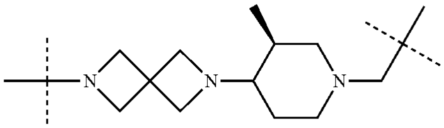
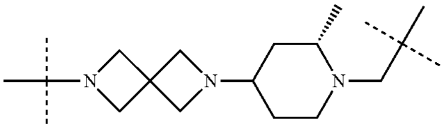
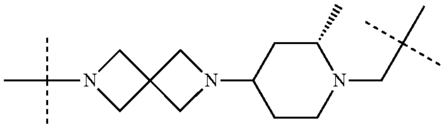
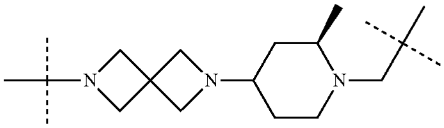
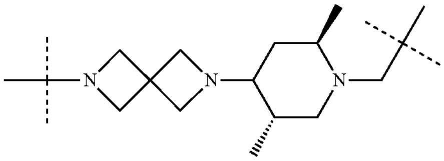
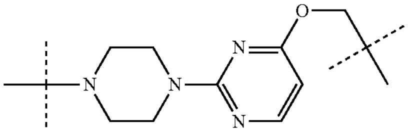
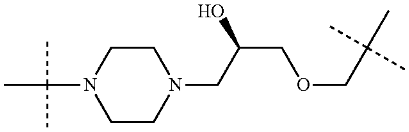
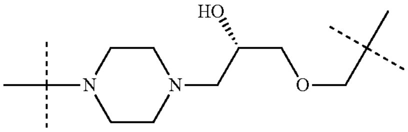
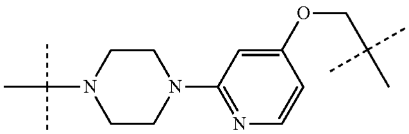
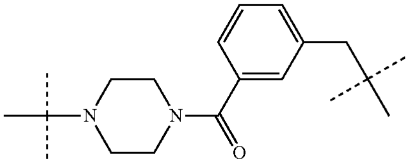
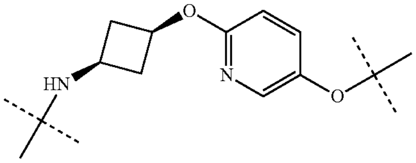
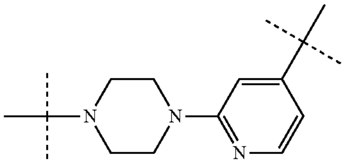
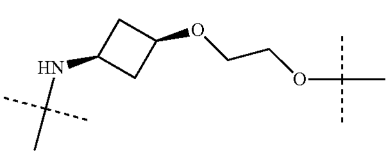
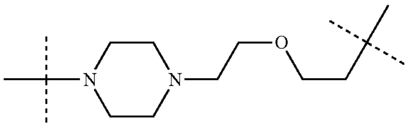

-continued
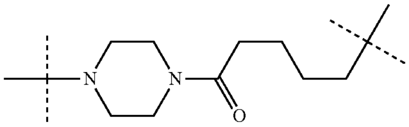
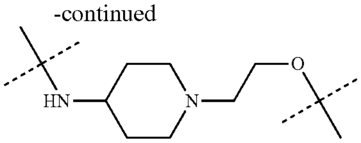
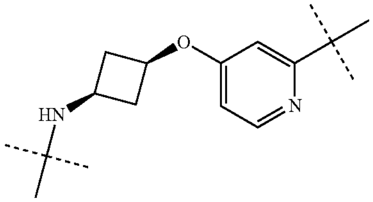
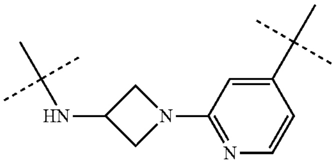
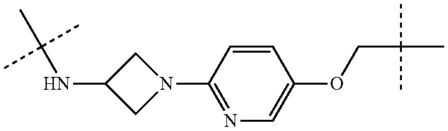
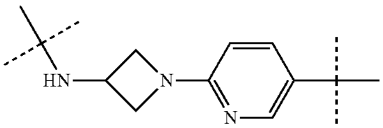
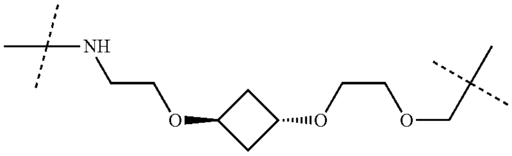
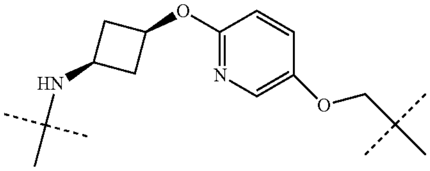
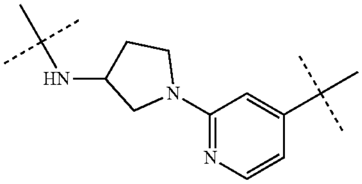
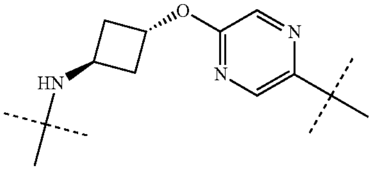
and
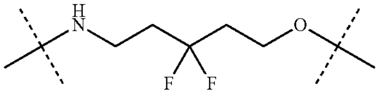
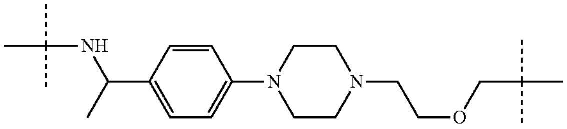
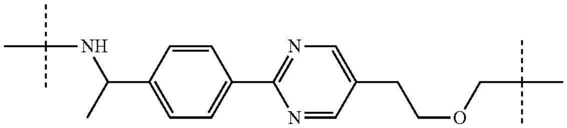
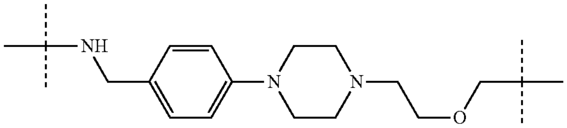
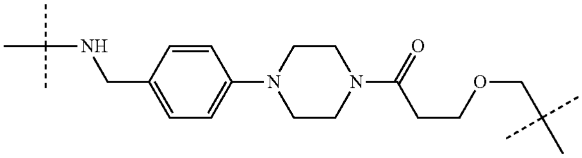
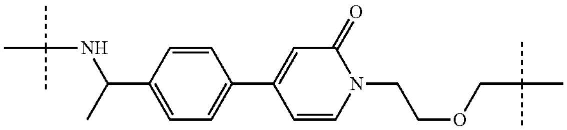
-continued
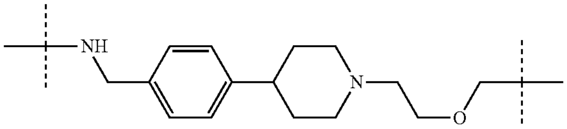
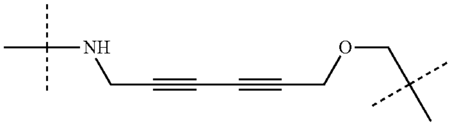
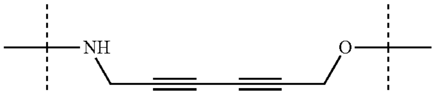
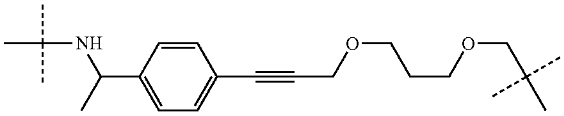
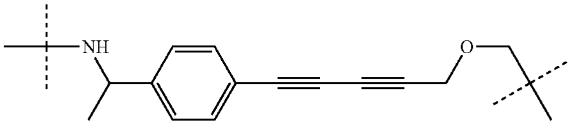

-continued
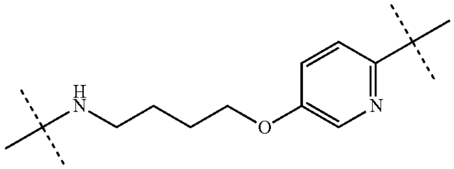
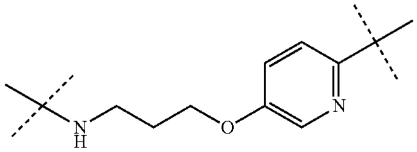
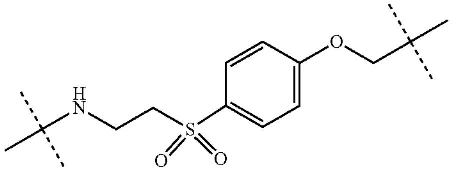
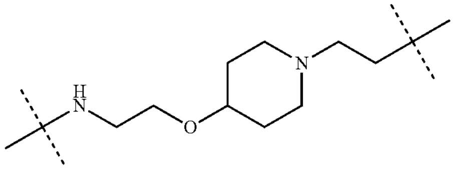
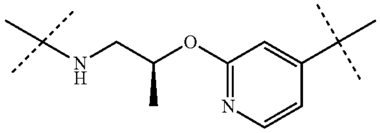
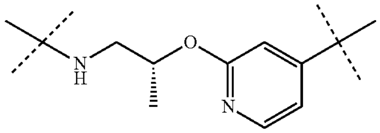
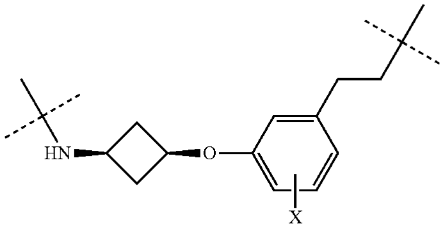
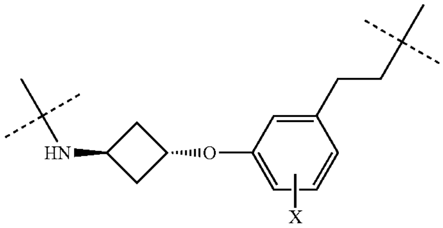
X = H, F
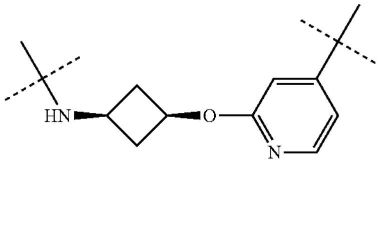
-continued
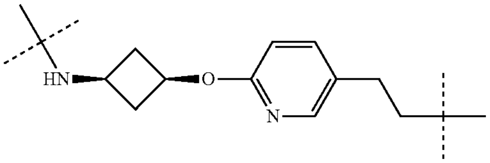
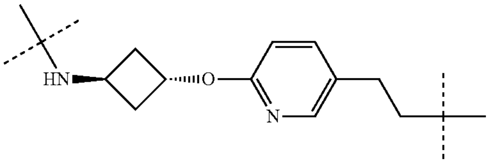
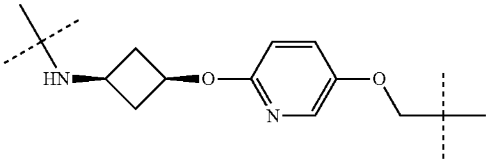
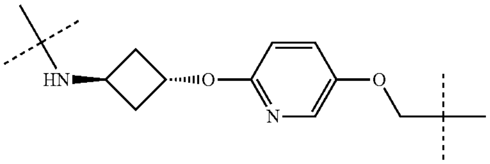
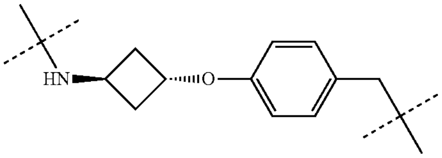
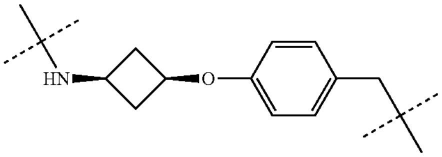
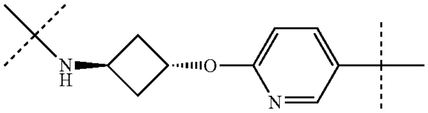
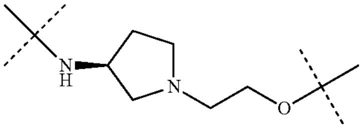
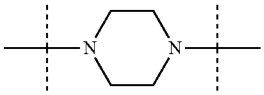
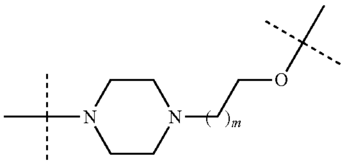
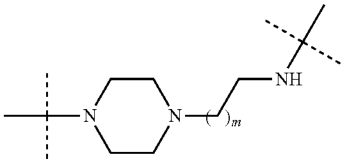

-continued
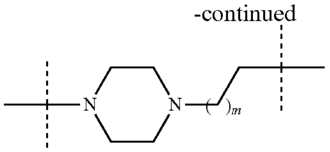
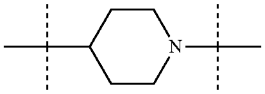
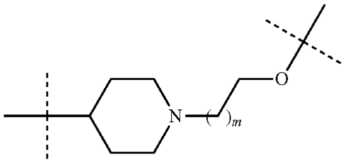
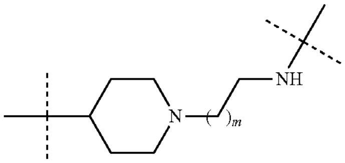
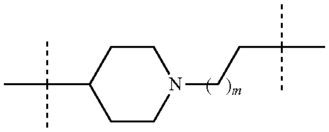
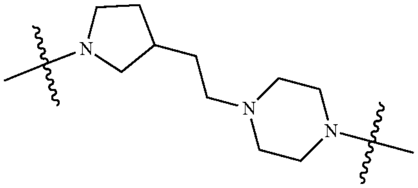
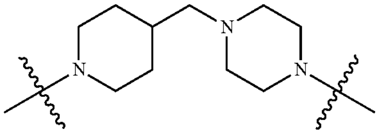
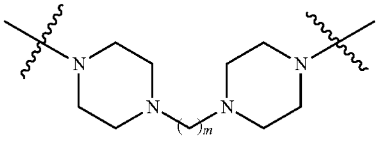
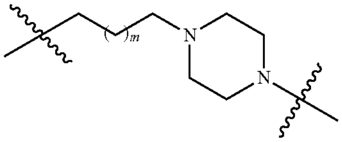
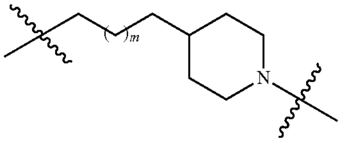
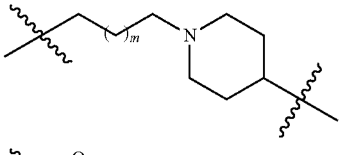
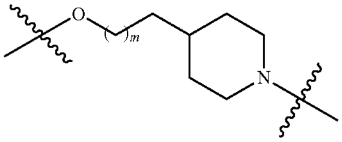
-continued
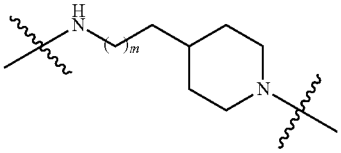
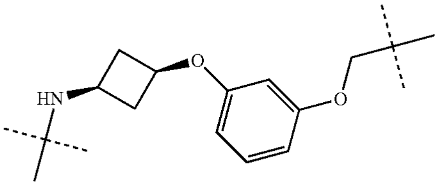
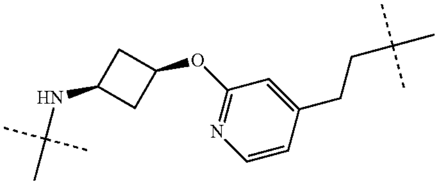
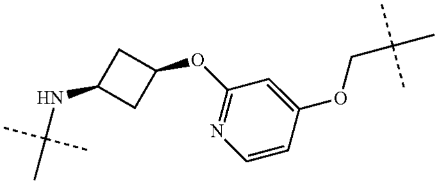
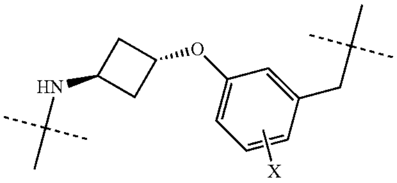
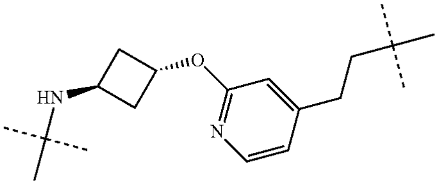
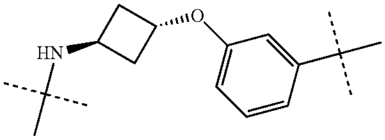
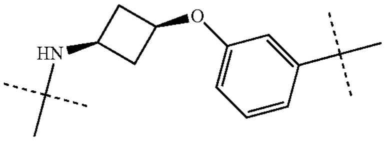
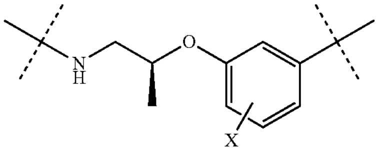

-continued
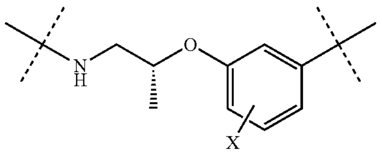
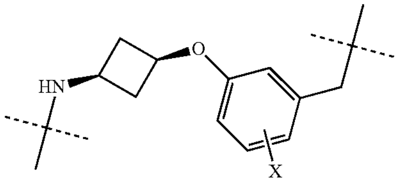
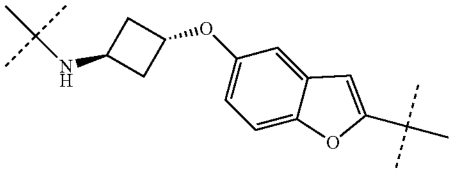
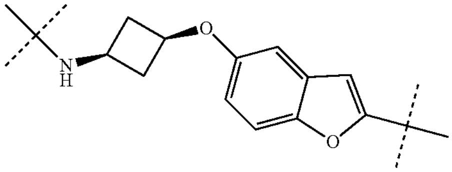
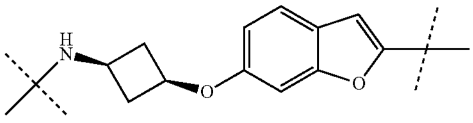
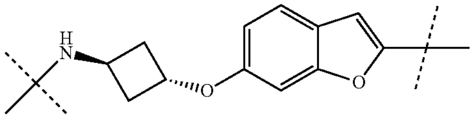
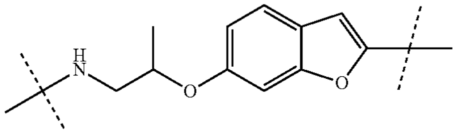
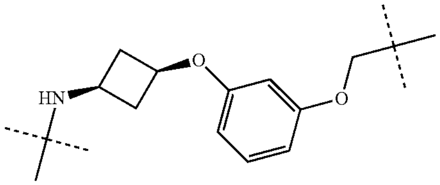
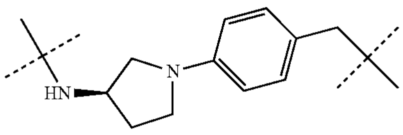
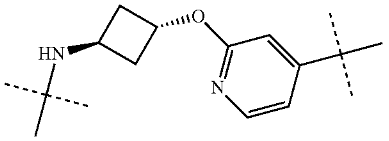
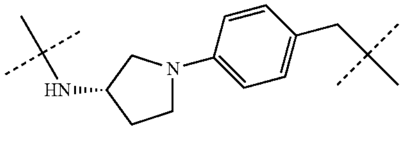
-continued
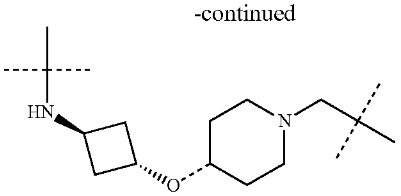
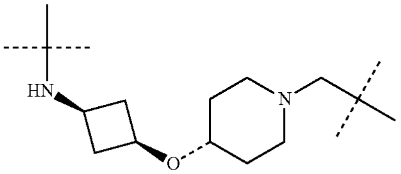
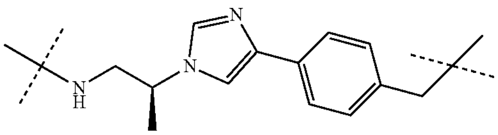
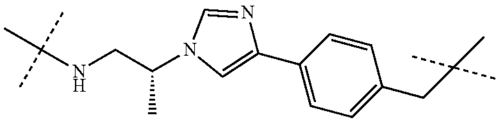
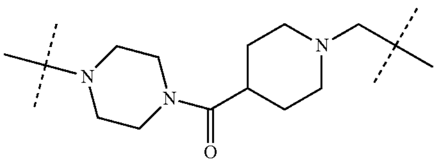
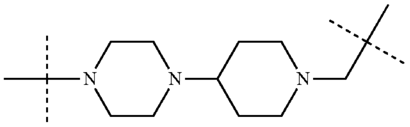
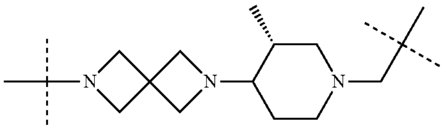
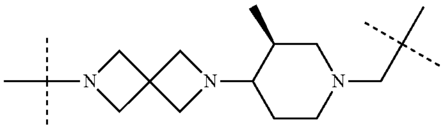
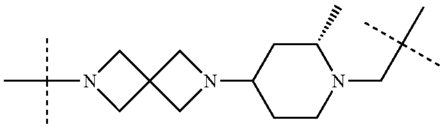
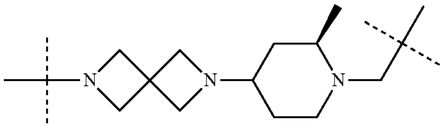
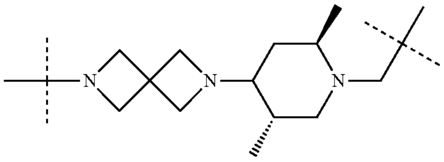
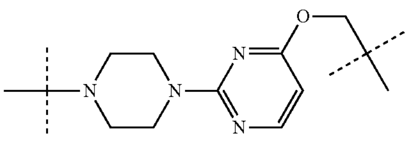

-continued
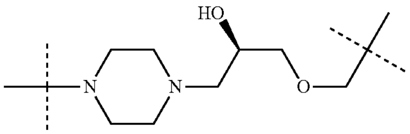
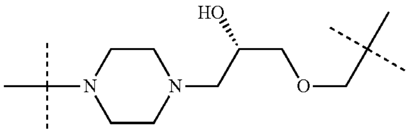
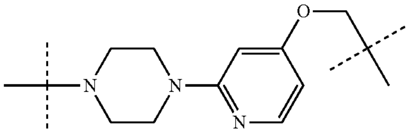
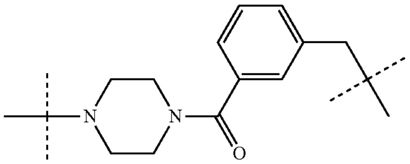
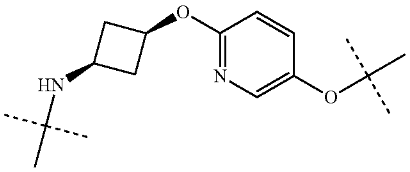
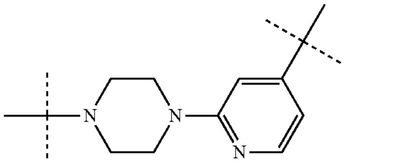
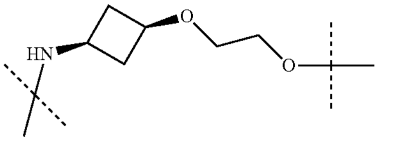
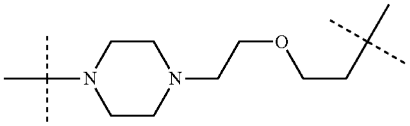
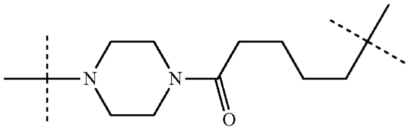
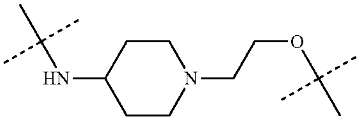
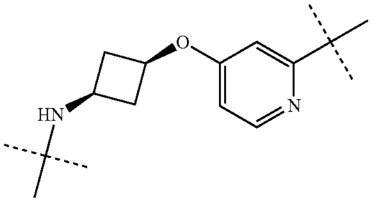
-continued
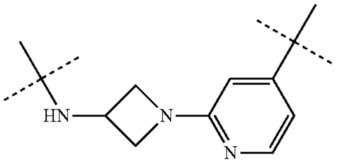
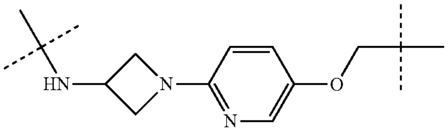
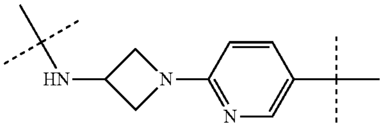
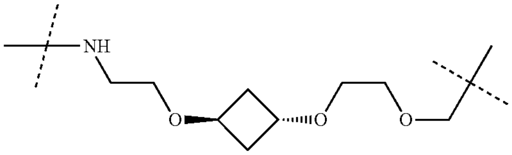
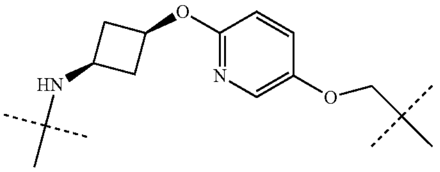
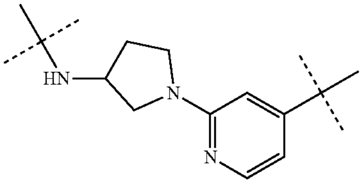
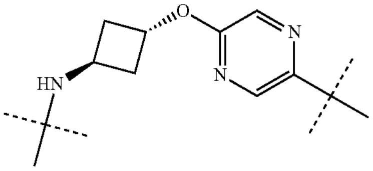
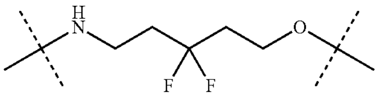
wherein
m, n, o, p, q, and r of the linker are independently 0, 1, 2, 3, 4, 5, or 6;
when the number is zero, there is no N—O or O—O bond in the linker;
R is H, methyl, or ethyl; and
X is H and F.
10. The compound of claim 1, or a pharmaceutically acceptable salt thereof, wherein the L is selected from the group consisting of:

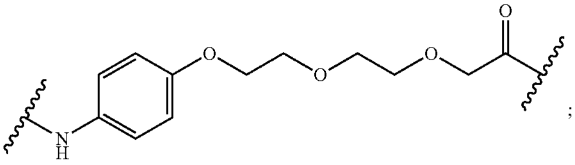
;
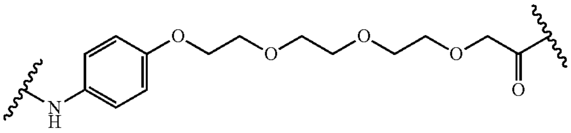
;
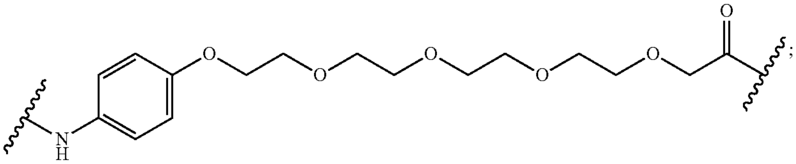
;
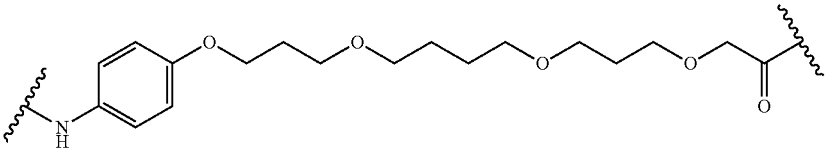
;
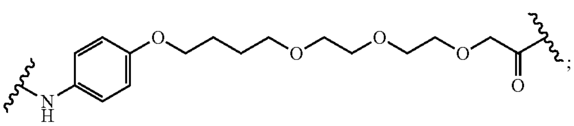
;
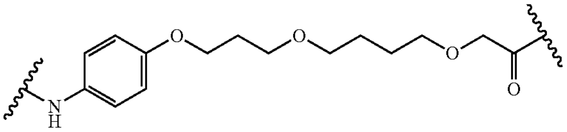
;
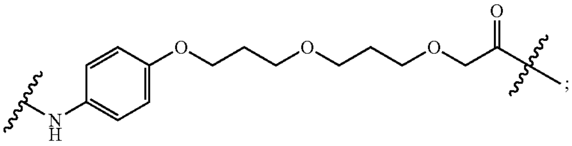
;
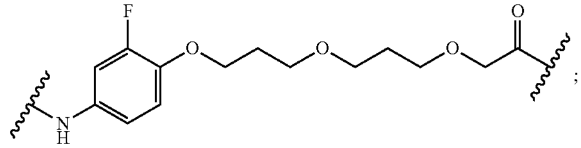
;
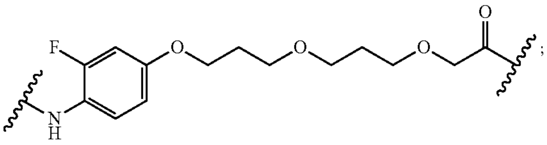
;
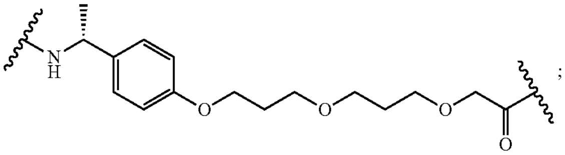
;
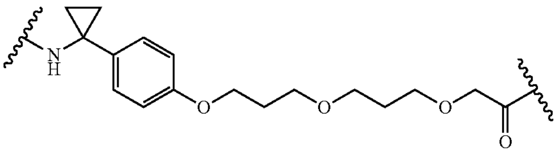
;
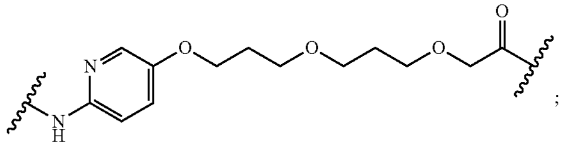
;
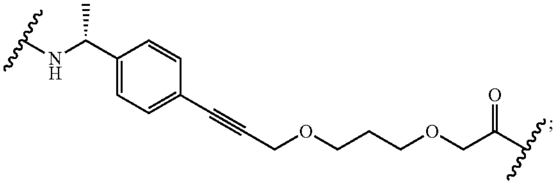
;
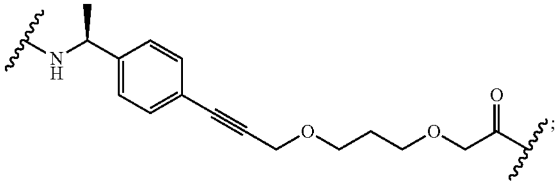
;
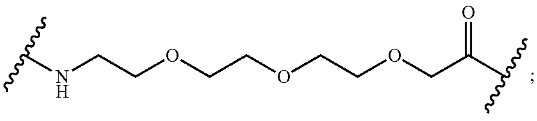
;
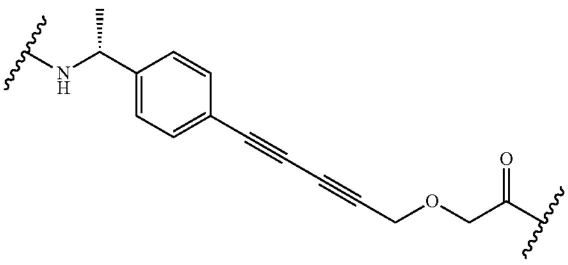
;

-continued
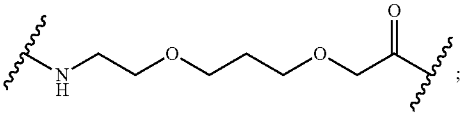
;
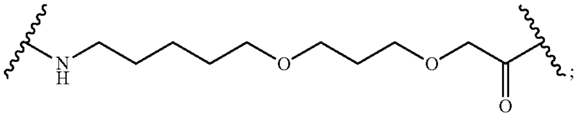
;
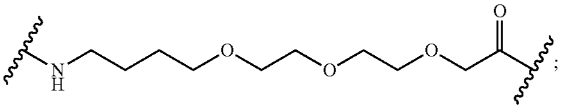
;
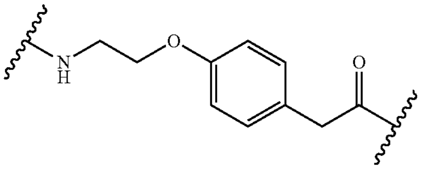
;
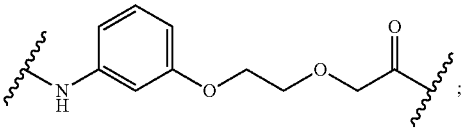
;
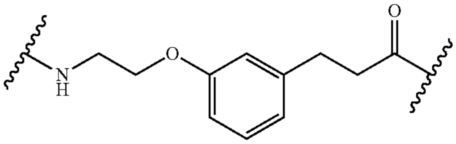
;
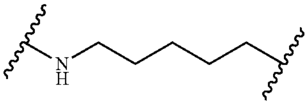
;
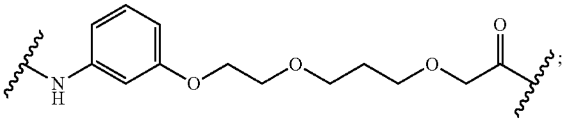
;
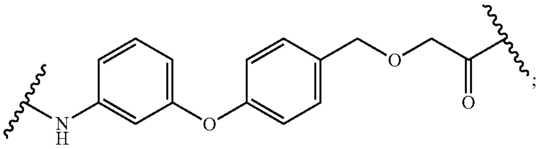
;
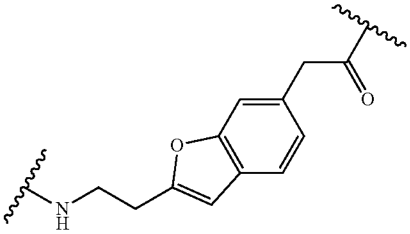
;
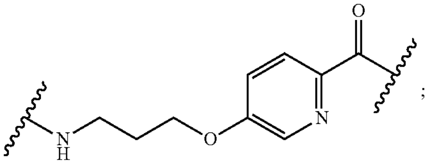
;
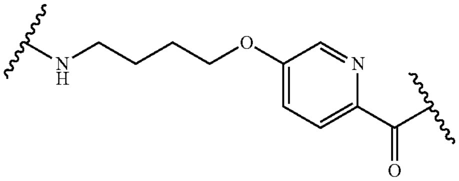
;
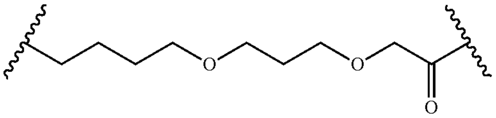
;
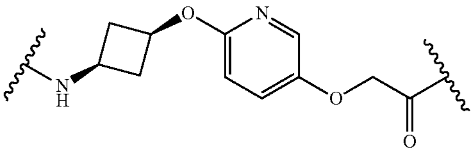
;
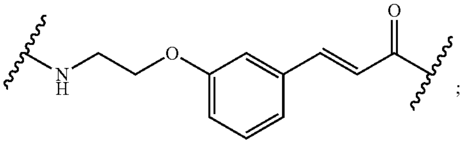
;
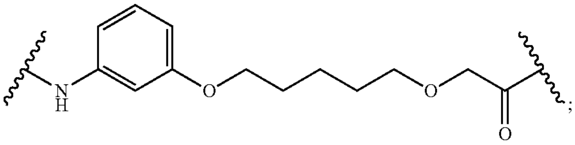
;
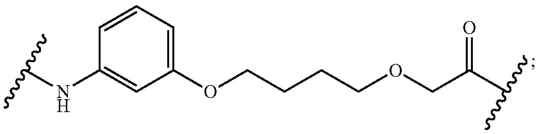
;
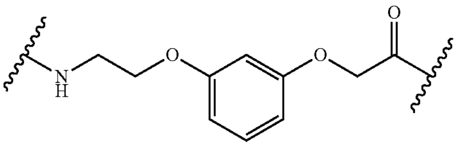
;
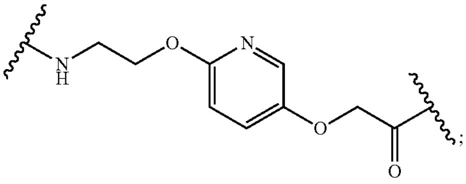
;
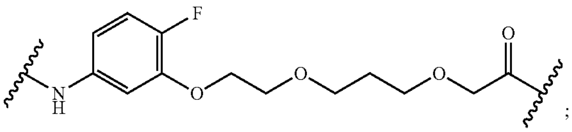
;

-continued
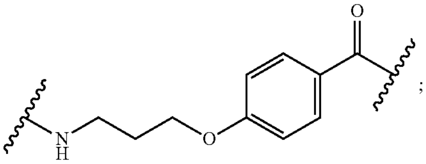;
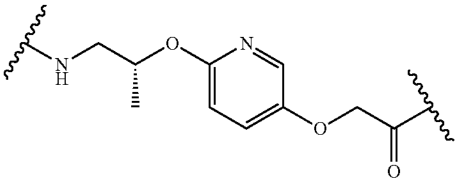;
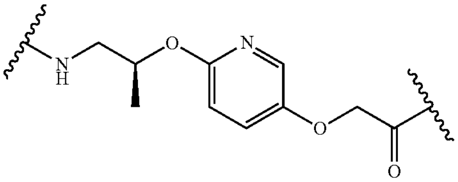;
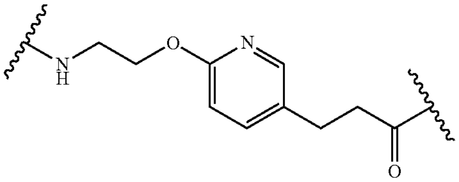;
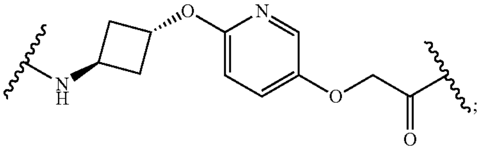;
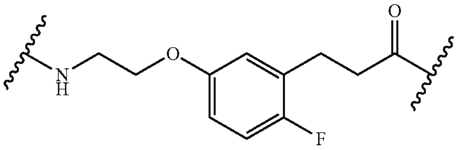;
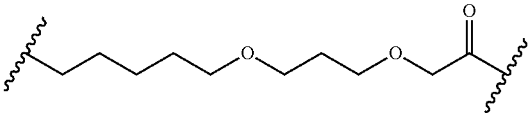;
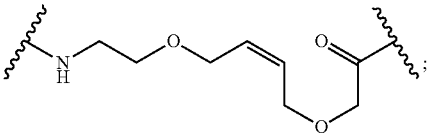;
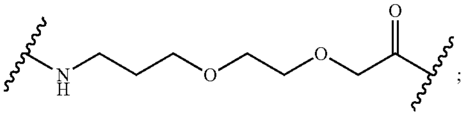;
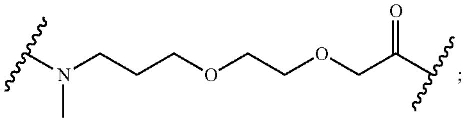;
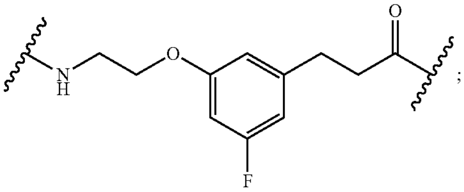;
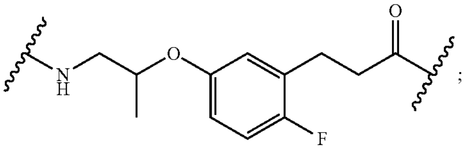;
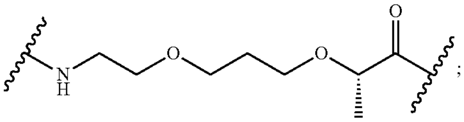;
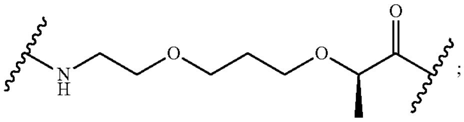;
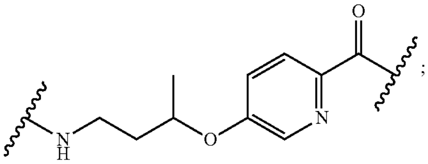;
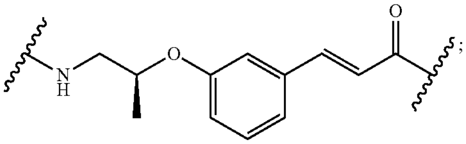;
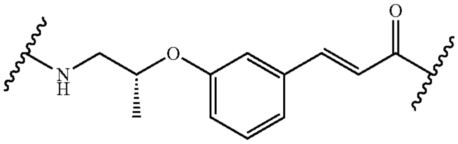;
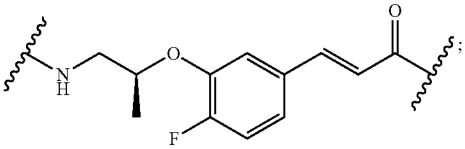;
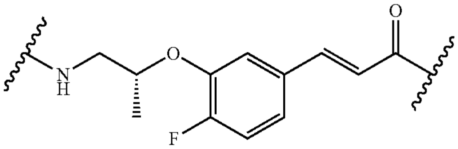;
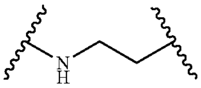;
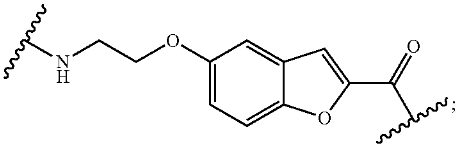;
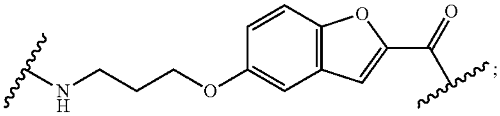;

-continued
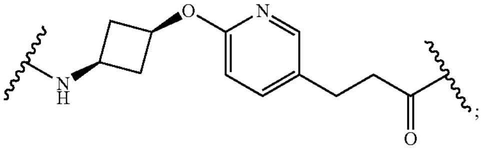;
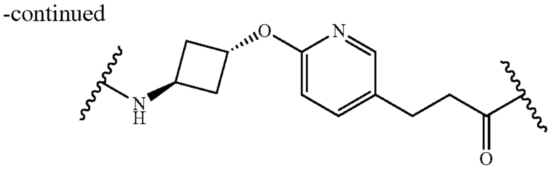;
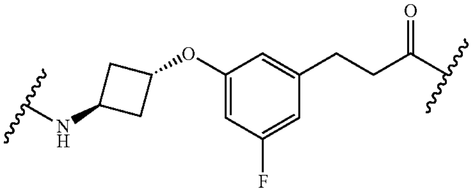;
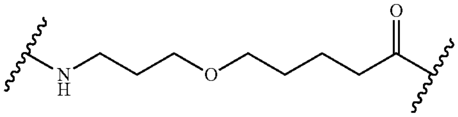;
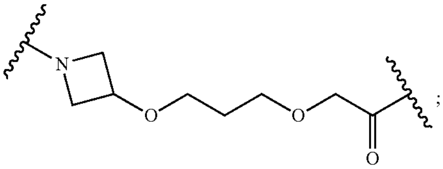;
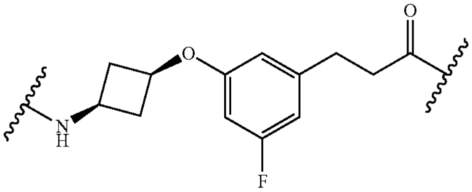;
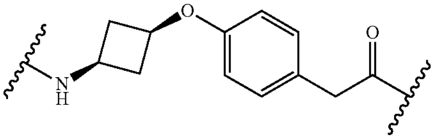;
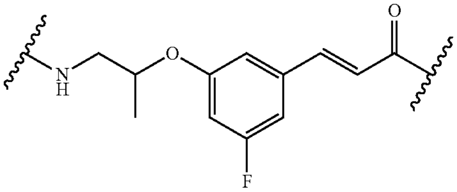;
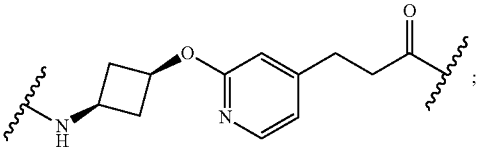;
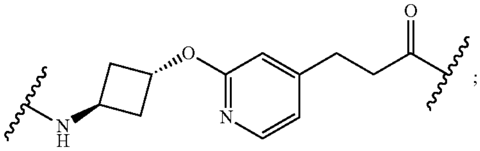;
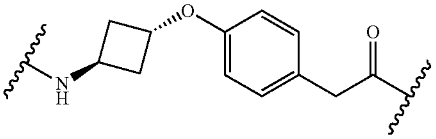;
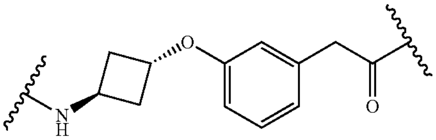;
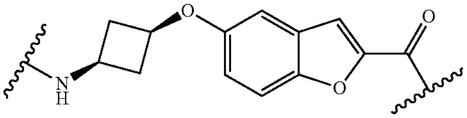;
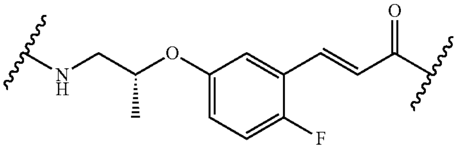;
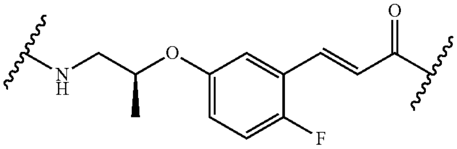;
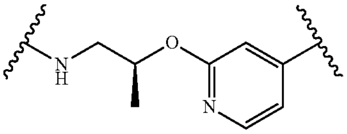;
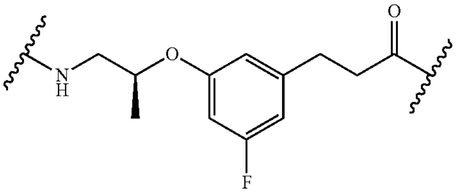;
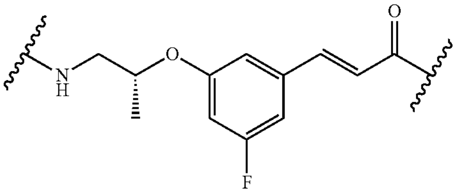;
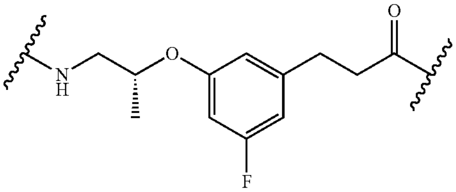;
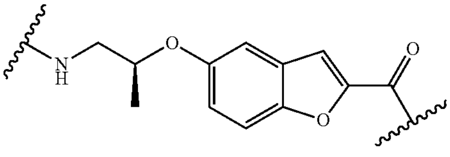;

-continued
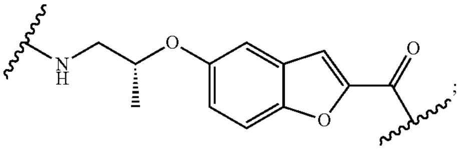
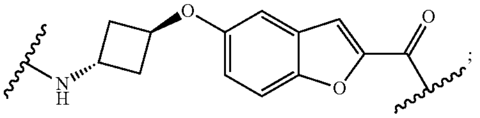
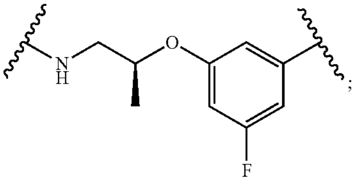
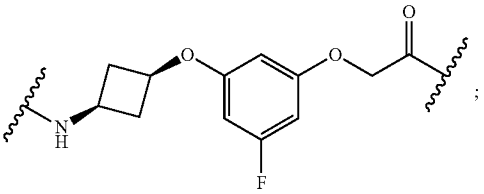
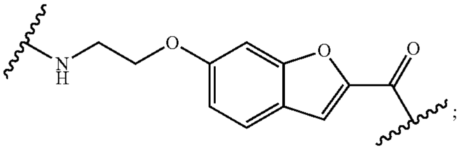
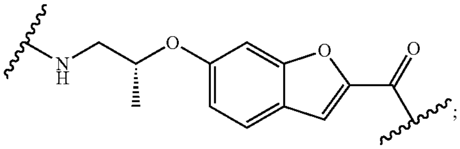
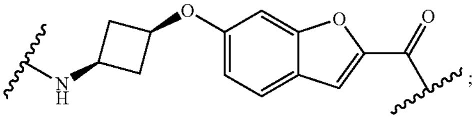
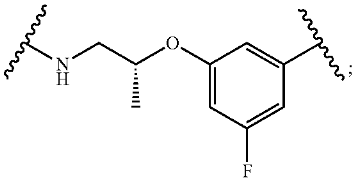
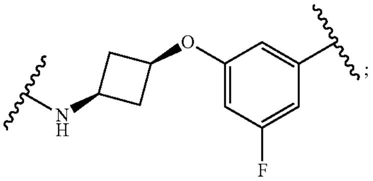
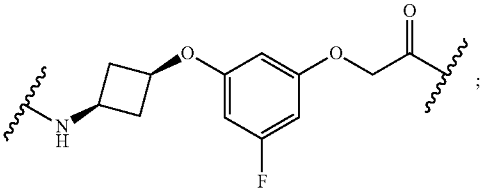
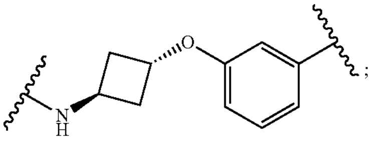
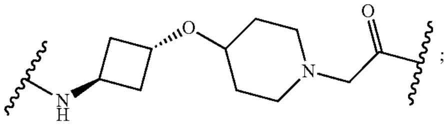
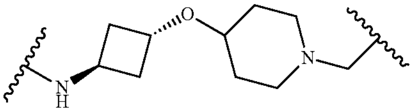
and
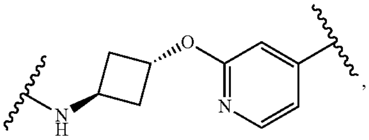
11. The compound of claim 1, or a pharmaceutically acceptable salt thereof, wherein the L is selected from the group consisting of:
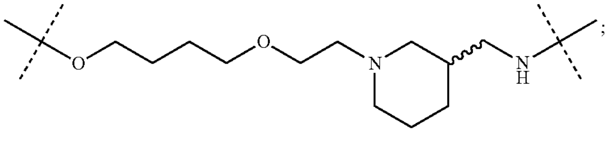
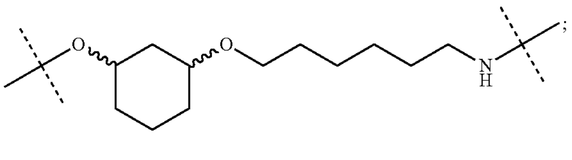
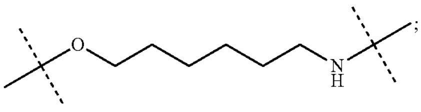

-continued
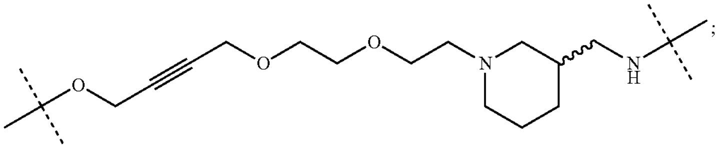
;
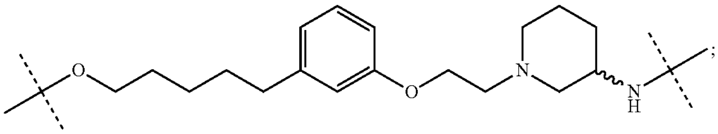
;
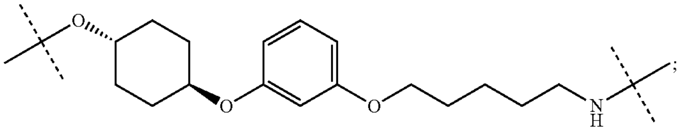
;
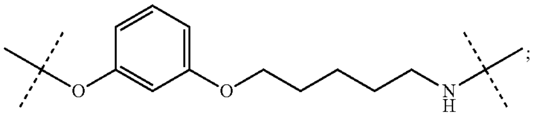
;
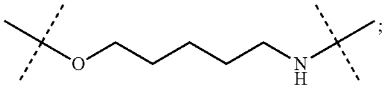
;
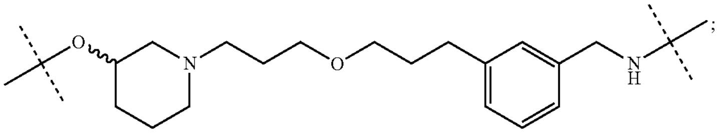
;
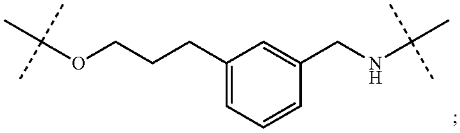
;
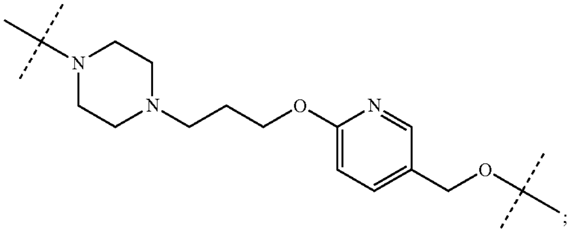
;
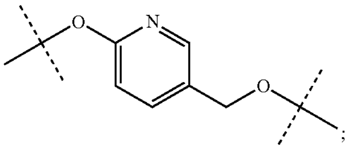
;
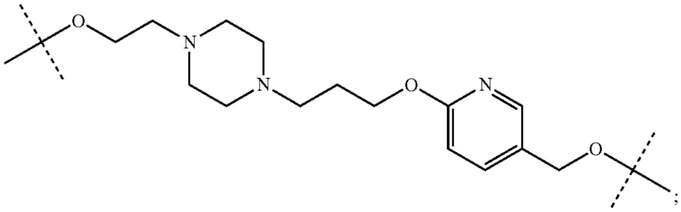
;
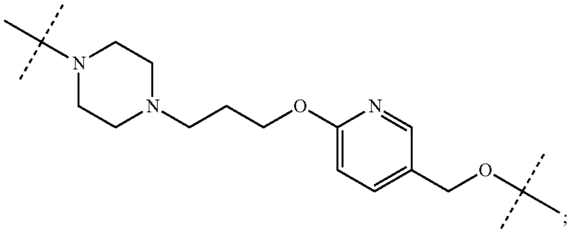
;
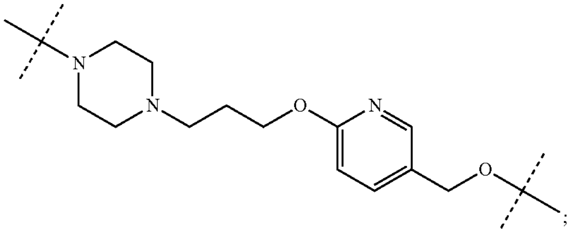
;

-continued
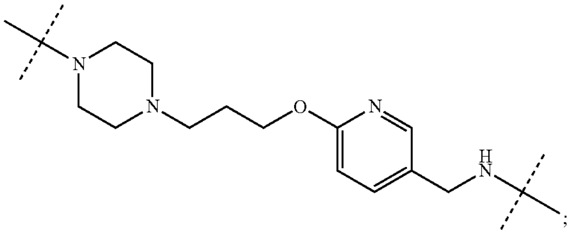 ;
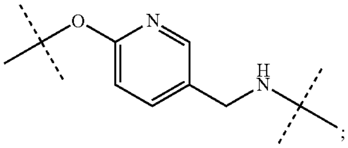 ;
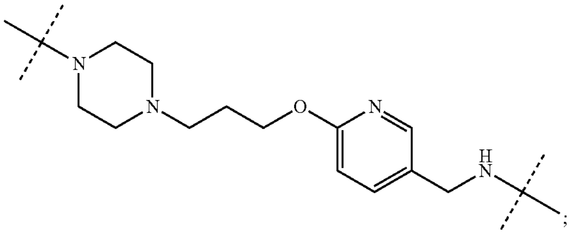 ;
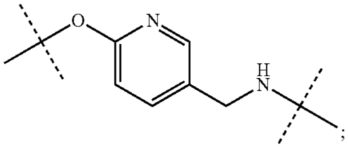 ;
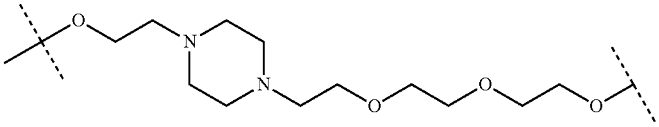 ;
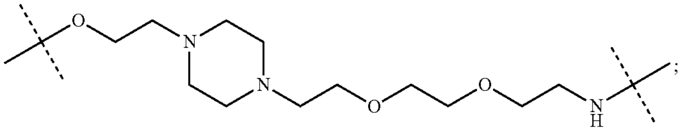 ;
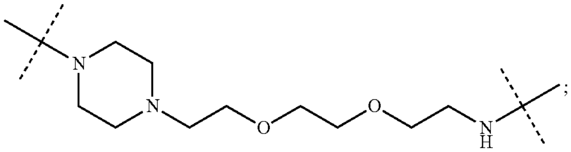 ;
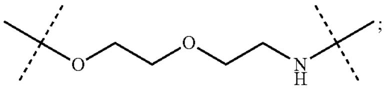 ;
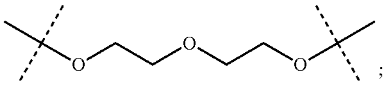 ;
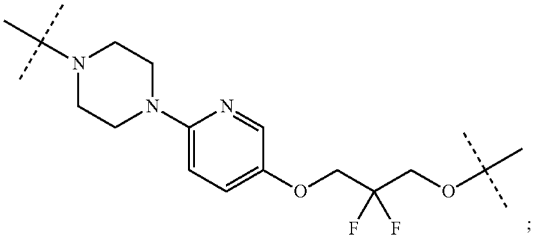 ;
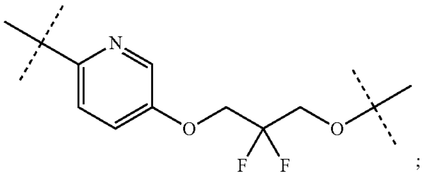 ;
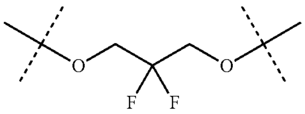 ;
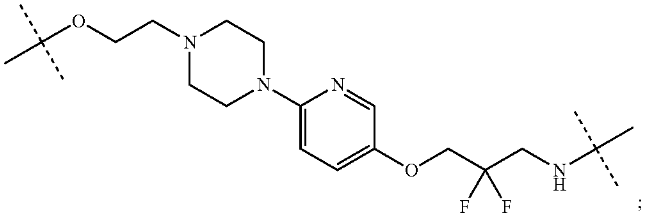 ;

-continued
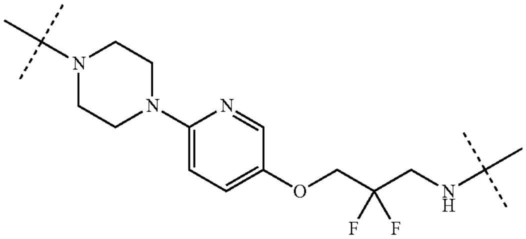
;
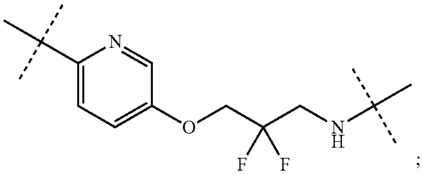
;
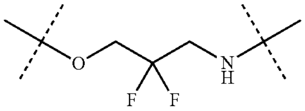
;
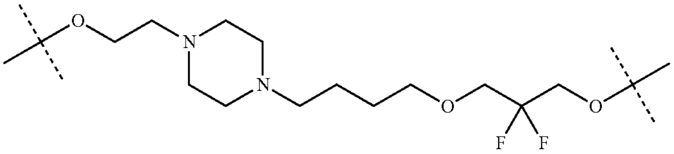
;
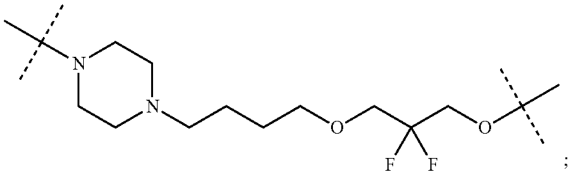
;
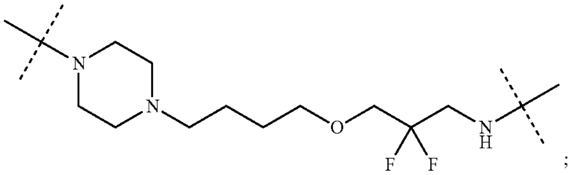
;
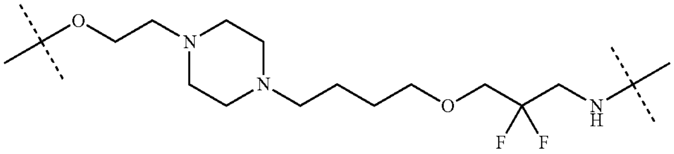
;
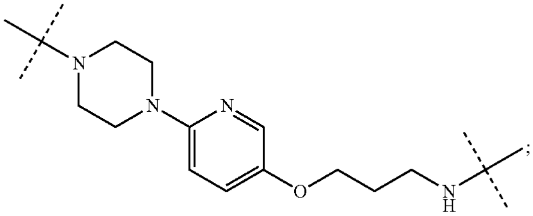
;
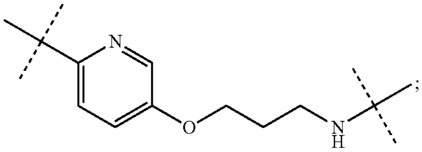
;
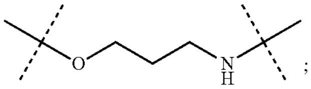
;
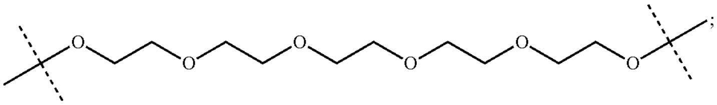
;
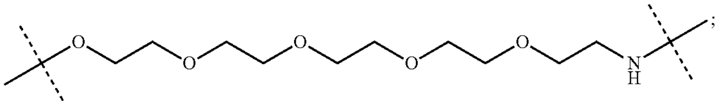
;
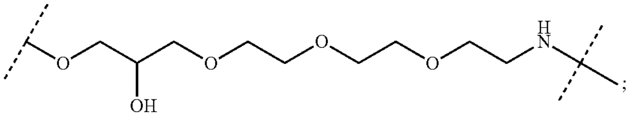
;
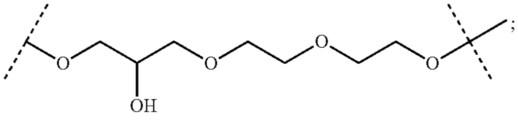
;
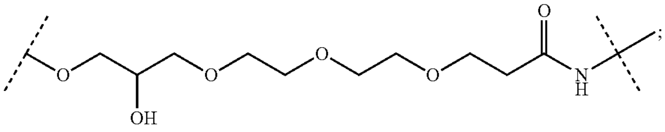
;

-continued
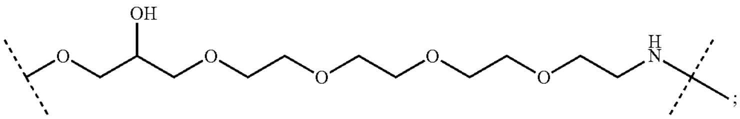
;
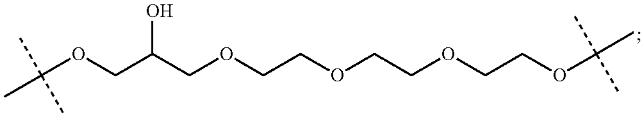
;
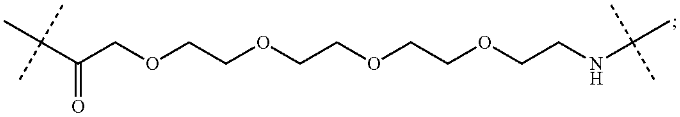
;
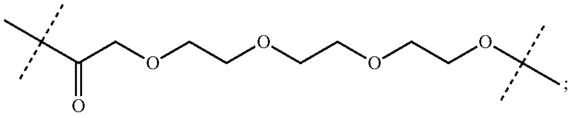
;
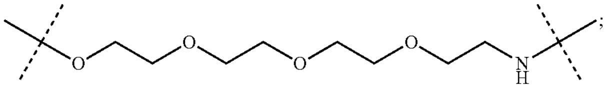
;
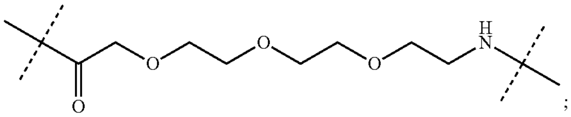
;
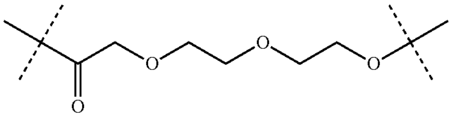
;
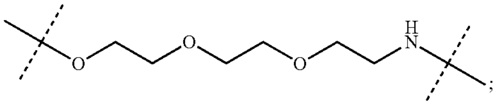
;
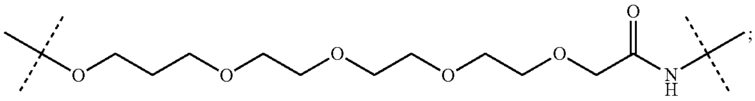
;
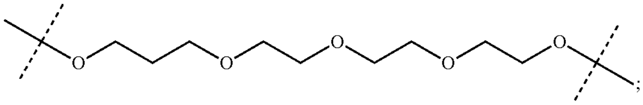
;
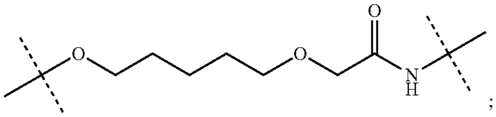
;
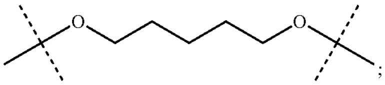
;
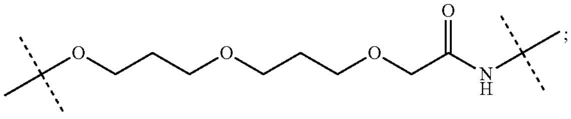
;
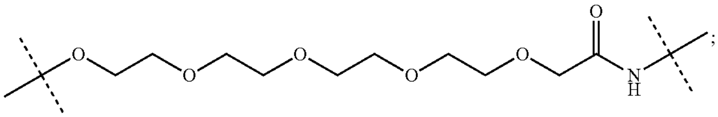
;
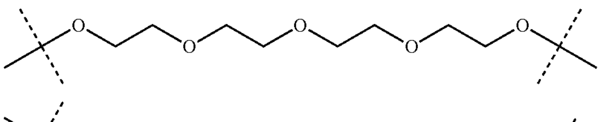
;
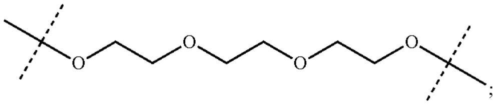
;
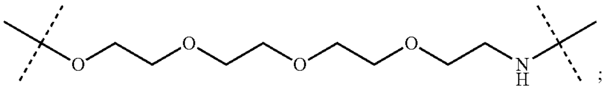
;
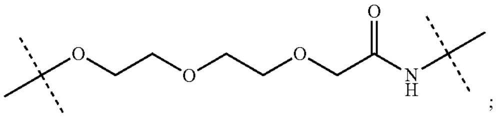
;
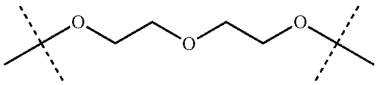
; and -continued
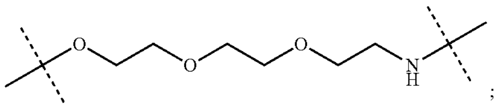
12. The compound of claim 1, or a pharmaceutically acceptable salt thereof, wherein the L is selected from the group consisting of:
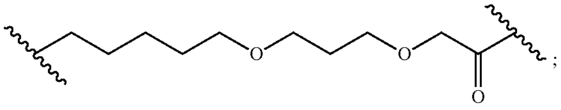
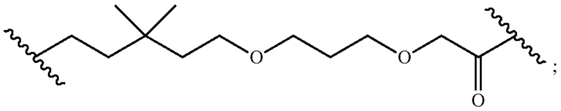
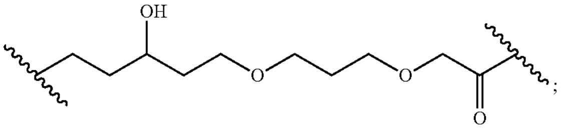
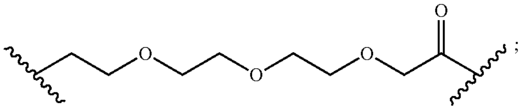
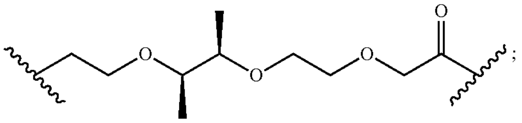
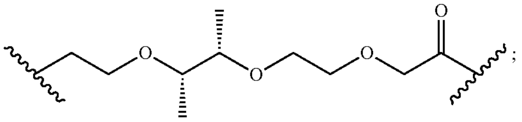
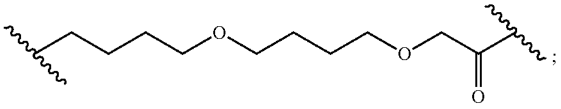
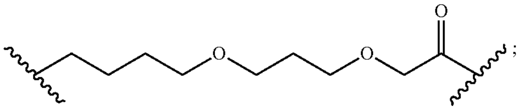
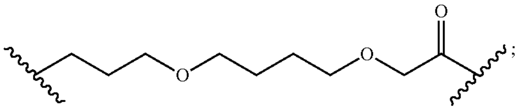
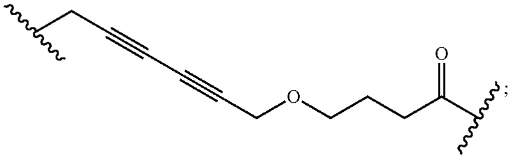
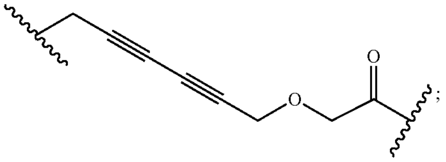
-continued
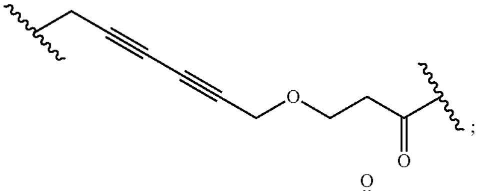
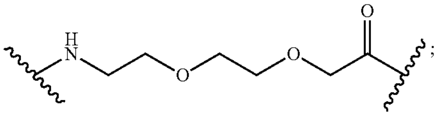
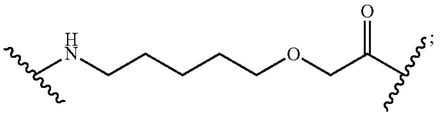
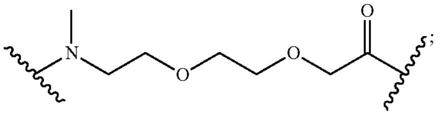
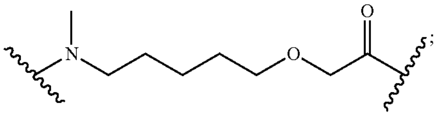
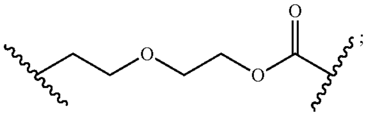
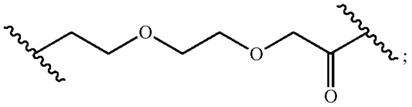
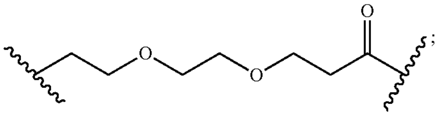
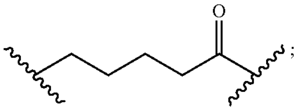
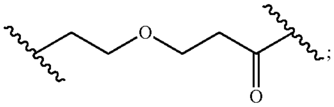
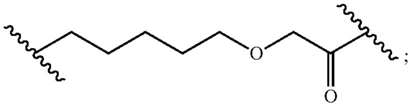
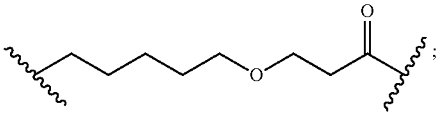
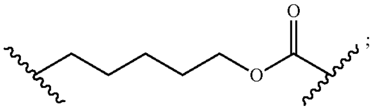

-continued
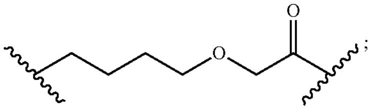
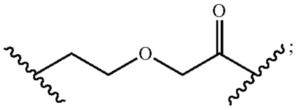
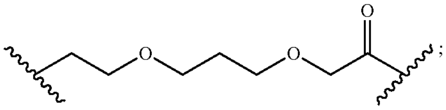
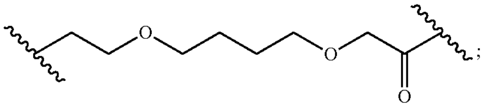
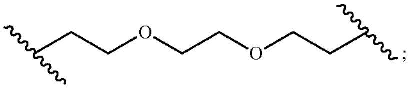
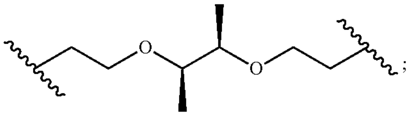
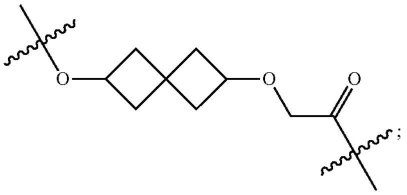
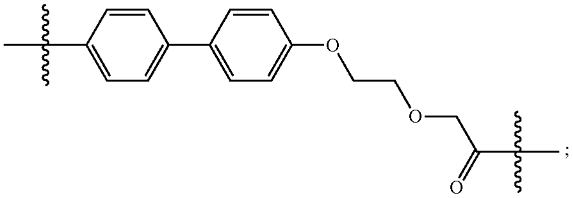
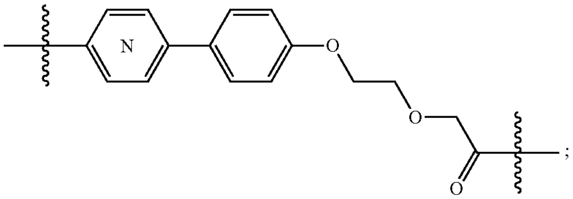
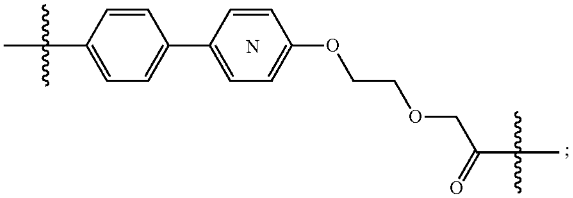
-continued
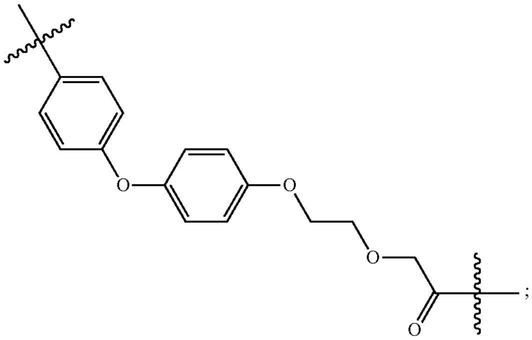
; and
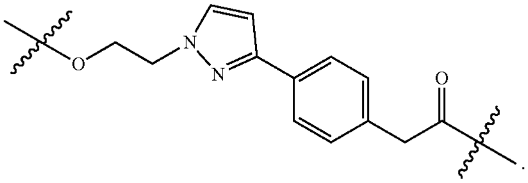 [SMILES: *OCCn1ccc(-c2ccc(CC(*)=O)cc2)n1]
13. The compound of claim 1, or a pharmaceutically acceptable salt thereof, wherein the L is selected from the group consisting of:
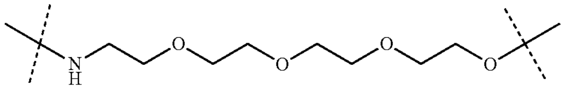
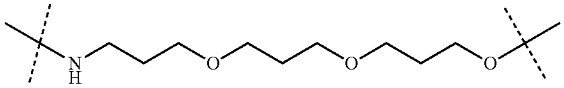
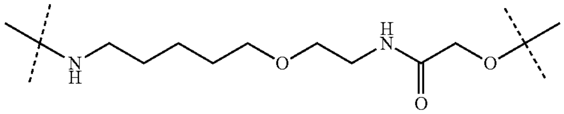
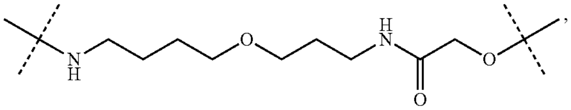
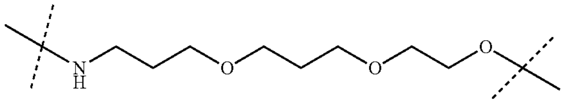
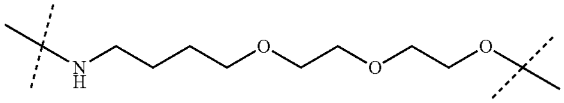
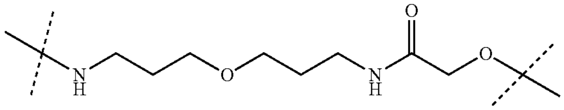
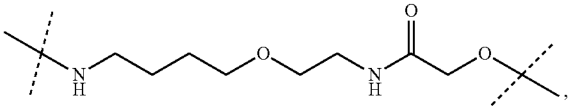
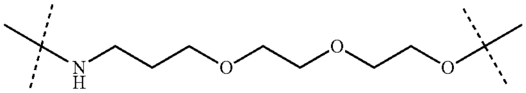
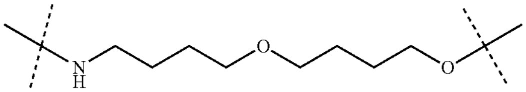

-continued
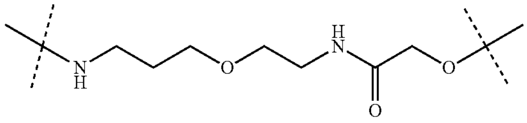
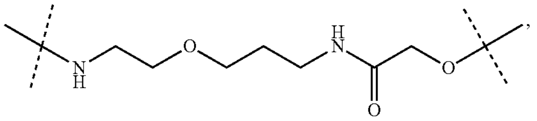
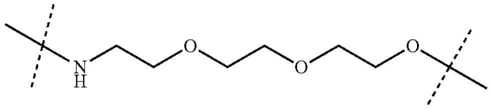
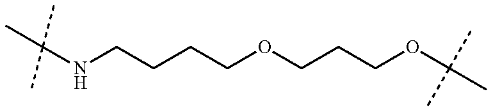
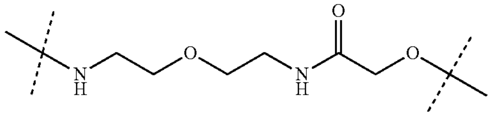
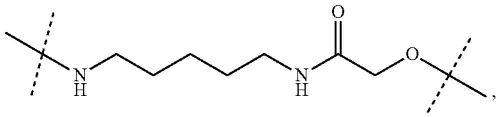
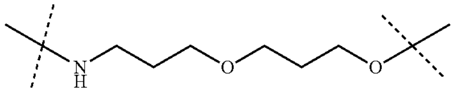
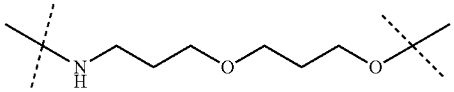
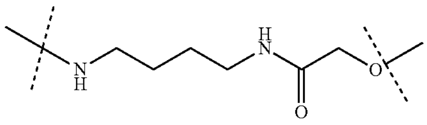
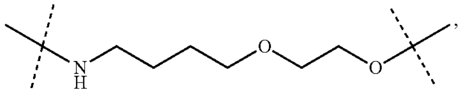
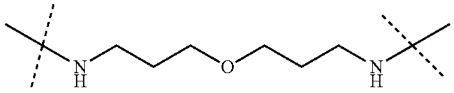
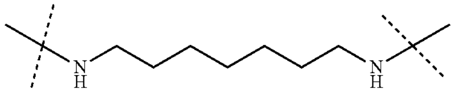
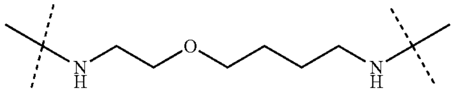
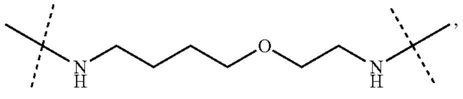
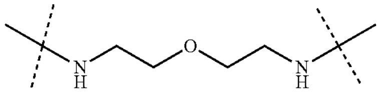
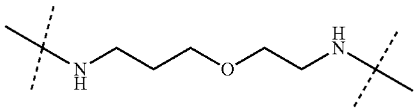
-continued
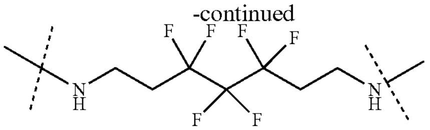
and
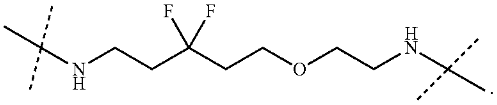
14. The compound of claim 1, or a pharmaceutically acceptable salt thereof, wherein the L is selected from the group consisting of:
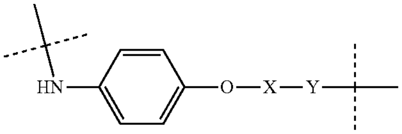
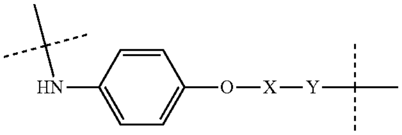
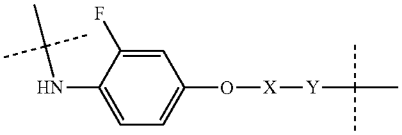
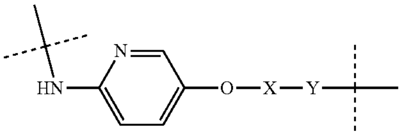
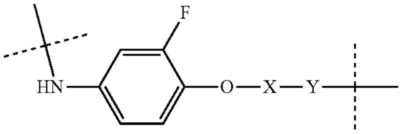
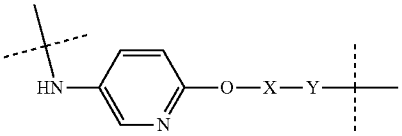
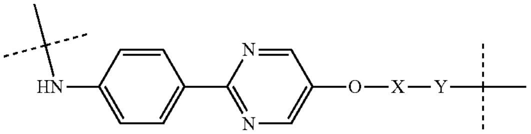
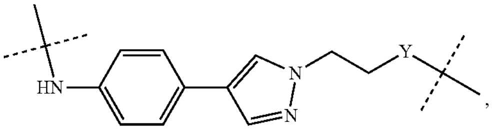
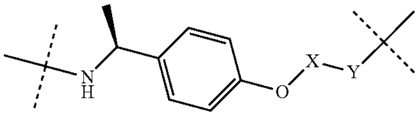
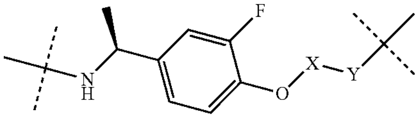

-continued

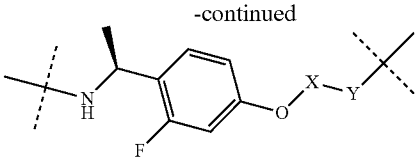

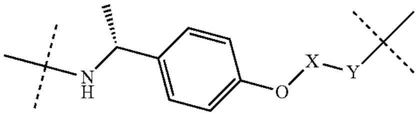

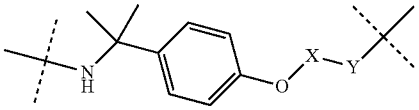

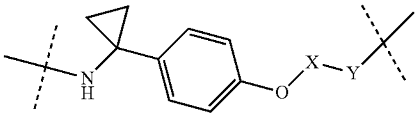

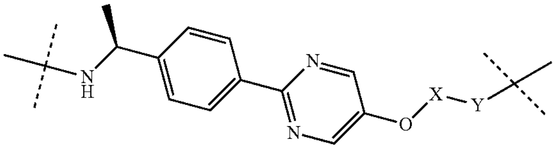

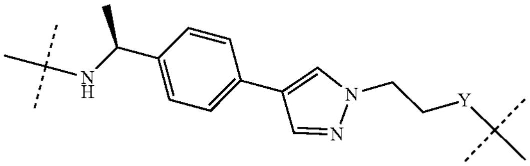

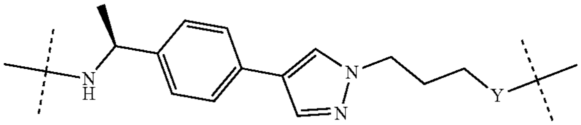

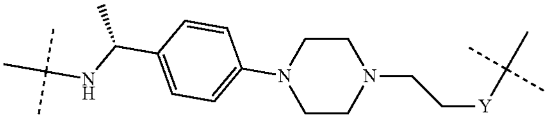

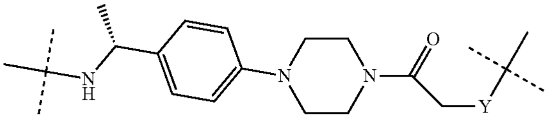

-continued

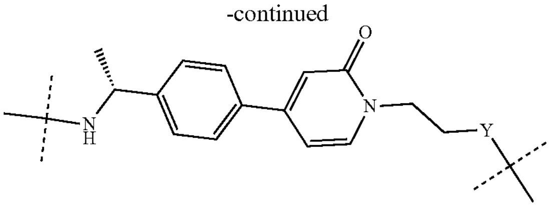

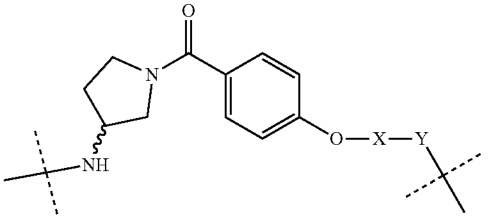

and

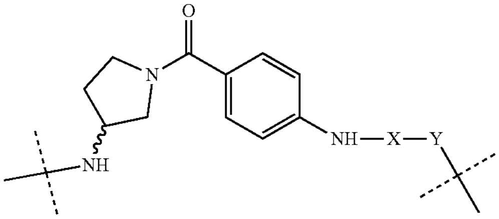

wherein

X is a linear chain with atoms ranging from 2 to 14 optionally substituted to contain heteroatoms, and Y is O, N, or S (O) n, wherein n is 0, 1, or 2.

15. The compound of claim 6, or a pharmaceutically acceptable salt thereof, wherein the L is selected from the group consisting of:

—N(R)—(CH2)$_m$—O(CH2)$_n$—O(CH2)$_o$—O(CH2)$_p$—O (CH2)$_q$—O(CH2)$_r$—OCH$_2$—, —O—(CH2)$_m$—O (CH2)$_n$—O(CH2)$_o$—O(CH2)$_p$—O (CH2)$_q$—O(CH2)$_r$—OCH$_2$—, —O—(CH2)$_m$—O(CH2)$_n$—O (CH2)$_o$—O(CH2)$_p$—O (CH2)$_q$—O(CH2)$_r$—O—;

—N(R)—(CH2)$_m$—O(CH2)$_n$—O(CH2)$_o$—O(CH2)$_p$—O (CH2)$_q$—O(CH2)$_r$—O—;

—(CH2)$_m$—O(CH2)$_n$—O(CH2)$_o$—O(CH2)$_p$—O (CH2)$_q$—O(CH2)$_r$—O—;

—(CH2)$_m$—O(CH2)$_n$—O(CH2)$_o$—O(CH2)$_p$—O (CH2)$_q$—O(CH2)$_r$—OCH$_2$—;

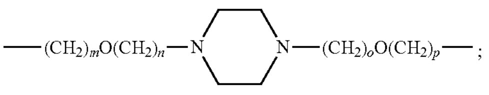

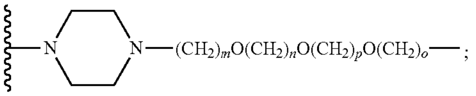

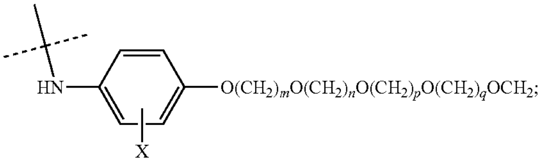

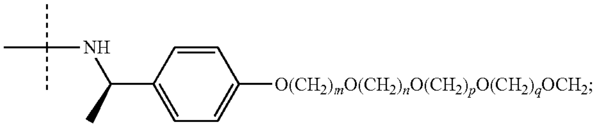

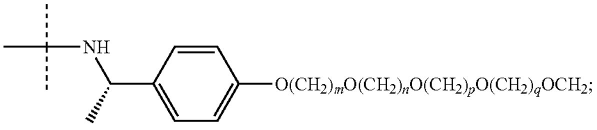

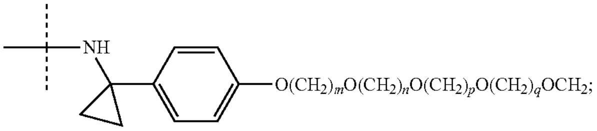

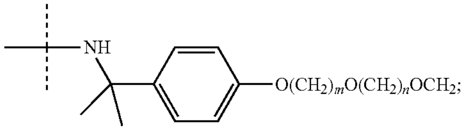

-continued
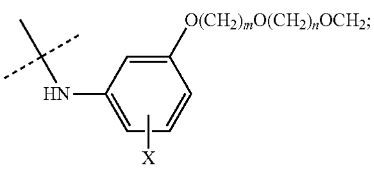
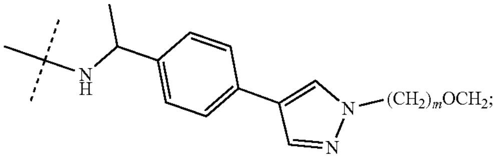
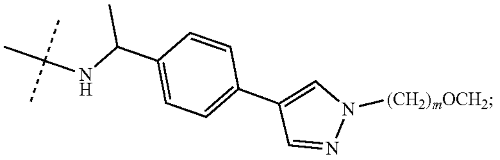
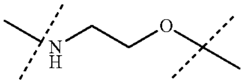
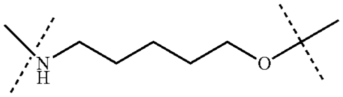
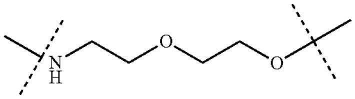
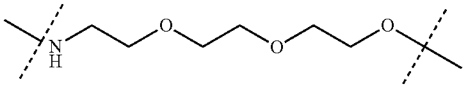
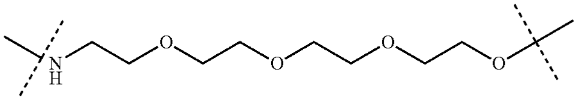
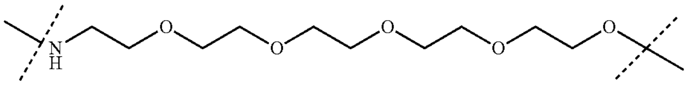
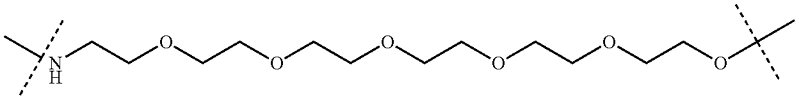
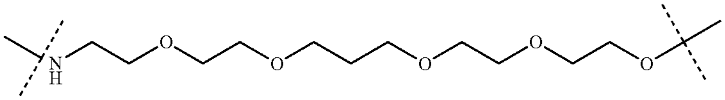
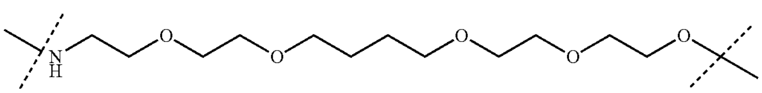
;
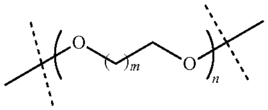
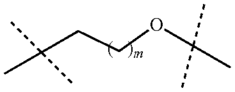
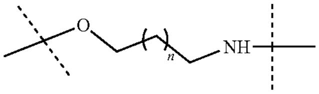
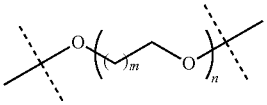
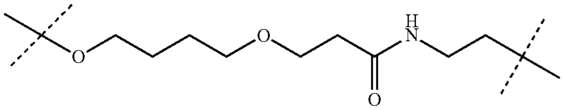
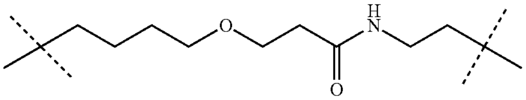
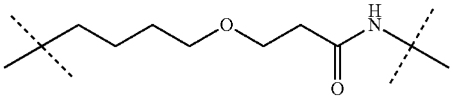
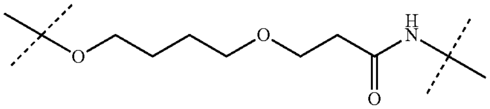
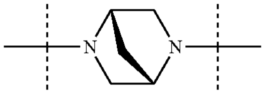
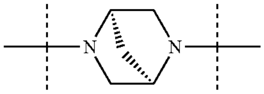
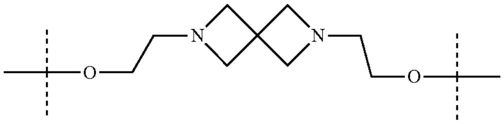
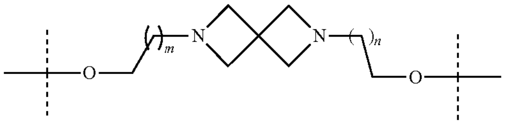
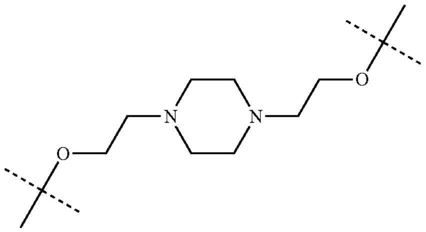

-continued
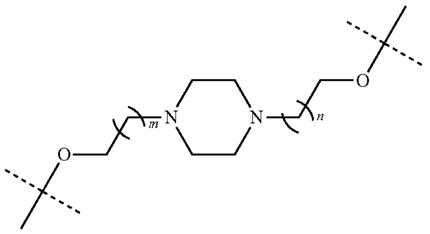
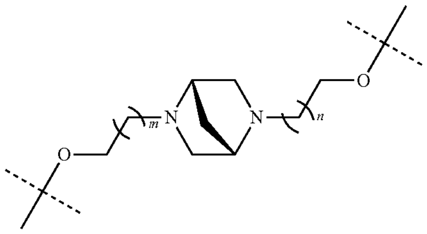
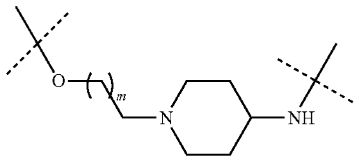
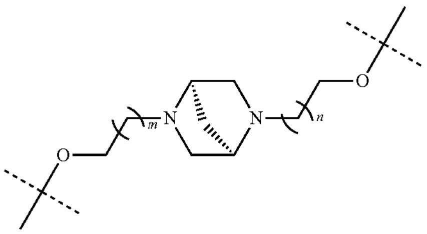
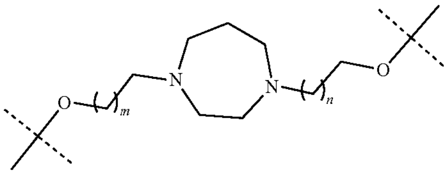
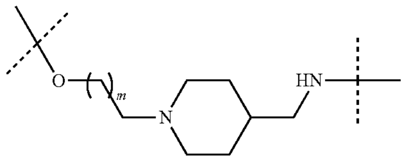
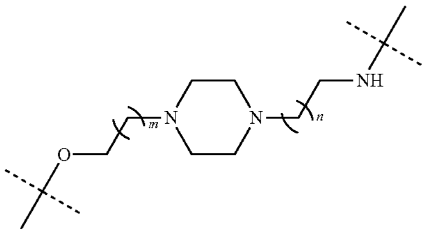
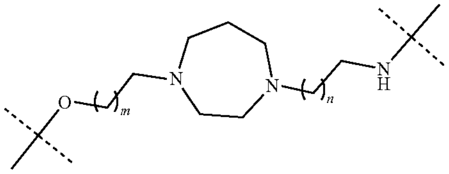
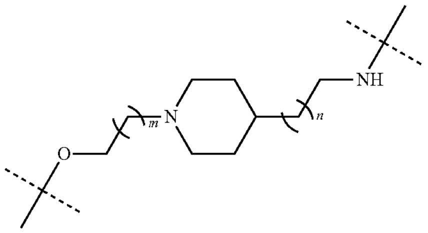
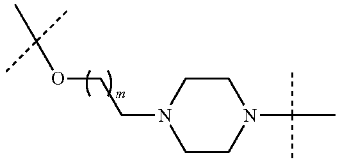
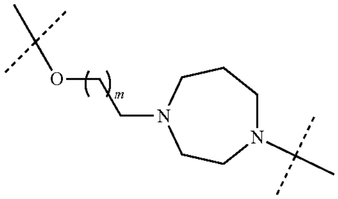
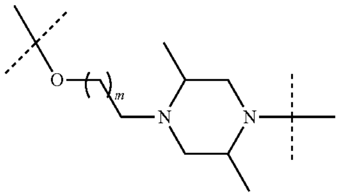
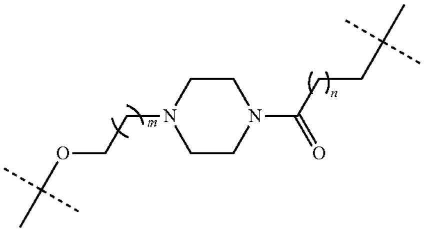
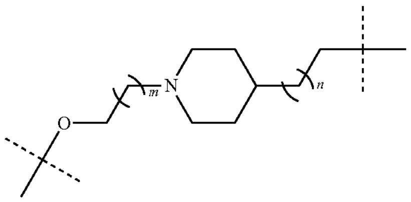
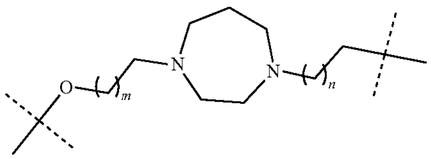

-continued
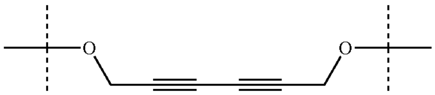
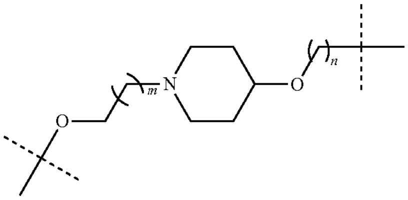
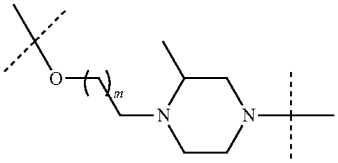
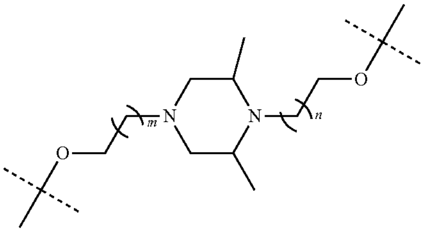
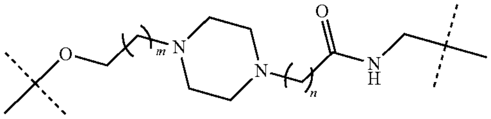
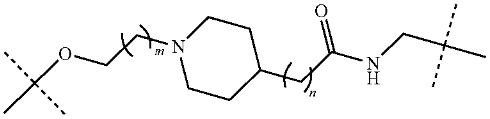
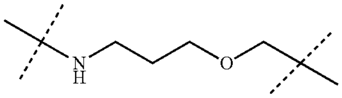
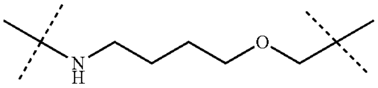
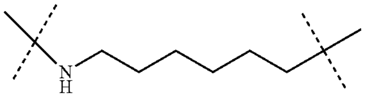
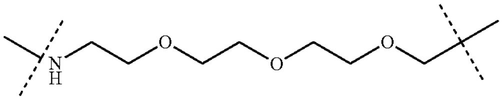
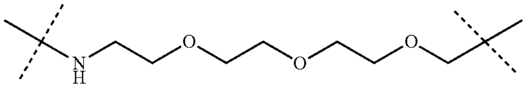
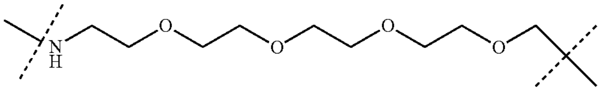
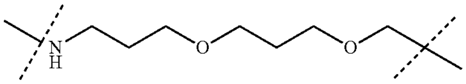
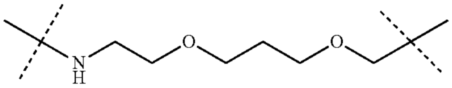
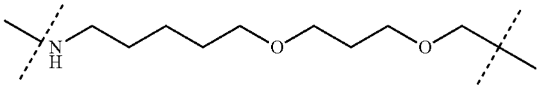
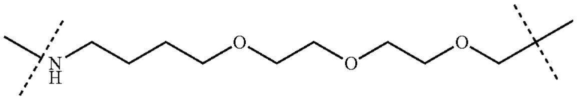
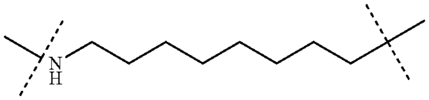
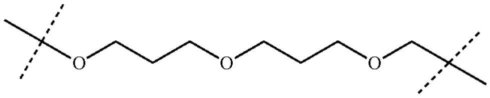
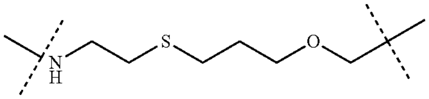
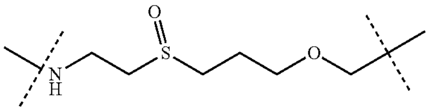
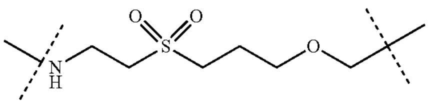
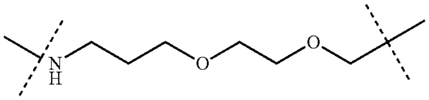
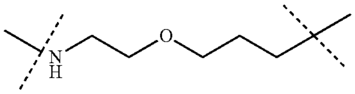
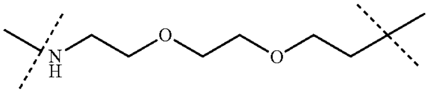
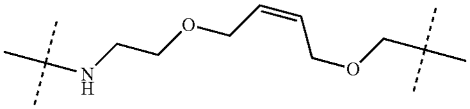
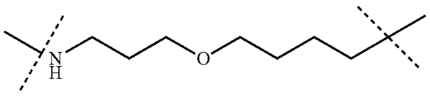

-continued
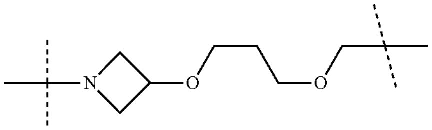
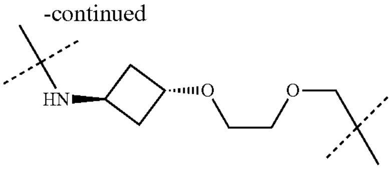
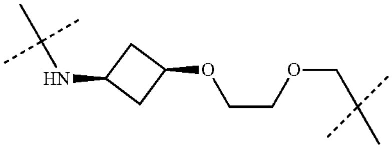
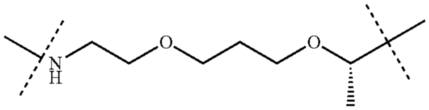
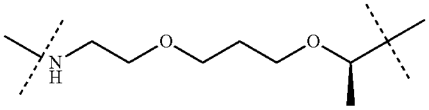
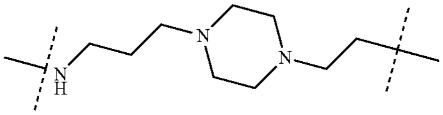
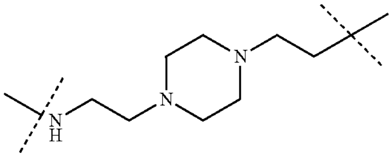
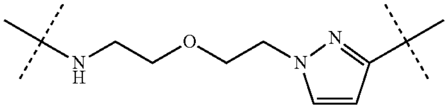
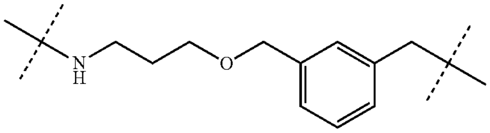
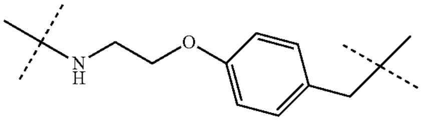
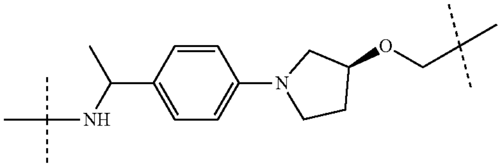
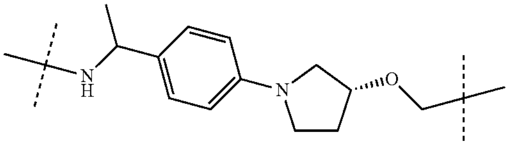
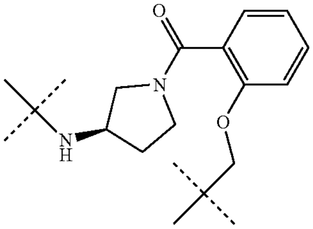
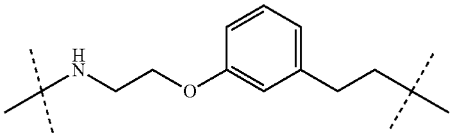
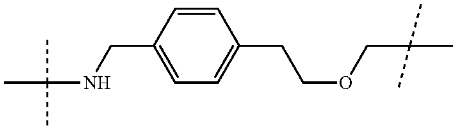
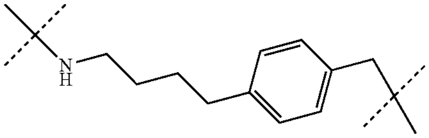
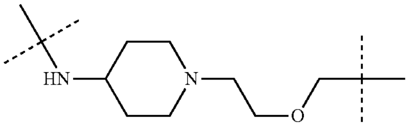
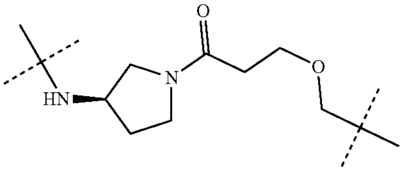
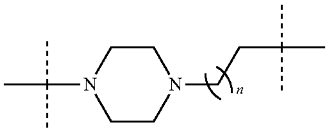
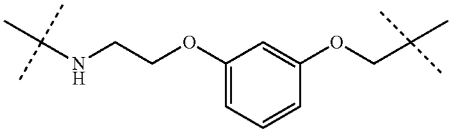
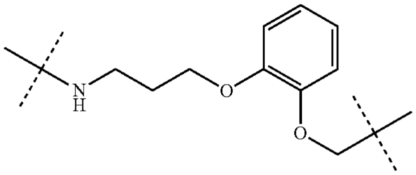
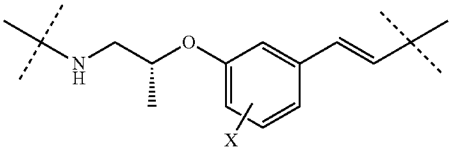

-continued
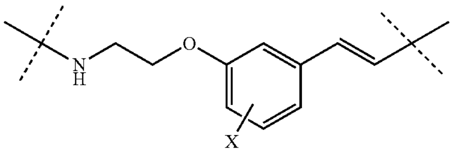
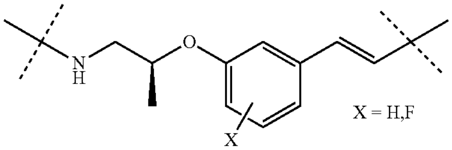
X = H,F
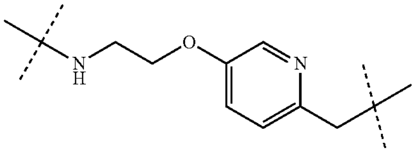
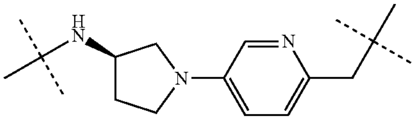
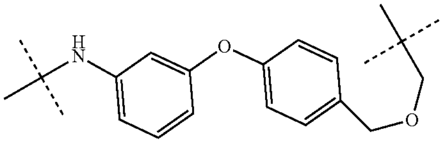
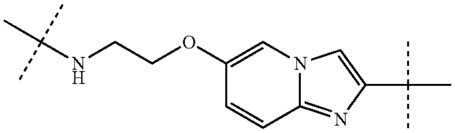
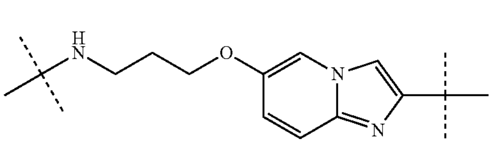
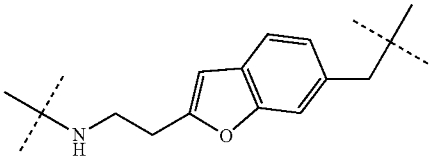
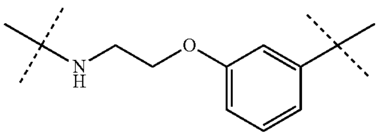
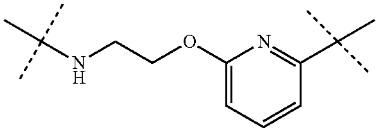
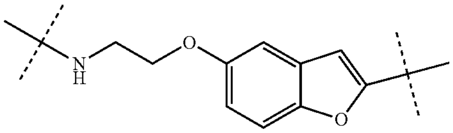
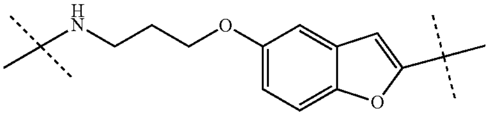
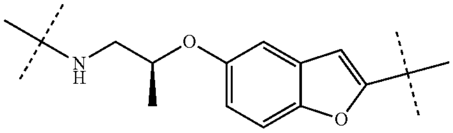
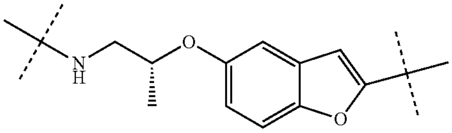
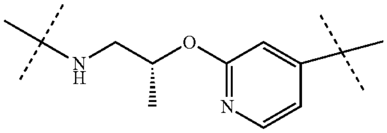
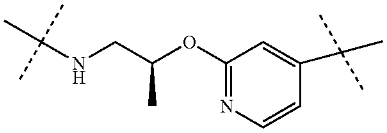
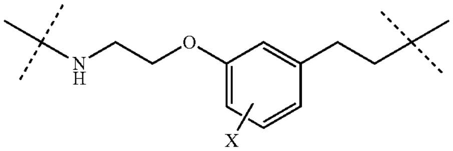
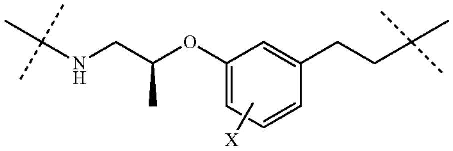
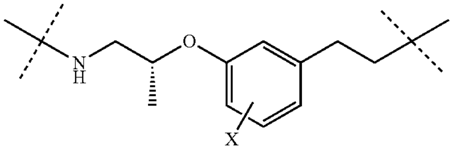
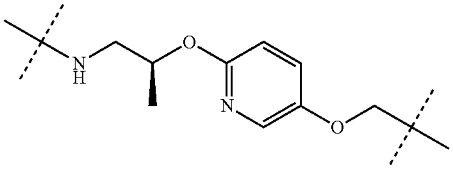
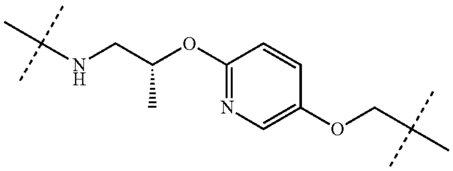
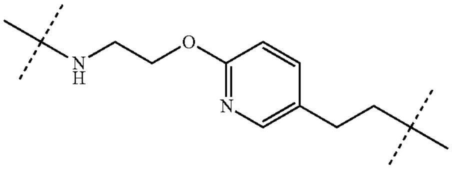

-continued
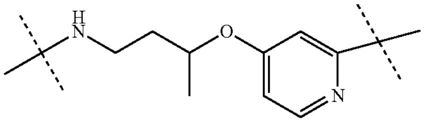
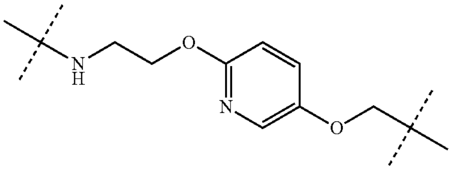
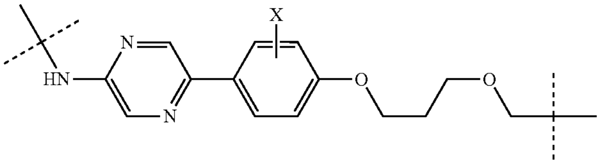
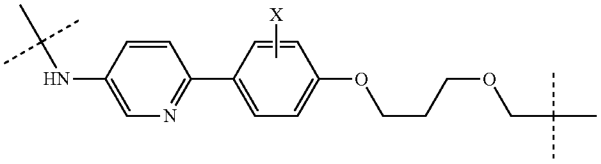
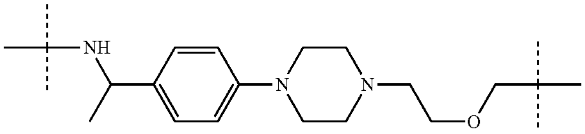
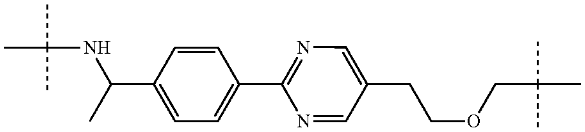
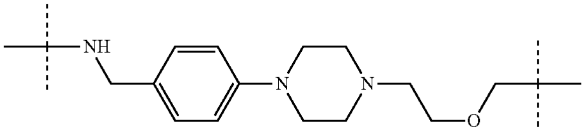
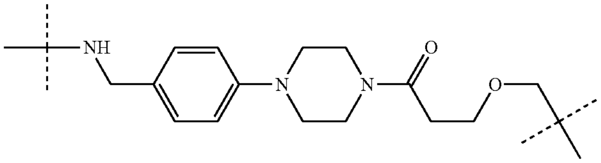
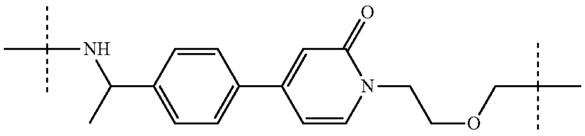
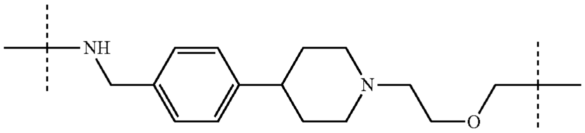
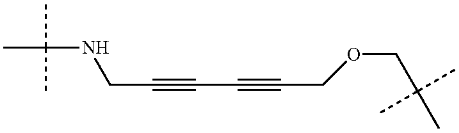
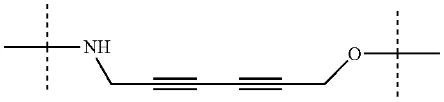
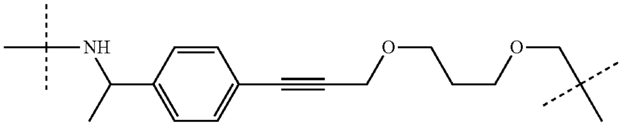
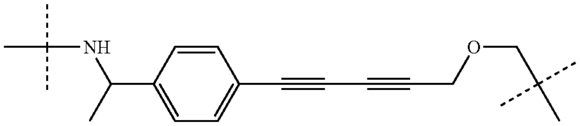
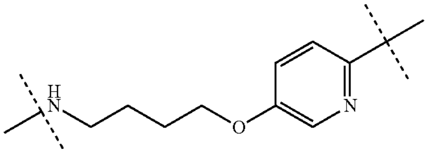

-continued
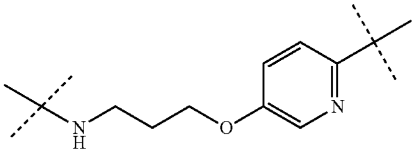
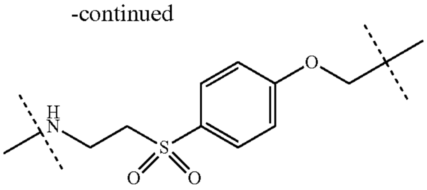
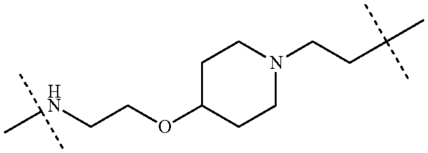
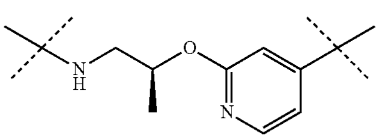
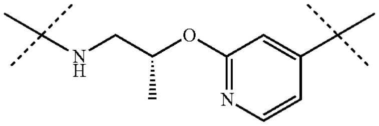
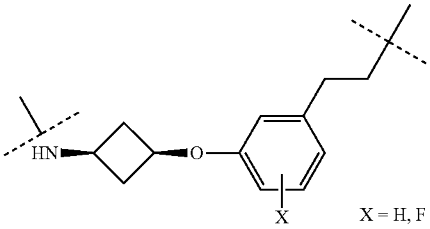
X = H, F
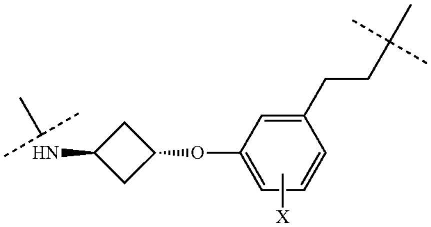
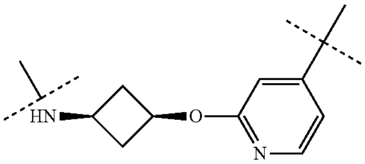
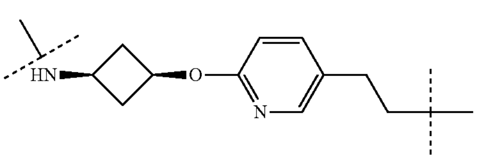
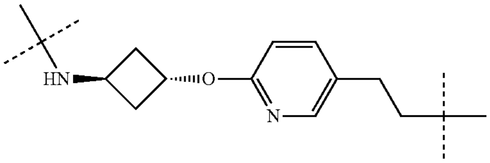
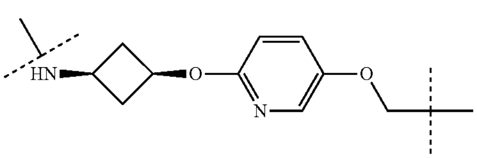
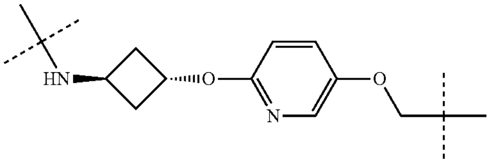
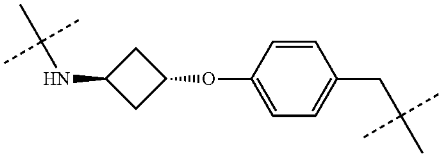
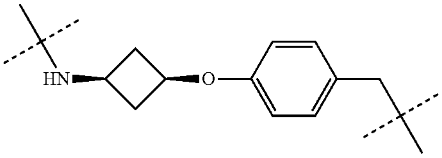
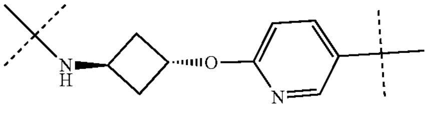
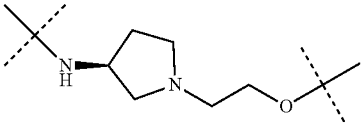
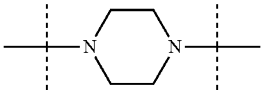
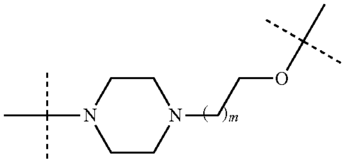
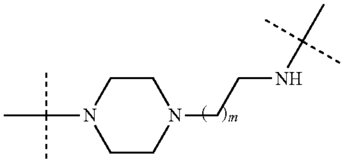
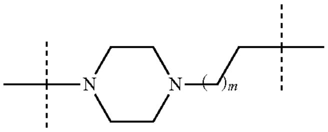
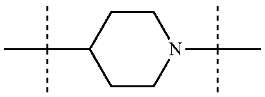
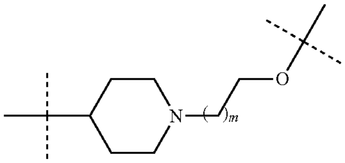
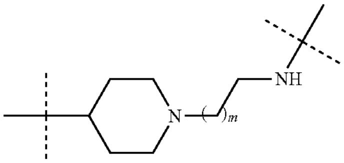

-continued
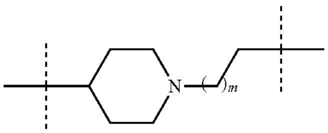
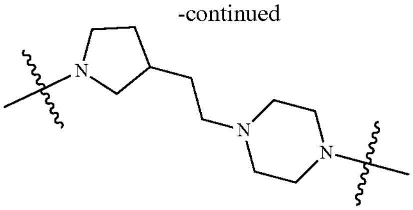
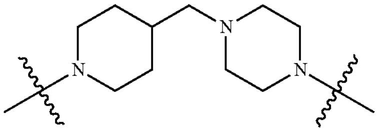
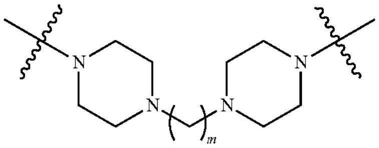
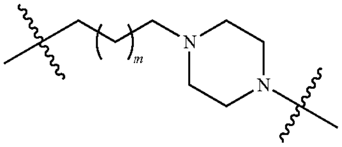
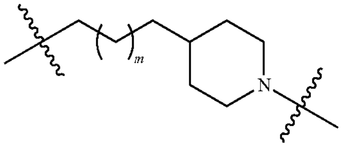
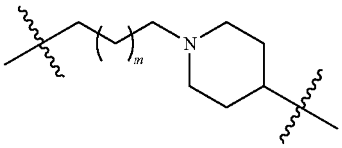
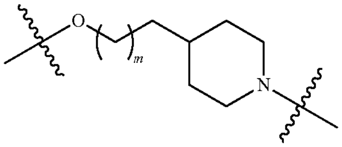
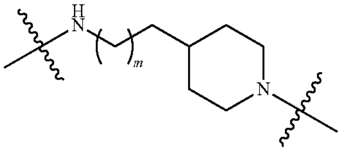
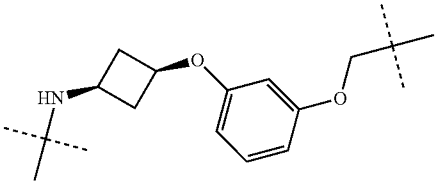
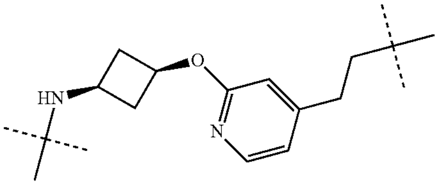
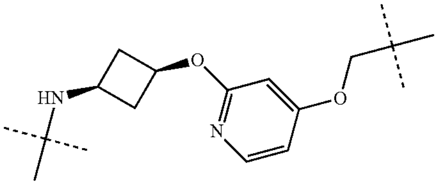
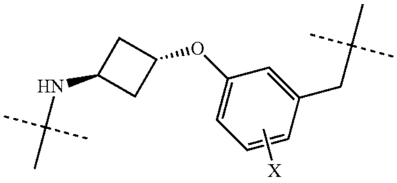
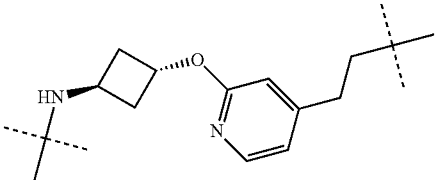
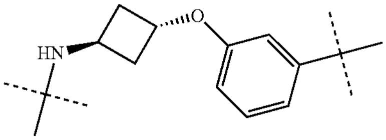
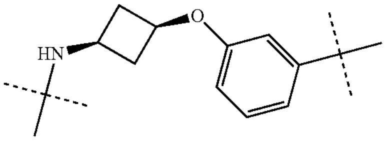
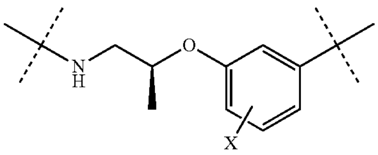
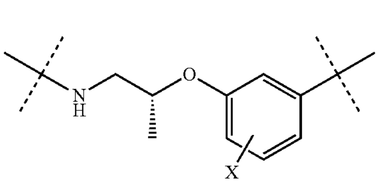
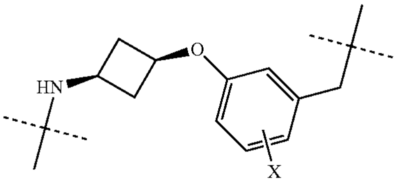
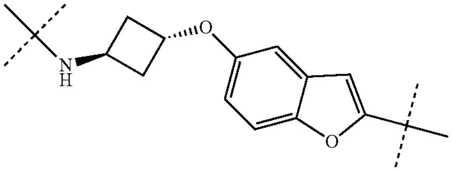
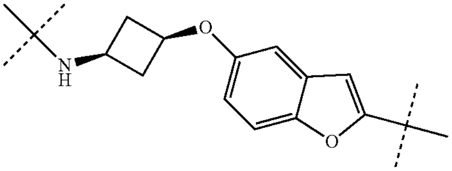
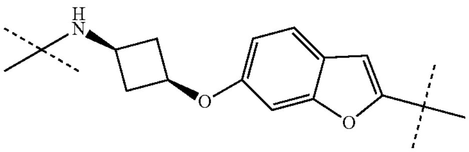
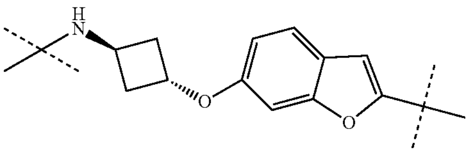

-continued
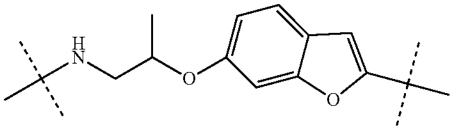
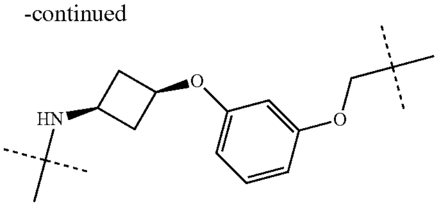
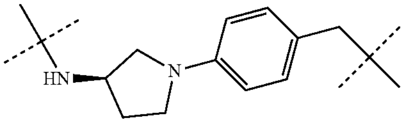
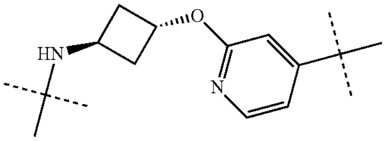
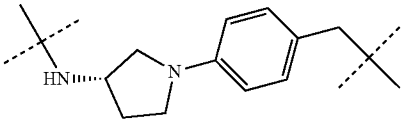
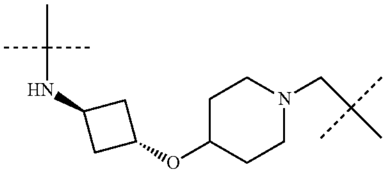
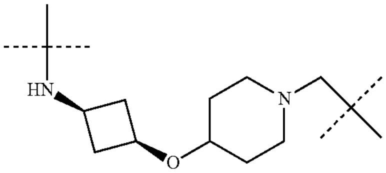
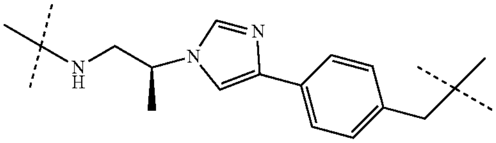
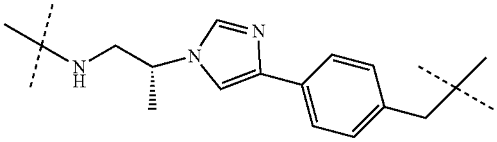
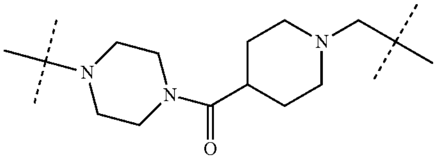
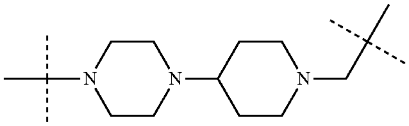
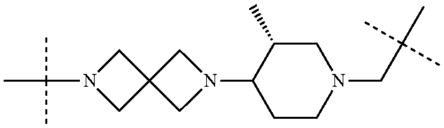
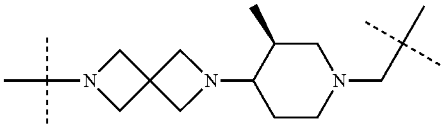
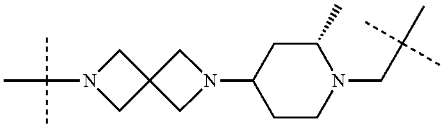
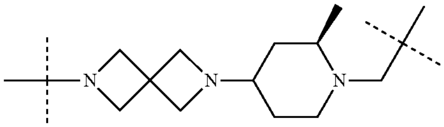
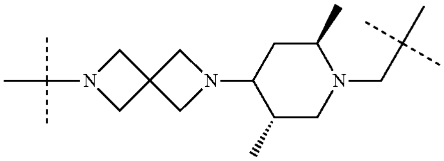
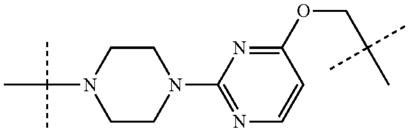
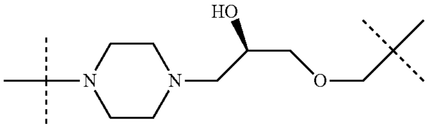
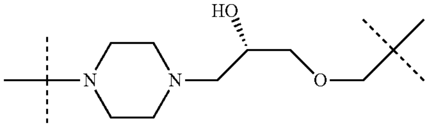
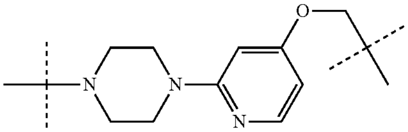
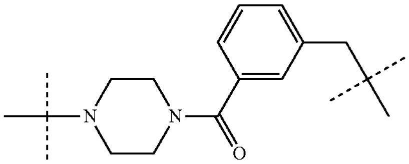
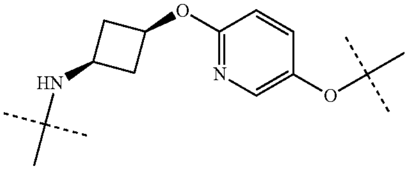

-continued
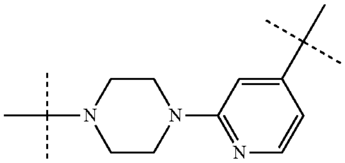
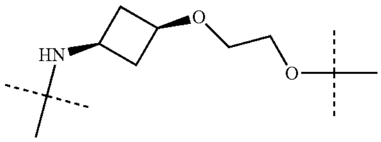
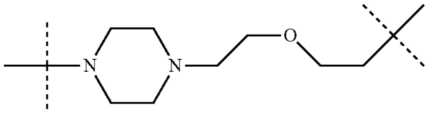
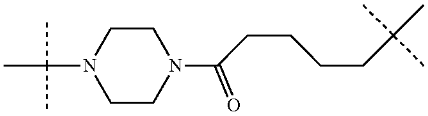
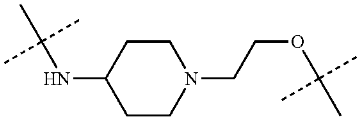
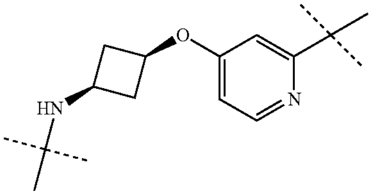
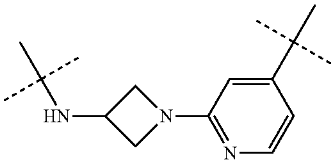
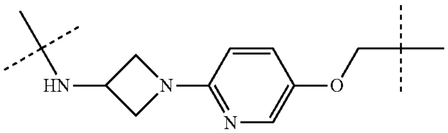
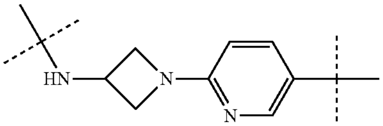
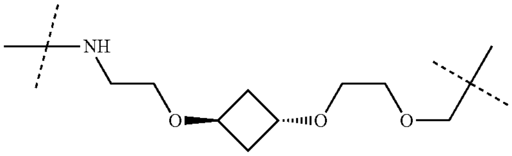
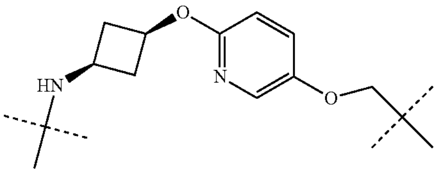
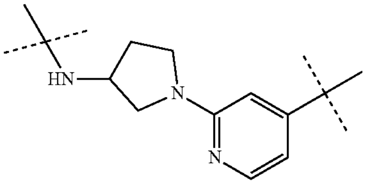
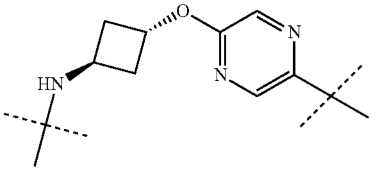
and
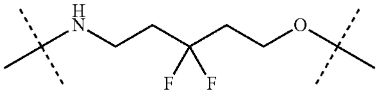
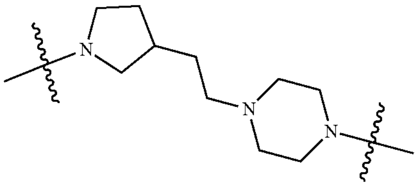
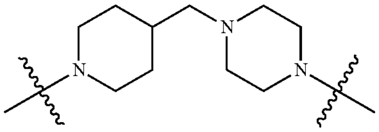
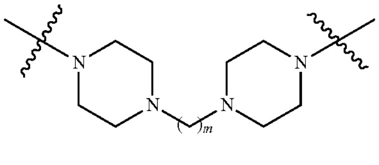
-continued
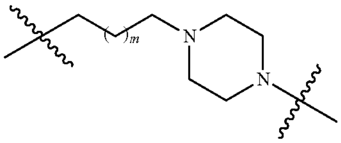
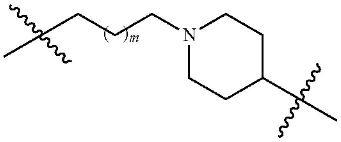
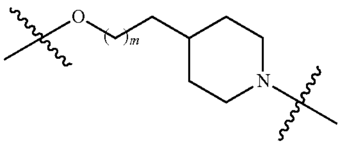

-continued
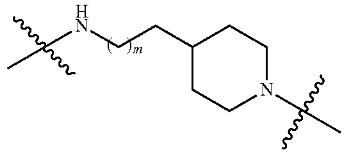
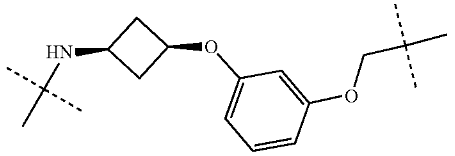
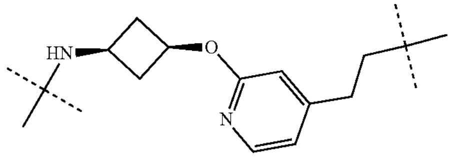
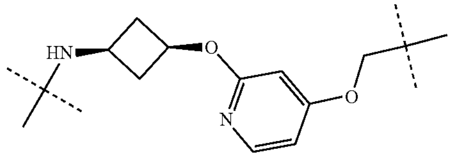
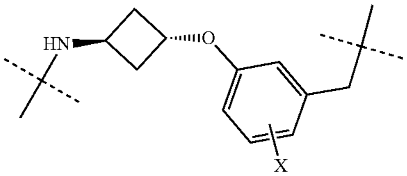
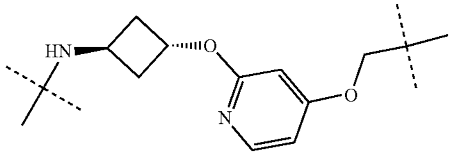
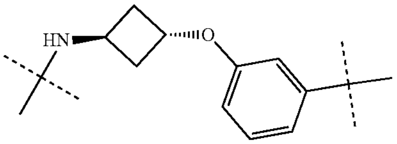
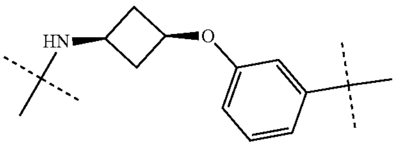
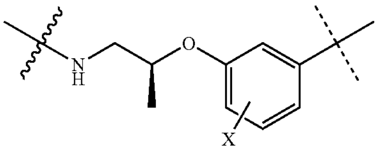
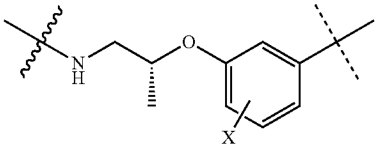
-continued
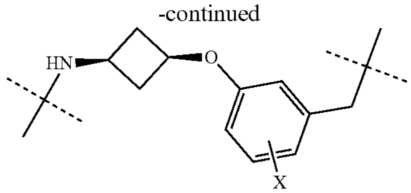
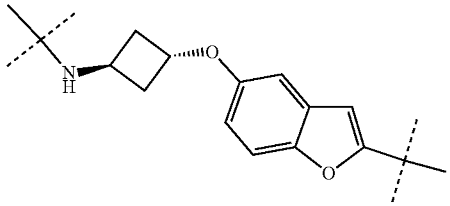
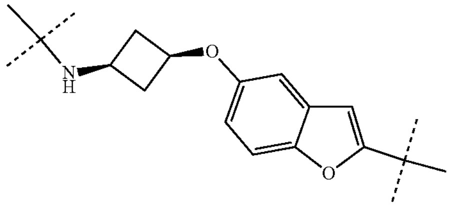
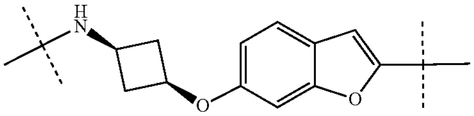
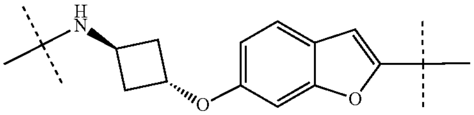
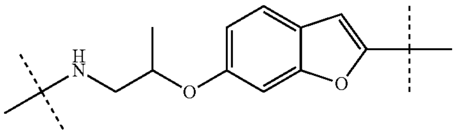
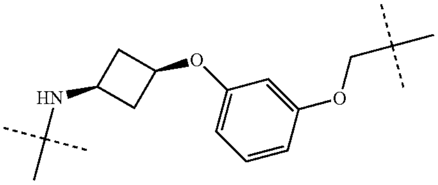
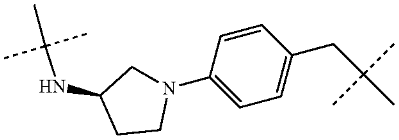
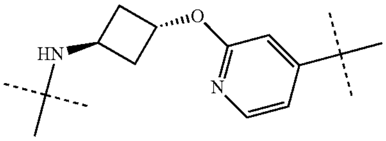
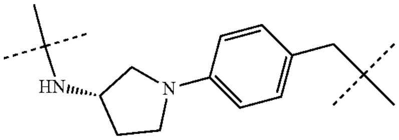
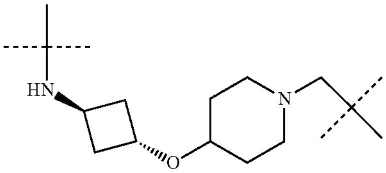

-continued
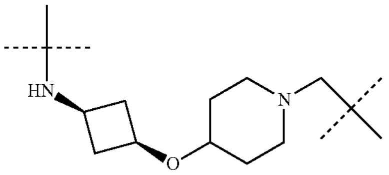
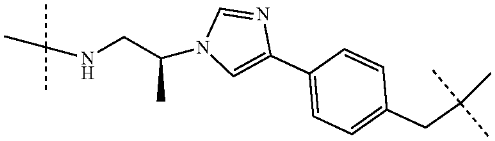
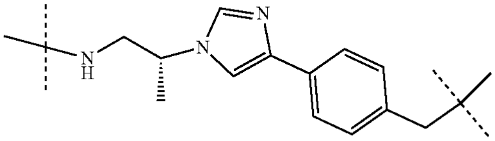
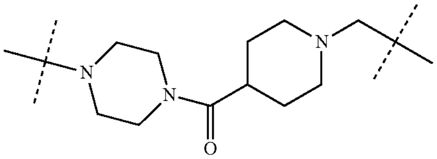
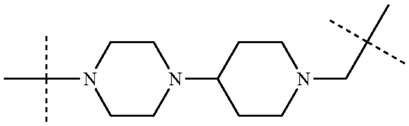
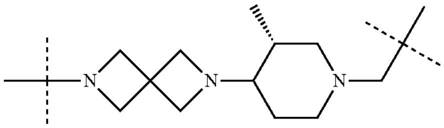
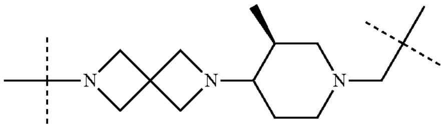
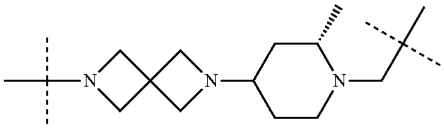
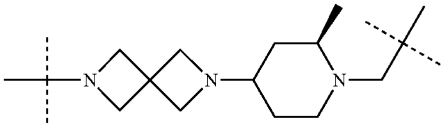
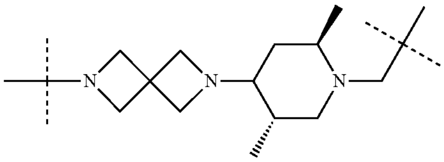
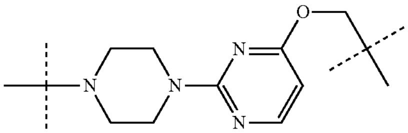
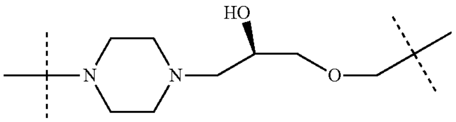
-continued
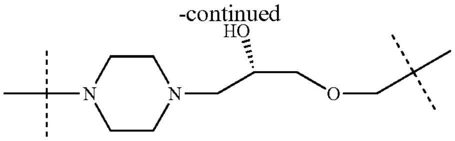
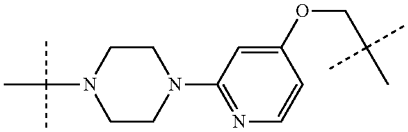
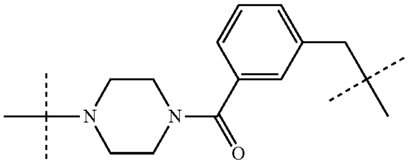
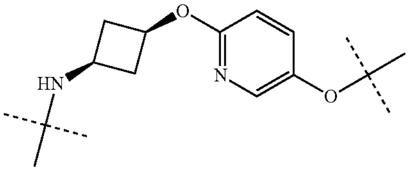
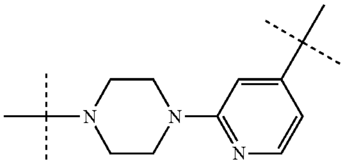
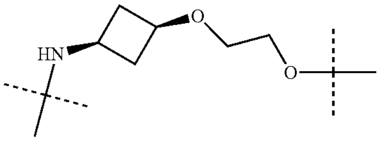
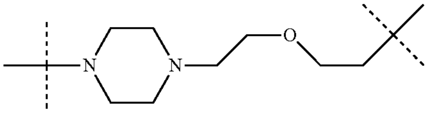
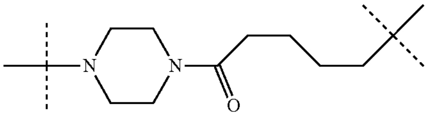
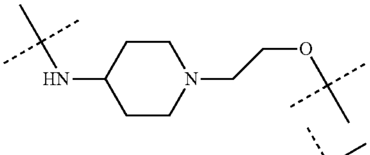
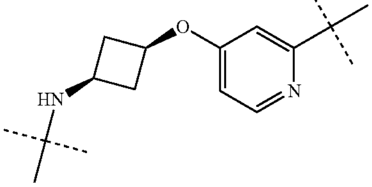
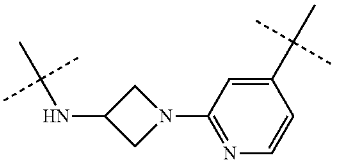
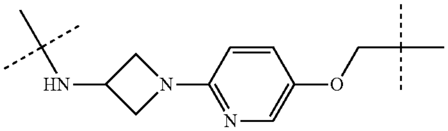

-continued
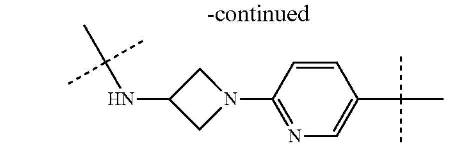
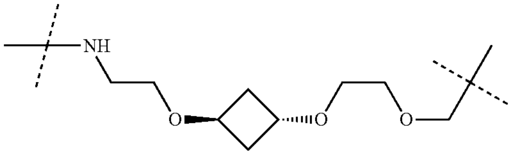
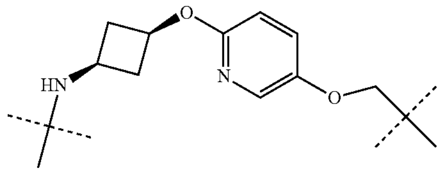
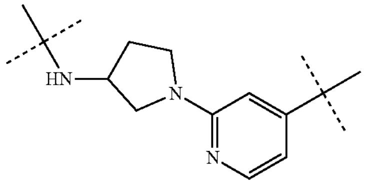
-continued
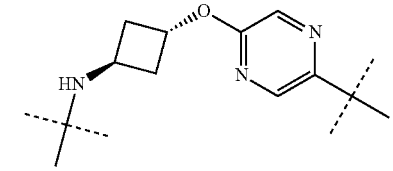
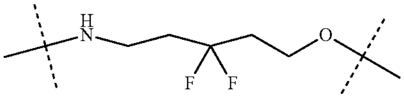
wherein
m, n, o, p, q, and r of the linker are independently 0, 1, 2, 3, 4, 5, or 6;
when the number is zero, there is no N—O or O—O bond in the linker;
R is H, methyl, or ethyl; and
X is H and F.
16. The compound of claim 6, or a pharmaceutically acceptable salt thereof, wherein the L is selected from the group consisting of:
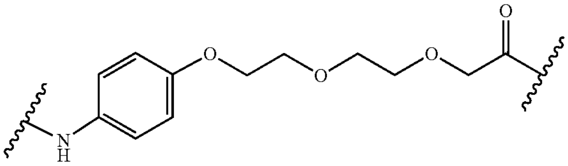
;
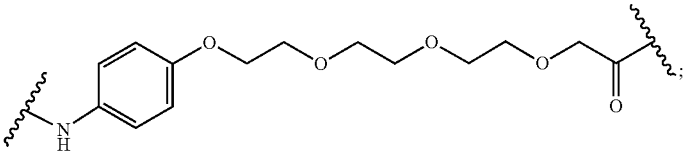
;
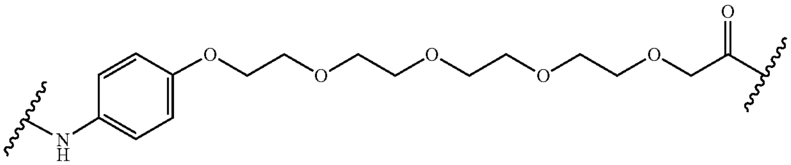
;
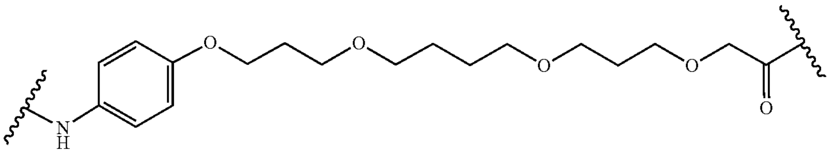
;
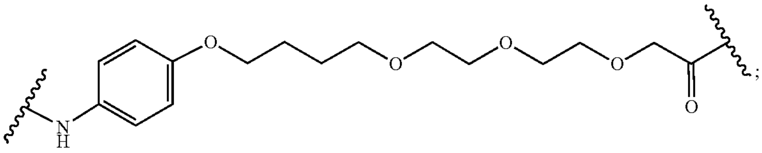
;
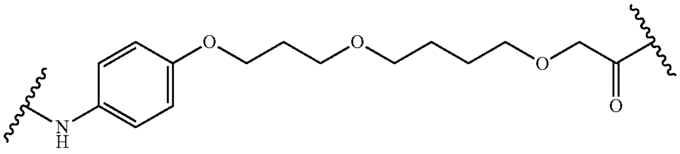
;

-continued
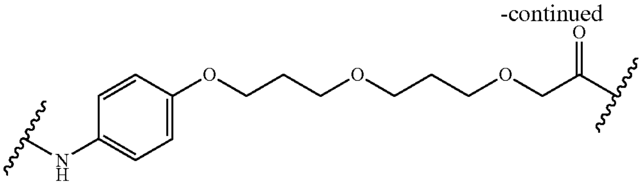
;
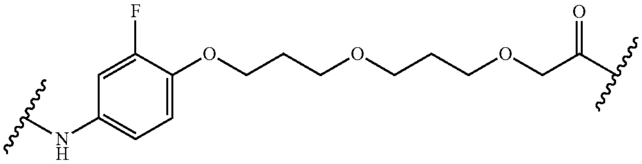
;
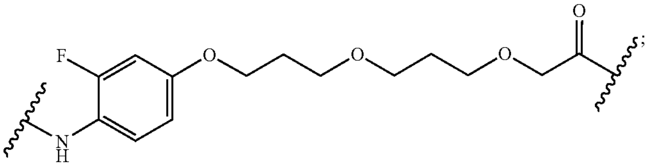
;
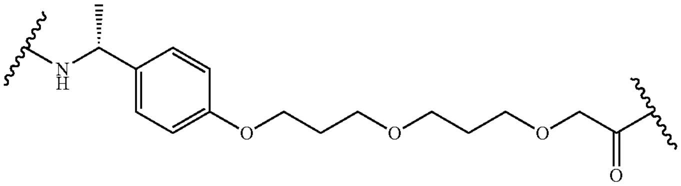
;
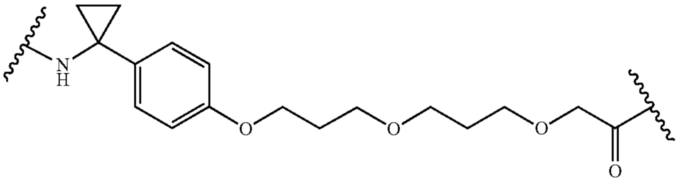
;
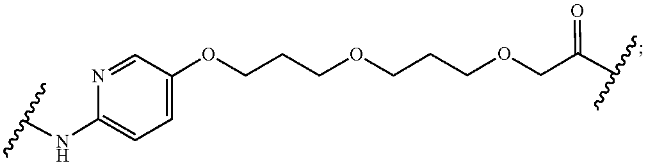
;
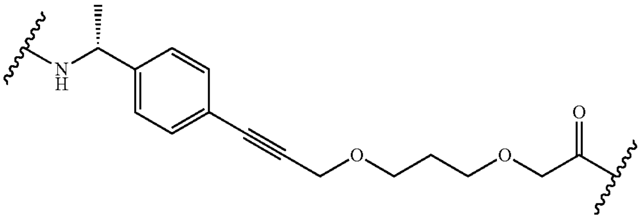
;
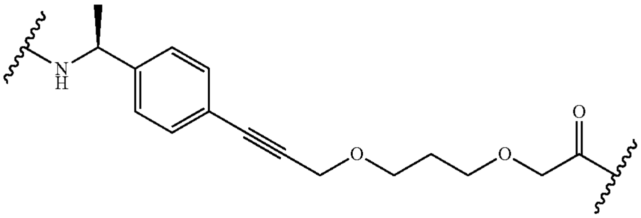
;
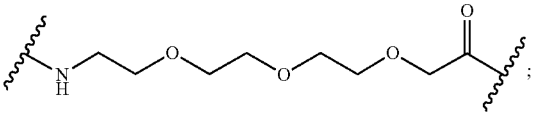
;
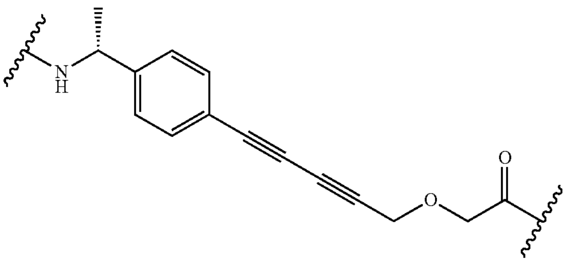
;

-continued
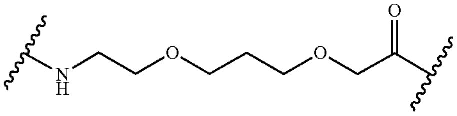
;
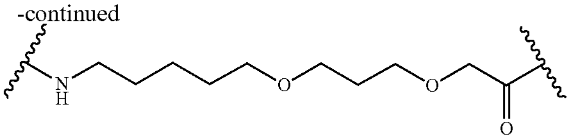
;
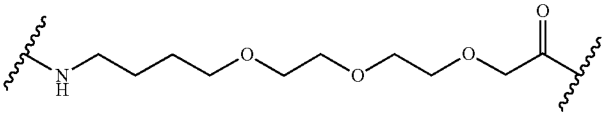
;
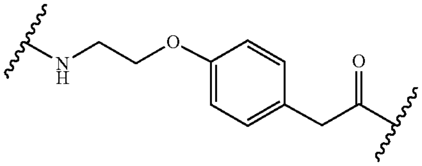
;
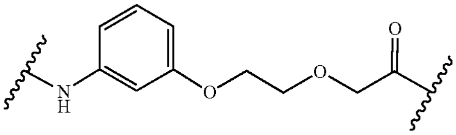
;
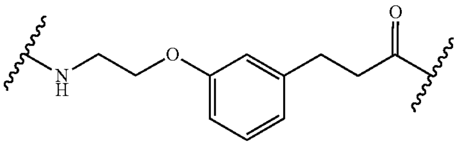
;
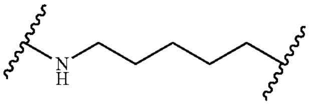
;
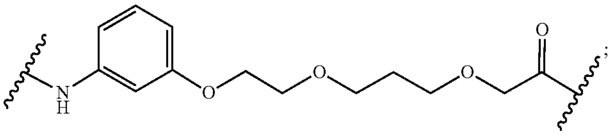
;
-continued
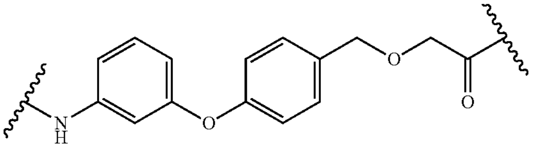
;
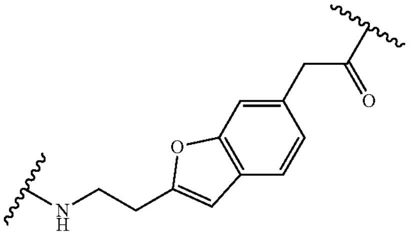
;
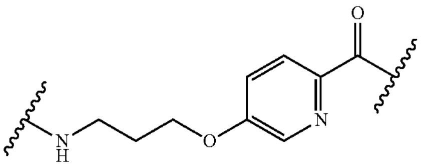
;
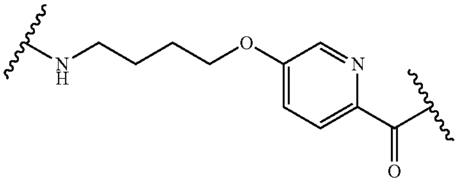
;
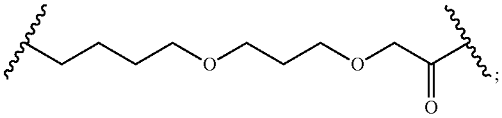
;
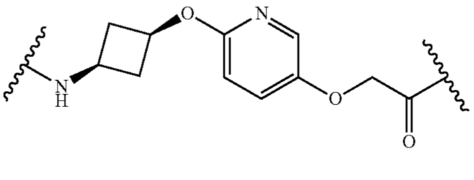
;
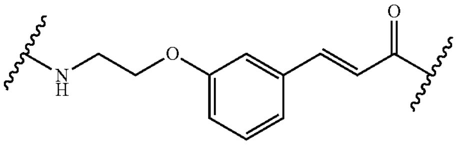
;
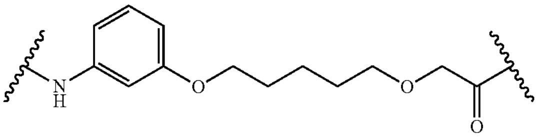
;
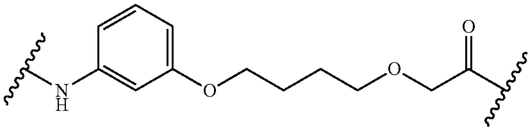
;
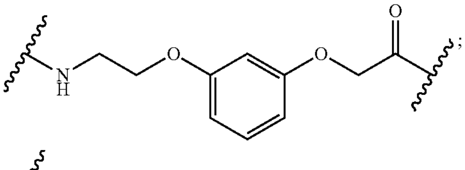
;
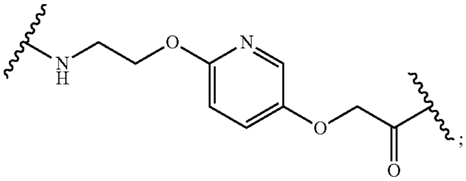
;
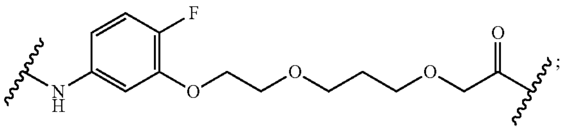
;
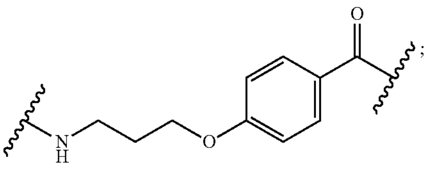
;

-continued
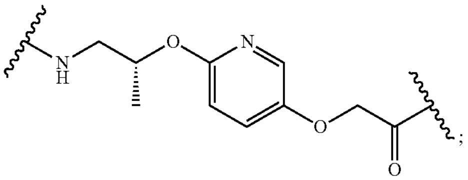
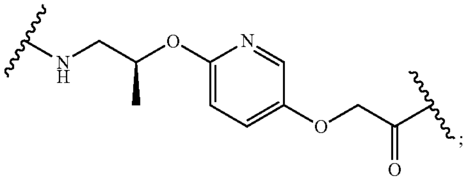
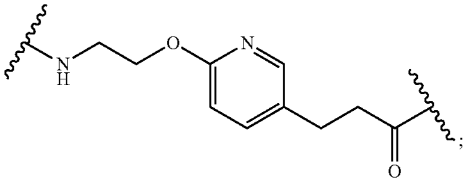
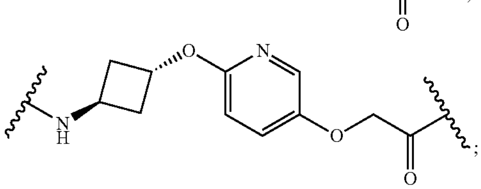
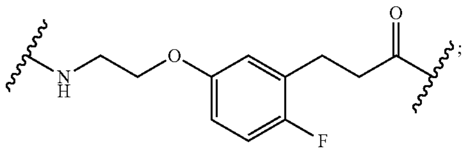
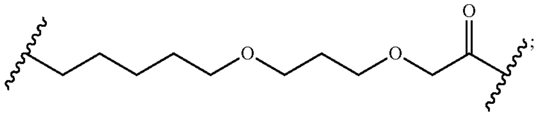
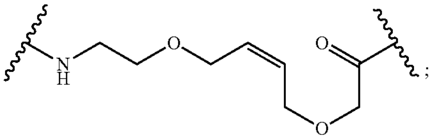
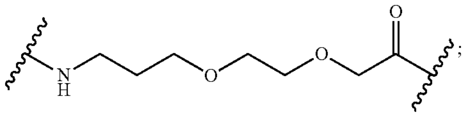
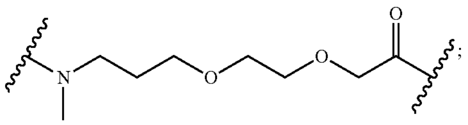
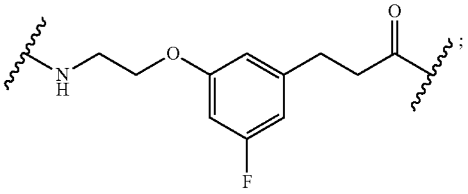
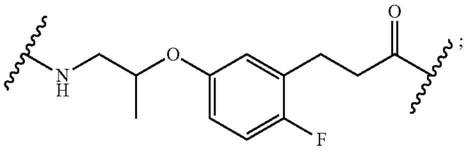
-continued
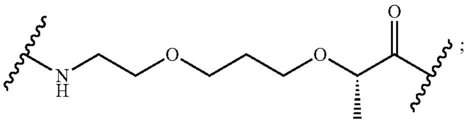
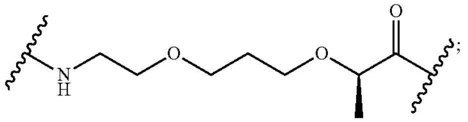
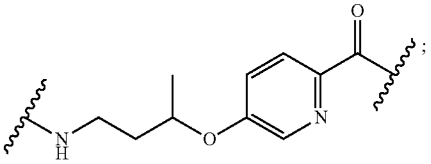
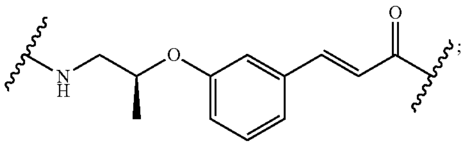
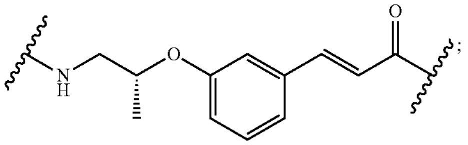
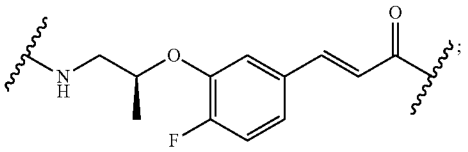
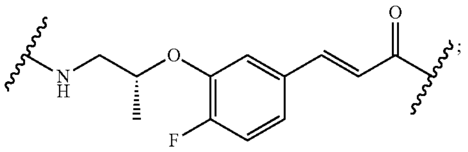
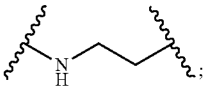
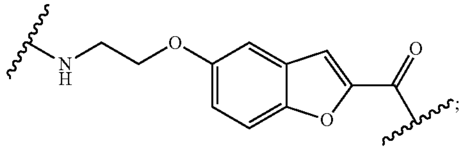
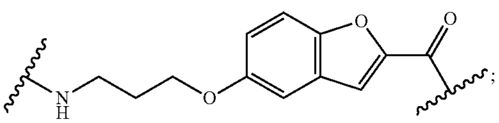
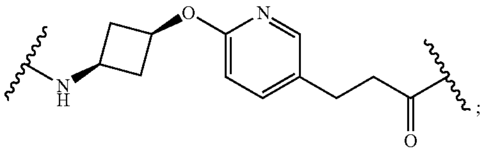
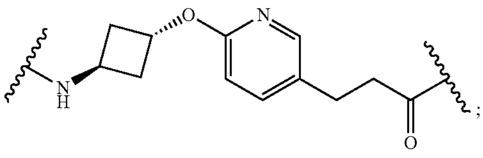

-continued
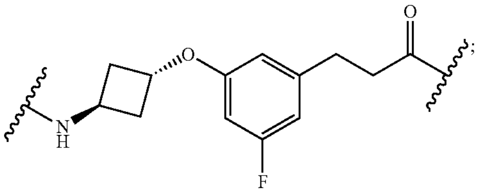
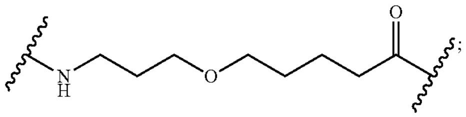
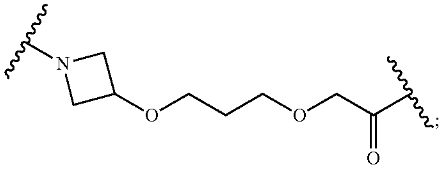
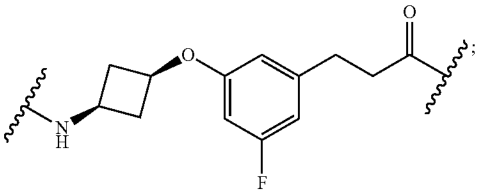
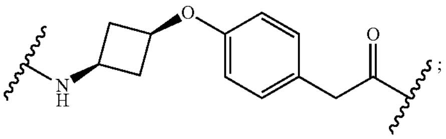
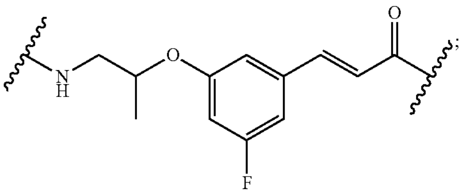
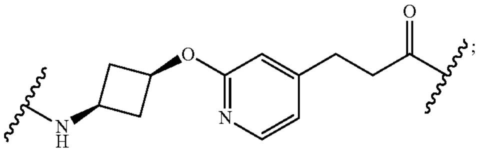
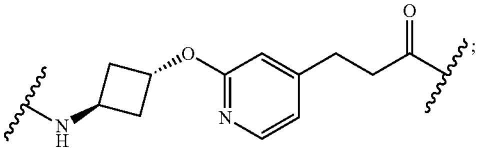
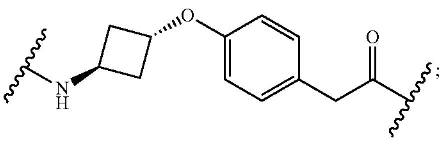
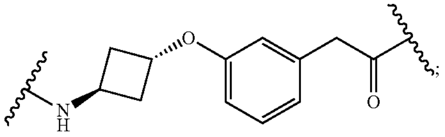
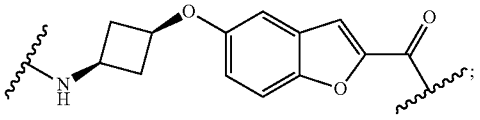
-continued
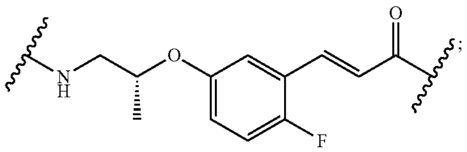
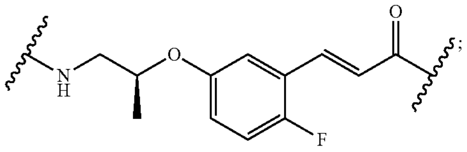
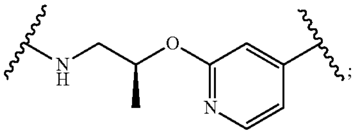
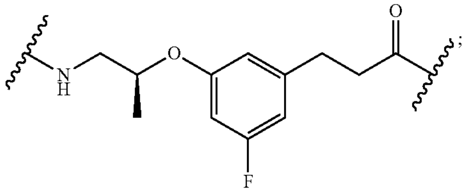
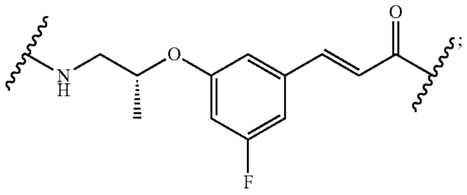
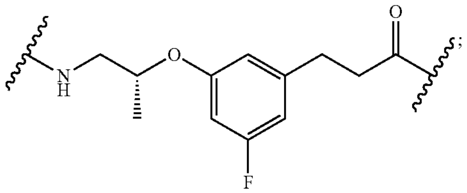
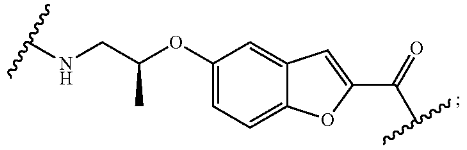
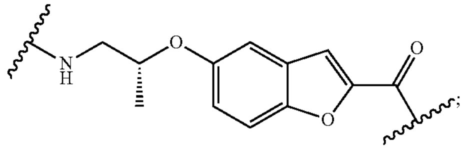
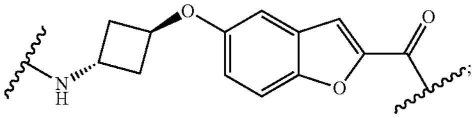
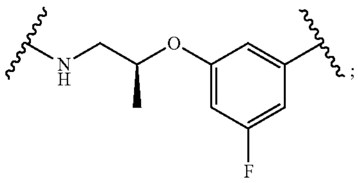

-continued
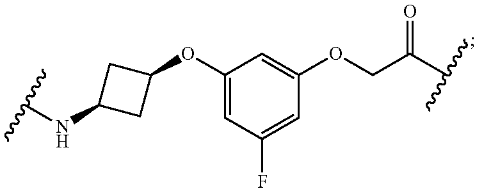
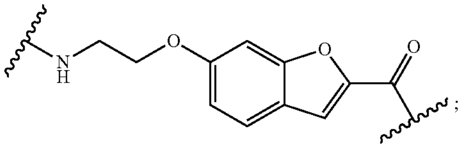
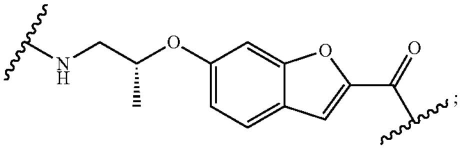
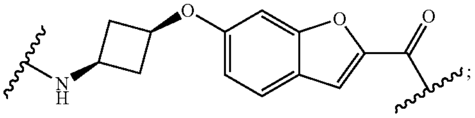
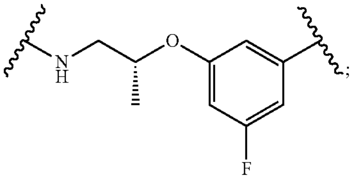
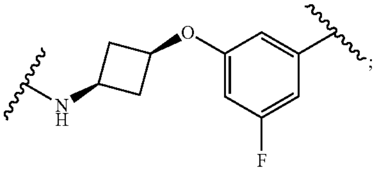
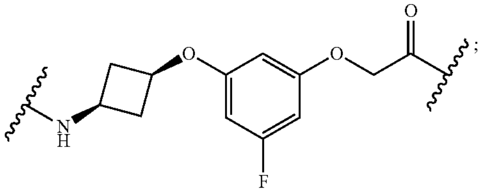
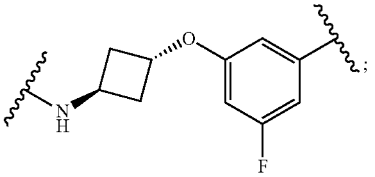
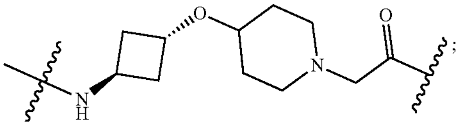
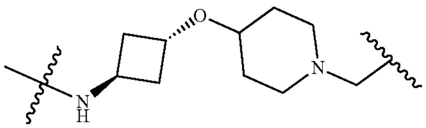
and
-continued
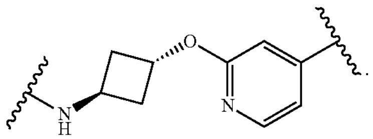
17. The compound of claim 6, or a pharmaceutically acceptable salt thereof, wherein the L is selected from the group consisting of:
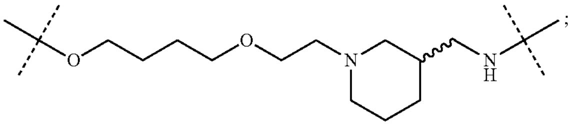
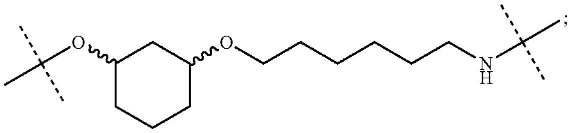
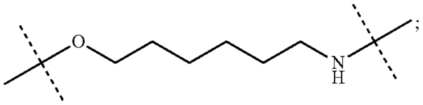
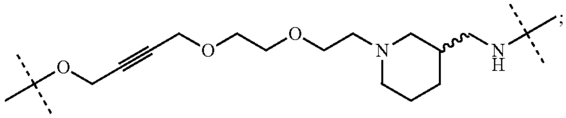
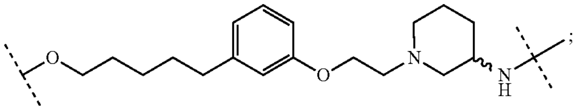
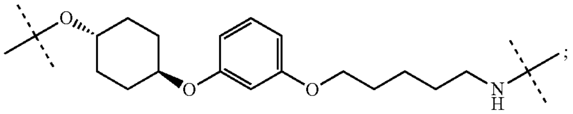
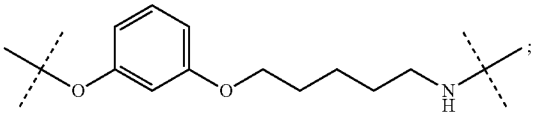
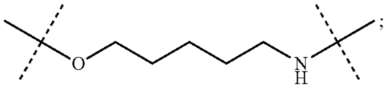
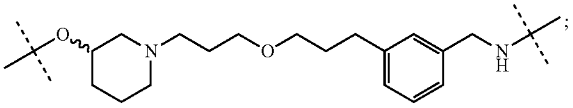
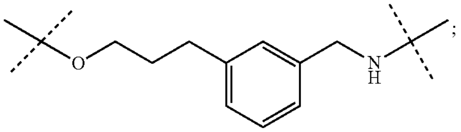
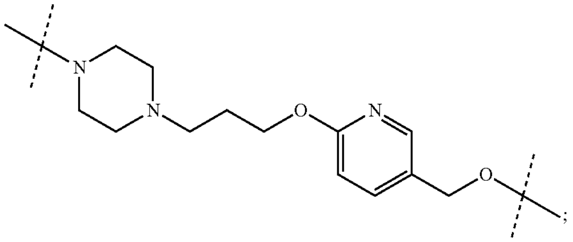

-continued
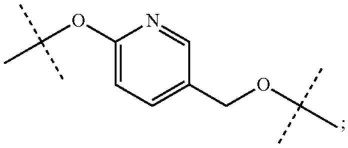
;
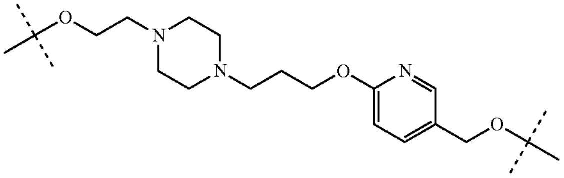
;
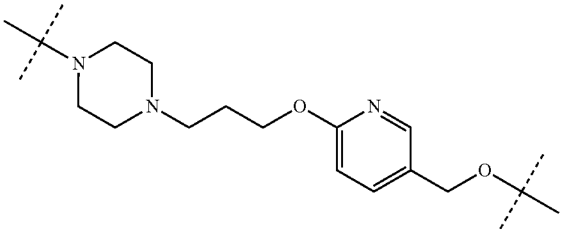
;
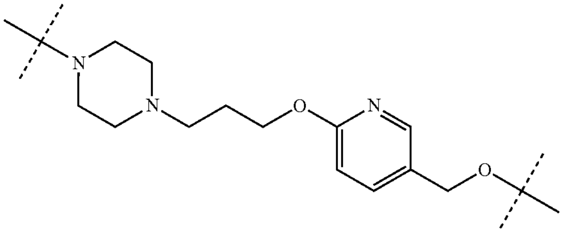
;
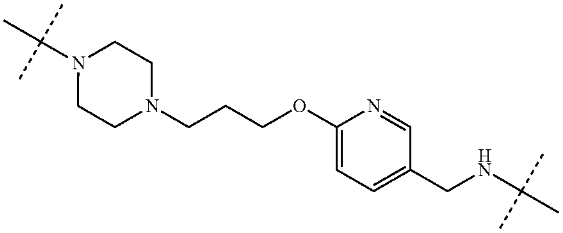
;
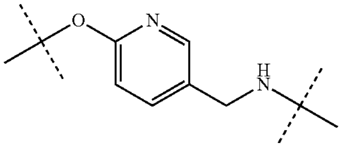
;
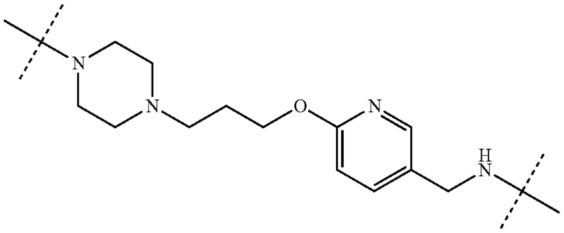
;
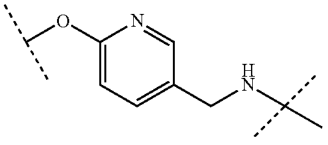
;
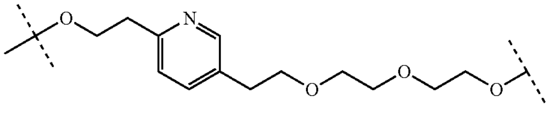
;
-continued
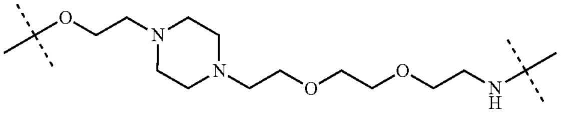
;
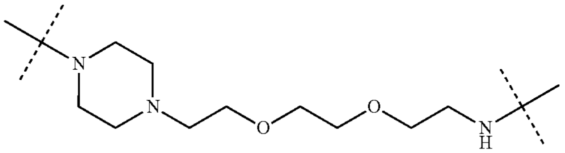
;
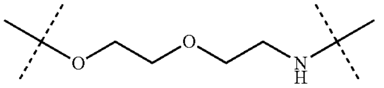
;
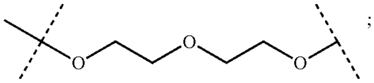
;
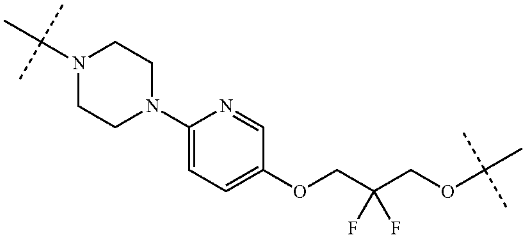
;
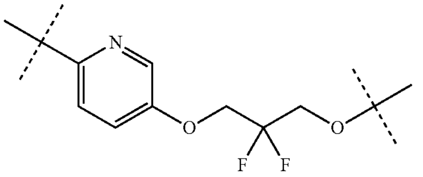
;
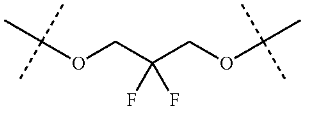
;
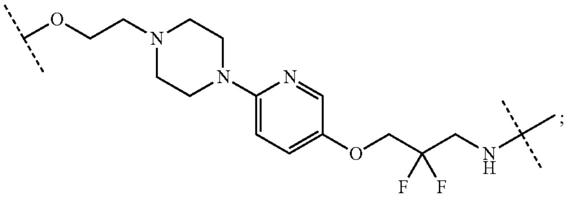
;
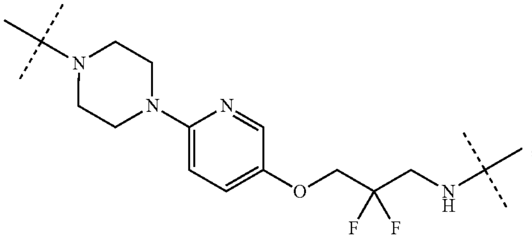
;
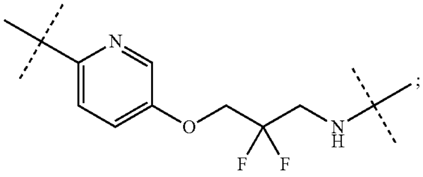
;
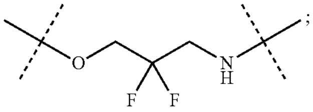
;

-continued
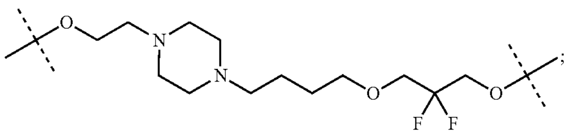
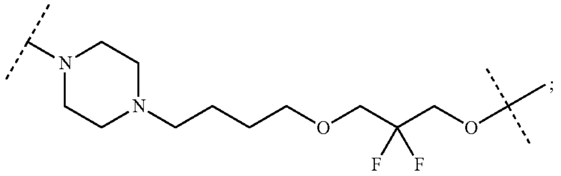
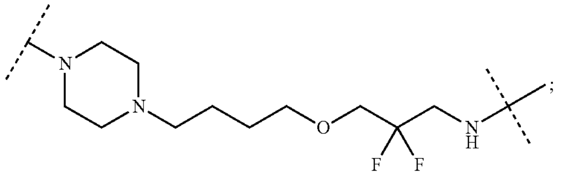
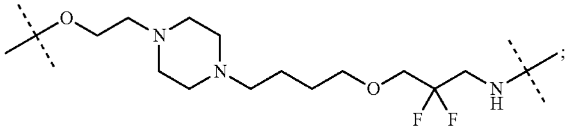
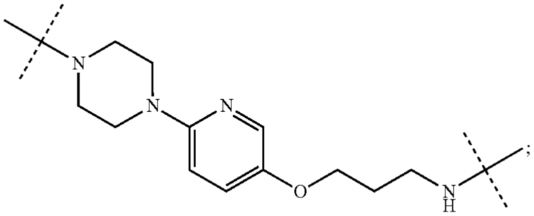
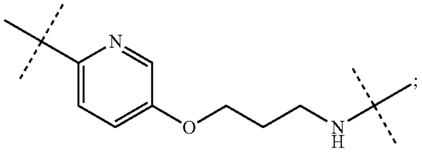
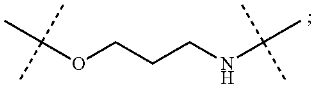
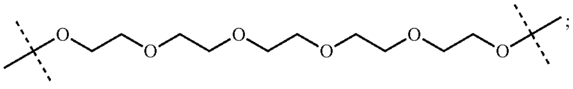
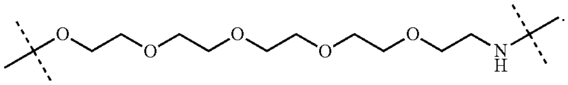
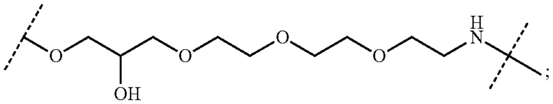
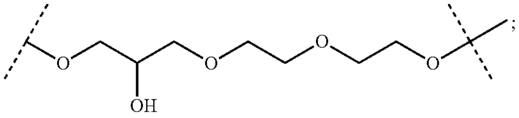
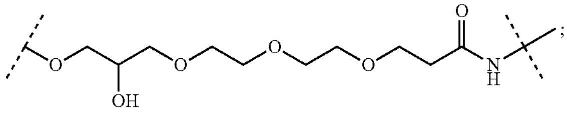
-continued
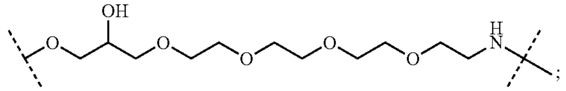
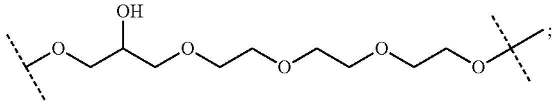
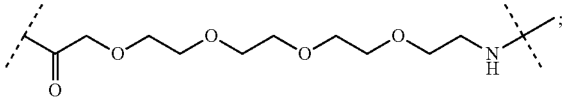
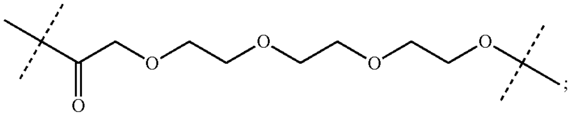
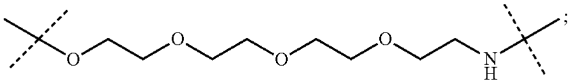
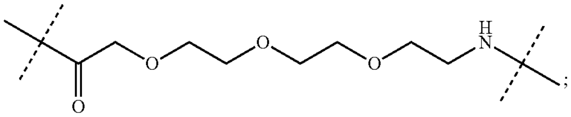
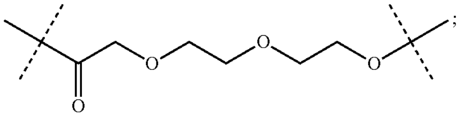
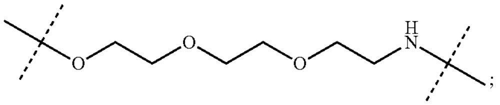
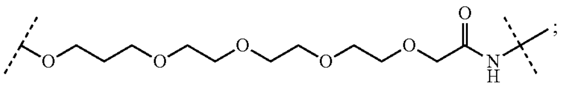
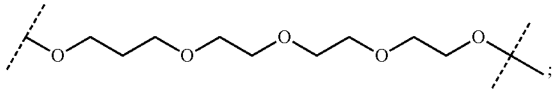
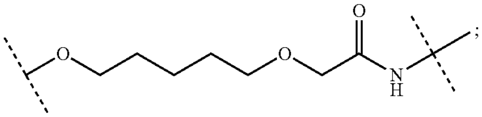
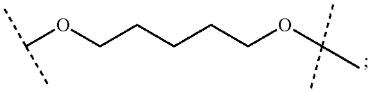
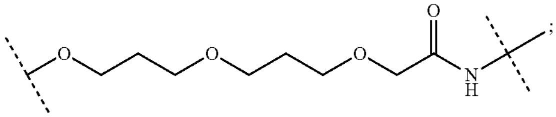
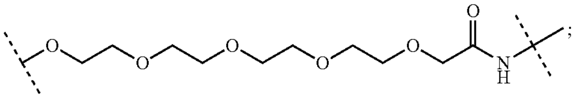
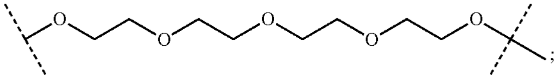
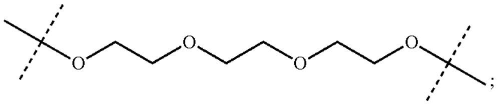
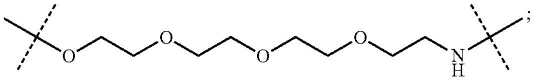

-continued
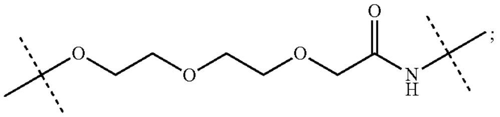
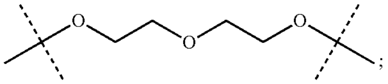
and
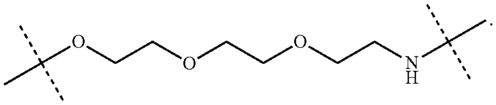
18. The compound of claim 6, or a pharmaceutically acceptable salt thereof, wherein the L is selected from the group consisting of:
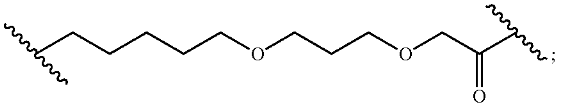
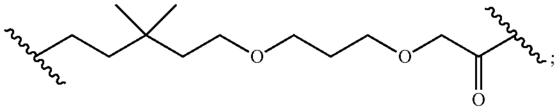
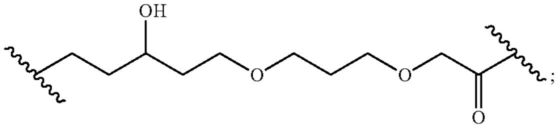
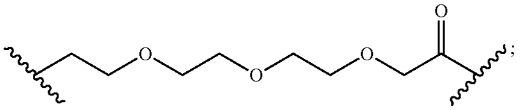
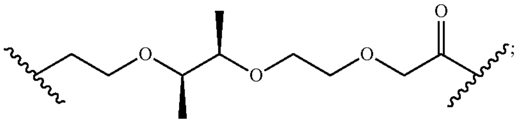
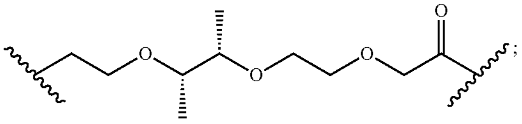
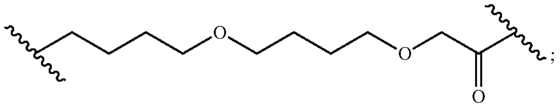
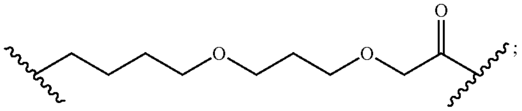
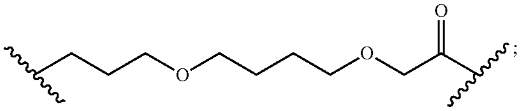
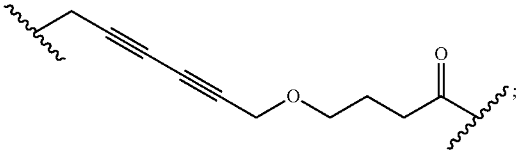
-continued
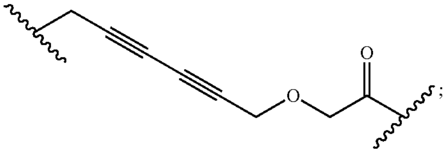
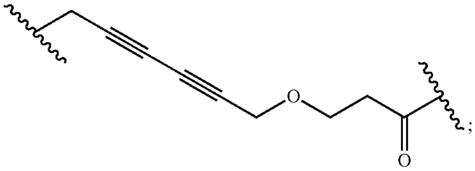
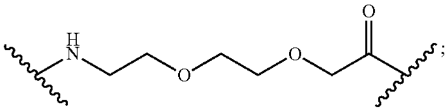
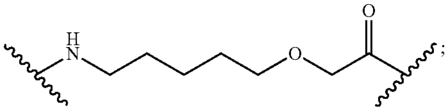
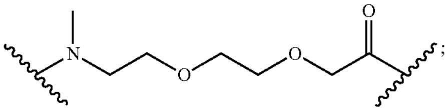
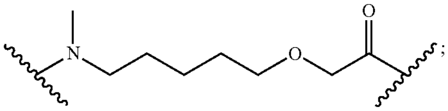
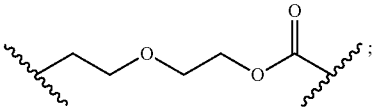
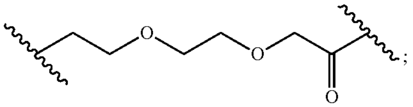
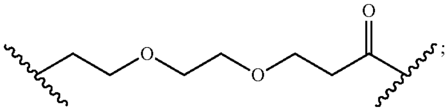
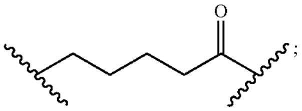
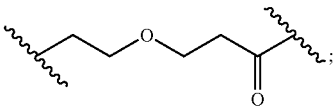
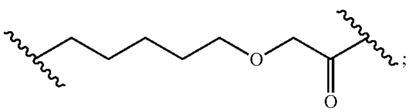
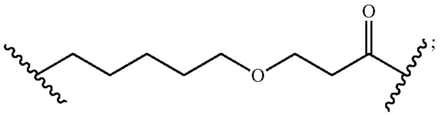
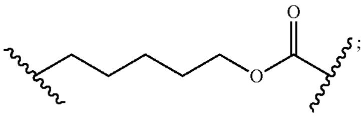

-continued
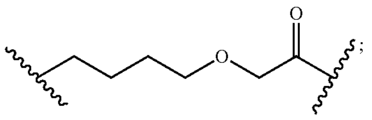
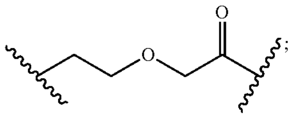
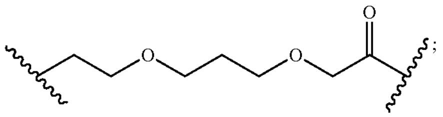
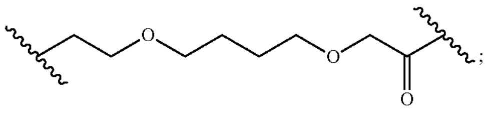
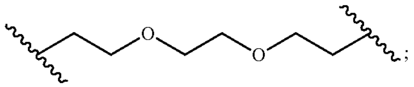
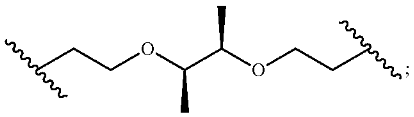
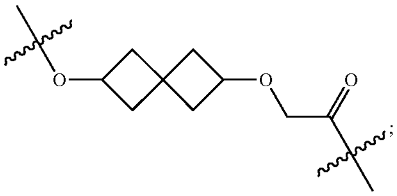
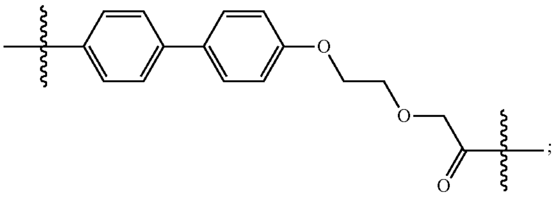
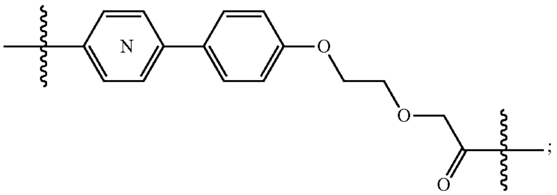
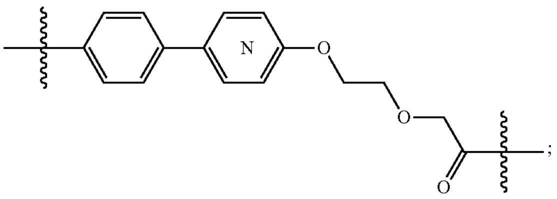
-continued
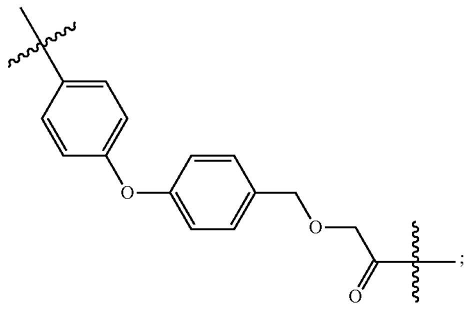
and
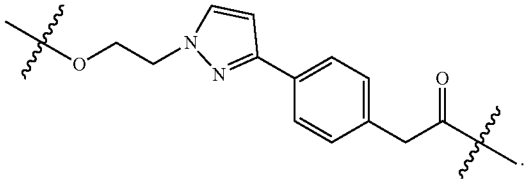 [SMILES: *OCCn1ccc(-c2ccc(CC(*)=O)cc2)n1]
19. The compound of claim 6, or a pharmaceutically acceptable salt thereof, wherein the L is selected from the group consisting of:
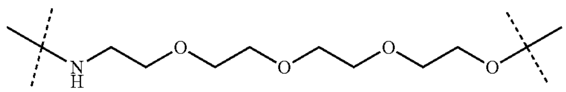
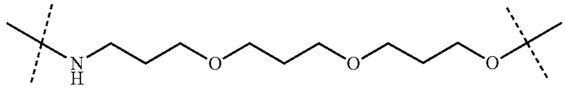
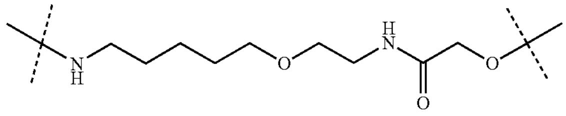
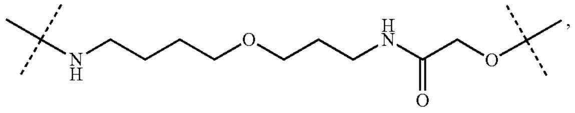
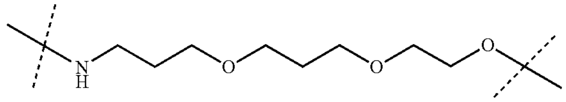
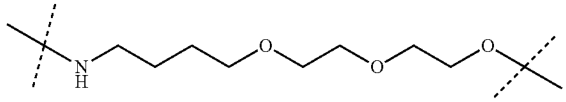
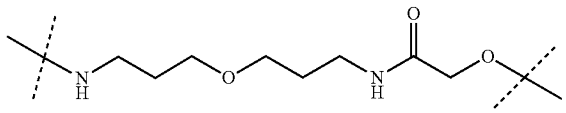
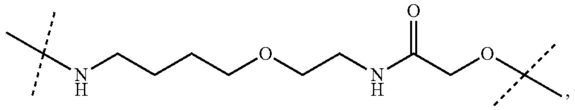
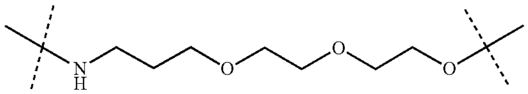
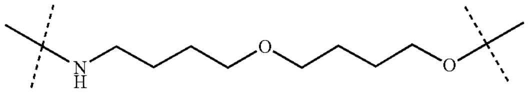

-continued
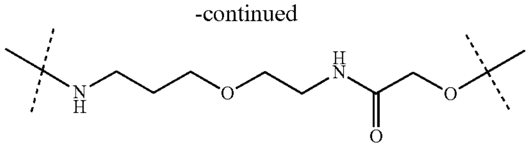
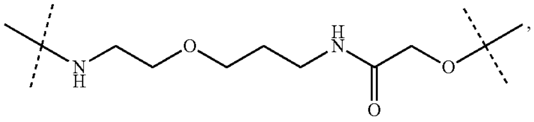
,
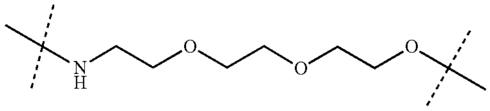
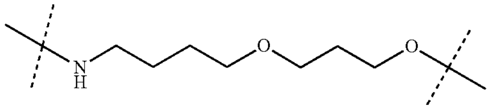
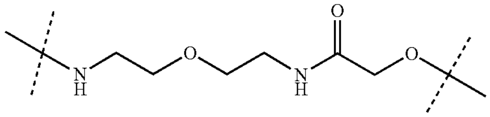
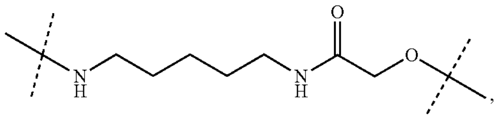
,
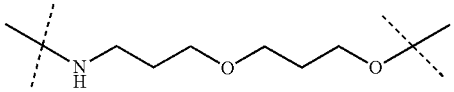
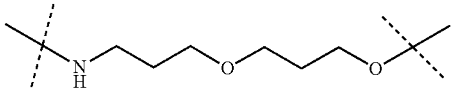
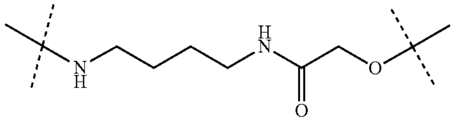
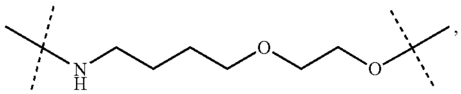
,
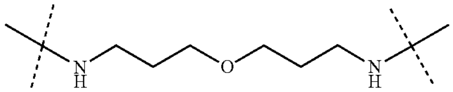
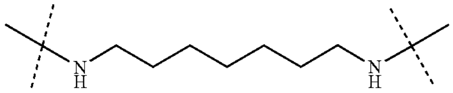
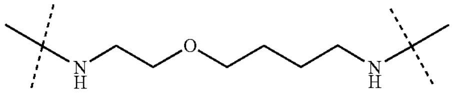
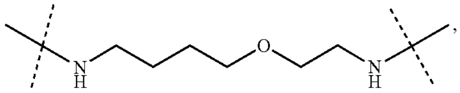
,
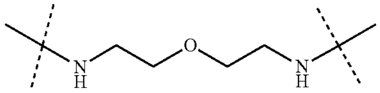
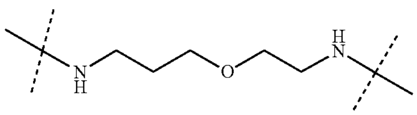
-continued
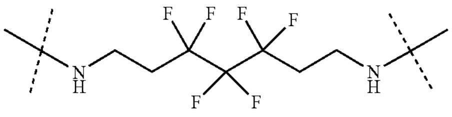
and
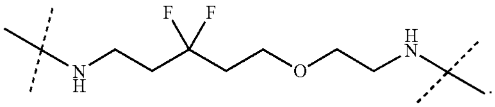
.
20. The compound of claim 6, or a pharmaceutically acceptable salt thereof, wherein the L is selected from the group consisting of:
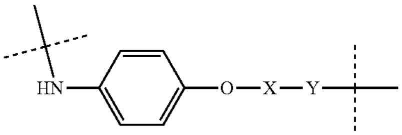
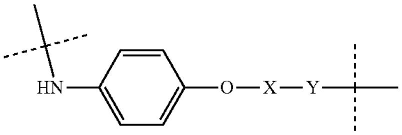
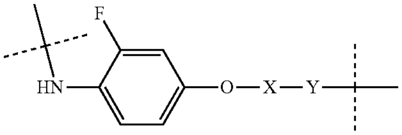
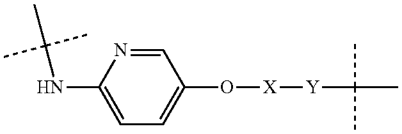
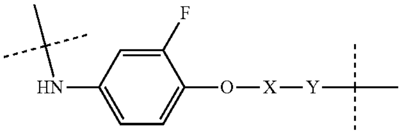
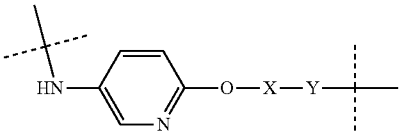
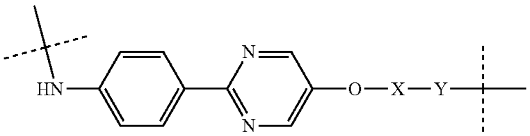
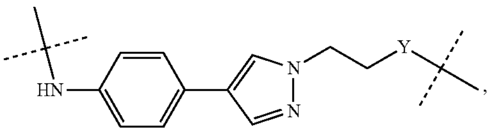
,
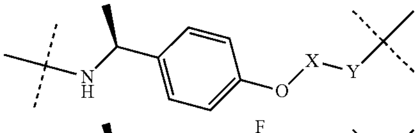
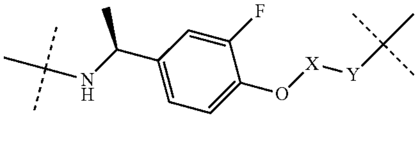

-continued
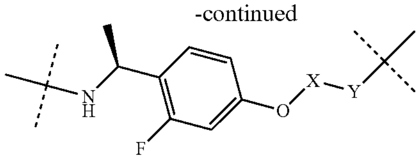
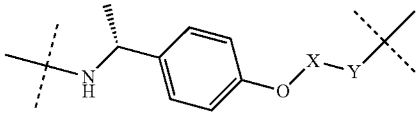
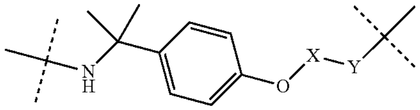
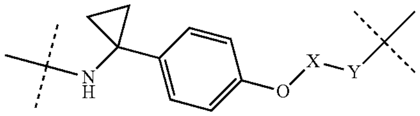
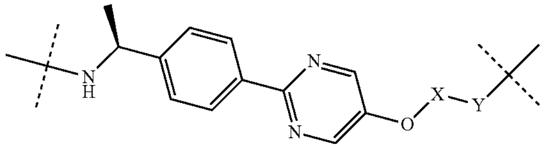
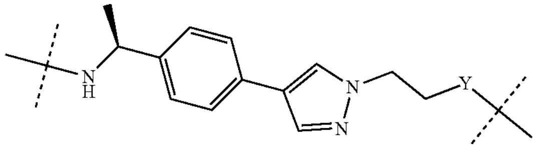
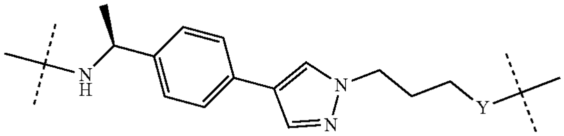
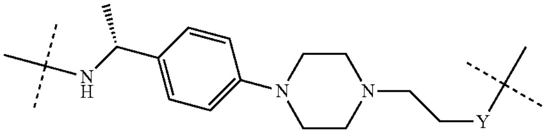
-continued
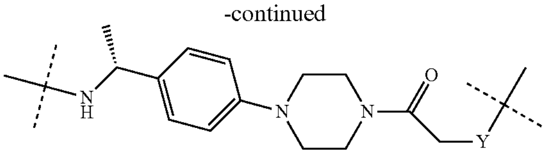
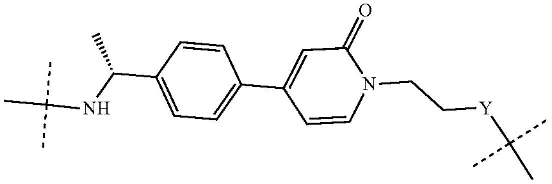
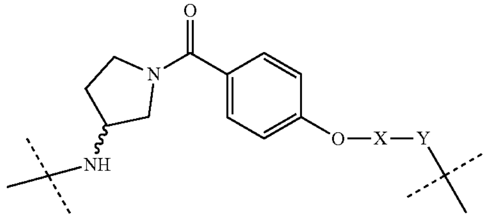
and
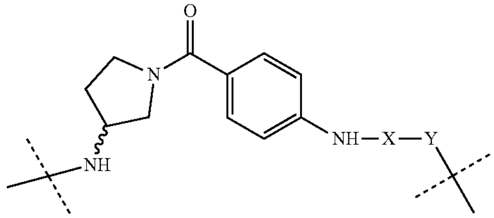
wherein
X is a linear chain with atoms ranging from 2 to 14 optionally substituted to contain heteroatoms, and
Y is O, N, or S (O) n, wherein n is 0, 1, or 2.
* * * * *